United States Patent
Zbieg et al.

(10) Patent No.: US 12,275,745 B2
(45) Date of Patent: Apr. 15, 2025

(54) THERAPEUTIC COMPOUNDS AND METHODS OF USE

(71) Applicant: Genentech, Inc., South San Francisco, CA (US)

(72) Inventors: Jason Robert Zbieg, Montara, CA (US); Paul Powell Beroza, Belmont, CA (US); Vishal Anil Verma, San Carlos, CA (US); Bing-Yan Zhu, Palo Alto, CA (US); Ramsay Beveridge, Montreal (CA); Liang Zhao, Montreal (CA); Melissa Leblanc, Montreal (CA); Lisa Marie Barton, Burlingame, CA (US); Bryan Ka Ip Chan, Foster City, CA (US); Samir Bouayad-Gervais, Montreal (CA); Anwesha Dey, Cupertino, CA (US); Marie Anne Evangelista, San Francisco, CA (US); Russell Tyler Smith, San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 18/057,742

(22) Filed: Nov. 21, 2022

(65) Prior Publication Data

US 2023/0203062 A1 Jun. 29, 2023

Related U.S. Application Data

(60) Provisional application No. 63/344,027, filed on May 19, 2022, provisional application No. 63/283,119, filed on Nov. 24, 2021.

(51) Int. Cl.

| | | |
|---|---|---|
| C07D 513/04 | (2006.01) |
| C07D 215/12 | (2006.01) |
| C07D 235/14 | (2006.01) |
| C07D 239/74 | (2006.01) |
| C07D 241/42 | (2006.01) |
| C07D 263/56 | (2006.01) |
| C07D 307/81 | (2006.01) |
| C07D 403/06 | (2006.01) |
| C07D 405/08 | (2006.01) |
| C07D 413/04 | (2006.01) |
| C07D 471/04 | (2006.01) |
| C07D 487/04 | (2006.01) |
| C07D 491/048 | (2006.01) |
| C07D 491/052 | (2006.01) |
| C07D 498/04 | (2006.01) |

(52) U.S. Cl.
CPC ......... *C07D 513/04* (2013.01); *C07D 215/12* (2013.01); *C07D 235/14* (2013.01); *C07D 239/74* (2013.01); *C07D 241/42* (2013.01); *C07D 263/56* (2013.01); *C07D 307/81* (2013.01); *C07D 403/06* (2013.01); *C07D 405/08* (2013.01); *C07D 413/04* (2013.01); *C07D 471/04* (2013.01); *C07D 487/04* (2013.01); *C07D 491/048* (2013.01); *C07D 491/052* (2013.01); *C07D 498/04* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell |
| 4,485,045 A | 11/1984 | Regen |
| 4,544,545 A | 10/1985 | Ryan |
| 4,670,447 A | 6/1987 | Strupczewski |
| 4,943,533 A | 7/1990 | Mendelsohn |
| 5,004,697 A | 4/1991 | Pardridge |
| 5,112,596 A | 5/1992 | Malfroy-camine |
| 5,212,290 A | 5/1993 | Vogelstein |
| 5,268,164 A | 12/1993 | Kozarich et al. |
| 5,457,105 A | 10/1995 | Barker |
| 5,475,001 A | 12/1995 | Barker |
| 5,506,206 A | 4/1996 | Kozarich et al. |
| 5,616,582 A | 4/1997 | Barker |
| 5,654,307 A | 8/1997 | Bridges |
| 5,679,683 A | 10/1997 | Bridges |
| 5,686,416 A | 11/1997 | Kozarich et al. |
| 5,747,498 A | 5/1998 | Schnur |
| 5,760,041 A | 6/1998 | Wissner |
| 5,770,599 A | 6/1998 | Gibson |
| 5,804,396 A | 9/1998 | Plowman |
| 5,866,572 A | 2/1999 | Barker |
| 5,891,996 A | 4/1999 | Mateo |
| 6,002,008 A | 12/1999 | Wissner |

(Continued)

FOREIGN PATENT DOCUMENTS

| | | |
|---|---|---|
| EP | 0102324 A2 | 3/1984 |
| EP | 0133988 A2 | 3/1985 |

(Continued)

OTHER PUBLICATIONS

Database Registry Chemical Abstracts Service, Columbus, Ohio, Accession No. RN 2102543-07-5, Entered STN: Jul. 20, 2017.*

(Continued)

*Primary Examiner* — Samantha L Shterengarts
(74) *Attorney, Agent, or Firm* — Morrison & Foerster LLP

(57) ABSTRACT

This disclosure relates to compounds and methods of using said compounds, as well as pharmaceutical compositions containing such compounds, for treating diseases and conditions mediated by TEAD, such as cancer.

20 Claims, 24 Drawing Sheets

Specification includes a Sequence Listing.

(56) References Cited

U.S. PATENT DOCUMENTS

| | | |
|---|---|---|
| 6,084,095 A | 7/2000 | Bridges |
| 6,140,332 A | 10/2000 | Traxler |
| 6,235,883 B1 | 5/2001 | Jakobovits |
| 6,265,410 B1 | 7/2001 | Bridges |
| 6,344,455 B1 | 2/2002 | Bridges |
| 6,344,459 B1 | 2/2002 | Bridges |
| 6,391,874 B1 | 5/2002 | Cockerill |
| 6,399,602 B1 | 6/2002 | Barker |
| 6,455,534 B2 | 9/2002 | Bridges |
| 6,521,620 B1 | 2/2003 | Bridges |
| 6,596,726 B1 | 7/2003 | Bridges |
| 6,602,863 B1 | 8/2003 | Bridges |
| 6,713,484 B2 | 3/2004 | Bridges |
| 8,217,149 B2 | 7/2012 | Irving |
| 9,205,148 B2 | 12/2015 | Langermann et al. |
| 9,212,139 B2 | 12/2015 | Kyle et al. |
| 9,266,880 B2 | 2/2016 | Austin et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0129186 A1 | 7/2003 | Beliveau et al. |
| 2003/0162695 A1 | 8/2003 | Schatzberg et al. |
| 2004/0131692 A1 | 7/2004 | Kreuter et al. |
| 2004/0204354 A1 | 10/2004 | Nelson et al. |
| 2005/0089473 A1 | 4/2005 | Black et al. |
| 2005/0124533 A1 | 6/2005 | Schatzberg et al. |
| 2006/0223708 A1 | 10/2006 | Hoffmann et al. |
| 2013/0034559 A1 | 2/2013 | Queva |
| 2015/0210769 A1 | 7/2015 | Freeman et al. |
| 2016/0108123 A1 | 4/2016 | Freeman |
| 2016/0376367 A1 | 12/2016 | Yuan et al. |
| 2018/0334454 A1 | 11/2018 | Lanman et al. |
| 2019/0144444 A1 | 5/2019 | Blake et al. |
| 2020/0054653 A1 | 2/2020 | Lagarde et al. |
| 2020/0299285 A1 | 9/2020 | Fletcher et al. |
| 2021/0009688 A1 | 1/2021 | Chen et al. |
| 2021/0213014 A1 | 7/2021 | Cosmopoulos et al. |
| 2021/0230142 A9 | 7/2021 | Malhotra et al. |
| 2023/0202984 A1 | 6/2023 | Zbieg et al. |

FOREIGN PATENT DOCUMENTS

| | | |
|---|---|---|
| EP | 0659439 A2 | 6/1995 |
| EP | 3712129 A1 | 9/2020 |
| WO | 199630347 A1 | 10/1996 |
| WO | 199633978 A1 | 10/1996 |
| WO | 199633980 A1 | 10/1996 |
| WO | 199640210 A1 | 12/1996 |
| WO | 199738983 A1 | 10/1997 |
| WO | 199814451 A1 | 4/1998 |
| WO | 199843960 A1 | 10/1998 |
| WO | 199850038 A1 | 11/1998 |
| WO | 199850433 A2 | 11/1998 |
| WO | 199906378 A1 | 2/1999 |
| WO | 199906396 A1 | 2/1999 |
| WO | 199909016 A1 | 2/1999 |
| WO | 199924037 A1 | 5/1999 |
| WO | 2006121168 A1 | 11/2006 |
| WO | 2007005874 A2 | 1/2007 |
| WO | 2009114335 A2 | 9/2009 |
| WO | 2010027827 A2 | 3/2010 |
| WO | 2010077634 A1 | 7/2010 |
| WO | 2011066342 A2 | 6/2011 |
| WO | 2011066389 A1 | 6/2011 |
| WO | 2011113798 A2 | 9/2011 |
| WO | 2011161699 A2 | 12/2011 |
| WO | 2012145493 A1 | 10/2012 |
| WO | 2012168944 A1 | 12/2012 |
| WO | 2013132317 A1 | 9/2013 |
| WO | 2013144704 A1 | 10/2013 |
| WO | 2013181634 A2 | 12/2013 |
| WO | 2014179664 A2 | 11/2014 |
| WO | 2014194302 A2 | 12/2014 |
| WO | 2014206107 A1 | 12/2014 |
| WO | 2015033299 A1 | 3/2015 |
| WO | 2015033301 A1 | 3/2015 |
| WO | 2015033303 A1 | 3/2015 |
| WO | 2015035606 A1 | 3/2015 |
| WO | 2015036927 A1 | 3/2015 |
| WO | 2015044900 A1 | 4/2015 |
| WO | 2015085847 A1 | 6/2015 |
| WO | 2015112800 A1 | 7/2015 |
| WO | 2015112805 A1 | 7/2015 |
| WO | 2015112900 A1 | 7/2015 |
| WO | 2015119923 A1 | 8/2015 |
| WO | 2015119930 A1 | 8/2015 |
| WO | 2016000619 A1 | 1/2016 |
| WO | 2016032927 A1 | 3/2016 |
| WO | 2016061142 A1 | 4/2016 |
| WO | 2016089873 A1 | 6/2016 |
| WO | 2016106160 A1 | 6/2016 |
| WO | 2020081572 A1 | 4/2020 |
| WO | 2020211563 A1 | 10/2020 |
| WO | 2021081212 A1 | 4/2021 |
| WO | 2021097110 A1 | 5/2021 |
| WO | 2021124222 A1 | 6/2021 |
| WO | 2021127333 A1 | 6/2021 |
| WO | 2021204823 A1 | 10/2021 |
| WO | 2022037568 A1 | 2/2022 |
| WO | 2022166469 A1 | 8/2022 |
| WO | 2022204452 A1 | 9/2022 |

OTHER PUBLICATIONS

Ahn, E.Y. et al. (Jul. 2013), "RASSF1A-Mediated Regulation of AREG via the Hippo Pathway in Hepatocellular Carcinoma," Mol. Cancer. Res. 11(7):748-758.

Avruch, J. et al. (Mar. 15, 2012). "YAP Oncogene Overexpression Supercharges Colon Cancer Proliferation," Cell Cycle 11(6):1090-1096.

Baia, G.S. et al. (Jul. 2012), "Yes-Associated Protein 1 is Activated and Functions as an Oncogene in Meningiomas," Mol. Cancer Res. 10(7):904-913.

Bao, Y. et al. (2011). "Mammalian Hippo Pathway: From Development to Cancer and Beyond," J. Biochem. 149(4):361-379.

Bobo, R.H. et al. (Mar. 1994). "Convection-Enhanced Delivery of Macromolecules in the Brain," Proc. Natl. Acad. Sci. U.S.A. 91:2076-2080.

Bundgaard, H. (1985). "Design of Prodrugs: Bioreversible Derivatives for Various Functional Groups and Chemical Entities," in Design of Prodrugs, 3 pages.

Bundgaard, H. (Jan.-Feb. 1992). "(C) Means to Enhance Penetration: (1) Prodrugs as a Means to Improve the Delivery of Peptide Drugs," Advanced Drug Delivery Reviews 8(1):1-38.

CAS Registry No. 1422184-00-6 (Feb. 5, 2019). AMP-224, 7 pages.

CAS Registry No. 1859072-53-9 (Feb. 5, 2019). PDR 001, 8 pages.

CAS Registry No. 2181546-09-6 (Feb. 28, 2018), supplied by Aurora Fine Chemicals, 1 page.

CAS Registry No. 2181546-13-2 (Feb. 28, 2018), supplied by Aurora Fine Chemicals, 1 page,.

CAS Registry No. 2181892-26-0 (Mar. 1, 2018), supplied by Aurora Fine Chemicals, 1 page.

CAS Registry No. 2182408-04-2 (Mar. 1, 2018), supplied by Aurora Fine Chemicals, 1 page.

CAS Registry No. 2185523-08-2 (Mar. 6, 2018), supplied by Aurora Fine Chemicals, 1 page.

CAS Registry No. 2645601-32-5 (Jun. 13, 2021), supplied by Aurora Fine Chemicals, 1 page.

CAS Registry No. 1374853-91-4 (2014). Pembrolizumab, 29 pages.

CAS Registry No. 1422185-06-5 (2023). Atezolizumab, 2 pages.

CAS Registry No. 1428935-60-7, Oct. 18, 2019, 2 pages.

CAS Registry No. 1537032-82-8, Oct. 18, 2019, 2 pages.

CAS Registry No. 946414-94-4 (2014). Nivolumab, 29 pages.

Chan, S.W. et al. (Apr. 15, 2008). "A Role for TAZ in Migration, Invasion, and Tumorigenesis of Breast Cancer Cells," Cancer Res. 68(8):2592-2598.

Database (Feb. 15, 2021). "2589189-68-2—Aurora Fine Chemicals" Acetamide, N-[[7-(4-fluorophenyl) [1,2,5] oxadiazolo [3,4-b] pyridine-5-yl] methyl]-. 1 page.

(56) References Cited

OTHER PUBLICATIONS

De Yebenes, J.G. et al. (1987). "Continuous Intracerebroventricular Infusion of Dopamine and Dopamine Agonists Through a Totally Implanted Drug Delivery System in Animal Models of Parkinson's Disease," Mov. Disord. 2(3):143-158.

Epstein, D.A. et al. (Jun. 1985). "Biological Activity of Lipsome-Encapsulated Murine Interferon γ is Mediated by Cell Membrane Receptor," Proc. Natl. Acad. Sci. USA 82:3688-3692.

Fleisher, D. et al. (May 22, 1996). "Improved Oral Drug Delivery: Solubility Limitations Overcome by the use of Prodrugs," Advanced Drug Delivery Reviews 19(2):115-130.

Fujii, M. et al. (2012). "TGF-β Synergizes with Defects in the Hippo Pathway to Stimulate Human Malignant Mesothelioma Growth," J. Exp. Med. 209(3):479-494.

Gasparotto, D. et al. (Dec. 22, 2011). "Overexpression of TWIST2 Correlates with Poor Prognosis in Head and Neck Squamous Cell Carcinomas," Oncotarget. 2(12):1165-1175.

Gill, S.S. et al. (May 2003, e-pub. Mar. 31, 2003). "Direct Brain Infusion of Glial Cell Line-Derived Neurotrophic Factor in Parkinson Disease," Nature Med. 9(5):589-595.

Halder, G. et al. (2011). "Hippo Signaling: Growth Control and Beyond," Development 138:9-22.

Hall, C.A. et al. (Nov. 1, 2010). "Hippo Pathway Effector Yap is an Ovarian Cancer Oncogene," Cancer Res. 70(21):8517-8525, 15 pages.

Hallin, J. et al. (Jan. 2020). "The KRASG12C Inhibitor, MRTX849, Provides Insight Toward Therapeutic Susceptibility of KRAS Mutant Cancers in Mouse Models and Patients," Cancer Discov. 10(1):54-71, 31 pages.

Harbaugh, R.E. (1987). "Intracerbroventricular Cholinergic Drug Administration in Alzheimer's Disease: Preliminary Results of a Double-Blind Study," J. Neural Transm. Suppl. 24:271-277.

Harvey, K.F. et al. (Apr. 2013, e-pub. Mar. 7, 2013). "The Hippo Pathway and Human Cancer," Nat. Rev. Cancer 13:246-257.

Hong, D.S. et al. (Sep. 24, 2020). "KRASG12C Inhibition with Sotorasib in Advanced Solid Tumors," N. Engl. J. Med. 383(13):1207-1217.

Hwang, K.J. et al. (Jul. 1980). "Hepatic Uptake and Degradation of Unilamellar Sphingomyelin/Cholesterol Liposomes: A Kinetic Study." Proc. Natl. Acad. Sci. USA 77:4030-4034.

International Search Report and Written Opinion, mailed Apr. 3, 2023, for PCT Application No. PCT/US2022/080279, filed Nov. 21, 2022, 22 pages.

International Search Report and Written Opinion, mailed Feb. 15, 2023, for PCT Application No. PCT/US2022/080281, filed Nov. 21, 2022, 7 pages.

Invitation To Pay Additional Fees, mailed Feb. 13, 2023, for PCT Application No. PCT/US2022/080279, filed Nov. 21, 2022, 16 pages,.

Jie, L. et al. (2013). "The Hippo-Yes Association Protein Pathway in Liver Cancer," Gastroenterol. Res. Pract. 2013 (187070):1-7.

Jimenez-Velasco, A. et al. (2005, e-pub. Oct. 6, 2005). "Downregulation of the Large Tumor Suppressor 2 (LATS2/KPM) Gene is Associated with Poor Prognosis in Acute Lymphoblastic Leukemia," Leukemia 19:2347-2350.

Johns, F.G. et al. (Jul. 16, 2004, e-pub. Apr. 9, 2004). "Identification of the Epitope for the Epidermal Growth Factor Receptor-Specific Monoclonal Antibody 806 Reveals that it Preferentially Recognizes an Untethered Form of the Receptor," J. Biol. Chem. 279(29):30375-30374.

Kakeya, N. et al. (Feb. 1984). "Studies on Prodrugs of Cephalosporins. I. Synthesis and Biological Properties of Glycyloxybenzoyloxymethyl and Glycylaminobenzoyloxymethyl Esters of 7 beta-[2-(2-aminothiazol-4-yl)-(Z)-2-methoxyiminoacetamido]-3-methyl-3-cephem-4-carboxylic Acid," Chem. Pharm. Bull., 32(2):692-698.

Lamar, J.M. et al. (2012, e-pub Aug. 13, 2012). "The Hippo Pathway Target, YAP, Promotes Metastasis Through its TEAD-Interaction Domain," Proc. Natl. Acad. Sci, USA, pp. E2441-E2250.

Langer, R. et al. (1981). "Biocompatibility of Polymeric Delivery Systems for Marcomolecules," J. Biomed. Mater. Res. 15:267-277.

Lei, Q.-Y. et al. (Apr. 2008). "TAZ Promotes Cell Proliferation and Epithelial-Mesenchymal Transition and is Inhibited by the Hippo Pathway," Mol. Cell. Biol. 28(7):2426-2436.

Liu, A.M. et al. (2012). "An Update on Targeting Hippo-YAP Signaling in Liver Cancer," Expert. Opin. Ther. Targets 16(3):243-247.

Mizuno, T. et al. (2012, e-pub. Jan. 30, 2012). "YAP Induces Malignant Mesothelioma Cell Proliferation by Upregulating Transcription of cell Cycle-Promoting Genes," Oncogene 31:5117-5122.

Moore, A.R. et al. (Aug. 2020). "RAS-Targeted Therapies: is the Undruggable Drugged?" Nat. Rev. Drug. Discov. 19(8):533-552, 43 pages.

Nicolaou, K.C. et al. (1994). "Calicheamicin ⊖1[1]: A Rationally Designed Molecule with Extremely Potent and Selective DNA Cleaving Properties and Apoptosis Inducing Activity," Angew. Chem. Intl. Ed. Engl. 33(2):183-186.

Orr, B.A. et al. (Jul. 2011). "Yes-Associated Protein 1 Is Widely Expressed in Human Brain Tumors and Promotes Glioblastoma Growth," J. Neuropathol. Exp. Neurol. 70(7):568-577.

Papanastassiou, V. et al. (2002). "The Potential for Efficacy of the Modified (ICP 34.5-) Herpes Simplex Virus HSV1716 Following Intratumoural Injection Into Human Malignant Glioma: A Proof of Principle Study," Gene Therapy 9:398-406.

Robinson, R.P. et al. (Jan. 5, 1996). "Discovery of the Hemifumarate and (α-L-Alanyloxy)methyl Ether as Prodrugs of an Antirheumatic Oxindole: Prodrugs for the Enolic OH Group," J. Med. Chem. 39(1):10-18.

Seidel, C. et al. (2007). "Frequent Hypermethylation of MST1 and MST2 in Soft Tissue Sarcoma," Mol. Carcinogenesis 46:865-871.

Sekido Y. (2011). "Inactivation of Merlin in Malignant Mesothelioma Cells and the Hippo Signaling Cascade Dysregulation," Pathol. Int. 61:331-344.

Sidman, K.R. et al. (1983). "Controlled Release of Macromolecules and Pharmaceuticals from Synthetic Polypeptides Based on Glutamic Acid," Biopolymers 22:547-556.

Skoulidis, F. et al. (Jun. 14, 2021). "Sotorasib for Lung Cancers with KRAS p.G12C Mutation," N. Engl. J. Med. 384(25):2371-2381.

Steinhardt, A.A. et al. (Nov. 2008). "Expression of Yes-Associated Protein, YAP, in Common Solid Tumors," Hum. Pathol. 39(11):1582-1589, 15 pages.

Steinmann, K. et al. (2009). "Frequent Promoter Hypermethylation of Tumor-Related Genes in Head and Neck Squamous Cell Carcinoma," Oncol. Rep. 22:1519-1526.

Stragliotto, G. et al. (Apr. 1996). "Multiple Infusion of Anti-Epidermal Growth Factor Receptor (EGFR) Monocional Antibody (EMD 55,900) in Patient with Recurrent Malignant Gliomas," Eur. J. Cancer 32A(4):636-640.

Striedinger, K, et al. (Nov. 2008). "The Neurofibromatosis 2 Tumor Suppressor Gene Product, Merlin, Regulates Human Meningioma Cell Growth by Signaling through YAP," Neoplasia 10(11):1204-1212.

UniProtKB/Swiss-Prot Accession No. (May 3, 2023). "Q9NZQ7. 1—RecName: Full=Programmed cell death 1 ligand 1; Short=PD-L1; Short=PDCD1 ligand 1; Short=Programmed death ligand 1; Short=hPD-L1; AltName: Full=B7 homolog 1; Short=B7-H1; AltName: CD_antigen=CD274; Flags: Precursor, ", 9 pages.

Vassilev, A. et al. (2001). "TEAD/TEF Transcription Factors Utilize the Activation Domain of YAP65, a Src/Yes-Associated Protein Localized in the Cytoplasm," Genes and Development 15:1229-1241.

Wang, X. et al. (2012, e-pub. Nov. 5, 2011). "Yes-Associated Protein Promotes Tumour Development in Luminal Epithelial Derived Breast Cancer," Eur. J. Cancer 48:1227-1234.

Wang, Y. et al. (2010, e-pub. Mar. 10, 2010). "Overexpression of Yes-Associated Protein Contributes to Progression and Poor Prognosis of Non-Small-Cell Lung Cancer," Cancer Sci. 101:1279-1285.

Widder, K. et al. (1985). Methods in Enzymology, vol. 42, 112:309-396, 92 pages.

Yuen, H.-F. et al. (Jan. 23, 2013). "TAZ Expression as a Prognostic Indicator in Colorectal Cancer," PLoS One 8(1):e54211, 17 pages.

(56) References Cited

OTHER PUBLICATIONS

Zeng, Q. et al. (Mar. 2008). "The Emerging Role of the Hippo Pathway in Cell Contact Inhibition, Organ Size Control, and Cancer Development in Mammals," Cancer Cell 13:188-192.
Zhao, B. at al. (2010). "Hippo Signaling at a Glance," J. Cell Sci. 123(23):4001-4006.
Zhao, B. et al. (2007). "Inactivation of YAP Oncoprotein by the Hippo Pathway is Involved in Cell Contact Inhibition and Tissue Growth Control," Genes Dev. 21:2747-2761.
Zhao, B. et al. (2010). "The Hippo-YAP Pathway in Organ Size Control and Tumorigenesis: An Updated Version," Genes Dev. 24:862-874.
Zhao, B. et al. (2012). "Cell Detachment Activates the Hippo Pathway via Cytoskeleton Reorganization to Induce Anoikis," Genes Dev.26:54-68.
Zhao, B. et al. (Aug. 2011). "The Hippo Pathway in Organ Size Control, Tissue Regeneration and Stem Cell Self-Renewal," Nature Cell Biology 13(8):877-883.
Zhao, B. et al. (Feb. 1, 2009). "Both TEAD-Binding and WW Domains Are Required for the Growth Stimulation and Oncogenic Transformation Activity of Yes-Associated Protein," Cancer Res. 69(3):1089-1098.
Zhou, Z. et al. (2011, e-pub. Jan. 24, 2011). "TAZ is a Novel Oncogene in Non-Small Cell Lung Cancer," Oncogene 30:2181-2186.
Pubchem CID 14032648 (Feb. 9, 2007). "1-Acetyl-4-[1-[4-(trifluoromethyl)phenyl]-1H-indazol-3-yl]piperidine," 9 pages.
U.S. Appl. No. 18/510,227, filed Nov. 15, 2023, Dey et al. (Copy not submitted herewith pursuant to the waiver of 37 C.F.R. §1.98(a)(2)(iii) issued by the Office on Sep. 21, 2004).
Zhang, B. et al. (Aug. 2021, e-pub. Jun. 20, 2021). "Focal Adhesion Kinase (FAK) Inhibition Synergizes with KRAS G12C Inhibitors in Treating Cancer Through the Regulation of the FAK-YAP Signaling," Advanced Science 8(16):1-15.
International Preliminary Report on Patentability, issued May 2, 2024, for PCT Application No. PCT/US2022/080279, filed Nov. 21, 2022, 12 pages.
International Preliminary Report on Patentability, issued May 2, 2024, for PCT Application No. PCT/US2022/080281, filed Nov. 21, 2022, 7 pages.

* cited by examiner

SEQUENCE LISTING

```
Sequence total quantity: 18
SEQ ID NO: 1              moltype = AA   length = 440
FEATURE                   Location/Qualifiers
source                    1..440
                          mol_type = protein
                          organism = synthetic construct
SEQUENCE: 1
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                              440

SEQ ID NO: 2              moltype = AA   length = 214
FEATURE                   Location/Qualifiers
source                    1..214
                          mol_type = protein
                          organism = synthetic construct
SEQUENCE: 2
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 3              moltype = AA   length = 447
FEATURE                   Location/Qualifiers
source                    1..447
                          mol_type = protein
                          organism = synthetic construct
SEQUENCE: 3
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 4              moltype = AA   length = 218
FEATURE                   Location/Qualifiers
source                    1..218
                          mol_type = protein
                          organism = synthetic construct
SEQUENCE: 4
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 5              moltype = AA   length = 10
FEATURE                   Location/Qualifiers
source                    1..10
                          mol_type = protein
                          organism = synthetic construct
SEQUENCE: 5
GFTFSDSWIH                                                          10

SEQ ID NO: 6              moltype = AA   length = 18
FEATURE                   Location/Qualifiers
source                    1..18
                          mol_type = protein
                          organism = synthetic construct
SEQUENCE: 6
AWISPYGGST YYADSVKG                                                 18

SEQ ID NO: 7              moltype = AA   length = 9
FEATURE                   Location/Qualifiers
source                    1..9
                          mol_type = protein
                          organism = synthetic construct
SEQUENCE: 7
RHWPGGFDY                                                           9

SEQ ID NO: 8              moltype = AA   length = 11
```

```
FEATURE              Location/Qualifiers
source               1..11
                     mol_type = protein
                     organism = synthetic construct
SEQUENCE: 8
RASQDVSTAV A                                                                      11

SEQ ID NO: 9         moltype = AA   length = 7
FEATURE              Location/Qualifiers
source               1..7
                     mol_type = protein
                     organism = synthetic construct
SEQUENCE: 9
SASFLYS                                                                            7

SEQ ID NO: 10        moltype = AA   length = 9
FEATURE              Location/Qualifiers
source               1..9
                     mol_type = protein
                     organism = synthetic construct
SEQUENCE: 10
QQYLYHPAT                                                                          9

SEQ ID NO: 11        moltype = AA   length = 118
FEATURE              Location/Qualifiers
source               1..118
                     mol_type = protein
                     organism = synthetic construct
SEQUENCE: 11
EVQLVESGGG LVQPGGSLRL SCAASGFTFS DSWIHWVRQA PGKGLEWVAW ISPYGGSTYY                  60
ADSVKGRFTI SADTSKNTAY LQMNSLRAED TAVYYCARRH WPGGFDYWGQ GTLVTVSS                   118

SEQ ID NO: 12        moltype = AA   length = 108
FEATURE              Location/Qualifiers
source               1..108
                     mol_type = protein
                     organism = synthetic construct
SEQUENCE: 12
DIQMTQSPSS LSASVGDRVT ITCRASQDVS TAVAWYQQKP GKAPKLLIYS ASFLYSGVPS                  60
RFSGSGSGTD FTLTISSLQP EDFATYYCQQ YLYHPATFGQ GTKVEIKR                              108

SEQ ID NO: 13        moltype = AA   length = 447
FEATURE              Location/Qualifiers
source               1..447
                     mol_type = protein
                     organism = synthetic construct
SEQUENCE: 13
EVQLVESGGG LVQPGGSLRL SCAASGFTFS DSWIHWVRQA PGKGLEWVAW ISPYGGSTYY                  60
ADSVKGRFTI SADTSKNTAY LQMNSLRAED TAVYYCARRH WPGGFDYWGQ GTLVTVSSAS                 120
TKGPSVFPLA PSSKSTSGGT AALGCLVKDY FPEPVTVSWN SGALTSGVHT FPAVLQSSGL                 180
YSLSSVVTVP SSSLGTQTYI CNVNHKPSNT KVDKKVEPKS CDKTHTCPPC PAPELLGGPS                 240
VFLFPPKPKD TLMISRTPEV TCVVVDVSHE DPEVKFNWYV DGVEVHNAKT KPREEQYAST                 300
YRVVSVLTVL HQDWLNGKEY KCKVSNKALP APIEKTISKA KGQPREPQVY TLPPSREEMT                 360
KNQVSLTCLV KGFYPSDIAV EWESNGQPEN NYKTTPPVLD SDGSFFLYSK LTVDKSRWQQ                 420
GNVFSCSVMH EALHNHYTQK SLSLSPG                                                    447

SEQ ID NO: 14        moltype = AA   length = 214
FEATURE              Location/Qualifiers
source               1..214
                     mol_type = protein
                     organism = synthetic construct
SEQUENCE: 14
DIQMTQSPSS LSASVGDRVT ITCRASQDVS TAVAWYQQKP GKAPKLLIYS ASFLYSGVPS                  60
RFSGSGSGTD FTLTISSLQP EDFATYYCQQ YLYHPATFGQ GTKVEIKRTV AAPSVFIFPP                 120
SDEQLKSGTA SVVCLLNNFY PREAKVQWKV DNALQSGNSQ ESVTEQDSKD STYSLSSTLT                 180
LSKADYEKHK VYACEVTHQG LSSPVTKSFN RGEC                                            214

SEQ ID NO: 15        moltype = AA   length = 449
FEATURE              Location/Qualifiers
source               1..449
                     mol_type = protein
                     organism = synthetic construct
SEQUENCE: 15
EVQLLESGGG LVQPGGSLRL SCAASGFTFS SYIMMWVRQA PGKGLEWVSS IYPSGGITFY                  60
ADTVKGRFTI SRDNSKNTLY LQMNSLRAED TAVYYCARIK LGTVTTVDYW GQGTLVTVSS                 120
ASTKGPSVFP LAPSSKSTSG GTAALGCLVK DYFPEPVTVS WNSGALTSGV HTFPAVLQSS                 180
GLYSLSSVVT VPSSSLGTQT YICNVNHKPS NTKVDKKVEP KSCDKTHTCP PCPAPELLGG                 240
PSVFLFPPKP KDTLMISRTP EVTCVVVDVS HEDPEVKFNW YVDGVEVHNA KTKPREEQYN                 300
STYRVVSVLT VLHQDWLNGK EYKCKVSNKA LPAPIEKTIS KAKGQPREPQ VYTLPPSRDE                 360
```

```
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPG                                     449

SEQ ID NO: 16           moltype = AA  length = 216
FEATURE                 Location/Qualifiers
source                  1..216
                        mol_type = protein
                        organism = synthetic construct
SEQUENCE: 16
QSALTQPASV SGSPGQSITI SCTGTSSDVG GYNYVSWYQQ HPGKAPKLMI YDVSNRPSGV     60
SNRFSGSKSG NTASLTISGL QAEDEADYYC SSYTSSSTRV FGTGTKVTVL GQPKANPTVT    120
LFPPSSEELQ ANKATLVCLI SDFYPGAVTV AWKADGSPVK AGVETTKPSK QSNNKYAASS    180
YLSLTPEQWK SHRSYSCQVT HEGSTVEKTV APTECS                             216

SEQ ID NO: 17           moltype = AA  length = 450
FEATURE                 Location/Qualifiers
source                  1..450
                        mol_type = protein
                        organism = synthetic construct
SEQUENCE: 17
EVQLVESGGG LVQPGGSLRL SCAASGFTFS RYWMSWVRQA PGKGLEWVAN IKQDGSEKYY     60
VDSVKGRFTI SRDNAKNSLY LQMNSLRAED TAVYYCAREG GWFGELAFDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKRVE PKSCDKTHTC PPCPAPEFEG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPASIEKTI SKAKGQPREP QVYTLPPSRE    360
EMTKNQVSLT CLVKGFYPSD IAVEWESNGQ PENNYKTTPP VLDSDGSFFL YSKLTVDKSR    420
WQQGNVFSCS VMHEALHNHY TQKSLSLSPG                                    450

SEQ ID NO: 18           moltype = AA  length = 215
FEATURE                 Location/Qualifiers
source                  1..215
                        mol_type = protein
                        organism = synthetic construct
SEQUENCE: 18
EIVLTQSPGT LSLSPGERAT LSCRASQRVS SSYLAWYQQK PGQAPRLLIY DASSRATGIP     60
DRFSGSGSGT DFTLTISRLE PEDFAVYYCQ QYGSLPWTFG QGTKVEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215
```

THERAPEUTIC COMPOUNDS AND METHODS OF USE

CROSS-REFERENCE TO RELATED APPLICATIONS

This application claims priority to and benefit of U.S. Provisional Patent Application No. 63/283,119, filed Nov. 24, 2021, and U.S. Provisional Patent Application No. 63/344,027, filed May 19, 2022, the disclosures of which are hereby incorporated herein by reference in their entireties.

SUBMISSION OF ELECTRONIC SEQUENCE LISTING

The content of the electronic Sequence Listing (file name: 146392054800SeqList.xml, date created: Nov. 21, 2022, size: 20,029 bytes) is herein incorporated by reference in its entirety.

FIELD OF THE DISCLOSURE

The present disclosure relates to compounds useful for therapy and/or prophylaxis in a mammal, and in particular as inhibitors of TEAD useful for treating cancer.

BRIEF DESCRIPTION

The Hippo pathway is a signaling pathway that regulates cell proliferation and cell death and determines organ size. The pathway is believed to play a role as a tumor suppressor in mammals, and disorders of the pathway are often detected in human cancers. The pathway is involved in and/or may regulate the self-renewal and differentiation of stem cells and progenitor cells. In addition, the Hippo pathway may be involved in wound healing and tissue regeneration. Furthermore, it is believed that as the Hippo pathway cross-talks with other signaling pathways such as Wnt, Notch, Hedgehog, and MAPK/ERK, it may influence a wide variety of biological events, and that its dysfunction could be involved in many human diseases in addition to cancer. For reviews, see, for example, Halder et al., 2011, Development 138:9-22; Zhao et al., 2011, Nature Cell Biology 13:877-883; Bao et al., 2011, J. Biochem. 149:361-379; Zhao at al., 2010, J. Cell Sci. 123:4001-4006.

The Hippo signaling pathway is conserved from drosophila to mammals (Vassilev et al., Genes and Development, 2001, 15, 1229-1241; Zeng and Hong, Cancer Cell, 2008, 13, 188-192). The core of the pathway consists of a cascade of kinases (Hippo-MSTI-2 being upstream of Lats 1-2 and NDRI-2) leading to the phosphorylation of two transcriptional co-activators, YAP (Yes-Associated Protein) and TAZ (Transcription co-activator with PDZ binding motif or tafazzin; Zhao et al., Cancer Res., 2009, 69, 1089-1098; Lei et al., Mol. Cell. Biol., 2008, 28, 2426-2436).

Because the Hippo signaling pathway is a regulator of animal development, organ size control and stem cell regulation, it has been implicated in cancer development (Review in Harvey et al., Nat. Rev. Cancer, 2013, 13, 246-257; Zhao et al., Genes Dev. 2010, 24, 862-874). In vitro, the overexpression of YAP or TAZ in mammary epithelial cells induces cell transformation, through interaction of both proteins with the TEAD family of transcription factors. Increased YAP/TAZ transcriptional activity induces oncogenic properties such as epithelial-mesenchymal transition and was also shown to confer stem cells properties to breast cancer cells. In vivo, in mouse liver, the overexpression of YAP or the genetic knockout of its upstream regulators MST1-2 triggers the development of hepatocellular carcinomas. Furthermore, when the tumor suppressor NF2 is inactivated in the mouse liver, the development of hepatocellular carcinomas can be blocked completely by the co-inactivation of YAP.

It is believed that deregulation of the Hippo tumor suppressor pathway is a major event in the development of a wide range of malignancies, including with no limitations, lung cancer (NSCLC; Zhou et al., Oncogene, 2011, 30, 2181-2186; Wang et al., Cancer Sci., 2010, 101, 1279-1285), breast cancer (Chan et al., Cancer Res., 2008, 68, 2592-2598; Lamar et al., Proc. Natl. Acad. Sci, USA, 2012; 109, E2441-E2250; Wang et al., Eur. J. Cancer, 2012, 48, 1227-1234), head and neck cancer (Gasparotto et al., Oncotarget., 2011, 2, 1165-1175; Steinmann et al., Oncol. Rep., 2009, 22, 1519-1526), colon cancer (Angela et al., Hum. Pathol., 2008, 39, 1582-1589; Yuen et al., PLoS One, 2013, 8, e54211; Avruch et al., Cell Cycle, 2012, 11, 1090-1096), ovarian cancer (Angela et al., Hum. Pathol., 2008, 39, 1582-1589; Chad et al., Cancer Res., 2010, 70, 8517-8525; Hall et al., Cancer Res., 2010, 70, 8517-8525), liver cancer (Jie et al., Gastroenterol. Res. Pract., 2013, 2013, 187070; Ahn et al., Mol. Cancer. Res., 2013, 11, 748-758; Liu et al., Expert. Opin. Ther. Targets, 2012, 16, 243-247), brain cancer (Orr et al., J Neuropathol. Exp. Neurol. 2011, 70, 568-577; Baia et al., Mol. Cancer Res., 2012, 10, 904-913; Striedinger et al., Neoplasia, 2008, 10, 1204-1212) and prostate cancer (Zhao et al., Genes Dev., 2012, 26, 54-68; Zhao et al., Genes Dev., 2007, 21, 2747-2761), mesotheliomas (Fujii et al., J. Exp. Med., 2012, 209, 479-494; Mizuno et al., Oncogene, 2012, 31, 5117-5122; Sekido Y., Pathol. Int., 2011, 61, 331-344), sarcomas (Seidel et al., Mol. Carcinog., 2007, 46, 865-871) and leukemia (Jimenez-Velasco et al., Leukemia, 2005, 19, 2347-2350).

Two of the core components of the mammalian Hippo pathway are Lats1 and Lats2, which are nuclear Dbf2-related (NDR) family protein kinases homologous to Drosophila Warts (Wts). The Lats1/2 proteins are activated by association with the scaffold proteins Mob1A/B (Mps one binder kinase activator-like 1A and 1B), which are homologous to Drosophila Mats. Lats1/2 proteins are also activated by phosphorylation by the STE20 family protein kinases Mst1 and Mst2, which are homologous to Drosophila Hippo. Lats1/2 kinases phosphorylate the downstream effectors YAP (Yes-associated protein) and TAZ (transcriptional coactivator with PDZ-binding motif; WWTR1), which are homologous to Drosophila Yorkie. The phosphorylation of YAP and TAZ by Lats1/2 are crucial events within the Hippo signaling pathway. Lats1/2 phosphorylates YAP at multiple sites, but phosphorylation of Ser127 is critical for YAP inhibition. Phosphorylation of YAP generates a protein-binding motif for the 14-3-3 family of proteins, which upon binding of a 14-3-3 protein, leads to retention and/or sequestration of YAP in the cell cytoplasm. Likewise, Lats1/2 phosphorylates TAZ at multiple sites, but phosphorylation of Ser89 is critical for TAZ inhibition. Phosphorylation of TAZ leads to retention and/or sequestration of TAZ in the cell cytoplasm. In addition, phosphorylation of YAP and TAZ is believed to destabilize these proteins by activating phosphorylation-dependent degradation catalyzed by YAP or TAZ ubiquitination. Thus, when the Hippo pathway is "on", YAP and/or TAZ is phosphorylated, inactive, and generally sequestered in the cytoplasm; in contrast, when the Hippo pathway is "off", YAP and/or TAZ is non-phosphorylated, active, and generally found in the nucleus.

Non-phosphorylated, activated YAP is translocated into the cell nucleus where its major target transcription factors are the four proteins of the TEAD-domain-containing family (TEAD1-TEAD4, collectively "TEAD"). YAP together with TEAD (or other transcription factors such as Smad1, RUNX, ErbB4 and p73) has been shown to induce the expression of a variety of genes, including connective tissue growth factor (CTGF), Gli2, Birc5, Birc2, fibroblast growth factor 1 (FGF1), and amphiregulin (AREG). Like YAP, non-phosphorylated TAZ is translocated into the cell nucleus where it interacts with multiple DNA-binding transcription factors, such as peroxisome proliferator-activated receptor γ (PPARγ), thyroid transcription factor-1 (TTF-1), Pax3, TBX5, RUNX, TEAD1 and Smad2/3/4. Many of the genes activated by YAP/TAZ-transcription factor complexes mediate cell survival and proliferation. Therefore, under some conditions YAP and/or TAZ acts as an oncogene and the Hippo pathway acts as a tumor suppressor. Hence, pharmacological targeting of the Hippo cascade through inhibition of TEAD would be valuable approach for the treatment of cancers that harbor functional alterations of this pathway.

Ras is a small GTP-binding protein that functions as a nucleotide-dependent switch for central growth signaling pathways. In response to extracellular signals, Ras is converted from a GDP-bound ($Ras^{GDP}$) to a GTP-bound ($Ras^{GTP}$) state, as catalyzed by guanine nucleotide exchange factors (GEFs), notably the SOS1 protein. Active $Ras^{GTP}$ mediates its diverse growth-stimulating functions through its direct interactions with effectors including Raf, P13K, and RaI guanine nucleotide dissociation stimulator. The intrinsic GTPase activity of Ras then hydrolyzes GTP to GDP to terminate Ras signaling. The Ras GTPase activity can be further accelerated by its interactions with GTPase-activating proteins (GAPs), including the neurofibromin 1 tumor suppressor.

Mutant Ras has a reduced GTPase activity, which prolongs its activated conformation, thereby promoting Ras-dependent signaling and cancer cell survival or growth. Mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer. Mutations in any one of the three main isoforms of RAS (H-Ras, N-Ras, or K-Ras) genes are common events in human tumorigenesis. Among the three Ras isoforms (K, N, and H), K-Ras is most frequently mutated.

The most common K-Ras (or KRAS) mutations are found at residue G12 and G13 in the P-loop and at residue Q61. G12C is a frequent mutation of K-Ras gene (glycine-12 to cysteine). G12C is a single point mutation with a glycine-to-cysteine substitution at codon 12. This substitution favors the activated state of KRAS, amplifying signaling pathways that lead to oncogenesis (see, e.g., Hallin et al. (Cancer Discov, 2020, 10(1): 54-71), Skoulidis et al. (N. Engl. J. Med., 2021, 384(25): 2371-2381), and Hong et al. (N. Engl. J. Med., 2020, 383(13): 1207-1217)). G12D, G12V, and G13D are other frequent mutations. Mutations of Ras in cancer are associated with poor prognosis.

Inactivation of oncogenic Ras in mice results in tumor shrinkage. Thus, Ras is widely considered an oncology target of exceptional importance. However, treatment with inhibitors of Ras (for example, KRAS) can lead to resistance through bypass of KRAS/MAPK pathway dependence, and activation of the Hippo pathway.

There is, therefore, a need for therapies that improve the ability of inhibitors of Ras (for example, KRAS) and inhibitors of YAP, TAZ, TEAD, and/or the YAP:TEAD protein-protein interaction to treat a range of diseases, disorders, and conditions, including cancer.

SUMMARY OF THE DISCLOSURE

In some aspect, provided is a compound for formula (II-AB'):

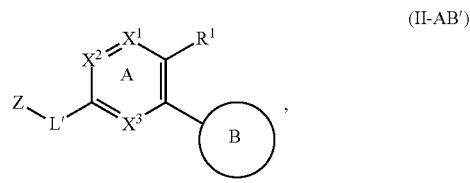

or a stereoisomer or tautomer thereof, or a pharmaceutically acceptable salt thereof, wherein:

L' is *—N(R³)-L-** or

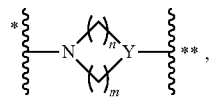

or Z-L' is

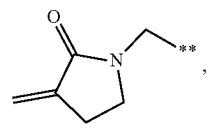

wherein * denotes the point of attachment to Z, and ** denotes the point of attachment to

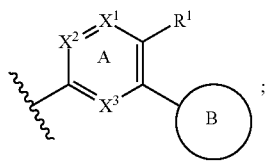

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;

wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

$X^2$ is N or $CR^s$, wherein $R^s$ is selected from H, halo, $C_{1-15}$alkyl, hydroxyl$C_{1-6}$alkynyl, $C_{6-20}$aryl, 5 to 15 membered heteroaryl, $C_{3-20}$cycloalkyl, 3 to 15 membered heterocyclyl, —OH, —CN, $C_{1-15}$-alkoxy, —$NR^dCOR^e$, —$CONR^dR^e$, —$SO_2R^d$, —$S(O)NHR^d$, —$SO_2NR^dR^e$, —$NR^dSO_2R^e$, and —$NR^dR^e$; wherein the $C_{1-15}$alkyl and $C_{1-15}$alkoxy of $R^s$ are each independently optionally substituted with one or more $R^{t1}$, wherein $R^{t1}$ is independently at each occurrence halo, oxo, —OH, —CN, 5-6 membered heteroaryl, or —$NR^dR^e$, wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently at each occurrence selected from halo, oxo, —OH, —CN and $C_{1-6}$alkyl; and wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

$X^3$ is N or CH;

B is
  i) phenyl or 5 to 6 membered heteroaryl; wherein the phenyl and 5 to 6 membered heteroaryl of B are each independently substituted with one or more $R^2$, wherein $R^2$ is independently, at each occurrence, halo; $S(R^y)_5$, wherein each $R_y$ is halo; $C_{1-6}$alkoxy optionally substituted with one or more halo; or
  ii) —O-phenyl substituted with halo$C_{1-3}$alkyl, provided that when B is —O-phenyl substituted with halo$C_{1-3}$alkyl, L' is *—$N(R^3)$-L-**, Z is —C(O)CHCH$_2$, $X^1$ is C, $X^2$ is $CR^s$, and $X^3$ is CH; or
  iii) bicyclopentane substituted by $C_{1-3}$alkyl, provided that when B is bicyclopentane substituted by $C_{1-3}$alkyl, L' is *—$N(R^3)$-L-** and Z is —C(O)CHCH$_2$; or
  iv) phenyl substituted with ethynyl or halo$C_{1-3}$alkyl, provided that when B is phenyl substituted with ethynyl or halo$C_{1-3}$alkyl, L' is *—$N(R^3)$-L-**, Z is —C(O)CHCH$_2$, and $R^s$ is $C_{1-3}$alkyl substituted with one or more —OH; or
  v) piperidine substituted with halo$C_{1-3}$alkyl or halo$C_{1-3}$alkoxy, provided that when B is piperidine substituted with halo$C_{1-3}$alkyl or halo$C_{1-3}$alkoxy, L' is *—$N(R^3)$-L-** and Z is —C(O)CHCH$_2$;

$R^3$ is H or $C_{1-6}$alkyl;

Z is —OH, —$NR^dR^e$, $C_{1-6}$alkoxy, —$C(O)R^a$, or —$S(O)_2R^b$,
  wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;
  $R^a$ and $R^b$ are each independently i) $C_{2-6}$alkenyl optionally substituted with one or more substituents selected from deuterium, $C_{1-6}$alkyl, hydroxyl $C_{1-6}$alkyl, halo and halo$C_{1-6}$alkyl; ii) $C_{1-6}$alkyl, optionally substituted with one or more halo; or iii) cyclobutenyl or bicyclobutanyl;

L is methylene or ethylene, wherein the methylene of L is optionally substituted with one $C_{1-6}$alkyl;

Y is CH or C(CN), and n and m are each independently 1 or 2;

provided that:
  i) when i-1) $X^1$ is taken together with $R^1$ and the atoms to which they are attached to form a phenyl, and i-2) $X^2$ or $X^3$ is N, B of formula (II-AB') is phenyl and $R^2$ is halo$C_{1-6}$alkoxyl; and
  ii) when n=1 and m=2, or n=2 and m=1, B is phenyl substituted by halomethyoxyl; and
  iii) the compound of formula (II-AB') is not any one of following:

N-((8-(4-fluorophenyl)imidazo[1,2-a]pyrazin-6-yl)methyl) acrylamide;

N-((8-(4-(trifluoromethoxy)phenyl)imidazo[1,2-a]pyrazin-6-yl)methyl)acrylamide;

N-((7-fluoro-4-(4-(trifluoromethoxy)phenyl)quinazolin-2-yl)methyl)acrylamide;

N-((8-(4-(difluoromethoxy)phenyl)imidazo[1,2-a]pyrazin-6-yl)methyl)acrylamide;

1-(4-(4-(4-methoxyphenyl)-1-methyl-1H-imidazo[4,5-c]pyridin-6-yl)piperidin-1-yl)ethan-1-one;

4-(4-methoxyphenyl)-1-methyl-6-(1-(methylsulfonyl)piperidin-4-yl)-1H-imidazo[4,5-c]pyridine;

6-(1-(ethylsulfonyl)piperidin-4-yl)-4-(4-methoxyphenyl)-1-methyl-1H-imidazo[4,5-c]pyridine;

6-(1-(ethylsulfonyl)piperidin-4-yl)-1-isopropyl-4-(4-methoxyphenyl)-1H-imidazo[4,5-c]pyridine;

4-(4-methoxyphenyl)-1-methyl-6-(1-((trifluoromethyl)sulfonyl)piperidin-4-yl)-1H-imidazo[4,5-c]pyridine; and N-((4-(4-fluorophenyl)-1,8-naphthyridin-2-yl)methyl)acetamide.

In some aspects, provided is a compound of formula (II-AB):

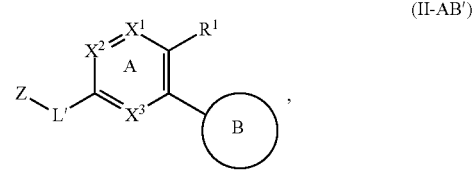

(II-AB')

or a stereoisomer or tautomer thereof, or a pharmaceutically acceptable salt thereof, wherein:

L' is selected from the group consisting of *—$N(R^3)$-L-** and

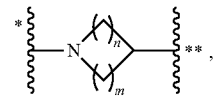

wherein * denotes the point of attachment to Z, and ** denotes the point of attachment to

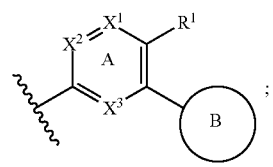

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;

wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$; and wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

$X^2$ is N or $CR^s$, wherein $R^s$ is selected from H, halo, $C_{1-15}$alkyl, hydroxyl$C_{1-6}$alkynyl, $C_{6-20}$aryl, 5 to 15 membered heteroaryl, $C_{3-20}$cycloalkyl, 3 to 15 membered heterocyclyl, —OH, —CN, $C_{1-15}$-alkoxy, —$NR^dCOR^e$, —$CONR^dR^e$, —$SO_2R^d$, —$S(O)NHR^d$, —$SO_2NR^dR^e$, —$NR^dSO_2R^1$, and —$NR^dR^e$;

wherein the $C_{1-15}$alkyl and $C_{1-15}$alkoxy of $R^s$ are each independently optionally substituted with one or more W, wherein $R^{t1}$ is independently at each occurrence halo, oxo, —OH, —CN, 5-6 membered heteroaryl, or —$NR^dR^e$, wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently at each occurrence selected from halo, oxo, —OH, —CN and $C_{1-6}$alkyl; and wherein $R^d$ and RC are each independently H or $C_{1-6}$alkyl, and wherein the $C_{1-6}$alkyl of $R^d$ or $R^e$ is optionally substituted with one or more substituents selected from halo, oxo, —OH and —CN;

$X^3$ is N or CH;

B is phenyl or 5 to 6 membered heteroaryl; wherein the phenyl and 5 to 6 membered heteroaryl of B are each independently substituted with one or more $R^2$, wherein $R^2$ is independently, at each occurrence, halo; $S(R^y)_5$; wherein each $R^y$ is halo; or $C_{1-6}$alkoxy optionally substituted with one or more halo;

$R^3$ is H or $C_{1-6}$alkyl;

Z is —OH, —$NR^dR^e$, $C_{1-6}$alkoxy, —$C(O)R^a$, or —$S(O)_2R^b$, wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

$R^a$ and $R^b$ are each independently i) $C_{2-6}$alkenyl optionally substituted with one or more substituents selected from deuterium, $C_{1-6}$alkyl, hydroxyl $C_{1-6}$alkyl, halo and halo$C_{1-6}$ alkyl; or ii) $C_{1-6}$alkyl, optionally substituted with one or more halo;

L is methylene, optionally substituted with one or more $C_{1-6}$alkyl; and n and m are 1; or n and m are 2;

provided that when 1) $X^1$ is taken together with $R^1$ and the atoms to which they are attached to form a phenyl, 2) $X^2$ or $X^3$ is N, and 3) L' is

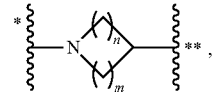

B of formula (II-AB) is phenyl and $R^2$ is halo$C_{1-6}$alkoxyl.

In some aspects, provided herein is a compound of formula (II-A) or (II-B):

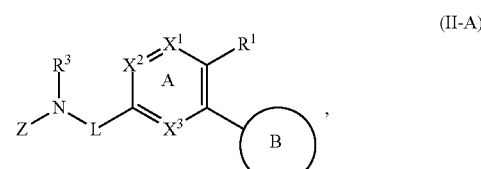

(II-A)

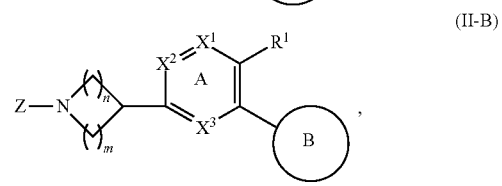

(II-B)

or a stereoisomer or tautomer thereof, or a pharmaceutically acceptable salt thereof, wherein:

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;

wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$; and wherein $R^d$ and $R^e$ are each independently H or $C_{1-6}$alkyl and wherein the $C_{1-6}$alkyl of $R^d$ or $R^e$ is optionally substituted with one or more substituents selected from halo, oxo, —OH and —CN;

$X^2$ is N or $CR^s$, wherein $R^s$ is selected from the group consisting of H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein the $C_{1-15}$alkyl and $C_{1-15}$alkoxy of $R^s$ are each independently optionally substituted with one or more $R^{t1}$, wherein $R^{t1}$ is independently at each occurrence halo, oxo, —OH, —CN, or —$NR^dR^e$, wherein $R^d$ and $R^e$ are each independently H or $C_{1-6}$alkyl; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^2$, wherein $R^{t2}$ is independently at each occurrence selected from halo, oxo, —OH, —CN and $C_{1-6}$alkyl; and $R^d$ and $R^e$ are each independently H or $C_{1-6}$alkyl, wherein the $C_{1-6}$alkyl of $R^d$ or $R^e$ is optionally substituted with one or more substituents selected from halo, oxo, —OH and —CN;

$X^3$ is N or CH;

B is phenyl or 5 to 6 membered heteroaryl; wherein the phenyl and 5 to 6 membered heteroaryl of B are each independently substituted with one or more $R^2$, wherein $R^2$ is independently, at each occurrence, halo; $S(R^y)_5$, wherein each $R^y$ is halo; or $C_{1-6}$alkoxy optionally substituted with one or more halo;

$R^3$ is H or $C_{1-6}$alkyl;

Z is —OH, —$NR^dR^e$, $C_{1-6}$alkoxy, —$C(O)R^a$, or —$S(O)_2R^b$, wherein $R^d$ and RC are each independently H or $C_{1-6}$alkyl and wherein the $C_{1-6}$alkyl of $R^d$ or $R^e$ is optionally substituted with one or more substituents selected from halo, oxo, —OH and —CN;

$R^a$ and $R^b$ are each independently i) $C_{2-6}$alkenyl optionally substituted with one or more substituents selected from deuterium, $C_{1-6}$alkyl, halo and halo$C_{1-6}$alkyl; or ii) $C_{1-6}$alkyl, optionally substituted with one or more halo;

L is methylene, optionally substituted with one or more $C_{1-6}$alkyl; and n and m are each independently 1 or 2.

In some aspects, a pharmaceutical composition comprising a compound of formula (II-A) or a stereoisomer, tautomer, or pharmaceutically acceptable salt thereof, and a pharmaceutically acceptable carrier, diluent or excipient, is provided.

In some aspects, a pharmaceutical composition comprising a compound of formula (II-B) or a stereoisomer, tautomer, or pharmaceutically acceptable salt thereof, and a pharmaceutically acceptable carrier, diluent or excipient, is provided.

In some aspects, a pharmaceutical composition comprising a compound of formula (II-AB) or a stereoisomer, tautomer, or pharmaceutically acceptable salt thereof, and a pharmaceutically acceptable carrier, diluent or excipient, is provided.

In some aspects, a pharmaceutical composition comprising a compound of formula (II-AB') or a stereoisomer, tautomer, or pharmaceutically acceptable salt thereof, and a pharmaceutically acceptable carrier, diluent or excipient, is provided.

In some aspects, a compound of formula (II-A) or formula (II-B), or a stereoisomer, tautomer, or pharmaceutically acceptable salt thereof, is provided for use in medical therapy.

In some aspects, a compound of formula (II-AB), or a stereoisomer, tautomer, or pharmaceutically acceptable salt thereof, is provided for use in medical therapy.

In some aspects, a compound of formula (II-AB'), or a stereoisomer, tautomer, or pharmaceutically acceptable salt thereof, is provided for use in medical therapy.

In some aspects, a compound of formula (II-A) or formula (II-B), or a stereoisomer, tautomer, or pharmaceutically acceptable salt thereof, is provided for the treatment or prophylaxis of cancer.

In some aspects, a compound of formula (II-AB), or a stereoisomer, tautomer, or pharmaceutically acceptable salt thereof, is provided for the treatment or prophylaxis of cancer.

In some aspects, a compound of formula (II-AB'), or a stereoisomer, tautomer, or pharmaceutically acceptable salt thereof, is provided for the treatment or prophylaxis of cancer.

In some aspects, a compound of formula (II-A) or formula (II-B), or a stereoisomer, tautomer, or pharmaceutically acceptable salt thereof, is provided for the preparation of a medicament for the treatment or prophylaxis of cancer.

In some aspects, a compound of formula (II-AB), or a stereoisomer, tautomer, or pharmaceutically acceptable salt thereof, is provided for the preparation of a medicament for the treatment or prophylaxis of cancer.

In some aspects, a compound of formula (II-AB'), or a stereoisomer, tautomer, or pharmaceutically acceptable salt thereof, is provided for the preparation of a medicament for the treatment or prophylaxis of cancer.

In some aspects, a method for treating cancer in a mammal is provided, the method comprising, administering a therapeutically effective amount of a compound of formula (II-A) or formula (II-B), or a stereoisomer, tautomer, or pharmaceutically acceptable salt thereof, to the mammal.

In some aspects, a method for treating cancer in a mammal is provided, the method comprising, administering a therapeutically effective amount of a compound of formula (II-AB), or a stereoisomer, tautomer, or pharmaceutically acceptable salt thereof, to the mammal.

In some aspects, a method for treating cancer in a mammal is provided, the method comprising, administering a therapeutically effective amount of a compound of formula (II-AB'), or a stereoisomer, tautomer, or pharmaceutically acceptable salt thereof, to the mammal.

In some aspects, a method for treating cancer in a mammal is provided, the method comprising administering a therapeutically effective amount of a compound of formula (II-A) or formula (II-B), or a stereoisomer, tautomer, or pharmaceutically acceptable salt thereof, to the mammal in combination with a second therapeutic agent.

In some aspects, a method for treating cancer in a mammal is provided, the method comprising administering a therapeutically effective amount of a compound of formula (II-AB), or a stereoisomer, tautomer, or pharmaceutically acceptable salt thereof, to the mammal in combination with a second therapeutic agent.

In some aspects, a method for treating cancer in a mammal is provided, the method comprising administering a therapeutically effective amount of a compound of formula (II-AB'), or a stereoisomer, tautomer, or pharmaceutically acceptable salt thereof, to the mammal in combination with a second therapeutic agent.

In some aspects, a compound of formula (II-A) or formula (II-B), or a stereoisomer, tautomer, or pharmaceutically acceptable salt thereof, is provided for modulating TEAD activity.

In some aspects, a compound of formula (II-AB), or a stereoisomer, tautomer, or pharmaceutically acceptable salt thereof, is provided for modulating TEAD activity.

In some aspects, a compound of formula (II-AB'), or a stereoisomer, tautomer, or pharmaceutically acceptable salt thereof, is provided for modulating TEAD activity.

In some aspects, a compound of formula (II-A) or formula (II-B), or a stereoisomer, tautomer, or pharmaceutically acceptable salt thereof, is provided for the treatment or prophylaxis of a disease or condition mediated by TEAD activity.

In some aspects, a compound of formula (II-AB), or a stereoisomer, tautomer, or pharmaceutically acceptable salt thereof, is provided for the treatment or prophylaxis of a disease or condition mediated by TEAD activity.

In some aspects, a compound of formula (II-AB'), or a stereoisomer, tautomer, or pharmaceutically acceptable salt thereof, is provided for the treatment or prophylaxis of a disease or condition mediated by TEAD activity.

In some aspects, a compound of formula (II-A) or formula (II-B), or a stereoisomer, tautomer, or pharmaceutically acceptable salt thereof, is provided for use for the preparation of a medicament for the treatment or prophylaxis of a disease or condition that is mediated by TEAD activity.

In some aspects, a compound of formula (II-AB), or a stereoisomer, tautomer, or pharmaceutically acceptable salt thereof, is provided for use for the preparation of a medicament for the treatment or prophylaxis of a disease or condition that is mediated by TEAD activity.

In some aspects, a compound of formula (II-AB'), or a stereoisomer, tautomer, or pharmaceutically acceptable salt thereof, is provided for use for the preparation of a medicament for the treatment or prophylaxis of a disease or condition that is mediated by TEAD activity.

In some aspects, a method for modulating TEAD activity is provided, the method comprising contacting TEAD with a therapeutically effective amount of a compound of formula (II-A) or formula (II-B), or a stereoisomer, tautomer, or pharmaceutically acceptable salt thereof.

In some aspects, a method for modulating TEAD activity is provided, the method comprising contacting TEAD with a therapeutically effective amount of a compound of formula (II-AB), or a stereoisomer, tautomer, or pharmaceutically acceptable salt thereof.

In some aspects, a method for modulating TEAD activity is provided, the method comprising contacting TEAD with a therapeutically effective amount of a compound of formula (II-AB'), or a stereoisomer, tautomer, or pharmaceutically acceptable salt thereof.

In some aspects, a method for treating a disease or condition mediated by TEAD activity in a mammal is provided, the method comprising administering a therapeutically effective amount of a compound of formula (II-A) or formula (II-B), or a stereoisomer, tautomer, or pharmaceutically acceptable salt thereof, to the mammal.

In some aspects, a method for treating a disease or condition mediated by TEAD activity in a mammal is provided, the method comprising administering a therapeutically effective amount of a compound of formula (II-AB), or a stereoisomer, tautomer, or pharmaceutically acceptable salt thereof, to the mammal.

In some aspects, a method for treating a disease or condition mediated by TEAD activity in a mammal is provided, the method comprising administering a therapeutically effective amount of a compound of formula (II-AB'), or a stereoisomer, tautomer, or pharmaceutically acceptable salt thereof, to the mammal.

In one aspect, the present disclosure is directed to a combination comprising: (i) one or more YAP/TAZ-TEAD inhibitors, or a pharmaceutically acceptable salt thereof; and (ii) one or more KRAS inhibitors, or a pharmaceutically acceptable salt thereof. In some aspects, one or more YAP/TAZ-TEAD inhibitors and one or more KRAS inhibitors are co-administered to an individual. In some aspects, the combination is administered to an individual in the same composition. In some aspects, the combination is administered to an individual in different compositions. Thus, it is understood that the one or more YAP/TAZ-TEAD inhibitors and the one or more KRAS inhibitors may be administered simultaneously or sequentially to the individual. In some aspects, provided herein are compositions comprising one or more YAP/TAZ-TEAD inhibitors and one or more KRAS inhibitors. In another aspect, the present disclosure is directed to methods of modulating or inhibiting KRAS activity in a cell, comprising administering to the cell an effective amount of such combinations. In another aspect, the present disclosure is directed to methods of treating cancer in a subject in need thereof, comprising administering to the subject an effective amount of such combinations. In another aspect, the present disclosure is directed to methods of reducing resistance of a subject to treatment comprising a KRAS inhibitor, wherein the method comprises administering to the subject a therapeutically effective amount of a TEAD inhibitor.

In one aspect, the present disclosure is directed to processes of preparing one or more TEAD inhibitors described herein.

BRIEF DESCRIPTION OF THE DRAWINGS

The following embodiments are representative of some aspects of the disclosure.

DETAILED DESCRIPTION

Definitions

Figure 1:
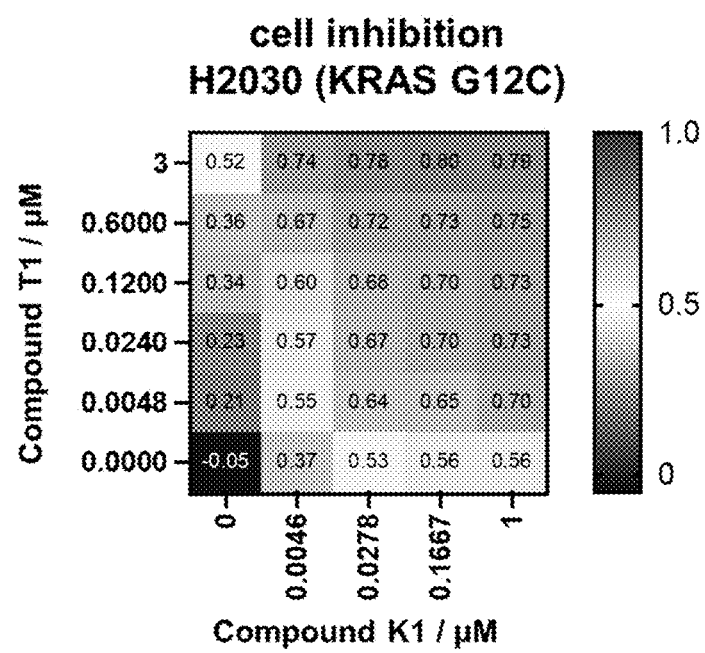
FIG. 1 depicts % inhibition of H2030 cells (KRAS G12C) following administration of a combination comprising Compound T1 (a YAP/TAZ-TEAD inhibitor) and Compound K1 (a KRAS inhibitor).

Unless otherwise indicated, the following specific terms and phrases used in the description and claims are defined as follows.

The term "moiety" refers to an atom or group of chemically bonded atoms that is attached to another atom or molecule by one or more chemical bonds thereby forming part of a molecule.

The term "substituted" refers to the fact that at least one of the hydrogen atoms of that moiety is replaced by another substituent or moiety.

The term "alkyl" refers to an aliphatic straight-chain or branched-chain saturated hydrocarbon moiety having 1 to 20 carbon atoms, such as 1 to 12 carbon atoms, or 1 to 6 carbon atoms. Alkyl groups may be optionally substituted.

In some embodiments, alkyl is unsubstituted.

In some embodiments, "hydroxylalkyl" is alkyl substituted with one or more —OH.

In some embodiments, "alkoxy" is —O-alkyl.

The term "cycloalkyl" means a saturated or partially unsaturated carbocyclic moiety having mono- or bicyclic (including bridged bicyclic) rings and 3 to 10 carbon atoms in the ring. In particular aspects, cycloalkyl may contain from 3 to 8 carbon atoms (i.e., ($C_3$-$C_8$)cycloalkyl). In other particular aspects cycloalkyl may contain from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a spirocycle fashion such as spirocyclopropyl:

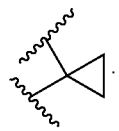

The term "haloalkyl" refers to an alkyl group wherein one or more of the hydrogen atoms of the alkyl group has been replaced by the same or different halogen atoms, such as fluoro atoms. Examples of haloalkyl include monofluoro-, difluoro- or trifluoromethyl, -ethyl or -propyl, for example 3,3,3-trifluoropropyl, 2-fluoroethyl, 2,2,2-trifluoroethyl, fluoromethyl, or trifluoromethyl. Haloalkyl groups may be optionally substituted.

In some embodiments, haloalkyl is unsubstituted.

The term "alkenyl" refers to a straight or branched chain alkyl or substituted alkyl group as defined elsewhere herein having at least one carbon-carbon double bond. Alkenyl groups may be optionally substituted.

In some embodiments, alkenyl is unsubstituted.

The term "alkynyl" refers to a straight or branched chain alkyl or substituted alkyl group as defined elsewhere herein having at least one carbon-carbon triple bond. Alkynyl groups may be optionally substituted.

In some embodiments, alkynyl is unsubstituted. In some embodiments, hydroxylalkynyl is alkynyl substituted with one or more —OH.

The terms "heterocyclyl" and "heterocycle" refer to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4) heteroatoms selected from oxygen, nitrogen and sulfur in the ring with the remaining ring atoms being carbon. When used in reference to a ring atom of a heterocycle, a nitrogen or sulfur may also be in an oxidized form, and a nitrogen may be substituted. The heterocycle can be attached to its pendant group at any heteroatom or carbon atom that results in a stable structure and any of the ring atoms can be optionally substituted. Examples of such saturated or partially unsaturated heterocycles include, without limitation, oxiranyl, oxetanyl, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazolyl, thiazepinyl, morpholinyl, and quinuclidinyl. The term heterocycle also includes groups in which a heterocycle is fused to one or more aryl, heteroaryl, or cycloalkyl rings, such as benzothiazolyl, benzofuranyl, furopyridinyl, indolinyl, 3H-indolyl, chromanyl, 2-azabicyclo[2.2.1]heptanyl, octahydroindolyl, or tetrahydroquinolinyl. Heterocyclyl groups may be optionally substituted.

In some embodiments, heterocyclyl is unsubstituted.

The term "aryl" refers to a cyclic aromatic hydrocarbon moiety having a mono-, bi- or tricyclic aromatic ring of 5 to 20 carbon ring atoms. Examples of aryl moieties include, but are not limited to, phenyl, naphthyl, benzyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted. In some aspects, monocyclic aryl rings may have 5 or 6 carbon ring atoms. Aryl groups may be optionally substituted.

In some embodiments, aryl is unsubstituted.

The term "heteroaryl" refers an aromatic heterocyclic mono- or bicyclic ring system of 1 to 20 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Heteroaryl groups may be optionally substituted.

In some embodiments, heteroaryl is unsubstituted.

The terms "halo" and "halogen" refer fluoro, chloro, bromo and iodo. In some aspects, halo is fluoro or chloro.

The term "oxo" refers to the =O moiety.

The term "cyano" refers to the —C≡N moiety.

The terms "spirocycle" and "spirocyclyl" refer to carbogenic bicyclic ring systems comprising between 5 and 13 carbon atoms with both rings connected through a single atom. The rings can be different in size and nature, or identical in size and nature. Examples include spiropentane, spirohexane, spiroheptane, spirooctane, spirononane, or spirodecane. One or more of the carbon atoms in the spirocycle can be substituted with a heteroatom (e.g., 0, N, S, or P). Spirocycle groups may be optionally substituted.

In some embodiments, the spirocycle is unsubstituted.

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The term "prodrug" refers to those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

In some prodrug aspects, prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present disclosure. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

In some other prodrug aspects, a free carboxyl group of a compound of the disclosure can be derivatized as an amide or alkyl ester. In yet other prodrug aspects, prodrugs comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$) alkoxycarbonyloxymethyl, N—($C_{1-6}$)alkoxycarbonylaminomethyl, succinoyl, ($C_{1-6}$)alkanoyl, alpha-amino($C_{1-4}$) alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present disclosure provides for metabolites of compounds of the disclosure. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^{3}H$) isotope of a compound of the disclosure, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure can exist in multiple crystalline or amorphous forms. In general, all physical forms are equivalent for the uses contemplated by the present disclosure and are intended to be within the scope of the present disclosure.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain aspects the compound is enriched by at least about 90% by weight with a single diastereomer or enantiomer. In other aspects the compound is enriched by at least about 95%, 98%, or 99% by weight with a single diastereomer or enantiomer.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure.

The compounds of the present disclosure may also exist in different tautomeric forms, and all such forms are embraced within the scope of the disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise indicated, the term "a compound of the formula" or "a compound of formula" or "compounds of the formula" or "compounds of formula" refers to any compound selected from the genus of compounds as defined by the formula. In some embodiments or aspects, the term also includes a pharmaceutically acceptable salt or ester of any such compound, a stereoisomer, or a tautomer of such compound. The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this disclosure can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

In some embodiments, the term "a therapeutically effective amount" of a compound means an amount of compound that is effective to alleviate or ameliorate symptoms of disease or prolong the survival of the subject being treated. Determination of a therapeutically effective amount is within the skill in the art. The therapeutically effective amount or dosage of a compound according to this disclosure can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

In embodiments herein, a therapeutically effective amount of a compound may be an amount of compound that is effective to alleviate or ameliorate a condition or disease, or symptoms thereof, or prolong the survival of the subject being treated.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with a compound of the disclosure, use thereof in the compositions of the disclosure is contemplated. Supplementary active compounds can also be incorporated into the compositions.

COMPOUNDS

In some aspects, provided is a compound for formula (II-AB'):

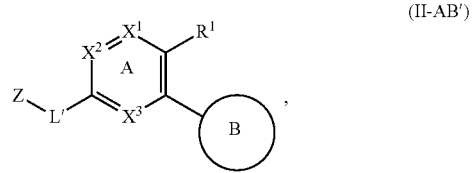

(II-AB')

or a stereoisomer or tautomer thereof, or a pharmaceutically acceptable salt thereof, wherein:

L' is *—N(R$^3$)-L-** or

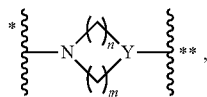

or Z-L' is

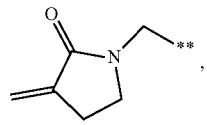

wherein * denotes the point of attachment to Z, and ** denotes the point of attachment to

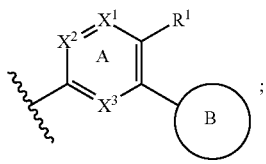

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;
   wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-6}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^1$, and —NR$^d$R$^e$; and
   wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN;
$X^2$ is N or CR$^s$, wherein R$^s$ is selected from H, halo, $C_{1-15}$alkyl, hydroxyl$C_{1-6}$alkynyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —NR$^d$COR$^e$, —CONR$^d$R$^e$, —SO$_2$R$^d$, —S(O)NHR$^d$, —SO$_2$NR$^d$R$^e$, —NR$^d$SO$_2$R$^1$, and —NR$^d$R$^e$;
   wherein the $C_{1-5}$alkyl and $C_{1-15}$alkoxy of R$^s$ are each independently optionally substituted with one or more R$^t$, wherein R$^t$ is independently at each occurrence halo, oxo, —OH, —CN, 5-6 membered heteroaryl, or —NR$^d$R$^e$, wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN; and
   wherein the $C_{6-20}$aryl, 5 to 15 membered heteroaryl, $C_{3-20}$cycloalkyl, and 3 to 15 membered heterocyclyl of R$^s$ are each independently optionally substituted with one or more R$^{t2}$, wherein R$^{t2}$ is independently at each occurrence selected from halo, oxo, —OH, —CN and $C_{1-6}$alkyl; and
   wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN;
$X^3$ is N or CH;
B is
   i) phenyl or 5 to 6 membered heteroaryl; wherein the phenyl and 5 to 6 membered heteroaryl of B are each independently substituted with one or more $R^2$,
      wherein $R^2$ is independently, at each occurrence, halo; S(R$^y$)$_5$, wherein each R$_y$ is halo; or $C_{1-6}$alkoxy optionally substituted with one or more halo;
   ii) —O-phenyl substituted with halo$C_{1-3}$alkyl, provided that when B is —O-phenyl substituted with halo$C_{1-3}$alkyl, L' is *—N(R$^3$)-L-**, Z is —C(O)CHCH$_2$, $X^1$ is C, $X^2$ is CR$^s$, and $X^3$ is CH; or
   iii) bicyclopentane substituted by $C_{1-3}$alkyl, provided that when B is bicyclopentane substituted by $C_{1-3}$alkyl, L' is *—N(R$^3$)-L-** and Z is —C(O)CHCH$_2$; or
   iv) phenyl substituted with ethynyl or halo$C_{1-3}$alkyl, provided that when B is phenyl substituted with ethynyl or halo$C_{1-3}$alkyl, L' is *—N(R$^3$)-L-**, Z is —C(O)CHCH$_2$, and R$^s$ is $C_1$-3alkyl substituted with one or more —OH; or
   v) piperidine substituted with halo$C_{1-3}$alkyl or halo$C_{1-3}$alkoxy, provided that when B is piperidine substituted with halo$C_{1-3}$alkyl or halo$C_{1-3}$alkoxy, L' is *—N(R$^3$)-L-** and Z is —C(O)CHCH$_2$;
$R^3$ is H or $C_{1-6}$alkyl;
Z is —OH, —NR$^d$R$^e$, $C_{1-6}$alkoxy, —C(O)R$^a$, or —S(O)$_2$R$^b$,
   wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN;
R$^a$ and R$^b$ are each independently i) $C_{2-6}$alkenyl optionally substituted with one or more substituents selected from deuterium, $C_{1-6}$alkyl, hydroxyl $C_{1-6}$alkyl, halo and halo$C_{1-6}$ alkyl; ii) $C_{1-6}$alkyl, optionally substituted with one or more halo; or iii) cyclobutenyl or bicyclobutanyl;
L is methylene or ethylene, wherein the methylene of L is optionally substituted with one $C_{1-6}$ alkyl;
Y is CH or C(CN), and
n and m are each independently 1 or 2;
provided that:
   i) when i-1) $X^1$ is taken together with $R^1$ and the atoms to which they are attached to form a phenyl, and i-2) $X^2$ or $X^3$ is N, B of formula (II-AB') is phenyl and $R^2$ is halo$C_{1-6}$alkoxyl; and
   ii) when n=1 and m=2, or n=2 and m=1, B is phenyl substituted by halomethyoxyl; and
   iii) the compound of formula (II-AB') is not any one of following:
N-((8-(4-fluorophenyl)imidazo[1,2-a]pyrazin-6-yl)methyl)acrylamide;
N-((8-(4-(trifluoromethoxy)phenyl)imidazo[1,2-a]pyrazin-6-yl)methyl)acrylamide;
N-((7-fluoro-4-(4-(trifluoromethoxy)phenyl)quinazolin-2-yl)methyl)acrylamide;

N-((8-(4-(difluoromethoxy)phenyl)imidazo[1,2-a]pyrazin-6-yl)methyl)acrylamide; 1-(4-(4-(4-methoxyphenyl)-1-methyl-1H-imidazo[4,5-c]pyridin-6-yl)piperidin-1-yl)ethan-1-one;
4-(4-methoxyphenyl)-1-methyl-6-(1-(methylsulfonyl)piperidin-4-yl)-1H-imidazo[4,5-c]pyridine;
6-(1-(ethylsulfonyl)piperidin-4-yl)-4-(4-methoxyphenyl)-1-methyl-1H-imidazo[4,5-c]pyridine;
6-(1-(ethylsulfonyl)piperidin-4-yl)-1-isopropyl-4-(4-methoxyphenyl)-1H-imidazo[4,5-c]pyridine;
4-(4-methoxyphenyl)-1-methyl-6-(1-((trifluoromethyl)sulfonyl)piperidin-4-yl)-1H-imidazo[4,5-c]pyridine; and
N-((4-(4-fluorophenyl)-1,8-naphthyridin-2-yl)methyl)acetamide.

Any embodiments, aspects, variations, described herein with respect to one formula, may, where applicable, be applied to any other formula listed herein. For example, any embodiments, aspects, variations, described herein with respect to any one or more of formula (II-AB), (II-A), and (II-B) apply to formula (II-AB'), the same as if each and every embodiments, aspects, and variations is specifically and individually listed with respect to formula (II-AB'). It is understood that such embodiments apply to structural features of compounds, as well as methods of making and using such compounds. For example, it is understood that methods of using any one or more of formula (II-AB), (II-A), and (II-B), where applicable, apply to methods of using compounds of formula (II-AB'), the same as if each and every embodiments, aspects, and variations is specifically and individually listed with respect to formula (II-AB').

In some embodiments, in conjunction with embodiments above or below, L' of formula (II-AB') is *—N(R³)-L-**. In some embodiments, in conjunction with embodiments above or below, L' of formula (II-AB') is

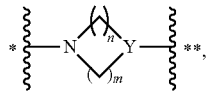

In some embodiments, provided is a compound of formula (II-AB):

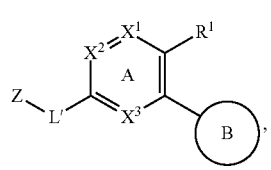

(II-AB)

or a stereoisomer or tautomer thereof, or a pharmaceutically acceptable salt thereof, wherein:
L' is selected from the group consisting of *—N(R³)-L-** and

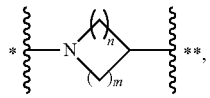

wherein * denotes the point of attachment to Z, and ** denotes the point of attachment to

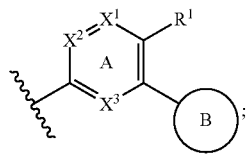

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;
  wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-5}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and
  wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;
$X^2$ is N or CR$^s$, wherein $R^s$ is selected from H, halo, $C_{1-15}$alkyl, hydroxyl$C_{1-6}$alkynyl, $C_{6-20}$aryl, 5 to 15 membered heteroaryl, $C_{3-20}$cycloalkyl, 3 to 15 membered heterocyclyl, —OH, —CN, $C_{1-15}$-alkoxy, —NR$^d$COR$^e$, —CONR$^d$R$^e$, —SO$_2$R$^d$, —S(O)NHR$^d$, —SO$_2$NR$^d$R$^e$, —NR$^d$SO$_2$R$^e$, and —NR$^d$R$^e$;
  wherein the $C_{1-15}$alkyl and $C_{1-15}$alkoxy of $R^s$ are each independently optionally substituted with one or more $R^{t1}$, wherein $R^{t1}$ is independently at each occurrence halo, oxo, —OH, —CN, 5-6 membered heteroaryl, or —NR$^d$R$^e$, wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN; and
  wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently at each occurrence selected from halo, oxo, —OH, —CN and $C_{1-6}$alkyl; and
  wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;
$X^3$ is N or CH;
B is phenyl or 5 to 6 membered heteroaryl; wherein the phenyl and 5 to 6 membered heteroaryl of B are each independently substituted with one or more $R^2$, wherein
$R^2$ is independently, at each occurrence, halo; S(R$^y$)$_5$, wherein each $R^y$ is halo; or $C_{1-6}$alkoxy optionally substituted with one or more halo;
$R^3$ is H or $C_{1-6}$alkyl;
Z is —OH, —NR$^d$R$^e$, $C_{1-6}$alkoxy, —C(O)R$^a$, —S(O)$_2$R$^b$, wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

R$^a$ and R$^b$ are each independently i) C$_{2-6}$alkenyl optionally substituted with one or more substituents selected from deuterium, C$_{1-6}$alkyl, hydroxyl C$_{1-6}$alkyl, halo and haloC$_{1-6}$alkyl; or ii) C$_{1-6}$alkyl, optionally substituted with one or more halo;

L is methylene, optionally substituted with one or more C$_{1-6}$alkyl; and n and m are 1; or n and m are 2;

provided that when 1) X$^1$ is taken together with R$^1$ and the atoms to which they are attached to form a phenyl, and 2) X$^2$ or X$^3$ is N, B of formula (II-AB) is phenyl and R$^2$ is haloC$_{1-6}$alkoxyl.

In some aspects, a compound or a stereoisomer, tautomer, or pharmaceutically acceptable salt thereof of the following formula (II-A) or formula (II-B) is provided:

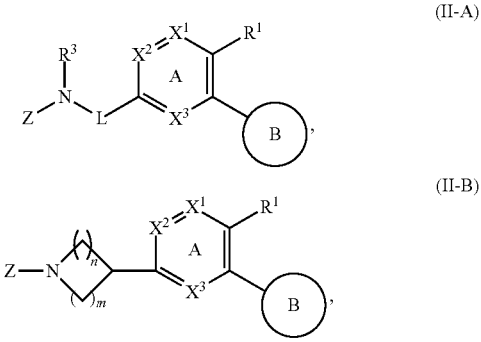

(II-A)

(II-B)

or a stereoisomer or tautomer thereof, or a pharmaceutically acceptable salt thereof, wherein:

X$^1$ is C or N, and X$^1$ is taken together with R$^1$ and the atoms to which they are attached, to form a 5 to 6 membered heteroaryl, 5 to 6 membered heterocyclyl, phenyl, or C$_{5-6}$cycloalkyl that is fused to ring A;

wherein the 5 to 6 membered heteroaryl, 5 to 6 membered heterocyclyl, phenyl, and C$_{5-6}$cycloalkyl formed by X$^1$ and R$^1$ are each independently optionally substituted with one or more R$^t$, wherein R$^t$ is independently, at each occurrence, selected from C$_{1-3}$alkyl, —OH, oxo, C$_{1-3}$alkoxy, and —NR$^d$R$^e$; and wherein R$^d$ and R$^e$ are each independently H or C$_{1-6}$alkyl, wherein the C$_{1-6}$alkyl of R$^d$ or R$^e$ is optionally substituted with one or more substituents selected from halo, oxo, —OH and —CN;

X$^2$ is N or CR$^s$, wherein R$^s$ is selected from the group consisting of H, halo, C$_{1-15}$alkyl, C$_{6-20}$aryl, 5 to 15 membered heteroaryl, C$_{3-20}$cycloalkyl, 3 to 15 membered heterocyclyl, —OH, —CN, C$_{1-15}$alkoxy, —NR$^d$-COR$^e$, —CONR$^d$R$^e$, —SO$_2$R$^d$, —SO$_2$NR$^d$R$^e$, —NR$^d$SO$_2$R$^e$, and —NR$^d$R$^e$;

wherein the C$_{1-15}$alkyl and C$_{1-25}$alkoxy of R$^s$ are each independently optionally substituted with one or more R$^{t1}$, wherein R$^{t1}$ is independently at each occurrence halo, oxo, —OH, —CN, or —NR$^d$R$^e$, wherein R$^d$ and R$^e$ are each independently H or C$_{1-6}$alkyl; and wherein the C$_{6-20}$aryl, 5 to 15 membered heteroaryl, C$_{3-20}$cycloalkyl, and 3 to 15 membered heterocyclyl of R$^s$ are each independently optionally substituted with one or more R$^{t2}$, wherein R$^{t2}$ is independently at each occurrence selected from halo, oxo, —OH, —CN and C$_{1-6}$alkyl; and wherein R$^d$ and R$^e$ are each independently H or C$_{1-6}$alkyl, wherein the C$_{1-6}$alkyl of R$^d$ or R$^e$ is optionally substituted with one or more substituents selected from halo, oxo, —OH and —CN;

X$^3$ is N or CH;

B is phenyl or 5 to 6 membered heteroaryl; wherein the phenyl and 5 to 6 membered heteroaryl of B are each independently substituted with one to five R$^2$;

R$^2$ is independently, at each occurrence, i) halo; ii) S(R$^y$)$_5$, wherein each R$^y$ is halo; or iii) C$_{1-6}$ alkoxy, optionally substituted with one or more halo;

R$^3$ is H or C$_{1-6}$alkyl;

Z is —OH, —NR$^d$R$^e$, C$_{1-6}$alkoxy, —C(O)R$^a$, —S(O)$_2$R$^a$, wherein R$^d$ and R$^e$ are each independently H or C$_{1-6}$alkyl and wherein the C$_{1-6}$alkyl of R$^d$ or R$^e$ is optionally substituted with one or more substituents selected from halo, oxo, —OH and —CN;

R$^a$ is i) C$_{2-6}$alkenyl optionally substituted with one or more deuterium, C$_{1-6}$alkyl, halo, haloC$_{1-6}$ alkyl; or ii) C$_{1-6}$alkyl, optionally substituted with one or more halo;

L is methylene, optionally substituted with one or more C$_{1-6}$alkyl; and n and m are each independently 1 or 2.

In some embodiments, provided is a compound of formula (II-A) or (II-B):

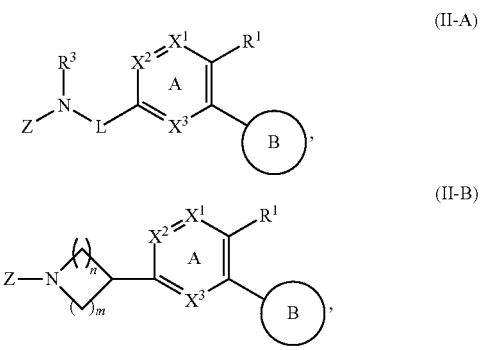

(II-A)

(II-B)

or a stereoisomer or tautomer thereof, or a pharmaceutically acceptable salt thereof, wherein:

X$^1$ is C or N, and X$^1$ is taken together with R$^1$ and the atoms to which they are attached, to form a 5 to 6 membered heteroaryl, 5 to 6 membered heterocyclyl, phenyl, or C$_{5-6}$cycloalkyl fused to ring A;

wherein the 5 to 6 membered heteroaryl, 5 to 6 membered heterocyclyl, phenyl, and C$_{5-6}$cycloalkyl formed by X$^1$ and R$^1$ are each independently optionally substituted with one or more R$^t$, wherein R$^t$ is independently, at each occurrence, selected from the group consisting of halo, C$_{1-15}$alkyl, haloC$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and wherein R$^d$ and R$^e$ are each independently H or C$_{1-6}$alkyl, and wherein the C$_{1-6}$alkyl of R$^d$ or R$^e$ is optionally substituted with one or more substituents selected from halo, oxo, —OH and —CN;

X$^2$ is N or CR$^s$, wherein R$^s$ is selected from H, halo, C$_{1-15}$alkyl, hydroxylC$_{1-6}$alkynyl, C$_{6-20}$aryl, 5 to 15 membered heteroaryl, C$_{3-20}$cycloalkyl, 3 to 15 membered heterocyclyl, —OH, —CN, C$_{1-15}$alkoxy, —NR$^d$-COR$^e$, —CONR$^d$R$^e$, —SO$_2$R$^d$, —S(O)NHR$^d$, —SO$_2$NR$^d$R$^e$, —NR$^d$SO$_2$R$^e$, and —NR$^d$R$^e$;

wherein the C$_{1-6}$alkyl and C$_{1-15}$alkoxy of R$^s$ are each independently optionally substituted with one or more R$^{t1}$, wherein R$^t$ is independently at each occurrence halo, oxo, —OH, —CN, 5-6 membered heteroaryl, or —NR$^d$R$^e$, wherein R$^d$ and R$^e$ are each independently H or C$_{1-6}$alkyl, and wherein the C$_{1-6}$alkyl of R$^d$ or R$^e$ is optionally substituted with one or more substituents selected from halo, oxo, —OH and —CN; and wherein the C$_{6-20}$aryl, 5 to 15 membered heteroaryl, C$_{3-20}$cycloalkyl, and 3 to 15 membered heterocyclyl of R$^s$ are each independently optionally substituted with one or more R$^2$, wherein R$^{t2}$ is independently at each occurrence selected from halo, oxo, —OH, —CN and C$_{1-6}$alkyl; and wherein R$^d$ and R$^e$ are each independently H or C$_{1-6}$alkyl, and wherein the C$_{1-6}$alkyl of R$^d$ or R$^e$ is optionally substituted with one or more substituents selected from halo, oxo, —OH and —CN;

X$^3$ is N or CH;

B is phenyl or 5 to 6 membered heteroaryl; wherein the phenyl and 5 to 6 membered heteroaryl of B are each independently substituted with one or more R$^2$, wherein R$^2$ is independently, at each occurrence, halo; S(R$^y$)$_5$, wherein each R$_y$ is halo; or C$_{1-6}$alkoxy optionally substituted with one or more halo;

R$^3$ is H or C$_{1-6}$alkyl;

Z is —OH, —NR$^d$R$^e$, C$_{1-6}$alkoxy, —C(O)R$^a$, or —S(O)$_2$R$^b$, wherein R$^d$ and R$^e$ are each independently H or C$_{1-6}$alkyl, and wherein the C$_{1-6}$alkyl of R$^d$ or R$^e$ is optionally substituted with one or more substituents selected from halo, oxo, —OH and —CN;

R$^a$ and R$^b$ are each independently i) C$_{2-6}$alkenyl optionally substituted with one or more substituents selected from deuterium, C$_{1-6}$alkyl, hydroxyl C$_{1-6}$alkyl, halo and haloC$_{1-6}$ alkyl; or ii) C$_{1-6}$alkyl, optionally substituted with one or more halo;

L is methylene, optionally substituted with one or more C$_{1-6}$alkyl; and n and m are 1; or n and m are 2;

provided that when 1) X$^1$ is taken together with R$^1$ and the atoms to which they are attached to form a phenyl, and 2) X$^2$ or X$^3$ is N, B of formula (II-B) is phenyl and R$^2$ is haloC$_{1-6}$alkoxyl.

In some embodiments, provided herein is a compound of formula (II-AB), or a stereoisomer, tautomer, or pharmaceutically acceptable salt thereof, wherein L' is *—N(R$^3$)-L-**, wherein * denotes the point of attachment to Z, and ** denotes the point of attachment to

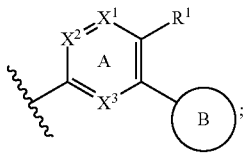

In some embodiments, provided herein is a compound of formula (II-AB), or a stereoisomer, tautomer, or pharmaceutically acceptable salt thereof, wherein L' is

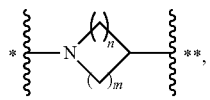

wherein * denotes the point of attachment to Z, and ** denotes the point of attachment to

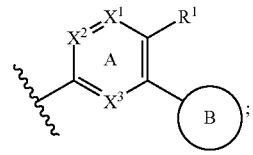

In some embodiments, provided herein is a compound of formula (II-AB), or a stereoisomer, tautomer, or pharmaceutically acceptable salt thereof, wherein X$^1$ is taken together with R$^1$ and the atoms to which they are attached, to form a 5 to 6 membered heteroaryl, 5 to 6 membered heterocyclyl, phenyl, or C$_{5-6}$cycloalkyl that is fused to ring A, wherein the 5 to 6 membered heteroaryl, 5 to 6 membered heterocyclyl, phenyl, and C$_{5-6}$cycloalkyl formed by X$^1$ and R$^1$ are each independently optionally substituted with one or more R$^t$, wherein R$^t$ is independently, at each occurrence, selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, or —NR$^d$R$^e$, wherein R$^d$ and R$^e$ are each independently H or C$_{1-6}$alkyl. In some embodiments, R$^d$ and R$^e$ are each independently H or C$_{1-6}$alkyl. In some embodiments, R$^d$ is H or C$_{1-6}$alkyl. In some embodiments, R$^d$ is H. In some embodiments, R$^d$ is C$_{1-6}$alkyl. In some embodiments, R$^e$ is H or C$_{1-6}$alkyl. In some embodiments, R$^e$ is H or C$_{1-6}$alkyl. In some embodiments, R$^e$ is H. In some embodiments, R$^e$ is C$_{1-6}$alkyl.

In some embodiments, provided herein is a compound of formula (II-AB), or a stereoisomer, tautomer, or pharmaceutically acceptable salt thereof, wherein X$^1$ is taken together with R$^1$ and the atoms to which they are attached, to form a 5 to 6 membered heteroaryl, wherein the 5 to 6 membered heteroaryl is substituted with one or more R$^t$, wherein R$^t$ is independently, at each occurrence, selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^1$ is taken together with R$^1$ and the atoms to which they are attached, to form a 5 to 6 membered heteroaryl, wherein the 5 to 6 membered heteroaryl is substituted with one or more R$^t$, wherein R$^t$ is independently, at each occurrence, selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^1$ is taken together with R$^1$ and the atoms to which they are attached, to form a 5 to 6 membered heteroaryl, wherein the 5 to 6 membered heteroaryl is substituted with one or more R$^t$, wherein R$^t$ is halo. In some embodiments, X$^1$ is taken together with R$^1$ and the atoms to which they are attached, to form a 5 to 6 membered heteroaryl, wherein the 5 to 6 membered heteroaryl is substituted with one or more R$^t$, wherein R$^t$ is C$_{1-15}$alkyl. In some embodiments, X$^1$ is taken together with R$^1$ and the atoms to which they are attached, to form a 5 to 6 membered heteroaryl, wherein the 5 to 6 membered heteroaryl is substituted with one or more R$^t$, wherein R$^t$ is C$_{6-20}$aryl. In some embodiments, X$^1$ is taken together with R$^1$ and the atoms to which they are attached, to form a 5 to 6 membered heteroaryl, wherein the 5 to 6 membered heteroaryl is substituted with one or more $R^t$, wherein $R^t$ is 5 to 15 membered heteroaryl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is $C_{3-20}$cycloalkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is 3 to 15 membered heterocyclyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —OH. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is —CN. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is oxo. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is $C_{1-15}$alkoxy. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$COR$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is —CONR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —SO$_2$R$^d$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —SO$_2$NR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is —NR$^d$SO$_2$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$R$^e$, wherein $R^d$ and $R^e$ are each independently H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is —NR$^d$R$^e$, wherein $R^d$ is H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$R$^e$, wherein $R^d$ is H. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$R$^e$, wherein $R^d$ is $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$R$^e$, wherein $R^e$ is H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$R$^e$, wherein $R^e$ is H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is —NR$^d$R$^e$, wherein $R^e$ is H. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$R$^e$, wherein $R^e$ is $C_{1-6}$alkyl.

In some embodiments, provided herein is a compound of formula (II-AB), or a stereoisomer, tautomer, or pharmaceutically acceptable salt thereof, wherein $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is independently, at each occurrence, selected from the group consisting of halo, $C_{1-15}$-alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is halo. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{1-15}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{6-20}$aryl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is 5 to 15 membered heterocyclyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{3-20}$cycloalkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is 3 to 15 membered heterocyclyl. In some embodiments, X, is taken together with $R^1$ and the atoms to which they are attached, to form a 5 to 6 membered heterocyclyl, wherein the 5 to 6 membered heterocyclyl is substituted with one or more $R^t$, wherein $R^t$ is —OH. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —CN. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is oxo. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{1-15}$alkoxy. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dCOR^e$. In some embodiments, $X^1$ is taken together with R, and the atoms to which they are attached, to form a 5 to 6 membered heterocyclyl, wherein the 5 to 6 membered heterocyclyl is substituted with one or more $R^t$, wherein $R^t$ is —$CONR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$SO_2R^d$. In some embodiments, $X^1$ is taken together with $R^t$ and the atoms to which they are attached, to form a 5 to 6 membered heterocyclyl, wherein the 5 to 6 membered heterocyclyl is substituted with one or more $R^t$, wherein $R^t$ is —$SO_2NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dSO_2R^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dRC$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^d$ and RC are each independently H or $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^d$ is H. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is —$NR^dR^e$, wherein $R^d$ is $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^1$, wherein $R^t$ is —$NR^dR^e$, wherein $R^e$ is H or $C_{1-6}$alkyl. In some embodiments, $R^e$ is H or $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^e$ is H. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is —$NR^dR^e$, wherein $R^e$ is $C_{1-6}$alkyl.

In some embodiments, provided herein is a compound of formula (II-AB), or a stereoisomer, tautomer, or pharmaceutically acceptable salt thereof, wherein $X^1$ is taken together with $R^1$ and the atoms to which they are attached, to form a phenyl, wherein the phenyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^1$, and —$NR^dR^e$. In some embodiments, $X^1$ is taken together with $R^1$ and the atoms to which they are attached, to form a phenyl, wherein the phenyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^1$, and —$NR^dR^e$. In some embodiments, $X^1$ is taken together with $R^1$ and the atoms to which they are attached, to form a phenyl, wherein the phenyl is substituted with one or more $R^t$, wherein $R^t$ is halo. In some embodiments, $X^1$ is taken together with $R^1$ and the atoms to which they are attached, to form a phenyl, wherein the phenyl is substituted with one or more $R^t$, wherein $R^1$ is $C_{1-15}$alkyl. In some embodiments, $X^1$ is taken together with $R^1$ and the atoms to which they are attached, to form a phenyl, wherein the phenyl is substituted with one or more $R^t$, wherein $R^t$ is $C_{6-20}$aryl. In some embodiments, $X^1$ is taken together with $R^1$ and the atoms to which they are attached, to form a phenyl, wherein the phenyl is substituted with one or more $R^t$, wherein $R^t$ is 5 to 15 membered heteroaryl. In some embodiments, $X^1$ is taken together with $R^1$ and the atoms to which they are attached, to form a phenyl, wherein the phenyl is substituted with one or more $R^t$, wherein $R^t$ is $C_{3-20}$cycloalkyl. In some embodiments, $X^1$ is taken together with $R^1$ and the atoms to which they are attached, to form a phenyl, wherein the phenyl is substituted with one or more $R^t$, wherein $R^t$ is 3 to 15 membered heterocyclyl. In some embodiments, $X^1$ is taken together with $R^1$ and the atoms to which they are attached, to form a phenyl, wherein the phenyl is substituted with one or more $R^t$, wherein $R^t$ is —OH. In some embodiments, $X^1$ is taken together with $R^1$ and the atoms to which they are attached, to form a phenyl, wherein the phenyl is substituted with one or more $R^t$, wherein $R^t$ is —CN. In some embodiments, $X^1$ is taken together with $R^1$ and the atoms to which they are attached, to form a phenyl, wherein the phenyl is substituted with one or more $R^t$, wherein $R^t$ is oxo. In some embodiments, $X^1$ is taken together with $R^1$ and the atoms to which they are attached, to form a phenyl, wherein the phenyl is substituted with one or more $R^t$, wherein $R^t$ is $C_{1-15}$alkoxy. In some embodiments, $X^1$ is taken together with $R^1$ and the atoms to which they are attached, to form a phenyl, wherein the phenyl is substituted with one or more $R^t$, wherein $R^t$ is —$NR^dCOR^e$. In some embodiments, $X^1$ is taken together with $R^1$ and the atoms to which they are attached, to form a phenyl, wherein the phenyl is substituted with one or more $R^t$, wherein $R^t$ is —$CONR^dR^e$. In some embodiments, $X^1$ is taken together with $R^1$ and the atoms to which they are attached, to form a phenyl, wherein the phenyl is substituted with one or more $R^t$, wherein $R^t$ is —$SO_2R^d$. In some embodiments, $X^1$ is taken together with $R^1$ and the atoms to which they are attached, to form a phenyl, wherein the phenyl is substituted with one or more $R^t$, wherein $R^t$ is —$SO_2NR^dR^e$. In some embodiments, $X^1$ is taken together with $R^1$ and the atoms to which they are attached, to form a phenyl, wherein the phenyl is substituted with one or more $R^t$, wherein $R^t$ is —$NR^dSO_2R^e$. In some embodiments, $X^1$ is taken together with $R^1$ and the atoms to which they are attached, to form a phenyl, wherein the phenyl is substituted with one or more $R^t$, wherein $R^t$ is —$NR^dR^e$. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^d$ and $R^e$ are each independently H or $C_{1-6}$alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^d$ is H. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^d$ is $C_{1-6}$alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^e$ is H. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^e$ is $C_{1-6}$alkyl.

In some embodiments, provided herein is a compound of formula (II-AB), or a stereoisomer, tautomer, or pharmaceutically acceptable salt thereof, wherein $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is halo. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{1-15}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{6-20}$aryl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is 5 to 15 membered heteroaryl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{3-20}$cycloalkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is 3 to 15 membered heterocyclyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —OH. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —CN. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is oxo. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{1-15}$alkoxy. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dCOR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$CONR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$SO_2R^d$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$SO_2NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dSO_2R^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ and $R^e$ are each independently H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is H. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is H. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is $C_{1-6}$alkyl.

In some embodiments, provided herein is a compound of formula (II-AB), or a stereoisomer, tautomer, or pharmaceutically acceptable salt thereof, wherein $X^2$ is N or $CR^s$, wherein $R^s$ is H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, or —$NR^dR^e$. In some embodiments, $X^2$ is N. In some embodiments, $X^2$ is $CR^s$. In some embodiments, $X^2$ is $CR^s$, wherein $R^s$ is H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, or —$NR^dR^e$. In some embodiments, $X^2$ is $CR^s$, wherein $R^s$ is H. In some embodiments, $X^2$ is $CR^s$, wherein $R^s$ is halo. In some embodiments, $X^2$ is $CR^s$, wherein $R^s$ is $C_{1-15}$alkyl. In some embodiments, $X^2$ is $CR^s$, wherein $R^s$ is $C_{6-20}$aryl. In some embodiments, $X^2$ is $CR^s$, wherein $R^s$ is 5 to 15 membered heteroaryl. In some embodiments, $X^2$ is $CR^s$, wherein $R^s$ is $C_{3-20}$cycloalkyl. In some embodiments, $X^2$ is $CR^s$, wherein $R^s$ is 3 to 15 membered heterocyclyl. In some embodiments, $X^2$ is $CR^s$, wherein $R^s$ is —OH. In some embodiments, $X^2$ is $CR^s$, wherein $R^s$ is —CN. In some embodiments, $X^2$ is $CR^s$, wherein $R^s$ is $C_{1-15}$alkoxy. In other embodiments, $X^2$ is $CR^s$, wherein $R^s$ is —$NR^dCOR^e$. In other embodiments, $X^2$ is $CR^s$, wherein $R^s$ is —$CONR^dR^e$. In other embodiments, $X^2$ is $CR^s$, wherein $R^s$ is —$SO_2R^d$. In other embodiments, $X^2$ is $CR^s$, wherein $R^s$ is —$SO_2NR^dR^e$. In other embodiments, $X^2$ is $CR^s$, wherein $R^s$ is —$NR^dSO_2R^e$. In some embodiments, $X^2$ is $CR^s$, wherein $R^s$ is —$NR^dR^e$. In some embodiments, $X^2$ is $CR^s$, wherein $R^s$ is —$NR^dR^e$, wherein $R^d$ and $R^e$ are each independently H or $C_{1-6}$alkyl. In some embodiments, $X^2$ is $CR^s$, wherein $R^s$ is —$NR^dR^e$, wherein $R^d$ is H or $C_{1-6}$alkyl. In some embodiments, $X^2$ is $CR^s$, wherein $R^s$ is —$NR^dR^e$, wherein $R^d$ is H. In some embodiments, $X^2$ is $CR^s$, wherein $R^s$ is —$NR^dR^e$, wherein $R^d$ is $C_{1-6}$alkyl. In some embodiments, $X^2$ is $CR^s$, wherein $R^s$ is —$NR^dR^e$, wherein $R^e$ is H or $C_{1-6}$alkyl. In some embodiments, $X^2$ is $CR^s$, wherein $R^s$ is —$NR^dR^e$, wherein $R^e$ is H or $C_{1-6}$alkyl. In some embodiments, $X^2$ is $CR^s$, wherein $R^s$ is —$NR^dR^e$, wherein $R^e$ is H. In some embodiments, $X^2$ is $CR^s$, wherein $R^s$ is —$NR^dR^e$, wherein $R^e$ is $C_{1-6}$alkyl.

In some embodiments, provided herein is a compound of formula (II-AB), or a stereoisomer, tautomer, or pharmaceutically acceptable salt thereof, wherein $X^2$ is $CR^s$, wherein $R^s$ is $C_{1-15}$alkyl or $C_{1-15}$alkoxy, wherein the $C_{1-15}$alkyl and $C_{1-15}$alkoxy of $R^s$ are each independently optionally substituted with one or more $R^{t1}$, wherein $R^t$ is independently at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{1-15}$alkyl, optionally substituted with one or more $R^t$, wherein $R^t$ is independently at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^1$, and —$NR^dR^e$. In some embodiments, $X^2$ is $CR^s$, wherein $R^s$ is $C_{1-15}$alkyl, optionally substituted with one or more $R^{t1}$, wherein $R^t$ is halo. In some embodiments, $X^2$ is $CR^s$, wherein $R^s$ is $C_{1-15}$alkyl, optionally substituted with one or more $R^{t1}$, wherein $R^t$ is oxo. In some embodiments, $X^2$ is $CR^s$, wherein $R^s$ is $C_{1-15}$alkyl, optionally substituted with one or more $R^{t1}$, wherein $R^t$ is —OH. In some embodiments, $X^2$ is $CR^s$, wherein $R^s$ is $C_{1-15}$alkyl, optionally substituted with one or more $R^{t1}$, wherein $R^t$ is —CN. In some embodiments, $X^2$ is $CR^s$, wherein $R^s$ is $C_{1-15}$alkyl, optionally substituted with one or more $R^t$, wherein $R^t$ is —$NR^dR^e$.

In some embodiments, provided herein is a compound of formula (II-AB), or a stereoisomer, tautomer, or pharmaceutically acceptable salt thereof, wherein $X^2$ is $CR^s$, wherein $R^s$ is $C_{1-15}$alkoxy, optionally substituted with one or more $R^{t1}$, wherein $R^t$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{1-15}$alkoxy, optionally substituted with one or more $R^1$, wherein $R^t$ is halo. In some embodiments, $X^2$ is $CR^s$, wherein $R^s$ is $C_{1-15}$alkoxy, optionally substituted with one or more $R^{t1}$, wherein $R^{t1}$ is oxo. In some embodiments, $X^2$ is $CR^s$, wherein $R^s$ is $C_{1-15}$alkoxy, optionally substituted with one or more $R^{t1}$, wherein $R^{t1}$ is —OH. In some embodiments, $X^2$ is $CR^s$, wherein $R^s$ is $C_{1-15}$alkoxy, optionally substituted with one or more $R^{t1}$, wherein $R^{t1}$ is —CN. In some embodiments, $X^2$ is $CR^s$, wherein $R^s$ is $C_{1-15}$alkoxy, optionally substituted with one or more $R^{t1}$, wherein $R^{t1}$ is —$NR^dR^e$.

In some embodiments, provided herein is a compound of formula (II-AB), or a stereoisomer, tautomer, or pharmaceutically acceptable salt thereof, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ and $R^{t1}$ are each independently H or $C_{1-6}$alkyl, and the $C_{1-6}$alkyl of $R^d$ or $R^e$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^{t1}$, is —$NR^dR^e$, wherein $R^d$ is H. In some embodiments, $X^2$ is $CR^s$, wherein $R^s$ is $C_{1-15}$alkoxy, optionally substituted with one or more $R^{t1}$, wherein $R^t$ is —$NR^dR^e$, wherein $R^d$ is $C_{1-6}$alkyl. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^e$ is H. In some embodiments, $X^2$ is $CR^s$, wherein $R^s$ is $C_{1-15}$alkoxy, optionally substituted with one or more $R^{t1}$, wherein $R^t$ is —$NR^dR^e$, wherein $R^e$ is $C_{1-6}$alkyl. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ or $R^e$ are independently $C_{1-6}$alkyl, the $C_{1-6}$alkyl of $R^d$ or $R^e$ is optionally substituted with one or more halo, oxo, —OH, or —CN. In some embodiments, $X^2$ is $CR^s$, wherein $R^s$ is $C_{1-15}$alkoxy, optionally substituted with one or more $R^t$, wherein $R^{t1}$ is —$NR^dR^e$, wherein $R^d$ is $C_{1-6}$alkyl, the $C_{1-6}$alkyl of $R^d$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ is $C_{1-6}$alkyl, the $C_{1-6}$alkyl of $R^d$ is optionally substituted with one or more halo. In some embodiments, $X^2$ is $CR^s$, wherein $R^s$ is $C_{1-15}$alkoxy, optionally substituted with one or more $R^{t1}$, wherein $R^t$ is —$NR^dR^e$, wherein $R^d$ is $C_{1-6}$alkyl, the $C_{1-6}$alkyl of $R^d$ is optionally substituted with one or more oxo. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ is $C_{1-6}$alkyl, the $C_{1-6}$alkyl of $R^d$ is optionally substituted with one or more —OH. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ is $C_{1-6}$alkyl, the $C_{1-6}$alkyl of $R^d$ is optionally substituted with one or more —CN. In some embodiments, $X^2$ is $CR^s$, wherein $R^s$ is $C_{1-6}$alkoxy, optionally substituted with one or more $R^{t1}$, wherein $R^t$ is —$NR^dR^e$, wherein $R^e$ is $C_{1-6}$alkyl, the $C_{1-6}$alkyl of $R^e$ is optionally substituted with one or more halo, oxo, —OH, or —CN. In some embodiments, $X^2$ is $CR^s$, wherein $R^s$ is $C_{1-15}$alkoxy, optionally substituted with one or more W, wherein $R^t$ is —$NR^dR^e$, wherein $R^e$ is $C_{1-6}$alkyl, the $C_{1-6}$alkyl of $R^e$ is optionally substituted with one or more halo. In some embodiments, $X^2$ is $CR^s$, wherein $R^1$ is $C_{1-15}$alkoxy, optionally substituted with one or more $R^{t1}$, wherein $R^{t1}$ is —$NR^dR^e$, wherein $R^e$ is $C_{1-6}$alkyl, the $C_{1-6}$alkyl of $R^e$ is optionally substituted with one or more oxo. In some embodiments, $X^2$ is $CR^s$, wherein $R^s$ is $C_{1-15}$alkoxy, optionally substituted with one or more $R^{t1}$, wherein $R^t$ is —$NR^dR^e$, wherein $R^e$ is $C_{1-6}$alkyl, the $C_{1-6}$alkyl of $R^e$ is optionally substituted with one or more —OH. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^e$ is $C_{1-6}$alkyl, the $C_{1-6}$alkyl of $R^e$ is optionally substituted with one or more —CN.

In some embodiments, provided herein is a compound of formula (II-AB), or a stereoisomer, tautomer, or pharmaceutically acceptable salt thereof, wherein $X^2$ is $CR^s$, wherein $R^s$ is $C_{6-20}$aryl, 5 to 15 membered heteroaryl, $C_{3-20}$cycloalkyl, or 3 to 15 membered heterocyclyl, wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^1$ is $C_{6-20}$aryl, the $C_{6-20}$aryl of $R^s$ is optionally substituted with one or more $R^{t2}$, wherein $R^{t2}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^1$ is $C_{6-20}$aryl, the $C_{6-20}$aryl of $R^s$ is optionally substituted with $R^{t2}$, wherein $R^{t2}$ is halo. In some embodiments, $X^2$ is $CR^s$, wherein $R^s$ is $C_{6-20}$aryl, the $C_{6-20}$aryl of $R^s$ is optionally substituted with $R^{t2}$, wherein $R^2$ is oxo. In some embodiments, $X^2$ is $CR^s$, wherein $R^s$ is $C_{6-20}$aryl, the $C_{6-20}$aryl of $R^s$ is optionally substituted with $R^2$, wherein $R^{t2}$ is —OH. In some embodiments, $X^2$ is $CR^s$, wherein $R^s$ is $C_{6-20}$aryl, the $C_{6-20}$aryl of $R^s$ is optionally substituted with $R^{t2}$, wherein $R^{t2}$ is —CN. In some embodiments, $X^2$ is $CR^s$, wherein $R^1$ is $C_{6-20}$aryl, the $C_{6-20}$aryl of $R^s$ is optionally substituted with $R^{t2}$, wherein $R^{t2}$ is $C_{1-6}$alkyl.

In some embodiments, provided herein is a compound of formula (II-AB), or a stereoisomer, tautomer, or pharmaceutically acceptable salt thereof, wherein $X^2$ is $CR^s$, wherein $R^s$ is 5 to 15 membered heteroaryl, the 5 to 15 membered heteroaryl of $R^1$ is optionally substituted with one or more $R^{t2}$, wherein $R^{t2}$ is independently at each occurrence selected from the group consisting of halo, $C_{1-6}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^1$, and —$NR^dR^e$. In some embodiments, $X^2$ is $CR^s$, wherein $R^s$ is 5 to 15 membered heteroaryl, the 5 to 15 membered heteroaryl of $R^s$ is optionally substituted with $R^2$, wherein $R^{t2}$ is halo. In some embodiments, $X^2$ is $CR^s$, wherein $R^s$ is 5 to 15 membered heteroaryl, the 5 to 15 membered heteroaryl of $R^s$ is optionally substituted with $R^2$, wherein $R^{t2}$ is oxo. In some embodiments, $X^2$ is $CR^s$, wherein $R^s$ is 5 to 15 membered heteroaryl, the 5 to 15 membered heteroaryl of $R^s$ is optionally substituted with $R^{t2}$, wherein $R^{t2}$ is —OH. In some embodiments, $X^2$ is $CR^s$, wherein $R^s$ is 5 to 15 membered heteroaryl, the 5 to 15 membered heteroaryl of $R^s$ is optionally substituted with $R^e$, wherein $R^2$ is —CN. In some embodiments, $X^2$ is $CR^s$, wherein $R^s$ is 5 to 15 membered heteroaryl, the 5 to 15 membered heteroaryl of $R^s$ is optionally substituted with $R^{t2}$, wherein $R^2$ is $C_{1-6}$alkyl.

In some embodiments, provided herein is a compound of formula (II-AB), or a stereoisomer, tautomer, or pharmaceutically acceptable salt thereof, wherein $X^2$ is $CR^s$, wherein $R^s$ is $C_{6-20}$cycloalkyl, the $C_{6-20}$cycloalkyl of $R^s$ is optionally substituted with one or more $R^2$, wherein $R^{t2}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is halo. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is oxo. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is —OH. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is —CN. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is $C_{1-6}$alkyl.

In some embodiments, provided herein is a compound of formula (II-AB), or a stereoisomer, tautomer, or pharmaceutically acceptable salt thereof, wherein $X^2$ is $CR^s$, wherein $R^s$ is 5 to 15 membered heterocyclyl, the 5 to 15 membered heterocyclyl of $R^s$ is optionally substituted with one or more $R^{t2}$, wherein $R^{t2}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is 5 to 15 membered heterocyclyl, the 5 to 15 membered heterocyclyl of $R^s$ is optionally substituted with $R^{t2}$, wherein $R^{t2}$ is halo. In some embodiments, $X^2$ is $CR^s$, wherein $R^s$ is 5 to 15 membered heterocyclyl, the 5 to 15 membered heterocyclyl of $R^s$ is optionally substituted with $R^{t2}$, wherein $R^2$ is oxo. In some embodiments, $X^2$ is $CR^s$, wherein $R^s$ is 5 to 15 membered heterocyclyl, the 5 to 15 membered heterocyclyl of $R^s$ is optionally substituted with $R^tz$, wherein $R^{t2}$ is —OH. In some embodiments, $X^2$ is $CR^s$, wherein $R^s$ is 5 to 15 membered heterocyclyl, the 5 to 15 membered heterocyclyl of $R^s$ is optionally substituted with $R^2$, wherein $R^{t2}$ is —CN. In some embodiments, $X^2$ is $CR^s$, wherein $R^s$ is 5 to 15 membered heterocyclyl, the 5 to 15 membered heterocyclyl of $R^s$ is optionally substituted with $R^{t2}$, wherein $R^{t2}$ is $C_{1-6}$alkyl.

In some embodiments, provided herein is a compound of formula (II-AB), or a stereoisomer, tautomer, or pharmaceutically acceptable salt thereof, wherein $X^3$ is N or CH. In some embodiments, $X^3$ is N. In some embodiments, $X^3$ is CH.

In some embodiments, provided herein is a compound of formula (II-AB), or a stereoisomer, tautomer, or pharmaceutically acceptable salt thereof, wherein B is phenyl or 5 to 6 membered heteroaryl; wherein the phenyl and 5 to 6 membered heteroaryl of B are each independently substituted with one to five $R^2$. In some embodiments, B is phenyl independently substituted with one to five $R^2$. In some embodiments, B is 5 to 6 membered heteroaryl independently substituted with one to five $R^2$.

In some embodiments, provided herein is a compound of formula (II-AB), or a stereoisomer, tautomer, or pharmaceutically acceptable salt thereof, wherein $R^2$ is independently, at each occurrence, i) halo; ii) $S(R^y)_5$, wherein each $R^y$ is halo; or iii) $C_{1-6}$ alkoxy, optionally substituted with one or more halo. In some embodiments, $R^2$ is halo. In some embodiments, $R^2$ is $S(R^y)_5$, wherein each $R_y$ is halo. In some embodiments, $R^2$ is $C_{1-6}$ alkoxy, optionally substituted with one or more halo. In some embodiments, $R^2$ is unsubstituted $C_{1-6}$alkoxy.

In some embodiments, provided herein is a compound of formula (II-AB), or a stereoisomer, tautomer, or pharmaceutically acceptable salt thereof, wherein $R^3$ is H or $C_{1-6}$ alkyl. In some embodiments, $R^3$ is H. In some embodiments, $R^3$ is $C_{1-6}$alkyl.

In some embodiments, provided herein is a compound of formula (II-AB), or a stereoisomer, tautomer, or pharmaceutically acceptable salt thereof, wherein Z is —OH, —$NR^dR^e$, $C_{1-6}$alkoxy, —$C(O)R^a$, —$S(O)_2R^a$. In some embodiments, Z is —OH. In some embodiments, Z is $NR^dR^e$, wherein $R^d$ and $R^e$ are each independently H or $C_{1-6}$alkyl. In some embodiments, Z is $NR^dR^e$, wherein $R^d$ is H. In some embodiments, Z is $NR^dR^e$, wherein $R^d$ is $C_{1-6}$alkyl. In some embodiments, Z is $NR^dR^e$, wherein $R^e$ is H. In some embodiments, Z is $NR^dR^e$, wherein $R^e$ is $C_{1-6}$alkyl. In some embodiments, Z is —$C(O)R^a$. In some embodiments, Z is —$C(O)R^a$, wherein $R^a$ is i) $C_{2-6}$alkenyl optionally substituted with one or more deuterium, $C_{1-6}$alkyl, halo, halo$C_{1-6}$ alkyl; or ii) $C_{1-6}$alkyl, optionally substituted with one or more halo. In some embodiments, Z is —$C(O)R^a$, wherein $R^a$ is $C_{2-6}$alkenyl optionally substituted with one or more deuterium, $C_{1-6}$alkyl, halo, halo$C_{1-6}$alkyl. In some embodiments, Z is —$C(O)R^a$, wherein $R^a$ is $C_{1-6}$alkyl, optionally substituted with one or more halo. In some embodiments, Z is —$C(O)R^a$, wherein $R^a$ is $C_{2-6}$alkenyl optionally substituted with one or more deuterium. In some embodiments, Z is —$C(O)R^a$, wherein $R^a$ is $C_{1-6}$alkyl. In some embodiments, Z is —$C(O)R^a$, wherein $R^a$ is halo$C_{1-6}$alkyl.

In some embodiments, provided herein is a compound of formula (II-AB), or a stereoisomer, tautomer, or pharmaceutically acceptable salt thereof, wherein Z is —$C(O)R^a$, wherein $R^a$ is $C_{2-6}$alkenyl optionally substituted with one or more deuterium, $C_{1-6}$alkyl, halo, halo$C_{1-6}$alkyl; and B is phenyl substituted with one or more $R^2$, wherein $R^2$ is $C_{1-6}$alkoxy optionally substituted with one or more halo. In some embodiments, Z is —$C(O)R^a$, wherein $R^a$ is $C_{2-6}$alkenyl optionally substituted with one or more deuterium; and B is phenyl substituted with one or more $R^2$, wherein $R^2$ is $C_{1-6}$alkoxy optionally substituted with one or more halo. In some embodiments, Z is —$C(O)R^a$, wherein $R^a$ is $C_{2-6}$alkenyl optionally substituted with one or more halo; and B is phenyl substituted with one or more $R^2$, wherein $R^2$ is $C_{1-6}$alkoxy optionally substituted with one or more halo. In some embodiments, Z is —$C(O)R^a$, wherein $R^a$ is $C_{2-6}$-alkenyl optionally substituted with one or more $C_{1-6}$alkyl; and B is phenyl substituted with one or more $R^2$, wherein $R^2$ is $C_{1-6}$alkoxy optionally substituted with one or more halo. In some embodiments, Z is —$C(O)R^a$, wherein $R^a$ is $C_{2-6}$alkenyl optionally substituted with one or more halo$C_{1-6}$alkyl; and B is phenyl substituted with one or more $R^2$, wherein $R^2$ is $C_{1-6}$alkoxy optionally substituted with one or more halo.

In some embodiments, provided herein is a compound of formula (II-AB), or a stereoisomer, tautomer, or pharmaceutically acceptable salt thereof, wherein $X^1$ is C or N, and $X^1$ is taken together with $R^1$, and the atoms to which they are attached, to form a 5 to 6 membered heteroaryl, 5 to 6 membered heterocyclyl, phenyl, or $C_5$ cycloalkyl fused to ring A; $X^2$ is N or $CR^s$, wherein $R^s$ is selected from $C_{1-15}$alkyl optionally substituted with —OH, 5-membered heteroaryl and —CN; $X^3$ is N or CH; B is phenyl or 5-membered heteroaryl, wherein the phenyl and 5 to 6 membered heteroaryl of B are each independently substituted with one or more $R^2$, wherein $R^2$ is independently, at each occurrence, $S(R^y)_5$, wherein each $R_y$ is independently halo, or $C_{1-6}$alkoxy optionally substituted with one or more halo; L is methylene, optionally substituted with $C_{1-6}$alkyl; $R^3$ is H or $C_{1-6}$alkyl; and Z is —$C(O)R^a$, —$S(O)_2R^b$, wherein $R^a$ is $C_{2-6}$alkenyl optionally substituted with deuterium, or $C_{1-6}$alkyl substituted with halo, and $R^b$ is $C_{1-6}$alkyl substituted with halo. In some embodiments, $R^s$ is methyl or ethyl. In some embodiments, each $R^y$ is fluoro. In some embodiments, $R^2$ is trifluoromethoxy. In some embodiments, $R^a$ is ethenyl. In some embodiments, $R^a$ is chloromethyl. In some embodiments, $R^b$ is chloromethyl.

In some embodiments, provided herein is a compound of formula (II-A), or a stereoisomer, tautomer, or pharmaceutically acceptable salt thereof, wherein $X^1$ is C or N. In some embodiments, $X^1$ is C. In some embodiments, $X^1$ is N. In some embodiments, $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A. In some embodiments, $X^1$ is C and is taken together with $R^1$ and the atoms to which they are attached, to form a 5 to 6 membered heteroaryl, 5 to 6 membered heterocyclyl, phenyl, or $C_{5-6}$cycloalkyl that is fused to ring A. In some embodiments, $X^1$ is C and is taken together with $R^t$ and the atoms to which they are attached to form a 5 to 6 membered heteroaryl that is fused to ring A. In some embodiments, $X^1$ is C and is taken together with $R^1$ and the atoms to which they are attached to form a 5 to 6 membered heterocyclyl that is fused to ring A. In some embodiments, $X^1$ is C and is taken together with $R^1$ and the atoms to which they are attached to form a phenyl that is fused to ring A. In some embodiments, $X^1$ is C and is taken together with $R^1$ and the atoms to which they are attached to form a $C_{5-6}$cycloalkyl that is fused to ring A. In some embodiments, $X^1$ is N and is taken together with $R^1$ and the atoms to which they are attached, to form a 5 to 6 membered heteroaryl or a 5 to 6 membered heterocyclyl that is fused to ring A. In some embodiments, $X^1$ is N and is taken together with $R^1$ and the atoms to which they are attached to form a 5 to 6 membered heteroaryl that is fused to ring A. In some embodiments, $X^1$ is N and is taken together with $R^1$ and the atoms to which they are attached to form a 5 to 6 membered heterocyclyl that is fused to ring A.

In some embodiments, provided herein is a compound of formula (II-A), or a stereoisomer, tautomer, or pharmaceutically acceptable salt thereof, wherein $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A, wherein the 5 to 6 membered heteroaryl, 5 to 6 membered heterocyclyl, phenyl, or $C_{5-6}$ cycloalkyl that is fused to ring A is selected from the group consisting of

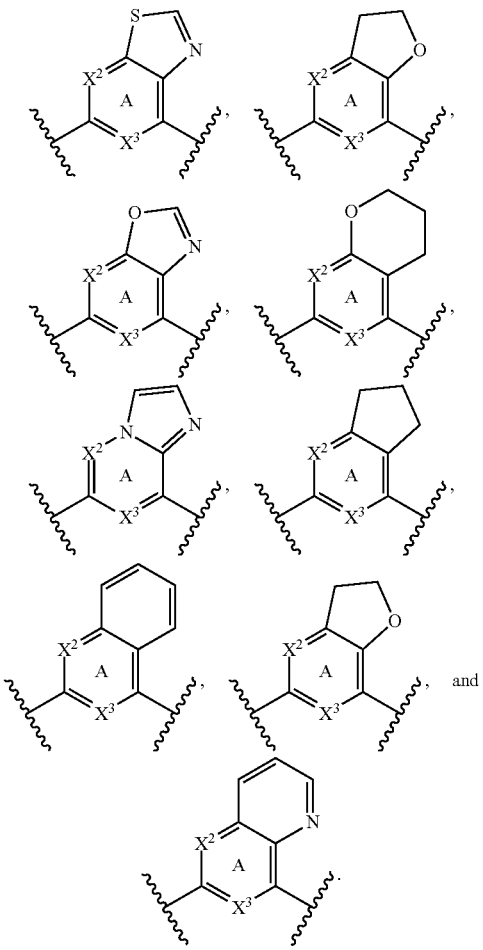

and

In some embodiments, in conjunction with embodiments above or below, the 5 to 6 membered heteroaryl, 5 to 6 membered heterocyclyl, phenyl, or $C_{5-6}$cycloalkyl that is fused to ring A is not substituted with one or more $R^t$.

It is understood that embodiments described herein with respect to any one of formula (II-AB), (II-A), or (II-B) apply to formula (II-AB'), the same as if each and every embodiment is specifically and individually listed with respect to formula (II-AB').

In some embodiments, provided herein is a compound of formula (II-AB), (II-A), or (II-B), or a stereoisomer, tautomer, or pharmaceutically acceptable salt thereof, wherein $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A, wherein the 5 to 6 membered heteroaryl, 5 to 6 membered heterocyclyl, phenyl, or $C_{5-6}$cycloalkyl that is fused to ring A is selected from the group consisting of

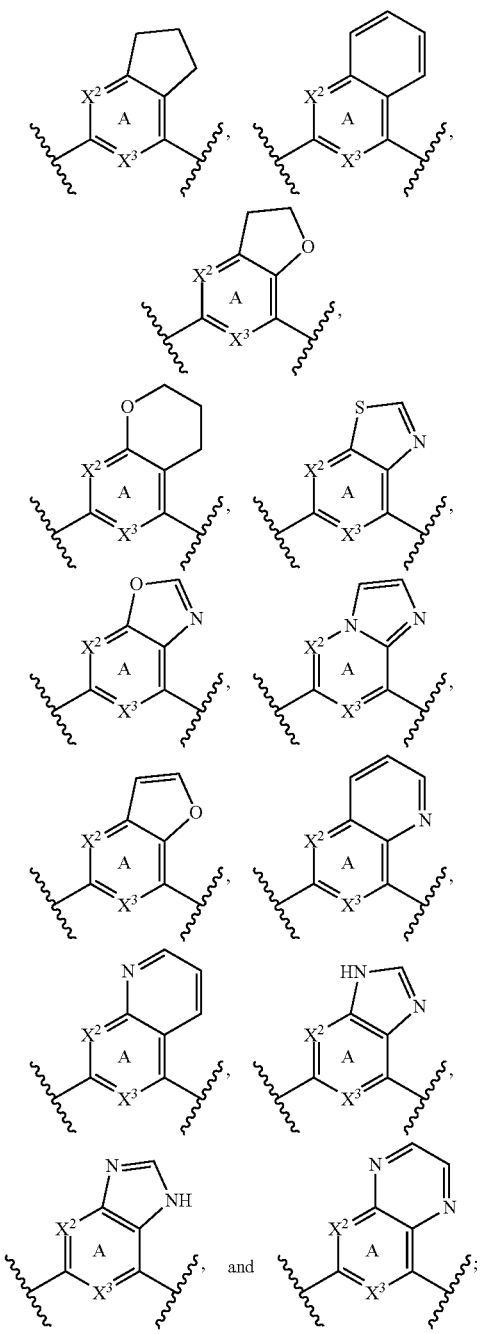

and each of which is optionally substituted with one or more $R^t$. In some embodiments, each $R^1$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$; and wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN. In some embodiments, $R^1$ is selected from the group consisting of methyl and —$CHF_2$.

In some embodiments, in conjunction with embodiments above or below, the 5 to 6 membered heteroaryl, 5 to 6 membered heterocyclyl, phenyl, or $C_{5-6}$cycloalkyl that is fused to ring A is not substituted with one or more $R^t$.

In some embodiments, provided herein is a compound of formula (II-AB), (II-A), or (II-B), or a stereoisomer, tautomer, or pharmaceutically acceptable salt thereof, wherein $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A, wherein the 5 to 6 membered heteroaryl, 5 to 6 membered heterocyclyl, phenyl, or $C_{5-6}$cycloalkyl that is fused to ring A is selected from the group consisting of

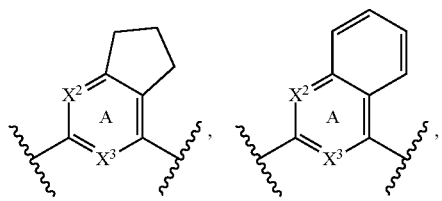

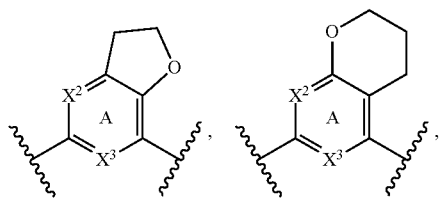

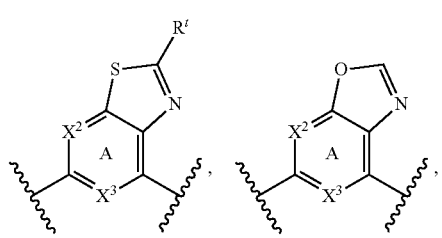

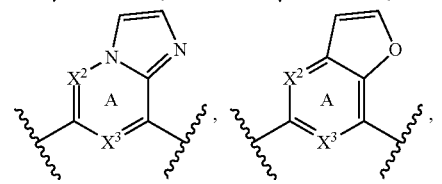


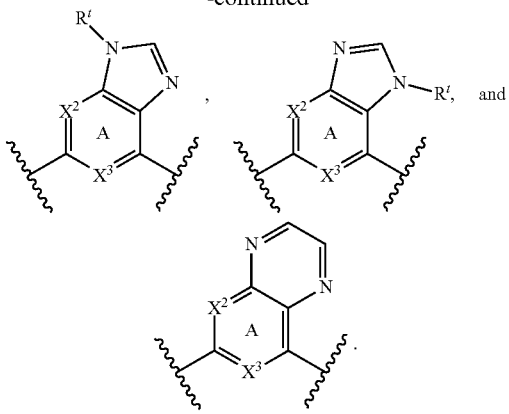

In some embodiments, each $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$; and wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN. In some embodiments, $R^t$ is selected from the group consisting of methyl and —$CHF_2$.

In some embodiments, in conjunction with embodiments above or below, the 5 to 6 membered heteroaryl, 5 to 6 membered heterocyclyl, phenyl, or $C_{5-6}$cycloalkyl that is fused to ring A is not substituted with one or more $R^t$.

In some embodiments, provided herein is a compound of formula (II-AB), (II-A), or (II-B), or a stereoisomer, tautomer, or pharmaceutically acceptable salt thereof, wherein $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A, wherein the 5 to 6 membered heteroaryl, 5 to 6 membered heterocyclyl, phenyl, or $C_{5-6}$cycloalkyl that is fused to ring A is selected from the group consisting of

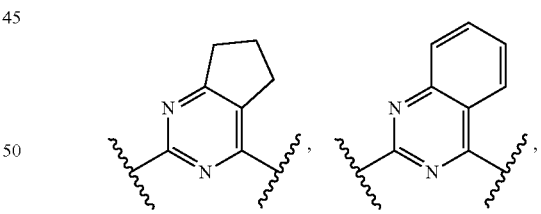

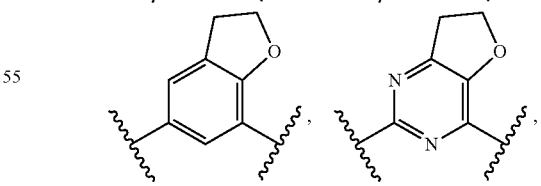


-continued

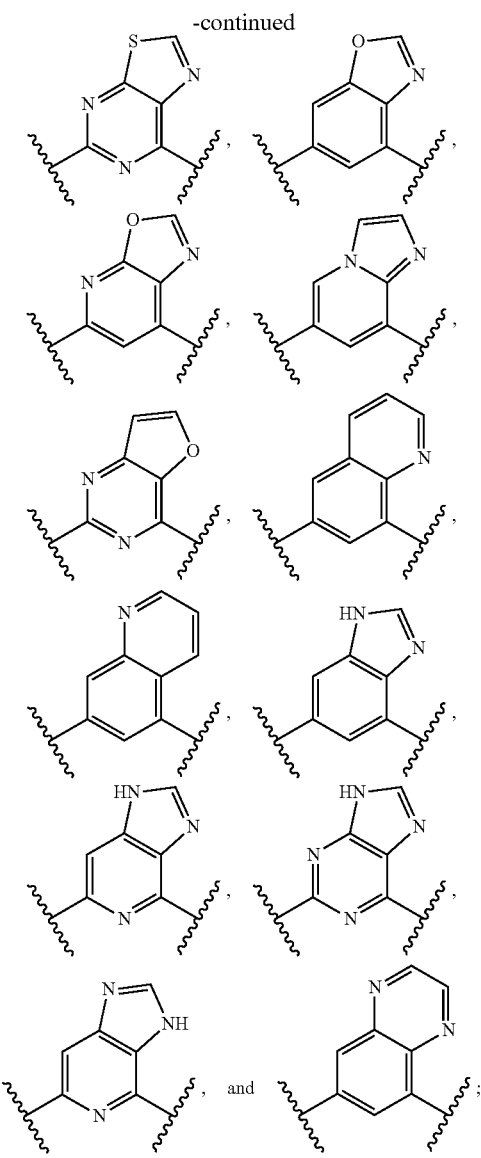

, and each of which is optionally substituted with one or more $R^t$. In some embodiments, each $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and wherein R$^d$ and R$^e$ are each independently H or $C_{1-6}$ alkyl, and wherein the $C_{1-6}$alkyl of R$^d$ or R$^e$ is optionally substituted with one or more substituents selected from halo, oxo, —OH and —CN. In some embodiments, $R^t$ is selected from the group consisting of methyl and —CHF$_2$.

In some embodiments, in conjunction with embodiments above or below, the 5 to 6 membered heteroaryl, 5 to 6 membered heterocyclyl, phenyl, or $C_{5-6}$cycloalkyl that is fused to ring A is not substituted with one or more $R^t$.

In some embodiments, provided herein is a compound of formula (II-AB), (II-A), or (II-B), or a stereoisomer, tautomer, or pharmaceutically acceptable salt thereof, wherein $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A, wherein the 5 to 6 membered heteroaryl, 5 to 6 membered heterocyclyl, phenyl, or $C_{5-6}$cycloalkyl that is fused to ring A is selected from the group consisting of

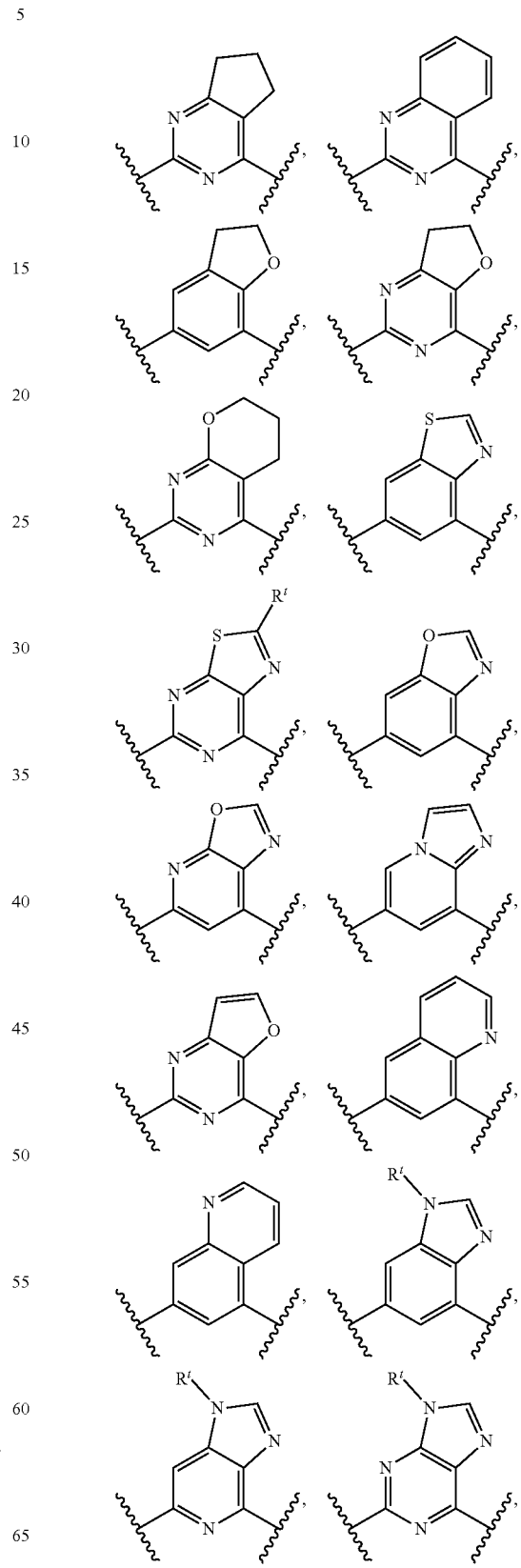

-continued

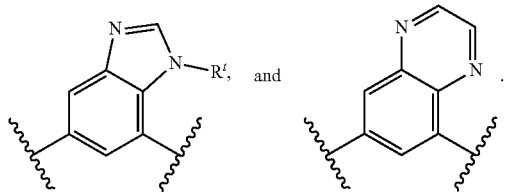

In some embodiments, each $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN. In some embodiments, $R^1$ is selected from the group consisting of methyl and —CHF$_2$.

In some embodiments, in conjunction with embodiments above or below, the 5 to 6 membered heteroaryl, 5 to 6 membered heterocyclyl, phenyl, or $C_{5-6}$cycloalkyl that is fused to ring A is not substituted with one or more $R^t$.

In some embodiments, provided herein is a compound of formula (II-A), or a stereoisomer, tautomer, or pharmaceutically acceptable salt thereof, wherein $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A, wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, or —NR$^d$R$^e$, wherein $R^d$ and $R^e$ are each independently H or $C_{1-6}$alkyl. In some embodiments, $R^d$ and $R^e$ are each independently H or $C_{1-6}$alkyl. In some embodiments, $R^d$ is H or $C_{1-6}$alkyl. In some embodiments, $R^d$ is H. In some embodiments, $R^d$ is $C_{1-6}$alkyl. In some embodiments, $R^e$ is H or $C_{1-6}$alkyl. In some embodiments, $R^e$ is H. In some embodiments, $R^e$ is $C_{1-6}$alkyl.

In some embodiments, provided herein is a compound of formula (II-A), or a stereoisomer, tautomer, or pharmaceutically acceptable salt thereof, wherein $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is halo. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is $C_{1-15}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is $C_{6-20}$aryl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is 5 to 15 membered heteroaryl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is $C_{3-20}$cycloalkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is 3 to 15 membered heterocyclyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —OH. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein R is —CN. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is oxo. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is $C_{1-15}$alkoxy. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$COR$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —CONR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —SO$_2$R$^d$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —SO$_2$NR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$SO$_2$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —NR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is —$NR^dR^e$, wherein $R^d$ and $R^1$ are each independently H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^d$ is H1. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^d$ is $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^e$ is H. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^e$ is $C_{1-6}$alkyl.

In embodiments, in conjunction with embodiments above or below, $X^1$ is taken together with $R^1$ and the atoms to which they are attached, to form a 5 to 6 membered heteroaryl, wherein the 5 to 6 membered heteroaryl is not substituted with one or more $R^t$.

In some embodiments, provided herein is a compound of formula (II-A), or a stereoisomer, tautomer, or pharmaceutically acceptable salt thereof, wherein X, is taken together with $R^1$ and the atoms to which they are attached, to form a 5 to 6 membered heterocyclyl, wherein the 5 to 6 membered heterocyclyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is halo. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{1-15}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{6-20}$aryl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is 5 to 15 membered heterocyclyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{3-20}$cycloalkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is 3 to 15 membered heterocyclyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is —OH. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —CN. In some embodiments, $X^1$ is taken together with $R^1$ and the atoms to which they are attached, to form a 5 to 6 membered heterocyclyl, wherein the 5 to 6 membered heterocyclyl is substituted with one or more $R^1$, wherein $R^t$ is oxo. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{1-15}$alkoxy. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dCOR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$CONR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$SO_2R^d$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$SO_2NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^1$, wherein $R^t$ is —$NR^dSO_2R^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^d$ and $R^e$ are each independently H or $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —NR$^d$R$^e$, wherein R$^d$ is H or C$_{1-6}$alkyl. In some embodiments, X$^1$ is taken together with R$^1$ and the atoms to which they are attached, to form a 5 to 6 membered heterocyclyl, wherein the 5 to 6 membered heterocyclyl is substituted with one or more R$^t$, wherein R$^t$ is —NR$^d$R$^e$, wherein R$^d$ is H. In some embodiments, X$^1$ is taken together with R$^1$ and the atoms to which they are attached, to form a 5 to 6 membered heterocyclyl, wherein the 5 to 6 membered heterocyclyl is substituted with one or more R$^t$, wherein R$^t$ is —NR$^d$R$^e$, wherein R$^d$ is C$_{1-6}$alkyl. In some embodiments, X$^1$ is taken together with R$^1$ and the atoms to which they are attached, to form a 5 to 6 membered heterocyclyl, wherein the 5 to 6 membered heterocyclyl is substituted with one or more R$^t$, wherein R$^t$ is —NR$^d$R$^e$, wherein R$^e$ is H or C$_{1-6}$alkyl. In some embodiments, R$^e$ is H or C$_{1-6}$alkyl. In some embodiments, X$^1$ is taken together with R$^1$ and the atoms to which they are attached, to form a 5 to 6 membered heterocyclyl, wherein the 5 to 6 membered heterocyclyl is substituted with one or more R$^t$, wherein R$^t$ is —NR$^d$R$^e$, wherein R$^e$ is H. In some embodiments, X$^1$ is taken together with R$^1$ and the atoms to which they are attached, to form a 5 to 6 membered heterocyclyl, wherein the 5 to 6 membered heterocyclyl is substituted with one or more R$^t$, wherein R$^t$ is —NR$^d$R$^e$, wherein R$^e$ is C$_{1-6}$alkyl.

In embodiments, in conjunction with embodiments above or below, X$^1$ is taken together with R$^1$ and the atoms to which they are attached, to form a 5 to 6 membered heterocyclyl, wherein the 5 to 6 membered heterocyclyl is not substituted with one or more R$^t$.

In some embodiments, provided herein is a compound of formula (II-A), or a stereoisomer, tautomer, or pharmaceutically acceptable salt thereof, wherein X$^1$ is taken together with R$^1$ and the atoms to which they are attached, to form a phenyl, wherein the phenyl is substituted with one or more R$^t$, wherein R$^t$ is independently, at each occurrence, selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^1$ is taken together with R$^1$ and the atoms to which they are attached, to form a phenyl, wherein the phenyl is substituted with one or more R$^t$, wherein R$^t$ is independently, at each occurrence, selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^1$ is taken together with R$^1$ and the atoms to which they are attached, to form a phenyl, wherein the phenyl is substituted with one or more R$^t$, wherein R$^t$ is halo. In some embodiments, X$^1$ is taken together with R$^1$ and the atoms to which they are attached, to form a phenyl, wherein the phenyl is substituted with one or more R$^t$, wherein R$^t$ is C$_{1-15}$alkyl. In some embodiments, X$^1$ is taken together with R$^1$ and the atoms to which they are attached, to form a phenyl, wherein the phenyl is substituted with one or more R$^t$, wherein R$^t$ is C$_{6-20}$aryl. In some embodiments, X$^1$ is taken together with R$^1$ and the atoms to which they are attached, to form a phenyl, wherein the phenyl is substituted with one or more R$^t$, wherein R$^t$ is 5 to 15 membered heteroaryl. In some embodiments, X$^1$ is taken together with R$^1$ and the atoms to which they are attached, to form a phenyl, wherein the phenyl is substituted with one or more R$^t$, wherein R$^t$ is C$_{3-20}$cycloalkyl. In some embodiments, X$^1$ is taken together with R$^1$ and the atoms to which they are attached, to form a phenyl, wherein the phenyl is substituted with one or more R$^t$, wherein R$^t$ is 3 to 15 membered heterocyclyl. In some embodiments, X$^1$ is taken together with R$^1$ and the atoms to which they are attached, to form a phenyl, wherein the phenyl is substituted with one or more R$^t$, wherein R$^t$ is —OH. In some embodiments, X$^1$ is taken together with R$^1$ and the atoms to which they are attached, to form a phenyl, wherein the phenyl is substituted with one or more R$^t$, wherein R$^t$ is —CN. In some embodiments, X$^1$ is taken together with R$^1$ and the atoms to which they are attached, to form a phenyl, wherein the phenyl is substituted with one or more R$^t$, wherein R$^t$ is oxo. In some embodiments, X$^1$ is taken together with R$^1$ and the atoms to which they are attached, to form a phenyl, wherein the phenyl is substituted with one or more R$^t$, wherein R$^t$ is C$_{1-15}$alkoxy. In some embodiments, X$^1$ is taken together with R$^1$ and the atoms to which they are attached, to form a phenyl, wherein the phenyl is substituted with one or more R$^t$, wherein R$^t$ is —NR$^d$COR$^e$. In some embodiments, X$^1$ is taken together with R$^1$ and the atoms to which they are attached, to form a phenyl, wherein the phenyl is substituted with one or more R$^t$, wherein R$^t$ is —CONR$^d$R$^e$. In some embodiments, X$^1$ is taken together with R$^1$ and the atoms to which they are attached, to form a phenyl, wherein the phenyl is substituted with one or more R$^t$, wherein R$^t$ is —SO$_2$R$^d$. In some embodiments, X$^1$ is taken together with R$^1$ and the atoms to which they are attached, to form a phenyl, wherein the phenyl is substituted with one or more R$^t$, wherein R$^t$ is —SO$_2$NR$^d$R$^e$. In some embodiments, X$^1$ is taken together with R$^1$ and the atoms to which they are attached, to form a phenyl, wherein the phenyl is substituted with one or more R$^t$, wherein R$^t$ is —NR$^d$SO$_2$R$^e$. In some embodiments, X$^1$ is taken together with R$^1$ and the atoms to which they are attached, to form a phenyl, wherein the phenyl is substituted with one or more R$^t$, wherein R$^t$ is —NR$^d$R$^e$. In some embodiments, X$^1$ is taken together with R$^1$ and the atoms to which they are attached, to form a phenyl, wherein the phenyl is substituted with one or more R$^t$, wherein R$^1$ is —NR$^d$R$^e$, wherein R$^d$ and R$^e$ are each independently H or C$_{1-6}$alkyl. In some embodiments, X$^1$ is taken together with R$^1$ and the atoms to which they are attached, to form a phenyl, wherein the phenyl is substituted with one or more R$^t$, wherein R$^t$ is —NR$^d$R$^e$, wherein R$^d$ is H or C$_{1-6}$alkyl. In some embodiments, X$^1$ is taken together with R$^1$ and the atoms to which they are attached, to form a phenyl, wherein the phenyl is substituted with one or more R$^t$, wherein R$^t$ is —NR$^d$R$^e$, wherein R$^d$ is H. In some embodiments, X$^1$ is taken together with R$^1$ and the atoms to which they are attached, to form a phenyl, wherein the phenyl is substituted with one or more R$^t$, wherein R$^t$ is —NR$^d$R$^e$, wherein R$^d$ is C$_{1-6}$alkyl. In some embodiments, X$^1$ is taken together with R$^1$ and the atoms to which they are attached, to form a phenyl, wherein the phenyl is substituted with one or more R$^t$, wherein R$^t$ is —NR$^d$R$^e$, wherein R$^e$ is H or C$_{1-6}$alkyl. In some embodiments, X$^1$ is taken together with R$^1$ and the atoms to which they are attached, to form a phenyl, wherein the phenyl is substituted with one or more R$^t$, wherein R$^1$ is —NR$^d$R$^e$, wherein R$^e$ is H or C$_{1-6}$alkyl. In some embodiments, X$^1$ is taken together with R$^1$ and the atoms to which they are attached, to form a phenyl, wherein the phenyl is substituted with one or more R$^t$, wherein R$^t$ is —NR$^d$R$^e$, wherein R$^e$ is H. In some embodiments, X$^1$ is taken together with R$^1$ and the atoms to which they are attached, to form a phenyl, wherein the phenyl is substituted with one or more R$^t$, wherein R$^t$ is —NR$^d$R$^e$, wherein R$^e$ is C$_{1-6}$alkyl.

In embodiments, in conjunction with embodiments above or below, X$^1$ is taken together with R$^1$ and the atoms to which they are attached, to form phenyl, wherein the phenyl is not substituted with one or more $R^t$.

In some embodiments, provided herein is a compound of formula (II-A), or a stereoisomer, tautomer, or pharmaceutically acceptable salt thereof, wherein $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is halo. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{1-15}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{6-20}$aryl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is 5 to 15 membered heteroaryl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{3-20}$cycloalkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is 3 to 15 membered heterocyclyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —OH. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —CN. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is oxo. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{1-15}$alkoxy. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dCOR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$CONR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$SO_2R^d$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$SO_2NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dSO_2R^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ and $R^e$ are each independently H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is H. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^1$ is —$NR^dR^e$, wherein RC is H. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is $C_{1-6}$alkyl.

In embodiments, in conjunction with embodiments above or below, $X^1$ is taken together with $R^1$ and the atoms to which they are attached, to form a $C_{5-6}$cycloalkyl, wherein the $C_{5-6}$cycloalkyl is not substituted with one or more $R^t$.

In some embodiments, provided herein is a compound of formula (II-A), or a stereoisomer, tautomer, or pharmaceutically acceptable salt thereof, wherein $X^2$ is N or $CR^s$, wherein $R^s$ is H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, or —$NR^dR^e$. In some embodiments, $X^2$ is N. In some embodiments, $X^2$ is $CR^s$. In some embodiments, $X^2$ is $CR^s$, wherein $R^s$ is H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, or —$NR^dR^e$. In some embodiments, $X^2$ is $CR^s$, wherein $R^s$ is H. In some embodiments, $X^2$ is $CR^s$, wherein $R^s$ is halo. In some embodiments, $X^2$ is $CR^s$, wherein $R^s$ is $C_{1-15}$alkyl. In some embodiments, $X^2$ is $CR^s$, wherein $R^s$ is $C_{6-20}$aryl. In some embodiments, $X^2$ is $CR^s$, wherein $R^s$ is 5 to 15 membered heteroaryl. In some embodiments, $X^2$ is $CR^s$, wherein $R^s$ is $C_{3-20}$cycloalkyl. In some embodiments, $X^2$ is $CR^s$, wherein $R^s$ is 3 to 15 membered heterocyclyl. In some embodiments, $X^2$ is $CR^s$, wherein $R^s$ is —OH. In some embodiments, $X^2$ is $CR^s$, wherein $R^s$ is —CN. In some embodiments, $X^2$ is $CR^s$, wherein $R^s$ is $C_{1-15}$alkoxy. In other embodiments, $X^2$ is $CR^s$, wherein $R^s$ is —NR$^d$COR$^e$. In other embodiments, $X^2$ is $CR^s$, wherein $R^s$ is —CONR$^d$R$^e$. In other embodiments, $X^2$ is $CR^s$, wherein $R^s$ is —SO$_2$R$^d$. In other embodiments, $X^2$ is $CR^s$, wherein $R^s$ is —SO$_2$NR$^d$R$^e$. In other embodiments, $X^2$ is $CR^s$, wherein $R^s$ is —NR$^d$SO$_2$R$^e$. In some embodiments, $X^2$ is $CR^s$, wherein $R^s$ is —NR$^d$R$^e$. In some embodiments, $X^2$ is $CR^s$, wherein $R^s$ is —NR$^d$R$^e$, wherein $R^d$ and $R^e$ are each independently H or $C_{1-6}$alkyl. In some embodiments, $X^2$ is $CR^s$, wherein $R^s$ is —NR$^d$R$^e$, wherein $R^d$ is H or $C_{1-6}$alkyl. In some embodiments, $X^2$ is $CR^s$, wherein $R^s$ is —NR$^d$R$^e$, wherein $R^d$ is H. In some embodiments, $X^2$ is $CR^s$, wherein $R^s$ is —NR$^d$R$^e$, wherein $R^d$ is $C_{1-6}$alkyl. In some embodiments, $X^2$ is $CR^s$, wherein $R^s$ is —NR$^d$R$^e$, wherein $R^e$ is H or $C_{1-6}$alkyl. In some embodiments, $X^2$ is $CR^s$, wherein $R^s$ is —NR$^d$R$^e$, wherein $R^e$ is H or $C_{1-6}$alkyl. In some embodiments, $X^2$ is $CR^s$, wherein $R^s$ is —NR$^d$R$^e$, wherein $R^e$ is H. In some embodiments, $X^2$ is $CR^s$, wherein $R^s$ is —NR$^d$R$^e$, wherein $R^e$ is $C_{1-6}$alkyl.

In some embodiments, provided herein is a compound of formula (II-A), or a stereoisomer, tautomer, or pharmaceutically acceptable salt thereof, wherein $X^2$ is $CR^s$, wherein $R^s$ is $C_{1-15}$alkyl or $C_{1-15}$alkoxy, wherein the $C_{1-15}$alkyl and $C_{1-15}$alkoxy of $R^s$ are each independently optionally substituted with one or more $R^{t1}$, wherein $R^{t1}$ is independently at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^2$ is $CR^s$, wherein $R^s$ is $C_{1-15}$alkyl, optionally substituted with one or more $R^{t1}$, wherein $R^{t1}$ is independently at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^2$ is $CR^s$, wherein $R^s$ is $C_{1-15}$alkyl, optionally substituted with one or more $R^{t1}$, wherein $R^{t1}$ is halo. In some embodiments, $X^2$ is $CR^s$, wherein $R^s$ is $C_{1-15}$alkyl, optionally substituted with one or more $R^{t1}$, wherein $R^{t1}$ is oxo. In some embodiments, $X^2$ is $CR^s$, wherein $R^s$ is $C_{1-5}$alkyl, optionally substituted with one or more $R^{t1}$, wherein $R^{t1}$ is —OH. In some embodiments, $X^2$ is $CR^s$, wherein $R^s$ is $C_{1-15}$alkyl, optionally substituted with one or more $R^{t1}$, wherein $R^t$ is —CN. In some embodiments, $X^2$ is $CR^s$, wherein $R^s$ is $C_{1-15}$alkyl, optionally substituted with one or more $R^{t1}$, wherein $R^t$ is —NR$^d$R$^e$.

In some embodiments, provided herein is a compound of formula (II-A), or a stereoisomer, tautomer, or pharmaceutically acceptable salt thereof, wherein $X^2$ is $CR^s$, wherein $R^s$ is $C_{1-15}$alkoxy, optionally substituted with one or more $R^{t1}$, wherein $R^t1$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^2$ is $CR^s$, wherein $R^s$ is $C_{1-15}$alkoxy, optionally substituted with one or more $R^{t1}$, wherein $R^{t1}$ is halo. In some embodiments, $X^2$ is $CR^s$, wherein $R^s$ is $C_{1-15}$alkoxy, optionally substituted with one or more $R^{t1}$, wherein $R^1$ is oxo. In some embodiments, $X^2$ is $CR^s$, wherein $R^s$ is $C_{1-15}$alkoxy, optionally substituted with one or more $R^{t1}$, wherein $R^t$ is —OH. In some embodiments, $X^2$ is $CR^s$, wherein $R^s$ is $C_{1-15}$alkoxy, optionally substituted with one or more $R^{t1}$, wherein $R^{t1}$ is —CN. In some embodiments, $X^2$ is $CR^s$, wherein $R^s$ is $C_{1-15}$alkoxy, optionally substituted with one or more $R^{t1}$, wherein $R^t$ is —NR$^d$R$^e$.

In some embodiments, provided herein is a compound of formula (II-A), or a stereoisomer, tautomer, or pharmaceutically acceptable salt thereof, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^t$ is —NR$^d$R$^e$, wherein $R^d$ is H. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^d$ is $C_{1-6}$alkyl. In some embodiments, $X^2$ is $CR^s$, wherein $R^s$ is $C_{1-15}$alkoxy, optionally substituted with one or more $R^{t1}$, wherein $R^t$ is —NR$^d$R$^e$, wherein $R^e$ is H. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^e$ is $C_{1-6}$alkyl. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^d$ or $R^e$ are independently $C_{1-6}$alkyl, the $C_{1-6}$alkyl of $R^d$ or $R^e$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^d$ is $C_{1-6}$alkyl, the $C_{1-6}$alkyl of $R^d$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^d$ is $C_{1-6}$alkyl, the $C_{1-6}$alkyl of $R^d$ is optionally substituted with one or more halo. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^d$ is $C_{1-6}$alkyl, the $C_{1-6}$alkyl of $R^d$ is optionally substituted with one or more oxo. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^d$ is $C_{1-6}$alkyl, the $C_{1-6}$alkyl of $R^d$ is optionally substituted with one or more —OH. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^d$ is $C_{1-6}$alkyl, the $C_{1-6}$alkyl of $R^d$ is optionally substituted with one or more —CN. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^e$ is $C_{1-6}$alkyl, the $C_{1-6}$alkyl of $R^e$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein $R^e$ is $C_{1-6}$alkyl, the $C_{1-6}$alkyl of $R^e$ is optionally substituted with one or more halo. In some embodiments, $X^2$ is $CR^s$, wherein $R^s$ is $C_{1-15}$alkoxy, optionally substituted with one or more $R^{t1}$, wherein $R^{t1}$ is —NR$^d$R$^e$, wherein RC is $C_{1-6}$alkyl, the $C_{1-6}$alkyl of $R^e$ is optionally substituted with one or more oxo. In some embodiments, $X^2$ is $CR^s$, wherein $R^s$ is $C_{1-15}$alkoxy, optionally substituted with one or more $R^t$, wherein $R^{t1}$ is —NR$^d$R$^e$, wherein $R^e$ is $C_{1-6}$alkyl, the $C_{1-6}$alkyl of $R^e$ is optionally substituted with one or more —OH. In some embodiments, $X^2$ is $CR^s$, wherein $R^s$ is $C_{1-15}$alkoxy, optionally substituted with one or more $R^{t1}$, wherein R is —NR$^d$R$^e$, wherein R$^e$ is C$_{1-6}$alkyl, the C$_{1-6}$alkyl of RC is optionally substituted with one or more —CN.

In some embodiments, provided herein is a compound of formula (II-A), or a stereoisomer, tautomer, or pharmaceutically acceptable salt thereof, wherein X$^2$ is CR$^s$, wherein R$^s$ is C$_{6-20}$aryl, 5 to 15 membered heteroaryl, C$_{3-20}$cycloalkyl, or 3 to 15 membered heterocyclyl, wherein the C$_{6-20}$aryl, 5 to 15 membered heteroaryl, C$_{3-20}$cycloalkyl, and 3 to 15 membered heterocyclyl of R$^s$ are each independently optionally substituted with one or more R$^{t2}$, wherein R$^{t2}$ is independently at each occurrence selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^2$ is CR$^s$, wherein R$^s$ is C$_{6-20}$aryl, the C$_{6-20}$aryl of R$^s$ is optionally substituted with one or more R$^{t2}$, wherein R$^{t2}$ is independently at each occurrence selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^2$ is CR$^s$, wherein R$^s$ is C$_{6-20}$aryl, the C$_{6-20}$aryl of R$^s$ is optionally substituted with R$^{t2}$, wherein R$^{t2}$ is halo. In some embodiments, X$^2$ is CR$^s$, wherein R$^s$ is C$_{6-20}$aryl, the C$_{6-20}$aryl of R$^s$ is optionally substituted with R$^{t2}$, wherein R$^{t2}$ is oxo. In some embodiments, X$^2$ is CR$^s$, wherein R$^s$ is C$_{6-20}$aryl, the C$_{6-20}$aryl of R$^s$ is optionally substituted with R$^{t2}$, wherein R$^{t2}$ is —OH. In some embodiments, X$^2$ is CR$^s$, wherein R$^s$ is C$_{6-20}$aryl, the C$_{6-20}$aryl of R$^s$ is optionally substituted with R$^{t2}$, wherein R$^{t2}$ is —CN. In some embodiments, X$^2$ is CR$^s$, wherein R$^s$ is C$_{6-20}$aryl, the C$_{6-20}$aryl of R$^s$ is optionally substituted with R$^a$, wherein R$^{t2}$ is C$_{1-6}$alkyl.

In some embodiments, provided herein is a compound of formula (II-A), or a stereoisomer, tautomer, or pharmaceutically acceptable salt thereof, wherein X$^2$ is CR$^s$, wherein R$^s$ is 5 to 15 membered heteroaryl, the 5 to 15 membered heteroaryl of R$^s$ is optionally substituted with one or more R$^{t2}$, wherein R$^{t2}$ is independently at each occurrence selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-25}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^2$ is CR$^s$, wherein R$^s$ is 5 to 15 membered heteroaryl, the 5 to 15 membered heteroaryl of R$^s$ is optionally substituted with R$^2$, wherein R$^{t2}$ is halo. In some embodiments, X$^2$ is CR$^s$, wherein R$^s$ is 5 to 15 membered heteroaryl, the 5 to 15 membered heteroaryl of R$^s$ is optionally substituted with R$^{t2}$, wherein R$^t$a is oxo. In some embodiments, X$^2$ is CR$^s$, wherein R$^s$ is 5 to 15 membered heteroaryl, the 5 to 15 membered heteroaryl of R$^1$ is optionally substituted with R$^{t2}$, wherein R$^{t2}$ is —OH. In some embodiments, X$^2$ is CR$^s$, wherein R$^s$ is 5 to 15 membered heteroaryl, the 5 to 15 membered heteroaryl of R$^s$ is optionally substituted with R$^2$, wherein R$^{t2}$ is —CN. In some embodiments, X$^2$ is CR$^s$, wherein R$^s$ is 5 to 15 membered heteroaryl, the 5 to 15 membered heteroaryl of R$^s$ is optionally substituted with R$^{t2}$, wherein R$^{t2}$ is C$_{1-6}$alkyl.

In some embodiments, provided herein is a compound of formula (II-A), or a stereoisomer, tautomer, or pharmaceutically acceptable salt thereof, wherein X$^2$ is CR$^s$, wherein R$^s$ is C$_{6-20}$cycloalkyl, the C$_{6-20}$cycloalkyl of R$^s$ is optionally substituted with one or more R$^2$, wherein R$^{t2}$ is independently at each occurrence selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^2$ is CR$^s$, wherein R$^s$ is C$_{6-20}$cycloalkyl, the C$_{6-20}$cycloalkyl of R$^s$ is optionally substituted with R$^{t2}$, wherein R$^2$ is halo. In some embodiments, X$^2$ is CR$^s$, wherein R$^s$ is C$_{6-20}$cycloalkyl, the C$_{6-20}$cycloalkyl of R$^s$ is optionally substituted with R$^{t2}$, wherein R$^{t2}$ is oxo. In some embodiments, X$^2$ is CR$^s$, wherein R$^s$ is C$_{6-20}$cycloalkyl, the C$_{6-20}$cycloalkyl of R$^s$ is optionally substituted with R$^{t2}$, wherein R$^{t2}$ is —OH. In some embodiments, X$^2$ is CR$^s$, wherein R$^s$ is C$_{6-20}$cycloalkyl, the C$_{6-20}$cycloalkyl of R$^s$ is optionally substituted with R$^{t2}$, wherein R$^{t2}$ is —CN. In some embodiments, X$^2$ is CR$^s$, wherein R$^s$ is C$_{6-20}$cycloalkyl, the C$_{6-20}$cycloalkyl of R$^s$ is optionally substituted with R$^{t2}$, wherein R$^{t2}$ is C$_{1-6}$alkyl.

In some embodiments, provided herein is a compound of formula (II-A), or a stereoisomer, tautomer, or pharmaceutically acceptable salt thereof, wherein X$^2$ is CR$^s$, wherein R$^s$ is 5 to 15 membered heterocyclyl, the 5 to 15 membered heterocyclyl of R$^s$ is optionally substituted with one or more R$^{t2}$, wherein R$^{t2}$ is independently at each occurrence selected from the group consisting of halo, C$_{1-15}$alkyl, C$_{6-20}$aryl, 5 to 15 membered heteroaryl, C$_{3-20}$cycloalkyl, 3 to 15 membered heterocyclyl, —OH, —CN, oxo, C$_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, X$^2$ is CR$^s$, wherein R$^s$ is 5 to 15 membered heterocyclyl, the 5 to 15 membered heterocyclyl of R$^s$ is optionally substituted with R$^{t2}$, wherein R$^{t2}$ is halo. In some embodiments, X$^2$ is CR$^s$, wherein R$^s$ is 5 to 15 membered heterocyclyl, the 5 to 15 membered heterocyclyl of R$^s$ is optionally substituted with R$^2$, wherein R$^{t2}$ is oxo. In some embodiments, X$^2$ is CR$^s$, wherein R$^s$ is 5 to 15 membered heterocyclyl, the 5 to 15 membered heterocyclyl of R$^s$ is optionally substituted with R$^a$, wherein R$^{t2}$ is —OH. In some embodiments, X$^2$ is CR$^s$, wherein R$^s$ is 5 to 15 membered heterocyclyl, the 5 to 15 membered heterocyclyl of R$^s$ is optionally substituted with R$^{t2}$, wherein R$^{t2}$ is —CN. In some embodiments, X$^2$ is CR$^s$, wherein R$^s$ is 5 to 15 membered heterocyclyl, the 5 to 15 membered heterocyclyl of R$^s$ is optionally substituted with R$^{t2}$, wherein R$^{t2}$ is C$_{1-6}$alkyl.

In some embodiments, provided herein is a compound of formula (II-A), or a stereoisomer, tautomer, or pharmaceutically acceptable salt thereof, wherein X$^3$ is N or CH. In some embodiments, X$^3$ is N. In some embodiments, X$^3$ is CH.

In some embodiments, provided herein is a compound of formula (II-A), or a stereoisomer, tautomer, or pharmaceutically acceptable salt thereof, wherein B is phenyl or 5 to 6 membered heteroaryl; wherein the phenyl and 5 to 6 membered heteroaryl of B are each independently substituted with one to five R$^2$. In some embodiments, B is phenyl independently substituted with one to five R$^2$. In some embodiments, B is 5 to 6 membered heteroaryl independently substituted with one to five R$^2$.

In some embodiments, in conjunction with embodiments above or below, B is 5 to 6 membered heteroaryl independently substituted with one R$^2$.

In some embodiments, provided herein is a compound of formula (II-A), or a stereoisomer, tautomer, or pharmaceutically acceptable salt thereof, wherein R$^2$ is independently, at each occurrence, i) halo; ii) S(R$^y$)$_5$, wherein each R$^y$ is halo; or iii) C$_{1-6}$ alkoxy, optionally substituted with one or more halo. In some embodiments, R$^2$ is halo. In some embodiments, $R^2$ is $S(R^y)_5$, wherein each $R^y$ is halo. In some embodiments, $R^2$ is $C_{1-6}$ alkoxy, optionally substituted with one or more halo. In some embodiments, $R^2$ is unsubstituted $C_{1-6}$alkoxy.

In some embodiments, provided herein is a compound of formula (II-A), or a stereoisomer, tautomer, or pharmaceutically acceptable salt thereof, wherein $R^3$ is H or $C_{1-6}$ alkyl. In some embodiments, $R^3$ is H. In some embodiments, $R^3$ is $C_{1-6}$alkyl.

In some embodiments, provided herein is a compound of formula (II-A), or a stereoisomer, tautomer, or pharmaceutically acceptable salt thereof, wherein Z is —OH, —NR$^d$R$^e$, $C_{1-6}$alkoxy, —C(O)R$^a$, —S(O)$_2$R$^a$. In some embodiments, Z is —OH. In some embodiments, Z is NR$^d$R$^e$, wherein R$^d$ and RC are each independently H or $C_{1-6}$alkyl. In some embodiments, Z is NR$^d$R$^e$, wherein R$^d$ is H. In some embodiments, Z is NR$^d$R$^e$, wherein R$^d$ is $C_{1-6}$alkyl. In some embodiments, Z is NR$^d$R$^e$, wherein R$^e$ is H. In some embodiments, Z is NR$^d$R$^e$, wherein R$^e$ is $C_{1-6}$alkyl. In some embodiments, Z is —C(O)R$^a$. In some embodiments, Z is —C(O)R$^a$, wherein R$^a$ is i) $C_{2-6}$alkenyl optionally substituted with one or more deuterium, $C_{1-6}$alkyl, halo, haloC$_{1-6}$ alkyl; or ii) $C_{1-6}$alkyl, optionally substituted with one or more halo. In some embodiments, Z is —C(O)R$^a$, wherein R$^a$ is $C_{2-6}$alkenyl optionally substituted with one or more deuterium, $C_{1-6}$ alkyl, halo, haloC$_{1-6}$alkyl. In some embodiments, Z is —C(O)R$^a$, wherein R$^a$ is $C_{1-6}$alkyl, optionally substituted with one or more halo. In some embodiments, Z is —C(O)R$^a$, wherein R$^a$ is $C_{2-6}$alkenyl optionally substituted with one or more deuterium. In some embodiments, Z is —C(O)R$^a$, wherein R$^a$ is $C_{1-6}$alkyl. In some embodiments, Z is —C(O)R$^a$, wherein R$^a$ is haloC$_{1-6}$alkyl.

In some embodiments, provided herein is a compound of formula (II-A), or a stereoisomer, tautomer, or pharmaceutically acceptable salt thereof, wherein Z is —C(O)R$^a$, wherein R$^a$ is $C_{2-6}$alkenyl optionally substituted with one or more deuterium, $C_{1-6}$alkyl, halo, haloC$_{1-6}$alkyl; and B is phenyl substituted with one or more R$^2$, wherein R$^2$ is $C_{1-6}$alkoxy optionally substituted with one or more halo. In some embodiments, Z is —C(O)R$^a$, wherein R$^a$ is $C_{2-6}$alkenyl optionally substituted with one or more deuterium; and B is phenyl substituted with one or more R$^2$, wherein R$^2$ is $C_{1-6}$alkoxy optionally substituted with one or more halo. In some embodiments, Z is —C(O)R$^a$, wherein R$^a$ is $C_{2-6}$alkenyl optionally substituted with one or more halo; and B is phenyl substituted with one or more R$^2$, wherein R$^2$ is $C_{1-6}$alkoxy optionally substituted with one or more halo. In some embodiments, Z is —C(O)R$^a$, wherein R$^a$ is $C_{2-6}$-alkenyl optionally substituted with one or more $C_{1-6}$alkyl; and B is phenyl substituted with one or more R$^2$, wherein R$^2$ is $C_{1-6}$alkoxy optionally substituted with one or more halo. In some embodiments, Z is —C(O)R$^a$, wherein R$^a$ is $C_{2-6}$alkenyl optionally substituted with one or more haloC$_{1-6}$alkyl; and B is phenyl substituted with one or more R$^2$, wherein R$^2$ is $C_{1-6}$alkoxy optionally substituted with one or more halo.

In some embodiments, provided herein is a compound of formula (II-A), or a stereoisomer, tautomer, or pharmaceutically acceptable salt thereof, wherein $X^1$ is C or N, and $X^1$ is taken together with R$^1$, and the atoms to which they are attached, to form a 5 to 6 membered heteroaryl, 5 to 6 membered heterocyclyl, phenyl, or $C_5$ cycloalkyl fused to ring A; $X^2$ is N or CR$^s$, wherein R$^s$ is selected from $C_{1-15}$alkyl optionally substituted with —OH, 5-membered heteroaryl and —CN; $X^3$ is N or CH; B is phenyl or 5-membered heteroaryl, wherein the phenyl and 5 to 6 membered heteroaryl of B are each independently substituted with one or more R$^2$, wherein R$^2$ is independently, at each occurrence, $S(R^y)_5$, wherein each R$^y$ is independently halo, or $C_{1-6}$alkoxy optionally substituted with one or more halo; L is methylene, optionally substituted with $C_{1-6}$alkyl; R$^s$ is H or $C_{1-6}$alkyl; and Z is —C(O)R$^a$, —S(O)$_2$R$^b$, wherein R$^a$ is $C_{2-6}$alkenyl optionally substituted with deuterium, or $C_{1-6}$alkyl substituted with halo, and R$^b$ is $C_{1-6}$alkyl substituted with halo. In some embodiments, R$^s$ is methyl or ethyl. In some embodiments, each R$^y$ is fluoro. In some embodiments, R$^2$ is trifluoromethoxy. In some embodiments, R$^a$ is ethenyl. In some embodiments, R$^a$ is chloromethyl. In some embodiments, R$^b$ is chloromethyl.

In some embodiments, provided herein is a compound of formula (II-AB), (II-A), or (II-B), or a stereoisomer, tautomer, or pharmaceutically acceptable salt thereof, wherein $X^2$ is CR$^s$. In some embodiments, $X^2$ is CR$^s$ and R$^s$ is hydroxylC$_{1-6}$alkynyl.

In some embodiments, provided herein is a compound of formula (II-AB), (II-A), or (II-B), or a stereoisomer, tautomer, or pharmaceutically acceptable salt thereof, wherein $X^2$ is CR$^s$. In some embodiments, $X^2$ is CR$^s$ and R$^s$ is —S(O)NHR$^d$, wherein R$^d$ is selected from the group consisting of H and $C_{1-6}$alkyl optionally substituted by one or more substituents selected from the group consisting of halo, oxo, —OH and —CN. In some embodiments, $X^2$ is CR$^s$, R$^s$ is —S(O)NHR$^d$, and R$^d$ is H. In some embodiments, $X^2$ is CR$^s$, R$^s$ is —S(O)NHR$^d$, and R$^d$ is unsubstituted $C_{1-6}$alkyl. In some embodiments, $X^2$ is CR$^s$, R$^s$ is —S(O)NHR$^d$, and R$^d$ is $C_{1-6}$ alkyl substituted with one or more halo. In some embodiments, $X^2$ is CR$^s$, R$^s$ is —S(O)NHR$^d$, and R$^d$ is $C_{1-6}$alkyl substituted with one or more oxo. In some embodiments, $X^2$ is CR$^s$, R$^s$ is —S(O)NHR$^d$, and R$^d$ is $C_{1-6}$alkyl substituted with one or more —OH. In some embodiments, $X^2$ is CR$^s$, R$^s$ is —S(O)NHR$^d$, and R$^d$ is $C_{1-6}$alkyl substituted with one or more —CN.

In some embodiments, provided herein is a compound of formula (II-AB), (II-A), or (II-B), or a stereoisomer, tautomer, or pharmaceutically acceptable salt thereof, wherein $X^2$ is CR$^s$. In some embodiments, $X^2$ is CR$^s$ and R$^s$ is selected from the group consisting of —CN, —CH$_3$,

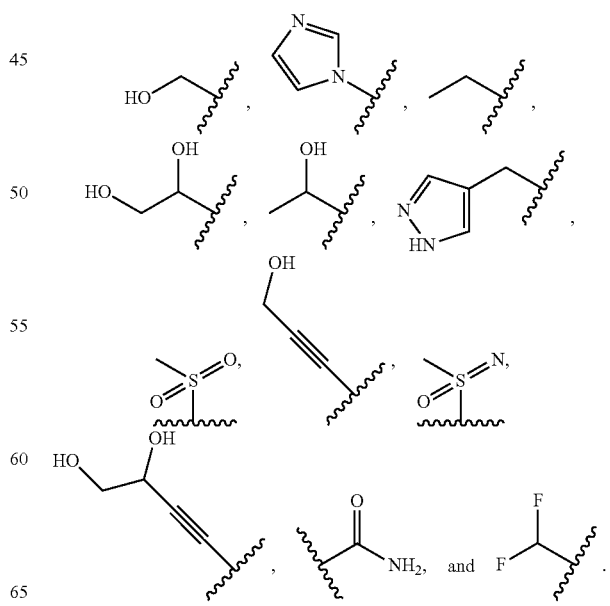

In some embodiments, $X^2$ is $CR^s$ and $R^s$ is —CN. In some embodiments, $X^2$ is $CR^s$ and $R^s$ is —CH$_3$. In some embodiments, $X^2$ is $CR^s$ and $R^s$ is

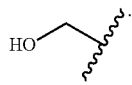

In some embodiments, $X^2$ is $CR^s$ and $R^s$ is

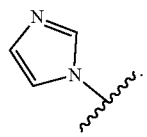

In some embodiments, $X^2$ is $CR^s$ and $R^s$ is

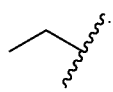

In some embodiments, $X^2$ is $CR^s$ and $R^s$ is.

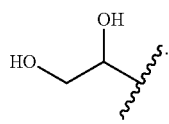

In some embodiments, $X^2$ is $CR^s$ and $R^s$ is

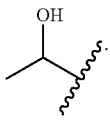

In some embodiments, $X^2$ is $CR^s$ and $R^s$ is

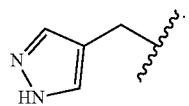 [SMILES: *Cc1cn[nH]c1]

In some embodiments, $X^2$ is $CR^s$ and $R^s$ is

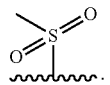

In some embodiments, $X^2$ is $CR^s$ and $R^s$ is

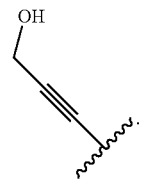 [SMILES: *C#CCO]

In some embodiments, $X^2$ is $CR^s$ and $R^s$ is

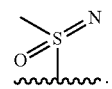

In some embodiments, $X^2$ is $CR^s$ and $R^s$ is

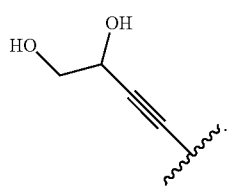

In some embodiments, $X^2$ is $CR^s$ and $R^s$ is

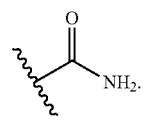

In some embodiments, $X^2$ is $CR^s$ and $R^s$ is

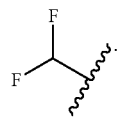

In some embodiments, provided herein is a compound of formula (II-B), or a stereoisomer, tautomer, or pharmaceutically acceptable salt thereof, wherein $X^1$ is C or N. In some embodiments, $X^1$ is C. In some embodiments, X is N. In some embodiments, X is taken together with $R^1$ and the atoms to which they are attached, to form a 5 to 6 membered heteroaryl, 5 to 6 membered heterocyclyl, phenyl, or $C_{5-6}$cycloalkyl that is fused to ring A. In some embodiments, $X^1$ is C and is taken together with $R^1$ and the atoms to which they are attached, to form a 5 to 6 membered heteroaryl, 5 to 6 membered heterocyclyl, phenyl, or $C_{5-6}$cycloalkyl that is fused to ring A. In some embodiments, $X^1$ is C and is taken together with $R^1$ and the atoms to which they are attached to form a 5 to 6 membered heteroaryl that is fused to ring A. In some embodiments, $X^1$ is C and is taken together with $R^1$ and the atoms to which they are attached to form a 5 to 6 membered heterocyclyl that is fused to ring A. In some embodiments, $X^1$ is C and is taken together with $R^1$ and the atoms to which they are attached to form a phenyl that is fused to ring A. In some embodiments, $X^1$ is C and is taken together with $R^1$ and the atoms to which they are attached to form a $C_{5-6}$cycloalkyl that is fused to ring A. In some embodiments, $X^1$ is N and is taken together with $R^1$ and the atoms to which they are attached, to form a 5 to 6 membered heteroaryl or a 5 to 6 membered heterocyclyl that is fused to ring A. In some embodiments, $X^1$ is N and is taken together with $R^1$ and the atoms to which they are attached to form a 5 to 6 membered heteroaryl that is fused to ring A. In some embodiments, $X^1$ is N and is taken together with $R^1$ and the atoms to which they are attached to form a 5 to 6 membered heterocyclyl that is fused to ring A.

In some embodiments, provided herein is a compound of formula (II-B), or a stereoisomer, tautomer, or pharmaceutically acceptable salt thereof, wherein $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A, wherein the 5 to 6 membered heteroaryl, 5 to 6 membered heterocyclyl, phenyl, or $C_{5-6}$ cycloalkyl that is fused to ring A is selected from the group consisting of

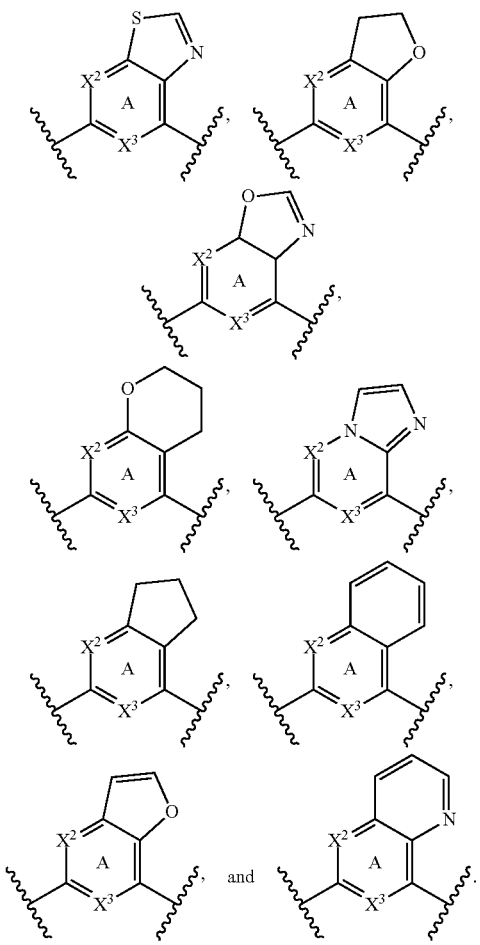

In some embodiments, provided herein is a compound of formula (II-B), or a stereoisomer, tautomer, or pharmaceutically acceptable salt thereof, wherein $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A, wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$, wherein R$^d$ and R$^e$ are each independently H or $C_{1-6}$alkyl. In some embodiments, R$^d$ and R$^e$ are each independently H or $C_{1-6}$alkyl. In some embodiments, R$^d$ is H or $C_{1-6}$alkyl. In some embodiments, R$^d$ is H. In some embodiments, R$^d$ is $C_{1-6}$alkyl. In some embodiments, R$^e$ is H or $C_{1-6}$alkyl. In some embodiments, R$^e$ is H or $C_{1-6}$alkyl. In some embodiments, R$^e$ is H. In some embodiments, R$^e$ is $C_{1-6}$alkyl.

In some embodiments, provided herein is a compound of formula (II-B), or a stereoisomer, tautomer, or pharmaceutically acceptable salt thereof, wherein $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is halo. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is $C_{1-15}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is $C_{6-20}$aryl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is 5 to 15 membered heteroaryl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is $C_{3-20}$cycloalkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is 3 to 15 membered heterocyclyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^1$ is —OH. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —CN. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is oxo. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is $C_{1-15}$alkoxy. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dCOR^t$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$CONR^dR^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$SO_2R^d$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$SO_2NR^dR^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dSO_2R^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^d$ and $R^e$ are each independently H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^d$ is H. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^d$ is $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^e$ is H. In some embodiments, $X^1$ is taken together with $R^1$ and the atoms to which they are attached, to form a 5 to 6 membered heteroaryl, wherein the 5 to 6 membered heteroaryl is substituted with one or more $R^t$, wherein $R^t$ is —$NR^dR^e$, wherein $R^e$ is $C_{1-6}$alkyl.

In some embodiments, provided herein is a compound of formula (II-B), or a stereoisomer, tautomer, or pharmaceutically acceptable salt thereof, wherein $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is independently, at each occurrence, selected from the group consisting of halo, $C_{1-15}$ alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is halo. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{1-15}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{6-20}$aryl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is 5 to 15 membered heterocyclyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is $C_{3-20}$cycloalkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is 3 to 15 membered heterocyclyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —OH. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^1$ is —CN. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is oxo. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is $C_{1-15}$alkoxy. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dCOR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$CONR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$SO_2R^d$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$SO_2NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dSO_2R^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^d$ and $R^e$ are each independently H or $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^d$ is H. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^d$ is $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^e$ is H or $C_{1-6}$alkyl. In some embodiments, $R^e$ is H or $C_{1-6}$alkyl. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^e$ is H. In some embodiments, $X^1$ is taken together with $R^1$ and the atoms to which they are attached, to form a 5 to 6 membered heterocyclyl, wherein the 5 to 6 membered heterocyclyl is substituted with one or more $R^t$, wherein $R^t$ is —$NR^dR^e$, wherein $R^e$ is $C_{1-6}$alkyl.

In some embodiments, provided herein is a compound of formula (II-B), or a stereoisomer, tautomer, or pharmaceutically acceptable salt thereof, wherein $X^1$ is taken together with $R^1$ and the atoms to which they are attached, to form a phenyl, wherein the phenyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^1$, and —$NR^dR^e$. In some embodiments, $X^1$ is taken together with $R^1$ and the atoms to which they are attached, to form a phenyl, wherein the phenyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a phenyl, wherein the phenyl is substituted with one or more $R^t$, wherein $R^t$ is halo. In some embodiments, $X^1$ is taken together with $R^1$ and the atoms to which they are attached, to form a phenyl, wherein the phenyl is substituted with one or more $R^t$, wherein $R^t$ is $C_{1-15}$alkyl. In some embodiments, $X^1$ is taken together with $R^1$ and the atoms to which they are attached, to form a phenyl, wherein the phenyl is substituted with one or more $R^t$, wherein R is $C_{6-20}$aryl. In some embodiments, $X^1$ is taken together with $R^1$ and the atoms to which they are attached, to form a phenyl, wherein the phenyl is substituted with one or more $R^t$, wherein $R^t$ is 5 to 15 membered heteroaryl. In some embodiments, $X^1$ is taken together with $R^1$ and the atoms to which they are attached, to form a phenyl, wherein the phenyl is substituted with one or more $R^t$, wherein $R^t$ is $C_{3-20}$cycloalkyl. In some embodiments, $X^1$ is taken together with $R^t$ and the atoms to which they are attached, to form a phenyl, wherein the phenyl is substituted with one or more $R^t$, wherein $R^t$ is 3 to 15 membered heterocyclyl. In some embodiments, $X^1$ is taken together with $R^1$ and the atoms to which they are attached, to form a phenyl, wherein the phenyl is substituted with one or more $R^t$, wherein $R^t$ is —OH. In some embodiments, $X^1$ is taken together with $R^1$ and the atoms to which they are attached, to form a phenyl, wherein the phenyl is substituted with one or more $R^t$, wherein $R^t$ is —CN. In some embodiments, $X^1$ is taken together with $R^1$ and the atoms to which they are attached, to form a phenyl, wherein the phenyl is substituted with one or more $R^t$, wherein $R^t$ is oxo. In some embodiments, $X^1$ is taken together with $R^1$ and the atoms to which they are attached, to form a phenyl, wherein the phenyl is substituted with one or more $R^t$, wherein $R^1$ is $C_{1-15}$alkoxy. In some embodiments, $X^1$ is taken together with $R^1$ and the atoms to which they are attached, to form a phenyl, wherein the phenyl is substituted with one or more $R^t$, wherein $R^1$ is —$NR^dCOR^e$. In some embodiments, $X^1$ is taken together with $R^1$ and the atoms to which they are attached, to form a phenyl, wherein the phenyl is substituted with one or more $R^t$, wherein $R^t$ is —$CONR^dR^e$. In some embodiments, $X^1$ is taken together with $R^1$ and the atoms to which they are attached, to form a phenyl, wherein the phenyl is substituted with one or more $R^t$, wherein $R^1$ is —$SO_2R^d$. In some embodiments, $X^1$ is taken together with $R^1$ and the atoms to which they are attached, to form a phenyl, wherein the phenyl is substituted with one or more $R^t$, wherein $R^1$ is —$SO_2NR^dR^e$. In some embodiments, $X^1$ is taken together with $R^1$ and the atoms to which they are attached, to form a phenyl, wherein the phenyl is substituted with one or more $R^t$, wherein $R^1$ is —$NR^dSO_2R^e$. In some embodiments, $X^1$ is taken together with $R^1$ and the atoms to which they are attached, to form a phenyl, wherein the phenyl is substituted with one or more $R^t$, wherein $R^1$ is —$NR^dR^e$. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^d$ and $R^{t1}$ are each independently H or $C_{1-6}$ alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^d$ is H. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^d$ is $C_{1-6}$alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^e$ is H. In some embodiments, $X^1$ is taken together with $R^1$ and the atoms to which they are attached, to form a phenyl, wherein the phenyl is substituted with one or more $R^t$, wherein $R^t$ is —$NR^dR^e$, wherein $R^e$ is $C_{1-6}$alkyl.

In some embodiments, provided herein is a compound of formula (II-B), or a stereoisomer, tautomer, or pharmaceutically acceptable salt thereof, wherein $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$-alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is halo. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{1-15}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{6-20}$aryl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is 5 to 15 membered heteroaryl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{3-20}$cycloalkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is 3 to 15 membered heterocyclyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^1$ is —OH. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —CN. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^1$ is oxo. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is $C_{1-15}$alkoxy. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dCOR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$CONR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$SO_2R^d$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$SO_2NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dSO_2R^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ and $R^e$ are each independently H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is H. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^d$ is $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^{t1}$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is H or $C_{1-6}$alkyl. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is H. In some embodiments, $X^1$ is taken together with $R^1$ and the atoms to which they are attached, to form a $C_{5-6}$cycloalkyl, wherein the $C_{5-6}$cycloalkyl is substituted with one or more $R^t$, wherein $R^t$ is —$NR^dR^e$, wherein $R^e$ is $C_{1-6}$alkyl.

In some embodiments, provided herein is a compound of formula (II-B), or a stereoisomer, tautomer, or pharmaceutically acceptable salt thereof, wherein $X^2$ is N or $CR^s$, wherein $R^s$ is H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, or —$NR^dR^e$. In some embodiments, $X^2$ is N. In some embodiments, $X^2$ is $CR^s$. In some embodiments, $X^2$ is $CR^s$, wherein $R^s$ is H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, or —$NR^dR^e$. In some embodiments, $X^2$ is $CR^s$, wherein $R^s$ is H. In some embodiments, $X^2$ is $CR^s$, wherein $R^s$ is halo. In some embodiments, $X^2$ is $CR^s$, wherein $R^s$ is $C_{1-15}$alkyl. In some embodiments, $X^2$ is $CR^s$, wherein $R^s$ is $C_{6-20}$aryl. In some embodiments, $X^2$ is $CR^s$, wherein $R^s$ is 5 to 15 membered heteroaryl. In some embodiments, $X^2$ is $CR^s$, wherein $R^s$ is $C_{3-20}$cycloalkyl. In some embodiments, $X^2$ is $CR^s$, wherein $R^s$ is 3 to 15 membered heterocyclyl. In some embodiments, $X^2$ is $CR^s$, wherein $R^s$ is —OH. In some embodiments, $X^2$ is $CR^s$, wherein $R^s$ is —CN. In some embodiments, $X^2$ is $CR^s$, wherein $R^s$ is $C_{1-15}$alkoxy. In other embodiments, $X^2$ is $CR^s$, wherein $R^s$ is —$NR^dCOR^e$. In other embodiments, $X^2$ is $CR^s$, wherein $R^s$ is —$CONR^dR^e$. In other embodiments, $X^2$ is $CR^s$, wherein $R^s$ is —$SO_2R^d$. In other embodiments, $X^2$ is $CR^s$, wherein $R^s$ is —$SO_2NR^dR^e$. In other embodiments, $X^2$ is $CR^s$, wherein $R^s$ is —$NR^dSO_2R^e$. In some embodiments, $X^2$ is $CR^s$, wherein $R^s$ is —$NR^dR^e$. In some embodiments, $X^2$ is $CR^s$, wherein $R^s$ is —$NR^dR^e$, wherein $R^d$ and $R^e$ are each independently H or $C_{1-6}$alkyl. In some embodiments, $X^2$ is $CR^s$, wherein $R^s$ is —$NR^dR^e$, wherein $R^d$ is H or $C_{1-6}$ alkyl. In some embodiments, $X^2$ is $CR^s$, wherein $R^s$ is —$NR^dR^e$, wherein $R^d$ is H. In some embodiments, $X^2$ is $CR^s$, wherein $R^s$ is —$NR^dR^e$, wherein $R^d$ is $C_{1-6}$alkyl. In some embodiments, $X^2$ is $CR^s$, wherein $R^s$ is —$NR^dR^e$, wherein $R^e$ is H or $C_{1-6}$alkyl. In some embodiments, $X^2$ is $CR^s$, wherein $R^s$ is —$NR^dR^e$, wherein $R^e$ is H or $C_{1-6}$alkyl. In some embodiments, $X^2$ is $CR^s$, wherein $R^s$ is —$NR^dR^e$, wherein $R^e$ is H. In some embodiments, $X^2$ is $CR^s$, wherein $R^s$ is —$NR^dR^e$, wherein $R^e$ is $C_{1-6}$alkyl.

In some embodiments, provided herein is a compound of formula (II-B), or a stereoisomer, tautomer, or pharmaceutically acceptable salt thereof, wherein $X^2$ is $CR^s$, wherein $R^s$ is $C_{1-15}$alkyl or $C_{1-15}$alkoxy, wherein the $C_{1-15}$alkyl and $C_{1-15}$alkoxy of $R^s$ are each independently optionally substituted with one or more $R^{t1}$, wherein $R^{t1}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{1-15}$alkyl, optionally substituted with one or more $R^{t1}$, wherein $R^{t1}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{1-15}$alkyl, optionally substituted with one or more $R^{t1}$, wherein $R^{t1}$ is halo. In some embodiments, $X^2$ is $CR^s$, wherein $R^s$ is $C_{1-15}$alkyl, optionally substituted with one or more $R^{t1}$, wherein $R^{t1}$ is oxo. In some embodiments, $X^2$ is $CR^s$, wherein $R^s$ is $C_{1-15}$alkyl, optionally substituted with one or more $R^{t1}$, wherein $R^{t1}$ is —OH. In some embodiments, $X^2$ is $CR^s$, wherein $R^s$ is $C_{1-15}$alkyl, optionally substituted with one or more $R^{t1}$, wherein $R^{t1}$ is —CN. In some embodiments, $X^2$ is $CR^s$, wherein $R^s$ is $C_{1-15}$alkyl, optionally substituted with one or more $R^{t1}$, wherein $R^{t1}$ is —$NR^dR^e$.

In some embodiments, provided herein is a compound of formula (II-B), or a stereoisomer, tautomer, or pharmaceutically acceptable salt thereof, wherein $X^2$ is $CR^s$, wherein $R^s$ is $C_{1-15}$alkoxy, optionally substituted with one or more $R^{t1}$, wherein $R^1$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{1-15}$alkoxy, optionally substituted with one or more $R^{t1}$, wherein $R^{t1}$ is halo. In some embodiments, $X^2$ is $CR^s$, wherein $R^s$ is $C_{1-15}$alkoxy, optionally substituted with one or more $R^{t1}$, wherein $R^{t1}$ is oxo. In some embodiments, $X^2$ is $CR^s$, wherein $R^s$ is $C_{1-15}$alkoxy, optionally substituted with one or more $R^{t1}$, wherein $R^{t}$ is —OH. In some embodiments, $X^2$ is $CR^s$, wherein $R^s$ is $C_{1-15}$alkoxy, optionally substituted with one or more $R^{t1}$, wherein $R^t$ is —CN. In some embodiments, $X^2$ is $CR^s$, wherein $R^s$ is $C_{1-15}$alkoxy, optionally substituted with one or more $R^{t1}$, wherein $R^{t1}$ is —$NR^dR^e$.

In some embodiments, provided herein is a compound of formula (II-B), or a stereoisomer, tautomer, or pharmaceutically acceptable salt thereof, wherein $X^2$ is $CR^s$, wherein $R^s$ is $C_{1-15}$alkoxy, optionally substituted with one or more $R^t$, wherein $R^t$ is —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ is H. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ is $C_{1-6}$alkyl. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^e$ is H. In some embodiments, $X^2$ is $CR^s$, wherein $R^s$ is $C_{1-15}$alkoxy, optionally substituted with one or more $R^t$, wherein $R^t$ is —$NR^dR^e$, wherein $R^e$ is $C_{1-6}$ alkyl. In some embodiments, $X^2$ is $CR^s$, wherein $R^s$ is $C_{1-15}$alkoxy, optionally substituted with one or more $R^{t1}$, wherein $R^t$ is —$NR^dR^e$, wherein $R^d$ or $R^e$ are independently $C_{1-6}$alkyl, the $C_{1-6}$ alkyl of $R^d$ or $R^e$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ is $C_{1-6}$alkyl, the $C_{1-6}$alkyl of $R^d$ is optionally substituted with one or more halo, oxo, —OH, or —CN. In some embodiments, $X^2$ is $CR^s$, wherein $R^s$ is $C_{1-15}$-alkoxy, optionally substituted with one or more $R^{t1}$, wherein $R^t$ is —$NR^dR^e$, wherein $R^d$ is $C_{1-6}$ alkyl, the $C_{1-6}$alkyl of $R^d$ is optionally substituted with one or more halo. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ is $C_{1-6}$alkyl, the $C_{1-6}$alkyl of $R^d$ is optionally substituted with one or more oxo. In some embodiments, $X^2$ is $CR^s$, wherein $R^s$ is $C_{1-15}$alkoxy, optionally substituted with one or more $R^t$, wherein $R^t$ is —$NR^dR^e$, wherein $R^d$ is $C_{1-6}$alkyl, the $C_{1-6}$alkyl of $R^d$ is optionally substituted with one or more —OH. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^d$ is $C_{1-6}$alkyl, the $C_{1-6}$alkyl of $R^d$ is optionally substituted with one or more —CN. In some embodiments, $X^2$ is $CR^s$, wherein $R^s$ is $C_{1-15}$alkoxy, optionally substituted with one or more $R^{t1}$, wherein $R^t$ is —$NR^dR^e$, wherein $R^e$ is $C_{1-6}$alkyl, the $C_{1-6}$alkyl of $R^e$ is optionally substituted with one or more halo, oxo, —OH, or —CN. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^e$ is $C_{1-6}$alkyl, the $C_{1-6}$alkyl of $R^e$ is optionally substituted with one or more halo. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^e$ is $C_{1-6}$alkyl, the $C_{1-6}$alkyl of $R^e$ is optionally substituted with one or more oxo. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^e$ is $C_{1-6}$alkyl, the $C_{1-6}$alkyl of $R^e$ is optionally substituted with one or more —OH. In some embodiments, $X^2$ is $CR^s$, wherein $R^s$ is $C_{1-15}$alkoxy, optionally substituted with one or more $R^{t1}$, wherein $R^{t1}$ is —$NR^dR^e$, wherein $R^e$ is $C_{1-6}$alkyl, the $C_{1-6}$alkyl of $R^e$ is optionally substituted with one or more —CN.

In some embodiments, provided herein is a compound of formula (II-B), or a stereoisomer, tautomer, or pharmaceutically acceptable salt thereof, wherein $X^2$ is $CR^s$, wherein $R^s$ is $C_{6-20}$aryl, 5 to 15 membered heteroaryl, $C_{3-20}$cycloalkyl, or 3 to 15 membered heterocyclyl, wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{6-20}$aryl, the $C_{6-20}$aryl of $R^s$ is optionally substituted with one or more $R^{t2}$, wherein $R^{t2}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{6-20}$aryl, the $C_{6-20}$aryl of $R^s$ is optionally substituted with $R^{t2}$, wherein $R^{t2}$ is halo. In some embodiments, $X^2$ is $CR^s$, wherein $R^s$ is $C_{6-20}$aryl, the $C_{6-20}$aryl of $R^s$ is optionally substituted with $R^{t2}$, wherein $R^2$ is oxo. In some embodiments, $X^2$ is $CR^s$, wherein $R^s$ is $C_{6-20}$aryl, the $C_{6-20}$aryl of $R^s$ is optionally substituted with $R^{t2}$, wherein $R^{t2}$ is —OH. In some embodiments, $X^2$ is $CR^s$, wherein $R^s$ is $C_{6-20}$aryl, the $C_{6-20}$aryl of $R^s$ is optionally substituted with $R^2$, wherein $R^{t2}$ is —CN. In some embodiments, $X^2$ is $CR^s$, wherein $R^s$ is $C_{6-20}$aryl, the $C_{6-20}$aryl of $R^s$ is optionally substituted with $R^{t2}$, wherein $R^{t2}$ is $C_{1-6}$alkyl.

In some embodiments, provided herein is a compound of formula (II-B), or a stereoisomer, tautomer, or pharmaceutically acceptable salt thereof, wherein $X^2$ is $CR^s$, wherein $R^s$ is 5 to 15 membered heteroaryl, the 5 to 15 membered heteroaryl of $R^s$ is optionally substituted with one or more $R^2$, wherein $R^{t2}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is 5 to 15 membered heteroaryl, the 5 to 15 membered heteroaryl of $R^s$ is optionally substituted with $R^{t2}$, wherein $R^{t2}$ is halo. In some embodiments, $X^2$ is $CR^s$, wherein $R^s$ is 5 to 15 membered heteroaryl, the 5 to 15 membered heteroaryl of $R^s$ is optionally substituted with $R^{t2}$, wherein $R^{t2}$ is oxo. In some embodiments, $X^2$ is $CR^s$, wherein $R^s$ is 5 to 15 membered heteroaryl, the 5 to 15 membered heteroaryl of $R^s$ is optionally substituted with $R^{t2}$, wherein $R^2$ is —OH. In some embodiments, $X^2$ is $CR^s$, wherein $R^s$ is 5 to 15 membered heteroaryl, the 5 to 15 membered heteroaryl of $R^s$ is optionally substituted with $R^{t2}$, wherein $R^2$ is —CN. In some embodiments, $X^2$ is $CR^s$, wherein $R^s$ is 5 to 15 membered heteroaryl, the 5 to 15 membered heteroaryl of $R^s$ is optionally substituted with $R^{t2}$, wherein $R^{t2}$ is $C_{1-6}$alkyl.

In some embodiments, provided herein is a compound of formula (II-B), or a stereoisomer, tautomer, or pharmaceutically acceptable salt thereof, wherein $X^2$ is $CR^s$, wherein $R^s$ is $C_{6-20}$cycloalkyl, the $C_{6-20}$cycloalkyl of $R^s$ is optionally substituted with one or more $R^{t2}$, wherein $R^{t2}$ is independently at each occurrence selected from the group consisting of halo, $C_{1-15}$-alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is halo. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is oxo. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is —OH. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is —CN. In some embodiments, $X^2$ is $CR^s$, wherein $R^s$ is $C_{6-20}$cycloalkyl, the $C_{6-20}$cycloalkyl of $R^s$ is optionally substituted with $R^{t2}$, wherein $R^{t2}$ is $C_{1-6}$alkyl.

In some embodiments, provided herein is a compound of formula (II-B), or a stereoisomer, tautomer, or pharmaceutically acceptable salt thereof, wherein $X^2$ is $CR^s$, wherein $R^s$ is 5 to 15 membered heterocyclyl, the 5 to 15 membered heterocyclyl of $R^s$ is optionally substituted with one or more $R^{t2}$, wherein $R^{t2}$ is independently at each occurrence selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In some embodiments, $X^2$ is $CR^s$, wherein $R^s$ is 5 to 15 membered heterocyclyl, the 5 to 15 membered heterocyclyl of $R^s$ is optionally substituted with $R^{t2}$, wherein $R^{t2}$ is halo. In some embodiments, $X^2$ is $CR^s$, wherein $R^s$ is 5 to 15 membered heterocyclyl, the 5 to 15 membered heterocyclyl of $R^s$ is optionally substituted with $R^{t2}$, wherein $R^{t2}$ is oxo. In some embodiments, $X^2$ is $CR^s$, wherein $R^s$ is 5 to 15 membered heterocyclyl, the 5 to 15 membered heterocyclyl of $R^s$ is optionally substituted with $R^{t2}$, wherein $R^{t2}$ is —OH. In some embodiments, $X^2$ is $CR^s$, wherein $R^s$ is 5 to 15 membered heterocyclyl, the 5 to 15 membered heterocyclyl of $R^s$ is optionally substituted with $R^{t2}$, wherein $R^{t2}$ is —CN. In some embodiments, $X^2$ is $CR^s$, wherein $R^s$ is 5 to 15 membered heterocyclyl, the 5 to 15 membered heterocyclyl of $R^s$ is optionally substituted with $R^{t2}$, wherein $R^2$ is $C_{1-6}$alkyl.

In some embodiments, provided herein is a compound of formula (II-B), or a stereoisomer, tautomer, or pharmaceutically acceptable salt thereof, wherein $X^3$ is N or CH. In some embodiments, $X^3$ is N. In some embodiments, $X^3$ is CH.

In some embodiments, provided herein is a compound of formula (II-B), or a stereoisomer, tautomer, or pharmaceutically acceptable salt thereof, wherein B is phenyl or 5 to 6 membered heteroaryl; wherein the phenyl and 5 to 6 membered heteroaryl of B are each independently substituted with one to five $R^2$. In some embodiments, B is phenyl independently substituted with one to five $R^2$. In some embodiments, B is 5 to 6 membered heteroaryl independently substituted with one to five $R^2$.

In some embodiments, in conjunction with embodiments above or below, B is 5 to 6 membered heteroaryl independently substituted with one $R^2$.

In some embodiments, provided herein is a compound of formula (II-B), or a stereoisomer, tautomer, or pharmaceutically acceptable salt thereof, wherein $R^2$ is independently, at each occurrence, i) halo; ii) $S(R^y)_5$, wherein each $R^y$ is halo; or iii) $C_{1-6}$ alkoxy, optionally substituted with one or more halo. In some embodiments, $R^2$ is halo. In some embodiments, $R^2$ is $S(R^y)_5$, wherein each $R^y$ is halo. In some embodiments, $R^2$ is $C_{1-6}$ alkoxy, optionally substituted with one or more halo. In some embodiments, $R^2$ is unsubstituted $C_{1-6}$alkoxy.

In some embodiments, provided herein is a compound of formula (II-B), or a stereoisomer, tautomer, or pharmaceutically acceptable salt thereof, wherein Z is —OH, —NR$^d$R$^e$, $C_{1-6}$alkoxy, —C(O)R$^a$, —S(O)$_2$R$^a$. In some embodiments, Z is —OH. In some embodiments, Z is NR$^d$R$^e$, wherein R$^d$ and RC are each independently H or $C_{1-6}$alkyl. In some embodiments, Z is NR$^d$R$^e$, wherein R$^d$ is H. In some embodiments, Z is NR$^d$R$^e$, wherein R$^d$ is $C_{1-6}$alkyl. In some embodiments, Z is NR$^d$R$^e$, wherein R$^e$ is H. In some embodiments, Z is NR$^d$R$^e$, wherein R$^e$ is $C_{1-6}$alkyl. In some embodiments, Z is —C(O)R$^a$. In some embodiments, Z is —C(O)R$^a$, wherein R$^a$ is i) $C_{2-6}$alkenyl optionally substituted with one or more deuterium, $C_{1-6}$alkyl, halo, haloC$_{1-6}$ alkyl; or ii) $C_{1-6}$alkyl, optionally substituted with one or more halo. In some embodiments, Z is —C(O)R$^a$, wherein R$^a$ is $C_{2-6}$alkenyl optionally substituted with one or more deuterium, $C_{1-6}$ alkyl, halo, haloC$_{1-6}$alkyl. In some embodiments, Z is —C(O)R$^a$, wherein R$^a$ is $C_{1-6}$alkyl, optionally substituted with one or more halo. In some embodiments, Z is —C(O)R$^a$, wherein R$^a$ is $C_{2-6}$alkenyl optionally substituted with one or more deuterium. In some embodiments, Z is —C(O)R$^a$, wherein R$^a$ is $C_{1-6}$alkyl. In some embodiments, Z is —C(O)R$^a$, wherein R$^a$ is haloC$_{1-6}$alkyl.

In some embodiments, provided herein is a compound of formula (II-B), or a stereoisomer, tautomer, or pharmaceutically acceptable salt thereof, wherein Z is —C(O)R$^a$, wherein R$^a$ is $C_{2-6}$alkenyl optionally substituted with one or more deuterium, $C_{1-6}$alkyl, halo, haloC$_{1-6}$alkyl; and B is phenyl substituted with one or more $R^2$, wherein $R^2$ is $C_{1-6}$alkoxy optionally substituted with one or more halo. In some embodiments, Z is —C(O)R$^a$, wherein R$^a$ is $C_{2-6}$alkenyl optionally substituted with one or more deuterium; and B is phenyl substituted with one or more $R^2$, wherein $R^2$ is $C_{1-6}$alkoxy optionally substituted with one or more halo. In some embodiments, Z is —C(O)R$^a$, wherein R$^a$ is $C_{2-6}$alkenyl optionally substituted with one or more halo; and B is phenyl substituted with one or more $R^2$, wherein $R^2$ is $C_{1-6}$alkoxy optionally substituted with one or more halo. In some embodiments, Z is —C(O)R$^a$, wherein R$^a$ is $C_{2-6}$-alkenyl optionally substituted with one or more $C_{1-6}$alkyl; and B is phenyl substituted with one or more $R^2$, wherein $R^2$ is $C_{1-6}$alkoxy optionally substituted with one or more halo. In some embodiments, Z is —C(O)R$^a$, wherein R$^a$ is $C_{2-6}$alkenyl optionally substituted with one or more haloC$_{1-6}$alkyl; and B is phenyl substituted with one or more $R^2$, wherein $R^2$ is $C_{1-6}$alkoxy optionally substituted with one or more halo.

In some embodiments, provided herein is a compound of formula (II-B), or a stereoisomer, tautomer, or pharmaceutically acceptable salt thereof, wherein n and m are each independently 1 or 2. In some embodiments, n is 1. In some embodiments, n is 2. In some embodiments, m is 1. In some embodiments, m is 2. In some embodiments, n is 1 and m is 1. In some embodiments, n is 1 and m is 2. In some embodiments, n is 2 and m is 1. In some embodiments, n is 2 and m is 2.

In some embodiments, in conjunction with embodiments above or below, provided herein is a compound of formula (II-AB'), or a stereoisomer, tautomer, or pharmaceutically acceptable salt thereof, wherein B is i) phenyl or 5 to 6 membered heteroaryl; wherein the phenyl and 5 to 6 membered heteroaryl of B are each independently substituted with one or more $R^2$, wherein $R^2$ is independently, at each occurrence, halo; $S(R^y)_5$, wherein each $R^y$ is halo; $C_{1-6}$alkoxy optionally substituted with one or more halo; or ii)—O-phenyl substituted with haloC$_{1-3}$alkyl, provided that when B is —O-phenyl substituted with haloC$_1$-3alkyl, L' is *—N(R$^3$)-L-**, Z is —C(O)CHCH$_2$, $X^1$ is C, $X^2$ is CR$^s$, and $X^3$ is CH; or iii) bicyclopentane substituted by $C_{1-3}$alkyl, provided that when B is bicyclopentane substituted by $C_{1-3}$alkyl, L' is *—N(R$^3$)-L-** and Z is —C(O)CHCH$_2$; or iv) phenyl substituted with ethynyl or haloC$_{1-3}$alkyl, provided that when B is phenyl substituted with ethynyl or haloC$_{1-3}$alkyl, L' is *—N(R$^3$)-L-**, Z is —C(O)CHCH$_2$, and R$^s$ is $C_{1-3}$alkyl substituted with one or more —OH; or v) piperidine substituted with haloC$_{1-3}$alkyl or haloC$_1$-3alkoxy, provided that when B is piperidine substituted with haloC$_{1-3}$alkyl or haloC$_{1-3}$alkoxy, L' is *—N(R$^3$)-L-** and Z is —C(O)CHCH$_2$. In some embodiments, B is phenyl or 5 to 6 membered heteroaryl; wherein the phenyl and 5 to 6 membered heteroaryl of B are each independently substituted with one or more $R^2$, wherein $R^2$ is independently, at each occurrence, halo; $S(R^y)_5$, wherein each R$_y$ is halo; $C_{1-6}$alkoxy optionally substituted with one or more halo. In some embodiments, B is —O-phenyl substituted with haloC$_{1-3}$alkyl, provided that when B is —O-phenyl substituted with haloC$_{1-3}$alkyl, L' is *—N(R$^3$)-L-**, Z is —C(O)CHCH$_2$, $X^1$ is C, $X^2$ is CR$^s$, and $X^3$ is CH. In some embodiments, B is bicyclopentane substituted by $C_{1-3}$alkyl, provided that when B is bicyclopentane substituted by $C_{1-3}$alkyl, L' is *—N(R$^3$)-L-** and Z is —C(O)CHCH$_2$. In some embodiments, B is phenyl substituted with ethynyl or haloC$_{1-3}$alkyl, provided that when B is phenyl substituted with ethynyl or haloC$_{1-3}$alkyl, L' is *—N(R$^3$)-L-**, Z is —C(O)CHCH$_2$, and R$^s$ is $C_{1-3}$alkyl substituted with one or more —OH. In some embodiments, B is piperidine substituted with haloC$_{1-3}$alkyl or haloC$_{1-3}$alkoxy, provided that when B is piperidine substituted with haloC$_{1-3}$alkyl or haloC$_1$-3alkoxy, L' is *—N(R$^3$)-L-** and Z is —C(O)CHCH$_2$.

In some embodiments, in conjunction with embodiments above or below, provided herein is a compound of formula (II-AB'), or a stereoisomer, tautomer, or pharmaceutically acceptable salt thereof, wherein Z is —OH, —NR$^d$R$^e$, $C_{1-6}$alkoxy, —C(O)R$^a$, or —S(O)$_2$R$^b$, wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN; R$^a$ and R$^b$ are each independently i) $C_{2-6}$alkenyl optionally substituted with one or more substituents selected from deuterium, $C_{1-6}$alkyl, hydroxyl $C_{1-6}$alkyl, halo and haloC$_{1-6}$ alkyl; ii) $C_{1-6}$alkyl, optionally substituted with one or more halo; or iii) cyclobutenyl or bicyclobutanyl. In some embodiments, Z is —C(O)R$^a$ or —S(O)$_2$R$^b$, wherein R$^a$ and $R^b$ are each independently $C_{2-6}$alkenyl optionally substituted with one or more substituents selected from deuterium, $C_{1-6}$alkyl, hydroxyl $C_{1-6}$alkyl, halo and halo$C_{1-6}$alkyl. In some embodiments, Z is —C(O)$R^a$ or —S(O)$_2R^b$, wherein $R^a$ and $R^b$ are each independently $C_{1-6}$alkyl, optionally substituted with one or more halo. In some embodiments, Z is —C(O)$R^a$ or —S(O)$_2R^b$, wherein $R^a$ and $R^b$ are each independently cyclobutenyl or bicyclobutanyl.

In some embodiments, in conjunction with embodiments above or below, provided herein is a compound of formula (II-AB'), or a stereoisomer, tautomer, or pharmaceutically acceptable salt thereof, wherein L is methylene or ethylene, wherein the methylene of L is optionally substituted with one $C_{1-6}$alkyl. In some embodiments, L is methylene optionally substituted with one $C_{1-6}$alkyl. In some embodiments, L is ethylene.

In some embodiments, in conjunction with embodiments above or below, provided herein is a compound of formula (II-AB'), or a stereoisomer, tautomer, or pharmaceutically acceptable salt thereof, wherein L' is

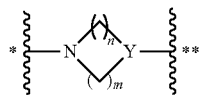

and Y is CH or C(CN). In some embodiments, in conjunction with embodiments above or below, provided herein is a compound of formula (II-AB'), or a stereoisomer, tautomer, or pharmaceutically acceptable salt thereof, wherein Z-L' is

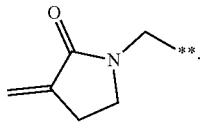

In some embodiments, in conjunction with embodiments above or below, provided herein is a compound of formula (II-AB'), or a stereoisomer, tautomer, or pharmaceutically acceptable salt thereof, wherein n and m are each independently 1 or 2.

In some embodiments, in conjunction with embodiments above or below, provided herein is a compound of formula (II-AB'), or a stereoisomer, tautomer, or pharmaceutically acceptable salt thereof, wherein when $X^1$ is taken together with $R^1$ and the atoms to which they are attached to form a phenyl, and $X^2$ or $X^3$ is N, B is phenyl and $R^2$ is halo$C_{1-6}$ alkoxyl; wherein when n=1 and m=2, or n=2 and m=1, B is phenyl substituted by halomethyoxyl; and wherein the compound of formula (II-AB') is not any one of following: N-((8-(4-fluorophenyl)imidazo[1,2-a]pyrazin-6-yl)methyl)acrylamide; N-((8-(4-(trifluoromethoxy)phenyl)imidazo[1,2-a]pyrazin-6-yl)methyl)acrylamide; N-((7-fluoro-4-(4-(trifluoromethoxy)phenyl)quinazolin-2-yl)methyl)acrylamide; N-((8-(4-(difluoromethoxy)phenyl)imidazo[1,2-a]pyrazin-6-yl)methyl)acrylamide; 1-(4-(4-(4-methoxyphenyl)-1-methyl-1H-imidazo[4,5-c]pyridin-6-yl)piperidin-1-yl)ethan-1-one; 4-(4-methoxyphenyl)-1-methyl-6-(1-(methylsulfonyl)piperidin-4-yl)-1H-imidazo[4,5-c]pyridine; 6-(1-(ethylsulfonyl)piperidin-4-yl)-4-(4-methoxyphenyl)-1-methyl-1H-imidazo[4,5-c]pyridine; 6-(1-(ethylsulfonyl)piperidin-4-yl)-1-isopropyl-4-(4-methoxyphenyl)-1H-imidazo[4,5-c]pyridine; 4-(4-methoxyphenyl)-1-methyl-6-(1-((trifluoromethyl)sulfonyl)piperidin-4-yl)-1H-imidazo[4,5-c]pyridine; and N-((4-(4-fluorophenyl)-1,8-naphthyridin-2-yl)methyl)acetamide.

In some embodiments, in conjunction with embodiments above or below, reference to "one or more" may be 1 to 5, 1 to 4, 1 to 3, 1 to 2, 5, 4, 3, 2, or 1.

In some embodiments, in conjunction with embodiments above or below, reference to "one or more substituents", for example, "one or more substituents of $C_{1-6}$alkyl", may be 1 to 3 substituents, 1 to 2 substituents, 2 substituents, or 1 substituent.

In some embodiments, in conjunction with embodiments above or below, wherein when B is optionally substituted with one or more $R^t$, $R^t$ is $C_{1-15}$alkoxy optionally substituted with 1-3 halo. In some embodiments, in conjunction with embodiments above or below, $R^t$ is $C_{1-15}$alkoxy substituted with 1-3 halo. In some embodiments, in conjunction with embodiments above or below, $R^t$ is OCF$_3$.

In some embodiments, in conjunction with embodiments above or below, wherein when $X^1$ is CR$^s$, $R^s$ is

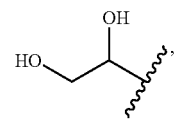

or a stereoisomer thereof. In some embodiments, R$^s$ is

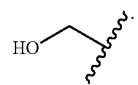

In some embodiments, in conjunction with embodiments above or below, n and m are each 1.

In some aspects, a compound or a stereoisomer, tautomer, or pharmaceutically acceptable salt thereof of the following formula (II-A-1) is provided:

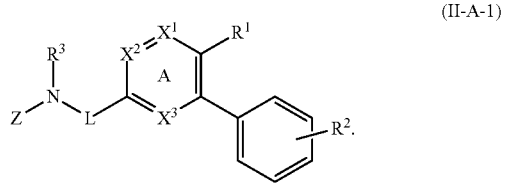

(II-A-1)

In one aspect, $X^1$, $X^2$, $X^3$, $R^1$, $R^2$, $R^3$, L, A, and Z of formula (II-A-1) are as defined in formula (II-AB'). In one aspect, $X^1$, $X^2$, $X^3$, $R^1$, $R^2$, $R^3$, L, A, and Z of formula (II-A-1) are as defined in formula (II-AB). In one aspect, $X^1$, $X^2$, $X^3$, $R^1$, $R^2$, $R^3$, L, A, and Z of formula (II-A-1) are as defined in formula (II-A). It is understood that embodiments of $X^1$, $X^2$, $X^3$, $R^1$, $R^2$, $R^3$, L, A, and Z described for formula (II-AB'), (II-AB) or (II-A) may, where applicable, apply in some embodiments to formula (II-A-1).

In some aspects, a compound or a stereoisomer, tautomer, or pharmaceutically acceptable salt thereof of the following formula (II-A-2) is provided:

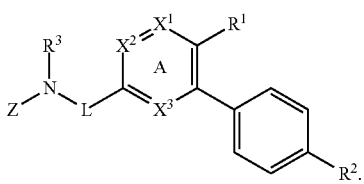

(II-A-2)

In one aspect, $X^1$, $X^2$, $X^3$, $R^1$, $R^2$, $R^3$, L, A, and Z of formula (II-A-2) are as defined in formula (II-AB'). In one aspect, $X^1$, $X^2$, $X^3$, $R^1$, $R^2$, $R^3$, L, A, and Z of formula (II-A-2) are as defined in formula (II-AB). In one aspect, $X^1$, $X^2$, $X^3$, $R^1$, $R^2$, $R^3$, L, A, and Z of formula (II-A-2) are as defined in formula (II-A). It is understood that embodiments of $X^1$, $X^2$, $X^3$, $R^1$, $R^2$, $R^3$, L, A, and Z described for formula (II-AB'), (II-AB), or (II-A) may, where applicable, apply in some embodiments to formula (II-A-2).

In some aspects, a compound or a stereoisomer, tautomer, or pharmaceutically acceptable salt thereof of the following formula (II-A-3) is provided:

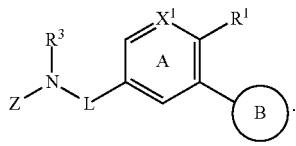

(II-A-3)

In one aspect, $X^1$, $R^1$, $R^3$, L, A, B, and Z of formula (II-A-3) are as defined in formula (II-AB'). In one aspect, $X^1$, $R^1$, $R^3$, L, A, B, and Z of formula (II-A-3) are as defined in formula (II-AB). In one aspect, $X^1$, $R^1$, $R^3$, L, A, B, and Z of formula (II-A-3) are as defined in formula (II-A). It is understood that embodiments of $X^1$, $R^1$, $R^3$, L, A, B, and Z described for formula (II-AB'), (II-AB), or (II-A) may, where applicable, apply in some embodiments to formula (II-A-3).

In some aspects, a compound or a stereoisomer, tautomer, or pharmaceutically acceptable salt thereof of the following formula (II-A-4) is provided:

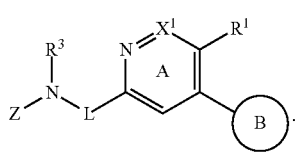

(II-A-4)

In one aspect, $X^1$, $R^1$, $R^3$, L, A, B, and Z of formula (II-A-4) are as defined in formula (II-AB'). In one aspect, $X^1$, $R^1$, $R^3$, L, A, B, and Z of formula (II-A-4) are as defined in formula (II-AB). In one aspect, $X^1$, $R^1$, $R^3$, L, A, B, and Z of formula (II-A-4) are as defined in formula (II-A). It is understood that embodiments of $X^1$, $R^1$, $R^3$, L, A, B, and Z described for formula (II-AB'), (II-AB), or (II-A) may, where applicable, apply in some embodiments to formula (II-A-4).

In some aspects, a compound or a stereoisomer, tautomer, or pharmaceutically acceptable salt thereof of the following formula (II-A-5) is provided:

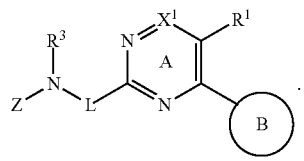

(II-A-5)

In one aspect, $X^1$, $R^1$, $R^3$, L, A, B, and Z of formula (II-A-5) are as defined in formula (II-AB'). In one aspect, $X^1$, $R^1$, $R^3$, L, A, B, and Z of formula (II-A-5) are as defined in formula (II-AB). In one aspect, $X^1$, $R^1$, $R^3$, L, A, B, and Z of formula (II-A-5) are as defined in formula (II-A). It is understood that embodiments of $X^1$, $R^1$, $R^3$, L, A, B, and Z described for formula (II-AB'), (II-AB), or (II-A) may, where applicable, apply in some embodiments to formula (II-A-5).

In some aspects, a compound or a stereoisomer, tautomer, or pharmaceutically acceptable salt thereof of the following formula (II-A-6) is provided:

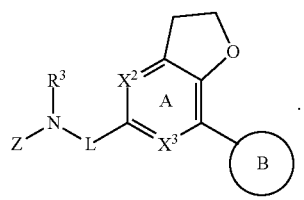

(II-A-6)

In one aspect, $X^2$, $X^3$, $R^3$, L, A, B, and Z of formula (II-A-6) are as defined in formula (II-AB'). In one aspect, $X^2$, $X^3$, $R^3$, L, A, B, and Z of formula (II-A-6) are as defined in formula (II-AB). In one aspect, $X^2$, $X^3$, $R^3$, L, A, B, and Z of formula (II-A-6) are as defined in formula (II-A). It is understood that embodiments of $X^2$, $X^3$, $R^3$, L, A, B, and Z described for formula (II-AB'), (II-AB), or (II-A) may, where applicable, apply in some embodiments to formula (II-A-6).

In some aspects, a compound or a stereoisomer, tautomer, or pharmaceutically acceptable salt thereof of the following formula (II-A-7) is provided:

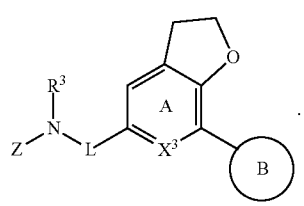

(II-A-7)

In one aspect, $X^3$, $R^3$, L, A, B, and Z of formula (II-A-7) are as defined in formula (II-AB'). In one aspect, $X^3$, $R^3$, L, A, B, and Z of formula (II-A-7) are as defined in formula (II-AB). In one aspect, $X^3$, $R^3$, L, A, B, and Z of formula (II-A-7) are as defined in formula (II-A). It is understood that embodiments of $X^3$, $R^3$, L, A, B, and Z described for formula (II-AB'), (II-AB), or (II-A) may, where applicable, apply in some embodiments to formula (II-A-7).

In some aspects, a compound or a stereoisomer, tautomer, or pharmaceutically acceptable salt thereof of the following formula (II-A-8) is provided:

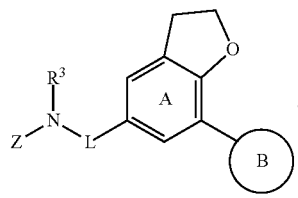

(II-A-8)

In one aspect, $R^3$, L, A, B, and Z of formula (II-A-8) are as defined in formula (II-AB'). In one aspect, $R^3$, L, A, B, and Z of formula (II-A-8) are as defined in formula (II-AB). In one aspect, $R^3$, L, A, B, and Z of formula (II-A-8) are as defined in formula (II-A). It is understood that embodiments of $R^3$, L, A, B, and Z described for formula (II-AB'), (II-AB), or (II-A) may, where applicable, apply in some embodiments to formula (II-A-8).

In some aspects, a compound or a stereoisomer, tautomer, or pharmaceutically acceptable salt thereof of the following formula (II-A-9) is provided:

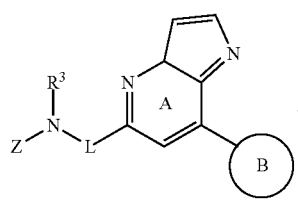

(II-A-9)

In one aspect, $R^3$, L, A, B, and Z of formula (II-A-9) are as defined in formula (II-AB'). In one aspect, $R^3$, L, A, B, and Z of formula (II-A-9) are as defined in formula (II-AB). In one aspect, $R^3$, L, A, B, and Z of formula (II-A-9) are as defined in formula (II-A). It is understood that embodiments of $R^3$, L, A, B, and Z described for formula (II-AB'), (II-AB), or (II-A) may, where applicable, apply in some embodiments to formula (II-A-9).

In some aspects, a compound or a stereoisomer, tautomer, or pharmaceutically acceptable salt thereof of the following formula (II-A-10) is provided:

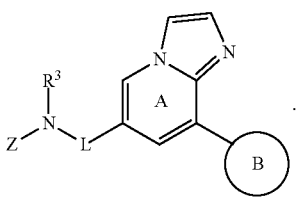

(II-A-10)

In one aspect, $R^3$, L, A, B, and Z of formula (II-A-10) are as defined in formula (II-AB'). In one aspect, $R^3$, L, A, B, and Z of formula (II-A-10) are as defined in formula (II-AB). In one aspect, $R^3$, L, A, B, and Z of formula (II-A-10) are as defined in formula (II-A). It is understood that embodiments of $R^3$, L, A, B, and Z described for formula (II-AB'), (II-AB), or (II-A) may, where applicable, apply in some embodiments to formula (II-A-10).

In some aspects, a compound or a stereoisomer, tautomer, or pharmaceutically acceptable salt thereof of the following formula (II-A-11) is provided:


(II-A-11)

In one aspect, $R^3$, L, A, B, and Z of formula (II-A-11) are as defined in formula (II-AB'). In one aspect, $R^3$, L, A, B, and Z of formula (II-A-11) are as defined in formula (II-AB). In one aspect, $R^3$, L, A, B, and Z of formula (II-A-11) are as defined in formula (II-A). It is understood that embodiments of $R^3$, L, A, B, and Z described for formula (II-AB'), (II-AB), or (II-A) may, where applicable, apply in some embodiments to formula (II-A-11).

In some aspects, a compound or a stereoisomer, tautomer, or pharmaceutically acceptable salt thereof of the following formula (II-A-12) is provided:

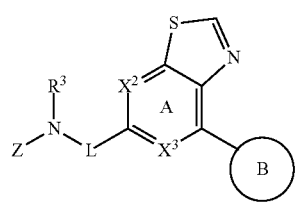

(II-A-12)

In one aspect, $X^2$, $X^3$, $R^3$, L, A, B, and Z of formula (II-A-12) are as defined in formula (II-AB'). In one aspect, $X^2$, $X^3$, $R^3$, L, A, B, and Z of formula (II-A-12) are as defined in formula (II-AB). In one aspect, $X^2$, $X^3$, $R^3$, L, A, B, and Z of formula (II-A-12) are as defined in formula (II-A). It is understood that embodiments of $X^2$, $X^3$, $R^3$, L, A, B, and Z described for formula (II-AB'), (II-AB), or (II-A) may, where applicable, apply in some embodiments to formula (II-A-12).

In some aspects, a compound or a stereoisomer, tautomer, or pharmaceutically acceptable salt thereof of the following formula (II-A-13) is provided:

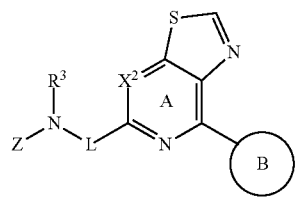

(II-A-13)

In one aspect, $X^2$, $R^3$, L, A, B, and Z of formula (II-A-13) are as defined in formula (II-AB'). In one aspect, $X^2$, $R^3$, L, A, B, and Z of formula (II-A-13) are as defined in formula (II-AB). In one aspect, $X^2$, $R^3$, L, A, B, and Z of formula (II-A-13) are as defined in formula (II-A). It is understood that embodiments of $X^2$, $R^3$, L, A, B, and Z described for formula (II-AB'), (II-AB), or (II-A) may, where applicable, apply in some embodiments to formula (II-A-13).

In some aspects, a compound or a stereoisomer, tautomer, or pharmaceutically acceptable salt thereof of the following formula (II-A-14) is provided:

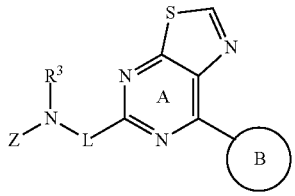

(II-A-14)

In one aspect, $R^3$, L, A, B, and Z of formula (II-A-14) are as defined in formula (II-AB'). In one aspect, $R^3$, L, A, B, and Z of formula (II-A-14) are as defined in formula (II-AB). In one aspect, $R^3$, L, A, B, and Z of formula (II-A-14) are as defined in formula (II-A). It is understood that embodiments of $R^3$, L, A, B, and Z described for formula (II-AB'), (II-AB), or (II-A) may, where applicable, apply in some embodiments to formula (II-A-14).

In some aspects, a compound or a stereoisomer, tautomer, or pharmaceutically acceptable salt thereof of the following formula (II-A-15) is provided:

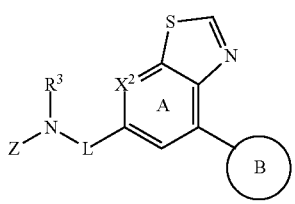

(II-A-15)

In one aspect, $R^3$, L, A, B, and Z of formula (II-A-15) are as defined in formula (II-AB'). In one aspect, $R^3$, L, A, B, and Z of formula (II-A-15) are as defined in formula (II-AB). In one aspect, $R^3$, L, A, B, and Z of formula (II-A-15) are as defined in formula (II-A). It is understood that embodiments of $R^3$, L, A, B, and Z described for formula (II-AB'), (II-AB), or (II-A) may, where applicable, apply in some embodiments to formula (II-A-15).

In some aspects, a compound or a stereoisomer, tautomer, or pharmaceutically acceptable salt thereof of the following formula (II-A-16) is provided:

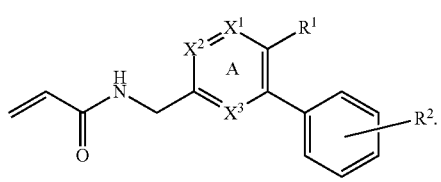

(II-A-16)

In one aspect, $R^1$, $R^2$, $X^1$, $X^2$, $X^3$, and A of formula (II-A-16) are as defined in formula (IL-AB'). In one aspect, $R^1$, $R^2$, $X^1$, $X^2$, $X^3$, and A of formula (II-A-16) are as defined in formula (II-AB). In one aspect, $R^1$, $R^2$, $X^1$, $X^2$, $X^3$, and A of formula (II-A-16) are as defined in formula (II-A). It is understood that embodiments of $R^1$, $R^2$, $X^1$, $X^2$, $X^3$, and A described for formula (II-AB'), (II-AB), or (II-A) may, where applicable, apply in some embodiments to formula (II-A-16).

In some aspects, a compound or a stereoisomer, tautomer, or pharmaceutically acceptable salt thereof of the following formula (II-A-17) is provided:

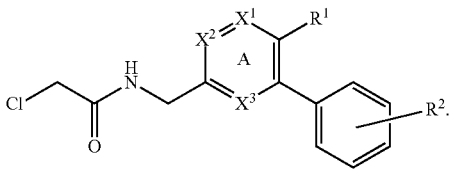

(II-A-17)

In one aspect, $R^1$, $R^2$, $X^1$, $X^2$, $X^3$, and A of formula (II-A-17) are as defined in formula (II-AB'). In one aspect, $R^1$, $R^2$, $X^1$, $X^2$, $X^3$, and A of formula (II-A-17) are as defined in formula (II-AB). In one aspect, $R^1$, $R^2$, $X^1$, $X^2$, $X^3$, and A of formula (II-A-17) are as defined in formula (II-A). It is understood that embodiments of $R^1$, $R^2$, $X^1$, $X^2$, $X^3$, and A described for formula (II-AB'), (II-AB), or (II-A) may, where applicable, apply in some embodiments to formula (II-A-17).

In some aspects, a compound or a stereoisomer, tautomer, or pharmaceutically acceptable salt thereof of the following formula (II-A-18) is provided:

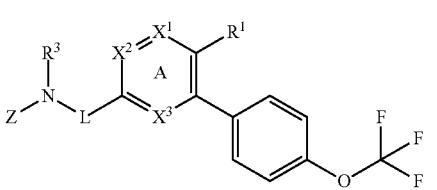

(II-A-18)

In one aspect, $R^1$, $R^3$, $X^1$, $X^2$, $X^3$, L, A, and Z of formula (II-A-18) are as defined in formula (II-AB'). In one aspect, $R^1$, $R^3$, $X^1$, $X^2$, $X^3$, L, A, and Z of formula (II-A-18) are as defined in formula (II-AB). In one aspect, $R^1$, $R^3$, $X^1$, $X^2$, $X^3$, L, A, and Z of formula (II-A-18) are as defined in formula (II-A). It is understood that embodiments of $R^1$, $R^3$, $X^1$, $X^2$, $X^3$, L, A, and Z described for formula (II-AB'), (II-AB), or (II-A) may, where applicable, apply in some embodiments to formula (II-A-18).

In some aspects, a compound or a stereoisomer, tautomer, or pharmaceutically acceptable salt thereof of the following formula (II-A-19) is provided:

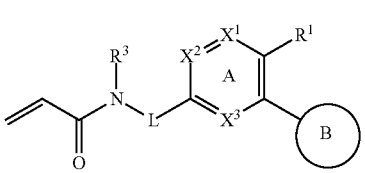

(II-A-19)

In one aspect, $R^1$, $R^3$, $X^1$, $X^2$, $X^3$, A, B, and L of formula (II-A-19) are as defined in formula (II-AB'). In one aspect, $R^1$, $R^3$, $X^1$, $X^2$, $X^3$, A, B, and L of formula (II-A-19) are as defined in formula (II-AB). In one aspect, $R^1$, $R^3$, $X^1$, $X^2$, $X^3$, A, B, and L of formula (II-A-19) are as defined in formula (II-A). It is understood that embodiments of $R^1$, $R^3$, $X^1$, $X^2$, $X^3$, A, B, and L described for formula (II-AB'), (II-AB), or (II-A) may, where applicable, apply in some embodiments to formula (II-A-19).

In some aspects, a compound or a stereoisomer, tautomer, or pharmaceutically acceptable salt thereof of the following formula (II-A-20) is provided:

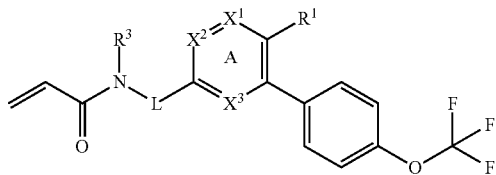

(II-A-20)

In one aspect, $R^1$, $R^3$, $X^1$, $X^2$, $X^3$, A, and L of formula (II-A-20) are as defined in formula (II-AB'). In one aspect, $R^1$, $R^3$, $X^1$, $X^2$, $X^3$, A, and L of formula (II-A-20) are as defined in formula (II-AB). In one aspect, $R^1$, $R^3$, $X^1$, $X^2$, $X^3$, A, and L of formula (II-A-20) are as defined in formula (II-A). It is understood that embodiments of $R^1$, $R^3$, $X^1$, $X^2$, $X^3$, A, and L described for formula (II-AB'), (II-AB), or (II-A) may, where applicable, apply in some embodiments to formula (II-A-20).

In some aspects, a compound or a stereoisomer, tautomer, or pharmaceutically acceptable salt thereof of the following formula (II-A-21) is provided:

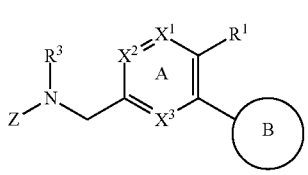

(II-A-21)

In one aspect, $R^1$, $R^3$, $X^1$, $X^2$, $X^3$, A, B, and Z of formula (II-A-21) are as defined in formula (II-AB'). In one aspect, $R^1$, $R^3$, $X^1$, $X^2$, $X^3$, A, B, and Z of formula (II-A-21) are as defined in formula (II-AB). In one aspect, $R^1$, $R^3$, $X^1$, $X^2$, $X^3$, A, B, and Z of formula (II-A-21) are as defined in formula (II-A). It is understood that embodiments of $R^1$, $R^3$, $X^1$, $X^2$, $X^3$, A, B, and Z described for formula (II-AB'), (II-AB), or (II-A) may, where applicable, apply in some embodiments to formula (II-A-21).

In some aspects, a compound or a stereoisomer, tautomer, or pharmaceutically acceptable salt thereof of the following formula (II-A-22) is provided:

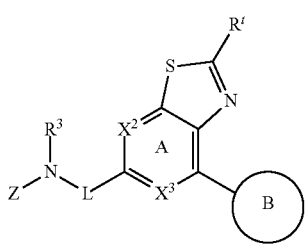

(II-A-22)

In one aspect, $R^t$, $R^3$, $X^2$, $X^3$, A, B, L, and Z of formula (II-A-22) are as defined in formula (II-AB'). In one aspect, R, $R^3$, $X^2$, $X^3$, A, B, L, and Z of formula (II-A-22) are as defined in formula (II-AB). In one aspect, $R^t$, $R^3$, $X^2$, $X^3$, A, B, L, and Z of formula (II-A-22) are as defined in formula (II-A). It is understood that embodiments of $R^t$, $R^3$, $X^2$, $X^3$, A, B, L, and Z described for formula (II-AB'), (II-AB), or (II-A) may, where applicable, apply in some embodiments to formula (II-A-22).

In some aspects, a compound or a stereoisomer, tautomer, or pharmaceutically acceptable salt thereof of the following formula (II-A-23) is provided:

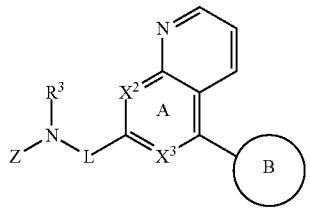

(II-A-23)

In one aspect, $R^3$, $X^2$, $X^3$, A, B, L, and Z of formula (II-A-23) are as defined in formula (II-AB'). In one aspect, $R^3$, $X^2$, $X^3$, A, B, L, and Z of formula (II-A-23) are as defined in formula (II-AB). In one aspect, $R^3$, $X^2$, $X^3$, A, B, L, and Z of formula (II-A-23) are as defined in formula (II-A). It is understood that embodiments of $R^3$, $X^2$, $X^3$, A, B, L, and Z described for formula (II-AB'), (II-AB), or (II-A) may, where applicable, apply in some embodiments to formula (II-A-23).

In some aspects, a compound or a stereoisomer, tautomer, or pharmaceutically acceptable salt thereof of the following formula (II-A-24) is provided:

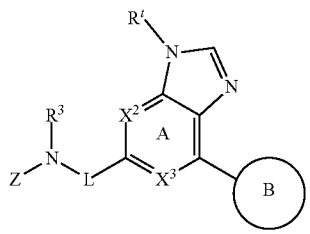

(II-A-24)

In one aspect, R, $R^3$, $X^2$, $X^3$, A, B, L, and Z of formula (II-A-24) are as defined in formula (II-AB'). In one aspect, $R^t$, $R^3$, $X^2$, $X^3$, A, B, L, and Z of formula (II-A-24) are as defined in formula (II-AB). In one aspect, R, $R^3$, $X^2$, $X^3$, A, B, L, and Z of formula (II-A-24) are as defined in formula (II-A). It is understood that embodiments of R, $R^3$, $X^2$, $X^3$, A, B, L, and Z described for formula (II-AB'), (II-AB), or (II-A) may, where applicable, apply in some embodiments to formula (II-A-24).

In some aspects, a compound or a stereoisomer, tautomer, or pharmaceutically acceptable salt thereof of the following formula (II-A-25) is provided:

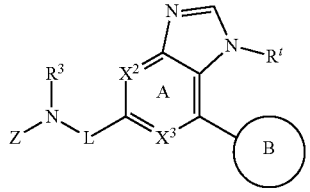

(II-A-25)

In one aspect, $R^t$, $R^3$, $X^2$, $X^3$, A, B, L, and Z of formula (II-A-25) are as defined in formula (II-AB'). In one aspect, $R^t$, $R^3$, $X^2$, $X^3$, A, B, L, and Z of formula (II-A-25) are as defined in formula (II-AB). In one aspect, R', R³, X², X³, A, B, L, and Z of formula (II-A-25) are as defined in formula (II-A). It is understood that embodiments of R', R³, X², X³, A, B, L, and Z described for formula (II-AB'), (II-AB), or (II-A) may, where applicable, apply in some embodiments to formula (II-A-25).

In some aspects, a compound or a stereoisomer, tautomer, or pharmaceutically acceptable salt thereof of the following formula (II-A-26) is provided:

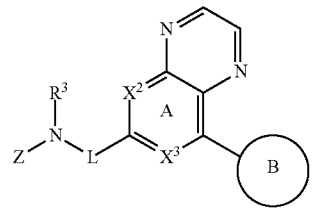

(II-A-26)

In one aspect, R³, X², X³, A, B, L, and Z of formula (II-A-26) are as defined in formula (II-AB'). In one aspect, R³, X², X³, A, B, L, and Z of formula (II-A-26) are as defined in formula (II-AB). In one aspect, R³, X², X³, A, B, L, and Z of formula (II-A-26) are as defined in formula (II-A). It is understood that embodiments of R³, X², X³, A, B, L, and Z described for formula (II-AB'), (II-AB), or (II-A) may, where applicable, apply in some embodiments to formula (II-A-26).

In some aspects, a compound or a stereoisomer, tautomer, or pharmaceutically acceptable salt thereof of the following formula (II-B-1) is provided:

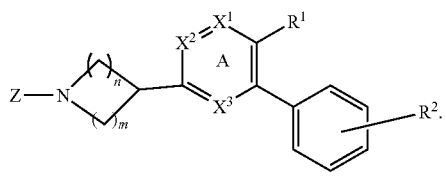

(II-B-1)

In one aspect, R¹, R², X¹, X², X³, n, m, A, and Z of formula (II-B-1) are as defined in formula (II-AB'). In one aspect, R¹, R², X¹, X², X³, n, m, A, and Z of formula (II-B-1) are as defined in formula (II-AB). In one aspect, R¹, R², X¹, X², X³, n, m, A, and Z of formula (II-B-1) are as defined in formula (IL-B). It is understood that embodiments of R¹, R², X¹, X², X³, n, m, A, and Z described for formula (II-AB'), (II-AB), or (II-B) may, where applicable, apply in some embodiments to formula (II-B-1).

In some aspects, a compound or a stereoisomer, tautomer, or pharmaceutically acceptable salt thereof of the following formula (II-B-2) is provided:

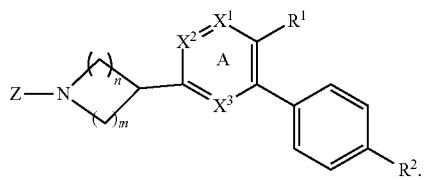

(II-B-2)

In one aspect, R¹, R², X¹, X², X³, n, m, A, and Z of formula (II-B-2) are as defined in formula (II-AB'). In one aspect, R¹, R², X¹, X², X³, n, m, A, and Z of formula (II-B-2) are as defined in formula (II-AB). In one aspect, R¹, R², X¹, X², X³, n, m, A, and Z of formula (II-B-2) are as defined in formula (II-B). It is understood that embodiments of R¹, R², X¹, X², X³, n, m, A, and Z described for formula (II-AB'), (II-AB), or (II-B) may, where applicable, apply in some embodiments to formula (II-B-2).

In some aspects, a compound or a stereoisomer, tautomer, or pharmaceutically acceptable salt thereof of the following formula (II-B-3) is provided:

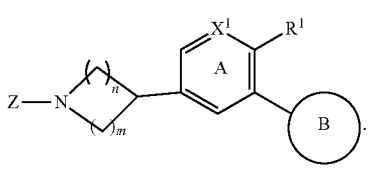

(II-B-3)

In one aspect, R¹, X¹, n, m, A, B, and Z of formula (II-B-3) are as defined in formula (II-AB'). In one aspect, R¹, X¹, n, m, A, B, and Z of formula (II-B-3) are as defined in formula (II-AB). In one aspect, R¹, X¹, n, m, A, B, and Z of formula (II-B-3) are as defined in formula (II-B). It is understood that embodiments of R¹, X¹, n, m, A, B, and Z described for formula (II-AB'), (II-AB), or (II-B) may, where applicable, apply in some embodiments to formula (II-B-3).

In some aspects, a compound or a stereoisomer, tautomer, or pharmaceutically acceptable salt thereof of the following formula (II-B-4) is provided:

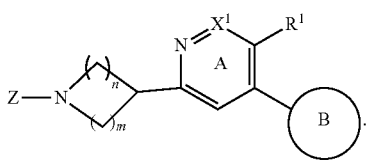

(II-B-4)

In one aspect, R¹, X¹, n, m, A, B, and Z of formula (II-B-4) are as defined in formula (II-AB'). In one aspect, R¹, X¹, n, m, A, B, and Z of formula (II-B-4) are as defined in formula (II-AB). In one aspect, R¹, X¹, n, m, A, B, and Z of formula (II-B-4) are as defined in formula (II-B). It is understood that embodiments of R¹, X¹, n, m, A, B, and Z described for formula (II-AB'), (II-AB), or (II-B) may, where applicable, apply in some embodiments to formula (II-B-4).

In some aspects, a compound or a stereoisomer, tautomer, or pharmaceutically acceptable salt thereof of the following formula (II-B-5) is provided:

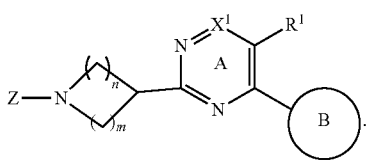

(II-B-5)

In one aspect, R¹, X¹, n, m, A, B, and Z of formula (II-B-5) are as defined in formula (II-AB'). In one aspect, R¹, X¹, n, m, A, B, and Z of formula (II-B-5) are as defined in formula (II-AB). In one aspect, $R^1$, $X^1$, n, m, A, B, and Z of formula (II-B-5) are as defined in formula (II-B). It is understood that embodiments of $R^1$, $X^1$, n, m, A, B, and Z described for formula (II-AB'), (II-AB), or (IL-B) may, where applicable, apply in some embodiments to formula (II-B-5).

In some aspects, a compound or a stereoisomer, tautomer, or pharmaceutically acceptable salt thereof of the following formula (II-B-6) is provided:

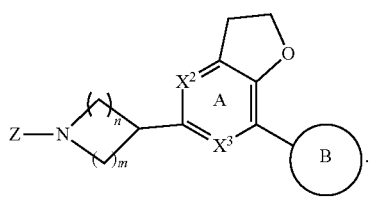

(II-B-6)

In one aspect, $X^2$, $X^3$, n, m, A, B, and Z of formula (II-B-6) are as defined in formula (II-AB'). In one aspect, $X^2$, $X^3$, n, m, A, B, and Z of formula (II-B-6) are as defined in formula (II-AB). In one aspect, $X^2$, $X^3$, n, m, A, B, and Z of formula (II-B-6) are as defined in formula (II-B). It is understood that embodiments of $X^2$, $X^3$, n, m, A, B, and Z described for formula (II-AB'), (II-AB), or (II-B) may, where applicable, apply in some embodiments to formula (II-B-6).

In some aspects, a compound or a stereoisomer, tautomer, or pharmaceutically acceptable salt thereof of the following formula (II-B-7) is provided:

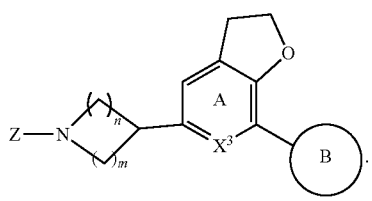

(II-B-7)

In one aspect, $X^3$, n, m, A, B, and Z of formula (II-B-7) are as defined in formula (II-AB'). In one aspect, $X^3$, n, m, A, B, and Z of formula (II-B-7) are as defined in formula (II-AB). In one aspect, $X^3$, n, m, A, B, and Z of formula (II-B-7) are as defined in formula (II-B). It is understood that embodiments of $X^3$, n, m, A, B, and Z described for formula (II-AB'), (II-AB), or (II-B) may, where applicable, apply in some embodiments to formula (II-B-7).

In some aspects, a compound or a stereoisomer, tautomer, or pharmaceutically acceptable salt thereof of the following formula (II-B-8) is provided:

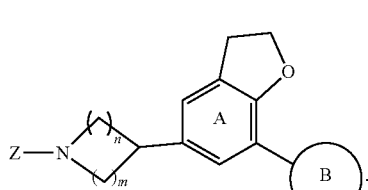

(II-B-8)

In one aspect, n, m, A, B, and Z of formula (II-B-8) are as defined in formula (II-AB'). In one aspect, n, m, A, B, and Z of formula (II-B-8) are as defined in formula (II-B). It is understood that embodiments of n, m, A, B, and Z described for formula (II-AB'), (II-AB), or (II-B) may, where applicable, apply in some embodiments to formula (II-B-8).

In some aspects, a compound or a stereoisomer, tautomer, or pharmaceutically acceptable salt thereof of the following formula (II-B-9) is provided:

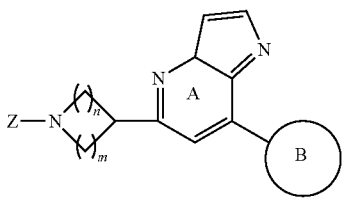

(II-B-9)

In one aspect, n, m, A, B, and Z of formula (II-B-9) are as defined in formula (II-AB'). In one aspect, n, m, A, B, and Z of formula (II-B-9) are as defined in formula (II-AB). In one aspect, n, m, A, B, and Z of formula (II-B-9) are as defined in formula (II-B). It is understood that embodiments of n, m, A, B, and Z described for formula (II-AB'), (II-AB), or (II-B) may, where applicable, apply in some embodiments to formula (II-B-9).

In some aspects, a compound or a stereoisomer, tautomer, or pharmaceutically acceptable salt thereof of the following formula (II-B-10) is provided:

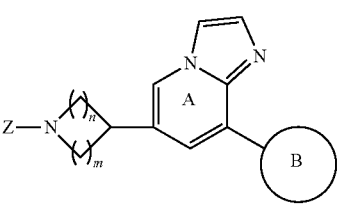

(II-B-10)

In one aspect, n, m, A, B, and Z of formula (II-B-10) are as defined in formula (II-AB'). In one aspect, n, m, A, B, and Z of formula (II-B-10) are as defined in formula (II-AB). In one aspect, n, m, A, B, and Z of formula (II-B-10) are as defined in formula (II-B). It is understood that embodiments of n, m, A, B, and Z described for formula (II-AB'), (II-AB), or (II-B) may, where applicable, apply in some embodiments to formula (II-B-10).

In some aspects, a compound or a stereoisomer, tautomer, or pharmaceutically acceptable salt thereof of the following formula (II-B-11) is provided:

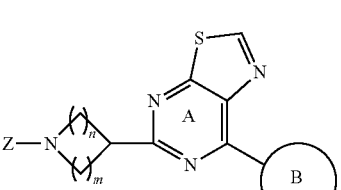

(II-B-11)

In one aspect, n, m, A, B, and Z of formula (II-B-11) are as defined in formula (II-AB'). In one aspect, n, m, A, B, and Z of formula (II-B-11) are as defined in formula (II-AB). In one aspect, n, m, A, B, and Z of formula (II-B-11) are as defined in formula (II-B). It is understood that embodiments of n, m, A, B, and Z described for formula (II-AB'), (II-AB), or (II-B) may, where applicable, apply in some embodiments to formula (II-B-11).

In some aspects, a compound or a stereoisomer, tautomer, or pharmaceutically acceptable salt thereof of the following formula (II-B-12) is provided:

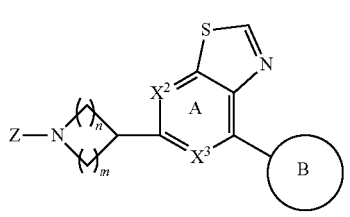

(II-B-12)

In one aspect, $X^1$, $X^2$, n, m, A, B, and Z of formula (II-B-12) are as defined in formula (II-AB'). In one aspect, $X^1$, $X^2$, n, m, A, B, and Z of formula (II-B-12) are as defined in formula (II-AB). In one aspect, $X^1$, $X^2$, n, m, A, B, and Z of formula (II-B-12) are as defined in formula (II-B). It is understood that embodiments of $X^1$, $X^2$, n, m, A, B, and Z described for formula (II-AB'), (II-AB), or (II-B) may, where applicable, apply in some embodiments to formula (II-B-12).

In some aspects, a compound or a stereoisomer, tautomer, or pharmaceutically acceptable salt thereof of the following formula (II-B-13) is provided:

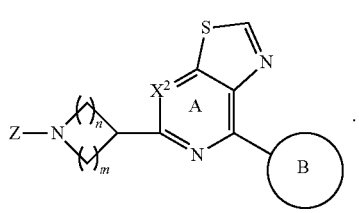

(II-B-13)

In one aspect, $X^2$, n, m, A, B, and Z of formula (II-B-13) are as defined in formula (II-AB'). In one aspect, $X^2$, n, m, A, B, and Z of formula (II-B-13) are as defined in formula (II-AB). In one aspect, $X^2$, n, m, A, B, and Z of formula (II-B-13) are as defined in formula (II-B). It is understood that embodiments of $X^2$, n, m, A, B, and Z described for formula (II-AB'), (II-AB), or (II-B) may, where applicable, apply in some embodiments to formula (II-B-13).

In some aspects, a compound or a stereoisomer, tautomer, or pharmaceutically acceptable salt thereof of the following formula (II-B-14) is provided:

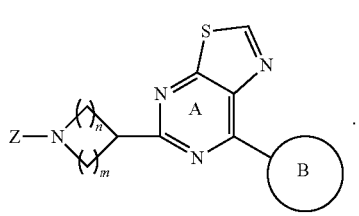

(II-B-14)

In one aspect, n, m, A, B, and Z of formula (II-B-14) are as defined in formula (II-AB'). In one aspect, n, m, A, B, and Z of formula (II-B-14) are as defined in formula (II-AB). In one aspect, n, m, A, B, and Z of formula (II-B-14) are as defined in formula (II-B). It is understood that embodiments of n, m, A, B, and Z described for formula (II-AB'), (II-AB), or (II-B) may, where applicable, apply in some embodiments to formula (II-B-14).

In some aspects, a compound or a stereoisomer, tautomer, or pharmaceutically acceptable salt thereof of the following formula (II-B-15) is provided:

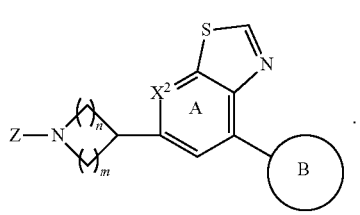

(II-B-15)

In one aspect, $X^2$, n, m, A, B, and Z of formula (II-B-15) are as defined in formula (II-AB'). In one aspect, $X^2$, n, m, A, B, and Z of formula (II-B-15) are as defined in formula (II-AB). In one aspect, $X^2$, n, m, A, B, and Z of formula (II-B-15) are as defined in formula (II-B). It is understood that embodiments of $X^2$, n, m, A, B, and Z described for formula (II-AB'), (II-AB), or (II-B) may, where applicable, apply in some embodiments to formula (II-B-15).

In some aspects, a compound or a stereoisomer, tautomer, or pharmaceutically acceptable salt thereof of the following formula (II-B-16) is provided

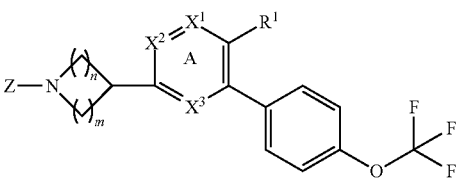

(II-B-16)

In one aspect, $R^1$, $X^1$, $X^2$, $X^3$, n, m, A, and Z of formula (II-B-16) are as defined in formula (II-AB'). In one aspect, $R^1$, $X^1$, $X^2$, $X^3$, n, m, A, and Z of formula (II-B-16) are as defined in formula (II-AB). In one aspect, $R^1$, $X^1$, $X^2$, $X^3$, n, m, A, and Z of formula (II-B-16) are as defined in formula (II-B). It is understood that embodiments of $R^1$, $X^1$, $X^2$, $X^3$, n, m, A, and Z described for formula (II-AB'), (II-AB), or (II-B) may, where applicable, apply in some embodiments to formula (II-B-16).

In some aspects, a compound or a stereoisomer, tautomer, or pharmaceutically acceptable salt thereof of the following formula (II-B-17) is provided

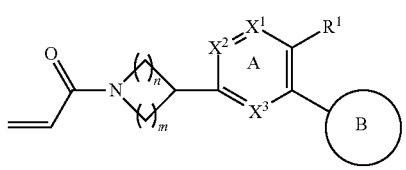

(II-B-17)

In one aspect, $R^1$, $X^1$, $X^2$, $X^3$, n, m, A, and B of formula (II-B-17) are as defined in formula (II-AB'). In one aspect, $R^1$, $X^1$, $X^2$, $X^3$, n, m, A, and B of formula (II-B-17) are as defined in formula (II-AB). In one aspect, $R^1$, $X^1$, $X^2$, $X^3$, n, m, A, and B of formula (II-B-17) are as defined in formula (II-B). It is understood that embodiments of $R^1$, $X^1$, $X^2$, $X^3$, n, m, A, and B described for formula (II-AB'), (II-AB), or (IL-B) may, where applicable, apply in some embodiments to formula (II-B-17).

In some aspects, a compound or a stereoisomer, tautomer, or pharmaceutically acceptable salt thereof of the following formula (II-B-18) is provided

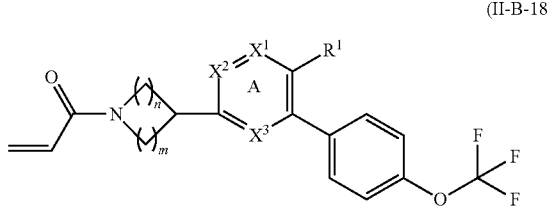

(II-B-18)

In one aspect, $R^1$, $X^1$, $X^2$, $X^3$, n, m, and A of formula (II-B-18) are as defined in formula (II-AB'). In one aspect, $R^1$, $X^1$, $X^2$, $X^3$, n, m, and A of formula (II-B-18) are as defined in formula (II-AB). In one aspect, $R^1$, $X^1$, $X^2$, $X^3$, n, m, and A of formula (II-B-18) are as defined in formula (II-B). It is understood that embodiments of $R^1$, $X^1$, $X^2$, $X^3$, n, m, and A described for formula (II-AB'), (II-AB), or (II-B) may, where applicable, apply in some embodiments to formula (II-B-18).

In some aspects, a compound or a stereoisomer, tautomer, or pharmaceutically acceptable salt thereof of the following formula (II-B-19) is provided

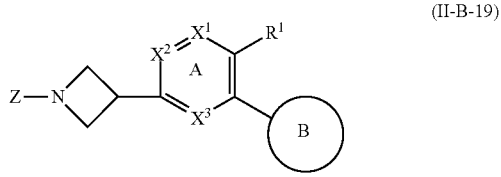

(II-B-19)

In one aspect, $R^1$, $X^1$, $X^2$, $X^3$, A, B, and Z of formula (II-B-19) are as defined in formula (II-AB'). In one aspect, $R^1$, $X^1$, $X^2$, $X^3$, A, B, and Z of formula (II-B-19) are as defined in formula (II-AB). In one aspect, $R^1$, $X^1$, $X^2$, $X^3$, A, B, and Z of formula (II-B-19) are as defined in formula (II-B). It is understood that embodiments of $R^1$, $X^1$, $X^2$, $X^3$, A, B, and Z described for formula (II-AB'), (II-AB), or (II-B) may, where applicable, apply in some embodiments to formula (II-B-19).

In some aspects, a compound or a stereoisomer, tautomer, or pharmaceutically acceptable salt thereof of the following formula (II-B-20) is provided

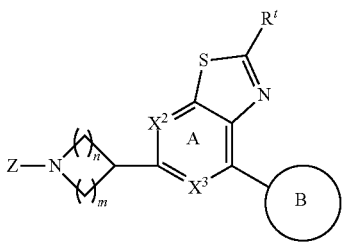

(II-B-20)

In one aspect, $R^1$, $X^2$, $X^3$, n, m, A, B, and Z of formula (II-B-20) are as defined in formula (II-AB'). In one aspect, $R^t$, $X^2$, $X^3$, n, m, A, B, and Z of formula (II-B-20) are as defined in formula (II-AB). In one aspect, $R^1$, $X^2$, $X^3$, n, m, A, B, and Z of formula (II-B-20) are as defined in formula (II-B). It is understood that embodiments of $R^1$, $X^2$, $X^3$, n, m, A, B, and Z described for formula (II-AB'), (II-AB), or (II-B) may, where applicable, apply in some embodiments to formula (II-B-20).

In some aspects, a compound or a stereoisomer, tautomer, or pharmaceutically acceptable salt thereof of the following formula (II-B-21) is provided

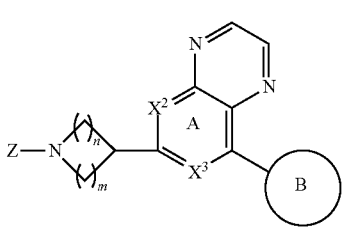

(II-B-21)

In one aspect, $X^2$, $X^3$, n, m, A, B, and Z of formula (II-B-21) are as defined in formula (II-AB'). In one aspect, $X^2$, $X^3$, n, m, A, B, and Z of formula (II-B-21) are as defined in formula (II-AB). In one aspect, $X^2$, $X^3$, n, m, A, B, and Z of formula (II-B-21) are as defined in formula (II-B). It is understood that embodiments of $X^2$, $X^3$, n, m, A, B, and Z described for formula (II-AB'), (II-AB), or (II-B) may, where applicable, apply in some embodiments to formula (II-B-21).

In some aspects, a compound or a stereoisomer, tautomer, or pharmaceutically acceptable salt thereof of the following formula (II-B-22) is provided

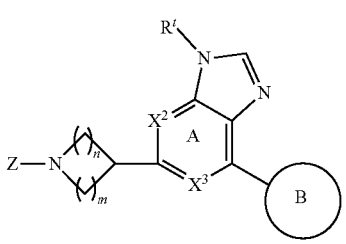

(II-B-22)

In one aspect, $R^t$, $X^2$, $X^3$, n, m, A, B, and Z of formula (II-B-22) are as defined in formula (II-AB'). In one aspect, $R^t$, $X^2$, $X^3$, n, m, A, B, and Z of formula (II-B-22) are as defined in formula (II-AB). In one aspect, $R^t$, $X^2$, $X^3$, n, m, A, B, and Z of formula (II-B-22) are as defined in formula (II-B). It is understood that embodiments of $R^t$, $X^2$, $X^3$, n, m, A, B, and Z described for formula (II-AB'), (II-AB), or (II-B) may, where applicable, apply in some embodiments to formula (II-B-22).

In some aspects, a compound or a stereoisomer, tautomer, or pharmaceutically acceptable salt thereof of the following formula (II-B-23) is provided

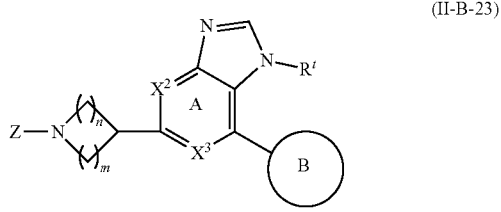

(II-B-23)

In one aspect, $R^t$, $X^2$, $X^3$, n, m, A, B, and Z of formula (II-B-23) are as defined in formula (II-AB'). In one aspect, R %, $X^2$, $X^3$, n, m, A, B, and Z of formula (II-B-23) are as defined in formula (II-AB). In one aspect, $R^t$, $X^2$, $X^3$, n, m, A, B, and Z of formula (II-B-23) are as defined in formula (II-B). It is understood that embodiments of R, $X^2$, $X^3$, n, m, A, B, and Z described for formula (II-AB'), (II-AB), or (II-B) may, where applicable, apply in some embodiments to formula (II-B-23).

In some aspects, a compound or a stereoisomer, tautomer, or pharmaceutically acceptable salt thereof of the following formula (II-B-24) is provided

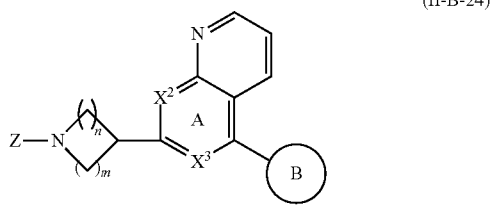

(II-B-24)

In one aspect, $X^2$, $X^3$, n, m, A, B, and Z of formula (II-B-24) are as defined in formula (II-AB'). In one aspect, $X^2$, $X^3$, n, m, A, B, and Z of formula (II-B-24) are as defined in formula (II-AB). In one aspect, $X^2$, $X^3$, n, m, A, B, and Z of formula (II-B-24) are as defined in formula (II-B). It is understood that embodiments of $X^2$, $X^3$, n, m, A, B, and Z described for formula (II-AB'), (II-AB), or (II-B) may, where applicable, apply in some embodiments to formula (II-B-24).

In some embodiments, in conjunction with embodiments above or below, wherein when B is phenyl substituted with one or more $R^2$, $R^2$ cannot be halo. In some embodiments, in conjunction with embodiments above or below, L' of formula (II-AB') or (II-AB) is *—N($R^3$)-L**.

In some embodiments, in conjunction with embodiments above or below, wherein when L' of formula (II-AB') or (II-AB) is

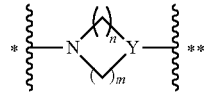

and B is phenyl substituted with one or more alkoxy, the one or more alkoxy is substituted with one or more halo (e.g., F, Cl, or Br).

In some embodiments, in conjunction with embodiments above or below, wherein when $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A, and wherein when the 5 to 6 membered heteroaryl, 5 to 6 membered heterocyclyl, phenyl, and $C_{5-6}$cycloalkyl formed by $X^1$ and $R^1$ are each independently substituted with one or more $R^t$, $R^t$ cannot be oxo.

In some embodiments, in conjunction with embodiments above or below, wherein when L' of formula (II-AB') or (II-AB) is *—N($R^3$)-L-**, Z is —C(O)$R^a$ or —S(O)$_2R^b$, wherein $R^a$ and $R^b$ are $C_{2-6}$alkenyl optionally substituted with one or more substituents selected from deuterium, $C_{1-6}$alkyl, hydroxyl $C_{1-6}$alkyl, halo and halo$C_{1-6}$alkyl.

In some embodiments, in conjunction with embodiments above or below, wherein when L' of formula (II-AB') or (II-AB) is

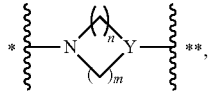

Z is —C(O)$R^a$, wherein $R^a$ is $C_{2-6}$alkenyl optionally substituted with one or more substituents selected from deuterium, $C_{1-6}$alkyl, hydroxyl $C_{1-6}$alkyl, halo and halo$C_{1-6}$alkyl.

In some aspects, compounds of formula (II-AB'), (II-AB), (II-A), or (II-B), or any variation or embodiment thereof, as appropriate, are selected from the compounds listed in Table 1 below, including racemic mixtures and resolved isomers:

| Compound Number | Structure | Compound Name |
|---|---|---|
| 1 | 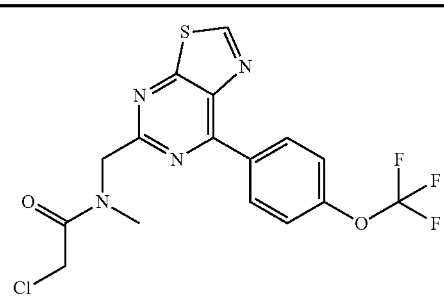 | 2-chloro-N-methyl-N-[[7-[4-(trifluoromethoxy)phenyl]thiazolo[5,4-d]pyrimidin-5-yl]methyl]acetamide |

| Compound Number | Structure | Compound Name |
|---|---|---|
| 2 | 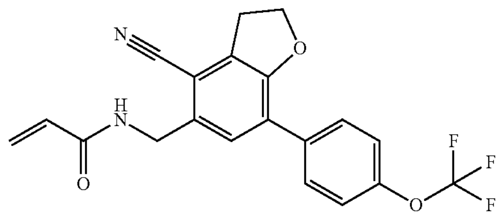 [SMILES: C=CC(=O)NCc1cc(-c2ccc(OC(F)(F)F)cc2)c2c(c1C#N)CCO2] | N-[[4-cyano-7-[4-(trifluoromethoxy)phenyl]-2,3-dihydrobenzofuran-5-yl]methyl]prop-2-enamide |
| 3 | 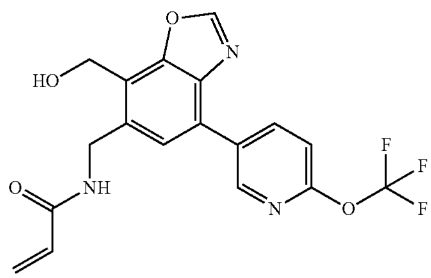 [SMILES: C=CC(=O)NCc1cc(-c2ccc(OC(F)(F)F)nc2)c2ncoc2c1CO] | N-[[7-(hydroxymethyl)-4-[6-(trifluoromethoxy)-3-pyridyl]-1,3-benzoxazol-6-yl]methyl]prop-2-enamide |
| 4 | 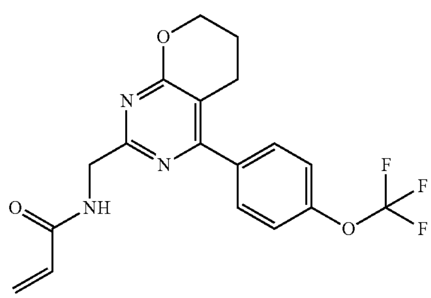 [SMILES: C=CC(=O)NCc1nc2c(c(-c3ccc(OC(F)(F)F)cc3)n1)CCCO2] | N-[[4-[4-(trifluoromethoxy)phenyl]-6,7-dihydro-5H-pyrano[2,3-d]pyrimidin-2-yl]methyl]prop-2-enamide |
| 5 | 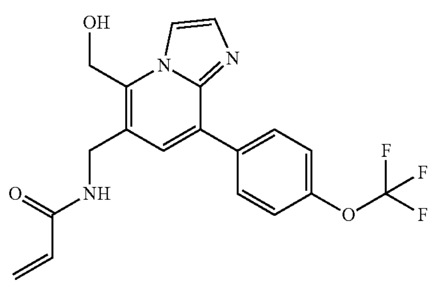 [SMILES: C=CC(=O)NCc1cc(-c2ccc(OC(F)(F)F)cc2)c2nccn2c1CO] | N-[[5-(hydroxymethyl)-8-[4-(trifluoromethoxy)phenyl]imidazo[1,2-a]pyridin-6-yl]methyl]prop-2-enamide |
| 6 | 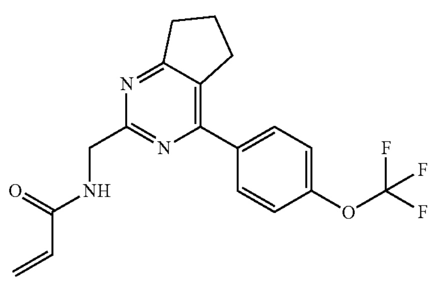 [SMILES: C=CC(=O)NCc1nc2c(c(-c3ccc(OC(F)(F)F)cc3)n1)CCC2] | N-[[4-[4-(trifluoromethoxy)phenyl]-6,7-dihydro-5H-cyclopenta[d]pyrimidin-2-yl]methyl]prop-2-enamide |

-continued

| Compound Number | Structure | Compound Name |
|---|---|---|
| 7 | 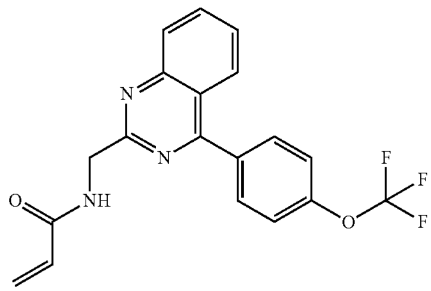 [SMILES: C=CC(=O)NCc1nc(-c2ccc(OC(F)(F)F)cc2)c2ccccc2n1] | N-[[4-[4-(trifluoromethoxy)phenyl]quinazolin-2-yl]methyl]prop-2-enamide |
| 8 | 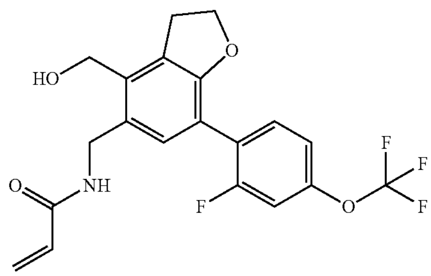 [SMILES: C=CC(=O)NCc1cc(-c2ccc(OC(F)(F)F)cc2F)c2c(c1CO)CCO2] | N-[[7-[2-fluoro-4-(trifluoromethoxy)phenyl]-4-(hydroxymethyl)-2,3-dihydrobenzofuran-5-yl]methyl]prop-2-enamide |
| 9 | 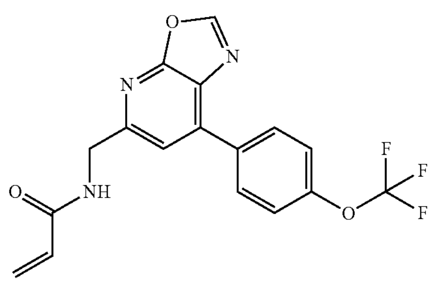 [SMILES: C=CC(=O)NCc1cc(-c2ccc(OC(F)(F)F)cc2)c2ncoc2n1] | N-[[7-4-(trifluoromethoxy)phenyl]oxazolo[5,4-b]pyridin-5-yl]methyl]prop-2-enamide |
| 10 | 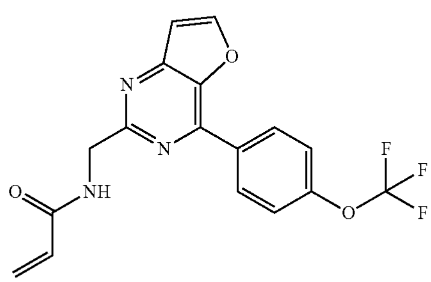 [SMILES: C=CC(=O)NCc1nc(-c2ccc(OC(F)(F)F)cc2)c2occc2n1] | N-[[4-[4-(trifluoromethoxy)phenyl]furo[3,2-d]pyrimidin-2-yl]methyl]prop-2-enamide |
| 11 | 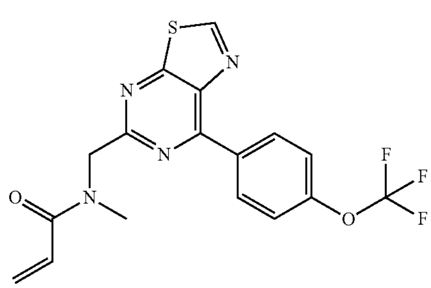 [SMILES: C=CC(=O)N(C)Cc1nc(-c2ccc(OC(F)(F)F)cc2)c2ncsc2n1] | N-methyl-N-[[7-[4-(trifluoromethoxy)phenyl]thiazolo[5,4-d]pyrimidin-5-yl]methyl]prop-2-enamide |

-continued

| Compound Number | Structure | Compound Name |
|---|---|---|
| 12 | 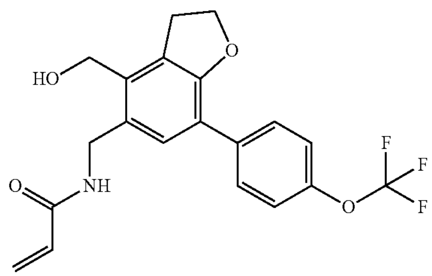 [SMILES: C=CC(=O)NCc1cc(-c2ccc(OC(F)(F)F)cc2)c2c(c1CO)CCO2] | N-[[4-(hydroxymethyl)-7-[4-(trifluoromethoxy)phenyl]-2,3-dihydrobenzofuran-5-yl]methyl]prop-2-enamide |
| 13 | 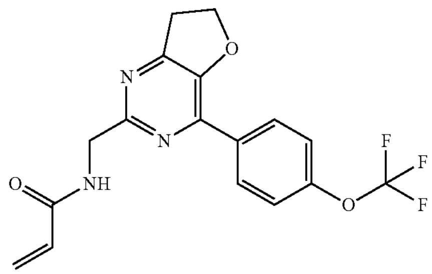 [SMILES: C=CC(=O)NCc1nc2c(c(-c3ccc(OC(F)(F)F)cc3)n1)OCC2] | N-[[4-[4-(trifluoromethoxy)phenyl]-6,7-dihydrofuro[3,2-d]pyrimidin-2-yl]methyl]prop-2-enamide |
| 14 | 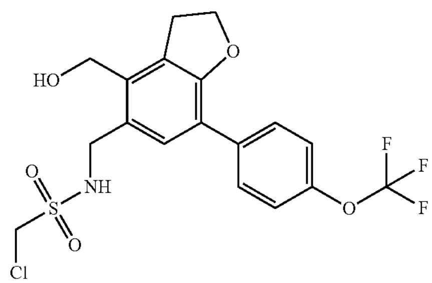 [SMILES: O=S(=O)(CCl)NCc1cc(-c2ccc(OC(F)(F)F)cc2)c2c(c1CO)CCO2] | 1-chloro-N-[[4-(hydroxymethyl)-7-[4-(trifluoromethoxy)phenyl]-2,3-dihydrobenzofuran-5-yl]methyl]methanesulfonamide |
| 15 | 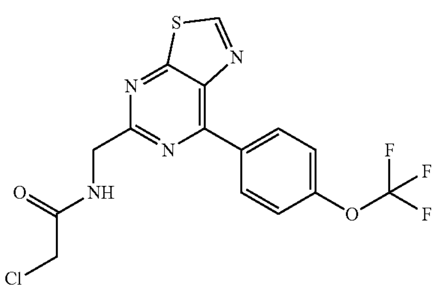 [SMILES: O=C(CCl)NCc1nc(-c2ccc(OC(F)(F)F)cc2)c2ncsc2n1] | 2-chloro-N-[[7-[4-(trifluoromethoxy)phenyl]thiazolo[5,4-d]pyrimidin-5-yl]methyl]acetamide |
| 16 | 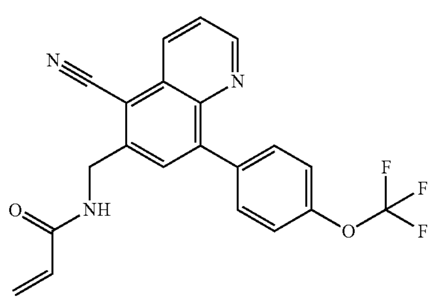 [SMILES: C=CC(=O)NCc1cc(-c2ccc(OC(F)(F)F)cc2)c2ncccc2c1C#N] | N-[[5-cyano-8-[4-(trifluoromethoxy)phenyl]-6-quinolyl]methyl]prop-2-enamide |

-continued

| Compound Number | Structure | Compound Name |
|---|---|---|
| 17 | 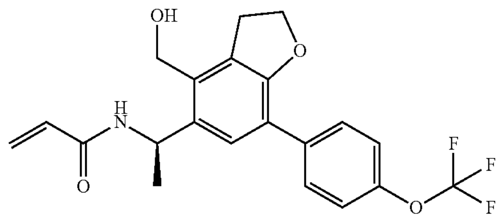 [SMILES: C=CC(=O)N[C@H](C)c1cc(-c2ccc(OC(F)(F)F)cc2)c2c(c1CO)CCO2] | N-[(1R)-1-[4-(hydroxymethyl)-7-[4-(trifluoromethoxy)phenyl]-2,3-dihydrobenzofuran-5-yl]ethyl]prop-2-enamide |
| 18 | 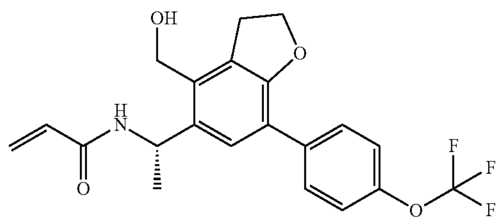 [SMILES: C=CC(=O)N[C@@H](C)c1cc(-c2ccc(OC(F)(F)F)cc2)c2c(c1CO)CCO2] | N-[(1S)-1-[4-(hydroxymethyl)-7-[4-(trifluoromethoxy)phenyl]-2,3-dihydrobenzofuran-5-yl]ethyl]prop-2-enamide |
| 19 | 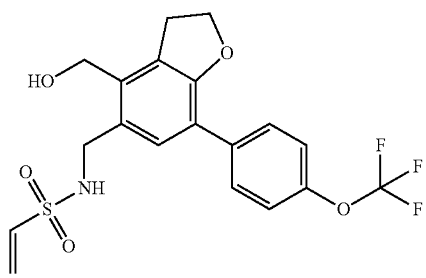 [SMILES: C=CS(=O)(=O)NCc1cc(-c2ccc(OC(F)(F)F)cc2)c2c(c1CO)CCO2] | N-[[4-(hydroxymethyl)-7-[4-(trifluoromethoxy)phenyl]-2,3-dihydrobenzofuran-5-yl]methyl]ethenesulfonamide |
| 20 | 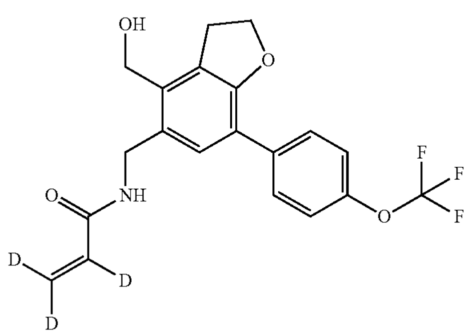 [SMILES: [2H]C([2H])=C([2H])C(=O)NCc1cc(-c2ccc(OC(F)(F)F)cc2)c2c(c1CO)CCO2] | 2,3,3-trideuterio-N-[[4-(hydroxymethyl)-7-[4-(trifluoromethoxy)phenyl]-2,3-dihydrobenzofuran-5-yl]methyl]prop-2-enamide |
| 21 | 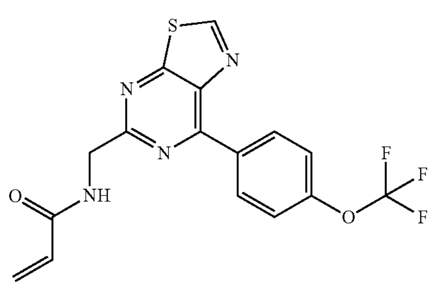 [SMILES: C=CC(=O)NCc1nc(-c2ccc(OC(F)(F)F)cc2)c2ncsc2n1] | N-[[7-4-(trifluoromethoxy)phenyl]thiazolo[5,4-d]pyrimidin-5-yl]methyl]prop-2-enamide |

-continued

| Compound Number | Structure | Compound Name |
|---|---|---|
| 22 | 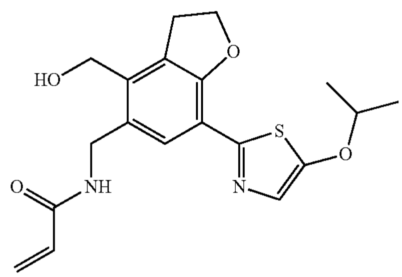 [SMILES: C=CC(=O)NCc1cc(-c2ncc(OC(C)C)s2)c2c(c1CO)CCO2] | N-[[4-(hydroxymethyl)-7-(5-isopropoxythiazol-2-yl)-2,3-dihydrobenzofuran-5-yl]methyl]prop-2-enamide |
| 23 | 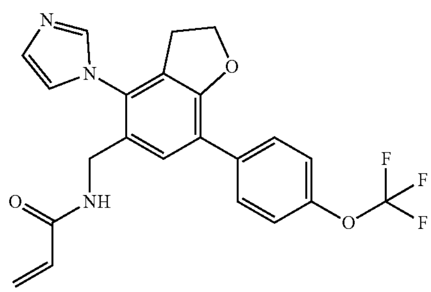 [SMILES: C=CC(=O)NCc1cc(-c2ccc(OC(F)(F)F)cc2)c2c(c1-n1ccnc1)CCO2] | N-[[4-imidazol-1-yl-7-[4-(trifluoromethoxy)phenyl]-2,3-dihydrobenzofuran-5-yl]methyl]prop-2-enamide |
| 24 | 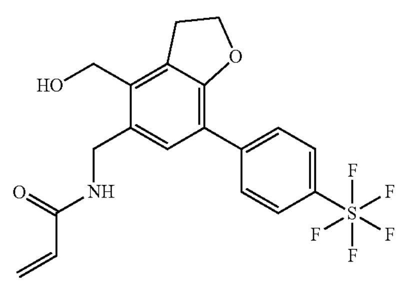 [SMILES: C=CC(=O)NCc1cc(-c2ccc(S(F)(F)(F)(F)F)cc2)c2c(c1CO)CCO2] | N-[[4-(hydroxymethyl)-7-[4-(pentafluoro-lambda6-sulfanyl)phenyl]-2,3-dihydrobenzofuran-5-yl]methyl]prop-2-enamide |
| 25 | 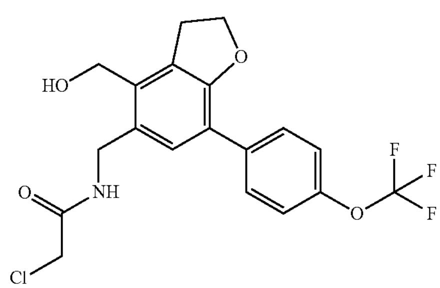 [SMILES: O=C(CCl)NCc1cc(-c2ccc(OC(F)(F)F)cc2)c2c(c1CO)CCO2] | 2-chloro-N-[[4-(hydroxymethyl)-7-[4-(trifluoromethoxy)phenyl]-2,3-dihydrobenzofuran-5-yl]methyl]acetamide |
| 26 | 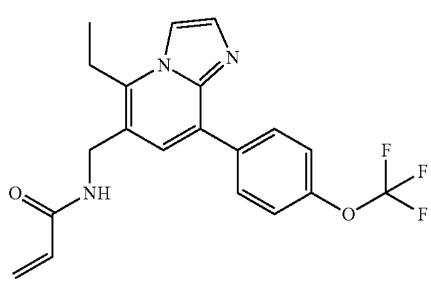 [SMILES: C=CC(=O)NCc1cc(-c2ccc(OC(F)(F)F)cc2)c2nccn2c1CC] | N-[[5-ethyl-8-[4-(trifluoromethoxy)phenyl]imidazo[1,2-a]pyridin-6-yl]methyl]prop-2-enamide |

| Compound Number | Structure | Compound Name |
|---|---|---|
| 27 | 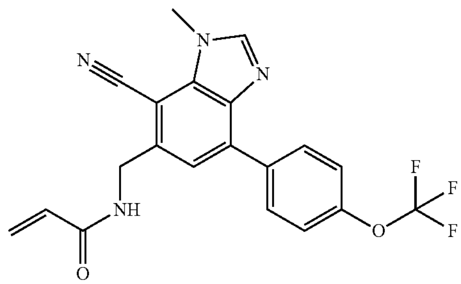 [SMILES: C=CC(=O)NCc1cc(-c2ccc(OC(F)(F)F)cc2)c2ncn(C)c2c1C#N] | N-[[4-cyano-3-methyl-7-[4-(trifluoromethoxy)phenyl]benzimidazol-5-yl]methyl]prop-2-enamide |
| 28 | 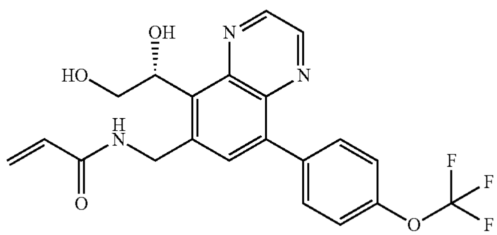 | N-[[5-[(1R)-1,2-dihydroxyethyl]-8-[4-(trifluoromethoxy)phenyl]quinoxalin-6-yl]methyl]prop-2-enamide |
| 29 | 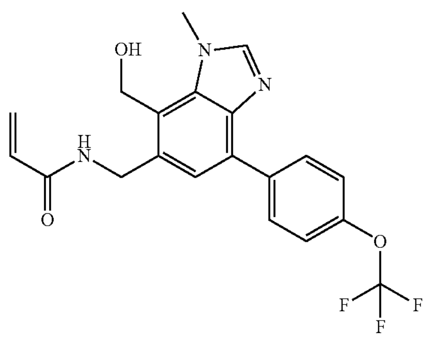 [SMILES: C=CC(=O)NCc1cc(-c2ccc(OC(F)(F)F)cc2)c2ncn(C)c2c1CO] | N-[[4-(hydroxymethyl)-3-methyl-7-[4-(trifluoromethoxy)phenyl]benzimidazol-5-yl]methyl]prop-2-enamide |
| 30 | 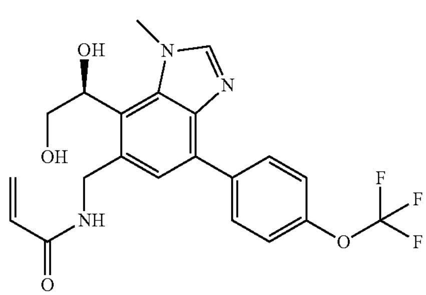 [SMILES: C=CC(=O)NCc1cc(-c2ccc(OC(F)(F)F)cc2)c2ncn(C)c2c1[C@H](O)CO] | N-[[3-methyl-4-[(1S)-1,2-dihydroxyethyl]-7-[4-(trifluoromethoxy)phenyl]benzimidazol-5-yl]methyl]prop-2-enamide |
| 31 | 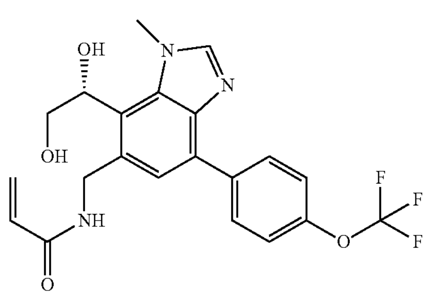 [SMILES: C=CC(=O)NCc1cc(-c2ccc(OC(F)(F)F)cc2)c2ncn(C)c2c1[C@@H](O)CO] | N-[[3-methyl-4-[(1R)-1,2-dihydroxyethyl]-7-[4-(trifluoromethoxy)phenyl]benzimidazol-5-yl]methyl]prop-2-enamide |

| Compound Number | Structure | Compound Name |
|---|---|---|
| 32 | 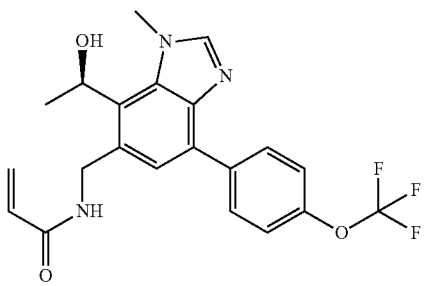 [SMILES: C=CC(=O)NCc1cc(-c2ccc(OC(F)(F)F)cc2)c2ncn(C)c2c1[C@@H](C)O] | N-[[3-methyl-4-[(1R)-1-hydroxyethyl]-7-[4-(trifluoromethoxy)phenyl]benzimidazol-5-yl]methyl]prop-2-enamide |
| 33 | 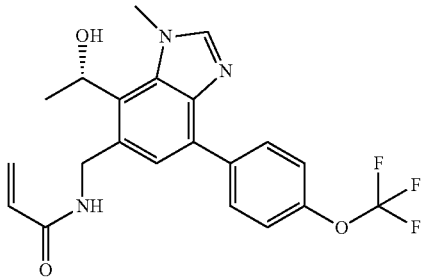 [SMILES: C=CC(=O)NCc1cc(-c2ccc(OC(F)(F)F)cc2)c2ncn(C)c2c1[C@H](C)O] | N-[[3-methyl-4-[(1S)-1-hydroxyethyl]-7-[4-(trifluoromethoxy)phenyl]benzimidazol-5-yl]methyl]prop-2-enamide |
| 34 | 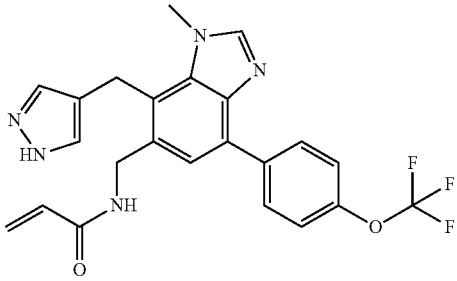 [SMILES: C=CC(=O)NCc1cc(-c2ccc(OC(F)(F)F)cc2)c2ncn(C)c2c1Cc1cn[nH]c1] | N-[[3-methyl-4-(1H-pyrazol-4-ylmethyl)-7-[4-(trifluoromethoxy)phenyl]benzimidazol-5-yl]methyl]prop-2-enamide |
| 35 | 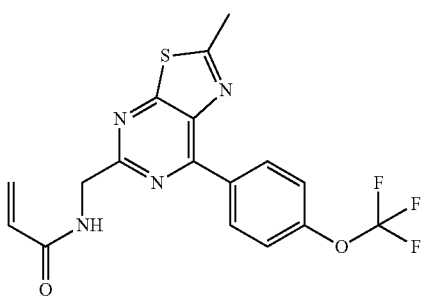 [SMILES: C=CC(=O)NCc1nc(-c2ccc(OC(F)(F)F)cc2)c2nc(C)sc2n1] | N-[[2-methyl-7-[4-(trifluoromethoxy)phenyl]thiazolo[5,4-d]pyrimidin-5-yl]methyl]prop-2-enamide |
| 36 | 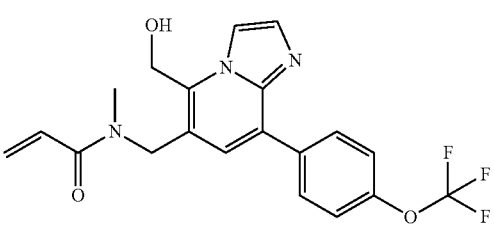 [SMILES: C=CC(=O)N(C)Cc1cc(-c2ccc(OC(F)(F)F)cc2)c2nccn2c1CO] | N-[[5-(hydroxymethyl)-8-[4-(trifluoromethoxy)phenyl]imidazo[1,2-a]pyridin-6-yl]methyl]-N-methyl-prop-2-enamide |

| Compound Number | Structure | Compound Name |
| --- | --- | --- |
| 37 | 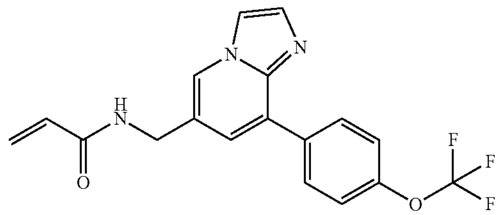 | N-[[8-[4-(trifluoromethoxy)phenyl]imidazo[1,2-a]pyridin-6-yl]methyl]prop-2-enamide) |
| 38 | 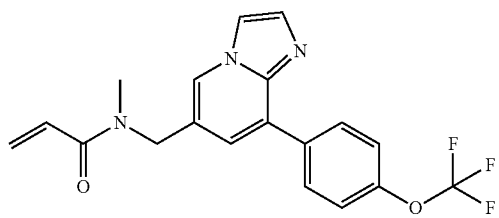 [SMILES: C=CC(=O)N(C)Cc1cc(-c2ccc(OC(F)(F)F)cc2)c2nccn2c1] | N-methyl-N-[[8-[4-(trifluoromethoxy)phenyl]imidazo[1,2-a]pyridin-6-yl]methyl]prop-2-enamide |
| 39 | 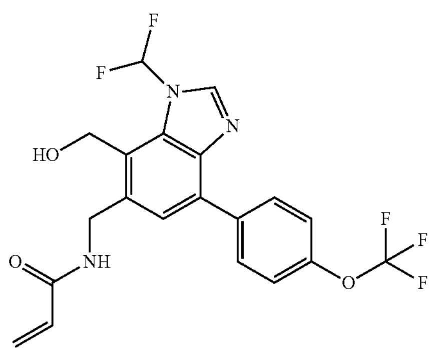 [SMILES: C=CC(=O)NCc1cc(-c2ccc(OC(F)(F)F)cc2)c2ncn(C(F)F)c2c1CO] | N-[[3-(difluoromethyl)-4-(hydroxymethyl)-7-[4-(trifluoromethoxy)phenyl]benzimidazol-5-yl]methyl]prop-2-enamide |
| 40 | 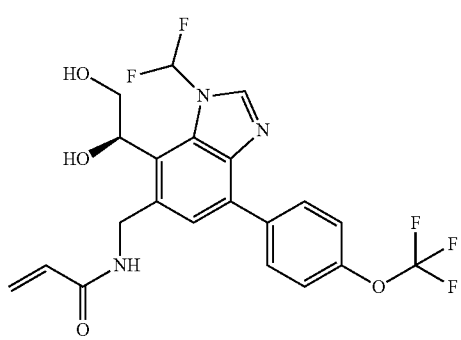 [SMILES: C=CC(=O)NCc1cc(-c2ccc(OC(F)(F)F)cc2)c2ncn(C(F)F)c2c1[C@@H](O)CO] | (R)-N-((1-(difluoromethyl)-7-(1,2-dihydroxyethyl)-4-(4-(trifluoromethoxy)phenyl)-1H-benzo[d]imidazol-6-yl)methyl)acrylamide |
| 41 | 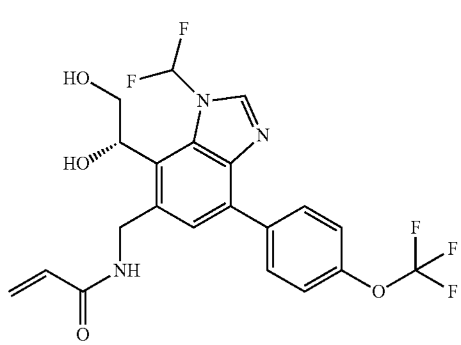 [SMILES: C=CC(=O)NCc1cc(-c2ccc(OC(F)(F)F)cc2)c2ncn(C(F)F)c2c1[C@H](O)CO] | (S)-N-(difluoromethyl)-7-(1,2-dihydroxyethyl)-4-(4-(trifluoromethoxy)phenyl)-1H-benzo[d]imidazol-6-yl)methyl)acrylamide |

-continued

| Compound Number | Structure | Compound Name |
|---|---|---|
| 42 | 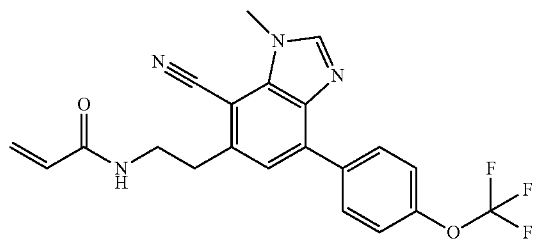 [SMILES: C=CC(=O)NCCc1cc(-c2ccc(OC(F)(F)F)cc2)c2ncn(C)c2c1C#N] | N-[2-[4-cyano-3-methyl-7-[4-(trifluoromethoxy)phenyl]benzimidazol-5-yl]ethyl]prop-2-enamide |
| 43 | 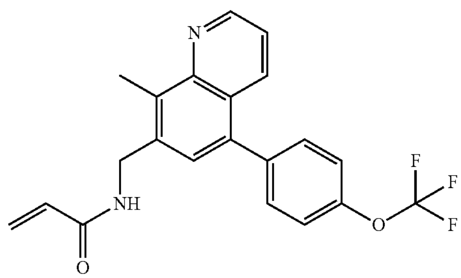 [SMILES: C=CC(=O)NCc1cc(-c2ccc(OC(F)(F)F)cc2)c2cccnc2c1C] | N-[[8-methyl-5-[4-(trifluoromethoxy)phenyl]-7-quinolyl]methyl]prop-2-enamide |
| 44 | 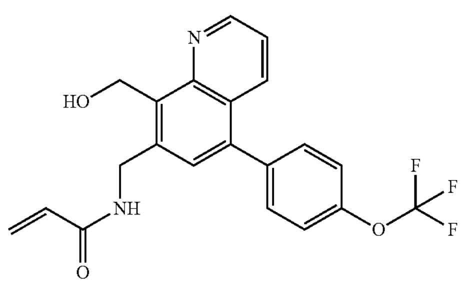 [SMILES: C=CC(=O)NCc1cc(-c2ccc(OC(F)(F)F)cc2)c2cccnc2c1CO] | N-[[8-(hydroxymethyl)-5-[4-(trifluoromethoxy)phenyl]-7-quinolyl]methyl]prop-2-enamide |
| 45 | 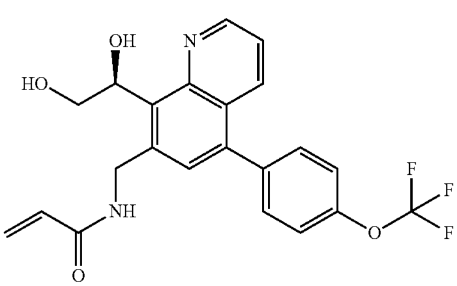 [SMILES: C=CC(=O)NCc1cc(-c2ccc(OC(F)(F)F)cc2)c2cccnc2c1[C@H](O)CO] | (S)-N-((8-(1,2-dihydroxyethyl)-5-(4-(trifluoromethoxy)phenyl)quinolin-7-yl)methyl)acrylamide |
| 46 | 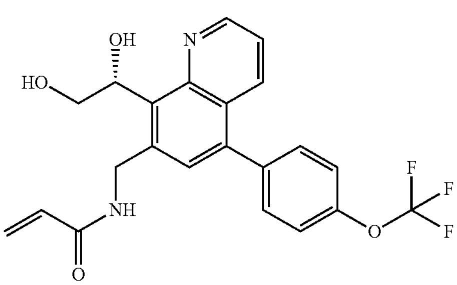 [SMILES: C=CC(=O)NCc1cc(-c2ccc(OC(F)(F)F)cc2)c2cccnc2c1[C@@H](O)CO] | (R)-N-((8-(1,2-dihydroxyethyl)-5-(4-(trifluoromethoxy)phenyl)quinolin-7-yl)methyl)acrylamide |

-continued

| Compound Number | Structure | Compound Name |
|---|---|---|
| 47 | 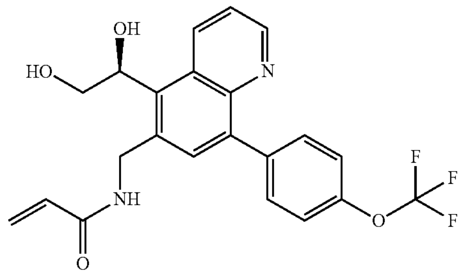 [SMILES: C=CC(=O)NCc1cc(-c2ccc(OC(F)(F)F)cc2)c2ncccc2c1[C@H](O)CO] | (S)-N-((5-(1,2-dihydroxyethyl)-8-(4-(trifluoromethoxy)phenyl)quinolin-6-yl)methyl)acrylamide |
| 48 | 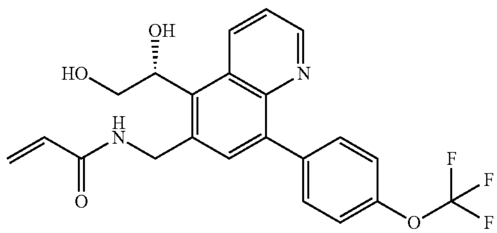 [SMILES: C=CC(=O)NCc1cc(-c2ccc(OC(F)(F)F)cc2)c2ncccc2c1[C@@H](O)CO] | (R)-N-((5-(1,2-dihydroxyethyl)-8-(4-(trifluoromethoxy)phenyl)quinolin-6-yl)methyl)acrylamide |
| 49 | 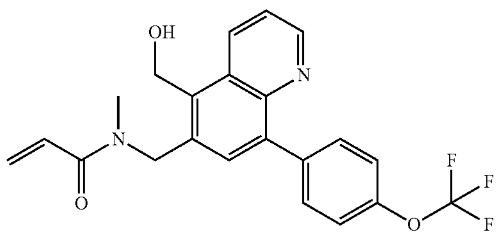 [SMILES: C=CC(=O)N(C)Cc1cc(-c2ccc(OC(F)(F)F)cc2)c2ncccc2c1CO] | N-[[5-(hydroxymethyl)-8-[4-(trifluoromethoxy)phenyl]-6-quinolyl]methyl]-N-methyl-prop-2-enamide |
| 50 | 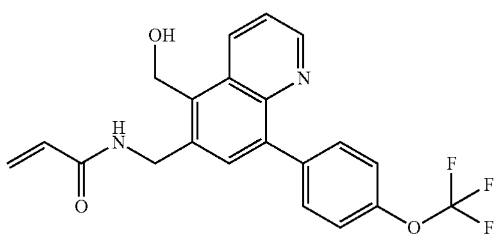 | N-[[5-(hydroxymethyl)-8-[4-(trifluoromethoxy)phenyl]-6-quinolyl]methyl]prop-2-enamide |
| 51 | 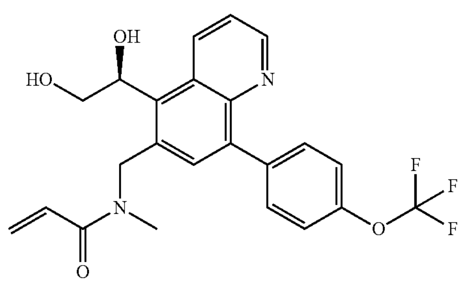 [SMILES: C=CC(=O)N(C)Cc1cc(-c2ccc(OC(F)(F)F)cc2)c2ncccc2c1[C@H](O)CO] | N-[[5-[[(1S)-1,2-dihydroxyethyl]-8-[4-(trifluoromethoxy)phenyl]-6-quinolyl]methyl]-N-methyl-prop-2-enamide |
| 52 | 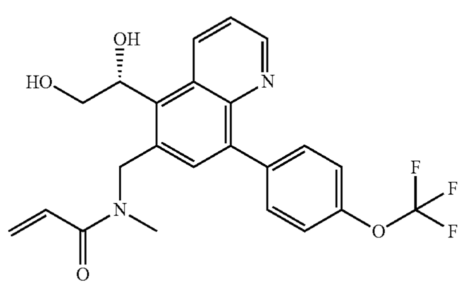 [SMILES: C=CC(=O)N(C)Cc1cc(-c2ccc(OC(F)(F)F)cc2)c2ncccc2c1[C@@H](O)CO] | N-[[5-[(1R)-1,2-dihydroxyethyl]-8-[4-(trifluoromethoxy)phenyl]-6-quinolyl]methyl]-N-methyl-prop-2-enamide |

-continued

| Compound Number | Structure | Compound Name |
|---|---|---|
| 53 | 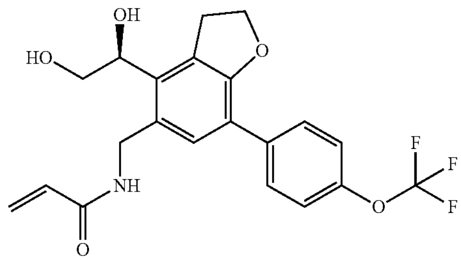 [SMILES: C=CC(=O)NCc1cc(-c2ccc(OC(F)(F)F)cc2)c2c(c1[C@H](O)CO)CCO2] | (S)-N-((4-(1,2-dihydroxyethyl)-7-(4-(trifluoromethoxy)phenyl)-2,3-dihydrobenzofuran-5-yl)methyl)acrylamide |
| 54 | 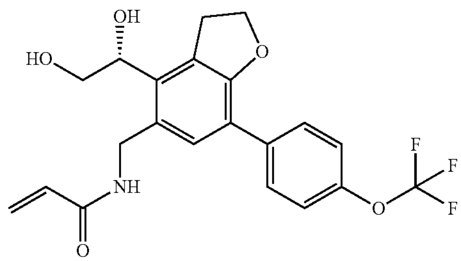 [SMILES: C=CC(=O)NCc1cc(-c2ccc(OC(F)(F)F)cc2)c2c(c1[C@@H](O)CO)CCO2] | (R)-N-((4-(1,2-dihydroxyethyl)-7-(4-(trifluoromethoxy)phenyl)-2,3-dihydrobenzofuran-5-yl)methyl)acrylamide |
| 55 | 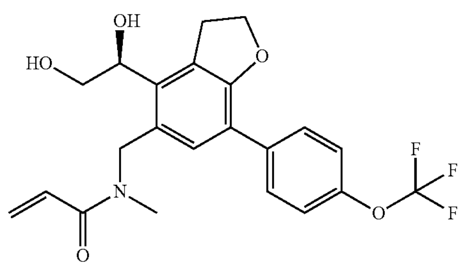 [SMILES: C=CC(=O)N(C)Cc1cc(-c2ccc(OC(F)(F)F)cc2)c2c(c1[C@H](O)CO)CCO2] | (S)-N-((4-(1,2-dihydroxyethyl)-7-(4-(trifluoromethoxy)phenyl)-2,3-dihydrobenzofuran-5-yl)methyl)-N-methylacrylamide |
| 56 | 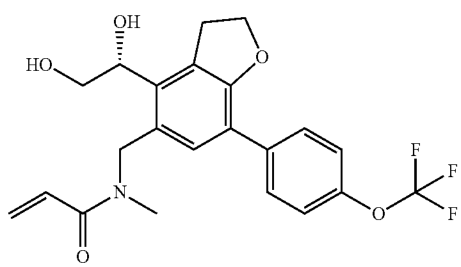 [SMILES: C=CC(=O)N(C)Cc1cc(-c2ccc(OC(F)(F)F)cc2)c2c(c1[C@@H](O)CO)CCO2] | (R)-N-((4-(1,2-dihydroxyethyl)-7-(4-(trifluoromethoxy)phenyl)-2,3-dihydrobenzofuran-5-yl)methyl)-N-methylacrylamide |
| 57 | 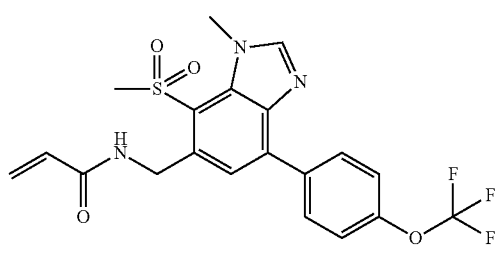 [SMILES: C=CC(=O)NCc1cc(-c2ccc(OC(F)(F)F)cc2)c2ncn(C)c2c1S(C)(=O)=O] | N-[[3-methyl-4-methylsulfonyl-7-[4-(trifluoromethoxy)phenyl]benzimidazol-5-yl]methyl]prop-2-enamide |
| 58 | 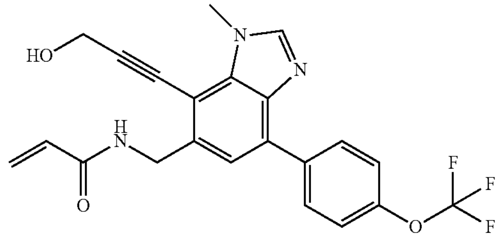 [SMILES: C=CC(=O)NCc1cc(-c2ccc(OC(F)(F)F)cc2)c2ncn(C)c2c1C#CCO] | N-[[4-(3-hydroxyprop-1-ynyl)-3-methyl-7-[4-(trifluoromethoxy)phenyl]benzimidazol-5-yl]methyl]prop-2-enamide |

| Compound Number | Structure | Compound Name |
|---|---|---|
| 59 | 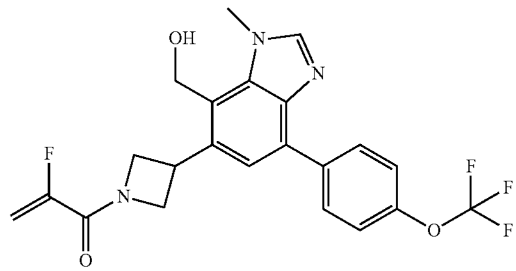 [SMILES: C=C(F)C(=O)N1CC(c2cc(-c3ccc(OC(F)(F)F)cc3)c3ncn(C)c3c2CO)C1] | 2-fluoro-1-[3-[4-(hydroxymethyl)-3-methyl-7-[4-(trifluoromethoxy)phenyl]benzimidazol-5-yl]azetidin-1-yl]prop-2-en-1-one |
| 60 | 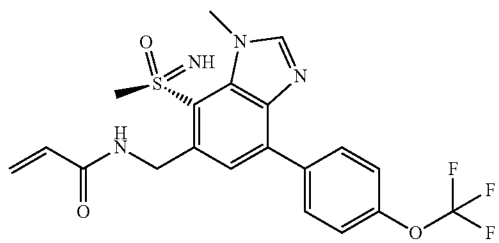 [SMILES: C=CC(=O)NCc1cc(-c2ccc(OC(F)(F)F)cc2)c2ncn(C)c2c1[S@@](C)(=N)=O] | (S)-N-((1-methyl-7-(S-methylsulfonimidoyl)-4-(4-(trifluoromethoxy)phenyl)-1H-benzo[d]imidazol-6-yl)methyl)acrylamide |
| 61 | 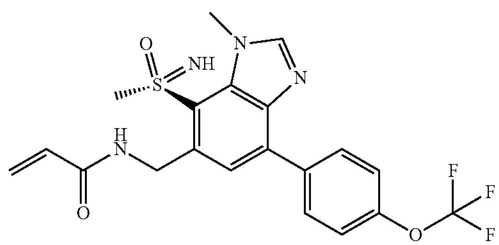 [SMILES: C=CC(=O)NCc1cc(-c2ccc(OC(F)(F)F)cc2)c2ncn(C)c2c1[S@](C)(=N)=O] | (R)-N-((1-methyl-7-(S-methylsulfonimidoyl)-4-(4-(trifluoromethoxy)phenyl)-1H-benzo[d]imidazol-6-yl)methyl)acrylamide |
| 62 | 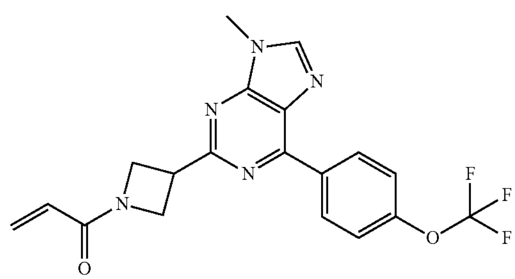 [SMILES: C=CC(=O)N1CC(c2nc(-c3ccc(OC(F)(F)F)cc3)c3ncn(C)c3n2)C1] | 1-[3-[9-methyl-6-[4-(trifluoromethoxy)phenyl]purin-2-yl]azetidin-1-yl]prop-2-en-1-one |
| 63 | 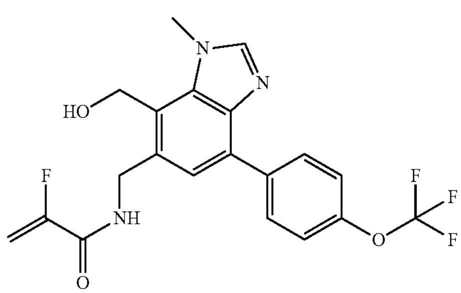 [SMILES: C=C(F)C(=O)NCc1cc(-c2ccc(OC(F)(F)F)cc2)c2ncn(C)c2c1CO] | 2-fluoro-N-[[4-(hydroxymethyl)-3-methyl-7-[4-(trifluoromethoxy)phenyl]benzimidazol-5-yl]methyl]prop-2-enamide |

-continued

| Compound Number | Structure | Compound Name |
|---|---|---|
| 64 | 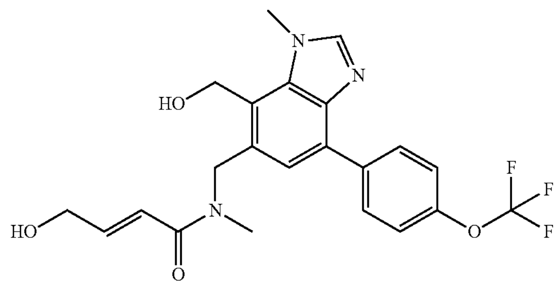 [SMILES: CN(Cc1cc(-c2ccc(OC(F)(F)F)cc2)c2ncn(C)c2c1CO)C(=O)/C=C/CO] | (E)-4-hydroxy-N-[[4-(hydroxymethyl)-3-methyl-7-[4-(trifluoromethoxy)phenyl]benzimidazol-5-yl]methyl]-N-methyl-but-2-enamide |
| 65 | 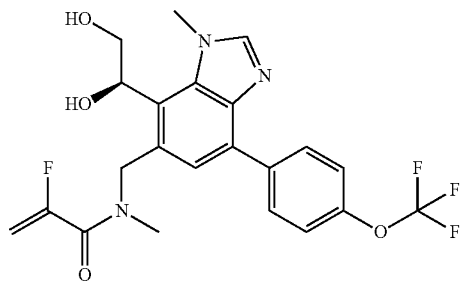 [SMILES: C=C(F)C(=O)N(C)Cc1cc(-c2ccc(OC(F)(F)F)cc2)c2ncn(C)c2c1[C@@H](O)CO] | (R)-N-((1-(1,2-dihydroxyethyl)-1-methyl-4-(4-(trifluoromethoxy)phenyl)-1H-benzo[d]imidazol-6-yl)methyl)-2-fluoro-N-methylacrylamide |
| 66 | 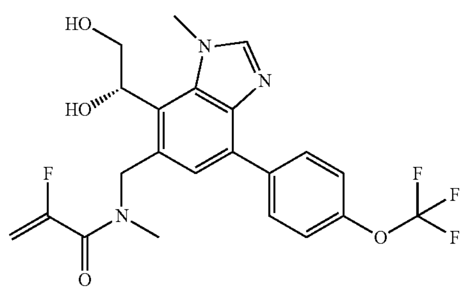 [SMILES: C=C(F)C(=O)N(C)Cc1cc(-c2ccc(OC(F)(F)F)cc2)c2ncn(C)c2c1[C@H](O)CO] | (S)-N-((7-(1,2-dihydroxyethyl)-1-methyl-4-(4-(trifluoromethoxy)phenyl)-1H-benzo[d]imidazol-6-yl)methyl)-2-fluoro-N-methylacrylamide |
| 67 | 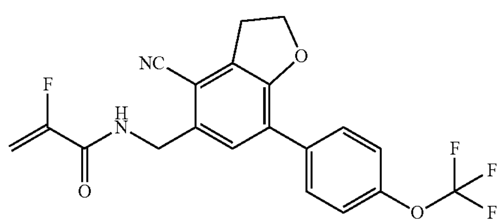 [SMILES: C=C(F)C(=O)NCc1cc(-c2ccc(OC(F)(F)F)cc2)c2c(c1C#N)CCO2] | N-[[4-cyano-7-[4-(trifluoromethoxy)phenyl]-2,3-dihydrobenzofuran-5-yl]methyl]-2-fluoro-prop-2-enamide |
| 68 | 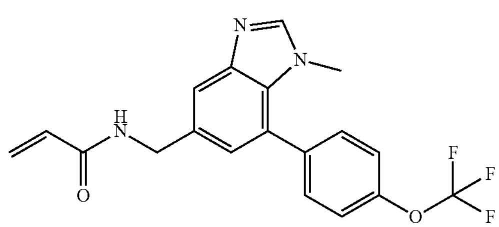 [SMILES: C=CC(=O)NCc1cc(-c2ccc(OC(F)(F)F)cc2)c2c(c1)ncn2C] | N-[[1-methyl-7-[4-(trifluoromethoxy)phenyl]benzimidazol-5-yl]methyl]prop-2-enamide |
| 69 | 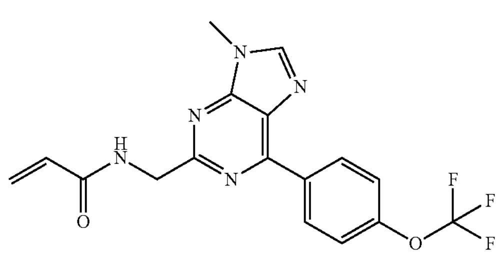 [SMILES: C=CC(=O)NCc1nc(-c2ccc(OC(F)(F)F)cc2)c2ncn(C)c2n1] | N-[[9-methyl-6-[4-(trifluoromethoxy)phenyl]purin-2-yl]methyl]prop-2-enamide |

-continued

| Compound Number | Structure | Compound Name |
|---|---|---|
| 70 | 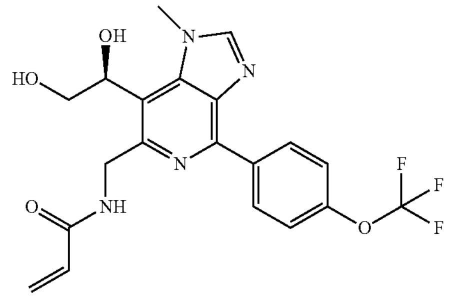 [SMILES: C=CC(=O)NCc1nc(-c2ccc(OC(F)(F)F)cc2)c2ncn(C)c2c1[C@H](O)CO] | N-[[7-[(1S)-1,2-dihydroxyethyl]-1-methyl-4-[4-(trifluoromethoxy)phenyl]imidazo[4,5-c]pyridin-6-yl]methyl]prop-2-enamide |
| 71 | 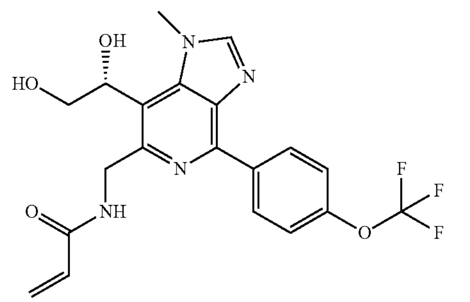 [SMILES: C=CC(=O)NCc1nc(-c2ccc(OC(F)(F)F)cc2)c2ncn(C)c2c1[C@@H](O)CO] | N-[[7-[(1R)-1,2-dihydroxyethyl]-1-methyl-4-[4-(trifluoromethoxy)phenyl]imidazo[4,5-c]pyridin-6-yl]methyl]prop-2-enamide |
| 72 | 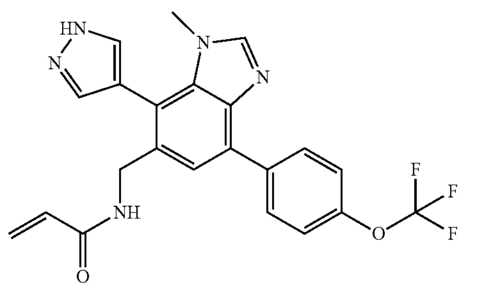 [SMILES: C=CC(=O)NCc1cc(-c2ccc(OC(F)(F)F)cc2)c2ncn(C)c2c1-c1cn[nH]c1] | N-[[3-methyl-4-(1H-pyrazol-4-yl)-7-[4-(trifluoromethoxy)phenyl]benzimidazol-5-yl]methyl]prop-2-enamide |
| 73 | 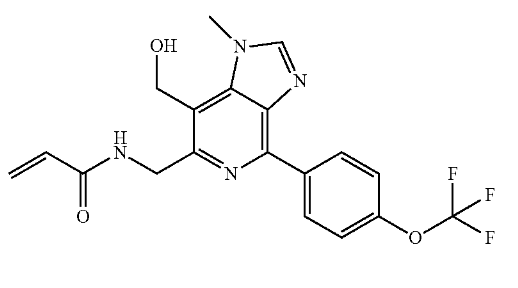 [SMILES: C=CC(=O)NCc1nc(-c2ccc(OC(F)(F)F)cc2)c2ncn(C)c2c1CO] | N-((7-(hydroxymethyl)-1-methyl-4-(4-(trifluoromethoxy)phenyl)-1H-imidazo[4,5-c]pyridin-6-yl)methyl)acrylamide |
| 74 | 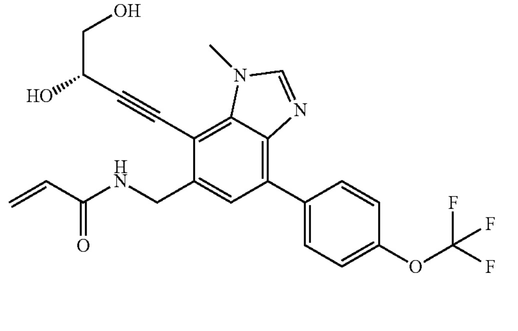 [SMILES: C=CC(=O)NCc1cc(-c2ccc(OC(F)(F)F)cc2)c2ncn(C)c2c1C#C[C@H](O)CO] | (S)-N-((7-(3,4-dihydroxybut-1-yn-1-yl)-1-methyl-4-(4-(trifluoromethoxy)phenyl)-1H-benzo[d]imidazol-6-yl)methyl)acrylamide |

-continued

| Compound Number | Structure | Compound Name |
|---|---|---|
| 75 | 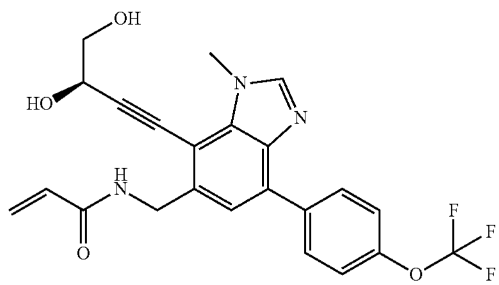 [SMILES: C=CC(=O)NCc1cc(-c2ccc(OC(F)(F)F)cc2)c2ncn(C)c2c1C#C[C@@H](O)CO] | (R)-N-((7-(3,4-dihydroxybut-1-yn-1-yl)-1-methyl-4-(4-(trifluoromethoxy)phenyl)-1H-benzo[d]imidazol-6-yl)methyl)acrylamide |
| 76 | 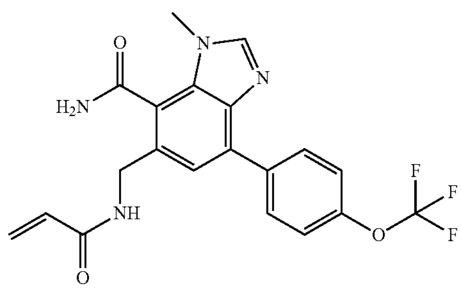 [SMILES: C=CC(=O)NCc1cc(-c2ccc(OC(F)(F)F)cc2)c2ncn(C)c2c1C(N)=O] | 3-methyl-5-[(prop-2-enoylamino)methyl]-7-[4-(trifluoromethoxy)phenyl]benzimidazole-4-carboxamide |
| 77 | 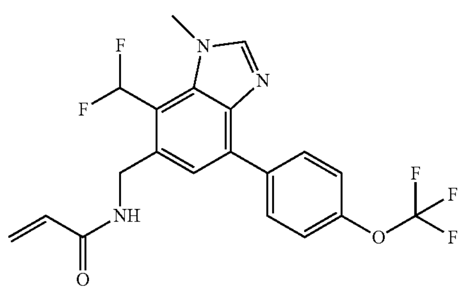 [SMILES: C=CC(=O)NCc1cc(-c2ccc(OC(F)(F)F)cc2)c2ncn(C)c2c1C(F)F] | N-[[4-(difluoromethyl)-3-methyl-7-[4-(trifluoromethoxy)phenyl]benzimidazol-5-yl]methyl]prop-2-enamide |
| 78 | 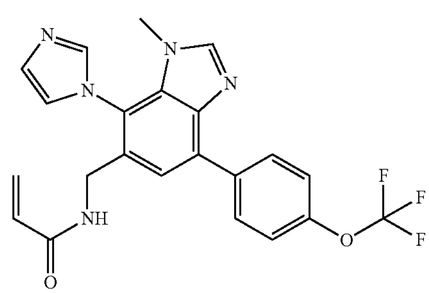 [SMILES: C=CC(=O)NCc1cc(-c2ccc(OC(F)(F)F)cc2)c2ncn(C)c2c1-n1ccnc1] | N-((7-(1H-imidazol-1-yl)-1-methyl-4-(4-(trifluoromethoxy)phenyl)-1H-benzo[d]imidazol-6-yl)methyl)acrylamide |
| 79 | 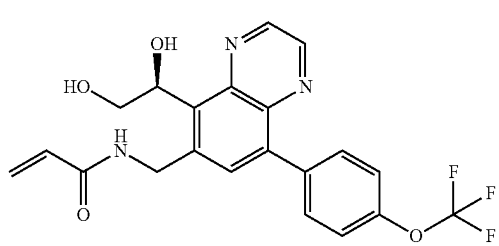 [SMILES: C=CC(=O)NCc1cc(-c2ccc(OC(F)(F)F)cc2)c2nccnc2c1[C@H](O)CO] | (S)-N-((5-(1,2-Dihydroxyethyl)-8-(4-(trifluoromethoxy)phenyl)quinoxalin-6-yl)methyl)acrylamide |

| Compound Number | Structure | Compound Name |
| --- | --- | --- |
| 80 | 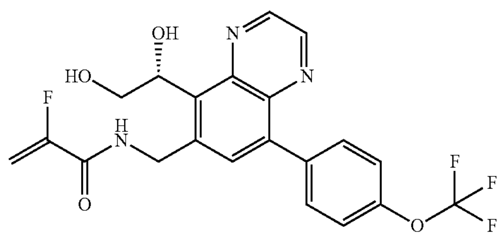 [SMILES: C=C(F)C(=O)NCc1cc(-c2ccc(OC(F)(F)F)cc2)c2nccnc2c1[C@@H](O)CO] | (R)-N-((5-(1,2-Dihydroxyethyl)-8-(4-(trifluoromethoxy)phenyl)quinoxalin-6-yl)methyl)-2-fluoroacrylamide |
| 81 | 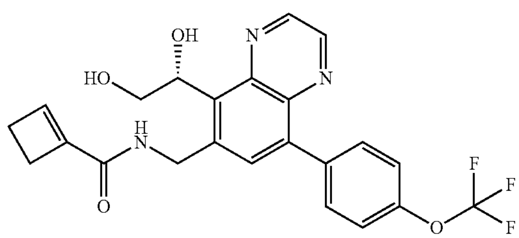 [SMILES: O=C(NCc1cc(-c2ccc(OC(F)(F)F)cc2)c2nccnc2c1[C@@H](O)CO)C1=CCC1] | (R)-N-((5-(1,2-Dihydroxyethyl)-8-(4-(trifluoromethoxy)phenyl)quinoxalin-6-yl)methyl)cyclobut-1-ene-1-carboxamide |
| 82 | 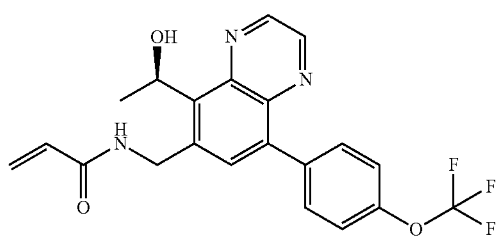 [SMILES: C=CC(=O)NCc1cc(-c2ccc(OC(F)(F)F)cc2)c2nccnc2c1[C@@H](C)O] | (R)-N-((5-(1-Hydroxyethyl)-8-(4-(trifluoromethoxy)phenyl)quinoxalin-6-yl)methyl)acrylamide |
| 83 | 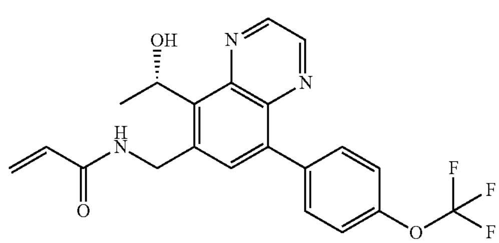 | (S)-N-((5-(1-hydroxyethyl)-8-(4-(trifluoromethoxy)phenyl)quinoxalin-6-yl)methyl)acrylamide |
| 84 | 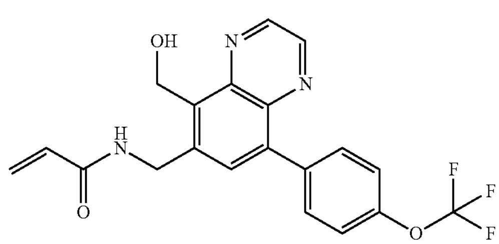 [SMILES: C=CC(=O)NCc1cc(-c2ccc(OC(F)(F)F)cc2)c2nccnc2c1CO] | N-((5-(Hydroxymethyl)-8-(4-(trifluoromethoxy)phenyl)quinoxalin-6-yl)methyl)acrylamide |
| 85 | 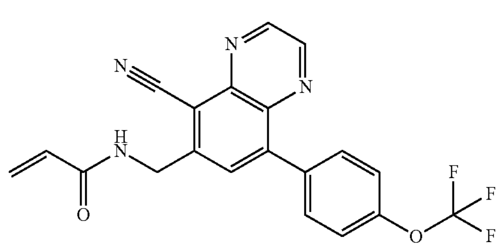 [SMILES: C=CC(=O)NCc1cc(-c2ccc(OC(F)(F)F)cc2)c2nccnc2c1C#N] | N-((5-Cyano-8-(4-(trifluoromethoxy)phenyl)quinoxalin-6-yl)methyl)acrylamide |

-continued

| Compound Number | Structure | Compound Name |
|---|---|---|
| 86 | 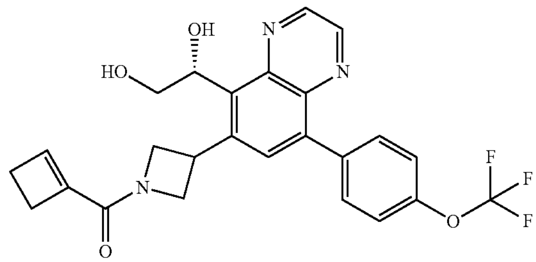 [SMILES: O=C(C1=CCC1)N1CC(c2cc(-c3ccc(OC(F)(F)F)cc3)c3nccnc3c2[C@@H](O)CO)C1] | (R)-Cyclobut-1-en-1-yl(3-(5-(1,2-dihydroxyethyl)-8-(4-(trifluoromethoxy)phenyl)quinoxalin-6-yl)azetidin-1-yl)methanone |
| 87 | 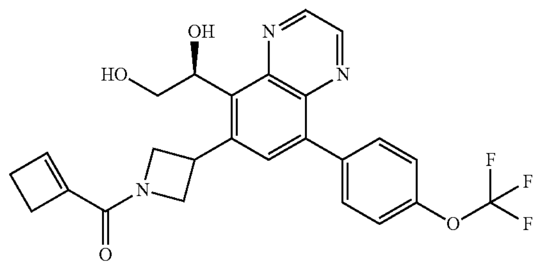 [SMILES: O=C(C1=CCC1)N1CC(c2cc(-c3ccc(OC(F)(F)F)cc3)c3nccnc3c2[C@H](O)CO)C1] | (S)-Cyclobut-1-en-1-yl(3-(5-(1,2-dihydroxyethyl)-8-(4-(trifluoromethoxy)phenyl)quinoxalin-6-yl)azetidin-1-yl)methanone |
| 88 | 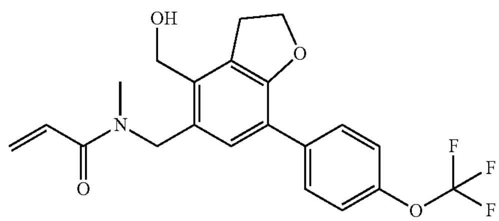 [SMILES: C=CC(=O)N(C)Cc1cc(-c2ccc(OC(F)(F)F)cc2)c2c(c1CO)CCO2] | N-((4-(Hydroxymethyl)-7-(4-(trifluoromethoxy)phenyl)-2,3-dihydrobenzofuran-5-yl)methyl)-N-methylacrylamide |
| 89 | 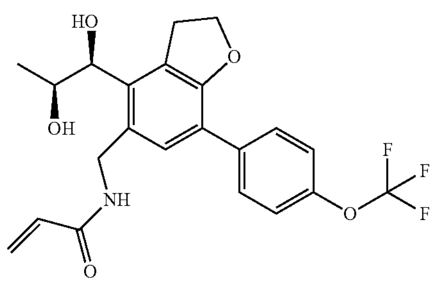 [SMILES: C=CC(=O)NCc1cc(-c2ccc(OC(F)(F)F)cc2)c2c(c1[C@H](O)[C@H](C)O)CCO2] | N-((4-((1S,2S)-1,2-Dihydroxypropyl)-7-(4-(trifluoromethoxy)phenyl)-2,3-dihydrobenzofuran-5-yl)methyl)acrylamide |
| 90 | 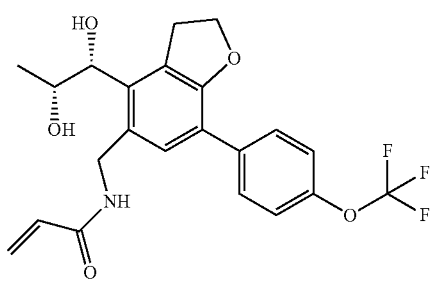 [SMILES: C=CC(=O)NCc1cc(-c2ccc(OC(F)(F)F)cc2)c2c(c1[C@@H](O)[C@@H](C)O)CCO2] | N-((4-((1R,2R)-1,2-dihydroxypropyl)-7-(4-(trifluoromethoxy)phenyl)-2,3-dihydrobenzofuran-5-yl)methyl)acrylamide |
| 91 | 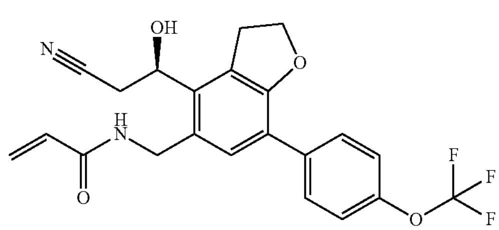 [SMILES: C=CC(=O)NCc1cc(-c2ccc(OC(F)(F)F)cc2)c2c(c1[C@H](O)CC#N)CCO2] | (R)-N-((4-(2-Cyano-1-hydroxyethyl)-7-(4-(trifluoromethoxy)phenyl)-2,3-dihydrobenzofuran-5-yl)methyl)acrylamide |

-continued

| Compound Number | Structure | Compound Name |
|---|---|---|
| 92 | 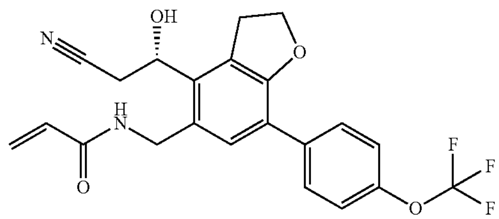 | (S)-N-((4-(2-cyano-1-hydroxyethyl)-7-(4-(trifluoromethoxy)phenyl)-2,3-dihydrobenzofuran-5-yl)methyl)acrylamide |
| 93 | 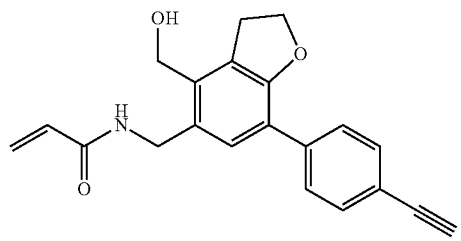 | N-((7-(4-Ethynylphenyl)-4-(hydroxymethyl)-2,3-dihydrobenzofuran-5-yl)methyl)acrylamide |
| 94 | 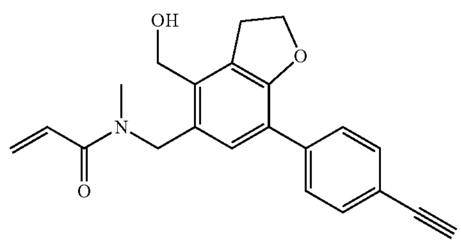 [SMILES: C#Cc1ccc(-c2cc(CN(C)C(=O)C=C)c(CO)c3c2OCC3)cc1] | N-((7-(4-Ethynylphenyl)-4-(hydroxymethyl)-2,3-dihydrobenzofuran-5-yl)methyl)-N-methylacrylamide |
| 95 | 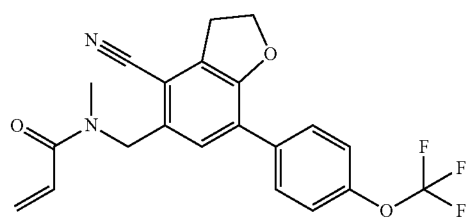 [SMILES: C=CC(=O)N(C)Cc1cc(-c2ccc(OC(F)(F)F)cc2)c2c(c1C#N)CCO2] | N-((4-cyano-7-(4-(trifluoromethoxy)phenyl)-2,3-dihydrobenzofuran-5-yl)methyl)-N-methylacrylamide |
| 96 | 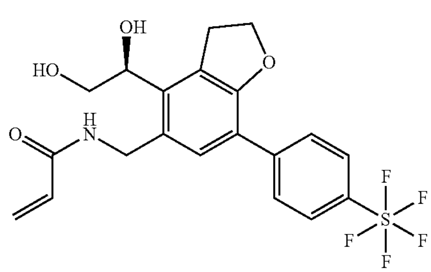 [SMILES: C=CC(=O)NCc1cc(-c2ccc(S(F)(F)(F)(F)F)cc2)c2c(c1[C@H](O)CO)CCO2] | N-[[7-[4-(Pentafluoro-6-sulfanyl)phenyl]-4-[rac-(1R)-1,2-dihydroxyethyl]-2,3-dihydrobenzofuran-5-yl]methyl]prop-2-enamide |
| 97 | 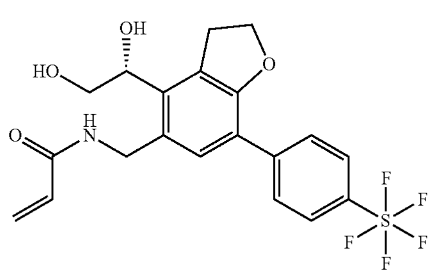 [SMILES: C=CC(=O)NCc1cc(-c2ccc(S(F)(F)(F)(F)F)cc2)c2c(c1[C@@H](O)CO)CCO2] | N-[[7-[4-(pentafluoro-6-sulfanyl)phenyl]-4-[rac-(1S)-1,2-dihydroxyethyl]-2,3-dihydrobenzofuran-5-yl]methyl]prop-2-enamide |

-continued

| Compound Number | Structure | Compound Name |
|---|---|---|
| 98 | 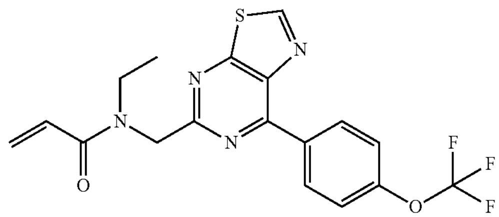 [SMILES: C=CC(=O)N(CC)Cc1nc(-c2ccc(OC(F)(F)F)cc2)c2ncsc2n1] | N-ethyl-N-((7-(4-(trifluoromethoxy)phenyl)thiazolo[5,4-d]pyrimidin-5-yl)methyl)acrylamide |
| 99 | 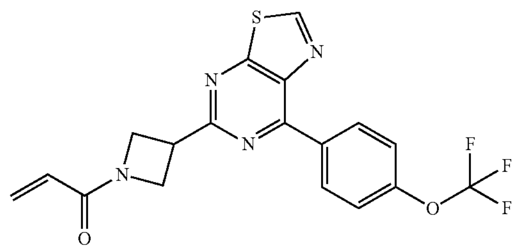 [SMILES: C=CC(=O)N1CC(c2nc(-c3ccc(OC(F)(F)F)cc3)c3ncsc3n2)C1] | 1-(3-(7-(4-(Trifluoromethoxy)phenyl)thiazolo[5,4-d]pyrimidin-5-yl)azetidin-1-yl)prop-2-en-1-one |
| 100 | 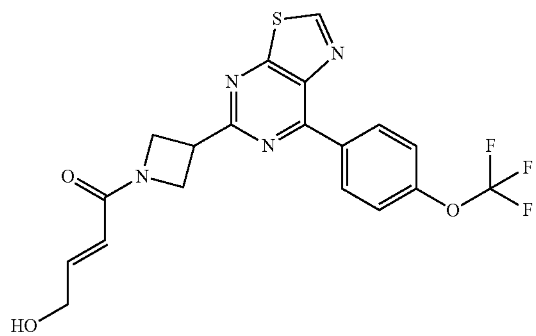 [SMILES: O=C(/C=C/CO)N1CC(c2nc(-c3ccc(OC(F)(F)F)cc3)c3ncsc3n2)C1] | (E)-4-Hydroxy-1-(3-(7-(4-(trifluoromethoxy)phenyl)thiazolo[5,4-d]pyrimidin-5-yl)azetidin-1-yl)but-2-en-1-one |
| 101 | 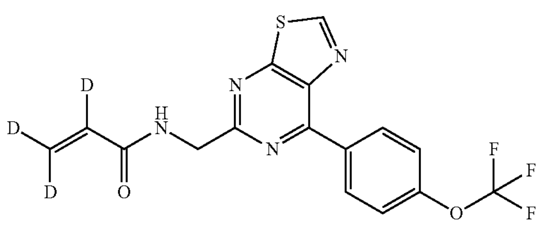 [SMILES: [2H]C([2H])=C([2H])C(=O)NCc1nc(-c2ccc(OC(F)(F)F)cc2)c2ncsc2n1] | N-((7-(4-(trifluoromethoxy)phenyl)thiazolo[5,4-d]pyrimidin-5-yl)methyl)acrylamide-2,3,3-$d_3$ |
| 102 | 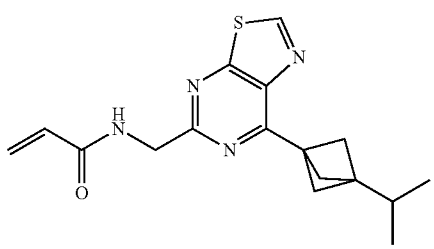 [SMILES: C=CC(=O)NCc1nc(C23CC(C(C)C)(C2)C3)c2ncsc2n1] | N-((7-(3-Isopropylbicyclo[1.1.1]pentan-1-yl)thiazolo[5,4-d]pyrimidin-5-yl)methyl)acrylamide |
| 103 | 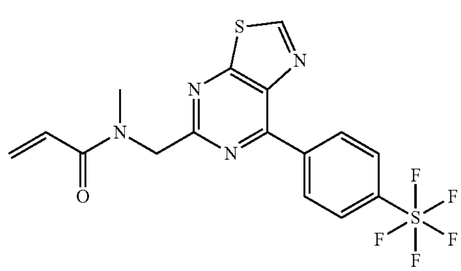 [SMILES: C=CC(=O)N(C)Cc1nc(-c2ccc(S(F)(F)(F)(F)F)cc2)c2ncsc2n1] | N-methyl-N-[[7-[4-(pentafluoro-6-sulfanyl)phenyl]thiazolo[5,4-d]pyrimidin-5-yl]methyl]prop-2-enamide |

| Compound Number | Structure | Compound Name |
|---|---|---|
| 104 | 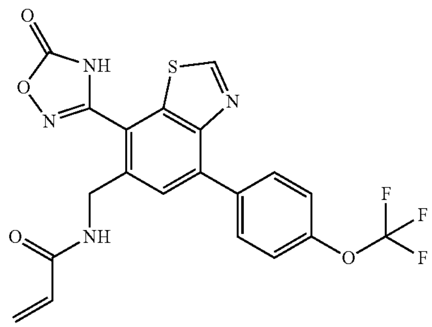 [SMILES: C=CC(=O)NCc1cc(-c2ccc(OC(F)(F)F)cc2)c2ncsc2c1-c1noc(=O)[nH]1] | N-((7-(5-Oxo-4,5-dihydro-1,2,4-oxadiazol-3-yl)-4-(4-(trifluoromethoxy)phenyl)benzo[d]thiazol-6-yl)methyl)acrylamide |
| 105 | 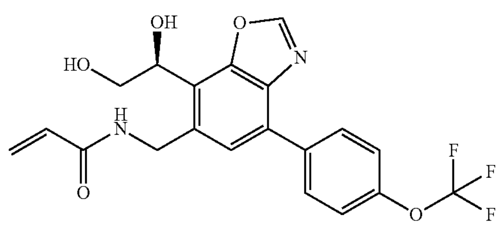 [SMILES: C=CC(=O)NCc1cc(-c2ccc(OC(F)(F)F)cc2)c2ncoc2c1[C@H](O)CO] | (S)-N-((7-(1,2-Dihydroxyethyl)-4-(4-(trifluoromethoxy)phenyl)benzo[d]oxazol-6-yl)methyl)acrylamide |
| 106 | 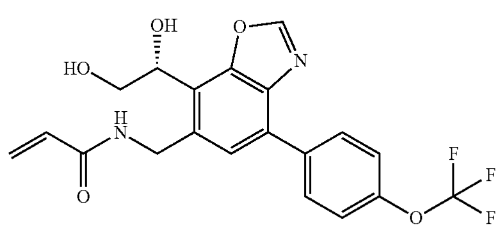 | (R)-N-((7-(1,2-dihydroxyethyl)-4-(4-(trifluoromethoxy)phenyl)benzo[d]oxazol-6-yl)methyl)acrylamide |
| 107 | 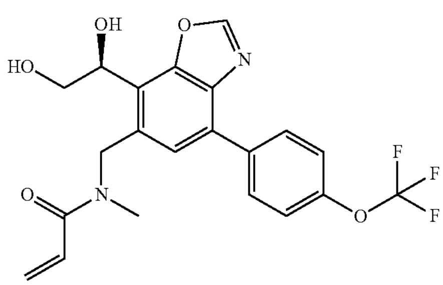 [SMILES: C=CC(=O)N(C)Cc1cc(-c2ccc(OC(F)(F)F)cc2)c2ncoc2c1[C@H](O)CO] | (S)-N-((7-(1,2-Dihydroxyethyl)-4-(4-(trifluoromethoxy)phenyl)benzo[d]oxazol-6-yl)methyl)-N-methylacrylamide |
| 108 | 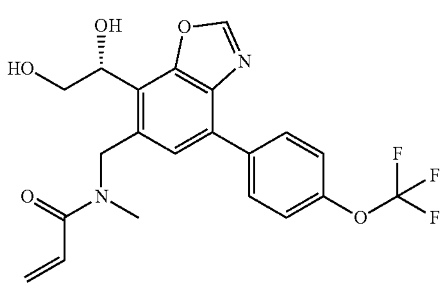 [SMILES: C=CC(=O)N(C)Cc1cc(-c2ccc(OC(F)(F)F)cc2)c2ncoc2c1[C@@H](O)CO] | (R)-N-((7-(1,2-dihydroxyethyl)-4-(4-(trifluoromethoxy)phenyl)benzo[d]oxazol-6-yl)methyl)-N-methylacrylamide |

| Compound Number | Structure | Compound Name |
|---|---|---|
| 109 | 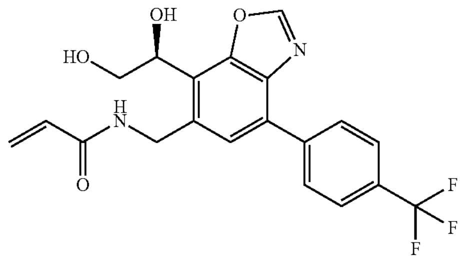 [SMILES: C=CC(=O)NCc1cc(-c2ccc(C(F)(F)F)cc2)c2ncoc2c1[C@H](O)CO] | (S)-N-((7-(1,2-Dihydroxyethyl)-4-(4-(trifluoromethyl)phenyl)benzo[d]oxazol-6-yl)methyl)acrylamide |
| 110 | 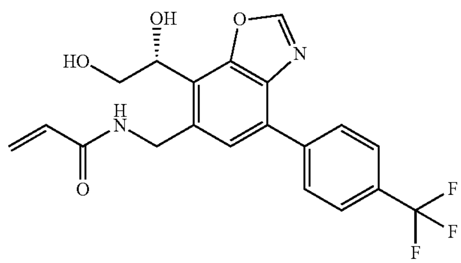 [SMILES: C=CC(=O)NCc1cc(-c2ccc(C(F)(F)F)cc2)c2ncoc2c1[C@@H](O)CO] | (R)-N-((7-(1,2-dihydroxyethyl)-4-(4-(trifluoromethyl)phenyl)benzo[d]oxazol-6-yl)methyl)acrylamide |
| 111 | 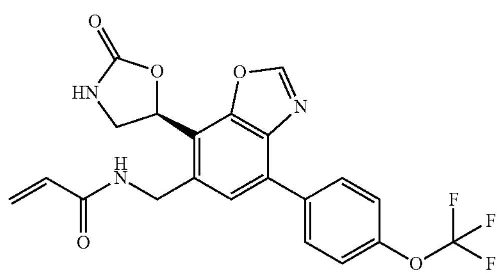 [SMILES: C=CC(=O)NCc1cc(-c2ccc(OC(F)(F)F)cc2)c2ncoc2c1[C@H]1CNC(=O)O1] | (S)-N-((7-(2-Oxooxazolidin-5-yl)-4-(4-(trifluoromethoxy)phenyl)benzo[d]oxazol-6-yl)methyl)acrylamide |
| 112 | 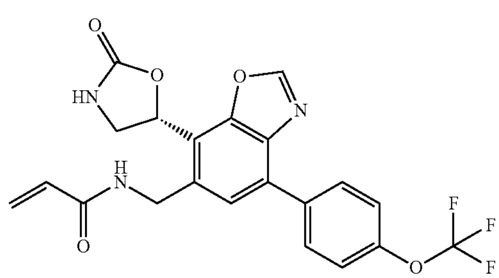 [SMILES: C=CC(=O)NCc1cc(-c2ccc(OC(F)(F)F)cc2)c2ncoc2c1[C@@H]1CNC(=O)O1] | (R)-N-((7-(2-oxooxazolidin-5-yl)-4-(4-(trifluoromethoxy)phenyl)benzo[d]oxazol-6-yl)methyl)acrylamide |
| 113 | 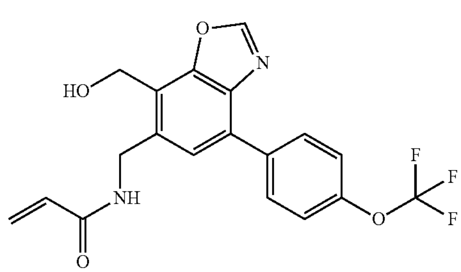 [SMILES: C=CC(=O)NCc1cc(-c2ccc(OC(F)(F)F)cc2)c2ncoc2c1CO] | N-((7-(Hydroxymethyl)-4-(4-(trifluoromethoxy)phenyl)benzo[d]oxazol-6-yl)methyl)acrylamide |

-continued

| Compound Number | Structure | Compound Name |
|---|---|---|
| 114 | 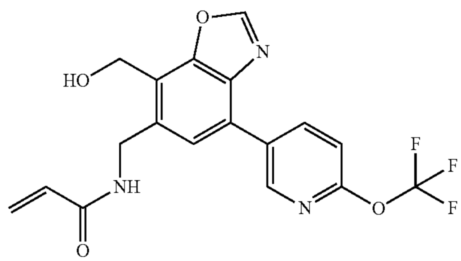 | N-((7-(Hydroxymethyl)-4-(6-(trifluoromethoxy)pyridin-3-yl)benzo[d]oxazol-6-yl)methyl)acrylamide |
| 115 | 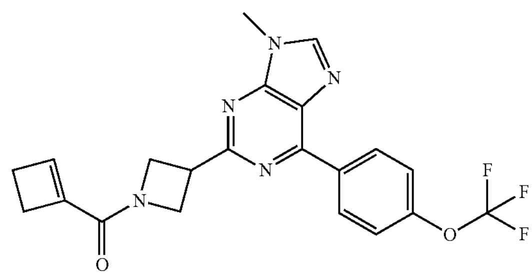 [SMILES: Cn1cnc2c(-c3ccc(OC(F)(F)F)cc3)nc(C3CN(C(=O)C4=CCC4)C3)nc21] | Cyclobut-1-en-1-yl(3-(9-methyl-6-(4-(trifluoromethoxy)phenyl)-9H-purin-2-yl)azetidin-1-yl)methanone |
| 116 | 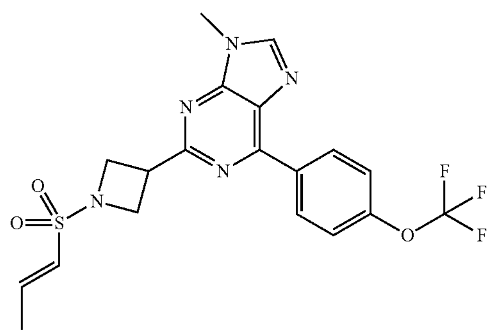 [SMILES: C/C=C/S(=O)(=O)N1CC(c2nc(-c3ccc(OC(F)(F)F)cc3)c3ncn(C)c3n2)C1] | (E)-9-Methyl-2-(1-(prop-1-en-1-ylsulfonyl)azetidin-3-yl)-6-(4-(trifluoromethoxy)phenyl)-9H-purine |
| 117 | 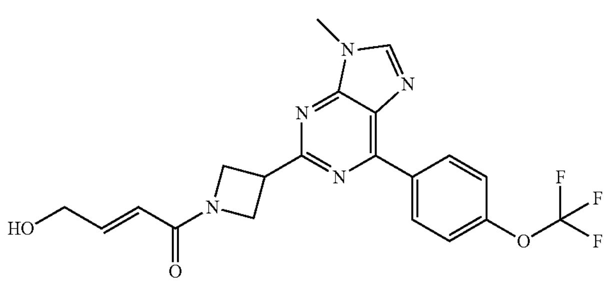 [SMILES: Cn1cnc2c(-c3ccc(OC(F)(F)F)cc3)nc(C3CN(C(=O)/C=C/CO)C3)nc21] | (E)-4-Hydroxy-1-(3-(9-methyl-6-(4-(trifluoromethoxy)phenyl)-9H-purin-2-yl)azetidin-1-yl)but-2-en-1-one |
| 118 | 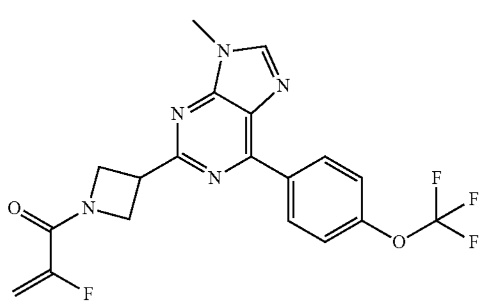 [SMILES: C=C(F)C(=O)N1CC(c2nc(-c3ccc(OC(F)(F)F)cc3)c3ncn(C)c3n2)C1] | 2-Fluoro-1-(3-(9-methyl-6-(4-(trifluoromethoxy)phenyl)-9H-purin-2-yl)azetidin-1-yl)prop-2-en-1-one |

| Compound Number | Structure | Compound Name |
|---|---|---|
| 119 | 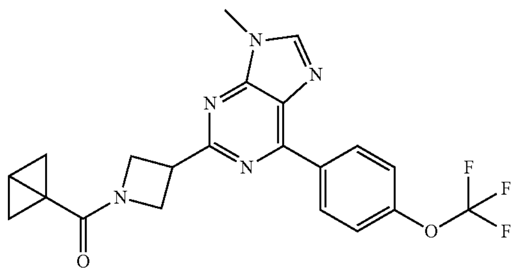 [SMILES: Cn1cnc2c(-c3ccc(OC(F)(F)F)cc3)nc(C3CN(C(=O)C45CC4C5)C3)nc21] | Bicyclo[1.1.0]butan-1-yl(3-(9-methyl-6-(4-(trifluoromethoxy)phenyl)-9H-purin-2-yl)azetidin-1-yl)methanone |
| 120 | 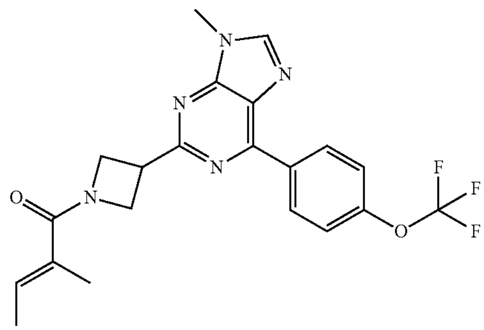 [SMILES: C/C=C(\C)C(=O)N1CC(c2nc(-c3ccc(OC(F)(F)F)cc3)c3ncn(C)c3n2)C1] | (E)-2-Methyl-1-(3-(9-methyl-6-(4-(trifluoromethoxy)phenyl)-9H-purin-2-yl)azetidin-1-yl)but-2-en-1-one |
| 121 | 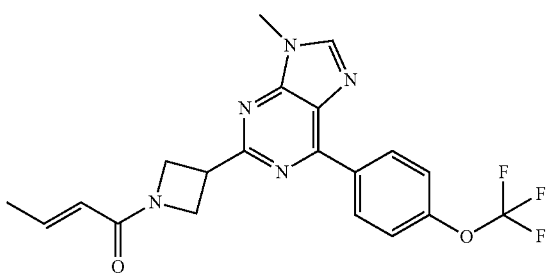 [SMILES: C/C=C/C(=O)N1CC(c2nc(-c3ccc(OC(F)(F)F)cc3)c3ncn(C)c3n2)C1] | (E)-1-(3-(9-Methyl-6-(4-(trifluoromethoxy)phenyl)-9H-purin-2-yl)azetidin-1-yl)but-2-en-1-one |
| 122 | 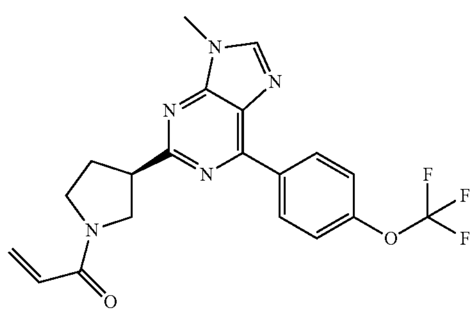 [SMILES: C=CC(=O)N1CC[C@@H](c2nc(-c3ccc(OC(F)(F)F)cc3)c3ncn(C)c3n2)C1] | (R)-1-(3-(9-Methyl-6-(4-(trifluoromethoxy)phenyl)-9H-purin-2-yl)pyrrolidin-1-yl)prop-2-en-1-one |
| 123 | 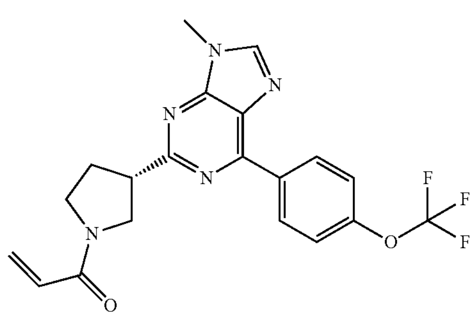 [SMILES: C=CC(=O)N1CC[C@H](c2nc(-c3ccc(OC(F)(F)F)cc3)c3ncn(C)c3n2)C1] | (S)-1-(3-(9-methyl-6-(4-(trifluoromethoxy)phenyl)-9H-purin-2-yl)pyrrolidin-1-yl)prop-2-en-1-one |

-continued

| Compound Number | Structure | Compound Name |
|---|---|---|
| 124 | 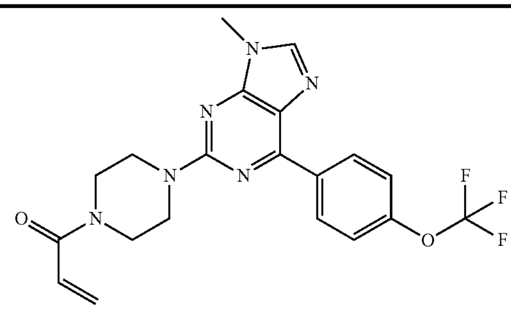 | 1-(4-(9-Methyl-6-(4-(trifluoromethoxy)phenyl)-9H-purin-2-yl)piperazin-1-yl)prop-2-en-1-one |
| 125 | 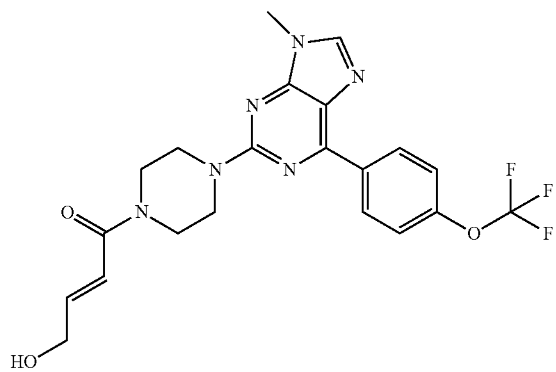 [SMILES: Cn1cnc2c(-c3ccc(OC(F)(F)F)cc3)nc(N3CCN(C(=O)/C=C/CO)CC3)nc21] | (E)-4-Hydroxy-1-(4-(9-methyl-6-(4-(trifluoromethoxy)phenyl)-9H-purin-2-yl)piperazin-1-yl)but-2-en-1-one |
| 126 | 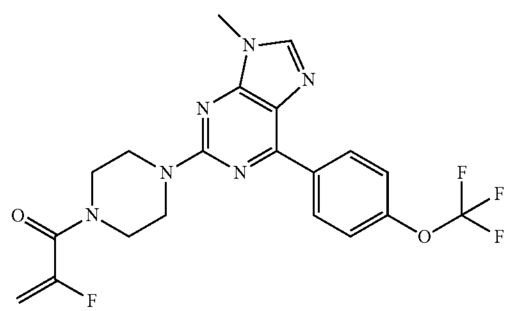 [SMILES: C=C(F)C(=O)N1CCN(c2nc(-c3ccc(OC(F)(F)F)cc3)c3ncn(C)c3n2)CC1] | 2-Fluoro-1-(4-(9-methyl-6-(4-(trifluoromethoxy)phenyl)-9H-purin-2-yl)piperazin-1-yl)prop-2-en-1-one |
| 127 | 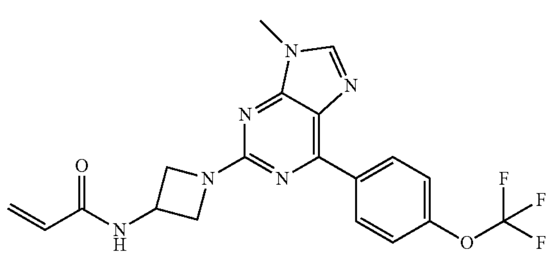 [SMILES: C=CC(=O)NC1CN(c2nc(-c3ccc(OC(F)(F)F)cc3)c3ncn(C)c3n2)C1] | N-(1-(9-Methyl-6-(4-(trifluoromethoxy)phenyl)-9H-purin-2-yl)azetidin-3-yl)acrylamide |
| 128 | 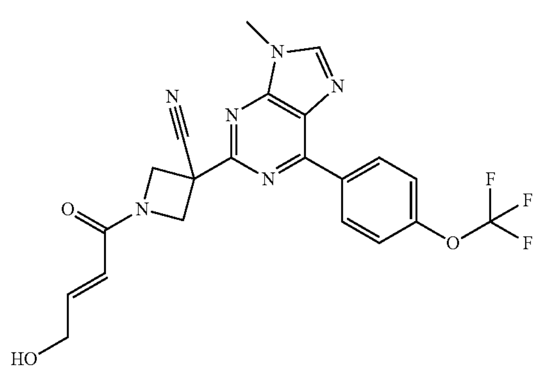 [SMILES: Cn1cnc2c(-c3ccc(OC(F)(F)F)cc3)nc(C3(C#N)CN(C(=O)/C=C/CO)C3)nc21] | (E)-1-(4-Hydroxybut-2-enoyl)-3-(9-methyl-6-(4-(trifluoromethoxy)phenyl)-9H-purin-2-yl)azetidine-3-carbonitrile |

| Compound Number | Structure | Compound Name |
|---|---|---|
| 129 | 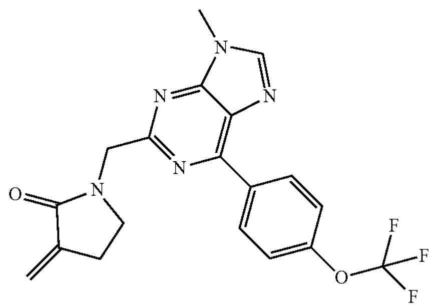 [SMILES: C=C1CCN(Cc2nc(-c3ccc(OC(F)(F)F)cc3)c3ncn(C)c3n2)C1=O] | 1-((9-Methyl-6-(4-(trifluoromethoxy)phenyl)-9H-purin-2-yl)methyl)-3-methylenepyrrolidin-2-one |
| 130 | 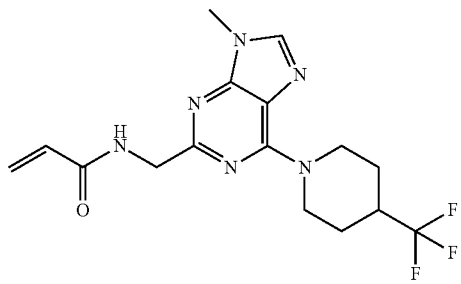 [SMILES: C=CC(=O)NCc1nc(N2CCC(C(F)(F)F)CC2)c2ncn(C)c2n1] | N-((9-Methyl-6-(4-(trifluoromethyl)piperidin-1-yl)-9H-purin-2-yl)methyl)acrylamide |
| 131 | 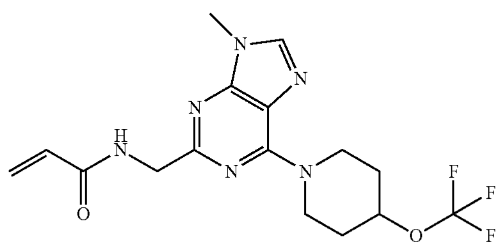 [SMILES: C=CC(=O)NCc1nc(N2CCC(OC(F)(F)F)CC2)c2ncn(C)c2n1] | N-((9-Methyl-6-(4-(trifluoromethoxy)piperidin-1-yl)-9H-purin-2-yl)methyl)acrylamide |
| 132 | 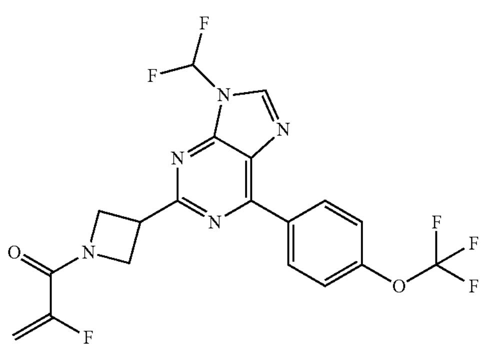 [SMILES: C=C(F)C(=O)N1CC(c2nc(-c3ccc(OC(F)(F)F)cc3)c3ncn(C(F)F)c3n2)C1] | 1-(3-(9-(Difluoromethyl)-6-(4-(trifluoromethoxy)phenyl)-9H-purin-2-yl)azetidin-1-yl)-2-fluoroprop-2-en-1-one |
| 133 | 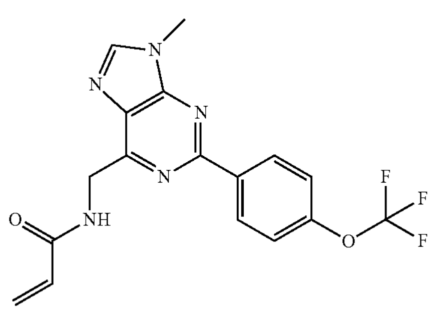 [SMILES: C=CC(=O)NCc1nc(-c2ccc(OC(F)(F)F)cc2)nc2c1ncn2C] | N-((9-Methyl-2-(4-(trifluoromethoxy)phenyl)-9H-purin-6-yl)methyl)acrylamide |

-continued

| Compound Number | Structure | Compound Name |
|---|---|---|
| 134 | 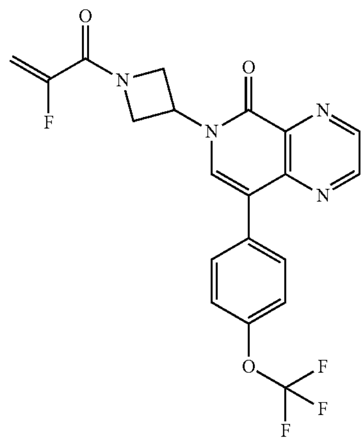 [SMILES: C=C(F)C(=O)N1CC(n2cc(-c3ccc(OC(F)(F)F)cc3)c3nccnc3c2=O)C1] | 6-(1-(2-Fluoroacryloyl)azetidin-3-yl)-8-(4-(trifluoromethoxy)phenyl)pyrido[3,4-b]pyrazin-5(6H)-one |
| 135 | 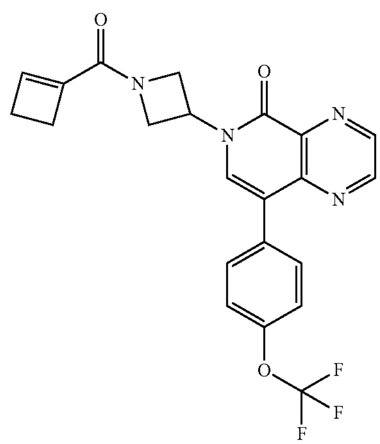 [SMILES: O=C(C1=CCC1)N1CC(n2cc(-c3ccc(OC(F)(F)F)cc3)c3nccnc3c2=O)C1] | 6-(1-(Cyclobut-1-ene-1-carbonyl)azetidin-3-yl)-8-(4-(trifluoromethoxy)phenyl)pyrido[3,4-b]pyrazin-5(6H)-one |
| 136 | 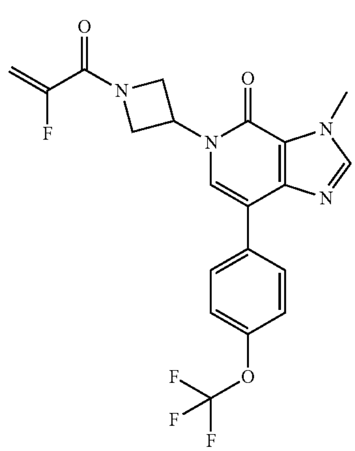 [SMILES: C=C(F)C(=O)N1CC(n2cc(-c3ccc(OC(F)(F)F)cc3)c3ncn(C)c3c2=O)C1] | 5-(1-(2-Fluoroacryloyl)azetidin-3-yl)-3-methyl-7-(4-(trifluoromethoxy)phenyl)-3,5-dihydro-4H-imidazo[4,5-c]pyridin-4-one |

| Compound Number | Structure | Compound Name |
|---|---|---|
| 137 | 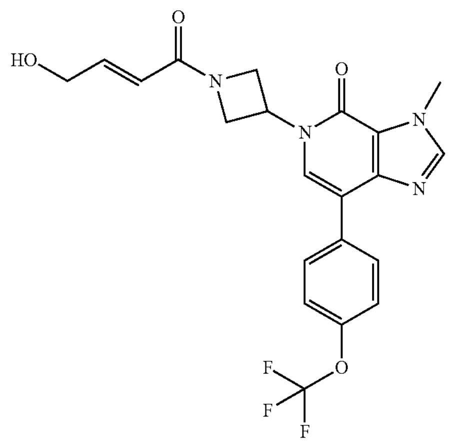 [SMILES: Cn1cnc2c(-c3ccc(OC(F)(F)F)cc3)cn(C3CN(C(=O)/C=C/CO)C3)c(=O)c21] | (E)-5-(1-(4-Hydroxybut-2-enoyl)azetidin-3-yl)-3-methyl-7-(4-(trifluoromethoxy)phenyl)-3,5-dihydro-4H-imidazo[4,5-c]pyridin-4-one |
| 138 | 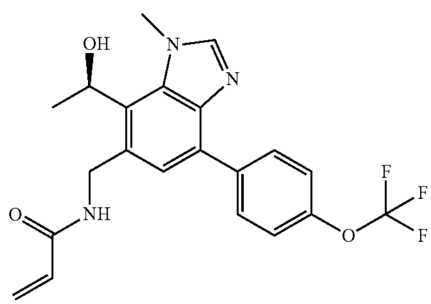 [SMILES: C=CC(=O)NCc1cc(-c2ccc(OC(F)(F)F)cc2)c2ncn(C)c2c1[C@@H](C)O] | (R)-N-((7-(1-Hydroxyethyl)-1-methyl-4-(4-(trifluoromethoxy)phenyl)-1H-benzo[d]imidazol-6-yl)methyl)acrylamide |
| 139 | 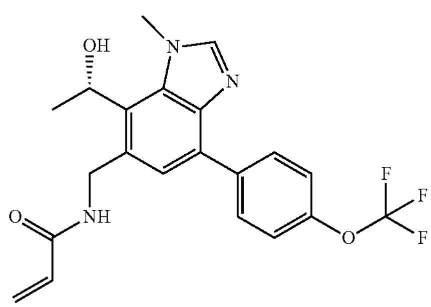 [SMILES: C=CC(=O)NCc1cc(-c2ccc(OC(F)(F)F)cc2)c2ncn(C)c2c1[C@H](C)O] | (S)-N-((7-(1-hydroxyethyl)-1-methyl-4-(4-(trifluoromethoxy)phenyl)-1H-benzo[d]imidazol-6-yl)methyl)acrylamide |
| 140 | 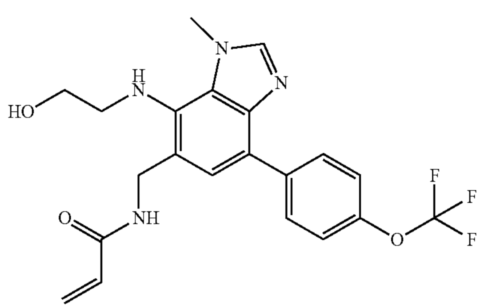 [SMILES: C=CC(=O)NCc1cc(-c2ccc(OC(F)(F)F)cc2)c2ncn(C)c2c1NCCO] | N-((7-((2-Hydroxyethyl)amino)-1-methyl-4-(4-(trifluoromethoxy)phenyl)-1H-benzo[d]imidazol-6-yl)methyl)acrylamide |

-continued

| Compound Number | Structure | Compound Name |
|---|---|---|
| 141 | 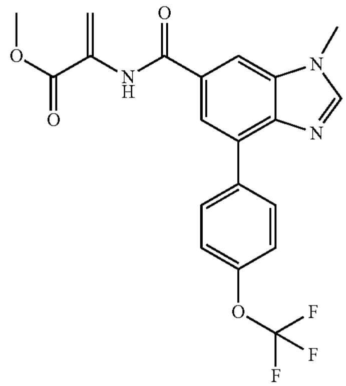 [SMILES: C=C(NC(=O)c1cc(-c2ccc(OC(F)(F)F)cc2)c2ncn(C)c2c1)C(=O)OC] | Methyl 2-(1-methyl-4-(4-(trifluoromethoxy)phenyl)-1H-benzo[d]imidazole-6-carboxamido)acrylate |
| 142 | 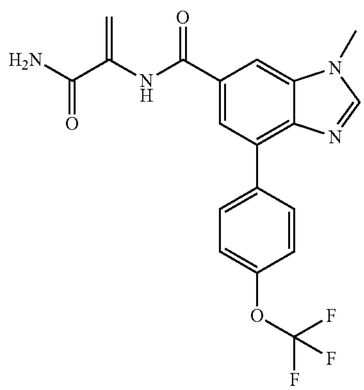 [SMILES: C=C(NC(=O)c1cc(-c2ccc(OC(F)(F)F)cc2)c2ncn(C)c2c1)C(N)=O] | N-(3-Amino-3-oxoprop-1-en-2-yl)-1-methyl-4-(4-(trifluoromethoxy)phenyl)-1H-benzo[d]imidazole-6-carboxamide |
| 143 | 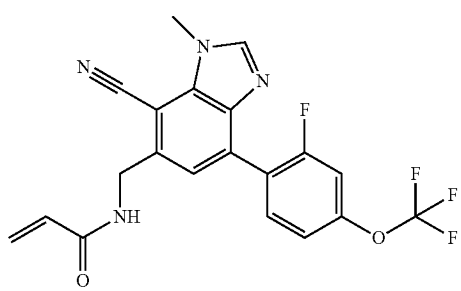 [SMILES: C=CC(=O)NCc1cc(-c2ccc(OC(F)(F)F)cc2F)c2ncn(C)c2c1C#N] | N-((7-Cyano-4-(2-fluoro-4-(trifluoromethoxy)phenyl)-1-methyl-1H-benzo[d]imidazol-6-yl)methyl)acrylamide |
| 144 | 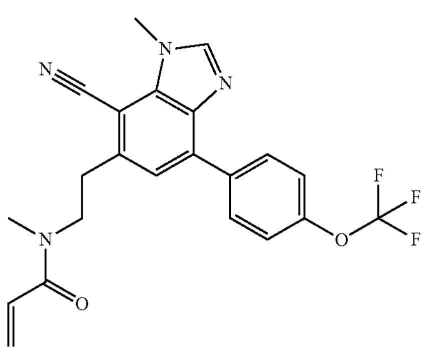 [SMILES: C=CC(=O)N(C)CCc1cc(-c2ccc(OC(F)(F)F)cc2)c2ncn(C)c2c1C#N] | N-(2-(7-Cyano-1-methyl-4-(4-(trifluoromethoxy)phenyl)-1H-benzo[d]imidazol-6-yl)ethyl)-N-methylacrylamide |

| Compound Number | Structure | Compound Name |
|---|---|---|
| 145 | 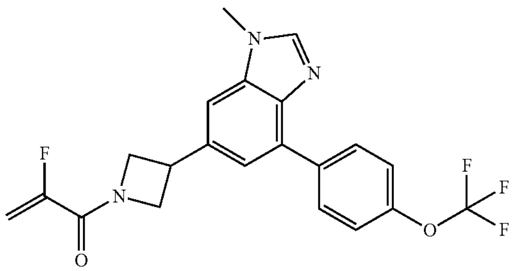 [SMILES: C=C(F)C(=O)N1CC(c2cc(-c3ccc(OC(F)(F)F)cc3)c3ncn(C)c3c2)C1] | 2-Fluoro-1-(3-(1-methyl-4-(4-(trifluoromethoxy)phenyl)-1H-benzo[d]imidazol-6-yl)azetidin-1-yl)prop-2-en-1-one |
| 146 | 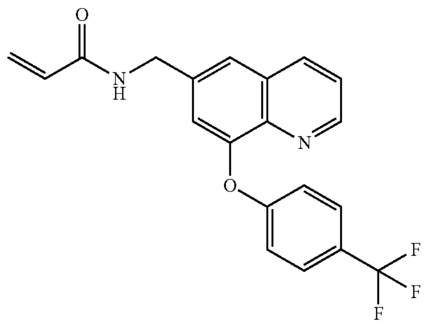 [SMILES: C=CC(=O)NCc1cc(Oc2ccc(C(F)(F)F)cc2)c2ncccc2c1] | N-((8-(4-(Trifluoromethyl)phenoxy)quinolin-6-yl)methyl)acrylamide |
| 147 | 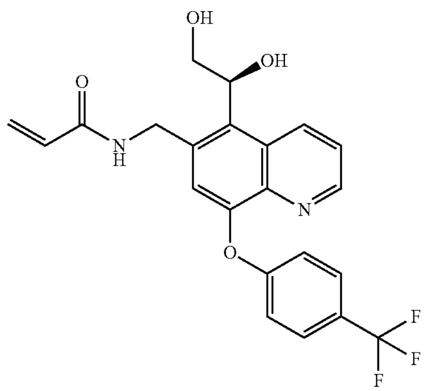 [SMILES: C=CC(=O)NCc1cc(Oc2ccc(C(F)(F)F)cc2)c2ncccc2c1[C@H](O)CO] | (S)-N-((5-(1,2-Dihydroxyethyl)-8-(4-(trifluoromethyl)phenoxy)quinolin-6-yl)methyl)acrylamide |
| 148 | 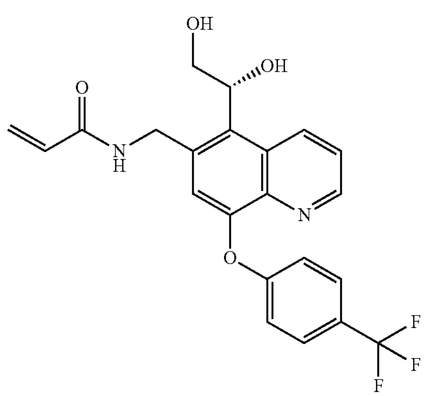 | (R)-N-((5-(1,2-dihydroxyethyl)-8-(4-(trifluoromethyl)phenoxy)quinolin-6-yl)methyl)acrylamide |

Provided herein is a compound selected from the group consisting of:

2-chloro-N-methyl-N-[[7-[4-(trifluoromethoxy)phenyl]thiazolo[5,4-d]pyrimidin-5-yl]methyl]acetamide N-[[4-cyano-7-[4-(trifluoromethoxy)phenyl]-2,3-dihydrobenzofuran-5-yl]methyl]prop-2-enamide N-[[7-(hydroxymethyl)-4-[6-(trifluoromethoxy)-3-pyridyl]-1,3-benzoxazol-6-yl]methyl]prop-2-enamide N-[[4-[4-(trifluoromethoxy)phenyl]-6,7-dihydro-5H-pyrano[2,3-d]pyrimidin-2-yl]methyl]prop-2-enamide N-[[5-(hydroxymethyl)-8-[4-(trifluoromethoxy)phenyl]imidazo[1,2-a]pyridin-6-yl]methyl]prop-2-enamide N-[[4-[4-(trifluoromethoxy)phenyl]-6,7-dihydro-5H-cyclopenta[d]pyrimidin-2-yl]methyl]prop-2-enamide N-[[4-[4-(trifluoromethoxy)phenyl]quinazolin-2-yl]methyl]prop-2-enamide N-[[7-[2-fluoro-4-(trifluoromethoxy)phenyl]-4-(hydroxymethyl)-2,3-dihydrobenzofuran-5-yl]methyl]prop-2-enamide N-[[7-[4-(trifluoromethoxy)phenyl]oxazolo[5,4-b]pyridin-5-yl]methyl]prop-2-enamide N-[[4-[4-(trifluoromethoxy)phenyl]furo[3,2-d]pyrimidin-2-yl]methyl]prop-2-enamide N-methyl-N-[[7-[4-(trifluoromethoxy)phenyl]thiazolo[5,4-d]pyrimidin-5-yl]methyl]prop-2-enamide N-[[4-(hydroxymethyl)-7-[4-(trifluoromethoxy)phenyl]-2,3-dihydrobenzofuran-5-yl]methyl]prop-2-enamide N-[[4-[4-(trifluoromethoxy)phenyl]-6,7-dihydrofuro[3,2-d]pyrimidin-2-yl]methyl]prop-2-enamide 1-chloro-N-[[4-(hydroxymethyl)-7-[4-(trifluoromethoxy)phenyl]-2,3-dihydrobenzofuran-5-yl]methyl]methanesulfonamide 2-chloro-N-[[7-[4-(trifluoromethoxy)phenyl]thiazolo[5,4-d]pyrimidin-5-yl]methyl]acetamide N-[[5-cyano-8-[4-(trifluoromethoxy)phenyl]-6-quinolyl]methyl]prop-2-enamide N-[(1R)-1-[4-(hydroxymethyl)-7-[4-(trifluoromethoxy)phenyl]-2,3-dihydrobenzofuran-5-yl]ethyl]prop-2-enamide N-[(1S)-1-[4-(hydroxymethyl)-7-[4-(trifluoromethoxy)phenyl]-2,3-dihydrobenzofuran-5-yl]ethyl]prop-2-enamide N-[[4-(hydroxymethyl)-7-[4-(trifluoromethoxy)phenyl]-2,3-dihydrobenzofuran-5-yl]methyl]ethenesulfonamide 2,3,3-trideuterio-N-[[4-(hydroxymethyl)-7-[4-(trifluoromethoxy)phenyl]-2,3-dihydrobenzofuran-5-yl]methyl]prop-2-enamide N-[[7-[4-(trifluoromethoxy)phenyl]thiazolo[5,4-d]pyrimidin-5-yl]methyl]prop-2-enamide N-[[4-(hydroxymethyl)-7-(5-isopropoxythiazol-2-yl)-2,3-dihydrobenzofuran-5-yl]methyl]prop-2-enamide N-[[4-imidazol-1-yl-7-[4-(trifluoromethoxy)phenyl]-2,3-dihydrobenzofuran-5-yl]methyl]prop-2-enamide N-[[4-(hydroxymethyl)-7-[4-(pentafluoro-lambda6-sulfanyl)phenyl]-2,3-dihydrobenzofuran-5-yl]methyl]prop-2-enamide 2-chloro-N-[[4-(hydroxymethyl)-7-[4-(trifluoromethoxy)phenyl]-2,3-dihydrobenzofuran-5-yl]methyl]acetamide N-[[5-ethyl-8-[4-(trifluoromethoxy)phenyl]imidazo[1,2-a]pyridin-6-yl]methyl]prop-2-enamide;

N-[[4-cyano-3-methyl-7-[4-(trifluoromethoxy)phenyl]benzimidazol-5-yl]methyl]prop-2-enamide;

N-[[5-[(1R)-1,2-dihydroxyethyl]-8-[4-(trifluoromethoxy)phenyl]quinoxalin-6-yl]methyl]prop-2-enamide;

N-[[4-(hydroxymethyl)-3-methyl-7-[4-(trifluoromethoxy)phenyl]benzimidazol-5-yl]methyl]prop-2-enamide;

N-[[3-methyl-4-[(1S)-1,2-dihydroxyethyl]-7-[4-(trifluoromethoxy)phenyl]benzimidazol-5-yl]methyl]prop-2-enamide;

N-[[3-methyl-4-[(1R)-1,2-dihydroxyethyl]-7-[4-(trifluoromethoxy)phenyl]benzimidazol-5-yl]methyl]prop-2-enamide;

N-[[3-methyl-4-[(1R)-1-hydroxyethyl]-7-[4-(trifluoromethoxy)phenyl]benzimidazol-5-yl]methyl]prop-2-enamide;

N-[[3-methyl-4-[(1S)-1-hydroxyethyl]-7-[4-(trifluoromethoxy)phenyl]benzimidazol-5-yl]methyl]prop-2-enamide;

N-[[3-methyl-4-(1H-pyrazol-4-ylmethyl)-7-[4-(trifluoromethoxy)phenyl]benzimidazol-5-yl]methyl]prop-2-enamide;

N-[[2-methyl-7-[4-(trifluoromethoxy)phenyl]thiazolo[5,4-d]pyrimidin-5-yl]methyl]prop-2-enamide;

N-[[5-(hydroxymethyl)-8-[4-(trifluoromethoxy)phenyl]imidazo[1,2-a]pyridin-6-yl]methyl]-N-methyl-prop-2-enamide;

N-[[8-[4-(trifluoromethoxy)phenyl]imidazo[1,2-a]pyridin-6-yl]methyl]prop-2-enamide); N-methyl-N-[[8-[4-(trifluoromethoxy)phenyl]imidazo[1,2-a]pyridin-6-yl]methyl]prop-2-enamide;

N-[[3-(difluoromethyl)-4-(hydroxymethyl)-7-[4-(trifluoromethoxy)phenyl]benzimidazol-5-yl]methyl]prop-2-enamide;

(R)—N-((1-(difluoromethyl)-7-(1,2-dihydroxyethyl)-4-(4-(trifluoromethoxy)phenyl)-1H-benzo[d]imidazol-6-yl)methyl)acrylamide;

(S)—N-((1-(difluoromethyl)-7-(1,2-dihydroxyethyl)-4-(4-(trifluoromethoxy)phenyl)-1H-benzo[d]imidazol-6-yl)methyl)acrylamide;

N-[2-[4-cyano-3-methyl-7-[4-(trifluoromethoxy)phenyl]benzimidazol-5-yl]ethyl]prop-2-enamide;

N-[[8-methyl-5-[4-(trifluoromethoxy)phenyl]-7-quinolyl]methyl]prop-2-enamide;

N-[[8-(hydroxymethyl)-5-[4-(trifluoromethoxy)phenyl]-7-quinolyl]methyl]prop-2-enamide;

(S)—N-((8-(1,2-dihydroxyethyl)-5-(4-(trifluoromethoxy)phenyl)quinolin-7-yl)methyl)acrylamide;

(R)—N-((8-(1,2-dihydroxyethyl)-5-(4-(trifluoromethoxy)phenyl)quinolin-7-yl)methyl)acrylamide;

(S)—N-((5-(1,2-dihydroxyethyl)-8-(4-(trifluoromethoxy)phenyl)quinolin-6-yl)methyl) acrylamide;

(R)—N-((5-(1,2-dihydroxyethyl)-8-(4-(trifluoromethoxy)phenyl)quinolin-6-yl)methyl) acrylamide;

N-[[5-(hydroxymethyl)-8-[4-(trifluoromethoxy)phenyl]-6-quinolyl]methyl]-N-methyl-prop-2-enamide;

N-[[5-(hydroxymethyl)-8-[4-(trifluoromethoxy)phenyl]-6-quinolyl]methyl]prop-2-enamide;

N-[[5-[(1S)-1,2-dihydroxyethyl]-8-[4-(trifluoromethoxy)phenyl]-6-quinolyl]methyl]-N-methyl-prop-2-enamide;

N-[[5-[(1R)-1,2-dihydroxyethyl]-8-[4-(trifluoromethoxy)phenyl]-6-quinolyl]methyl]-N-methyl-prop-2-enamide;

(S)—N-((4-(1,2-dihydroxyethyl)-7-(4-(trifluoromethoxy)phenyl)-2,3-dihydrobenzofuran-5-yl)methyl)acrylamide;

(R)—N-((4-(1,2-dihydroxyethyl)-7-(4-(trifluoromethoxy)phenyl)-2,3-dihydrobenzofuran-5-yl)methyl)acrylamide;

(S)—N-((4-(1,2-dihydroxyethyl)-7-(4-(trifluoromethoxy)phenyl)-2,3-dihydrobenzofuran-5-yl)methyl)-N-methylacrylamide;

(R)—N-((4-(1,2-dihydroxyethyl)-7-(4-(trifluoromethoxy)phenyl)-2,3-dihydrobenzofuran-5-yl)methyl)-N-methylacrylamide;

N-[[3-methyl-4-methylsulfonyl-7-[4-(trifluoromethoxy)phenyl]benzimidazol-5-yl]methyl]prop-2-enamide;

N-[[4-(3-hydroxyprop-1-ynyl)-3-methyl-7-[4-(trifluoromethoxy)phenyl]benzimidazol-5-yl]methyl]prop-2-enamide;

2-fluoro-1-[3-[4-(hydroxymethyl)-3-methyl-7-[4-(trifluoromethoxy)phenyl]benzimidazol-5-yl]azetidin-1-yl]prop-2-en-1-one;

(S)—N-((1-methyl-7-(S-methylsulfonimidoyl)-4-(4-(trifluoromethoxy)phenyl)-1H-benzo[d]imidazol-6-yl)methyl)acrylamide;

(R)—N-((1-methyl-7-(S-methylsulfonimidoyl)-4-(4-(trifluoromethoxy)phenyl)-1H-benzo[d]imidazol-6-yl)methyl)acrylamide;

1-[3-[9-methyl-6-[4-(trifluoromethoxy)phenyl]purin-2-yl]azetidin-1-yl]prop-2-en-1-one;

- 2-fluoro-N-[[4-(hydroxymethyl)-3-methyl-7-[4-(trifluoromethoxy)phenyl]benzimidazol-5-yl]methyl]prop-2-enamide;
- (E)-4-hydroxy-N-[[4-(hydroxymethyl)-3-methyl-7-[4-(trifluoromethoxy)phenyl]benzimidazol-5-yl]methyl]-N-methyl-but-2-enamide;
- (R)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide;
- (S)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide;
- N-[[4-cyano-7-[4-(trifluoromethoxy)phenyl]-2,3-dihydrobenzofuran-5-yl]methyl]-2-fluoro-prop-2-enamide;
- N-[[1-methyl-7-[4-(trifluoromethoxy)phenyl]benzimidazol-5-yl]methyl]prop-2-enamide;
- N-[[9-methyl-6-[4-(trifluoromethoxy)phenyl]purin-2-yl]methyl]prop-2-enamide;
- N-[[7-[(1S)-1,2-dihydroxyethyl]-1-methyl-4-[4-(trifluoromethoxy)phenyl]imidazo[4,5-c]pyridin-6-yl]methyl]prop-2-enamide;
- N-[[7-[(1R)-1,2-dihydroxyethyl]-1-methyl-4-[4-(trifluoromethoxy)phenyl]imidazo[4,5-c]pyridin-6-yl]methyl]prop-2-enamide;
- N-[[3-methyl-4-(1H-pyrazol-4-yl)-7-[4-(trifluoromethoxy)phenyl]benzimidazol-5-yl]methyl]prop-2-enamide;
- N-((7-(hydroxymethyl)-1-methyl-4-(4-(trifluoromethoxy)phenyl)-1H-imidazo[4,5-c]pyridin-6-yl)methyl)acrylamide;
- (S)—N-((7-(3,4-dihydroxybut-1-yn-1-yl)-1-methyl-4-(4-(trifluoromethoxy)phenyl)-1H-benzo[d]imidazol-6-yl)methyl)acrylamide;
- (R)—N-((7-(3,4-dihydroxybut-1-yn-1-yl)-1-methyl-4-(4-(trifluoromethoxy)phenyl)-1H-benzo[d]imidazol-6-yl)methyl)acrylamide;
- 3-methyl-5-[(prop-2-enoylamino)methyl]-7-[4-(trifluoromethoxy)phenyl]benzimidazole-4-carboxamide;
- N-[[4-(difluoromethyl)-3-methyl-7-[4-(trifluoromethoxy)phenyl]benzimidazol-5-yl]methyl]prop-2-enamide;
- N-((7-(1H-imidazol-1-yl)-1-methyl-4-(4-(trifluoromethoxy)phenyl)-1H-benzo[d]imidazol-6-yl)methyl)acrylamide;
- (S)—N-((5-(1,2-Dihydroxyethyl)-8-(4-(trifluoromethoxy)phenyl)quinoxalin-6-yl)methyl)acrylamide;
- (R)—N-((5-(1,2-Dihydroxyethyl)-8-(4-(trifluoromethoxy)phenyl)quinoxalin-6-yl)methyl)-2-fluoroacrylamide;
- (R)—N-((5-(1,2-Dihydroxyethyl)-8-(4-(trifluoromethoxy)phenyl)quinoxalin-6-yl)methyl)cyclobut-1-ene-1-carboxamide;
- (R)—N-((5-(1-Hydroxyethyl)-8-(4-(trifluoromethoxy)phenyl)quinoxalin-6-yl)methyl)acrylamide;
- (S)—N-((5-(1-hydroxyethyl)-8-(4-(trifluoromethoxy)phenyl)quinoxalin-6-yl)methyl)acrylamide;
- N-((5-(Hydroxymethyl)-8-(4-(trifluoromethoxy)phenyl)quinoxalin-6-yl)methyl)acrylamide;
- N-((5-Cyano-8-(4-(trifluoromethoxy)phenyl)quinoxalin-6-yl)methyl)acrylamide;
- (R)-Cyclobut-1-en-1-yl(3-(5-(1,2-dihydroxyethyl)-8-(4-(trifluoromethoxy)phenyl)quinoxalin-6-yl)azetidin-1-yl)methanone;
- (S)-Cyclobut-1-en-1-yl(3-(5-(1,2-dihydroxyethyl)-8-(4-(trifluoromethoxy) phenyl)quinoxalin-6-yl)azetidin-1-yl)methanone;
- N-((4-(Hydroxymethyl)-7-(4-(trifluoromethoxy)phenyl)-2,3-dihydrobenzofuran-5-yl)methyl)-N-methylacrylamide;
- N-((4-((1S,2S)-1,2-Dihydroxypropyl)-7-(4-(trifluoromethoxy)phenyl)-2,3-dihydrobenzofuran-5-yl)methyl)acrylamide;
- N-((4-((1R,2R)-1,2-dihydroxypropyl)-7-(4-(trifluoromethoxy)phenyl)-2,3-dihydrobenzofuran-5-yl)methyl)acrylamide;
- (R)—N-((4-(2-Cyano-1-hydroxyethyl)-7-(4-(trifluoromethoxy)phenyl)-2,3-dihydrobenzofuran-5-yl)methyl)acrylamide;
- (S)—N-((4-(2-cyano-1-hydroxyethyl)-7-(4-(trifluoromethoxy)phenyl)-2,3-dihydrobenzofuran-5-yl)methyl)acrylamide;
- N-((7-(4-Ethynylphenyl)-4-(hydroxymethyl)-2,3-dihydrobenzofuran-5-yl)methyl)acrylamide;
- N-((7-(4-Ethynylphenyl)-4-(hydroxymethyl)-2,3-dihydrobenzofuran-5-yl)methyl)-N-methylacrylamide;
- N-((4-cyano-7-(4-(trifluoromethoxy)phenyl)-2,3-dihydrobenzofuran-5-yl)methyl)-N-methylacrylamide;
- N-[[7-[4-(Pentafluoro-6-sulfanyl)phenyl]-4-[rac-(1R)-1,2-dihydroxyethyl]-2,3-dihydrobenzofuran-5-yl]methyl]prop-2-enamide;
- N-[[7-[4-(pentafluoro-6-sulfanyl)phenyl]-4-[rac-(1S)-1,2-dihydroxyethyl]-2,3-dihydrobenzofuran-5-yl]methyl]prop-2-enamide;
- N-ethyl-N-((7-(4-(trifluoromethoxy)phenyl)thiazolo[5,4-d]pyrimidin-5-yl)methyl)acrylamide;
- 1-(3-(7-(4-(Trifluoromethoxy)phenyl)thiazolo[5,4-d]pyrimidin-5-yl)azetidin-1-yl)prop-2-en-1-one;
- (E)-4-Hydroxy-1-(3-(7-(4-(trifluoromethoxy)phenyl)thiazolo[5,4-d]pyrimidin-5-yl)azetidin-1-yl)but-2-en-1-one;
- N-((7-(4-(trifluoromethoxy)phenyl)thiazolo[5,4-d]pyrimidin-5-yl)methyl)acrylamide-2,3,3-d3;
- N-((7-(3-Isopropylbicyclo[1.1.1]pentan-1-yl)thiazolo[5,4-d]pyrimidin-5-yl)methyl)acrylamide;
- N-methyl-N-[[7-[4-(pentafluoro-6-sulfanyl)phenyl]thiazolo[5,4-d]pyrimidin-5-yl]methyl]prop-2-enamide;
- N-((7-(5-Oxo-4,5-dihydro-1,2,4-oxadiazol-3-yl)-4-(4-(trifluoromethoxy)phenyl)benzo[d]thiazol-6-yl)methyl)acrylamide;
- (S)—N-((7-(1,2-Dihydroxyethyl)-4-(4-(trifluoromethoxy)phenyl)benzo[d]oxazol-6-yl)methyl)acrylamide;
- (R)—N-((7-(1,2-dihydroxyethyl)-4-(4-(trifluoromethoxy)phenyl)benzo[d]oxazol-6-yl)methyl)acrylamide;
- (S)—N-((7-(1,2-dihydroxyethyl)-4-(4-(trifluoromethoxy)phenyl)benzo[d]oxazol-6-yl)methyl)-N-methylacrylamide;
- (R)—N-((7-(1,2-dihydroxyethyl)-4-(4-(trifluoromethoxy)phenyl)benzo[d]oxazol-6-yl)methyl)-N-methylacrylamide;
- (S)—N-((7-(1,2-Dihydroxyethyl)-4-(4-(trifluoromethyl)phenyl)benzo[d]oxazol-6-yl)methyl)acrylamide;
- (R)—N-((7-(1,2-dihydroxyethyl)-4-(4-(trifluoromethyl)phenyl)benzo[d]oxazol-6-yl)methyl)acrylamide;
- (S)—N-((7-(2-Oxooxazolidin-5-yl)-4-(4-(trifluoromethoxy)phenyl)benzo[d]oxazol-6-yl)methyl)acrylamide;
- (R)—N-((7-(2-oxooxazolidin-5-yl)-4-(4-(trifluoromethoxy)phenyl)benzo[d]oxazol-6-yl)methyl)acrylamide;
- N-((7-(Hydroxymethyl)-4-(4-(trifluoromethoxy)phenyl)benzo[d]oxazol-6-yl)methyl)acrylamide;
- N-((7-(Hydroxymethyl)-4-(6-(trifluoromethoxy)pyridin-3-yl)benzo[d]oxazol-6-yl)methyl)acrylamide; Cyclobut-1-en-1-yl(3-(9-methyl-6-(4-(trifluoromethoxy)phenyl)-9H-purin-2-yl)azetidin-1-yl)methanone;
- (E)-9-Methyl-2-(1-(prop-1-en-1-ylsulfonyl)azetidin-3-yl)-6-(4-(trifluoromethoxy)phenyl)-9H-purine;
- (E)-4-Hydroxy-1-(3-(9-methyl-6-(4-(trifluoromethoxy)phenyl)-9H-purin-2-yl)azetidin-1-yl)but-2-en-1-one;
- 2-Fluoro-1-(3-(9-methyl-6-(4-(trifluoromethoxy)phenyl)-9H-purin-2-yl)azetidin-1-yl)prop-2-en-1-one;

Bicyclo[1.1.0]butan-1-yl(3-(9-methyl-6-(4-(trifluoromethoxy)phenyl)-9H-purin-2-yl)azetidin-1-yl)methanone;

(E)-2-Methyl-1-(3-(9-methyl-6-(4-(trifluoromethoxy)phenyl)-9H-purin-2-yl)azetidin-1-yl)but-2-en-1-one;

(E)-1-(3-(9-Methyl-6-(4-(trifluoromethoxy)phenyl)-9H-purin-2-yl)azetidin-1-yl)but-2-en-1-one;

(R)-1-(3-(9-Methyl-6-(4-(trifluoromethoxy)phenyl)-9H-purin-2-yl)pyrrolidin-1-yl)prop-2-en-1-one;

(S)-1-(3-(9-methyl-6-(4-(trifluoromethoxy)phenyl)-9H-purin-2-yl)pyrrolidin-1-yl)prop-2-en-1-one;

1-(4-(9-Methyl-6-(4-(trifluoromethoxy)phenyl)-9H-purin-2-yl)piperazin-1-yl)prop-2-en-1-one;

(E)-4-Hydroxy-1-(4-(9-methyl-6-(4-(trifluoromethoxy)phenyl)-9H-purin-2-yl)piperazin-1-yl)but-2-en-1-one;

2-Fluoro-1-(4-(9-methyl-6-(4-(trifluoromethoxy)phenyl)-9H-purin-2-yl)piperazin-1-yl)prop-2-en-1-one;

N-(1-(9-Methyl-6-(4-(trifluoromethoxy)phenyl)-9H-purin-2-yl)azetidin-3-yl)acrylamide;

(E)-1-(4-Hydroxybut-2-enoyl)-3-(9-methyl-6-(4-(trifluoromethoxy)phenyl)-9H-purin-2-yl)azetidine-3-carbonitrile;

1-((9-Methyl-6-(4-(trifluoromethoxy)phenyl)-9H-purin-2-yl)methyl)-3-methylenepyrrolidin-2-one;

N-((9-Methyl-6-(4-(trifluoromethyl)piperidin-1-yl)-9H-purin-2-yl)methyl)acrylamide;

N-((9-Methyl-6-(4-(trifluoromethoxy)piperidin-1-yl)-9H-purin-2-yl)methyl)acrylamide;

1-(3-(9-(Difluoromethyl)-6-(4-(trifluoromethoxy)phenyl)-9H-purin-2-yl)azetidin-1-yl)-2-fluoroprop-2-en-1-one;

N-((9-Methyl-2-(4-(trifluoromethoxy)phenyl)-9H-purin-6-yl)methyl)acrylamide;

6-(1-(2-Fluoroacryloyl)azetidin-3-yl)-8-(4-(trifluoromethoxy)phenyl)pyrido[3,4-b]pyrazin-5(6H)-one;

6-(1-(Cyclobut-1-ene-1-carbonyl)azetidin-3-yl)-8-(4-(trifluoromethoxy)phenyl) pyrido[3,4-b]pyrazin-5(6H)-one;

5-(1-(2-Fluoroacryloyl)azetidin-3-yl)-3-methyl-7-(4-(trifluoromethoxy)phenyl)-3,5-dihydro-4H-imidazo[4,5-c]pyridin-4-one;

(E)-5-(I-(4-Hydroxybut-2-enoyl)azetidin-3-yl)-3-methyl-7-(4-(trifluoromethoxy)phenyl)-3,5-dihydro-4H-imidazo[4,5-c]pyridin-4-one;

(R)—N-((7-(1-Hydroxyethyl)-1-methyl-4-(4-(trifluoromethoxy)phenyl)-1H-benzo[d]imidazol-6-yl)methyl) acrylamide;

(S)—N-((7-(1-hydroxyethyl)-1-methyl-4-(4-(trifluoromethoxy)phenyl)-1H-benzo[d]imidazol-6-yl)methyl) acrylamide;

N-((7-((2-Hydroxyethyl)amino)-1-methyl-4-(4-(trifluoromethoxy)phenyl)-1H-benzo[d]imidazol-6-yl)methyl) acrylamide;

Methyl 2-(1-methyl-4-(4-(trifluoromethoxy)phenyl)-1H-benzo[d]imidazole-6-carboxamido)acrylate;

N-(3-Amino-3-oxoprop-1-en-2-yl)-1-methyl-4-(4-(trifluoromethoxy)phenyl)-1H-benzo[d]imidazole-6-carboxamide;

N-((7-Cyano-4-(2-fluoro-4-(trifluoromethoxy)phenyl)-1-methyl-1H-benzo[d]imidazol-6-yl)methyl)acrylamide;

N-(2-(7-Cyano-1-methyl-4-(4-(trifluoromethoxy)phenyl)-1H-benzo[d]imidazol-6-yl)ethyl)-N-methylacrylamide;

2-Fluoro-1-(3-(1-methyl-4-(4-(trifluoromethoxy)phenyl)-1H-benzo[d]imidazol-6-yl)azetidin-1-yl)prop-2-en-1-one;

N-((8-(4-(Trifluoromethyl)phenoxy)quinolin-6-yl)methyl) acrylamide;

(S)—N-((5-(1,2-Dihydroxyethyl)-8-(4-(trifluoromethyl) phenoxy)quinolin-6-yl)methyl)acrylamide; and (R)—N-((5-(1,2-dihydroxyethyl)-8-(4-(trifluoromethyl) phenoxy)quinolin-6-yl)methyl)acrylamide;

or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, tautomers, or mixtures thereof in any ratio, including racemic mixtures.

In some embodiments, provided herein is a compound selected from the group consisting of:

2-chloro-N-methyl-N-[[7-[4-(trifluoromethoxy)phenyl]thiazolo[5,4-d]pyrimidin-5-yl]methyl]acetamide N-[[4-cyano-7-[4-(trifluoromethoxy)phenyl]-2,3-dihydrobenzofuran-5-yl]methyl]prop-2-enamide N-[[7-(hydroxymethyl)-4-[6-(trifluoromethoxy)-3-pyridyl]-1,3-benzoxazol-6-yl]methyl]prop-2-enamide N-[[4-[4-(trifluoromethoxy)phenyl]-6,7-dihydro-5H-pyrano[2,3-d]pyrimidin-2-yl]methyl]prop-2-enamide N-[[5-(hydroxymethyl)-8-[4-(trifluoromethoxy)phenyl]imidazo[1,2-a]pyridin-6-yl]methyl]prop-2-enamide N-[[4-[4-(trifluoromethoxy)phenyl]-6,7-dihydro-5H-cyclopenta[d]pyrimidin-2-yl]methyl]prop-2-enamide N-[[4-[4-(trifluoromethoxy)phenyl]quinazolin-2-yl]methyl]prop-2-enamide N-[[7-[2-fluoro-4-(trifluoromethoxy)phenyl]-4-(hydroxymethyl)-2,3-dihydrobenzofuran-5-yl]methyl]prop-2-enamide N-[[7-[4-(trifluoromethoxy)phenyl]oxazolo[5,4-b]pyridin-5-yl]methyl]prop-2-enamide N-[[4-[4-(trifluoromethoxy)phenyl]furo[3,2-d]pyrimidin-2-yl]methyl]prop-2-enamide N-methyl-N-[[7-[4-(trifluoromethoxy)phenyl]thiazolo[5,4-d]pyrimidin-5-yl]methyl]prop-2-enamide N-[[4-(hydroxymethyl)-7-[4-(trifluoromethoxy)phenyl]-2,3-dihydrobenzofuran-5-yl]methyl]prop-2-enamide N-[[4-[4-(trifluoromethoxy)phenyl]-6,7-dihydrofuro[3,2-d]pyrimidin-2-yl]methyl]prop-2-enamide 1-chloro-N-[[4-(hydroxymethyl)-7-[4-(trifluoromethoxy)phenyl]-2,3-dihydrobenzofuran-5-yl]methyl]methanesulfonamide 2-chloro-N-[[7-[4-(trifluoromethoxy)phenyl]thiazolo[5,4-d]pyrimidin-5-yl]methyl]acetamide N-[[5-cyano-8-[4-(trifluoromethoxy)phenyl]-6-quinolyl]methyl]prop-2-enamide N-[(1R)-1-[4-(hydroxymethyl)-7-[4-(trifluoromethoxy)phenyl]-2,3-dihydrobenzofuran-5-yl]ethyl]prop-2-enamide N-[(1S)-1-[4-(hydroxymethyl)-7-[4-(trifluoromethoxy)phenyl]-2,3-dihydrobenzofuran-5-yl]ethyl]prop-2-enamide N-[[4-(hydroxymethyl)-7-[4-(trifluoromethoxy)phenyl]-2,3-dihydrobenzofuran-5-yl]methyl]ethenesulfonamide 2,3,3-trideuterio-N-[[4-(hydroxymethyl)-7-[4-(trifluoromethoxy)phenyl]-2,3-dihydrobenzofuran-5-yl]methyl]prop-2-enamide N-[[7-[4-(trifluoromethoxy)phenyl]thiazolo[5,4-d]pyrimidin-5-yl]methyl]prop-2-enamide N-[[4-(hydroxymethyl)-7-(5-isopropoxythiazol-2-yl)-2,3-dihydrobenzofuran-5-yl]methyl]prop-2-enamide N-[[4-imidazol-1-yl-7-[4-(trifluoromethoxy)phenyl]-2,3-dihydrobenzofuran-5-yl]methyl]prop-2-enamide N-[[4-(hydroxymethyl)-7-[4-(pentafluoro-lambda6-sulfanyl)phenyl]-2,3-dihydrobenzofuran-5-yl]methyl]prop-2-enamide 2-chloro-N-[[4-(hydroxymethyl)-7-[4-(trifluoromethoxy)phenyl]-2,3-dihydrobenzofuran-5-yl]methyl]acetamide N-[[5-ethyl-8-[4-(trifluoromethoxy)phenyl]imidazo[1,2-a]pyridin-6-yl]methyl]prop-2-enamide;

N-[[4-cyano-3-methyl-7-[4-(trifluoromethoxy)phenyl]benzimidazol-5-yl]methyl]prop-2-enamide;
N-[[5-[(1R)-1,2-dihydroxyethyl]-8-[4-(trifluoromethoxy)phenyl]quinoxalin-6-yl]methyl]prop-2-enamide;
N-[[4-(hydroxymethyl)-3-methyl-7-[4-(trifluoromethoxy)phenyl]benzimidazol-5-yl]methyl]prop-2-enamide;
N-[[3-methyl-4-[(1S)-1,2-dihydroxyethyl]-7-[4-(trifluoromethoxy)phenyl]benzimidazol-5-yl]methyl]prop-2-enamide;
N-[[3-methyl-4-[(1R)-1,2-dihydroxyethyl]-7-[4-(trifluoromethoxy)phenyl]benzimidazol-5-yl]methyl]prop-2-enamide;
N-[[3-methyl-4-[(1R)-1-hydroxyethyl]-7-[4-(trifluoromethoxy)phenyl]benzimidazol-5-yl]methyl]prop-2-enamide;
N-[[3-methyl-4-[(1S)-1-hydroxyethyl]-7-[4-(trifluoromethoxy)phenyl]benzimidazol-5-yl]methyl]prop-2-enamide;
N-[[3-methyl-4-(1H-pyrazol-4-ylmethyl)-7-[4-(trifluoromethoxy)phenyl]benzimidazol-5-yl]methyl]prop-2-enamide;
N-[[2-methyl-7-[4-(trifluoromethoxy)phenyl]thiazolo[5,4-d]pyrimidin-5-yl]methyl]prop-2-enamide;
N-[[5-(hydroxymethyl)-8-[4-(trifluoromethoxy)phenyl]imidazo[1,2-a]pyridin-6-yl]methyl]-N-methyl-prop-2-enamide;
N-[[8-[4-(trifluoromethoxy)phenyl]imidazo[1,2-a]pyridin-6-yl]methyl]prop-2-enamide);
N-methyl-N-[[8-[4-(trifluoromethoxy)phenyl]imidazo[1,2-a]pyridin-6-yl]methyl]prop-2-enamide;
N-[[3-(difluoromethyl)-4-(hydroxymethyl)-7-[4-(trifluoromethoxy)phenyl]benzimidazol-5-yl]methyl]prop-2-enamide;
(R)—N-((1-(difluoromethyl)-7-(1,2-dihydroxyethyl)-4-(4-(trifluoromethoxy)phenyl)-1H-benzo[d]imidazol-6-yl)methyl)acrylamide;
(S)—N-((1-(difluoromethyl)-7-(1,2-dihydroxyethyl)-4-(4-(trifluoromethoxy)phenyl)-1H-benzo[d]imidazol-6-yl)methyl)acrylamide;
N-[2-[4-cyano-3-methyl-7-[4-(trifluoromethoxy)phenyl]benzimidazol-5-yl]ethyl]prop-2-enamide;
N-[[8-methyl-5-[4-(trifluoromethoxy)phenyl]-7-quinolyl]methyl]prop-2-enamide;
N-[[8-(hydroxymethyl)-5-[4-(trifluoromethoxy)phenyl]-7-quinolyl]methyl]prop-2-enamide;
(S)—N-((8-(1,2-dihydroxyethyl)-5-(4-(trifluoromethoxy)phenyl)quinolin-7-yl)methyl)acrylamide;
(R)—N-((8-(1,2-dihydroxyethyl)-5-(4-(trifluoromethoxy)phenyl)quinolin-7-yl)methyl)acrylamide;
(S)—N-((5-(1,2-dihydroxyethyl)-8-(4-(trifluoromethoxy)phenyl)quinolin-6-yl)methyl) acrylamide;
(R)—N-((5-(1,2-dihydroxyethyl)-8-(4-(trifluoromethoxy)phenyl)quinolin-6-yl)methyl) acrylamide;
N-[[5-(hydroxymethyl)-8-[4-(trifluoromethoxy)phenyl]-6-quinolyl]methyl]-N-methyl-prop-2-enamide;
N-[[5-(hydroxymethyl)-8-[4-(trifluoromethoxy)phenyl]-6-quinolyl]methyl]prop-2-enamide;
N-[[5-[(1S)-1,2-dihydroxyethyl]-8-[4-(trifluoromethoxy)phenyl]-6-quinolyl]methyl]-N-methyl-prop-2-enamide;
N-[[5-[(1R)-1,2-dihydroxyethyl]-8-[4-(trifluoromethoxy)phenyl]-6-quinolyl]methyl]-N-methyl-prop-2-enamide;
(S)—N-((4-(1,2-dihydroxyethyl)-7-(4-(trifluoromethoxy)phenyl)-2,3-dihydrobenzofuran-5-yl)methyl)acrylamide;
(R)—N-((4-(1,2-dihydroxyethyl)-7-(4-(trifluoromethoxy)phenyl)-2,3-dihydrobenzofuran-5-yl)methyl)acrylamide;
(S)—N-((4-(1,2-dihydroxyethyl)-7-(4-(trifluoromethoxy)phenyl)-2,3-dihydrobenzofuran-5-yl)methyl)-N-methyl-acrylamide;
(R)—N-((4-(1,2-dihydroxyethyl)-7-(4-(trifluoromethoxy)phenyl)-2,3-dihydrobenzofuran-5-yl)methyl)-N-methyl-acrylamide;
N-[[3-methyl-4-methylsulfonyl-7-[4-(trifluoromethoxy)phenyl]benzimidazol-5-yl]methyl]prop-2-enamide;
N-[[4-(3-hydroxyprop-1-ynyl)-3-methyl-7-[4-(trifluoromethoxy)phenyl]benzimidazol-5-yl]methyl]prop-2-enamide;
2-fluoro-1-[3-[4-(hydroxymethyl)-3-methyl-7-[4-(trifluoromethoxy)phenyl]benzimidazol-5-yl]azetidin-1-yl]prop-2-en-1-one;
(S)—N-((1-methyl-7-(S-methylsulfonimidoyl)-4-(4-(trifluoromethoxy)phenyl)-1H-benzo[d]imidazol-6-yl)methyl)acrylamide;
(R)—N-((1-methyl-7-(S-methylsulfonimidoyl)-4-(4-(trifluoromethoxy)phenyl)-1H-benzo[d]imidazol-6-yl)methyl)acrylamide;
1-[3-[9-methyl-6-[4-(trifluoromethoxy)phenyl]purin-2-yl]azetidin-1-yl]prop-2-en-1-one;
2-fluoro-N-[[4-(hydroxymethyl)-3-methyl-7-[4-(trifluoromethoxy)phenyl]benzimidazol-5-yl]methyl]prop-2-enamide;
(E)-4-hydroxy-N-[[4-(hydroxymethyl)-3-methyl-7-[4-(trifluoromethoxy)phenyl]benzimidazol-5-yl]methyl]-N-methyl-but-2-enamide;
(R)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide;
(S)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide;
N-[[4-cyano-7-[4-(trifluoromethoxy)phenyl]-2,3-dihydrobenzofuran-5-yl]methyl]-2-fluoro-prop-2-enamide;
N-[[1-methyl-7-[4-(trifluoromethoxy)phenyl]benzimidazol-5-yl]methyl]prop-2-enamide;
N-[[9-methyl-6-[4-(trifluoromethoxy)phenyl]purin-2-yl]methyl]prop-2-enamide;
N-[[7-[(1S)-1,2-dihydroxyethyl]-1-methyl-4-[4-(trifluoromethoxy)phenyl]imidazo[4,5-c]pyridin-6-yl]methyl]prop-2-enamide;
N-[[7-[(1R)-1,2-dihydroxyethyl]-1-methyl-4-[4-(trifluoromethoxy)phenyl]imidazo[4,5-c]pyridin-6-yl]methyl]prop-2-enamide;
N-[[3-methyl-4-(1H-pyrazol-4-yl)-7-[4-(trifluoromethoxy)phenyl]benzimidazol-5-yl]methyl]prop-2-enamide;
N-((7-(hydroxymethyl)-1-methyl-4-(4-(trifluoromethoxy)phenyl)-1H-imidazo[4,5-c]pyridin-6-yl)methyl)acrylamide;
(S)—N-((7-(3,4-dihydroxybut-1-yn-1-yl)-1-methyl-4-(4-(trifluoromethoxy)phenyl)-H-benzo[d]imidazol-6-yl)methyl)acrylamide;
(R)—N-((7-(3,4-dihydroxybut-1-yn-1-yl)-1-methyl-4-(4-(trifluoromethoxy)phenyl)-1H-benzo[d]imidazol-6-yl)methyl)acrylamide; 3-methyl-5-[(prop-2-enoylamino)methyl]-7-[4-(trifluoromethoxy)phenyl]benzimidazole-4-carboxamide;
N-[[4-(difluoromethyl)-3-methyl-7-[4-(trifluoromethoxy)phenyl]benzimidazol-5-yl]methyl]prop-2-enamide; and;
N-((7-(1H-imidazol-1-yl)-1-methyl-4-(4-(trifluoromethoxy)phenyl)-1H-benzo[d]imidazol-6-yl)methyl)acrylamide;
or a pharmaceutically acceptable salt thereof. Also provided herein are, where applicable, any and all stereoisomers of the compounds depicted herein, including geometric isomers (e.g., cis/trans isomers or E/Z iso- In one aspect, provided herein is a compound, or a stereoisomer, tautomer, or pharmaceutically acceptable salt thereof, selected from the group consisting of:
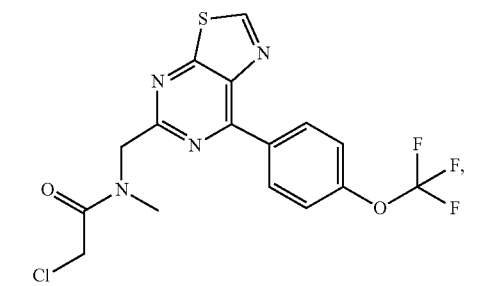
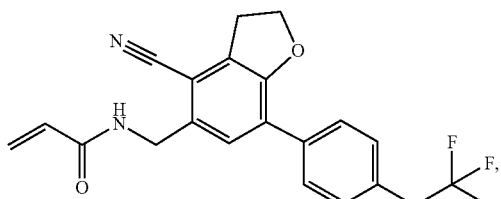
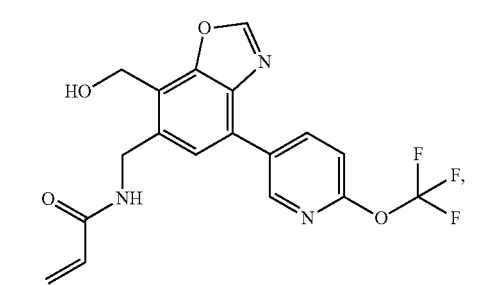
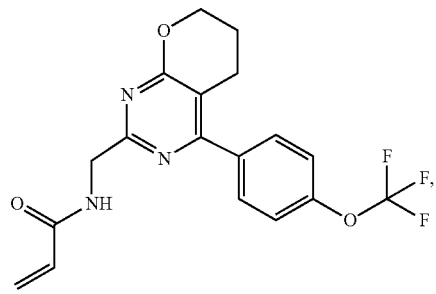
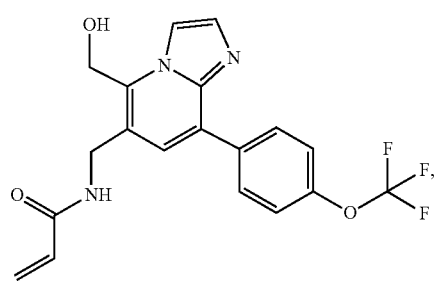
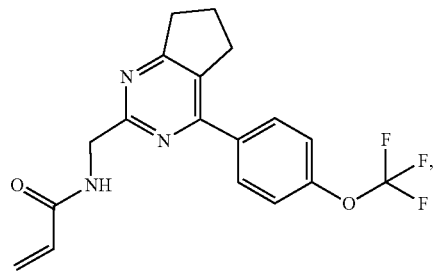
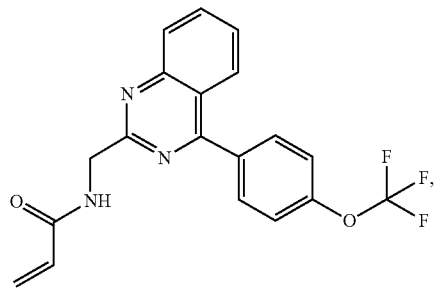
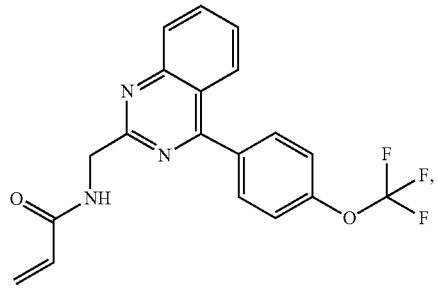
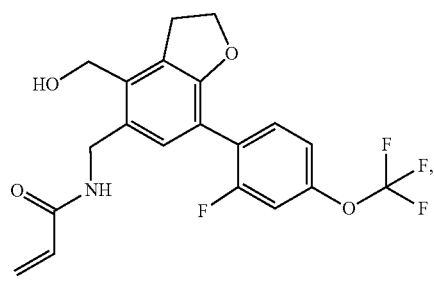
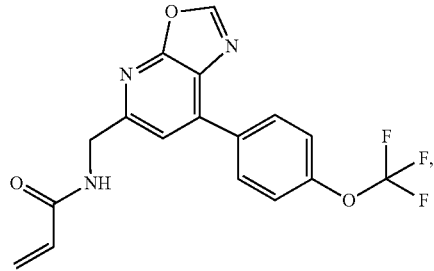
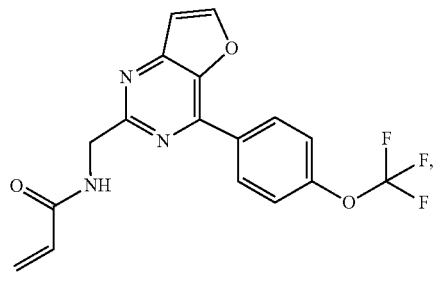

165
-continued
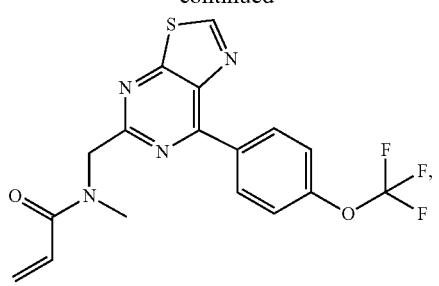
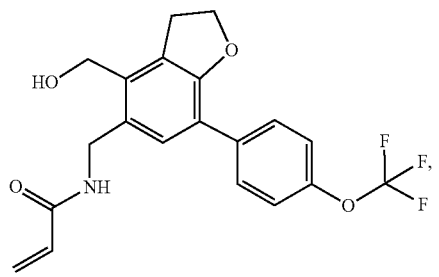
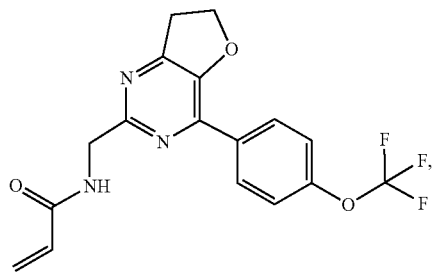
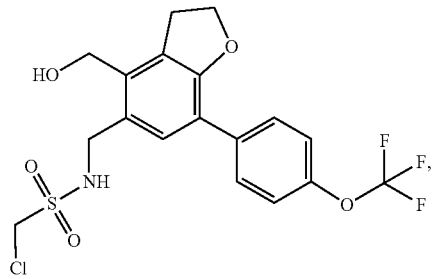
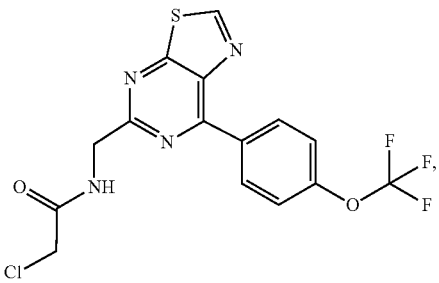
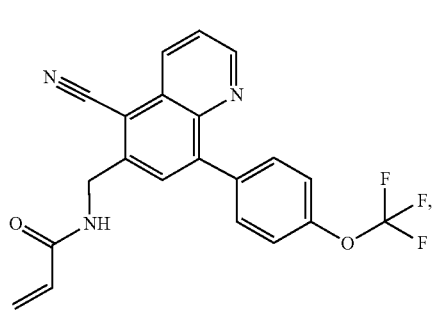
166
-continued
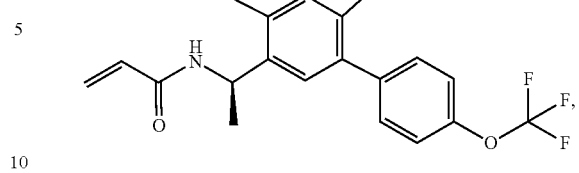
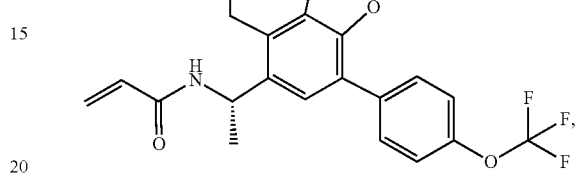
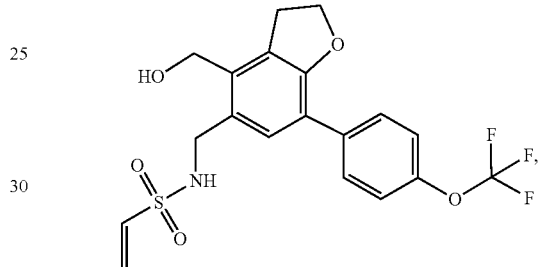
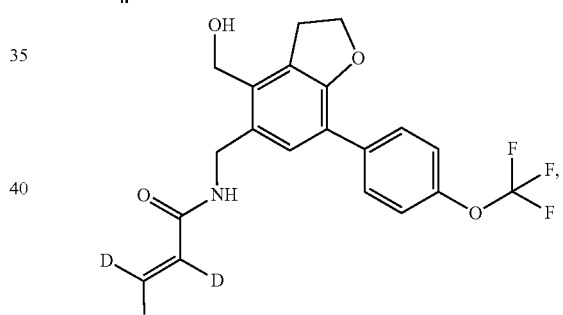
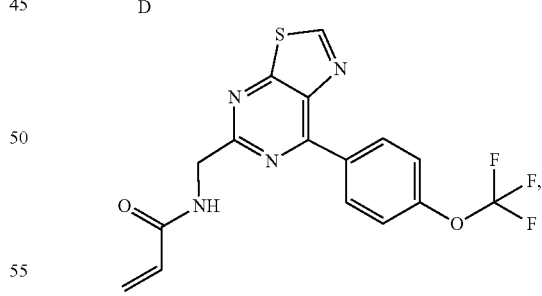
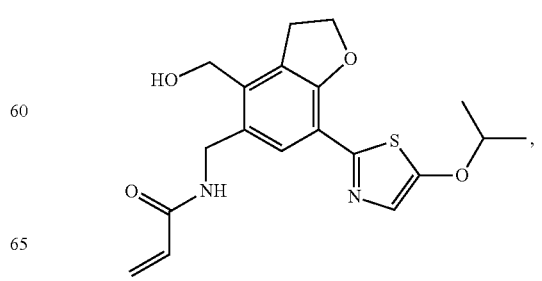

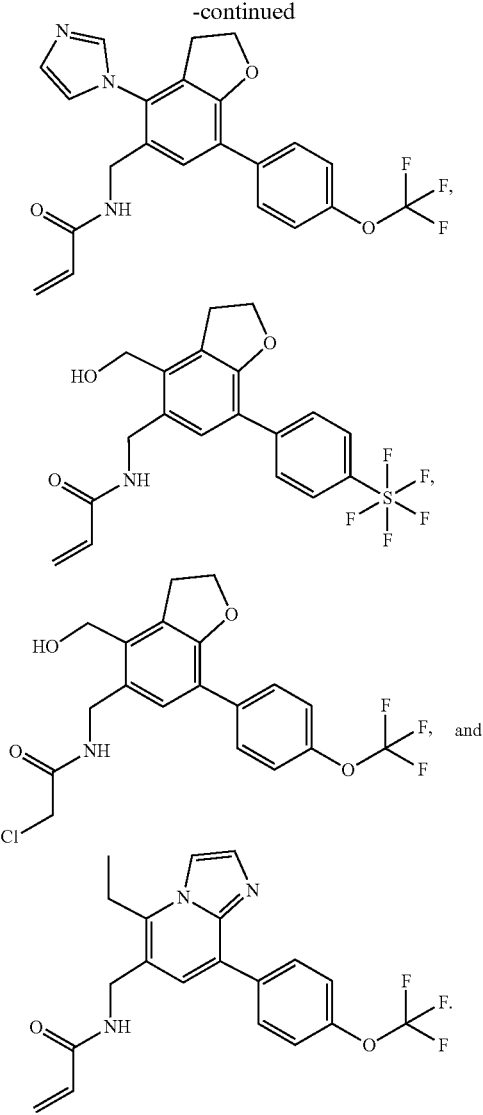

In some aspects, the compounds of the disclosure are isotopically labeled by having one or more atoms therein replaced by an atom having a different atomic mass or mass number. Such isotopically-labeled (i.e., radiolabeled) compounds of formula (II-A) or formula (II-B) are considered to be within the scope of this disclosure. Examples of isotopes that can be incorporated into the compounds of formula (II-A) or formula (II-B) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action, or binding affinity to TEAD. Certain isotopically-labeled compounds of formula (II-A) or formula (II-B), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (II-A) or formula (II-B) can be enriched with 1, 2, 5, 10, 25, 50, 75, 90, 95, or 99 percent of a given isotope.

In some aspects, any of the ways in which compounds of formula (II-A) or formula (II-B) may be isotopically labeled, and any of the ways in which isotopically-labeled compounds of formula (II-A) or formula (II-B) may be used (as described, e.g. in the previous paragraph) also apply to compounds of formula (II-AB).

In some aspects, any of the ways in which compounds of formula (II-A) or formula (II-B) may be isotopically labeled, and any of the ways in which isotopically-labeled compounds of formula (II-A) or formula (II-B) may be used (as described, e.g. in the previous paragraph) also apply to compounds of formula (II-AB').

Substitution with heavier isotopes such as deuterium, i.e. 2H, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (II-A) or formula (II-B) can generally be prepared by conventional techniques known to those skilled in the art or by processes analogous to those described in the Examples as set out below using an appropriate isotopically-labeled reagent in place of the non-labeled reagent previously employed.

In some aspects, any of the ways in which compounds of formula (II-A) or formula (II-B) may be isotopically labeled, and any of the ways in which isotopically-labeled compounds of formula (II-A) or formula (II-B) may be used (as described, e.g. in the previous paragraph) also apply to compounds of formula (II-AB).

In some aspects, any of the ways in which compounds of formula (II-A) or formula (II-B) may be isotopically labeled, and any of the ways in which isotopically-labeled compounds of formula (II-A) or formula (II-B) may be used (as described, e.g. in the previous paragraph) also apply to compounds of formula (II-AB').

Also provided herein is a pharmaceutically acceptable salt or ester of any compound provided herein, as well as a stereoisomer, a geometric isomer, a tautomer, a solvate, a metabolite, an isotope or a prodrug of such compound or a pharmaceutically acceptable salt of such compound.

PROCESS OF PREPARATION

In one aspect, the present disclosure is directed to processes of preparing one or more TEAD inhibitors described herein. In some embodiments, a process of preparing a TEAD inhibitor is described herein in one or more examples.

In some embodiments, provided is a process for preparing a compound of formula (II-AB'):

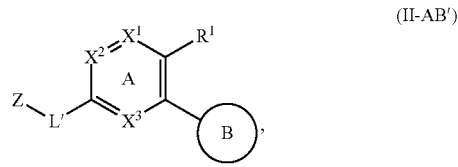

(II-AB')

or a stereoisomer or tautomer thereof, or a pharmaceutically acceptable salt thereof, wherein:

L' is *—N(R³)-L-** or

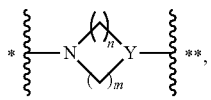

m, or Z-L' is

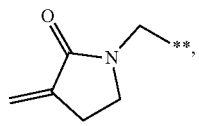

wherein * denotes the point of attachment to Z, and ** denotes the point of attachment to

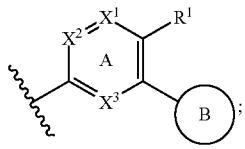

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;
wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN;
$X^2$ is N or CR$^s$, wherein R$^s$ is selected from H, halo, $C_{1-15}$alkyl, hydroxyl$C_{1-6}$alkynyl, $C_{6-20}$aryl, 5 to 15 membered heteroaryl, $C_{3-20}$cycloalkyl, 3 to 15 membered heterocyclyl, —OH, —CN, $C_{1-15}$-alkoxy, —NR$^d$COR$^e$, —CONR$^d$R$^e$, —SO$_2$R$^d$, —S(O)NHR$^d$, —SO$_2$NR$^d$R$^e$, —NR$^d$SO$_2$R$^e$, and —NR$^d$R$^e$;
wherein the $C_{1-15}$alkyl and $C_{1-15}$alkoxy of R$^s$ are each independently optionally substituted with one or more R$^{t1}$, wherein R$^t$ is independently at each occurrence halo, oxo, —OH, —CN, 5-6 membered heteroaryl, or —NR$^d$R$^e$, wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN; and wherein the $C_{6-20}$aryl, 5 to 15 membered heteroaryl, $C_{3-20}$cycloalkyl, and 3 to 15 membered heterocyclyl of R$^s$ are each independently optionally substituted with one or more R$^{t2}$, wherein R$^{t2}$ is independently at each occurrence selected from halo, oxo, —OH, —CN and $C_{1-6}$alkyl; and
wherein R$^d$ and R$^e$ are each independently H or $C_{1-6}$alkyl, and wherein the $C_{1-6}$alkyl of R$^d$ or R$^e$ is option-
ally substituted with one or more substituents selected from halo, oxo, —OH and —CN;
$X^3$ is N or CH;
B is
  i) phenyl or 5 to 6 membered heteroaryl; wherein the phenyl and 5 to 6 membered heteroaryl of B are each independently substituted with one or more $R^2$, wherein $R^2$ is independently, at each occurrence, halo; S(R$^y$)$_5$, wherein each R$^y$ is halo; $C_{1-6}$alkoxy optionally substituted with one or more halo; or
  ii) —O-phenyl substituted with halo$C_{1-3}$alkyl, provided that when B is —O-phenyl substituted with halo$C_{1-3}$alkyl, L' is *—N(R³)-L-**, Z is —C(O)CHCH$_2$, $X^1$ is C, $X^2$ is CR$^s$, and $X^3$ is CH; or
  iii) bicyclopentane substituted by $C_{1-3}$alkyl, provided that when B is bicyclopentane substituted by $C_{1-3}$alkyl, L' is *—N(R³)-L-** and Z is —C(O)CHCH$_2$; or
  iv) phenyl substituted with ethynyl or halo$C_{1-3}$alkyl, provided that when B is phenyl substituted with ethynyl or halo$C_{1-3}$alkyl, L' is *—N(R³)-L-**, Z is —C(O)CHCH$_2$, and R$^s$ is $C_1$-3alkyl substituted with one or more —OH; or
  v) piperidine substituted with halo$C_{1-3}$alkyl or halo$C_{1-3}$alkoxy, provided that when B is piperidine substituted with halo$C_{1-3}$alkyl or halo$C_{1-3}$alkoxy, L' is *—N(R³)-L-** and Z is —C(O)CHCH$_2$;
$R^3$ is H or $C_{1-6}$alkyl;
Z is —OH, —NR$^d$R$^e$, $C_{1-6}$alkoxy, —C(O)R$^a$, or —S(O)$_2$R$^b$,
  wherein R$^d$ and R$^e$ are each independently H or $C_{1-6}$alkyl, and wherein the $C_{1-6}$alkyl of R$^d$ or R* is optionally substituted with one or more substituents selected from halo, oxo, —OH and —CN;
R$^a$ and R$^b$ are each independently i) $C_{2-6}$alkenyl optionally substituted with one or more substituents selected from deuterium, $C_{1-6}$alkyl, hydroxyl $C_{1-6}$alkyl, halo and halo$C_{1-6}$ alkyl; ii) $C_{1-6}$alkyl, optionally substituted with one or more halo; or iii) cyclobutenyl or bicyclobutanyl;
L is methylene or ethylene, wherein the methylene of L is optionally substituted with one $C_{1-6}$ alkyl;
Y is CH or C(CN), and
n and m are each independently 1 or 2;
provided that:
  i) when i-1) $X^1$ is taken together with $R^1$ and the atoms to which they are attached to form a phenyl, and i-2) $X^2$ or $X^3$ is N, B of formula (II-AB') is phenyl and $R^2$ is halo$C_{1-6}$alkoxyl; and
  ii) when n=1 and m=2, or n=2 and m=1, B is phenyl substituted by halomethyoxyl; and
  iii) the compound of formula (II-AB') is not any one of following:
N-((8-(4-fluorophenyl)imidazo[1,2-a]pyrazin-6-yl)methyl)acrylamide;
N-((8-(4-(trifluoromethoxy)phenyl)imidazo[1,2-a]pyrazin-6-yl)methyl)acrylamide;
N-((7-fluoro-4-(4-(trifluoromethoxy)phenyl)quinazolin-2-yl)methyl)acrylamide;
N-((8-(4-(difluoromethoxy)phenyl)imidazo[1,2-a]pyrazin-6-yl)methyl)acrylamide;
1-(4-(4-(4-methoxyphenyl)-1-methyl-1H-imidazo[4,5-c]pyridin-6-yl)piperidin-1-yl)ethan-1-one;
4-(4-methoxyphenyl)-1-methyl-6-(1-(methylsulfonyl)piperidin-4-yl)-1H-imidazo[4,5-c]pyridine;
6-(1-(ethylsulfonyl)piperidin-4-yl)-4-(4-methoxyphenyl)-1-methyl-1H-imidazo[4,5-c]pyridine;

6-(1-(ethylsulfonyl)piperidin-4-yl)-1-isopropyl-4-(4-methoxyphenyl)-1H-imidazo[4,5-c]pyridine;
4-(4-methoxyphenyl)-1-methyl-6-(1-((trifluoromethyl)sulfonyl)piperidin-4-yl)-1H-imidazo[4,5-c]pyridine; and
N-((4-(4-fluorophenyl)-1,8-naphthyridin-2-yl)methyl)acetamide.

PHARMACEUTICAL COMPOSITIONS AND ADMINISTRATION

In addition to one or more of the compounds provided above (including stereoisomers, geometric isomers, tautomers, solvates, metabolites, isotopes, pharmaceutically acceptable salts, or prodrugs thereof), the disclosure also provides for compositions and medicaments comprising a compound of the present disclosure or an embodiment or aspect thereof and at least one pharmaceutically acceptable carrier. The compositions of the disclosure can be used to selectively inhibit TEAD in patients (e.g., humans).

In one aspect, the disclosure provides for pharmaceutical compositions or medicaments comprising a compound of the disclosure (or embodiments and aspects thereof including stereoisomers, geometric isomers, tautomers, solvates, metabolites, isotopes, pharmaceutically acceptable salts, and prodrugs) and a pharmaceutically acceptable carrier, diluent or excipient. In another aspect, the disclosure provides for preparing compositions (or medicaments) comprising compounds of the disclosure. In another aspect, the disclosure provides for administering compounds of the disclosure and compositions comprising compounds of the disclosure to a patient (e.g., a human patient) in need thereof.

The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of a compound of the disclosure which are prepared by dissolving solid compounds of the disclosure in water to produce an aqueous solution, and rendering the solution sterile. Suitable pharmaceutical excipients include starch, cellulose, talc, glucose, lactose, tale, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of a compound of the disclosure together with a suitable carrier so as to prepare the proper dosage form for proper administration to the recipient.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TEAD activity as required to prevent or treat the undesired disease or disorder, such as for example, pain. For example, such amount may be below the amount that is toxic to normal cells, or the mammal as a whole.

In one example, the therapeutically effective amount of the compound of the disclosure administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain aspects, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present disclosure may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compositions comprising compounds of the disclosure (or embodiments or aspects thereof including stereoisomers, geometric isomers, tautomers, solvates, metabolites, isotopes, pharmaceutically acceptable salts, and prodrugs thereof) are normally formulated in accordance with standard pharmaceutical practice as a pharmaceutical composition. A typical formulation is prepared by mixing a compound of the present disclosure and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present disclosure or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). An active pharmaceutical ingredient of the disclosure (e.g., a compound of formula (I), or an embodiment or aspect thereof) can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005)$_{21S}$t Edition, Lippincott Williams & Wilkins, Philadelphia, PA. The particular carrier, diluent or excipient used will depend upon the means and purpose for which a compound of the present disclosure is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

Sustained-release preparations of a compound of the disclosure (e.g., compound of formula (II-A) or formula (II-B), or an embodiment or aspect thereof) can be prepared. Suitable examples of sustained-release preparations include semipermeable matrices of solid hydrophobic polymers containing a compound of formula (II-A) or formula (II-B), or an embodiment or aspect thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

Sustained-release preparations of a compound of formula (II-AB) may be prepared in the same way as sustained-release preparations of a compound of formula (II-A) or formula (II-B) (as described, e.g. in the preceding paragraph).

Sustained-release preparations of a compound of formula (II-AB') may be prepared in the same way as sustained-release preparations of a compound of formula (II-A) or formula (II-B) (as described, e.g. in the preceding paragraph).

In one example, compounds of the disclosure or an embodiment or aspect thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of the disclosure (or an embodiment or aspect thereof) is formulated in an acetate buffer, at pH 5. In another aspect, the compounds of the disclosure or an embodiment thereof are sterile. The compound may be stored, for example, as a solid or amorphous composition, as a lyophilized formulation or as an aqueous solution Formulations of a compound of the disclosure suitable for oral administration can be prepared as discrete units such as pills, capsules, cachets or tablets each containing a predetermined amount of a compound of the disclosure.

Compressed tablets can be prepared by compressing in a suitable machine a compound of the disclosure in a free-flowing form such as a powder or granules, optionally mixed with a binder, lubricant, inert diluent, preservative, surface active or dispersing agent. Molded tablets can be made by molding in a suitable machine a mixture of a powdered compound of the disclosure moistened with an inert liquid diluent. The tablets can optionally be coated or scored and optionally are formulated so as to provide slow or controlled release of a compound of the disclosure therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the disclosure intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing a compound of the disclosure in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 0.1 mg, about 1 mg, about 5 mg, about 10 mg, about 25 mg, about 30 mg, about 50 mg, about 80 mg, about 100 mg, about 150 mg, about 250 mg, about 300 mg and about 500 mg of the compounds (or an embodiment or aspect thereof) of the disclosure compounded with a filler (e.g., lactose, such as about 90-30 mg anhydrous lactose), a disintegrant (e.g, croscarellose, such as about 5-40 mg sodium croscarmellose), a polymer (e.g. polyvinylpyrrolidone (PVP), a cellulose (e.g., hydroxypropylmethyl cellulose (HPMe), and/or copovidone, such as about 5-30 mg PVP, HPMe or copovidone), and a lubricant (e.g., magnesium stearate, such as about 1-10 mg). Wet granulation, dry granulation or dry blending may be used. In one wet granulation aspect, powdered ingredients are first mixed together and then mixed with a solution or suspension of the polymer (e.g., PVP). The resulting composition can be dried, granulated, mixed with lubricant and compressed to tablet form using conventional equipment. An example of an aerosol formulation can be prepared by dissolving the compound, for example 5-400 mg, of the disclosure in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the compounds of the disclosure in an amount of, for example, 0.075 to 20% w/w. When formulated in an ointment, the compounds of the disclosure can be employed with either a paraffinic or a water-miscible ointment base. Alternatively, the compounds of the disclosure can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of a compound of the disclosure through the skin or other affected areas. Examples of such dermal penetration enhancers include dimethyl sulfoxide and related analogs.

For topical formulations, it is desired to administer an effective amount of a pharmaceutical composition according to the disclosure to target area, e.g., skin surfaces, mucous membranes, and the like, which are adjacent to peripheral neurons which are to be treated. This amount will generally range from about 0.0001 mg to about 1 g of a compound of the disclosure (or an embodiment or aspect thereof) per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of a compound of the disclosure is used per cc of ointment base. The pharmaceutical composition can be formulated as transdermal compositions or transdermal delivery devices ("patches"). Such compositions include, for example, a backing, compound of the disclosure reservoir, a control membrane, liner and contact adhesive. Such transdermal patches may be used to provide continuous pulsatile, or on demand delivery of the compounds of the present disclosure as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of a compound of the disclosure.

When the binding target is located in the brain, certain aspects of the disclosure provide for a compound of the disclosure (or an embodiment or aspect thereof) to traverse the blood-brain barrier. Certain neurodegenerative diseases are associated with an increase in permeability of the blood-brain barrier, such that a compound of the disclosure (or an embodiment or aspect thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of the disclosure (or an embodiment or aspect thereof) across the blood-brain barrier include, but are not limited to, circumventing the blood- brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91 :2076-2080, 1994), and implanting a delivery device in the brain (see, e.g., Gill et al., Nature Med. 9:589-595, 2003; and Gliadel Wafers™, Guildford Pharmaceutical).

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686, 416).

Lipid-based methods of transporting a compound of formula of the disclosure (or an embodiment or aspect thereof) across the blood-brain barrier include, but are not limited to, encapsulating the a compound of the disclosure (or an embodiment or aspect thereof) in liposomes that are coupled to antibody binding fragments that bind to receptors on the vascular endothelium of the blood- brain barrier (see, e.g., U.S. Patent Application Publication No. 2002/0025313), and coating a compound of the disclosure (or an embodiment or aspect thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of the disclosure (or an embodiment or aspect thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/ 0089473), inhibiting ABC drug transporters (see, e.g., U.S. Patent Application Publication No. 2003/0073713); coating a compound of the disclosure (or an embodiment or aspect thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain aspects, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic mini pumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

INDICATIONS AND METHODS OF TREATMENT

Representative compounds of the disclosure have been shown to modulate TEAD activity.

In some embodiments, a compound that modulates TEAD activity is a compound of formula (II-A), or a stereoisomer, tautomer, or pharmaceutically acceptable salt thereof:

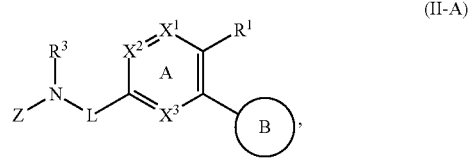

(II-A)

wherein:
$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A;
wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from $C_{1-3}$alkyl, —OH, oxo, $C_{1-3}$alkoxy, and —$NR^dR^e$; and
wherein $R^d$ and $R^e$ are each independently H or $C_{1-6}$alkyl, wherein the $C_{1-6}$alkyl of $R^d$ or $R^e$ is optionally substituted with one or more substituents selected from halo, oxo, —OH and —CN;
$X^2$ is N or $CR^s$, wherein $R^s$ is selected from the group consisting of H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^d$-$COR^e$, —$CONR^dR^e$, —$SO_2R^d$, —$SO_2NR^dR^e$, —$NR^dSO_2R^1$, and —$NR^dR^e$;
wherein the $C_{1-15}$alkyl and $C_{1-15}$alkoxy of $R^s$ are each independently optionally substituted with one or more $R^{t1}$, wherein $R^{t1}$ is independently at each occurrence halo, oxo, —OH, —CN, or —$NR^dR^e$, wherein $R^d$ and $R^e$ are each independently H or $C_{1-6}$alkyl; and
wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently at each occurrence selected from halo, oxo, —OH, —CN and $C_{1-6}$alkyl; and
wherein $R^d$ and $R^e$ are each independently H or $C_{1-6}$alkyl, wherein the $C_{1-6}$alkyl of $R^d$ or $R^e$ is optionally substituted with one or more substituents selected from halo, oxo, —OH and —CN;

$X^3$ is N or CH;
B is phenyl or 5 to 6 membered heteroaryl; wherein the phenyl and 5 to 6 membered heteroaryl of B are each independently substituted with one to five $R^2$;
$R^2$ is independently, at each occurrence, i) halo; ii) $S(R^y)_5$, wherein each $R^y$ is halo; or iii) $C_{1-6}$ alkoxy, optionally substituted with one or more halo;
$R^3$ is H or $C_{1-6}$alkyl;
Z is —OH, —$NR^dR^e$, $C_{1-6}$alkoxy, —$C(O)R^a$, —$S(O)_2R^a$, wherein $R^d$ and $R^e$ are each independently H or $C_{1-6}$alkyl;
$R^a$ is i) $C_{2-6}$alkenyl optionally substituted with one or more deuterium, $C_{1-6}$alkyl, halo, halo$C_{1-6}$ alkyl; or ii) $C_{1-6}$alkyl, optionally substituted with one or more halo; and
L is methylene, optionally substituted with one or more $C_{1-6}$alkyl.

In some embodiments, a compound that modulates TEAD activity is a compound of formula (II-B), or a stereoisomer, tautomer, or pharmaceutically acceptable salt thereof:

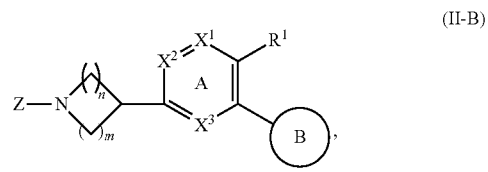

(II-B)

wherein:
$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl that is fused to ring A;
wherein the 5 to 6 membered heteroaryl, 5 to 6 membered heterocyclyl, phenyl, and $C_{5-6}$ cycloalkyl formed by $X^1$ and $R^1$ are each independently optionally substituted with one or more $R^t$, wherein $R^t$ is independently, at each occurrence, selected from $C_{1-3}$alkyl, —OH, oxo, $C_{1-3}$alkoxy, and —$NR^dR^e$; and
wherein $R^d$ and RC are each independently H or $C_{1-6}$alkyl, wherein the $C_{1-6}$alkyl of $R^d$ or $R^e$ is optionally substituted with one or more substituents selected from halo, oxo, —OH and —CN;
$X^2$ is N or $CR^s$, wherein $R^s$ is selected from the group consisting of H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;
wherein the $C_{1-15}$alkyl and $C_{1-15}$alkoxy of $R^s$ are each independently optionally substituted with one or more $R^{t1}$, wherein $R^{t1}$ is independently at each occurrence halo, oxo, —OH, —CN, or —$NR^dR^e$, wherein $R^d$ and $R^e$ are each independently H or $C_{1-6}$alkyl; and
wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently at each occurrence selected from halo, oxo, —OH, —CN and $C_{1-6}$alkyl; and
wherein $R^d$ and $R^e$ are each independently H or $C_{1-6}$alkyl, wherein the $C_{1-6}$alkyl of $R^d$ or $R^e$ is optionally substituted with one or more substituents selected from halo, oxo, —OH and —CN;

$X^3$ is N or CH;

B is phenyl or 5 to 6 membered heteroaryl; wherein the phenyl and 5 to 6 membered heteroaryl of B are each independently substituted with one to five $R^2$;

$R^2$ is independently, at each occurrence, i) halo; ii) $S(R^y)_5$, wherein each $R^y$ is halo; or iii) $C_{1-6}$ alkoxy, optionally substituted with one or more halo;

Z is —OH, —$NR^dR^e$, $C_{1-6}$alkoxy, —$C(O)R^a$, —$S(O)_2R^a$, wherein $R^d$ and $R^e$ are each independently H or $C_{1-6}$alkyl;

$R^a$ is i) $C_{2-6}$alkenyl optionally substituted with one or more deuterium, $C_{1-6}$alkyl, halo, halo$C_{1-6}$ alkyl; or ii) $C_{1-6}$alkyl, optionally substituted with one or more halo; and n and m are each independently 1 or 2.

In some embodiments, the compound that modulates TEAD activity is a compound of formula (II-AB):

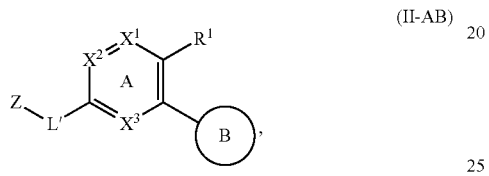

(II-AB)

or a stereoisomer or tautomer thereof, or a pharmaceutically acceptable salt thereof, wherein:

L' is selected from the group consisting of *—$N(R^3)$-L-** and

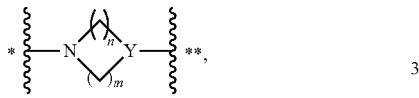

wherein * denotes the point of attachment to Z, and ** denotes the point of attachment to

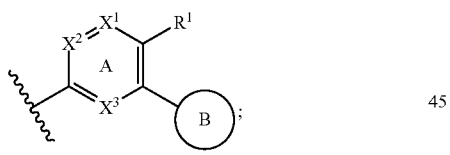

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;
wherein the 5 to 6 membered heteroaryl, 5 to 6 membered heterocyclyl, phenyl, and $C_{5-6}$cycloalkyl formed by $X^1$ and $R^1$ are each independently optionally substituted with one or more $R^t$, wherein $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$; and
wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

$X^2$ is N or $CR^s$, wherein $R^s$ is selected from H, halo, $C_{1-15}$alkyl, hydroxyl$C_{1-6}$alkynyl, $C_{6-20}$aryl, 5 to 15 membered heteroaryl, $C_{3-20}$cycloalkyl, 3 to 15 membered heterocyclyl, —OH, —CN, $C_{1-15}$ alkoxy, —$NR^d$-$COR^e$, —$CONR^dR^e$, —$SO_2R^d$, —$S(O)NHR^d$, —$SO_2NR^dR^e$, —$NR^dSO_2R^e$, and —$NR^dR^e$;
wherein the $C_{1-15}$alkyl and $C_{1-15}$alkoxy of $R^s$ are each independently optionally substituted with one or more $R^4$, wherein $R^{t1}$ is independently at each occurrence halo, oxo, —OH, —CN, 5-6 membered heteroaryl, or —$NR^dR^e$, wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{ta}$ is independently at each occurrence selected from halo, oxo, —OH, —CN and $C_{1-6}$alkyl; and
wherein $R^d$ and RC are each independently H or $C_{1-6}$alkyl, and wherein the $C_{1-6}$alkyl of $R^d$ or $R^e$ is optionally substituted with one or more substituents selected from halo, oxo, —OH and —CN;

$X^3$ is N or CH;

B is phenyl or 5 to 6 membered heteroaryl; wherein the phenyl and 5 to 6 membered heteroaryl of B are each independently substituted with one or more $R^2$, wherein $R^2$ is independently, at each occurrence, halo; $S(R^y)_5$, wherein each $R^y$ is halo; or $C_{1-6}$alkoxy optionally substituted with one or more halo;

$R^3$ is H or $C_{1-6}$alkyl;

Z is —OH, —$NR^dR^e$, $C_{1-6}$alkoxy, —$C(O)R^a$, —$S(O)_2R^b$, wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

$R^a$ and $R^b$ are each independently i) $C_{2-6}$alkenyl optionally substituted with one or more substituents selected from deuterium, $C_{1-6}$alkyl, hydroxyl $C_{1-6}$alkyl, halo and halo$C_{1-6}$ alkyl; or ii) $C_{1-6}$alkyl, optionally substituted with one or more halo;

L is methylene, optionally substituted with one or more $C_{1-6}$alkyl; and n and m are 1; or n and m are 2;

provided that when 1) $X^1$ is taken together with $R^1$ and the atoms to which they are attached to form a phenyl, and 2) $X^2$ or $X^3$ is N, B of formula (II-B) is phenyl and $R^2$ is halo$C_{1-6}$alkoxyl.

The compounds of the disclosure (or any embodiment or aspect thereof) are useful as a medical therapy for treating diseases and conditions mediated by TEAD activity. Such diseases and conditions include but are not limited to proliferative disorders such as cancer including acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In a specific embodiment, compounds of the disclosure (or any embodiment or aspect thereof) can be administered as a medical therapy to treat proliferative disorders such as cancer.

In one specific aspect, compounds of the disclosure (or any embodiment or aspect thereof) are administered as a medical therapy to treat proliferative disorders such as cancer.

In another aspect, the disclosure provides for a method for treating proliferative disorders such as cancer, comprising the step of administering a therapeutically effective amount of a compound according to formula (II-A) or formula (II-B) (or an embodiment or aspect thereof) as described elsewhere herein to a subject in need thereof.

In another aspect, the disclosure provides for a method for treating any of the indications enumerated herein, comprising the step of administering a therapeutically effective amount of a compound according to formula (II-AB) (or an embodiment or aspect thereof) as described elsewhere herein to a subject in need thereof.

In another aspect, the disclosure provides for a method for treating any of the indications enumerated herein, comprising the step of administering a therapeutically effective amount of a compound according to formula (II-AB') (or an embodiment or aspect thereof) as described elsewhere herein to a subject in need thereof.

In another aspect, the disclosure provides for a compound of formula (II-A) or formula (II-B) as described elsewhere herein (or any embodiment or aspect thereof) for modulating TEAD activity. In some embodiments, the disclosure provides for a pharmaceutically acceptable salt of a compound of formula (II-A) or formula (II-B) for modulating TEAD activity.

In another aspect, the disclosure provides for a compound of formula (II-AB) as described elsewhere herein (or any embodiment or aspect thereof) for modulating TEAD activity. In some embodiments, the disclosure provides for a pharmaceutically acceptable salt of a compound of formula (II-AB) for modulating TEAD activity.

In another aspect, the disclosure provides for a compound of formula (II-AB') as described elsewhere herein (or any embodiment or aspect thereof) for modulating TEAD activity. In some embodiments, the disclosure provides for a pharmaceutically acceptable salt of a compound of formula (II-AB') for modulating TEAD activity.

In another aspect, the disclosure provides for a compound of formula (II-A) or formula (II-B) as described elsewhere herein, or an embodiment or aspect thereof, such as a pharmaceutically acceptable salt thereof, for use in medical therapy.

In another aspect, the disclosure provides for a compound of formula (II-AB) as described elsewhere herein, or an embodiment or aspect thereof, such as a pharmaceutically acceptable salt thereof, for use in medical therapy.

In another aspect, the disclosure provides for a compound of formula (II-AB') as described elsewhere herein, or an embodiment or aspect thereof, such as a pharmaceutically acceptable salt thereof, for use in medical therapy.

In another aspect, the disclosure provides for a method for treatment or prophylaxis of proliferative disorders such as cancer, comprising the step of administering a therapeutically effective amount of a compound according to formula (II-A) or formula (II-B) (or an embodiment or aspect thereof) as described elsewhere herein, to a subject in need thereof.

In another aspect, the disclosure provides for a method for treatment or prophylaxis of any of the indications enumerated herein, comprising the step of administering a therapeutically effective amount of a compound according to formula (II-AB) (or an embodiment or aspect thereof) as described elsewhere herein, to a subject in need thereof.

In another aspect, the disclosure provides for a method for treatment or prophylaxis of any of the indications enumerated herein, comprising the step of administering a therapeutically effective amount of a compound according to formula (II-AB') (or an embodiment or aspect thereof) as described elsewhere herein, to a subject in need thereof.

In another aspect, the disclosure provides for a compound of formula (II-A) or formula (II-B), as described elsewhere herein, or an embodiment or aspect thereof, such as a pharmaceutically acceptable salt thereof, for the treatment or prophylaxis of proliferative disorders such as cancer.

In another aspect, the disclosure provides for a compound of formula (II-AB), as described elsewhere herein, or an embodiment or aspect thereof, such as a pharmaceutically acceptable salt thereof, for the treatment or prophylaxis of any of the indications enumerated herein.

In another aspect, the disclosure provides for a compound of formula (II-AB'), as described elsewhere herein, or an embodiment or aspect thereof, such as a pharmaceutically acceptable salt thereof, for the treatment or prophylaxis of any of the indications enumerated herein.

In another aspect, the disclosure provides for the use of a compound of formula (II-A) or formula (II-B), as described elsewhere herein, or an embodiment or aspect thereof, such as a pharmaceutically acceptable salt thereof, for the preparation of a medicament for the treatment or prophylaxis of proliferative disorders such as cancer.

In another aspect, the disclosure provides for the use of a compound of formula (II-AB), as described elsewhere herein, or an embodiment or aspect thereof, such as a pharmaceutically acceptable salt thereof, for the preparation of a medicament for the treatment or prophylaxis of any of the indications enumerated herein.

In another aspect, the disclosure provides for the use of a compound of formula (II-AB'), as described elsewhere herein, or an embodiment or aspect thereof, such as a pharmaceutically acceptable salt thereof, for the preparation of a medicament for the treatment or prophylaxis of any of the indications enumerated herein.

In another aspect, the disclosure provides for a method for treating proliferative disorders such as cancer in a mammal (e.g., a human) comprising administering a compound of formula (II-A) or formula (II-B) as described elsewhere herein or an embodiment or aspect thereof such as a pharmaceutically acceptable salt thereof to the mammal.

In another aspect, the disclosure provides for a method for treating any of the indications enumerated herein, comprising administering a compound of formula (II-AB) as described elsewhere herein or an embodiment or aspect thereof such as a pharmaceutically acceptable salt thereof to the mammal.

In another aspect, the disclosure provides for a method for treating any of the indications enumerated herein, comprising administering a compound of formula (II-AB') as described elsewhere herein or an embodiment or aspect thereof such as a pharmaceutically acceptable salt thereof to the mammal.

In another aspect, the disclosure provides for a method for modulating TEAD activity, comprising contacting TEAD with a compound of formula (II-A) or formula (II-B), as described elsewhere herein, or an embodiment or aspect thereof, such as a pharmaceutically acceptable salt thereof.

In another aspect, the disclosure provides for a method for modulating TEAD activity, comprising contacting TEAD with a compound of formula (II-AB), as described elsewhere herein, or an embodiment or aspect thereof, such as a pharmaceutically acceptable salt thereof.

In another aspect, the disclosure provides for a method for modulating TEAD activity, comprising contacting TEAD with a compound of formula (II-AB'), as described elsewhere herein, or an embodiment or aspect thereof, such as a pharmaceutically acceptable salt thereof.

It is understood that, in some embodiments, in conjunction with embodiments above or below, a compound of formula (II-AB'), (II-AB), (II-A), or (II-B) as described elsewhere herein, or an embodiment or aspect thereof, such as a pharmaceutically acceptable salt thereof, may be used in a therapeutically effective amount.

In another aspect, the disclosure provides for a compound of formula (II-A) or formula (II-B), as described elsewhere herein, or an embodiment or aspect thereof, such as a pharmaceutically acceptable salt thereof, for the treatment or prophylaxis of a disease or condition mediated by TEAD activity.

In another aspect, the disclosure provides for a compound of formula (II-AB), as described elsewhere herein, or an embodiment or aspect thereof, such as a pharmaceutically acceptable salt thereof, for the treatment or prophylaxis of a disease or condition mediated by TEAD activity. Within aspects of this embodiment, the disease or condition is any of the indications enumerated herein.

In another aspect, the disclosure provides for a compound of formula (II-AB'), as described elsewhere herein, or an embodiment or aspect thereof, such as a pharmaceutically acceptable salt thereof, for the treatment or prophylaxis of a disease or condition mediated by TEAD activity. Within aspects of this embodiment, the disease or condition is any of the indications enumerated herein.

In another aspect, the disclosure provides for the use of a compound of formula (II-A) or formula (II-B), as described elsewhere herein, or an embodiment or aspect thereof, such as a pharmaceutically acceptable salt thereof for the preparation of a medicament for the treatment or prophylaxis of a disease or condition that is mediated by TEAD activity. Within aspects of this embodiment, the disease or condition is proliferative disorders such as cancer.

In another aspect, the disclosure provides for the use of a compound of formula (II-AB), as described elsewhere herein, or an embodiment or aspect thereof, such as a pharmaceutically acceptable salt thereof for the preparation of a medicament for the treatment or prophylaxis of a disease or condition that is mediated by TEAD activity. Within aspects of this embodiment, the disease or condition is any of the diseases enumerated herein.

In another aspect, the disclosure provides for the use of a compound of formula (II-AB'), as described elsewhere herein, or an embodiment or aspect thereof, such as a pharmaceutically acceptable salt thereof for the preparation of a medicament for the treatment or prophylaxis of a disease or condition that is mediated by TEAD activity. Within aspects of this embodiment, the disease or condition is any of the diseases enumerated herein.

In one aspect, compounds of the disclosure demonstrate higher potency as compared to other analogues.

COMBINATION THERAPY

The compounds of formula (II-A) or formula (II-B), or stereoisomers, tautomers, or pharmaceutically acceptable salts thereof, may be employed alone or in combination with other agents for treatment. For example, the second agent of the pharmaceutical combination formulation or dosing regimen may have complementary activities to the compound of formula (II-A) or formula (II-B), such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (II-A) or formula (II-B), or stereoisomers, tautomers, or pharmaceutically acceptable salts thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Any of the methods of using a compound of formula (II-A) or (II-B) described in the preceding paragraphs may also be applied to a compound of formula (II-AB).

Any of the methods of using a compound of formula (II-A) or (II-B) described in the preceding paragraphs may also be applied to a compound of formula (II-AB').

Those additional agents may be administered separately from a composition comprising a disclosed compound, as part of a multiple dosage regimen. Alternatively, those agents may be part of a single dosage form, mixed together with a disclosed compound in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this disclosure. For example, a compound of the present disclosure may be administered with another therapeutic agent simultaneously or sequentially in separate unit dosage forms or together in a single unit dosage form. Accordingly, the present disclosure provides a single unit dosage form comprising a compound of formula I or formula II, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of a disclosed compound can be administered.

Typically, any agent that has activity against a disease or condition being treated may be co-administered. Examples of such agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (II-A) or formula (II-B), or stereoisomers, tautomers, or pharmaceutically acceptable salts thereof, and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Any of the treatment methods involving a compound of formula (II-A) or (II-B) or stereoisomers, tautomers, or pharmaceutically acceptable salts thereof, also apply to a compound or stereoisomers, tautomers, or pharmaceutically acceptable salts thereof, of formula (II-AB).

Any of the treatment methods involving a compound of formula (II-A) or (II-B) or stereoisomers, tautomers, or pharmaceutically acceptable salts thereof, also apply to a compound or stereoisomers, tautomers, or pharmaceutically acceptable salts thereof, of formula (II-AB').

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signalling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®., Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5a-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid;

2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CR$_L$ HB 8506), MAb 455 (ATCC CR$_L$ HB8507), MAb 225 (ATCC CR$_L$ 8508), MAb 528 (ATCC CR$_L$ 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc.); and mAb 806 or humanized mAb 806 (Johns et al., J Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3-fluorophenyl)methoxy]phenyl]-6[5[[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc.); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/p2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18- OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CC1-779; tipifarnib ($R^1$ 1577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2*a*, interferon alfa-2*b*, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

In another embodiment, provided are methods of using a compound of formula (II-A) or formula (II-B), or a stereoisomer, tautomer, or pharmaceutically acceptable salt thereof, as described elsewhere herein, or an embodiment or aspect thereof, to treat cancer in combination with a PD-1 axis binding antagonist.

In another embodiment, provided are methods of using a compound of formula (II-AB), or a stereoisomer, tautomer, or pharmaceutically acceptable salt thereof, as described elsewhere herein, or an embodiment or aspect thereof, to treat cancer in combination with a PD-1 axis binding antagonist.

In another embodiment, provided are methods of using a compound of formula (II-AB'), or a stereoisomer, tautomer, or pharmaceutically acceptable salt thereof, as described elsewhere herein, or an embodiment or aspect thereof, to treat cancer in combination with a PD-1 axis binding antagonist.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. Specific examples of PD-1 binding antagonists are provided infra.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1I binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. Specific examples of PD-L1 binding antagonists are provided infra.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

PD-1 Axis Binding Antagonists

Provided herein are methods for treating cancer in an individual comprising administering to the individual an effective amount of a PD-1 axis binding antagonist and a compound of formula (II-A) or formula (II-B), or a stereoisomer, tautomer, or pharmaceutically acceptable salt thereof, as described elsewhere herein. Also provided herein are methods of enhancing immune function or response in an individual (e.g., an individual having cancer) comprising administering to the individual an effective amount of a PD-1 axis binding antagonist and a compound of formula (II-A) or formula (II-B), or a stereoisomer, tautomer, or pharmaceutically acceptable salt thereof, as described elsewhere herein.

Provided herein are methods for treating cancer in an individual comprising administering to the individual an effective amount of a PD-1 axis binding antagonist and a compound of formula (II-AB), or a stereoisomer, tautomer, or pharmaceutically acceptable salt thereof, as described elsewhere herein. Also provided herein are methods of enhancing immune function or response in an individual (e.g., an individual having cancer) comprising administering to the individual an effective amount of a PD-1 axis binding antagonist and a compound of formula (II-AB), or a stereoisomer, tautomer, or pharmaceutically acceptable salt thereof, as described elsewhere herein.

Provided herein are methods for treating cancer in an individual comprising administering to the individual an effective amount of a PD-1 axis binding antagonist and a compound of formula (II-AB'), or a stereoisomer, tautomer, or pharmaceutically acceptable salt thereof, as described elsewhere herein. Also provided herein are methods of enhancing immune function or response in an individual (e.g., an individual having cancer) comprising administering to the individual an effective amount of a PD-1 axis binding antagonist and a compound of formula (II-AB'), or a stereoisomer, tautomer, or pharmaceutically acceptable salt thereof, as described elsewhere herein.

In such methods, the PD-1 axis binding antagonist includes a PD-1 binding antagonist, a PDL1 binding antagonist, and/or a PDL2 binding antagonist. Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 binding antagonist is a molecule that inhibits the binding of PD-1 to its ligand binding partner(s). In a specific aspect the PD-A ligand binding partners are PDL1 and/or PDL2. In another embodiment, a PDL1 binding antagonist is a molecule that inhibits the binding of PDL1 to its binding partner(s). In a specific aspect, PDL1 binding partner(s) are PD-1 and/or B7-1. In another embodiment, the PDL2 binding antagonist is a molecule that inhibits the binding of PDL2 to its binding partner(s). In a specific aspect, a PDL2 binding partner is PD-1. The antagonist may be an antibody, an antigen binding fragment thereof, an immunoadhesin, a fusion protein, an oligopeptide or a small molecule. If the antagonist is an antibody, in some embodiments the antibody comprises a human constant region selected from the group consisting of IgG1, IgG2, IgG3 and IgG4

Anti-PD-1 Antibodies

In some embodiments, the PD-1 binding antagonist is an anti-PD-1 antibody. A variety of anti-PDL1 antibodies can be utilized in the methods disclosed herein. In any of the embodiments herein, the PD-1 antibody can bind to a human PD-1 or a variant thereof. In some embodiments the anti-PD-1 antibody is a monoclonal antibody. In some embodiments, the anti-PD-1 antibody is an antibody fragment selected from the group consisting of Fab, Fab', Fab'-SH, Fv, scFv, and (Fab')$_2$ fragments. In some embodiments, the anti-PD-1 antibody is a chimeric or humanized antibody. In other embodiments, the anti-PD-1 antibody is a human antibody.

In some embodiments, the anti-PD-1 antibody is nivolumab (CAS Registry Number: 946414-94-4). Nivolumab (Bristol-Myers Squibb/Ono), also known as MDX-1106-04, MDX-1 106, ON0-4538, BMS-936558, and OPDIVO®, is an anti-PD-1 antibody described in WO2006/121168. Nivolumab comprises a heavy chain and a light chain sequence, wherein:

(a) the heavy chain comprises the amino acid sequence.
(SEQ ID NO: 1)
QVQLVESGGGVVQPGRSLRLDCKASGITFSNSGMHWVRQAPGKGLEWVA

VIWYDGSKRYYADSVKGRFTISRDNSKNTLFLQMNSLRAEDTAVYYCAT

NDDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK, and (b) the light chain comprises the amino acid sequence:
(SEQ ID NO: 2)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some embodiments, the anti-PD-1 antibody comprises the six HVR sequences from SEQ ID NO:1 and SEQ ID NO:2 (e.g., the three heavy chain HVRs from SEQ ID NO:1 and the three light chain HVRs from SEQ ID NO:2). In some embodiments, the anti-PD-1 antibody comprises the heavy chain variable domain from SEQ ID NO:1 and the light chain variable domain from SEQ ID NO:2.

In some embodiments, the anti-PD-1 antibody is pembrolizumab (CAS Registry Number: 1374853-91-4). Pembrolizumab (Merck), also known as MK-3475, Merck 3475, lambrolizumab, SCH-900475, and KEYTRUDA® is an anti-PD-1 antibody described in WO2009/114335. Pembrolizumab comprises a heavy chain and a light chain sequence, wherein:

(a) the heavy chain comprises the amino acid sequence:
(SEQ ID NO: 3)
QVQLVQSGVEVKKPGASVKVSCKASGYTFTNYYMYWVRQAPGQGLEWMG

GINPSNGGTNFNEKFKNRVTLTTDSSTTTAYMELKSLQFDDTAVYYCAR

RDYRFDMGFDYWGQGTTVTVSSASTKGPSVFPLAPCSRSTSESTAALGC

LVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSL

SLSLGK, and (b) the light chain comprises the amino acid sequence:
(SEQ ID NO: 4)
EIVLTQSPATLSLSPGERATLSCRASKGVSTSGYSYLHWYQQKPGQAPR

LLIYLASYLESGVPARFSGSGSGTDFTLTISSLEPEDFAVYYCQHSRDL

PLTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.

In some embodiments, the anti-PD-1 antibody comprises the six HVR sequences from SEQ ID NO:3 and SEQ ID NO:4 (e.g., the three heavy chain HVRs from SEQ ID NO:3 and the three light chain HVRs from SEQ ID NO:4). In some embodiments, the anti-PD-1 antibody comprises the heavy chain variable domain from SEQ ID NO:3 and the light chain variable domain from SEQ ID NO:4.

In some embodiments, the anti-PD-1 antibody is MEDI-0680 (AMP-514; AstraZeneca). MEDI-0680 is a humanized IgG4 anti-PD-1 antibody.

In some embodiments, the anti-PD-1 antibody is PDR001 (CAS Registry No. 1859072-53-9; Novartis). PDR001 is a humanized IgG4 anti-PD1 antibody that blocks the binding of PDL1 and PDL2 to PD-1.

In some embodiments, the anti-PD-1 antibody is REGN2810 (Regeneron). REGN2810 is a human anti-PD1 antibody.

In some embodiments, the anti-PD-1 antibody is BGB-108 (BeiGene). In some embodiments, the anti-PD-1 antibody is BGB-A317 (BeiGene).

In some embodiments, the anti-PD-1 antibody is JS-001 (Shanghai Junshi). JS-001 is a humanized anti-PD1 antibody.

In some embodiments, the anti-PD-1 antibody is STI-A1110 (Sorrento). STI-A 1110 is a human anti-PD1 antibody.

In some embodiments, the anti-PD-1 antibody is INCSHR-1210 (Incyte). INCSHR-1210 is a human IgG4 anti-PD1 antibody.

In some embodiments, the anti-PD-1 antibody is PF-06801591 (Pfizer).

In some embodiments, the anti-PD-1 antibody is TSR-042 (also known as ANB011; Tesaro/AnaptysBio).

In some embodiments, the anti-PD-1 antibody is AM0001 (ARMO Biosciences).

In some embodiments, the anti-PD-1 antibody is ENUM 244C8 (Enumeral Biomedical Holdings). ENUM 244C8 is an anti-PD1 antibody that inhibits PD-1 function without blocking binding of PDL1 to PD-1.

In some embodiments, the anti-PD-1 antibody is ENUM 388D4 (Enumeral Biomedical Holdings). ENUM 388D4 is an anti-PD1 antibody that competitively inhibits binding of PDL1 to PD-1.

In some embodiments, the PD-1 antibody comprises the six HVR sequences (e.g., the three heavy chain HVRs and the three light chain HVRs) and/or the heavy chain variable domain and light chain variable domain from a PD-1 antibody described in WO2015/112800 (Applicant: Regeneron), WO2015/112805 (Applicant: Regeneron), WO2015/112900 (Applicant: Novartis), US20150210769 (Assigned to Novartis), WO2016/089873 (Applicant: Celgene), WO2015/035606 (Applicant: Beigene), WO2015/085847 (Applicants: Shanghai Hengrui Pharmaceutical/Jiangsu Hengrui Medicine), WO2014/206107 (Applicants: Shanghai Junshi Biosciences/Junmeng Biosciences), WO2012/145493 (Applicant: Amplimmune), U.S. Pat. No. 9,205,148 (Assigned to MedImmune), WO2015/119930 (Applicants: Pfizer/Merck), WO2015/119923 (Applicants: Pfizer/Merck), WO2016/032927 (Applicants: Pfizer/Merck), WO2014/179664 (Applicant: AnaptysBio), WO2016/106160 (Applicant: Enumeral), and WO2014/194302 (Applicant: Sorrento).

Anti-PDL1 Antibodies

In some embodiments, the PD-1 axis binding antagonist is an anti-PDL1 antibody. A variety of anti-PDL1 antibodies are contemplated and described herein. In any of the embodiments herein, the isolated anti-PDL1 antibody can bind to a human PDL1, for example a human PDL1 as shown in UniProtKB/Swiss-Prot Accession No.Q9NZQ7.1, or a variant thereof. In some embodiments, the anti-PDL1 antibody is capable of inhibiting binding between PDL1 and PD-1 and/or between PDL1 and B7-1. In some embodiments, the anti-PDL1 antibody is a monoclonal antibody. In some embodiments, the anti-PDL1 antibody is an antibody fragment selected from the group consisting of Fab, Fab'-SH, Fv, scFv, and (Fab')$_2$ fragments. In some embodiments, the anti-PDL1 antibody is a chimeric or humanized antibody. In some embodiments, the anti-PDL1 antibody is a human antibody. Examples of anti-PDL1 antibodies useful in the methods of this invention and methods of making them are described in PCT patent application WO 2010/077634 and U.S. Pat. No. 8,217,149, both of which are incorporated herein.

In some embodiments, the anti-PDL1 antibody is atezolizumab (CAS Registry Number: 1422185-06-5). Atezolizumab (Genentech), also known as MPDL3280A, is an anti-PDL1 antibody.

Atezolizumab comprises:

```
(a) an HVR-H1, HVR-H2, and HVR-H3 sequence of
                                        (SEQ ID NO: 5)
GFTFSDSWIH, (SEQ ID NO: 6)
AWISPYGGSTYYADSVKG
and (SEQ ID NO: 7)
RHWPGGFDY,
respectively, and (b) an HVR-L1, HVR-L2, and HVR-L3 sequence of
                                        (SEQ ID NO: 8)
RASQDVSTAVA, (SEQ ID NO: 9)
SASFLYS
and (SEQ ID NO: 10)
QQYLYHPAT,
respectively.
```

Atezolizumab comprises a heavy chain and a light chain sequence, wherein:

```
(a) the heavy chain variable region sequence
comprises the amino acid sequence:
                                        (SEQ ID NO: 11
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS,
and
```

```
(b) the light chain variable region sequence
comprises the amino acid sequence:
                                        (SEQ ID NO: 12)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKR.
```

Atezolizumab comprises a heavy chain and a light chain sequence, wherein:

```
(a) the heavy chain comprises the amino acid
sequence:
                                        (SEQ ID NO: 13)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPG,
and
```

```
(b) the light chain comprises the amino acid
sequence:
                                        (SEQ ID NO: 14)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.
```

In some embodiments, the anti-PDL1 antibody is avelumab (CAS Registry Number: 1537032-82-8). Avelumab, also known as MSB0010718C, is a human monoclonal IgG1 anti-PDL1 antibody (Merck KGaA, Pfizer). Avelumab comprises a heavy chain and a light chain sequence, wherein:

```
(a) the heavy chain comprises the amino acid
sequence:
                                        (SEQ ID NO: 15)
EVQLLESGGGLVQPGGSLRLSCAASGFTFSSYIMMWVRQAPGKGLEWVS

SIYPSGGITFYADTVKGRFTISRDNSKNTLYLQMNSLRAEDTAVYYCAR

IKLGTVTTVDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN
```

-continued
NYKTTPPVLDSDGSFFLYSKLTVDKSRWQQGNVFSCSVMHEALHNHYTQ

KSLSLSPG,
and (b) the light chain comprises the amino acid
sequence:
(SEQ ID NO: 16)
QSALTQPASVSGSPGQSITISCTGTSSDVGGYNYVSWYQQHPGKAPKLM

IYDVSNRPSGVSNRFSGSKSGNTASLTISGLQAEDEADYYCSSYTSSST

RVFGTGTKVTVLGQPKANPTVTLFPPSSEELQANKATLVCLISDFYPGA

VTVAWKADGSPVKAGVETTKPSKQSNNKYAASSYLSLTPEQWKSHRSYS

CQVTHEGSTVEKTVAPTECS.

In some embodiments, the anti-PDL1 antibody comprises the six HVR sequences from SEQ ID NO:15 and SEQ ID NO:16 (e.g., the three heavy chain HVRs from SEQ ID NO:15 and the three light chain HVRs from SEQ ID NO:16). In some embodiments, the anti-PDL1 antibody comprises the heavy chain variable domain from SEQ ID NO:15 and the light chain variable domain from SEQ ID NO:16.

In some embodiments, the anti-PDL1 antibody is durvalumab (CAS Registry Number: 1428935-60-7). Durvalumab, also known as MEDI4736, is an Fc-optimized human monoclonal IgG1 kappa anti-PDL1 antibody (MedImmune, AstraZeneca) described in WO2011/066389 and US2013/034559. Durvalumab comprises a heavy chain and a light chain sequence, wherein:

(a) the heavy chain comprises the amino acid
sequence:
(SEQ ID NO: 17)
EVQLVESGGGLVQPGGSLRLSCAASGFTFSRYWMSWVRQAPGKGLEWVA

NIKQDGSEKYYVDSVKGRFTISRDNAKNSLYLQMNSLRAEDTAVYYCAR

EGGWFGELAFDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKRVEPKSCDKTHTCPPCPAPEFEGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPASIEKTISKA

KGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYT

QKSLSLSPG,
and (b) the light chain comprises the amino acid
sequence:
(SEQ ID NO: 18)
EIVLTQSPGTLSLSPGERATLSCRASQRVSSSYLAWYQQKPGQAPRLLI

YDASSRATGIPDRFSGSGSGTDFTLTISRLEPEDFAVYYCQQYGSLPWT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC.

In some embodiments, the anti-PDL1 antibody comprises the six HVR sequences from SEQ ID NO:17 and SEQ ID NO:18 (e.g., the three heavy chain HVRs from SEQ ID NO:17 and the three light chain HVRs from SEQ ID NO:18). In some embodiments, the anti-PDL1 antibody comprises the heavy chain variable domain from SEQ ID NO:17 and the light chain variable domain from SEQ ID NO:18.

In some embodiments, the anti-PDL1 antibody is MDX-1105 (Bristol Myers Squibb). MDX-1105, also known as BMS-936559, is an anti-PDL1 antibody described in WO2007/005874.

In some embodiments, the anti-PDL1 antibody is LY3300054 (Eli Lilly).

In some embodiments, the anti-PDL1 antibody is STI-A1014 (Sorrento). STI-A1014 is a human anti-PDL1 antibody.

In some embodiments, the anti-PDL1 antibody is KN035 (Suzhou Alphamab). KN035 is single-domain antibody (dAB) generated from a camel phage display library.

In some embodiments, the anti-PDL1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some embodiments, the anti-PDL1 antibody is CX-072 (CytomX Therapeutics).

In some embodiments, the PDL1 antibody comprises the six HVR sequences (e.g., the three heavy chain HVRs and the three light chain HVRs) and/or the heavy chain variable domain and light chain variable domain from a PDL1 antibody described in US20160108123 (Assigned to Novartis), WO2016/000619 (Applicant: Beigene), WO2012/145493 (Applicant: Amplimmune), U.S. Pat. No. 9,205,148 (Assigned to MedImmune), WO2013/181634 (Applicant: Sorrento), and WO2016/061142 (Applicant: Novartis).

In a still further specific aspect, the PD-1 or PDL1 antibody has reduced or minimal effector function. In a still further specific aspect the minimal effector function results from an "effector-less Fc mutation" or aglycosylation mutation. In still a further embodiment, the effector-less Fc mutation is an N297A or D265A/N297A substitution in the constant region. In some embodiments, the isolated anti-PDL1 antibody is aglycosylated. Glycosylation of antibodies is typically either N-linked or O—linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

Other PD-1 Antagonists

In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. AMP-224 (CAS Registry No. 1422184-00-6; GlaxoSmithKline/MedImmune), also known as B7-DCIg, is a PDL2-Fc fusion soluble receptor described in WO2010/027827 and WO2011/066342.

In some embodiments, the PD-1 binding antagonist is a peptide or small molecule compound. In some embodiments, the PD-1 binding antagonist is AUNP-12 (PierreFabre/Aurigene). See, e.g., WO2012/168944, WO2015/036927, WO2015/044900, WO2015/033303, WO2013/144704, WO2013/132317, and WO2011/161699.

In some embodiments, the PDL1 binding antagonist is a small molecule that inhibits PD-1. In some embodiments, the PDL1 binding antagonist is a small molecule that inhibits PDL1. In some embodiments, the PDL1 binding antagonist is a small molecule that inhibits PDL1 and VISTA. In some embodiments, the PDL1 binding antagonist is CA-170 (also known as AUPM-170). In some embodiments, the PDL1 binding antagonist is a small molecule that inhibits PDL1 and TIM3. In some embodiments, the small molecule is a compound described in WO2015/033301 and WO2015/033299.

In some embodiments, the treatment method includes the co-administration of a compound of formula (II-A) or formula (II-B), or stereoisomers or tautomers thereof, or pharmaceutically acceptable salts of any of the foregoing, and at least one mitogen-activated protein kinase (MAPK) inhibitor. In some embodiments, the treatment method includes the co-administration of a compound of formula (II-A) or formula (II-B), or stereoisomers or tautomers thereof, or pharmaceutically acceptable salts of any of the foregoing, and at least one inhibitor of the RAS/MAPK pathway. In some embodiments, the treatment method includes the co-administration of a compound of formula (II-A) or formula (II-B), or stereoisomers or tautomers thereof, or pharmaceutically acceptable salts of any of the foregoing, and at least one epidermal growth factor receptor (EGFR) inhibitor. In some embodiments, the inhibitor of the RAS/MAPK pathway is a KRAS inhibitor, a RAF inhibitor, such as a BRAF monomer or RAF dimer inhibitor, a MEK inhibitor, an ERK inhibitor, an EGFR inhibitor, or a MAPK inhibitor, or any combination thereof. In certain embodiments, the inhibitor of the RAS/MAPK pathway is an EGFR inhibitor or a MAPK inhibitor, or a combination thereof. Examples of EGFR inhibitors, MAPK inhibitors, and/or RAS/MAPK pathway inhibitors are disclosed in Moore, A. R., Rosenberg, S. C., McCormick, F. et al. RAS-targeted therapies: is the undruggable drugged?. *Nat Rev Drug Discov* (2020), incorporated herein by reference and include, but are not limited to: sotorasib (AMG 510 from Amgen), MRTX849 (from Mirati Therapeutics), JNJ-74699157/ARs-3248 (from J&J Wellspring Biosciences), LY3499446 (from Eli Lilly), GDCBI 1701963 (from Boehringer Ingelheim), mRNA-5671 (from Moderna Therapeutics), G12D inhibitor (from Mirati Therapeutics), RAS(ON) inhibitors (from Revolution Medicines), BBP-454 (from BridgeBio Pharma), SP600125, PLX4032, GW5074, AZD6244, PD98059, simvastatin, alisertib, teriflunomide, NSC95397, PD325901, PD98059, lovastatin, sorafenib (NEXAVAR®*, Bayer Labs), vermurafenib (ZELBORAF®, Hoffman L$^a$ Roche Inc.), dabrafenib (TAFLINAR®, Novartis Pharmaceuticals Corporation), selumetinib (KOSELUGO™, AstraZeneca Pharmaceuticals LP), trametinib (MEKINIST®, Novartis Pharmaceuticals Corporation), ulixertinib, silimarin, sirolimus (RAPAMUNE®, PV Prism CV), lapatinib (TYKERB®*/TYVERB*, GlaxoSmithKline), crizotinib (XALKORI®, PF Prism CV), taselisib (Roche), PF-0491502, PF502, enterolactone, PLX4720, PD0325901, PD184352, SC-514, alisterib (MLN8237), SB415286, PLX4720, obtaoclax (GX15-070), pimasterib, venetoclax (ABT-199/VENCLEXTA®/VENCLYXTO®), eprenetapopt (APR-246), gemcitabine (GEMZAR®*), birinapant (TL32711), pexmetinib (ARRY-614), afuresertib, ralimetinib (LY2228820, Eli Lilly), cobimetinib (COTELLIC®, Exelixis/Genentech), prexasertib (LY2606368), erlotinib (TARCEVA®, OSI Pharmaceuticals), bevacizumab (AVASTIN®, Genentech), belvarafenib (Hanmi Pharm./Genentech, Inc.), and binimetinib (MEKTOVI®, Array Biopharma Inc.).

In some embodiments, the any of the treatment methods using compounds of formula (II-A) or formula (II-B), or stereoisomers or tautomers thereof, or pharmaceutically acceptable salts of any of the foregoing, also apply to a compound of formula (II-AB), or stereoisomers or tautomers thereof, or pharmaceutically acceptable salts of any of the foregoing.

In some embodiments, the any of the treatment methods using compounds of formula (II-A) or formula (II-B), or stereoisomers or tautomers thereof, or pharmaceutically acceptable salts of any of the foregoing, also apply to a compound of formula (II-AB'), or stereoisomers or tautomers thereof, or pharmaceutically acceptable salts of any of the foregoing.

As used herein "combination" refers to any mixture or permutation of one or more compounds of the disclosure (or an embodiment or aspect thereof) and one or more other compounds of the disclosure or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the disclosure with another therapeutic agent. Unless the context makes clear otherwise, "combination" may include routes of administration of a compound of the disclosure with another therapeutic agent. Unless the context makes clear otherwise, "combination" may include formulations of a compound of the disclosure with another therapeutic agent. Dosage forms, routes of administration and pharmaceutical compositions include, but are not limited to, those described herein.

In some embodiments, provided herein are compositions, methods, and kits, comprising: (i) one or more TEAD inhibitors (e.g., any one of the TEAD inhibitors described herein, including but not limited to, any one of compounds of formula (II-AB'), (II-AB), (II-A), or (II-B), or any variations or embodiments thereof), or a pharmaceutically acceptable salt thereof; and (ii) one or more KRAS inhibitors (e.g., any one of compounds of formula (K—I), (K-II), (K—III), or (K—IV) or any variations or embodiments thereof), or a pharmaceutically acceptable salt thereof. TEAD inhibitors may, in some embodiments, be referred to as YAP/TAZ-TEAD inhibitors. In some embodiments, the one or more KRAS inhibitor is a G12C KRAS inhibitor.

In some embodiments, provided herein are methods of reducing resistance of a subject to treatment with a KRAS inhibitor, wherein the method comprises administering to a subject in need thereof one or more TEAD inhibitors, such as a TEAD inhibitor provided herein, or a pharmaceutically acceptable salt thereof. In some embodiments, the TEAD inhibitor is co-administered to the subject with the KRAS inhibitor. Also provided herein are kits comprising one or more TEAD inhibitors, or a pharmaceutically acceptable salt thereof, and optionally one or more KRAS inhibitors, or a pharmaceutically acceptable salt thereof, and instructions for use in reducing resistance of a subject to treatment with a KRAS inhibitor. In some embodiments, the reduction in resistance is sufficient for the subject to overcome resistance to treatment with a KRAS inhibitor. In some embodiments, the subject has experienced resistance to treatment with a KRAS inhibitor. In some embodiments, treatment with a KRAS inhibitor and a TEAD inhibitor decreases the likelihood of a subject receiving treatment with a KRAS inhibitor to develop resistance to such KRAS inhibitor.

In some embodiments, in conjunction with embodiments above or below, the one or more KRAS inhibitors comprise a compound of formula (K—I):

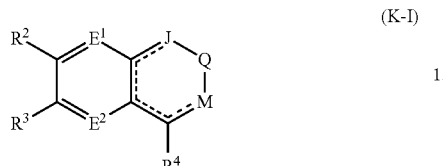
(K-I)

wherein E1 and E2 are each independently N or $CR^1$; J is N, $NR^{10}$, or $CR^{10}$; M is N, $NR^{13}$, or $CR^{13}$; === is a single or double bond as necessary to give every atom its normal valence; $R^1$ is independently H, hydroxy, $C_{1-4}$alkyl, $C_{1-4}$haloalkyl, $C_{1-4}$alkoxy, $NHC_{1-4}$alkyl, $N(C_{1-4}alkyl)_2$, cyano, or halo; $R^2$ is halo, $C_{1-6}$alkyl, $C_{1-6}$haloalkyl, OR', $N(R')_2$, $C_2$-3alkenyl, $C_2$-3alkynyl, $C_{0-3}$alkylene-$C_{3-8}$cycloalkyl, $C_{0-3}$alkylene-$C_2$-7heterocycloalkyl, $C_{0-3}$alkylenearyl, or $C_{0-3}$alkyleneheteroaryl, and each $R^1$ is independently H, $C_{1-6}$alkyl, $C_{1-6}$haloalkyl, $C_3$-4cycloalkyl, $C_2$-3alkenyl, $C_2$-3alkynyl, aryl, or heteroaryl, or two $R^1$ substituents, together with the nitrogen atom to which they are attached, form a 3-7-membered ring; $R^3$ is halo, $C_{1-3}$alkyl, $C_{1-2}$haloalkyl, $C_{1-3}$alkoxy, $C_3$-4cycloalkyl, $C_2$-3alkenyl, $C_2$-3alkynyl, aryl, or heteroaryl; $R^4$ is

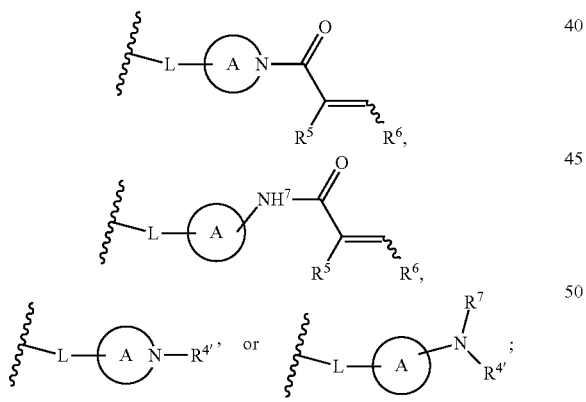

ring A is a monocyclic 4-7 membered ring or a bicyclic, bridged, fused, or Spiro 6-11 membered ring; L is a bond, $C_{1-6}$alkylene, —O—$C_0$-5alkylene, —S—$C_0$-5alkylene, or —NH—$C_0$-5 alkylene, and for $C_{2-6}$alkylene, —O—$C_{2-5}$alkylene, —S—$C_{2-5}$alkylene, and NH—$C_{2-5}$ alkylene, one carbon atom of the alkylene group can optionally be replaced with O, S, or NH; $R^{4'}$ is H, $C_1$-8-alkyl, $C_2$-8alkynyl, $C_{1-6}$alkylene-O—$C_{1-4}$ alkyl, $C_{1-6}$alkylene-OH, $C_{1-6}$haloalkyl, $C_{0-3}$alkylene-$C_{3-8}$-cycloalkyl, $C_{0-3}$alkylene-$C_2$-7heterocycloalkyl, $C_{0-3}$alkylenearyl, or selected from

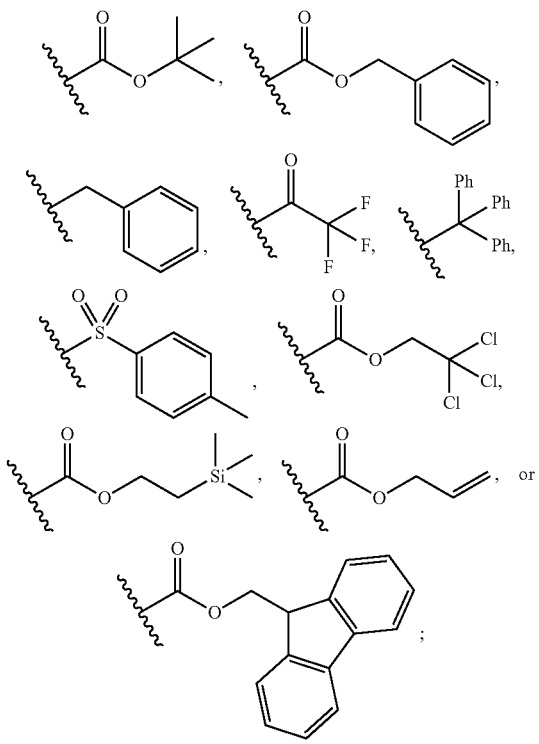

$R^5$ and $R^6$ are each independently H, halo, $C_{1-6}$alkyl, $C_{2-5}$alkynyl, $C_{1-6}$alkylene-O—$C_{1-4}$-alkyl, $C_{1-6}$alkylene-OH, $C_{1-6}$haloalkyl, $C_{1-6}$alkyleneamine, $C_0$-6alkyleneamide, $C_{0-3}$alkylene-C(O)OH, $C_{0-3}$alkylene-C(O)OC$_{1-4}$alkyl, $C_{1-6}$alkylene-O-aryl, $C_{0-3}$alkylene-C(O)C$_{1-4}$alkylene-OH, $C_{0-3}$alkylene-$C_{3-8}$cycloalkyl, $C_{0-3}$alkylene-$C_2$-7heterocycloalkyl, $C_{0-3}$alkylenearyl, or cyano, or $R^5$ and $R^6$, together with the atoms to which they are attached, form a 4-6 membered ring; $R^7$ is H or $C_{1-3}$alkyl, or $R^7$ and $R^8$, together with the atoms to which they are attached, form a 4-6 membered ring; Q is $CR^8R^9$, $C=CR^8R^9$, $C=O$, $C=S$, or $C=NR^8$; $R^8$ and $R^9$ are each independently H, $C_{1-3}$alkyl, hydroxy, $C_{1-3}$alkoxy, cyano, nitro, or $C_3$-6cycloalkyl, or $R^8$ and $R^9$, taken together with the carbon atom to which they are attached, can form a 3-6 membered ring; $R^{10}$ is $C_{1-6}$alkyl, $C_{0-3}$alkylenearyl, $C_{0-3}$alkyleneheteroaryl, $C_{0-3}$alkylene-$C_{3-5}$cycloalkyl, $C_{0-3}$ alkylene-$C_2$-7heterocycloalkyl, $C_{1-6}$alkoxy, O—$C_{0-3}$alkylenearyl, O—$C_{0-3}$alkyleneheteroaryl, O—$C_{0-3}$alkylene-$C_{3-5}$cycloalkyl, O—$C_{0-3}$alkylenearyl, O—$C_{0-3}$alkylene-$C_2$-7heterocycloalkyl, NH—$C_1$-8-alkyl, N($C_1$-8alkyl)$_2$, NH—$C_{0-3}$alkylenearyl, NH—$C_{0-3}$alkyleneheteroaryl, NH—$C_{0-3}$alkylene-$C_{3-8}$-cycloalkyl, NH—$C_{0-3}$alkylene-$C_2$-7heterocycloalkyl, halo, cyano, or $C_{1-6}$alkyleneamine; and $R^{13}$ is $C_{1-4}$alkyl, $C_{1-3}$haloalkyl, $C_{1-3}$alkyleneamine, and $C_{3-5}$cycloalkyl, or a stereoisomer or tautomer thereof, or a pharmaceutically acceptable salt or any of the foregoing, with the proviso that (1) when J is $NR^{10}$, M is N or $CR^{13}$; (2) when M is $NR^{13}$, J is N or $CR^{10}$; (3) when J is $CR^{10}$, M is N or $NR^3$; and (4) when M is $CR^{13}$, J is N or $NR^{10}$.

Description of formula (K—I) can be found in US2018/0334454A1, the entirety of which is incorporated herein by reference. Formula (K—I) is described as formula (II) in US2018/0334454A1 (see, e.g., paragraphs [0033]-[0053]), which paragraphs and description of formula (II) and methods of making compounds of formula (II) are hereby incorporated herein by reference. Moieties of formula (K—I), such as J, Q, M, $E^1$, $E^2$, $R^2$, $R^3$, and $R^4$ are as defined in US2018/0334454A1, including any variations or embodiments thereof.

In some embodiments, in conjunction with embodiments above or below, the one or more KRAS inhibitors comprise a compound of formula (K—I-A):

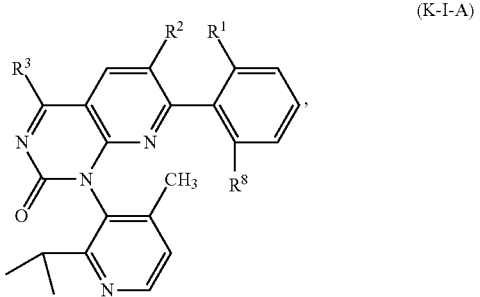

wherein
$R^1$ is H, halo, or —$CH_3$;
$R^2$ is H, halo, or —$CH_3$;
R is

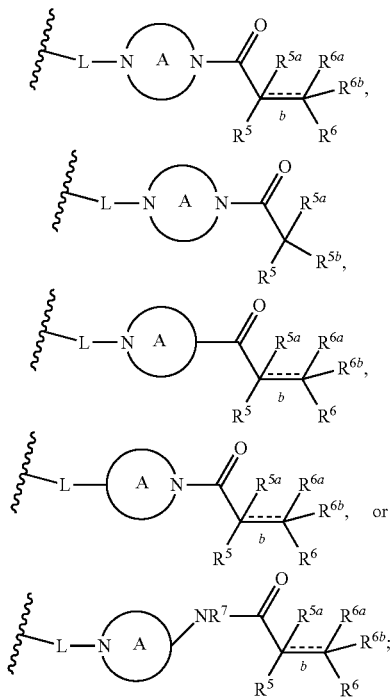

b is optionally a single or a double bond;
ring A is a monocyclic 4-7 membered ring or a bicyclic, bridged, fused, or spiro 6-11 membered ring;
L is a bond or $NR^4$;
$R^4$ is H, —$C_{1-6}$alkyl, —$C_{2-6}$alkynyl, $C_{1-6}$alkylene-O—$C_{1-4}$alkyl, $C_{1-6}$alkylene-OH, $C_{1-6}$haloalkyl, —$C_{1-6}$alkyleneamine, —$C_0$-6alkylene-amide, —C(O)OH, —C(O)O$C_{1-4}$alkyl, —$C_{1-6}$alkylene-O-aryl, —N=N, —$C_{0-3}$alkylene-C(O)$C_{1-4}$alkylene-OH, cycloalkyl, heterocycloalkyl, aryl, heteroaryl, —$C_{0-3}$ alkylene-$C_{3-14}$cycloalkyl, —$C_{0-3}$alkylene-$C_{2-14}$ heterocycloalkyl, —$C_{0-3}$alkylene-$C_{6-14}$aryl, or —$C_{0-3}$ alkylene-$C_{2-14}$heteroaryl;
$R^5$ is H, halo, an —$C_{1-6}$alkyl, —$C_{2-6}$alkynyl, —$C_0$-6alkylene-O—$C_{1-4}$alkyl, —$C_{1-6}$alkylene-O—$C_{1-4}$alkyl, —$C_{1-6}$alkylene-OH, —$C_{1-6}$haloalkyl, —$C_{1-6}$alkyleneamine, —$C_0$-6 alkylene-amide, —C(O)OH, —C(O)O$C_{1-4}$alkyl, —$C_0$-6 alkylene-O—$C_{6-14}$aryl, —$C_{0-3}$alkylene-C(O)C1-4alkylene-OH, cyclocalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$-alkylene-$C_{6-14}$aryl, —$C_{0-3}$alkylene-$C_{2-14}$heteroaryl, or cyano;
$R^{5a}$ is selected from H, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_0$-6 alkylene-amide, —C(O)OH, —C(O)O$C_{1-4}$alkyl, —$C_0$-6 alkylene-O—$C_{6-14}$aryl, —$C_{0-3}$alkylene-C(O) $C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$-aryl, or —$C_{0-3}$alkylene-$C_{2-14}$heteroaryl;
$R^{5b}$ is selected from H, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_0$-6 alkylene-amide, —C(O)OH, —C(O)O$C_{1-4}$alkyl, , —$C_0$-6 alkylene-O—$C_{6-14}$aryl, —$C_{0-3}$alkylene-C(O) $C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$-aryl, or —$C_{0-3}$alkylene-$C_{2-14}$heteroaryl;
or $R^{5a}$ and $R^{5b}$ together, may represent an =O or =N=N;
$R^6$ is H, halo, —$C_{1-6}$alkyl, —$C_{2-6}$alkynyl, —$C_{1-6}$alkylene-O—$C_{1-4}$alkyl, —$C_{1-6}$alkylene-OH, —$C_{1-6}$haloalkyl, —$C_{1-6}$alkyleneamine, —$C_0$-6 alkylene-amide, —C(O)OH, —C(O)O$C_{1-4}$alkyl, —$C_0$-6alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_6$-4aryl, or —$C_{0-3}$alkylene-$C_{2-14}$heteroaryl; $R^{5a}$ and $R^{6a}$, together with the atoms to which they are attached, may form a 3-6 membered ring that optionally includes one or two heteroatoms selected from O, S or N; or
$R^{5a}$ and $R^{6a}$ are absent when b is a double bond;
$R^{6a}$ is H, or —$C_{1-6}$alkyl;
$R^{6b}$ is H, —$C_{1-6}$alkyl, —$C_{2-6}$alkynyl, —$C_{1-6}$ alkylene-O—$C_{1-6}$alkyl, —$C_{1-6}$alkylene-OH, —$C_{1-6}$haloalkyl, —$C_{1-6}$alkyleneamine, —$C_0$-6 alkylene-amide, —C(O)OH, —C(O)O$C_{1-4}$alkyl, —$C_0$-6 alkylene-O—$C_{6-14}$-aryl, —$C_{0-3}$alkylene-C(O)$C_{1-4}$alkylene-OH, cycloalkyl, heterocycloalkyl, aryl, heteroaryl, —$C_{0-3}$ alkylene-$C_{3-14}$cycloalkyl, —$C_{0-3}$alkylene-$C_{2-14}$heterocycloalkyl, —$C_{0-3}$alkylene-$C_{6-14}$aryl, —$C_{0-3}$ alkylene-$C_{2-14}$heteroaryl, or cyano;
or $R^{6a}$ and $R^{6b}$ together, may represent an =O;
$R^7$ is H or $C_{1-6}$alkyl;
$R^8$ is H, OH, $NR^aR^b$;
wherein $R^a$ and $R^b$ are each independently H, halo, —$C_{1-6}$alkyl, —$C_{2-6}$alkynyl;
wherein the ring A or the —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_0$-6 alkylene-amide, —C(O)O$C_{1-4}$alkyl, —$C_{1-6}$ alkylene-O-aryl, —$C_{0-3}$alkylene-C(O)$C_{1-4}$alkylene-OH, cycloalkyl, heterocycloalkyl, aryl, heteroaryl, —C$_{0-3}$alkylene-C$_{3-14}$cycloalkyl, —C$_{0-3}$alkylene-C$_{2-14}$heterocycloalkyl, —C$_{0-3}$alkylene-C$_{6-14}$aryl, or —C$_{0-3}$alkylene-C$_{2-14}$heteroaryl groups of any of the R$^4$, R$^5$, R$^{5a}$, R$^{5b}$, R$^6$, R$^{6a}$, R$^{6b}$, R$^7$ and R$^8$ may be unsubstituted or substituted with 1, 2, 3, or 4 substituents, as allowed, independently selected from halo, —C$_{1-6}$alkyl, —O—C$_{1-6}$alkyl, —OH, or —C$_{1-6}$alkyl-CN; or a stereoisomer or tautomer thereof, or a pharmaceutically acceptable salt of any of the foregoing.

Description of formula (K—I-A) can be found in WO2021/081212A1, the entirety of which is incorporated herein by reference. Formula (K—I-A) is described as formula (I) in WO2021/081212A1 (see, e.g., Embodiment 1, paragraph [0037]), which paragraphs and description of formula (I) and methods of making compounds of formula (I) are hereby incorporated herein by reference. Moieties of formula (K—I-A), such as R$^1$, R$^2$, R$^3$, and R$^s$ are as defined in WO2021/081212A1, including any variations or embodiments thereof.

In some embodiments, in conjunction with embodiments above or below, a compound of formula (K—I) or (K—I-A) is sotorasib (Compound K1), or a stereoisomer or tautomer thereof, or a pharmaceutically acceptable salt of any of the foregoing. Sotorasib is chemically described as 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one, having the structure below:

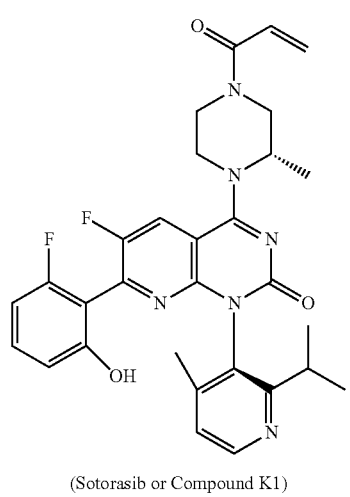

(Sotorasib or Compound K1)

Description of sotorasib (Compound K1) and methods of making sotorasib can be found in US2018/0334454A1, the entirety of which is incorporated herein by reference. Description of sotorasib (Compound K1) and methods of making sotorasib can be found in, e.g., Example 41, pages 210-212 of US2018/0334454A1.

In some embodiments, in conjunction with embodiments above or below, the one or more KRAS inhibitors comprise a compound of formula (K-II):

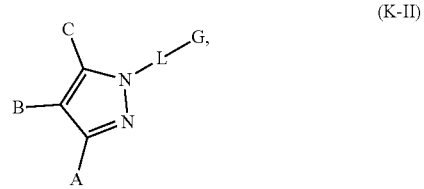

(K-II)

wherein,
A is selected from the group consisting of:
(a) C$_5$-C$_7$ cycloalkylene which is unsubstituted or substituted with one or more, preferably 1, 2 or 3, substituents independently selected from fluoro and C$_1$-C$_4$ alkyl;
(b) a 5-7 membered unsaturated heterocyclyl containing one carbon-carbon double bond and one oxygen atom as ring member, wherein said heterocyclyl is unsubstituted or substituted with one or more, preferably 1, 2 or 3, substituents, independently selected from fluoro and C$_1$-C$_4$ alkyl, preferably 1, 2 or 3, C$_1$-C$_4$ alkyl;
(c) C$_6$-C$_{10}$ aryl which is unsubstituted or substituted with 1, 2 or 3 R$^{A2}$;
(d) a 5-6 membered heteroaryl ring containing 1,2 or 3 heteroatoms independently selected from N, O and S as ring members, wherein said heteroaryl ring is unsubstituted or substituted on one or more (e.g., 1, 2 or 3) carbon atoms with R$^{A3}$, and wherein a nitrogen atom, when present in the heteroaryl ring, is unsubstituted or substituted with a substituent selected from the group consisting of: C$_1$-C$_4$ alkyl, —(CH$_2$)$_{1-2}$—C$_3$-4-cycloalkyl, C$_3$-C$_6$ cycloalkyl, hydroxy-C$_1$-C$_4$ alkyl, fluoro-C$_1$-C$_4$ alkyl, C$_1$-C$_4$ alkoxy-C$_1$-C$_4$ alkyl, N(R$^9$)(R$^{10}$)—C$_1$-C$_4$ alkyl, —SO$_2$—C$_1$-C$_4$ alkyl, —SO$_2$—C$_3$-C$_4$ cycloalkyl, —(CH$_2$)$_p$-Het$^{py}$, and —(CH$_2$)$_p$—N(R$^9$)(R$^{10}$);
(e) an 8-10 membered heteroaryl ring containing 1 to 3 heteroatoms independently selected from nitrogen, oxygen and sulfur, or an 8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 S(=O)$_2$ group in the hetero-bicyclic ring, wherein said heteroaryl ring or hetero-bicyclic ring is unsubstituted or substituted on a carbon atom with 1, 2, 3, 4, or 5 R$^{A4}$, and wherein the hetero-bicyclic ring is further optionally substituted on a carbon atom by oxo and wherein a nitrogen atom, when present, is unsubstituted or substituted with a substituent which is —(CO)—C$_1$-C$_4$ alkyl or C$_1$-C$_4$ alkyl, and wherein said C$_1$-C$_4$ alkyl is optionally substituted with 1 or 2 substituents independently selected from cyano, hydroxy, oxo, fluoro, C$_1$-C$_4$ alkoxy, C$_1$-C$_4$ alkoxy-C$_1$-C$_4$ alkyl-oxy, Het$^b$ and NR$^9$R$^{10}$; and
wherein Het$^b$ is a 4- or 5- or 6-membered heterocyclic ring comprising 1 or 2 heteroatoms or groups independently selected from N, O, S, SO and SO$_2$, wherein said heterocyclic ring Het$^b$ is unsubstituted or substituted on a carbon atom with one or two substituents independently selected from C$_1$-C$_4$ alkyl, hydroxy, cyano, fluoro, C$_1$-C$_4$ alkoxy-hydroxy-C$_1$-C$_4$ alkyl, hydroxy-C$_1$-C$_4$ alkyl, C$_1$-C$_4$ alkoxy, fluoro-C$_1$-C$_4$ alkoxy and fluoro C$_1$-C$_4$ alkyl, and wherein said heterocyclic ring Het$^b$ is further optionally substituted on a carbon atom by oxo, and wherein the nitrogen atom when present in Het$^b$ is optionally further substituted with C$_1$-C$_4$ alkyl which is optionally substituted with 1 to 3 substituents independently selected from fluoro, hydroxy and $C_1$-$C_4$ alkoxy;

wherein A is attached to the rest of the compound of Formula (I) by a carbon atom on A which is $sp^2$ hybridized;

wherein

B is selected from the group consisting of $B^1$ and $B^2$;

wherein $B^1$ is $C_{6-10}$ aryl which is unsubstituted or substituted with 1, 2, 3 or 4 $R^{Ba}$;

$B^2$ is a 6-13 membered heteroaryl which comprises 1, 2 or 3 nitrogen atoms, wherein $B^2$ is unsubstituted or substituted with 1, 2, 3 or 4 $R^{Bb}$;

C is selected from the group consisting of hydrogen, $C_1$-$C_3$ alkyl, $C_3$-$C_5$ cycloalkyl, fluoro-$C_1$-$C_3$ alkyl, cyano, —$CH_2$—CN, —CH(CN)—$CH_3$, —$CH_2$—OH, —CH(OH)—$CH_3$ and halo;

L is selected from the group consisting of:

[structures shown]

wherein n is 1, 2 or 3, $R_L$ is selected from hydrogen, methyl, ethyl, —$CH_2$—CN and —$CH_2$—OH, where G* represents the point of attachment to G;

G is selected from the group consisting of

[structures shown]

wherein $R^2$ is selected from hydrogen, $C_1$-$C_3$ alkyl, —C(O)—$C_1$-$C_3$ alkyl, and fluoro;

$R^3$ is hydrogen;

$R^4$ is selected from hydrogen, methyl, —$CH_2F$, —$CH_2$—OCH3 and —$CH_2$—N($CH_3)_2$;

$R^5$ is selected from hydrogen and methyl;

$R^6$ is hydrogen;

$R^7$ is selected from hydrogen and methyl;

wherein $R^{42}$ is independently selected from the group consisting of: $NR^9R^{10}$, cyano, —$(CH_2)_p$—CN, halo, OH, hydroxy-$C_1$-$C_4$ alkyl, —(COOH), —$(CH_2)_p$—COOH, $C_1$-$C_4$ alkyl, fluoro-$C_1$-$C_4$ alkyl, $C_1$-$C_4$ alkoxy, $C_1$-$C_4$ alkoxy-$C_1$-$C_4$ alkyl, $N(R^9)(R^{10})$—$C_1$-$C_4$alkyl, $N(R^9)(R^{10})$—$C_1$-$C_4$ alkyl-oxy, $N(R^9)(R^{10})$—$C_1$-$C_4$ alkoxy, $C_1$-$C_4$ alkyl-carbonyl-oxy-$C_1$-$C_4$ alkyl-oxy, hydroxy-$C_1$-$C_4$ alkyl-oxy, $C_1$-$C_4$ alkoxy-$C_1$-$C_4$ alkyl-oxy, $C_1$-$C_4$ alkoxy-$C_1$-$C_4$ alkyl-oxy-$C_1$-$C_4$ alkyl, —$SO_2$—$C_1$-$C_4$ alkyl, —$SO_2$—$C_3$-$C_4$ cycloalkyl, —$(CH_2)_{1-2}$—$C_3$-$C_4$ cycloalkyl, $Het^{py}$, —$(CH_2)_p$-$Het^{py}$, —C(=O)—$NR^9R^{10}$, —$(CH_2)_p$-C(=O)$NR^9R^{10}$;

wherein $R^{43}$ is independently selected from the group consisting of oxo, $NR^9R^{10}$, cyano, —$(CH_2)_p$—CN, halo, OH, hydroxy-$C_1$-$C_4$ alkyl, —(COOH), —$(CH_2)_p$—COOH, $C_1$-$C_4$alkyl, fluoro-$C_1$-$C_4$ alkyl, $C_1$-$C_4$ alkoxy, $C_1$-$C_4$ alkoxy-$C_1$-$C_4$ alkyl, $N(R^9)(R^{10})$—$C_1$-$C_4$ alkyl, $N(R^9)(R^{10})$—$C_1$-$C_4$ alkyl-oxy, $N(R^9)(R^{10})$—$C_1$-$C_4$ alkoxy, $C_1$-$C_4$ alkyl-carbonyl-oxy-$C_1$-$C_4$ alkyl-oxy, hydroxy-$C_1$-$C_4$ alkyl-oxy, $C_1$-$C_4$ alkoxy-$C_1$-$C_4$ alkyl-oxy, $C_1$-$C_4$ alkoxy-$C_1$-$C_4$ alkyl-oxy-$C_1$-$C_4$ alkyl, —$SO_2$—$C_1$-$C_4$ alkyl, —$SO_2$—$C_3$-$C_4$ cycloalkyl, —$(CH_2)_{1-2}$—$C_3$-$C_4$ cycloalkyl, $Het^{py}$, —$(CH_2)_p$-$Het^{py}$, —C(=O)—$NR^9R^{10}$, —$(CH_2)_p$-C(=O)$NR^9R^{10}$, $(CH_2)_p$-$NR^9R^{10}$;

wherein $R^{44}$ is independently selected from the group consisting of cyano, $CO_2H$, halo, $C_1$-$C_4$ alkyl, fluoro-$C_1$-$C_4$ alkyl, hydroxy, hydroxy-$C_1$-$C_4$ alkyl, hydroxy-$C_1$-$C_4$ alkyl-oxy, $C_1$-$C_4$ alkoxy, $C_1$-$C_4$ alkoxy-$C_1$-$C_4$ alkyl, $C_1$-$C_4$ alkoxy-$C_1$-$C_4$ alkyl-oxy, $NR^9R^{10}$, $N(R^9)(R^{10})$—$C_1$-$C_4$ alkyl, $N(R^9)(R^{10})$—$C_1$-$C_4$ alkyl-oxy, —(CO)—$C_1$-$C_4$ alkyl, and $R^9R^{10}N$—$C_1$-$C_4$ alkyl-oxy-(CO)—$C_1$-$C_4$ alkyl;

wherein p is 1 or 2 or 3;

$R^9$ is selected from hydrogen and $C_1$-$C_4$ alkyl;

$R^{10}$ is selected from the group consisting of hydrogen, $C_1$-$C_4$ alkyl, hydroxyl-$C_1$-$C_4$ alkyl, $C_1$-$C_4$ alkoxy-$C_1$-$C_4$ alkyl and di-$C_1$-$C_4$ alkyl-amino-$C_1$-$C_4$ alkyl;

$Het^{py}$ is a 4-, 5-, 6- or 7-membered saturated heterocyclic ring comprising one or two heteroatoms independently selected from O, N and S, or comprising an S-oxide (SO) or S-dioxide ($SO_2$) group, and wherein said heterocyclic ring is optionally substituted with oxo on one carbon atom, and wherein said heterocyclic ring is optionally further substituted on one or more carbon atoms with 1, 2 or 3 substituents independently selected from $C_1$-$C_4$ alkoxy, halo, $C_1$-$C_4$ alkyl, hydroxy-$C_1$-$C_4$ alkyl, and fluoro-$C_1$-$C_4$ alkyl, and wherein the nitrogen atom, if present in said heterocycle, is optionally further substituted with $R^{10}$;

or $Het^{py}$ is a 5- or 6-membered heteroaryl ring, comprising 1, 2 or 3 nitrogen atoms and wherein said heteroaryl ring is optionally substituted with one or more (e.g., 1, 2 3) substituents independently selected from $NR^9R^{10}$, —C(=O)—$NR^9R^{10}$, halo, $C_1$-$C_4$ alkyl, hydroxy-$C_1$-$C_4$ alkyl, fluoro-$C_1$-$C_4$ alkyl, cyano, OH, and $C_1$-$C_4$ alkoxy;

each $R^{Ba}$ is independently selected from the group consisting of hydroxy, $NH_2$, $C_1$-$C_4$ alkyl and halo;

each $R^{Bb}$ is independently selected from the group consisting of $C_1$-$C_4$ alkyl, cyclopropyl, fluoro-$C_1$-$C_3$ alkyl, cyano, halo, $NH_2$, and $C_1$-$C_3$ alkoxy, or a stereoisomer or tautomer thereof, or a pharmaceutically acceptable salt of any of the foregoing.

Description of formula (K-II) can be found in WO2021/124222A1, the entirety of which is incorporated herein by reference. Formula (K-II) is described as Formula (I) in WO2021/124222A1 (see, e.g., pages 5-13 and Embodiment I pages 29-32), which paragraphs and description of Formula (I) and methods of making compounds of Formula (I) are hereby incorporated herein by reference. Moieties of formula (K-II), such as A, B, C, L, and G are as defined in WO2021/124222A1, including any variations or embodiments thereof.

In some embodiments, in conjunction with embodiments above or below, the one or more KRAS inhibitors comprise a compound of formula (K-II-A):

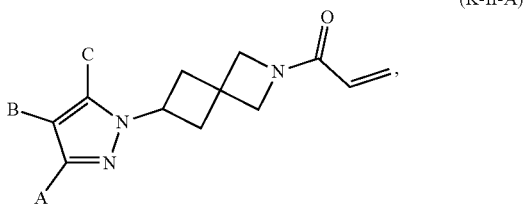

or a stereoisomer or tautomer thereof, or a pharmaceutically acceptable salt of any of the foregoing, wherein A, B, and C are as defined in formula (K-II). It is understood that A, B, and C of such embodiments of compounds of Formula (K-II-A) may include A, B, and C as described for Formula (K-II). Formula (K-II-A) is described as formula (Ia) in, e.g., Embodiment 21, of WO2021/124222A1, which paragraphs and description of formula (Ia) and methods of making compounds of formula (Ia) are hereby incorporated herein by reference. Moieties of formula (K-II-A), such as A, B, and C are as defined in WO2021/124222A1, including any variations or embodiments thereof.

In some embodiments, in conjunction with embodiments above or below, the one or more KRAS inhibitors comprise a compound of formula (K-II-B) or (K-II-C):

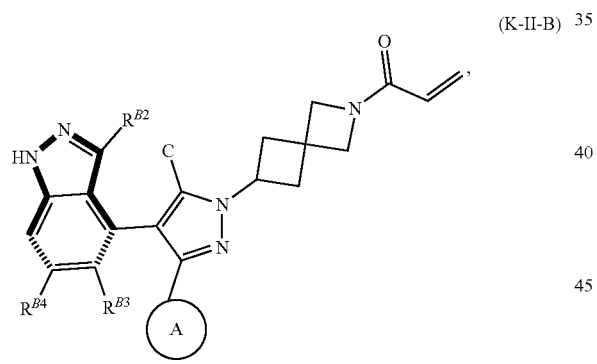

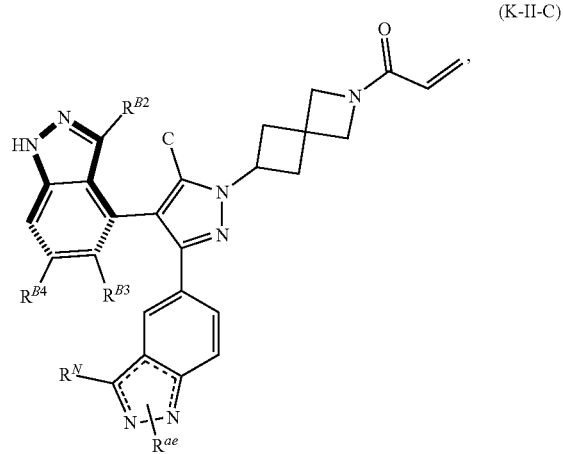

wherein, $R^{B2}$ is independently selected from hydrogen, halo, $C_1$-$C_4$-alkyl, cyclopropyl and $NH_2$;

$R^{B3}$ is independently selected from hydrogen, halo, cyclopropyl and $C_1$-$C_4$-alkyl;

$R^{B4}$ is independently selected from hydrogen, halo and $C_1$-$C_4$-alkyl, or $R^{B3}$ and $R^{B4}$ together with the atoms to which they are attached, form a 4-6 membered ring fused to the aromatic ring to which $R^{B3}$ and $R^{B4}$ are attached;

$R^N$ is hydrogen, halo, $C_{1-4}$alkyl, or halo or fluoro-$C_{1-4}$alkyl;

$R^{ac}$ is selected from the group consisting of hydrogen and $C_{1-4}$alkyl, wherein said alkyl is optionally substituted with 1 or 2 substituents selected from cyano, hydroxyl, fluoro, $C_{1-4}$alkoxy, $C_{1-4}$alkoxy-$C_{1-4}$alkyl-oxy, Het$^b$ and $NR^9R^{10}$;

$R^9$ is selected from hydrogen and $C_{1-4}$alkyl;

$R^{10}$ is selected from hydrogen, $C_{1-4}$alkyl, hydroxy-$C_{1-4}$alkyl, $C_{1-4}$alkoxy-$C_{1-4}$alkyl and di-$C_{1-4}$alkyl-amino-$C_{1-4}$alkyl;

wherein Het$^b$ is a 4- or 5- or 6-membered heterocyclic ring comprising 1 or 2 heteroatoms or groups independently selected from N, O, S, SO and $SO_2$, wherein said heterocyclic ring Het$^b$ is unsubstituted or substituted on a carbon atom with one or two substituents independently selected from $C_{1-4}$alkyl, hydroxy, cyano, fluoro, hydroxy-$C_{1-4}$alkyl, $C_{1-4}$alkoxy and fluoro-$C_{1-4}$-alkyl, and wherein said heterocyclic ring Het$^b$ is further optionally substituted on a carbon atom by oxo, and wherein the nitrogen atom when present in Het$^b$ is optionally further substituted with $C_{1-4}$alkyl which is optionally substituted with 1 to 3 substituents independently selected from fluoro, hydroxy and $C_{1-4}$akloxy;

or a stereoisomer or tautomer thereof, or a pharmaceutically acceptable salt of any of the foregoing, wherein A and C are as defined in Formula (K-II). It is understood that A and C of such embodiments of compounds of Formulae (K-II-B) and (K-II-C) may include A and C as described for Formula (K-II).

Formulae (K-II-B) and (K-II-C) are described as formula (Ib*) and (Id*), respectively in, e.g., Embodiment 39 and 41, of WO2021/124222A 1, which paragraphs and description of formula (Ib*) or (Id*) and methods of making compounds of formula (Ib*) or (Id*) are hereby incorporated herein by reference. Moieties of formula (K-II-B) or (K-II-C), such as A, C, $R^{B2}$, $R^{B3}$, $R^{B4}$, $R^N$, and $R^{ae}$ are as defined in WO2021/124222A1, including any variations or embodiments thereof.

In some embodiments, in conjunction with embodiments above or below, a compound of formula (K-II), (K-II-A), (K-II-B), or (K-II-C) is Compound K2, or a stereoisomer or tautomer thereof, or a pharmaceutically acceptable salt of any of the foregoing. Compound K2 is chemically described as 1-[6-[4-(5-chloro-6-methyl-1H-indazol-4-yl)-5-methyl-3-(1-methylindazol-5-yl)pyrazol-1-yl]-2-azaspiro[3.3]heptan-2-yl]prop-2-en-1-one, having the structure below:

(Compound K2)

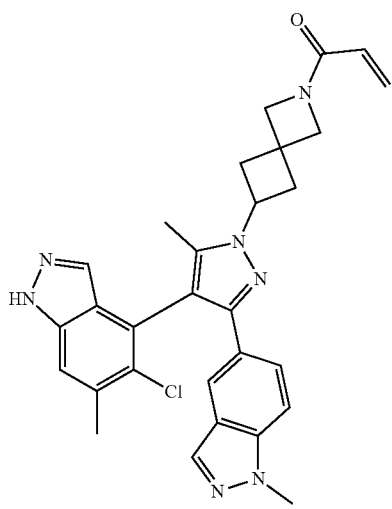

Description of Compound K2 and methods of making Compound K2 can be found in, e.g., Method 1-Synthetic Scheme on pages 111 to 114 of WO2021/124222A1.

In some embodiments, in conjunction with embodiments above or below, the one or more KRAS inhibitors comprise a compound of formula (K—III):

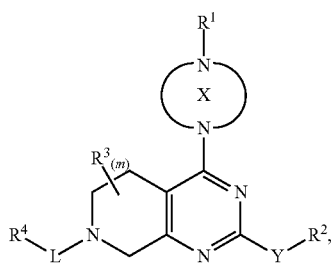

(K-III)

wherein:
X is a 4-12 membered saturated or partially saturated monocyclic, bridged or spirocyclic ring, wherein the saturated or partially saturated monocyclic ring is optionally substituted with one or more $R^8$;
Y is a bond, O, S or $NR^s$;
$R^1$ is $-C(O)C(R^A)$ === $C(R^B)_p$ or $-SO_2C(R^A)$ === $C(R^B)_p$; $R^2$ is hydrogen, alkyl, hydroxyalkyl, dihydroxyalkyl, alkylaminylalkyl, dialkylaminylalkyl, $-Z-NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;
each Z is C1-C4 alkylene;
each $R^3$ is independently C1-C3 alkyl, oxo, haloalkyl, hydroxyl or halogen;
L is a bond, $-C(O)-$, or C1-C3 alkylene;
$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$, $R^7$ or $R^8$;
each $R^5$ is independently hydrogen or $C_1$-$C_3$ alkyl;
$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;
each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;
$R^8$ is oxo, C1-C3 alkyl, C2-C4 alkynyl, heteroalkyl, cyano, $-C(O)OR^5$, $-C(O)N(R^5)_2$, $-N(R^s)_2$, wherein the C1-C3 alkyl may be optionally substituted with cyano, halogen, $-OR^1$, $-N(R^5)_2$, or heteroaryl;
each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;
each $R^{10}$ is independently hydrogen, acyl, C1-C3 alkyl, heteroalkyl or hydroxyalkyl;
$R^{11}$ is haloalkyl;
$R^A$ is absent, hydrogen, deuterium, cyano, halogen, C1-C3 alkyl, haloalkyl, heteroalkyl, $-C(O)N(R^s)_2$, or hydroxyalkyl;
each $R^B$ is independently hydrogen, deuterium, cyano, C1-C3 alkyl, hydroxyalkyl, heteroalkyl, C1-C3 alkoxy, halogen, haloalkyl, $-ZNR^5R^{11}$, $-C(O)N(R^s)_2$, $-NHC(O)C1-C3$ alkyl, $-CH_2NHC(O)C1-C3$ alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;
or when === is a double bond and p is two, one $R^B$ is hydrogen and $R^A$ and one $R^B$ and the carbon atoms to which they are attached form a 4-8 membered partially saturated cycloalkyl substituted with oxo;
m is zero or an integer between 1 and 2;
p is one or two; and wherein,
when === is a triple bond then $R^A$ is absent, p equals one and $R^B$ is hydroxyalkyl,
or when === is a double bond then $R^A$ is present, $R^B$ is present and p equals two, wherein when $R^A$ is hydrogen or C1-C3 alkyl, at least one $R^B$ is deuterium, cyano, halogen, haloalkyl, hydroxyalkyl, heteroalkyl, heteroaryl, heteroarylalkyl, $-ZNR^5R^{11}$, $-C(O)N(R^s)_2$, $-NHC(O)C1-C3$ alkyl, $-CH_2NHC(O)C1-C3$ alkyl or heterocyclylalkyl, wherein the heterocyclyl portion is substituted with one or more substituents independently selected from halogen, hydroxyl, alkoxy and C1-C3 alkyl; or when each $R^B$ is hydrogen, then $R^A$ is deuterium, cyano, halogen, haloalkyl, $-C(O)N(R^5)_2$, hydroxyalkyl or heteroalkyl;
or a stereoisomer or tautomer thereof, or a pharmaceutically acceptable salt of any of the foregoing.

Description of formula (K—III) can be found in US2019/0144444A1, the entirety of which is incorporated herein by reference. Formula (K—III) is described as Formula (II) in US2019/0144444A1 (see, e.g., paragraphs [0169]-[0193]), which paragraphs and description of Formula (II) and methods of making compounds of Formula (II) are hereby incorporated herein by reference. Moieties of formula (K—III), such as X, Y, L, m, $R^1$, $R^2$, $R^3$, and $R^4$ are as defined in US2019/0144444A1, including any variations or embodiments thereof.

215

In some embodiments, in conjunction with embodiments above or below, the one or more KRAS inhibitors comprise a compound of formula (K—III-A):

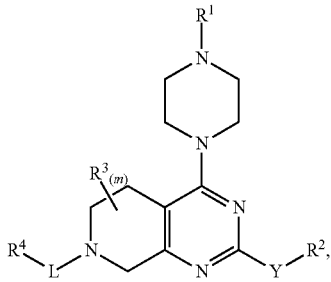

(K-III-A)

where the piperazinyl ring is optionally substituted with $R^8$; or a stereoisomer or tautomer thereof, or a pharmaceutically acceptable salt of any of the foregoing, wherein $R^1$, $R^3$, $R^4$, $R^8$, L, and m are as defined in Formula (K—III). It is understood that $R^1$, $R^3$, $R^4$, $R^1$, L, and m of such embodiments of compounds of Formula (K—III-A) may include $R^1$, $R^3$, $R^4$, $R^8$, L, and m as described for Formula (K—III). Formula (K—III-A) is described as Formula (II-B) in, e.g., paragraphs [0231]-[0241] of US2019/0144444A1, which paragraphs and description of Formula (II-B) and methods of making compounds of Formula (II-B) are hereby incorporated herein by reference. Moieties of formula (K—III-A), such as L, m, $R^1$, $R^2$, $R^3$, and $R^4$ are as defined in US2019/0144444A1, including any variations or embodiments thereof.

In some embodiments, in conjunction with embodiments above or below, a compound of formula (K—III) or (K—III-A) is adagrasib (Compound K3), or a stereoisomer or tautomer thereof, or a pharmaceutically acceptable salt of any of the foregoing. Adagrasib is chemically described as 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile, having the structure below:

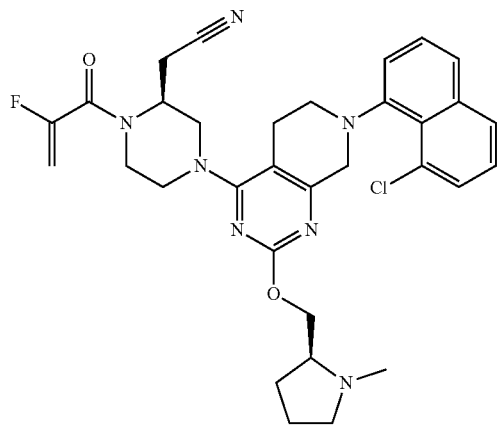

(Adagrasib or Compound K3)

Description of adagrasib (Compound K3) and methods of making adagrasib can be found in, e.g., Example 478 on pages 668-669 of US2019/0144444A1.

In some embodiments, in conjunction with embodiments above or below, the one or more KRAS inhibitors comprise a compound of formula (K—IV):

216

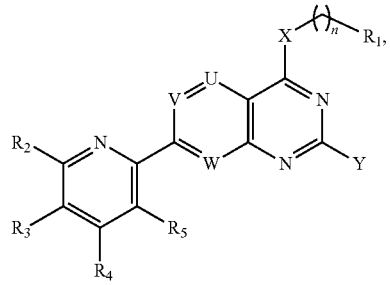

(K-IV)

wherein, $R_1$ is an electrophilic moiety capable of forming a covalent bond with a cysteine residue at position 12 of a K-Ras G12C mutant protein; $R_2$ is selected from a group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkenyl)NH(CH$_3$)—($C_{1-6}$ alkylenyl)N(CH$_3$)$_2$, and —($C_{1-3}$ alkylenyl)(3-7 membered-heterocyclyl);

$R_3$ and $R_4$ are each independently selected from the group consisting of H, $NH_2$, halo, $C_{1-6}$ alkyl, $C_{1-6}$ haloakyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;

$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl, Wherein at least one of $R_2$, $R_3$, $R_4$, and $R_5$ is other than H; or $R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of -L-$Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ haloalkoxy, $C_{1-6}$ haloalkyl, 5- to 10-membered heteroaryl, 4- to 10-membered heterocyclyl, a 4- to 10-membered heterocyclyl substituted with methyl, hydroxyl, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy $C_{1-6}$alkyl, $C_{1-6}$ haloalkyl, oxo, hydroxyl, $NH_2$, cyano, $C_{1-6}$ carboxyalkyl, $C_{1-6}$ cyanoalkyl, $C_{1-6}$ hydroxyalkyl, and $C_{1-6}$ haloalkoxy;

L is selected from the group consisting of a bond, O, S, and $N(L^a)$;

$L^a$ is selected from the group consisting of hydrogen and $C_{1-3}$ alkyl;

U is $C(R_{6a})$;

V is $C(R_{6b})$;

W is $C(R_{6c})$ or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_3$-7 cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2;

or a stereoisomer or tautomer thereof, or a pharmaceutically acceptable salt of any of the foregoing.

Description of formula (K—IV) can be found in US2021/0230142A9, the entirety of which is incorporated herein by reference. Formula (K—IV) is described as Formula (I) in US2021/0230142A9 (see, e.g., paragraphs [0113]-[0132]), which paragraphs and description of Formula (I) and methods of making compounds of Formula (I) are hereby incorporated herein by reference. Moieties of formula (K—IV), such as U, V, W, X, Y, $R_1$, $R_2$, $R_3$, $R_4$ and $R_5$ are as defined in US2021/0230142A9, including any variations or embodiments thereof.

In some embodiments, in conjunction with embodiments above or below, the one or more KRAS inhibitors comprise a compound of formula (K—IV-A):

(II)

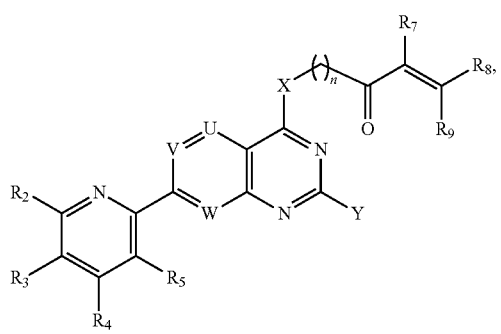

(K-IV-A)

wherein, $R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)$NH(CH_3)$—($C_{1-6}$ alkylenyl)$N(CH_3)_2$, and —($C_{1-3}$ alkylenyl)(3-7 membered-heterocyclyl);

$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;

$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_3$-7 cycloalkyl, wherein at least one of $R_2$, $R_3$, $R_4$, and $R_5$ is other than H; or $R_2$ and $R_3$, $R_3$ and $R_4$, or $R_4$ and $R_5$, together with the atoms to which they are each bonded, form a $C_3$-7 cycloalkyl, 3 to 7 membered heterocycloalkyl, $C_{6-14}$ aryl, or 5- to 10-membered heteroaryl;

each of which is optionally substituted with 1 to 4 substituents, wherein each substituent is independently selected from the group consisting of OH, $NH_2$, halo, $C_{1-3}$ alkyl, $C_{1-3}$ haloalkyl, $C_1$-3 alkoxy, and $C_{1-3}$ haloalkoxy;

$R_7$ is selected from the group consisting of H, cyano, and halo; and $R_8$ and $R_9$ are each independently selected from the group consisting of H, $C_{1-6}$ alkyl, $C_{1-6}$ haloalkyl, $C_{1-6}$ hydroxyalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

or $R_7$ and $R_8$ together form a triple bond between the carbons to which they are attached, or $R_7$ and $R_8$ together with the carbons to which they are each bonded form a $C_3$-7 cycloalkenyl optionally substituted with one or two halo substituents; and $R_9$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_3$-7 cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_3$-7 spirocycloalkyl or 4- to 7-membered spiroheterocyclyl;

Y is selected from the group consisting of -L-$Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_3$-7 cycloalkyl, $C_3$-7 cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy;

L is selected from the group consisting of a bond, O, S, and $N(L^a)$;

$L^a$ is selected from the group consisting of hydrogen and $C_{1-3}$ alkyl;

U is $C(R_{6a})$;

V is $C(R_{6b})$;

W is $C(R_{6c})$ or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_3$-7 cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2;

or a stereoisomer or tautomer thereof, or a pharmaceutically acceptable salt of any of the foregoing.

Formula (K—IV-A) is described as Formula (II) in, e.g., paragraph [0137] of US2021/0230142A9, which paragraphs and description of Formula (II) and methods of making compounds of Formula (II) are hereby incorporated herein by reference. Moieties of formula (K—IV-A), such as U, V, W, X, Y, $R^1$, $R^2$, $R^3$, $R^4$, $R^s$, $R^7$, $R^8$, and $R^9$ are as defined in US2021/0230142A9, including any variations or embodiments thereof.

In some embodiments, in conjunction with embodiments above or below, the one or more KRAS inhibitors comprise a compound of formula (K-IV-B) or (K-IV-C):

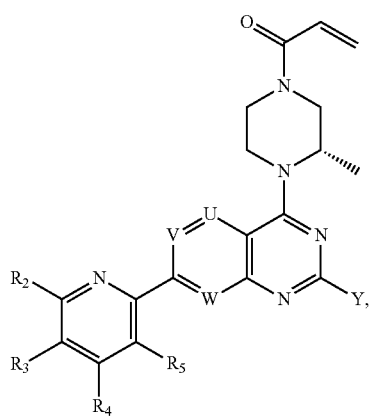

(K-IV-B)

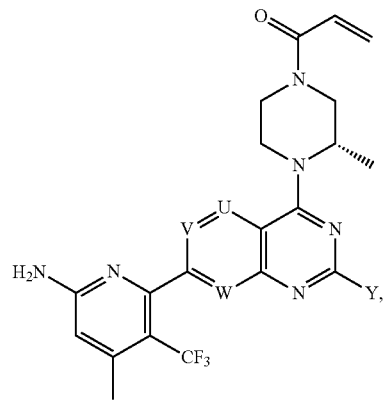

(K-IV-C)

or a stereoisomer or tautomer thereof, or a pharmaceutically acceptable salt of any of the foregoing, wherein U, V, W, Y, $R_2$, $R_3$, $R_4$, and $R_5$ are as defined in Formula (K—IV). It is understood that U, V, W, Y, $R_2$, $R_3$, $R_4$, and $R_5$ of such embodiments of compounds of Formulae (K-IV-B) and (K-IV-C) may include U, V, W, Y, $R_2$, $R_3$, $R_4$, and $R_5$ as described for Formula (K—IV). Formulae (K-IV-B) and (K-IV-C) are described as Formulae (Ib) and (IVb), respectively, in, e.g., paragraphs [0277] and [0285] of US2021/0230142A9, which paragraphs and description of Formula (Ib) or (IVb) and methods of making compounds of Formula (Ib) or (IVb) are hereby incorporated herein by reference. Moieties of formulae (K-IV-B) and (K-IV-C), such as U, V, W, Y, $R^2$, $R^3$, $R^4$, and $R^5$ are as defined in US2021/0230142A9, including any variations or embodiments thereof.

In some embodiments, in conjunction with embodiments above or below, a compound of formula (K—IV), (K—IV-A), (K-IV-B), or (K-IV-C) is Compound K4, or a stereoisomer or tautomer thereof, or a pharmaceutically acceptable salt of any of the foregoing. Compound K2 is chemically described as 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one, having the structure below:

(Compound K4)

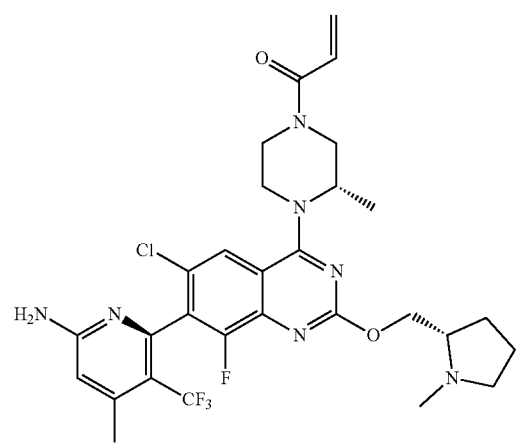

Description of Compound K4 and methods of making Compound K4 can be found in, e.g., Example 17a & 17b on pages 130 to 135 of US2021/0230142A9.

In some embodiments, in conjunction with embodiments above or below, the one or more KRAS inhibitors comprise a G12C KRAS inhibitor (e.g., any one of Compound K1, Compound K2, Compound K3, and Compound K4). G12C KRAS inhibitors are described in, for example, Hallin et al. (Cancer Discov, 2020, 10(1): 54-71), Skoulidis et al. (N. Engl. J. Med., 2021, 384(25): 2371-2381), and Hong et al. (N. Engl. J. Med., 2020, 383(13): 1207-1217), each of which is incorporated herein by reference in its entirety and specifically with respect to G12C KRAS inhibitors described therein.

In some embodiments, in conjunction with embodiments above or below, the one or more TEAD inhibitors are selected from the group consisting of compounds T1, T2, T3, and T4 as listed in Table 2, or a stereoisomer or tautomer thereof, or a pharmaceutically acceptable salt of any of the foregoing. In some embodiments, in conjunction with embodiments above or below, the one or more TEAD inhibitors are selected from the group consisting of the compounds listed in Table 1, or a stereoisomer or tautomer thereof, or a pharmaceutically acceptable salt of any of the foregoing. In some embodiments, in conjunction with embodiments above or below, the one or more KRAS inhibitors are selected from the group consisting of compounds K1, K2, K3, and K4 as listed in Table 2, or a stereoisomer or tautomer thereof, or a pharmaceutically acceptable salt of any of the foregoing.

TABLE 2

| Compound Number | Structure | Chemical name |
|---|---|---|
| T1 (also referred to as Compound 12) | 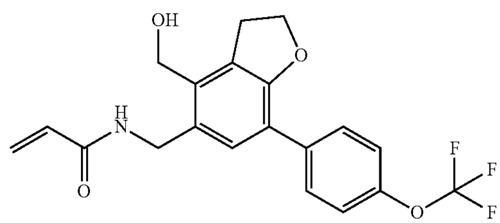 [SMILES: C=CC(=O)NCc1cc(-c2ccc(OC(F)(F)F)cc2)c2c(c1CO)CCO2] | N-[[4-(hydroxymethyl)-7-[4-(trifluoromethoxy)05phenyl]-2,3-dihydrobenzofuran-5-yl]methyl]prop-2-enamide |
| T2 (also referred to as Compound 27) | 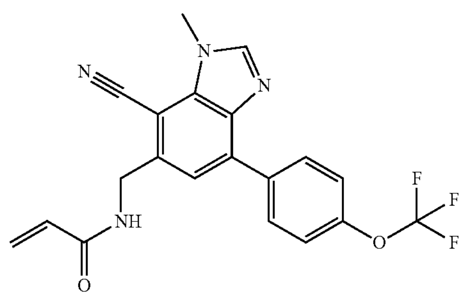 [SMILES: C=CC(=O)NCc1cc(-c2ccc(OC(F)(F)F)cc2)c2ncn(C)c2c1C#N] | N-[[4-cyano-3-methyl-7-[4-(trifluoromethoxy)phenyl]benzimidazol-5-yl]methyl]prop-2-enamide |
| T3 (also referred to as Compound 28) | 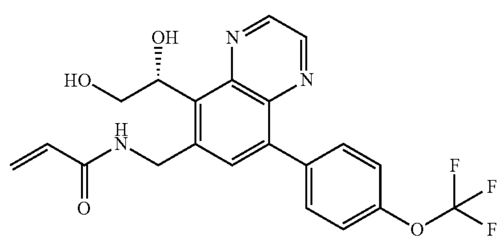 | N-[[5-[(1R)-1,2-dihydroxyethyl]-8-[4-(trifluoromethoxy)phenyl]quinoxalin-6-yl]methyl]prop-2-enamide |
| T4 (also referred to as Compound 29) | 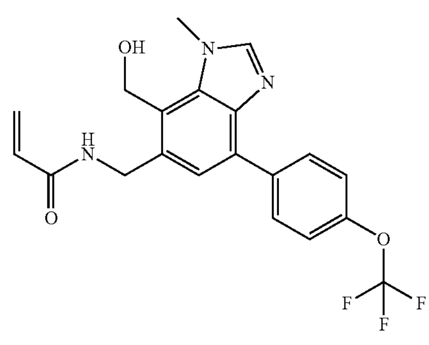 [SMILES: C=CC(=O)NCc1cc(-c2ccc(OC(F)(F)F)cc2)c2ncn(C)c2c1CO] | N-[[4-(hydroxymethyl)-3-methyl-7-[4-(trifluoromethoxy)phenyl]benzimidazol-5-yl]methyl]prop-2-enamide |

TABLE 2-continued

| Compound Number | Structure | Chemical name |
|---|---|---|
| K1 | 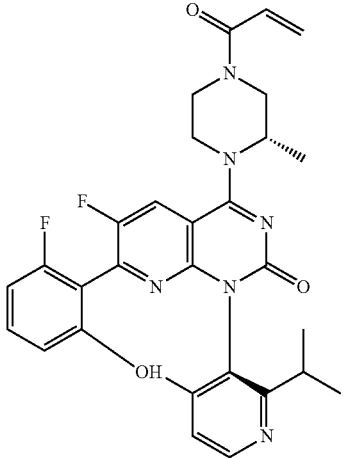 | 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one |
| K2 | 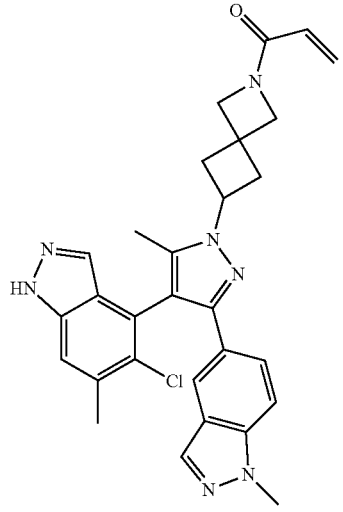 [SMILES: C=CC(=O)N1CC2(CC(n3nc(-c4ccc5c(cnn5C)c4)c(-c4c(Cl)c(C)cc5[nH]ncc45)c3C)C2)C1] | 1-[6-[4-(5-chloro-6-methyl-1H-indazol-4-yl)-5-methyl-3-(1-methylindazol-5-yl)pyrazol-1-yl]-2-azaspiro[3.3]heptan-2-yl]prop-2-en-1-one |
| K3 | 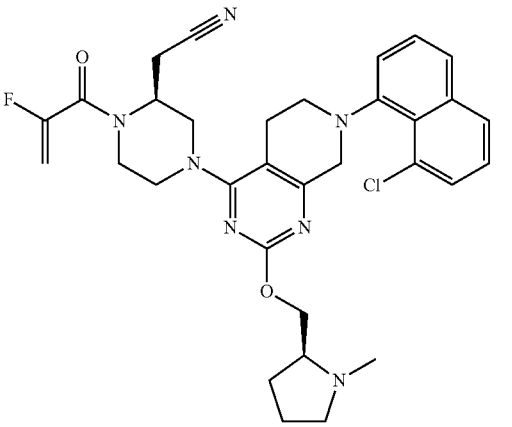 [SMILES: C=C(F)C(=O)N1CCN(c2nc(OC[C@@H]3CCCN3C)nc3c2CCN(c2cccc4cccc(Cl)c24)C3)C[C@@H]1CC#N] | 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile |

TABLE 2-continued

| Compound Number | Structure | Chemical name |
|---|---|---|
| K4 | 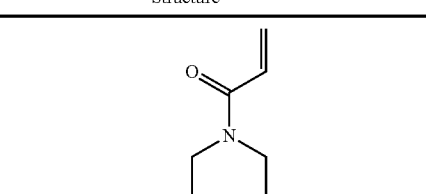 | 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one |

In some embodiments, the YAP/TAZ-TEAD inhibitors are selected from the group consisting of:
N-[[4-(hydroxymethyl)-7-[4-(trifluoromethoxy)$_{0.5}$phenyl]-2,3-dihydrobenzofuran-5-yl]methyl]prop-2-enamide;
N-[[4-cyano-3-methyl-7-[4-(trifluoromethoxy)phenyl]benzimidazol-5-yl]methyl]prop-2-enamide;
N-((5-(1,2-dihydroxyethyl)-8-(4-(trifluoromethoxy)phenyl)quinoxalin-6-yl)methyl)acrylamide; and
N-[[4-(hydroxymethyl)-3-methyl-7-[4-(trifluoromethoxy)phenyl]benzimidazol-5-yl]methyl]prop-2-enamide,
or a stereoisomer or tautomer thereof, or a pharmaceutically acceptable salt of any of the foregoing.

In some embodiments, the one or more KRAS inhibitors are selected from the group consisting of:
4-(4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one;
1-[6-[4-(5-chloro-6-methyl-1H-indazol-4-yl)-5-methyl-3-(1-methylindazol-5-yl)pyrazol-1-yl]-2-azaspiro[3.3]heptan-2-yl]prop-2-en-1-one;
2-(4-(7-(8-chloronaphthalen-1-yl)-2-((1-methylpyrrolidin-2-yl)methoxy)-5,6,7,8-tetrahydropyrido[3,4-d]pyrimidin-4-yl)-1-(2-fluoroaciyloyl)piperazin-2-yl)acetonitrile; and
1-(4-(7-(6-amino-4-methyl-3-(trifluoromethyl)pyridin-2-yl)-6-chloro-8-fluoro-2-((I-methylpyrrolidin-2-yl)methoxy)quinazolin-4-yl)-3-methylpiperazin-1-yl)prop-2-en-1-one,
or a stereoisomer or tautomer thereof, or a pharmaceutically acceptable salt of any of the foregoing.

In some embodiments, the compositions, methods, or kits, comprise one or more TEAD inhibitors (e.g., any one of the TEAD inhibitors described herein, including but not limited to, any one of compounds of formula (II-AB'), (II-AB), (II-A), (II-A-20), (II-B), or (II-B-18), or any variations or embodiments thereof) and one or more KRAS inhibitors (e.g., any one of compounds of formula (K—I), (K—I-A), (K-II), (K-II-A), (K-II-B), (K-II-C), (K—III), (K—III-A), (K—IV), (K—IV-A), (K-IV-B), or (K-IV-C) or any variations or embodiments thereof). TEAD inhibitors may, in some embodiments, be referred to as YAP/TAZ-TEAD inhibitors. In some embodiments, in conjunction with embodiments above or below, the one or more KRAS inhibitors may be a G12C KRAS inhibitor (e.g., Compound K1, Compound K2, Compound K3, or Compound K4). Each and every combination of TEAD inhibitor and KRAS inhibitor is intended the same as if each and every combination is specifically and individually listed. Thus, for example, it is intended that any combination of: (1) a compound of formula (II-AB'), (II-AB), (II-A), (II-A-20), (II-B), or (II-B-18), or any variation or embodiment thereof; and (2) a compound of formula (K—I), (K—I-A), (K-II), (K-II-A), (K-II-B), (K-II-C), (K—III), (K—III-A), (K—IV), (K—IV-A), (K-IV-B), or (K-IV-C), or any variation or embodiment thereof, is provided herein.

In some embodiments, the one or more TEAD inhibitors comprise a compound of formula (II-AB'), (II-AB), (II-A), or (II-A-20) (e.g., Compound T1, Compound T2, Compound T3, or Compound T4) and the one or more KRAS inhibitors comprise a compound of formula (K—I) (e.g., Compound K1). In some embodiments, the one or more TEAD inhibitors comprise a compound of formula (II-AB'), (II-AB), (II-A), or (II-A-20) (e.g., Compound T1, Compound T2, Compound T3, or Compound T4) and the one or more KRAS inhibitors comprise a compound of formula (K-II) (e.g., Compound K2). In some embodiments, the one or more TEAD inhibitors comprise a compound of formula (II-AB'), (II-AB), (II-A), or (II-A-20) (e.g., Compound T1, Compound T2, Compound T3, or Compound T4) and the one or more KRAS inhibitors comprise a compound of formula (K—III) (e.g., Compound K3). In some embodiments, the one or more TEAD inhibitors comprise a compound of formula (II-AB'), (II-AB), (II-A), or (II-A-20) (e.g., Compound T1, Compound T2, Compound T3, or Compound T4) and the one or more KRAS inhibitors comprise a compound of formula (K—IV) (e.g., Compound K4).

In some embodiments, the one or more TEAD inhibitors are selected from compounds of formula (II-AB'), (II-AB), (II-A), (II-A-20), or (II-B), and the one or more KRAS inhibitors are selected from compounds of formula (K—IV), (K—IV-A), (K-IV-B), or (K-IV-C). In some embodiments, in conjunction with the embodiments above or below, the one or more KRAS inhibitors comprise Compound K4. In some embodiments, in conjunction with the embodiments above or below, the one or more TEAD inhibitors comprise Compound T1. In some embodiments, in conjunction with the embodiments above or below, the one or more TEAD inhibitors comprise Compound T2. In some embodiments, in conjunction with the embodiments above or below, the one or more TEAD inhibitors comprise Compound T3. In some embodiments, in conjunction with the embodiments above or below, the one or more TEAD inhibitors comprise Compound T4.

In some embodiments, the one or more TEAD inhibitors are selected from compounds of formula (II-AB'), (II-AB), (II-A), (II-A-20), or (II-B), and the one or more KRAS inhibitors are selected from compounds of formula (K—III) or (K—III-A). In some embodiments, in conjunction with the embodiments above or below, the one or more KRAS inhibitors comprise Compound K3. In some embodiments, in conjunction with the embodiments above or below, the one or more TEAD inhibitors comprise Compound T1. In some embodiments, in conjunction with the embodiments above or below, the one or more TEAD inhibitors comprise Compound T2. In some embodiments, in conjunction with the embodiments above or below, the one or more TEAD inhibitors comprise Compound T3. In some embodiments, in conjunction with the embodiments above or below, the one or more TEAD inhibitors comprise Compound T4.

In some embodiments, the one or more TEAD inhibitors are selected from compounds of formula (II-AB'), (II-AB), (II-A), (II-A-20), or (II-B), and the one or more KRAS inhibitors are selected from compounds of formula (K-II), (K-II-A), (K-II-B), or (K-III-C). In some embodiments, in conjunction with the embodiments above or below, the one or more KRAS inhibitors comprise Compound K2. In some embodiments, in conjunction with the embodiments above or below, the one or more TEAD inhibitors comprise Compound T1. In some embodiments, in conjunction with the embodiments above or below, the one or more TEAD inhibitors comprise Compound T2. In some embodiments, in conjunction with the embodiments above or below, the one or more TEAD inhibitors comprise Compound T3. In some embodiments, in conjunction with the embodiments above or below, the one or more TEAD inhibitors comprise Compound T4.

In some embodiments, the one or more TEAD inhibitors are selected from compounds of formula (II-AB'), (II-AB), (II-A), (II-A-20), or (II-B), and the one or more KRAS inhibitors are selected from compounds of formula (K—I) or (K—I-A). In some embodiments, in conjunction with the embodiments above or below, the one or more KRAS inhibitors comprise Compound K1. In some embodiments, in conjunction with the embodiments above or below, the one or more TEAD inhibitors comprise Compound T1. In some embodiments, in conjunction with the embodiments above or below, the one or more TEAD inhibitors comprise Compound T2. In some embodiments, in conjunction with the embodiments above or below, the one or more TEAD inhibitors comprise Compound T3. In some embodiments, in conjunction with the embodiments above or below, the one or more TEAD inhibitors comprise Compound T4.

In some embodiments, the one or more TEAD inhibitors are selected from compounds of Table 1, and the one or more KRAS inhibitors are selected from compounds of formula (K—IV), (K—IV-A), (K-IV-B), or (K-IV-C). In some embodiments, the one or more KRAS inhibitors comprise Compound K4. In some embodiments, the one or more TEAD inhibitors are selected from compounds of Table 1, and the one or more KRAS inhibitors are selected from compounds of formula (K—III) or (K—III-A). In some embodiments, the one or more KRAS inhibitors comprise Compound K3. In some embodiments, the one or more TEAD inhibitors are selected from compounds of Table 1, and the one or more KRAS inhibitors are selected from compounds of formula (K-II), (K-II-A), (K-II-B), or (K-II-C). In some embodiments, the one or more KRAS inhibitors comprise Compound K2. In some embodiments, the one or more TEAD inhibitors are selected from compounds of Table 1, and the one or more KRAS inhibitors are selected from compounds of formula (K—I) or (K—I-A). In some embodiments, the one or more KRAS inhibitors comprise Compound K1.

In some embodiments, the one or more TEAD inhibitors comprise Compound T1, and the one or more KRAS inhibitors are selected from compounds of formula (K—IV), (K—IV-A), (K-IV-B), or (K-IV-C). In some embodiments, the one or more TEAD inhibitors comprise Compound T1, and the one or more KRAS inhibitors are selected from compounds of formula (K—III) or (K—III-A). In some embodiments, the one or more TEAD inhibitors comprise Compound T1, and the one or more KRAS inhibitors are selected from compounds of formula (K-II), (K-II-A), (K-II-B), or (K-II-C). In some embodiments, the one or more TEAD inhibitors comprise Compound T1, and the one or more KRAS inhibitors are selected from compounds of formula (K—I) or (K—I-A). In some embodiments, the one or more TEAD inhibitors comprise Compound T1, and the one or more KRAS inhibitors comprise Compound K4. In some embodiments, the one or more TEAD inhibitors comprise Compound T1, and the one or more KRAS inhibitors comprise Compound K3. In some embodiments, the one or more TEAD inhibitors comprise Compound T1, and the one or more KRAS inhibitors comprise Compound K2. In some embodiments, the one or more TEAD inhibitors comprise Compound T1, and the one or more KRAS inhibitors comprise Compound K1.

In some embodiments, the one or more TEAD inhibitors comprise Compound T2, and the one or more KRAS inhibitors are selected from compounds of formula (K—IV), (K—IV-A), (K-IV-B), or (K-IV-C). In some embodiments, the one or more TEAD inhibitors comprise Compound T2, and the one or more KRAS inhibitors are selected from compounds of formula (K—III) or (K—III-A). In some embodiments, the one or more TEAD inhibitors comprise Compound T2, and the one or more KRAS inhibitors are selected from compounds of formula (K-II), (K-II-A), (K-II-B), or (K-II-C). In some embodiments, the one or more TEAD inhibitors comprise Compound T2, and the one or more KRAS inhibitors are selected from compounds of formula (K—I) or (K—I-A). In some embodiments, the one or more TEAD inhibitors comprise Compound T2, and the one or more KRAS inhibitors comprise Compound K4. In some embodiments, the one or more TEAD inhibitors comprise Compound T2, and the one or more KRAS inhibitors comprise Compound K3. In some embodiments, the one or more TEAD inhibitors comprise Compound T2, and the one or more KRAS inhibitors comprise Compound K2. In some embodiments, the one or more TEAD inhibitors comprise Compound T2, and the one or more KRAS inhibitors comprise Compound K1.

In some embodiments, the one or more TEAD inhibitors comprise Compound T3, and the one or more KRAS inhibitors are selected from compounds of formula (K—IV), (K—IV-A), (K-IV-B), or (K-IV-C). In some embodiments, the one or more TEAD inhibitors comprise Compound T3, and the one or more KRAS inhibitors are selected from compounds of formula (K—III) or (K—III-A). In some embodiments, the one or more TEAD inhibitors comprise Compound T3, and the one or more KRAS inhibitors are selected from compounds of formula (K-II), (K-II-A), (K-II-B), or (K-II-C). In some embodiments, the one or more TEAD inhibitors comprise Compound T3, and the one or more KRAS inhibitors are selected from compounds of formula (K—I) or (K—I-A). In some embodiments, the one or more TEAD inhibitors comprise Compound T3, and the one or more KRAS inhibitors comprise Compound K4. In some embodiments, the one or more TEAD inhibitors comprise Compound T3, and the one or more KRAS inhibitors comprise Compound K3. In some embodiments, the one or more TEAD inhibitors comprise Compound T3, and the one or more KRAS inhibitors comprise Compound K2. In some embodiments, the one or more TEAD inhibitors comprise Compound T3, and the one or more KRAS inhibitors comprise Compound K1.

In some embodiments, the one or more TEAD inhibitors comprise Compound T4, and the one or more KRAS inhibitors are selected from compounds of formula (K—IV), (K—IV-A), (K-IV-B), or (K-IV-C). In some embodiments, the one or more TEAD inhibitors comprise Compound T4, and the one or more KRAS inhibitors are selected from compounds of formula (K—III) or (K—III-A). In some embodiments, the one or more TEAD inhibitors comprise Compound T4, and the one or more KRAS inhibitors are selected from compounds of formula (K-II), (K-II-A), (K-II-B), or (K-II-C). In some embodiments, the one or more TEAD inhibitors comprise Compound T4, and the one or more KRAS inhibitors are selected from compounds of formula (K—I) or (K—I-A). In some embodiments, the one or more TEAD inhibitors comprise Compound T4, and the one or more KRAS inhibitors comprise Compound K4. In some embodiments, the one or more TEAD inhibitors comprise Compound T4, and the one or more KRAS inhibitors comprise Compound K3. In some embodiments, the one or more TEAD inhibitors comprise Compound T4, and the one or more KRAS inhibitors comprise Compound K2. In some embodiments, the one or more TEAD inhibitors comprise Compound T4, and the one or more KRAS inhibitors comprise Compound K1.

In some embodiments, the one or more TEAD inhibitors are selected from the group consisting of:

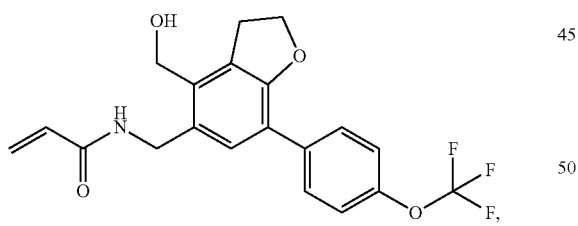

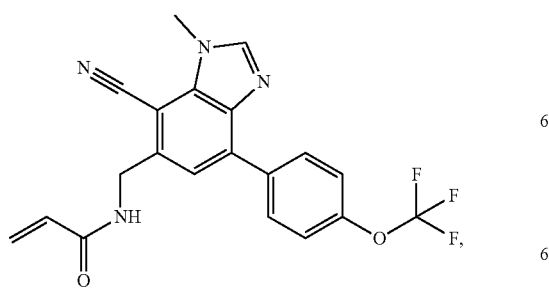

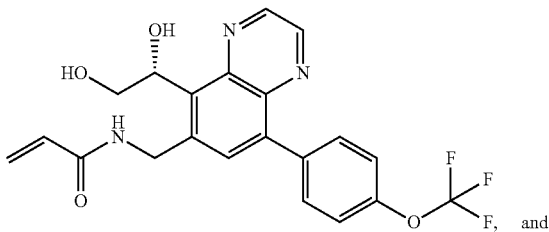

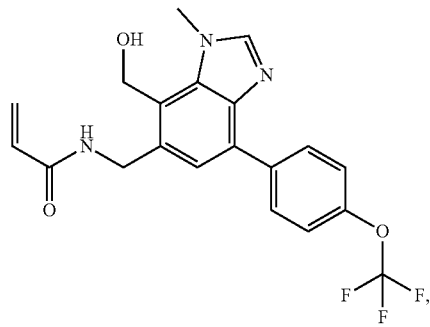

stereoisomer or tautomer thereof, or a pharmaceutically acceptable salt of any of the foregoing; and the one or more KRAS inhibitors are selected from the group consisting of:

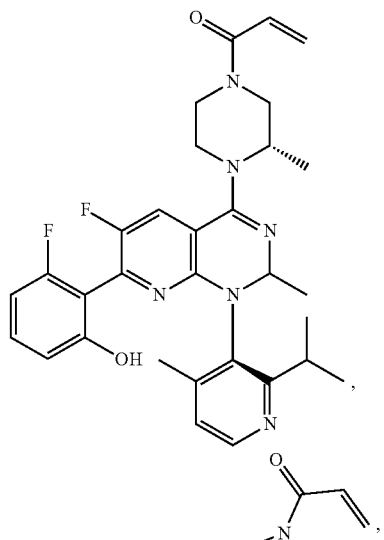

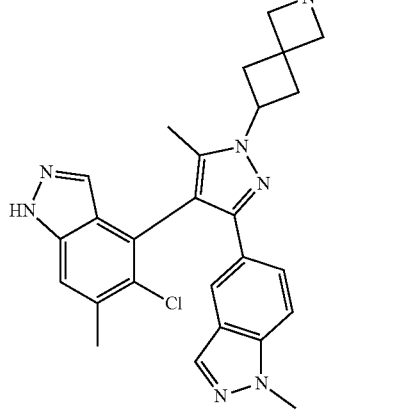

-continued

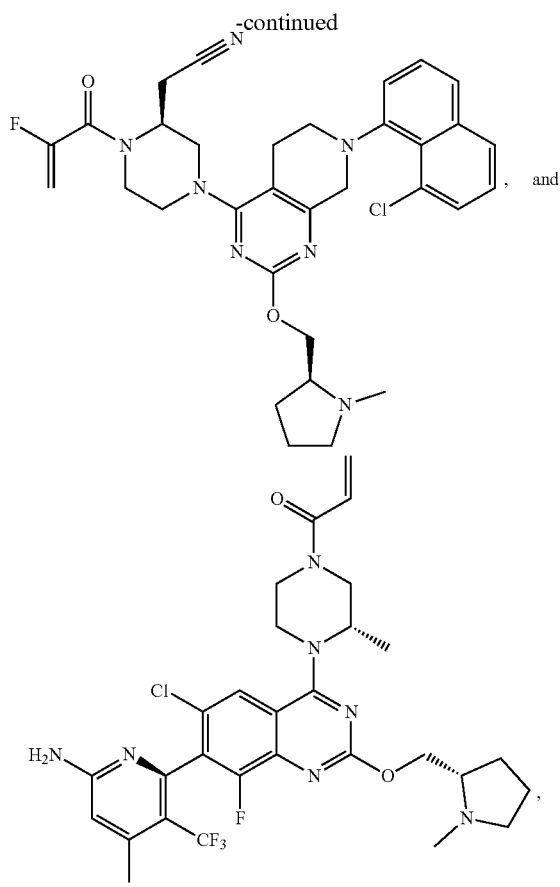

and or a stereoisomer or tautomer thereof, or a pharmaceutically acceptable salt of any of the foregoing.

In some embodiments, provided herein are methods of treating cancer in a subject in need thereof, comprising administering to the subject an effective amount of a combination, comprising one or more TEAD inhibitors (e.g., any one of the TEAD inhibitors described herein, including but not limited to, any one of compounds of formula (II-AB'), (II-AB), (II-A), or (II-B), or any variations or embodiments thereof) and one or more KRAS inhibitors (e.g., any one of compounds of formula (K—I), (K-II), (K—III), or (K—IV), or any variations or embodiments thereof). In some embodiments, the KRAS inhibitor is a G12C KRAS inhibitor.

In some aspects, provided herein is a method of treating a disease or condition mediated by KRAS activity in a subject in need thereof, comprising administering to the subject an effective amount of a combination, comprising: i) one or more TEAD inhibitors; and (ii) one or more KRAS inhibitors. In some embodiments, the disease or condition mediated by KRAS activity is cancer.

In some aspects, provided herein is a method of treating a disease or condition mediated by TEAD activity in a subject in need thereof, comprising administering to the subject an effective amount of a combination, comprising: i) one or more TEAD inhibitors; and (ii) one or more KRAS inhibitors. In some embodiments, the disease or condition mediated by TEAD activity is cancer.

In another aspect, provided herein is a method of reducing resistance of a subject to treatment comprising one or more KRAS inhibitors (e.g., any one of compounds of formula (K—I), (K-IL), (K—III), or (K—IV), or any variations or embodiments thereof), wherein the method comprises administering to the subject a therapeutically effective amount of one or more TEAD inhibitors (e.g., any one of the TEAD inhibitors described herein, including but not limited to, any one of compounds of formula (II-AB'), (II-AB), (II-A), or (II-B), or any variations or embodiments thereof).

In some embodiments, provided herein are kits, comprising (i) one or more TEAD inhibitors (e.g., any one of the TEAD inhibitors described herein, including but not limited to, any one of compounds of formula (II-AB'), (II-AB), (II-A), or (II-B), or any variations or embodiments thereof); (ii) one or more KRAS inhibitors (e.g., any one of compounds of formula (K—I), (K-II), (K—III), or (K—IV), or any variations or embodiments thereof); and (iii) instructions for administering the combination to treat cancer in a subject in need thereof. In some embodiments, the KRAS inhibitor is a G12C KRAS inhibitor.

ENUMERATED EMBODIMENTS

In one aspect provided herein is a list of embodiments as enumerated below: Embodiment 1. A compound of formula (II-A) or (II-B):

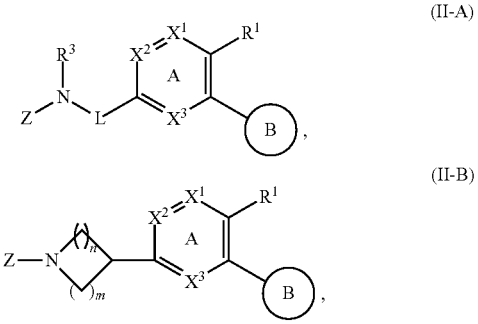

or a stereoisomer or tautomer thereof, or a pharmaceutically acceptable salt thereof, wherein:

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;

wherein the 5 to 6 membered heteroaryl, 5 to 6 membered heterocyclyl, phenyl, and $C_{5-6}$ cycloalkyl formed by $X^1$ and $R^1$ are each independently optionally substituted with one or more $R^t$, wherein $R^t$ is independently, at each occurrence, selected from the group consisting of halo, $C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN;

$X^2$ is N or CR$^s$, wherein R$^s$ is selected from H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$;

wherein the $C_{1-15}$alkyl and $C_{1-15}$alkoxy of R$^s$ are each independently optionally substituted with one or more R$^t$, wherein R$^t$ is independently at each occurrence halo, oxo, —OH, —CN, or —NR$^d$R$^e$, wherein R$^d$ and R$^e$ are each independently H or $C_{1-6}$alkyl; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^t$, wherein $R^t$ is independently at each occurrence selected from halo, oxo, —OH, —CN and $C_{1-6}$alkyl; and wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

$X^3$ is N or CH;

B is phenyl or 5 to 6 membered heteroaryl; wherein the phenyl and 5 to 6 membered heteroaryl of B are each independently substituted with one or more $R^2$, wherein $R^2$ is independently, at each occurrence, halo; $S(R^y)_5$, wherein each $R^y$ is halo; or $C_{1-6}$alkoxy optionally substituted with one or more halo;

$R^3$ is H or $C_{1-6}$alkyl;

Z is —OH, —$NR^dR^e$, $C_{1-6}$alkoxy, —C(O)$R^a$, —S(O)$_2R^b$, wherein $R^d$ and $R^e$ are each independently H or $C_{1-6}$alkyl, and wherein the $C_{1-6}$alkyl of $R^d$ or $R^e$ is optionally substituted with one or more substituents selected from halo, oxo, —OH and —CN;

$R^a$ and $R^b$ are each independently i) $C_{2-6}$alkenyl optionally substituted with one or more substituents selected from deuterium, $C_{1-6}$alkyl, halo and halo$C_{1-6}$alkyl; or ii) $C_{1-6}$alkyl, optionally substituted with one or more halo;

L is methylene, optionally substituted with one or more $C_{1-6}$alkyl; and n and m are each independently 1 or 2.

Embodiment 2. The compound of embodiment 1, or a stereoisomer or tautomer thereof, or a pharmaceutically acceptable salt thereof, wherein Z is —C(O)$R^a$ or —S(O)$_2R^b$, $R^a$ and $R^b$ are each independently i) $C_{2-6}$alkenyl optionally substituted with one or more substituents selected from deuterium, $C_{1-6}$alkyl, halo and halo$C_{1-6}$alkyl; or ii) $C_{1-6}$alkyl, optionally substituted with one or more halo.

Embodiment 3. The compound of embodiment 1 or 2, or a stereoisomer or tautomer thereof, or a pharmaceutically acceptable salt thereof, wherein Z is —C(O)$R^a$ and $R^a$ is $C_{2-6}$alkenyl optionally substituted with one or more substituents selected from deuterium, $C_{1-6}$alkyl, halo and halo$C_{1-6}$alkyl.

Embodiment 4. The compound of embodiment 1 or 2, or a stereoisomer or tautomer thereof, or a pharmaceutically acceptable salt thereof, wherein Z is —C(O)$R^a$ and $R^a$ is $C_{1-6}$alkyl, optionally substituted with one or more halo.

Embodiment 5. The compound of any one of embodiments 1 to 4, or a stereoisomer or tautomer thereof, or a pharmaceutically acceptable salt thereof, wherein B is phenyl substituted with one or more $R^2$, $R^2$ is independently, at each occurrence, halo; $S(R^y)_5$, wherein each $R^y$ is halo; or $C_{1-6}$ alkoxy optionally substituted with one or more halo.

Embodiment 6. The compound of any one of embodiments 1 to 4, or a stereoisomer or tautomer thereof, or a pharmaceutically acceptable salt thereof, wherein B is 5 to 6 membered heteroaryl substituted with one or more $R^2$, $R^2$ is independently, at each occurrence, halo; $S(R^y)_5$, wherein each $R^y$ is halo; or $C_{1-6}$ alkoxy optionally substituted with one or more halo.

Embodiment 7. The compound of embodiment 5 or 6, or a stereoisomer or tautomer thereof, or a pharmaceutically acceptable salt thereof, wherein $R^2$ is halomethoxy.

Embodiment 8. The compound of any one of embodiments 1 to 7, wherein $X^1$ is C or N;

$X^2$ is $CR^s$, wherein $R^s$ is selected from the group consisting of H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$; and $X^3$ is N or CH.

Embodiment 9. The compound of embodiment 8, wherein one of $X^1$ and $X^3$ is N.

Embodiment 10. The compound of embodiment 8, wherein $X^1$ is C and $X^3$ is CH.

Embodiment 11. The compound of any one of embodiments 8 to 10, wherein $X^2$ is $CR^s$, wherein $R^s$ is $C_{1-15}$alkyl, 5 to 15 membered heteroaryl, —CN, or $C_{1-15}$alkoxy.

Embodiment 12. The compound of any one of embodiments 1 to 5, wherein $X_1$ is C; $X^2$ is N; and $X^3$ is N or CH.

Embodiment 13. The compound of any one of embodiments 1 to 12, wherein $X_1$ is taken together with $R^1$ and the atoms to which they are attached, to form a 5 to 6 membered heteroaryl fused to ring A.

Embodiment 14. The compound of embodiment 13, wherein the 5 to 6 membered heteroaryl fused to ring A is selected from the group consisting of:

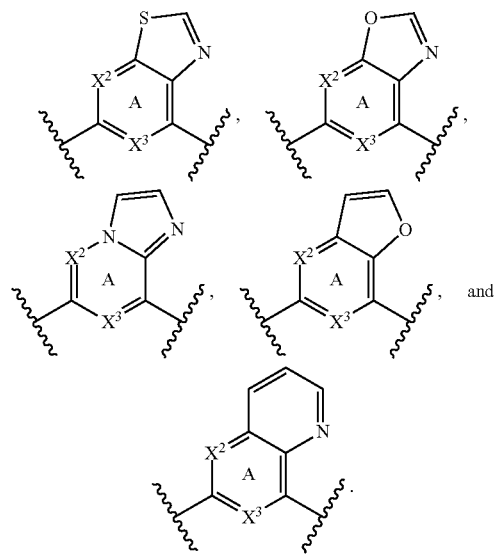

Embodiment 15. The compound of embodiment 13, or a stereoisomer or tautomer thereof, or a pharmaceutically acceptable salt thereof, wherein the compound is selected from the group consisting of:

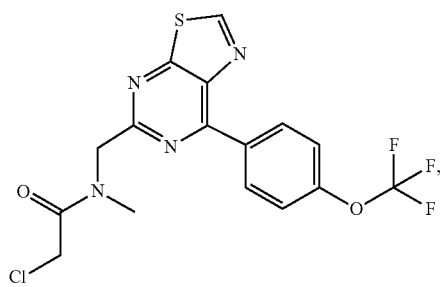

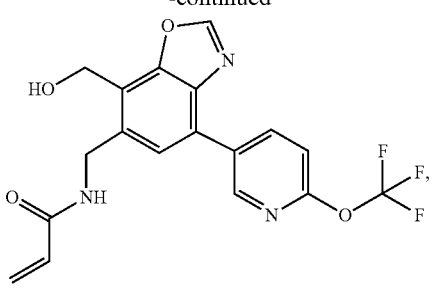

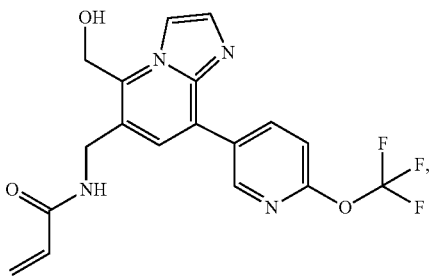

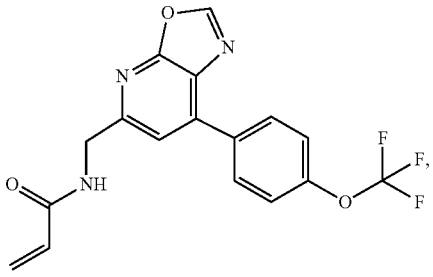

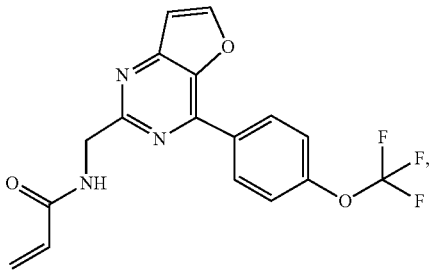

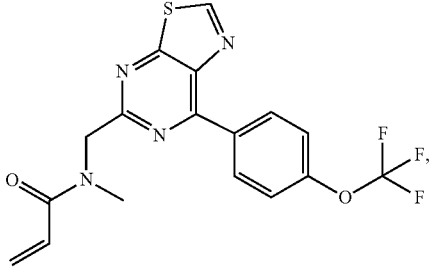

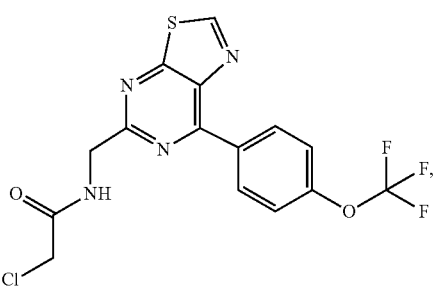

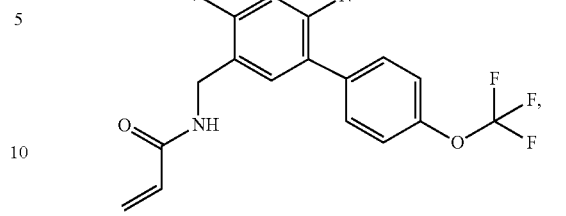

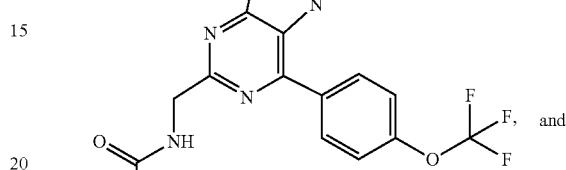

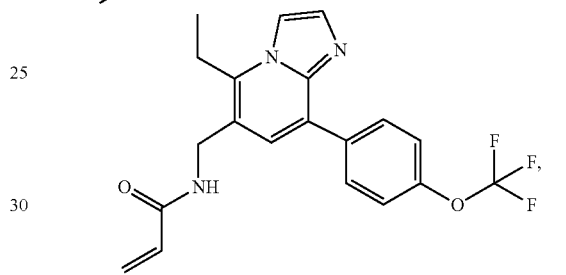

or a stereoisomer or tautomer thereof, or a pharmaceutically acceptable salt thereof.

16. The compound of any one of embodiments 1 to 12, wherein $X^1$ is taken together with $R^1$ and the atoms to which they are attached, to form a 5 to 6 membered heterocyclyl fused to ring A.

Embodiment 17. The compound of embodiment 16, wherein the 5 to 6 membered heterocyclyl fused to ring A is

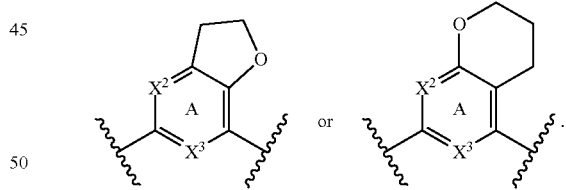

Embodiment 18. The compound of embodiment 17, or a stereoisomer or tautomer thereof, or a pharmaceutically acceptable salt thereof, wherein the compound is selected from the group consisting of:

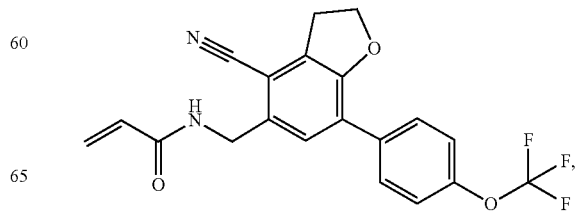

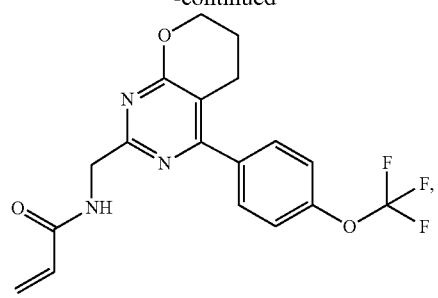
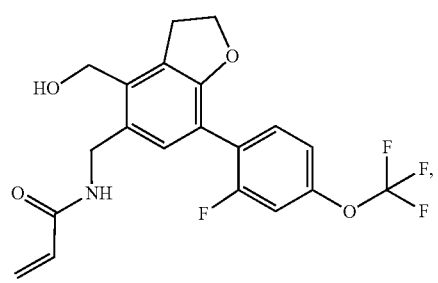
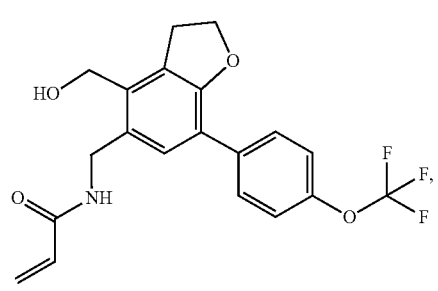
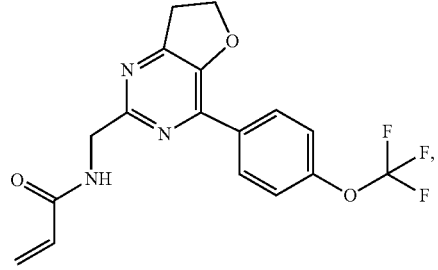
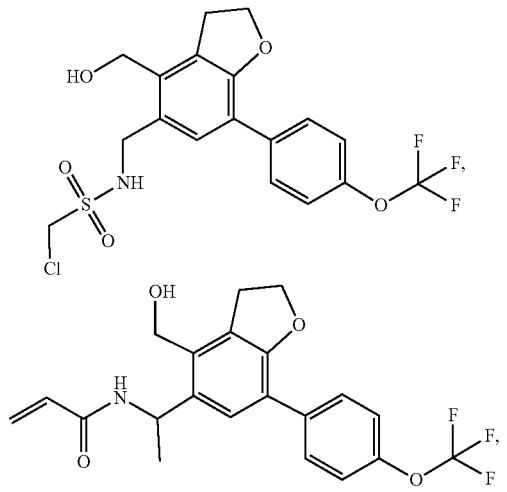
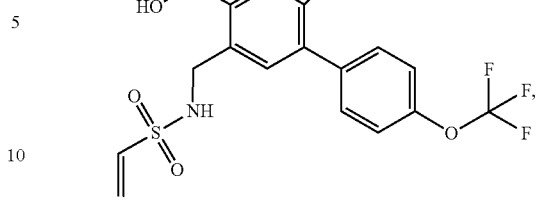
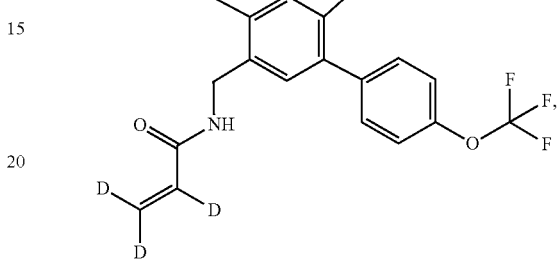
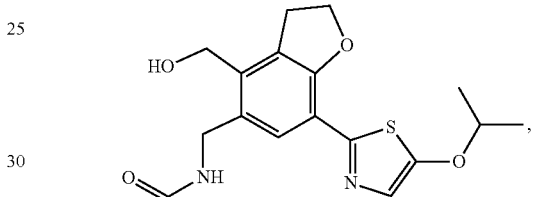
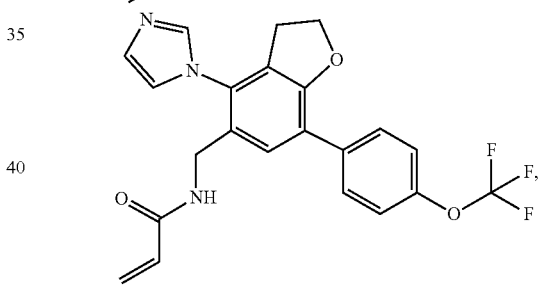
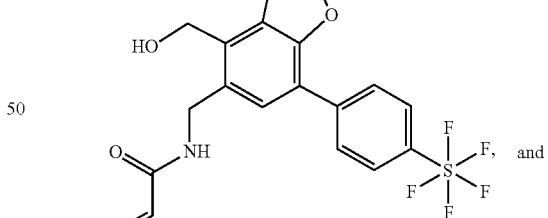
and
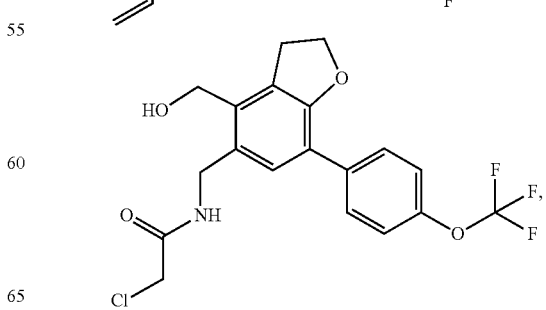

or a stereoisomer or tautomer thereof, or a pharmaceutically acceptable salt thereof.

Embodiment 19. The compound of embodiment 17, or a pharmaceutically acceptable salt thereof, wherein the compound is

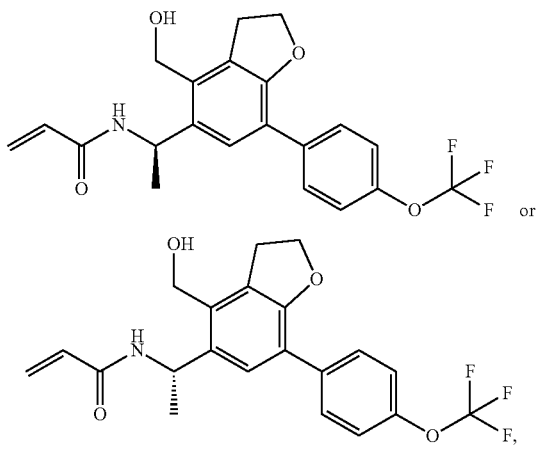

or a pharmaceutically acceptable salt thereof.

Embodiment 20. The compound of any one of embodiments 1 to 12, wherein $X^1$ is taken together with $R^1$ and the atoms to which they are attached, to form a phenyl fused to ring A,

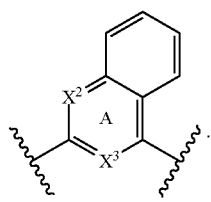

Embodiment 21. The compound of embodiment 20, or a stereoisomer or tautomer thereof, or a pharmaceutically acceptable salt thereof, wherein the compound is

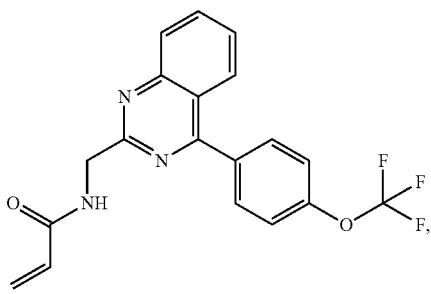 [SMILES: C=CC(=O)NCc1nc(-c2ccc(OC(F)(F)F)cc2)c2ccccc2n1]

or a stereoisomer or tautomer thereof, or a pharmaceutically acceptable salt thereof.

Embodiment 22. The compound of any one of embodiments 1 to 12, wherein X, is taken together with $R^1$ and the atoms to which they are attached, to form a $C_{5-6}$cycloalkyl fused to ring A,

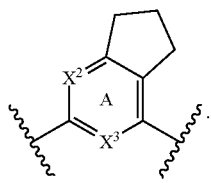

Embodiment 23. The compound of embodiment 22, or a stereoisomer or tautomer thereof, or a pharmaceutically acceptable salt thereof, wherein the compound is

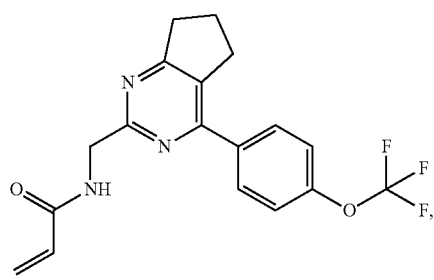 [SMILES: C=CC(=O)NCc1nc2c(c(-c3ccc(OC(F)(F)F)cc3)n1)CCC2]

or a stereoisomer or tautomer thereof, or a pharmaceutically acceptable salt thereof.

Embodiment 24. The compound of embodiment 1, or a stereoisomer or tautomer thereof, or a pharmaceutically acceptable salt thereof, wherein Z is —C(O)R$^a$ and R$^a$ is $C_{2-6}$alkenyl optionally substituted with one or more substituents selected from deuterium, $C_{1-6}$alkyl, halo and haloC$_{1-6}$alkyl; and B is phenyl substituted with one or more R$^2$, wherein R$^2$ is $C_{1-6}$alkoxy optionally substituted with one or more halo.

Embodiment 25. The compound of embodiment 24, or a stereoisomer or tautomer thereof, or a pharmaceutically acceptable salt thereof, wherein the compound is selected from the group consisting of:

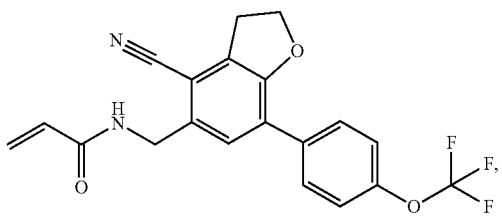

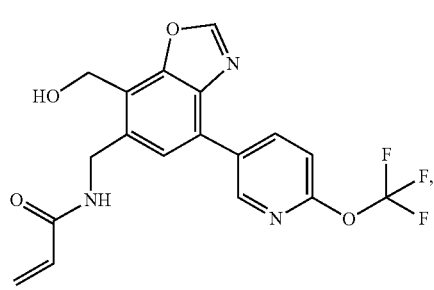

241
-continued
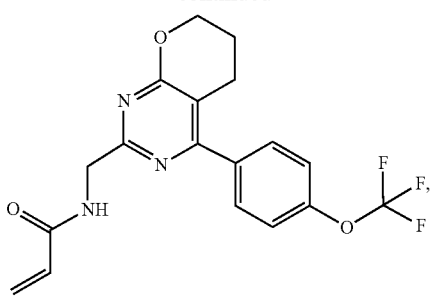
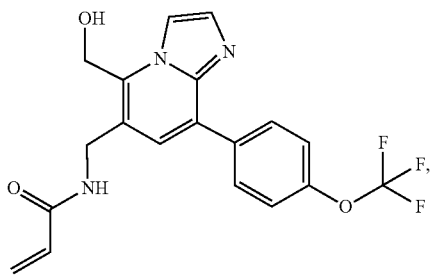
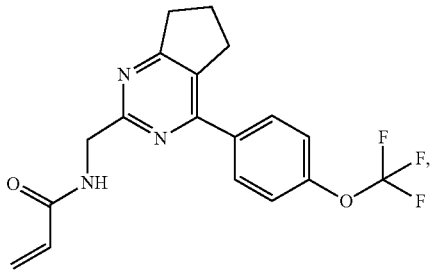
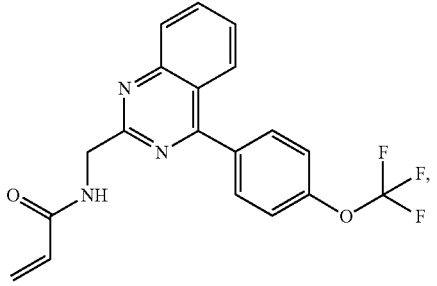
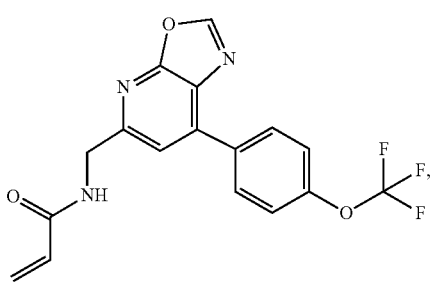
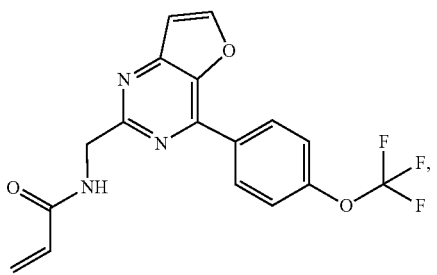
242
-continued
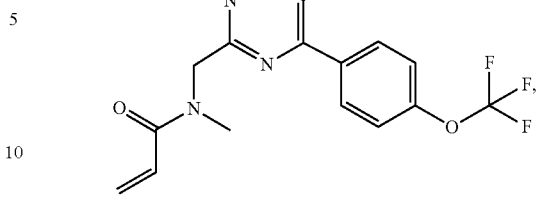
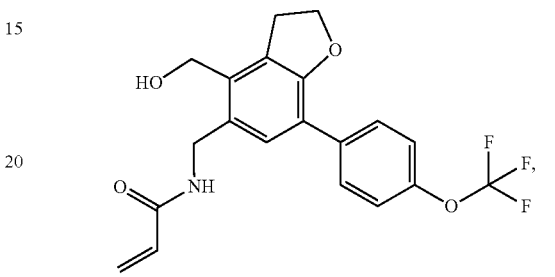
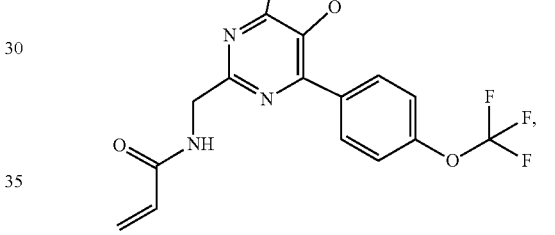
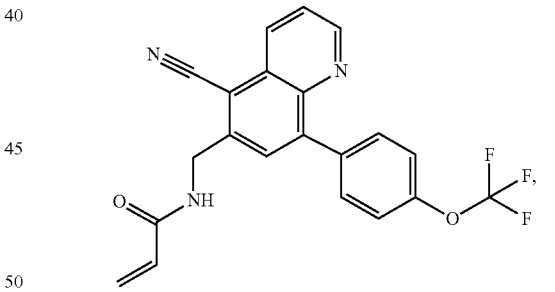
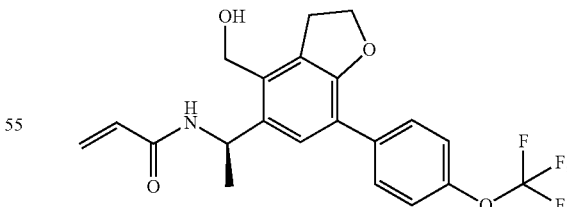
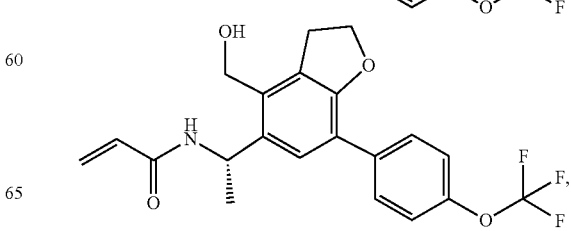

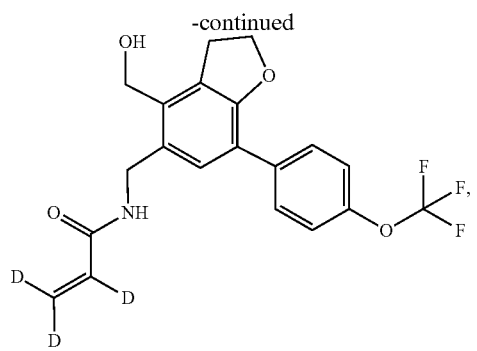

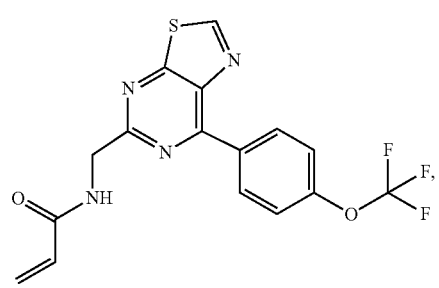

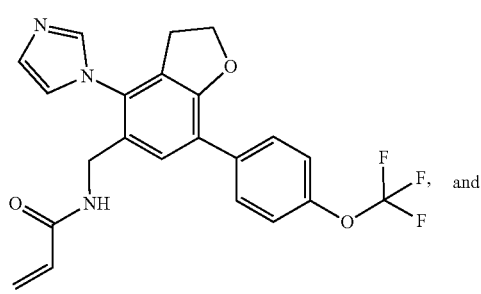

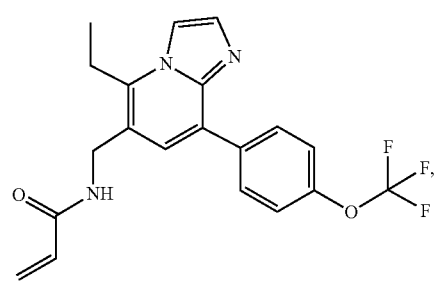

or a stereoisomer or tautomer thereof, or a pharmaceutically acceptable salt thereof.

Embodiment 26. The compound of embodiment 1, or a stereoisomer or tautomer thereof, or a pharmaceutically acceptable salt thereof, wherein
- Z is —C(O)R$^a$ and R$^a$ is C$_{1-6}$alkyl, optionally substituted with one or more halo,
- B is phenyl substituted with one or more R$^2$, wherein R$^2$ is C$_{1-6}$alkoxy optionally substituted with one or more halo.

Embodiment 27. The compound of embodiment 26, or a stereoisomer or tautomer thereof, or a pharmaceutically acceptable salt thereof, wherein the compound is selected from the group consisting of:

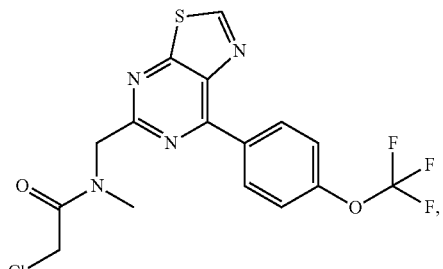

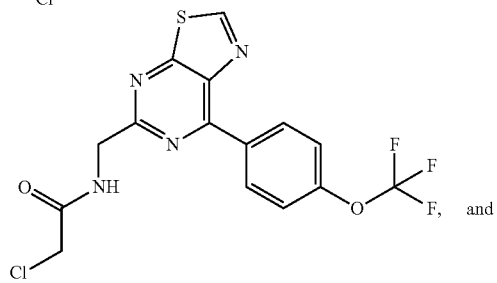

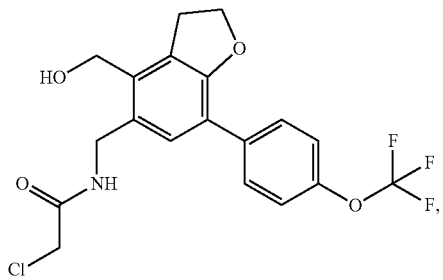

or a stereoisomer or tautomer thereof, or a pharmaceutically acceptable salt thereof.

Embodiment 28. The compound of any one of embodiments 1 to 27, or a stereoisomer or tautomer thereof, or a pharmaceutically acceptable salt thereof, wherein R$^3$ is H.

Embodiment 29. The compound of embodiment 1, or a stereoisomer or tautomer thereof, or a pharmaceutically acceptable salt thereof, wherein the compound is selected from the group consisting of:

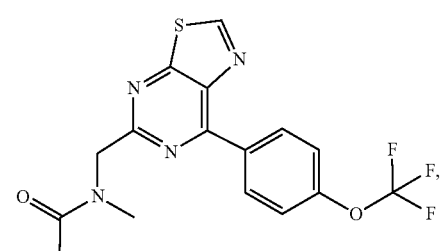

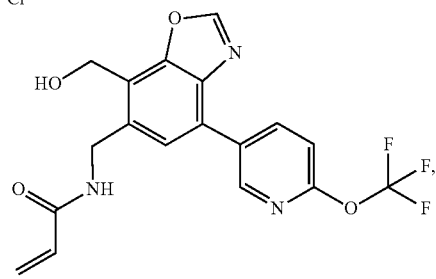

245
-continued
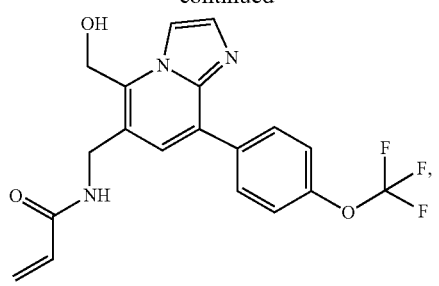
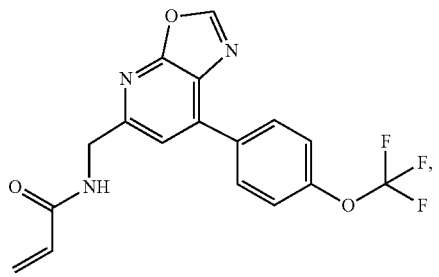
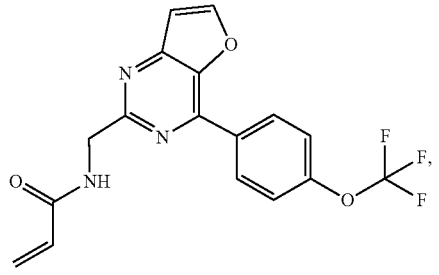
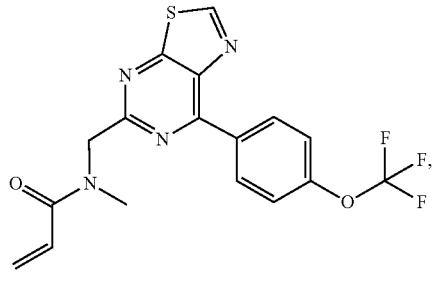
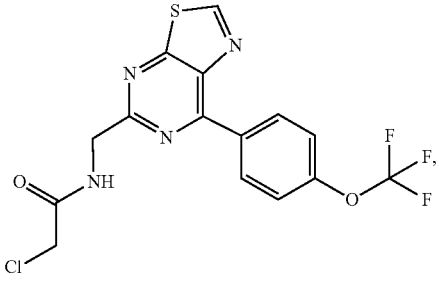
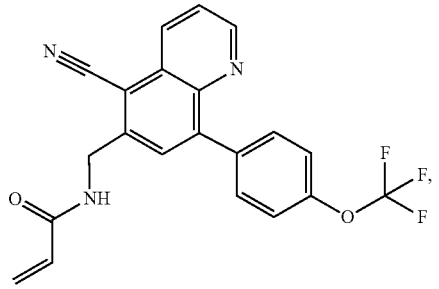
246
-continued
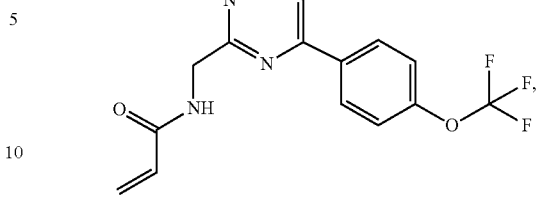
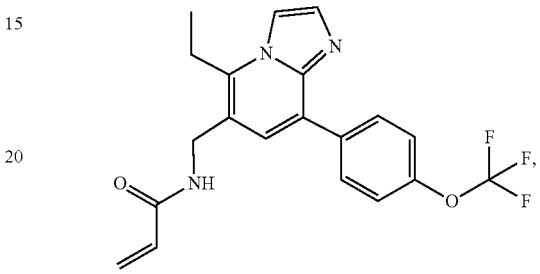
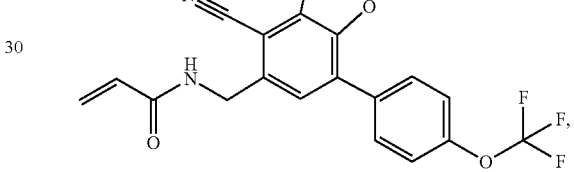
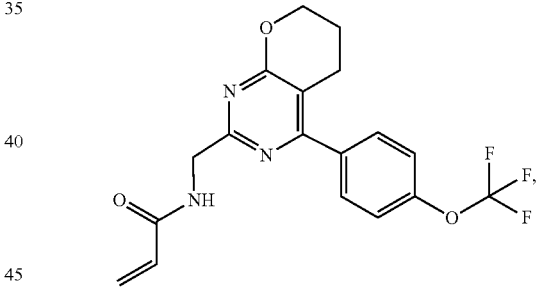
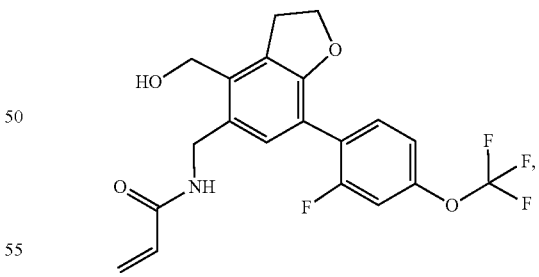
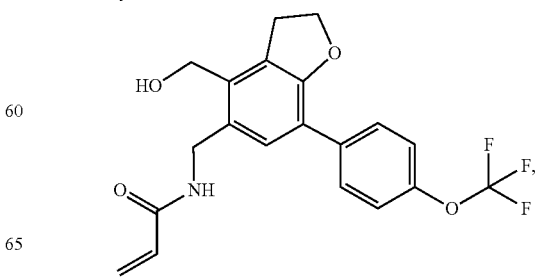

247
-continued
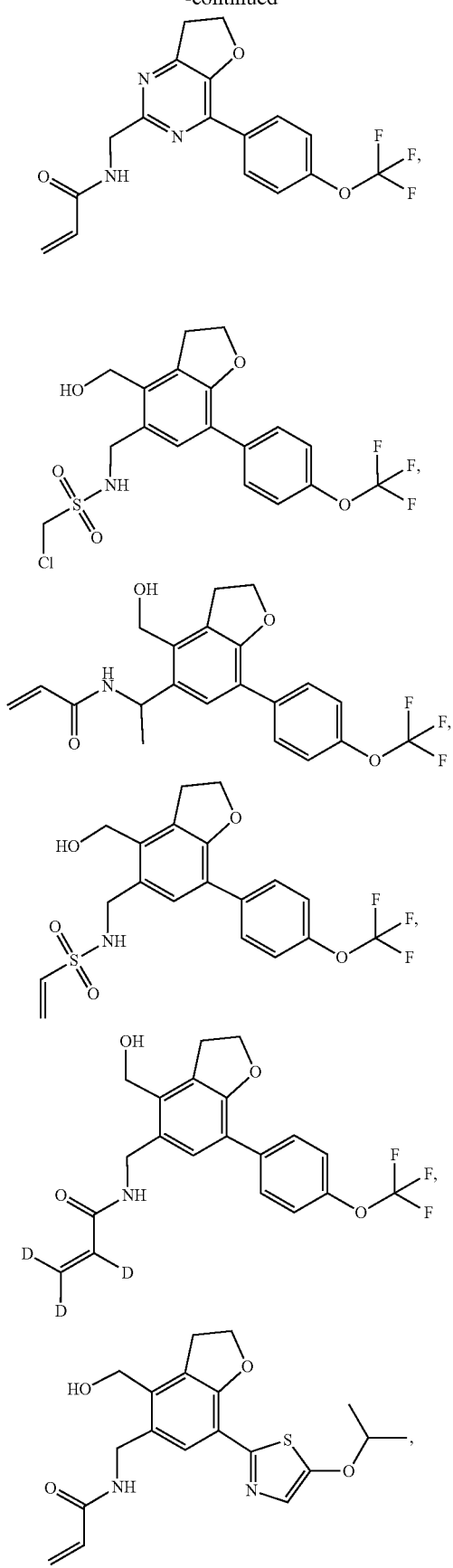
248
-continued
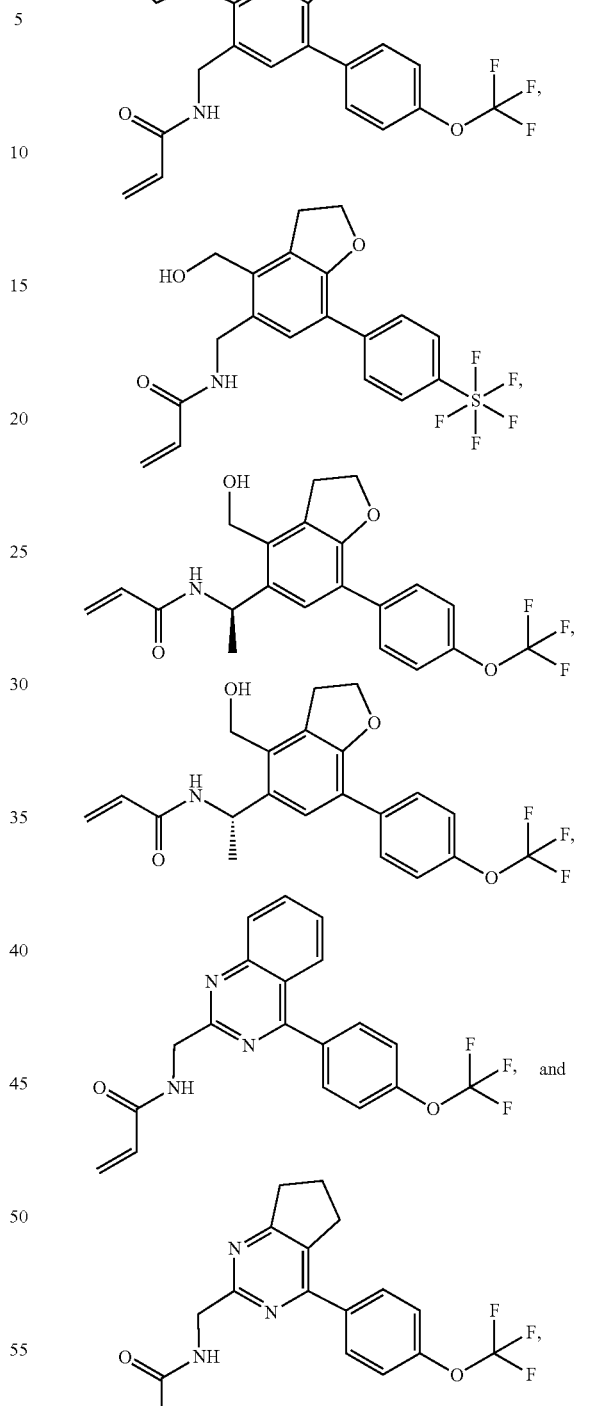
or a stereoisomer or tautomer thereof, or a pharmaceutically acceptable salt thereof.
Embodiment 30. A pharmaceutical composition, comprising (i) a compound as described in any one of embodiments 1-29, or a stereoisomer, tautomer, or pharmaceutically acceptable salt thereof, and (ii) a pharmaceutically acceptable carrier, diluent, or excipient.

Embodiment 31. A compound as described in any one of embodiments 1-29, or a stereoisomer, tautomer, or pharmaceutically acceptable salt thereof, for use in medical therapy.

Embodiment 32. A compound as described in any one of embodiments 1-29, or a stereoisomer, tautomer, or pharmaceutically acceptable salt thereof, for use in the treatment and/or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 33. A method for treating cancer in a mammal, comprising administering a compound as described in any one of embodiments 1-29, or a stereoisomer, tautomer, or pharmaceutically acceptable salt thereof, to the mammal.

Embodiment 34. A compound as described in any one of embodiments 1-29, or a stereoisomer, tautomer, or pharmaceutically acceptable salt thereof, for use in modulating TEAD activity.

Embodiment 35. A compound as described in any one of embodiments 1-29, or a stereoisomer, tautomer, or pharmaceutically acceptable salt thereof, for use in the treatment and/or prophylaxis of a disease or condition mediated by TEAD activity.

Embodiment 36. The compound for the use of embodiment 35, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, cinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 37. The use of a compound as described in any one of embodiments 1-29, or a stereoisomer, tautomer, or pharmaceutically acceptable salt thereof, for the preparation of a medicament for the treatment of prophylaxis of a disease or condition that is mediated by TEAD activity.

Embodiment 38. The use of embodiment 33, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 39. A method for modulating TEAD activity, comprising contacting TEAD with a compound as described in any one of embodiments 1-29, or a stereoisomer, tautomer, or pharmaceutically acceptable salt thereof.

Embodiment 40. A method for treating a disease or condition mediated by TEAD activity in a mammal, comprising administering a compound as described in any one of embodiments 1-29, or a pharmaceutically acceptable salt thereof, to the mammal.

Embodiment 41. The method of embodiment 40, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 42. The use of a compound as described in any one of embodiments 1-29, or a stereoisomer, tautomer, or pharmaceutically acceptable salt thereof, for modulating TEAD activity.

Embodiment 43. The use of a compound as described in any one of embodiments 1-29, or a stereoisomer, tautomer, or pharmaceutically acceptable salt thereof, for the treatment and/or prophylaxis of a disease or condition mediated by TEAD activity.

Embodiment 44. The use of embodiment 43, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment A1. A compound of formula (II-AB):

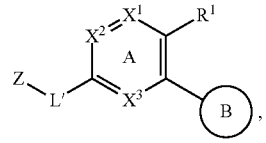

(II-AB)

or a stereoisomer or tautomer thereof, or a pharmaceutically acceptable salt thereof, wherein:
L' is selected from the group consisting of *—N(R$^3$)-L-** and

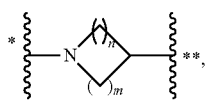

wherein * denotes the point of attachment to Z, and ** denotes the point of attachment to

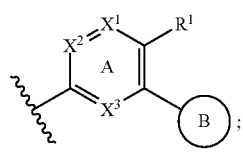

$X^1$ is C or N, and $X^1$ is taken together with $R^1$ and the atoms to which they are attached, to form a 5 to 6 membered heteroaryl, 5 to 6 membered heterocyclyl, phenyl, or $C_{5-6}$cycloalkyl fused to ring A;

wherein the 5 to 6 membered heteroaryl, 5 to 6 membered heterocyclyl, phenyl, and $C_{5-6}$ cycloalkyl formed by $X^1$ and $R^1$ are each independently optionally substituted with one or more $R^t$, wherein $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN; $X^2$ is N or CR$^s$, wherein R$^s$ is selected from H, halo, $C_{1-15}$alkyl, hydroxyl$C_{1-6}$alkynyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —NR$^d$COR$^e$, —CONR$^d$R$^e$, —SO$_2$R$^d$, —S(O)NHR$^d$, —SO$_2$NR$^d$R$^e$, —NR$^d$SO$_2$R$^e$, and —NR$^d$R$^e$;

wherein the $C_{1-15}$alkyl and $C_{1-15}$alkoxy of R$^s$ are each independently optionally substituted with one or more $R^{t1}$, wherein $R^{t1}$ is independently at each occurrence halo, oxo, —OH, —CN, 5-6 membered heteroaryl, or —NR$^d$R$^e$, wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN; and wherein the $C_{6-20}$aryl, 5 to 15 membered heteroaryl, $C_{3-20}$cycloalkyl, and 3 to 15 membered heterocyclyl of R$^s$ are each independently optionally substituted with one or more $R^{t2}$, wherein $R^{t2}$ is independently at each occurrence selected from halo, oxo, —OH, —CN and $C_{1-6}$alkyl; and wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN;

$X^3$ is N or CH;

B is phenyl or 5 to 6 membered heteroaryl; wherein the phenyl and 5 to 6 membered heteroaryl of B are each independently substituted with one or more $R^2$, wherein $R^2$ is independently, at each occurrence, halo; S(R$^y$)$_5$, wherein each R$^y$ is halo; or $C_{1-6}$alkoxy optionally substituted with one or more halo;

$R^3$ is H or $C_{1-6}$alkyl;

Z is —OH, —NR$^d$R$^e$, $C_{1-6}$alkoxy, —C(O)R$^a$, —S(O)$_2$R$^b$, wherein R$^d$ and R$^e$ are each independently H or $C_{1-6}$alkyl, and wherein the $C_{1-6}$alkyl of R$^d$ or R$^e$ is optionally substituted with one or more substituents selected from halo, oxo, —OH and —CN; R$^a$ and R$^b$ are each independently i) $C_{2-6}$alkenyl optionally substituted with one or more substituents selected from deuterium, $C_{1-6}$alkyl, hydroxyl $C_{1-6}$alkyl, halo and halo$C_{1-6}$alkyl; or ii) $C_{1-6}$alkyl, optionally substituted with one or more halo;

L is methylene, optionally substituted with one or more $C_{1-6}$alkyl; and n and m are 1; or n and m are 2;

provided that when 1) $X^1$ is taken together with $R^1$ and the atoms to which they are attached to form a phenyl, and 2) $X^2$ or $X^3$ is N, B of formula (II-B) is phenyl and $R^2$ is halo$C_{1-6}$alkoxyl.

Embodiment A2. A compound of embodiment A1, or a stereoisomer or tautomer thereof, or a pharmaceutically acceptable salt thereof, wherein the compound is a compound of formula (II-A):

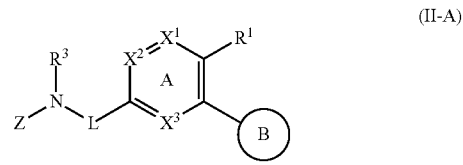

(II-A)

or a stereoisomer or tautomer thereof, or a pharmaceutically acceptable salt thereof.

Embodiment A3. A compound of embodiment A1, or a stereoisomer or tautomer thereof, or a pharmaceutically acceptable salt thereof, wherein the compound is a compound of formula (II-B):

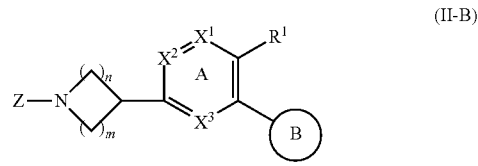

(II-B)

or a stereoisomer or tautomer thereof, or a pharmaceutically acceptable salt thereof.

Embodiment A4. The compound of any one of embodiments A1-A3, or a stereoisomer or tautomer thereof, or a pharmaceutically acceptable salt thereof, wherein Z is —C(O)R$^a$ or —S(O)$_2$R$^b$, R$^a$ and R$^b$ are each independently i) $C_{2-6}$alkenyl optionally substituted with one or more substituents selected from deuterium, $C_{1-6}$alkyl, hydroxyl $C_{1-6}$alkyl, halo and halo$C_{1-6}$ alkyl; or ii) $C_{1-6}$alkyl, optionally substituted with one or more halo.

Embodiment A5. The compound of embodiment A4, or a stereoisomer or tautomer thereof, or a pharmaceutically acceptable salt thereof, wherein Z is —C(O)R$^a$ and R$^a$ is $C_{2-6}$alkenyl optionally substituted with one or more substituents selected from deuterium, $C_{1-6}$alkyl, hydroxyl $C_{1-6}$alkyl, halo and halo$C_{1-6}$alkyl.

Embodiment A6. The compound of embodiment A5, or a stereoisomer or tautomer thereof, or a pharmaceutically acceptable salt thereof, wherein Z is —C(O)R$^a$ and R$^a$ is ethenyl optionally substituted with one or more substituents selected from deuterium and halo. Embodiment A7. The compound of embodiment A6, or a stereoisomer or tautomer thereof, or a pharmaceutically acceptable salt thereof, wherein Z is —C(O)R$^a$ and R$^a$ is C$_{1-6}$alkyl, optionally substituted with one or more halo.

Embodiment A8. The compound of embodiment A5, or a stereoisomer or tautomer thereof,

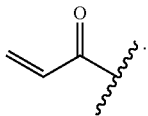

or a pharmaceutically acceptable salt thereof, wherein Z is.

Embodiment A9. The compound of any one of embodiments A1 to A8, or a stereoisomer or tautomer thereof, or a pharmaceutically acceptable salt thereof, wherein B is phenyl substituted with one or more R$^2$, wherein R$^2$ is independently, at each occurrence, halo; S(R$^y$)$_5$, wherein each R$^y$ is halo; or C$_{1-6}$alkoxy optionally substituted with one or more halo.

Embodiment A10. The compound of any one of embodiments A1 to A9, or a stereoisomer or tautomer thereof, or a pharmaceutically acceptable salt thereof, wherein B is phenyl substituted with one or more R$^2$, wherein R$^2$ is independently, at each occurrence, halomethoxy.

Embodiment 11. The compound of any one of embodiments A1 to A10, or a stereoisomer or tautomer thereof, or a pharmaceutically acceptable salt thereof, wherein B is

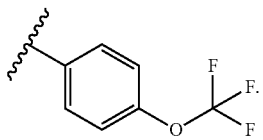 [SMILES: *c1ccc(OC(F)(F)F)cc1]

Embodiment A12. The compound of any one of embodiments A1 to A8, or a stereoisomer or tautomer thereof, or a pharmaceutically acceptable salt thereof, wherein B is 5 to 6 membered heteroaryl substituted with one or more R$^2$, wherein R$^2$ is independently, at each occurrence, halo; S(R$^y$)$_5$, wherein each R$^y$ is halo; or C$_{1-6}$ alkoxy optionally substituted with one or more halo.

Embodiment A13. The compound of embodiment A1, or a stereoisomer or tautomer thereof, or a pharmaceutically acceptable salt thereof, wherein Z is —C(O)R$^a$ and R$^a$ is C$_{2-6}$alkenyl optionally substituted with one or more substituents selected from deuterium, C$_{1-6}$alkyl, halo and haloC$_{1-6}$alkyl; and B is phenyl substituted with one or more R$^2$, wherein R$^2$ is C$_{1-6}$alkoxy optionally substituted with one or more halo.

Embodiment A14. The compound of embodiment A1, or a stereoisomer or tautomer thereof, or a pharmaceutically acceptable salt thereof, wherein
  Z is —C(O)R$^a$ and R$^a$ is C$_{1-6}$alkyl, optionally substituted with one or more halo,
  B is phenyl substituted with one or more R$^2$, wherein R$^2$ is C$_{1-6}$alkoxy optionally substituted with one or more halo.

Embodiment A15. The compound of embodiment A2, or a stereoisomer or tautomer thereof, or a pharmaceutically acceptable salt thereof, wherein the compound is a compound of formula (II-A-20)

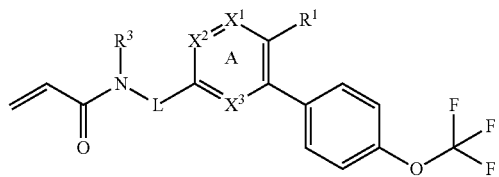

(II-B-18)

or a stereoisomer or tautomer thereof, or a pharmaceutically acceptable salt thereof.

Embodiment A16. The compound of embodiment A3, or a stereoisomer or tautomer thereof, or a pharmaceutically acceptable salt thereof, wherein the compound is a compound of formula (II-B-18)

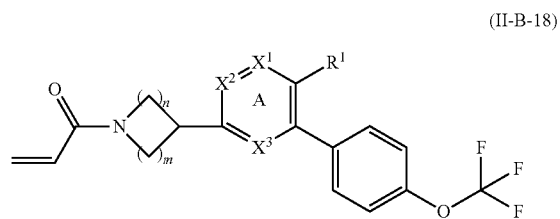

(II-B-18)

or a stereoisomer or tautomer thereof, or a pharmaceutically acceptable salt thereof.

Embodiment A17. The compound of any one of embodiments A1 to A15, or a stereoisomer or tautomer thereof, or a pharmaceutically acceptable salt thereof, wherein R$^3$ is H.

Embodiment A18. The compound of any one of embodiments A1 to A17, or a stereoisomer or tautomer thereof, or a pharmaceutically acceptable salt thereof, wherein
  X$^1$ is C or N;
  X$^2$ is CR$^s$, wherein R$^s$ is selected from the group consisting of H, halo, C$_{1-15}$alkyl, hydroxylC$_{1-6}$ alkynyl, C$_{6-20}$aryl, 5 to 15 membered heteroaryl, C$_{3-20}$cycloalkyl, 3 to 15 membered heterocyclyl, —OH, —CN, C$_{1-15}$alkoxy, —NR$^d$COR$^e$, —CONR$^d$R$^e$, —SO$_2$R$^d$, —S(O)NHR$^d$, —SO$_2$NR$^d$R$^e$, —NR$^d$SO$_2$R$^e$, and —NR$^d$R$^e$; and
  X$^3$ is N or CH.

Embodiment A19. The compound of any one of embodiments A1-A18, or a stereoisomer or tautomer thereof, or a pharmaceutically acceptable salt thereof, wherein one of X$^1$ and X$^3$ is N.

Embodiment A20. The compound of any one of embodiments A1-A18, or a stereoisomer or tautomer thereof, or a pharmaceutically acceptable salt thereof, wherein X$^1$ is C and X$^3$ is CH.

Embodiment A21. The compound of any one of embodiments A1-A20, or a stereoisomer or tautomer thereof, or a pharmaceutically acceptable salt thereof, wherein X$^2$ is CR$^s$, wherein R$^s$ is C$_{1-15}$alkyl, 5 to 15 membered heteroaryl, —CN, or C$_{1-15}$alkoxy.

Embodiment A22. The compound of any one of embodiments A1-A18, or a stereoisomer or tautomer thereof, or a pharmaceutically acceptable salt thereof, wherein X$^1$ is C; X$^2$ is N; and X$^3$ is N or CH.

Embodiment A23. The compound of any one of embodiments A1 to A22, or a stereoisomer or tautomer thereof, or a pharmaceutically acceptable salt thereof, wherein X$^1$ is taken together with R¹ and the atoms to which they are attached, to form a 5 to 6 membered heteroaryl fused to ring A.

Embodiment A24. The compound of embodiment A23, or a stereoisomer or tautomer thereof, or a pharmaceutically acceptable salt thereof, wherein the 5 to 6 membered heteroaryl fused to ring A is selected from the group consisting of:

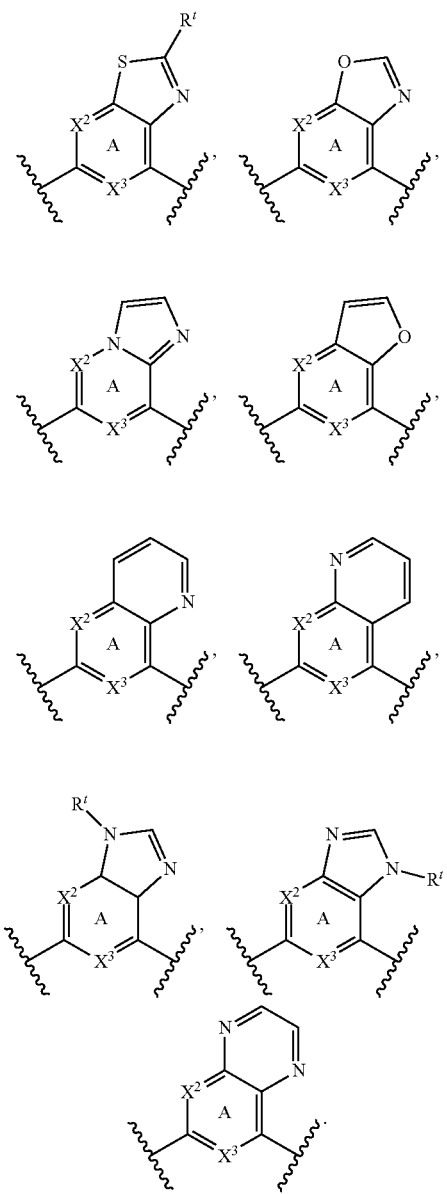

Embodiment A25. The compound of any one of embodiments A1 to A22, or a stereoisomer or tautomer thereof, or a pharmaceutically acceptable salt thereof, wherein X¹ is taken together with R¹ and the atoms to which they are attached, to form a 5 to 6 membered heterocyclyl fused to ring A.

Embodiment A26. The compound of embodiment A25, or a stereoisomer or tautomer thereof, or a pharmaceutically acceptable salt thereof, wherein the 5 to 6 membered heterocyclyl fused to ring A is

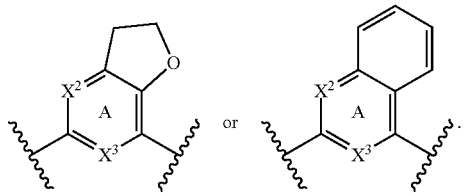

Embodiment A27. The compound of any one of embodiments A1 to A1-A18 and A20-A22, or a stereoisomer or tautomer thereof, or a pharmaceutically acceptable salt thereof, wherein X¹ is taken together with R¹ and the atoms to which they are attached, to form a phenyl fused to ring A,

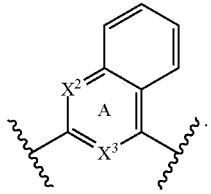

Embodiment A28. The compound of any one of embodiments A1 to A1-A18 and A20-A22, or a stereoisomer or tautomer thereof, or a pharmaceutically acceptable salt thereof, wherein X¹ is taken together with R¹ and the atoms to which they are attached, to form a $C_{5-6}$cycloalkyl fused to ring A,

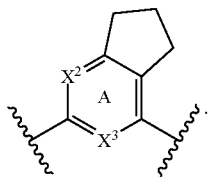

Embodiment A29. The compound of any one of embodiments A1 to A15, or a stereoisomer or tautomer thereof, or a pharmaceutically acceptable salt thereof, wherein Embodiment A30. A pharmaceutical composition, comprising (i) a compound as described in any one of embodiments A1-A29, or a stereoisomer, tautomer, or pharmaceutically acceptable salt thereof, and (ii) a pharmaceutically acceptable carrier, diluent, or excipient.

Embodiment A31. A compound as described in any one of embodiments A1-A29, or a stereoisomer, tautomer, or pharmaceutically acceptable salt thereof, for use in medical therapy.

Embodiment A32. A compound as described in any one of embodiments A1-A29, or a stereoisomer, tautomer, or pharmaceutically acceptable salt thereof, for use in the treatment and/or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment A33. A compound as described in any one of embodiments A1-A29, or a stereoisomer, tautomer, or pharmaceutically acceptable salt thereof, for use in modulating TEAD activity.

Embodiment A34. A compound as described in any one of embodiments A1-A29, or a stereoisomer, tautomer, or pharmaceutically acceptable salt thereof, for use in the treatment and/or prophylaxis of a disease or condition mediated by TEAD activity.

Embodiment A35. The use of a compound as described in any one of embodiments A1-A29, or a stereoisomer, tautomer, or pharmaceutically acceptable salt thereof, for the preparation of a medicament for the treatment of prophylaxis of a disease or condition that is mediated by TEAD activity.

Embodiment A36. A method for treating cancer in a mammal, comprising administering a compound as described in any one of embodiments A1-A29, or a stereoisomer, tautomer, or pharmaceutically acceptable salt thereof, to the mammal.

Embodiment A37. A method for modulating TEAD activity, comprising contacting TEAD with a compound as described in any one of embodiments A1-A29, or a stereoisomer, tautomer, or pharmaceutically acceptable salt thereof.

Embodiment A38. A method for treating a disease or condition mediated by TEAD activity in a mammal, comprising administering a compound as described in any one of embodiments A1-A29, or a pharmaceutically acceptable salt thereof, to the mammal.

Embodiment A39. The use of a compound as described in any one of embodiments A1-A29, or a stereoisomer, tautomer, or pharmaceutically acceptable salt thereof, for modulating TEAD activity.

Embodiment A40. The use of a compound as described in any one of embodiments A1-A29, or a stereoisomer, tautomer, or pharmaceutically acceptable salt thereof, for the treatment and/or prophylaxis of a disease or condition mediated by TEAD activity.

PREPARATION OF COMPOUNDS

The following synthetic reaction schemes detailed in the General Schemes and Examples are merely illustrative of some of the methods by which the compounds of the present disclosure (or an embodiment or aspect thereof) can be synthesized. Various modifications to these synthetic reaction schemes can be made and will be suggested to one skilled in the art having referred to the disclosure contained in this Application.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C.

Although certain exemplary embodiments are depicted and described herein, the compounds of the present disclosure (or an embodiment or aspect thereof) can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography, and/or by Preparative Thin Layer Chromatography (Prep TLC).

Mass spectrometry (MS) was performed using a (1) Sciex 15 mass spectrometer in ES+ mode, or (2) Shimadzu liquid chromatography-mass spectrometry (LCMS) 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

The following generalized schemes are used to prepare the disclosed compounds, intermediates, and pharmaceutically acceptable salts thereof. Disclosed compounds and intermediates may be prepared using standard organic syn-

SYNTHETIC PROCEDURES

Intermediate 1: Methyl 5-amino-7-chloro-2,3-dihydrobenzofuran-4-carboxylate

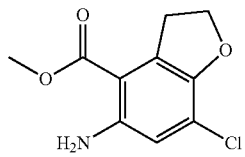

Step 1: 4-Bromo-1-chloro-2-(2,2-diethoxyethoxy)benzene

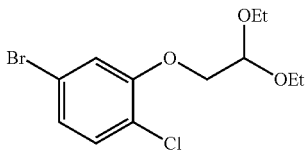 [SMILES: CCOC(COc1cc(Br)ccc1Cl)OCC]

A reaction flask was charged with a mixture of 5-bromo-2-chlorophenol (90.0 g, 433.8 mmol), K$_2$CO$_3$ (90 g, 650.8 mmol) and 2-bromo-1,1-diethoxyethane (94.0 g, 477.2 mmol) in DMF (900 mL) and was stirred at 135° C. for 16 hours. The reaction mixture was concentrated and diluted with ethyl acetate (1 L), washed with brine (1 L×5). The organic layer was dried over Na$_2$SO$_4$, filtered and concentrated to afford the title compound (140.0 g, 99%) as a brown oil. The crude product was used for next step without further purification. $^1$H NMR (400 MHz, CDCl$_3$): δ 7.22 (d, J=8.4 Hz, 1H), 7.10 (d, J=2.0 Hz, 1H), 7.04 (dd, J=8.4, 2.0 Hz, 1H), 4.87 (t, J=5.2 Hz, 1H), 4.05 (d, J=5.2 Hz, 2H), 3.83-3.76 (m, 2H), 3.73-3.68 (m, 2H), 1.26 (t, J=7.2 Hz, 6H).

Step 2: 4-Bromo-7-chlorobenzofuran

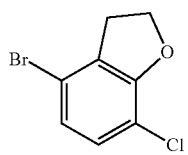 [SMILES: Clc1ccc(Br)c2c1OCC2]

The reaction mixture of 4-bromo-1-chloro-2-(2,2-diethoxyethoxy)benzene (140.0 g, 432.6 mmol) and PPA (140 g) in toluene (1.4 L) was stirred at 110° C. for 5 hours. The reaction mixture was quenched with sat. aq. NaHCO$_3$, extracted with ethyl acetate (1 L×3). The combined organic layers were dried over Na$_2$SO$_4$, filtered and concentrated under vacuum. The residue was purified by chromatography on silica gel (100% petroleum ether) to afford the title compound (44.0 g, 44%) as a white solid. $^1$H NMR (400 MHz, CDCl$_3$): δ 7.74 (d, J=2.0 Hz, 1H), 7.35 (d, J=8.4 Hz, 1H), 7.20 (d, J=8.4 Hz, 1H), 6.87 (d, J=2.0 Hz, 1H).

Step 3: 4-Bromo-7-chloro-2,3-dihydrobenzofuran

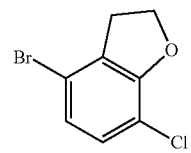 [SMILES: Clc1ccc(Br)c2c1OCC2]

A mixture of Rh/C (10.0 g, 95.0 mmol) and 4-bromo-7-chlorobenzofuran (44.0 g, 190 mmol) in EtOH (440 mL) was stirred at room temperature for 2 hours under H2 (15 psi). The reaction was filtered and the filtrate was concentrated. The residue was purified by chromatography on silica gel (100% petroleum ether) to afford the title compound (33.0 g, 74%) as a white solid. $^1$H NMR (400 MHz, CDCl$_3$): δ 7.01 (d, J=8.8 Hz, 1H), 6.93 (d, J=8.8 Hz, 1H), 4.72 (t, J=8.8 Hz, 2H), 3.30 (t, J=8.8 Hz, 2H).

Step 4: 4-Bromo-7-chloro-5-nitro-2,3-dihydrobenzofuran

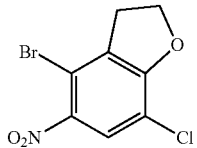

To the mixture of 4-bromo-7-chloro-2,3-dihydrobenzofuran (30.0 g, 128.5 mmol) in TFA (300 mL) was added HNO$_3$ (11.4 mL, 257.0 mmol) at 0° C. dropwise slowly. The reaction mixture was stirred for 2 hours at 0° C. The reaction mixture was quenched with aq. NaOH, and the mixture was extracted with ethyl acetate (1 L×3), the combined organic layers were dried over Na$_2$SO$_4$, filtered and concentrated. The residue was purified by chromatography on silica gel (0-10% ethyl acetate in petroleum ether) to afford the title compound (27.0 g, 76%) as a white solid. $^1$H NMR (400 MHz, CDCl$_3$): δ 7.97 (s, 1H), 4.88 (t, J=8.8 Hz, 2H), 3.42 (t, J=8.8 Hz, 2H).

Step 5: 4-Bromo-7-chloro-2,3-dihydrobenzofuran-5-amine

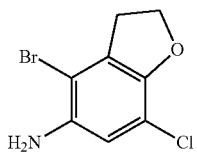 [SMILES: O=[N+]([O-])c1cc(Cl)c2c(c1Br)CCO2]

To a solution of 4-bromo-7-chloro-5-nitro-2,3-dihydrobenzofuran (20.0 g, 72 mmol) in MeOH (200 mL) was added iron powder (20.0 g, 360 mmol) and HOAc (21 mL, 360 mmol). The reaction mixture was then stirred at 60° C. for 16 hours. The reaction mixture was filtered and the filtrate was concentrated in vacuo. The residue was dissolved in water (300 mL) and adjusted to pH=8 by 2M aq. NaOH. The mixture was extracted with ethyl acetate (500 mL×3), the combined organic layers were dried over $Na_2SO_4$ and concentrated under vacuum to afford the title compound (17.0 g, 95%) as a yellow solid. The crude product was used for next step directly without further purification. $^1$H NMR (400 MHz, $CDCl_3$): δ 6.61 (s, 1H), 4.65 (t, J=8.8 Hz, 2H), 3.79 (s, 2H), 3.26 (t, J=8.8 Hz, 2H); LCMS (ESI): m/z 247.8 $(M+H)^+$.

Step 6: Methyl 5-amino-7-chloro-2,3-dihydrobenzofuran-4-carboxylate

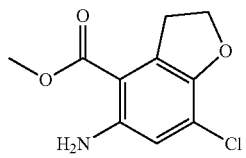

A solution of $Pd(OAc)_2$ (1.5 g, 6.8 mmol), $Na_2CO_3$ (22.0 g, 205 mmol), 4-bromo-7-chloro-2,3-dihydrobenzofuran-5-amine (17.0 g, 68 mmol) and Xantphos (4.0 g, 6.8 mmol) in DMF (100 mL) and MeOH (100 mL) was stirred at 100° C. for 16 hours under CO (15 psi). The reaction mixture was filtered and the filtrate was concentered under vacuum. The residue was purified by flash column chromatography on silica gel (0-10% ethyl acetate in petroleum ether) to afford the title compound (3.2 g, 21%) as a yellow solid. $^1$H NMR (400 MHz, $CDCl_3$) δ 6.54 (s, 1H), 5.39 (s, 2H), 4.58 (t, J=8.8 Hz, 2H), 3.87 (s, 3H), 3.52 (t, J=8.8 Hz, 2H).

Intermediate A 8-(4-(Trifluoromethoxy)phenyl)quinoxalin-6-amine

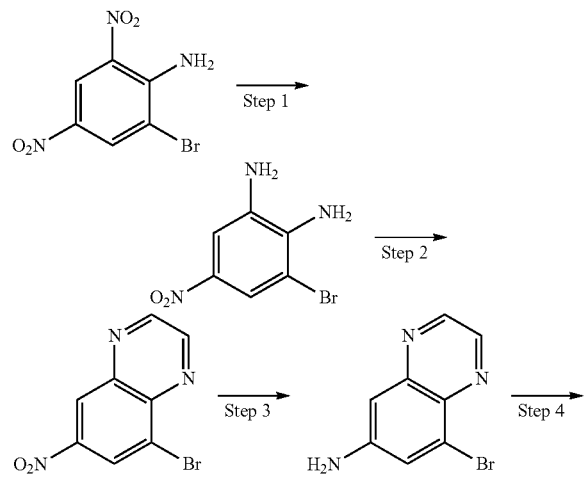

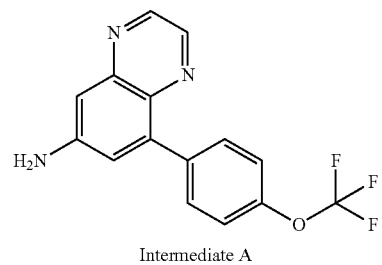

Intermediate A

Step 1: 3-bromo-5-nitrobenzene-1,2-diamine

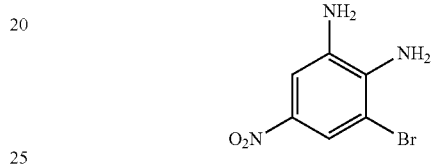

A mixture of $NH_4Cl$ (26.95 g, 503.78 mmol) and sulfur (16.15 g, 503.78 mmol) in a mixture of 120 mL of water and 480 mL of ethanol was stirred at 100° C. under nitrogen for 1 h. The solution was added into a stirred suspension of 2-bromo-4,6-dinitroaniline (120.0 g, 457.98 mmol) and $Na_2S·9H_2O$ (110.0 g, 457.98 mmol) in ethanol (480 mL) and water (840 mL). The mixture was stirred at 80° C. for 16 h. Then 540 mL of 2N NaOH solution was added into dropwise during a period of 30 min and the mixture was then stirred for a further 15 minutes at 80° C. After cooling, the mixture was poured into a mixture of 2N HCl (540 mL), 1 kg ice and 1 L of water, and then the mixture was stirred for 15 min to complete the reaction. The reaction mixture was filtered to afford the title compound (100.0 g, 94%) as a brown solid, which was used for the next step without further purification. LCMS (ESI): m/z 232.0 $(M+H)^+$.

Step 2: 5-bromo-7-nitroquinoxaline

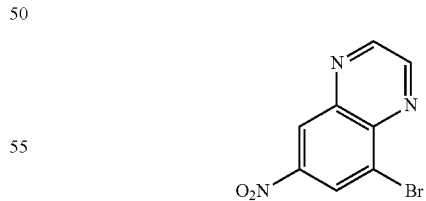

To the mixture of 3-bromo-5-nitrobenzene-1,2-diamine (100.0 g, 430.98 mmol) in water (2 L) was added 40% aq.oxalaldehyde (98.87 mL, 861.96 mmol). The mixture was stirred at 100° C. for 4 hours. After cooled to 10° C. The precipitate was filtered and washed with water (200 mL×2). The filter cake was dried under reduced pressure to afford the title compound (100.0 g, crude) as a rust-colored solid. LCMS (ESI): m/z 254.0 $(M+H)^+$.

Step 3: 8-bromoquinoxalin-6-amine

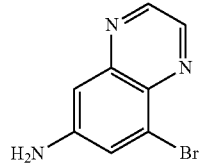

To the mixture of 5-bromo-7-nitroquinoxaline (400.0 g, 1.57 mol) in ethanol (1.5 L) and water (1.0 L) was added iron (440 g, 7.87 mol) and NH$_4$Cl (422 g, 7.87 mol). The mixture was stirred at 90° C. for 2 hours. The reaction mixture was cooled to room temperature, and filtered. The filter cake was washed with ethyl acetate (1.5 L). The filtrate was concentrated and the residue was diluted with water (5.0 L) and filtered to afford the title compound (300.0 g, 85%) as a yellow solid. LCMS (ESI): m/z 223.8 (M+H)$^+$.

Step 4: 8-(4-(trifluoromethoxy)phenyl)quinoxalin-6-amine

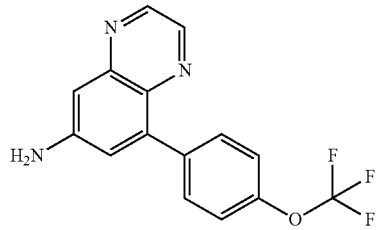

A solution of 8-bromoquinoxalin-6-amine (200.0 g, 892.62 mmol), Pd(dppf)Cl$_2$ (26.13 g, 35.7 mmol), K$_2$CO$_3$ (370.11 g, 2.68 mol) and (4-(trifluoromethoxy)phenyl)boronic acid (183.82 g, 892.62 mmol) in 1,4-dioxane (1500 mL) and water (400 mL) was stirred at 100° C. under N2 atmosphere for 16 h. The reaction mixture was diluted with water (1 L), extracted with ethyl acetate (1.5 L×2) and washed with saturated brine (1 L). The organic layer was dried over Na$_2$SO$_4$ and concentrated. The residue was purified by chromatography on silica (0-50% ethyl acetate in petroleum ether) to afford the title compound (200.0 g, 73%) as a yellow solid. $^1$H NMR (400 MHz, CDCl$_3$): δ 8.68 (d, J=1.6 Hz, 1H), 8.59 (d, J=1.6 Hz, 1H), 7.70-7.64 (m, 2H), 7.34 (d, J=8.0 Hz, 2H), 7.23-7.18 (m, 2H); LCMS (ESI): m/z 305.9 (M+H)$^+$.

Intermediate B

5-Bromo-8-(4-(trifluoromethoxy)phenyl)quinoxalin-6-amine

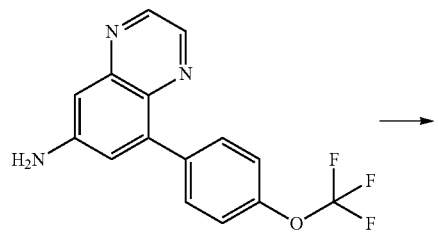

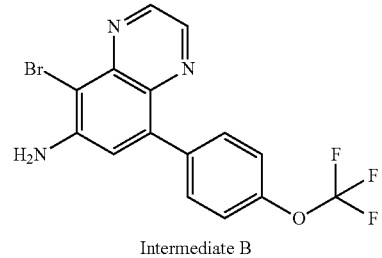

Intermediate B

To a mixture of 8-(4-(trifluoromethoxy)phenyl)quinoxalin-6-amine (300.0 g, 982.8 mmol) in DCM (2.5 L) was added NBS (174.92 g, 982.8 mmol) at 0° C. The resulting solution was stirred at 0° C. for 30 min. The reaction was quenched with water (1 L) and washed with brine (1 L×3). The organic layers were dried over anhydrous sodium sulfate and concentrated under reduced. The residue was purified by chromatography on silica gel (0-20% ethyl acetate in petroleum ether) to afford the title compound (300.0 g, 80%) as a yellow solid. 2D-NMR confirmed it. $^1$H NMR (400 MHz, CDCl$_3$): δ 8.84 (d, J=1.6 Hz, 1H), 8.64 (d, J=1.6 Hz, 1H), 7.70-7.63 (m, 2H), 7.38-7.31 (m, 3H), 4.83 (s, 2H).

Intermediate C tert-Butyl (R)-((5-(1,2-dihydroxyethyl)-8-(4-(trifluoromethoxy)phenyl)quinoxalin-6-yl)methyl)carbamate

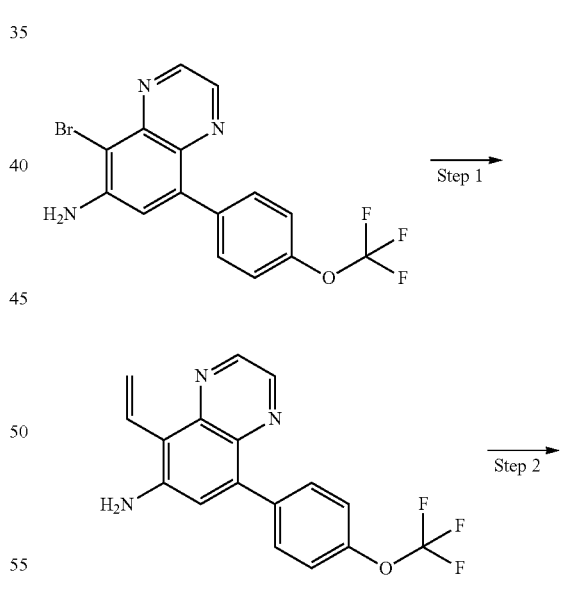

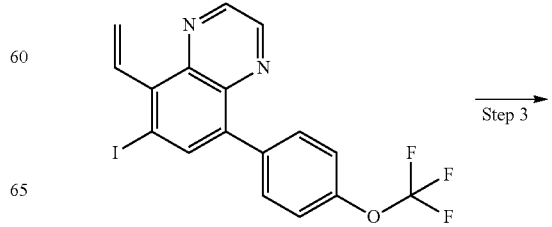

-continued

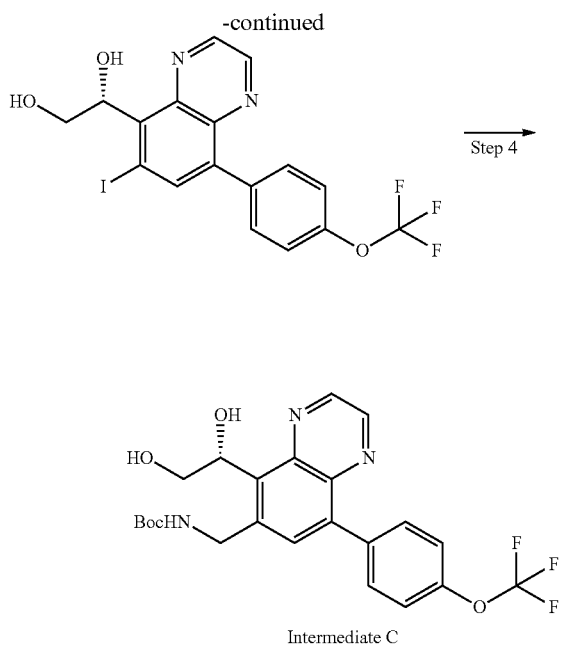

Step 1: 8-(4-(trifluoromethoxy)phenyl)-5-vinylquinoxalin-6-amine

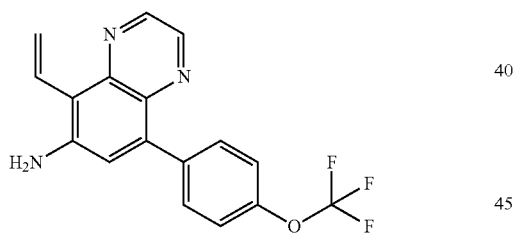

A solution of 5-bromo-8-(4-(trifluoromethoxy)phenyl)quinoxalin-6-amine (100.0 g, 260.31 mmol), $K_2CO_3$ (107.93 g, 780.94 mmol), Pd(dppf)Cl$_2$ (7.62 g, 10.41 mmol), 4,4,5,5-tetramethyl-2-vinyl-1,3,2-dioxaborolane (60.14 g, 390.47 mmol) in 1,4-dioxane (1 L) and water (300 mL) was stirred at 120° C. for 16 h under N2 atmosphere. The reaction mixture was quenched with water (500 mL) and extracted with ethyl acetate (1 L×2). The combined organic layers were dried over anhydrous sodium sulfate and concentrated under vacuum. The residue was purified by chromatography on silica gel (0-20% ethyl acetate in petroleum ether) to afford the title compound (70.0 g, 81%) as a yellow solid. $^1$H NMR (400 MHz, CDCl$_3$): δ 8.75 (d, J=1.6 Hz, 1H), 8.61 (d, J=1.6 Hz, 1H), 7.68 (t, J=8.8 Hz, 2H), 7.47 (dd, J=18.4, 12.0 Hz, 1H), 7.34 (d, J=8.4 Hz, 2H), 7.27 (s, 1H), 5.88-5.80 (m, 2H), 4.63 (s, 2H); LCMS (ESI): m/z 332.1 (M+H)$^+$.

Step 2: 6-iodo-8-(4-(trifluoromethoxy)phenyl)-5-vinylquinoxaline

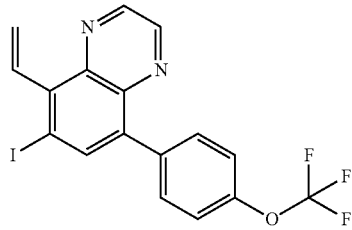 [SMILES: C=Cc1c(I)cc(-c2ccc(OC(F)(F)F)cc2)c2nccnc12]

To a solution of 8-(4-(trifluoromethoxy)phenyl)-5-vinylquinoxalin-6-amine (50.0 g, 150.93 mmol) in acetonitrile (500 mL) was added 6M HCl (250 mL) at −10° C. The reaction mixture was stirred −10° C. at for 5 mins. Solution of NaNO$_2$ (10.93 g, 158.47 mmol) in water (400 mL) was added drop wise at −10° C. and the reaction mixture was stirred at −10° C. for 1 h. Solution of KI (50.11 g, 301.85 mmol) in water (200 mL) was added drop wise to the reaction mixture at -10° C. and the solution was stirred at −10° C. for 30 mins. The reaction mixture was quenched with aq. NaHCO$_3$ and extracted with ethyl acetate (800 mL×2). The organic layer was dried over anhydrous sodium sulfate and concentrated. The residue was purified by flash chromatography on silica gel (0-10% ethyl acetate in petroleum ether) to afford the title compound (23.0 g, 35%) as a yellow solid. $^1$H NMR (400 MHz, CDCl$_3$): δ 8.91-8.90 (m, 2H), 8.30 (s, 1H), 7.71-7.64 (m, 2H), 7.36 (d, J=8.0 Hz, 2H), 7.13 (dd, J=17.6, 12.0 Hz, 1H), 6.08 (dd, J=17.6, 1.6 Hz, 1H), 5.92 (dd, J=12.0, 1.6 Hz, 1H); LCMS (ESI): m/z 442.9 (M+H)$^+$.

Step 3: (R)-1-(6-iodo- 8-(4-(trifluoromethoxy)phenyl)quinoxalin-5-yl)ethane-1,2-diol

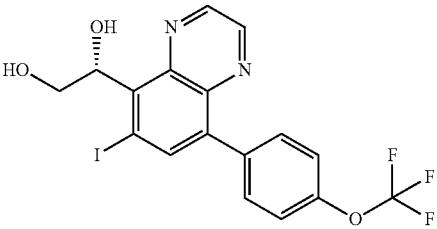 [SMILES: OC[C@H](O)c1c(I)cc(-c2ccc(OC(F)(F)F)cc2)c2nccnc12]

A mixture of K$_3$Fe(CN)$_6$ (478.65 g, 1.09 mol), methanesulfonamide (51.63 g, 542.78 mmol), K$_2$OsO$_4$·2H$_2$O (2.0 g, 5.43 mmol), (DHQD)$_2$PHAL (6.34 g, 8.14 mmol) and K$_2$CO$_3$ (150.03 g, 1.09 mol) in t-BuOH (1.2 L) and water (1.2 L) was stirred at room temperature for 20 min. And then 6-iodo- 8-(4-(trifluoromethoxy)phenyl)-5-vinylquinoxaline (240.0 g, 542.78 mmol) was added into the reaction mixture at 0° C. The resulting mixture was stirred at room temperature for 16 h. The reaction mixture was diluted with water (2 L). The precipitate was filtered and washed with water (2 L) to afford the title compound (220.0 g, 85%) as a white solid. 2D-NMR confirmed it. $^1$H NMR (400 MHz, DMSO-d$_6$): δ 9.03 (d, J=1.6 Hz, 1H), 8.97 (d, J=1.6 Hz, 1H), 8.29 (s, 1H), 7.77 (d, J=8.4 Hz, 2H), 7.49 (d, J=8.4 Hz, 2H), 5.90 (d, J=9.2

Hz, 1H), 5.45 (d, J=5.6 Hz, 1H), 4.93 (t, J=6.0 Hz, 1H), 3.98-3.87 (m, 1H), 3.79-3.73 (m, 1H); LCMS (ESI): m/z 477.0 (M+H)⁺.

Step 4: tert-butyl (R)-((5-(1,2-dihydroxyethyl)-8-(4-(trifluoromethoxy)phenyl)quinoxalin-6-yl)methyl) carbamate

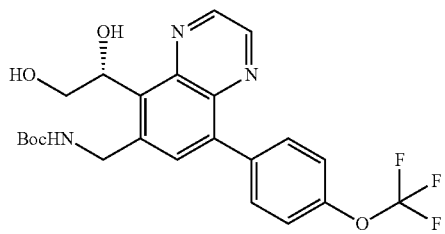 [SMILES: CC(C)(C)OC(=O)NCc1cc(-c2ccc(OC(F)(F)F)cc2)c2nccnc2c1[C@@H](O)CO]

A mixture of (R)-1-(6-iodo-8-(4-(trifluoromethoxy)phenyl)quinoxalin-5-yl)ethane-1,2-diol (11.0 g, 23.1 mmol), potassium (((tert-butoxycarbonyl)amino)methyl)trifluoroborate (8.21 g, 34.65 mmol), Cs₂CO₃ (22.58 g, 69.3 mmol) and CATACXIUM A Pd G₂ (0.93 g, 1.39 mmol) in 1,4-dioxane (100 mL) and water (20 mL) was stirred at 100° C. for 2 h under N2 atmosphere. The mixture was diluted with ethyl acetate (500 mL×3) and washed with water (500 mL×3). The organic was dried over Na₂SO₄ and concentrated. The residue was purified by flash chromatography on silica gel (0-10% methanol in DCM) to afford the title compound (9.0 g, 81%) as a brown solid. LCMS (ESI): m/z 480.2 (M+H)⁺.

Intermediate D tert-Butyl (R)-((5-(1,2-dihydroxyethyl)-8-(4-(trifluoromethoxy)phenyl)quinoxalin-6-yl)methyl)carbamate

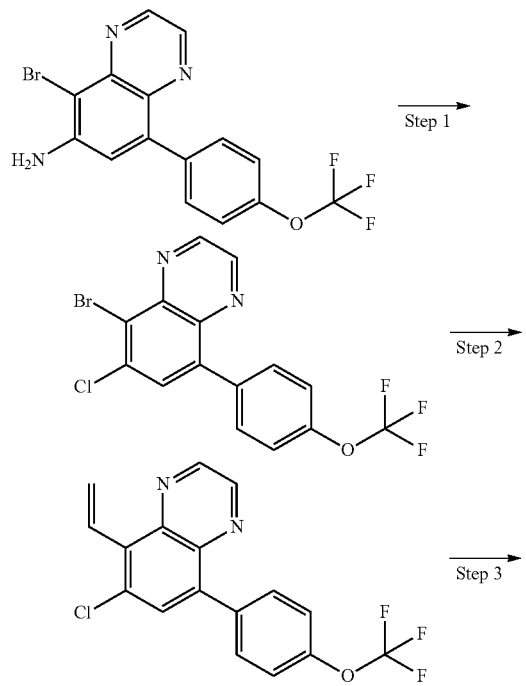

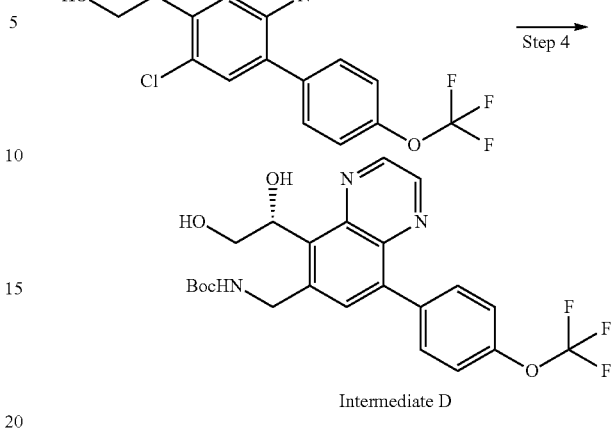

Intermediate D

Step 1: 5-bromo-6-chloro-8-(4-(trifluoromethoxy)phenyl)quinoxaline

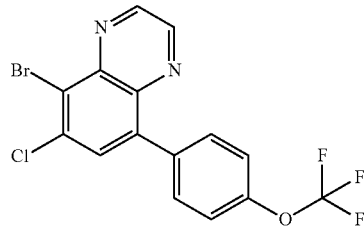

To a mixture of 5-bromo-8-(4-(trifluoromethoxy)phenyl)quinoxalin-6-amine (50.0 g, 130.16 mmol), TBAC (36.17 g, 130.16 mmol) and CuCl₂ (17.5 g, 130.16 mmol) in acetonitrile (1.0 L) was added t-BuONO (13.42 g, 130.16 mmol) at room temperature. Then the reaction was stirred at 60° C. for 16 h. The solution was concentrated. The residue was purified by flash chromatography on silica gel (0-10% ethyl acetate in petroleum ether) to afford the title compound (37.0 g, 70%) as a white solid. ¹H NMR (400 MHz, CDCl₃): δ 9.04-9.01 (m, 1H), 8.93-8.90 (m, 1H), 7.90 (s, 1H), 7.71-7.66 (m, 2H), 7.38 (d, J=8.0 Hz, 2H); LCMS (ESI): m/z 402.9 (M+H)⁺.

Step 2: 6-chloro-8-(4-(trifluoromethoxy)phenyl)-5-vinylquinoxaline

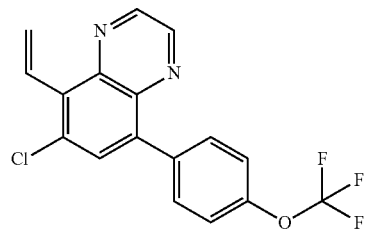 [SMILES: C=Cc1c(Cl)cc(-c2ccc(OC(F)(F)F)cc2)c2nccnc12]

A solution of 5-bromo-6-chloro-8-(4-(trifluoromethoxy)phenyl)quinoxaline (100.0 g, 247.78 mmol), K₂CO₃ (85.61 g, 619.46 mmol), 4,4,5,5-tetramethyl-2-vinyl-1,3,2-dioxaborolane (57.24 g, 371.67 mmol) and Pd(dppf)Cl$_2$ (9.07 g, 12.39 mmol) in 1,4-dioxane (1.0 L) and water (300 mL) was stirred at 100° C. for 3 h under N2 atmosphere. The mixture was diluted with ethyl acetate (1 L) and washed with water (500 mL×3). The organic layer was dried over Na$_2$SO$_4$ and concentrated. The residue was purified by chromatography on silica gel (0-10% ethyl acetate in petroleum ether) to afford the title compound (73.0 g, 84%) as a yellow solid. $^1$H NMR (400 MHz, CDCl$_3$) δ 8.92 (d, J=1.6 Hz, 1H), 8.89 (d, J=1.6 Hz, 1H), 7.84 (s, 1H), 7.72-7.69 (m, 2H), 7.46-7.34 (m, 3H), 6.35 (dd, J=18.0, 1.6 Hz, 1H), 5.98 (dd, J=12.0, 1.6 Hz, 1H); LCMS (ESI): m/z 351.0 (M+H)$^+$.

Step 3: (R)-1-(6-chloro-8-(4-(trifluoromethoxy)phenyl)quinoxalin-5-yl)ethane-1,2-diol

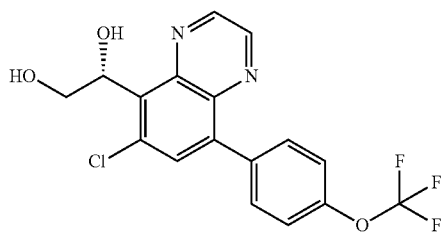 [SMILES: OC[C@H](O)c1c(Cl)cc(-c2ccc(OC(F)(F)F)cc2)c2nccnc12]

A mixture of K$_2$CO$_3$ (57.53 g, 416.29 mmol), (DHQD)$_2$PHAL (3.24 g, 4.16 mmol), methanesulfonamide (19.8 g, 208.14 mmol), K$_3$Fe(CN)$_6$ (137.06 g, 416.29 mmol) and K$_2$OsO$_4$·2H$_2$O (770 mg, 2.08 mmol) in t-BuOH(1 L) and water (800 mL) was stirred at room temperature for 20 min. And then 6-chloro-8-(4-(trifluoromethoxy)phenyl)-5-vinylquinoxaline (73.0 g, 208.14 mmol) was added into the reaction mixture at 0° C. The resulting mixture was stirred at room temperature for 16 h. The reaction mixture was diluted with water (1 L). The precipitate was filtered and washed with water (500 mL×2). The filter cake was dried under reduced pressure to afford the title compound (58.0 g, 72%) as a white solid. $^1$H NMR (400 MHz, DMSO-d$_6$): δ 9.03-9.02 (m, 2H), 7.95 (s, 1H), 7.80 (d, J=8.4 Hz, 2H), 7.50 (d, J=8.4 Hz, 2H), 5.81-5.69 (m, 2H), 4.88 (t, J=6.0 Hz, 1H), 4.01-3.94 (m, 1H), 3.85-3.77 (m, 1H); LCMS (ESI): m/z 385.1 (M+H)$^+$.

Step 4: tert-butyl (R)-((5-(1,2-dihydroxyethyl)-8-(4-(trifluoromethoxy)phenyl)quinoxalin-6-yl)methyl)carbamate

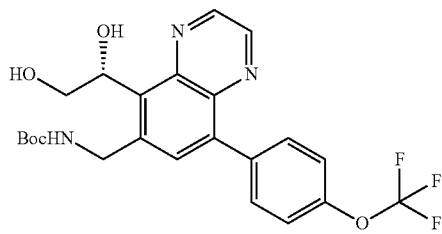 [SMILES: CC(C)(C)OC(=O)NCc1cc(-c2ccc(OC(F)(F)F)cc2)c2nccnc2c1[C@@H](O)CO]

A mixture of (R)-1-(6-chloro-8-(4-(trifluoromethoxy)phenyl)quinoxalin-5-yl)ethane-1,2-diol (58.0 g, 150.75 mmol), potassium (((tert-butoxycarbonyl)amino)methyl)trifluoroborate (37.53 g, 158.29 mmol), Cs$_2$CO$_3$ (147.35 g, 452.25 mmol) and CATACXIUM A Pd G$_2$ (2.02 g, 3.02 mmol) in 1,4-dioxane (600 mL) and water (100 mL) was stirred at 100° C. for 2 h under N2 atmosphere. The mixture was diluted with ethyl acetate (1 L) and washed with water (500 mL×3). The organic layer was dried over Na$_2$SO$_4$ and concentrated. The residue was purified by chromatography on silica gel (0-10% methanol in DCM) to afford the title compound (40.0 g, 55%) as a brown solid. $^1$H NMR (400 MHz, DMSO-d$_6$): δ 8.97 (d, J=1.6 Hz, 1H), 8.94 (d, J=1.6 Hz, 1H), 7.85 (s, 1H), 7.77-7.71 (m, 2H), 7.51 (d, J=8.0 Hz, 2H), 7.37 (t, J=6.0 Hz, 1H), 6.11-6.04 (m, 1H), 5.75 (d, J=6.0 Hz, 1H), 4.89 (t, J=6.0 Hz, 1H), 4.80 (dd, J=16.0, 6.4 Hz, 1H), 4.61 (dd, J=16.0, 5.6 Hz, 1H), 3.90-3.80 (m, 1H), 3.67-3.60 (m, 1H), 1.39 (s, 9H); LCMS (ESI): m/z 480.2 (M+H)$^+$.

Intermediate E (R)-1-(6-(Aminomethyl)-8-(4-(trifluoromethoxy)phenyl)quinoxalin-5-yl)ethane-1,2-diol

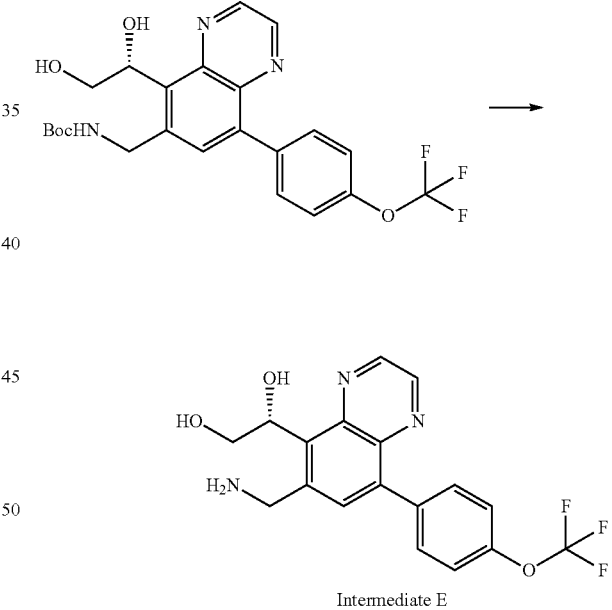

Intermediate E

To a solution of tert-butyl (R)-((5-(1,2-dihydroxyethyl)-8-(4-(trifluoromethoxy)phenyl)quinoxalin-6-yl)methyl)carbamate (100.0 g, 208.57 mmol) in THF (1 L) was added con.HCl (250 mL) at 0° C. dropwise. Then the reaction was stirred at room temperature for 16 h. The reaction was diluted with water (100 mL) and adjusted to pH=8 with sat.NaHCO$_3$. The mixture was extracted with ethyl acetate (1 L×3). The combined organic layers were dried over Na$_2$SO$_4$ and concentrated in vacuo to afford the title compound (75.0 g, crude) as a yellow solid. The crude was used for next step without further purification. LCMS (ESI): m/z 380.2 (M+H)$^+$.

Intermediate F

6-Iodo-8-(4-(trifluoromethoxy)phenyl)quinoxaline-5-carbaldehyde

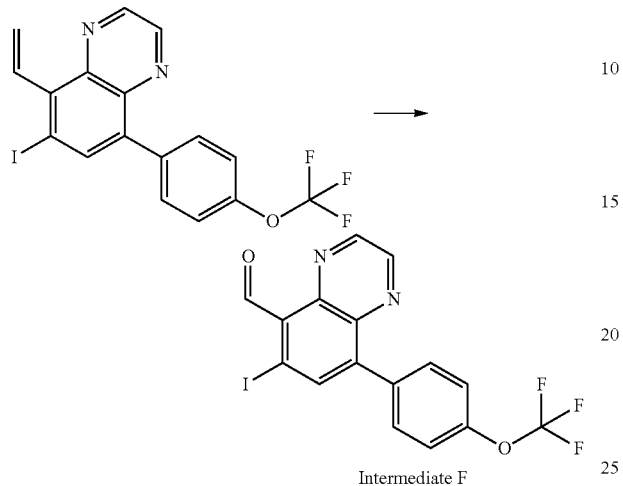

Intermediate F

To a mixture of 6-iodo-8-(4-(trifluoromethoxy)phenyl)-5-vinylquinoxaline (200 mg, 0.44 mmol) in THF (2 mL) and water (0.5 mL) was added K$_2$OsO$_4$·2H$_2$O (17 mg, 0.04 mmol) and NaIO$_4$ (474 mg, 2.21 mmol) at 0° C. The mixture was stirred at room temperature for 16 h. The reaction mixture was quenched with saturated sodium sulfite (20 mL). The reaction mixture was diluted with ethyl acetate (60 mL), washed with brine (60 mL), dried over Na$_2$SO$_4$ and concentrated to dryness. The residue was purified by flash column chromatography on silica gel (10-25% ethyl acetate in petroleum ether) to afford the title compound (150 mg, 75%) as a white solid. $^1$H NMR (400 MHz, CDCl$_3$): δ 11.13 (s, 1H), 9.02-9.00 (m, 2H), 8.44 (s, 1H), 7.76 (d, J=8.8 Hz, 2H), 7.41 (d, J=8.8 Hz, 2H).

Intermediate G tert-Butyl 3-(8-(4-(trifluoromethoxy)phenyl)-5-vinylquinoxalin-6-yl)azetidine-1-carboxylate

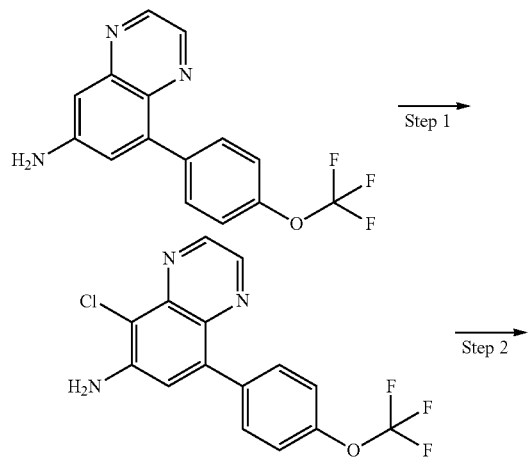

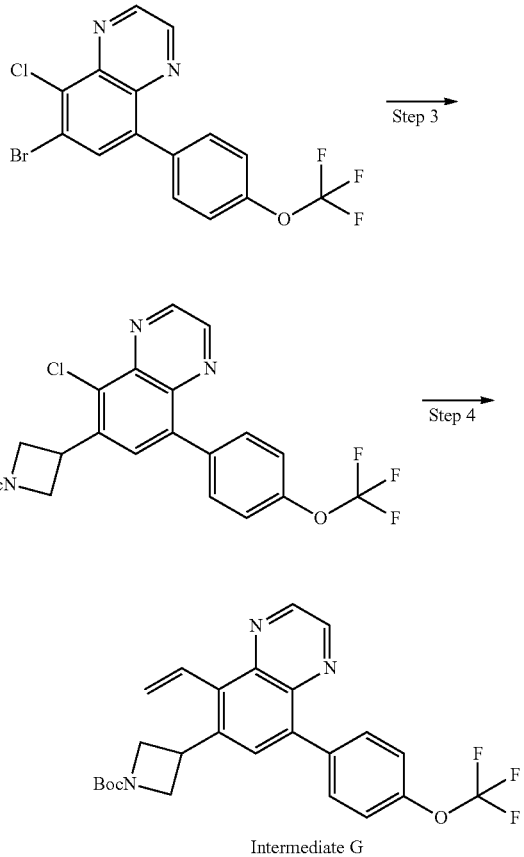

Intermediate G

Step 1: 5-chloro-8-(4-(trifluoromethoxy)phenyl)quinoxalin-6-amine

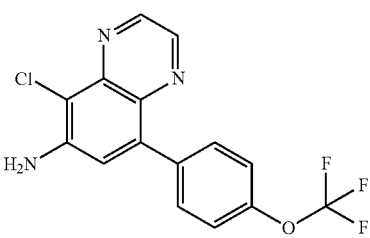

To a solution of 8-(4-(trifluoromethoxy)phenyl)quinoxalin-6-amine (5.0 g, 16.38 mmol) in dichloromethane (50 mL) was added NCS (2.19 g, 16.38 mmol) at 0° C. The resulting solution was stirred at 0° C. for 30 min. The mixture was quenched with water (100 mL), extracted with ethyl acetate (100 mL×3). The combined organic layer was washed with brine (100 mL), dried over Na$_2$SO$_4$, filtered and concentrated. The residue was purified by column chromatography on silica gel (0-20% ethyl acetate in petroleum ether) to afford the title compound (5.5 g, 99%) as a yellow solid. LCMS (ESI): m/z 339.9 (M+H)$^+$.

Step 2: 6-bromo-5-chloro-8-(4-(trifluoromethoxy)phenyl)quinoxaline

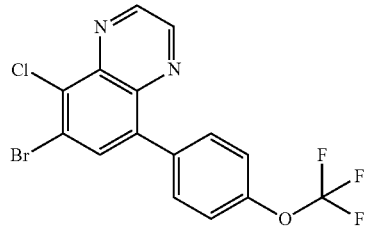

To a mixture of 5-chloro-8-(4-(trifluoromethoxy)phenyl)quinoxalin-6-amine (5.6 g, 16.49 mmol), CuBr$_2$ (3.68 g, 16.49 mmol) and TBAB (5.31 g, 16.49 mmol) in acetonitrile (200 mL) was added tert-butyl nitrite (1.96 mL, 16.49 mmol) at room temperature. The reaction was stirred at 60° C. for 3 h. The reaction was concentrated and the residue was purified by column chromatography on silica gel (0-10% ethyl acetate in petroleum ether) to afford the title compound (5.2 g, 78%) as a white solid. LCMS (ESI): m/z 402.8 (M+H)$^+$.

Step 3: tert-butyl 3-(5-chloro-8-(4-(trifluoromethoxy)phenyl)quinoxalin-6-yl)azetidine-1-carboxylate

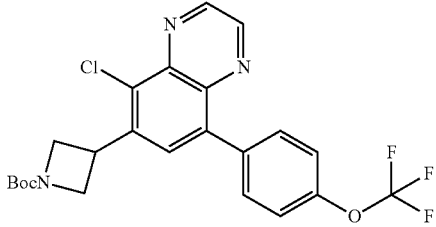 [SMILES: CC(C)(C)OC(=O)N1CC(c2cc(-c3ccc(OC(F)(F)F)cc3)c3nccnc3c2Cl)C1]

A mixture of 6-bromo-5-chloro-8-(4-(trifluoromethoxy)phenyl)quinoxaline (500 mg, 1.35 mmol), tert-butyl 3-bromoazetidine-1-carboxylate (480 mg, 2.03 mmol), Ir[dF(CF$_3$)ppy]$_2$(dtbbpy)PF$_6$ (15 mg, 0.01 mmol), NiCl$_2$·glyme (30 mg, 0.14 mmol), TTMSS (0.5 mL, 1.63 mmol), Na$_2$CO$_3$ (359 mg, 3.39 mmol) and dtbbpy (55 mg, 0.20 mmol) in DME (30 mL) was sealed and taken out from glove box, irradiated with 72W Blue_LED-Strip-Light for 16 h with cooling from a fan. The mixture was concentrated in vacuo. The residue was purified by column chromatography on silica gel (0-16% ethyl acetate in petroleum ether) to afford the title compound (180 mg, 28%) as a yellow oil. LCMS (ESI): m/z 480.1 (M+H)$^+$.

Step 4: tert-butyl 3-(8-(4-(trifluoromethoxy)phenyl)-5-vinylquinoxalin-6-yl)azetidine-1-carboxylate

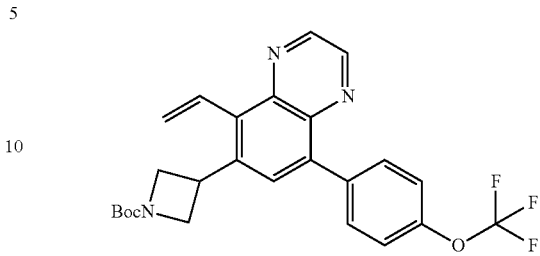

A mixture of tert-butyl 3-(5-chloro-8-(4-(trifluoromethoxy)phenyl)quinoxalin-6-yl)azetidine-1-carboxylate (1.8 g, 3.43 mmol), Xphos (164 mg, 0.34 mmol), Xphos Pd G$_2$ (270 mg, 0.34 mmol), 4,4,5,5-tetramethyl-2-vinyl-1,3,2-dioxaborolane (2.33 mL, 10.30 mmol) and K$_3$PO4 (2.19 g, 10.30 mmol) in 1,4-dioxane (50 mL) and water (5 mL) was stirred at 100° C. under N2 atmosphere for 2 h. The mixture was concentrated. The residue was purified by column chromatography on silica gel (0-16% ethyl acetate in petroleum ether) to afford the title compound (1.4 g, 87%) as a brown oil. $^1$H NMR (400 MHz, CDCl$_3$): δ 8.90 (d, J=1.6 Hz, 1H), 8.87 (d, J=1.6 Hz, 1H), 7.99 (s, 1H), 7.75-7.71 (m, 2H), 7.46-7.36 (m, 3H), 5.85 (dd, J=11.6, 1.6 Hz, 1H), 5.46 (dd, J=17.6, 1.6 Hz, 11H), 4.54-4.49 (m, 11H), 4.46-4.40 (m, 2H), 4.14-4.07 (m, 2H), 1.48 (s, 9H).

Intermediate H (R)-1-(6-(Azetidin-3-yl)-8-(4-(trifluoromethoxy)phenyl)quinoxalin-5-yl)ethane-1,2-diol

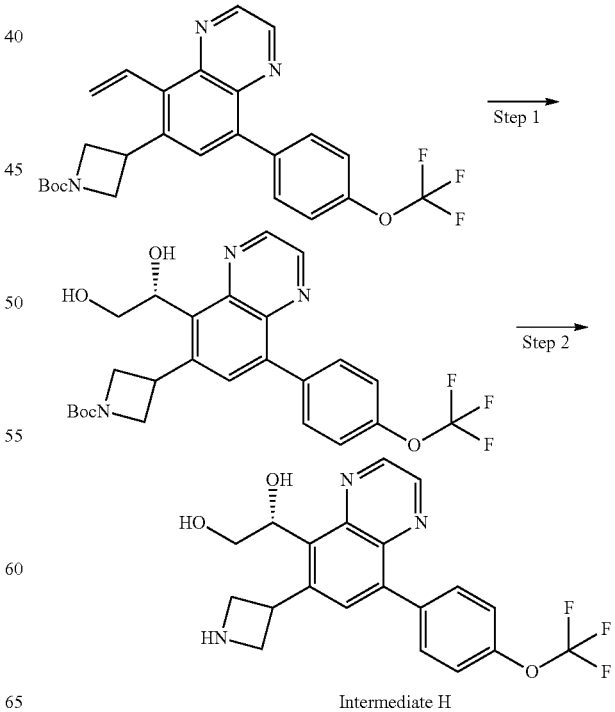

Intermediate H

Step 1: tert-butyl (R)-3-(5-(1,2-dihydroxyethyl)-8-(4-(trifluoromethoxy)phenyl)quinoxalin-6-yl)azetidine-1-carboxylate

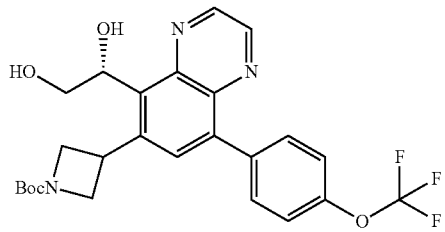 [SMILES: CC(C)(C)OC(=O)N1CC(c2cc(-c3ccc(OC(F)(F)F)cc3)c3nccnc3c2[C@@H](O)CO)C1]

A mixture of K₂CO₃ (469 mg, 3.39 mmol), (DHQD)₂PHAL (66 mg, 0.08 mmol), methanesulfonamide (161 mg, 1.7 mmol), K₃Fe(CN)₆ (1.12 g, 3.39 mmol) and K₂OsO₄·2H₂O (6 mg, 0.02 mmol) in 2-methylpropan-2-ol (200 mL) and water (200 mL) was stirred at room temperature for 20 min. Then tert-butyl 3-(8-(4-(trifluoromethoxy)phenyl)-5-vinylquinoxalin-6-yl)azetidine-1-carboxylate (800 mg, 1.7 mmol) was added into the reaction mixture at 0° C. The resulting mixture was stirred at room temperature for 16 h. The reaction was quenched with water (20 mL) and extracted with ethyl acetate (100 mL×3). The combined organic layer was washed with brine (50 mL), dried over Na₂SO₄, filtered and concentrated. The residue was purified by column chromatography on silica gel (0-5% methanol in dichloromethane) to afford the title compound (600 mg, 70%) as a brown solid. LCMS (ESI): m/z 506.1 (M+H)⁺.

Step 2: (R)-1-(6-(azetidin-3-yl)-8-(4-(trifluoromethoxy)phenyl)quinoxalin-5-yl)ethane-1,2-diol

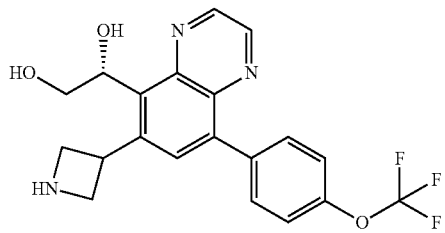 [SMILES: OC[C@H](O)c1c(C2CNC2)cc(-c2ccc(OC(F)(F)F)cc2)c2nccnc12]

A solution of tert-butyl (R)-3-(5-(1,2-dihydroxyethyl)-8-(4-(trifluoromethoxy)phenyl)quinoxalin-6-yl)azetidine-1-carboxylate (600 mg, 1.19 mmol) and 5% TFA in HFIP (10 mL) was stirred at room temperature for 1 h. The mixture was quenched with water (100 mL), then adjusted pH to 8 with aq.NaHCO₃ solution, extracted with ethyl acetate (100 mL×3). The combined organic layer was washed with water (150 mL), dried over Na₂SO₄, filtered and concentrated to afford the title compound (450 mg, crude) as a brown solid. LCMS (ESI): m/z 406.2 (M+H)⁺.

Intermediate I (S)-1-(6-(Azetidin-3-yl)-8-(4-(trifluoromethoxy)phenyl)quinoxalin-5-yl)ethane-1,2-diol

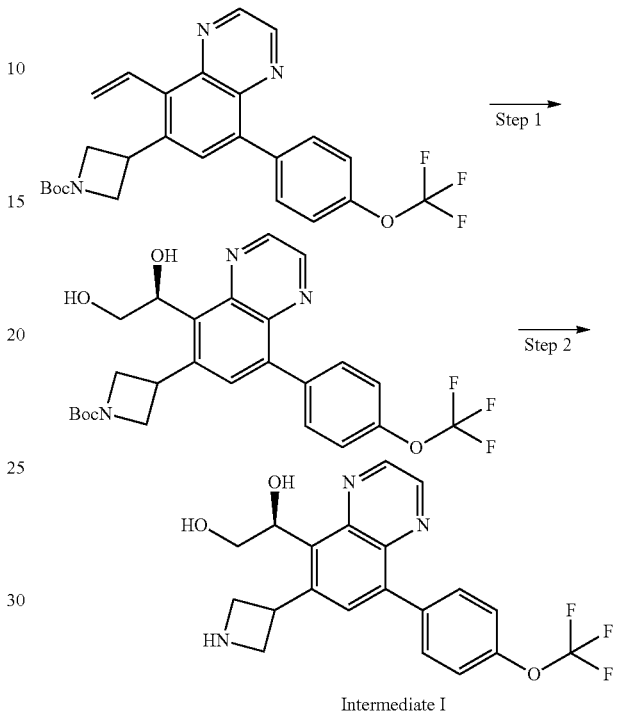

Intermediate I

Step 1: tert-butyl (S)-3-(5-(1,2-dihydroxyethyl)-8-(4-(trifluoromethoxy)phenyl)quinoxalin-6-yl)azetidine-1-carboxylate

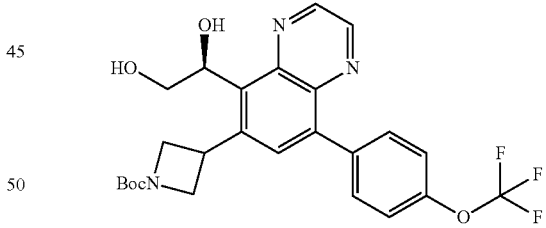

A mixture of K₂CO₃ (469 mg, 3.39 mmol), (DHQ)₂PHAL (66 mg, 0.08 mmol), methanesulfonamide (162 mg, 1.7 mmol), K₃Fe(CN)₆ (1.12 g, 3.39 mmol) and K₂OsO₄·2H₂O (7 mg, 0.02 mmol) in 2-methylpropan-2-ol (200 mL) and water (200 mL) was stirred at room temperature for 20 min. And then tert-butyl3-(8-(4-(trifluoromethoxy)phenyl)-5-vinylquinoxalin-6-yl)azetidine-1-carboxylate (800 mg, 1.7 mmol) was added into the reaction mixture at 0° C. The resulting mixture was stirred at room temperature for 16 h. The reaction was diluted with water (20 mL) and extracted with ethyl acetate (100 mL×3). The organic layers were washed with brine (50 mL×2), dried over sodium sulfate, filtered and concentrated. The residue was purified by flash chromatography on silica gel (0-5% methanol in DCM) to afford the title compound (800 mg, 93%) as a brown solid. LCMS (ESI): m/z 506.2 (M+H)+

Step 2: (S)-1-(6-(azetidin-3-yl)-8-(4-(trifluoromethoxy)phenyl)quinoxalin-5-yl)ethane-1,2-diol

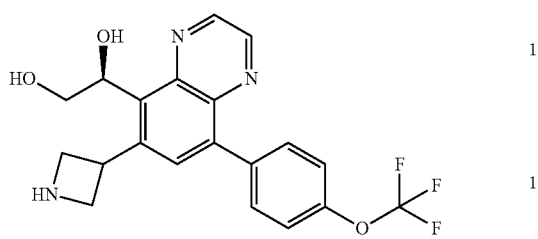

A solution of tert-butyl (S)-3-(5-(1,2-dihydroxyethyl)-8-(4-(trifluoromethoxy)phenyl)quinoxalin-6-yl)azetidine-1-carboxylate (800 mg, 1.58 mmol) and 5% TFA in HFIP (10 mL) was stirred for at room temperature 1 h. The mixture was quenched with water (100 mL) then adjusted pH to 8 with aq.NaHCO₃ solution. The solution was diluted with ethyl acetate (100 mL) and washed with water (100 mL×3). The organic layer was dried over Na₂SO₄ and concentrated to afford the title compound (600 mg crude) as a brown solid. LCMS (ESI): m/z 406.2 (M+H)+.

Intermediate J

5-Bromo-7-chloro-2,3-dihydrobenzofuran-4-carbaldehyde

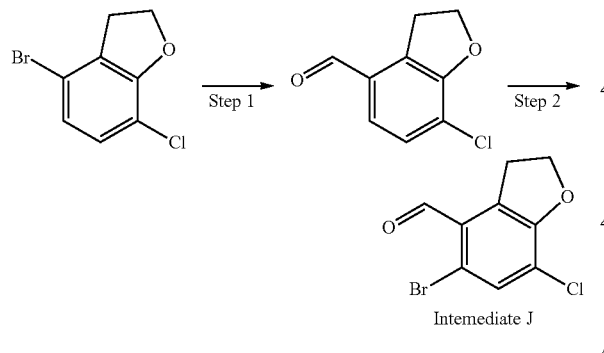

Step 1:
7-chloro-2,3-dihydrobenzofuran-4-carbaldehyde

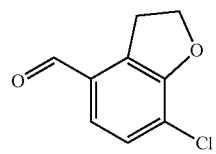 [SMILES: O=Cc1ccc(Cl)c2c1CCO2]

To a solution of 4-bromo-7-chloro-2,3-dihydrobenzofuran (10.0 g, 42.8 mmol) in THF (100 mL) was added n-BuLi (2.5 M in hexane, 10.0 mL, 51.4 mmol) at −70° C. The solution was stirred at −70° C. for 1 h. Then the reaction mixture was added DMF (3.2 g, 85.6 mmol) and the solution was stirred at −70° C. for 1 h. The mixture was quenched with NH₄Cl (100 mL), extracted with ethyl acetate (200 mL×3) and washed with water (200 mL×3). The organic layer was dried over Na₂SO₄ and concentrated. The residue was purified by chromatography on silica gel (0-5% ethyl acetate in petroleum ether) to afford the title compound (5.5 g, 70%) as a white solid. ¹H NMR (400 MHz, CDCl₃): δ 10.01 (s, 1H), 7.32 (d, J=8.0 Hz, 1H), 7.26 (d, J=8.0 Hz, 1H), 4.77 (t, J=8.8 Hz, 2H), 3.63 (t, J=8.8 Hz, 2H).

Step 2: 5-bromo-7-chloro-2,3-dihydrobenzofuran-4-carbaldehyde

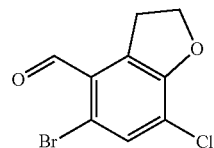 [SMILES: O=Cc1c(Br)cc(Cl)c2c1CCO2]

To a solution of 7-chloro-2,3-dihydrobenzofuran-4-carbaldehyde (4.7 g, 25.8 mmol) in AcOH (40 mL) was added Br₂ (2.0 mL, 38.8 mmol) dropwise at 0° C. The mixture was stirred at room temperature for 2 h. The mixture was quenched with water (50 mL) and filtration. After filtration, the filtrate cake was diluted with ethyl acetate (200 mL) and washed with sat.NaHCO₃ (200 mL). The organic layer was dried over Na₂SO₄ and concentrated. The residue was purified by chromatography on silica gel (0-5% ethyl acetate in petroleum ether) to afford the title compound (4.1 g, 60%) as white solid. ¹H NMR (400 MHz, CDCl₃) δ10.36 (s, 1H), 7.48 (s, 1H), 4.76 (t, J=8.8 Hz, 2H), 3.65 (t, J=8.8 Hz, 2H).

Intermediate K

5-Chloro-7-(4-(trifluoromethoxy)phenyl)thiazolo[5,4-d]pyrimidine

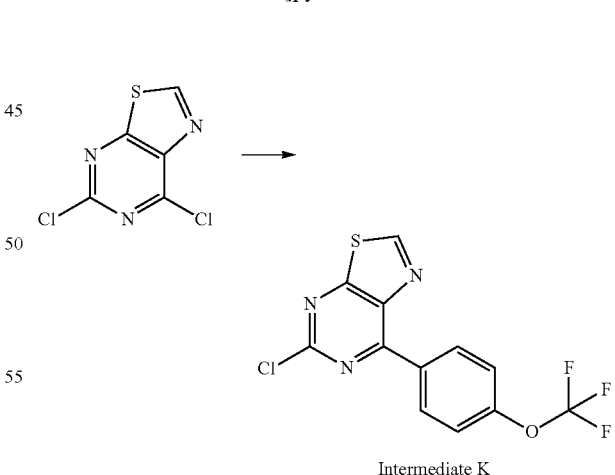

A mixture of K₃PO₄ (1.03 g, 4.85 mmol), (4-(trifluoromethoxy)phenyl)boronic acid (550 mg, 2.67 mmol), 5,7-dichlorothiazolo[5,4-d]pyrimidine (500 mg, 2.43 mmol) and Pd(dppf)Cl₂ (178 mg, 0.24 mmol) in 1,4-dioxane (5 mL) and water (0.30 mL) was stirred at 100° C. for 10 min under N2 atmosphere. The mixture was quenched with water (30 mL), extracted with ethyl acetate (30 mL×3) and washed with brine (30 mL). The organic layers were dried over Na₂SO₄ and concentrated under reduced. The residue was purified by flash chromatography on silica gel (0-30% ethyl acetate in petroleum ether) to afford the title compound (450 mg, 56%) as a white solid. ¹H NMR (400 MHz, CDCl₃): δ 9.16 (s, 1H), 8.84 (d, J=8.4 Hz, 2H), 7.41 (d, J=8.4 Hz, 2H); LCMS (ESI): m/z 332.0 (M+H)⁺.

Intermediate L 5-(Azetidin-3-yl)-7-(4-(trifluoromethoxy)phenyl)thiazolo[5,4-d]pyrimidine

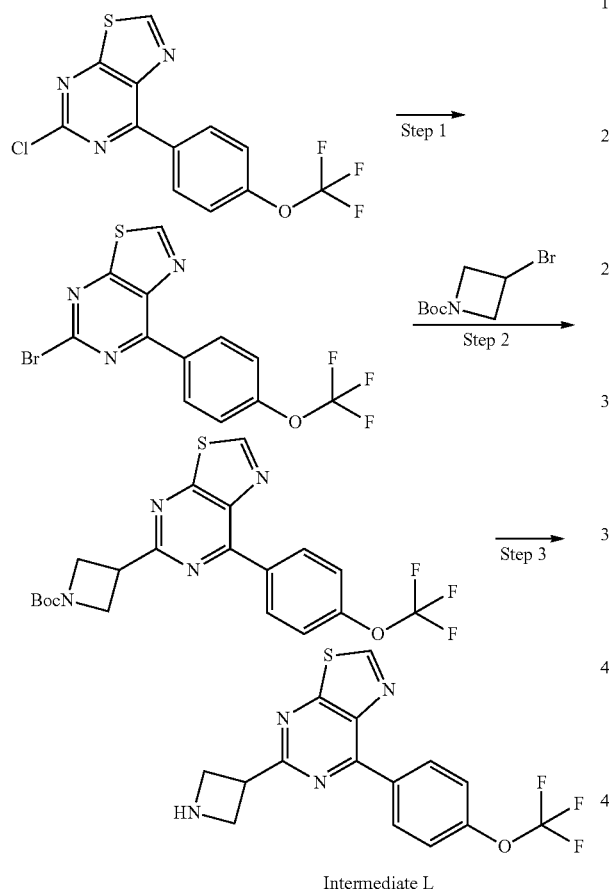

Intermediate L

Step 1: 5-bromo-7-(4-(trifluoromethoxy)phenyl)thiazolo[5,4-d]pyrimidine

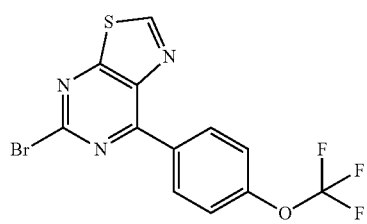 [SMILES: FC(F)(F)Oc1ccc(-c2nc(Br)nc3scnc23)cc1]

A solution of 5-chloro-7-(4-(trifluoromethoxy)phenyl)thiazolo[5,4-d]pyrimidine (2.0 g, 6.03 mmol) in 33% HBr in HOAc (15 mL) was stirred at 80° C. for 2 h. The reaction mixture was concentrated under reduced pressure. The residue was purified by flash chromatography on silica gel (0-10% ethyl acetate in petroleum ether) to afford the title compound (2.1 g, 93%) as a white solid. ¹H NMR (400 MHz, DMSO-d₆): δ 9.70 (s, 1H), 8.77-8.72 (m, 2H), 7.63 (d, J=8.0 Hz, 2H); LCMS (ESI): m/z 375.7 (M+H)⁺.

Step 2: tert-butyl 3-(7-(4-(trifluoromethoxy)phenyl)thiazolo[5,4-d]pyrimidin-5-yl)azetidine-1-carboxylate

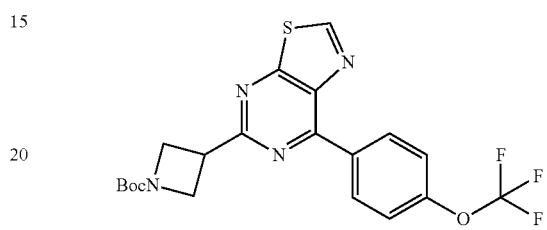

To a mixture of tert-butyl 3-bromoazetidine-1-carboxylate (189 mg, 0.80 mmol), 5-bromo-7-(4-(trifluoromethoxy)phenyl)thiazolo[5,4-d]pyrimidine (200 mg, 0.53 mmol) in DME (10 mL) was added Na₂CO₃ (141 mg, 1.33 mmol), Ir[dF(CF₃)ppy]₂(dtbbpy)PF₆ (6 mg, 0.01 mmol) and TTMSS (159 mg, 0.64 mmol) in glove box. The solution NiCl₂-glyme (12 mg, 0.05 mmol) and dtbbpy (22 mg, 0.08 mmol) in DME (4 mL) was added into the mixture in glove box at room temperature. The reaction mixture was stirred under a Lumidox Screen Kit at room temperature for 16 hours. The solution was diluted with water (20 mL), extracted with ethyl acetate (20 mL×3), dried over Na₂SO₄ and concentrated. The residue was purified by pre-TLC (20% ethyl acetate in petroleum ether ) to afford the title compound (100 mg, 42%) as a white solid, 2D-NMR confirmed. ¹H NMR (400 MHz, CDCl₃): δ 9.16 (s, 1H), 8.87-8.81 (m, 2H), 7.41 (d, J=8.4 Hz, 2H), 4.43-4.40 (m, 4H), 4.27-4.18 (m, 1H), 1.49 (m, 9H); LCMS (ESI): m/z 397.1 (M+H−56)⁺.

Step 3: 5-(azetidin-3-yl)-7-(4-(trifluoromethoxy)phenyl)thiazolo[5,4-d]pyrimidine

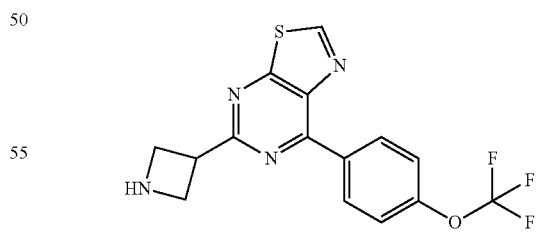

To a mixture of tert-butyl 3-(7-(4-(trifluoromethoxy)phenyl)thiazolo[5,4-d]pyrimidin-5-yl)azetidine-1-carboxylate (90 mg, 0.20 mmol) in DCM (2 mL) was added TFA (0.2 mL) at 0° C., the resulting mixture was stirred at room temperature for 2 h. The reaction was quenched with ammonia (1 mL). The mixture was concentrated under vacuum to afford the title compound (70 mg, crude) as a white solid. LCMS (ESI): m/z 353.1 (M+H)⁺.

283

Intermediate M 1-(6-Iodo-4-(4-(trifluoromethoxy)phenyl)benzo[d]oxazol-7-yl)ethane-1,2-diol

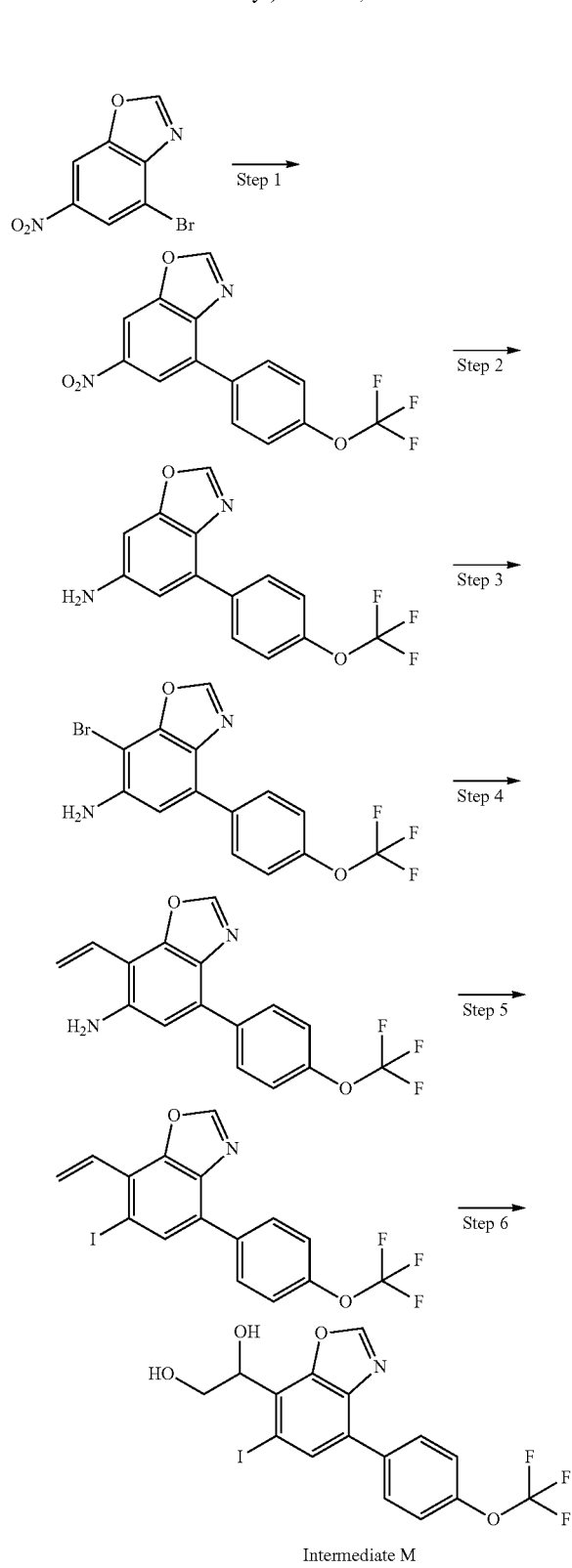

Intermediate M

284

Step 1: 6-nitro-4-(4-(trifluoromethoxy)phenyl)benzo[d]oxazole

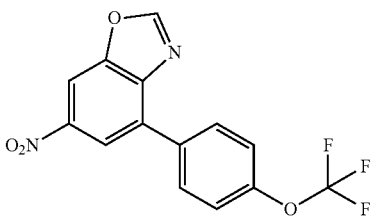

A mixture of 4-bromo-6-nitrobenzo[d]oxazole (5.0 g, 20.58 mmol), Pd(dppf)Cl$_2$ (1.51 g, 2.06 mmol), (4-(trifluoromethoxy)phenyl)boronic acid (5.08 g, 24.69 mmol) and Na$_2$CO$_3$ (4.36 g, 41.15 mmol) in 1,4-dioxane (50 mL) and water (5 mL) was stirred at 80° C. for 3 h under N2 atmosphere. The reaction mixture was diluted with water (50 mL) and extracted with ethyl acetate (50 mL×3), the combined organic layers were dried over Na$_2$SO$_4$ and concentrated in vacuo. The residue was purified by flash chromatography on silica gel (0-20% ethyl acetate in petroleum ether) to afford the title compound (2.5 g, 37%) as a yellow solid. $^1$H NMR (400 MHz, CDCl$_3$): δ 8.54-8.51 (m, 2H), 8.40 (s, 1H), 8.06 (d, J=8.8 Hz, 2H), 7.42 (d, J=8.0 Hz, 2H); LCMS (ESI): m/z 325.0 (M+H)$^+$.

Step 2: 4-(4-(trifluoromethoxy)phenyl)benzo[d]oxazol-6-amine

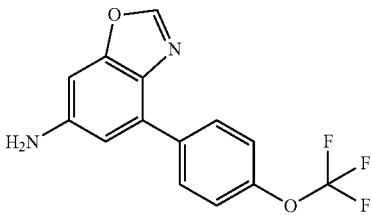

A mixture of 6-nitro-4-(4-(trifluoromethoxy)phenyl)benzo[d]oxazole (2.8 g, 8.64 mmol) and 10% Pd/C (92 mg, 0.86 mmol) in ethanol (5 mL) was stirred at room temperature for 16 h under H$_2$ (15 psi). The reaction was filtered and the filtrate was concentrated under vacuum to afford the title compound (2.52 g, crude) as a black solid. The crude product was used for next step without further purification. LCMS (ESI): m/z 295.1 (M+H)$^+$.

Step 3: 7-bromo-4-(4-(trifluoromethoxy)phenyl)benzo[d]oxazol-6-amine

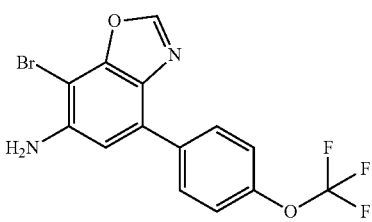

To a solution of 4-(4-(trifluoromethoxy)phenyl)benzo[d]oxazol-6-amine (1.5 g, 5.1 mmol) in dichloromethane (20 mL) was added the solution NBS (908 mg, 5.1 mmol) in THF (20 mL) at −15° C., after addition, the resulting solution was stirred at −15° C. for 5 min. The reaction was diluted with water (50 mL) and extracted with ethyl acetate (30 mL×3). The combined organic layers were dried over Na$_2$SO$_4$ and concentrated in vacuo. The residue was purified by flash chromatography on silica gel (0-10% ethyl acetate in petroleum ether) to afford the title compound (1.7 g, 89%) as a bule solid. 2D-NMR confirmed it. $^1$H NMR (400 MHz, DMSO-d$_6$): δ 8.58 (s, 1H), 8.01 (d, J=8.8 Hz, 2H), 7.51 (d, J=8.0 Hz, 2H), 7.12 (s, 1H), 5.74 (s, 2H); LCMS (ESI): m/z 373.0 (M+H)$^+$.

Step 4: 4-(4-(trifluoromethoxy)phenyl)-7-vinyl-benzo[d]oxazol-6-amine

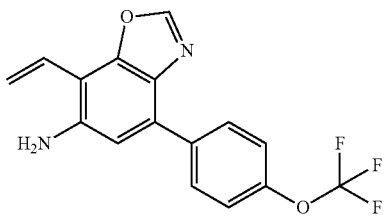 [SMILES: C=Cc1c(N)cc(-c2ccc(OC(F)(F)F)cc2)c2ncoc12]

To a solution of 7-bromo-4-(4-(trifluoromethoxy)phenyl)benzo[d]oxazol-6-amine (10.0 g, 26.8 mmol) in 1,4-dioxane (150 mL) was added tributyl(vinyl)stannane (15.67 mL, 53.6 mmol) and Pd(PPh$_3$)$_4$ (6.19 g, 5.36 mmol). The mixture was stirred at 110° C. for 16 hours under N2 atmosphere. The reaction mixture was diluted with ethyl acetate (200 mL) and washed with brine (200 mL×3). The organic layer was separated, dried over anhydrous sodium sulfate and concentrated under reduced pressure. The residue was purified by column chromatography on silica gel (0-20% ethyl acetate in petroleum ether) to afford the title compound (4.6 g, 54%) as a yellow solid. $^1$H NMR (400 MHz, CDCl$_3$): δ 8.05 (s, 1H), 7.94 (d, J=8.8 Hz, 2H), 7.34 (d, J=8.4 Hz, 2H), 6.90 (s, 1H), 6.83 (dd, J=17.6, 11.6 Hz, 1H), 6.17 (d, J=17.6 Hz, 1H), 5.69 (d, J=11.6 Hz, 1H); LCMS (ESI): m/z 320.9 (M+H)$^+$.

Step 5: 6-iodo-4-(4-(trifluoromethoxy)phenyl)-7-vinylbenzo[d]oxazole

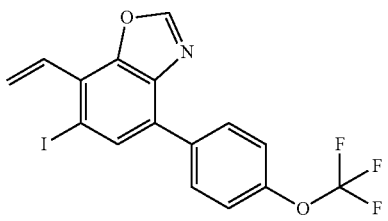 [SMILES: C=Cc1c(I)cc(-c2ccc(OC(F)(F)F)cc2)c2ncoc12]

To a solution of 4-(4-(trifluoromethoxy)phenyl)-7-vinyl-benzo[d]oxazol-6-amine (2.0 g, 6.24 mmol) in acetonitrile (15 mL) was added con.HCl (1.04 mL, 12.49 mmol) at 0° C. and the reaction mixture was stirred at 0° C. at for 5 mins. Solution of NaNO$_2$ (453 mg, 6.56 mmol) in water (2 mL) was added into it drop wise at 0° C. and the reaction mixture was stirred at 0° C. for 20 mins. The reaction mixture turned into clear pale yellow solution. Solution of KI (2.07 g, 12.49 mmol) in water(2 mL) was added drop wise to the reaction mixture at 0° C. Then the solution was stirred at 0° C. for 30 mins. The reaction mixture was quenched with cold water (100 mL) and extracted with ethyl acetate (80 mL×2). The organic layer was dried over anhydrous sodium sulfate and concentrated. The residue was purified by flash chromatography on silica gel (0-15% ethyl acetate in petroleum ether) to afford the title compound (895 mg, 33%) as a yellow solid. $^1$H NMR (400 MHz, DMSO-d$_6$): δ 8.88 (s, 1H), 8.20-8.13 (m, 3H), 7.52 (d, J=8.4 Hz, 2H), 6.88 (dd, J=17.6, 11.6 Hz, 1H), 6.32 (dd, J=17.6 Hz, 1H), 5.83 (d, J=11.6 Hz, 1H); LCMS (ESI): m/z 431.9 (M+H)$^+$.

Step 6: 1-(6-iodo-4-(4-(trifluoromethoxy)phenyl)benzo[d]oxazol-7-yl)ethane-1,2-diol

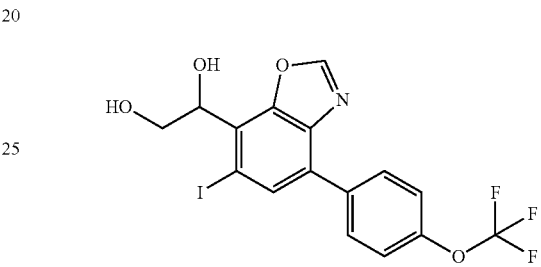

To a solution of 6-iodo-4-(4-(trifluoromethoxy)phenyl)-7-vinylbenzo[d]oxazole (1.5 g, 3.48 mmol) and K$_2$OsO$_4$·2H$_2$O (129 mg, 0.35 mmol) in THF (15 mL) and water (3 mL) was added NMO (530 mg, 4.52 mmol) at room temperature. The resulting mixture was stirred at room temperature for 16 h. The reaction mixture was diluted with ethyl acetate (100 mL), washed with water (100 mL×2) and brine (100 mL×2). The organic layer was dried over Na$_2$SO$_4$ and concentrated. The residue was purified by flash chromatography on silica gel (0-50% ethyl acetate in petroleum ether) to afford the title compound (1.1 g, 68%) as a white solid. $^1$H NMR (400 MHz, CDCl$_3$): δ 8.81 (s, 1H), 8.11 (d, J=8.8 Hz, 2H), 8.05 (s, 1H), 7.52 (d, J=8.4 Hz, 2H), 5.73 (d, J=4.0 Hz, 1H), 5.06-5.00 (m, 1H), 4.94 (t, J=6.0 Hz, 1H), 3.81-3.71 (m, 2H); LCMS (ESI): m/z 466.0 (M+H)$^+$.

Intermediate N

Ethyl 4-bromo-6-methylbenzo[d]oxazole-7-carboxylate

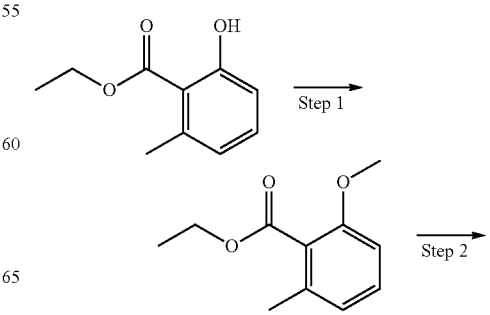

287

-continued

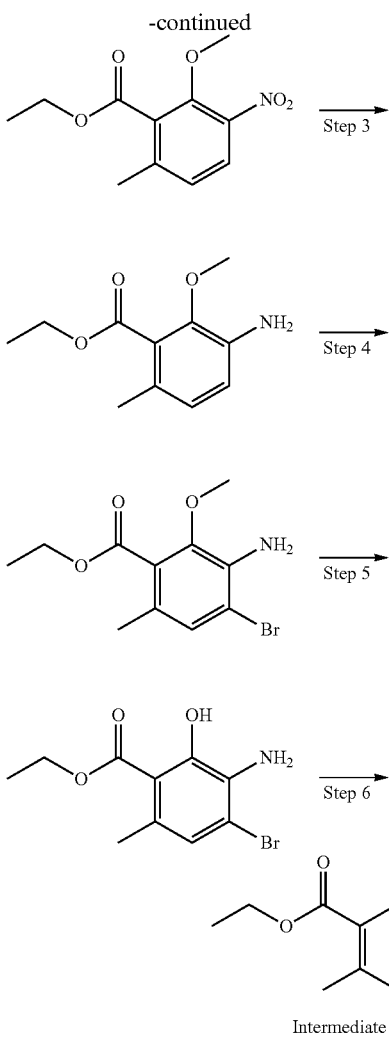

Intermediate N

Step 1: ethyl 2-methoxy-6-methylbenzoate

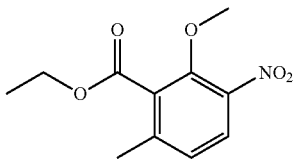 [SMILES: CCOC(=O)c1c(C)ccc([N+](=O)[O-])c1OC]

To a stirred solution of ethyl 2-hydroxy-6-methylbenzoate (40.0 g, 222.0 mmol) in acetone (400 mL) was added $Na_2CO_3$ (60.0 g, 444.0 mmol) and MeI (68.5 mL, 1.11 mol). The reaction mixture was stirred at 60° C. for 16 hours under nitrogen atmosphere. The reaction mixture was poured into ice water (1 L). The mixture was extracted with ethyl acetate (500 mL×3). The combined organic layer was washed with saturated aqueous $NH_4Cl$ solution (500 mL×3) and brine (500 mL×3), dried over $Na_2SO_4$ and concentrated to afford the title compound (40.0 g, 93%). $^1H$ NMR (400 MHz, $CDCl_3$) δ7.26-7.22 (m, 1H), 6.81-6.75 (m, 2H), 4.41 (q, J=7.2 Hz, 2H), 3.83 (s, 3H), 2.31 (s, 3H), 1.39 (t, J=7.2 Hz, 3H); LCMS (ESI): m/z 195.1 (M+H)$^+$.

288

Step 2: ethyl 2-methoxy-6-methyl-3-nitrobenzoate

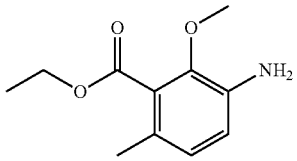

To a solution of ethyl 2-methoxy-6-methylbenzoate (1.0 g, 5.15 mmol) in 2,2,2-trifluoroacetic acid (30 mL) was added $HNMO_3$ (0.46 mL, 6.18 mmol) at −10° C., the resulting solution was stirred at −10° C. for 2 h. The reaction mixture was quenched with ice water (100 mL) and adjusted to pH=8 by 2M aq.NaOH. The solution was extracted with ethyl acetate (20 mL×3). The combined organic layers were washed with brine (20 mL×2) and dried with $Na_2SO_4$ and concentrated. The residue was purified by column chromatography on silica gel (0-10% ethyl acetate in petroleum ether ) to afford the title compound (700 mg, 57%) as a yellow solid. Note: the region-isomer (ethyl 6-methoxy-2-methyl-3-nitrobenzoate) can be removed by column. $^1H$ NMR (400 MHz, $CDCl_3$) δ7.87 (d, J=8.4 Hz, 1H), 7.08 (d, J=8.4 Hz, 1H), 4.45 (q, J=7.2 Hz, 2H), 3.95 (s, 3H), 2.39 (s, 3H), 1.42 (t, J=7.2 Hz, 3H).

Step 3: ethyl 3-amino-2-methoxy-6-methylbenzoate

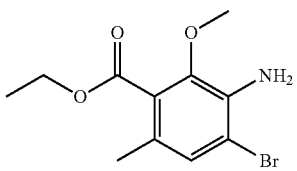 [SMILES: CCOC(=O)c1c(C)cc(Br)c(N)c1OC]

A solution of ethyl 2-methoxy-6-methyl-3-nitrobenzoate (20.0 g, 83.7 mmol) and 10% Pd/C (4.5 g, 42.0 mmol) in ethanol (200 mL) was stirred at room temperature for 16 hours under $H_2$ (15 psi). The reaction mixture was filtered. The filtrate was concentrated to afford the title compound (15.0 g, 86%) as a yellow solid. $^1H$ NMR (400 MHz, $CDCl_3$): δ 6.81-6.74 (m, 2H), 4.42 (q, J=7.2 Hz, 2H), 3.82 (s, 3H), 2.22 (s, 3H), 1.40 (t, J=7.2 Hz, 3H).

Step 4: ethyl 3-amino-4-bromo-2-methoxy-6-methylbenzoate

To a mixture of ethyl 3-amino-2-methoxy-6-methylbenzoate (12.5 g, 59.6 mmol) in DCM (150 mL) was added NBS (10.0 g, 60 mmol) at 0° C. The reaction solution was stirred at 0° C. for 1 hour. The reaction mixture was filtered and the filtrate was concentrated under vacuum. The residue was purified by flash chromatography on silica gel (0-10% ethyl acetate in petroleum ether) to afford the title compound (15.0 g, 86%) as a yellow solid. $^1$H NMR (400 MHz, CDCl$_3$): δ 7.08 (s, 1H), 4.41 (q, J=7.2 Hz, 2H), 3.82 (s, 3H), 2.20 (s, 3H), 1.40 (t, J=7.2 Hz, 3H).

Step 5: ethyl 3-amino-4-bromo-2-hydroxy-6-methylbenzoate

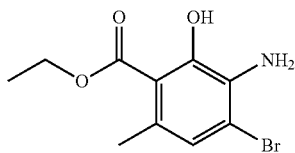

To a solution of ethyl 3-amino-4-bromo-2-methoxy-6-methylbenzoate (8.0 g, 28.0 mmol) in DCM (120 mL) was added BBr$_3$ (2.7 mL, 28.0 mmol) in DCM (10 mL) at −78° C. The mixture was stirred at −78° C. for 2 hours. The mixture was quenched with H$_2$O (300 mL), then the solution was adjusted pH to 8 with 2M NaOH. Then the solution was extracted with ethyl acetate (500 mL×3). The organic layer was dried over Na$_2$SO$_4$, filtered and the filtrate was concentrated under vacuum. The residue was purified by flash chromatography on silica gel (0-10% ethyl acetate in petroleum ether) to afford the title compound (15.0 g, 86%) as white solid. $^1$H NMR (400 MHz, CDCl$_3$): δ 6.85 (s, 1H), 4.44 (q, J=7.2 Hz, 2H), 2.44 (s, 3H), 1.44 (t, J=7.2 Hz, 3H).

Step 6: ethyl 4-bromo-6-methylbenzo[d]oxazole-7-carboxylate

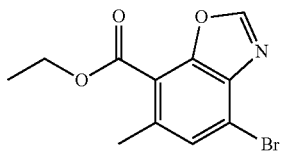 [SMILES: CCOC(=O)c1c(C)cc(Br)c2ncoc12]

A mixture of ethyl 3-amino-4-bromo-2-hydroxy-6-methyl-benzoate (900 mg, 3.28 mmol), trimethoxymethane (20 mL, 182.81 mmol) and p-toluenesulfonic acid monohydrate (62 mg, 0.33 mmol) was stirred at 80° C. for 16 hours. The reaction mixture was concentrated. The residue was purified with flash chromatography on silica gel (0-10% ethyl acetate in petroleum ether) to afford the title compound as a white solid. $^1$H NMR (400 MHz, CDCl$_3$): δ 8.17 (s, 1H), 7.50 (s, 1H), 4.48 (q, J=7.2 Hz, 2H), 2.68 (s, 3H), 1.46 (t, J=7.2 Hz, 3H); LCMS (ESI): m/z 284.0 (M+H)$^+$.

Intermediate O

2-Chloro-9-methyl-6-(4-(trifluoromethoxy)phenyl)-9H-purine

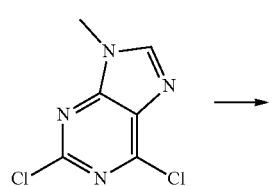

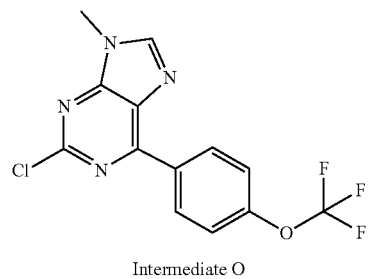

Intermediate O

A solution of Pd(dppf)Cl$_2$ (5.41 g, 7.39 mmol), (4-(trifluoromethoxy)phenyl)boronic acid (15.21 g, 73.88 mmol), K$_3$PO$_4$ (31.37 g, 147.76 mmol) and 2,6-dichloro-9-methyl-9H-purine (15.0 g, 73.88 mmol) in 1,4-dioxane (150 mL) and water (15 mL) was stirred at 80° C. for 4 h under N2 atmosphere. The mixture was diluted with ethyl acetate (500 mL) and washed with water (500 mL×3). The organic was dried over Na$_2$SO$_4$ and concentrated. The residue was purified by chromatography on silica gel (0-10% ethyl acetate in petroleum ether) to afford the title compound (21.0 g, 87%) as a white solid. $^1$H NMR (400 MHz, DMSO-d$_6$): δ 8.86 (d, J=8.8 Hz, 2H), 8.67 (s, 1H), 7.59 (d, J=8.4 Hz, 2H), 3.83 (s, 3H); LCMS (ESI): m/z 328.9 (M+H)$^+$.

Intermediate P

2-Bromo-9-methyl-6-(4-(trifluoromethoxy)phenyl)-9H-purine

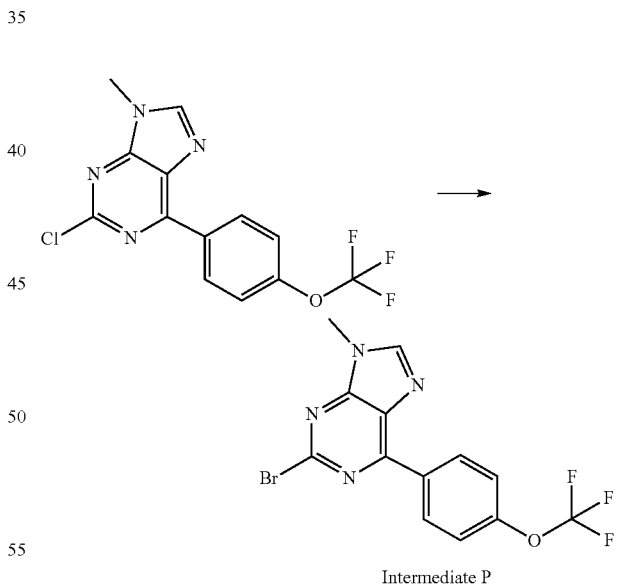

Intermediate P

A solution of 2-chloro-9-methyl-6-(4-(trifluoromethoxy)phenyl)-9H-purine (600 mg, 1.83 mmol) and 33% HBr in acetic acid (10 mL) was stirred at 80° C. for 2 h. The reaction mixture was concentrated under reduced pressure. The residue was diluted with DCM (5 mL), the precipitate was filtered and washed with DCM (5 mL). The filter cake was dried in vacuo to afford the title compound (650 mg, crude) as a white solid. LCMS (ESI): m/z 372.8 (M+H)$^+$.

Intermediate Q 2-(Azetidin-3-yl)-9-methyl-6-(4-(trifluoromethoxy)phenyl)-9H-purine

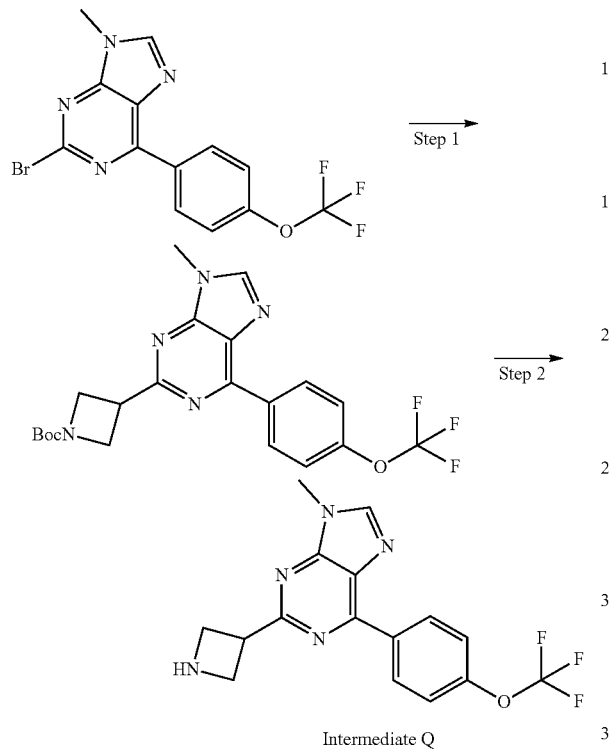

Intermediate Q

Step 1: tert-butyl 3-(9-methyl-6-(4-(trifluoromethoxy)phenyl)-9H-purin-2-yl)azetidine-1-carboxylate

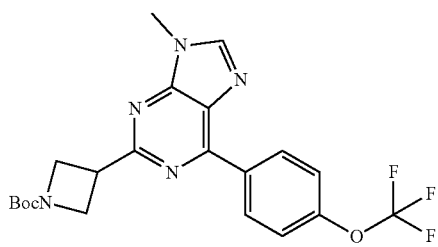 [SMILES: Cn1cnc2c(-c3ccc(OC(F)(F)F)cc3)nc(C3CN(C(=O)OC(C)(C)C)C3)nc21]

In glove box, a mixture of tert-butyl 3-bromoazetidine-1-carboxylate (950 mg, 4.02 mmol), 2-bromo-9-methyl-6-(4-(trifluoromethoxy)phenyl)-9H-purine (1.0 g, 2.68 mmol), Na$_2$CO$_3$ (710 mg, 6.70 mmol), Ir[dF(CF$_3$)ppy]$_2$(dtbbpy)PF$_6$ (30 mg, 0.03 mmol), TTMSS (800 mg, 3.22 mmol), NiCl$_2$·glyme (60 mg, 0.27 mmol) and dtbbpy (110 mg, 0.40 mmol) in DME (5 mL) was stirred under a Lumidox Screen Kit at room temperature for 16 hours. The reaction mixture was diluted with water (50 mL) and extracted with ethyl acetate (20 mL×3). The combined organic layers were dried over Na$_2$SO$_4$ and concentrated in vacuo. The residue was purified by flash chromatography on silica gel (0-50% ethyl acetate in petroleum ether) to afford the title compound (650 mg, 54%) as a yellow solid. $^1$H NMR (400 MHz, CDCl$_3$): δ 8.91 (d, J=8.8 Hz, 2H), 8.10 (s, 1H), 7.39 (d, J=8.4 Hz, 2H), 4.45-4.36 (m, 4H), 4.24-4.10 (m, 11H), 3.94 (s, 3H), 1.50 (s, 9H); LCMS (ESI): m/z 450.0 (M+H)$^+$.

Step 2: 2-(azetidin-3-yl)-9-methyl-6-(4-(trifluoromethoxy)phenyl)-9H-purine

A mixture of tert-butyl 3-(9-methyl-6-(4-(trifluoromethoxy)phenyl)-9H-purin-2-yl)azetidine-1-carboxylate (200 mg, 0.45 mmol) and 5% TFA in HFIP (10 mL) was stirred at room temperature for 16 h. The reaction mixture was quenched with sat.NaHCO$_3$ (30 mL), extracted with ethyl acetate (30 mL×3), the combined organic layers were washed with water (20 mL×2), dried over Na$_2$SO$_4$ and concentrated to afford the crude title compound (155 mg, crude) as a white solid. The crude product was used for next step without further purification. LCMS (ESI): m/z 349.9 (M+H)$^+$.

Intermediate R

9-Methyl-2-(piperazin-1-yl)-6-(4-(trifluoromethoxy)phenyl)-9H-purine

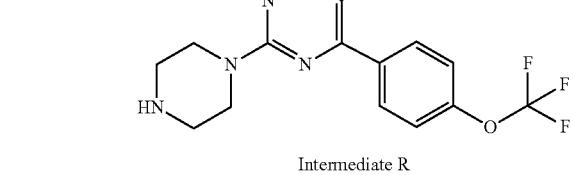

Intermediate R

Step 1: tert-butyl 4-(9-methyl-6-(4-(trifluoromethoxy)phenyl)-9H-purin-2-yl)piperazine-1-carboxylate

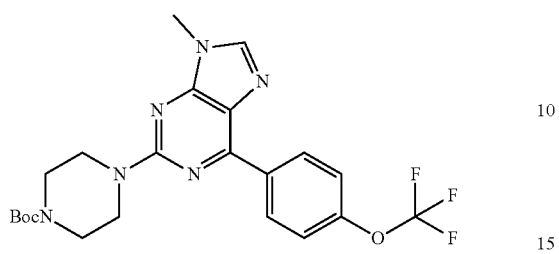

To a solution of 2-bromo-9-methyl-6-(4-(trifluoromethoxy)phenyl)-9H-purine (1.0 g, 2.68 mmol) in 1,4-dioxane (30 mL) was added tert-butyl piperazine-1-carboxylate (749 mg, 4.02 mmol), $Cs_2CO_3$ (2.62 g, 8.04 mmol), RuPhos (187 mg, 0.40 mmol) and RuPhos Pd $G_2$ (112 mg, 0.13 mmol). The mixture was stirred at 100° C. for 16 h under N2 atmosphere. The mixture was diluted with ethyl acetate (50 mL) and washed with water (30 mL×3). The organic layer was dried over $Na_2SO_4$ and concentrated. The residue was purified by chromatography on silica gel (0-50% ethyl acetate in petroleum ether) to afford the title compound (600 mg, 47%) as a yellow solid. LCMS (ESI): m/z 479.1 (M+H)+.

Step 2: 9-methyl-2-(piperazin-1-yl)-6-(4-(trifluoromethoxy)phenyl)-9H-purine 2,2,2-trifluoroacetate

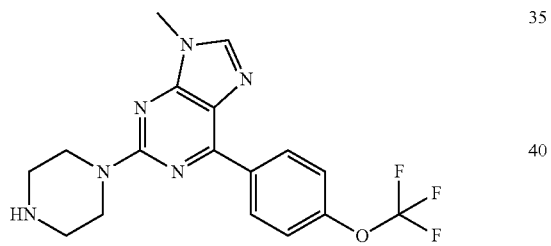

A mixture of tert-butyl 4-(9-methyl-6-(4-(trifluoromethoxy)phenyl)-9H-purin-2-yl)piperazine-1-carboxylate (100 mg, 0.21 mmol) and 5% TFA in HFIP (110 mg) was stirred at room temperature for 1 h. The mixture was concentrated to afford the title compound (100 mg, crude) as a yellow oil. The crude would be used in the next step directly.

Intermediate S 6-(Azetidin-3-yl)-8-(4-(trifluoromethoxy)phenyl)pyrido[3,4-b]pyrazin-5(6H)-one

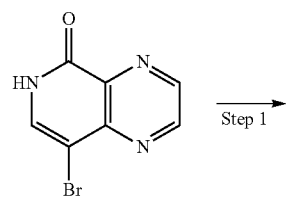

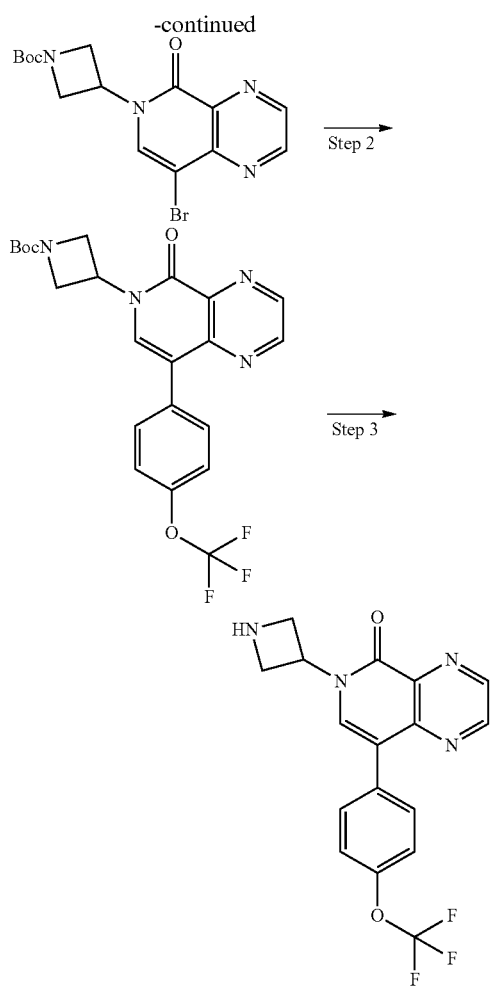

Intermediate S

Step 1: tert-butyl 3-(8-bromo-5-oxopyrido[3,4-b]pyrazin-6(5H)-yl)azetidine-1-carboxylate

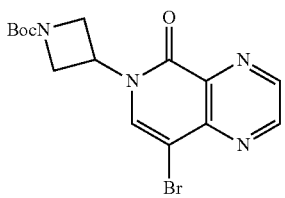 [SMILES: CC(C)(C)OC(=O)N1CC(n2cc(Br)c3nccnc3c2=O)C1]

To a solution of 8-bromopyrido[3,4-b]pyrazin-5(6H)-one (650 mg, 2.88 mmol) and tert-butyl 3-bromoazetidine-1-carboxylate (1.02 g, 4.31 mmol) in DMF (10 mL) was added $K_2CO_3$ (1.19 g, 8.63 mmol) at room temperature. The mixture was stirred at 80° C. for 12 h under $N_2$ atmosphere. The reaction mixture was diluted with $H_2O$ (20 mL) and extracted with ethyl acetate (20 mL×3). The combined organic layers were washed with brine (50 mL), dried over anhydrous $Na_2SO_4$, filtered and concentrated under reduced pressure to give a residue. The residue was purified by column chromatography on silica gel (0-50% ethyl acetate in petroleum ether) to afford the title compound (410 mg, 37%) as a white solid. 2D-NMR confirmed it. ¹H NMR (400 MHz, DMSO-d₆): b 9.07 (d, J=2.4 Hz, 1H), 8.90 (d, J=2.4 Hz, 1H), 8.29 (s, 1H), 5.37-5.28 (m, 1H), 4.25-4.18 (m, 4H), 1.41 (s, 9H).

Step 2: tert-butyl 3-(5-oxo-8-(4-(trifluoromethoxy) phenyl)pyrido[3,4-b]pyrazin-6(5H)-yl)azetidine-1-carboxylate

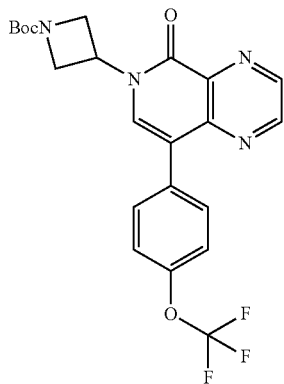 [SMILES: CC(C)(C)OC(=O)N1CC(n2cc(-c3ccc(OC(F)(F)F)cc3)c3nccnc3c2=O)C1]

To a solution of tert-butyl 3-(8-bromo-5-oxopyrido[3,4-b]pyrazin-6(5H)-yl)azetidine-1-carboxylate (370 mg, 0.970 mmol) and (4-(trifluoromethoxy)phenyl)boronic acid (299 mg, 1.46 mmol) in dioxane (5 mL) and H₂O (1 mL) was added K₂CO₃ (268 mg, 1.94 mmol) and Pd(dppf)Cl₂ (71 mg, 0.097 mmol). The mixture was stirred at 80° C. for 12 h under N₂ atmosphere. The reaction mixture was diluted with H₂O (10 mL) and extracted with ethyl acetate (10 mL×3). The combined organic layers were washed with brine (50 mL), dried over anhydrous Na₂SO₄, filtered and concentrated under reduced pressure to give a residue. The residue was purified by column chromatography on silica gel (0-50% ethyl acetate in petroleum ether) to afford the title compound (370 mg, 82%) as a white solid. ¹H NMR (400 MHz, DMSO-d₆): δ 8.99 (d, J=2.0 Hz, 1H), 8.90 (d, J=2.0 Hz, 1H), 7.97 (s, 1H), 7.78-7.69 (m, 2H), 7.46 (d, J=8.0 Hz, 2H), 5.46-5.39 (m, 1H), 4.33-4.24 (m, 4H), 1.41 (s, 9H).

Step 3: 6-(azetidin-3-yl)-8-(4-(trifluoromethoxy) phenyl)pyrido[3,4-b]pyrazin-5(6H)-one

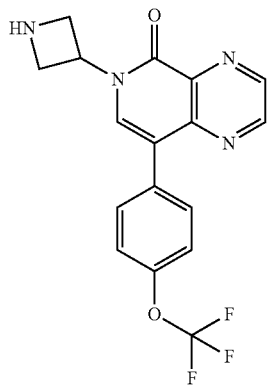 [SMILES: O=c1c2nccnc2c(-c2ccc(OC(F)(F)F)cc2)cn1C1CNC1]

A mixture of tert-butyl 3-(5-oxo-8-(4-(trifluoromethoxy) phenyl)pyrido[3,4-b]pyrazin-6(5H)-yl)azetidine-1-carboxylate (100 mg, 0.21 mmol) and 5% TFA in HFIP (2 mL) was stirred at room temperature for 12 h under N₂ atmosphere. The reaction mixture was poured into aq.NaHCO₃ (10 mL) and extracted with ethyl acetate (20 mL×2), dried over Na₂SO₄ and concentrated under reduced pressure to afford the title compound (60 mg, crude) as a light yellow solid. The residue was used directly for next step.

Intermediate T 5-(Azetidin-3-yl)-3-methyl-7-(4-(trifluoromethoxy) phenyl)-3,5-dihydro-4H-imidazo[4,5-c]pyridin-4-one

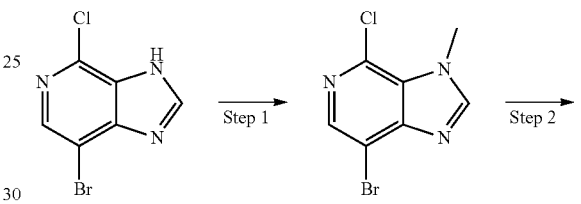

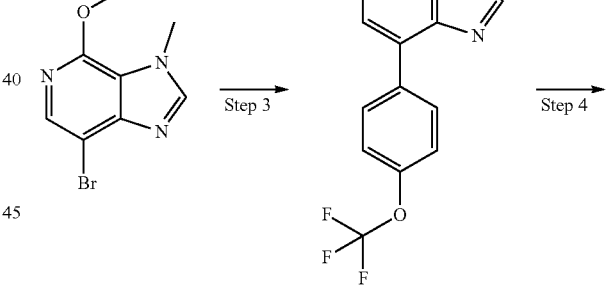

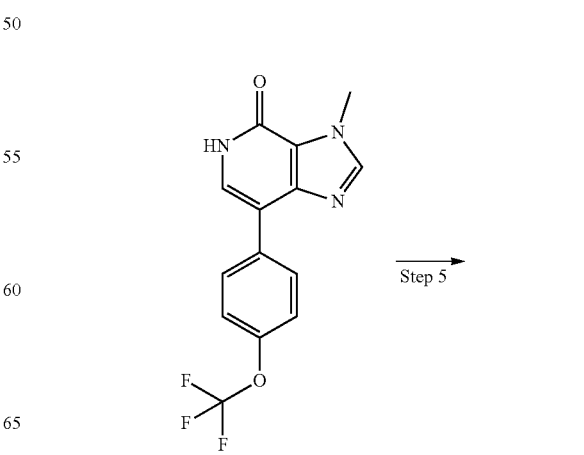

-continued

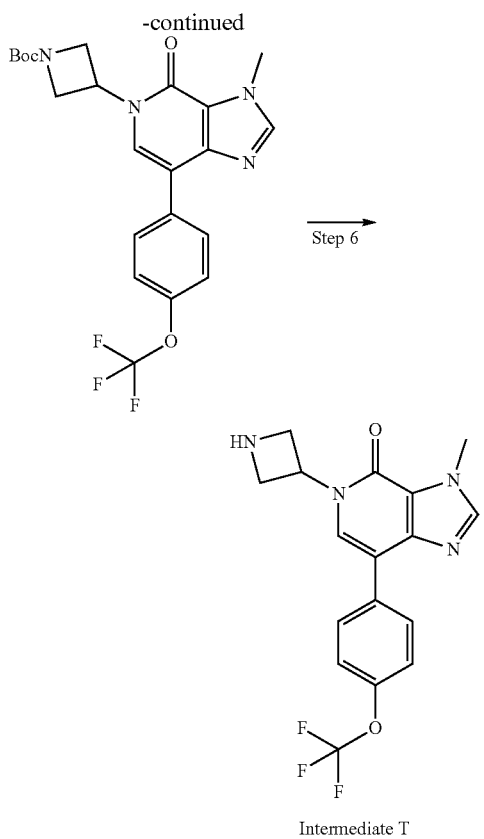

Intermediate T

Step 1: 7-bromo-4-chloro-3-methyl-3H-imidazo[4,5-c]pyridine

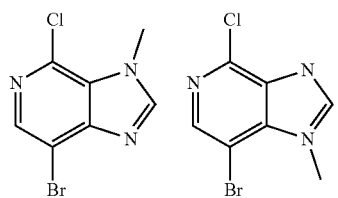

To a solution of 7-bromo-4-chloro-3H-imidazo[4,5-c]pyridine (5.0 g, 21.51 mmol) in DMF (50 mL) was added K₂CO₃ (6.0 g, 43.02 mmol) and MeI (5.4 mL, 86.03 mmol) at room temperature, the mixture was stirred at 60° C. for 1 hour under N₂ atmosphere. The mixture was quenched with water (100 mL), extracted with ethyl acetate (100 mL×3), the organic layers were washed with water (50 mL×5), dried over Na₂SO₄, filtered and concentrated. The residue was purified by flash chromatography on silica gel (0-70% ethyl acetate in petroleum ether) to afford a mixture of desired compound and the region-isomer 7-bromo-4-chloro-1-methyl-1H-imidazo[4,5-c]pyridine (5.0 g, 94%) as a yellow solid, ¹H NMR showed the ratio 1:1, and the region-isomers are not separated by column. ¹H NMR (400 MHz, CDCl₃): δ 8.32 (s, 1H), 8.26 (s, 1H), 8.04 (s, 1H), 7.94 (s, 1H), 4.19 (s, 3H), 4.18 (s, 3H). LCMS (ESI): m/z 245.7 (M+H)⁺.

Step 2: 7-bromo-4-methoxy-3-methyl-3H-imidazo [4,5-c]pyridine

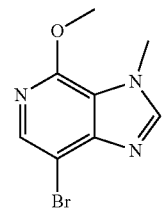

To a solution of region-isomers 7-bromo-4-chloro-3-methyl-3H-imidazo[4,5-c]pyridine and 7-bromo-4-chloro-1-methyl-1H-imidazo[4,5-c]pyridine (5.0 g, 20.12 mmol) in methanol (80 mL) was added KOH (5.7 g, 100.61 mmol) at room temperature. The mixture was stirred at 75° C. for 16 hours. The mixture was concentrated, diluted with water (50 mL), extracted with ethyl acetate (40 mL×3), the organic layers were washed with water(50 mL×3), dried over Na₂SO₄ and concentrated. The residue was purified by chromatography on silica gel (0-71% ethyl acetate in petroleum ether) to afford the title compound (1.45 g, 30%) as a white solid, 2D-NMR confirmed the configuration. ¹H NMR (400 MHz, CDCl₃): δ 7.98 (s, 1H), 7.86 (s, 1H), 4.07 (s, 3H), 4.05 (s, 3H); LCMS (ESI): m/z 241.7 (M+H)⁺.

Step 3: 4-methoxy-3-methyl-7-(4-(trifluoromethoxy) phenyl)-3H-imidazo[4,5-c]pyridine

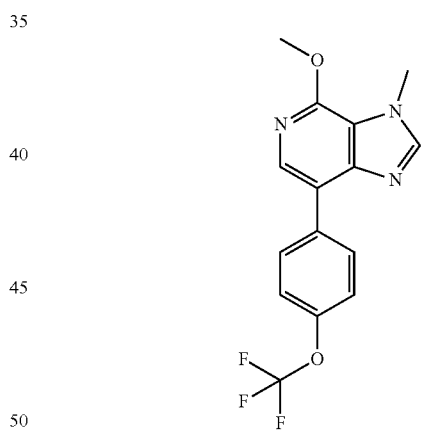

A solution of 7-bromo-4-methoxy-3-methyl-3H-imidazo [4,5-c]pyridine (500 mg, 2.07 mmol) and (4-(trifluoromethoxy)phenyl)boronic acid (510 mg, 2.48 mmol), K₃PO4 (1.1 g, 5.16 mmol) and Pd(dppf)Cl₂ (151 mg, 0.21 mmol) in 1,4-dioxane (10 mL) and water (2 mL) was stirred at 100° C. for 1 hour under N₂ atmosphere. The mixture was diluted with water (20 mL), extracted with ethyl acetate (20 mL×3), the organic layer was washed with water (40 mL×3), dried over Na₂SO₄ and concentrated. The residue was purified by flash chromatography on silica gel (0-40% ethyl acetate in petroleum ether) to afford the title compound (590 mg, 88%) as a white solid. ¹H NMR (400 M Hz, CDCl₃): δ 8.06 (s, 1H), 7.95 (d, J=8.4 Hz, 2H), 7.89 (s, 1H), 7.34 (d, J=8.4 Hz, 2H), 4.15 (s, 3H), 4.11 (s, 3H); LCMS (ESI): m/z 323.9 (M+H)⁺.

Step 4: 3-methyl-7-(4-(trifluoromethoxy)phenyl)-3,5-dihydro-4H-imidazo[4,5-c]pyridin-4-one

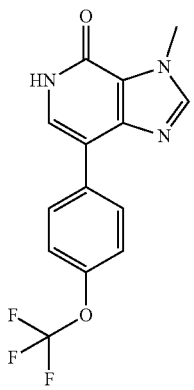

A mixture of HBr (4.0 mL, 1.83 mmol, 40% in H₂O) and 4-methoxy-3-methyl-7-(4-(trifluoromethoxy)phenyl)-3H-imidazo[4,5-c]pyridine (590 mg, 1.83 mmol) in EtOH (8 mL) was stirred at 100° C. for 1 hour. The mixture was quenched with sat.NaHCO₃ (150 mL), extracted with ethyl acetate (100 mL×3), the organic layer was washed with water (150 mL×3), dried over Na₂SO₄ and concentrated to afford the title compound (430 mg, 76%) as a white solid. $^1$H NMR (400 MHz, DMSO-$d_6$): δ 11.60 (d, J=4.8 Hz, 1H), 8.21 (s, 1H), 8.09 (d, J=8.8 Hz, 2H), 7.43-7.39 (m, 3H), 4.06 (s, 3H); LCMS (ESI): m/z 309.9 (M+H)⁺.

Step 5: tert-butyl 3-(3-methyl-4-oxo-7-(4-(trifluoromethoxy)phenyl)-3,4-dihydro-5H-imidazo[4,5-c]pyridin-5-yl)azetidine-1-carboxylate

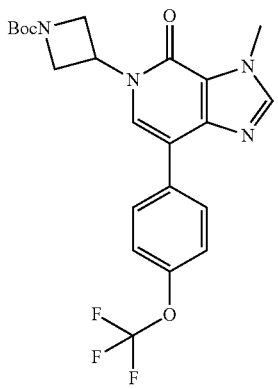 [SMILES: Cn1cnc2c(-c3ccc(OC(F)(F)F)cc3)cn(C3CN(C(=O)OC(C)(C)C)C3)c(=O)c21]

A mixture of 3-methyl-7-(4-(trifluoromethoxy)phenyl)-3,5-dihydro-4H-imidazo[4,5-c]pyridin-4-one (430 mg, 1.39 mmol), K₂CO₃ (576 mg, 4.17 mmol) and tert-butyl 3-bromoazetidine-1-carboxylate (492 mg, 2.09 mmol) in DMF (7 mL) was stirred at 100° C. for 16 hours. The mixture was quenched with water (10 mL), extracted with ethyl acetate (10 mL×3), the organic layer was washed with water (20 mL×3), dried over Na₂SO₄, concentrated. The residue was purified by flash chromatography on silica gel (0-41% ethyl acetate in petroleum ether) to afford the title compound (280 mg, 43%) as a white solid, 2D-NMR confirmed it. $^1$H NMR (400 MHz, CDCl₃) δ 7.86-7.83 (m, 3H), 7.49 (s, 1H), 7.33 (d, J=8.4 Hz, 2H), 5.85-5.79 (m, 1H), 4.53-4.48 (m, 2H), 4.17 (s, 3H), 4.14-4.10 (m, 2H), 1.48 (s, 9H); LCMS (ESI): m/z 465.5 (M+H)⁺.

Step 6: 5-(azetidin-3-yl)-3-methyl-7-(4-(trifluoromethoxy)phenyl)-3,5-dihydro-4H-imidazo[4,5-c]pyridin-4-one

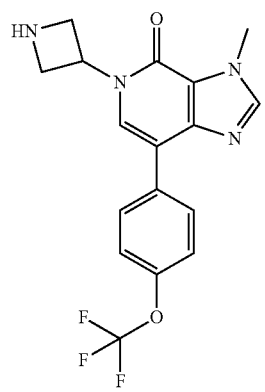 [SMILES: Cn1cnc2c(-c3ccc(OC(F)(F)F)cc3)cn(C3CNC3)c(=O)c21]

A solution of tert-butyl 3-(3-methyl-4-oxo-7-(4-(trifluoromethoxy)phenyl)-3,4-dihydro-5H-imidazo[4,5-c]pyridin-5-yl)azetidine-1-carboxylate (230 mg, 0.50 mmol) and 5% TFA in HFIP (6.0 mL) was stirred at room temperature for 16 hours. The solution was quenched with sat.NaHCO₃ (10 mL), extracted with ethyl acetate (10 mL×3), the combined organic layers were washed with water (20 mL×3), dried over Na₂SO₄, filtered and concentrated to afford the title compound (180 mg, crude) as a yellow oil. LCMS (ESI): m/z 365.0 (M+H)⁺.

Intermediate U

Methyl 4-bromo-1H-benzo[d]imidazole-6-carboxylate

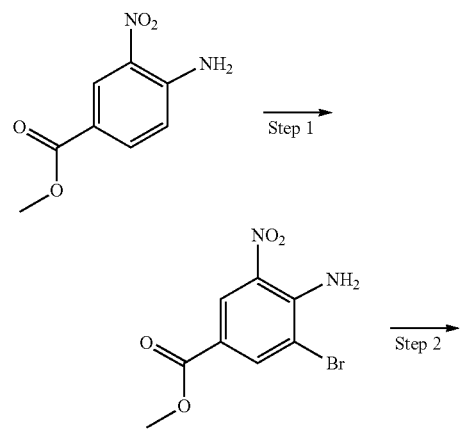

Step 1: methyl 4-amino-3-bromo-5-nitrobenzoate

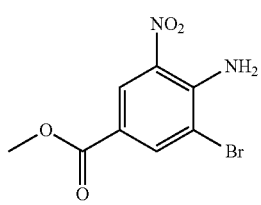

To a solution of methyl 4-amino-3-nitrobenzoate (50.0 g, 204 mmol) in DCM (500 mL) was added Br₂(21 mL, 382.34 mmol) at 0° C., then the solution was stirred at 40° C. for 2 hours. The reaction was quenched with sat.Na₂SO₃ (1.5 L) and extracted with ethyl acetate (500 mL×3). The organics were combined, dried over sodium sulfate, filtered and concentrated to afford the title compound (70.0 g, crude) as a yellow solid. $^1$H NMR (400 MHz, CDCl₃): δ 8.85 (d, J=1.6 Hz, 1H), 8.35 (d, J=1.6 Hz, 11H), 3.92 (s, 3H).

Step 2: methyl 3,4-diamino-5-bromobenzoate

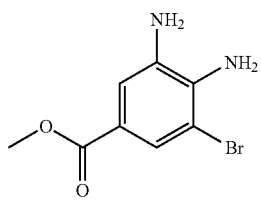

A solution of methyl 4-amino-3-bromo-5-nitrobenzoate (50.0 g, 181.78 mmol), NH₄Cl (48.6 g, 908.89 mmol) and iron power (50.8 g, 908.89 mmol) in EtOH (500 mL) was stirred at 70° C. for 2 h. The reaction mixture was filtered and the filtrate was diluted with ethyl acetate (2 L) and washed with water (1 L×3), the organic layer was dried over Na₂SO₄ and concentrated under vacuum to afford the title compound (40.0 g, crude) as a yellow solid. The crude was used for next step without further purification. $^1$H NMR (400 MHz, CDCl₃) δ 7.74 (d, J=1.6 Hz, 1H), 7.35 (d, J=1.6 Hz, 1H), 4.24 (s, 2H), 3.86 (s, 3H), 3.66 (s, 2H).

Step 3: methyl 4-bromo-1H-benzo[d]imidazole-6-carboxylate

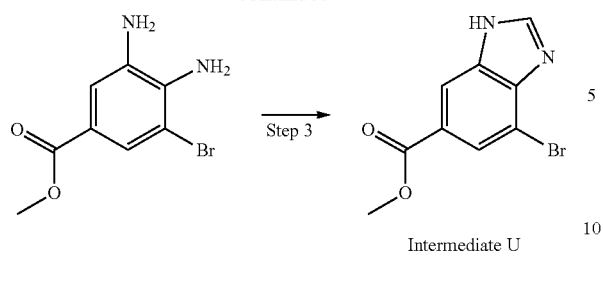

Intermediate U

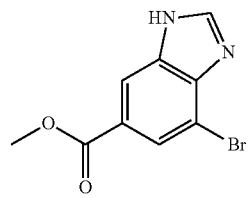

A mixture of methyl 3,4-diamino-5-bromobenzoate (75.0 g, 306.04 mmol), 4-methylbenzenesulfonic acid hydrate (5.8 g, 30.6 mmol), triethoxymethane (102 mL, 612.07 mmol) in THF (1 L) was stirred at room temperature for 16 h. The mixture was concentrated under vacuum, the residue was diluted with ethyl acetate (100 mL) and the solution was stirred at room temperature for 10 min. Then the mixture was filtered to afford the title compound (75.0 g, crude) as a white solid. $^1$H NMR (400 MHz, DMSO-d₆): δ 9.11 (s, 1H), 8.70 (d, J=1.2 Hz, 1H), 8.49 (d, J=1.2 Hz, 1H), 4.40 (s, 3H).

Intermediate V

Methyl 1-methyl-4-(4-(trifluoromethoxy)phenyl)-1H-benzo[d]imidazole-6-carboxylate

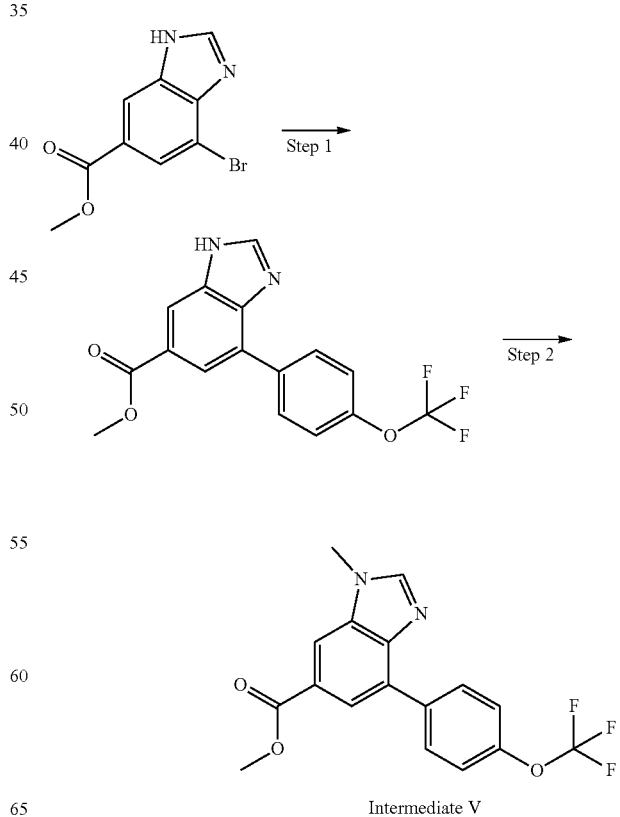

Intermediate V

303

Step 1: methyl 4-(4-(trifluoromethoxy)phenyl)-1H-benzo[d]imidazole-6-carboxylate

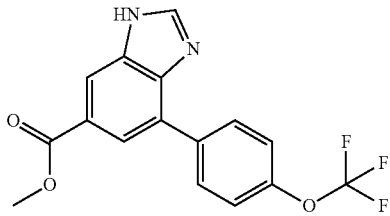 [SMILES: COC(=O)c1cc(-c2ccc(OC(F)(F)F)cc2)c2nc[nH]c2c1]

A solution of methyl 4-bromo-1H-benzo[d]imidazole-6-carboxylate (100.0 g, 392.05 mmol), Pd(dppf)Cl₂ (14.0 g, 19.62 mmol), (4-(trifluoromethoxy)phenyl)boronic acid (89.0 g, 431.25 mmol) and K₃PO₄ (166 g, 784.1 mmol) in 1,4-dioxane (1.5 L) and water (40 mL) was stirred at 100° C. for 16 h under N₂ atmosphere. After filtration, the filtrate was concentrated under reduced pressure. The residue was diluted with water (1 L) and extracted with ethyl acetate (1 L×3), the combined organic layers were dried over anhydrous Na₂SO₄ and concentrated under vacuum. The residue was purified by chromatography on silica gel (0-50% EE (ethyl acetate:EtOH=3:1) in petroleum ether) to afford the title compound (100.0 g, 76%) as a white solid. ¹H NMR (400 MHz, CDCl₃) δ 8.38 (s, 1H), 8.27 (s, 1H), 8.12 (s, 1H), 7.88 (d, J=8.0 Hz, 2H), 7.36 (d, J=8.0 Hz, 2H), 3.98 (s, 3H).

Step 2: methyl 1-methyl-4-(4-(trifluoromethoxy)phenyl)-1H-benzo[d]imidazole-6-carboxylate

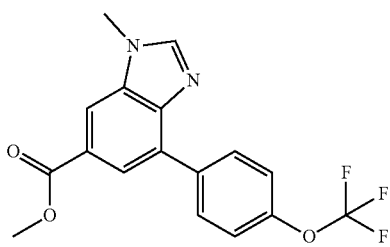 [SMILES: COC(=O)c1cc(-c2ccc(OC(F)(F)F)cc2)c2ncn(C)c2c1]

To a mixture of K₃PO4 (105.0 g, 743.45 mmol) and methyl 4-(4-(trifluoromethoxy)phenyl)-1H-benzo[d]imidazole-6-carboxylate (50.0 g, 148.69 mmol) in DMF (800 mL) was added MeI (24.6 mL, 297.38 mmol) at 0° C. After addition, the resulting mixture was stirred at room temperature for 16 h. The reaction was diluted with ethyl acetate (1 L) and filtered, the filtrate was washed with water (800 mL) and brine (800 mL×3), the organic layer was dried over Na₂SO₄ and concentrated in vacuo. The residue was purified by flash chromatography on silica gel (0-50% ethyl acetate in petroleum ether) to afford the title compound (30.0 g, 57%) as a white solid. ¹H NMR (400 MHz, CDCl₃) δ 58.18 (d, J=1.2 Hz, 1H), 8.15 (d, J=1.2 Hz, 1H), 8.07-8.03 (m, 3H), 7.37 (d, J=8.0 Hz, 2H), 4.00 (s, 3H), 3.97 (s, 3H).

304

Intermediate W 7-Bromo-1-methyl-4-(4-(trifluoromethoxy)phenyl)-1H-benzo[d]imidazol-6-amine

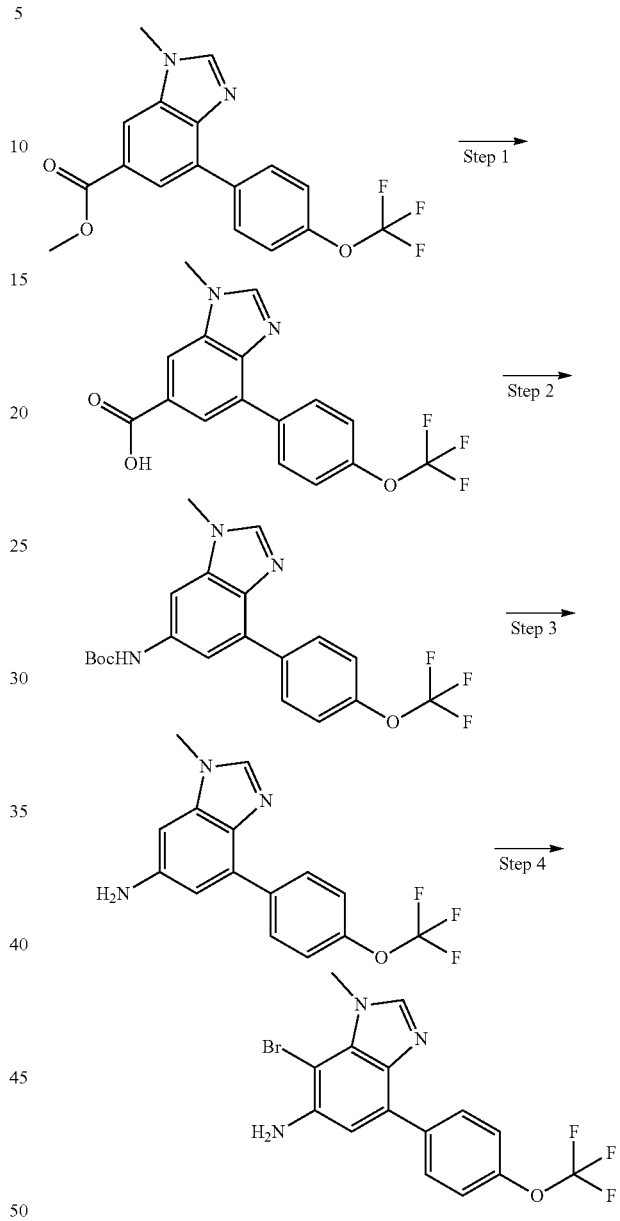

Step 1: 1-methyl-4-(4-(trifluoromethoxy)phenyl)-1H-benzo[d]imidazole-6-carboxylic acid

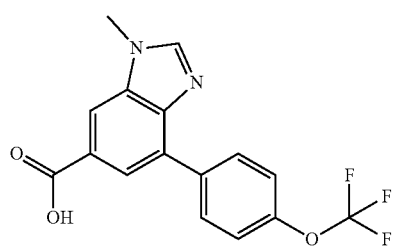 [SMILES: Cn1cnc2c(-c3ccc(OC(F)(F)F)cc3)cc(C(=O)O)cc21]

A mixture of methyl 1-methyl-4-(4-(trifluoromethoxy)phenyl)-1H-benzo[d]imidazole-6-carboxylate (12.0 g, 34.24 mmol) and lithium hydroxide monohydrate (3.3 g, 137.0 mmol) in THF (150 mL) and water (30 mL) was stirred at 40° C. for 16 h. The reaction was diluted with water (500 mL) and adjusted pH=3 with 2 M HCL. The mixture was extracted with ethyl acetate (300 mL×3), the combined organic layers were washed with brine (300 mL×2), dried over Na$_2$SO$_4$ and concentrated under reduced pressure to afford the title compound (10.0 g, 87%) as a white solid. LCMS (ESI): m/z 336.9 (M+H)$^+$.

Step 2: tert-butyl (1-methyl-4-(4-(trifluoromethoxy)phenyl)-1H-benzo[d]imidazol-6-yl)carbamate

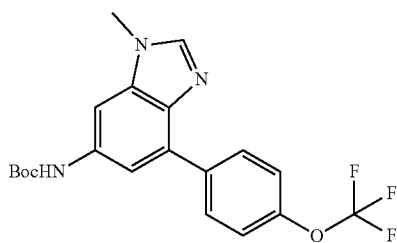 [SMILES: Cn1cnc2c(-c3ccc(OC(F)(F)F)cc3)cc(NC(=O)OC(C)(C)C)cc21]

To a mixture of I-methyl-4-(4-(trifluoromethoxy)phenyl)-1H-benzo[d]imidazole-6-carboxylic acid (10.0 g, 29.76 mmol) in t-BuOH (100 mL) was added DPPA (6.4 mL, 29.7 mmol) and DIPEA (4.5 mL, 32.7 mmol) at room temperature. The mixture was stirred at 80° C. for 16 hours. The reaction was diluted with ethyl acetate (200 mL) and filtered, the filtrate was washed with water (200 mL) and brine (200 mL×3), the organic layer was dried over Na$_2$SO$_4$ and concentrated in vacuo. The residue was purified by flash chromatography on silica gel (0-50% ethyl acetate in petroleum ether) to afford the title compound (10.0 g, 82%) as a white solid. $^1$H NMR (400 MHz, DMSO-d$_6$): δ 9.50 (m, 1H), 8.18-8.13 (m, 3H), 7.83 (s, 1H), 7.52-7.45 (m, 3H), 3.82 (s, 3H), 1.51 (s, 9H).

Step 3: 1-methyl-4-(4-(trifluoromethoxy)phenyl)-1H-benzo[d]imidazol-6-amine

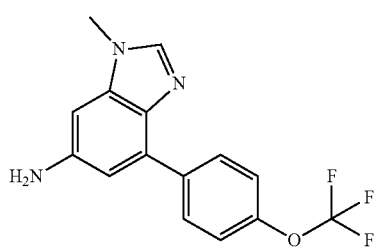 [SMILES: Cn1cnc2c(-c3ccc(OC(F)(F)F)cc3)cc(N)cc21]

To a stirred solution of tert-butyl (1-methyl-4-(4-(trifluoromethoxy)phenyl)-1H-benzo[d]imidazol-6-yl)carbamate (12.0 g, 29.4 mmol) in DCM (120 mL) was added TFA (11 mL, 147.28 mmol) at 0° C. The mixture was stirred at 0° C. for 2 h. The reaction was diluted with water (300 mL) and adjusted pH=8 with sat.NaHCO$_3$, the mixture was extracted with ethyl acetate (300 mL×3), the combined organic layers were dried over Na$_2$SO$_4$ and concentrated under reduced pressure to afford the title compound (9.0 g, crude). The crude product would be directly used in the next step without purification. LCMS (ESI): m/z 308.1 (M+H)$^+$.

Step 4: 7-bromo-1-methyl-4-(4-(trifluoromethoxy)phenyl)-1H-benzo[d]imidazol-6-amine

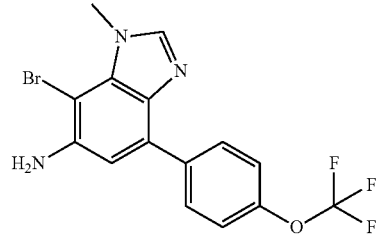 [SMILES: Cn1cnc2c(-c3ccc(OC(F)(F)F)cc3)cc(N)c(Br)c21]

To a solution of 1-methyl-4-(4-(trifluoromethoxy)phenyl)-1H-benzo[d]imidazol-6-amine (9.0 g, 29.29 mmol) in DCM (100 mL) was added NBS (5.2 g, 29.29 mmol) in THF (15 ml) was added at 0° C. The resulting solution was stirred at 0° C. for 10 min under N$_2$ atmosphere. The reaction was quenched with water (200 mL). The mixture was extracted with ethyl acetate (200 mL×3) and washed with brine (200 mL). The combined organic layers were dried over Na$_2$SO$_4$ and concentrated under reduced. The residue was purified by flash chromatography on silica gel (0-50% ethyl acetate in petroleum ether) to afford the title compound (7.0 g, 62%) as a white solid. 2D-NMR confirmed it. $^1$H NMR (400 MHz, DMSO-d$_6$): δ 8.06-8.02 (m, 2H), 7.94 (s, 1H), 7.45 (d, J=8.0 Hz, 2H), 7.00 (s, 1H), 5.30 (s, 2H), 4.03 (s, 3H).

Intermediate X 6-Bromo-1-methyl-4-(4-(trifluoromethoxy)phenyl)-1H-benzo[d]imidazole-7-carbonitrile

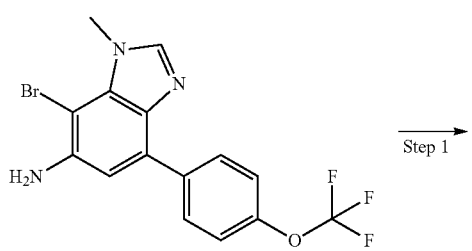

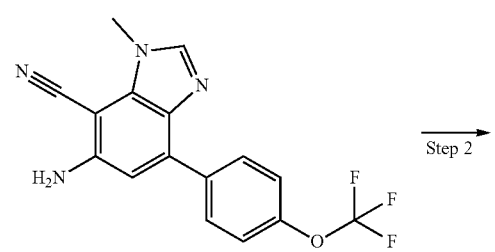

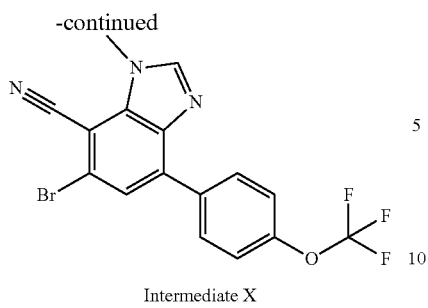

Intermediate X

Step 1: 6-amino-1-methyl-4-(4-(trifluoromethoxy)phenyl)-1H-benzo[d]imidazole-7-carbonitrile

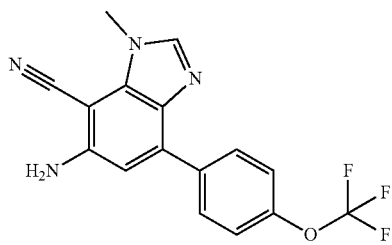 [SMILES: Cn1cnc2c(-c3ccc(OC(F)(F)F)cc3)cc(N)c(C#N)c21]

To a mixture of 7-bromo-1-methyl-4-(4-(trifluoromethoxy)phenyl)-1H-benzo[d]imidazol-6-amine and (1.4 g, 3.63 mmol) and Zn(CN)₂ in DMAc (15 mL) was added t-BuXphos Pd G₃ (288 mg, 0.36 mmol). The mixture was stirred at 140° C. for 16 hours under N₂ atmosphere. The mixture was quenched with water (50 mL), extracted with ethyl acetate (100 mL×3), the organic layer was washed with water (50 mL×2) and brine (50 mL×3), dried over Na₂SO₄ and concentrated. The residue was purified by flash chromatography on silica gel (0-20% ethyl acetate in petroleum ether) to afford the title compound (150 mg, 13%) as a yellow solid. ¹H NMR (400 MHz, CDCl₃): δ 7.97-7.91 (m, 2H), 7.74 (s, 1H), 7.35 (d, J=8.0 Hz, 2H), 6.77 (s, 1H), 4.58 (s, 2H), 4.09 (s, 3H).

Step 2: 6-bromo-1-methyl-4-(4-(trifluoromethoxy)phenyl)-1H-benzo[d]imidazole-7-carbonitrile

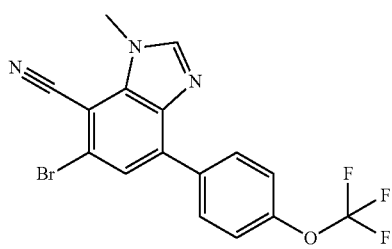 [SMILES: Cn1cnc2c(-c3ccc(OC(F)(F)F)cc3)cc(Br)c(C#N)c21]

To a solution of 6-amino-1-methyl-4-(4-(trifluoromethoxy)phenyl)-1H-benzo[d]imidazole-7-carbonitrile (1.7 g, 5.1 mmol) and CuBr (1.47 g, 10.2 mmol) in MeCN (20 mL) was added t-BuONO (1.2 mL, 10.2 mmol) at room temperature. Then the solution was stirred at 60° C. for 3 hours. The reaction was diluted with water (200 mL) and extracted with ethyl acetate (200 mL×3). The organics were washed with brine (150 mL×2), dried over sodium sulfate, filtered and concentrated. The residue was purified by flash chromatography on silica gel (0-25% ethyl acetate in petroleum ether) to afford the title compound (1.0 g, 49%) as a white solid. ¹H NMR (400 MHz, CDCl₃): δ 8.01 (d, J=8.8 Hz, 2H), 7.96 (s, 1H), 7.69 (s, 1H), 7.38 (d, J=8.0 Hz, 2H), 4.20 (s, 3H).

Intermediate Y (8-(4-(Trifluoromethyl)phenoxy)quinolin-6-yl)methanamine

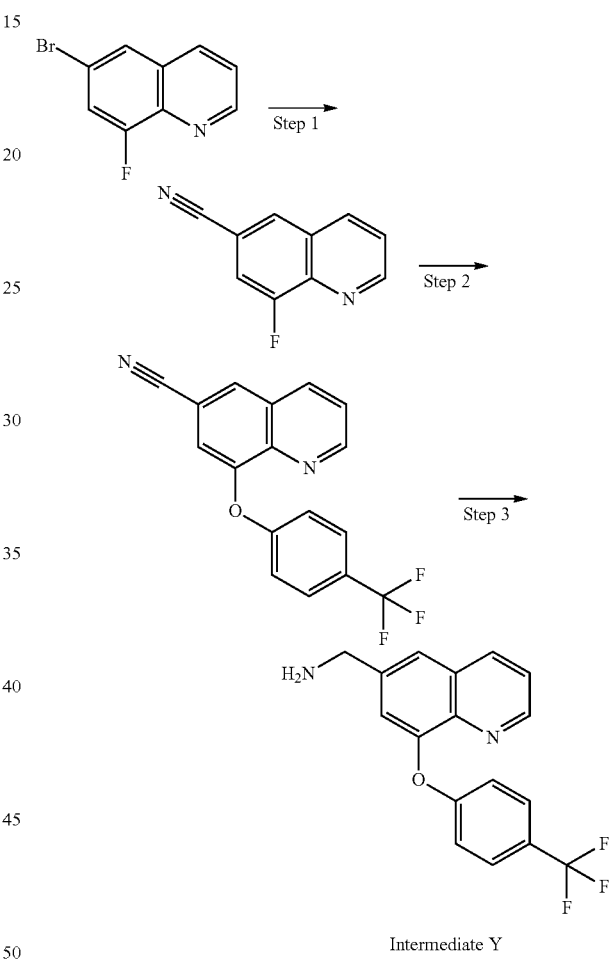

Intermediate Y

Step 1: 8-fluoroquinoline-6-carbonitrile

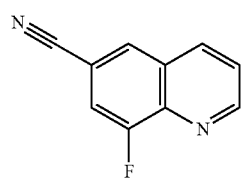 [SMILES: N#Cc1cc(F)c2ncccc2c1]

A solution of 6-bromo-8-fluoroquinoline (25.0 g, 110.6 mmol), Pd(PPh₃)₄ (12.78 g, 11.06 mmol) and ZnCN (15.36 g, 168.1 mmol) in DMF (100 mL) was stirred at 150° C. for 3 h under N₂ atmosphere. After filtration, the filtrate cake was worked up with the water phase. The solution was extracted with ethyl acetate (1 L) and water (1 L×3). The organic layer was dried over Na₂SO₄ and concentrated. The residue was purified by flash chromatography on silica gel (0-30% ethyl acetate in petroleum ether) to afford the title compound (16.6 g, 87%) as a light yellow solid. ¹H NMR (400 MHz, DMSO-d₆): δ 9.14 (dd, J=4.0, 1.6 Hz, 1H), 8.59-8.54 (m, 2H), 8.11-8.08 (m, 1H), 7.82 (dd, J=8.4, 4.0 Hz, 11H).

Step 2: 8-(4-(trifluoromethyl)phenoxy)quinoline-6-carbonitrile

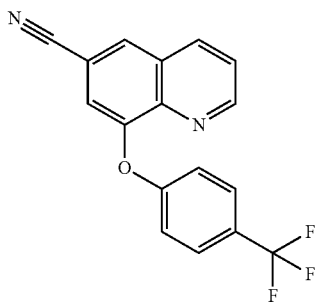 [SMILES: N#Cc1cc(Oc2ccc(C(F)(F)F)cc2)c2ncccc2c1]

A solution of 8-fluoroquinoline-6-carbonitrile (8.0 g, 46.47 mmol), 4-(trifluoromethyl)phenol (9.04 g, 55.76 mmol) and Cs₂CO₃ (37.85 g, 116.17 mmol) in DMF (200 mL) was stirred at 90° C. under N₂ atmosphere for 16 hours. The reaction mixture was diluted with ethyl acetate (500 mL), the combined organic layers were washed with brine (300 mL×3). The organic layer was dried over Na₂SO₄ and concentrated in vacuo. The residue was purified by flash column chromatography on silica gel (0-25% ethyl acetate in petroleum ether) to afford the title compound (12.0 g, 82%) as a white solid. LCMS (ESI): m/z 315.1 (M+H)⁺.

Step 3: (8-(4-(trifluoromethyl)phenoxy)quinolin-6-yl)methanamine

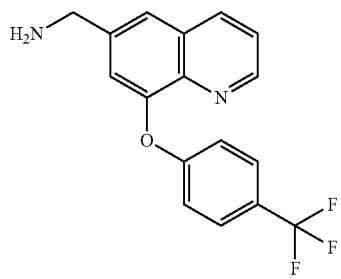 [SMILES: NCc1cc(Oc2ccc(C(F)(F)F)cc2)c2ncccc2c1]

A solution of Raney Ni (112 mg, 1.91 mmol) and 8-(4-(trifluoromethyl)phenoxy)quinoline-6-carbonitrile (6.0 g, 19.09 mmol) in methanol (70 mL) and NH₃H₂O (30 mL) was stirred at room temperature for 16 hours under H₂ balloon. After filtration, the mixture was concentrated to afford the title compound (6.0 g, crude) as a brown solid. LCMS (ESI): m/z 319.1 (M+H)⁺.

Example 1

N-((4-(Hydroxymethyl)-7-(4-(trifluoromethoxy)phenyl)-2,3-dihydrobenzofuran-5-yl)methyl)acrylamide (Compound 12)

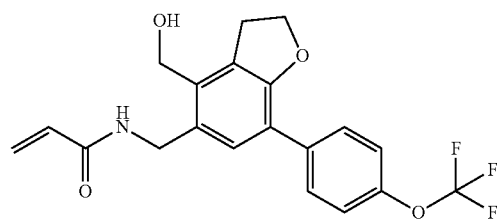 [SMILES: C=CC(=O)NCc1cc(-c2ccc(OC(F)(F)F)cc2)c2c(c1CO)CCO2]

Step 1: Methyl 5-amino-7-(4-(trifluoromethoxy)phenyl)-2,3-dihydrobenzofuran-4-carboxylate

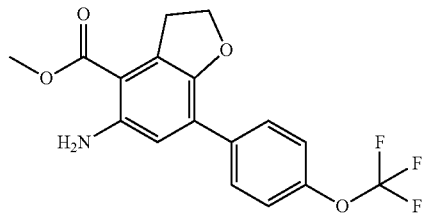 [SMILES: COC(=O)c1c(N)cc(-c2ccc(OC(F)(F)F)cc2)c2c1CCO2]

A mixture of (4-(trifluoromethoxy)phenyl)boronic acid (1.1 g, 5.3 mmol), methyl 5-amino-7-chloro-2,3-dihydrobenzofuran-4-carboxylate (1.0 g, 4.4 mmol), KOAc (860 mg, 8.8 mmol), Xphos (210 mg, 0.44 mmol) and Xphos Pd G₂ (345 mg, 0.44 mmol) in 1,4-Dioxane (20 mL) and Water (2 mL) was stirred at 100° C. for 2 hours under N₂ atmosphere. The reaction was quenched with water (50 mL) and extracted with ethyl acetate (30 mL×2), the combined organic layers were dried over Na₂SO₄ and concentrated. The residue was purified by chromatography on silica gel (0-10% ethyl acetate in petroleum ether) to afford the title compound (1.4 g, 90%) as a yellow solid. ¹H NMR (400 MHz, CDCl₃): δ 7.71 (d, J=8.0 Hz, 2H), 7.27 (d, J=8.0 Hz, 2H), 6.63 (s, 1H), 5.42 (s, 2H), 4.55 (t, J=8.8 Hz, 2H), 3.90 (s, 3H), 3.52 (t, J=8.8 Hz, 2H); LCMS (ESI): m/z 353.9 (M+H)⁺.

Step 2: Methyl 5-bromo-7-(4-(trifluoromethoxy)phenyl)-2,3-dihydrobenzofuran-4-carboxylate

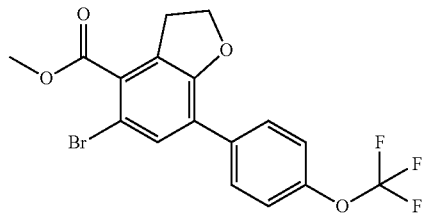 [SMILES: COC(=O)c1c(Br)cc(-c2ccc(OC(F)(F)F)cc2)c2c1CCO2]

To a solution of methyl 5-amino-7-(4-(trifluoromethoxy)phenyl)-2,3-dihydrobenzofuran-4-carboxylate (1.4 g, 4.0 mmol) and CuBr₂ (1.8 g, 8.0 mmol) in MeCN (10 mL) was added t-BuONO (820 mg, 8.0 mmol) under $N_2$ atmosphere, the resulting mixture was stirred for 2 hours at 80° C. The reaction was diluted with water (20 mL) and extracted with ethyl acetate (20 mL×3). The organics were washed with brine (50 mL×2), dried over sodium sulfate, filtered and concentrated. The residue was purified by flash chromatography on silica gel (0-5% ethyl acetate in petroleum ether) to afford methyl the title compound (780 mg, 47%) as a yellow oil. $^1$H NMR (400 MHz, CDCl$_3$): δ 7.71 (d, J=8.8 Hz, 2H), 7.53 (s, 1H), 7.29 (d, J=8.8 Hz, 2H), 4.68 (t, J=8.8 Hz, 2H), 3.97 (s, 3H), 3.42 (t, J=8.8 Hz, 2H).

Step 3: Methyl 5-cyano-7-(4-(trifluoromethoxy)phenyl)-2,3-dihydrobenzofuran-4-carboxylate

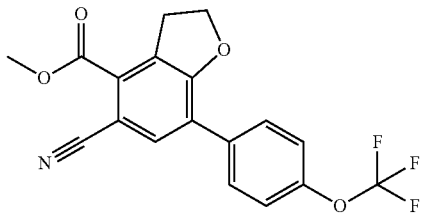 [SMILES: COC(=O)c1c(C#N)cc(-c2ccc(OC(F)(F)F)cc2)c2c1CCO2]

To a solution of methyl 5-bromo-7-(4-(trifluoromethoxy)phenyl)-2,3-dihydrobenzofuran-4-carboxylate (780 mg, 1.9 mmol) in DMF (10 mL) was added CuCN (335 mg, 3.8 mmol). The resulting mixture was stirred at 100° C. for 16 hours. Then the reaction mixture was quenched with water (30 mL) and extracted with ethyl acetate (30 mL×2). The combined organic layers were washed with brine (50 mL×4). The organic layer was dried over Na$_2$SO$_4$ filtered and concentrated. The residue was purified by flash chromatography on silica gel (0-30% ethyl acetate in petroleum ether to afford the title compound (430 mg, 63%) as a white solid. $^1$H NMR (400 MHz, CDCl$_3$): δ 7.77-7.69 (m, 3H), 7.32 (d, J=8.8 Hz, 2H), 4.78 (t, J=8.8 Hz, 2H), 4.02 (s, 3H), 3.65 (t, J=8.8 Hz, 2H).

Step 4: (5-(Aminomethyl)-7-(4-(trifluoromethoxy)phenyl)-2,3-dihydrobenzofuran-4-yl)methanol

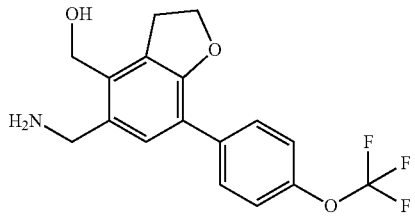 [SMILES: NCc1cc(-c2ccc(OC(F)(F)F)cc2)c2c(c1CO)CCO2]

To a solution of methyl 5-cyano-7-(4-(trifluoromethoxy)phenyl)-2,3-dihydrobenzofuran-4-carboxylate (430 mg, 1.2 mmol) in THF (2 mL) was added LiAlH$_4$ (225 mg, 6.0 mmol) slowly at 0° C. Then the reaction mixture was stirred at 0° C. for 1 hour. The reaction was quenched with sat. aq. KHSO$_4$ and dried over MgSO$_4$. The mixture was filtered and the filtrate was concentrated to afford the title compound (310 mg, 77%) as a yellow oil. The crude was used for next step directly without further purification. $^1$H NMR (400 MHz, DMSO-d$_6$): δ 7.80 (d, J=8.4 Hz, 2H), 7.42 (d, J=8.4 Hz, 2H), 7.29 (s, 1H), 4.59 (t, J=8.8 Hz, 2H), 4.48 (s, 2H), 3.79 (s, 2H), 3.27 (t, J=8.8 Hz, 2H); LCMS (ESI): m/z 323.1 (M-NH$_2$)$^+$.

Step 5: N-((4-(Hydroxymethyl)-7-(4-(trifluoromethoxy)phenyl)-2,3-dihydrobenzofuran-5-yl)methyl)acrylamide

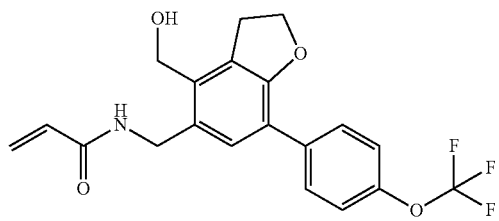 [SMILES: C=CC(=O)NCc1cc(-c2ccc(OC(F)(F)F)cc2)c2c(c1CO)CCO2]

To a solution of (5-(aminomethyl)-7-(4-(trifluoromethoxy)phenyl)-2,3-dihydrobenzofuran-4-yl)methanol (310 mg, 0.9 mmol) and sat. aq. NaHCO$_3$(I mL) in THF (5 mL) was added acryloyl chloride (0.08 mL, 1.0 mmol) at 0° C. Then the reaction was stirred at 0° C. for 1 hour. The reaction was diluted with water (20 mL) and extracted with ethyl acetate (10 mL×3). The organics were washed with brine (10 mL×2), dried over sodium sulfate, filtered and concentrated. The resulting residue was purified by reverse phase chromatography (Welch Xtimate C18 150*25 mm*5 um, acetonitrile 40-70% /water (0.225% FA)-ACN) to afford the title compound (118.29 mg, 33%) as a white solid. $^1$H NMR (400 MHz, DMSO-d$_6$): δ 5 8.40 (t, J=5.2 Hz, 1H), 7.76 (d, J=8.4 Hz, 2H), 7.43 (d, J=8.4 Hz, 2H), 7.25 (s, 1H), 6.23 (dd, J=16.8, 10.0 Hz, 1H), 6.10 (dd, J=16.8, 2.0 Hz, 1H), 5.57 (dd, J=10.0, 2.0 Hz, 1H), 5.04 (t, J=5.6 Hz, 1H), 4.60 (t, J=8.8 Hz, 2H), 4.51 (d, J=5.6 Hz, 2H), 4.43 (d, J=5.6 Hz, 2H), 3.28 (t, J=8.8 Hz, 2H); LCMS (ESI): m/z 416.1 (M+Na)$^+$.

Example 2

2-Chloro-N-((4-(hydroxymethyl)-7-(4-(trifluoromethoxy)phenyl)-2,3-dihydrobenzofuran-5-yl)methyl)acetamide (Compound 25)

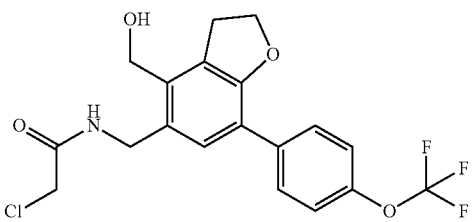 [SMILES: O=C(CCl)NCc1cc(-c2ccc(OC(F)(F)F)cc2)c2c(c1CO)CCO2]

To a solution of (5-(aminomethyl)-7-(4-(trifluoromethoxy)phenyl)-2,3-dihydrobenzofuran-4-yl)methanol (70 mg, 0.21 mmol) in THF (5 mL) was added sat. aq. NaHCO$_3$ (1 mL) and 2-chloroacetyl chloride (25 mg, 0.23 mmol) at 0° C. Then the reaction was stirred at 0° C. for 30 minutes. The reaction was diluted with water (20 mL) and extracted with ethyl acetate (100 mL×3). The organics were washed with brine (100 mL×2), dried over sodium sulfate, filtered and concentrated. The residue was purified by prep-HPLC (Welch Xtimate C18 150*25 mm*5 um, water (0.225% FA)-ACN, 46-76%) to afford the title compound (10.06 mg, 10%) as a white solid. $^1$H NMR (400 MHz, DMSO-d$_6$): δ 8.52 (s, 1H), 7.77 (d, J=8.0 Hz, 2H), 7.43 (d, J=8.0 Hz, 2H), 7.27 (s, 1H), 5.06 (t, J=5.2 Hz, 1H), 4.60 (t, J=8.8 Hz, 2H), 4.51 (d, J=5.2 Hz, 2H), 4.40 (d, J=6.0 Hz, 2H), 4.09 (s, 2H), 3.30 (t, J=8.8 Hz, 2H); LCMS (ESI): m/z 437.8 (M+Na)$^+$.

Example 3

N-((4-(Hydroxymethyl)-7-(4-(trifluoromethoxy)phenyl)-2,3-dihydrobenzofuran-5-yl)methyl)ethenesulfonamide (Compound 19)

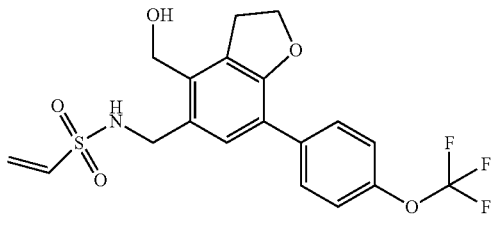 [SMILES: C=CS(=O)(=O)NCc1cc(-c2ccc(OC(F)(F)F)cc2)c2c(c1CO)CCO2]

A mixture of 2-chloroethanesulfonyl chloride (106 mg, 0.65 mmol) and TEA (0.90 mL, 0.65 mmol) in THF (2 mL) was stirred at −78° C. for 1 hour. (5-(aminomethyl)-7-(4-(trifluoromethoxy)phenyl)-2,3-dihydrobenzofuran-4-yl)methanol (200 mg, 0.59 mmol) and TEA (0.80 mL, 0.59 mmol) in THF (3 mL) was added into the reaction mixture at −78° C. The resulting mixture was stirred at room temperature for 2 hours. The reaction mixture was concentrated under vacuum. The resulting residue was purified by reverse phase chromatography (3_Phenomenex Luna C18 75*30 mm*3 um, acetonitrile 65-95%/water(0.2% FA)-ACN) to afford the title compound (8.84 mg, 4%) as white solid. $^1$H NMR (400 MHz, DMSO-d$_6$): δ 7.78 (d, J=8.4 Hz, 2H), 7.53 (s, 1H), 7.44 (d, J=8.4 Hz, 2H), 7.31 (s, 1H), 6.70 (dd, J=16.8, 10.0 Hz, 1H), 6.06 (d, J=16.8 Hz, 1H), 5.98 (d, J=10.0 Hz, 1H), 5.05 (s, 1H), 4.60 (t, J=8.8 Hz, 2H), 4.50 (s, 2H), 4.15 (s, 2H), 3.28 (t, J=8.8 Hz, 2H); LCMS (ESI): m/z 452.0 (M+Na)$^+$.

Example 4

2,3,3-Trideuterio-N-((4-(hydroxymethyl)-7-(4-(trifluoromethoxy)phenyl)-2,3-dihydrobenzofuran-5-yl)methyl]prop-2-enamide (Compound 20)

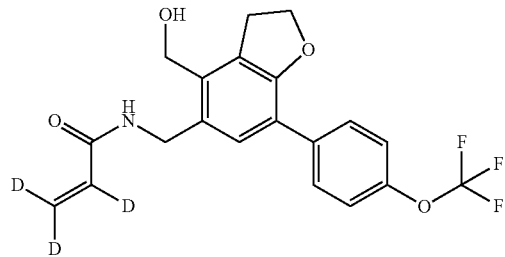 [SMILES: [2H]C([2H])=C([2H])C(=O)NCc1cc(-c2ccc(OC(F)(F)F)cc2)c2c(c1CO)CCO2]

To a solution of (5-(aminomethyl)-7-(4-(trifluoromethoxy)phenyl)-2,3-dihydrobenzofuran-4-yl)methanol (100 mg, 0.29 mmol) and 2,3,3-trideuterioprop-2-enoic acid (27 mg, 0.35 mmol) in DCM (2 mL) was added EEDQ (146 mg, 0.59 mmol) at −78° C. The resulting solution was stirred at room temperature for 2 hours. The reaction solution was concentrated under vacuum. The resulting residue was purified by reverse phase chromatography (Phenomenex Gemi-nutesi-NX C18 75*30 mm*3 um, acetonitrile 40-70% /water (0.225% FA)-ACN) to afford the title compound (41.93 mg, 36%) as a white solid. $^1$H NMR (400 MHz, DMSO-d$_6$): δ 8.35 (t, J=4.8 Hz, 1H), 7.76 (d, J=8.8 Hz, 2H), 7.42 (d, J=8.8 Hz, 2H), 7.25 (s, 1H), 5.01 (t, J=5.6 Hz, 1H), 4.60 (t, J=8.8 Hz, 2H), 4.52 (d, J=5.2 Hz, 2H), 4.44 (d, J=5.6 Hz, 2H), 3.28 (t, J=8.8 Hz, 211); LCMS (ESI): m/z 419.0 (M+Na)$^+$.

Example 5

1-Chloro-N-((4-(hydroxymethyl)-7-(4-(trifluoromethoxy)phenyl)-2,3-dihydrobenzofuran-5-yl)methyl)methanesulfonamide (Compound 14)

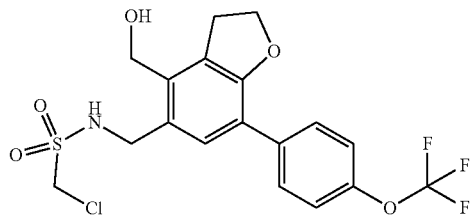 [SMILES: O=S(=O)(CCl)NCc1cc(-c2ccc(OC(F)(F)F)cc2)c2c(c1CO)CCO2]

To a solution of (5-(aminomethyl)-7-(4-(trifluoromethoxy)phenyl)-2,3-dihydrobenzofuran-4-yl)methanol (200 mg, 0.59 mmol) and DIPEA (0.15 mL, 0.88 mmol) in THF (2 mL) was added chloromethanesulfonyl chloride (88 mg, 0.59 mmol) at 0° C. The resulting solution was stirred at room temperature for 16 hours. The reaction was quenched with water (5 mL) and extracted with ethyl acetate (10 mL×2). The combined organic layers were dried over Na$_2$SO$_4$ and concentrated under vacuum. The resulting residue was purified by reverse phase chromatography (Welch Xtimate C18 150*25 mm*5 um, acetonitrile 47-77% /water (FA)-ACN) to afford the title compound (18.12 mg, 7%) as a yellow solid. $^1$H NMR (400 MHz, DMSO-d$_6$): δ 8.02 (t, J=5.6 Hz, 1H), 7.79 (d, J=8.8 Hz, 2H), 7.45 (d, J=8.8 Hz, 2H), 7.38 (s, 1H), 5.07 (t, J=5.6 Hz, 1H), 4.89 (s, 2H), 4.61 (t, J=8.8 Hz, 2H), 4.52 (d, J=5.6 Hz, 2H), 4.32 (d, J=5.6 Hz, 2H), 3.29 (t, J=8.8 Hz, 2H). LCMS (ESI): m/z 450.0 (M−H)$^−$.

Example 6

N-((4-(Hydroxymethyl)-7-(4-(pentafluoro-16-sulfaneyl)phenyl)-2,3-dihydrobenzofuran-5-yl)methyl)acrylamide (Compound 24)

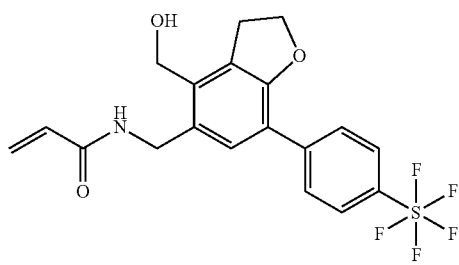 [SMILES: C=CC(=O)NCc1cc(-c2ccc(S(F)(F)(F)(F)F)cc2)c2c(c1CO)CCO2]

Step 1: Methyl 5-amino-7-(4-(pentafluoro-16-sulfaneyl)phenyl)-2,3-dihydrobenzofuran-4-carboxylate

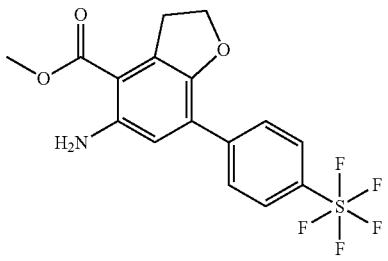 [SMILES: COC(=O)c1c(N)cc(-c2ccc(S(F)(F)(F)(F)F)cc2)c2c1CCO2]

A mixture of 4,4,5,5-tetramethyl-2-(4-(pentafluoro-16-sulfaneyl)phenyl)-1,3,2-dioxaborolane (1.6 g, 4.8 mmol), methyl 5-amino-7-chloro-2,3-dihydrobenzofuran-4-carboxylate (900 mg, 4.0 mmol), KOAc (786 mg, 8.0 mmol), Xphos (190 mg, 0.4 mmol) and Xphos Pd $G_2$ (311 mg, 0.4 mmol) in 1,4-Dioxane (20 mL) and Water (2 mL) was stirred at 100° C. for 16 hours. The reaction was quenched with water (50 mL) and extracted with ethyl acetate (50 mL×2), the organics were washed with brine (50 mL×2), dried over $Na_2SO_4$, filtered and concentrated. The residue was purified by flash column chromatography on silica gel (0-10% ethyl acetate in petroleum ether) to afford the title compound (700 mg, 44%) as an orange oil. $^1$H NMR (400 MHz, CDCl$_3$): δ 7.82-7.72 (m, 4H), 6.69 (s, 1H), 4.57 (t, J=8.8 Hz, 2H), 3.92 (s, 3H), 3.57-3.50 (m, 2H); LCMS (ESI): m/z 396.1 (M+H)$^+$.

Step 2: Methyl 5-bromo-7-(4-(pentafluoro-16-sulfaneyl)phenyl)-2,3-dihydrobenzofuran-4-carboxylate

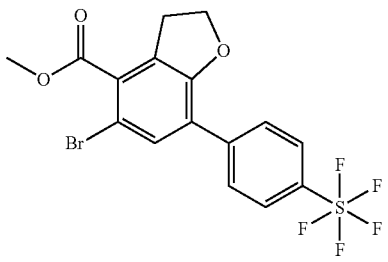 [SMILES: COC(=O)c1c(Br)cc(-c2ccc(S(F)(F)(F)(F)F)cc2)c2c1CCO2]

To a mixture of methyl 5-amino-7-(4-(pentafluoro-16-sulfaneyl)phenyl)-2,3-dihydrobenzofuran-4-carboxylate (700 mg, 1.8 mmol) and CuBr$_2$ (791 mg, 3.6 mmol) in MeCN (10 mL) was added t-BuONO (365 mg, 3.6 mmol) at room temperature under N$_2$ atmosphere. After the addition, the resulting mixture was stirred at 60° C. for 2 hours. The reaction was concentrated under vacuum. The residue was purified by flash column chromatography on silica gel (0-10% ethyl acetate in petroleum ether) to afford the title compound (330 mg, 41%) as a yellow solid. $^1$H NMR (400 MHz, CDCl$_3$): δ 7.82 (d, J=8.8 Hz, 2H), 7.76 (d, J=8.8 Hz, 2H), 7.55 (s, 1H), 4.69 (t, J=8.8 Hz, 2H), 3.97 (s, 3H), 3.43 (t, J=8.8 Hz, 2H).

Step 3: Methyl 5-cyano-7-(4-(pentafluoro-16-sulfaneyl)phenyl)-2,3-dihydrobenzofuran-4-carboxylate

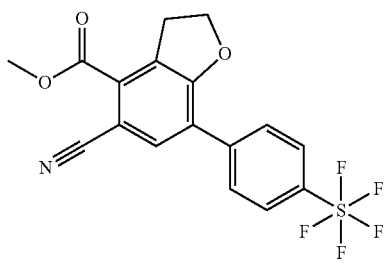 [SMILES: COC(=O)c1c(C#N)cc(-c2ccc(S(F)(F)(F)(F)F)cc2)c2c1CCO2]

To a solution of methyl 5-bromo-7-(4-(pentafluoro-16-sulfaneyl)phenyl)-2,3-dihydrobenzofuran-4-carboxylate (330 mg, 0.7 mmol) in DMF (5 mL) was added CuCN (130 mg, 1.4 mmol). The mixture was stirred at 100° C. for 16 hours. Then the reaction mixture was filtered and the filtrate was concentrated under vacuum. The residue was purified by flash chromatography on silica gel (0-10% ethyl acetate in petroleum ether) to afford the title compound (120 mg, 41%) as a white solid. $^1$H NMR (400 MHz, CDCl$_3$): δ 7.86 (d, J=8.8 Hz, 2H), 7.79 (d, J=8.8 Hz, 2H), 7.77 (s, 1H), 4.80 (t, J=8.8 Hz, 2H), 4.03 (s, 3H), 3.66 (t, J=8.8 Hz, 2H).

Step 4: (5-(Aminomethyl)-7-(4-(pentafluoro-16-sulfaneyl)phenyl)-2,3-dihydrobenzofuran-4-yl)methanol

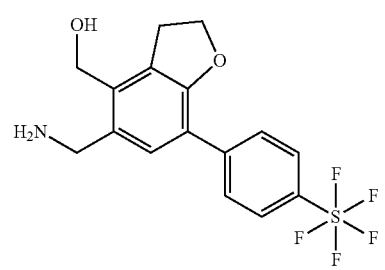 [SMILES: NCc1cc(-c2ccc(S(F)(F)(F)(F)F)cc2)c2c(c1CO)CCO2]

To a mixture of methyl 5-cyano-7-(4-(pentafluoro-16-sulfaneyl)phenyl)-2,3-dihydrobenzofuran-4-carboxylate (110 mg, 0.27 mmol) in THF (5 mL) was added LiAlH$_4$ (52 mg, 1.35 mmol) slowly at 0° C. Then the reaction mixture was stirred at 0° C. for 1 hour. The reaction was quenched with sat. aq. KHSO$_4$ and dried over MgSO$_4$. The mixture was filtered and the filtrate was concentrated to the title compound (60 mg, 58%) as a yellow solid. LCMS (ESI): m/z 364.9 (M-NH$_2$)$^+$.

Step 5: N-((4-(Hydroxymethyl)-7-(4-(trifluoromethoxy)phenyl)-2,3-dihydrobenzofuran-5-yl)methyl)acrylamide

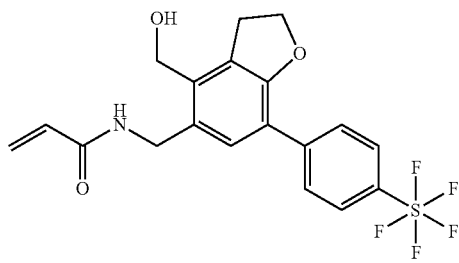 [SMILES: C=CC(=O)NCc1cc(-c2ccc(S(F)(F)(F)(F)F)cc2)c2c(c1CO)CCO2]

To a solution of (5-(aminomethyl)-7-(4-(pentafluoro-16-sulfaneyl)phenyl)-2,3-dihydrobenzofuran-4-yl)methanol (60 mg, 0.16 mmol) in THF (1 mL) was added sat. aq. NaHCO₃ (0.2 mL) and acryloyl chloride (0.10 mL, 0.17 mmol) at 0° C. Then the reaction was stirred at 0° C. for 1 hour. The reaction was diluted with water (10 mL) and extracted with ethyl acetate (10 mL×3). The organics were washed with brine (10 mL×2), dried over sodium sulfate, filtered and concentrated. The resulting residue was purified by reverse phase chromatography (Welch Xtimate C18 150*25 mm*5 um, acetonitrile 42-72% /water(NH₄HCO₃)-ACN) and pre-TLC (50% ethyl acetate in petroleum ether) to afford the title compound (2.45 mg, 4%) as a white solid. ¹H NMR (400 MHz, DMSO-d₆): δ 8.40 (t, J=5.2 Hz, 1H), 7.96 (d, J=8.8 Hz, 2H), 7.87 (d, J=8.8 Hz, 2H), 7.31 (s, 11H), 6.23 (dd, J=17.2, 10.0 Hz, 1H), 6.10 (dd, J=17.2, 2.4 Hz, 1H), 5.59 (dd, J=10.0, 2.4 Hz, 1H), 5.06 (t, J=5.6 Hz, 1H), 4.62 (t, J=8.8 Hz, 2H), 4.52 (d, J=5.6 Hz, 2H), 4.44 (d, J=5.6 Hz, 2H), 3.29 (t, J=8.8 Hz, 2H); LCMS (ESI): m/z 458.0 (M+Na)⁺.

Example 7

N-((7-(2-Fluoro-4-(trifluoromethoxy)phenyl)-4-(hydroxymethyl)-2,3-dihydrobenzofuran-5-yl)methyl)acrylamide (Compound 8)

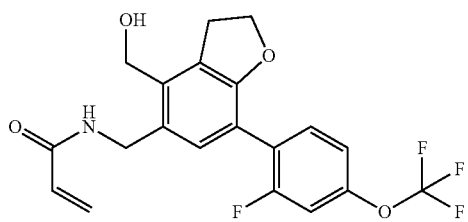 [SMILES: C=CC(=O)NCc1cc(-c2ccc(OC(F)(F)F)cc2F)c2c(c1CO)CCO2]

Step 1: 2-(2-Fluoro-4-(trifluoromethoxy)phenyl)-4,4,5,5-tetramethyl-1,3,2-dioxaborolane

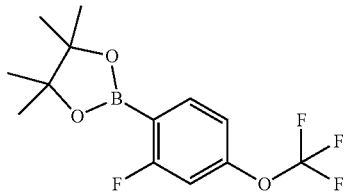 [SMILES: CC1(C)OB(c2ccc(OC(F)(F)F)cc2F)OC1(C)C]

A mixture of 1-bromo-2-fluoro-4-(trifluoromethoxy)benzene (2.5 g, 9.6 mmol), 4,4,4',4',5,5,5',5'-octamethyl-2,2'-bi(1,3,2-dioxaborolane) (2.9 g, 11.6 mmol), KOAc (2.4 g, 24.1 mmol), Pd(dppf)Cl₂ (706 mg, 1.0 mmol) in 1,4-Dioxane (25 mL) was stirred at 90° C. for 16 hours under N₂ atmosphere. Then the solvent was removed in vacuo and the residue was extracted with ethyl acetate (500 mL×3) and water (300 mL). The organic layer was washed with brine (300 mL), dried over anhydrous sodium sulfate and concentrated under reduced pressure. The residue was purified by flash column chromatography on silica gel (0-50% ethyl acetate in petroleum ether) to afford the title compound (1.5 g, 51%) as a white solid. ¹H NMR (400 MHz, CDCl₃): δ 7.80 (dd, J=8.0, 6.8 Hz, 1H), 7.03 (d, J=8.0 Hz, 1H), 6.94 (d, J=9.6 Hz, 1H), 1.38 (s, 12H).

Step 2: Methyl 5-amino-7-(2-fluoro-4-(trifluoromethoxy)phenyl)-2,3-dihydrobenzofuran-4-carboxylate

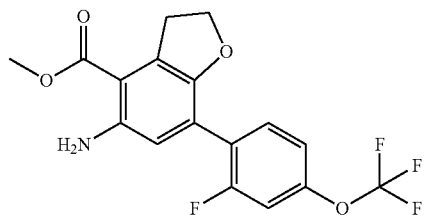 [SMILES: COC(=O)c1c(N)cc(-c2ccc(OC(F)(F)F)cc2F)c2c1CCO2]

A mixture of 2-(2-fluoro-4-(trifluoromethoxy)phenyl)-4,4,5,5-tetramethyl-1,3,2-dioxaborolane (800 mg, 2.6 mmol), methyl 5-amino-7-chloro-2,3-dihydrobenzofuran-4-carboxylate (500 mg, 2.2 mmol), KOAc (431 mg, 4.4 mmol), Xphos (105 mg, 0.2 mmol) and Xphos Pd G₂ (173 mg, 0.2 mmol) in 1,4-Dioxane (10 mL) and Water (1 mL) was stirred at 100° C. for 16 hours under N₂ atmosphere. The reaction was quenched with water (50 mL) and extracted with ethyl acetate (50 mL×2). The organics were washed with brine (50 mL×3), dried over anhydrous sodium sulfate, filtered and concentrated. The residue was purified by flash column chromatography on silica gel (0-6% ethyl acetate in petroleum ether) to afford the title compound (600 mg, 73%) as an orange oil. ¹H NMR (400 MHz, CDCl₃): δ 7.54 (t, J=8.4, 1H), 7.12-7.02 (m, 2H), 6.75 (s, 1H), 4.55 (t, J=8.8 Hz, 2H), 3.92 (s, 3H), 3.54 (t, J=8.8 Hz, 2H); LCMS (ESI): m/z 372.1 (M+H)⁺.

Step 3: Methyl 5-bromo-7-(2-fluoro-4-(trifluoromethoxy)phenyl)-2,3-dihydrobenzofuran-4-carboxylate

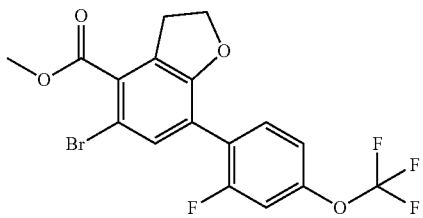 [SMILES: COC(=O)c1c(Br)cc(-c2ccc(OC(F)(F)F)cc2F)c2c1CCO2]

To a mixture of methyl 5-amino-7-(2-fluoro-4-(trifluoromethoxy)phenyl)-2,3-dihydrobenzofuran-4-carboxylate (600 mg, 1.6 mmol) and CuBr$_2$ (722 mg, 3.2 mmol) in acetonitrile (10 mL) was added t-BuONO (333 mg, 3.2 mmol) at room temperature. After the addition, the resulting mixture was stirred at 80° C. for 16 hours. The reaction was concentrated under vacuum. The residue was purified by flash chromatography on silica gel (0-5% Ethyl acetate in petroleum ether) to afford the title compound (600 mg, 85%) as a yellow solid. $^1$H NMR (400 MHz, CDCl$_3$): δ 7.54-7.43 (m, 2H), 7.13-7.05 (m, 2H), 4.63 (d, J=8.8 Hz, 2H), 3.97 (s, 3H), 3.43 (d, J=8.8 Hz, 2H); LCMS (ESI): m/z 435.0 (M+H)$^+$.

Step 4: Methyl 5-cyano-7-(2-fluoro-4-(trifluoromethoxy)phenyl)-2,3-dihydrobenzofuran-4-carboxylate

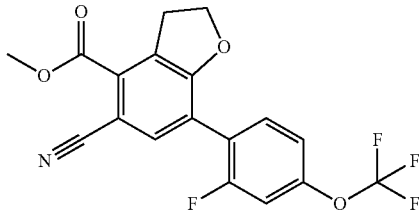 [SMILES: COC(=O)c1c(C#N)cc(-c2ccc(OC(F)(F)F)cc2F)c2c1CCO2]

To a solution of methyl 5-bromo-7-(2-fluoro-4-(trifluoromethoxy)phenyl)-2,3-dihydrobenzofuran-4-carboxylate (300 mg, 0.7 mmol) in DMF (5 mL) was added CuCN (322 mg, 3.6 mmol). The mixture was stirred at 100° C. for 16 hours. The reaction mixture was filtered and the filtrate was concentrated under vacuum. The residue was purified by flash chromatography on silica gel (0-10% ethyl acetate in petroleum ether) to afford the title compound (150 mg, 57%) as a yellow solid. $^1$H NMR (400 MHz, CDCl$_3$): δ 7.69 (s, 1H), 7.53 (t, J=8.0 Hz, 1H), 7.15-7.08 (m, 2H), 4.76 (t, J=8.8 Hz, 2H), 4.03 (s, 3H), 3.65 (t, J=8.8 Hz, 2H); LCMS (ESI): m/z 382.1 (M+H)$^+$.

Step 5: (5-(Aminomethyl)-7-(2-fluoro-4-(trifluoromethoxy)phenyl)-2,3-dihydrobenzofuran-4-yl)methanol

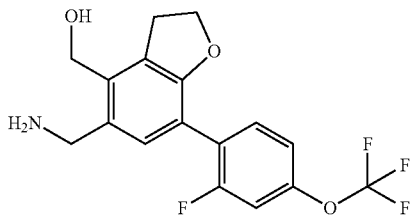 [SMILES: NCc1cc(-c2ccc(OC(F)(F)F)cc2F)c2c(c1CO)CCO2]

To a mixture of methyl 5-cyano-7-(2-fluoro-4-(trifluoromethoxy)phenyl)-2,3-dihydrobenzofuran-4-carboxylate (150 mg, 0.4 mmol) in THF (2 mL) was added LiAlH$_4$ (76 mg, 2.0 mmol) slowly at 0° C. Then the reaction mixture was stirred at 0° C. for 1 hour. The reaction was quenched with sat. aq. KHSO$_4$ and dried over MgSO$_4$. The mixture was filtered and the filtrate was concentrated to afford the title compound (90 mg, 64%) as a yellow solid. LCMS (ESI): m/z 341.1 (M-NH$_2$)$^+$.

Step 6: N-((7-(2-Fluoro-4-(trifluoromethoxy)phenyl)-4-(hydroxymethyl)-2,3-dihydrobenzofuran-5-yl)methyl)acrylamide To a mixture of (5-(aminomethyl)-7-(2-fluoro-4-(trifluoromethoxy)phenyl)-2,3-dihydrobenzofuran-4-yl)nethanol (80 mg, 0.2 mmol), sat. aq. NaHCO$_3$ (0.2 mL) in THF (5 mL) was added acryloyl chloride (20 mg, 0.2 mmol) at 0° C. The reaction was stirred at 0° C. for 2 hours. The mixture was diluted with water (10 mL) and extracted with ethyl acetate (10 mL×3). The organics were washed with brine (10 mL×3), dried over sodium sulfate, filtered and concentrated. The residue was purified by reverse phase chromatography (acetonitrile 49-79/0.225% FA in water) to afford the title compound (11.87 mg, 12%) as a white solid. $^1$H NMR (400 MHz, DMSO-d$_6$): δ 8.40 (t, J=4.8 Hz, 1H), 7.55 (t, J=8.4 Hz, 1H), 7.46 (d, J=10.4 Hz, 1H), 7.31 (d, J=8.4 Hz, 1H), 7.07 (s, 1H), 6.22 (dd, J=17.2, 10.0 Hz, 1H), 6.09 (dd, J=17.2, 2.0 Hz, 11H), 5.58 (dd, J=10.0, 2.0 Hz, 1H), 5.07 (t, J=5.6 Hz, 1H), 4.58-4.49 (m, 4H), 4.42 (d, J=5.6 Hz, 2H), 3.28 (t, J=8.8 Hz, 3H); LCMS (ESI): m/z 434.0 (M+Na)$^+$.

Example 8

N-((4-(Hydroxymethyl)-7-(5-isopropoxythiazol-2-yl)-2,3-dihydrobenzofuran-5-yl)methyl)acrylamide (Compound 22)

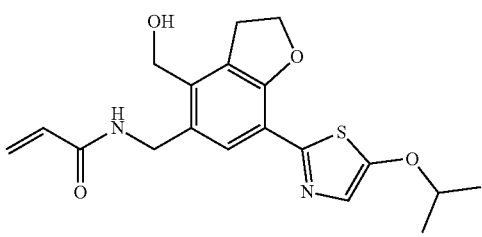 [SMILES: C=CC(=O)NCc1cc(-c2ncc(OC(C)C)s2)c2c(c1CO)CCO2]

Step 1: Methyl 5-amino-7-(5-isopropoxythiazol-2-yl)-2,3-dihydrobenzofuran-4-carboxylate

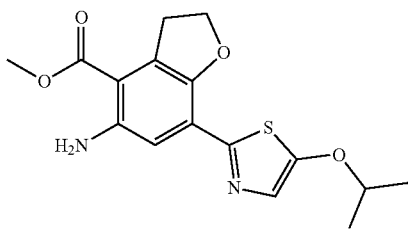 [SMILES: COC(=O)c1c(N)cc(-c2ncc(OC(C)C)s2)c2c1CCO2]

To the mixture of methyl 5-amino-7-chloro-2,3-dihydrobenzofuran-4-carboxylate (1.0 g, 4.39 mmol), Ni(PMe₃)₂Cl2 (124 mg, 0.44 mmol) and CsF (1.33 g, 8.79 mmol), 4,4,4',4',5,5,5',5'-octamethyl-2,2'-bi(1,3,2-dioxaborolane) (1.23 g, 4.83 mmol) in THF (20 mL) was added trimethyl(2,2,2-trifluoroethoxy)silane (1.59 g, 9.23 mmol) at room temperature. The reaction mixture was stirred at 100° C. for 16 hours under a N₂ atmosphere. Then the reaction mixture was cooled to room temperature and 2-bromo-5-isopropoxythiazole (1.07 g, 4.83 mmol), Na₂CO₃ (1.39 g, 13.16 mmol), Pd(dppf)Cl₂ (321 mg, 0.44 mmol) and water (1 mL) were added into the reaction solution. Then the solution was stirred at 100° C. for 2 hours. The reaction was cooled to RT then quenched with water (100 mL) and extracted with ethyl acetate (20 mL×3). The organic layer was dried over Na₂SO₄, filtered and concentrated. The residue was purified by flash chromatography on silica gel (0-30% ethyl acetate in petroleum ether) to afford the title compound (1.4 g, 95%) as a white solid. ¹H NMR (400 MHz, CDCl₃): δ 7.22 (s, 1H), 7.18 (s, 1H), 4.64 (t, J=8.8 Hz, 2H), 4.39-4.27 (m, 1H), 3.83 (s, 3H), 3.46 (t, J=8.8 Hz, 2H), 1.35 (d, J=6.0 Hz, 6H); LCMS (ESI): m/z 335.1 (M+H)⁺.

Step 2: Methyl 5-iodo-7-(5-isopropoxythiazol-2-yl)-2,3-dihydrobenzofuran-4-carboxylate

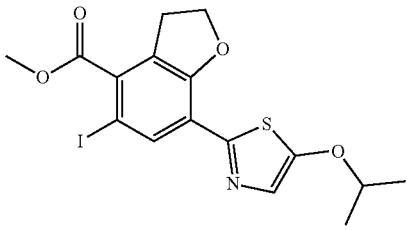 [SMILES: COC(=O)c1c(I)cc(-c2ncc(OC(C)C)s2)c2c1CCO2]

To a mixture of tert-butyl nitrite (0.16 mL, 1.32 mmol) and methyl 5-amino-7-(5-isopropoxythiazol-2-yl)-2,3-dihydrobenzofuran-4-carboxylate (400 mg, 1.2 mmol) in acetonitrile (8 mL) was added CH₂I₂ (0.98 mL, 12.11 mmol) at 0° C. The mixture was stirred at room temperature for 16 hours. The reaction solution was quenched with H₂O (10 mL), extracted with ethyl acetate (20 mL), dried over Na₂SO₄, filtered and concentrated. The residue was purified by flash chromatography on silica gel (0-15% ethyl acetate in petroleum ether) to afford the title compound (130 mg, 24%) as a yellow solid. ¹H NMR (400 MHz, DMSO-d₆): δ 8.31 (s, 1H), 7.40 (s, 1H), 4.78 (t, J=8.8 Hz, 2H), 4.55-4.44 (m, 1H), 3.87 (s, 3H), 3.38 (t, J=8.8 Hz, 2H), 1.33 (d, J=6.4 Hz, 6H).

Step 3: Methyl 5-cyano-7-(5-isopropoxythiazol-2-yl)-2,3-dihydrobenzofuran-4-carboxylate

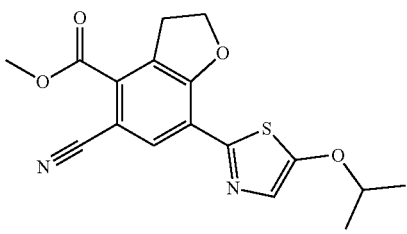 [SMILES: COC(=O)c1c(C#N)cc(-c2ncc(OC(C)C)s2)c2c1CCO2]

To a solution of methyl 5-iodo-7-(5-isopropoxythiazol-2-yl)-2,3-dihydrobenzofuran-4-carboxylate (130 mg, 0.33 mmol) in DMF (5 mL) was added CuCN (60 mg, 0.66 mmol). The mixture was stirred at 80° C. for 16 hours. The reaction mixture was filtered and the filtrate was concentrated under vacuum. The residue was purified by flash chromatography on silica gel (0-15% ethyl acetate in petroleum ether) to afford the title compound (100 mg, 89%) as a yellow solid. ¹H NMR (400 MHz, DMSO-d₆): δ 8.29 (s, 1H), 7.48 (s, 1H), 4.89 (t, J=8.8 Hz, 2H), 4.57-4.47 (m, 1H), 3.91 (s, 3H), 3.56 (t, J=8.8 Hz, 2H), 1.34 (d, J=6.0 Hz, 6H); LCMS (ESI): m/z 345.1 (M+H)⁺.

323

Step 4: (5-(Aminomethyl)-7-(5-isopropoxythiazol-2-yl)-2,3-dihydrobenzofuran-4-yl)methanol

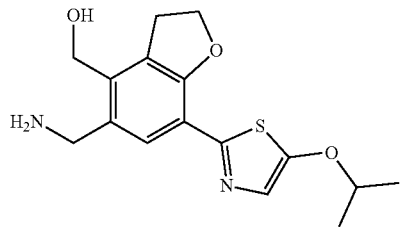 [SMILES: CC(C)Oc1cnc(-c2cc(CN)c(CO)c3c2OCC3)s1]

To a solution of methyl 5-cyano-7-(5-isopropoxythiazol-2-yl)-2,3-dihydrobenzofuran-4-carboxylate (90 mg, 0.26 mmol) in THF (5 mL) was added LiAlH$_4$ (49.6 mg, 1.31 mmol) slowly at 0° C. Then the reaction mixture was stirred at 0° C. for 1 hour. The reaction was quenched with sat. aq. KHSO$_4$ and dried over MgSO$_4$. The mixture was filtered and the filtrate was concentrated to afford the title compound (83 mg, 99%) as a yellow solid. LCMS (ESI): m/z 321.1 (M+H)$^+$.

Step 5: N-((4-(Hydroxymethyl)-7-(5-isopropoxythiazol-2-yl)-2,3-dihydrobenzofuran-5-yl)methyl)acrylamide

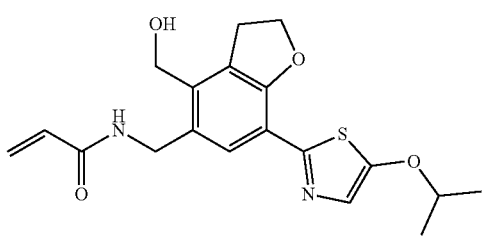 [SMILES: C=CC(=O)NCc1cc(-c2ncc(OC(C)C)s2)c2c(c1CO)CCO2]

To a mixture of (5-(aminomethyl)-7-(5-isopropoxythiazol-2-yl)-2,3-dihydrobenzofuran-4-yl)methanol (60 mg, 0.09 mmol) in THF (5 mL) was added saturated sat. aq. NaHCO$_3$ (0.2 mL) and acryloyl chloride (8.5 mg, 0.09 mmol) at 0° C. The reaction was stirred at 0° C. for 1 hour. The mixture was diluted with water (10 mL) and extracted with ethyl acetate (30 mL×3). The organics were washed with brine (20 mL×2), dried over sodium sulfate, filtered and concentrated. The residue was purified by reverse phase chromatography (acetonitrile 30-60/0.225% FA in water) to afford the title compound (7.83 mg, 22%) as a white solid. $^1$H NMR (400 MHz, DMSO-d$_6$): b 8.49 (t, J=5.2 Hz, 1H), 7.76 (s, 1H), 7.28 (s, 1H), 6.28 (dd, J=16.8, 10.4 Hz, 1H), 6.11 (dd, J=16.8, 2.0 Hz, 1H), 5.61 (dd, J=10.4, 2.0 Hz, 1H), 5.08 (t, J=5.6 Hz, 1H), 4.73 (t, J=8.8 Hz, 2H), 4.51 (d, J=5.6 Hz, 2H), 4.47-4.40 (m, 3H), 3.30 (t, J=8.8 Hz, 2H), 1.32 (d, J=6.0 Hz, 6H); LCMS (ESI): m/z 375.0 (M+H)$^+$.

324

Example 9

(R)—N-(1-(4-(Hydroxymethyl)-7-(4-(trifluoromethoxy)phenyl)-2,3-dihydrobenzofuran-5-yl)ethyl)acrylamide& (S)—N-(1-(4-(hydroxymethyl)-7-(4-(trifluoromethoxy)phenyl)-2,3-dihydrobenzofuran-5-yl)ethyl)acrylamide (Compounds 17-18)

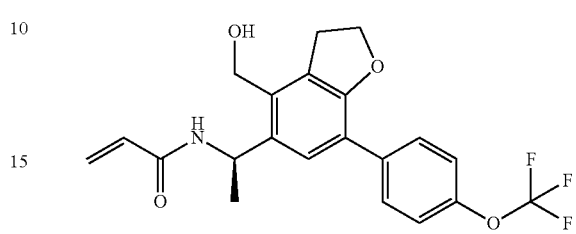

Step 1: Methyl 5-acetyl-7-(4-(trifluoromethoxy)phenyl)-2,3-dihydrobenzofuran-4-carboxylate

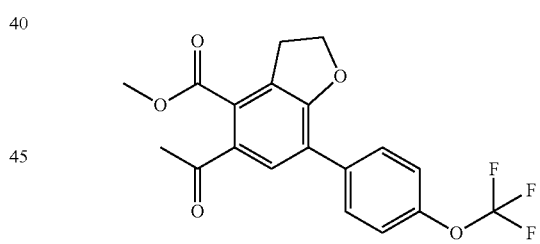

To a solution of methyl 5-bromo-7-(4-(trifluoromethoxy)phenyl)-2,3-dihydrobenzofuran-4-carboxylate (500 mg, 1.2 mmol) in 1,4-Dioxane (6 mL) was added tributyl(1-ethoxyvinyl)stannane (0.81 mL, 2.4 mmol), Pd(PPh$_3$)$_2$Cl$_2$ (253 mg, 0.36 mmol). The mixture was stirred at 100° C. for 2 hours under N$_2$ atmosphere. The reaction was diluted with water (20 mL), the mixture was stirred with dilute aqueous hydrochloric acid (2 M, 40 mL) for 1 hour, extracted with ethyl acetate (50 mL). The organics were washed with water (50 mL), dried over Na$_2$SO$_4$, filtered and concentrated. The residue was purified by column chromatography on silica gel (0-20% ethyl acetate in petroleum ether) to afford the title compound (420 mg, 92% yield) as a yellow solid. $^1$H NMR (400 MHz, CDCl$_3$): δ 7.71 (d, J=8.8 Hz, 2H), 7.67 (s, 1H), 7.31 (d, J=8.8 Hz, 2H), 4.75 (t, J=8.8 Hz, 2H), 3.94 (s, 3H), 3.39 (t, J=8.8 Hz, 2H), 2.58 (s, 3H); LCMS (ESI): m/z 381.1 (M+H)$^+$.

Step 2: 1-(4-(Hydroxymethyl)-7-(4-(trifluoromethoxy)phenyl)-2,3-dihydrobenzofuran-5-yl)ethanol

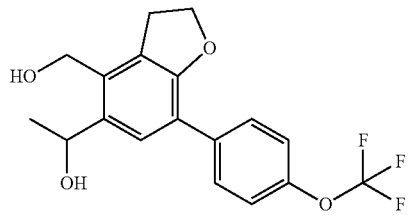

To the mixture of methyl 5-acetyl-7-(4-(trifluoromethoxy)phenyl)-2,3-dihydrobenzofuran-4-carboxylate (320 mg, 0.84 mmol) in THF (10 mL) was added LiAlH$_4$ (160 mg, 4.20 mmol) at 0° C. The reaction mixture was then stirred at 0° C. for 2 hours. The mixture was quenched with water (0.1 mL), 1 M aq. NaOH (0.1 mL) and water (0.1 mL). The resulting mixture was dried over sodium sulfate, filtered and concentrated to afford the title compound (290 mg, 97%) as a yellow solid. $^1$H NMR (400 MHz, DMSO-d$_6$): b 7.78 (d, J=8.8 Hz, 2H), 7.43-7.41 (m, 3H), 5.11-4.98 (m, 3H), 4.58 (t, J=8.8 Hz, 2H), 4.51 (s, 2H), 3.29 (t, J=8.8 Hz, 2H), 1.36 (d, J=6.4 Hz, 3H).

Step 3: 1-(4-(((tert-Butyldimethylsilyl)oxy)methyl)-7-(4-(trifluoromethoxy)phenyl)-2,3-dihydrobenzofuran-5-yl)ethanol

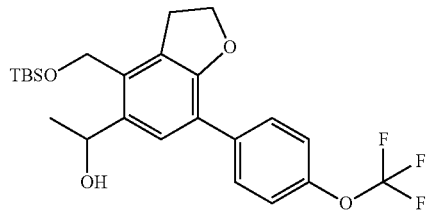 [SMILES: CC(O)c1cc(-c2ccc(OC(F)(F)F)cc2)c2c(c1CO[Si](C)(C)C(C)(C)C)CCO2]

To a solution of 1-(4-(hydroxymethyl)-7-(4-(trifluoromethoxy)phenyl)-2,3-dihydrobenzofuran-5-yl)ethanol (150 mg, 0.42 mmol) and sodium hydride (100 mg, 2.5 mmol, 60% in mineral oil) in THF (10 mL) was stirred at 0° C. for 10 minutes. tert-Butyldimethylsilyl chloride (75 mg, 0.50 mmol) was added into the solution at 0° C. The reaction was stirred at 0° C. for 2 hours. The mixture was quenched with water (10 mL), extracted with ethyl acetate (30 mL×2), the combined organic layers were dried over Na$_2$SO$_4$ and concentrated. The residue was purified by flash chromatography on silica gel (0-15% ethyl acetate in petroleum ether) to afford the title compound (190 mg, 95%) as a colorless oil. $^1$H NMR (400 MHz, DMSO-d$_6$): δ 7.77 (d, J=8.8 Hz, 2H), 7.43-7.41 (m, 3H), 5.07-4.98 (m, 2H), 4.74-4.65 (m, 2H), 4.59 (t, J=8.8 Hz, 2H), 3.30-3.17 (m, 2H), 1.34 (d, J=6.4 Hz, 3H), 0.89 (s, 9H), 0.12 (s, 3H), 0.11 (s, 3H).

Step 4: (5-(1-Azidoethyl)-7-(4-(trifluoromethoxy)phenyl)-2,3-dihydrobenzofuran-4-yl)methanol

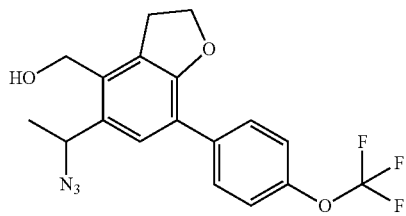 [SMILES: CC(N=[N+]=[N-])c1cc(-c2ccc(OC(F)(F)F)cc2)c2c(c1CO)CCO2]

A mixture of TMSN$_3$ (0.06 mL, 0.48 mmol), Cu(OTf)$_2$ (5.7 mg, 0.02 mmol) and 1-(4-(((tert-butyldimethylsilyl)oxy)methyl)-7-(4-(trifluoromethoxy)phenyl)-2,3-dihydrobenzofuran-5-yl)ethanol (150 mg, 0.32 mmol) in DCM (3 mL) was stirred at 0° C. for 30 minutes. The mixture was diluted with water (10 mL) and extracted with ethyl acetate (30 mL×3), the organics were washed with brine (20 mL×2), dried over sodium sulfate, filtered and concentrated. The residue was purified by flash chromatography on silica gel (0-30% ethyl acetate in petroleum ether) to afford the title compound (100 mg, 82%) as a colorless oil. $^1$H NMR (400 MHz, DMSO-d$_6$): 7.79 (d, J=8.0 Hz, 2H), 7.43 (d, J=8.0 Hz, 2H), 7.35 (s, 1H), 5.19-5.12 (m, 1H), 5.13 (t, J=5.6 Hz, 1H), 4.62 (t, J=8.8 Hz, 2H), 4.56-4.47 (m, 2H), 3.33-3.26 (m, 2H), 1.50 (d, J=6.8 Hz, 3H).

Step 5: (5-(1-Aminoethyl)-7-(4-(trifluoromethoxy)phenyl)-2,3-dihydrobenzofuran-4-yl)methanol

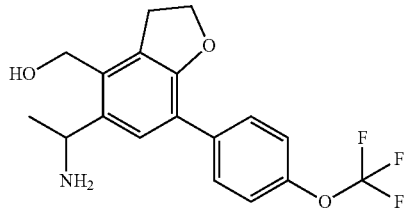 [SMILES: CC(N)c1cc(-c2ccc(OC(F)(F)F)cc2)c2c(c1CO)CCO2]

To a solution of PPh$_3$ (72 mg, 0.27 mmol) and (5-(1-azidoethyl)-7-(4-(trifluoromethoxy)phenyl)-2,3-dihydrobenzofuran-4-yl)methanol (100 mg, 0.26 mmol) in THF (1.5 mL) and Water (0.5 mL) was stirred at 60° C. for 16 hours. The mixture was then concentrated. The residue was purified by prep-TLC (20% MeOH in DCM) to afford the title compound (30 mg, 32%) as a colorless oil. $^1$H NMR (400 MHz, DMSO-d$_6$): δ 7.86 (d, J=8.8 Hz, 2H), 7.63 (s, 1H), 7.46 (d, J=8.8 Hz, 2H), 7.16 (s, 2H), 4.68-4.60 (m, 3H), 4.53 (s, 2H), 3.31-3.26 (m, 2H), 1.52 (d, J=6.8 Hz, 3H).

Step 6: N-(1-(4-(Hydroxymethyl)-7-(4-(trifluoromethoxy)phenyl)-2,3-dihydrobenzofuran-5-yl)ethyl)acrylamide

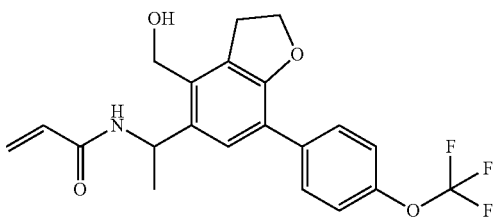 [SMILES: C=CC(=O)NC(C)c1cc(-c2ccc(OC(F)(F)F)cc2)c2c(c1CO)CCO2]

To a mixture of (5-(1-aminoethyl)-7-(4-(trifluoromethoxy)phenyl)-2,3-dihydrobenzofuran-4-yl)methanol (28 mg, 0.08 mmol), sat. aq. NaHCO$_3$ (0.2 mL) in THF (5 mL) was added acryloyl chloride (8 mg, 0.08 mmol) at 0° C. The reaction was stirred at 0° C. for 1 hour. The mixture was diluted with water (10 mL) and extracted with ethyl acetate (30 mL×3). The organics were washed with brine (20 mL×2), dried over sodium sulfate, filtered and concentrated. The residue was purified by reverse phase chromatography (acetonitrile 50-80/0.225% FA in water) to afford the title compound (6 mg, 18%) as a white solid. LCMS (ESI): m/z 430 (M+Na)$^+$.

Step 7: (R)—N-(1-(4-(Hydroxymethyl)-7-(4-(trifluoromethoxy)phenyl)-2,3-dihydrobenzofuran-5-yl)ethyl)acrylamide & (S)—N-(1-(4-(hydroxymethyl)-7-(4-(trifluoromethoxy)phenyl)-2,3-dihydrobenzofuran-5-yl)ethyl)acrylamide

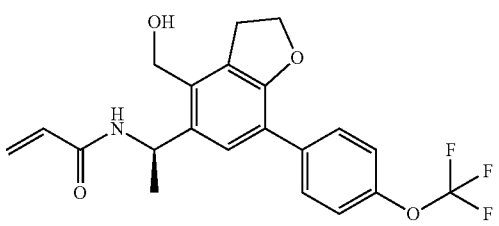

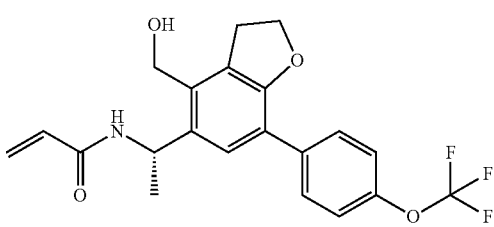

N-(1-(4-(Hydroxymethyl)-7-(4-(trifluoromethoxy)phenyl)-2,3-dihydrobenzofuran-5-yl)ethyl)acrylamide (6.0 mg, 0.01 mmol) was separated by Chiral SFC (Instrument: SFC-12; Column: OD(250 mm*30 mm,10 um); Condition: Neu-ETOH; Begin B:30%; Flow Rate (ml/minutes): 70) to afford the first peak (R)—N-(1-(4-(hydroxymethyl)-7-(4-(trifluoromethoxy)phenyl)-2,3-dihydrobenzofuran-5-yl)ethyl)acrylamide (1.95 mg, 31%) and the second peak (S)—N-(1-(4-(hydroxymethyl)-7-(4-(trifluoromethoxy)phenyl)-2,3-dihydrobenzofuran-5-yl)ethyl)acrylamide (2.06 mg, 32%) both as white solid.

(R)—N-(1-(4-(hydroxymethyl)-7-(4-(trifluoromethoxy)phenyl)-2,3-dihydrobenzofuran-5-yl)ethyl)acrylamide: $^1$H NMR (400 MHz, DMSO-d$_6$): δ 8.58 (d, J=8.4 Hz, 1H), 7.77 (d, J=8.8 Hz, 2H), 7.44 (d, J=8.8 Hz, 2H), 7.37 (s, 1H), 6.22 (dd, J=17.2, 10.0 Hz, 1H), 6.05 (dd, J=17.2, 2.0 Hz, 1H), 5.56 (dd, J=10.0, 2.0 Hz, 1H), 5.33-5.29 (m, 1H), 5.07 (s, 1H), 4.61-4.50 (m, 4H), 3.31-3.20 (m, 2H), 1.42 (d, J=6.8 Hz, 3H); LCMS (ESI): m/z 430 (M+Na)$^+$.

(S)—N-(1-(4-(hydroxymethyl)-7-(4-(trifluoromethoxy)phenyl)-2,3-dihydrobenzofuran-5-yl)ethyl)acrylamide: $^1$H NMR (400 MHz, DMSO-d$_6$): δ 8.58 (d, J=8.4 Hz, 1H), 7.77 (d, J=8.8 Hz, 2H), 7.44 (d, J=8.8 Hz, 2H), 7.37 (s, 1H), 6.22 (dd, J=17.2, 10.0 Hz, 1H), 6.05 (dd, J=17.2, 2.0 Hz, 1H), 5.56 (dd, J=10.0, 2.0 Hz, 1H), 5.33-5.29 (m, 1H), 5.07 (s, 1H), 4.61-4.50 (m, 4H), 3.31-3.20 (m, 2H), 1.42 (d, J=6.8 Hz, 3H); LCMS (ESI): m/z 430.1 (M+Na)$^+$.

Example 10

N-((4-(1H-Imidazol-1-yl)-7-(4-(trifluoromethoxy)phenyl)-2,3-dihydrobenzofuran-5-yl)methyl)acrylamide (Compound 23)

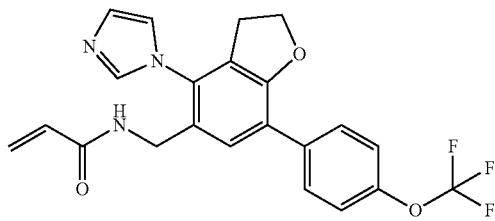 [SMILES: C=CC(=O)NCc1cc(-c2ccc(OC(F)(F)F)cc2)c2c(c1-n1ccnc1)CCO2]

Step 1: 7-Chloro-4-(JH-imidazol-1-yl)-2,3-dihydrobenzofuran-5-amine

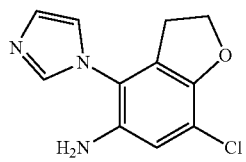 [SMILES: Nc1cc(Cl)c2c(c1-n1ccnc1)CCO2]

The mixture of imidazole (1.23 g, 18.11 mmol), 4-bromo-7-chloro-2,3-dihydrobenzofuran-5-amine (3.0 g, 12.07 mmol), Cs$_2$CO$_3$ (7.92 g, 24.14 mmol), Cu$_2$O (86 mg, 0.60 mmol) and quinolin-8-ol (350 mg, 2.41 mmol) in pentanenitrile (32 mL, 306 mmol) were stirred at 135° C. for 16 hours under a N$_2$ atmosphere. The reaction was diluted with water (200 mL) and extracted with ethyl acetate (200 mL×3). The organics were washed with brine (100 mL), dried over Na$_2$SO$_4$, filtered and concentrated. The residue was purified by flash chromatography on silica gel (0-100% ethyl acetate in petroleum ether) to afford the title compound (1.25 g, 44%) as a brown solid. 1H NMR (400 MHz, CDCl$_3$): δ 7.60 (s, 1H), 7.28 (s, 1H), 7.05 (s, 1H), 6.67 (s, 1H), 4.64 (t, J=8.8 Hz, 2H), 3.37 (s, 2H), 3.08 (t, J=8.8 Hz, 2H); LCMS (ESI): m/z 236.1 (M+H)$^+$.

Step 2: 4-(1H-Imidazol-1-yl)-7-(4-(trifluoromethoxy)phenyl)-2,3-dihydrobenzofuran-5-amine

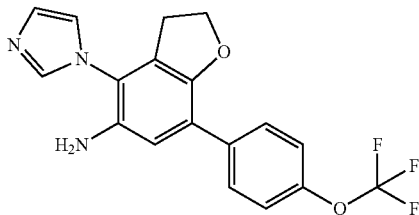 [SMILES: Nc1cc(-c2ccc(OC(F)(F)F)cc2)c2c(c1-n1ccnc1)CCO2]

The mixture of (4-(trifluoromethoxy)phenyl)boronic acid (1.31 g, 6.36 mmol), 7-chloro-4-(1H-imidazol-1-yl)-2,3-dihydrobenzofuran-5-amine (1.25 g, 5.3 mmol), KOAc (1.56 g, 15.91 mmol), Xphos (253 mg, 0.53 mmol) and Xphos Pd $G_2$(417 mg, 0.53 mmol) in 1,4-Dioxane (10 mL) and Water (1 mL) was stirred at 100° C. for 16 hours. The reaction was quenched with water (200 mL) and extracted with ethyl acetate (150 mL×3). The combined organic layers were dried over $Na_2SO_4$ and concentrated. The residue was purified by chromatography on silica gel (0-3% methanol in dichloromethane) to afford crude product. The crude product was purified by prep-HPLC (Xtimate C18 150*40 mm*5 um, water (0.05% $NH_3H_2O$ )-ACN, 43-73%, 55 mL/minutes) to afford the title compound (830 mg, 43%) as a white solid. $^1$H NMR (400 MHz, DMSO-$d_6$): δ 7.81 (s, 1H), 7.74 (d, J=8.8 Hz, 2H), 7.44 (d, J=8.8 Hz, 2H), 7.34 (s, 11H), 7.13 (s, 1H), 6.88 (s, 1H), 4.54-4.44 (m, 4H), 2.99 (t, J=8.8 Hz, 2H); LCMS (ESI): m/z 362.1 (M+H)$^+$.

Step 3: 1-(5-Bromo-7-(4-(trifluoromethoxy)phenyl)-2,3-dihydrobenzofuran-4-yl)-1H-imidazole

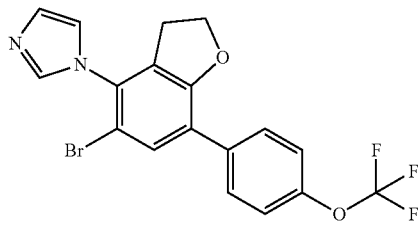 [SMILES: FC(F)(F)Oc1ccc(-c2cc(Br)c(-n3ccnc3)c3c2OCC3)cc1]

A mixture of 4-(1H-imidazol-1-yl)-7-(4-(trifluoromethoxy)phenyl)-2,3-dihydrobenzofuran-5-amine (770 mg, 2.13 mmol), $CuBr_2$ (571 mg, 2.56 mmol) in acetonitrile (10 mL) was added tert-butyl nitrite (439 mg, 4.26 mmol) at 0° C. under $N_2$ atmosphere. The mixture was stirred at 60° C. for 4 hours. The reaction was diluted with water (30 mL) and extracted with ethyl acetate (25 mL×2). The organics were washed with brine (20 mL), dried over $Na_2SO_4$, filtered and concentrated. The residue was purified by flash chromatography on silica gel (0-60% ethyl acetate in petroleum ether) to afford the title compound (600 mg, 66%) as a white solid. $^1$H NMR (400 MHz, DMSO-$d_6$): δ 7.89 (s, 1H), 7.87 (d, J=8.0 Hz, 2H), 7.78 (s, 1H), 7.48 (d, J=8.0 Hz, 2H), 7.42 (s, 1H), 7.14 (s, 1H), 4.68 (t, J=8.8 Hz, 2H), 3.15 (t, J=8.8 Hz, 2H); LCMS (ESI): m/z 425.0 (M+H)$^+$.

Step 4: 1-(7-(4-(Trifluoromethoxy)phenyl)-5-vinyl-2,3-dihydrobenzofuran-4-yl)-1H-imidazole

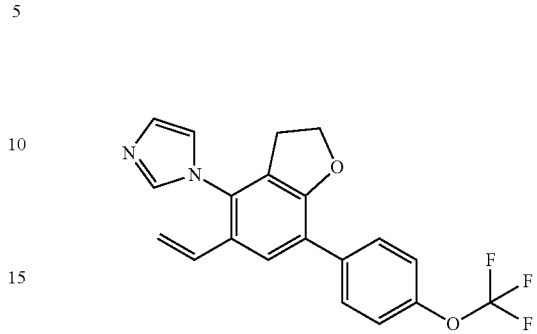

To a mixture of $Na_2CO_3$ (149 mg, 1.41 mmol), 4,4,5,5-tetramethyl-2-vinyl-1,3,2-dioxaborolane (79 mg, 0.52 mmol) in 1,4-Dioxane (3 mL) and $H_2O$ (1 mL) was added 1-(5-bromo-7-(4-(trifluoromethoxy)phenyl)-2,3-dihydrobenzofuran-4-yl)-1H-imidazole (200 mg, 0.47 mmol) and Pd(dppf)$Cl_2$ (34 mg, 0.05 mmol). The reaction mixture was stirred under $N_2$ atmosphere at 100° C. for 2 hours. Water (3 mL) was added, the reaction mixture was extracted with ethyl acetate (10 mL×3) and washed with brine (10 mL). The organic layers were dried over anhydrous sodium sulfate and concentrated. The residue was purified by flash column chromatography on silica gel (0-30% ethyl acetate in petroleum ether) to afford the title compound (170 mg, 97%) as a yellow solid. $^1$H NMR (400 MHz, $CDCl_3$): δ 7.78-7.76 (m, 3H), 7.58 (s, 1H), 7.34-7.30 (m, 2H), 7.26-7.18 (m, 2H), 6.29 (dd, J=17.6, 11.2 Hz, 1H), 5.61 (d, J=17.6 Hz, 1H), 5.22 (d, J=11.2 Hz, 1H), 4.71 (t, J=8.8 Hz, 2H), 3.14 (t, J=8.8 Hz, 2H); LCMS (ESI): m/z 373.1 (M+H)$^+$.

Step 5: 4-(JH-Imidazol-1-yl)-7-(4-(trifluoromethoxy)phenyl)-2,3-dihydrobenzofuran-5-carbaldehyde

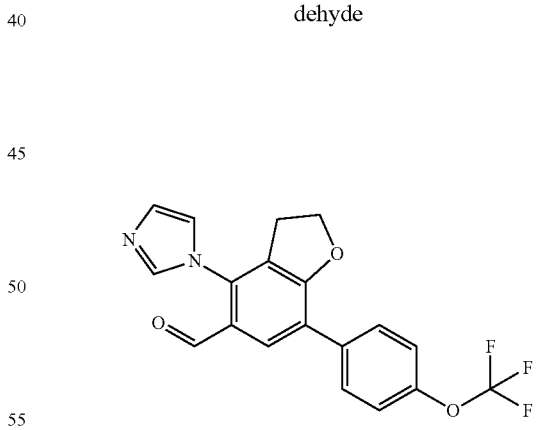

To a solution of 1-(7-(4-(trifluoromethoxy)phenyl)-5-vinyl-2,3-dihydrobenzofuran-4-yl)-1H-imidazole (170 mg, 0.46 mmol) in THF (1 mL) and Water (0.2 mL) at 0° C. was added $OsO_4$ (17.0 mg, 0.07 mmol) and $NaIO_4$ (391 mg, 1.83 mmol). The reaction mixture was stirred at room temperature for 2.5 hours. The reaction mixture was quenched with sat aq. $NaHSO_3$. The resulting mixture was extracted with ethyl acetate (30 mL×3). Combined organic layers were dried over $Na_2SO_4$, filtered and concentrated to afford the title compound (120 mg, 70%) as brown solid. LCMS (ESI): m/z 375.1 (M+H)$^+$.

Step 6: N-((4-(1H-Imidazol-1-yl)-7-(4-(trifluoromethoxy)phenyl)-2,3-dihydrobenzofuran-5-yl)methyl)-2-methylpropane-2-sulfinamide

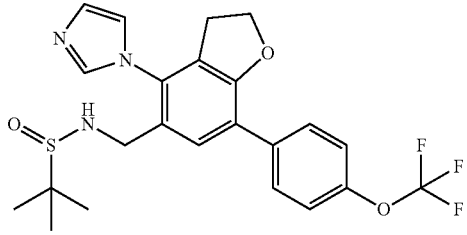 [SMILES: CC(C)(C)S(=O)NCc1cc(-c2ccc(OC(F)(F)F)cc2)c2c(c1-n1ccnc1)CCO2]

The mixture of 4-(1H-imidazol-1-yl)-7-(4-(trifluoromethoxy)phenyl)-2,3-dihydrobenzofuran-5-carbaldehyde (160 mg, 0.43 mmol), 2-methylpropane-2-sulfinamide (52 mg, 0.43 mmol) and titanium ethoxide (195 mg, 0.85 mmol) in THF (10 mL) was stirred at 60° C. for 16 hours under $N_2$ atmosphere. Then NaBH$_4$ (25 mg, 0.67 mmol) was added into the reaction. The reaction mixture was stirred at room temperature for 2 hours under $N_2$ atmosphere again. The reaction mixture was diluted with ethyl acetate (30 mL), which was washed with water (30 mL). The organic layer was separated and dried with Na$_2$SO$_4$. After filtration, the organic layer was concentrated to dryness. The residue was purified by flash chromatography on silica gel (0-10% methanol in dichloromethane) to afford the title compound (150 mg, 73%) as yellow solid. LCMS (ESI): m/z 480.2 (M+H)$^+$.

Step 7: (4-(JH-Imidazol-1-yl)-7-(4-(trifluoromethoxy)phenyl)-2,3-dihydrobenzofuran-5-yl)methanamine

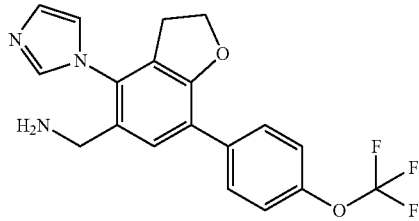 [SMILES: NCc1cc(-c2ccc(OC(F)(F)F)cc2)c2c(c1-n1ccnc1)CCO2]

A mixture of N-((4-(1H-imidazol-1-yl)-7-(4-(trifluoromethoxy)phenyl)-2,3-dihydrobenzofuran-5-yl)methyl)-2-methylpropane-2-sulfinamide (140 mg, 0.29 mmol), HCl (1 mL, 4 mmol) in 1,4-Dioxane (2 mL) was stirred at room temperature for 2 hours. The residue was quenched with sat. aq. NaHCO$_3$ (10 mL), extracted by ethyl acetate (20 mL×2). The organic layer was dried over Na$_2$SO$_4$ and evaporated. The residue was purified by pre-HPLC (Welch Xtimate C18 150*25 mm*5 um, water (0.225% FA)-CAN, 15% -45%) to afford the title compound (20 mg, 18%) as a white solid. LCMS (ESI): m/z 376.1 (M+H)$^+$.

Step 8: N-((4-(1H-Imidazol-1-yl)-7-(4-(trifluoromethoxy)phenyl)-2,3-dihydrobenzofuran-5-yl)methyl)acrylamide

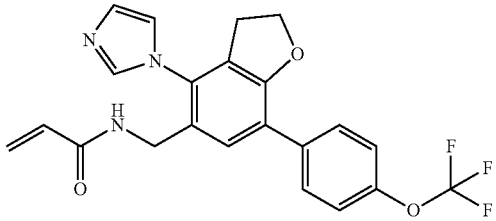 [SMILES: C=CC(=O)NCc1cc(-c2ccc(OC(F)(F)F)cc2)c2c(c1-n1ccnc1)CCO2]

A mixture of (4-(1H-imidazol-1-yl)-7-(4-(trifluoromethoxy)phenyl)-2,3-dihydrobenzofuran-5-yl)methanamine (20 mg, 0.05 mmol), sat. aq. NaHCO$_3$ (0.02 mL) and acryloyl chloride (6 mg, 0.06 mmol) in THF (2 mL) was stirred at 0° C. for 30 minutes. The mixture was diluted with water (20 mL) and extracted with ethyl acetate (30 mL×3). The organics were washed with brine (20 mL×2), dried over sodium sulfate, filtered and concentrated. The residue was purified by pre-HPLC (Welch Xtimate C18 150*25 mm*5 um, water(0.225% FA)-CAN, 16%-46%) to afford the title compound (0.62 mg, 2.7%) as a white solid. $^1$H NMR (400 MHz, CDCl$_3$): δ 7.73-7.70 (m, 3H), 7.53 (s, 1H), 7.33-7.30 (m, 311), 7.22-7.15 (m, 1H), 6.31-6.28 (m, 1H), 6.05-6.06 (m, 1H), 5.66 (s, 1H), 4.72-4.70 (m, 2H), 4.31-4.29 (m, 2H), 3.13-3.11 (m, 2H); LCMS (ESI): m/z 430.0 (M+H)$^+$.

Example 11

N-((7-(Hydroxymethyl)-4-(6-(trifluoromethoxy)pyridin-3-yl)benzo[d]oxazol-6-yl)methyl)acrylamide (Compound 3)

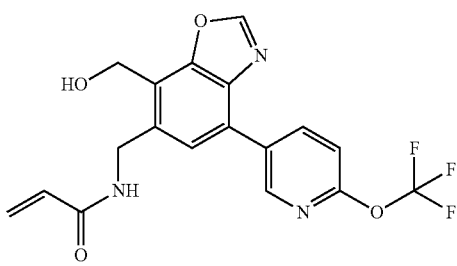

Step 1: 5-Bromo-2-(trifluoromethoxy)pyridine

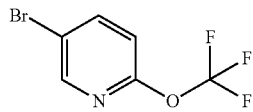 [SMILES: FC(F)(F)Oc1ccc(Br)cn1]

A solution of 1-trifluoromethyl-1,2-benziodoxol-3-(1H)-one (35.0 g, 110.74 mmol) in MeNO$_2$ (580 mL) was added 5-bromopyridin-2-ol (57.82 g, 332.3 mmol) was stirred at 100° C. for 5 hours under N$_2$ atmosphere. The reaction mixture was concentrated and the residue was purified by flash column chromatography on silica gel (100% petroleum ether) to afford the title compound (3.8 g, 14%) as a colorless oil. $^1$H NMR (400 MHz, CDCl$_3$): δ 8.39 (d, J=2.4 Hz, 11H), 7.90 (dd, J1=8.4, 2.4 Hz, 11H), 6.95 (d, J=8.4 Hz, 11H).

Step 2: Ethyl 2-methoxy-6-methylbenzoate

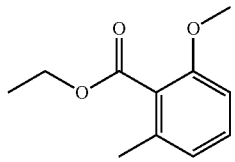

To a stirred solution of ethyl 2-hydroxy-6-methylbenzoate (40.0 g, 222.0 mmol) in acetone (400 mL) was added Na$_2$CO$_3$ (60.0 g, 444.0 mmol) and MeI (68.5 mL, 1.11 mol). The reaction mixture was stirred at 60° C. for 16 hours under a nitrogen atmosphere. The reaction mixture was then poured into ice water (1 L). The mixture was extracted with ethyl acetate (500 mL×3). The combined organic layer was washed with sat. aq. NH$_4$Cl solution (500 mL×3) and brine (500 mL×3), dried over Na$_2$SO$_4$ and concentrated to afford the title compound (40.0 g, 93%). $^1$H NMR (400 MHz, CDCl$_3$): δ 7.26-7.22 (m, 1H), 6.81-6.75 (m, 2H), 4.41 (q, J=7.2 Hz, 2H), 3.83 (s, 3H), 2.31 (s, 3H), 1.39 (t, J=7.2 Hz, 3H); LCMS (ESI): m/z 195.1 (M+H)$^+$.

Step 3: Ethyl 2-methoxy-6-methyl-3-nitrobenzoate

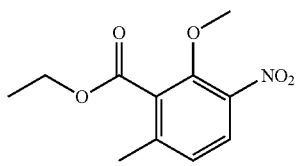 [SMILES: CCOC(=O)c1c(C)ccc([N+](=O)[O-])c1OC]

To a solution of ethyl 2-methoxy-6-methylbenzoate (20.0 g, 103.0 mmol) in Ac$_2$O (200 mL) was added HNO$_3$ (9.3 mL, 123.0 mmol) at 0° C., the resulting solution was stirred for 1 hour at 0° C. The reaction mixture was filtered and the filtrate was concentrated under vacuum. The residue was purified by flash chromatography on silica gel (0-10% ethyl acetate in petroleum ether) to afford the title compound (25.0 g, 99%) as a yellow solid. $^1$H NMR (400 MHz, CDCl$_3$): δ 7.87 (d, J=8.4 Hz, 1H), 7.08 (d, J=8.4 Hz, 1H), 4.45 (q, J=7.2 Hz, 2H), 3.95 (s, 3H), 2.39 (s, 3H), 1.42 (t, J=7.2 Hz, 3H).

Step 4: Ethyl 3-amino-2-methoxy-6-methylbenzoate

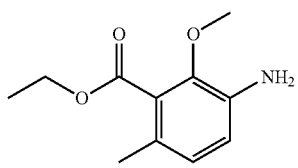

A solution of ethyl 2-methoxy-6-methyl-3-nitrobenzoate (20.0 g, 83.7 mmol), 10% Pd/C (4.5 g, 42.0 mmol) in EtOH (200 mL) was stirred at room temperature for 16 hours under a H$_2$ atmosphere (15 psi). Then the reaction mixture was filtered through Celite®. The filtrate was concentrated to afford the title compound (15.0 g, 86%) as a yellow solid. $^1$H NMR (400 MHz, CDCl$_3$) δ6.83-6.71 (m, 2H), 4.42 (q, J=7.2 Hz, 2H), 3.82 (s, 3H), 2.22 (s, 3H), 1.40 (t, J=7.2 Hz, 3H).

Step 5: Ethyl 3-amino-4-bromo-2-methoxy-6-methylbenzoate

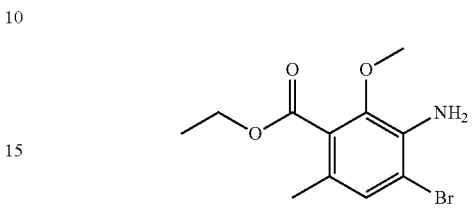

To a mixture of ethyl 3-amino-2-methoxy-6-methylbenzoate (12.5 g, 59.6 mmol) in DCM (150 mL) was added NBS (10 g, 60 mmol) at 0° C. The reaction solution was stirred at 0° C. for 1 hour. The reaction mixture was filtered and the filtrate was concentrated under vacuum. The residue was purified by flash chromatography on silica gel (0-10% ethyl acetate in petroleum ether) to afford the title compound (15.0 g, 86%) as a yellow solid. $^1$H NMR (400 MHz, CDCl$_3$): δ 7.08 (s, 1H), 4.41 (q, J=7.2 Hz, 2H), 3.82 (s, 3H), 2.20 (s, 3H), 1.40 (t, J=7.2 Hz, 3H).

Step 6: Ethyl 3-amino-4-bromo-2-hydroxy-6-methylbenzoate

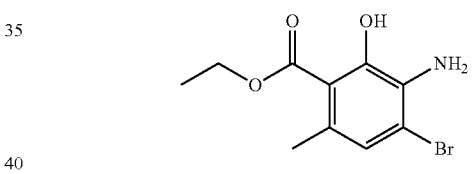

To a solution of ethyl 3-amino-4-bromo-2-methoxy-6-methylbenzoate (8.0 g, 28.0 mmol) in DCM (120 mL) was added BBr$_3$ (2.7 mL, 28.0 mmol) in DCM (10 mL) at −78° C. The mixture was stirred at −78° C. for 2 hours. The mixture was then quenched with H$_2$O (300 mL) and the solution was adjusted to pH 8 with 2M aq. NaOH. Then the solution was extracted with ethyl acetate (500 mL×3). The organic layer was dried over Na$_2$SO$_4$, filtered and concentrated under vacuum. The residue was purified by flash chromatography on silica gel (0-10% ethyl acetate in petroleum ether) to afford the title compound as white solid. $^1$H NMR (400 MHz, CDCl$_3$): δ 6.85 (s, 1H), 4.44 (q, J=7.2 Hz, 2H), 2.44 (s, 3H), 1.44 (t, J=7.2 Hz, 3H).

Step 7: Ethyl 4-bromo-6-methylbenzo[d]oxazole-7-carboxylate

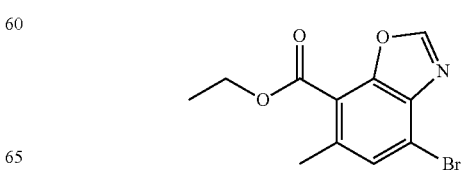

A mixture of ethyl 3-amino-4-bromo-2-hydroxy-6-methyl-benzoate (900 mg, 3.28 mmol) trimethoxymethane (20 mL, 182.81 mmol) and p-toluenesulfonic acid monohydrate (62 mg, 0.33 mmol) was stirred at 80° C. for 16 hours. Then the reaction mixture was concentrated. The residue was purified with flash chromatography on silica gel (0-10% ethyl acetate in petroleum ether) to afford the title compound (700 mg, 75%) as a white solid. ¹H NMR (400 MHz, CDCl₃) δ 8.17 (s, 1H), 7.50 (s, 1H), 4.48 (q, J=7.2 Hz, 2H), 2.68 (s, 3H), 1.46 (t, J=7.2 Hz, 3H); LCMS (ESI): m/z 284.0 (M+H)⁺.

Step 8: Ethyl 6-methyl-4-(tributylstannyl)benzo[d]oxazole-7-carboxylate

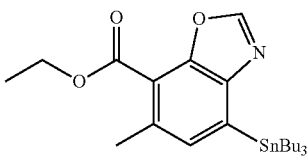

A mixture of ethyl 4-bromo-6-methylbenzo[d]oxazole-7-carboxylate (3.0 g, 10.56 mmol), Pd(PPh₃)₂Cl₂ (741 mg, 1.06 mmol) and 1,1,1,2,2,2-hexabutyldistannane (6.94 mL, 13.73 mmol) in 1,4-dioxane (50 mL) was stirred at 100° C. for 16 hours under N₂ atmosphere. The mixture was quenched with water (300 mL) and extracted with ethyl acetate (300 mL). The organic layer was washed with water (300 mL×3), dried over Na₂SO₄ and concentrated. The residue was purified by flash chromatography on silica gel (0-15% ethyl acetate in petroleum ether) to afford the title compound (3.8 g, 73%) as a yellow oil.

Step 9: Ethyl 6-methyl-4-(6-(trifluoromethoxy)pyridin-3-yl)benzo[d]oxazole-7-carboxylate

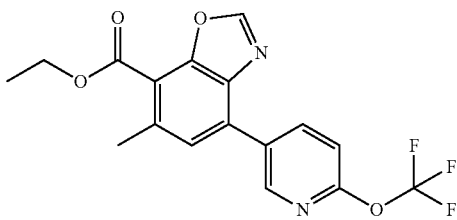 [SMILES: CCOC(=O)c1c(C)cc(-c2ccc(OC(F)(F)F)nc2)c2ncoc12]

A mixture of ethyl 6-methyl-4-(tributylstannyl)benzo[d]oxazole-7-carboxylate (1.5 g, 3.03 mmol), Pd(PPh₃)₂C12 (213 mg, 0.30 mmol), CsF (1.36 g, 9.1 mmol), CuCl (30 mg, 0.30 mmol) and 5-bromo-2-(trifluoromethoxy)pyridine (881 mg, 3.64 mmol) in 1,4-dioxane (20 mL) was stirred at 100° C. for 16 hours under N₂ atmosphere. The mixture was quenched with water (100 mL) and extracted with ethyl acetate (100 mL). Then the organic layer was then washed with water (100 mL×3). The organics where collected, dried over Na₂SO₄ and concentrated. The residue was purified by flash chromatography on silica gel (0-10% ethyl acetate in petroleum ether) to afford the title compound (1.0 g, 90%) as a white solid. ¹H NMR (400 MHz, CDCl₃): δ 8.87 (d, J=2.0 Hz, 1H), 8.47 (dd, J=8.4, 2.0 Hz, 1H), 8.19 (s, 1H), 7.44 (s, 1H), 7.18 (d, J=8.4 Hz, 1H), 4.52 (q, J=7.2 Hz, 2H), 2.77 (s, 3H), 1.48 (t, J=7.2 Hz, 3H); LCMS (ESI): m/z 367.1 (M+H)⁺.

Step 10: Ethyl 6-(bromomethyl)-4-(6-(trifluoromethoxy)pyridin-3-yl)benzo[d]oxazole-7-carboxylate

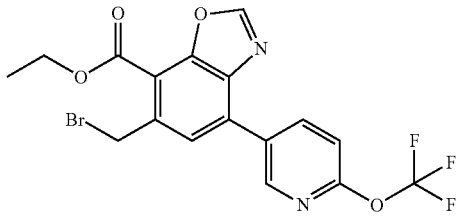 [SMILES: CCOC(=O)c1c(CBr)cc(-c2ccc(OC(F)(F)F)nc2)c2ncoc12]

To a mixture of ethyl 6-methyl-4-(6-(trifluoromethoxy)pyridin-3-yl)benzo[d]oxazole-7-carboxylate (900 mg, 2.46 mmol) in CC14 (10 mL) was added AIBN (80 mg, 0.49 mmol) and NBS (524 mg, 2.95 mmol) at 0° C. The reaction solution was stirred at 80° C. for 16 hours, at which point the solution was concentrated. The residue was purified by flash chromatography on silica gel (0-10% Ethyl acetate in petroleum ether) to afford the title compound (900 mg, 82%) as a yellow solid. LCMS (ESI): m/z 445.0 (M+H)⁺.

Step 11: Ethyl 6-(azidomethyl)-4-(6-(trifluoromethoxy)pyridin-3-yl)benzo[d]oxazole-7-carboxylate

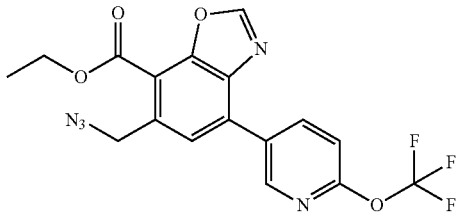

To a mixture of ethyl 6-(bromomethyl)-4-(6-(trifluoromethoxy)pyridin-3-yl)benzo[d]oxazole-7-carboxylate (500 mg, 1.12 mmol) in DMF (10 mL) was added NaN₃ (80 mg, 1.24 mmol) at room temperature. Then the reaction was stirred at room temperature for 16 hours. The reaction solution was quenched with water (200 mL), extracted in ethyl acetate (300 mL), dried over MgSO4, filtered and concentrated to afford the title compound (0.40 g, 87%) as a yellow solid. LCMS (ESI): m/z 408.1 (M+H)⁺.

Step 12: (6-(Aminomethyl)-4-(6-(trifluoromethoxy)pyridin-3-yl)benzo[d]oxazol-7-yl)methanol

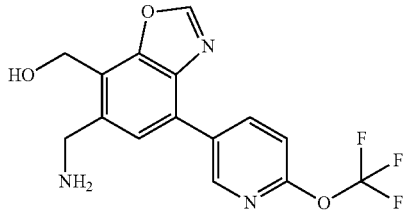

To a mixture of ethyl 6-(azidomethyl)-4-(6-(trifluoromethoxy)pyridin-3-yl)benzo[d]oxazole-7-carboxylate (100 mg, 0.25 mmol) in THF (5 mL) was added LiAlH₄ (0.22 mL, 0.54 mmol, 2.5 mol/L in THF) at 0° C. Then the reaction was stirred at 0° C. for 1 hour. The reaction was quenched with water (1 mL) and sat. aq. NaHCO₃ solution (1 mL). The organic layer was dried over Na₂SO₄, filtered and concentrated to afford the title compound (80 mg, crude) as a brown liquid. LCMS (ESI): m/z 340.1 (M+H)⁺.

Step 13: N-((7-(Hydroxymethyl)-4-(6-(trifluoromethoxy)pyridin-3-yl)benzo[d]oxazol-6-yl)methyl)acrylamide

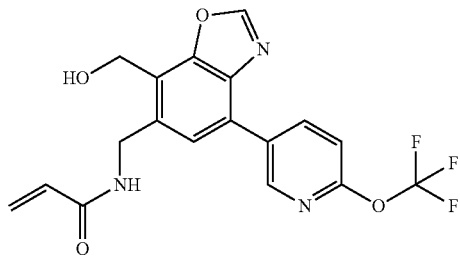

To a solution of (6-(Aminomethyl)-4-(6-(trifluoromethoxy)pyridin-3-yl)benzo[d]oxazol-7-yl)methanol (80 mg, 0.24 mmol) in THF (5 mL) was added sat. aq. NaHCO₃ solution (1 mL) and acryloyl chloride (25 mg, 0.28 mmol) at 0° C. Then the reaction was stirred at 0° C. for 30 minutes. The reaction was diluted with water (20 mL) and extracted with ethyl acetate (100 mL×3). The organic layers were washed with brine (100 mL×2), dried over sodium sulfate, filtered and concentrated. The residue was purified by flash chromatography on silica gel (0-50% ethyl acetate in petroleum ether) and prep-HPLC (Welch Xtimate C18 150*25 mm*5 um, water (NH₄HCO₃)-ACN,30-60%) to afford the title compound (6.28 mg, 7%) as a white solid. ¹H NMR (400 MHz, DMSO-d₆): δ 8.94 (d, J=2.4 Hz, 1H), 8.89 (s, 1H), 8.61 (s, 1H), 8.57 (dd, J=8.8, 2.4 Hz, 1H), 7.70 (s, 1H), 7.49 (d, J=8.4 Hz, 1H), 6.27 (dd, J=17.2, 10.0 Hz, 1H), 6.12 (dd, J=17.2, 2.4 Hz, 1H), 5.62 (dd, J=10.0, 2.4 Hz, 1H), 5.39 (s, 1H), 4.88 (d, J=5.2 Hz, 2H), 4.67 (d, J=6.0 Hz, 2H); LCMS (ESI): m/z 416.0 (M+Na)⁺.

Example 12

N-((4-cyano-7-(4-(trifluoromethoxy)phenyl)-2,3-dihydrobenzofuran-5-yl)methyl)acrylamide (Compound 2)

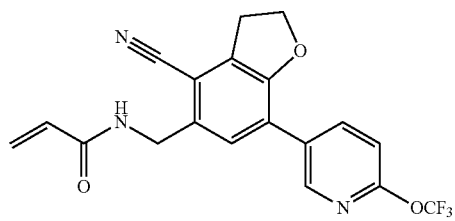 [SMILES: C=CC(=O)NCc1cc(-c2ccc(OC(F)(F)F)nc2)c2c(c1C#N)CCO2]

Step 1: 7-chloro-5-nitro-2,3-dihydrobenzofuran-4-carbonitrile

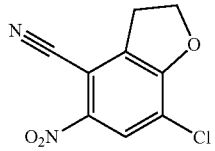

A vial was charged with 4-bromo-7-chloro-5-nitro-2,3-dihydrobenzofuran (1000 mg, 3.59 mmol) and copper(I) cyanide (354 mg, 3.95 mmol). NMP (5 mL) was added and the vial was capped and irradiated at 150° C. for 20 minutes in a microwave reactor. The reaction was then diluted with EtOAc (75 mL), washed with 50% NH₄OH (2×25 mL) and saturated aqueous NaCl (3×25 mL), dried over Na₂SO₄, filtered, and concentrated under reduced pressure. The crude was purified by flash column chromatography on silica gel (Silica, 0-100% EtOAc/heptanes) to provide 7-chloro-5-nitro-2,3-dihydrobenzofuran-4-carbonitrile (564 mg, 70% in yield) as a yellow solid. LCMS (ESI) [M−H]⁻=223.2.

Step 2: 5-nitro-7-[4-(trifluoromethoxy)phenyl]-2,3-dihydrobenzofuran-4-carbonitrile

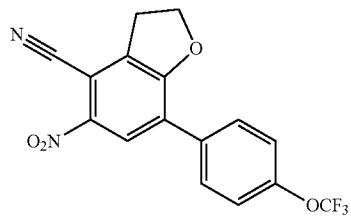 [SMILES: N#Cc1c([N+](=O)[O-])cc(-c2ccc(OC(F)(F)F)cc2)c2c1CCO2]

A vial was charged with 4-(trifluoromethoxy)phenylboronic acid (568.8 mg, 2.76 mmol), 7-chloro-5-nitro-2,3-dihydrobenzofuran-4-carbonitrile (564 mg, 2.51 mmol), and Pd(PPh₃)₄ (145.1 mg, 0.13 mmol). The vial was capped and dioxane (10 mL) was added followed by addition of 1M Na₂CO₃ (3.77 mL, 3.77 mmol). The mixture was purged with nitrogen for 5 minutes and irradiated at 150° C. in a microwave reactor for 10 minutes. The reaction was diluted with EtOAc (40 mL), filtered through Celite® using EtOAc (2×10 mL), and concentrated under reduced pressure. The crude was purified by flash column chromatography (Silica, 0-100% EtOAc/heptanes) to provide 5-nitro-7-[4-(trifluoromethoxy)phenyl]-2,3-dihydrobenzofuran-4-carbonitrile (679 mg, 77% in yield) as a yellow solid. LCMS (ESI) [M−H]⁻=349.0.

Step 3: 5-amino-7-[4-(trifluoromethoxy)phenyl]-2,3-dihydrobenzofuran-4-carbonitrile

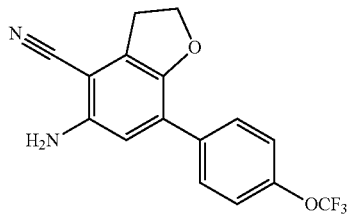

A flask was charged with 5-nitro-7-[4-(trifluoromethoxy)phenyl]-2,3-dihydrobenzofuran-4-carbonitrile (529 mg, 1.51 mmol) and 10% w/w Pd/C (97 mg, wet). The flask was capped, purged with nitrogen for 5 minutes, and charged with EtOAc (25 mL). The reaction was purged 10 minutes with $H_2$ then stirred under an atmosphere of $H_2$ at room temperature for 16 hours till completion. The reaction mixture was purged with $N_2$ then filtered through Celite® using EtOAc (30 mL) followed by MeOH (30 mL). Filtrate was concentrated under reduced pressure to provide crude 5-amino-7-[4-(trifluoromethoxy)phenyl]-2,3-dihydrobenzofuran-4-carbonitrile (445 mg, 92% in yield) as a green solid, which was carried to the next step without further purification. LCMS (ESI) $[M+H]^+=321.1$.

Step 4: 5-formyl-7-[4-(trifluoromethoxy)phenyl]-2,3-dihydrobenzofuran-4-carbonitrile

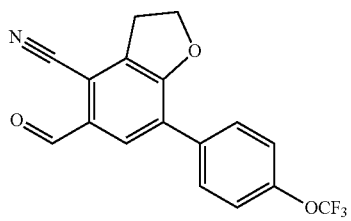 [SMILES: N#Cc1c(C=O)cc(-c2ccc(OC(F)(F)F)cc2)c2c1CCO2]

A flask was charged with $CuBr_2$ (369.6 mg, 1.65 mmol) and MeCN (4 mL) followed by addition of tert-butyl nitrite (0.25 mL, 2.07 mmol). The flask was then heated to 65° C. and a solution of 5-amino-7-[4-(trifluoromethoxy)phenyl]-2,3-dihydrobenzofuran-4-carbonitrile (265 mg, 0.83 mmol) in MeCN (3 mL) was added by syringe. The reaction was stirred for 1 hour, cooled to room temperature, diluted with EtOAc (75 mL), washed with 1N aq. HCl (25 mL), dried over $Na_2SO_4$, filtered, and concentrated under reduced pressure to provide crude 5-bromo-7-[4-(trifluoromethoxy)phenyl]-2,3-dihydrobenzofuran-4-carbonitrile (343 mg) as a brown solid. This solid was mixed with potassium trifluoro(vinyl)boron (379.7 mg, 2.83 mmol) and Pd(dppf)$Cl_2$ (70.1 mg, 0.09 mmol). Dioxane (12 mL) and $H_2O$ (2 mL) were added followed by addition of triethylamine (0.4 mL, 2.83 mmol). The mixture was heated to 100° C. for 16 hours. The mixture was then cooled to room temperature, diluted with EtOAc (75 mL), dried with $Na_2SO_4$, filtered through a plug of silica topped with Celite® using EtOAc (50 mL), and concentrated under reduced pressure to provide crude 7-[4-(trifluoromethoxy)phenyl]-5-vinyl-2,3-dihydrobenzofuran-4-carbonitrile (397 mg) as a brown waxy semi-solid. This solid was dissolved in a mixture of acetone (10 mL) and water (5 mL). Sodium (meta)periodate (978 mg, 4.58 mmol) was added followed by a 4% aqueous solution of osmium tetroxide (0.29 mL, 0.05 mmol) and stirred at room temperature for 16 hours. The reaction mixture was then diluted with EtOAc (75 mL) and washed with water (25 mL), 10% $Na_2S_2O_3$ (2×10 mL), dried over $Na_2SO_4$, filtered, and concentrated under reduced pressure. The crude mixture was purified by flash column chromatography (Silica, 0-100% EtOAc/heptanes) to provide 5-formyl-7-[4-(trifluoromethoxy)phenyl]-2,3-dihydrobenzofuran-4-carbonitrile (74 mg, 19% in yield) as a white solid. LCMS (ESI) $[M+H]^+=324.1$.

Step 5: 5-(azidomethyl)-7-[4-(triuoromethoxy)phenyl]-2,3-dihydrobenzofuran-4-carbonitrile

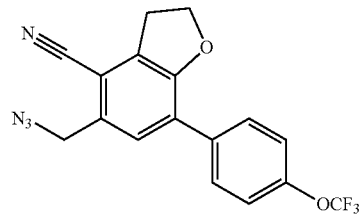 [SMILES: N#Cc1c(CN=[N+]=[N-])cc(-c2ccc(OC(F)(F)F)cc2)c2c1CCO2]

5-formyl-7-[4-(trifluoromethoxy)phenyl]-2,3-dihydrobenzofuran-4-carbonitrile (74 mg, 0.22 mmol) was dissolved in MeOH (10 mL) and cooled to 0° C. NaBH$_4$ (12.6 mg, 0.33 mmol) was added and stirred for 10 minutes. The reaction mixture was then concentrated to dryness, re-dissolved in MeOH (3 mL) and concentrated to dryness again in triplicate. The crude residue was dissolved in EtOAc (80 mL) and washed with sat. aq. NaHCO$_3$ (20 mL). The organic extract was dried over Na$_2$SO$_4$, filtered, and concentrated to dryness to provide 5-(hydroxymethyl)-7-[4-(trifluoromethoxy)phenyl]-2,3-dihydrobenzofuran-4-carbonitrile (85 mg) as a yellow solid. This solid was dissolved in DCM (3 mL) and cooled to 0° C. Triethylamine (0.05 mL, 0.38 mmol) was added followed by methanesulfonyl chloride (0.02 mL, 0.28 mmol) The reaction was stirred for 90 minutes at which point it was diluted with DCM (50 mL), washed with sat. aq. NaHCO$_3$ (10 mL), dried over Na$_2$SO$_4$, filtered, and concentrated under reduced pressure to provide [4-cyano-7-[4-(trifluoromethoxy)phenyl]-2,3-dihydrobenzofuran-5-yl]methyl methanesulfonate (108 mg) as a brown solid. The solid was then dissolved in DMF (2 mL). Sodium azide (25 mg, 0.39 mmol) added and the reaction was stirred at 55° C. overnight. The reaction mixture was then diluted with EtOAc (40 mL), washed with H$_2$O , dried over Na$_2$SO$_4$, filtered, and concentrated. The reaction was purified by flash column chromatography (Silica, 0-100% EtOAc/heptane) to provide 5-(azidomethyl)-7-[4-(trifluoromethoxy)phenyl]-2,3-dihydrobenzofuran-4-carbonitrile (23 mg, 24% in yield) as a white solid. LCMS (ESI) $[M+H]^+=361.9$. $^1$H NMR (400 MHz, CDCl$_3$) δ 7.79-7.68 (m, 2H), 7.36 (s, 1H), 7.33-7.28 (m, 2H), 4.77 (t, J=8.9 Hz, 2H), 4.54 (s, 2H), 3.49 (t, J=8.9 Hz, 2H).

Step 6: N-[[4-cyano-7-[4-(trifluoromethoxy)phenyl]-2,3-dihydrobenzofuran-5-yl]methyl]prop-2-enamide

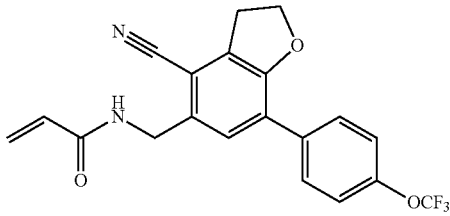 [SMILES: C=CC(=O)NCc1cc(-c2ccc(OC(F)(F)F)cc2)c2c(c1C#N)CCO2]

A flask was charged with 5-(azidomethyl)-7-[4-(trifluoromethoxy)phenyl]-2,3-dihydrobenzofuran-4-carbonitrile (23 mg, 0.06 mmol) and 10% w/w Pd/C (9 mg). The flask was purged with nitrogen for 5 minutes then charged with EtOAc (3 mL). The flask was then purged with hydrogen for 10 minutes and stirred for 90 minutes under an atmosphere of hydrogen till completion. The reaction was purged with nitrogen, diluted with EtOAc (10 mL), and filtered through Celite® using EtOAc (20 mL) followed by MeOH (20 mL). The filtrate was concentrated to dryness to provide crude 5-(aminomethyl)-7-[4-(trifluoromethoxy)phenyl]-2,3-dihydrobenzofuran-4-carbonitrile (15 mg) as a brown wax. This was dissolved in a mixture of THF (2 mL) and sat. aq. NaHCO$_3$ (2 mL). A solution of acryloyl chloride (4.4 □L, 0.05 mmol) in THF (0.1 mL) was added and the mixture was stirred at room temperature for 20 minutes. The reaction was then diluted with water (20 mL) and extracted with EtOAc (2×40 mL). The organic extracts were combined and concentrated. The organic material was purified by flash column chromatography (Silica, 0-100% EtOAc/heptanes). The obtained solid was lyophilized to provide N-[[4-cyano-7-[4-(trifluoromethoxy)phenyl]-2,3-dihydrobenzofuran-5-yl]methyl]prop-2-enamide (7 mg, 30% in yield) as a white powder. LCMS (ESI) [M+H]$^+$=389.1. $^1$H NMR (400 MHz, DMSO-d$_6$) δ 8.66 (t, J=5.3 Hz, 1H), 7.87-7.75 (m, 2H), 7.53-7.37 (m, 3H), 6.27 (dd, J=17.1, 10.1 Hz, 1H), 6.12 (dd, J=17.1, 2.2 Hz, 1H), 5.62 (dd, J=10.1, 2.2 Hz, 1H), 4.73 (t, J=8.8 Hz, 2H), 4.47 (d, J=5.6 Hz, 2H), 3.44 (t, J=8.8 Hz, 2H).

Example 13

N-((4-(4-(trifluoromethoxy)phenyl)quinazolin-2-yl)methyl)acrylamide (Compound 7)

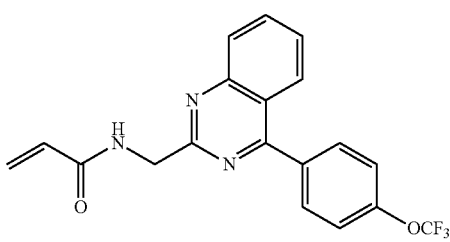 [SMILES: C=CC(=O)NCc1nc(-c2ccc(OC(F)(F)F)cc2)c2ccccc2n1]

Step 1: 2-chloro-4-[4-(trifluoromethoxy)phenyl]quinazoline

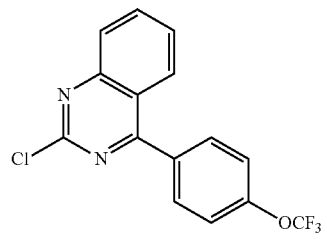 [SMILES: FC(F)(F)Oc1ccc(-c2nc(Cl)nc3ccccc23)cc1]

A mixture of 2,4-dichloroquinazoline (300 mg, 1.51 mmol), 4-(trifluoromethoxy)phenylboronic acid (295 mg, 1.43 mmol), K$_3$PO4 (642 mg, 3.03 mmol), 1,4-dioxane (8 mL) and water (2 mL) was stirred for 5 minutes while purging with nitrogen. Pd(dppf)Cl$_2$ (115 mg, 0.16 mmol) was added and the reaction was heated to 100° C. for 30 minutes. The reaction was then cooled to room temperature, diluted with water, extracted twice with EtOAc, dried over MgSO$_4$ and solvent was removed under reduced pressure. The crude mixture was purified by flash column chromatography (Silica, 0 to 5% EtOAc/heptanes) to yield 2-chloro-4-[4-(trifluoromethoxy)phenyl]quinazoline (90 mg, 18% in yield). LCMS (ESI) [M+H]$^+$=325.0. 1H NMR (400 MHz, CDCl$_3$) δ 8.09 (td, J=9.1, 0.5 Hz, 2H), 7.97 (ddd, J=8.4, 6.9, 1.4 Hz, 1H), 7.90-7.82 (m, 2H), 7.66 (ddd, J=8.3, 6.9, 1.2 Hz, 11H), 7.49-7.40 (m, 2H).

Step 2: 4-[4-(trifluoromethoxy)phenyl]quinazoline-2-carbonitrile

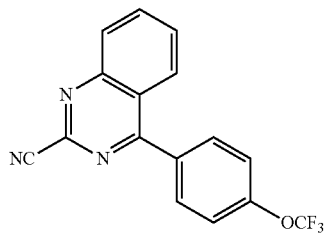 [SMILES: N#Cc1nc(-c2ccc(OC(F)(F)F)cc2)c2ccccc2n1]

A mixture of 2-chloro-4-[4-(trifluoromethoxy)phenyl]quinazoline (90 mg, 0.28 mmol) and zinc cyanide (0.04 mL, 0.55 mmol) in DMF (2 mL) was degassed 5 minutes before the addition of Pd(PPh$_3$)$_4$ (32 mg, 0.03 mmol). The mixture was heated 1 h at 100° C. The reaction mixture was diluted with EtOAc, washed three times with H$_2$O, dried over MgSO$_4$. The organic solution was concentrated under reduced pressure and purified by flash column chromatography (Silica, 0 to 20% EtOAc/heptanes) to yield 4-[4-(trifluoromethoxy)phenyl]quinazoline-2-carbonitrile (82 mg, 94% in yield). LCMS (ESI) [M+H]$^+$=316.1.

Step 3: N-[[4-[4-(trifluoromethoxy)phenyl]quinazolin-2-yl]methyl]prop-2-enamide

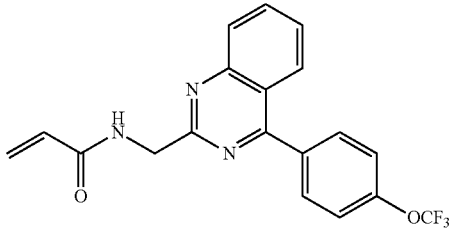 [SMILES: C=CC(=O)NCc1nc(-c2ccc(OC(F)(F)F)cc2)c2ccccc2n1]

A solution of 4-[4-(trifluoromethoxy)phenyl]quinazoline-2-carbonitrile (44 mg, 0.14 mmol) in toluene (4 mL) was cooled to 0° C. DIBAL-H in heptanes (1.0 M, 0.68 mL, 0.68 mmol) was slowly added to the solution with stirring. The reaction was then slowly warmed to room temperature and stirred for 30 minutes. The reaction mixture was diluted with water, extracted twice with EtOAc, dried over MgSO$_4$, and solvent was removed under reduced pressure to give crude [4-[4-(trifluoromethoxy)phenyl]quinazolin-2-yl]methanamine (40 mg). LCMS (ESI) [M+H]$^+$=320.1. This crude material was dissolved in THF (3 mL) and saturated aqueous solution of NaHCO$_3$ (0.25 mL). Acryloyl chloride (0.02 mL, 0.20 mmol) was added and the mixture was stirred at room temperature for 30 minutes. Solvent was removed under reduced pressure and the residue was purified by PreµLCMS (CSH column, 35-55% MeCN/10 mM AmF water) to yield N-[[4-[4-(trifluoromethoxy)phenyl]quinazolin-2-yl]methyl]prop-2-enamide (5 mg, 11% in yield). LCMS (ESI) [M+H]$^+$=374.1. 1H NMR (400 MHz, DMSO-d$_6$) δ 8.81 (t, J=5.5 Hz, 1H), 8.10-8.01 (m, 3H), 7.94 (d, J=8.6 Hz, 2H), 7.77-7.70 (m, 1H), 7.63 (d, J=8.4 Hz, 2H), 6.43 (dd, J=17.1, 10.2 Hz, 1H), 6.14 (dd, J=17.1, 2.0 Hz, 1H), 5.65 (dd, J=10.2, 2.0 Hz, 1H), 4.76 (d, J=5.8 Hz, 2H).

Example 14

N-[[7-[4-(trifluoromethoxy)phenyl]thiazolo[5,4-d]pyrimidin-5-yl]methyl]prop-2-enamide (Compound 21)

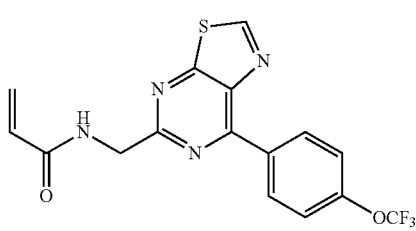 [SMILES: C=CC(=O)NCc1nc(-c2ccc(OC(F)(F)F)cc2)c2ncsc2n1]

Step 1: 5-chloro-7-[4-(trifluoromethoxy)phenyl]thiazolo[5,4-d]pyrimidine

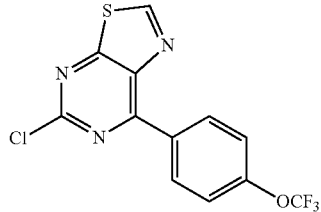 [SMILES: FC(F)(F)Oc1ccc(-c2nc(Cl)nc3scnc23)cc1]

4-(trifluoromethoxy)phenylboronic acid (500 mg, 2.43 mmol), 5,7-dichlorothiazolo[5,4-d]pyrimidine (500 mg, 2.43 mmol), Pd(dppf)Cl$_2$ (177.38 mg, 0.24 mmol), K$_3$PO$_4$ (1029 mg, 4.85 mmol) were mixed in 1,4-dioxane (5 mL)/water (0.30 mL) and the mixture was stirred at room temperature for 20 minutes then heated at 100° C. for 2 minutes. The reaction was quickly diluted with water/ethyl acetate (10 mL/20 mL) and organic layer was separated and dried over Na$_2$SO$_4$, filtered and concentrated in vacuo with silica. The crude was purified by flash column chromatography (Silica, 0-40% EtOAc/heptanes) to give 5-chloro-7-[4-(trifluoromethoxy)phenyl]thiazolo[5,4-d]pyrimidine (460 mg, 57% in yield). LCMS (ESI) [M+H]$^+$=332.5

Step 2: 7-[4-(trifluoromethoxy)phenyl]thiazolo[5,4-d]pyrimidine-5-carbonitrile

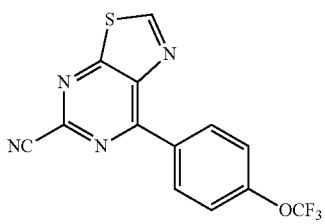 [SMILES: N#Cc1nc(-c2ccc(OC(F)(F)F)cc2)c2ncsc2n1]

5-chloro-7-[4-(trifluoromethoxy)phenyl]thiazolo[5,4-d]pyrimidine (460 mg, 1.39 mmol), Zn(CN)$_2$ (163 mg, 1.39 mmol), Pd(PPh$_3$)$_4$ (80 mg, 0.07 mmol) were added to DMF (3 mL) in a microwave vial. The mixture was purged with N$_2$ for 5 minutes and heated at 180° C. in microwave for 30 minutes. The reaction was then diluted with EtOAc (75 mL) and washed with sat. aq. NaHCO$_3$ (25 mL), brine (3×25 mL), dried over Na$_2$SO$_4$, filtered and concentrated in vacuo with silica. Crude material was purified by flash column chromatography (Silica, 0-50% EtOAc/heptanes) to give 7-[4-(trifluoromethoxy)phenyl]thiazolo[5,4-d]pyrimidine-5-carbonitrile (250 mg, 56% in yield) as a yellow solid. LCMS (ESI) [M+H]$^+$=323.5

Step 3: tert-butyl N-[[7-[4-(trifluoromethoxy)phenyl]thiazolo[5,4-d]pyrimidin-5-yl]methyl]carbamate

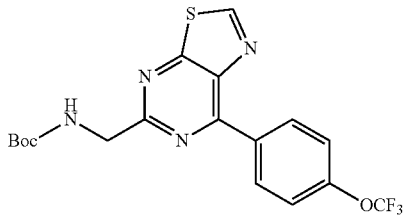 [SMILES: CC(C)(C)OC(=O)NCc1nc(-c2ccc(OC(F)(F)F)cc2)c2ncsc2n1]

7-[4-(trifluoromethoxy)phenyl]thiazolo[5,4-d]pyrimidine-5-carbonitrile (250 mg, 0.78 mmol) was dissolved in methanol (10 mL) and to the solution was added di-tert-butyl dicarbonate (846 mg, 3.88 mmol) and raney nickel (332 mg). The reaction was stirred at room temperature under a hydrogen atmosphere (1 atm) for 3 days till starting material was consumed. The reaction is filtered through Celite® and concentrated in vacuo. The crude was purified by flash column chromatography (Silica, 0-50% EtOAc/heptanes) to give tert-butyl N-[[7-[4-(trifluoromethoxy)phenyl]thiazolo[5,4-d]pyrimidin-5-yl]methyl]carbamate (190 mg, 57% in yield). LCMS (ESI) [M+H]$^+$=427.1.

Step 4: N-[[7-[4-(trifluoromethoxy)phenyl]thiazolo[5,4-d]pyrimidin-5-yl]methyl]prop-2-enamide

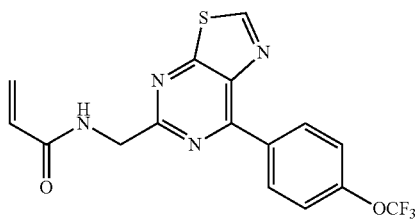 [SMILES: C=CC(=O)NCc1nc(-c2ccc(OC(F)(F)F)cc2)c2ncsc2n1]

tert-butyl-N-[[7-[4-(trifluoromethoxy)phenyl]thiazolo[5,4-d]pyrimidin-5-yl]methyl]carbamate (66 mg, 0.15 mmol) was dissolved in DCM (4 mL) and to the solution was added TFA (1 mL). The reaction was stirred at room temperature for 1 hour till completion. To the mixture was added toluene (3 mL) and concentrated in vacuo. The crude was dissolved in 1,4-dioxane/sat. aq. Na$_2$CO$_3$ (3 mL/0.5 mL) and stirred for 10 minutes. To the mixture was added acryloyl chloride (16 uL, 0.20 mmol) and stirred for 10 minutes till completion. The reaction was then diluted with water (10 mL) and extracted with EtOAc (30 mL). The organic layer was separated and washed with brine, dried over Na$_2$SO$_4$, filtered and concentrated. The crude was purified by flash column chromatography (C18, 35-55% MeCN/10 mM AmF water) to give N-[[7-[4-(trifluoromethoxy)phenyl]thiazolo[5,4-d]pyrimidin-5-yl]methyl]prop-2-enamide (15 mg, 25% in yield). LCMS (ESI) [M+H]$^+$=381.1. 1H NMR (400 MHz, DMSO-d$_6$) 9.69 (s, 1H), 8.90-8.79 (m, 3H), 7.64 (d, J=8.9 Hz, 2H), 6.43 (dd, J=17.1, 10.3 Hz, 1H), 6.15 (dd, J=17.1, 2.1 Hz, 1H), 5.66 (dd, J=10.2, 2.1 Hz, 1H), 4.77 (d, J=5.9 Hz, 2H)$^+$.

EXAMPLE 15

2-chloro-N-[[7-[4-(trifluoromethoxy)phenyl]thiazolo[5,4-d]pyrimidin-5-yl]methyl]acetamide (Compound 15)

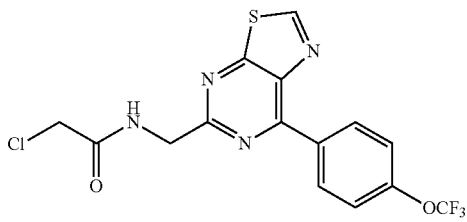 [SMILES: O=C(CCl)NCc1nc(-c2ccc(OC(F)(F)F)cc2)c2ncsc2n1]

tert-butyl-N-[[7-[4-(trifluoromethoxy)phenyl]thiazolo[5,4-d]pyrimidin-5-yl]methyl]carbamate (30 mg, 0.07 mmol) (described in Example 14, step 3) was dissolved in DCM (1 mL) and to the solution was added TFA (0.3 mL). The reaction was stirred at room temperature for 30 minutes. The crude reaction mixture was diluted with toluene (2 mL) and then concentrated. The crude intermediate was then dissolved in DCM (1 mL) and to the solution was added TEA (97 uL, 0.70 mmol), followed by chloroacetyl chloride (6 uL, 0.08 mmol). The reaction mixture was stirred at room temperature for 2 hours. LCMS indicated some of SM remaining and another chloroacetyl chloride (6 uL, 0.08 mmol) was added. Stirring continued for 30 minutes till all the starting material was consumed, as indicated by LCMS analysis. The reaction was then quenched with sat. aq. NaHCO$_3$ (20 mL) and the product was extracted with DCM (20 mL×3). The organic layers were combined and dried with anhydrous Na$_2$SO$_4$, filtered and concentrated. The crude product is purified by flash column chromatography (Silica, 0-20% DCM/MeOH) to give2-chloro-N-[[7-[4-(trifluoromethoxy)phenyl]thiazolo[5,4-d]pyrimidin-5-yl]methyl]acetamide (16 mg, 56% in yield). LCMS (ESI) [M+H]$^+$=403.5. $^1$H NMR (400 MHz, DMSO-d$_6$) δ 9.67 (s, 1H), 8.94 (s, 1H), 8.82 (d, J=8.4 Hz, 2H), 7.62 (d, J=8.4 Hz, 2H), 4.70 (d, J=5.7 Hz, 2H), 4.23 (s, 2H).

Example 16

N-[[7-[4-(trifluoromethoxy)phenyl]thiazolo[5,4-d]pyrimidin-5-yl]methyl]prop-2-enamide (Compound 11)

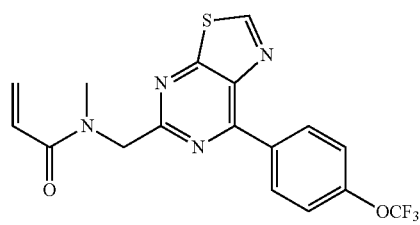 [SMILES: C=CC(=O)N(C)Cc1nc(-c2ccc(OC(F)(F)F)cc2)c2ncsc2n1]

Step 1: N-methyl-1-[7-[4-(trifluoromethoxy)phenyl]thiazolo[5,4-d]pyrimidin-5-yl]methanamine

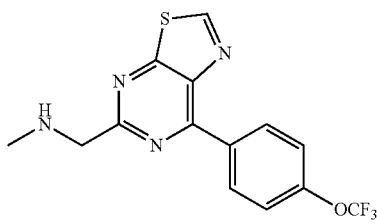 [SMILES: CNCc1nc(-c2ccc(OC(F)(F)F)cc2)c2ncsc2n1]

tert-butyl-N-[[7-[4-(trifluoromethoxy)phenyl]thiazolo[5,4-d]pyrimidin-5-yl]methyl]carbamate (58mg, 0.14 mmol) (described in Example 15, step 3) was dissolved in DCM (1 mL) and TFA (0.3 mL) was added. The reaction was stirred for 30 minutes till completion, diluted with toluene (3 mL) and concentrated in vacuo. The crude material was dissolved in EtOAc/sat. aq. NaHCO$_3$ (10 mL/2 mL) and the organic layer was separated, dried over Na$_2$SO$_4$. The solvent was removed in vacuo and HFIP (1 mL) was added to this crude. Methyl trifluoromethanesulfonate (23 uL, 0.20 mmol) was then added to this solution at room temperature. The reaction was stirred at room temperature for 90 minutes. The reaction mixture was passed through a silica pad (60 mL of silica) washed with EtOAc/heptanes (1/1 ratio in a total of 100 mL) and the filtrate was discarded. The silica pad was then washed with MeOH/DCM (4/1 ratio in a total of 200 mL) to elute the product out and the filtrate was concentrated in vacuo to give the crude N-methyl-1-[7-[4-(trifluoromethoxy)phenyl]thiazolo[5,4-d]pyrimidin-5-yl]methanamine (45 mg, 97% in yield) together with starting material and bis-methylated byproduct as an inseparable mixture. This crude was carried to the next step without further purification. LCMS (ESI) [M+H]$^+$=341.5.

Step 2: N-methyl-1-[7-[4-(trifluoromethoxy)phenyl]thiazolo[5,4-d]pyrimidin-5-yl]methanamine

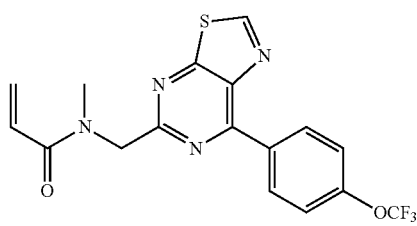 [SMILES: C=CC(=O)N(C)Cc1nc(-c2ccc(OC(F)(F)F)cc2)c2ncsc2n1]

N-methyl-1-[7-[4-(trifluoromethoxy)phenyl]thiazolo[5,4-d]pyrimidin-5-yl]methanamine (15 mg, 0.05 mmol) was dissolved in THF (1 mL) and to the solution was added sat. aq. Na$_2$CO$_3$ (200 uL) and water (0.50 mL). Acryloyl chloride (4 uL, 0.05 mmol) was added to the solution. The reaction mixture was stirred at room temperature for 20 minutes. The crude reaction mixture was diluted with ethyl acetate/water (20 mL/10 mL), the organic layer was separated, dried over Na$_2$SO$_4$, filtered and concentrated in vacuo. The crude organic mixture was purified by preµLCMS (CSH column, 35-55% MeCN/10 mM AmF water) to give N-methyl-N-[[7-[4-(trifluoromethoxy)phenyl]thiazolo[5,4-d]pyrimidin-5-yl]methyl]prop-2-enamide (5.8 mg, 32% in yield). LCMS (ESI) [M+H]$^+$=395.6. $^1$H NMR (400 MHz, DMSO-d$_6$) δ 9.67 (s, 1H), 8.87-8.72 (m, 2H), 7.66-7.58 (m, 2H), 7.07-6.72 (m, 1H), 6.13 (d, J=16.4 Hz, 1H), 5.66 (dd, J=58.3, 10.3 Hz, 1H), 4.99 (d, J=42.6 Hz, 2H), 3.01 (s, 3H).

Example 17

2-chloro-N-methyl-N-[[7-[4-(trifluoromethoxy)phenyl]thiazolo[5,4-d]pyrimidin-5-yl]methyl]acetamide
(Compound 1)

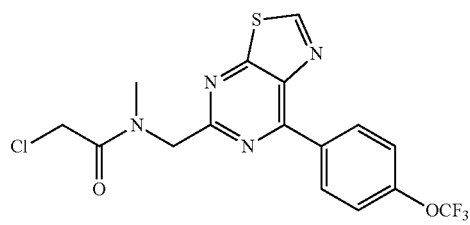 [SMILES: CN(Cc1nc(-c2ccc(OC(F)(F)F)cc2)c2ncsc2n1)C(=O)CCl]

N-methyl-1-[7-[4-(trifluoromethoxy)phenyl]thiazolo[5,4-d]pyrimidin-5-yl]methanamine (15 mg, 0.05 mmol) (described in Example 16, step 1) was dissolved in DCM (1 mL) and to the solution was added TEA (63 uL, 0.45 mmol) followed by chloroacetyl chloride (4 uL, 0.05 mmol). The reaction mixture was stirred at room temperature for 20 minutes. The reaction mixture was then concentrated in vacuo and purified by preµLCMS (CSH column, 35-55% MeCN/10 mM AmF water) to give 2-chloro-N-methyl-N-[[7-[4-(trifluoromethoxy)phenyl]thiazolo[5,4-d]pyrimidin-5-yl]methyl]acetamide (6.8 mg, 36% in yield). LCMS (ESI) [M+H]$^+$=417.5. $^1$H NMR (400 MHz, DMSO-d$_6$) δ 9.68 (d, J=8.1 Hz, 1H), 8.99-8.71 (m, 2H), 7.61 (t, J=8.1 Hz, 2H), 5.07-4.85 (m, 2H), 4.52 (d, J=25.8 Hz, 2H), 3.11 (d, J=102.1 Hz, 3H).

Example 18

N-[[4-[4-(trifluoromethoxy)phenyl]-6,7-dihydro-5H-cyclopenta[d]pyrimidin-2-yl]methyl]prop-2-enamide
(Compound 6)

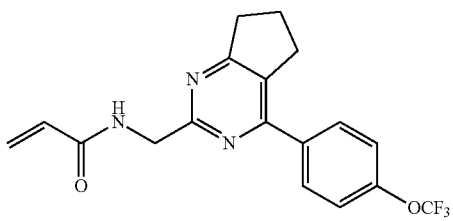 [SMILES: C=CC(=O)NCc1nc2c(c(-c3ccc(OC(F)(F)F)cc3)n1)CCC2]

349

Step 1: 2-chloro-4-[4-(trifluoromethoxy)phenyl]-6,7-dihydro-5H-cyclopenta[d]pyrimidine

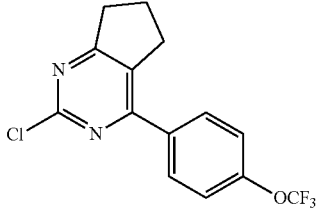 [SMILES: FC(F)(F)Oc1ccc(-c2nc(Cl)nc3c2CCC3)cc1]

4-(trifluoromethoxy)phenylboronic acid (762 mg, 3.7 mmol), 2,4-dichloro-6,7-dihydro-5H-cyclopenta[d]pyrimidine (700 mg, 3.7 mmol), Pd(dppf)Cl$_2$ (135 mg, 0.19 mmol), K$_3$PO$_4$ (1570 mg, 7.41 mmol) were added in 1,4-dioxane (10 mL)/water (2 mL) and the mixture was stirred at 85° C. in a sealed tube for 30 minutes at which point LC-MS analysis indicated consumption of the starting material. The reaction was diluted with EtOAc/water (100 mL/30 mL), dried over Na$_2$SO$_4$, concentrated and the crude was purified by flash column chromatography (Silica, load with toluene, 0-100% EA/heptanes) to provide 2-chloro-4-[4-(trifluoromethoxy)phenyl]-6,7-dihydro-5H-cyclopenta[d]pyrimidine (710 mg, 61% in yield) as a white solid. LCMS (ESI) [M+H]$^+$=315.5.

Step 2: 4-[4-(trifluoromethoxy)phenyl]-6,7-dihydro-5H-cyclopenta[d]pyrimidine-2-carbonitrile

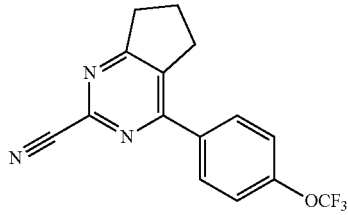 [SMILES: N#Cc1nc2c(c(-c3ccc(OC(F)(F)F)cc3)n1)CCC2]

2-chloro-4-[4-(trifluoromethoxy)phenyl]-6,7-dihydro-5H cyclopenta[d]pyrimidine (710 mg, 2.26 mmol), Zn(CN)$_2$ (265 mg, 2.26 mmol), Pd(PPh$_3$)$_4$ (130 mg, 0.11 mmol) were combined in DMF (6 mL) in a vial. The mixture was purged with N$_2$ for 5 minutes then heated at 180° C. in a microwave reactor for 30 minutes. The reaction was then diluted with EtOAc (75 mL) and washed with sat. aq. NaHCO$_3$ (25 mL), followed by brine (3×25 mL), dried over Na$_2$SO$_4$, filtered and concentrated in vacuo. Crude material was purified by flash column chromatography (Silica, 0-100% EA/heptanes) to give 4-[4-(trifluoromethoxy)phenyl]-6,7-dihydro-5H-cyclopenta[d]pyrimidine-2-carbonitrile (470 mg, 68% in yield) as a yellow solid. LCMS (ESI) [M+H]$^+$=306.5

350

Step 3: [4-[4-(trifluoromethoxy)phenyl]-6,7-dihydro-5H-cyclopenta[d]pyrimidin-2-yl]methanamine

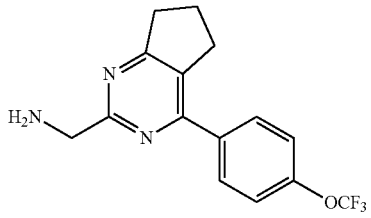 [SMILES: NCc1nc2c(c(-c3ccc(OC(F)(F)F)cc3)n1)CCC2]

4-[4-(trifluoromethoxy)phenyl]-6,7-dihydro-5H-cyclopenta[d]pyrimidine-2-carbonitrile (470 mg, 1.54 mmol) was dissolved in anhydrous THF (15 mL) and the solution was cooled to 0° C. To the solution was added DIBAL-H (4.62 mL, 4.62 mmol, 1 M in heptane) drop wise and stirred for 20 minutes. LCMS indicated full consumption of the starting material and the reaction mixture was poured into aq. 0.5 M HCl (50 mL) and washed with EtOAc (50 mL). The organic layer was discarded and the aqueous layer was basified with NaOH (10 M, 50 mL) and the product was extracted with EtOAc (50 mL×2). The combined organic layers wash washed with brine, dried over Na$_2$SO$_4$, filtered and concentrated to give[4-[4-(trifluoromethoxy)phenyl]-6,7-dihydro-5H-cyclopenta[d]pyrimidin-2-yl]methanamine (152 mg, 32% in yield). The crude product was carried to the next step without further purification. LCMS (ESI) [M+H]$^+$=310.5

Step 4: N-[[4-[4-(trifluoromethoxy)phenyl]-6,7-dihydro-5H-cyclopenta[d]pyrimidin-2-yl]methyl]prop-2-enamide

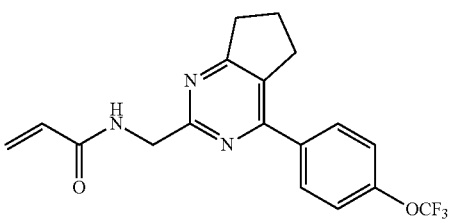 [SMILES: C=CC(=O)NCc1nc2c(c(-c3ccc(OC(F)(F)F)cc3)n1)CCC2]

[4-[4-(trifluoromethoxy)phenyl]-6,7-dihydro-5H-cyclopenta[d]pyrimidin-2-yl]methanamine (152 mg, 0.49 mmol) was dissolved in THF/sat. aq. Na$_2$CO$_3$ (5 mL/1 mL). To the solution was added acryloyl chloride (0.04 mL, 0.54 mmol) and stirred for 10 minutes till completion. The reaction was then diluted with EtOAc/water (50 mL/30 mL). The organic layer was washed with brine, dried over Na$_2$SO$_4$, filtered and concentrated in vacuo. The crude mixture was purified by preμLCMS (CSH column, 30-50% MeCN/10 mM AmF water) to give N-[[4-[4-(trifluoromethoxy)phenyl]-6,7-dihydro-5H-cyclopenta[d]pyrimidin-2-yl]methyl]prop-2-enamide (112 mg, 63% in yield). LCMS (ESI) [M+H]$^+$=364.2. $^1$H NMR (400 MHz, DMSO-d$_6$) δ 8.66 (s, 1H), 8.07 (d, J=8.7 Hz, 2H), 7.52 (d, J=8.2 Hz, 2H), 6.38 (dd, J=17.1, 10.2 Hz, 1H), 6.10 (dd, J=17.1, 1.7 Hz, 1H), 5.61 (dd, J=10.2, 1.7 Hz, 1H), 4.55 (d, J=5.8 Hz, 2H), 3.15 (t, J=7.2 Hz, 2H), 2.96 (t, J=7.7 Hz, 2H), 2.12-1.97 (m, 2H).

Example 19

N-[[4-[4-(trifluoromethoxy)phenyl]-6,7-dihydro-5H-cyclopenta[d]pyrimidin-2-yl]methyl]prop-2-enamide (Compound 4)

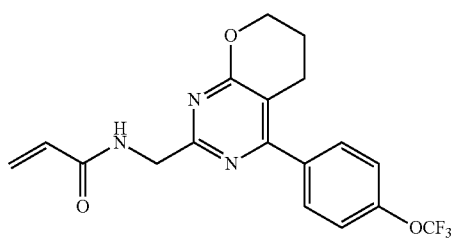 [SMILES: C=CC(=O)NCc1nc2c(c(-c3ccc(OC(F)(F)F)cc3)n1)CCCO2]

Step 1: 2-chloro-4-[4-(trifluoromethoxy)phenyl]-6,7-dihydro-5H-pyrano[2,3-d]pyrimidine

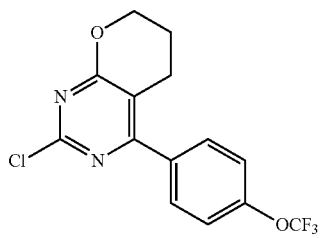 [SMILES: FC(F)(F)Oc1ccc(-c2nc(Cl)nc3c2CCCO3)cc1]

4-(trifluoromethoxy)phenylboronic acid (100 mg, 0.49 mmol), 2,4-dichloro-6,7-dihydro-5H-pyrano[2,3-d]pyrimidine (100 mg, 0.50 mmol), Pd(dppf)Cl$_2$ (35 mg, 0.034 mmol) and K$_3$PO$_4$ (41 mg, 0.97 mmol) were mixed in 1,4-dioxane/water (1.5 mL/0.25 mL) and the mixture was stirred at 100° C. for 20 minutes, at which point the starting materials where consumed. The reaction was then diluted with water/ethyl acetate (10 mL/30 mL). The organic layer was separated and dried over Na$_2$SO$_4$, filtered and concentrated in vacuo with silica. The crude was purified by flash column chromatography (Silica, 0-40% EtOAc/heptanes) to give 2-chloro-4-[4-(trifluoromethoxy)phenyl]-6,7-dihydro-5H-pyrano[2,3-d]pyrimidine (22 mg, 14% in yield). LCMS (ESI) [M+H]$^+$=331.6.

Step 2: 4-[4-(trifluoromethoxy)phenyl]-6,7-dihydro-5H-pyrano[2,3-d]pyrimidine-2-carbonitrile

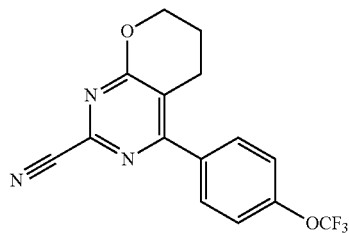 [SMILES: N#Cc1nc2c(c(-c3ccc(OC(F)(F)F)cc3)n1)CCCO2]

2-chloro-4-[4-(trifluoromethoxy)phenyl]-6,7-dihydro-5H-pyrano[2,3-d]pyrimidine (120 mg, 0.36 mmol), Zn(CN)$_2$ (85 mg, 0.73 mmol), Tetrakis(triphenylphosphine)palladium(0) (42 mg, 0.04 mmol) were dissolved in DMF (0.50 mL) and the mixture was purged with nitrogen for 5 minutes. The reaction was stirred at 160° C. for 1 hour. The crude was diluted with ethyl acetate/water (30 mL/20 mL), the organic layer was separated, washed with brine, dried over Na$_2$SO$_4$, filtered and concentrated. The crude was purified by flash column chromatography (Silica, 0-70% EtOAc/heptanes) to give 4-[4-(trifluoromethoxy)phenyl]-6,7-dihydro-5H-pyrano[2,3-d]pyrimidine-2-carbonitrile (56 mg, 48% in yield). LCMS (ESI) [M+H]$^+$=322.6.

Step 3: [4-[4-(trifluoromethoxy)phenyl]-6,7-dihydro-5H-pyrano[2,3-d]pyrimidin-2-yl]methanamine

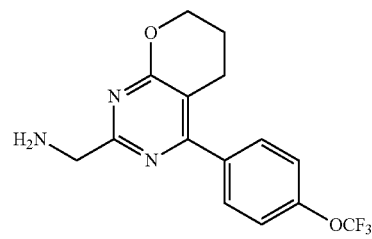 [SMILES: NCc1nc2c(c(-c3ccc(OC(F)(F)F)cc3)n1)CCCO2]

4-[4-(trifluoromethoxy)phenyl]-6,7-dihydro-5H-pyrano[2,3-d]pyrimidine-2-carbonitrile (56 mg, 0.17 mmol) was dissolved in toluene (5 mL) and the solution was cooled to 0° C. under a nitrogen atmosphere. To the solution was slowly added DIBAL-H (1 M in toluene) (435 uL, 0.44 mmol) slowly and stirred for 20 minutes till completion. To the solution was added Na$_2$SO$_4$·10H$_2$O (500 mg) to quench the reaction and stirred for 10 minutes. The mixture as filtered and concentrated in vacuo. The crude material was purified by flash column chromatography (C18, 0-55% MeCN/10 mM AmF water). Fractions from the purification were combined and concentrated to around 20 mL. Sat. aq. Na$_2$CO$_3$ (5 mL) was added to the residue and the product was extracted with ethyl acetate (30 mL×2). The organic layer was washed with brine, dried over Na$_2$SO$_4$, filtered and concentrated to give [4-[4-(trifluoromethoxy)phenyl]-6,7-dihydro-5H-pyrano[2,3-d]pyrimidin-2-yl]methanamine (29 mg, 51% in yield). LCMS (ESI) [M+H]$^+$=326.6.

Step 4: N-[[4-[4-(trifluoromethoxy)phenyl]-6, 7-dihydro-5H-cyclopenta[d]pyrimidin-2-yl]methyl]prop-2-enamide

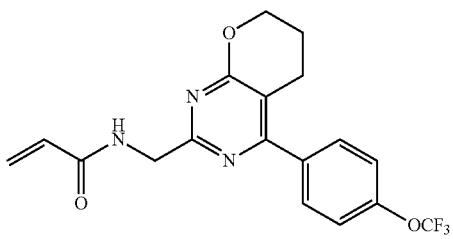 [SMILES: C=CC(=O)NCc1nc2c(c(-c3ccc(OC(F)(F)F)cc3)n1)CCCO2]

tert-butyl-N-[[4-[4-(trifluoromethoxy)phenyl]-6,7-dihydro-5H-pyrano[2,3-d]pyrimidin-2-yl]methyl]carbamate (29 mg, 0.07 mmol) was dissolved in 1,4-dioxane (1 mL) and to the solution was added sat. aq. Na$_2$CO$_3$ (0.2 mL)

followed by acryloyl chloride (7 uL, 0.09 mmol) and stirred for 10 minutes till completion. The reaction was then diluted with water (10 mL) and extracted with EtOAc (30 mL). The organic layer was separated and washed with brine, dried over $Na_2SO_4$, filtered and concentrated in vacuo. The crude mixture was purified by Prep LCMS (CSH column, 35-55% MeCN/10 mM AmF water) to give N-[[4-[4-(trifluoromethoxy)phenyl]-6,7-dihydro-5H-pyrano[2,3-d]pyrimidin-2-yl]methyl]prop-2-enamide (18 mg, 70% in yield). LCMS (ESI) $[M+H]^+$=380.7. $^1$H NMR (400 MHz, DMSO-$d_6$) δ 8.57 (s, 1H), 8.40 (t, J=6.6 Hz, 2H), 7.45 (t, J=8.0 Hz, 2H), 6.40 (dd, J=17.1, 10.2 Hz, 1H), 6.13 (d, J=17.0 Hz, 1H), 5.64 (d, J=10.1 Hz, 1H), 4.45 (d, J=5.5 Hz, 2H), 4.36 (dd, J=8.0, 5.9 Hz, 2H), 2.76 (t, J=5.9 Hz, 2H), 2.03-1.96 (m, 2H).

Example 20

N-[[5-cyano-8-[4-(trifluoromethoxy)phenyl]-6-quinolyl]methyl]prop-2-enamide (Compound 16)

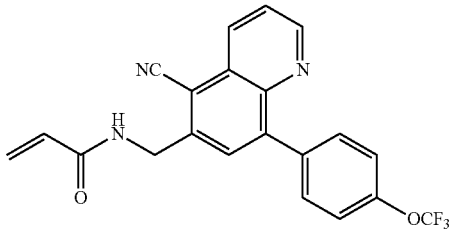 [SMILES: C=CC(=O)NCc1cc(-c2ccc(OC(F)(F)F)cc2)c2ncccc2c1C#N]

Step 1: 5-bromo-8-chloro-6-methyl-quinoline

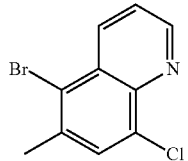

8-chloro-6-methyl-quinoline (1000 mg, 5.63 mmol) was dissolved in DMF (6 mL) and to the solution was added NBS (4000 mg, 22.52 mmol). The reaction was stirred at 60° C. overnight. The reaction was diluted with ethyl acetate/water (50 mL/20 mL), the organic layer was separated and washed with brine. The organic layer was then concentrated in vacou onto silica. The crude mixture was purified by flash column chromatography (Silica, 0-50% EtOAc/heptanes) to give 5-bromo-8-chloro-6-methyl-quinoline (1.3 g, 90% in yield). LCMS (ESI) $[M+H]^+$=258.0

Step 2: 4-chloro-2-methyl-naphthalene-1-carbonitrile

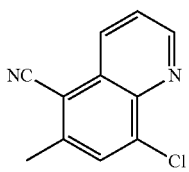

1-bromo-4-chloro-2-methyl-naphthalene (480 mg, 1.88 mmol), $Zn(CN)_2$ (110 mg, 0.94 mmol), $Pd(PPh_3)_4$ (108 mg, 0.09 mmol) were added to DMF (7 mL) and the reaction was purged with $N_2$ for 5 minutes. The mixture was heated at 180° C. in a microwave for 15 minutes. The reaction was then diluted with ethyl acetate/water (50 mL/20 mL) and the organic layer was washed with water twice followed by brine. The organic layer was separated and concentrated in vacuo onto silica. The reaction was purified by flash column chromatography (Silica, from 0% EA in heptanes to 50% EA in heptanes) to give 4-chloro-2-methyl-naphthalene-1-carbonitrile (288 mg, 76% in yield). LCMS (ESI) $[M+H]^+$=203.4

Step 3: 6-methyl- 8-[4-(trifluoromethoxy)phenyl]quinoline-5-carbonitrile

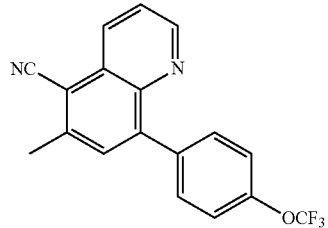 [SMILES: Cc1cc(-c2ccc(OC(F)(F)F)cc2)c2ncccc2c1C#N]

8-chloro-6-methyl-quinoline-5-carbonitrile (40 mg, 0.20 mmol), 4-(trifluoromethoxy)phenylboronic acid (61 mg, 0.30 mmol), $Pd(PPh_3)_4$ (45.6 mg, 0.04 mmol) and $Na_2CO_3$ (42 mg, 0.39 mmol) were added to 1,4-dioxane (1 mL)/water (0.30 mL). The mixture was degassed with nitrogen for 5 minutes and heated at 150° C. in a microwave for 15 minutes. The reaction was then diluted with EtOAc/water (30 mL/20 mL). The organic layer was separated, washed with brine, dried over $Na_2SO_4$, filtered and concentrated in vacuo. The crude was purified by flash column chromatography (Silica, loaded with toluene, 0-40% EtOAc/heptanes silica) to give 6-methyl-8-[4-(trifluoromethoxy)phenyl]-quinoline-5-carbonitrile (45 mg, 69% in yield). LCMS (ESI) $[M+H]^+$=329.6

Step 4: 6-(bromomethyl)-8-[4-(trifluoromethoxy)phenyl]quinoline-5-carbonitrile

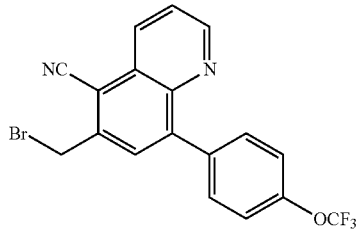

A solution of 6-methyl-8-[4-(trifluoromethoxy)phenyl]quinoline-5-carbonitrile (200 mg, 0.61 mmol), NBS (141 mg, 0.79 mmol) and benzoyl peroxide (15 mg, 0.06 mmol) in carbon tetrachloride (4 mL) was stirred at reflux for 3 hours. Then the reaction mixture was cooled to room temperature, loaded on silica column directly and purified by flash column chromatography (Silica, 0-50% EtOAc/heptanes) to give 6-(bromomethyl)-8-[4-(trifluoromethoxy)phenyl]quinoline-5-carbonitrile (240 mg, 97% in yield). (ESI) [M+H]⁺=409.5

Step 5: [5-cyano- 8-[4-(trifluoromethoxy)phenyl]-6-quinolyl]methyl-diazonio-azanide

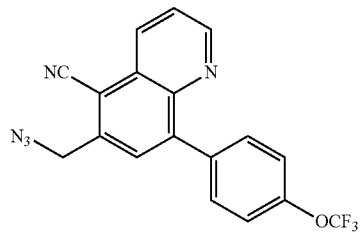 [SMILES: N#Cc1c(CN=[N+]=[N-])cc(-c2ccc(OC(F)(F)F)cc2)c2ncccc12]

6-(bromomethyl)-8-[4-(trifluoromethoxy)phenyl]quinoline-5-carbonitrile (240 mg, 0.59 mmol) and NaN₃ (46 mg, 0.71 mmol) were added to DMF (2 mL) and stirred at room temperature for 2 hours. The reaction was then diluted with water/EtOAc (20 mL/20 mL). The organic layer was washed with water, brine, dried over Na₂SO₄, filtered. The crude solution was concentrated in vacuo onto silica and purified by flash column chromatography (Silica, 0-40% EtOAc/heptanes) to give [5-cyano-8-[4-(trifluoromethoxy)phenyl]-6-quinolyl]methyl-diazonio-azanide (130 mg, 59% in yield). (ESI) [M+H]⁺=370.6

Step 6: N-[[5-cyano-8-[4-(trifluoromethoxy)phenyl]-6-quinolyl]methyl]prop-2-enamide

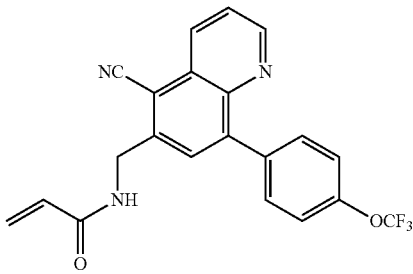 [SMILES: C=CC(=O)NCc1cc(-c2ccc(OC(F)(F)F)cc2)c2ncccc2c1C#N]

[5-cyano-8-[4-(trifluoromethoxy)phenyl]-6-quinolyl]methyl-diazonio-azanide (80 mg, 0.22 mmol) and Pd/C (10% wet) (80 mg) was suspended in EtOAc (5 mL). The reaction is stirred at room temperature under a H₂ atmosphere (1 atm) for 30 minutes and LCMS analysis showed full consumption of the starting material. The reaction mixture is filtered through Celite® and concentrated in vacuo. The crude mixture was dissolved in THF (3 mL) and sat. aq. Na₂CO₃ (0.5 mL) was added. To the mixture was added acryloyl chloride (19 uL, 0.24 mmol) and reaction is stirred at room temperature for 20 minutes. The reaction was diluted with EtOAc/water (20 mL/10 mL) and the organic layer separated. The organics were washed with brine, dried over Na₂SO₄, filtered and concentrated in vacuo. The crude was purified by semi-prep-LCMS (CSH column, 35-55% MeCN/10 mM AmF water) to give N-[[5-cyano-8-[4-(trifluoromethoxy)phenyl]-6-quinolyl]methyl]prop-2-enamide (23 mg, 26% in yield). (ESI) [M+H]⁺=398.6. 1H NMR (400 MHz, DMSO-d₆) δ 9.05 (ddd, J=5.8, 4.1, 1.7 Hz, 1H), 8.93 (t, J=5.7 Hz, 1H), 8.57 (dd, J=8.5, 1.7 Hz, 1H), 7.87 (s, 1H), 7.85-7.81 (m, 1H), 7.79-7.75 (m, 2H), 7.52 (d, J=7.9 Hz, 2H), 6.27 (dd, J=17.1, 10.1 Hz, 1H), 6.12 (dd, J=17.1, 2.1 Hz, 1H), 5.63 (dd, J=10.1, 2.1 Hz, 1H), 4.77 (d, J=5.8 Hz, 2H).

Example 21

N-((5-ethyl-8-(4-(trifluoromethoxy)phenyl)imidazo[1,2-a]pyridin-6-yl)methyl)acrylamide, (Compound 26)

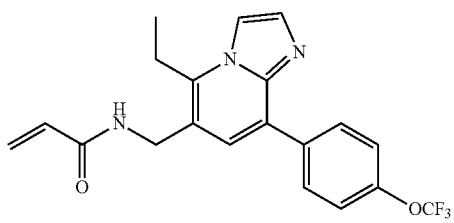

Step 1: 6-amino-2-chloronicotinonitrile

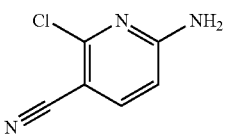

To 20 mL microwave vial with 2,6-dichloropyridine-3-carbonitrile (1.73 g, 10.02 mmol) was added ammonia 7N in MeOH (15 mL, 105 mmol). The vial was sealed and heated at 120° C. for 25 minutes. This reaction was repeated three time for a total of 5.20 g of 2,6-dichloropyridine-3-carbonitrile. The three reactions were concentrated to dryness onto silica gel. The crude was purified by flash column chromatography (Silica, 10-60% EtOAc/heptanes) to afford 6-amino-2-chloronicotinonitrile (2.78 g, 60.2% in yield) as a white solid. LCMS (ESI) [M+H]⁺=154.2; ¹H NMR (400 MHz, DMSO-d₆) δ 7.78 (d, J=8.6 Hz, 1H), 7.51 (s, 2H), 6.45 (d, J=8.6 Hz, 1H).

Step 2: 6-amino-5-bromo-2-chloronicotinonitrile

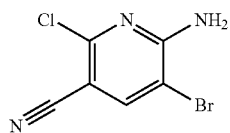 [SMILES: N#Cc1cc(Br)c(N)nc1Cl]

To 6-amino-2-chloro-pyridine-3-carbonitrile (2.78 g, 18.1 mmol) in DCM (60.3 mL) and MeCN (60.3 mL) was added N-bromosuccinimide (6.44 g, 36.2 mmol). The mixture was stirred at room temperature for 3 h. A precipitate was formed, solvent volume was reduced to half by concentration in vacuo and filtrated, rinsed with DCM and dried under vacuum to give 6-amino-5-bromo-2-chloronicotinonitrile (3.25 g, 77.2% in yield) as a cream solid. LCMS (ESI) [M+H]⁺=232.3, 234.3. ¹H NMR (400 MHz, DMSO-d₆) δ 8.30 (s, 1H), 5.75 (s, 2H)⁺.

Step 3: 8-bromo-5-chloroirnidazo[1,2-a]pyridine-6-carbonitrile

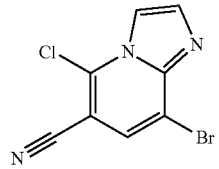 [SMILES: N#Cc1cc(Br)c2nccn2c1Cl]

In a sealed tube with 6-amino-5-bromo-2-chloro-pyridine-3-carbonitrile (3.25 g, 13.98 mmol) was added chloroacetaldehyde 50% in water (39 mL, 307.03 mmol) and the mixture was stirred at 100° C. for 2 hours. The solution was then cooled to room temperature and concentrated in vacuo. Acetone (75 mL) was added to the residue and the resulting mixture was stirred rapidly for 1.5 hours. The resulting solid was collected through filtration and dried to afford 8-bromo-5-chloroimidazo[1,2-a]pyridine-6-carbonitrile (3.38 g, 94.3% in yield) as a beige solid. LCMS (ESI) [M+H]⁺=256.3, 258.3 ¹H NMR (400 MHz, DMSO-d₆) δ 7.78 (d, J=2.0 Hz, 1H), 7.63 (s, 1H), 7.46 (d, J=1.9 Hz, 1H).

Step 4: 5-chloro-8-(4-(trifluoromethoxy)phenyl)imidazo[1,2-a]pyridine-6-carbonitrile

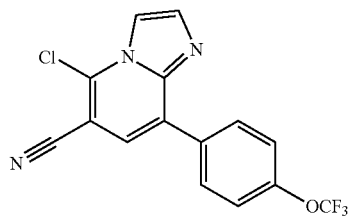 [SMILES: N#Cc1cc(-c2ccc(OC(F)(F)F)cc2)c2nccn2c1Cl]

A microwave vial was charged with 8-bromo-5-chloro-imidazo[1,2-a]pyridine-6-carbonitrile (195 mg, 0.76 mmol), 4-(trifluoromethoxy)phenylboronic acid (140.9 mg, 0.68 mmol) and K₂CO₃ (315.2 mg, 2.28 mmol). Degassed 1,4-dioxane/degassed water (4 mL/1 mL) mixture was added followed by (tetrakis(triphenylphosphine) palladium(0) (87.9 mg, 0.07 mmol). The reaction was purged with N₂ and heated for 10 minutes in microwave at 130° C. This process was repeated eight times using a total of 1.56 g of 8-bromo-5-chloro-imidazo[1,2-a]pyridine-6-carbonitrile. All reactions were combined and poured in EtOAc/water, extraction, washed with brine, dried over anhydrous sodium sulfate, filtered and concentrated. The crude was purified by flash column chromatography (Silica, 5-70% EtOAc/heptanes) to afford 5-chloro- 8-(4-(trifluoromethoxy)phenyl)imidazo[1,2-a]pyridine-6-carbonitrile (1.19 g, 57.8% in yield) as a white solid. LCMS (ESI) [M+H]⁺=338.1. ¹H NMR (400 MHz, CDCl₃) δ 8.03-7.97 (m, 3H), 7.95 (d, J=1.4 Hz, 1H), 7.51 (s, 1H), 7.40 (d, J=8.7 Hz, 2H)⁺.

Step 5: 8-(4-(trifluoromethoxy)phenyl)-5-vinylimidazo[1,2-a]pyridine-6-carbonitrile

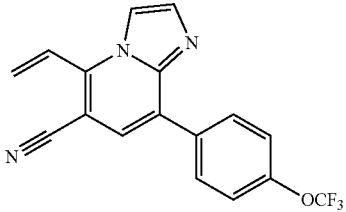 [SMILES: C=Cc1c(C#N)cc(-c2ccc(OC(F)(F)F)cc2)c2nccn12]

In a RBF purged with nitrogen was added 5-chloro-8-[4-(trifluoromethoxy)phenyl]imidazo[1,2-a]pyridine-6-carbonitrile (560 mg, 1.66 mmol) and potassium trifluoro(vinyl)boron (888.6 mg, 6.63 mmol). To the mixture was added degassed 1,4-dioxane (12 mL) followed by the addition of triethylamine (0.46 mL, 3.32 mmol) and 1,1-bis(diphenylphosphinos)ferrocene-palladium-dichloride (123 mg, 0.17 mmol). The reaction mixture was further degassed for 2 minutes and heated at 80° C. for 3 hours. The reaction was cooled to room temperature and concentrated onto silica gel. The crude was purified by flash column chromatography (Silica, 5-70% EtOAc/heptanes) to afford 8-(4-(trifluoromethoxy)phenyl)-5-vinylimidazo[1,2-a]pyridine-6-carbonitrile (382 mg, 69.9% in yield) as a yellow solid. LCMS (ESI) [M+H]⁺=330.0. ¹H NMR (400 MHz, CDCl₃) δ 8.01 (d, J=7.9 Hz, 2H), 7.90 (d, J=24.2 Hz, 2H), 7.55 (s, 1H), 7.41 (d, J=8.7 Hz, 2H), 6.97 (dd, J=17.6, 11.8 Hz, 1H), 6.51 (d, J=17.6 Hz, 1H), 6.24 (d, J=11.7 Hz, 1H)⁺.

Step 6: (5-ethyl-8-(4-(trifluoromethoxy)phenyl)imidazo[1,2-a]pyridin-6-yl)methanamine

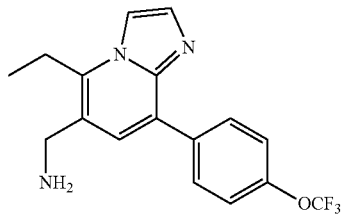 [SMILES: CCc1c(CN)cc(-c2ccc(OC(F)(F)F)cc2)c2nccn12]

To a suspension of 8-[4-(trifluoromethoxy)phenyl]-5-vinyl-imidazo[1,2-a]pyridine-6-carbonitrile (110 mg, 0.33 mmol) in methanol (3.34 mL) at 0° C. was added nickel(II) chloride hexahydrate (39.7 mg, 0.17 mmol) followed by sodium borohydride (50.5 mg, 1.34 mmol) in portions. The reaction mixture was stirred at 0° C. for 10 minutes then slowly warmed up to room temperature. To the reaction was added ammonium hydroxide (28% in H₂O, 0.5 mL) and the reaction was stirred at room temperature for 15 minutes. The reaction was extracted with EtOAc (20 mL×3). The organic layers were combined, washed with brine, dried over anhydrous sodium sulfate, filtered and concentrated. The crude was purified by flash column chromatography (Silica, 0-20% DCM/MeOH) to afford (5-ethyl-8-(4-(trifluoromethoxy)phenyl)imidazo[1,2-a]pyridin-6-yl)methanamine (44 mg, 39.3% in yield). LCMS (ESI) [M+H]⁺=336.2

Step 7: N-((5-ethyl-8-(4-(trifluoromethoxy)phenyl)
imidazo[1,2-a]pyridin-6-yl)methyl)acrylamide

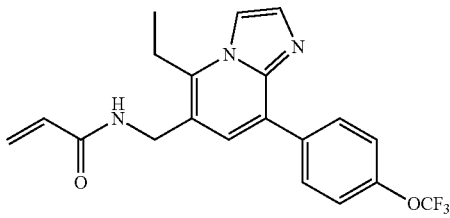 [SMILES: C=CC(=O)NCc1cc(-c2ccc(OC(F)(F)F)cc2)c2nccn2c1CC]

To (5-ethyl-8-(4-(trifluoromethoxy)phenyl)imidazo[1,2-a]pyridin-6-yl)methanamine (42 mg, 0.13 mmol) in THF (1.14 mL) and 1 mL of saturated aqueous NaHCO₃ solution was added acryloyl chloride (10.7 uL, 0.13 mmol). The mixture was stirred at room temperature for 30 minutes. Then EtOAc/water (20 mL/20 mL) were added. The organic layer was separated, dried over anhydrous sodium sulfate, filtered and concentrated. The crude was purified by PreμLCMS, (CSH column, 25-45% MeCN/10 mM AmF water). Pure fractions were collected and lyophilized to provide N-((5-ethyl-8-(4-(trifluoromethoxy)phenyl)imidazo[1,2-a]pyridin-6-yl)methyl)acrylamide (23.5 mg, 48% in yield). LCMS (ESI) [M+H]⁺=390.2 ¹H NMR (400 MHz, DMSO-d₆) δ 8.62 (s, 1H), 8.24 (d, J=8.7 Hz, 2H), 8.09 (s, 1H), 7.70 (s, 1H), 7.54 (s, 1H), 7.50 (d, J=8.4 Hz, 2H), 6.24 (dd, J=17.1, 10.0 Hz, 1H), 6.12 (dd, J=17.0, 2.1 Hz, 1H), 5.61 (dd, J=9.9, 2.1 Hz, 1H), 4.48 (d, J=5.5 Hz, 2H), 3.15 (q, J=7.3 Hz, 2H), 1.24 (t, J=7.4 Hz, 3H)⁺.

Example 22

N-((5-(hydroxymethyl)-8-(4-(trifluoromethoxy)phenyl)imidazo[1,2-a]pyridin-6-yl)methyl)acrylamide
(Compound 5)

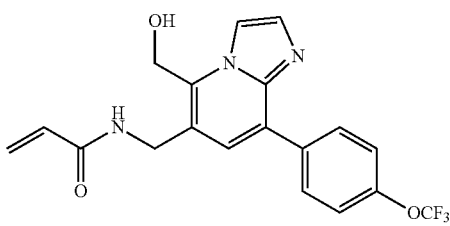

Step 1: 5-formyl-8-(4-(trifluoromethoxy)phenyl)
imidazo[1,2-a]pyridine-6-carbonitrile

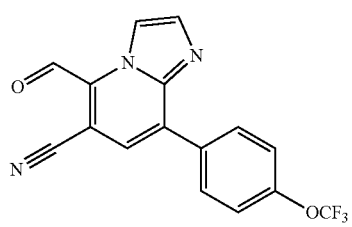 [SMILES: N#Cc1cc(-c2ccc(OC(F)(F)F)cc2)c2nccn2c1C=O]

To 8-(4-(trifluoromethoxy)phenyl)-5-vinylimidazo[1,2-a]pyridine-6-carbonitrile (100 mg, 0.30 mmol) (described in Example 25, step 5) in acetone (1.8 mL) and water (0.3 mL) was added osmium tetroxide (4% wt in water, 77.2 uL, 0.01 mmol) and sodium (meta)periodate (194.9 mg, 0.91 mmol). The reaction was stirred at room temperature for 14 hours. To the reaction was added EtOAc and saturated aqueous NaHCO₃ solution. Phased were separated, organic phase was washed with 10% aqueous Na₂S₂O₃ solution followed by brine, dried over anhydrous sodium sulfate, filtered and concentrated in vacuo. The crude was purified by flash column chromatography (Silica, 0-100% EtOAc/heptanes) to afford 5-formyl-8-(4-(trifluoromethoxy)phenyl)imidazo[1,2-a]pyridine-6-carbonitrile (79 mg, 78.5% in yield). LCMS (ESI) [M+H]⁺=332.1

Step 2: 5-(hydroxymethyl)-8-(4-(trifluoromethoxy)
phenyl)imidazo[1,2-a]pyridine-6-carbonitrile

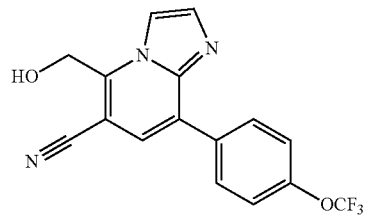 [SMILES: N#Cc1cc(-c2ccc(OC(F)(F)F)cc2)c2nccn2c1CO]

To 5-formyl-8-[4-(trifluoromethoxy)phenyl]imidazo[1,2-a]pyridine-6-carbonitrile (79 mg, 0.24 mmol) in methanol (2 mL) was added sodium borohydride (18.1 mg, 0.48 mmol). The reaction was stirred at room temperature for 35 minutes. To the reaction mixture was added a saturated aqueous NaHCO₃ solution, water/EtOAc and then extracted 3 times with EtOAc. The combined organic phases were washed with brine, dried over anhydrous sodium sulfate, filtered and concentrated to give 5-(hydroxymethyl)-8-(4-(trifluoromethoxy)phenyl)imidazo[1,2-a]pyridine-6-carbonitrile as a crude mixture that was used without further purification. LCMS (ESI) [M+H]⁺=334.1

Step 3: (6-(aminomethyl)-8-(4-(trifluoromethoxy)
phenyl)imidazo[1,2-a]pyridin-5-yl)methanol

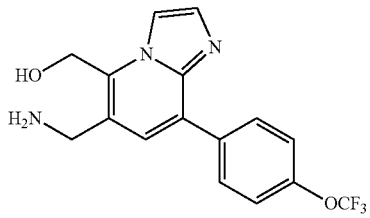 [SMILES: NCc1cc(-c2ccc(OC(F)(F)F)cc2)c2nccn2c1CO]

To a suspension of 5-(hydroxymethyl)-8-(4-(trifluoromethoxy)phenyl)imidazo[1,2-a]pyridine-6-carbonitrile (79 mg, 0.24 mmol) in methanol (2.4 mL) at 0° C. was added nickel(II) chloride hexahydrate (28.2 mg, 0.12 mmol) followed by a portion wise addition of sodium borohydride (35.9 mg, 0.95 mmol). The reaction mixture was stirred at 0° C. for 5 minutes and then slowly warmed up to room temperature for 2 hours. To the reaction was added ammonium hydroxide (28% in H₂O, 0.5 mL), water and the reaction was stirred at room temperature for 15 minutes. DCM was added and extracted 3 times with DCM. The combined organics were dried with anhydrous sodium sulfate, filtered and concentrated. The crude material obtained was purified by flash column chromatography (C18, 10-70% MeCN/10 mM AmF water). Appropriate fractions were combined and lyophilized to provide (6-(aminomethyl)-8-(4-(trifluoromethoxy)phenyl)imidazo[1,2-a]pyridin-5-yl)methanol (17 mg, 21% in yield). LCMS (ESI) [M+H]⁺=338.1

Step 4: N-((5-(hydroxymethyl)-8-(4-(trifluoromethoxy)phenyl)imidazo[1,2-a]pyridin-6-yl)methyl)acrylamide

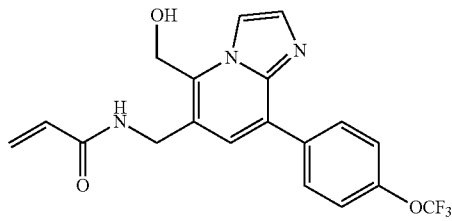 [SMILES: C=CC(=O)NCc1cc(-c2ccc(OC(F)(F)F)cc2)c2nccn2c1CO]

To (6-(aminomethyl)-8-(4-(trifluoromethoxy)phenyl)imidazo[1,2-a]pyridin-5-yl)methanol (17 mg, 0.05 mmol) in THF (0.5 mL) and saturated aqueous NaHCO₃ solution (0.5 mL) was added acryloyl chloride (4.3 uL, 0.05 mmol). The mixture was stirred at room temperature for 45 minutes. EtOAc and water were added and extracted with EtOAc. The combined organic layer was separated, dried over anhydrous sodium sulfate, filtered and concentrated. The crude was purified by PreμLCMS (CSH column, 25-45% MeCN/10 mM AmF water) to provide N-((5-(hydroxymethyl)-8-(4-(trifluoromethoxy)phenyl)imidazo[1,2-a]pyridin-6-yl)methyl)acrylamide (4.2 mg, 21% in yield). LCMS (ESI) [M+H]⁻=390.1. ¹H NMR (400 MHz, d₆-DMOS) 8.59 (t, J=5.0 Hz, 1H), 8.23 (d, J=8.5 Hz, 2H), 8.06 (s, 1H), 7.67 (s, 1H), 7.55-7.46 (m, J=6.6 Hz, 3H), 6.20 (dd, J=17.1, 9.9 Hz, 1H), 6.10 (dd, J=16.9, 1.7 Hz, 1H), 5.59 (dd, J=9.8, 1.7 Hz, 1H), 5.50 (bs, 1H), 4.92 (s, 2H), 4.52 (d, J=5.5 Hz, 2H).

Example 23

N-((7-(4-(trifluoromethoxy)phenyl)oxazolo[5,4-b]pyridin-5-yl)methyl)acrylamide (Compound 9)

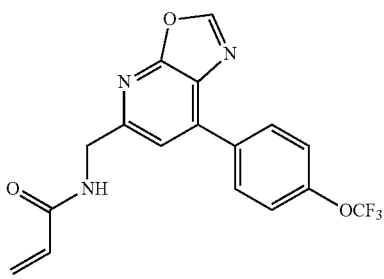 [SMILES: C=CC(=O)NCc1cc(-c2ccc(OC(F)(F)F)cc2)c2ncoc2n1]

Step 1: 6-methyl-3-nitro-4-[4-(trifluoromethoxy)phenyl]-JH-pyridin-2-one

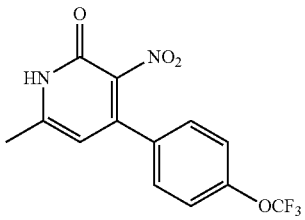 [SMILES: Cc1cc(-c2ccc(OC(F)(F)F)cc2)c([N+](=O)[O-])c(=O)[nH]1]

A flask was charged with 4-chloro-6-methyl-3-nitro-1H-pyridin-2-one (1.0 g, 5.3 mmol), 4-(trifluoromethoxy)phenylboronic acid (1.2 g, 5.83 mmol), K₂CO₃ (2.2 g, 15.91 mmol), 1,4-dioxane (21 mL) and water (5 mL). The mixture was degassed for 5 minutes before the addition of Pd(PPh₃)₄ (306.4 mg, 0.27 mmol) and degassed further for 2 minutes. The reaction was sealed and heated for 18 hours at 90° C. Water/EtOAc were added and the emulsion was passed through sand, then extracted 3 times with EtOAc. The organic phase was dried over Na₂SO₄, filtered and concentrated with silica gel. The crude was purified by flash column chromatography (Silica, 5-100% gradient of 1:4 MeOH:EtOAc/heptanes) to give 6-methyl-3-nitro-4-[4-(trifluoromethoxy)phenyl]-1H-pyridin-2-one (1.4 g, 85% in yield) as a yellow foam. LCMS (ESI) [M+H]⁺=315.6

Step 2: 3-amino-6-methyl-4-[4-(trifluoromethoxy)phenyl]-1H-pyridin-2-one

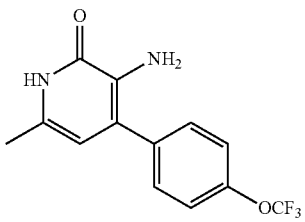 [SMILES: Cc1cc(-c2ccc(OC(F)(F)F)cc2)c(N)c(=O)[nH]1]

To a suspension of 6-methyl-3-nitro-4-[4-(trifluoromethoxy)phenyl]-1H-pyridin-2-one (1.37 g, 4.36 mmol) in methanol (21.8 mL) at 0° C. was added nickel(II) chloride hexahydrate (517.8 mg, 2.18 mmol) followed by portion wise addition of sodium borohydride (659.3 mg, 17.43 mmol). The reaction mixture was stirred at 0° C. for 10 minutes. Ammonium hydroxide (28% in H₂O, 5 mL) and water (20 mL) were added and the reaction was stirred at room temperature for 15 minutes. The reaction was then extracted with DCM 3 times. The combined organic phase was washed with brine, dried with anhydrous sodium sulfate, filtered and concentrated to give crude 3-amino-6-methyl-4-[4-(trifluoromethoxy)phenyl]-1H-pyridin-2-one (1.32 g, quantitative) as a brown solid which was used without further purification. LCMS (ESI) [M+H]⁺=285.5

Step 3: 5-methyl-7-[4-(trifluoromethoxy)phenyl]oxazolo[5,4-b]pyridine

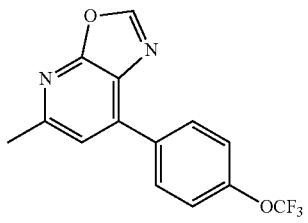 [SMILES: Cc1cc(-c2ccc(OC(F)(F)F)cc2)c2ncoc2n1]

To a suspension of 3-amino-6-methyl-4-[4-(trifluoromethoxy)phenyl]-1H-pyridin-2-one (600 mg, 2.11 mmol) in toluene (4.2 mL) were added p-toluenesulfonic acid monohydrate (20.0 mg, 0.11 mmol) and trimethylorthoformate (1.39 mL, 12.67 mmol). The reaction mixture was stirred at 100° C. for 90 minutes. Additional trimethylorthoformate (1.39 mL, 12.67 mmol) and p-toluenesulfonic acid monohydrate (20.1 mg, 0.11 mmol) were added and stirring was continued at 100° C. for 1.5 hours. The mixture was cooled and the solvent was evaporated under reduced pressure. The residue was purified by flash column chromatography (Silica, 0-70% EtOAc/heptane) to give 5-methyl-7-[4-(trifluoromethoxy)phenyl]oxazolo[5,4-b]pyridine (262 mg, 42% in yield). 1H NMR (400 MHz, DMSO-d$_6$) δ 8.90 (s, 1H), 8.38-8.27 (m, 2H), 7.75 (s, 1H), 7.59 (d, J=8.1 Hz, 2H), 2.65 (s, 3H).

Step 4: 5-(bromomethyl)-7-(4-(trifluoromethoxy)phenyl)oxazolo[5,4-b]pyridine

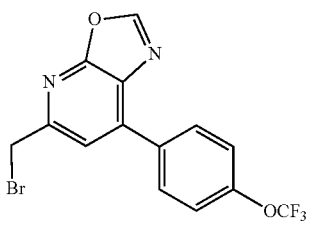 [SMILES: FC(F)(F)Oc1ccc(-c2cc(CBr)nc3ocnc23)cc1]

A solution of 5-methyl-7-[4-(trifluoromethoxy)phenyl]oxazolo[5,4-b]pyridine (260 mg, 0.88 mmol), N-bromosuccinimide (204.5 mg, 1.15 mmol) and benzoyl peroxide (32.1 mg, 0.13 mmol) in carbon tetrachloride (4.42 mL) was stirred at reflux for 18 hours. The reaction was cooled to room temperature and concentrated onto silica gel. The crude product was purified by flash column chromatography (Silica, 0-60% EtOAc/heptane) to give 5-(bromomethyl)-7-[4-(trifluoromethoxy)phenyl]oxazolo[5,4-b]pyridine (174 mg, 53% yield) LCMS (ESI) [M+H]$^+$=372.9, 374.9

Step 5: tert-butyl N-tert-butoxycarbonyl-N-[[7-[4-(trifluoromethoxy)phenyl]oxazolo[5,4-b]pyridin-5-yl]methyl]carbamate

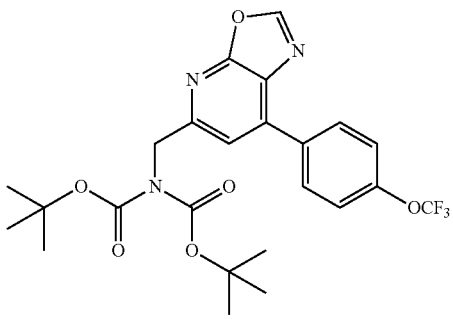 [SMILES: CC(C)(C)OC(=O)N(Cc1cc(-c2ccc(OC(F)(F)F)cc2)c2ncoc2n1)C(=O)OC(C)(C)C]

5-(bromomethyl)-7-[4-(trifluoromethoxy)phenyl]oxazolo[5,4-b]pyridine (174 mg, 0.47 mmol) and tert-butyl N-tert-butoxycarbonylcarbamate (131.7 mg, 0.61 mmol) were dissolved in DMF (2.3 mL) and cesium carbonate (305.7 mg, 0.93 mmol) was added while stirring. The reaction was stirred at room temperature for 18 hours. The reaction was diluted with ethyl acetate and water. The organic layer was collected, washed with brine, dried over Na$_2$SO$_4$, filtered and concentrated onto silica gel. The product was purified by flash column chromatography (Silica, 0-50% EtOAc/heptanes) to give tert-butyl N-tert-butoxycarbonyl-N-[[7-[4-(trifluoromethoxy)phenyl]oxazolo[5,4-b]pyridin-5-yl]methyl]carbamate (171 mg, 72% in yield). LCMS (ESI) [M+H−2Boc]$^+$=310.6.

Step 6: [7-[4-(trifluoromethoxy)phenyl]oxazolo[5,4-b]pyridin-5-yl]methanamine

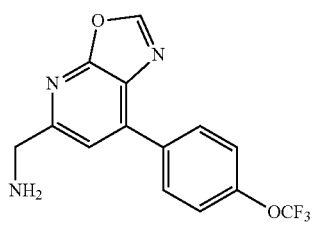 [SMILES: NCc1cc(-c2ccc(OC(F)(F)F)cc2)c2ncoc2n1]

tert-butyl-N-tert-butoxycarbonyl-N-[[7-[4-(trifluoromethoxy)phenyl]oxazolo[5,4-b]pyridin-5-yl]methyl]carbamate (171 mg, 0.34 mmol) was dissolved in DCM (1.2 mL). Trifluoroacetic acid (1.2 mL) was added and the reaction was stirred for 15 minutes at room temperature for 15 minutes. The reaction was concentrated to dryness, poured into DCM and neutralized with sat. aq. NaHCO$_3$. The aqueous phase was extracted with DCM which was then, dried over Na$_2$SO$_4$, filtered and concentrated to give [7-[4-(trifluoromethoxy)phenyl]oxazolo[5,4-b]pyridin-5-yl]methanamine (77 mg, 74% yield). LCMS (ESI) [M+H]$^+$=310.6.

Step 7: N-((7-(4-(trifluoromethoxy)phenyl)oxazolo[5,4-b]pyridin-5-yl)methyl)acrylamide

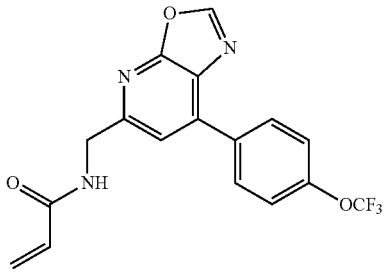 [SMILES: C=CC(=O)NCc1cc(-c2ccc(OC(F)(F)F)cc2)c2ncoc2n1]

To a solution of [7-[4-(trifluoromethoxy)phenyl]oxazolo[5,4-b]pyridin-5-yl]methanamine (77 mg, 0.25 mmol) in THF (1.25 mL) was added 1 mL of saturated NaHCO$_3$ solution followed by acryloyl chloride (21.2 uL, 0.26 mmol). The mixture was stirred at room temperature for 45 minutes. EtOAc and water were added the organic phase was collected, dried over Na$_2$SO$_4$, filtered and concentrated under reduced pressure. The product was then purified by prepµLCMS (CSH column, 30-50% MeCN/10 mM AmF water) to give N-((7-(4-(trifluoromethoxy)phenyl)oxazolo[5,4-b]pyridin-5-yl)methyl)acrylamide (4.5 mg, 5.0% in yield) LCMS (ESI) [M+H]$^+$=364.6. 1H NMR (400 MHz, DMSO-d$_6$) δ 8.98 (s, 1H), 8.82 (t, J=5.6 Hz, 1H), 8.30 (d, J=8.8 Hz, 2H), 7.78 (s, 1H), 7.62 (d, J=8.3 Hz, 2H), 6.35 (dd, J=17.1, 10.2 Hz, 1H), 6.14 (dd, J=17.1, 1.9 Hz, 1H), 5.65 (dd, J=10.2, 1.9 Hz, 1H), 4.62 (d, J=5.9 Hz, 2H).

Example 24

N-[[4-[4-(trifluoromethoxy)phenyl]furo[3,2-d]pyrimidin-2-yl]methyl]prop-2-enamide (Compound 10)

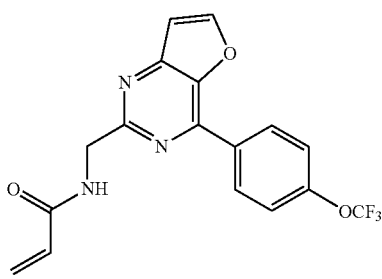 [SMILES: C=CC(=O)NCc1nc(-c2ccc(OC(F)(F)F)cc2)c2occc2n1]

Step 1: 2-chloro-4-[4-(triuoromethoxy)phenyl]furo[3,2-d]pyrimidine

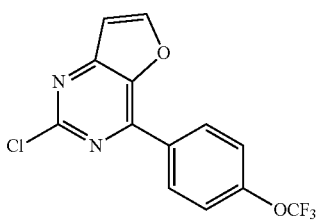 [SMILES: FC(F)(F)Oc1ccc(-c2nc(Cl)nc3ccoc23)cc1]

A flask was charged with 2,4-dichlorofuro[3,2-d]pyrimidine (300 mg, 1.59 mmol), 4-(trifluoromethoxy)phenylboronic acid (300 mg, 1.46 mmol), K$_3$PO4 (675 mg, 3.18 mmol), 1,4-dioxane (8 mL) and water (2 mL). The mixture was degassed 5 minutes before the addition of Pd(dppf)Cl$_2$ (120 mg, 0.16 mmol). The reaction was heated 30 minutes at 100° C. The reaction mixture, diluted with H$_2$O, extracted twice with AcOEt. The combined organic phase was dried with MgSO$_4$, concentrated in vacuo and purified by flash column chromatography (Silica, 0-20% AcOEt/heptanes) to afford 2-chloro-4-[4-(trifluoromethoxy)phenyl]furo[3,2-d]pyrimidine (360 mg, 72% in yield). LCMS (ESI) [M+H]$^+$=315.1.

Step 2: 4-[4-(trifluoromethoxy)phenyl]furo[3,2-d]pyrimidine-2-carbonitrile

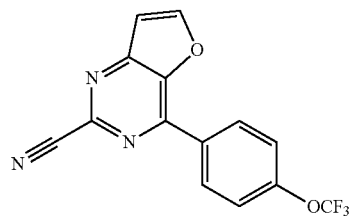 [SMILES: N#Cc1nc(-c2ccc(OC(F)(F)F)cc2)c2occc2n1]

A solution of 2-chloro-4-[4-(trifluoromethoxy)phenyl]furo[3,2-d]pyrimidine (310 mg, 0.99 mmol) and zinc cyanide (153 mg, 1.32 mmol) in DMF (8 mL) was degassed for 5 minutes by N$_2$ before the addition of Pd(PPh$_3$)$_4$ (124 mg, 0.11 mmol). The reaction was heated at 180° C. under microwave irradiation for 20 minutes. The reaction mixture was diluted with EtOAc, washed with water twice, dried with MgSO$_4$ and concentrated in vacuo. The residue was purified by flash column chromatography (Silica, 0-30% EtOAc/heptanes) to give 4-[4-(trifluoromethoxy)phenyl]furo[3,2-d]pyrimidine-2-carbonitrile (241 mg, 80% in yield). LCMS (ESI) [M+H]$^+$=306.1

Step 3: [4-[4-(trifluoromethoxy)phenyl]furo[3,2-d]pyrimidin-2-yl]methanamine

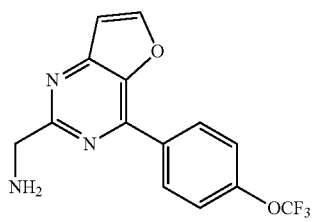 [SMILES: NCc1nc(-c2ccc(OC(F)(F)F)cc2)c2occc2n1]

A solution of 4-[4-(trifluoromethoxy)phenyl]furo[3,2-d]pyrimidine-2-carbonitrile (50 mg, 0.16 mmol) in toluene (2 mL) was cooled to 0° C. and DIBAL-H (1 M/heptanes, 0.41 mL, 0.41 mmol) was added slowly. The ice bath was removed and the reaction stirred at room temperature for 30 minutes. It was concentrated in vacuo, diluted with water, extracted twice with EtOAc, dried with MgSO$_4$ and fully concentrated to dryness. The crude mixture was not further purified and used directly for the next step. LCMS (ESI) [M+H]* =310.1

Step 4: N-[[4-[4-(trifluoromethoxy)phenyl]furo[3,2-d]pyrimidin-2-yl]methyl]prop-2-enamide

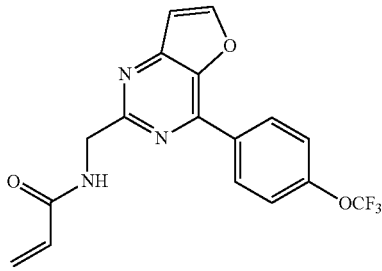 [SMILES: C=CC(=O)NCc1nc(-c2ccc(OC(F)(F)F)cc2)c2occc2n1]

To a solution of [4-[4-(trifluoromethoxy)phenyl]furo[3,2-d]pyrimidin-2-yl]methanamine (44 mg, 0.14 mmol) in THF (1 mL) was added sat. aq. NaHCO$_3$ (0.25 mL) followed by acryloyl chloride (0.02 mL, 0.22 mmol). The mixture was stirred at room temperature for 30 minutes till completion. The residue was diluted with water which was extracted twice with EtOAc. The combined organic phase was concentrated in vacuo and purified preµLCMS (CSH column, 30-50% MeCN/10 mM AmF water) to give N-[[4-[4-(trifluoromethoxy)phenyl]furo[3,2-d]pyrimidin-2-yl]methyl]prop-2-enamide (16 mg, 31% in yield). LCMS (ESI) [M+H]=364.1, 1H NMR (400 MHz, DMSO-d$_6$) δ 8.79 (t, J=5.5 Hz, 1H), 8.66 (d, J=2.3 Hz, 1H), 8.58 (d, J=8.9 Hz, 2H), 7.66 (d, J=8.3 Hz, 2H), 7.31 (d, J=2.2 Hz, 1H), 6.43 (dd, J=17.1, 10.2 Hz, 1H), 6.14 (dd, J=17.1, 2.1 Hz, 1H), 5.65 (dd, J=10.2, 2.1 Hz, 1H), 4.71 (d, J=5.9 Hz, 2H).

Example 25

N-[[4-[4-(trifluoromethoxy)phenyl]-6,7-dihydrofuro[3,2-d]pyrimidin-2-yl]methyl]prop-2-enamide
(Compound 13)

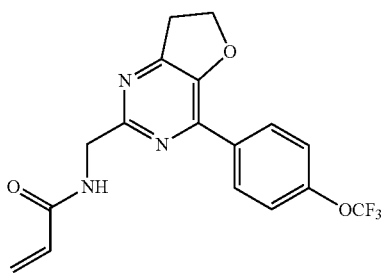 [SMILES: C=CC(=O)NCc1nc2c(c(-c3ccc(OC(F)(F)F)cc3)n1)OCC2]

Step 1: [4-[4-(trifluoromethoxy)phenyl]-6,7-dihydrofuro[3,2-d]pyrimidin-2-yl]methanamine

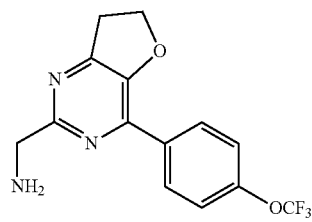

To a solution of 4-[4-(trifluoromethoxy)phenyl]furo[3,2-d]pyrimidine-2-carbonitrile (75 mg, 0.25 mmol) (described in Example 28, step 2) in ethanol (7.5 mL), was added HCl (1N, 0.75 mL, 0.74 mmol) followed by Pd(OH)$_2$ (20%/C wet, 75 mg). The reaction was stirred 18 hours at room temperature under a H$_2$ atmosphere (15 PSI). The reaction mixture was filtered on a pad of Celite® and rinsed with MeOH. The volatiles were evaporated in vacuo to provide [4-[4-(trifluoromethoxy)phenyl]-6,7-dihydrofuro[3,2-d]pyrimidin-2-yl]methanamine (76 mg, 99% in yield) as crude material which was used without further purification. LCMS (ESI) [M+H]$^+$=312.1.

Step 2: N-[[4-[4-(trifluoromethoxy)phenyl]-6,7-dihydrofuro[3,2-d]pyrimidin-2-yl]methyl]prop-2-enamide

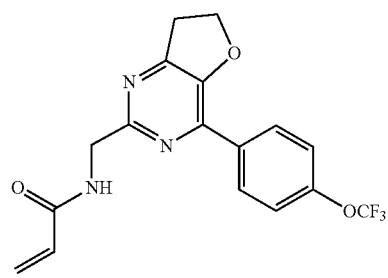 [SMILES: C=CC(=O)NCc1nc2c(c(-c3ccc(OC(F)(F)F)cc3)n1)OCC2]

To a solution of [4-[4-(trifluoromethoxy)phenyl]-6,7-dihydrofuro[3,2-d]pyrimidin-2-yl]methanamine (85 mg, 0.27 mmol) in THF (2 mL) was added sat. aq. NaHCO$_3$ (0.50 mL) followed by acryloyl chloride (0.03 mL, 0.42 mmol). The mixture was stirred at room temperature for 30 minutes until starting materials were consumed. The residue was diluted with H$_2$O and extracted twice with EtOAc. The combined organic phase was concentrated and purified by preµLCMS (CSH column, 30-50% MeCN/10 mM AmF water) to give N-[[4-[4-(trifluoromethoxy)phenyl]-6,7-dihydrofuro[3,2-d]pyrimidin-2-yl]methyl]prop-2-enamide (23 mg, 23% in yield). LCMS (ESI) [M+H]$^+$=366.1, 1H NMR (400 MHz, DMSO-d$_6$) δ 8.69 (t, J=5.7 Hz, 1H), 8.40 (d, J=8.9 Hz, 2H), 7.54 (d, J=8.4 Hz, 2H), 6.40 (dd, J=17.1, 10.2 Hz, 1H), 6.13 (dd, J=17.1, 2.0 Hz, 11H), 5.63 (dd, J=10.2, 2.0 Hz, 1H), 4.80 (t, J=8.9 Hz, 2H), 4.54 (d, J=5.9 Hz, 2H), 3.38 (t, J=8.9 Hz, 2H).

Example 26 (Compound 28)

(R)—N-((5-(1,2-Dihydroxyethyl)-8-(4-(trifluoromethoxy)phenyl)quinoxalin-6-yl)methyl)acrylamide

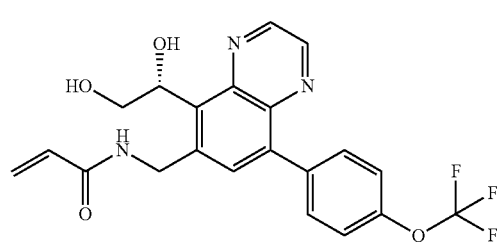

Step 1: 3-bromo-5-nitrobenzene-1,2-diamine

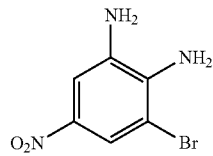 [SMILES: Nc1cc([N+](=O)[O-])cc(Br)c1N]

A mixture of sulfur (16.15 g, 503.78 mmol) and Na₂S 9H₂O (110.0 g, 457.98 mmol) in a mixture of water (120 mL) and ethanol (480 mL) was heated at reflux under nitrogen for 1 h. The solution was added to a stirred suspension of 2-bromo-4,6-dinitro-aniline (120.0 g, 457.98 mmol) and NH₄Cl (27.0 g, 503.78 mmol) in a mixture of water (840 mL) and ethanol (480 mL). The mixture was stirred at 80° C. for 16 h. Then aq. 2N NaOH (540 mL) solution was added dropwise and the mixture was then stirred for a further 15 minutes at 80° C. After cooling, the mixture was poured into a mixture of aq. 2N HCl (540 mL) and ice (500 g), stirred for 15 min to complete the reaction. The mixture was concentrated to remove EtOH. The residue was filtered to give the title compound (100 g, 95%, crude) as a rust-colored solid, which was used for the next step directly without further purification. ¹H NMR (400 MHz, DMSO-d₆): δ 7.64 (d, J=2.8 Hz, 1H), 7.39 (d, J=2.8 Hz, 1H), 6.08 (s, 2H), 5.49 (s, 2H).

Step 2: 5-bromo-7-nitroquinoxaline

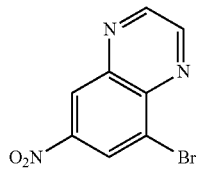

To the mixture of 3-bromo-5-nitrobenzene-1,2-diamine (27.0 g, 116.36 mmol) in water (1 L) was added oxalaldehyde (40% in H₂O, 32.0 mL). The mixture was stirred at 100° C. for 4 hours. After cooled to 10° C., the precipitate was filtered and washed with water (200 mL×2). The filter cake was dried under reduced pressure to afford the title compound (25.0 g, 84%, crude) as a rust-colored solid. ¹H NMR (400 MHz, DMSO-d₆): δ 9.26 (d, J=1.6 Hz, 1H), 9.23 (d, J=1.6 Hz, 1H), 8.94 (d, J=2.4 Hz, 1H), 8.89 (d, J=2.4 Hz, 1H).

Step 3: 8-bromoquinoxalin-6-amine

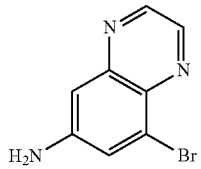

To the mixture of 5-bromo-7-nitroquinoxaline (25.0 g, 98.41 mmol) in EtOH (250 mL) and water (80 mL) was added Fe (27.5 g, 492.05 mmol) and NH₄Cl (26.3 g, 492.05 mmol). The mixture was stirred at 90° C. for 2 hours. The TLC indicated the reaction was completed. The reaction mixture was cooled to room temperature, and filtered. The filter cake was washed with EtOAc (500 mL). The filtrate was concentrated and the residue was diluted with water (400 mL), extracted with EtOAc (500 mL×2) and washed with saturated brine (200 mL), dried over Na₂SO₄ and concentrated. The residue was purified by column on silica gel (0-50% EtOAc in petroleum ether) to afford the title compound (16.0 g, 64%) as a yellow solid. ¹H NMR (400 MHz, CDCl₃): δ 8.62-8.59 (m, 2H), 7.56 (d, J=2.4 Hz, 1H), 7.05 (d, J=2.4 Hz, 1H).

Step 4: 8-(4-(trifluoromethoxy)phenyl)quinoxalin-6-amine

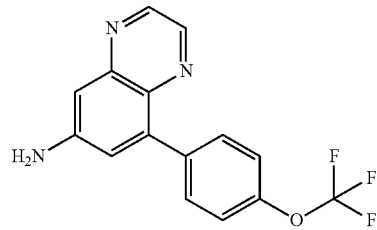 [SMILES: Nc1cc(-c2ccc(OC(F)(F)F)cc2)c2nccnc2c1]

The mixture of (4-(trifluoromethoxy)phenyl)boronic acid (2.0 g, 9.82 mmol), 8-bromoquinoxalin-6-amine (2.0 g, 8.93 mmol), Pd(dppf)Cl₂ (653 mg, 0.89 mmol) and Na₂CO₃ (1.9 g, 17.85 mmol) in 1,4-dioxane (5 mL) and water (1 mL) was stirred at 100° C. under N₂ atmosphere for 3 h. The TLC (50% ethyl acetate in petroleum ether, R_f=0.4) indicated the reaction was completed. The reaction mixture was diluted with water (50 mL), extracted with EtOAc (50 mL×2). The combined organic layers were washed with saturated brine (200 mL) and dried over Na₂SO₄ and concentrated. The residue was purified by column on silica gel (0-50% EtOAc in petroleum ether) to afford the title compound (1.5 g, 55%) as a yellow solid. ¹H NMR (400 MHz, CDCl₃): δ 8.69 (d, J=1.6 Hz, 1H), 8.59 (d, J=1.6 Hz, 1H), 7.72-7.63 (m, 2H), 7.35 (d, J=8.0 Hz, 2H), 7.22-7.20 (m, 2H), 4.14 (s, 2H).

Step 5: 5-bromo-8-(4-(trifluoromethoxy)phenyl)quinoxalin-6-amine

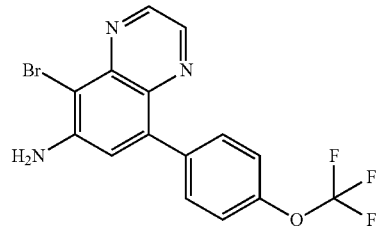 [SMILES: Nc1cc(-c2ccc(OC(F)(F)F)cc2)c2nccnc2c1Br]

To the mixture of 8-(4-(trifluoromethoxy)phenyl)quinoxalin-6-amine (1.0 g, 3.25 mmol) in DCM (10 mL) was added NBS (579 mg, 3.25 mmol) at 0° C. The resulting solution was stirred at 0° C. for 10 min. The TLC (20% EtOAc in Petroleum ether, R_f=0.5) indicated the reaction was completed. The reaction was quenched by water (10 mL). The mixture was extracted with ethyl acetate (20 mL×3) and washed with brine (10 mL). The organic layers were dried over anhydrous sodium sulfate and concentrated under reduced. The residue was purified by chromatography on silica gel (0-20% EtOAc in petroleum ether) to afford the title compound (1.2 g, 96%) as a yellow solid. $^1$H NMR (400 MHz, CDCl$_3$): δ 8.83 (d, J=1.2 Hz, 1H), 8.63 (d, J=1.2 Hz, 1H), 7.66 (d, J=8.4 Hz, 2H), 7.34 (d, J=8.4 Hz, 2H), 7.32 (s, 1H), 4.84 (s, 2H).

Step 6: 8-(4-(trifluoromethoxy)phenyl)-5-vinylquinoxalin-6-amine

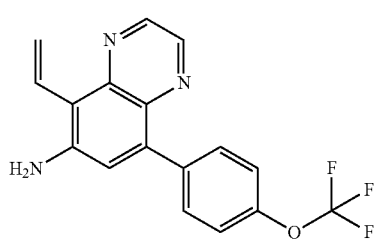

A solution of 5-bromo-8-(4-(trifluoromethoxy)phenyl) quinoxalin-6-amine (1.2 g, 3.12 mmol), Pd(dppf)Cl$_2$(229 mg, 0.3100 mmol), Na$_2$CO$_3$(0.66 g, 6.25 mmol) and 4,4,5,5-tetramethyl-2-vinyl-1,3,2-dioxaborolane (0.53 g, 3.44 mmol) in 1,4-Dioxane (15 mL) and Water (5 mL) was stirred at 120° C. for 16 h under N$_2$ atmosphere. The reaction mixture was diluted with water (50 mL) and extracted with EtOAc (200 mL×2). The organic layer was concentrated and purified by column on silica gel (0-20% EtOAc in hexanes) to afford the title compound (700 mg, 68%) as a yellow solid. $^1$H NMR (400 MHz, CDCl$_3$): δ 8.75 (d, J=1.6 Hz, 1H), 8.61 (d, J=1.6 Hz, 1H), 7.69 (d, J=8.4 Hz, 2H), 7.48 (dd, J=18.4, 12.0 Hz, 1H), 7.34 (d, J=8.4 Hz, 2H), 7.28 (s, 1H), 5.90-5.78 (m, 2H), 4.67 (br s, 2H).

Step 7: 6-iodo-8-(4-(trifluoromethoxy)phenyl)-5-vinylquinoxaline

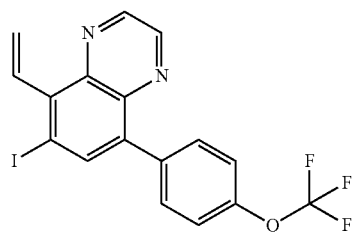 [SMILES: C=Cc1c(I)cc(-c2ccc(OC(F)(F)F)cc2)c2nccnc12]

To a solution of 6M HCl (10 mL) was added in 8-(4-(trifluoromethoxy)phenyl)-5-vinylquinoxalin-6-amine (1.0 g, 3.12 mmol) in acetonitrile (10 mL) at −10° C. And the reaction mixture was stirred at −10° C. for 5 mins. The solution of NaNO$_2$ (226.15 mg, 3.28 mmol) in water (5 mL) was added drop wise at −10° C., and the reaction mixture was stirred for 1 h. The reaction mixture turned into clear pale yellow solution. Solution of KI (1.03 g, 6.24 mmol) in water (5 mL) was added drop wise to the reaction mixture at −10° C. and the solution was stirred at −10° C. for 30 mins. The reaction mixture was quenched with cold water (100 mL) and extracted with EtOAc (80 mL×2). The organic layer was dried over anhydrous sodium sulfate. The organic layer was concentrated and the residue was purified by flash chromatography on silica gel (0-10% EtOAc in Petroleum ether) to afford the title compound (400 mg, 30%) as a white solid. $^1$H NMR (400 MHz, CDCl$_3$) δ 58.90 (s, 21), 8.29 (s, 1H), 7.69 (d, J=8.8 Hz, 2H), 7.36 (d, J=8.8 Hz, 2H), 7.13 (dd, J=17.6, 12.0 Hz, 1H), 6.08 (dd, J=17.6, 1.6 Hz, 1H), 5.92 (dd, J=12.0, 1.6 Hz, 1H).

Step 8: 1-(6-iodo-8-(4-(trifluoromethoxy)phenyl) quinoxalin-5-yl)ethane-1,2-diol

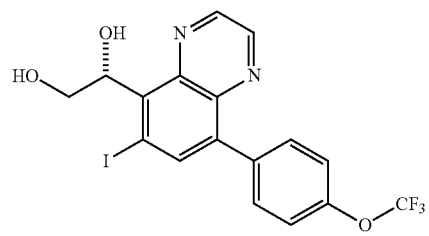 [SMILES: OC[C@H](O)c1c(I)cc(-c2ccc(OC(F)(F)F)cc2)c2nccnc12]

A mixture of K$_3$Fe(CN)$_6$ (2.87 g, 6.52 mmol), methanesulfonamide (310 mg, 3.26 mmol), K$_2$OsO$_4$·2H$_2$O (12.0 mg, 0.03 mmol), (DHQD)$_2$PHAL (127 mg, 0.16 mmol) and K$_2$CO$_3$ (900 mg, 6.52 mmol) in t-BuOH (20 mL) and Water (20 mL) was stirred at 25° C. for 20 min. The mixture was cooled to 0° C. and 6-iodo-8-(4-(trifluoromethoxy)phenyl)-5-vinylquinoxaline (1.5 g, 3.26 mmol) was added into the reaction mixture. The resulting mixture was stirred at 25° C. for 16 h. The TLC (10% MeOH in DCM, R$_f$=0.6) indicated the reaction was completed. The reaction mixture was diluted with water (100 mL) and extracted with EtOAc (200 mL×3). The combined organic layers were dried over Na$_2$SO$_4$ and concentrated in vacuo. The residue was purified by chromatography on silica gel (0-10% MeOH in DCM) to afford the title compound (0.9 g, 56%) as a white solid. $^1$H NMR (400 MHz, CDCl$_3$): δ 9.01 (s, 1H), 8.78 (s, 1H), 8.27 (s, 1H), 7.66 (d, J=8.4 Hz, 2H), 7.37 (d, J=8.4 Hz, 2H), 5.44-5.41 (m, 1H), 4.00-3.84 (m, 2H); LCMS (ESI): m/z 476.9 (M+H)$^+$.

Step 9: tert-butyl ((5-(1,2-dihydroxyethyl)-8-(4-(trifluoromethoxy)phenyl)quinoxalin-6-yl)methyl) carbamate

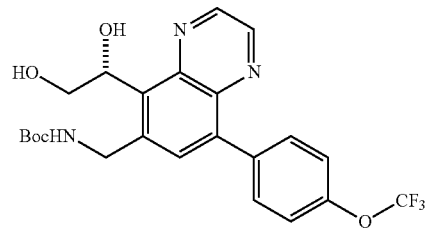 [SMILES: CC(C)(C)OC(=O)NCc1cc(-c2ccc(OC(F)(F)F)cc2)c2nccnc2c1[C@@H](O)CO]

A mixture of potassium (((tert-butoxycarbonyl)amino) methyl)trifluoroborate (1.31 g, 5.54 mmol), 1-(6-iodo-8-(4-(trifluoromethoxy)phenyl)quinoxalin-5-yl)ethane-1,2-diol (880 mg, 1.85 mmol), Cs$_2$CO$_3$ (1.81 g, 5.54 mmol) and CATACXIUM-A Pd G$_2$ (123 mg, 0.18 mmol) in 1,4-Dioxane (10 mL) and Water (2 mL) was stirred at 100° C. under N$_2$ atmosphere for 2 h. The TLC (10% MeOH in DCM, R$_f$=0.4) indicated the reaction was completed. The mixture was diluted with EtOAc (100 mL×3) and washed with water (50 mL×3). The organic was dried over Na₂SO₄ and concentrated. The residue was purified by column on silica gel (0-10% MeOH in DCM) to afford the title compound (850 mg, 95%) as a light brown solid. ¹H NMR (400 MHz, DMSO-d₆): δ 8.98 (d, J=1.6 Hz, 11H), 8.95 (d, J=1.6 Hz, 11H), 7.86 (s, 1H), 7.74 (d, J=8.4 Hz, 2H), 7.52 (d, J=8.4 Hz, 2H), 7.39 (t, J=6.0 Hz, 11H), 6.14-5.99 (m, 11H), 5.76 (d, J=5.6 Hz, 11H), 4.91 (t, J=5.6 Hz, 1H), 4.82-4.80 (m, 1H), 4.64-4.62 (m, 1H), 3.92-3.87 (m, 11H), 3.65-3.61 (m, 1H), 1.39 (s, 9H); LCMS (ESI): m/z 480.2 (M+H)⁺.

Step 10: 1-(6-(aminomethyl)-8-(4-(trifluoromethoxy)phenyl)quinoxalin-5-yl)ethane-1,2-diol

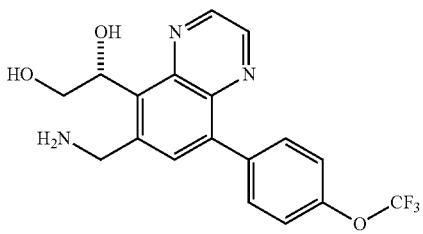 [SMILES: NCc1cc(-c2ccc(OC(F)(F)F)cc2)c2nccnc2c1[C@@H](O)CO]

A mixture of tert-butyl ((5-(1,2-dihydroxyethyl)-8-(4-(trifluoromethoxy)phenyl)quinoxalin-6-yl)methyl)carbamate (850 mg, 1.77 mmol) and con.HCl (3 mL) in Tetrahydrofuran (10 mL) was stirred at 20° C. for 16 h. The reaction was quenched with sat. AQ. NaHCO₃ to pH=7. The mixture was extracted with EtOAc (100 mL×3). The combined organic layers were dried over Na₂SO₄ and concentrated in vacuo to afford the title compound (650 mg, crude) as a yellow solid. The crude was used for next step without further purification. LCMS (ESI): m/z 380.1 (M+H)⁺.

Step 11: (R)—N-((5-(1,2-dihydroxyethyl)-8-(4-(trifluoromethoxy)phenyl)quinoxalin-6-yl)methyl)acrylamide

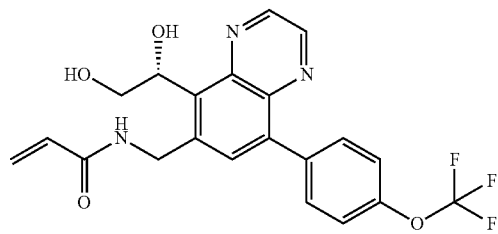

To a solution of 1-(6-(aminomethyl)-8-(4-(trifluoromethoxy)phenyl)quinoxalin-5-yl)ethane-1,2-diol (650 mg, 1.7 mmol) and sat. aq. NaHCO₃ (3 mL) in Tetrahydrofuran (10 mL) was added acrylicanhydride (238 mg, 1.88 mmol) at 0° C. The mixture was stirred at 0° C. for 1 h. The reaction was diluted with water (50 mL) and extracted with EtOAc (100 mL×3), the combined organic layers were dried over Na₂SO₄ and concentrated in vacuo. The residue was purified by pre-HPLC (Xtimate C18 150*40 mm*10 um, water(FA)-ACN, 35%-65%) to afford the title compound (350 mg, 47%) as a white solid. 1'H NMR (400 MHz, DMSO-d₆): δ 8.99 (d, J=1.6 Hz, 1H), 8.95 (d, J=2.0 Hz, 1H), 8.60 (t, J=5.6 Hz, 1H), 7.82 (s, 1H), 7.76-7.69 (m, 2H), 7.51 (d, J=8.0 Hz, 2H), 6.31 (dd, J=17.2, 10.0 Hz, 1H), 6.14-6.11 (m, 2H), 5.79 (d, J=6.0 Hz, 1H), 5.62 (dd, J=10.0, 2.0 Hz, 1H), 5.02-4.96 (m, 1H), 4.94-4.91 (m, 1H), 4.86-4.82 (m, 1H), 3.96-3.81 (m, 1H), 3.70-3.64 (m, 1H); LCMS (ESI): m/z 434.1 (M+H)⁺. Example 27 (Compound 29)

N-[[4-(hydroxymethyl)-3-methyl-7-[4-(trifluoromethoxy)phenyl]benzimidazol-5-yl]methyl]prop-2-enamide

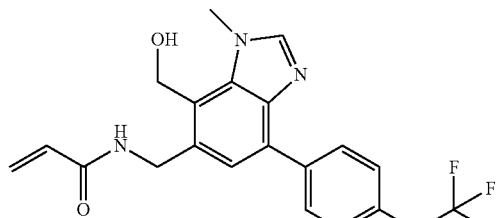

Step 1: Ethyl 7-[4-(trifluoromethoxy)phenyl]-3H-benzimidazole-5-carboxylate

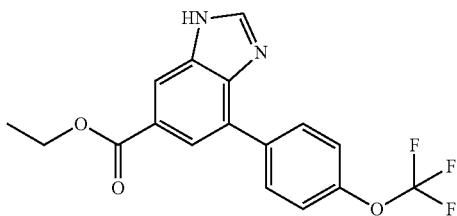 [SMILES: CCOC(=O)c1cc(-c2ccc(OC(F)(F)F)cc2)c2nc[nH]c2c1]

Ethyl 7-bromo-3H-benzimidazole-5-carboxylate (3.0 g, 11.1 mmol), 4-(trifluoromethoxy)-phenylboronic acid (2.75 g, 13.4 mmol), K₃PO₄ (5.91 g, 27.9 mmol) and Pd(dppf)Cl₂ (815 mg, 1.11 mmol) were added to 1,4-dioxane (25 mL) and water (8 mL). The mixture was equipped with a condenser and stirred at 100° C. for 17 h. The reaction was diluted with water (70 mL) and extracted with EtOAc (100 mL). The organic extract was washed with brine (20 mL) and concentrated with silica gel. The crude was purified by flash column chromatography (silica, 10-50% (30% MeOH in EtOAc)/heptanes) to afford the title compound (4.0 g, 99% yield) as a brown solid. LCMS (ESI): m/z 351.2 (M+H)⁺

Step 2: Ethyl 4-bromo-7-[4-(trifluoromethoxy)phenyl]-3H-benzimidazole-5-carboxylate

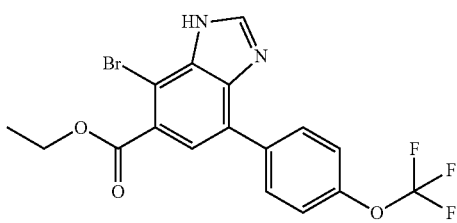 [SMILES: CCOC(=O)c1cc(-c2ccc(OC(F)(F)F)cc2)c2nc[nH]c2c1Br]

In a 250 mL flask ethyl 7-[4-(trifluoromethoxy)phenyl]-3H-benzimidazole-5-carboxylate (4.0 g, 11.3 mmol) was dissolved in chloroform (35 mL). To the mixture was added N-bromosuccinimide (4.91 g, 27.6 mmol), the flask was stirred at rt for 17 h. LCMS showed completion of the reaction with bis-brominated side-product. The reaction was quenched with 50 mL of 10% aqueous $Na_2S_2O_3$ solution and diluted with DCM (150 mL). The mixture was stirred for 10 min. Phases were separated and the organic phase was then washed with water (2×50 mL), dried over sodium sulfate, filtered and concentrated to approximatively 50 mL of crude solution. The crude product was purified by flash column chromatography (Silica, 0-90% DCM/EtOAc) to give a mixture of the title compound amd di-brominated side product (3.9 g, 76% yield). LCMS (ESI): m/z 429.2 (M+H)$^+$ Step 3: Ethyl 4-bromo-3-methyl-7-[4-(trifluoromethoxy)phenyl]benzimidazole-5-carboxylate

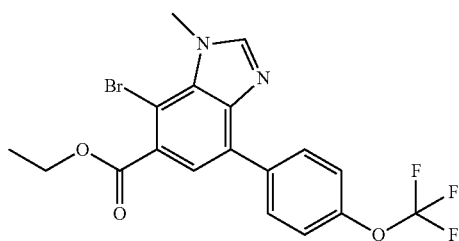 [SMILES: CCOC(=O)c1cc(-c2ccc(OC(F)(F)F)cc2)c2ncn(C)c2c1Br]

To ethyl 4-bromo-7-[4-(trifluoromethoxy)phenyl]-3H-benzimidazole-5-carboxylate (2.72 g, 6.34 mmol) in DMF (22 mL) was added $K_3P04$ (4.1 g, 19.0 mmol) followed by MeI (0.59 mL, 9.5 mmol) over 10 min. The mixture was stirred at rt for 45 min. The reaction was diluted with EtOAc (400 mL), washed with water (2×100 mL) and brine (50 mL), dried over sodium sulfate, filtered and concentrated with silica gel. The crude was purified by flash column chromatography (silica, 30-50% EtOAc/heptanes) to give the title compound (1.89 g, 67% yield) as a white solid. LCMS (ESI): m/z 445.1 (M+H)$^+$ Step 4: (5-(Aminomethyl)-7-(4-(trifluoromethoxy)phenyl)-2,3-dihydrobenzofuran-4-yl)methanol

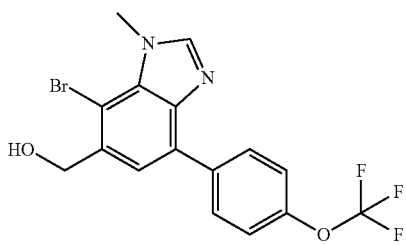 [SMILES: Cn1cnc2c(-c3ccc(OC(F)(F)F)cc3)cc(CO)c(Br)c21]

Ethyl 4-bromo-3-methyl-7-[4-(trifluoromethoxy)phenyl] benzimidazole-5-carboxylate (4.60 g, 10.4 mmol) was dissolved in THF (28 mL) and cooled to 0° C. Diisobutylaluminum hydride, 1.0 M in THF (51.9 mL, 51.9 mmol) was added to the solution dropwise. Stirred at rt for 1 h. The reaction was diluted with THF (100 mL). $Na_2SO_4$-$10H_2O$ (2 g) was added in small portions. The reaction was then stirred at rt for 20 min. The mixture was filtered through Celite, washed with EtOAc. The filtrate was concentrated to yield the crude title compound (4.10 g, 98% yield). LCMS (ESI): m/z 403.1 (M+H)$^+$ Step 5: 7-Bromo-6-(bromomethyl)-1-methyl-4-[4-(trifluoromethoxy)phenyl]-benzimidazole

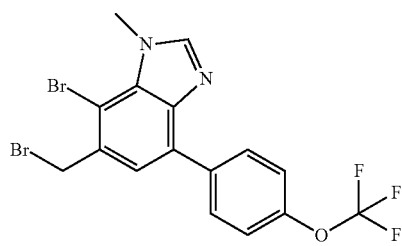 [SMILES: Cn1cnc2c(-c3ccc(OC(F)(F)F)cc3)cc(CBr)c(Br)c21]

[4-bromo-3-methyl-7-[4-(trifluoromethoxy)phenyl]benzimidazol-5-yl]methanol (4.47 g, 11.1 mmol) and triphenylphosphine (5.85 g, 22.3 mmol) were dissolved in DCM (55 mL). Carbon tetrabromide (7.39 g, 22.3 mmol) was slowly added and it was stirred for 1.5 h. The reaction was directly concentrated with silica and purified by flash column chromatography (silica, 20-40% EtOAc/heptanes) to afford the title compound (3.56 g, 69% yield) as a colorless solid. LCMS (ESI): m/z 465.0 (M+H)$^+$ Step 6: tert-Butyl N-[[4-bromo-3-methyl-7-[4-(trifluoromethoxy)phenyl]benzimidazol-5-yl]methyl]-N-tert-butoxycarbonyl-carbamate

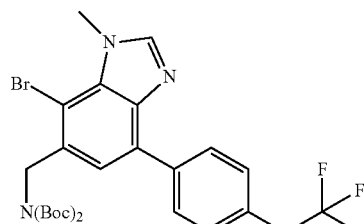

7-bromo-6-(bromomethyl)-1-methyl-4-[4-(trifluoromethoxy)phenyl]benzimidazole (3.56 g, 7.67 mmol), di-tert-butyl-iminodicarboxylate (1.67 g, 7.67 mmol) and cesium carbonate (2.51 g, 7.67 mmol) were added in a flask with DMF (20 mL). The reaction was stirred for 1.5 h. The reaction was diluted with EtOAc (200 mL) and washed with water (2×100 mL) followed by brine (50 mL). The organic phase was dried over sodium sulfate, filtered and concentrated to afford the title compound (4.6 g, 99% yield) as an off white solid which was used without further purification. LCMS (ESI): m/z 600.0 (M+H)$^+$

Step 7: tert-Butyl N-tert-butoxycarbonyl-N-[[3-methyl-7-[4-(trifluoromethoxy)-phenyl]-4-vinyl-benzimidazol-5-yl]methyl]carbamate

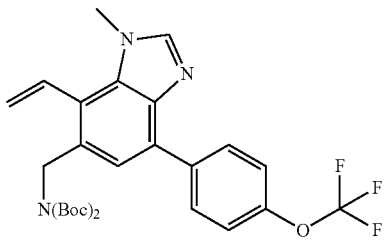

A reaction vessel was charged with tert-butyl N-[[4-bromo-3-methyl-7-[4-(trifluoromethoxy)-phenyl]benzimidazol-5-yl]methyl]-N-tert-butoxycarbonyl-carbamate (500 mg, 0.83 mmol), potassium; trifluoro(vinyl)boron (334 mg, 2.5 mmol), K$_3$PO$_4$ (337 mg, 3.33 mmol) and palladium tetrakis(triphenylphosphine) (96 mg, 0.08 mmol). 1,4-dioxane (6 mL) and water (2 mL) was added to the mixture and purged with N$_2$. The mixture was stirred at 110° C. for 3 h. The organic layer was taken out and concentrated with silica gel. The crude was purified by flash column chromatography (silica, 20-80% EA/heptanes) to give the title compound (270 mg, 59% yield). LCMS (ESI): m/z 548.3 (M+H)$^+$

Step 8: tert-Butyl N-tert-butoxycarbonyl-N-[[4-(hydroxymethyl)-3-methyl-7-[4-(trifluoromethoxy)phenyl]benzimidazol-5-yl]methyl]-carbamate

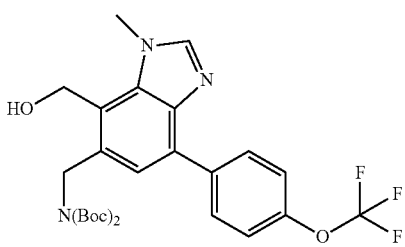

tert-Butyl-N-tert-butoxycarbonyl-N-[[3-methyl-7-[4-(trifluoromethoxy)phenyl]-4-vinyl-benzimidazol-5-yl]-methyl] carbamate (780 mg, 1.42 mmol) was dissolved in methanol (10 mL) and the mixture was cooled to −78° C. under N$_2$. Then ozone was bubbled for 3-5 min until the color changed to light blue. The reaction was stopped and N$_2$ was purged to the mixture at −78° C. for 3 min. To the mixture was added sodium borohydride (539 mg, 14.24 mmol) in small portions and the reaction was stirred for 5 min at −78° C. then slowly warmed to rt. The reaction was poured into a mixture of EtOAc (100 mL) and brine (50 mL). The organic layer was separated, washed with brine (10 mL), dried over sodium sulfate, filtered and concentrated with silica gel. The crude was purified by flash column chromatography (silica, 10-100% (30% MeOH in EtOAc)/heptanes) to give the title compound (650 mg, 82% yield). LCMS (ESI): m/z 552.3 (M+H)$^+$

Step 9: N-[[4-(hydroxymethyl)-3-methyl-7-[4-(trifluoromethoxy)phenyl]benzimidazol-5-yl]methyl] prop-2-enamide

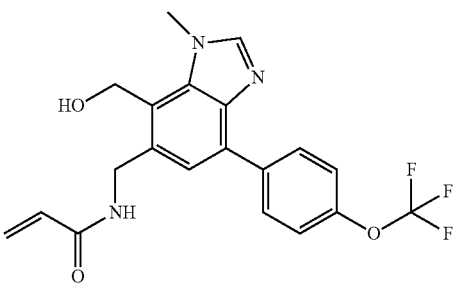 [SMILES: C=CC(=O)NCc1cc(-c2ccc(OC(F)(F)F)cc2)c2ncn(C)c2c1CO]

tert-Butyl-N-tert-butoxycarbonyl-N-[[4-(hydroxymethyl)-3-methyl-7-[4-(trifluoromethoxy)-phenyl]-benzimidazol-5-yl]methyl]-carbamate (650 mg, 1.18 mmol) was dissolved in DCM (5 mL) and TFA (1 mL) was added. The reaction was stirred at rt for 10 min. To the mixture was added toluene (2 mL) and concentrated. The residue was dissolved in THF (10 mL) and saturated aqueous Na$_2$CO$_3$ solution (3 mL) was added. To the mixture was added prop-2-enoyl prop-2-enoate (135 µL, 1.18 mmol) in THF (1 mL) dropwise. The reaction was stirred at rt for 40 min. The reaction was then diluted with EtOAc (50 mL) and water (20 mL). Organic layer was taken and concentrated with DMSO (2 mL) to remove EtOAc. The crude was purified by flash column chromatography (silica/C18, 0-50% MeCN/10 mM AmF water) to give the title compound (313 mg, 66% yield). LCMS (ESI): m/z 406.2 (M+H)$^+$. $^1$H NMR (400 MHz, DMSO-d$_6$) δ 8.48 (s, 1H), 8.19 (s, 1H), 8.13 (d, J=8.8 Hz, 2H), 7.46 (d, J=8.1 Hz, 2H), 7.41 (s, 1H), 6.23 (dd, J=17.1, 10.0 Hz, 1H), 6.10 (dd, J=17.1, 2.3 Hz, 1H), 5.58 (dd, J=10.0, 2.3 Hz, 1H), 5.28 (t, J=5.4 Hz, 1H), 4.90 (d, J=5.4 Hz, 2H), 4.61 (d, J=5.5 Hz, 2H), 4.13 (s, 3H).

Example 28 (Compound 27)

N-((7-cyano-1-methyl-4-(4-(trifluoromethoxy)phenyl)-1H-benzo[d]imidazol-6-yl)methyl)acrylamide

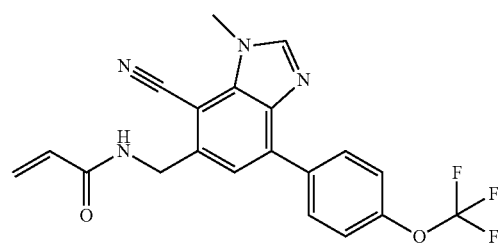 [SMILES: C=CC(=O)NCc1cc(-c2ccc(OC(F)(F)F)cc2)c2ncn(C)c2c1C#N]

Step 1: tert-Butyl N-tert-butoxycarbonyl-N-[[4-cyano-3-methyl-7-[4-(trifluoromethoxy)phenyl]benzimidazol-5-yl]methyl]carbamate

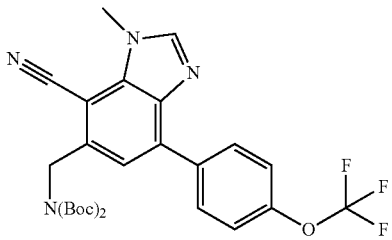

tert-Butyl-N-[[4-bromo-3-methyl-7-[4-(trifluoromethoxy)phenyl]benzimidazol-5-yl]methyl]-N-tert-butoxycarbonyl-carbamate (1.00 g, 1.67 mmol) (described in Example 27, step 6), tetrakistriphenylphosphine palladium (289 mg, 0.25 mmol) and zinc cyanide (584 mg, 5.0 mmol) were added to DMA (8 mL) and the mixture was degassed with $N_2$. The mixture was then stirred at 110° C. for 1 h. The reaction was then diluted with EtOAc (100 mL) and washed with water (2×50 mL) followed by brine (20 mL). The organic layer was concentrated with silica gel and purified by flash column chromatography (silica, 20-60% EtOAc/Heptanes) to give the title compound (810 mg, 89% yield). LCMS (ESI): m/z 547.3 (M+H)+.

Step 2: N-((7-cyano-1-methyl-4-(4-(trifluoromethoxy)phenyl)-1H-benzo[d]imidazol-6-yl)methyl)acrylamide

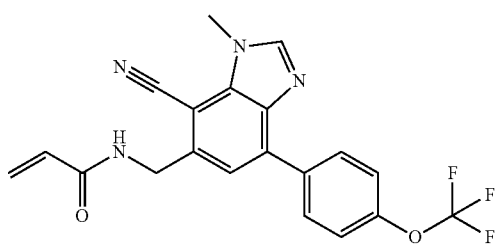 [SMILES: C=CC(=O)NCc1cc(-c2ccc(OC(F)(F)F)cc2)c2ncn(C)c2c1C#N]

tert-Butyl-N-tert-butoxycarbonyl-N-[[4-cyano-3-methyl-7-[4-(trifluoromethoxy)phenyl]benzimidazol-5-yl]methyl]carbamate (760 mg, 1.39 mmol) was dissolved in DCM (5 mL) and TFA (1.0 mL) was added. The reaction stirred at rt for 20 min. To the mixture was added toluene (2 mL) and concentrated. The residue was dissolved in THF (10 mL) and saturated aqueous $Na_2CO_3$ solution (3. mL) was added. To the mixture was added prop-2-enoyl prop-2-enoate (160 µL, 1.39 mmol) in THF (1 mL) dropwise. The reaction was stirred at rt for 20 min. The reaction was then diluted with EtOAc (100 mL) and water (30 mL). The organic layer was washed with water (50 mL) followed by brine (20 mL), dried over sodium sulfate, filtered and concentrated. The crude was purified by flash column chromatography (silica, 20-60% EtOAc/Heptanes) to give approximatively 400 mg of product (92% purity). The product was then suspended in EtOAc (10 mL), stirred at 80° C. EtOAc was added to the mixture until all the solid was dissolved. The mixture was then cool to 0° C. slowly with stirring. The precipitate was filtered to provide the title compound (312 mg, 56% yield).

LCMS (ESI): m/z 401.3 (M+H)+. 1H NMR (400 MHz, DMSO-$d_6$) δ 8.79 (t, J=5.3 Hz, 1H), 8.44 (s, 1H), 8.16 (d, J=8.8 Hz, 2H), 7.58 (s, 1H), 7.53 (d, J=8.3 Hz, 2H), 6.28 (dd, J=17.1, 10.1 Hz, 1H), 6.12 (dd, J=17.1, 2.1 Hz, 1H), 5.62 (dd, J=10.1, 2.1 Hz, 1H), 4.67 (d, J=5.6 Hz, 2H), 4.11 (s, 3H).

Example 29 (Compound 30 & 31)

N-[[3-methyl-4-[(1S)-1,2-dihydroxyethyl]-7-[4-(trifluoromethoxy)phenyl]benzimidazol-5-yl]methyl]prop-2-enamide and N-[[3-methyl-4-[(1R)-1,2-dihydroxyethyl]-7-[4-(trifluoromethoxy)phenyl]benzimidazol-5-yl]methyl]prop-2-enamide

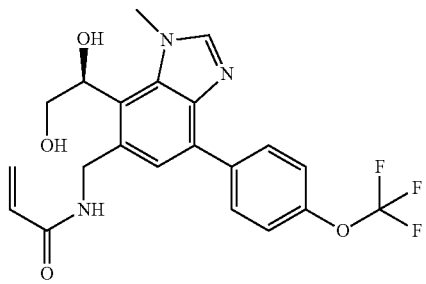

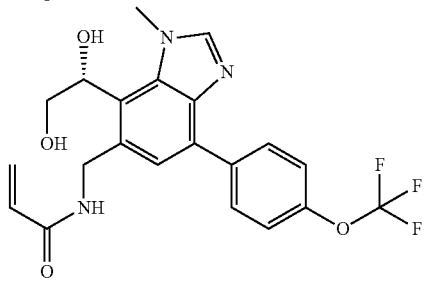

Step 1: 4-bromo-3-methyl-7-[4-(trifluoromethoxy)phenyl]benzimidazole-5-carboxylic acid

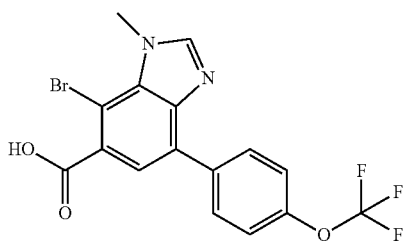 [SMILES: Cn1cnc2c(-c3ccc(OC(F)(F)F)cc3)cc(C(=O)O)c(Br)c21]

A flask was charged with ethyl 4-bromo-3-methyl-7-[4-(trifluoromethoxy)phenyl]-benzimidazole-5-carboxylate (450 mg, 1.0 mmol) (described in Example 27, , step 3), followed by addition of LiOH (4 M in water) (1 mL) and 1,4-dioxane (3 mL). The flask was stirred at 60° C. for 30 min. The reaction was diluted with EtOAc (50 mL) and 5% citric acid (20 mL). The organic layer was washed with brine (20 mL), dried over sodium sulfate, filtered and concentrated to give the crude title compound (421 mg, 99% yield). LCMS (ESI): m/z 417.0 (M+H)+.

Step 2: 4-bromo-3-methyl-7-[4-(trifluoromethoxy)phenyl]benzimidazole-5-carboxamide

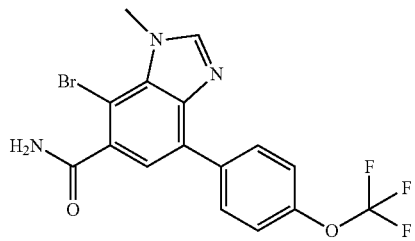 [SMILES: Cn1cnc2c(-c3ccc(OC(F)(F)F)cc3)cc(C(N)=O)c(Br)c21]

4-Bromo-3-methyl-7-[4-(trifluoromethoxy)phenyl]benzimidazole-5-carboxylic acid (421 mg, 1.0 mmol) was dissolved in DMF (5 mL) and to the solution was added HATU (1.156 g, 3.0 mmol), triethylamine (0.56 mL, 4.1 mmol) followed by ammonia (7 M in MeOH) (1.45 mL, 10 mmol). The reaction was stirred at rt and a precipitate was formed quickly. The reaction was then diluted with EtOAc (50 mL) and brine (20 mL). The organic layer was washed with water (20 mL) and brine (20 mL), dried over sodium sulfate, filtered and concentrated to give the title compound (421 mg, 100% yield). The crude was used without further purification. LCMS (ESI): m/z 416.4 (M+H)$^+$.

Step 3: 3-methyl-7-[4-(trifluoromethoxy)phenyl]-4-vinyl-benzimidazole-5-carboxamide

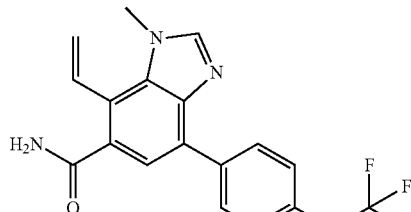

4-Bromo-3-methyl-7-[4-(trifluoromethoxy)phenyl]benzimidazole-5-carboxamide (421 mg, 1.0 mmol), potassium vinyltrifluoroborate (272 mg, 2.0 mmol), palladium tetrakis(triphenylphosphine) (117 mg, 0.10 mmol), K$_3$PO$_4$ (646 mg, 3.0 mmol) were added to a mixture of 1,4-dioxane (6 mL) and water (2 mL). The reaction was purged with N$_2$ for 5 min then was stirred at 150° C. for 30 min in microwave. The reaction was diluted with EtOAc (50 mL) and water (20 mL). Organic layer was concentrated with silica gel. The product was purified by flash column chromatography (silica, 0-100% (30% MeOH in EtOAc)/heptanes) to give the title compound (367 mg, 100% yield). LCMS (ESI): m/z 362.1 (M+H)$^+$.

Step 4: 3-methyl-7-[4-(trifluoromethoxy)phenyl]-4-vinyl-benzimidazole-5-carbonitrile

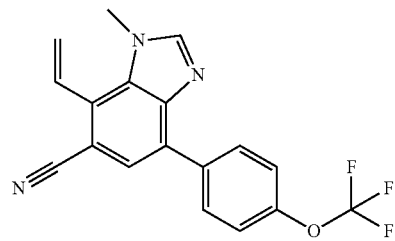 [SMILES: C=Cc1c(C#N)cc(-c2ccc(OC(F)(F)F)cc2)c2ncn(C)c12]

3-Methyl-7-[4-(trifluoromethoxy)phenyl]-4-vinyl-benzimidazole-5-carboxamide (432 mg, 1.2 mmol) was dissolved in DMF (5 mL) and to the solution was added cyanuric chloride (110 mg, 0.60 mmol). The mixture was stirred at rt for 1 h. To the mixture was added another portion of cyanuric chloride (110 mg, 0.60 mmol) and stirred for 1 h. The reaction was diluted with water (20 mL) and the product was extracted with EtOAc (50 mL). The organic layer was separated and washed with water (10 mL) and brine (10 mL), dried over sodium sulfate, filtered and concentrated. The crude was purified by flash column chromatography (silica, 0-100% (30% MeOH in EtOAc)/heptanes) to give the title compound (180 mg, 44% yield). LCMS (ESI): m/z 344.6 (M+H)$^+$.

Step 5: 4-(1,2-dihydroxyethyl)-3-methyl-7-[4-(trifluoromethoxy)phenyl]benzimidazole-5-carbonitrile

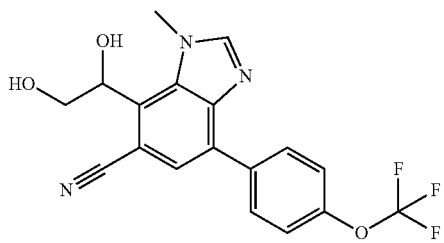 [SMILES: Cn1cnc2c(-c3ccc(OC(F)(F)F)cc3)cc(C#N)c(C(O)CO)c21]

3-Methyl-7-[4-(trifluoromethoxy)phenyl]-4-vinyl-benzimidazole-5-carbonitrile (180 mg, 0.52 mmol) was dissolved in acetone (3 mL) and to the mixture was added osmium tetraoxide 4% wt in water (166 mg, 0.03 mmol) followed by 4-methylmorpholine N-oxide (245 mg, 2.1 mmol). The reaction was stirred at rt for 8 h. The reaction was then diluted with EtOAc (50 mL) and water (20 mL). The organic layer was washed with brine (20 mL), dried over sodium sulfate, filtered and concentrated. The crude was purified by flash column chromatography (silica, 0-20% MeOH/DCM) to give the title compound (120 mg, 61% yield). LCMS (ESI): m/z 378.1 (M+H)$^+$.

Step 6: tert-Butyl N-[[4-(1,2-dihydroxyethyl)-3-methyl-7-[4-(trifluoromethoxy)phenyl]benzimidazol-5-yl]methyl]carbamate

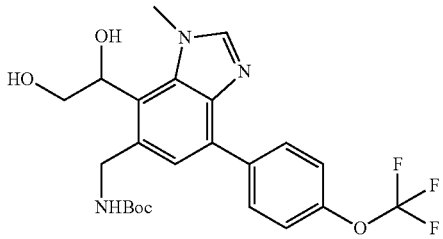 [SMILES: Cn1cnc2c(-c3ccc(OC(F)(F)F)cc3)cc(CNC(=O)OC(C)(C)C)c(C(O)CO)c21]

4-(1,2-Dihydroxyethyl)-3-methyl-7-[4-(trifluoromethoxy)phenyl]benzimidazole-5-carbonitrile (120 mg, 0.32 mmol) was dissolved in THF (3.0 mL) and to the mixture was added borane (1 M in THF) (0.64 mL, 0.64 mmol). The mixture was stirred at rt and was stopped at approximatively 60% conversion. The mixture was poured to saturated aqueous Na$_2$CO$_3$ solution (10 mL) and extracted with EtOAc (30 mL). The organic layer was washed with brine (10 mL), dried over sodium sulfate, filtered and concentrated. The crude was dissolved in DCM (5 mL), triethylamine (137 µL, 0.95 mmol) and di-tert-butyl dicarbonate (208 mg, 0.95 mmol) were added. The reaction was stirred at rt for 10 min and loaded on a silica column for purification without workup (silica, 0-20% MeOH/DCM) to provide the title compound (62 mg, 40% yield). LCMS (ESI): m/z 482.1 (M+H)$^+$.

Step 7: N-[[3-methyl-4-[(1S)-1,2-dihydroxyethyl]-7-[4-(trifluoromethoxy) phenyl]benzimidazol-5-yl]methyl]prop-2-enamide and N-[[3-methyl-4-[(1R)-1,2-dihydroxyethyl]-7-[4-(trifluoromethoxy)phenyl]benzimidazol-5-yl]methyl]prop-2-enamide

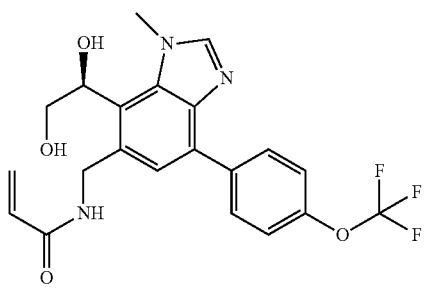

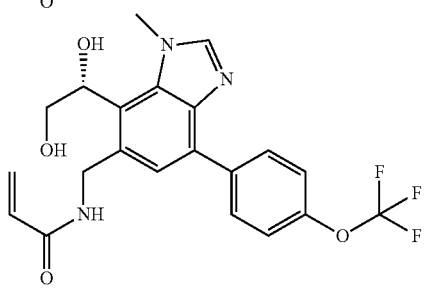

tert-Butyl-N-[[4-(1,2-dihydroxyethyl)-3-methyl-7-[4-(trifluoromethoxy)phenyl]-benzimidazol-5-yl]methyl]carbamate (50 mg, 0.10 mmol) was dissolved in DCM (3 mL) and TFA (0.5 mL) was added. The reaction was stirred at rt for 10 min. To the mixture was added toluene (2 mL) and concentrated. The residue was dissolved in THF (3 mL) and saturated aqueous Na$_2$CO$_3$ solution (0.3 mL) was added. To the mixture was added prop-2-enoyl prop-2-enoate (13 mg, 0.10 mmol) in THF (1 mL) dropwise. The reaction was stirred at rt for 20 min. The reaction was then diluted with EtOAc (30 mL) and water (10 mL), the organic layer was dried over sodium sulfate, filtered and concentrated. The crude was purified by flash column chromatography (silica, C18, 0-100% MeCN/10 mM ammonium formate water) to give (25 mg, 56% yield) of the desired product as a mixture of enantiomers.

The above racemate was further purified by chiral SFC (Column=IC; Column dimensions=250 mm×10 mm×5 pm; Flow rate=10 mL/min; Run time=18 min; Column temperature=40° C.) Mobile phase: 20% IPA+10 mM AmF, 80% supercritical CO$_2$) to afford:

N-[[3-methyl-4-[(1S)-1,2-dihydroxyethyl]-7-[4-(trifluoromethoxy)phenyl]-benzimidazol-5-yl]methyl]prop-2-enamide (9.4 mg, 21% yield) (peak 1, stereochemistry was arbitrarily assigned) LCMS (ESI): m/z 436.1 (M+H)$^+$. $^1$H NMR (400 MHz, DMSO-d$_6$) δ 8.37 (s, 1H), 8.17 (s, 1H), 8.06 (d, J=8.6 Hz, 2H), 7.45 (d, J=8.2 Hz, 2H), 7.36 (s, 1H), 6.27 (dd, J=17.1, 10.1 Hz, 1H), 6.10 (dd, J=17.0, 1.7 Hz, 1H), 5.74 (s, 2H), 5.58 (dd, J=10.1, 1.7 Hz, 1H), 5.46 (s, 1H), 5.00 (s, 1H), 4.80 (dd, J=14.7, 5.8 Hz, 1H), 4.57 (dt, J=23.1, 11.5 Hz, 1H), 4.11 (s, 3H), 3.89-3.79 (m, 1H), 3.66 (d, J=28.1 Hz, 1H). N-[[3-methyl-4-[(1R)-1,2-dihydroxyethyl]-7-[4-(trifluoromethoxy)phenyl]-benzimidazol-5-yl]methyl]prop-2-enamide (8.3 mg,18% yield) (peak 2, stereochemistry was arbitrarily assigned) LCMS (ESI): ,n/z 436.1 (M+H)$^+$. $^1$H NMR (400 MHz, DMSO-d$_6$) δ 8.37 (s, 1H), 8.17 (s, 1H), 8.06 (d, J=8.6 Hz, 2H), 7.45 (d, J=8.2 Hz, 2H), 7.36 (s, 1H), 6.27 (dd, J=17.1, 10.1 Hz, 1H), 6.10 (dd, J=17.0, 1.7 Hz, 1H), 5.74 (s, 2H), 5.58 (dd, J=10.1, 1.7 Hz, 1H), 5.46 (s, 1H), 5.00 (s, 1H), 4.80 (dd, J=14.7, 5.8 Hz, 1H), 4.57 (dt, J=23.1, 11.5 Hz, 1H), 4.11 (s, 3H), 3.89-3.79 (m, 1H), 3.66 (d, J=28.1 Hz, 1H).

Example 30 (Compound 32 & 33)

N-[[3-methyl-4-[(1R)-1-hydroxyethyl]-7-[4-(trifluoromethoxy)phenyl]benzimidazol-5-yl]methyl]prop-2-enamide and N-[[3-methyl-4-[(1S)-1-hydroxyethyl]-7-[4-(trifluoromethoxy)phenyl]benzimidazol-5-yl]methyl]prop-2-enamide

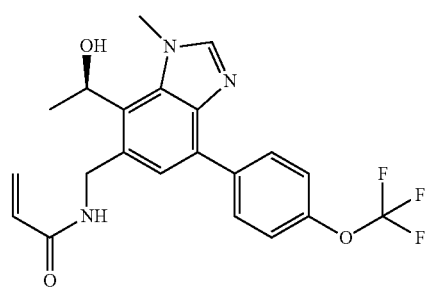

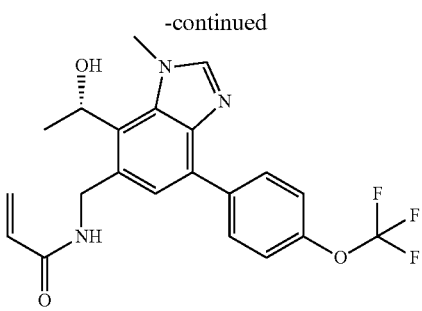

Step 1: tert-Butyl-N-tert-butoxycarbonyl-N-[[4-formyl-3-methyl-7-[4-(trifluoromethoxy)phenyl]benzimidazol-5-yl]methyl]carbamate

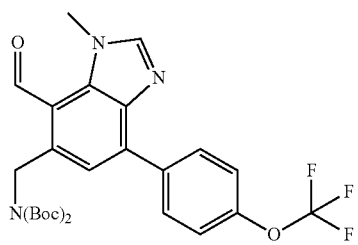

tert-Butyl-N-tert-butoxycarbonyl-N-[[3-methyl-7-[4-(trifluoromethoxy)phenyl]-4-vinyl-benzimidazol-5-yl]methyl]carbamate (134 mg, 0.24 mmol) (described in Example 27, step 7) and pyridine (20 μL, 0.24 mmol) were dissolved in DCM (8 mL) and the mixture was cooled to −78° C. under $N_2$. Then ozone was bubbled for 3-5 min until the color changed to blue. LCMS confirmed the consumption of the starting material. The reaction was stopped and $N_2$ was purged to the mixture at −78° C. for 3 min. To the mixture was added triphenylphosphine (129 mg, 0.49 mmol) and the mixture was warmed to rt with stirring. The crude was concentrated with silica gel and was purified by flash column chromatography (silica, 10-80%, (30% MeOH in EtOAc)/heptanes) to give the title compound (127 mg, 95% yield). LCMS (ESI): m/z 550.3 (M+H)$^+$.

Step 2: tert-Butyl-N-[[4-(1-hydroxyethyl)-3-methyl-7-[4-(trifluoromethoxy)phenyl]benzimidazol-5-yl]methyl]carbamate

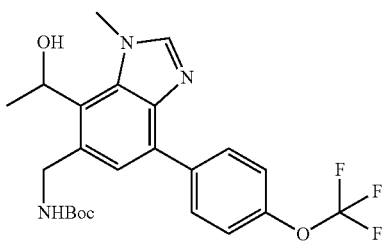 [SMILES: CC(O)c1c(CNC(=O)OC(C)(C)C)cc(-c2ccc(OC(F)(F)F)cc2)c2ncn(C)c12]

To methylmagnesium bromide (3.0 M in Et$_2$O) (200 μL, 0.60 mmol) in THF (2 mL) was added tert-butyl-N-tert-butoxycarbonyl-N-[[4-formyl-3-methyl-7-[4-(trifluoromethoxy)phenyl]benzimidazol-5-yl]methyl]carbamate (110 mg, 0.20 mmol) in THF (2.0 mL) at rt. The reaction was stirred at rt for 10 min. To the mixture was added another 5 equivalents of MeMgBr and stirred for 10 min. The reaction was quenched with saturated aqueous $NH_4C_1$ solution (10 mL) and extracted with EtOAc (20 mL). The organic layer was concentrated with silica gel and purified by flash column chromatography (silica, 10-70% (30% MeOH in EA)/heptanes) to give the title compound (52 mg, 56% yield). LCMS (ESI): m/z 466.3 (M+H)$^+$.

Step 3: N-[[3-methyl-4-[(1R)-1-hydroxyethyl]-7-[4-(trifluoromethoxy)phenyl]benzimidazol-5-yl]methyl]prop-2-enamide and N-[[3-methyl-4-[(1S)-1-hydroxyethyl]-7-[4-(trifluoromethoxy)phenyl]benzimidazol-5-yl]methyl]prop-2-enamide

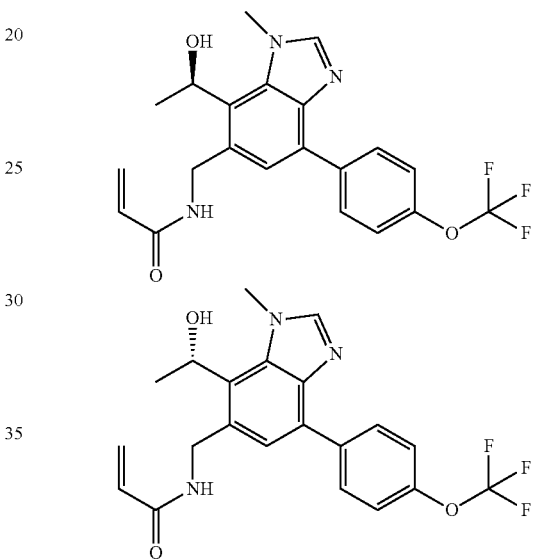

tert-Butyl-N-[[4-(1-hydroxyethyl)-3-methyl-7-[4-(trifluoromethoxy)phenyl]-benzimidazol-5-yl]methyl]carbamate (52 mg, 0.11 mmol) was dissolved in DCM (2 mL) and TFA (0.5 mL) was added. The reaction stirred at rt for 10 min. To the mixture was added toluene (2 mL) and concentrated. The residue was dissolved in THF (2 mL) and saturated aqueous Na$_2$CO$_3$ solution (0.3 mL) was added. To the mixture was added prop-2-enoyl prop-2-enoate (14 mg, 0.11 mmol) in THF (0.2 mL) slowly. The reaction was stirred at rt for 20 min and then diluted with EtOAc (30 mL) and water (10 mL). The organic layer was separated, dried over sodium sulfate, filtered and concentrated. The crude was purified by flash column chromatography (silica, C18, 0-100% MeCN/10 mM ammonium formate water) to give 22 mg of the desired product as a mixture of enantiomers.

The above racemate was further purified by chiral SFC (Column=Cel-4, Column dimensions=250 mm×10 mm×5 pm; Flow rate=10 mL/min; Run time=15 min; Column temperature=40° C., 20% ACN/EtOH (1:1)+10 mM AmF, 80% supercritical CO$_2$) to afford:

N-[[3-methyl-4-[(1R)-1-hydroxyethyl]-7-[4-(trifluoromethoxy)phenyl]benzimidazol-5-yl]methyl]prop-2-enamide (10 mg, 21% yield) (peak 1, stereochemistry was arbitrarily assigned) LCMS (ESI): m/z 420.1 (M+H)$^+$. $^1$H NMR (400 MHz, DMSO-d$_6$) δ 8.41 (s, 1H), 8.19 (s, 11H), 8.08 (d, J=8.7 Hz, 2H), 7.45 (d, J=8.3 Hz, 2H), 7.38 (s, 1H), 6.27 (dd, J=17.1, 10.1 Hz, 1H), 6.11 (dd, J=17.1, 2.2 Hz, 1H), 5.58 (dd, J=10.1, 2.2 Hz, 2H), 5.51 (d, J=6.7 Hz, 1H), 4.75 (dd, J=14.4, 6.0 Hz, 1H), 4.59 (dd, J=14.8, 4.4 Hz, 1H), 4.16 (s, 3H), 1.53 (d, J=6.7 Hz, 3H).

N-[[3-methyl-4-[(1S)-1-hydroxyethyl]-7-[4-(trifluoromethoxy)phenyl]benzimidazol-5-yl]methyl]prop-2-enamide (10 mg, 21% yield) (peak 2, stereochemistry was arbitrarily assigned) LCMS (ESI): m/z 420.1 (M+H)+. 1H NMR (400 MHz, DMSO-d6) δ 8.41 (s, 1H), 8.19 (s, 1H), 8.08 (d, J=8.7 Hz, 2H), 7.45 (d, J=8.3 Hz, 2H), 7.38 (s, 1H), 6.27 (dd, J=17.1, 10.1 Hz, 1H), 6.11 (dd, J=17.1, 2.2 Hz, 1H), 5.58 (dd, J=10.1, 2.2 Hz, 2H), 5.51 (d, J=6.7 Hz, 1H), 4.75 (dd, J=14.4, 6.0 Hz, 1H), 4.59 (dd, J=14.8, 4.4 Hz, 1H), 4.16 (s, 3H), 1.53 (d, J=6.7 Hz, 3H).

Example 31 (Compound 34)

N-[[3-methyl-4-(1H-pyrazol-4-ylmethyl)-7-[4-(trifluoromethoxy)phenyl]benzimidazol-5-yl]methyl]prop-2-enamide

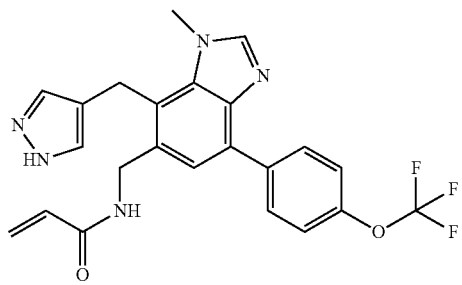 [SMILES: C=CC(=O)NCc1cc(-c2ccc(OC(F)(F)F)cc2)c2ncn(C)c2c1Cc1cn[nH]c1]

Step 1: tert-Butyl-N-[[4-(bromomethyl)-3-methyl-7-[4-(trifluoromethoxy)phenyl]benzimidazol-5-yl]methyl]-N-tert-butoxycarbonyl-carbamate

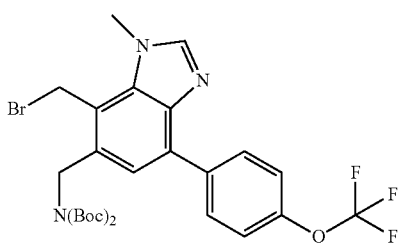

tert-Butyl-N-tert-butoxycarbonyl-N-[[4-(hydroxymethyl)-3-methyl-7-[4-(trifluoromethoxy)phenyl]benzimidazol-5-yl]methyl]carbamate (300 mg, 0.54 mmol) (described in Example 27, , step 9) and triphenylphosphine (156 mg, 0.6 mmol) were dissolved in DCM (5.0 mL). Carbon tetrabromide (198 mg, 0.60 mmol) in DCM (1 mL) was added slowly and stirred for 40 min. The reaction was directly purified by flash chromatography (silica, 10-60% (30% MeOH inEtOAc)/heptanes) to afford the tittle compound (243 mg, 73% yield) as colorless solid that should be used quickly. LCMS (ESI): m/z 616.3 (M+H)+.

Step 2: tert-Butyl 4-[[5-[[bis(tert-butoxycarbonyl)amino]methyl]-3-methyl-7-[4-(trifluoromethoxy)phenyl]benzimidazol-4-yl]methyl]pyrazole-1-carboxylate

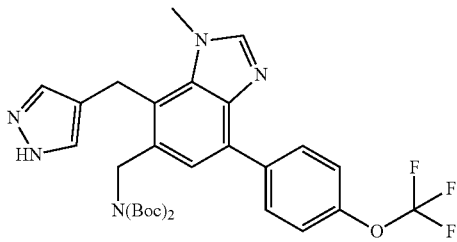

To a mixture of tert-butyl N-[[4-(bromomethyl)-3-methyl-7-[4-(trifluoromethoxy)phenyl]-benzimidazol-5-yl]methyl]-N-tert-butoxycarbonyl-carbamate (100 mg, 0.16 mmol), tert-butyl 4-(4,4,5,5-tetramethyl-1,3,2-dioxaborolan-2-yl)pyrazole-1-carboxylate (96 mg, 0.33 mmol), palladium tetrakis(triphenylphosphine) (19 mg, 0.02 mmol), $K_3PO_4$ (104 mg, 0.49 mmol) were DME (1 mL), ethanol (0.20 mL) and water (0.20 mL). The solution was degassed at rt for 2 min and the mixture was then heated at 60° C. for 1 h. The reaction was diluted with EtOAc (30 mL) and water (20 mL). Organic layer was separated and concentrated with silica gel. The crude was purified by flash column chromatography (silica, 0-70% (30% MeOH in EA)/heptanes) to give the title compound (96 mg, 84% yield). LCMS (ESI): m/z 702.5 (M+H)+.

Step 2: N-[[3-methyl-4-(1H-pyrazol-4-ylmethyl)-7-[4-(trifluoromethoxy)phenyl]benzimidazol-5-yl]methyl]prop-2-enamide

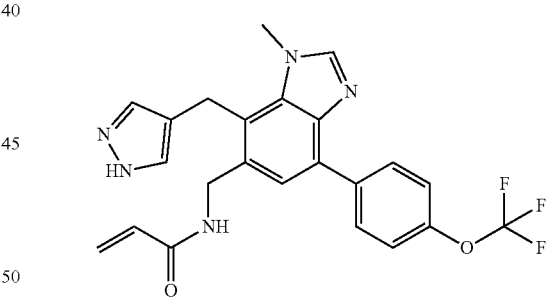

tert-Butyl-4-[[5-[[bis(tert-butoxycarbonyl)amino]methyl]-3-methyl-7-[4-(trifluoromethoxy) phenyl]benzimidazol-4-yl]methyl]pyrazole-1-carboxylate (100 mg, 0.14 mmol) was dissolved in DCM (0.50 mL) and TFA (0.5 mL) was added. The reaction was stirred at rt for 10 min and toluene (2 mL) was added then concentration. The residue was dissolved in THF (0.50 mL) and saturated aqueous $Na_2CO_3$ solution (0.3 mL) was added. To the mixture was added prop-2-enoyl prop-2-enoate (18 mg, 0.14 mmol) in THF (0.3 mL) slowly. The reaction was stirred at rt for 10 min then was diluted with EtOAc (20 mL) and water (10 mL). Organic layer was dried over sodium sulfate, filtered and concentrated. The residue was purified by prep-HPLC: (Column: CSH Prep C18 OBD, 5 μm, 30×75 mm. 20% MeCN in 10 mM AmF water to 40% MeCN) to give the title compound (7.5 mg, 11% yield). LCMS (ESI): m/z 456.2 (M+H)+. $^1$H NMR (400 MHz, DMSO-$d_6$) δ 12.59 (s, 1H), 8.51 (t, J=5.4 Hz, 1H), 8.20-8.13 (m, 2H), 8.12 (s, 1H), 7.46 (d, J=8.1 Hz, 2H), 7.43 (s, 1H), 7.26 (s, 2H), 6.20 (dd, J=17.1, 10.0 Hz, 1H), 6.07 (dd, J=17.1, 2.3 Hz, 1H), 5.55 (dd, J=10.0, 2.3 Hz, 1H), 4.51 (d, J=5.6 Hz, 2H), 4.28 (s, 2H), 3.94 (s, 3H).

Example 32 (Compound 35)

N-[[2-methyl-7-[4-(trifluoromethoxy)phenyl]thiazolo[5,4-d]pyrimidin-5-yl]methyl]prop-2-enamide

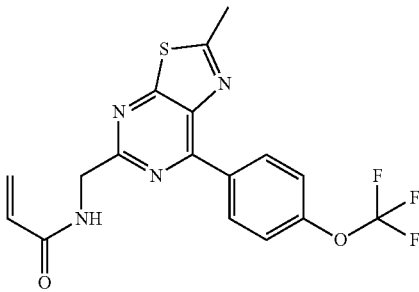 [SMILES: C=CC(=O)NCc1nc(-c2ccc(OC(F)(F)F)cc2)c2nc(C)sc2n1]

Step 1: 5-chloro-2-methyl-7-[4-(trifluoromethoxy) phenyl]thiazolo[5,4-d]pyrimidine

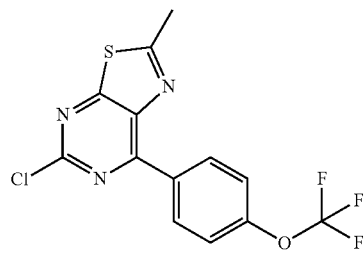 [SMILES: Cc1nc2c(-c3ccc(OC(F)(F)F)cc3)nc(Cl)nc2s1]

4-(trifluoromethoxy)phenylboronic acid (234 mg, 1.14 mmol), 5,7-dichloro-2-methyl-thiazolo[5,4-d]pyrimidine (250 mg, 1.14 mmol), Pd(dppf)Cl$_2$ (83 mg, 0.11 mmol), K$_3$PO4 (481 mg, 2.27 mmol) were mixed in 1,4-dioxane (2 mL) and water (200 µL) and the mixture was stirred at rt for 20 min and then heated at 100° C. for 2 min. The mixture was diluted with water (10 mL) and EtOAc (20 mL) and the organic layer was separated, dried over sodium sulfate, filtered and concentrated with silica gel. The crude was purified by flash column chromatography (silica, 0-40% EtOAc/heptanes) to give the title compound (255 mg, 65% yield). LCMS (ESI): m/z 346.0 (M+H)+.

Step 2: 2-methyl-7-[4-(trifluoromethoxy)phenyl]thiazolo[5,4-d]pyrimidine-5-carbonitrile

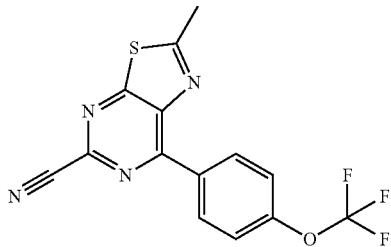 [SMILES: Cc1nc2c(-c3ccc(OC(F)(F)F)cc3)nc(C#N)nc2s1]

5-Chloro-2-methyl-7-[4-(trifluoromethoxy)phenyl]thiazolo[5,4-d]pyrimidine (255 mg, 0.74 mmol), zinc cyanide (86 mg, 0.74 mmol), palladium tetrakis(triphenylphosphine) (42 mg, 0.04 mmol) were added to anhydrous DMF (1 mL) and the mixture was purged with N$_2$ for 5 min. The mixture was heated at 180° C. in microwave for 30 min. The reaction was then diluted with EtOAc (30 mL) and water (15 mL), the organic layer was washed with water (2×30 mL) followed by brine (10 mL). The organic layer was concentrated with silica gel and purified by flash column chromatography (silica, 0-50% EtOAc/heptanes) to give the title compound (190 mg, 77% yield). LCMS (ESI): m/z 335.1 (M+H)+.

Step 3: [2-methyl-7-[4-(trifluoromethoxy)phenyl] thiazolo[5,4-d]pyrimidin-5-yl]methanamine

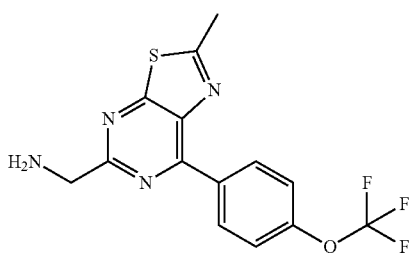 [SMILES: Cc1nc2c(-c3ccc(OC(F)(F)F)cc3)nc(CN)nc2s1]

To a solution of 2-methyl-7-[4-(trifluoromethoxy)phenyl] thiazolo[5,4-d]pyrimidine-5-carbonitrile (100 mg, 0.30 mmol) in methanol (3.0 mL) at 0° C. was added nickel(II) chloride hexahydrate (35 mg, 0.15 mmol) followed by portion wise addition of sodium borohydride (45 mg, 1.2 mmol) and stirred at rt for 15 min. NH$_4$OH (0.5 mL) and water (5 mL) were added and stirred for 15 min. The mixture was extracted with EtOAc (2×20 mL). The organic layers were combined, dried over sodium sulfate, filtered and concentrated to give the crude tittle compound (70 mg, 69% yield). LCMS (ESI): m/z 341.6 (M+H)+.

Step 4: N-[[2-methyl-7-[4-(trifluoromethoxy)phenyl]thiazolo[5,4-d]pyrimidin-5-yl]methyl]prop-2-enamide

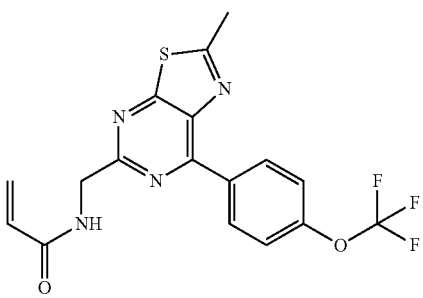 [SMILES: C=CC(=O)NCc1nc(-c2ccc(OC(F)(F)F)cc2)c2nc(C)sc2n1]

To [2-methyl-7-[4-(trifluoromethoxy)phenyl]thiazolo[5,4-d]pyrimidin-5-yl]methanamine (70 mg, 0.21 mmol) and DIPEA (107 μL, 0.62 mmol) in DCM (3 mL) at rt was added a solution of prop-2-enoyl prop-2-enoate (33 mg, 0.27 mmol) in DCM (0.50 mL) slowly. The mixture was stirred at 25° C. for 15 min. The crude was quenched with MeOH (1 mL) and concentrated. The crude was dissolved in DMF and purified by flash column chromatography (silica, C18, 0-80% MeCN/10 mM AmF) to give the title compound (29 mg, 36% yield). LCMS (ESI): m/z 395.1 (M+H)$^+$. $^1$H NMR (400 MHz, DMSO-d$_6$) δ 8.81 (t, J=5.9 Hz, 1H), 8.79-8.74 (m, 2H), 7.60 (d, J1=8.2 Hz, 2H), 6.40 (dd, J1=17.1, 10.2 Hz, 1H), 6.12 (dd, J=17.1, 2.1 Hz, 1H), 5.64 (dd, J=10.2, 2.1 Hz, 1H), 4.71 (d, J=5.9 Hz, 2H), 2.91 (s, 3H).

Example 33: (Compound 36)

N-[[5-(hydroxymethyl)-8-[4-(trifluoromethoxy)phenyl]imidazo[1,2-a]pyridin-6-yl]methyl]-N-methyl-prop-2-enamide

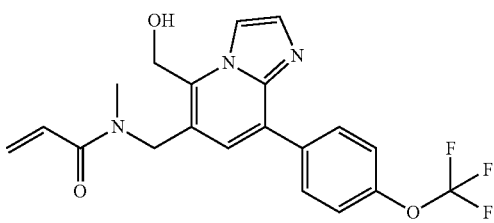 [SMILES: C=CC(=O)N(C)Cc1cc(-c2ccc(OC(F)(F)F)cc2)c2nccn2c1CO]

Step 1: 6-amino-2-chloronicotinonitrile

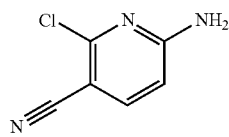

In 20 mL microwave vial and to 2,6-dichloropyridine-3-carbonitrile (1.73 g, 10.02 mmol) was added ammonia 7 N in MeOH (15 mL, 105 mmol). The vial was sealed and heated at 120° C. for 25 min in the microwave reactor, this process was repeated three time for a total of 5.20 g of 2,6-dichloropyridine-3-carbonitrile. The three reactions were concentrated to dryness with silica gel. The crude was purified with flash column chromatography (silica, 10% EtOAc/heptane to 60% EtOAc/heptane) to afford the title compound (2.78 g, 60.2% yield) as a white solid. LCMS (ESI): m/z 154.2 (M+H)* $^1$H NMR (400 MHz, d$_6$-DMSO-d$_6$) δ 7.78 (d, J=8.6 Hz, 1H), 7.51 (s, 2H), 6.45 (d, J=8.6 Hz, 1H).

Step 2: 6-amino-5-bromo-2-chloronicotinonitrile

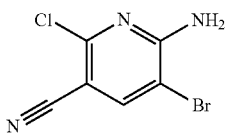 [SMILES: N#Cc1cc(Br)c(N)nc1Cl]

To 6-amino-2-chloro-pyridine-3-carbonitrile (2.78 g, 18.1 mmol) in DCM (60.3 mL) and MeCN (60.3 mL) was added N-bromosuccinimide (6.44 g, 36.2 mmol). The mixture was stirred at rt for 3 h. A precipitate was formed, removed small amount of solvent and filtrated, rinsed with DCM and dried under vacuum to give the title compound (3.25 g, 77.2% yield) as a cream solid. LCMS (ESI): m/z 232.3, 234.3 (M+H)$^+$. $^1$H NMR (400 MHz, DMSO-d$_6$) δ 8.30 (s, 1H), 5.75 (s, 2H)$^+$.

Step 3: 8-bromo-5-chloroimidazo[1,2-a]pyridine-6-carbonitrile

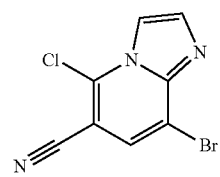 [SMILES: N#Cc1cc(Br)c2nccn2c1Cl]

In a seal tube and to 6-amino-5-bromo-2-chloro-pyridine-3-carbonitrile (3.25 g, 13.98 mmol) was added chloroacetaldehyde 50% in water (39 mL, 307.03 mmol) and the mixture was stirred at 100° C. for 2 h. The solution was then cooled to rt and concentrated to remove most of the water. Acetone (75 mL) was added to the residue and the resulting mixture was stirred rapidly for 1.5 h. The resulting solid was collected through filtration and dried to afford the title compound (3.38 g, 94% yield) as a beige solid. LCMS (ESI): m/z 256.3, 258.3 (M+H)$^+$. $^1$H NMR (400 MHz, DMSO-d$_6$) δ 7.78 (d, J=2.0 Hz, 1H), 7.63 (s, 1H), 7.46 (d, J=1.9 Hz, 1H).

Step 4: 5-chloro-8-(4-(trifluoromethoxy)phenyl)imidazo[1,2-a]pyridine-6-carbonitrile

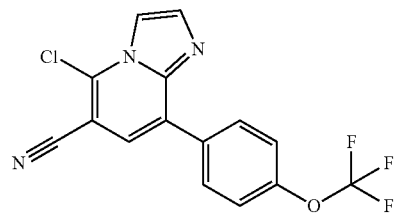 [SMILES: N#Cc1cc(-c2ccc(OC(F)(F)F)cc2)c2nccn2c1Cl]

A microwave vial was charged with 8-bromo-5-chloro-imidazo[1,2-a]pyridine-6-carbonitrile (195 mg, 0.76 mmol), 4-(trifluoromethoxy)phenylboronic acid (140.9 mg, 0.68 mmol), K₂CO₃ (315.2 mg, 2.28 mmol), degassed 1,4-dioxane (3.9 mL) and degassed water (0.98 mL) were added and the mixture was degassed for 1 min before the addition of tetrakis(triphenylphosphine) palladium (87.9 mg, 0.07 mmol). The reaction was heated 10 min, in the microwave reactor at 130° C. This process was repeated eight times for a total of 1.56 g of 8-bromo-5-chloro-imidazo[1,2-a]pyridine-6-carbonitrile. All reaction were combined and poured in EtOAc (200 mL) and water (75 mL), extraction, washed with brine, dried over sodium sulfate, filtered and concentrated. The crude was purified with flash column chromatography (silica, 5% EtOAc/heptane to 70% EtOAc/heptane) to afford the title compound (1.19 g, 57.8% yield) as a white solid. LCMS (ESI): m/z 338.1 (M+H)⁺. ¹H NMR (400 MHz, CDCl₃) δ 8.03-7.97 (m, 3H), 7.95 (d, J=1.4 Hz, 1H), 7.51 (s, 1H), 7.40 (d, J=8.7 Hz, 2H)⁺.

Step 5: 8-(4-(trifluoromethoxy)phenyl)-5-vinylimidazo[1,2-a]pyridine-6-carbonitrile

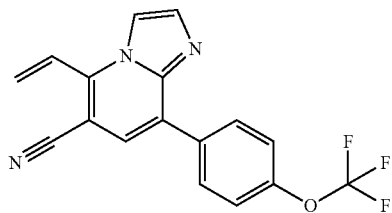 [SMILES: C=Cc1c(C#N)cc(-c2ccc(OC(F)(F)F)cc2)c2nccn12]

In a RBF flushed with nitrogen and containing 5-chloro-8-[4-(trifluoromethoxy)phenyl]imidazo[1,2-a]pyridine-6-carbonitrile (560 mg, 1.66 mmol) and potassium; trifluoro(vinyl)boron (888.6 mg, 6.63 mmol) was added degassed 1,4-dioxane (12 mL). The reaction mixture was degassed for 2 min, triethylamine (0.46 mL, 3.32 mmol) was added and degassed again for 2 min, 1,1-bis(diphenylphosphinos)ferroce-palladium-dichlorid (123 mg, 0.17 mmol) was added, degassed for 1 minute then heated in an oil bath at 80° C. for 3 h. Cooled down to rt, transferred in a flask with EtOAc and concentrated with silica gel. The crude was purified by flash column chromatography (silica, 5% EtOAc/heptane to 70% EtOAc/heptane) to afford the title compound (382 mg, 69.9% yield) as a yellow solid. LCMS (ESI): m/z 330.0 (M+H)⁺. ¹H NMR (400 MHz, CDCl₃) δ 8.01 (d, J=7.9 Hz, 2H), 7.90 (d, J=24.2 Hz, 2H), 7.55 (s, 1H), 7.41 (d, J=8.7 Hz, 2H), 6.97 (dd, J=17.6, 11.8 Hz, 1H), 6.51 (d, J=17.6 Hz, 1H), 6.24 (d, J=11.7 Hz, 1H)⁺.

Step 6: 5-formyl-8-[4-(trifluoromethoxy)phenyl]imidazo[1,2-a]pyridine-6-carbonitrile

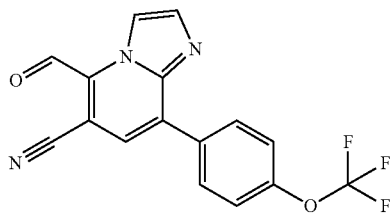 [SMILES: N#Cc1cc(-c2ccc(OC(F)(F)F)cc2)c2nccn2c1C=O]

To 8-[4-(trifluoromethoxy)phenyl]-5-vinyl-imidazo[1,2-a]pyridine-6-carbonitrile (940 mg, 2.85 mmol) in acetone (5.2 mL) and water (0.87 mL) was added osmium tetroxide, 4% wt in water (907.2 μL 0.14 mmol) and sodium (meta) periodate (2.442 g, 11.42 mmol). The reaction was stirred at rt for 18 h. To the reaction was added EtOAc (125 mL) and water (40 mL). Phased were separated, organic phase was washed with 10% aqueous Na₂S₂O₃ solution (40 mL) then with brine (30 mL), dried over sodium sulfate, filtered and concentrated. The crude was purified by flash column chromatography (silica, 5% EtOAc/heptane to 100% EtOAc/heptane) to afford the title compound (650 mg, 69% yield) as a yellow solid.

Step 7: 5-(hydroxymethyl)-8-[4-(trifluoromethoxy)phenyl]imidazo[1,2-a]pyridine-6-carbonitrile

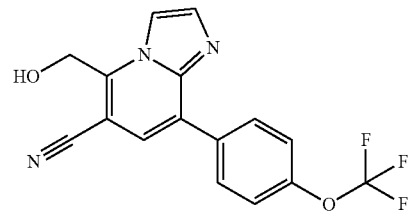 [SMILES: N#Cc1cc(-c2ccc(OC(F)(F)F)cc2)c2nccn2c1CO]

To 5-formyl-8-[4-(trifluoromethoxy)phenyl]imidazo[1,2-a]pyridine-6-carbonitrile (319 mg, 0.96 mmol) in methanol (4.8 mL) was added sodium borohydride (72.9 mg, 1.93 mmol). The reaction was stirred at rt for 15 min. To the reaction mixture was added a saturated aqueous NaHCO₃ solution (20 mL), water (20 mL) and EtOAc (50 mL) and then extracted 3 time with EtOAc (3×50 mL), combined organic phases were washed with brine (30 mL), dried over sodium sulfate, filtered and concentrated. The crude was purified with flash column chromatography (silica, DMC to 10% MeOH/DCM) to afford the title compound (205 mg, 64% yield) as a yellow solid. LCMS (ESI): m/z 334.64(M+H)⁺.

Step 8: [6-(aminomethyl)-8-[4-(trifluoromethoxy)phenyl]imidazo[1,2-a]pyridin-5-yl]methanol

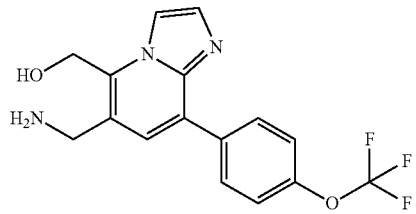 [SMILES: NCc1cc(-c2ccc(OC(F)(F)F)cc2)c2nccn2c1CO]

To a solution of 5-(hydroxymethyl)-8-[4-(trifluoromethoxy)phenyl]imidazo[1,2-a]pyridine-6-carbonitrile (420 mg, 1.26 mmol) in THF (6.2 mL) under nitrogen was added borane-THF complex 1 M in THF (3.8 mL, 3.78 mmol) and the solution was stirred at 65° C. for 2 h. The reaction was cooled down to rt, MeOH (8 mL) was added slowly followed by water (50 mL) and EtOAc (150 mL). Phase were separated and organic phase was washed with water (30 mL) then brine (30 mL), dried over sodium sulfate, filtered and concentrated. The crude was purified with flash column chromatography (silica, C18, 10% MeCN/water (10 mM ammonium formate pH 3.8 buffer) to 100% MeCN/water.) to provide the title compound (68 mg, 16% yield) as a yellow/orange solid. LCMS (ESI): m/z 338.6 (M+H)+.

Step 9: [6-(methylaminomethyl)-8-[4-(trifluoromethoxy)phenyl]imidazo[1,2-a]pyridin-5-yl]methanol

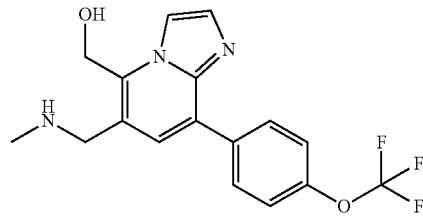 [SMILES: CNCc1cc(-c2ccc(OC(F)(F)F)cc2)c2nccn2c1CO]

To [6-(aminomethyl)-8-[4-(trifluoromethoxy)phenyl]imidazo[1,2-a]pyridin-5-yl]methanol (70 mg, 0.21 mmol) in solution in HFIP (0.98 mL, 9.31 mmol) was added methyl trifluoromethanesulfonate (35.2 μL 0.31 mmol) at rt. The reaction was stirred at rt for 2.5 h and then passed through a silica pad (30 mL of silica gel) washed with EtOAc/Hexanes (1/1, 100 mL) to remove HFIP and excess Methyltriflate. The silica pad was then washed with 20% MeOH in DCM (100 mL). DCM/MeOH filtrate was concentrated to give the crude title compound (72.9 mg, 100% yield).

Step 10: N-[[5-(hydroxymethyl)-8-[4-(trifluoromethoxy)phenyl]imidazo[1,2-a]pyridin-6-yl]methyl]-N-methyl-prop-2-enamide, (Compound 36)

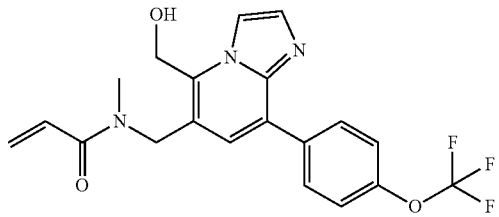 [SMILES: C=CC(=O)N(C)Cc1cc(-c2ccc(OC(F)(F)F)cc2)c2nccn2c1CO]

To [6-(methylaminomethyl)-8-[4-(trifluoromethoxy)phenyl]imidazo[1,2-a]pyridin-5-yl]methanol (70 mg, 0.20 mmol) in THF (1.3 mL) at 0° C. were added 1.3 mL of saturated aqueous NaHCO3 aqueous solution followed by acryloyl chloride (17 μL 0.21 mmol) slowly. The solution was poured in EtOAc (30 mL) and water (15 mL) were added, extraction, dried over sodium sulfate, filtered and concentrated. The residue was purified by prep-HPLC: Column: CSH Prep C18 OBD, 5 μm, 30×75 mm. 40% MeCN in 10 mM AmF water to 60% MeCN) to give the title compound (7 mg, 9% yield). LCMS (ESI): m/z 406.65 (M+H)+. NMR (400 MHz, DMSO-d6) δ 8.26 (d, J=8.9 Hz, 1H), 8.21 (d, J=8.5 Hz, 1H), 8.14-8.04 (m, 1H), 7.74-7.65 (m, 1H), 7.57-7.45 (m, 3H), 7.00-6.60 (m, 1H), 6.19 (d, J=16.4 Hz, 1H), 5.72 (dd, J=10.4, 2.4 Hz, 1H), 4.94 (d, J=6.3 Hz, 3H), 4.84 (s, 2H), 2 protons are missing. Example 34: (Compound 37) N-[[8-[4-(trifluoromethoxy)phenyl]imidazo[1,2-a]pyridin-6-yl]methyl]prop-2-enamide)

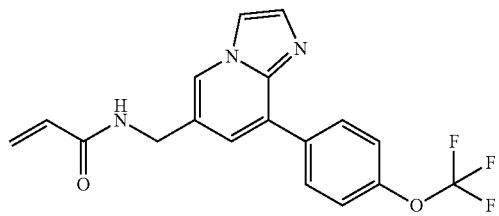 [SMILES: C=CC(=O)NCc1cc(-c2ccc(OC(F)(F)F)cc2)c2nccn2c1]

Step 1: [8-[4-(trifluoromethoxy)phenyl]imidazo[1,2-a]pyridin-6-yl]methanamine

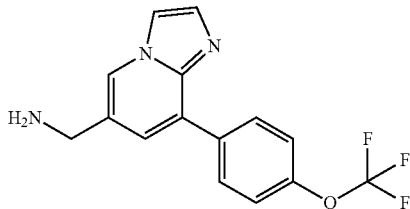 [SMILES: NCc1cc(-c2ccc(OC(F)(F)F)cc2)c2nccn2c1]

To 5-chloro-8-[4-(trifluoromethoxy)phenyl]imidazo[1,2-a]pyridine-6-carbonitrile (614 mg, 1.82 mmol) (described in example 33 (Compound 36), step 4) in THF (18 mL) at rt was added borane-THF complex 1 M in THF (7.3 mL, 7.3 mmol). The reaction was stirred at rt for the 18 h. MeOH (15 mL) and water (50 mL) were added very slowly until no more bubbled occurred. The reaction was poured in EtOAc (100 mL), extraction, washed with brine (30 mL), dried over sodium sulfate, filtered and concentrated as a crude mixture of [8-[4-(trifluoromethoxy)phenyl]imidazo[1,2-a]pyridin-6-yl]methanamine and [5-chloro-8-[4-(trifluoromethoxy)phenyl]imidazo[1,2-a]pyridin-6-yl]methanamine.

Step 2: N-[[8-[4-(trifluoromethoxy)phenyl]imidazo[1,2-a]pyridin-6-yl]methyl]carbamate

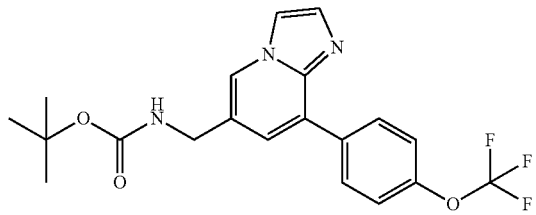 [SMILES: CC(C)(C)OC(=O)NCc1cc(-c2ccc(OC(F)(F)F)cc2)c2nccn2c1]

To a mixture of[5-chloro-8-[4-(trifluoromethoxy)phenyl]imidazo[1,2-a]pyridin-6-yl]methanamine and [8-[4-(trifluoromethoxy)phenyl]imidazo[1,2-a]pyridin-6-yl]methanamine (620 mg, 1.81 mmol) in DCE (12 mL) were added triethylamine (0.51 mL, 3.63 mmol) and di-tert-butyl dicarbonate (792 mg, 3.63 mmol). The solution was stirred at rt for 20 min. The crude was poured in DCM (125 mL) and water (50 mL), extraction, dried over sodium sulfate, filtered and concentrated with silica gel. The crude was purified with flash column chromatography (silica, 10% EtOAc/heptane to 100% EtOA) to afford the title compound (51 mg, 7% yield).

397

Step 3: N-[[8-[4-(trifluoromethoxy)phenyl]imidazo[1,2-a]pyridin-6-yl]methyl]prop-2-enamide (Compound 37)

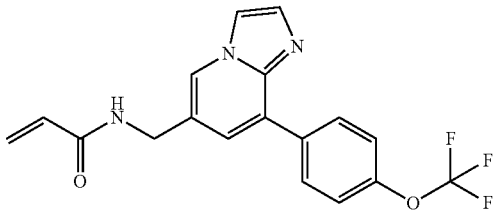 [SMILES: C=CC(=O)NCc1cc(-c2ccc(OC(F)(F)F)cc2)c2nccn2c1]

To tert-butyl N-[[8-[4-(trifluoromethoxy)phenyl]imidazo[1,2-a]pyridin-6-yl]methyl]carbamate (51 mg, 0.13 mmol) in DCM (0.63 mL) was added trifluoroacetic acid (0.24 mL, 3.12 mmol) and the solution was stirred at rt for 30 min. Toluene (5 mL) was added and concentrated to dryness (repeated twice, 2×5 mL). To the residue in THF (0.63 mL) at 0° C. was added 1.3 mL of saturated aqueous NaHCO₃ solution followed by acryloyl chloride (10.7 µL, 0.13 mmol) slowly. After 45 min, the solution was poured in EtOAc (30 mL) and water (15 mL) were added, extraction, dried over sodium sulfate, filtered and concentrated. The residue was purified by prep-HPLC: Column: CSH Prep C18 OBD, 5 µm, 30×75 mm. 20% MeCN in 10 mM AmF water to 40% MeCN) to give the title compound (10 mg, 22% yield) as a white solid. LCMS (ESI): m/z 362.62 (M+H)⁺. ¹H NMR (400 MHz, DMSO-d₆) δ 8.72 (s, 1H), 8.50 (s, 1H), 8.26 (d, J=8.7 Hz, 2H), 8.07 (s, 1H), 7.62 (s, 1H), 7.56-7.45 (m, 3H), 6.28 (dd, J=17.1, 10.1 Hz, 1H), 6.14 (dd, J=17.1, 1.9 Hz, 1H), 5.64 (dd, J=10.1, 1.9 Hz, 1H), 4.42 (d, J=5.7 Hz, 2H).

Example 35 (Compound 38)

N-methyl-N-[[8-[4-(trifluoromethoxy)phenyl]imidazo[1,2-a]pyridin-6-yl]methyl]prop-2-enamide

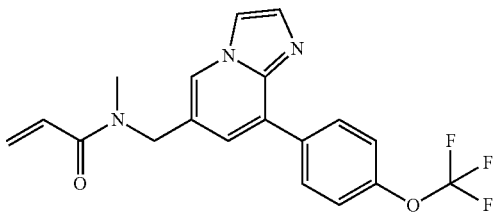 [SMILES: C=CC(=O)N(C)Cc1cc(-c2ccc(OC(F)(F)F)cc2)c2nccn2c1]

Step 1: N-methyl-1-[8-[4-(trifluoromethoxy)phenyl]imidazo[1,2-a]pyridin-6-yl]methanamine

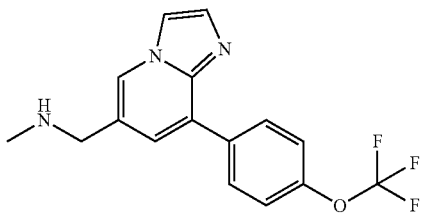 [SMILES: CNCc1cc(-c2ccc(OC(F)(F)F)cc2)c2nccn2c1]

398

To [8-[4-(trifluoromethoxy)phenyl]imidazo[1,2-a]pyridin-6-yl]methanamine (64 mg, 0.21 mmol) ) (described in example 34, step 1) in solution in HFIP (0.98 mL, 9.34 mmol) was added methyl trifluoromethanesulfonate (35.4 µL, 0.31 mmol) at rt. The reaction is stirred at rt for 2 h. The reaction was passed through a silica pad (30 mL of silica gel) washed with EtOAc/Hexanes (1/1, 100 mL) to remove HFIP and excess methyltriflate, the silica pad was then washed with 20% MeOH in DCM (150 mL). DCM/MeOH filtrate was concentrated to give the crude title compound.

Step 2: N-methyl-N-[[8-[4-(trifluoromethoxy)phenyl]imidazo[1,2-a]pyridin-6-yl]methyl]prop-2-enamide (Compound 38)

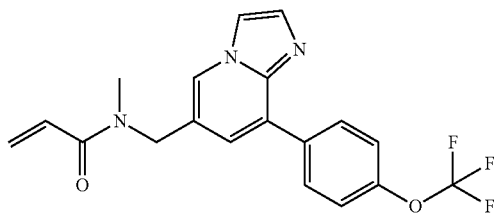 [SMILES: C=CC(=O)N(C)Cc1cc(-c2ccc(OC(F)(F)F)cc2)c2nccn2c1]

To N-methyl-1-[8-[4-(trifluoromethoxy)phenyl]imidazo[1,2-a]pyridin-6-yl]methanamine (67 mg, 0.21 mmol) and N,N-diisopropylethylamine (0.11 mL, 0.63 mmol) in DCM (1.4 mL) at −20° C. was added a solution of prop-2-enoyl prop-2-enoate (34.2 mg, 0.27 mmol) in DCM (0.47 mL) via cannula over 10 min. The mixture was stirred at −20° C. for 15 min then slowly warmed up to rt. The solution was poured in DCM (40 mL) and water (20 mL), phase were separated, washed with saturated aqueous NH₄Cl solution (10 mL), dried over sodium sulfate, filtered and concentrated. The residue was purified by prep-HPLC: Column: CSH Prep C18 OBD, 5 µm, 30×75 mm. 25% MeCN in 10 mM AmF water to 45% MeCN) to give the title compound (13 mg, 17% yield) as a white gum. LCMS (ESI): m/z 376.62 (M+H)⁺.

¹H NMR (400 MHz, DMSO-do) S 8.49 (d, J=21.3 Hz, 1H), 8.31-8.16 (m, 2H), 8.07 (d, J=7.6 Hz, 11H), 7.76-7.27 (m, 4H), 7.01-6.70 (m, 1H), 6.21 (d, J=16.7 Hz, 1H), 5.81-5.65 (m, 1H), 4.80-4.55 (m, 2H), 3.14-2.91 (m, 3H). NMR is complex due to rotamers.

Example 36: (Compound 39)

N-[[3-(difluoromethyl)-4-(hydroxymethyl)-7-[4-(trifluoromethoxy)phenyl]benzimidazol-5-yl]methyl]prop-2-enamide

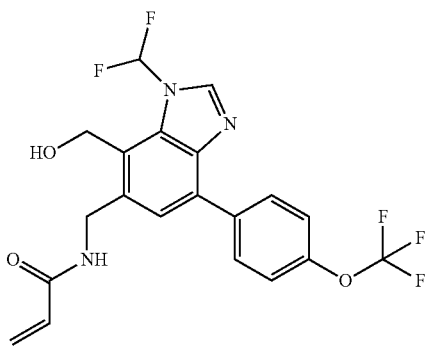 [SMILES: C=CC(=O)NCc1cc(-c2ccc(OC(F)(F)F)cc2)c2ncn(C(F)F)c2c1CO]

Step 1: ethyl 4-bromo-3-(difluoromethyl)-7-[4-(trifluoromethoxy)phenyl]benzimidazole-5-carboxylate

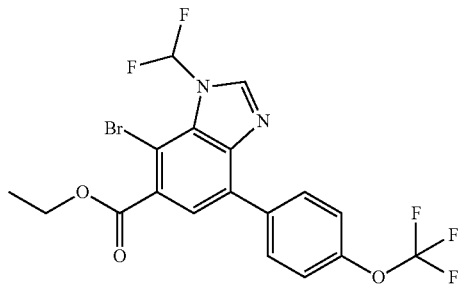 [SMILES: CCOC(=O)c1cc(-c2ccc(OC(F)(F)F)cc2)c2ncn(C(F)F)c2c1Br]

In a seal tube and to ethyl 4-bromo-7-[4-(trifluoromethoxy)phenyl]-3H-benzimidazole-5-carboxylate (3.41 g, 7.95 mmol) (described in Example 27, , step 2) in DMF (38 mL) were added ethyl bromodifluoroacetate (5.2 mL, 40.68 mmol) and potassium phosphate (8.68 g, 40.68 mmol). The reaction was stirred at rt for 19 h then at 35° C. for 5 h. The reaction was poured in EtOAc (500 mL), washed with water (2×150 mL) and brine (150 mL), dried over sodium sulfate, filtered and concentrated with silica gel. The crude was purified with flash column chromatography (silica, 10% ETOAc/heptane to 30% EtOAc/heptane) to give the title compound (1.12 g, 29%). LCMS (ESI): m/z 478.8, 480.7 (M+H)$^+$.

Step 2: [4-bromo-3-(difluoromethyl)-7-[4-(trifluoromethoxy)phenyl]benzimidazol-5-yl]methanol

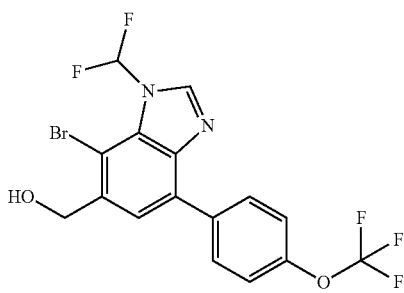 [SMILES: OCc1cc(-c2ccc(OC(F)(F)F)cc2)c2ncn(C(F)F)c2c1Br]

Ethyl4-bromo-3-(difluoromethyl)-7-[4-(trifluoromethoxy)phenyl]benzimidazole-5-carboxylate (1.01 g, 2.11 mmol) was dissolved in THF (10.5 mL) and cooled to 0° C., diisobutylaluminum hydride 1.0 M in toluene (5.3 mL, 5.27 mmol) was added dropwise. The solution was stirred at 0° C. then slowly increased to rt for 2 h. To the mixture was added EtOAc (100 ml) and sodium sulfate decahydrate, the suspension was stirred for 5 min then filtered through Celite, washed with plenty of EtOAc and concentrated to give the title compound (749 mg, 81% yield) as crude a white foam. LCMS (ESI): m/z 436.7, 438.6 (M+H)$^+$.

Step 3: 7-bromo-6-(bromomethyl)-1-(difluoromethyl)-4-[4-(trifluoromethoxy)phenyl]benzimidazole

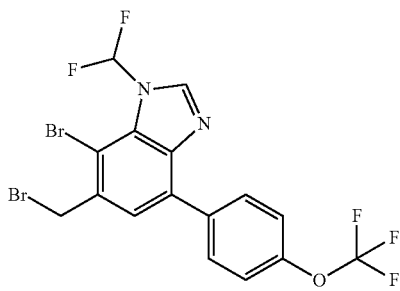 [SMILES: FC(F)n1cnc2c(-c3ccc(OC(F)(F)F)cc3)cc(CBr)c(Br)c21]

To [4-bromo-3-(difluoromethyl)-7-[4-(trifluoromethoxy)phenyl]benzimidazol-5-yl]methanol (749 mg, 1.71 mmol) in DCM (11.7 mL) were added triphenylphosphine (494.3 mg, 1.88 mmol) and carbon tetrabromide (625.0 mg, 1.88 mmol) and the mixture was stirred at rt for 17 h then silica gel was added and concentrated. The crude was purified with flash column chromatography (silica, 5% EtOAc/heptane to 60% EtOAc/heptane) to provide the title compound (472 mg, 55% yield) as a white solid. LCMS (ESI): m/z 498.5, 500.6, 502.5 (M+H)$^+$.

Step 4: tert-Butyl-N-[[4-bromo-3-(difluoromethyl)-7-[4-(trifluoromethoxy)phenyl]benzimidazol-5-yl]methyl]-N-tert-butoxycarbonyl-carbamate

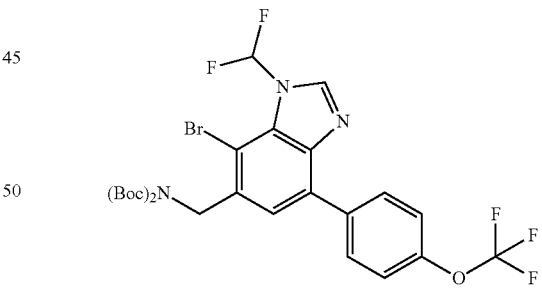

To 7-bromo-6-(bromomethyl)-1-(difluoromethyl)-4-[4-(trifluoromethoxy)phenyl]benzimidazole (472 mg, 0.94 mmol) in DMF (4.7 mL) were added di-tert-butyl-iminodicarboxylate (205.1 mg, 0.94 mmol) and cesium carbonate (309.5 mg, 0.94 mmol). The reaction was stirred for 5.5 h. The reaction was diluted with EtOAc (100 mL) and washed with water (2×50 mL), saturated aqueous LiCl solution (25 mL) and brine (25 mL). The combined organic phases were dried over sodium sulfate, filtered and concentrated to give the title compound (566 mg, 94% yield) as a clear oil that solidified upon standing which was used without further purification. LCMS (ESI): m/z 636.1, 638.2 (M+H)$^+$.

401

Step 5: tert-Butyl-N-tert-butoxycarbonyl-N-[[3-(difluoromethyl)-7-[4-(trifluoromethoxy) phenyl]-4-vinyl-benzimidazol-5-yl]methyl]carbamate

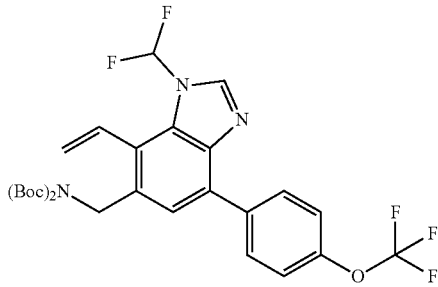

A flask was charged with tert-butyl-N-[[4-bromo-3-(difluoromethyl)-7-[4-(trifluoromethoxy)phenyl]benzimidazol-5-yl]methyl]-N-tert-butoxycarbonyl-carbamate (566 mg, 0.89 mmol), potassium; trifluoro(vinyl)boron (357.4 mg, 2.67 mmol) and $K_3PO_4$ (360 mg, 3.56 mmol). 1,4-Dioxane (6.6 mL) and water (2.3 mL) were added and purged with $N_2$. Palladium tetrakis(triphenylphosphine) (102.7 mg, 0.09 mmol) was added and the flask was heated at 90° C. under nitrogen for 17 h. The reaction was cooled down to rt, diluted with EtOAc, filtered over sodium sulfate, rinsed with EtOAc and concentrated with silica gel. The crude was purified with flash column chromatography (silica, 5% EtOAc/heptane to 40% EtOAc/heptane) to provide the title compound (289 mg, 56% yield) as a pale yellow solid. LCMS (ESI): m/z 584.2 (M+H)$^+$.

Step 6: tert-Butyl-N-tert-butoxycarbonyl-N-[[3-(difluoromethyl)-4-(hydroxymethyl)-7-[4-(trifluoromethoxy)phenyl]benzimidazol-5-yl]methyl]carbamate

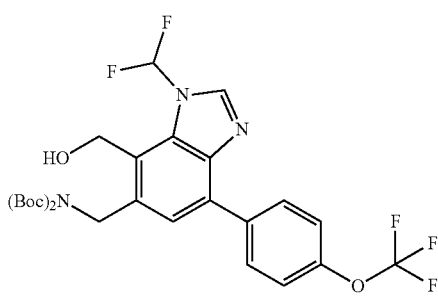

To tert-butyl-N-tert-butoxycarbonyl-N-[[3-(difluoromethyl)-7-[4-(trifluoromethoxy) phenyl]-4-vinyl-benzimidazol-5-yl]methyl]carbamate (115 mg, 0.20 mmol) in methanol (1 mL) and DCM (1 mL) at −78° C. was bubbled ozone for 10 min. Nitrogen was bubbled in the solution for 10 min then sodium borohydride (29.8 mg, 0.79 mmol) was added. The reaction was slowly warmed up to rt for 45 min. The solution was poured in DCM (50 mL) and saturated aqueous $NH_4Cl$ solution (25 mL), extraction with DCM (3×20 mL), dried over sodium sulfate, filtered and concentrated to give (110 mg, 95% yield) as a very pale brown solid. LCMS (ESI): m/z 588.2 (M+H)$^+$.

402

Step 7: N-[[3-(difluoromethyl)-4-(hydroxymethyl)-7-[4-(trifluoromethoxy)phenyl]benzimidazol-5-yl]methyl]prop-2-enamide (Compound 39)

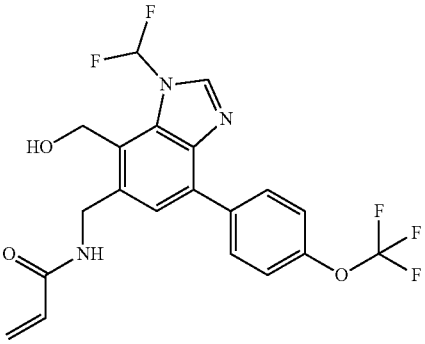 [SMILES: C=CC(=O)NCc1cc(-c2ccc(OC(F)(F)F)cc2)c2ncn(C(F)F)c2c1CO]

To tert-butyl-N-tert-butoxycarbonyl-N-[[3-(difluoromethyl)-4-(hydroxymethyl)-7-[4-(trifluoromethoxy)phenyl]benzimidazol-5-yl]methyl]carbamate (110 mg, 0.19 mmol) in DCM (1.2 mL) was added trifluoroacetic acid (0.43 mL, 5.62 mmol) and the mixture was stirred until complete deprotection. The reaction was concentrated, toluene (5 mL) was added, concentration again (2×5 mL). To the residue in DCM (1.2 mL) at −20° C. was added N,N-diisopropylethylamine (97.8 µL, 0.56 mmol) then a solution of prop-2-enoyl prop-2-enoate (23.6 µL, 0.21 mmol) in DCM (0.32 mL) was added very slowly. The mixture was stirred at -20° C. for 15 min then slowly warmed up to rt. Water and MeOH were added and the solution was concentrated. The crude was purified with flash column chromatography (silica, C18, 25% MeCN/water (10 mM ammonium formate pH 3.8 buffer) to 70% MeCN/water) to give the title compound (33.7 mg, 41% yield) as a white solid. LCMS (ESI): m/z 441.8 (M+H)$^+$. $^1$H NMR (400 MHz, DMSO-d$_6$) δ 8.82 (s, 1H), 8.55 (t, J=5.3 Hz, 1H), 8.24 (t, J=54.8 Hz, 1H), 8.09 (d, J=8.8 Hz, 2H), 7.58 (s, 1H), 7.53 (d, J=8.1 Hz, 2H), 6.24 (dd, J=17.1, 10.0 Hz, 1H), 6.13 (dd, J=17.1, 2.4 Hz, 1H), 5.66 (t, J=5.3 Hz, 1H), 5.61 (dd, J=10.0, 2.4 Hz, 1H), 4.83 (d, J=5.3 Hz, 2H), 4.65 (d, J=5.5 Hz, 2H).

Example 37 (Compounds 40 & 41) (R)—N-((1-(difluoromethyl)-7-(1,2-dihydroxyethyl)-4-(4-(trifluoromethoxy)phenyl)-1H-benzo[d]imidazol-6-yl)methyl)acrylamide and (S)—N-((1-(difluoromethyl)-7-(1,2-dihydroxyethyl)-4-(4-(trifluoromethoxy)phenyl)-1H-benzo[d]imidazol-6-yl)methyl)acrylamide

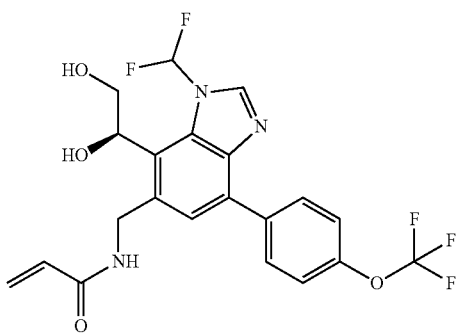

Step 1: tert-butyl-N-[[3-(difluoromethyl)-7-[4-(trifluoromethoxy)phenyl]-4-vinyl-benzimidazol-5-yl]methyl]carbamate

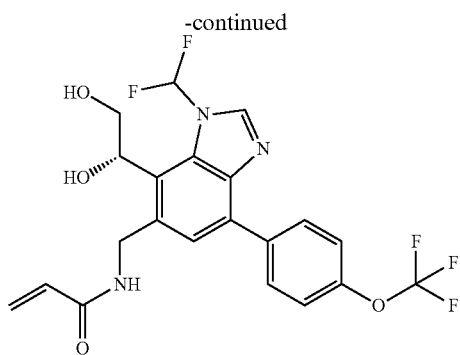

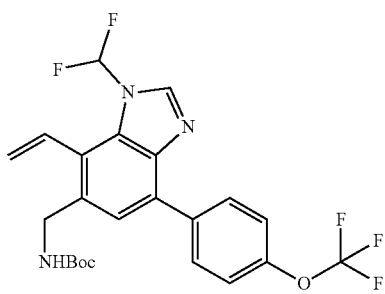 [SMILES: C=Cc1c(CNC(=O)OC(C)(C)C)cc(-c2ccc(OC(F)(F)F)cc2)c2ncn(C(F)F)c12]

To tert-butyl-N-tert-butoxycarbonyl-N-[[3-(difluoromethyl)-7-[4-(trifluoromethoxy )phenyl]-4-vinyl-benzimidazol-5-yl]methyl]carbamate (169 mg, 0.29 mmol) in MeCN (3 mL) was added magnesium perchlorate hexahydrate (31 mg, 0.09 mmol) and the mixture was stirred at 60° C. for 50 min. The reaction was cooled down and was added EtOAc (50 mL). The solution was washed with water (20 mL) and brine (20 mL), dried over sodium sulfate, filtered and concentrated to give the crude title compound (141 mg, 100% yield) as a cream solid. LCMS (ESI): m/z 484.3 (M+H)$^+$ Step 2: tert-butyl N-[[3-(difluoromethyl)-4-(1,2-dihydroxyethyl)-7-[4-(trifluoromethoxy) phenyl]benzimidazol-5-yl]methyl]carbamate

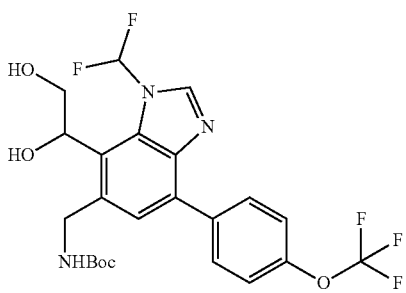 [SMILES: CC(C)(C)OC(=O)NCc1cc(-c2ccc(OC(F)(F)F)cc2)c2ncn(C(F)F)c2c1C(O)CO]

To tert-butyl-N-[[3-(difluoromethyl)-7-[4-(trifluoromethoxy)phenyl]-4-vinyl-benzimidazol-5-yl]methyl]carbamate (141 mg, 0.29 mmol) dissolved in DCM (1.5 mL) and acetone (0.5 mL) were added 4-methylmorpholine N-oxide (102.5 mg, 0.87 mmol) and osmium tetroxide, 4% wt in water (185.4 μL, 0.03 mmol). The mixture stirred at rt for 17 h then further acetone (0.5 mL), 4-methylmorpholine N-oxide (102.5 mg, 0.87 mmol) and osmium tetroxide, 4% wt in water (185.4 μL, 0.03 mmol) were added and the mixture continued to be stir at rt for 24 h. Further acetone (0.5 mL), 4-methylmorpholine N-oxide (102.5 mg, 0.87 mmol) and osmium tetroxide, 4% wt in water (185.4 μL, 0.03 mmol) were added and the mixture continued to be stir at rt for 3 days. More DCM (50 mL) and 10% aqueous Na$_2$S$_2$O$_3$ solution (20 mL) were added stirred for 5 min, phases were separated and the solid was extracted with DCM (3×15 mL). Combined organic phased were washed with NaHCO$_3$ (10 mL), dried over sodium sulfate, filtered and concentrated. The crude product was purified by flash column chromatography (silica, 5-70% (20% MeOH in EtOAc)/heptanes) to provide the title compound (86 mg, 57% yield) as a clear solid. LCMS (ESI): m/z 517.9 (M+H)$^+$ Step 3: (R)—N-((1-(difluoromethyl)-7-(1,2-dihydroxyethyl)-4-(4-(trifluoromethoxy)phenyl)-1H-benzo[d]imidazol-6-yl)methyl)acrylamide and (S)—N-((1-(difluoromethyl)-7-(1,2-dihydroxyethyl)-4-(4-(trifluoromethoxy)phenyl)-1H-benzo[d]imidazol-6-yl)methyl)acrylamide

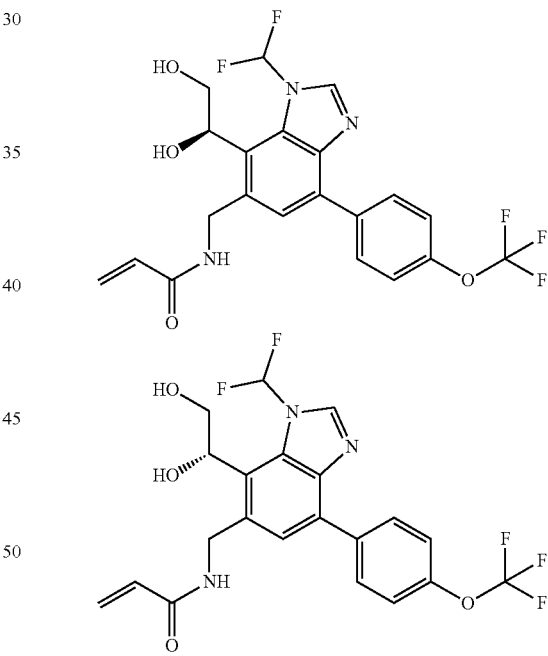

To tert-butyl-N-[[3-(difluoromethyl)-4-(1,2-dihydroxyethyl)-7-[4-(trifluoromethoxy) phenyl]benzimidazol-5-yl]methyl]carbamate (86 mg, 0.17 mmol) in DCM (1.2 mL) was added trifluoroacetic acid (0.8 mL, 10.38 mmol) and the mixture was stirred for 30 min. Toluene (5 mL) was added and the mixture was concentrated. To the residue in THF (1.2 mL) at 0° C. was added saturated aqueous Na$_2$CO$_3$ solution (0.5 mL) then a solution of prop-2-enoyl prop-2-enoate (0.21 μL, 0.18 mmol) in THF (0.32 mL) was added very slowly. The mixture was stirred at 0° C. for 40 min. Water (15 mL) was added and the product was extracted with 10% MeOH/DCM (3×30 mL), dried over sodium sulfate, filtered and concentration. The crude product was purified by flash column chromatography (silica, C18, 5% MeCN/water (10 mM ammonium formate pH 3.8 buffer) to 70% MeCN/water) to provide N-[[3-(difluoromethyl)-4-(1,2-dihydroxyethyl)-7-[4-(trifluoromethoxy)phenyl]benzimidazol-5-yl]methyl]prop-2-enamide (34 mg) as a mixture of enantiomers.

The above racemate was further purified by chiral chromatography (Anal. Column: ChiralPak IA, 250 mm×4.6 mm ID, 5 μm, Mobile Phase: 6:2:92 EtOH: DCM: hexanes; isocratic Flow: 1 mL/min, column temp.: ~26° C., run time: 35 min; wavelength: 280 nm) to afford:

(R)—N-((1-(difluoromethyl)-7-(1,2-dihydroxyethyl)-4-(4-(trifluoromethoxy)phenyl)-1H-benzo[d]imidazol-6-yl)methyl)acrylamide. LCMS (ESI): m/z 472.0 (M+H)+. 1H NMR (400 MHz, DMSO-d6) δ 9.07 (t, J=59.5 Hz, 1H), 8.79 (s, 1H), 8.55 (t, J=5.4 Hz, 1H), 8.09-8.00 (m, 2H), 7.58-7.48 (m, 3H), 6.27 (td, J=11.7, 10.2 Hz, 2H), 6.13 (dd, J=17.1, 2.3 Hz, 1H), 5.62 (dd, J=10.1, 2.3 Hz, 1H), 5.30 (dd, J=7.4, 3.6 Hz, 1H), 5.22 (t, J=5.0 Hz, 1H), 4.68-4.51 (m, 2H), 3.86-3.69 (m, 2H).

(S)—N-((1-(difluoromethyl)-7-(1,2-dihydroxyethyl)-4-(4-(trifluoromethoxy)phenyl)-1H-benzo[d]imidazol-6-yl)methyl)acrylamide. LCMS (ESI): m/z 472.0 (M+H)+. 1H NMR (400 MHz, DMSO-d6) δ 9.07 (t, J=59.5 Hz, 1H), 8.79 (s, 1H), 8.55 (t, J=5.4 Hz, 1H), 8.09-8.00 (m, 2H), 7.60-7.47 (m, 3H), 6.35-6.21 (m, 2H), 6.13 (dd, J=17.1, 2.3 Hz, 1H), 5.62 (dd, J=10.1, 2.3 Hz, 1H), 5.30 (dd, J=7.4, 3.5 Hz, 1H), 5.22 (t, J=4.9 Hz, 1H), 4.68-4.50 (m, 2H), 3.86-3.69 (m, 2H).

Example 38 (Compound 42)N-[2-[4-cyano-3-methyl-7-[4-(trifluoromethoxy)phenyl]benzimidazol-5-yl]ethyl]prop-2-enamide

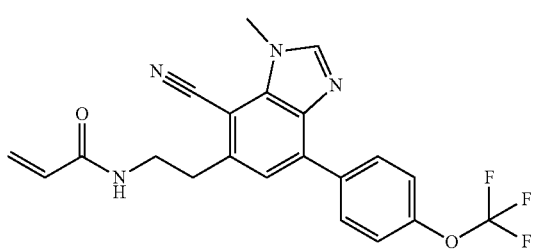 [SMILES: C=CC(=O)NCCc1cc(-c2ccc(OC(F)(F)F)cc2)c2ncn(C)c2c1C#N]

Step 1: methyl (7-cyano-1-methyl-4-(4-(trifluoromethoxy)phenyl)-1H-benzo[d]imidazol-6-yl)carbamate

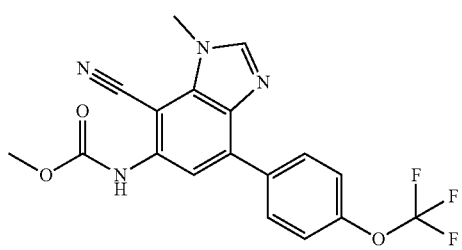 [SMILES: COC(=O)Nc1cc(-c2ccc(OC(F)(F)F)cc2)c2ncn(C)c2c1C#N]

In a 2-5 mL microwave vial a solution of methyl (7-bromo-1-methyl-4-(4-(trifluoromethoxy)phenyl)-1H-benzo[d]imidazol-6-yl)carbamate (1.0 g, 01.99 mmol) (described in example 55, , step 4) and zinc cyanine (303.9 mg, 2.59 mmol) in DMF (16 mL) was degassed 5 minutes before the addition of palladium tetrakis(triphenylphosphine) (161.1 mg, 0.14 mmol). The reaction was stirred at 140° C. for 20 min in the microwave reactor. The solution was poured in EtOAc (150 mL), washed with saturated aqueous NaHCO3 solution (40 mL), water (40 mL) then brine (2×30 mL), dried over sodium sulfate, filtered and concentrated. The crude was purified by flash column chromatography (silica, 10% EtOAc/heptane to 100% EtOAc) to give the title compound (816 mg, 85% yield) as a pale yellow solid.

Step 2: 5-amino-3-methyl-7-[4-(trifluoromethoxy)phenyl]benzimidazole-4-carbonitrile

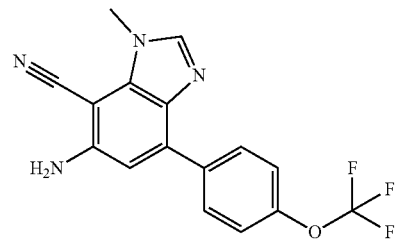 [SMILES: Cn1cnc2c(-c3ccc(OC(F)(F)F)cc3)cc(N)c(C#N)c21]

To methyl (7-cyano-1-methyl-4-(4-(trifluoromethoxy)phenyl)-1H-benzo[d]imidazol-6-yl)carbamate (801 mg, 1.79 mmol) in methanol (20 mL) was added sodium hydroxide 1M (11 mL, 11 mmol) and the solution was stirred at 50° C. for 20 h the more sodium hydroxide 1M (11 mL, 11 mmol) was added and the temperature was increased at 70° C. for 5 h. and then cooled down to rt and concentrated to remove most of MeOH. The residue was diluted with water (50 mL) and extracted with DCM (3×100 mL). The combined organic phases were dried over sodium sulfate, filtered and concentrated to give the title compound (593 mg, 100% yield) as beige solid. LCMS (ESI): m/z 332.9. (M+H)+.

Step 3: 5-bromo-3-methyl-7-[4-(trifluoromethoxy)phenyl]benzimidazole-4-carbonitrile

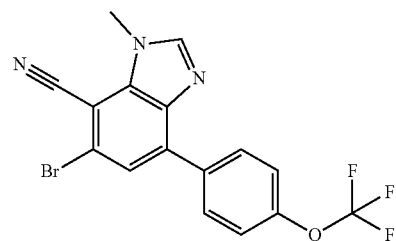 [SMILES: Cn1cnc2c(-c3ccc(OC(F)(F)F)cc3)cc(Br)c(C#N)c21]

5-amino-3-methyl-7-[4-(trifluoromethoxy)phenyl]benzimidazole-4-carbonitrile (573 mg, 1.72 mmol) was dissolved in MeCN (10.6 mL) and copper (I) bromide (494.7 4 mg, 3.45 mmol) was added. The reaction was heated to 60° C. and a solution of tert-butyl nitrite (512.8 uL, 4.31 mmol) in MeCN (6.6 mL) was added slowly dropwise. It was stirred at 60° C. for 40 min. The reaction was concentrated onto silica and purified by flash column chromatography (silica, 5-100% (20% MeOH in EtOAc)/heptanes) to provide the title compound (191 mg, 28% yield) as an orange solid. LCMS (ESI): m/z 396.2, 398.2 (M+H)⁺

Step 4: tert-butyl N-[2-[4-cyano-3-methyl-7-[4-(trifluoromethoxy)phenyl]benzimidazol-5-yl]ethyl]carbamate

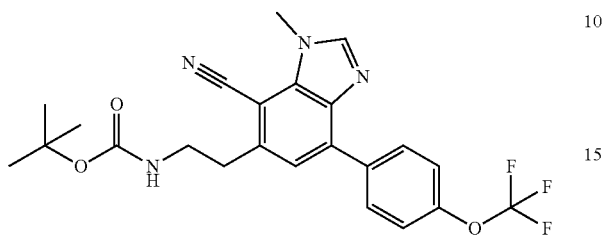

A 2-5 mL microwave vial under N₂ was charged with 5-bromo-3-methyl-7-[4-(trifluoromethoxy)phenyl]benzimidazole-4-carbonitrile (145 mg, 0.37 mmol), potassium tert-butyl N-[2-(trifluoroboranuidyl)ethyl]carbamate (321 mg, 1.28 mmol) and cesium carbonate (583.4 mg, 1.78 mmol). 1,4-Dioxane (4.5 mL) and water (0.9 mL) were added and degassed for 2 minutes then were added palladium(II) acetate (20 mg, 0.09 mmol) and butyldi-1-adamantylphosphine (64 mg, 0.1800 mmol), the solution was degassed 1 min and heated at 120° C. for 25 min in the microwave reactor. The mixture was diluted with EtOAc (60 mL), dried over sodium sulfate, filtered over Celite and concentrated with silica gel. The crude was purified by flash column chromatography (silica, 15-70% (20% MeOH in EtOAc)/heptanes) to provide the title compound (85 mg, 40% yield) as a beige solid. LCMS (ESI): m/z 461.2 (M+H)⁺

Step 5: N-[2-[4-cyano-3-methyl-7-[4-(trifluoromethoxy)phenyl]benzimidazol-5-yl]ethyl]prop-2-enamide

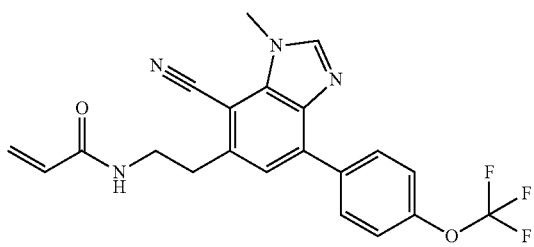 [SMILES: C=CC(=O)NCCc1cc(-c2ccc(OC(F)(F)F)cc2)c2ncn(C)c2c1C#N]

To tert-butyl N-[2-[4-cyano-3-methyl-7-[4-(trifluoromethoxy)phenyl]benzimidazol-5-yl]ethyl]carbamate (80 mg, 0.17 mmol) in DCM (1 mL) was added trifluoroacetic acid (0.5 mL, 6.49 mmol) and the mixture was stirred for 30 min then toluene (5 mL) and the mixture was concentrated. To residue in THF (1.2 mL) at 0° C. was added saturated aqueous Na₂CO₃ solution (0.6 mL) then a solution of prop-2-enoyl prop-2-enoate (21.9 uL, 0.19 mmol) in THF (0.32 mL) was added very slowly. The mixture was stirred at 0° C. for 5 min. Water (15 mL) was added and extracted 3 times with 10% MeOH/DCM, the combined organic phases were dried over sodium sulfate, filtered and concentrated. The residue was purified by prep-HPLC: Column: CSH Prep C18 OBD, 5 μm, 30×75 mm. 35% MeCN in 10 mM AmF water to 55% MeCN) to give the title compound (36 mg, 50% yield) as a white solid. LCMS (ESI): m/z 415.2 (M+H)⁺. ¹H NMR (400 MHz, DMSO-d₆) δ 8.41 (s, J=9.1 Hz, 1H), 8.31-8.24 (m, 1H), 8.23 (d, J=8.9 Hz, 2H), 7.58-7.48 (m, 3H), 6.19 (dd, J=17.1, 10.1 Hz, 1H), 6.05 (dd, J=17.1, 2.3 Hz, 1H), 5.56 (dd, J=10.1, 2.3 Hz, 1H), 4.11 (s, 3H), 3.54 (q, J=6.8 Hz, 2H), 3.14 (t, J=6.9 Hz, 2H). (Compound 42)

Example 39 (Compound 43) N-[[8-methyl-5-[4-(trifluoromethoxy)phenyl]-7-quinolyl]methyl]prop-2-enamide

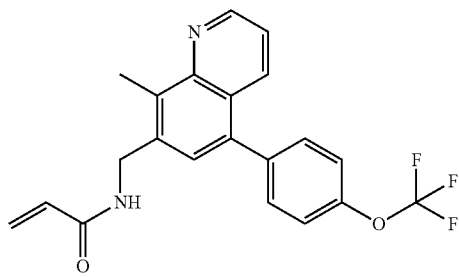 [SMILES: C=CC(=O)NCc1cc(-c2ccc(OC(F)(F)F)cc2)c2cccnc2c1C]

Step 1: 5-bromo-7-chloro-8-methyl-quinoline

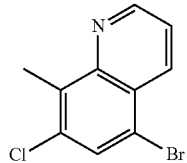

To a solution of 7-chloro-8-methyl-quinoline (10.51 g, 59.17 mmol) and silver sulfate (27.85 g, 88.75 mmol) in concentrated sulfuric acid (40 mL, 746.4 mmol) was added bromine (3.6 mL, 71 mmol) (100 μL at the time for 15 min). The reaction was stirred at rt for 2 h. Reaction was not complete so addition of more bromine (1.2 mL, 23.42 mmol) and continued to stir at rt for 20 h. The reaction was transferred very slowly to a 2 L erlenmeyer contained ice, NH₄OH 28% aqueous solution (300 mL) and 400 mL of EtOAc, then the mixture was stirred for 15 min. The basic solution was filtered through sand, rinsed with water and plenty of EtOAc. Phase were separated and then extracted with EtOAc (3×200 mL) and combined organic phases were washed with brine (200 mL), dried over sodium sulfate, filtered and concentrated with silica gel. The crude was purified with flash column chromatography (silica, 5% EtOAc/heptane to 50% EtOAc/heptane) to give the title compound (8.24 g, 54% yield) as a white solid. LCMS (ESI): m/z 256.4, 258.3 (M+H)⁺. ¹H NMR (400 MHz, CDCl₃) δ 8.96 (d, J=4.2 Hz, 1H), 8.49 (d, J=8.5 Hz, 1H), 7.84 (s, 1H), 7.50 (dd, J=8.5, 4.2 Hz, 1H), 2.84 (s, 3H)⁺.

Step 2: 7-chloro-8-methyl-5-[4-(trifluoromethoxy)phenyl]quinoline

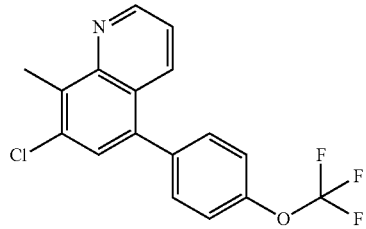 [SMILES: Cc1c(Cl)cc(-c2ccc(OC(F)(F)F)cc2)c2cccnc12]

A 10-20 mL microwave vial was charged with 5-bromo-7-chloro-8-methyl-quinoline (850 mg, 3.31 mmol), 4-(trifluoromethoxy)phenylboronic acid (648.2 mg, 3.15 mmol), $K_2CO_3$ (1.37 g, 9.94 mmol). 1,4-Dioxane (15 mL) and water (4 mL) were added and the mixture was degassed for 5 min before the addition of palladium tetrakis(triphenylphosphine) (268 mg, 0.23 mmol) and degassed again for 2 min. The reaction was heated in the microwave reactor at 130° C. for 20 min. The reaction was poured in EtOAc (100 mL), washed with water (40 mL) and brine (40 mL), dried over sodium sulfate, filtered and concentrated. The crude was purified by flash column chromatography (silica, 5% EtOAc/heptane to 60% EtOAc/heptane) to give the title compound (1.064 g, 95% yield) as a clear oil that solidified upon standing. LCMS (ESI): m/z 338.5, 340.3 $(M+H)^+$

Step 3: tert-Butyl-N-[[8-methyl-5-[4-(trifluoromethoxy)phenyl]-7-quinolyl]methyl]carbamate

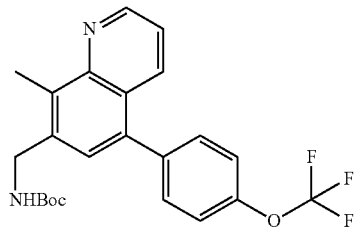 [SMILES: Cc1c(CNC(=O)OC(C)(C)C)cc(-c2ccc(OC(F)(F)F)cc2)c2cccnc12]

A 10-20 mL microwave vial under $N_2$ was charged with 7-chloro-8-methyl-5-[4-(trifluoromethoxy)phenyl]quinoline (900 mg, 2.66 mmol), potassium (((tert-butoxycarbonyl)amino)methyl)trifluoroborate (1.9 g, 7.99 mmol), potassium carbonate (3.31 g, 23.98 mmol), degassed 1,4-dioxane (15 mL) and degassed water (3 mL) were added and degassed for 2 min then was added Pd SPhos G2 (191.9 mg, 0.27 mmol), degassed 1 min. The mixture was heated in the microwave reactor at 130° C. for 25 min. The reaction was not complete, degassed for 2 min then were added potassium (((tert-butoxycarbonyl)amino)methyl)trifluoroborate (631.8 mg, 2.66 mmol) and Pd SPhos G2 (57.6 mg, 0.08 mmol), degassed for 2 min again. Vial was sealed and heated in the microwave at 130° C. for 30 min. The mixture was diluted with EtOAc (75 mL) and water (50 mL), extraction, dried over sodium sulfate, filtered and concentrated with silica gel. The crude was purified with flash column chromatography (silica, 5% EtOAc/heptane to 60% EtOAc/heptane) to give the title compound (955 mg, 83% yield) as a pale orange solid. LCMS (ESI): m/z 433.7 $(M+H)^+$. $^1$H NMR (400 MHz, $CDCl_3$) δ 8.98 (d, J=2.4 Hz, 1H), 8.16 (d, J=8.4 Hz, 1H), 7.49-7.42 (m, 3H), 7.41-7.30 (m, 3H), 4.86 (s, 1H), 4.60 (d, J=5.3 Hz, 2H), 2.88 (s, 3H), 1.46 (s, 9H).

Step 4: N-[[8-methyl-5-[4-(trifluoromethoxy)phenyl]-7-quinolyl]methyl]prop-2-enamide (Compound 43)

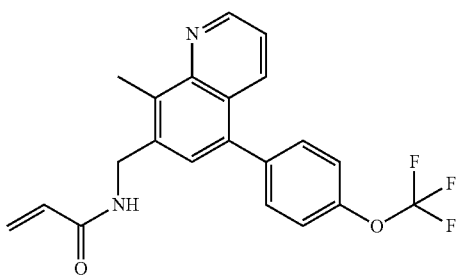 [SMILES: C=CC(=O)NCc1cc(-c2ccc(OC(F)(F)F)cc2)c2cccnc2c1C]

To tert-butyl-N-[[8-methyl-5-[4-(trifluoromethoxy)phenyl]-7-quinolyl]methyl]carbamate (155 mg, 0.36 mmol) in DCM (1 mL) was added trifluoroacetic acid (1 mL, 13.41 mmol) and stirred at rt for 30 min, then concentrated to dryness, addition of toluene (5 mL) and concentration again (2×5 mL). To residue in DCM (2 mL) was added N,N-diisopropylethylamine (0.19 mL, 1.08 mmol) at −20° C. then was added a solution of prop-2-enoyl prop-2-enoate (53.4 µL, 0.47 mmol) in DCM (0.7 mL) very slowly via cannula. The mixture was stirred at −20° C. for 15 min then slowly warmed up to rt and stirred for 17 h. The solution was poured in DCM (50 mL) and water (20 mL), phase were separated, washed with saturated aqueous $NH_4Cl$ solution (20 mL), dried over sodium sulfate, filtered and concentrated. The crude was purified with flash column chromatography (silica, C18, 5% MeCN/water (10 mM ammonium formate pH 3.8 buffer) to 70% MeCN/water) to give the title compound (116 mg, 84% yield) as a white solid. LCMS (ESI): m/z 387.7 $(M+H)^+$. $^1$H NMR (400 MHz, DMSO-$d_6$) δ 8.98 (dd, J=4.1, 1.7 Hz, 1H), 8.65 (t, J=5.5 Hz, 1H), 8.14 (dd, J=8.5, 1.7 Hz, 1H), 7.65-7.44 (m, 6H), 6.28 (dd, J=17.1, 10.1 Hz, 11H), 6.13 (dd, J=17.1, 2.2 Hz, 1H), 5.61 (dd, J=10.1, 2.2 Hz, 1H), 4.63 (d, J=5.7 Hz, 2H), 2.81 (s, 3H).

Example 40 (Compound 44) N-[[8-(hydroxymethyl)-5-[4-(trifluoromethoxy)phenyl]-7-quinolyl]methyl]prop-2-enamide

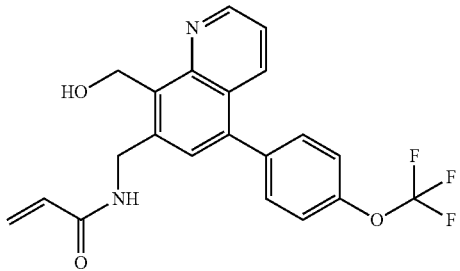 [SMILES: C=CC(=O)NCc1cc(-c2ccc(OC(F)(F)F)cc2)c2cccnc2c1CO]

Step 1: tert-Butyl-N-tert-butoxycarbonyl-N-[[8-methyl-5-[4-(trifluoromethoxy)phenyl]-7-quinolyl]methyl]carbamate

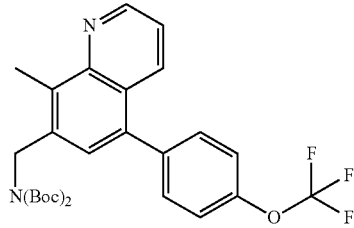

To a mixture of tert-butyl N-[[8-methyl-5-[4-(trifluoromethoxy)phenyl]-7-quinolyl]methyl]carbamate (2.75 g, 6.35 mmol) (described in Example 39, , step 3) and N,N-diisopropylethylamine (1.1 mL, 6.35 mmol) in MeCN (33.2 mL) was added 4-dimethylaminopyridine (116.5 mg, 0.95 mmol). The solution was stirred at rt for the 18 h. The crude was poured in DCM (150 mL) and water (50 mL), extraction, dried over sodium sulfate, filtered and concentrated with silica gel. The crude was purified with flash column chromatography (silica, 10% EtOAc/heptane to 100% EtOAc/heptane) to give the title compound (3.20 g, 95% yield) as white solid. LCMS (ESI): m/z 533.84 (M+H)$^+$.

Step 2: tert-Butyl-N-[[8-(bromomethyl)-5-[4-(trifluoromethoxy)phenyl]-7-quinolyl]methyl]-N-tert-butoxycarbonyl-carbamate

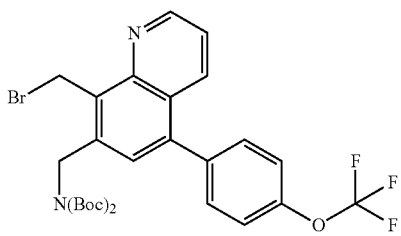

To tert-butyl N-tert-butoxycarbonyl-N-[[8-methyl-5-[4-(trifluoromethoxy)phenyl]-7-quinolyl]methyl]carbamate (1000 mg, 1.88 mmol) in carbon tetrachloride (14 mL) was added N-bromosuccinimide (334.2 mg, 1.88 mmol) followed by benzoyl peroxide (22.74 mg, 0.09 mmol). The reaction was stirred at 85° C. for 50 min. The reaction was cooled down to rt, solid was filtrated, rinsed with DCM and concentrated to give the title compound as crude product. LCMS (ESI): m/z 611.78, 613.76 (M+H)$^+$.

Step 3: tert-Butyl N-tert-butoxycarbonyl-N-[[8-(hydroxymethyl)-5-[4-(trifluoromethoxy)phenyl]-7-quinolyl]methyl]carbamate

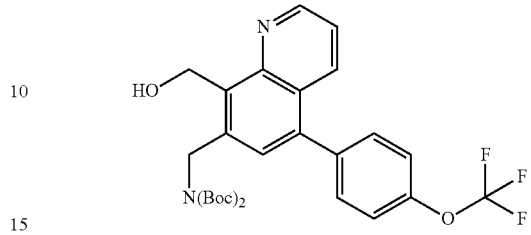

To tert-butyl-N-[[8-(bromomethyl)-5-[4-(trifluoromethoxy)phenyl]-7-quinolyl]methyl]-N-tert-butoxycarbonyl-carbamate (1.09 g, 1.78 mmol) in 1,4-dioxane (10 mL) and water (10 mL) was added calcium carbonate (1.82 g, 17.83 mmol). The reaction was stirred at 100° C. for 22 h. The suspension was cooled down to rt, poured in EtOAc (150 mL), brought to pH 7 with saturated aqueous NH$_4$Cl solution, washed with brine (50 mL), dried over sodium sulfate, filtered and concentrated to give a mixture of the title compound and tert-butyl N-[[8-(hydroxymethyl)-5-[4-(trifluoromethoxy)phenyl]-7-quinolyl]methyl]carbamate.

Step 4: N—[[8-(hydroxymethyl)-5-[4-(trifluoromethoxy)phenyl]-7-quinolyl]methyl]prop-2-enamide (Compound 44)

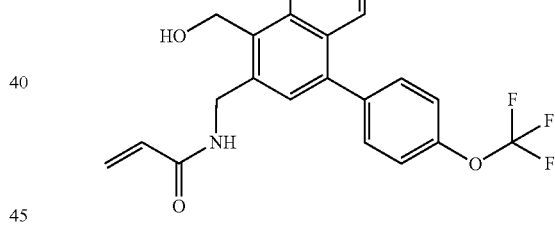

To tert-butyl N-tert-butoxycarbonyl-N-[[8-(hydroxymethyl)-5-[4-(trifluoromethoxy) phenyl]-7-quinolyl]methyl] carbamate (142 mg, 0.26 mmol) in DCM (0.70 mL) was added trifluoroacetic acid (1 mL, 12.98 mmol). The reaction was stirred at rt for 30 min then concentrated with toluene (5 mL). To residue in DCM (2 mL) was added N,N-diisopropylethylamine (0.14 mL, 0.78 mmol). A solution of prop-2-enoyl prop-2-enoate (38.6 µL, 0.34 mmol) in DCM (0.70 mL) was added very slowly via cannula. The mixture was stirred at −20° C. for 15 min then slowly warmed up to rt and stirred for 17 h. The reaction was poured in DCM (50 mL) and water (20 mL), phase were separated, washed with saturated aqueous NH$_4$Cl solution (15 mL), dried over sodium sulfate, filtered and concentrated. The residue was purified by prep-HPLC: Column: CSH Prep C18 OBD, 5 µm, 30×75 mm. 35% MeCN in 10 mM AmF water to 55% MeCN) to give the title compound (25 mg, 24% yield) as a white solid. LCMS (ESI): m/z 611.78, 613.76 (M+H)$^+$. $^1$H NMR (400 MHz, DMSO-d$_6$) δ 8.99 (dd, J=4.1, 1.7 Hz, 1H), 8.72 (t, J=5.7 Hz, 1H), 8.15 (dd, J=8.5, 1.7 Hz, 1H), 7.64-7.48 (m, 6H), 6.27 (dd, J=17.1, 10.1 Hz, 1H), 6.12 (dd, J=17.1, 2.2 Hz, 1H), 5.62 (dd, J=10.1, 2.2 Hz, 1H), 5.36 (d, J=5.5 Hz, 2H), 5.11 (t, J=5.5 Hz, 1H), 4.76 (d, J=5.9 Hz, 2H).

Example 41 (Compound 45) and Example 42 (Compound 46) (S)—N-((8-(1,2-dihydroxyethyl)-5-(4-(trifluoromethoxy)phenyl)quinolin-7-yl)methyl) acrylamide and (R)—N-((8-(1,2-dihydroxyethyl)-5-(4-(trifluoromethoxy)phenyl)quinolin-7-yl)methyl) acrylamide

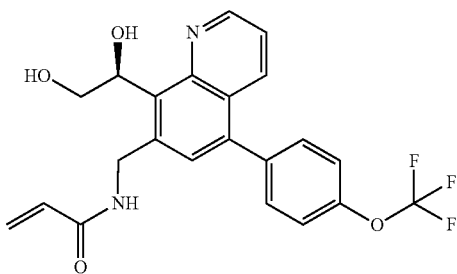

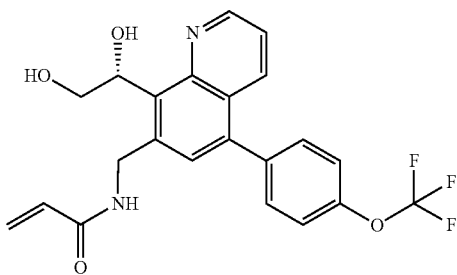

Step 1: tert-Butyl-N-tert-butoxycarbonyl-N-[[8-formyl-5-[4-(trifluoromethoxy)phenyl]-7-quinolyl] methyl]carbamate

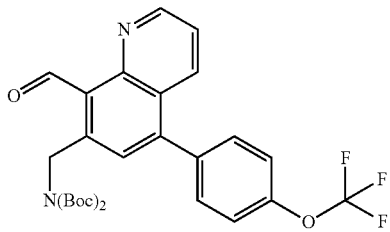

To tert-butyl-N-tert-butoxycarbonyl-N-[[8-(hydroxymethyl)-5-[4-(trifluoromethoxy) phenyl]-7-quinolyl]methyl] carbamate (797 mg, 1.45 mmol) (described in Example 40, , step 3) in DCM (7.3 mL) was added Dess-Martin periodinane (677.9 mg, 1.6 mmol). The solution was stirred at rt for 30 min. EtOAc (150 mL) and Na$_2$S$_2$O$_3$/NaHCO$_3$ (90 mL of mixture 1:1) were added and the mixture was stirred until a clear solution was obtained. The organic material was extracted with EtOAc (3×50 mL), dried over sodium sulfate, filtered and concentrated to give the crude title compound as a yellow tick oil. $^1$H NMR (400 MHz, CDCl$_3$) δ 11.70 (s, 1H), 9.03 (dd, J=4.1, 1.7 Hz, 1H), 8.20 (dd, J=8.6, 1.7 Hz, 1H), 7.49-7.39 (m, 4H), 7.38 (d, J=8.2 Hz, 2H), 5.46 (s, 2H), 1.40 (s, 18H).

Step 2: tert-Butyl-N-tert-butoxycarbonyl-N-[[5-[4-(trifluoromethoxy)phenyl]-8-vinyl-7-quinolyl] methyl]carbamate

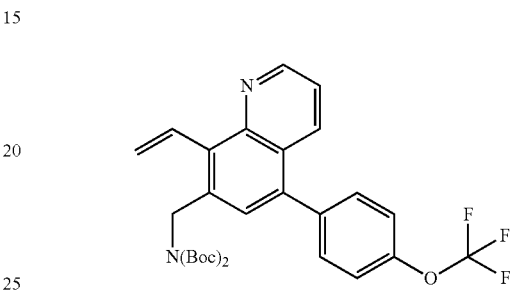

In an oven dried flask at 0° C. and to methyltriphenylphosphonium iodide (472 mg, 1.17 mmol) in THF (3.5 mL) was added potassium tert-butoxide 1 M in THF (1.2 mL, 1.2 mmol). The resulting yellow suspension was stirred at 0° C. for 45 min then at rt for 10 min. To the suspension was added a solution of tert-butyl-N-tert-butoxycarbonyl-N-[[8-formyl-5-[4-(trifluoromethoxy) phenyl]-7-quinolyl] methyl]carbamate (405 mg, 0.74 mmol) in THF (2 mL) dropwise via cannula. The resulting mixture was stirred at rt for 45 min. Heptane (60 mL) was added, stirred at rt for 30 min, the solid was removed by filtration and the filtrated was concentrated with silica gel. The crude was purified by flash column chromatography (silica, heptane to 40% EtOAc/heptane) to give the title compound (245 mg, 61% yield) as a clear oil that solidify upon standing. LCMS (ESI): m/z 545.98 (M+H)$^+$.

Step 3: tert-Butyl-N-[[5-[4-(trifluoromethoxy)phenyl]-8-vinyl-7-quinolyl]methyl]carbamate

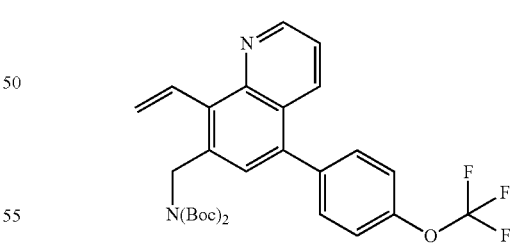

To tert-butyl-N-tert-butoxycarbonyl-N-[[5-[4-(trifluoromethoxy)phenyl]-8-vinyl-7-quinolyl]methyl]carbamate (307 mg, 0.56 mmol) in MeCN (0.37 mL) was added magnesium perchlorate hexahydrate (56 mg, 0.17 mmol) and the mixture was stirred at 60° C. for 1.5 h. The reaction was cooled down and was added EtOAc (75 mL). The solution was washed with water (30 mL), dried over sodium sulfate, filtered and concentrated to give the crude title compound (250 mg, 100% yield) as a cream solid. LCMS (ESI): m/z 445.85 (M+H)$^+$ LCMS (ESI) [M+H]$^+$=445.85.

Step 4: tert-Butyl-N-[[8-(1,2-dihydroxyethyl)-5-[4-(trifluoromethoxy)phenyl]-7-quinolyl]methyl]carbamate

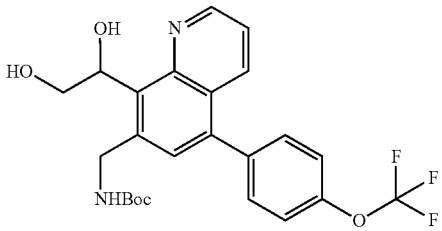 [SMILES: CC(C)(C)OC(=O)NCc1cc(-c2ccc(OC(F)(F)F)cc2)c2cccnc2c1C(O)CO]

tert-Butyl-N-[[5-[4-(trifluoromethoxy)phenyl]-8-vinyl-7-quinolyl]methyl]carbamate (262 mg, 0.59 mmol) and 4-methylmorpholine N-oxide (138.1 mg, 1.18 mmol) were dissolved in DCM (5.5 mL). To this solution were added osmium tetroxide, 4% wt in water (374.7 µL, 0.06 mmol) and acetone (1.8 mL). The mixture was stirred at rt for 3 h. More DCM (30 mL) and 10% aqueous $Na_2S_2O_3$ solution and saturated aqueous $NaHCO_3$ solution (10 mL each) were added, stirred for 5 min. The layers were separated and the aqueous layer was extracted with DCM (3×50 mL). The combined organic layers were dried over sodium sulfate, filtered and concentrated to afford crude title compound (282 mg, 100% yield). LCMS (ESI): m/z 479.5 (M+H)$^+$.

Step 5: (S)—N-((8-(1,2-dihydroxyethyl)-5-(4-(trifluoromethoxy)phenyl)quinolin-7-yl)methyl)acrylamide (Compound 45) and (R)—N-((8-(1,2-dihydroxyethyl)-5-(4-(trifluoromethoxy)phenyl)quinolin-7-yl)methyl)acrylamide (Compound 46)

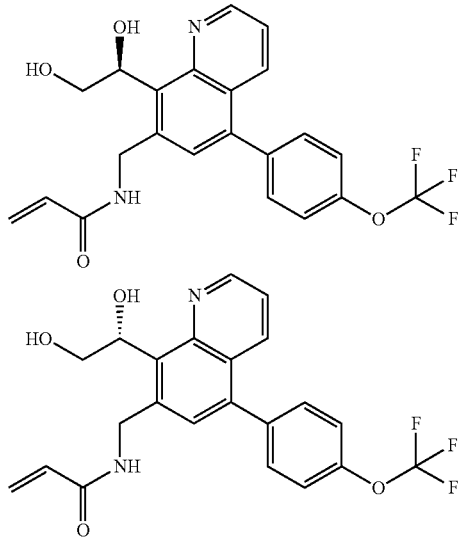

To tert-butyl-N-[[8-(1,2-dihydroxyethyl)-5-[4-(trifluoromethoxy)phenyl]-7-quinolyl]methyl]carbamate (282 mg, 0.61 mmol) in DCM (3 mL) was added trifluoroacetic acid (3 mL, 38.94 mmol) at rt. The mixture was stirred at rt for 2 h, toluene (10 mL) was added and concentrated. To the residue in DCM (9 mL) and N,N-diisopropylethylamine (0.48 mL, 2.74 mmol) at −20° C. was added a solution of prop-2-enoyl prop-2-enoate (136.2 µL, 1.19 mmol) in DCM (9 mL) very slowly dropwise. The mixture was stirred at −20° C. for 10 min then slowly warmed up to rt and stirred for 15 min. The reaction was diluted with water (10 mL) and saturated aqueous $NH_4Cl$ solution (10 mL) and the product was extracted using DCM (3×20 mL). The combined organic phases were dried over sodium sulfate, filtered and concentrated. The crude was purified with flash column chromatography (silica, C18, 0% MeCN/water (10 mM ammonium formate pH 3.8 buffer) to 100% MeCN/water) to give (68 mg, 17% yield) of the desired product as a mixture of enantiomers.

The above racemate was further purified by chiral SFC (Column=IG; Column dimensions=4.6×250 mm; Flow rate=3 mL/min; Run time=10 min; Column temperature=40° C.) 5 to 60 ACN_EtOH 10 mM AmFor—carbon dioxide) to afford:

(S)—N-((8-(1,2-dihydroxyethyl)-5-(4-(trifluoromethoxy)phenyl)quinolin-7-yl)methyl)acrylamide (19 mg, 6%), (peak 1, stereochemistry arbitrarily assigned). LCMS (ESI): m/z 433.2 (M+H)$^+$. $^1$H NMR (400 MHz, DMSO-$d_6$) δ 8.94 (dd, J=4.1, 1.7 Hz, 1H), 8.60 (t, J=5.8 Hz, 1H), 8.18 (dd, J=8.6, 1.7 Hz, 1H), 7.63-7.53 (m, 5H), 7.49 (s, 1H), 6.41 (d, J=7.5 Hz, 1H), 6.29 (dd, J=17.1, 10.1 Hz, 1H), 6.12 (dd, J=17.1, 2.2 Hz, 1H), 5.87 (dd, J=12.8, 7.0 Hz, 1H), 5.61 (dd, J=10.1, 2.2 Hz, 1H), 5.01-4.81 (m, 2H), 4.70 (dd, J=15.2, 5.5 Hz, 1H), 3.95-3.79 (m, 1H), 3.76-3.55 (m, 1H). (Compound 45)

(R)—N-((8-(1,2-dihydroxyethyl)-5-(4-(trifluoromethoxy)phenyl)quinolin-7-yl)methyl)acrylamide (18.7 mg, 6%), (peak 2, stereochemistry arbitrarily assigned). LCMS (ESI): m/z 433.2 (M+H)$^+$. $^1$H NMR (400 MHz, DMSO-$d_6$) δ 8.94 (dd, J=4.1, 1.7 Hz, 1H), 8.61 (t, J=5.8 Hz, 1H), 8.18 (dd, J=8.6, 1.7 Hz, 1H), 7.64-7.52 (m, 5H), 7.49 (s, 1H), 6.41 (d, J=7.5 Hz, 1H), 6.29 (dd, J=17.1, 10.1 Hz, 1H), 6.12 (dd, J=17.1, 2.2 Hz, 1H), 5.87 (dd, J=12.5, 6.9 Hz, 11H), 5.61 (dd, J=10.1, 2.2 Hz, 11H), 4.93 (dd, J=15.1, 6.2 Hz, 2H), 4.70 (dd, J=15.2, 5.5 Hz, 11H), 3.94-3.81 (m, 1H), 3.75-3.64 (m, 1H). (Compound 46)

Example 43 (Compound 47)

(S)—N-((5-(1,2-dihydroxyethyl)-8-(4-(trifluoromethoxy)phenyl)quinolin-6-yl)methyl) acrylamide

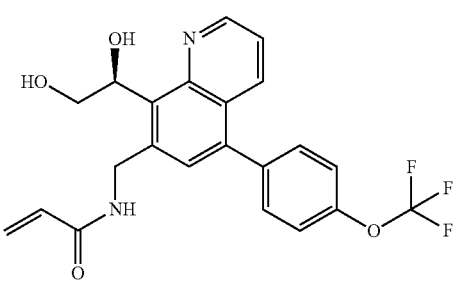 [SMILES: C=CC(=O)NCc1cc(-c2ccc(OC(F)(F)F)cc2)c2cccnc2c1[C@H](O)CO]

Step 1: 5-bromo-8-chloro-6-methyl-quinoline

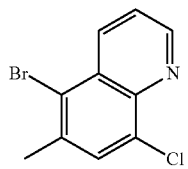

8-chloro-6-methyl-quinoline (1.00 g, 5.63 mmol) was dissolved in DMF (6 mL) and to the solution was added N-bromosuccinimide (2.00 g, 11.26 mmol). The reaction was stirred at rt for 1 h then heated to 60° C. for 16 h. The reaction was diluted with EtOAc (50 mL) and water (20 mL). The organic layer was separated and washed with brine (20 mL) then concentrated with silica gel. The crude was purified with flash column chromatography (silica, heptane to 50% EtOAc/heptane) to give the title compound (655 mg, 45% yield). LCMS (ESI): m/z 257.98 (M+H)$^+$ Step 2:
5-bromo-6-(bromomethyl)-8-chloro-quinoline

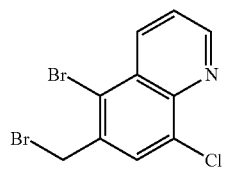 [SMILES: Clc1cc(CBr)c(Br)c2cccnc12]

A solution of 5-bromo-8-chloro-6-methyl-quinoline (200 mg, 0.78 mmol), N-bromosuccinimide (180.4 mg, 1.01 mmol) and benzoyl peroxide (18.9 mg, 0.08 mmol) in carbon tetrachloride (4.8 mL) was stirred at reflux for 3 h and then cooled to rt. The reaction mixture was filtered and filtrate was concentrated. The crude was purified with flash column chromatography (silica, heptane to 50% EtOAc/heptane) to give the title compound (260 mg, 100% yield). $^1$H NMR (400 MHz, CDCl$_3$) δ 9.07 (dd, J=4.2, 1.4 Hz, 1H), 8.69 (dd, J=9.7, 5.3 Hz, 1H), 7.95 (s, 1H), 7.62 (dd, J=9.7, 5.3 Hz, 1H), 4.79 (s, 2H).

Step 3: tert-Butyl-N-[(5-bromo-8-chloro-6-quinolyl)methyl]-N-tert-butoxycarbonyl-carbamate

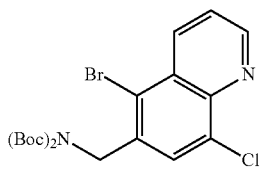

5-bromo-6-(bromomethyl)-8-chloro-quinoline (260 mg, 0.78 mmol) and tert-butyl-N-tert-butoxycarbonylcarbamate (218.9 mg, 1.01 mmol) was dissolved in DMF (2 mL) and cesium carbonate (330.4 mg, 1.01 mmol) was added with stirring. The reaction was stirred at rt for 2 h. The reaction was diluted with EtOAc (30 mL) and water (20 mL). Organic layer was washed with brine (20 mL), dried over sodium sulfate, filtered and concentrated. The crude was purified with flash column chromatography (silica, heptane to 50% EtOAc/heptane) to provide the title compound (190 mg, 52% yield). LCMS (ESI): m/z 471.1 (M+H)$^+$ Step 4: tert-Butyl N-[(5-bromo-8-chloro-6-quinolyl)methyl]carbamate

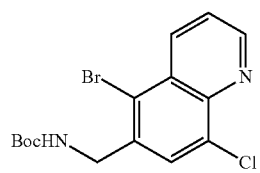 [SMILES: CC(C)(C)OC(=O)NCc1cc(Cl)c2ncccc2c1Br]

tert-Butyl-N-[(5-bromo-8-chloro-6-quinolyl)methyl]-N-tert-butoxycarbonyl-carbamate (100 mg, 0.21 mmol) and magnesium perchlorate hexahydrate (21.1 mg, 0.06 mmol) were added to MeCN (4 mL) and the mixture was stirred at 60° C. for 1 h. The reaction was then concentrated and the residue was dissolved in EtOAc (30 mL). The solution was washed with water (15 mL) and brine (15 mL), dried over sodium sulfate, filtered and concentrated to provide the crude title compound (78 mg, 100% yield). LCMS (ESI): m/z 372.9 (M+H)$^+$ Step 5: tert-Butyl-N-[(8-chloro-5-vinyl-6-quinolyl)methyl]carbamate

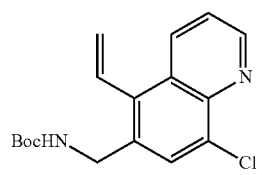

A seal tube was charged with tert-butyl-N-[(5-bromo-8-chloro-6-quinolyl)methyl]carbamate (50 mg, 0.13 mmol), potassium vinyltrifluoroborate (36.0 mg, 0.27 mmol), Pd(dppf)Cl$_2$ (9.8 mg, 0.010 mmol), cesium carbonate (87.7 mg, 0.27 mmol) and 1,4-dioxane (1.5 mL), water (0.3 mL) were added to the mixture. The reaction was stirred at 110° C. for 5 h. The reaction was diluted with water (20 mL) and EtOAc (30 mL), organic layer was separated, washed with brine (20 mL), dried over sodium sulfate, filtered and concentrated. The crude was purified with flash column chromatography (silica, heptane to 60% EtOAc/heptane) to provide the title compound (34 mg, 79% yield). LCMS (ESI): m/z 319.1 (M+H)$^+$

Step 6: tert-Butyl-N-[[8-[4-(trifluoromethoxy)phenyl]-5-vinyl-6-quinolyl]methyl]carbamate

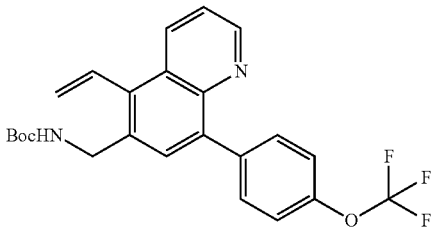 [SMILES: C=Cc1c(CNC(=O)OC(C)(C)C)cc(-c2ccc(OC(F)(F)F)cc2)c2ncccc12]

tert-Butyl-N-[(8-chloro-5-vinyl-6-quinolyl)methyl]carbamate (290 mg, 0.91 mmol), 4-(trifluoromethoxy)phenylboronic acid (281 mg, 1.36 mmol), palladium tetrakis(triphenylphosphine) (210.3 mg, 0.18 mmol), sodium carbonate (192.9 mg, 1.82 mmol) were added to DME (3.8 mL) and water (1 mL). The mixture was degassed for 5 min and heated at 150° C. in microwave reactor for 15 min. The reaction was then diluted with EtOAc (30 mL) and water (20 mL). Organic layer was then washed with brine (20 mL), dried over sodium sulfate, filtered and concentrated. The crude was purified with flash column chromatography (silica, heptane to 40% EtOAc/heptane) to provide the title compound (325 mg, 80% yield). LCMS (ESI): m/z 445.6 $(M+H)^+$

Step 7: (S)-tert-butyl-((5-(1,2-dihydroxyethyl)-8-(4-(trifluoromethoxy)phenyl)quinolin-6-yl)methyl)carbamate and (R)-tert-butyl-((5-(1,2-dihydroxyethyl)-8-(4-(trifluoromethoxy)phenyl)quinolin-6-yl)methyl)carbamate

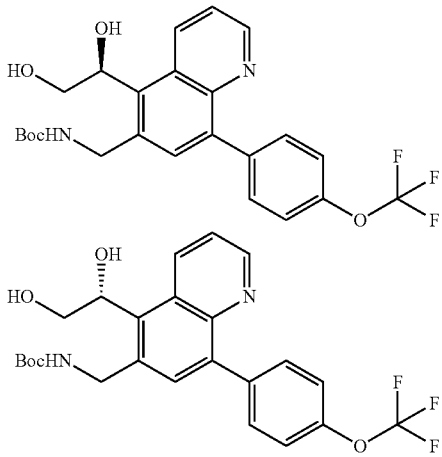

To a solution of tert-butyl N-[[8-[4-(trifluoromethoxy)phenyl]-5-vinyl-6-quinolyl]methyl]carbamate (120 mg, 0.27 mmol) in acetone (2 mL) and water (1 mL) was added 4-methylmorpholine N-oxide (126.5 mg, 1.08 mmol) followed by osmium tetraoxide 4% wt in water (171.6 μL, 0.03 mmol). The reaction was stirred for 4 h at rt. The reaction mixture was diluted with water (30 mL) and extracted twice with EtOAc (2×50 mL), dried over magnesium sulfate, filtered and concentrated. The crude was purified with flash column chromatography (silica, heptane to 100% EtOAc/heptane) to provide the title compound (110 mg, 85% yield). LCMS (ESI): m/z 479.7 $(M+H)^+$ 48 mg of the above racemate was further purified by chiral LC (Column=ChiralPak IB, 250 mm×4.6 mm ID, 5 μm; Flow rate=1 mL/min; Run time=30 min; Column temperature=26° C.) 3.8:0.2:96 MeOH:DCM:Hexane (0.1% DEA)) to afford:

(S)-tert-butyl ((5-(1,2-dihydroxyethyl)-8-(4-(trifluoromethoxy)phenyl)quinolin-6-yl)methyl) carbamate (peak 1, stereochemistry arbitrarily assigned) 23 mg.

(R)-tert-butyl ((5-(1,2-dihydroxyethyl)-8-(4-(trifluoromethoxy)phenyl)quinolin-6-yl)methyl) carbamate. (peak 2, stereochemistry arbitrarily assigned) 15 mg

Step 8: (S)—N-((5-(1,2-dihydroxyethyl)-8-(4-(trifluoromethoxy)phenyl)quinolin-6-yl)methyl) acrylamide. (Compound 47)

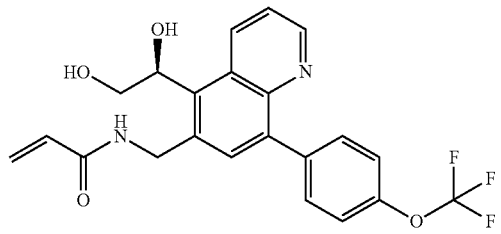

(S)-tert-butyl-((5-(1,2-dihydroxyethyl)-8-(4-(trifluoromethoxy)phenyl)quinolin-6-yl)methyl) carbamate (23 mg, 0.05 mmol) was dissolved in DCM (2 mL) and TFA (0.2 mL) was added. The reaction was stirred at rt for 1 h. The reaction was then concentrated with toluene (5 mL). The crude was dissolved in THF (2 mL) and saturated aqueous $Na_2CO_3$ solution (0.2 mL) was added. To the mixture was added acryloyl chloride (4.7 μL, 0.06 mmol) at rt and stirred for 10 min. The crude was diluted with EtOAc (10 mL) and water (5 mL). The organic layer was separated, dried over sodium sulfate, filtered and concentrated. The residue was purified by prep-HPLC: Column: CSH Prep C18 OBD, 5 μm, 30×75 mm. 25% MeCN in 10 mM AmF water to 55% MeCN) to give the title compound (8.6 mg, 41% yield). LCMS (ESI): m/z 433.3 $(M+H)^+$. $^1$H NMR (400 MHz, DMSO-$d_6$) δ 9.14 (d, J=8.2 Hz, 1H), 8.82 (d, J=2.6 Hz, 1H), 8.53 (t, J=3.6 Hz, 1H), 7.73-7.64 (m, 3H), 7.52-7.41 (m, 3H), 6.26 (dd, J=17.1, 10.1 Hz, 1H), 6.11 (dd, J=17.1, 2.2 Hz, 1H), 5.80 (d, J=3.6 Hz, 1H), 5.60 (dd, J=10.1, 2.2 Hz, 1H), 5.46 (s, 1H), 4.97 (t, J=5.4 Hz, 1H), 4.81 (dd, J=14.9, 5.8 Hz, 1H), 4.59 (dd, J=15.1, 5.3 Hz, 1H), 3.96-3.86 (m, 1H), 3.73 (dd, J=11.0, 5.6 Hz, 1H).

Example 44 (Compound 48)

(R)—N-((5-(1,2-dihydroxyethyl)-8-(4-(trifluoromethoxy)phenyl)quinolin-6-yl)methyl) acrylamide

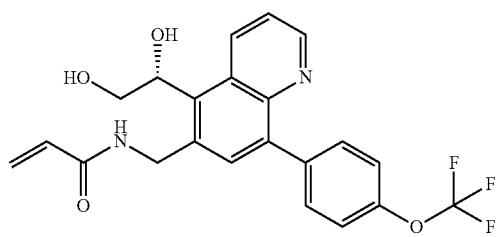 [SMILES: C=CC(=O)NCc1cc(-c2ccc(OC(F)(F)F)cc2)c2ncccc2c1[C@@H](O)CO]

tert-butyl-((5-(1,2-dihydroxyethyl)-8-(4-(trifluoromethoxy)phenyl)quinolin-6-yl)methyl) carbamate (75 mg, 0.16 mmol) (described in Example 43, , step 7) was dissolved in DCM (2 mL) and TFA (0.2 mL) was added. The reaction was stirred at rt for 1 h and toluene (5 mL) was added then concentrated. The crude was then dissolved in THF (2 mL) and saturated aqueous Na$_2$CO$_3$ solution (0.2 mL) was added. To the mixture was then added prop-2-enoyl prop-2-enoate (23.7 mg, 0.19 mmol) at rt and stirred for 10 min. The crude was directly purified with flash column chromatography (silica, C18, 0% MeCN/water (10 mM ammonium formate pH 3.8 buffer) to 100% MeCN/water) to give the title compound (63 mg, 93% yield). LCMS (ESI): m/z 433.2 (M+H)$^+$. $^1$H NMR (400 MHz, DMSO-d$_6$) δ 9.14 (d, J=8.6 Hz, 1H), 8.82 (d, J=3.9 Hz, 1H), 8.53 (s, 1H), 7.76-7.62 (m, 3H), 7.50 (dd, J=8.6, 3.9 Hz, 1H), 7.45 (d, J=8.1 Hz, 2H), 6.26 (dd, J=17.0, 10.0 Hz, 1H), 6.11 (d, J=17.1 Hz, 1H), 5.81 (s, 1H), 5.60 (d, J=10.1 Hz, 1H), 5.46 (s, 1H), 4.98 (s, 1H), 4.83-4.75 (dd, J=15.0, 5.0 Hz, 11H), 4.59 (dd, J=15.0, 5.0 Hz, 1H), 3.96-3.85 (m, 1H), 3.73 (s, 1H).

Example 45 (Compound 49)

N-[[5-(hydroxymethyl)-8-[4-(trifluoromethoxy)phenyl]-6-quinolyl]methyl]-N-methyl-prop-2-enamide

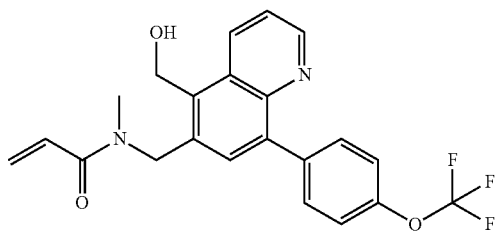

Step 1: 8-chloro-6-methyl-5-vinyl-quinoline

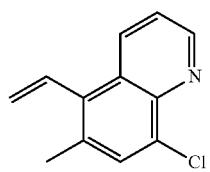

5-bromo-8-chloro-6-methyl-quinoline (330 mg, 1.29 mmol) (described in Example 43,, step 1), potassium vinyltrifluoroborate (258.5 mg, 1.93 mmol), Pd(dppf)Cl$_2$ (94 mg, 0.13 mmol) and K$_3$PO$_4$ (545.4 mg, 2.57 mmol) were added to 1,4-dioxane (5 mL) and water (1 mL). The mixture was heated at 110° C. for 16 h. The reaction was diluted with EtOAc (30 mL) and water (10 mL). The organic layer was separated, washed with brine (10 mL), dried over sodium sulfate, filtered and concentrated. The crude was purified with flash column chromatography (silica, heptane to 100% EtOAc/heptane) to provide the title compound (198 mg, 76% yield). LCMS (ESI): n/z 204.1 (M+H)$^+$.

Step 2: 6-methyl-8-[4-(trifluoromethoxy)phenyl]-5-vinyl-quinoline

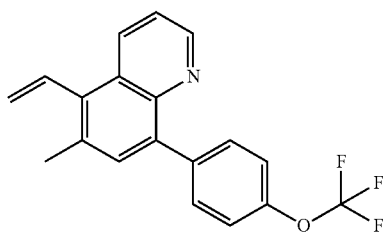 [SMILES: C=Cc1c(C)cc(-c2ccc(OC(F)(F)F)cc2)c2ncccc12]

8-chloro-6-methyl-5-vinyl-quinoline (198 mg, 0.97 mmol), 4-(trifluoromethoxy)phenylboronic acid (300.3 mg, 1.46 mmol), palladium tetrakis(triphenylphosphine) (224.8 mg, 0.19 mmol) and Na$_2$CO$_3$ (206.1 mg, 1.94 mmol) were added to 1,4-dioxane (3 mL) and water (0.5 mL). The mixture was degassed for 5 min and heated at 150° C. in microwave reactor for 1 h. The reaction was then diluted with EtOAc (30 mL) and water (20 mL). Organic layer was then washed with brine (20 mL), dried over sodium sulfate, filtered and concentrated. The crude was purified with flash column chromatography (silica, heptane to 100% EtOAc/heptane) to provide the title compound (208 mg, 65% yield). LCMS (ESI): m/z 330.55 (M+H)$^+$.

Step 3: 6-methyl-8-[4-(trifluoromethoxy)phenyl] quinoline-5-carbaldehyde

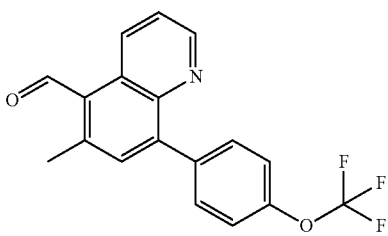 [SMILES: Cc1cc(-c2ccc(OC(F)(F)F)cc2)c2ncccc2c1C=O]

A solution of 6-methyl-8-[4-(trifluoromethoxy)phenyl]-5-vinyl-quinoline (185 mg, 0.56 mmol) in a mixture of THF (2 mL) and water (2 mL) was cooled down to 0° C. Sodium periodate (483.2 mg, 2.26 mmol) was added followed by osmium tetraoxide 4% wt in water (374 mg, 0.06 mmol) and the ice bath was removed. The reaction pursued at rt for 17 h and was then diluted with EtOAc (40 mL) and water (20 mL). The organic layer was separated, washed with brine (20 mL), dried over sodium sulfate, filtered and concentrated to afford the crude title compound (186 mg, 100% yield). LCMS (ESI): m/z 332.7 (M+H)$^+$

Step 4: [6-methyl-8-[4-(trifluoromethoxy)phenyl]-5-quinolyl]methanol

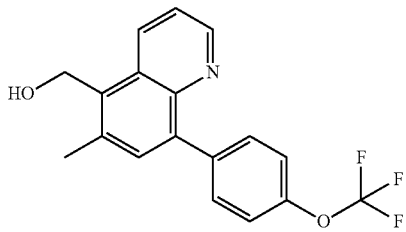 [SMILES: Cc1cc(-c2ccc(OC(F)(F)F)cc2)c2ncccc2c1CO]

6-methyl-8-[4-(trifluoromethoxy)phenyl]quinoline-5-carbaldehyde (186 mg, 0.57 mmol) was dissolved in methanol (3 mL) and cooled to 0° C. To the reaction was added sodium borohydride (87.2 mg, 2.29 mmol) and stirred for 10 min. The reaction was then quench by addition of water (1 mL) and stirred for 10 min at rt. The reaction was diluted with EtOAc (20 mL) and water (10 mL). Organic layer was separated, washed with brine (10 mL), dried over sodium sulfate, filtered and concentrated to provide the crude title compound (190 mg, 99% yield). LCMS (ESI): m/z 334.6 (M+H)$^+$

Step 5: [6-methyl-8-[4-(trifluoromethoxy)phenyl]-5-quinolyl]methyl acetate

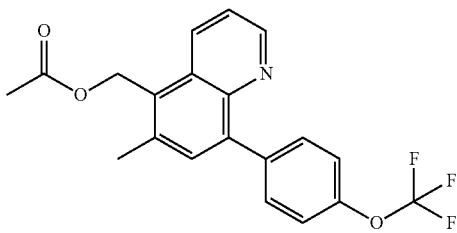 [SMILES: CC(=O)OCc1c(C)cc(-c2ccc(OC(F)(F)F)cc2)c2ncccc12]

[6-methyl-8-[4-(trifluoromethoxy)phenyl]-5-quinolyl]methanol (190 mg, 0.57 mmol) was dissolved in DCM (3 mL) and to the solution were added trimethylamine (287.9 mg, 2.85 mmol) and DMAP (3.5 mg, 0.03 mmol) followed by acetic anhydride (0.27 mL, 2.85 mmol). The reaction was stirred at rt for 30 min and concentrated with silica gel. The crude was purified with flash column chromatography (silica, heptane to 50% EtOAc/heptane) to provide the title compound (130 mg, 61% yield). LCMS (ESI): m/z 376.7 (M+H)$^+$

Step 6: [6-(bromomethyl)-8-[4-(trifluoromethoxy)phenyl]-5-quinolyl]methyl acetate

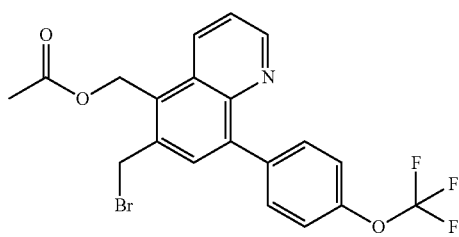 [SMILES: CC(=O)OCc1c(CBr)cc(-c2ccc(OC(F)(F)F)cc2)c2ncccc12]

[6-methyl-8-[4-(trifluoromethoxy)phenyl]-5-quinolyl] methyl acetate (130 mg, 0.35 mmol) was dissolved in CCl$_4$ (2 mL) and to the solution were added benzoyl peroxide (8.4 mg, 0.030 mmol) and N-bromosuccinimide (74 mg, 0.42 mmol). The mixture was stirred at reflux for 90 min. The reaction was purified directly with flash column chromatography (silica, heptane to 50% EtOAc/heptane) to provide the title compound (140 mg, 89% yield). LCMS (ESI): m/z 456.1 (M+H)$^+$

Step 7: [6-[[bis(tert-butoxycarbonyl)amino]methyl]-8-[4-(trifluoromethoxy)phenyl]-5-quinolyl]methyl acetate

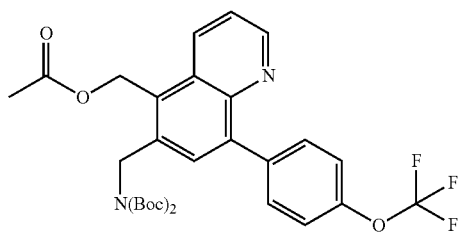

[6-(bromomethyl)-8-[4-(trifluoromethoxy)phenyl]-5-quinolyl]methyl acetate (140 mg, 0.31 mmol) was dissolved in DMF (5 mL) and to the solution was added tert-butyl N-tert-butoxycarbonylcarbamate (67 mg, 0.31 mmol) and Cs$_2$CO$_3$ (99.2 mg, 0.31 mmol). The mixture was stirred at rt for 30 min. The crude was dissolved in EtOAc (50 mL) and water (20 mL). Organic layer was washed with water (20 mL) and brine (20 mL), dried over sodium sulfate, filtered and concentrated with silica gel. The crude was purified with flash column chromatography (silica, heptane to 50% EtOAc/heptane) to provide the title compound (130 mg, 71% yield). LCMS (ESI): m/z 591.3 (M+H)$^+$

Step 8: [6-(aminomethyl)-8-[4-(trifluoromethoxy)phenyl]-5-quinolyl]methanol

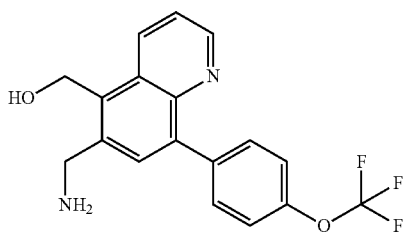 [SMILES: NCc1cc(-c2ccc(OC(F)(F)F)cc2)c2ncccc2c1CO]

[6-[[bis(tert-butoxycarbonyl)amino]methyl]-8-[4-(trifluoromethoxy)phenyl]-5-quinolyl]methyl acetate (130 mg, 0.22 mmol) was dissolved in methanol (2 mL) and HCl (4 M in dioxane) (2 mL) was added to the solution. The mixture was heated at 60° C. for 30 min. The crude was concentrated and diluted with EtOAc (30 mL) and saturated aqueous Na$_2$CO$_3$ solution (20 mL). The organic layer was washed with brine (20 mL), dried over sodium sulfate, filtered and concentrated to provide the crude title compound (70 mg, 91% yield). LCMS (ESI): m/z 349.5 (M+H)$^+$ Step 9: [6-(methylaminomethyl)-8-[4-(trifluoromethoxy)phenyl]-5-quinolyl]methanol

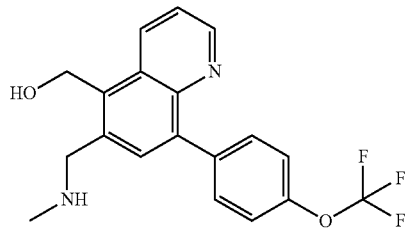 [SMILES: CNCc1cc(-c2ccc(OC(F)(F)F)cc2)c2ncccc2c1CO]

[6-(aminomethyl)-8-[4-(trifluoromethoxy)phenyl]-5-quinolyl]methanol (70 mg, 0.20 mmol) was dissolved in HFIP (1 mL) and to the solution was added methyl triflate (19.8 µL, 0.18 mmol). The mixture was stirred at rt for 1 h and around 7:3 ratio of starting material and product was observed. The reaction was then passed through a pad of silica gel and EtOAc/heptanes (150 mL, 1/1 ratio) was used to flush the reagent/solvent away. Then MeOH/DCM (150 mL, 3/10 ratio) was used to elute the mixture. The solution was concentrated to give a ratio of 7:3 starting material and product as a mixture (69 mg). LCMS (ESI): m/z 349.8 and 363.6 (M+H)$^+$ Step 10: N-[[5-(hydroxymethyl)-8-[4-(trifluoromethoxy)phenyl]-6-quinolyl]methyl]-N-methyl-prop-2-enamide (Compound 49)

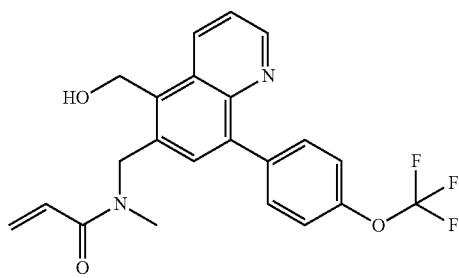 [SMILES: C=CC(=O)N(C)Cc1cc(-c2ccc(OC(F)(F)F)cc2)c2ncccc2c1CO]

The mixture of [6-(aminomethyl)-8-[4-(trifluoromethoxy)phenyl]-5-quinolyl]methanol and [6-(methylaminomethyl)-8-[4-(trifluoromethoxy)phenyl]-5-quinolyl]methanol (69 mg) was dissolved in THF (1 mL) and saturated aqueous Na$_2$CO$_3$ solution (0.3 mL) was added followed by prop-2-enoyl prop-2-enoate (24.8 mg, 0.20 mmol). The reaction was stirred at rt for 10 min then was diluted with EtOAc (20 mL) and water (10 mL). Organic layer was washed with brine (10 mL), dried over sodium sulfate, filtered and concentrated. The residue was purified by prep-HPLC: Column: CSH Prep C18 OBD, 5 gm, 30×75 mm. 30% MeCN in 10 mM AmF water to 50% MeCN) to give the title compound (3.8 mg, 6% yield). LCMS (ESI): m/z 417.2 (M+H)$^+$. $^1$H NMR (400 MHz, DMSO-d$_6$) δ 8.87 (d, J=3.9 Hz, 1H), 8.74 (d, J=8.5 Hz, 1H), 7.78-7.58 (m, 3H), 7.44 (dd, J=47.0, 38.8 Hz, 3H), 6.88-6.73 (m, 1H), 6.18 (d, J=16.7 Hz, 1H), 5.78-5.60 (m, 1H), 5.26 (dd, J=16.3, 11.2 Hz, 1H), 5.01 (dd, J=28.7, 23.6 Hz, 4H), 2.98 (d, J=32.8 Hz, 3H).

Example 46 (Compound 50)

N-[[5-(hydroxymethyl)-8-[4-(trifluoromethoxy)phenyl]-6-quinolyl]methyl]prop-2-enamide

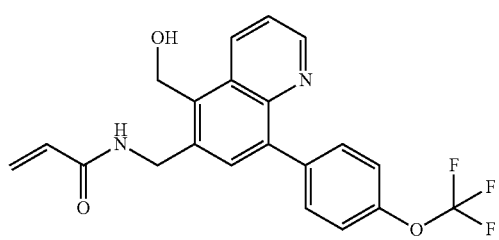

From the mixture described in Example 45, , step 10 is obtained N-[[5-(hydroxymethyl)-8-[4-(trifluoromethoxy)phenyl]-6-quinolyl]methyl]prop-2-enamide (11.6 mg, 20% yield). ). LCMS (ESI) [M+H]$^+$=403.2. $^1$H NMR (400 MHz, DMSO-d$_6$) δ 8.87 (dd, J=4.0, 1.5 Hz, 1H), 8.78-8.71 (m, 1H), 8.64 (s, 1H), 7.73 (d, J=9.0 Hz, 3H), 7.60 (dd, J=8.6, 4.1 Hz, 1H), 7.47 (d, J=8.1 Hz, 2H), 6.24 (dd, J=17.1, 10.1 Hz, 1H), 6.10 (dd, J=17.1, 2.3 Hz, 1H), 5.60 (dd, J=10.0, 2.2 Hz, 1H), 5.26 (t, J=5.4 Hz, 1H), 5.02 (d, J=5.4 Hz, 2H), 4.68 (d, J=5.7 Hz, 2H).

Example 47 (Compound 51) and Example 48 (Compound 52)

N-[[5-[(1S)-1,2-dihydroxyethyl]-8-[4-(trifluoromethoxy)phenyl]-6-quinolyl]methyl]-N-methyl-prop-2-enamide and N-[[5-[(1R)-1,2-dihydroxyethyl]-8-[4-(trifluoromethoxy)phenyl]-6-quinolyl]methyl]-N-methyl-prop-2-enamide

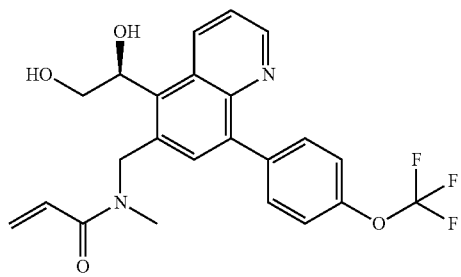

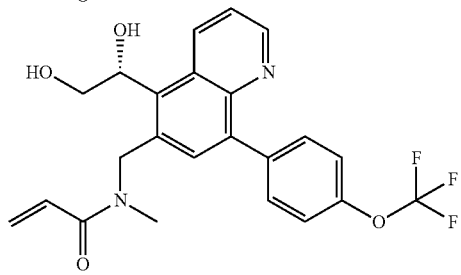

Step 1: 1-(5-bromo-8-chloro-6-quinolyl)-N-methyl-methanamine

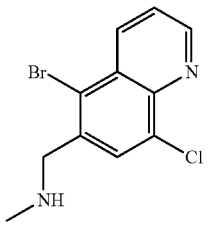

Methylamine, 40% in water (2.6 mL, 33.39 mmol) was dissolved in THF (5 mL) and to the solution was added 5-bromo-6-(bromomethyl)-8-chloro-quinoline (1.40 g, 4.17 mmol) (described in Example 43, , step 2) in THF (5 mL). The reaction was stirred at rt for 5 min. The reaction was diluted with water (30 mL) and EtOAc (50 mL). The organic layer was washed with water (15 mL) and brine (15 mL), dried over sodium sulfate, filtered and concentrated to give the crude title compound (1.20 g, 100% yield). LCMS (ESI): m/z 287.0 (M+H)$^+$

Step 2: tert-Butyl N-[(5-bromo-8-chloro-6-quinolyl)methyl]-N-methyl-carbamate

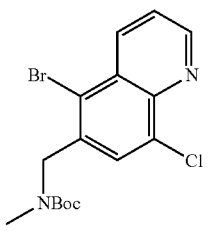 [SMILES: CN(Cc1cc(Cl)c2ncccc2c1Br)C(=O)OC(C)(C)C]

1-(5-bromo-8-chloro-6-quinolyl)-N-methyl-methanamine (1.192 g, 4.17 mmol) was dissolved in DCM (10 mL) and to the solution was added di-tert-butyl dicarbonate (2.73 mL, 12.52 mmol). The reaction was stirred at rt for 15 min. The reaction was concentrated with silica gel. The crude was purified with flash column chromatography (silica, heptane to 50% EtOAc/heptane) to provide the title compound (1.40 g, 87% yield). LCMS (ESI): m/z 387.1 (M+H)$^+$

Step 3: tert-Butyl-N-[(8-chloro-5-vinyl-6-quinolyl)methyl]-N-methyl-carbamate

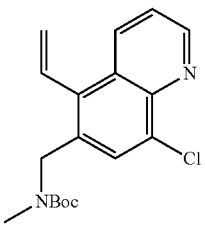 [SMILES: C=Cc1c(CN(C)C(=O)OC(C)(C)C)cc(Cl)c2ncccc12]

A seal tube was charged with tert-butyl-N-[(5-bromo-8-chloro-6-quinolyl)methyl]-N-methyl-carbamate (600 mg, 1.56 mmol), potassium vinyltrifluoroborate (625.2 mg, 4.67 mmol), Pd(dppf)Cl$_2$ (113.7 mg, 0.16 mmol), Cs$_2$CO$_3$ (1.014 g, 3.11 mmol) were added to a mixture of 1,4-dioxane (10 mL) and water (2 mL). The reaction was stirred at 110° C. for 10 h. The reaction was diluted with water (20 mL) and EtOAc (30 mL), organic layer was separated, washed with brine (20 mL), dried over sodium sulfate, filtered and concentrated. The crude was purified with flash column chromatography (silica, heptane to 60% EtOAc/heptane) to provide the title compound (344 mg, 66% yield). LCMS (ESI): m/z 333.2 (M+H)$^+$

Step 4: tert-Butyl-N-methyl-N-[[8-[4-(trifluoromethoxy)phenyl]-5-vinyl-6-quinolyl]methyl]carbamate

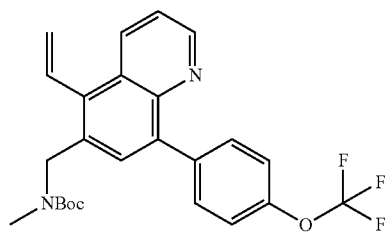 [SMILES: C=Cc1c(CN(C)C(=O)OC(C)(C)C)cc(-c2ccc(OC(F)(F)F)cc2)c2ncccc12]

tert-Butyl-N-[(8-chloro-5-vinyl-6-quinolyl)methyl]-N-methyl-carbamate (344 mg, 1.03 mmol), 4-(trifluoromethoxy)phenylboronic acid (319.3 mg, 1.55 mmol), palladium tetrakis(triphenylphosphine) (119.5 mg, 0.10 mmol) and Na$_2$CO$_3$ (219.1 mg, 2.07 mmol) were added to 1,4-dioxane (2 mL) and water (0.5 mL). The mixture was degassed for 5 min and heated at 150° C. in microwave reactor for 30 min. The reaction was then diluted with EtOAc (50 mL) and water (20 mL). Organic layer was then washed with brine (20 mL), dried over sodium sulfate, filtered and concentrated. The crude was purified with flash column chromatography (silica, heptane to 40% EtOAc/heptane) to provide the title compound (321 mg, 68% yield). LCMS (ESI): m/z 459.2 (M+H)$^+$

Step 5: tert-Butyl-N-[[5-(1,2-dihydroxyethyl)-8-[4-(trifluoromethoxy)phenyl]-6-quinolyl]methyl]-N-methyl-carbamate

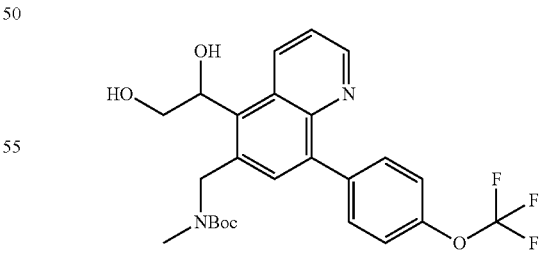

To a solution of tert-butyl-N-methyl-N-[[8-[4-(trifluoromethoxy)phenyl]-5-vinyl-6-quinolyl]methyl]carbamate (320 mg, 0.70 mmol) in DCM (4 mL) was added 4-methylmorpholine N-oxide (163.5 mg, 1.4 mmol) followed by osmium tetraoxide 4% wt in water (177.5 μL, 0.03 mmol). The reaction was stirred for 16 h at rt. The reaction was purified directly with flash column chromatography (silica, heptane to 100% EtOAc/heptane) to provide the title compound (190 mg, 55% yield). LCMS (ESI): m/z 493.2 (M+H)+

Step 6: N-[[5-[(1S)-1,2-dihydroxyethyl]-8-[4-(trifluoromethoxy)phenyl]-6-quinolyl]methyl]-N-methyl-prop-2-enamide (Compound 51) and N-[[5-[(1R)-1,2-dihydroxyethyl]-8-[4-(trifluoromethoxy)phenyl]-6-quinolyl]methyl]-N-methyl-prop-2-enamide (Compound 52)

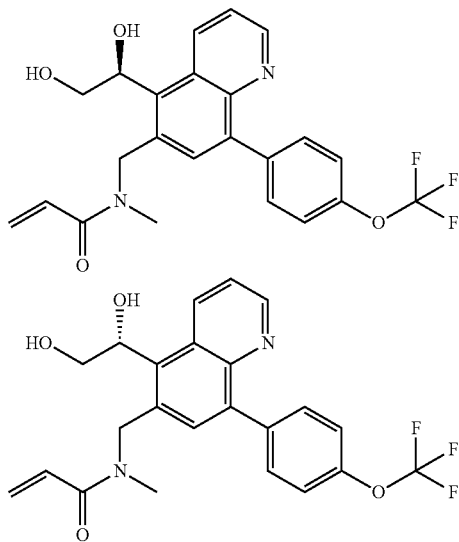

tert-Butyl-N-[[5-(1,2-dihydroxyethyl)-8-[4-(trifluoromethoxy)phenyl]-6-quinolyl]methyl]N-methyl-carbamate (190 mg, 0.39 mmol) was dissolved in DCM (3 mL) and TFA (0.5 mL) was added. The reaction was stirred at rt for 1 h and was then concentrated with toluene (5 mL). The crude was dissolved in THF (4 mL) and saturated aqueous Na$_2$CO$_3$ solution (0.5 mL) was added. To the mixture was then added prop-2-enoyl prop-2-enoate (58.5 mg, 0.46 mmol) at rt and stirred for 10 min. The crude was directly purified with flash column chromatography (silica, C18, 0% MeCN/water (10 mM ammonium formate pH 3.8 buffer) to 100% MeCN/water) to give 106 mg as a mixture of enantiomers.

The above racemate was further purified by chiral SFC (Column=AS; Column dimensions=10×250 mm; Flow rate=10 mL/min; Run time=7 min; Column temperature=40° C.) 20% IPA-10 mM AmF, 80% supercritical CO$_2$) to afford:

N-[[5-[(1S)-1,2-dihydroxyethyl]-8-[4-(trifluoromethoxy)phenyl]-6-quinolyl]methyl]-N-methyl-prop-2-enamide (peak 1, stereochemistry was arbitrarily assigned), (39 mg, 23%). LCMS (ESI): m/z 447.2 (M+H)+. $^1$H NMR (400 MHz, DMSO-d$_6$) δ 9.18 (s, 1H), 8.89 (s, 1H), 7.72 (t, J=8.5 Hz, 2H), 7.57 (dd, J=8.3, 3.9 Hz, 1H), 7.51-7.43 (m, 2H), 6.83 (ddd, J=55.1, 16.6, 10.4 Hz, 1H), 6.23 (d, J=16.7 Hz, 1H), 5.91 (s, 1H), 5.74 (dd, J=35.9, 10.1 Hz, 1H), 5.52 (s, 1H), 5.09 (ddd, J=70.8, 44.1, 16.2 Hz, 3H), 3.93 (d, J=7.6 Hz, 11H), 3.80 (dd, J=28.4, 6.4 Hz, 1H), 3.05 (d, J=24.4 Hz, 3H). (Compound 51)

N-[[5-[(1R)-1,2-dihydroxyethyl]-8-[4-(trifluoromethoxy)phenyl]-6-quinolyl]methyl]-N-methyl-prop-2-enamide (peak 2, stereochemistry was arbitrarily assigned), (33 mg, 19%). LCMS (ESI): m/z 447.2 (M+H)+. $^1$H NMR (400 MHz, DMSO-d$_6$) δ 9.18 (s, 1H), 8.89 (s, 1H), 7.72 (t, J=8.5 Hz, 2H), 7.57 (dd, J=8.3, 3.9 Hz, 1H), 7.51-7.43 (m, 2H), 6.83 (ddd, J=55.1, 16.6, 10.4 Hz, 1H), 6.23 (d, J=16.7 Hz, 1H), 5.91 (s, 1H), 5.74 (dd, J=35.9, 10.1 Hz, 1H), 5.52 (s, 1H), 5.09 (ddd, J=70.8, 44.1, 16.2 Hz, 3H), 3.93 (d, J=7.6 Hz, 1H), 3.80 (dd, J=28.4, 6.4 Hz, 1H), 3.05 (d, J=24.4 Hz, 3H). (Compound 51)

Example 49 (Compound 53) and Example 50 (Compound 54)

(S)—N-((4-(1,2-dihydroxyethyl)-7-(4-(trifluoromethoxy)phenyl)-2,3-dihydrobenzofuran-5-yl)methyl)acrylamide and (R)—N-((4-(1,2-dihydroxyethyl)-7-(4-(trifluoromethoxy)phenyl)-2,3-dihydrobenzofuran-5-yl)methyl)acrylamide

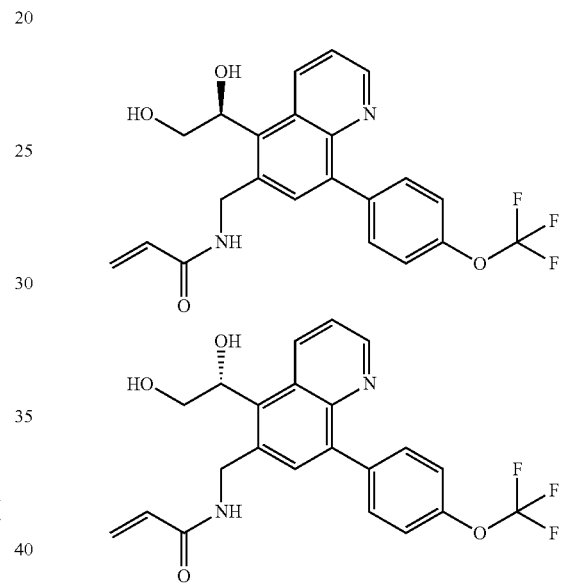

Step 1:
4-bromo-7-chloro-2,3-dihydrobenzofuran-5-amine

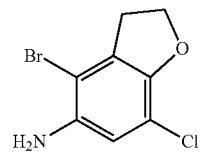

4-bromo-7-chloro-5-nitro-2,3-dihydrobenzofuran (5 g, 18 mmol) was dissolved in acetic acid (20.6 mL) and water (11.6 mL). The mixture was cooled to 0° C. and zinc powder (5.87 g, 90 mmol) was added slowly. The reaction was stirred at rt for 2 h. EtOAc (100 mL) and water was added and the reaction was basified with saturated aqueous Na$_2$CO$_3$ solution (200 mL). The organic phase was washed with brine (100 mL), dried over magnesium sulfate and concentrated under reduced pressure to yield the title compound (4.3 g, 96% yield) as an orange solid. LCMS (ESI): m/z 249.9 (M+H)+.

Step 2: 4-bromo-7-chloro-2,3-dihydrobenzofuran-5-carbonitrile

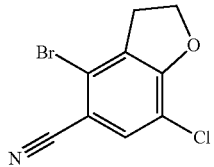 [SMILES: N#Cc1cc(Cl)c2c(c1Br)CCO2]

A flask was charged with CuCN (2.9 mg, 32 mmol) and capped with a septa. To this was then added MeCN (71 mL) and brought up to 65° C. tert-Butyl nitrite (4.8 mL, 40 mmol) was added followed by the dropwise addition of a solution of 4-bromo-7-chloro-2,3-dihydrobenzofuran-5-amine (4 g, 16.1 mmol) in MeCN (44.5 mL) over 20 min. After 30 min of heating, the mixture was cooled to rt and diluted with EtOAc (100 mL). The solution was washed with water (2×100 mL), dried with magnesium sulfate, filtered and concentrated onto silica gel. The crude was purified by flash column chromatography (silica, 0-10% EtOAc/heptanes) giving the title compound (1.2 g, 29% yield) as an orange solid.

Step 3: (4-bromo-7-chloro-2,3-dihydrobenzofuran-5-yl)methanamine

4-bromo-7-chloro-2,3-dihydrobenzofuran-5-carbonitrile (1.2 g, 4.6 mmol) dissolved in THF (46 mL) and 1 M borane in THF (9.3 mL, 9.3 mmol) added slowly. The solution was refluxed for 30 min and then quenched with 1 M NaOH (20 mL) solution. The mixture was extracted with EtOAc (3×75 mL). The combined organic phases were washed with brine (100 mL), dried over magnesium sulfate, filtered and concentrated to yield the crude title compound (1.05 g, 4 mmol, 86% yield) as an orange oil. LCMS (ESI): m/z 263.9 (M+H)$^+$.

Step 4: tert-Butyl-N-[(4-bromo-7-chloro-2,3-dihydrobenzofuran-5-yl)methyl]carbamate

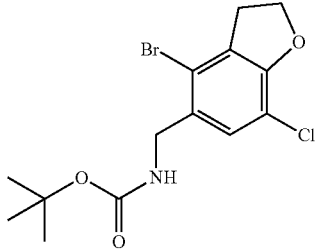 [SMILES: CC(C)(C)OC(=O)NCc1cc(Cl)c2c(c1Br)CCO2]

(4-bromo-7-chloro-2,3-dihydrobenzofuran-5-yl)methanamine (1.05 g, 4 mmol) was dissolved in DCM (10.5 mL) and di-tert-butyl dicarbonate (959 mg, 4.4 mmol) was added followed by triethylamine (0.84 mL, 6.0 mmol). The reaction was stirred at rt for 1 h. The reaction was diluted with DCM (10 mL) and washed with 1 M HCl (15 mL). The organic phase was dried over magnesium sulfate, filtered and concentrated with silica gel. The crude was purified by flash column chromatography (silica, 0-50% EtOAc/heptanes) giving the title compound (660 mg, 46% yield) as a red oil. LCMS (ESI): m/z 263.9 (M+H–Boc)$^+$.

Step 5: N-[(7-chloro-4-vinyl-2,3-dihydrobenzofuran-5-yl)methyl]carbamate

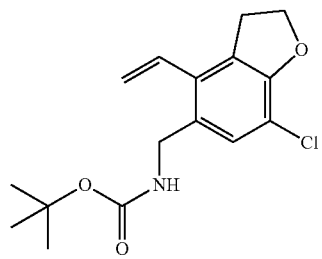 [SMILES: C=Cc1c(CNC(=O)OC(C)(C)C)cc(Cl)c2c1CCO2]

A vial was charged with tert-butyl-N-[(4-bromo-7-chloro-2,3-dihydrobenzofuran-5-yl)methyl]carbamate (660 mg, 1.8 mmol), potassium trifluoro(vinyl)boron (735 mg, 5.5 mmol), 1,4-dioxane (12.6 mL) and water (1.6 mL). The mixture was degassed 5 min before the addition of Pd(pddf)Cl$_2$ (274 mg, 0.37 mmol) followed by saturated aqueous Na$_2$CO$_3$ solution (1.4 mL). The reaction was heated for 16 h at 95° C. The reaction mixture was diluted with AcOEt (10 mL), concentrated on silica gel and purified by flash column chromatography (silica, 10-20% AcOEt/heptanes) giving the title compound (412 mg, 73% yield) as a yellow solid. LCMS (ESI): m/z 201.1 (M+H–Boc)$^+$.

Step 6: tert-Butyl-N-[[7-[4-(trifluoromethoxy)phenyl]-4-vinyl-2,3-dihydrobenzofuran-5-yl]methyl]carbamate

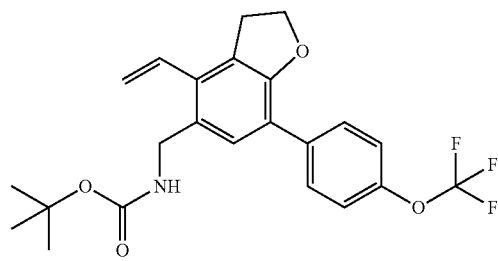 [SMILES: C=Cc1c(CNC(=O)OC(C)(C)C)cc(-c2ccc(OC(F)(F)F)cc2)c2c1CCO2]

A vial was charged with 4-(trifluoromethoxy)phenylboronic acid (317 mg, 1.5 mmol), tert-butyl-N-[(7-chloro-4-vinyl-2,3-dihydrobenzofuran-5-yl)methyl]carbamate (397 mg, 1.3 mmol) potassium acetate (0.3 mL, 5.1 mmol). The solids were dissolved in 1,4-dioxane (5.1 mL) and water (1.3 mL) was added. The mixture was degassed for 5 min before XPhos Pd G2 (50 mg, 0.06 mmol) was added. The reaction was heated at 80° C. for 4 h. The reaction was diluted with EtOAc (10 mL), concentrated on silica gel and purified by flash column chromatography (silica, 0-10% EtOAc/Heptanes) giving the title compound (453 mg, 1 mmol, 81% yield) as a yellow solid. LCMS (ESI): m/z 336.1 (M+H–Boc)⁺.

Step 7: tert-Butyl-N-[[4-(1,2-dihydroxyethyl)-7-[4-(trifluoromethoxy)phenyl]-2,3-dihydrobenzofuran-5-yl]methyl]carbamate

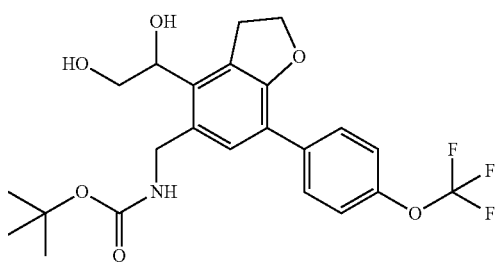 [SMILES: CC(C)(C)OC(=O)NCc1cc(-c2ccc(OC(F)(F)F)cc2)c2c(c1C(O)CO)CCO2]

To a solution of tert-butyl-N-[[7-[4-(trifluoromethoxy)phenyl]-4-vinyl-2,3-dihydrobenzofuran-5-yl]methyl]carbamate (398 mg, 0.91 mmol) in acetone (12 mL) was added 4-methylmorpholine N-oxide (268 mg, 2.3 mmol) followed by Osmium tetroxide, 4% wt in water (12 mg, 0.05 mmol). It was then stirred at rt for 1 h. The reaction was diluted with 50% aqueous sodium thiosultate (10 mL) and extracted with DCM (3×10 mL). The combined organic phases were dried over magnesium sulfate, filtered and concentrated to give the title compound (429 mg, 100% yield) as a brown solid. LCMS (ESI): m/z 352.2 (M+H–H₂O )⁺.

Step 8: (S)—N-((4-(1,2-dihydroxyethyl)-7-(4-(trifluoromethoxy)phenyl)-2,3-dihydrobenzofuran-5-yl)methyl)acrylamide and (R)—N-((4-(1,2-dihydroxyethyl)-7-(4-(trifluoromethoxy)phenyl)-2,3-dihydrobenzofuran-5-yl)methyl)acrylamide

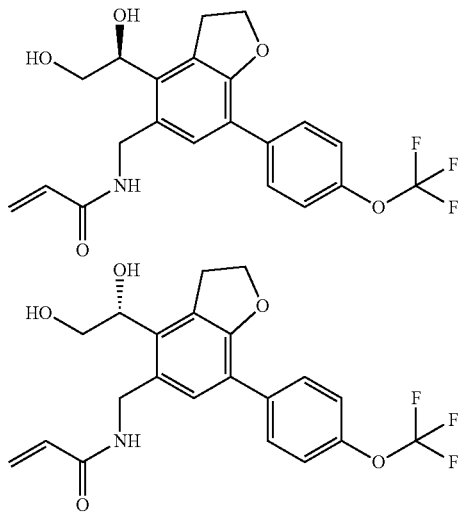

tert-Butyl-N-[[4-(1,2-dihydroxyethyl)-7-[4-(trifluoromethoxy)phenyl]-2,3-dihydrobenzofuran-5-yl]methyl] carbamate (200 mg, 0.43 mmol) was dissolved in DCM (15 mL) and TFA (2 mL, 25 mmol) was added. The reaction was stirred at rt for 1 h then was concentrated with toluene (5 mL). The crude was dissolved in THF (20 mL) and saturated aqueous Na₂CO₃ solution (2 mL) was added. To the mixture was then added acryloyl anhydride (48 mg, 0.38 mmol) and stirred at rt for 10 min. The crude was diluted with water (10 mL) and the aqueous phase was extracted with DCM (3×15 mL). The combined organic phases were dried over magnesium sulfate, filtered and concentrated. The crude was purified by preparative LCMS (C18 CSH, 30-50% MeCN/AmF 10 mM buffer) to give racemic product (90 mg, 50%).

The above racemate was further purified by chiral chromatography (Column=Chiralpak IA; Column dimensions=250 mm×4.6 mm×5 pm; Flow rate=1 mL/min; Run time=48 min; Column temperature=40° C.) 4:1:95 MeOH:DCM:Hexane) to afford:

(S)—N-((4-(1,2-dihydroxyethyl)-7-(4-(trifluoromethoxy)phenyl)-2,3-dihydrobenzofuran-5-yl)methyl)acrylamide (peak 1, stereochemistry is arbitrarily assigned) (26 mg, 15% yield) white solid. ¹H NMR (400 MHz, DMSO-d₆): δ 8.32 (s, 1H), 7.72 (d, J=7.8 Hz, 2H), 7.40 (d, J=7.8 Hz, 2H), 7.19 (s, 1H), 6.25 (dd, J=16.9, 10.1 Hz, 1H), 6.08 (d, J=16.3 Hz, 1H), 5.57 (d, J=10.1 Hz, 1H), 5.30 (s, 1H), 4.86 (s, 2H), 4.61-4.43 (m, 3H), 4.33 (d, J=10.9 Hz, 1H), 3.60 (s, 1H), 3.50 (s, 2H). LCMS (ESI): m/z 422.1 (M–H)⁻. (Compound 53)

(R)—N-((4-(1,2-dihydroxyethyl)-7-(4-(trifluoromethoxy)phenyl)-2,3-dihydrobenzofuran-5-yl)methyl)acrylamide (peak 2, stereochemistry is arbitrarily assigned) (24 mg, 14% yield) white solid. 1H NMR (400 MHz, DMSO-d₆): δ 8.34 (s, 1H), 7.74 (d, J=7.1 Hz, 2H), 7.42 (d, J=6.3 Hz, 2H), 7.21 (s, 1H), 6.35-6.20 (m, 1H), 6.10 (d, J=16.8 Hz, 11H), 5.58 (d, J=9.2 Hz, 1H), 5.32 (s, 1H), 4.88 (s, 2H), 4.53 (d, J=8.1 Hz, 3H), 4.35 (d, J=13.1 Hz, 1H), 3.61 (s, 1H), 3.52 (s, 2H). LCMS (ESI): m/z 422.1 (M–H)⁻. (Compound 54)

Example 51 (Compound 55) and Example 52 (Compound 56)

(S)—N-((4-(1,2-dihydroxyethyl)-7-(4-(trifluoromethoxy)phenyl)-2,3-dihydrobenzofuran-5-yl)methyl)-N-methylacrylamide and (R)—N-((4-(1,2-dihydroxyethyl)-7-(4-(trifluoromethoxy)phenyl)-2,3-dihydrobenzofuran-5-yl)methyl)-N-methylacrylamide

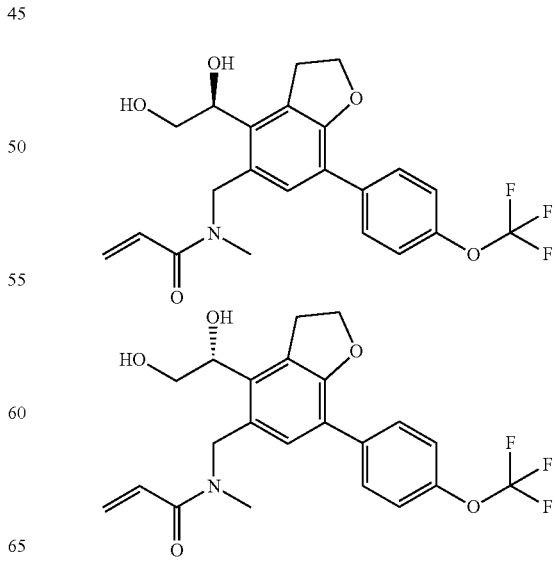

Step 1: tert-Butyl-N-[[4-(2,2-dimethyl-1,3-dioxolan-4-yl)-7-[4-(trifluoromethoxy)phenyl]-2,3-dihydrobenzofuran-5-yl]methyl]carbamate

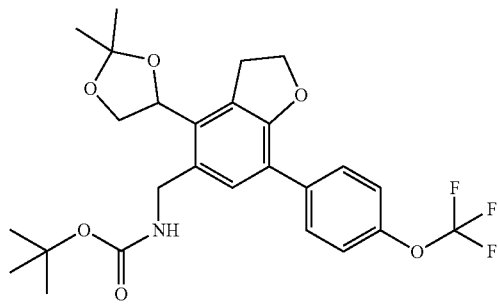 [SMILES: CC(C)(C)OC(=O)NCc1cc(-c2ccc(OC(F)(F)F)cc2)c2c(c1C1COC(C)(C)O1)CCO2]

tert-Butyl-N-[[4-(1,2-dihydroxyethyl)-7-[4-(trifluoromethoxy)phenyl]-2,3-dihydrobenzofuran-5-yl]methyl]carbamate (252 mg, 0.54 mmol) (described in Example 49,, step 7) was dissolved in acetone (1.8 mL). 2-Methoxypropene (192 μL, 2 mmol) was added followed by p-toluene sulfonic acid (4.6 mg, 0.03 mmol). The reaction was stirred at rt for 30 min. More 2-methoxypropene (192 μL, 2 mmol) was added and the reaction was stirred for another 30 min. More p-toluene sulfonic acid (4.6 mg, 0.03 mmol) was added along with more 2-methoxypropene (192 μL, 2 mmol). Then magnesium sulfate was added along with more 2-methoxypropene (192 μL, 2 mmol). Then pyridinium p-toluenesulfonate (13 mg, 0.05 mmol) was added. The reaction was diluted with EtOAc (10 mL) and washed with saturated aqueous $Na_2CO_3$ solution (2×5 mL). The organic phase was dried over magnesium sulfate and concentrated to give the title crude compound (273 mg, 99%) as a brown oil. LCMS (ESI): m/z 492.1 (M+H–$H_2O$ )+.

Step 2: tert-Butyl-N-[[4-(2,2-dimethyl-1,3-dioxolan-4-yl)-7-[4-(trifluoromethoxy)phenyl]-2,3-dihydrobenzofuran-5-yl]methyl]-N-methyl-carbamate

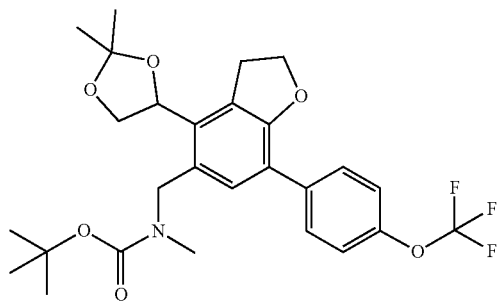 [SMILES: CN(Cc1cc(-c2ccc(OC(F)(F)F)cc2)c2c(c1C1COC(C)(C)O1)CCO2)C(=O)OC(C)(C)C]

tert-Butyl-N-[[4-(2,2-dimethyl-1,3-dioxolan-4-yl)-7-[4-(trifluoromethoxy)phenyl]-2,3-dihydrobenzofuran-5-yl]methyl]carbamate (270 mg, 0.53 mmol) was dissolved in anhydrous DMF (2.6 mL) and sodium hydride (42 mg, 1.1 mmol) was added under nitrogen at 0° C. The reaction was stirred for 2 min at 0° C. and brought to rt and stirred for an additional 10 min before iodomethane (66 μL, 1.1 mmol) was added. The reaction was stirred at rt for 1 h then was quenched with 80% brine (5 mL) and diluted with EtOAc (10 mL). The organic phase was removed, washed with water (1×10 mL), dried over magnesium sulfate, filtered and concentrated to provide the crude title compound (266 mg, 96%) as a black oil. LCMS (ESI): m/z 406.3 (M+Na-Boc-acetonide)+.

Step 3: tert-Butyl-N-[[4-(1,2-dihydroxyethyl)-7-[4-(trifluoromethoxy)phenyl]-2,3-dihydrobenzofuran-5-yl]methyl]-N-methyl-carbamate

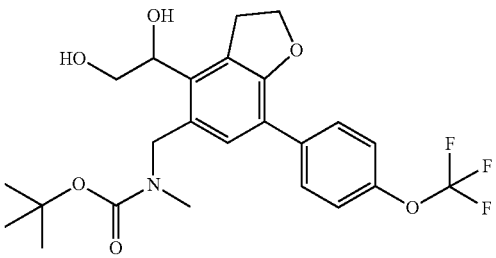 [SMILES: CN(Cc1cc(-c2ccc(OC(F)(F)F)cc2)c2c(c1C(O)CO)CCO2)C(=O)OC(C)(C)C]

tert-Butyl-N-[[4-(2,2-dimethyl-1,3-dioxolan-4-yl)-7-[4-(trifluoromethoxy)phenyl]-2,3-dihydrobenzofuran-5-yl]methyl]-N-methyl-carbamate (266 mg, 0.51 mmol) was dissolved in methanol (3.9 mL), water (0.6 mL) and trifluoroacetic acid (25 μL, 0.33 mmol) was added at 0° C. The reaction was stirred for 3 h and then was neutralized by addition of saturated aqueous $NaHCO_3$ solution (2 mL) and then was extracted with DCM (3×5 mL). The combined organic phases were dried over magnesium sulfate, filtered and concentrated with silica. The crude was purified by flash column chromatography (silica, 0-100% EtOAc/Heptanes) to provide the title compound (159 mg, 65% yield) as a beige solid. LCMS (ESI): m/z 366.2 (M+H–Boc-$H_2O$ )+.

Step 4: (S)—N-((4-(1,2-dihydroxyethyl)-7-(4-(trifluoromethoxy)phenyl)-2,3-dihydrobenzofuran-5-yl)methyl)-N-methylacrylamide and (R)—N-((4-(1,2-dihydroxyethyl)-7-(4-(trifluoromethoxy)phenyl)-2,3-dihydrobenzofuran-5-yl)methyl)-N-methylacrylamide

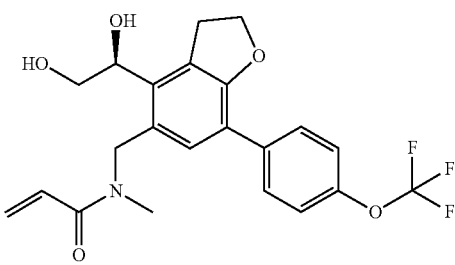

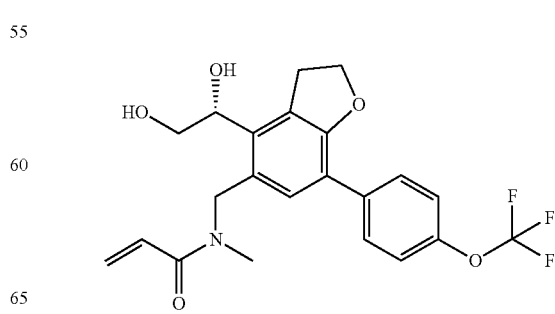

tert-Butyl-N-[[4-(1,2-dihydroxyethyl)-7-[4-(trifluoromethoxy)phenyl]-2,3-dihydrobenzofuran-5-yl]methyl]-N-methyl-carbamate (155 mg, 0.32 mmol) was dissolved in DCM (2.5 mL) and TFA (403 μL, 5 mmol) was added. The reaction was stirred at rt for 1 h then was concentrated with toluene (1 mL). The crude was dissolved in THF (3.3 mL) and saturated aqueous Na$_2$CO$_3$ solution (403 μL) was added. To the mixture was added prop-2-enoyl prop-2-enoate (49 mg, 0.38 mmol) at rt and stirred for 10 min. The reaction was diluted with water (2 mL), extracted with DCM (2×5 mL). The combined organic phases were dried over magnesium sulfate, filtered and concentrated. The crude was purified by flash column chromatography (silica, C18, 0-100% MeCN/10 mM AmF buffer) to give the desired product (50 mg, 36%) as a mixture of enantiomers.

The above racemate was further purified by chiral SFC (Column=AS; Column dimensions=250 mm×10 mm×5 pm; Flow rate=10 mL/min; Run time=7 min; Column temperature=40° C.) 20% IPA+10 mM AmF−80% carbon dioxide) to afford:

(S)—N-((4-(1,2-dihydroxyethyl)-7-(4-(trifluoromethoxy)phenyl)-2,3-dihydrobenzofuran-5-yl)methyl)-N-methylacrylamide (peak 1, stereochemistry is arbitrarily assigned) (19.4 mg, 14%) white solid. $^1$H NMR (400 MHz, DMSO-d$_6$): δ 7.66 (dd, J=20.5, 7.8 Hz, 2H), 7.40 (d, J=7.8 Hz, 2H), 7.01-6.57 (m, 2H), 6.15 (d, J=17.2 Hz, 1H), 5.65 (dd, J=30.5, 10.5 Hz, 1H), 5.33 (d, J=32.3 Hz, 1H), 4.91-4.46 (m, 6H), 3.53 (br, 2H), 2.93 (d, J=14.1 Hz, 3H). LCMS (ESI): m/z 460.1 (M+Na)$^+$. (Compound 55)

(R)—N-((4-(1,2-dihydroxyethyl)-7-(4-(trifluoromethoxy)phenyl)-2,3-dihydrobenzofuran-5-yl)methyl)-N-methylacrylamide (peak 2, stereochemistry is arbitrarily assigned) (19.3 mg, 14%) white solid. $^1$H NMR (400 MHz, DMSO-d$_6$): δ 7.66 (dd, J=20.5, 7.6 Hz, 2H), 7.40 (d, J=7.8 Hz, 2H), 7.00-6.56 (m, 2H), 6.15 (d, J=16.8 Hz, 1H), 5.65 (dd, J=30.7, 10.5 Hz, 1H), 5.32 (d, J=31.6 Hz, 1H), 4.91-4.46 (m, 6H), 3.53 (br, 2H), 2.93 (d, J=14.1 Hz, 3H). LCMS (ESI): m/z 460.1 (M+Na)$^+$. (Compound 56)

Example 53 (Compound 57)

N-[[3-methyl-4-methylsulfonyl-7-[4-(trifluoromethoxy)phenyl]benzimidazol-5-yl]methyl]prop-2-enamide

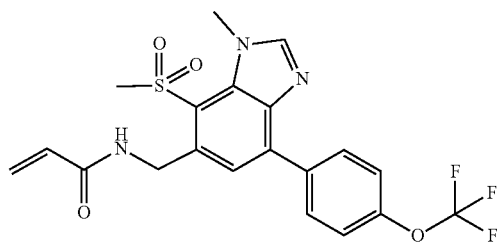 [SMILES: C=CC(=O)NCc1cc(-c2ccc(OC(F)(F)F)cc2)c2ncn(C)c2c1S(C)(=O)=O]

Step 1: tert-Butyl-N-[[3-methyl-4-methylsulfanyl-7-[4-(trifluoromethoxy)phenyl]benzimidazol-5-yl]methyl]carbamate

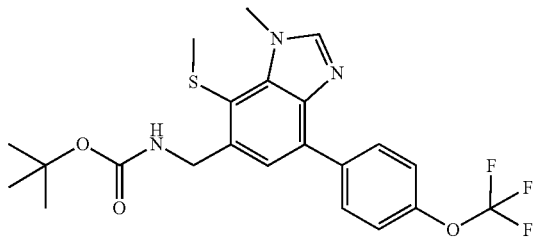 [SMILES: CSc1c(CNC(=O)OC(C)(C)C)cc(-c2ccc(OC(F)(F)F)cc2)c2ncn(C)c12]

tert-Butyl-N-[[4-bromo-3-methyl-7-[4-(trifluoromethoxy)phenyl]benzimidazol-5-yl]methyl]-N-tert-butoxycarbonyl-carbamate (500 mg, 0.83 mmol) (described in Example 27,, step 6), Pd$_2$(dba)$_3$ (152 mg, 0.17 mmol) and XantPhos (193 mg, 0.33 mmol) were put in a microwave vial. The vial was purged with nitrogen and toluene (2.8 mL) was added followed by triethylamine (0.58 mL, 4.2 mmol). The solution was degassed with nitrogen for 5 min and NaSMe (233 mg, 3.3 mmol) was added. The reaction was sealed and heated at 100° C. for 18 h. The mixture was cooled down and was concentrated onto silica gel and purified by flash column chromatography (silica, 0-100% EtOAc/Heptanes) to give the title compound (181 mg, 46% yield) as a yellow solid. LCMS (ESI): m/z 468.3 (M+H)$^+$.

Step 2: tert-Butyl-N-[[3-methyl-4-methylsulfonyl-7-[4-(trifluoromethoxy)phenyl]benzimidazol-5-yl]methyl]carbamate

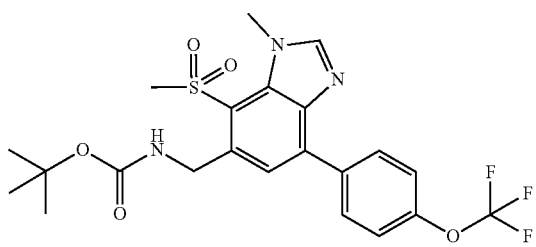 [SMILES: Cn1cnc2c(-c3ccc(OC(F)(F)F)cc3)cc(CNC(=O)OC(C)(C)C)c(S(C)(=O)=O)c21]

tert-Butyl-N-[[3-methyl-4-methylsulfanyl-7-[4-(trifluoromethoxy)phenyl]benzimidazol-5-yl]methyl]carbamate (58 mg, 0.12 mmol) was dissolved in DCM (620 L) and cooled to 0° C. 3-Chloroperbenzoic acid (MCPBA) (54 mg, 0.31 mmol) was added and it was stirred at rt for 18 h. The reaction was diluted with EtOAc (15 mL) and washed with 1M Na$_2$S$_2$O$_3$ solution (10 mL), saturated aqueous Na$_2$CO$_3$ solution (2×15 mL), dried over magnesium sulfate, concentrated on silica gel and purified by flash column chromatography (silica, 0-100% EtOAc/Heptanes) to give the title compound (62 mg, 0.12 mmol, 100% yield) as a colorless wax. LCMS (ESI): m/z 500.1 (M+H)$^+$.

Step 3: N-[[3-methyl-4-methylsulfonyl-7-[4-(trifluoromethoxy)phenyl]benzimidazol-5-yl]methyl]prop-2-enamide

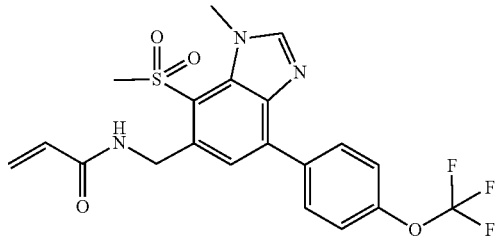 [SMILES: C=CC(=O)NCc1cc(-c2ccc(OC(F)(F)F)cc2)c2ncn(C)c2c1S(C)(=O)=O]

tert-Butyl-N-[[3-methyl-4-methylsulfonyl-7-[4-(trifluoromethoxy)phenyl]benzimidazol-5-yl]methyl]carbamate (15 mg, 0.03 mmol) was dissolved in DCM (260 μL) and TFA (40 μL, 0.5 mmol) was added. The reaction stirred at rt for 1 h then was added toluene (0.5 mL) and it was concentrated. The residue was dissolved in THF (340 μL) and saturated aqueous. Na$_2$CO$_3$ solution (35 μL) was added. To the mixture was added prop-2-enoyl prop-2-enoate (3.8 mg, 0.03 mmol) in THF (0.3 mL). The reaction was stirred at rt for 10 min then was diluted with water (1 mL) and was extracted twice with DCM (2 mL). The combined organic layers were dried over magnesium sulfate, filtered and concentrated. The crude was purified by flash column chromatography (silica, C18, 20-70% MeCN/10 mM AmF water) to give the title compound (4 mg, 0.009 mmol, 29% yield) as a colorless solid after lyophilization. $^1$H NMR (400 MHz, DMSO-d$_6$): δ 8.72 (t, J=5.7 Hz, 1H), 8.41 (s, 1H), 8.10 (d, J=8.6 Hz, 2H), 7.65 (s, 1H), 7.55 (d, J=8.4 Hz, 2H), 6.33 (dd, J=17.1, 10.2 Hz, 1H), 6.10 (dd, J=17.1, 1.9 Hz, 1H), 5.61 (dd, J=10.2, 1.9 Hz, 1H), 4.95 (d, J=6.0 Hz, 2H), 4.12 (s, 3H), 3.69 (s, 3H). ; LCMS (ESI): m/z 454.2 (M+H)$^+$.

Example 54 (Compound 58)

N-[[4-(3-hydroxyprop-1-ynyl)-3-methyl-7-[4-(trifluoromethoxy)phenyl]benzimidazol-5-yl]methyl]prop-2-enamide

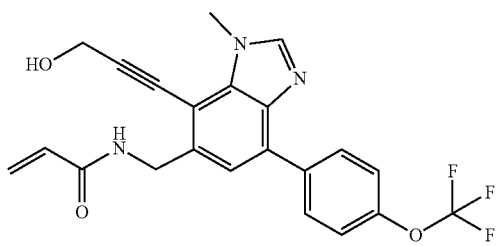 [SMILES: C=CC(=O)NCc1cc(-c2ccc(OC(F)(F)F)cc2)c2ncn(C)c2c1C#CCO]

Step 1: tert-Butyl-N-tert-butoxycarbonyl-N-[[4-[3-[tert-butyl(dimethyl)silyl]oxyprop-1-ynyl]-3-methyl-7-[4-(trifluoromethoxy)phenyl]benzimidazol-5-yl]methyl]carbamate

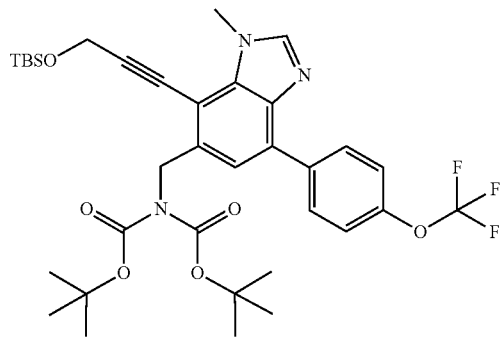 [SMILES: Cn1cnc2c(-c3ccc(OC(F)(F)F)cc3)cc(CN(C(=O)OC(C)(C)C)C(=O)OC(C)(C)C)c(C#CCO[Si](C)(C)C(C)(C)C)c21]

tert-butyldimethyl(2-Propynyloxy)silane (0.17 mL, 0.83 mmol), tert-butyl-N-[[4-bromo-3-methyl-7-[4-(trifluoromethoxy)phenyl]benzimidazol-5-yl]methyl]-N-tert-butoxycarbonyl-carbamate (100 mg, 0.17 mmol) (described in Example 27, , step 6), Pd(dppf)Cl$_2$ (7 mg, 0.01 mmol) were put in a vial and purged with nitrogen. DMF (833 μL) was added with CuI (2 mg, 0.01 mmol) followed by potassium carbonate (161 mg, 1.2 mmol). The reaction was heated at 80° C. for 18 h and diluted with EtOAc (15 mL), washed with 50% brine (3×10 mL). The organic phase was dried over magnesium sulfate and concentrated onto silica gel. The crude was purified by flash column chromatography (silica, 0-50% EtOAc/Heptanes) to give the title compound (67 mg, 58% yield) as a brown oil. LCMS (ESI): m/z 690.5 (M+H)$^+$.

Step 2: tert-Butyl-N-tert-butoxycarbonyl-N-[[4-(3-hydroxyprop-1-ynyl)-3-methyl-7-[4-(trifluoromethoxy)phenyl]benzimidazol-5-yl]methyl]carbamate

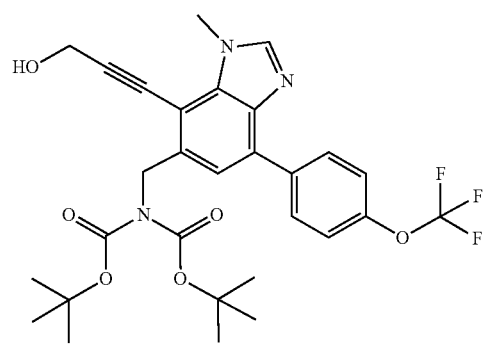 [SMILES: Cn1cnc2c(-c3ccc(OC(F)(F)F)cc3)cc(CN(C(=O)OC(C)(C)C)C(=O)OC(C)(C)C)c(C#CCO)c21]

tert-Butyl-N-tert-butoxycarbonyl-N-[[4-[3-[tert-butyl(dimethyl)silyl]oxyprop-1-ynyl]-3-methyl-7-[4-(trifluoromethoxy)phenyl]benzimidazol-5-yl]methyl]carbamate (67 mg, 0.1 mmol) was dissolved in THF (486 L) and tetrabutylammonium fluoride 1.0 M in THF (194 μL, 0.19 mmol) was added. The reaction was stirred at rt for 1 h and then was diluted with EtOAc (20 mL), washed with water (2×10 mL). The organic phase was dried over magnesium

441 sulfate and concentrated to give the title compound (55 mg, 0.1 mmol, 98% yield) as a brown oil. LCMS (ESI): m/z 573.3 (M+H)⁺.

Step 3: N-[[4-(3-hydroxyprop-1-ynyl)-3-methyl-7-[4-(trifluoromethoxy)phenyl]benzimidazol-5-yl]methyl]prop-2-enamide

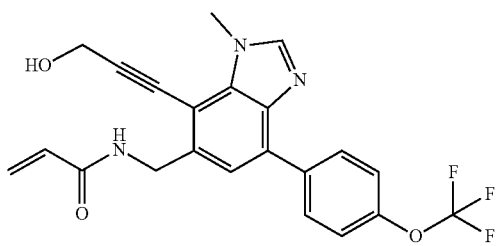 [SMILES: C=CC(=O)NCc1cc(-c2ccc(OC(F)(F)F)cc2)c2ncn(C)c2c1C#CCO]

tert-Butyl-N-tert-butoxycarbonyl-N-[[4-(3-hydroxyprop-1-ynyl)-3-methyl-7-[4-(trifluoromethoxy)phenyl]benzimidazol-5-yl]methyl]carbamate (55 mg, 0.1 mmol) was dissolved in DCM (0.83 mL) and TFA (100 μL, 1.3 mmol) was added. The reaction stirred at rt for 1 h, toluene (500 μL) was added and it was concentrated. The residue was dissolved in THF (1.1 mL) and saturated aqueous Na₂CO₃ solution (70 μL) was added. To the mixture was added prop-2-enoyl prop-2-enoate (12 mg, 0.1 mmol) in THF (0.3 mL). The reaction was stirred at rt for 10 min, then was diluted with water (1 mL) and it was extracted twice with DCM (2×5 mL). The organic layers were dried over magnesium sulfate, filtered and concentrated. The crude was purified by flash column chromatography (silica, C18, 20-100% MeCN/10 mM AmF water) to give the title compound (18 mg, 44% yield) as a colorless solid after lyophilization. ¹H NMR (400 MHz, DMSO-d₆): δ 8.59 (t, J=5.5 Hz, 1H), 8.25 (s, 1H), 8.13 (d, J=8.8 Hz, 2H), 7.48 (d, J=8.3 Hz, 2H), 7.40 (s, 1H), 6.31 (dd, J=17.1, 10.1 Hz, 1H), 6.12 (dd, J=17.1, 2.1 Hz, 1H), 5.61 (dd, J=10.1, 2.2 Hz, 1H), 5.42 (t, J=6.0 Hz, 1H), 4.64 (d, J=5.7 Hz, 2H), 4.43 (d, J=5.9 Hz, 2H), 4.14 (s, 3H). LCMS (ESI): m/z 430.2 (M+H)⁺.

Example 55 (Compound 59)

2-fluoro-1-[3-[4-(hydroxymethyl)-3-methyl-7-[4-(trifluoromethoxy)phenyl]benzimidazol-5-yl]azetidin-1-yl]prop-2-en-1-one

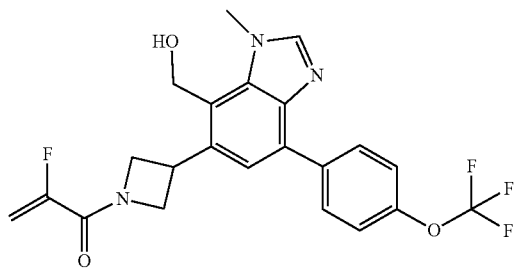 [SMILES: C=C(F)C(=O)N1CC(c2cc(-c3ccc(OC(F)(F)F)cc3)c3ncn(C)c3c2CO)C1]

442

Step 1: 4-bromo-3-methyl-7-[4-(trifluoromethoxy)phenyl]benzimidazole-5-carboxylic acid

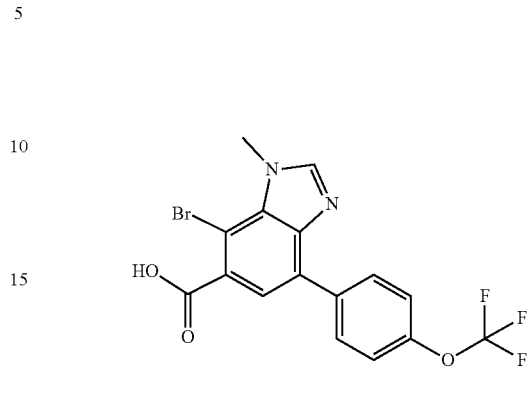

Ethyl4-bromo-3-methyl-7-[4-(trifluoromethoxy)phenyl]benzimidazole-5-carboxylate (4.33 g, 9.8 mmol) (described in Example 27, , step 3) was dissolved in 1,4-dioxane (38 mL) and a solution of LiOH (1.2 g, 48 mmol) in water (11 mL) was added. The solution was stirred at 70° C. for 2 h then was concentrated and diluted with 1M HCl to a pH of 6. This caused a precipitate to form which was filtered, washed with water with a pH of 6. The solid was dried to give the title compound (3.86 g, 9.3 mmol, 95% yield) as a brown solid. LCMS (ESI): m/z 417.0 (M+H)⁺.

Step 2: 4-bromo-3-methyl-7-[4-(trifluoromethoxy)phenyl]benzimidazole-5-carbonyl azide

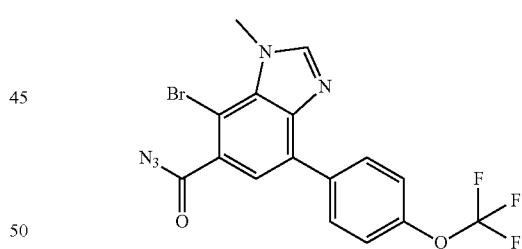

4-bromo-3-methyl-7-[4-(trifluoromethoxy)phenyl]benzimidazole-5-carboxylic acid (3.86 g, 9.3 mmol) was dissolved in DCE (180 mL) and one drop of DMF was added. Thionyl chloride (3.21 mL, 44 mmol) was added and it was heated at 80° C. for 2 h. The reaction was concentrated, redissolved in anhydrous THF (80 mL) and sodium azide (1.21 g, 18.6 mmol) was added along with 4-dimethylaminopyridine (77 mg, 0.63 mmol) and was stirred for 15 min. The mixture was diluted with water (200 mL) and extracted with EtOAc (3×100 mL). The combined organic phases were dried over magnesium sulfate, filtered and concentrated to give the crude title compound (4.1 g, 100% yield) as brown solid. LCMS (ESI): m/z 442.0 (M+H)⁺.

Step 3: 4-bromo-3-methyl-7-[4-(trifluoromethoxy)phenyl]benzimidazol-5-amine

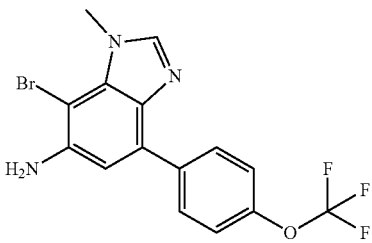 [SMILES: Cn1cnc2c(-c3ccc(OC(F)(F)F)cc3)cc(N)c(Br)c21]

Crude 4-bromo-3-methyl-7-[4-(trifluoromethoxy)phenyl]benzimidazole-5-carbonyl azide (4.1 g, 9.3 mmol) was dissolved in acetic acid (133 mL) and water (22 mL). The reaction was heated at 100° C. for 40 min then was diluted with EtOAc (100 mL) and basified with saturated aqueous Na₂CO₃ solution. The organic phase was dried over magnesium sulfate and concentrated onto silica gel. The crude was purified by flash column chromatography (silica, 0-70% EtOAc/Heptanes) to provide the title compound (1.05 g, 29% yield) as a light brown solid. LCMS (ESI): m/z 388.1 (M+H)⁺.

Step 4: Methyl N-[4-bromo-3-methyl-7-[4-(trifluoromethoxy)phenyl]benzimidazol-5-yl]carbamate

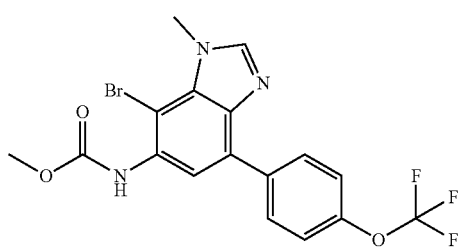 [SMILES: COC(=O)Nc1cc(-c2ccc(OC(F)(F)F)cc2)c2ncn(C)c2c1Br]

4-bromo-3-methyl-7-[4-(trifluoromethoxy)phenyl]benzimidazol-5-amine (1 g, 2.6 mmol) was dissolved in DCM (6 mL) and N,N-diisopropylethylamine (1.8 mL, 10.4 mmol). The solution was cooled to 0° C. and a solution of methyl chloroformate (220 μL, 2.9 mmol) in DCM (1 mL) was added and was stirred for 1.5 h. The reaction was diluted with DCM (100 mL) and washed with 1 M HCl (2×75 mL), brine (1×75 mL), dried over magnesium sulfate, filtered and concentrated to give the crude title compound. LCMS (ESI): m/z 446.1 (M+H)⁺.

Step 5: Methyl N-[3-methyl-7-[4-(trifluoromethoxy)phenyl]-4-vinyl-benzimidazol-5-yl]carbamate

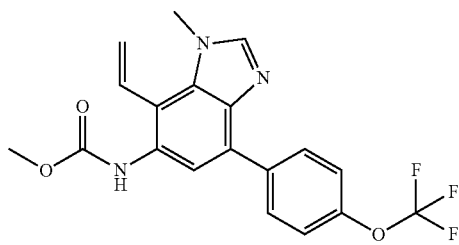 [SMILES: C=Cc1c(NC(=O)OC)cc(-c2ccc(OC(F)(F)F)cc2)c2ncn(C)c12]

Methyl N-[4-bromo-3-methyl-7-[4-(trifluoromethoxy)phenyl]benzimidazol-5-yl]carbamate (1.15 g, 2.6 mmol), potassium vinyltrifluoroborate (1.04 g, 7.8 mmol), potassium carbonate (1.79 g, 12.9 mmol) and Pd(dppf)Cl₂ (192 mg, 0.26 mmol) were put in a microwave vial and THF (12 mL) and water (1.2 mL) were added. The reaction was degassed with nitrogen for 5 min and then heated at 100° C. for 1.5 h. It was then directly concentrated onto silica and purified by flash column chromatography (silica, 30-100% EtOAc/Heptanes) to give the title compound (521 mg, 51% yield) as a yellow solid. LCMS (ESI): m/z 392.3 (M+H)⁺.

Step 6: Methyl N-[4-(hydroxymethyl)-3-methyl-7-[4-(trifluoromethoxy)phenyl]benzimidazol-5-yl]carbamate

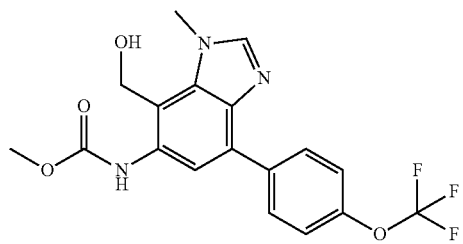 [SMILES: COC(=O)Nc1cc(-c2ccc(OC(F)(F)F)cc2)c2ncn(C)c2c1CO]

Methyl N-[3-methyl-7-[4-(trifluoromethoxy)phenyl]-4-vinyl-benzimidazol-5-yl]carbamate (521 mg, 1.33 mmol) was dissolved in methanol (31 mL) and cooled to −78° C. Ozone was gently bubbled for 1 h. The reaction was purged with nitrogen for 10 min and sodium borohydride (504 mg, 13.3 mmol) was added. The cooling bath was removed and it was stirred for 30 min. The reaction was diluted with 1 M HCl (20 mL) and stirred for 30 min then was concentrated to dryness under a flow of air leaving 2.5 g of a colorless residue which was used directly in the next step. LCMS (ESI): m/z 396.1 (M+H)⁺.

Step 7: [5-amino-3-methyl-7-[4-(trifluoromethoxy)phenyl]benzimidazol-4-yl]methanol

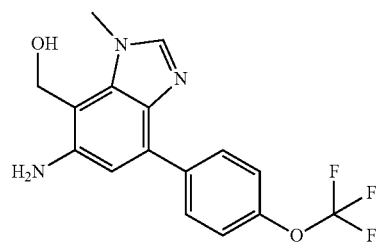 [SMILES: Cn1cnc2c(-c3ccc(OC(F)(F)F)cc3)cc(N)c(CO)c21]

Methyl N-[4-(hydroxymethyl)-3-methyl-7-[4-(trifluoromethoxy)phenyl]benzimidazol-5-yl]carbamate (526 mg, 1.33 mmol) was dissolved in methanol (63 mL) and 1M sodium hydroxide (8 mL, 8 mmol) was added. The reaction was heated at 75° C. for 3 h then was diluted with water (50 mL) and extracted with CHCl₃/IPA (3×50 mL). The combined organic phases were dried over magnesium sulfate, filtered and concentrated to give the crude title compound (312 mg, 70% yield) as an orange solid. LCMS (ESI): m/z 338.2 (M+H)⁺.

Step 8: 4-[[tert-Butyl-(dimethyl)silyl]oxymethyl]-3-methyl-7-[4-(trifluoromethoxy)phenyl]benzimidazol-5-amine

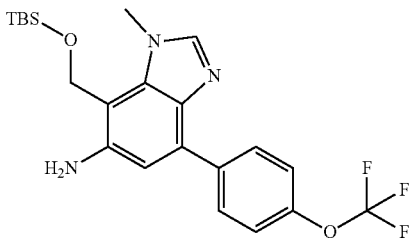

[5-amino-3-methyl-7-[4-(trifluoromethoxy)phenyl]benzimidazol-4-yl]methanol (300 mg, 0.89 mmol) was dissolved in DMF (3 mL) and imidazole (109 mg, 1.6 mmol) was added followed by tert-butyldimethylchlorosilane (201 mg, 1.3 mmol). The reaction was stirred at rt for 18 h then was diluted with EtOAc (15 mL) and washed with 0.5 M HCl (2×15 mL). The organic phase was dried over magnesium sulfate, filtered and concentrated to provide the crude title compound (305 mg, 76% yield) as an orange solid. LCMS (ESI): m/z 452.3 (M+H)+.

Step 9: [5-bromo-3-methyl-7-[4-(trifluoromethoxy)phenyl]benzimidazol-4-yl]methoxy-tert-butyl-dimethyl-silane

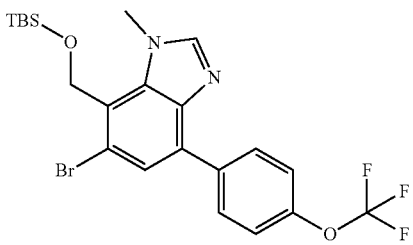

4-[[tert-butyl-(dimethyl)silyl]oxymethyl]-3-methyl-7-[4-(trifluoromethoxy)phenyl]benzimidazol-5-amine (305 mg, 0.68 mmol) was dissolved in MeCN (42 mL) and copper (I) bromide (194 mg, 1.35 mmol) was added. The mixture was heated to 60° C. and a solution of tert-butyl nitrite (201 μL, 1.7 mmol) in MeCN (26 mL) was added and stirred at 60° C. for 30 min. The reaction was concentrated onto silica gel and purified by flash column chromatography (silica, 0-50% EtOAc/Heptanes) to provide the title compound (63 mg, 18% yield) as an orange solid. LCMS (ESI): m/z 517.1 (M+H)+.

Step 10: Tert-butyl-3-[4-[[tert-butyl(dimethyl)silyl]oxymethyl]-3-methyl-7-[4-(trifluoromethoxy)phenyl]benzimidazol-5-yl]azetidine-1-carboxylate

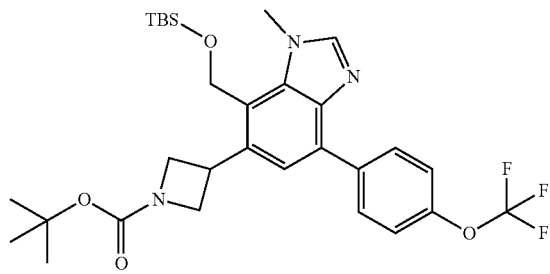

tert-Butyl-3-bromoazetidine-1-carboxylate (43 mg, 0.18 mmol), [5-bromo-3-methyl-7-[4-(trifluoromethoxy)phenyl]benzimidazol-4-yl]methoxy-tert-butyl-dimethyl-silane (63 mg, 0.12 mmol), nickel chloride dimethoxyethane adduct (2.7 mg, 0.01 mmol), zinc (16 mg, 0.24 mmol), sodium iodide (4.6 mg, 0.03 mmol) and imidazole-4-carbonitrile (1.1 mg, 0.01 mmol) were put in a vial and it was purged with nitrogen four times. DMA (0.4 mL) was degassed for 15 min and trifluoroacetic acid (0.94 μL, 0.01 mmol) was added. This solution was added to the reaction mixture and it was heated at 60° C. for 18 h. Water (2 mL) was added and it was diluted with EtOAc (10 mL). The organic phase was washed with 50% brine (2×10 mL), dried over magnesium sulfate, concentrated onto silica and purified by flash column chromatography (silica, 0-50% EtOAc/Heptanes) to provide the title compound (21 mg, 29% yield) as a white solid. LCMS (ESI): m/z 592.4 (M+H)+.

Step 11: 2-fluoro-1-[3-[4-(hydroxymethyl)-3-methyl-7-[4-(trifluoromethoxy)phenyl]benzimidazol-5-yl]azetidin-1-yl]prop-2-en-1-one

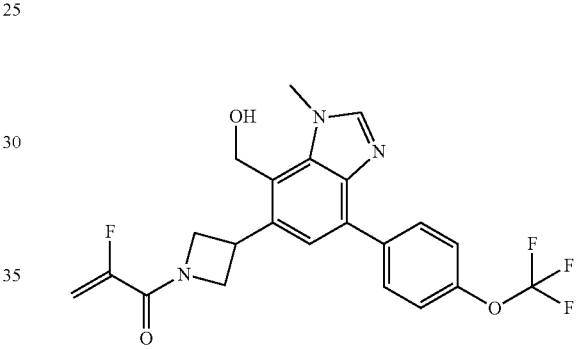

tert-Butyl-3-[4-[[tert-butyl(dimethyl)silyl]oxymethyl]-3-methyl-7-[4-(trifluoromethoxy) phenyl]benzimidazol-5-yl]azetidine-1-carboxylate (21 mg, 0.04 mmol) was dissolved in THF (600 μL) and tetrabutylammonium fluoride 1.0 M in THF (71 μL, 0.07 mmol) was added. It was stirred for 2 h and the reaction was diluted with EtOAc (10 mL) before being washed with water (2×10 mL) and brine (1×10 mL). The organic phase was dried over magnesium sulfate, filtered and concentrated.

The residue was dissolved in DCM (600 μL) and TFA (80 μL, 1.0 mmol) was added and stirred for 4 h then toluene (2 mL) was added and it was concentrated to dryness.

The residue was redissolved in methanol (225 μL) and DCM (225 μL), EEDQ (9.7 mg, 0.04 mmol) and 2-fluoroacrylic acid (3.52 mg, 0.04 mmol) were added followed by N,N-diisopropylethylamine (13.6 μL, 0.08 mmol). The reaction was stirred for 20 h before being diluted with water and extracted with DCM (3×2 mL). The combined organic phase were dried over magnesium sulfate, filtered and concentrated. The crude was purified by flash column chromatography (silica, C18, 25-45%, MeCN/AmF 10 mM buffer) to provide the title compound (4.5 mg, 28% yield) as a white solid after lyophilization. 1H NMR (400 MHz, DMSO-d6): δ 8.19 (s, 3H), 7.53 (s, 1H), 7.46 (s, 2H), 5.49 (d, J=48.2 Hz, 1H), 5.29 (d, J=16.6 Hz, 2H), 4.79 (s, 3H), 4.63-4.39 (m, 3H), 4.19 (s, 1H), 4.12 (s, 2H). LCMS (ESI): m/z 450.1 (M+H)+.

Example 56 (Compound 60) and Example 57 (Compound 61)

(S)—N-((1-methyl-7-(S-methylsulfonimidoyl)-4-(4-(trifluoromethoxy)phenyl)-1H-benzo[d]imidazol-6-yl)methyl)acrylamide and (R)—N-((1-methyl-7-(S-methylsulfonimidoyl)-4-(4-(trifluoromethoxy)phenyl)-1H-benzo[d]imidazol-6-yl)methyl) acrylamide

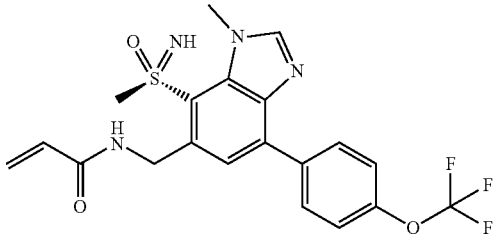

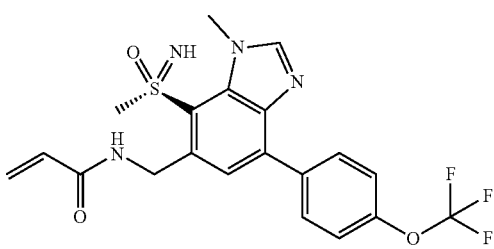

Step 1: Ethyl 3-methyl-4-methylsulfanyl-7-[4-(trifluoromethoxy)phenyl]benzimidazole-5-carboxylate

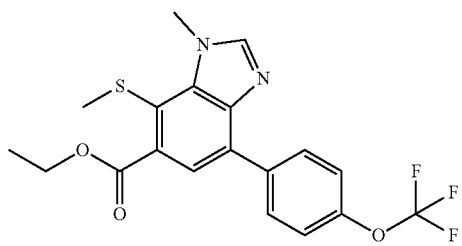 [SMILES: CCOC(=O)c1cc(-c2ccc(OC(F)(F)F)cc2)c2ncn(C)c2c1SC]

Ethyl4-bromo-3-methyl-7-[4-(trifluoromethoxy)phenyl]benzimidazole-5-carboxylate (500 mg, 1.1 mmol) (described in Example 27, , step 3), Pd$_2$(dba)$_3$ (206 mg, 0.23 mmol) and XantPhos (261 mg, 0.45 mmol) were put in a microwave vial. The vial was purged with nitrogen and toluene (5.6 mL) was added followed by triethylamine (786 µL, 5.6 mmol). The solution was degassed for 5 min and NaSMe (316 mg, 4.5 mmol) was added. The reaction was heated at 100° C. for 42 h and was concentrated onto silica and purified by flash column chromatography (silica, 0-100% EtOAc/Heptanes) to provide the title compound (463 mg, 100% yield) as a yellow solid. LCMS (ESI): m/z 411.3 (M+H)$^+$.

Step 2: [3-methyl-4-methylsulfanyl-7-[4-(trifluoromethoxy)phenyl]benzimidazol-5-yl]methanol

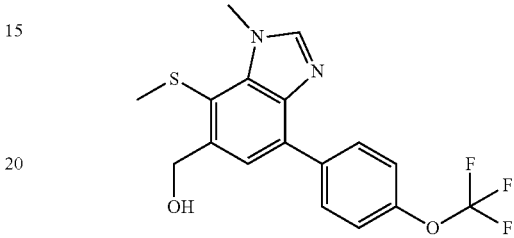

Ethyl 3-methyl-4-methylsulfanyl-7-[4-(trifluoromethoxy)phenyl]benzimidazole-5-carboxylate (486 mg, 1.2 mmol) was dissolved in THF (3 mL) and cooled to 0° C. Diisobutylaluminum hydride, 1.0 M in THF (6.2 mL, 6.2 mmol) added dropwise (internal temperature was kept below 2° C.). The mixture was stirred at rt for 1 h and THF (3 mL) was added followed by sodium sulfate decahydrate (200 mg). The suspension was stirred at rt for 1 h, filtered and concentrated on silica gel. The crude was purified by flash column chromatography (silica, 0-100% EtOAc/Heptanes) to provide the title compound (118 mg, 27% yield) as a colorless solid. LCMS (ESI): m/z 369.2 (M+H)$^+$.

Step 3: 6-(bromomethyl)-1-methyl-7-methylsulfanyl-4-[4-(trifluoromethoxy)phenyl]benzimidazole

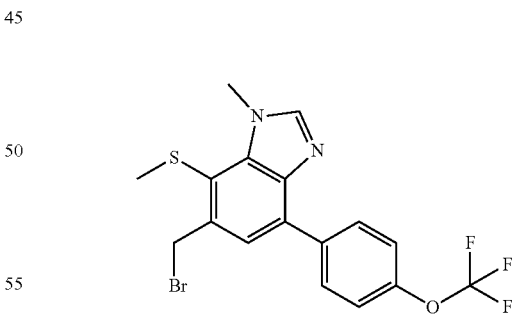

[3-methyl-4-methylsulfanyl-7-[4-(trifluoromethoxy)phenyl]benzimidazol-5-yl]methanol (70 mg, 0.19 mmol) and triphenylphosphine (50 mg, 0.19 mmol) were dissolved in DCM (0.95 mL). Carbon tetrabromide (63 mg, 0.19 mmol) was slowly added and it was stirred for 1.5 h. The reaction was directly concentrated onto silica gel and purified by flash chromatography (silica, 20-50% EtOAc/Heptanes) to provide the title compound (61 mg, 74% yield) as a colorless oil. LCMS (ESI): n/z 433.2 (M+H)$^+$.

Step 4: tert-Butyl-N-tert-butoxycarbonyl-N-[[3-methyl-4-methylsulfanyl-7-[4-(trifluoromethoxy)phenyl]benzimidazol-5-yl]methyl]carbamate

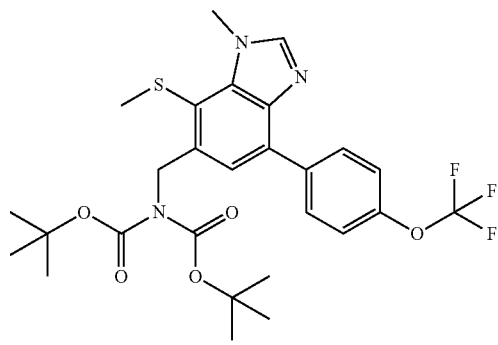 [SMILES: CSc1c(CN(C(=O)OC(C)(C)C)C(=O)OC(C)(C)C)cc(-c2ccc(OC(F)(F)F)cc2)c2ncn(C)c12]

6-(bromomethyl)-1-methyl-7-methylsulfanyl-4-[4-(trifluoromethoxy)phenyl]benzimidazole (81 mg, 0.19 mmol), di-tert-butyl-iminodicarboxylate (41 mg, 0.19 mmol) and cesium carbonate (62 mg, 0.19 mmol) were put in a flask. DMF (0.94 mL) was added and it was stirred for 30 min. The reaction was diluted with EtOAc (10 mL), washed with water (2×10 mL) and 50% brine (1×10 mL), dried over magnesium sulfate and concentrated to provide the title compound (96 mg, 90% yield) as an off white solid which was used without further purification. LCMS (ESI): m/z 568.5 (M+H)$^+$.

Step 5: tert-Butyl-N-tert-butoxycarbonyl-N-[[3-methyl-4-(methylsulfonimidoyl)-7-[4-(trifluoromethoxy)phenyl]benzimidazol-5-yl]methyl]carbamate

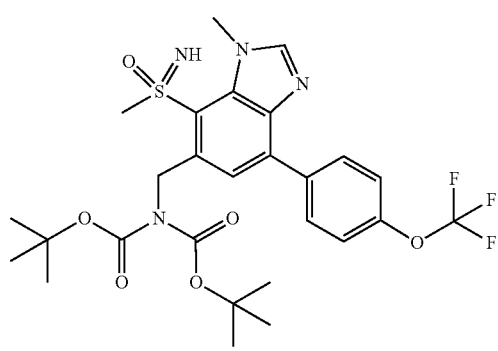 [SMILES: Cn1cnc2c(-c3ccc(OC(F)(F)F)cc3)cc(CN(C(=O)OC(C)(C)C)C(=O)OC(C)(C)C)c(S(C)(=N)=O)c21]

tert-Butyl-N-tert-butoxycarbonyl-N-[[3-methyl-4-methylsulfanyl-7-[4-(trifluoromethoxy) phenyl]benzimidazol-5-yl]methyl]carbamate (96 mg, 0.17 mmol) was dissolved in methanol (0.85 mL) and ammonium carbamate (26 mg, 0.34 mmol) was added. It was cooled to 0° C. and [bis(trifluoroacetoxy)iodo]benzene (145 mg, 0.34 mmol) was added then the mixture was stirred at rt for 25 min. The reaction was concentrated and purified by flash column chromatography (silica, C18, 40-80% MeCN/AmF 10 mM buffer) to provide the title compound (23 mg, 23% yield) as a white solid. LCMS (ESI): m/z 599.3 (M+H)$^+$.

Step 6: (S)—N-((1-methyl-7-(S-methylsulfonimidoyl)-4-(4-(trifluoromethoxy)phenyl)-1H-benzo[d]imidazol-6-yl)methyl)acrylamide and (R)—N-((1-methyl-7-(S-methylsulfonimidoyl)-4-(4-(trifluoromethoxy)phenyl)-1H-benzo[d]imidazol-6-yl)methyl)acrylamide

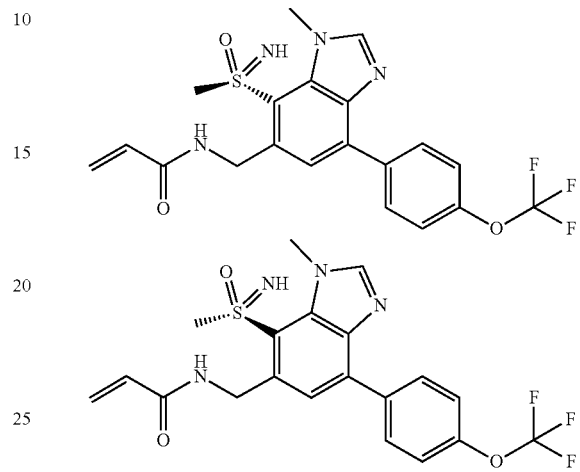

tert-Butyl-N-tert-butoxycarbonyl-N-[[3-methyl-4-(methylsulfonimidoyl)-7-[4-(trifluoromethoxy)phenyl]benzimidazol-5-yl]methyl]carbamate (23 mg, 0.04 mmol) was dissolved in DCM (0.33 mL) and TFA (84 µL, 1.1 mmol) was added. The reaction was stirred at rt for 3 h, toluene (0.5 mL) was added and it was concentrated. The residue was dissolved in THF (0.43 mL) and saturated aqueous Na$_2$CO$_3$ solution (75 µL) was added. To the mixture was added prop-2-enoyl prop-2-enoate (4.9 mg, 0.04 mmol) in THF (0.3 mL). The reaction was stirred at rt for 10 min then was diluted with water (1 mL) and extracted twice with DCM (2×5 mL). The combined organic layers were dried over magnesium sulfate, filtered and concentrated. The crude was purified by reverse phase chromatography (silica, C18, 40-80% MeCN/10 mM AmF water) to give mixture of enantiomers 7.5 mg, 43% yield as a colorless solid after lyophilization.

The 9 mg of the racemate was further purified by chiral chromatography (Column=ChiralPak IA; Column dimensions=250 mm×4.6 mm×5 gm; Flow rate=0.8 m/min; Run time=15 min; Column temperature=26° C.) 5:30:65 MeOH:EtOH to afford:

(S)—N-((1-methyl-7-(S-methylsulfonimidoyl)-4-(4-(trifluoromethoxy)phenyl)-1H-benzo[d]imidazol-6-yl)methyl)acrylamide (peak 1, stereochemistry is arbitrarily assigned) (5.5 mg, 32%) white solid. $^1$H NMR (400 MHz, DMSO-d$_6$): δ 8.37 (s, 1H), 8.17 (s, 1H), 8.06 (d, J=8.7 Hz, 2H), 7.45 (d, J=8.3 Hz, 2H), 7.36 (s, 1H), 6.27 (dd, J=17.1, 10.1 Hz, 1H), 6.10 (dd, J=17.0, 1.9 Hz, 1H), 5.58 (dd, J=10.1, 2.0 Hz, 1H), 5.46 (s, 1H), 4.80 (dd, J=14.9, 5.9 Hz, 1H), 4.58 (dd, J=14.6, 4.8 Hz, 1H), 4.11 (s, 3H), 3.84 (t, J=8.8 Hz, 1H), 3.69 (dd, J=9.4, 5.6 Hz, 1H). LCMS (ESI): m/z 453.3 (M+H)$^+$. (Compound 60)

(S)—N-((1-methyl-7-(S-methylsulfonimidoyl)-4-(4-(trifluoromethoxy)phenyl)-1H-benzo[d]imidazol-6-yl)methyl)acrylamide (peak 1, stereochemistry is arbitrarily assigned) (3.3 mg, 19%) white solid. $^1$H NMR (400 MHz, DMSO-d$_6$): δ 8.39 (s, 1H), 8.16 (s, 1H), 8.06 (d, J=8.6 Hz, 2H), 7.45 (d, J=8.3 Hz, 2H), 7.36 (s, 1H), 6.28 (dd, J=17.0, 10.2 Hz, 1H), 6.10 (dd, J=17.1, 2.1 Hz, 1H), 5.58 (dd, J=10.1, 2.2 Hz, 1H), 5.47 (s, 1H), 4.80 (dd, J=14.7, 6.0 Hz, 1H), 4.59 (dd, J=14.6, 4.9 Hz, 1H), 4.11 (s, 3H), 3.84 (dd, J=10.8, 7.1 Hz, 1H), 3.69 (dd, J=10.9, 6.1 Hz, 1H). LCMS (ESI): m/z 453.3 (M+H)+. (Compound 61)

Example 58 (Compound 62)

1-[3-[9-methyl-6-[4-(trifluoromethoxy)phenyl]purin-2-yl]azetidin-1-yl]prop-2-en-1-one

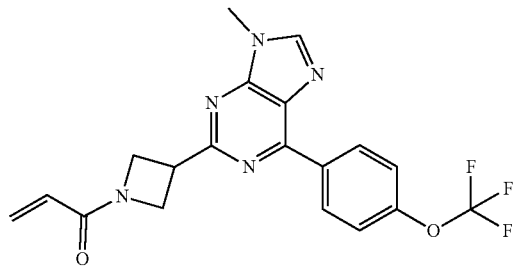 [SMILES: C=CC(=O)N1CC(c2nc(-c3ccc(OC(F)(F)F)cc3)c3ncn(C)c3n2)C1]

Step 1: 2-chloro-9-methyl-6-[4-(trifluoromethoxy)phenyl]purine

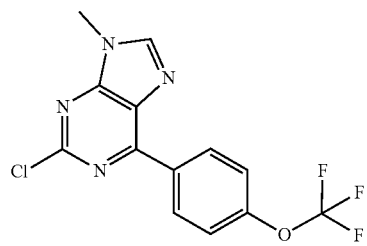 [SMILES: Cn1cnc2c(-c3ccc(OC(F)(F)F)cc3)nc(Cl)nc21]

4-(trifluoromethoxy)phenylboronic acid (2.03 g, 9.85 mmol), 2,6-dichloro-9-methyl-purine (2.00 g, 9.85 mmol) and potassium carbonate (5.45 g, 39.4 mmol) were dissolved in a 5:1 mixture of 1,4-dioxane (13.7 mL) and water (2.7 mL) and purged with nitrogen for 15 min. 1,1-bis(diphenylphosphino)ferrocene-palladium dichloride (146 mg, 0.20 mmol) was quickly added and the reaction was sealed and heated to 120° C. in a microwave reactor for 30 min. The reaction was then cooled to rt, extracted into EtOAc and concentrated to yield a crude solid which was then dissolved in DCM and MeOH (~20 mL each) and carefully concentrated until solids appeared. The white solids were collected and the cake was washed with MeOH to yield the title compound (1.28 g, 40% yield). LCMS (ESI): m/z 329.0 (M+H)+.

Step 2: tert-Butyl-3-[9-methyl-6-[4-(trifluoromethoxy)phenyl]purin-2-yl]azetidine-1-carboxylate

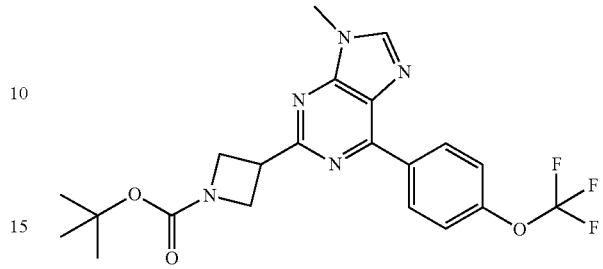

A vial was charged with tert-butyl 3-bromoazetidine-1-carboxylate (459 mg, 1.94 mmol), 2-chloro-9-methyl-6-[4-(trifluoromethoxy)phenyl]purine (426 mg, 1.3 mmol), nickel chloride dimethoxy ethane adduct (28 mg, 0.13 mmol), zinc (169 mg, 2.59 mmol), sodium iodide (49 mg, 0.32 mmol) and imidazole-4-carbonitrile (12 mg, 0.13 mmol) and the contents were placed under nitrogen. Inert atmosphere was insured by evacuating the flask using vacuum and re-introducing nitrogen three times. In another vial degassed DMA (4.3 mL) and trifluoroacetic acid (10 µL, 0.13 mmol) were added. This solution was added to the solids at rt. The reaction was sealed and heated at 60° C. for 18 h. Water (15 mL) was added and the product was extracted with DCM (2×15 mL). The combined organic phases were washed with a 1:1 mixture of brine and water (30 mL) and then dried over magnesium sulfate and directly concentrated onto silica gel. The product was purified by flash column chromatography (silica, 0-100% DCM/EtOAc) to afford the title compound (260 mg, 45% yield) as an off-white solid. LCMS (ESI): m/z 450.3 (M+H)+.

Step 3: 1-[3-[9-methyl-6-[4-(trifluoromethoxy)phenyl]purin-2-yl]azetidin-1-yl]prop-2-en-1-one (Compound 62)

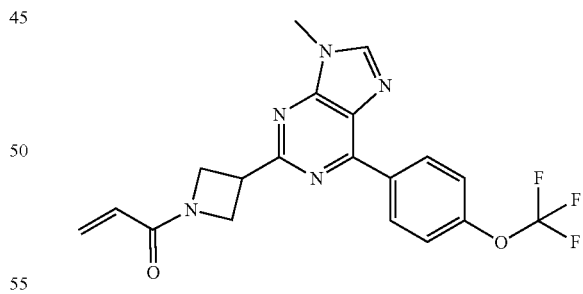

tert-Butyl-3-[9-methyl-6-[4-(trifluoromethoxy)phenyl]purin-2-yl]azetidine-1-carboxylate (30 mg, 0.07 mmol) was dissolved in DCM (0.57 mL) and trifluoroacetic acid (75 µL, 0.97 mmol) was added. The reaction was stirred at rt for 1 h and toluene was added and the reaction mixture was concentrated to dryness. The residue was then redissolved in THF (0.76 mL), saturated aqueous Na₂CO₃ solution (150 mL) was added followed by a solution of prop-2-enoyl prop-2-enoate (9.2 mg, 0.07 mmol) in THF (0.6 mL). The reaction mixture was stirred for 10 min and the reaction was diluted with water (3 mL). The product was extracted with DCM (3×3 mL), dried over magnesium sulfate, and concentrated. The compound was purified using prep-HPLC: Column: CSH Prep C18 OBD, 5 μm, 30×75 mm. (30% MeCN in 10 mM AmF water to 50% MeCN) to afford the title compound (18.3 mg, 68% yield) as a white solid. ¹H NMR (400 MHz, DMSO-d₆) δ 8.95 (d, J=8.7 Hz, 2H), 8.63 (s, 1H), 7.58 (t, J=13.6 Hz, 2H), 6.38 (dt, J=22.1, 11.0 Hz, 1H), 6.18-6.08 (m, 1H), 5.68 (dt, J=16.0, 8.0 Hz, 1H), 4.69 (t, J=8.6 Hz, 1H), 4.60-4.53 (m, 1H), 4.39 (t, J=9.3 Hz, 1H), 4.32 (t, J=7.7 Hz, 1H), 4.25 (ddd, J=14.8, 8.9, 6.0 Hz, 1H). LCMS (ESI): m/z 404.1 (M+H)⁺.

Example 59 (Compound 63)

2-fluoro-N-[[4-(hydroxymethyl)-3-methyl-7-[4-(trifluoromethoxy)phenyl]benzimidazol-5-yl]methyl]prop-2-enamide

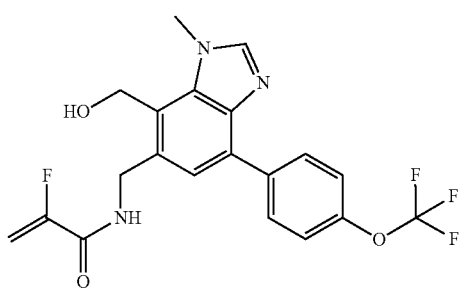 [SMILES: C=C(F)C(=O)NCc1cc(-c2ccc(OC(F)(F)F)cc2)c2ncn(C)c2c1CO]

Step 1: [5-(aminomethyl)-3-methyl-7-[4-(trifluoromethoxy)phenyl]benzimidazol-4-yl]methanol

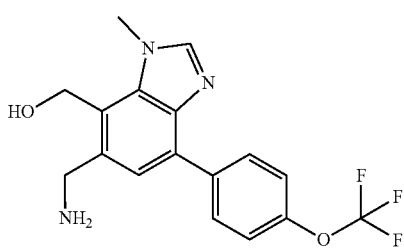 [SMILES: Cn1cnc2c(-c3ccc(OC(F)(F)F)cc3)cc(CN)c(CO)c21]

tert-Butyl-N-tert-butoxycarbonyl-N-[[4-(hydroxymethyl)-3-methyl-7-[4-(trifluoromethoxy)phenyl]benzimidazol-5-yl]methyl]carbamate (87 mg, 0.16 mmol) (described in example 27 step 8) was dissolved in DCM (1.6 mL) and trifluoroacetic acid (0.37 mL, 4.73 mmol) was added at rt. The reaction was stirred at this temperature for 1 h. Toluene (~3 mL) was added and the reaction mixture was concentrated to dryness. The crude reaction mixture was taken to the next step without further purification. LCMS (ESI): m/z 352.5 (M+H)⁺.

Step 2: 2-fluoro-N-[[4-(hydroxymethyl)-3-methyl-7-[4-(trifluoromethoxy)phenyl]benzimidazol-5-yl]methyl]prop-2-enamide (Compound 63)

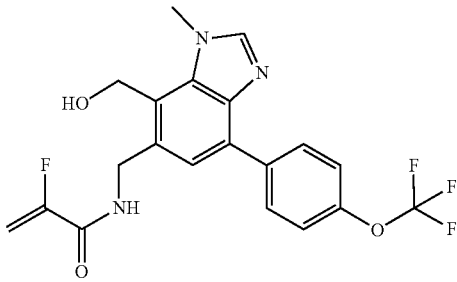 [SMILES: C=C(F)C(=O)NCc1cc(-c2ccc(OC(F)(F)F)cc2)c2ncn(C)c2c1CO]

To a solution of 2-fluoroprop-2-enoic acid (14 mg, 0.16 mmol), [5-(aminomethyl)-3-methyl-7-[4-(trifluoromethoxy)phenyl]benzimidazol-4-yl]methanol (55 mg, 0.16 mmol) and HATU (66 mg, 0.17 mmol) in DMF (1.6 mL) was added N,N-diisopropylethylamine (0.08 mL, 0.47 mmol) dropwise at 0° C. The reaction was stirred at this temperature for 5 min and then warmed to rt and then stirred for another 2 h. Water (10 mL) was added to the reaction and the product was extracted with 20% iPrOH in CHCl3 (3×10 mL). The organic layers were combined, dried over sodium sulfate, filtered and concentrated. The batch was combined with two other small batches and were purified by reverse phase chromatography (silica, C18, 40-80% MeCN/10 mM AmF water) ACN was removed and the residue was extracted with 20% iPrOH in CHCl3 (3×10 mL). The organic layers were combined, dried over sodium sulfate, filtered and concentrated. The product was further purified using Buchi prep. system (Luna column, 20-60% MeCN in 10 mM AmF water) to afford the title compound (26.6 mg, 40% yield) as a white solid. ¹H NMR (400 MHz, DMSO-d₆) δ 8.94 (t, J=5.1 Hz, 1H), 8.20 (s, 1H), 8.14 (d, J=8.7 Hz, 2H), 7.48 (ap d, J=9.7 Hz, 3H), 5.55 (dd, J=48.1, 3.3 Hz, 1H), 5.31 (t, J=5.0 Hz, 1H), 5.26 (dd, J1=15.7, 3.3 Hz, 1H), 4.97 (d, J=4.8 Hz, 2H), 4.66 (d, J=5.8 Hz, 2H), 4.15 (s, 3H). LCMS (ESI): m/z 424.2 (M+H)⁺.

Example 60 (Compound 64)

(E)-4-hydroxy-N-[[4-(hydroxymethyl)-3-methyl-7-[4-(trifluoromethoxy)phenyl]benzimidazol-5-yl]methyl]-N-methyl-but-2-enamide

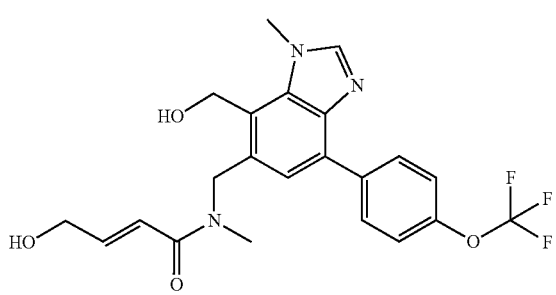 [SMILES: CN(Cc1cc(-c2ccc(OC(F)(F)F)cc2)c2ncn(C)c2c1CO)C(=O)/C=C/CO]

Step 1: tert-butyl-N-tert-butoxycarbonyl-N-[[4-[[tert-butyl(dimethyl)silyl]oxymethyl]-3-methyl-7-[4-(trifluoromethoxy)phenyl]benzimidazol-5-yl]methyl]carbamate

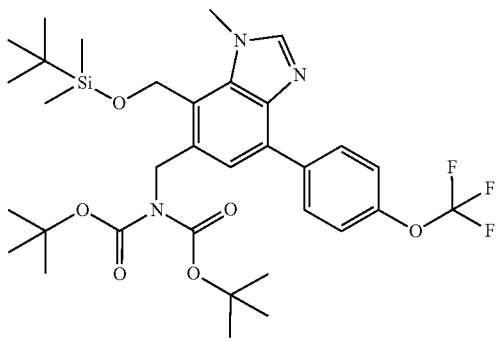 [SMILES: Cn1cnc2c(-c3ccc(OC(F)(F)F)cc3)cc(CN(C(=O)OC(C)(C)C)C(=O)OC(C)(C)C)c(CO[Si](C)(C)C(C)(C)C)c21]

tert-Butyl-N-tert-butoxycarbonyl-N-[[4-(hydroxymethyl)-3-methyl-7-[4-(trifluoromethoxy)phenyl]benzimidazol-5-yl]methyl]carbamate (400 mg, 0.73 mmol) (described in Example 27 step 8) was dissolved in DMF (2.1 mL) and imidazole (88.9 mg, 1.31 mmol) was added followed by tert-butyldimethylchlorosilane (120 mg, 0.800 mmol). The reaction was stirred at rt for 18 h. The reaction was diluted with EtOAc (5 mL) and washed with water (2×5 mL), dried over sodium sulfate, filtered and concentrated to afford the title compound (470 mg, 97% yield) as a white solid. LCMS (ESI): m/z 666.2 (M+H)⁺.

Step 2: tert-butyl N-[[4-[[tert-butyl(dimethyl)silyl]oxymethyl]-3-methyl-7-[4-(trifluoromethoxy)phenyl]benzimidazol-5-yl]methyl]carbamate

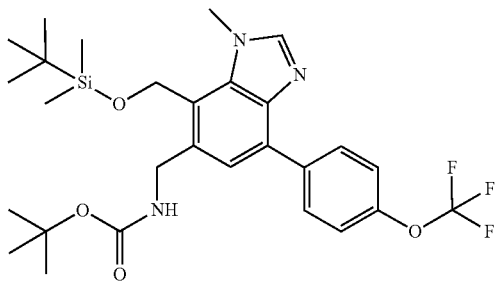 [SMILES: Cn1cnc2c(-c3ccc(OC(F)(F)F)cc3)cc(CNC(=O)OC(C)(C)C)c(CO[Si](C)(C)C(C)(C)C)c21]

tert-Butyl-N-tert-butoxycarbonyl-N-[[4-[[tert-butyl(dimethyl)silyl]oxymethyl]-3-methyl-7-[4-(trifluoromethoxy)phenyl]benzimidazol-5-yl]methyl]carbamate (470 mg, 0.71 mmol) was suspended in MeCN (7.1 mL) and magnesium perchlorate hexahydrate (0.03 mL, 0.21 mmol) was added at rt. The reaction mixture was then stirred at 60° C. for 1.5 h then diluted with EtOAc (20 mL) and the organic layer was washed with (1:1) H₂O:brine (2×20 mL). The organic phase was dried over sodium sulfate and concentrated to give the crude title compound (400 mg, 100% yield) as a white powder. LCMS (ESI): m/z 566.2 (M+H)⁺.

Step 3: tert-Butyl-N-[[4-[[tert-butyl(dimethyl)silyl]oxymethyl]-3-methyl-7-[4-(trifluoromethoxy)phenyl]benzimidazol-5-yl]methyl]-N-methyl-carbamate

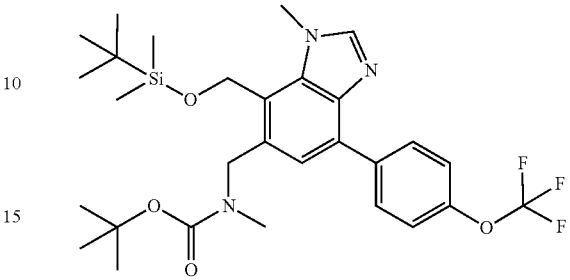

To a solution of tert-butyl-N-[[4-[[tert-butyl(dimethyl)silyl]oxymethyl]-3-methyl-7-[4-(trifluoromethoxy)phenyl]benzimidazol-5-yl]methyl]carbamate (400 mg, 0.71 mmol) and iodomethane (0.05 mL, 0.74 mmol) in THF (4.7 mL) was added sodium hydride (60% in mineral oil) (31 mg, 0.78 mmol) at 0° C. The reaction was stirred at 0° C. for 30 min and then warmed to rt and stirred at rt for an additional 3 h. The reaction was diluted with EtOAc (15 ml) and the organic layer was washed sequentially with saturated aqueous NH₄Cl solution (5 ml) and brine (15 ml). The organic layer was dried over sodium sulfate, filtered and concentrated. The crude reaction mixture was used as such in the next step without further purification. LCMS (ESI): m/z 580.3 (M+H)⁺.

Step 4: tert-butyl-N-[[4-(hydroxymethyl)-3-methyl-7-[4-(trifluoromethoxy)phenyl]benzimidazol-5-yl]methyl]-N-methyl-carbamate

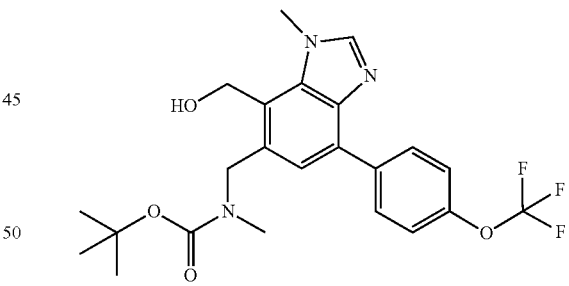

tert-Butyl N-[[4-[[tert-butyl(dimethyl)silyl]oxymethyl]-3-methyl-7-[4-(trifluoromethoxy) phenyl]benzimidazol-5-yl]methyl]-N-methyl-carbamate (392 mg, 0.680 mmol) was dissolved in THF (4.6 mL) and tetrabutyl ammonium fluoride [1.0 M in THF](1.35 mL, 1.35 mmol) was added. The reaction was stirred at rt for 1 h. The reaction was diluted with EtOAc (15 mL) and the organic layer was washed with water (2×15 mL). The organic phase was dried over magnesium sulfate, filtered and concentrated. The crude was then purified by flash column chromatography (silica, 20-40% [EtOAc:MeOH (7:3)] in heptane) to yield the title compound (218 mg, 69% yield) as a white solid. LCMS (ESI): m/z 466.1 (M+H)⁺.

Step 5: (E)-4-hydroxy-N-[[4-(hydroxymethyl)-3-methyl-7-[4-(trifluoromethoxy)phenyl]benzimidazol-5-yl]methyl]-N-methyl-but-2-enamide (Compound 64)

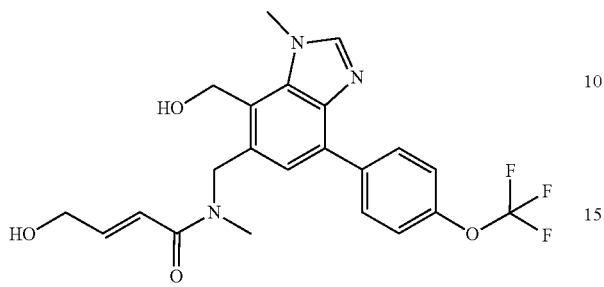

tert-Butyl-N-[[4-(hydroxymethyl)-3-methyl-7-[4-(trifluoromethoxy)phenyl]benzimidazol-5-yl]methyl]-N-methyl-carbamate (218 mg, 0.470 mmol) was dissolved in DCM (4.7 mL) and trifluoroacetic acid (0.36 mL, 4.9 mmol) was added at 0° C. The reaction was then stirred at rt for 1.5 h. Toluene was then added (~1 mL) and the reaction mixture was concentrated to dryness. The crude reaction mixture was dissolved in DMF (4.7 mL), N,N-diisopropylethylamine (0.33 mL, 1.87 mmol), and (E)-4-hydroxybut-2-enoic acid (0.13 mL, 1.64 mmol) were added followed by HATU (196 mg, 0.520 mmol). The reaction mixture was stirred at rt for 1.5 h and then diluted with water (10 mL) and the product was extracted with DCM (2×10 mL). The combined organic layers were dried over sodium sulfate and concentrated. The crude was purified using Buchi prep. system (Luna column, 20-40% MeCN in 10 mM ammonium formate) to afford the title compound (76 mg, 36% yield) as a white powder. $^1$H NMR (400 MHz, DMSO-d$_6$) 8.21 (d, J=7.4 Hz, 1H), 8.11 (d, J=8.6 Hz, 1H), 8.05 (d, J=8.5 Hz, 1H), 7.48 (d, J=8.3 Hz, 2H), 7.30-6.99 (m, J=109.2 Hz, 1H), 6.89-6.79 (m, 1H), 6.63-6.51 (m, J=16.3 Hz, 1H), 5.39-5.22 (m, J=37.8 Hz, 1H), 5.07-4.94 (m, J=15.1 Hz, 2H), 4.89 (s, 3H), 4.15 (s, 4H), 3.00-2.90 (m, J=15.5 Hz, 3H). LCMS (ESI): m/z 450.5 (M+H)$^+$.

Example 61 (Compound 65) and Example 62 (Compound 66)

(R)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide and (S)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide

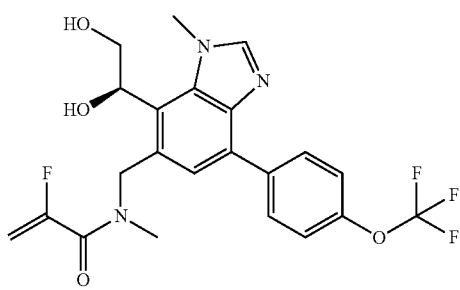

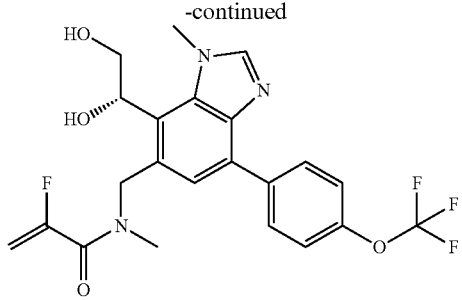

Step 1: tert-butyl-N-[[3-methyl-7-[4-(trifluoromethoxy)phenyl]-4-vinyl-benzimidazol-5-yl]methyl]carbamate

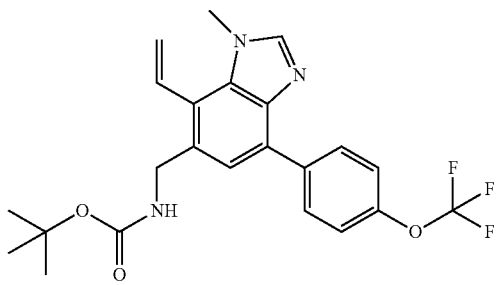 [SMILES: C=Cc1c(CNC(=O)OC(C)(C)C)cc(-c2ccc(OC(F)(F)F)cc2)c2ncn(C)c12]

tert-Butyl-N-tert-butoxycarbonyl-N-[[3-methyl-7-[4-(trifluoromethoxy)phenyl]-4-vinyl-benzimidazol-5-yl]methyl]carbamate (470 mg, 0.86 mmol) (described in Example 27, step 7, stepX) was suspended in MeCN (8.6 mL) and magnesium perchlorate hexahydrate (85 mg, 0.26 mmol) was added. The reaction was stirred at 60° C. for 1 h. The reaction was diluted with water (20 mL) and the product was extracted with EtOAc (3×20 mL). The combined organic phases were dried over magnesium sulfate, filtered and concentrated to afford the crude title compound (400 mg, 100% yield) as a white solid. LCMS (ESI): m/z 448.2 (M+H)$^+$.

Step 2: tert-butyl-N-methyl-N-[[3-methyl-7-[4-(trifluoromethoxy)phenyl]-4-vinyl-benzimidazol-5-yl]methyl]carbamate

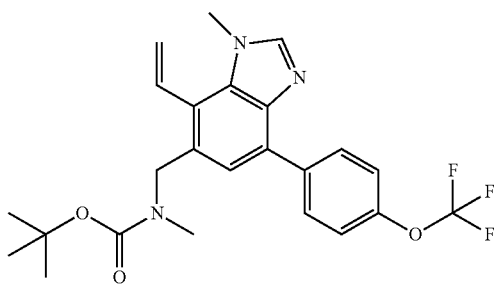 [SMILES: C=Cc1c(CN(C)C(=O)OC(C)(C)C)cc(-c2ccc(OC(F)(F)F)cc2)c2ncn(C)c12]

To a solution of tert-butyl-N-[[3-methyl-7-[4-(trifluoromethoxy)phenyl]-4-vinyl-benzimidazol-5-yl]methyl]carbamate (400 mg, 0.890 mmol) and iodomethane (0.06 mL, 0.94 mmol) in THF (6.0 mL) was added sodium hydride (60% in mineral oil) (39 mg, 0.98 mmol) at 0° C. The reaction was stirred at 0° C. for 30 min and then warmed to rt. After 2 h excess iodomethane (0.06 mL, 0.94 mmol) and sodium hydride (60% in mineral oil) (39 mg, 0.98 mmol) was added at 0° C. and the reaction was warmed to rt. After 3 h (5 h total), the reaction was cooled in an ice-bath and water (30 mL) was added dropwise. The product was extracted with EtOAc (3×30 mL). The organic layers were dried over sodium sulfate, filtered and concentrated. The crude was purified by flash column chromatography (silica, 0-100% EtOAc in heptanes) to afford the title compound (392 mg, 95% yield) as a yellow solid. LCMS (ESI): m/z 462.2 (M+H)$^+$.

Step 3: rac-tert-butyl-N-[[4-(1,2-dihydroxyethyl)-3-methyl-7-[4-(trifluoromethoxy)phenyl]benzimidazol-5-yl]methyl]-N-methyl-carbamate

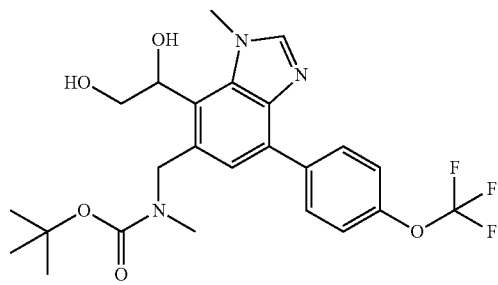 [SMILES: CN(Cc1cc(-c2ccc(OC(F)(F)F)cc2)c2ncn(C)c2c1C(O)CO)C(=O)OC(C)(C)C]

tert-Butyl-N-methyl-N-[[3-methyl-7-[4-(trifluoromethoxy)phenyl]-4-vinyl-benzimidazol-5-yl]methyl]carbamate (392 mg, 0.85 mmol) and 4-methylmorpholine N-oxide (119 mg, 1.02 mmol) was dissolved in acetone (6.8 mL) and water (1.7 mL). To this was then added osmium tetroxide (4% wt in water) (270 µL, 0.04 mmol) at 0° C. The reaction was stirred at rt for 2 h. Fresh osmium tetroxide (4% wt in water) (270 µL, 0.0400 mmol) was added and the reaction was stirred for an additional 15 h. The reaction was diluted with water (30 mL) and the product was extracted with DCM (3×30 mL). The organic layers were combined, dried over sodium sulfate, filtered and concentrated. The reaction mixture was re-subjected to the reaction conditions described above with the following modification CH$_3$CN (3.0 mL) water (1.0 mL) instead of acetone and water. The reaction was stirred at rt for 4 days. The above work-up procedure was repeated and the crude was purified by flash column chromatography (silica, 0-5% MeOH in DCM) to afford the title compound (214 mg, 51% yield) as a white solid. LCMS (ESI): m/z 496.2 (M+H)$^+$.

Step 4: (R)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide (Compound 65) and (S)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide (Compound 66)

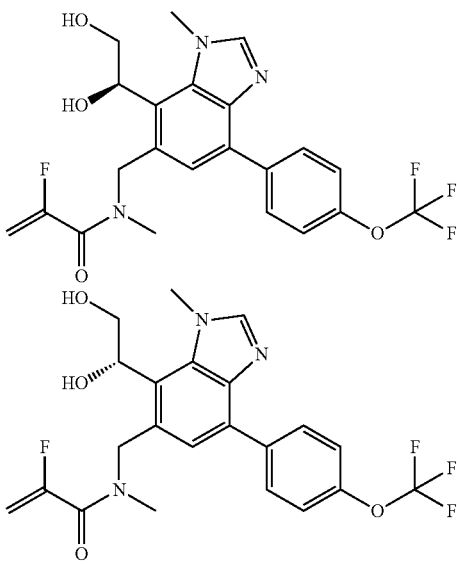

To a solution of tert-butyl-N-[[4-(1,2-dihydroxyethyl)-3-methyl-7-[4-(trifluoromethoxy)phenyl]benzimidazol-5-yl]methyl]-N-methyl-carbamate (214 mg, 0.43 mmol) in DCM (2.2 mL) was added trifluoroacetic acid (1.0 mL, 13 mmol) at rt. After 30 min toluene (~2 mL) was added and the mixture was concentrated. To residue was added EEDQ (98 mg, 0.40 mmol), 2-fluoroprop-2-enoic acid (33 mg, 0.36 mmol) and a mixture of DCM (0.9 mL) and methanol (0.9 mL). The reaction was cooled in an ice-bath and triethylamine (0.5 mL, 3.95 mmol) was added. The reaction was gradually warmed to rt and stirred at rt for 3 h. Excess EEDQ (98 mg, 0.40 mmol) and 2-fluoroprop-2-enoic acid (33 mg, 0.36 mmol) were added and the reaction was stirred at rt for an additional 3 h. Again excess EEDQ (98 mg, 0.40 mmol) and 2-fluoroprop-2-enoic acid (33 mg, 0.36 mmol) and triethylamine (0.11 mL, 0.79 mmol) were added and the reaction was stirred for an additional 16 h. Saturated aqueous NH$_4$Cl solution(5 mL) was added and the product was extracted using 20% iPrOH in CHCl$_3$ (3×5 mL) and the combined organic phase was dried over sodium sulfate, filtered and concentrated. The crude product was purified by flash column chromatography (silica, C18, 0-100% ACN in 10 mM ammonium formate). Fractions containing the desired product were combined and ACN was removed. The product was extracted with 20% iPrOH in CHCl$_3$ (3×50 mL), dried over sodium sulfate, filtered and concentrated. The product was further purified using Buchi prep system (Luna column, 30%-70% MeCN in 10 mM AmF water) to afford 35 mg as a mixture of enantiomers. LCMS (ESI): n/z 468.2 (M+H)$^+$.

The above racemate was further purified by chiral chromatography (Anal. Column: ChiralPak IA, 250 mm×4.6 mm ID, 5 pm, Mobile Phase: 6:12:82 MeOH: iPrOH: hexanes;

isocratic Flow: 1 mL/min, column temp.: ~26° C., run time: 20 min; wavelength: 280 nm) to afford:

(R)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide (12 mg, 34% yield) (peak 1, stereochemistry was arbitrarily assigned) as a white solid. $^1$H NMR (400 MHz, DMSO-$d_6$); mixture of roatmers: δ 8.20 (s, 1H), 8.05 (d, J=8.6 Hz, 2H), 7.47 (d, J=8.1 Hz, 2H), 7.24-7.04 (m, 1H), 5.76 (d, J=3.8 Hz, 11H), 5.65-5.04 (m, 4H), 5.02-4.76 (m, 2H), 4.13 (s, 3H), 3.91-3.76 (m, 1H), 3.73-3.59 (m, 1H), 3.04-2.78 (m, 3H). LCMS (ESI): m/z 468.3 (M+H)$^+$.

The other enantiomer (1S) was further purified using Buchi prep system (Luna column, 30%-80% MeCN in 10 mM AmF water). afford (S)—N-((7-(1,2-dihydroxyethyl)-1-methyl-4-(4-(trifluoromethoxy)phenyl)-1H-benzo[d]imidazol-6-yl)methyl)-2-fluoro-N-methylacrylamide (10.3 mg, 29% yield) (peak 2, stereochemistry was arbitrarily assigned) as a white solid. $^1$H NMR (400 MHz, DMSO-$d_6$); mixture of rotamers: 6 8.20 (d, J=4.6 Hz, 1H), 8.17-7.99 (m, 2H), 7.51-7.43 (m, 2H), 7.23-7.02 (m, 1H), 5.82-5.63 (m, 1H), 5.60-4.61 (m, 5H), 4.20-4.05 (m, 3H), 3.91-3.78 (m, 1H), 3.75-3.57 (m, 11H), 3.01-2.77 (m, 3H). LCMS (ESI): m/z 468.0 (M+H)$^+$.

Example 63 (Compound 67)

N-[[4-cyano-7-[4-(trifluoromethoxy)phenyl]-2,3-dihydrobenzofuran-5-yl]methyl]-2-fluoro-prop-2-enamide

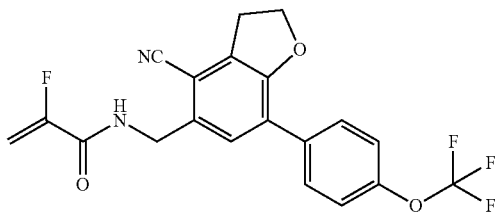 [SMILES: C=C(F)C(=O)NCc1cc(-c2ccc(OC(F)(F)F)cc2)c2c(c1C#N)CCO2]

To 2-Fluoroprop-2-enoic acid (8.1 mg, 0.090 mmol) and 5-(aminomethyl)-7-[4-(trifluoromethoxy)phenyl]-2,3-dihydrobenzofuran-4-carbonitrile (30 mg, 0.090 mmol) in DMF (1.2 mL) was added triethylamine (0.05 mL, 0.36 mmol). A 50% solution of propylphosphonic acid in EtOAc (0.11 mL, 0.18 mmol) was added and stirred for 30 min. DCM (2 mL) and water (2 mL) were added, then extraction with DCM (3×5 mL), dried over magnesium sulfate, filtered and concentrated. The crude was purified by flash column chromatography (silica, DCM to 80/18/2 DCM/MeOH/NH$_4$OH) to yield the title compound (8.0 mg, 22% yield) as a white solid.

$^1$H NMR (400 MHz, DMSO-$d_6$) δ 9.11 (s, 1H), 7.79 (d, J=8.9 Hz, 1H), 7.47 (d, J=10.8 Hz, 3H), 5.54 (dd, J=48.0, 3.5 Hz, 11H), 5.26 (dd, J=15.6, 3.5 Hz, 11H), 4.70 (t, J=8.8 Hz, 2H), 4.47 (d, J=5.7 Hz, 2H), 3.42 (t, J=8.6 Hz, 3H); LCMS (ESI): m/z 406.6 (M+H)$^+$.

Example 64 (Compound 68)

N-[[1-methyl-7-[4-(trifluoromethoxy)phenyl]benzimidazol-5-yl]methyl]prop-2-enamide

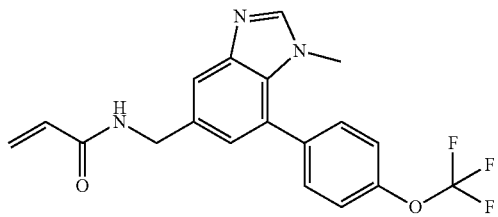 [SMILES: C=CC(=O)NCc1cc(-c2ccc(OC(F)(F)F)cc2)c2c(c1)ncn2C]

Step 1: 7-bromo-3-methyl-benzimidazole-5-carbonitrile and 7-bromo-1-methyl-benzimidazole-5-carbonitrile

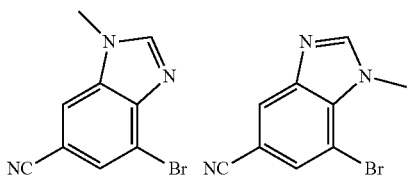

7-bromo-1H-benzimidazole-5-carbonitrile (400 mg, 1.8 mmol) was dissolved in DMF (9.0 mL) and cooled to 0° C. Sodium hydride (86 mg, 2.2 mmol) was added slowly followed by iodomethane (307 mg, 2.16 mmol) dropwise. The reaction was warmed to rt and stirred for 16 h. The mixture was quenched with water (10 mL) and extracted into EtOAc (3×20 mL), the combined organic phased were washed with brine (10 mL), dried over magnesium sulfate, filtered and concentrated. The crude was purified by flash column chromatography (silica, 0 to 30% MeOH/DCM) to yield a mixture of the above compounds (314 mg, 74% yield) in an approximately 1:1 ratio. LCMS (ESI): m/z 238.0 (M+H)$^+$.

Step 2: 3-methyl-7-[4-(trifluoromethoxy)phenyl] benzimidazole-5-carbonitrile and 1-methyl-7-[4-(trifluoromethoxy)phenyl]benzimidazole-5-carbonitrile

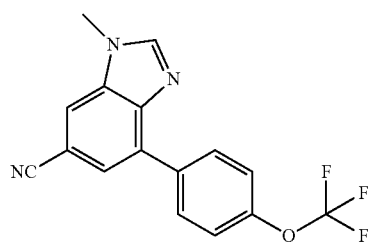

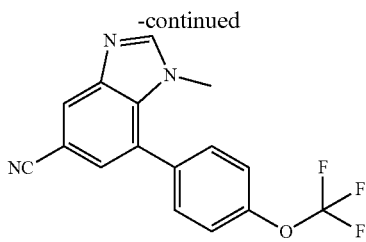

4-(trifluoromethoxy)phenylboronic acid (274 mg, 1.33 mmol), a mixture of 7-bromo-3-methyl-benzimidazole-5-carbonitrile and 7-bromo-1-methyl-benzimidazole-5-carbonitrile (314 mg, 1.33 mmol), 1,1-bis(diphenylphosphino) ferrocene palladium dichloride (49 mg, 0.07 mmol), and potassium carbonate (551 mg, 3.99 mmol) were placed under vacuum and refilled with an atmosphere of nitrogen. A mixture of 1,4-dioxane (5 mL) and water (1 mL) were added and heated to 80° C. for 16 h. The reaction was cooled to rt, magnesium sulfate was added and the mixture was filtered through Celite and concentrated. The crude was purified by flash column chromatography (silica, 0-100% EtOAc/heptanes) to yield 3-methyl-7-[4-(trifluoromethoxy) phenyl]benzimidazole-5-carbonitrile (220 mg, 52% yield) $^1$H NMR (400 MHz, CDCl$_3$) δ 8.16 (s, 1H), 8.03-7.95 (m, 2H), 7.74 (d, J=1.3 Hz, 1H), 7.68 (d, J=1.3 Hz, 1H), 7.37 (d, J=8.1 Hz, 2H), 3.95 (s, 3H); 1D NOESY obtained irradiating the peak at 3.95 ppm (methyl) resulted in the appearance of the peaks at 8.16 ppm (benzimidazole) and 7.74 ppm (benzimidazole); LCMS (ESI): m/z 318.4 (M+H)$^+$ and 1-methyl-7-[4-(trifluoromethoxy) phenyl]benzimidazole-5-carbonitrile (170 mg, 40% yield)$^1$H NMR (400 MHz, CDCl$_3$) δ 8.16 (s, 1H), 7.45 (d, J=7.9 Hz, 2H), 7.39 (s, 1H), 7.35 (d, J=7.4 Hz, 2H), 3.46 (s, 3H); 1D NOESY obtained irradiating the peak at 3.46 ppm (methyl) resulted in the appearance of the peaks at 8.16 ppm (benzimidazole) and 7.45 ppm (4-(trifluoromethoxy)phenyl); LCMS (ESI): m/z 318.4 (M+H)$^+$.

Step 3: N-[[1-methyl-7-[4-(trifluoromethoxy)phenyl]benzimidazol-5-yl]methyl]prop-2-enamide To 1-methyl-7-[4-(trifluoromethoxy)phenyl]benzimidazole-5-carbonitrile (100 mg, 0.32 mmol) in THF (3.2 mL) was added a 1 M solution of BH$_3$ in THF (0.63 mL, 0.63 mmol) slowly. The resulting solution was refluxed for 30 min then cooled down to rt and quenched with 1 M aqueous NaOH solution (3.2 mL) and extracted into EtOAc (3×10 mL). The combined organic phased were washed with brine (10 mL), dried over magnesium sulfate, filtered and concentrated to yield crude [1-methyl-7-[4-(trifluoromethoxy) phenyl]benzimidazol-5-yl]methanamine. LCMS (ESI): m/z 322.5 (M+H)$^+$.

This solid was combined with N-methylimidazole (102 mg, 1.24 mmol) and dissolved in DMF (3.1 mL). Triethylamine (0.17 mL, 1.24 mmol) was added followed by acrylic acid (0.03 mL, 0.47 mmol) and a 50% solution of propylphosphonic acid in EtOAc (0.46 mL, 0.78 mmol). The mixture was stirred at rt for 30 min. Water (5 mL) was added to quench the reaction and the mixture was extracted into EtOAc (3×10 mL). The combined organic phases was washed with brine (10 mL), dried over sodium sulfate, filtered and concentrated. The crude was purified by flash column chromatography (silica, C18, 30-70% MeCN/10 mM ammonium formate) to afford the title compound (21 mg, 18% yield). $^1$H NMR (400 MHz, DMSO-d$_6$) δ 8.62 (s, 1H), 8.17 (s, 11H), 7.58 (d, J=8.7 Hz, 3H), 7.45 (d, J=7.9 Hz, 2H), 7.01 (s, 11H), 6.26 (dd, J=17.1, 10.1 Hz, 1H), 6.10 (dd, J=17.1, 2.2 Hz, 1H), 5.59 (dd, J=10.1, 2.2 Hz, 1H), 4.46 (d, J=5.9 Hz, 2H), 3.35 (s, 3H). LCMS (ESI): m/z 376.2 (M+H)$^+$.

Example 65 (Compound 69)

N-[[9-methyl-6-[4-(trifluoromethoxy)phenyl]purin-2-yl]methyl]prop-2-enamide

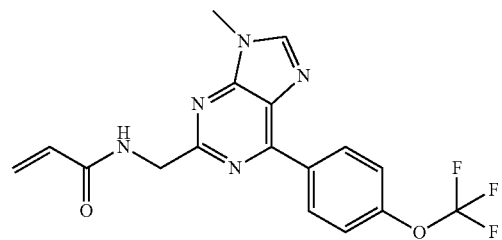 [SMILES: C=CC(=O)NCc1nc(-c2ccc(OC(F)(F)F)cc2)c2ncn(C)c2n1]

Step 1: 2-chloro-9-methyl-6-[4-(trifluoromethoxy) phenyl]purine

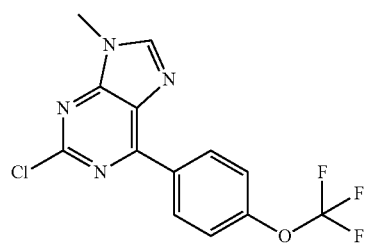 [SMILES: Cn1cnc2c(-c3ccc(OC(F)(F)F)cc3)nc(Cl)nc21]

4-(trifluoromethoxy)phenylboronic acid (1.01 g, 4.93 mmol), 2,6-dichloro-9-methyl-purine (1.0 g, 4.93 mmol) and potassium carbonate (2.72 mg, 19.7 mmol) were dissolved in a mixture of 1,4-dioxane (10 mL) and water (2 mL) and purged with nitrogen. 1,1-bis(diphenylphosphino)ferrocene palladium dichloride (183 mg, 0.25 mmol) was added. The reaction was sealed and heated to 120° C. in a microwave for 30 min. The mixture was extracted with EtOAc (3×15 mL) and solvent removed to yield a crude solid. The crude was dissolved in DCM (10 mL) and MeOH (10 mL), solvent was removed until the formation of a precipitate. The solid was filtered, washed with MeOH to yield the title compound (800 mg, 49% yield). LCMS (ESI): m/z 329.0 (M+H)$^+$.

Step 2: 9-methyl-6-[4-(trifluoromethoxy)phenyl]purine-2-carbonitrile

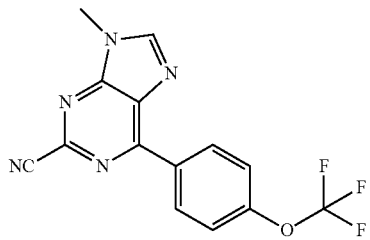 [SMILES: Cn1cnc2c(-c3ccc(OC(F)(F)F)cc3)nc(C#N)nc21]

2-chloro-9-methyl-6-[4-(trifluoromethoxy)phenyl]purine (800 mg, 2.43 mmol) and zinc cyanide (343 mg, 2.92 mmol) were added to anhydrous DMF (9.7 mL) and purged with $N_2$ for 5 min. Palladium tetrakis(triphenylphosphine) (141 mg, 0.12 mmol) was added and the mixture was heated to 180° C. in a microwave reactor for 30 min. The reaction was then diluted with EtOAc (50 mL) and water (15 mL), phased were separated and organic phase was washed with water (2×15 mL) followed by brine (15 mL) and was concentrated. The residue was dissolved in DCM (20 mL) and MeOH (10 mL), solvent was removed until the formation of a precipitate. The solid was filtered, washed with MeOH to yield the title compound (516 mg, 66% yield). LCMS (ESI): m/z 320.0 $(M+H)^+$.

Step 3: N-[[9-methyl-6-[4-(trifluoromethoxy)phenyl]purin-2-yl]methyl]prop-2-enamide

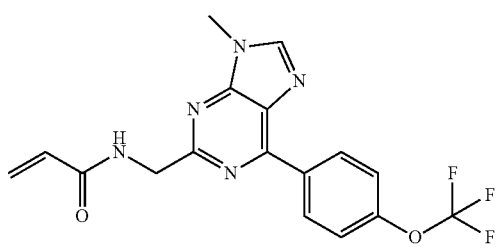 [SMILES: C=CC(=O)NCc1nc(-c2ccc(OC(F)(F)F)cc2)c2ncn(C)c2n1]

9-methyl-6-[4-(trifluoromethoxy)phenyl]purine-2-carbonitrile (240 mg, 0.75 mmol) was dissolved in THF (3.2 mL) and 1 M solution of $BH_3$ in THF (1.13 mL, 1.13 mmol) was added slowly. The resulting solution was refluxed for 30 min. The reaction was cooled down to rt and quenched with 1 M aqueous NaOH solution (5 mL) and extracted with EtOAc (3×10 mL). The combined organic phased were washed with brine (10 mL), dried over magnesium sulfate, filtered and concentrated to yield crude [9-methyl-6-[4-(trifluoromethoxy)phenyl]-7,8-dihydropurin-2-yl]methanamine. LCMS (ESI): m/z 326.1 $(M+H)^+$.

This solid was dissolved in DCM (3.1 mL), 2,3-dichloro-5,6-dicyano-p-benzoquinone (204 mg, 0.90 mmol) was added and stirred at rt for 30 min. 1 M aqueous NaOH solution (5 mL) was added and the mixture was extracted with DCM (3×10 mL), dried over sodium sulfate, filtered and concentrated to yield [9-methyl-6-[4-(trifluoromethoxy)phenyl]purin-2-yl]methanamine. LCMS (ESI): m/z 324.1 $(M+H)^+$.

This solid was dissolved in THF (7.5 mL) and 1 M aqueous $Na_2CO_3$ solution (2.99 mL, 2.99 mmol), N-meth-ylimidazole (246 mg, 2.99 mmol) were added followed by acrylic anhydride (0.103 mL, 0.90 mmol) and the mixture was stirred at rt for 30 min. The solution was extracted with EtOAc (3×20 mL), the combined organic phases were washed with brine (10 mL), dried over sodium sulfate, filtered and concentrated. The crude was purified by flash column chromatography (silica, C18, 0-100% MeCN/10 mM ammonium formate) to afford the title compound (96 mg, 34% yield). $^1$H NMR (400 MHz, DMSO-$d_6$) δ 8.96 (dd, J=9.3, 2.4 Hz, 2H), 8.75 (t, J=5.7 Hz, 1H), 8.61 (s, 1H), 7.59 (d, J=8.2 Hz, 2H), 6.42 (dd, J=17.1, 10.3 Hz, 1H), 6.13 (dd, J=17.1, 2.1 Hz, 1H), 5.64 (dd, J=10.2, 2.1 Hz, 1H), 4.69 (d, J=5.9 Hz, 2H), 3.84 (s, 3H); LCMS (ESI): m/z 378.2 $(M+H)^+$.

Example 66 (Compound 70) and Example 67 (Compound 71)

N-[[7-[(1S)-1,2-dihydroxyethyl]-1-methyl-4-[4-(trifluoromethoxy)phenyl]imidazo[4,5-c]pyridin-6-yl]methyl]prop-2-enamide and N-[[7-[(1R)-1,2-dihydroxyethyl]-1-methyl-4-[4-(trifluoromethoxy)phenyl]imidazo[4,5-c]pyridin-6-yl]methyl]prop-2-enamide

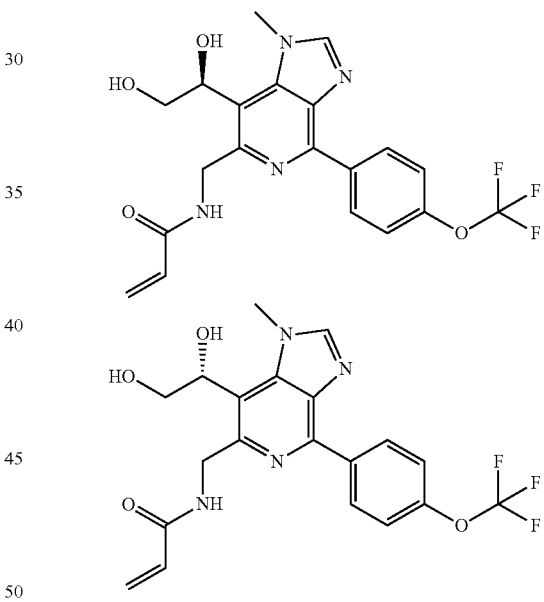

Step 1: 5-bromo-6-methyl-3-nitro-pyridine-2,4-diol

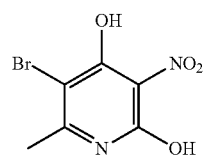

6-methyl-3-nitro-pyridine-2,4-diol (25 g, 146.96 mmol) was suspended in acetic acid (245 mL). Bromine (8.3 mL, 162 mmol) was then added and the mixture was stirred at rt for 17 h. Water (500 mL) was added to precipitate a solid.

The solids were washed with H₂O (3×100 mL) then with EtOH (3×100 mL) and dried to provide title compound (30.8 g, 84% yield) as a yellow solid. LCMS (ESI): m/z 248.9 (M+H)⁺.

Step 2:
5-bromo-2,4-dichloro-6-methyl-3-nitro-pyridine

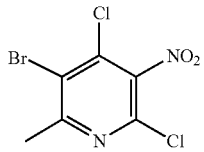

5-bromo-6-methyl-3-nitro-pyridine-2,4-diol (37.5 g, 151 mmol) was suspended in phosphorus oxychloride (140 mL, 1506 mmol) and the reaction was stirred at 100° C. for 18 h. Remaining POCl₃ was distilled off and the resulting was cooled to 0° C. and water (100 mL) was added dropwise. The mixture was extracted with EtOAc (3×100 mL) and the combined organic phased were washed with brine (100 mL), dried over sodium sulfate, filtered and concentrated. The crude was purified by flash column chromatography (silica, 0-40% EtOAc/heptanes) to yield the title compound (23.4 g, 54% yield) as a yellow solid. LCMS (ESI): m/z 284.9 (M+H)⁺.

Step 3: 3-bromo-6-chloro-N,2-dimethyl-5-nitropyridin-4-amine

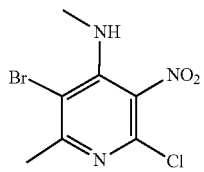

5-bromo-2,4-dichloro-6-methyl-3-nitro-pyridine (18.0 g, 63.0 mmol) was dissolved in THF (164 mL) and cooled to 0° C. A 33% solution of methylamine in ethanol (17.8 mL, 188.87 mmol) and triethylamine (0.88 mL, 6.3 mmol) were added. The reaction was stirred at rt for 15 min then water (200 mL) was added and the solution was extracted with EtOAc (3×200 mL). The combined organic phases were washed with 1 M aqueous HCl solution (100 mL) then with brine (100 mL), dried over sodium sulfate, filtered and concentrated to yield the title compound (17.6 g, 99% yield) as a yellow solid. LCMS (ESI): m/z 280 (M+H)⁺.

Step 4: 7-bromo-1,6-dimethyl-4-(4-(trifluoromethoxy)phenyl)-1H-imidazo[4,5-c]pyridine

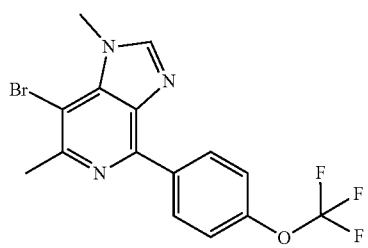 [SMILES: Cc1nc(-c2ccc(OC(F)(F)F)cc2)c2ncn(C)c2c1Br]

3-bromo-6-chloro-N,2-dimethyl-5-nitropyridin-4-amine (1.4 g, 4.99 mmol), 4-(trifluoromethoxy)phenylboronic acid (925 mg, 4.49 mmol) and potassium carbonate (2.07 g, 14.97 mmol) were dissolved in 1,4-dioxane (15 mL) and water (3 mL) and purged with nitrogen. Palladium tetrakis (triphenylphosphine) (404 mg, 0.35 mmol) was added and the solution was stirred at 75° C. for 17 h. The solution was cooled to rt, EtOAc (10 mL) was added, phases were separated and organic phase was and dried over sodium sulfate and filtered through Celite. The crude was purified by flash column chromatography (silica, 0-30% EtOAc/heptanes) to obtain a mixture of starting material, desire product and bis aryl side product (600 mg). LCMS (ESI): m/z 408.0 (M+H)⁺. To the mixture in ethanol (7 mL) was added tin(II) chloride dihydrate (1.35 g, 5.91 mmol) and heated to 45° C. for 17 h. The reaction was cooled down to rt and quenched with 2 M aqueous NaOH solution (7 mL), extracted with DCM (3×30 mL). The combined organic phases were washed with saturated aqueous NaHCO₃ solution (20 mL), dried over sodium sulfate and concentrated to yield crude 5-bromo-N4,6-dimethyl-2-[4-(trifluoromethoxy)phenyl] pyridine-3,4-diamine. LCMS (ESI): m/z 378.0 (M+H)⁺.

This solid was dissolved in formic acid (16.7 mL, 442.62 mmol) and heated to 90° C. for 2 h. Solvent was removed and the residual was dissolved in DCM (30 mL) then was washed with saturated aqueous Na₂CO₃ solution (10 mL) and brine (10 mL), dried over sodium sulfate, filtered and concentrated. The crude was purified by flash column chromatography (silica, 20-50% EtOAc/heptanes) to yield the title compound was a white solid (390 mg, 20% yield). LCMS (ESI): m/z 387.7 (M+H)⁺.

Step 5: 7-bromo-6-(bromomethyl)-1-methyl-4-[4-(trifluoromethoxy)phenyl]imidazo[4,5-c]pyridine

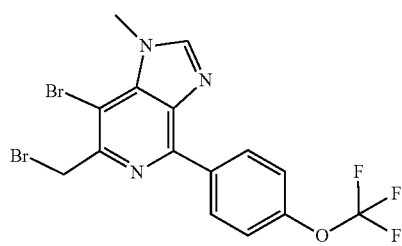 [SMILES: Cn1cnc2c(-c3ccc(OC(F)(F)F)cc3)nc(CBr)c(Br)c21]

A solution of 7-bromo-1,6-dimethyl-4-[4-(trifluoromethoxy)phenyl]imidazo[4,5-c]pyridine (390 mg, 1.01 mmol) and N-bromosuccinimide (216 mg, 1.21 mmol) in carbon tetrachloride (6.5 mL) was purged with nitrogen. Benzoyl peroxide (49 mg, 0.20 mmol) was added and the solution was stirred at 70° C. 17 h. The reaction mixture was cooled to rt and concentrated with silica gel. The crude was purified by flash column chromatography (silica, 30-70% EtOAc/heptane) to yield the title compound (400 mg, 85% yield). LCMS (ESI): m/z 466.0 (M+H)⁺.

Step 6: tert-butyl N-[[7-bromo-1-methyl-4-[4-(trifluoromethoxy)phenyl]imidazo[4,5-c]pyridin-6-yl]methyl]-N-tert-butoxycarbonyl-carbamate

Step 8: N-[[7-[(1S)-1,2-dihydroxyethyl]-1-methyl-4-[4-(trifluoromethoxy)phenyl]imidazo [4,5-c]pyridin-6-yl]methyl]prop-2-enamide and N-[[7-[(1R)-1,2-dihydroxyethyl]-1-methyl-4-[4-(trifluoromethoxy)phenyl]imidazo[4,5-c]pyridin-6-yl]methyl]prop-2-enamide

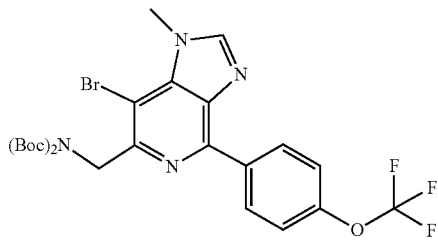

7-bromo-6-(bromomethyl)-1-methyl-4-[4-(trifluoromethoxy)phenyl]imidazo[4,5-c]pyridine (400 mg, 0.86 mmol) and tert-butyl-N-tert-butoxycarbonylcarbamate (243 mg, 1.12 mmol) were dissolved in MeCN (6.5 mL) and cesium carbonate (564 mg, 1.72 mmol) was added and stirred at rt for 90 min. The reaction was diluted with water (10 mL) and extracted with DCM (3×10 mL). The combined organic phases were dried over sodium sulfate, filtered and concentrated to yield the title compound (517 mg, 99% yield). LCMS (ESI): m/z 603.1 (M+H)⁺.

Step 7: tert-butyl-N-tert-butoxycarbonyl-N-[[1-methyl-4-[4-(trifluoromethoxy)phenyl]-7-vinyl-imidazo[4,5-c]pyridin-6-yl]methyl]carbamate

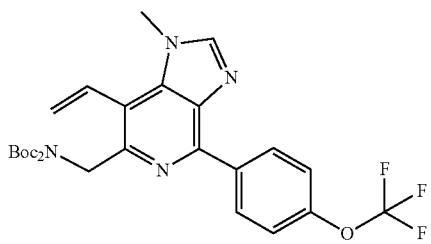

A flask was charged with tert-butyl-N-[[7-bromo-1-methyl-4-[4-(trifluoromethoxy)phenyl]imidazo[4,5-c]pyridin-6-yl]methyl]-N-tert-butoxycarbonyl-carbamate (517 mg, 0.86 mmol), potassium trifluoro(vinyl)boron (345 mg, 2.58 mmol) and 1,1-bis(diphenylphosphino)ferrocene palladium dichloride (64 mg, 0.090 mmol). 1,4-Dioxane:H₂O 5:1 (4 mL) was added followed by addition of triethylamine (0.36 mL, 2.58 mmol). The solution was heated to 80° C. for 17 h. The mixture was cooled to rt, diluted with EtOAc (20 mL), dried over sodium sulfate, filtered through Celite and concentrated. The crude was purified by flash column chromatography (silica, 20-60% EtOAC/heptanes) to yield the title compound (155 mg, 33% yield). LCMS (ESI): m/z 549.3 (M+H)⁺.

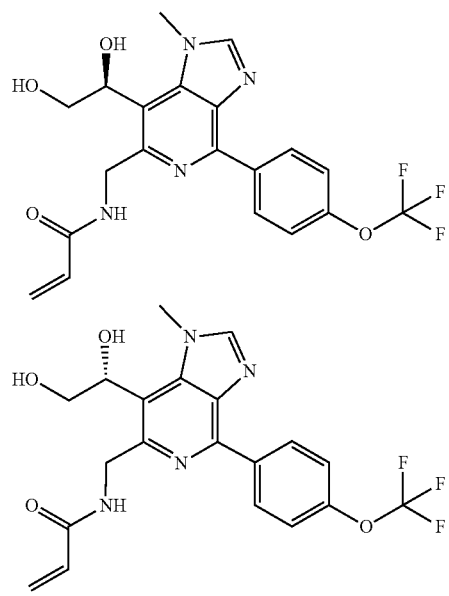

tert-butyl-N-tert-butoxycarbonyl-N-[[1-methyl-4-[4-(trifluoromethoxy)phenyl]-7-vinyl-imidazo[4,5-c]pyridin-6-yl]methyl]carbamate (150 mg, 0.300 mmol) and magnesium perchlorate hexahydrate (27.2 mg, 0.0100 mmol) were dissolved in MeCN (3 mL) and the mixture was stirred at 60° C. for 1 h. The reaction was then concentrated and dissolved in EtOAc (50 mL). The organic layer was washed with brine (10 mL), dried over sodium sulfate, filtered and concentrated to give crude tert-butyl N-[[1-methyl-4-[4-(trifluoromethoxy)phenyl]-7-vinyl-imidazo[4,5-c]pyridin-6-yl]methyl]carbamate (127 mg). LCMS (ESI): m/z 449.2 (M+H)⁺.

This crude material was dissolved in DCM (12 mL) and 4-methylmorpholine N-oxide (0.06 mL, 0.57 mmol) was added followed by osmium tetraoxide (4% wt in water) (180 µL, 0.03 mmol). The reaction was stirred for 20 h. More osmium tetraoxide (4% wt in water) (180 µL, 0.030 mmol) was added and the reaction was stirred for 72 h. The reaction was then diluted with saturated aqueous sodium thiosulfate solution (20 mL) and extracted with DCM (3×20 mL). The combined organic phases were dried over magnesium sulfate and concentrated to give tert-butyl N-[[7-(1,2-dihydroxyethyl)-1-methyl-4-[4-(trifluoromethoxy)phenyl]imidazo[4,5-c]pyridin-6-yl]methyl]carbamate (136 mg) as a black solid. LCMS (ESI): m/z 483.1 (M+H)⁺.

This black solid was dissolved in DCM (1.2 mL) and TFA (175 µL) was added. The reaction was stirred at rt for 1 h then was concentrated with toluene (2 mL). The crude material was dissolved in THF (1.7 mL) and saturated aqueous Na₂CO₃ solution (350 L) was added. To the mixture was added acrylic anhydride (20 mg, 0.16 mmol) at rt and stirred for 10 min. The reaction was diluted with DCM (10 mL) and washed with water (5 mL). The organic phase was dried over magnesium sulfate and concentrated. The crude was purified by flash column chromatography (silica, C18, 0-100% MeCN/10 mM ammonium formate) to yield a mixture of enantiomers (50 mg). The above racemate was purified by chiral SFC giving:

N-[[7-[(1S)-1,2-dihydroxyethyl]-1-methyl-4-[4-(trifluoromethoxy)phenyl]imidazo[4,5-c]pyridin-6-yl]methyl]prop-2-enamide (12.2 mg, 19%) (peak 1, stereochemistry was arbitrarily assigned) LCMS (ESI): m/z 437.1 (M+H)+; $^1$H NMR (400 MHz, DMSO-d$_6$) 8.85 (d, J=8.5 Hz, 2H), 8.44 (s, 1H), 8.38 (s, 1H), 7.50 (d, J=8.0 Hz, 2H), 6.42 (dd, J=17.1, 10.2 Hz, 1H), 6.13 (d, J=17.1 Hz, 1H), 5.92 (s, 1H), 5.61 (d, J=10.0 Hz, 1H), 5.42 (s, 1H), 5.04 (s, 1H), 4.93 (dd, J=14.7, 5.6 Hz, 1H), 4.64 (d, J=14.9 Hz, 1H), 4.15 (s, 3H), 3.92-3.78 (m, 1H), 3.71 (s, 1H).

N-[[7-[(1R)-1,2-dihydroxyethyl]-1-methyl-4-[4-(trifluoromethoxy)phenyl]imidazo[4,5-c]pyridin-6-yl]methyl]prop-2-enamide (11.3 mg, 18% yield) (peak 2, stereochemistry was arbitrarily assigned) LCMS (ESI): m/z 437.1 (M+H)+; $^1$H NMR (400 MHz, DMSO-d$_6$) 8.85 (d, J=8.4 Hz, 2H), 8.44 (s, 1H), 8.38 (s, 1H), 7.50 (d, J=8.2 Hz, 2H), 6.42 (dd, J=17.0, 10.1 Hz, 1H), 6.13 (d, J=17.3 Hz, 1H), 5.92 (s, 1H), 5.61 (d, J=10.1 Hz, 1H), 5.42 (s, 1H), 5.03 (s, 1H), 4.93 (dd, J=15.2, 5.7 Hz, 1H), 4.65 (dd, J=15.1, 4.6 Hz, 1H), 4.15 (s, 3H), 3.92-3.79 (m, 1H), 3.78-3.67 (m, 1H).

Example 68 (Compound 72)

N-[[3-methyl-4-(1H-pyrazol-4-yl)-7-[4-(trifluoromethoxy)phenyl]benzimidazol-5-yl]methyl]prop-2-enamide

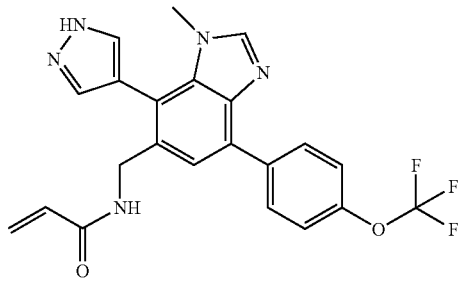 [SMILES: C=CC(=O)NCc1cc(-c2ccc(OC(F)(F)F)cc2)c2ncn(C)c2c1-c1cn[nH]c1]

tert-Butyl-N-[[4-bromo-3-methyl-7-[4-(trifluoromethoxy)phenyl]benzimidazol-5-yl]methyl]-N-tert-butoxycarbonyl-carbamate (250 mg, 0.42 mmol) (described in Example 27 step 6), tert-butyl 4-(4,4,5,5-tetramethyl-1,3,2-dioxaborolan-2-yl)pyrazole-1-carboxylate (122 mg, 0.42 mmol) and Pd SPhos G2 (15 mg, 0.020 mmol) were dissolved in 1,4-dioxane (1.7 mL) and water (0.2 mL). The mixture was purged with nitrogen, potassium carbonate (288 mg, 2.08 mmol) was added, further purged with nitrogen and then heated to 80° C. for 18 h. The reaction was cooled to rt and EtOAc (10 mL) was added. The solution was filtered through sodium sulfate and Celite and concentrated to yield a crude solid (286 mg). LCMS (ESI): m/z 688.4 (M+H)+. This crude solid was dissolved in DCM (1.8 mL) and TFA (1.6 mL, 21 mmol) was added and the mixture was stirred for 3 h. Toluene (2 mL) was added and solvent removed to yield a crude residue. LCMS (ESI): m/z 388.2 (M+H)+.

This crude residue was dissolved in THF (4 mL) and 1 M aqueous Na$_2$CO$_3$ solution (4.2 mL, 4.2 mmol) was added. N-methylimidazole (0.02 mL, 0.21 mmol) was added followed by acrylic anhydride (0.05 mL, 0.42 mmol) and the mixture was stirred at rt for 30 min. Water (5 mL) was added and extracted into EtOAc (3×20 mL). The combined organic phases was washed with brine (10 mL), dried over sodium sulfate, filtered and concentrated. The crude was purified by preparative HPLC to yield the title compound (18.1 mg, 10% yield) as a white solid. LCMS (ESI): m/z 442.2 (M+H)+. $^1$H NMR (400 MHz, DMSO-d$_6$) δ 13.11 (s, 1H), 8.36 (t, J=5.3 Hz, 1H), 8.16 (s, 1H), 8.14 (d, J=8.8 Hz, 2H), 7.92 (s, 1H), 7.63 (s, 1H), 7.48 (d, J=8.1 Hz, 2H), 7.46 (s, 1H), 6.26 (dd, J=17.1, 10.1 Hz, 1H), 6.07 (dd, J=17.1, 2.2 Hz, 1H), 5.56 (dd, J=10.1, 2.3 Hz, 1H), 4.23 (d, J=5.4 Hz, 2H), 3.31 (s, 4H).

Example 69 (Compound 73)

N-((7-(hydroxymethyl)-1-methyl-4-(4-(trifluoromethoxy)phenyl)-1H-imidazo[4,5-c]pyridin-6-yl)methyl)acrylamide

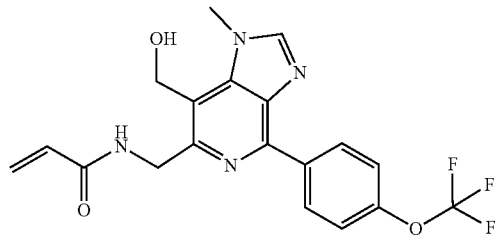 [SMILES: C=CC(=O)NCc1nc(-c2ccc(OC(F)(F)F)cc2)c2ncn(C)c2c1CO]

tert-Butyl-N-tert-butoxycarbonyl-N-[[1-methyl-4-[4-(trifluoromethoxy)phenyl]-7-vinyl-imidazo[4,5-c]pyridin-6-yl]methyl]carbamate (155 mg, 0.28 mmol) (described in Examples 66 and 67, step 7) was dissolved in methanol (3 mL) and cooled to −78° C. Ozone was bubbled for 15 min, the solution was purged with nitrogen for 5 min and then sodium borohydride (214 mg, 5.65 mmol) was added. The cooling bath was removed and it was stirred for 30 min then was diluted with 1 M aqueous HCl solution (5 mL) and extracted with DCM (3×10 mL). The combined organic phases were dried with magnesium sulfate, filtered and concentrated to give 156 mg as a brown solid. LCMS (ESI): m/z 553.3 (M+H)+.

This brown solid was dissolved in DCM (1.8 mL) and TFA (1.1 mL, 14 mmol) was added. The solution was stirred for 3 h then quenched with saturated aqueous NaHCO$_3$ solution (4 mL) and extracted with DCM (3×10 mL). The combined organic phases were dried over sodium sulfate, filtered and concentrated to yield a crude residue. LCMS (ESI): m/z 353.2 (M+H)+. This crude residue was dissolved in THF (7.5 mL), 1 M aqueous Na$_2$CO$_3$ solution (2.8 mL, 2.8 mmol) and N-methylimidazole (12 mg, 0.14 mmol) were added followed by acrylic anhydride (0.04 mL, 0.34 mmol) and the mixture was stirred at rt for 30 min. Water (5 mL) was added and extracted into EtOAc (3×20 mL). The combined organic phases were washed with brine (10 mL), dried over sodium sulfate, filtered and concentrated. The crude was purified by flash column chromatography (silica, C18, 5-80% MeCN/10 mM ammonium formate) to yield the title compound (22 mg, 19% yield) as a white solid. LCMS (ESI): m/z 407.2 (M+H)+. $^1$H NMR (400 MHz, DMSO-d$_6$) δ 8.85 (d, J=8.9 Hz, 2H), 8.59 (s, 1H), 8.38 (s, 1H), 7.50 (d, J=8.3 Hz, 2H), 6.34 (dd, J=17.1, 10.2 Hz, 1H), 6.11 (dd, J=17.1, 2.2 Hz, 1H), 5.59 (dd, J=10.2, 2.2 Hz, 1H), 5.45 (t, J=5.4 Hz, 1H), 4.93 (d, J=5.5 Hz, 2H), 4.74 (d, J=5.5 Hz, 2H), 4.13 (s, 3H).

Example 70 (Compound 74)

(S)—N-((7-(3,4-dihydroxybut-1-yn-1-yl)-1-methyl-4-(4-(trifluoromethoxy)phenyl)-1H-benzo[d]imidazol-6-yl)methyl)acrylamide

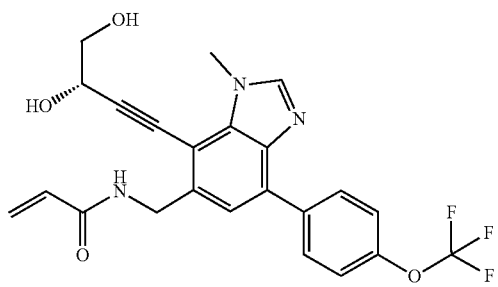 [SMILES: C=CC(=O)NCc1cc(-c2ccc(OC(F)(F)F)cc2)c2ncn(C)c2c1C#C[C@H](O)CO]

(4S)-4-ethynyl-2,2-dimethyl-1,3-dioxolane (84.04 mg, 0.67 mmol), tert-butyl N-[[4-bromo-3-methyl-7-[4-(trifluoromethoxy)phenyl]benzimidazol-5-yl]methyl]-N-tert-butoxycarbonylcarbamate (100 mg, 0.17 mmol) (described in Example 27 step 6), bis(triphenylphosphine)palladium(ll) dichloride (7.0 mg, 0.010 mmol), copper(I) iodide (3.8 mg, 0.020 mmol) and potassium carbonate (161 mg, 1.17 mmol) were dissolved in DMF (1.7 mL) and purged with nitrogen. The reaction was heated at 80° C. for 18 h and then cooled to rt, water (5 mL) was added and extracted with EtOAc (3×10 mL). The combined organic phases were washed with saturated aqueous LiCl solution (3×5 mL), dried over sodium sulfate, filtered and concentrated to yield tert-butyl N-tert-butoxycarbonyl-N-[[3-methyl-4-[2-[(4S)-2,2-dimethyl-1,3-dioxolan-4-yl]ethynyl]-7-[4-(trifluoromethoxy)phenyl]benzimidazol-5-yl]methyl]carbamate (107 mg) as a brown oil. LCMS (ESI): m/z 646.5 (M+H)$^+$.

This brown oil was dissolved in methanol (1.7 mL) and 1 M aqueous HCl solution (1.7 mL, 1.7 mmol) was added and was stirred at rt for 16 h. The reaction was quenched with saturated aqueous NaHCO$_3$ solution (2 mL), then extracted with EtOAc (3×10 mL). The combined organic phases were washed with brine (10 mL), dried over sodium sulfate, filtered and concentrated to give crude tert-butylN-tert-butoxycarbonyl-N-[[3-methyl-4-[(3S)-3,4-dihydroxybut-1-ynyl]-7-[4-(trifluoromethoxy) phenyl]benzimidazol-5-yl]methyl]carbamate (100 mg). LCMS (ESI): m/z 606.5 (M+H)$^+$.

This crude material was dissolved in DCM (1.7 mL) and TFA (1 mL, 0.17 mmol) was added and the solution was stirred for 30 min. Toluene (1 mL) was added and solvent removed under reduced pressure to yield crude (2S)-4-[5-(aminomethyl)-3-methyl-7-[4-(trifluoromethoxy) phenyl] benzimidazol-4-yl]but-3-yne-1,2-diol (66 mg). LCMS (ESI): m/z 406.3 (M+H)$^+$. This crude material was dissolved in THF (7.5 mL) and 1 M aqueous Na$_2$CO$_3$ (1.73 mL, 1.73 mmol), N-methylimidazole (6.9 µL, 0.090 mmol) were added followed by acrylic anhydride (24 µL, 0.21 mmol) and the mixture was stirred at rt for 30 min. Water (5 mL) was added and extracted into EtOAc (3×20 mL). The combined organic phases were washed with brine (10 mL), dried over sodium sulfate, filtered and concentrated. The crude was purified by flash column chromatography (silica, C18, 5-80% MeCN/10 mM ammonium formate) to yield the title compound (3.8 mg, 5% yield) as a white solid. LCMS (ESI): m/z 460.3 (M+H)$^+$. $^1$H NMR (400 MHz, DMSO-d$_6$) δ 8.57 (t, J=5.6 Hz, 1H), 8.24 (s, 1H), 8.14 (d, J=8.9 Hz, 2H), 7.48 (d, J=8.0 Hz, 2H), 7.41 (s, 1H), 6.30 (dd, J=17.1, 10.1 Hz, 1H), 6.12 (dd, J=17.1, 2.2 Hz, 1H), 5.61 (dd, J=10.1, 2.1 Hz, 1H), 5.59 (d, J1=5.9 Hz, 1H), 5.07 (t, J=6.0 Hz, 1H), 4.64 (d, J=5.8 Hz, 2H), 4.53 (q, J=6.0 Hz, 1H), 4.15 (s, 3H), 3.58 (t, J=6.1 Hz, 2H).

Example 71 (Compound 75)

(R)—N-((7-(3,4-dihydroxybut-1-yn-1-yl)-1-methyl-4-(4-(trifluoromethoxy)phenyl)-1H-benzo[d]imidazol-6-yl)methyl)acrylamide

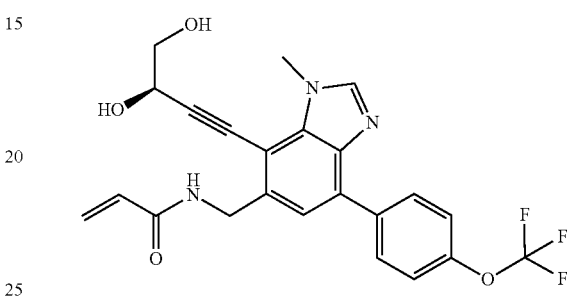

(4R)-4-ethynyl-2,2-dimethyl-1,3-dioxolane (168 mg, 1.33 mmol), tert-butyl N-[[4-bromo-3-methyl-7-[4-(trifluoromethoxy)phenyl]benzimidazol-5-yl]methyl]-N-tert-butoxycarbonyl-carbamate (200 mg, 0.33 mmol) (described in Example 27 step 6), bis(triphenylphosphine)palladium(11) dichloride (14 mg, 0.020 mmol), copper(I) iodide (7.7 mg, 0.040 mmol) and potassium carbonate (322 mg, 2.33 mmol) were dissolved in DMF (1.7 mL) and purged with nitrogen. The reaction heated at 80° C. for 18 h. The reaction was cooled to rt, water (5 mL) was added and extracted with EtOAc (3×10 mL). The combined organic phases were washed with saturated aqueous LiCl solution (3×5 mL), dried over sodium sulfate, filtered and concentrated to yields tert-butyl-N-tert-butoxycarbonyl-N-[[3-methyl-4-[2-[(4R)-2,2-dimethyl-1,3-dioxolan-4-yl]ethynyl]-7-[4-(trifluoromethoxy)phenyl]benzimidazol-5-yl]methyl]carbamate (215 mg) as a brown oil. LCMS (ESI): m/z 646.5 (M+H)$^+$.

This brown oil was dissolved in methanol (1.7 mL) and 1 M aqueous HCl solution (3.3 mL, 3.3 mmol) was added and stirred at rt for 17 h. The reaction was quenched with saturated aqueous NaHCO$_3$ solution (2 mL), then extracted with EtOAc (3×10 mL). The combined organic phases were washed with brine (10 mL), dried over sodium sulfate, filtered and concentrated to give crude tert-butyl-N-tert-butoxycarbonyl-N-[[3-methyl-4-[(3R)-3,4-dihydroxybut-1-ynyl]-7-[4-(trifluoromethoxy) phenyl]benzimidazol-5-yl] methyl]carbamate (200 mg). LCMS (ESI): m/z 606.5 (M+H)$^+$.

This crude material was dissolved in DCM (1.6 mL) and TFA (1 mL, 0.33 mmol) was added and the solution was stirred for 30 min. Toluene (1 mL) was added and solvent removed under reduced pressure to yield (2R)-4-[5-(aminomethyl)-3-methyl-7-[4-(trifluoromethoxy)phenyl]benzimidazol-4-yl]but-3-yne-1,2-diol (133 mg) as a crude brown residue. LCMS (ESI): m/z 406.3 (M+H)$^+$.

This residue was dissolved in THF (7 mL), 1 M aqueous Na$_2$CO$_3$ solution (3.28 mL, 3.28 mmol), N-methylimidazole (13 µL, 0.16 mmol) were added followed by acrylic anhydride (45 µL, 0.39 mmol) and the mixture was stirred at rt for 30 min. Water (5 mL) was added and extracted into EtOAc (3×20 mL). The combined organic phases were washed with brine (10 mL), dried over sodium sulfate, filtered and concentrated. The crude was purified by flash column chromatography (silica, C18, 5-80% MeCN/10 mM ammonium formate) to yield the title compound (4.4 mg, 3% yield). LCMS (ESI): m/z 460.3 (M+H)⁺. ¹H NMR (400 MHz, DMSO-d₆) δ 8.57 (t, J=5.5 Hz, 1H), 8.24 (s, 1H), 8.14 (d, J=8.8 Hz, 2H), 7.48 (d, J=8.3 Hz, 2H), 7.41 (s, 1H), 6.30 (dd, J=17.1, 10.2 Hz, 1H), 6.12 (dd, J=17.1, 2.2 Hz, 1H), 5.61 (dd, J=10.1, 2.2 Hz, 2H), 5.08 (s, 1H), 4.64 (d, J=5.7 Hz, 2H), 4.53 (t, J=6.0 Hz, 1H), 4.14 (s, 3H), 3.58 (d, J=5.8 Hz, 2H).

Example 72 (Compound 76) 3-methyl-5-[(prop-2-enoylamino)methyl]-7-[4-(trifluoromethoxy)phenyl]benzimidazole-4-carboxamide

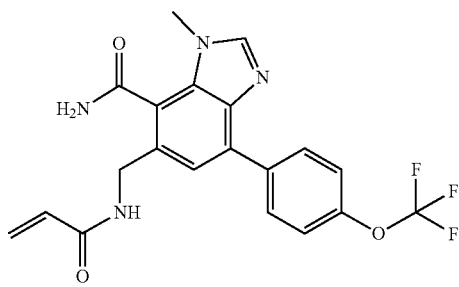 [SMILES: C=CC(=O)NCc1cc(-c2ccc(OC(F)(F)F)cc2)c2ncn(C)c2c1C(N)=O]

Step 1: tert-butyl N-[[4-cyano-3-methyl-7-[4-(trifluoromethoxy)phenyl]benzimidazol-5-yl]methyl]carbamate

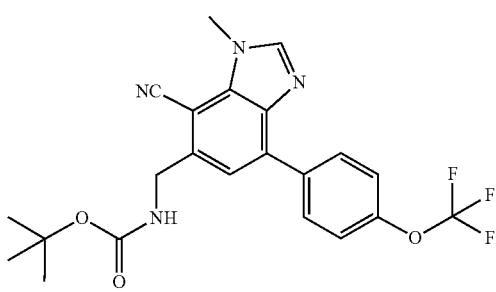 [SMILES: Cn1cnc2c(-c3ccc(OC(F)(F)F)cc3)cc(CNC(=O)OC(C)(C)C)c(C#N)c21]

tert-butyl-N-[[4-bromo-3-methyl-7-[4-(trifluoromethoxy)phenyl]benzimidazol-5-yl]methyl]-N-tert-butoxycarbonyl-carbamate (200 mg, 0.33 mmol) (described in Example 27 step 6), palladium tetrakis(triphenylphosphine) (58 mg, 0.050 mmol) and Zn(CN)₂ (117 mg, 1.0 mmol) were added to DMA (1.7 mL) and the mixture was degassed with N2. The mixture was then stirred at 110° C. for 17 h. The reaction was diluted with EtOAc (100 mL) and washed with water (2×50 mL) followed by brine (50 mL). The organic layer was concentrated with silica gel and purified by flash column chromatography (silica, 0-100% EtOAC/heptanes) to yield the title compound (20 mg, 13% yield) as an off-white solid. LCMS (ESI): m/z 447.4 (M+H)⁺.

Step 2: 3-methyl-5-[(prop-2-enoylamino)methyl]-7-[4-(trifluoromethoxy)phenyl]benzimidazole-4-carboxamide

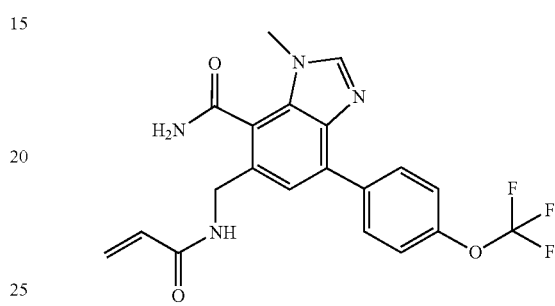

To a solution of tert-butyl-N-[[4-cyano-3-methyl-7-[4-(trifluoromethoxy)phenyl]benzimidazol-5-yl]methyl]carbamate (20 mg, 0.040 mmol) in ethanol (0.4 mL) was added a 1 M aqueous solution of LiOH (0.13 mL, 0.13 mmol) followed by a 30% aqueous solution of hydrogen peroxide solution (0.01 mL, 0.13 mmol) at 0° C. The reaction was warmed to rt and stirred for 3 days. Water (3 mL) was added and the product was extracted with 20% iPrOH in CHCl3 (3×3 mL). The organic layers were combined, dried over sodium sulfate and concentrated to yield tert-butyl-N-[[4-carbamoyl-3-methyl-7-[4-(trifluoromethoxy)phenyl]benzimidazol-5-yl]methyl]carbamate as a crude residue. LCMS (ESI): m/z 464.9 (M+H)⁺.

This residue was dissolved in 4 N HCl in dioxane (1.08 mL, 4.31 mmol) and stirred for 2 h. The reaction mixture was quenched with saturated aqueous NaHCO₃ solution (2 mL) then extracted with EtOAc (3×5 mL). The combined organic phases were washed with brine (5 mL), dried over sodium sulfate, filtered and concentrated to yield a crude residue. LCMS (ESI): m/z 365.2 (M+H)⁺.

This residue was dissolved in THF (7 mL), 1 M aqueous Na₂CO₃ solution (0.41 mL, 0.41 mmol), N-methylimidazole (1.7 mg, 0.020 mmol) were added followed by acrylic anhydride (0.01 mL, 0.050 mmol) and the mixture was stirred at rt for 30 min. Water (10 mL) was added and extracted into EtOAc (3×20 mL). The combined organic phases were washed with brine (10 mL), dried over sodium sulfate, filtered and concentrated. The crude was purified by preparative HPLC to yield the title compound (2.4 mg, 14% yield) as a white solid. LCMS (ESI): m/z 419.3 (M+H)*; ¹H NMR (400 MHz, DMSO-d₆) δ 8.53 (t, J=5.6 Hz, 1H), 8.26 (s, 1H), 8.22 (s, 1H), 8.10 (d, J=8.7 Hz, 2H), 8.00 (s, 1H), 7.48 (d, J=8.1 Hz, 2H), 7.39 (s, 1H), 6.29 (dd, J=17.1, 10.1 Hz, 1H), 6.11 (dd, J=17.1, 2.2 Hz, 1H), 5.60 (dd, J=10.1, 2.2 Hz, 1H), 4.53 (d, J=5.5 Hz, 2H), 3.86 (s, 3H).

Example 73 (Compound 77) N-[[4-(difluoromethyl)-3-methyl-7-[4-(trifluoromethoxy)phenyl]benzimidazol-5-yl]methyl]prop-2-enamide

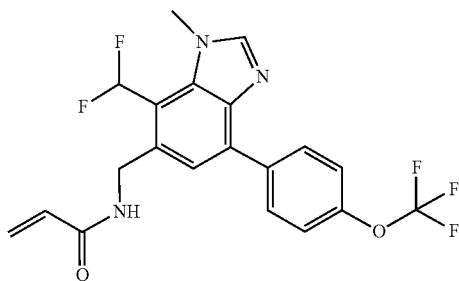 [SMILES: C=CC(=O)NCc1cc(-c2ccc(OC(F)(F)F)cc2)c2ncn(C)c2c1C(F)F]

Step 1: tert-butyl-N-tert-butoxycarbonyl-N-[[4-formyl-3-methyl-7-[4-(trifluoromethoxy) phenyl]benzimidazol-5-yl]methyl]carbamate

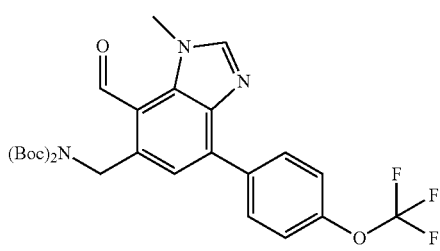

tert-Butyl-N-tert-butoxycarbonyl-N-[[3-methyl-7-[4-(trifluoromethoxy)phenyl]-4-vinyl-benzimidazol-5-yl]methyl]carbamate (320 mg, 0.58 mmol) (described in Example 27 step 7) was dissolved in DCM (8 mL) and the mixture was cooled to −78° C. under N2. Ozone was bubbled for 5 min until a blue color appeared. The mixture was purged with N2 at −78° C. for 5 min then was added triphenyl phosphine (307 mg, 1.17 mmol) and the mixture was warmed to rt. The crude was concentrated with silica gel and purified by flash column chromatography (silica, 20-40% (30% MeOH in EtOAc)/heptanes) to give the title compound (220 mg, 69% yield). LCMS (ESI): m/z 550.3 (M+H)+.

Step 2: tert-butyl N-tert-butoxycarbonyl-N-[[4-(difluoromethyl)-3-methyl-7-[4-(trifluoromethoxy)phenyl]benzimidazol-5-yl]methyl]carbamate

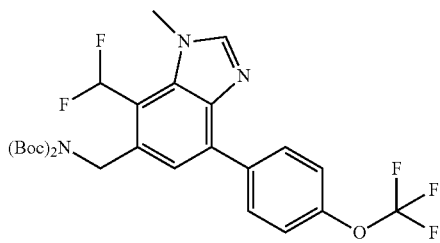

7-chloro-5-nitro-2,3-dihydrobenzofuran-4-carbaldehyde (100 mg, 0.18 mmol) was dissolved in DCM (0.5 mL) and cooled to 0° C. To the solution was added diethylaminosulfur trifluoride (0.024 mL, 0.18 mmol) in DCM (0.6 mL) and it was removed from the cooling bath and stirred for 18 h. The reaction was diluted with DCM (30 mL), washed with saturated aqueous NaHCO3 solution (10 mL), dried over sodium sulfate, filtered through 1 cm×1 cm silica plug topped with Celite and concentrated to give crude title compound (88 mg, 85% yield) as a yellow solid. LCMS (ESI): m/z 572.2 (M+H)+.

Step 3: N-[[4-(difluoromethyl)-3-methyl-7-[4-(trifluoromethoxy)phenyl]benzimidazol-5-yl]methyl]prop-2-enamide

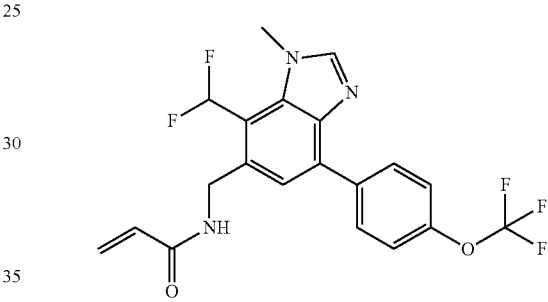

To tert-butyl-N-tert-butoxycarbonyl-N-[[4-(difluoromethyl)-3-methyl-7-[4-(trifluoromethoxy)phenyl]benzimidazol-5-yl]methyl]carbamate (88 mg, 0.15 mmol) in DCM (1.9 mL) was added TFA (1.0 mL, 0.15 mmol) and the solution was stirred for 30 min. Toluene (2 mL) was added and the mixture was concentrated to [4-(difluoromethyl)-3-methyl-7-[4-(trifluoromethoxy)phenyl]benzimidazol-5-yl]methanamine as a green oil. LCMS (ESI): m/z 372.3 (M+H)+.

This green oil was dissolved in THF (7 mL), 1 M aqueous Na2CO3 solution (1.5 mL, 1.5 mmol), N-methylimidazole (6.1 µL, 0.080 mmol) were added followed by acrylic anhydride (21 µL, 0.18 mmol) and the mixture was stirred at rt for 30 min. Water (5 mL) was added and extracted into EtOAc (3×20 mL). The combined organic phases were washed with brine (20 mL), dried over sodium and concentrated. The crude was purified by flash column chromatography (silica, C18, 5-80% MeCN/10 mM ammonium formate)) to yield the title compound (25.4 mg, 39% yield) as a white solid. LCMS (ESI): m/z 426.3 (M+H)+. 1H NMR (400 MHz, DMSO-d6) δ 8.74 (t, J=5.5 Hz, 1H), 8.36 (s, 1H), 8.13 (d, J=8.8 Hz, 2H), 7.61 (t, J=53.3 Hz, 1H), 7.53 (s, 1H), 7.51 (d, J=8.1 Hz, 2H), 6.22 (dd, J=17.1, 9.8 Hz, 1H), 6.12 (dd, J=17.1, 2.4 Hz, 1H), 5.61 (dd, J=9.8, 2.5 Hz, 1H), 4.70 (d, J=5.8 Hz, 2H), 3.97 (s, 3H).

Example 74 (Compound 78) N-((7-(1H-imidazol-1-yl)-1-methyl-4-(4-(trifluoromethoxy)phenyl)-1H-benzo[d]imidazol-6-yl)methyl)acrylamide

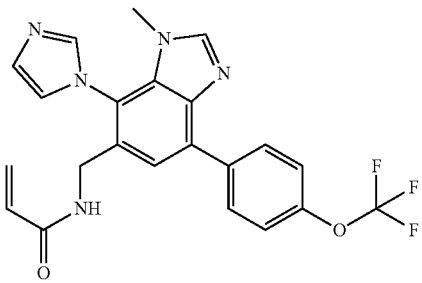 [SMILES: C=CC(=O)NCc1cc(-c2ccc(OC(F)(F)F)cc2)c2ncn(C)c2c1-n1ccnc1]

Step 1: Ethyl 4-imidazol-1-yl-3-methyl-7-[4-(trifluoromethoxy)phenyl]benzimidazole-5-carboxylate

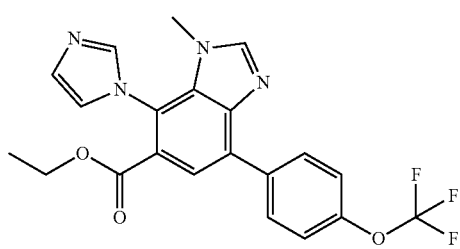 [SMILES: CCOC(=O)c1cc(-c2ccc(OC(F)(F)F)cc2)c2ncn(C)c2c1-n1ccnc1]

A vial was charged with ethyl 4-bromo-3-methyl-7-[4-(trifluoromethoxy)-phenyl]-benzimidazole-5-carboxylate (300 mg, 0.68 mmol) (described in Example 27,, step 3), imidazole (69 mg, 1.02 mmol), CuI (26 mg, 0.14 mmol) and $Cs_2CO_3$ (443 mg, 1.35 mmol). DMF (4 mL) was added and the vial was sealed and stirred at 120° C. for 3 h. The reaction was diluted with water (50 mL) and EtOAc (50 mL). The organic layer was washed with water (20 mL), brine (20 mL), dried over sodium sulfate, filtered and concentrated. The crude was purified by flash column chromatography (silica, 0-10% MeOH/DCM) to give the title compound (210 mg, 72% yield). LCMS (ESI): m/z 431.3 $(M+H)^+$.

Step 2: [4-imidazol-1-yl-3-methyl-7-[4-(trifluoromethoxy)phenyl]benzimidazol-5-yl]methanol

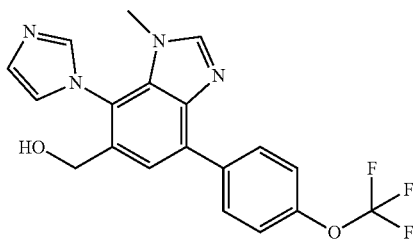 [SMILES: Cn1cnc2c(-c3ccc(OC(F)(F)F)cc3)cc(CN=[N+]=[N-])c(-n3ccnc3)c21]

Ethyl 4-imidazol-1-yl-3-methyl-7-[4-(trifluoromethoxy)phenyl]benzimidazole-5-carboxylate (210 mg, 0.49 mmol) was dissolved in THF (6 mL) and cooled to 0° C. Diisobutylaluminum hydride, 1.0 M in THF (2.54 mL, 2.54 mmol) was added dropwise to the mixture with stirring. The reaction was warmed to rt and stirred for 30 min. To the mixture was added 20 mL THF and 600 mg $Na_2SO_4$-$10H_2O$. The mixture was stirred at rt for 10 min and filtered through Celite. The filtrate was concentrated to give the title compound (155 mg, 82% yield) as crude product. LCMS (ESI): m/z 389.3 $(M+H)^+$.

Step 3: 6-(bromomethyl)-7-imidazol-1-yl-1-methyl-4-[4-(trifluoromethoxy)phenyl]benzimidazole

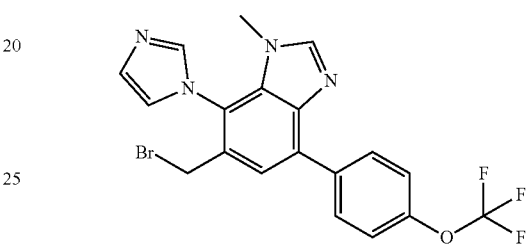

[4-imidazol-1-yl-3-methyl-7-[4-(trifluoromethoxy)phenyl]benzimidazol-5-yl]methanol (135 mg, 0.35 mmol) and triphenylphosphine (91 mg, 0.35 mmol) were dissolved in DCM (3 mL). Carbon tetrabromide (115 mg, 0.35 mmol) in DCM (0.5 mL) was added. The reaction was stirred for 10 min and was used quickly without purification to the next step. Assuming quantative yield. LCMS (ESI): m/z 453.2 (M+H).

Step 4: Diazonio-[[4-imidazol-1-yl-3-methyl-7-[4-(trifluoromethoxy)phenyl]benzimidazol-5-yl]methyl]azanide

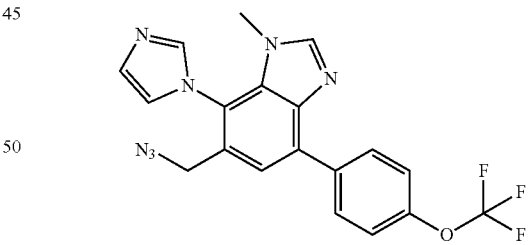

To a solution of sodium azide (225 mg, 3.46 mmol) in DMSO (10 mL) was added 6-(bromomethyl)-7-imidazol-1-yl-1-methyl-4-[4-(trifluoromethoxy)phenyl]benzimidazole (156 mg, 0.35 mmol) (DCM solution from previous step) with stirring. The reaction was stirred at rt for 10 min. The reaction was diluted with EtOAc (30 mL) and water (30 mL). Organic layer was separated, washed with water (30 mL) and brine (10 mL) and concentrated with silica gel. The crude was purified by flash column chromatography (silica, 0-100% (30% MeOH in EtOAc)/Heptanes) to give the title compound (105 mg, 73% yield). LCMS (ESI): m/z 414.3 $(M+H)^+$.

Step 5: N-[[4-imidazol-1-yl-3-methyl-7-[4-(trifluoromethoxy)phenyl]benzimidazol-5-yl]methyl]prop-2-enamide

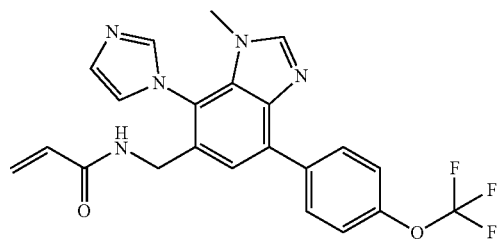 [SMILES: C=CC(=O)NCc1cc(-c2ccc(OC(F)(F)F)cc2)c2ncn(C)c2c1-n1ccnc1]

To diazonio-[[4-imidazol-1-yl-3-methyl-7-[4-(trifluoromethoxy)phenyl]benzimidazol-5-yl]methyl]azanide (107 mg, 0.26 mmol) in ethyl acetate (2.4 mL) was purged with nitrogen. 10% palladium on carbon (28 mg, 0.030 mmol) was added and the suspension was purged with hydrogen then stirred under hydrogen for 16 h. The reaction was purged with nitrogen, filtered through Celite and concentrated to yield [4-imidazol-1-yl-3-methyl-7-[4-(trifluoromethoxy)phenyl]benzimidazol-5-yl]methanamine as a crude solid. LCMS (ESI): m/z 388.3 (M+H)+.

This crude solid was dissolved in THF (2.6 mL), 1 M aqueous Na$_2$CO$_3$ solution (2.6 mL, 2.6 mmol), N-methylimidazole (21 μL, 0.26 mmol) were added followed by acrylic anhydride (36 μL, 0.31 mmol) and the mixture was stirred at rt for 30 min. Water (5 mL) was added and extracted into EtOAc (3×20 mL). The combined organic phases were washed with brine (10 mL), dried over sodium sulfate, filtered and concentrated. The crude was purified by flash column chromatography (silica, C18, 20-80% MeCN/10 mM ammonium formate) to yield the title compound (19 mg, 17% yield) as a white solid. LCMS (ESI): m/z 442.3 (M+H)+. $^1$H NMR (400 MHz, DMSO-d$_6$) δ 8.49 (t, J=5.5 Hz, 1H), 8.27 (s, 1H), 8.17-8.07 (m, 2H), 7.96 (s, 1H), 7.54-7.49 (m, 1H), 7.19 (s, 1H), 6.23 (dd, J=17.1, 10.1 Hz, 1H), 6.07 (dd, J=17.1, 2.2 Hz, 1H), 5.58 (dd, J=10.1, 2.2 Hz, 1H), 4.14 (dd, J=14.8, 5.6 Hz, 1H), 4.08 (dd, J=14.9, 5.5 Hz, 1H), 3.22 (s, 3H).

Example 75 (Compounds 79 and 28)

(S)—N-((5-(1,2-Dihydroxyethyl)-8-(4-(trifluoromethoxy)phenyl)quinoxalin-6-yl)methyl)acrylamide & (R)—N-((5-(1,2-dihydroxyethyl)-8-(4-(trifluoromethoxy)phenyl)quinoxalin-6-yl)methyl)acrylamide

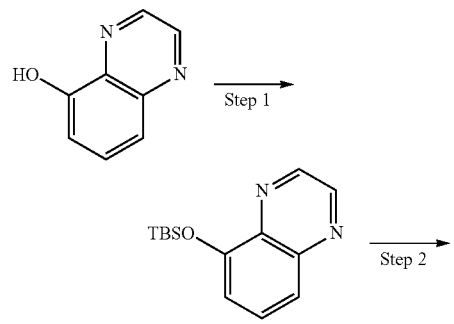

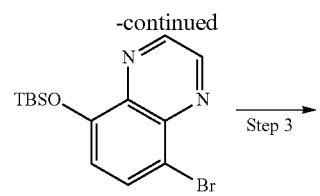

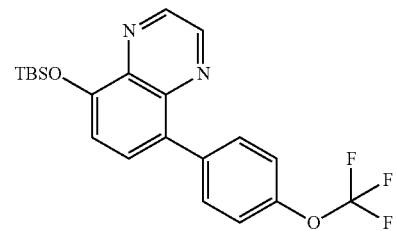 [SMILES: CC(C)(C)[Si](C)(C)Oc1ccc(-c2ccc(OC(F)(F)F)cc2)c2nccnc12]

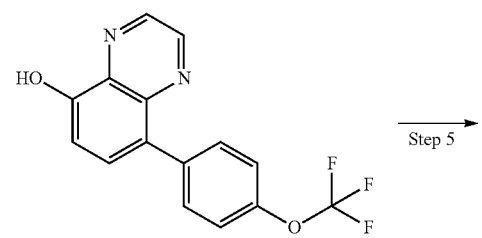

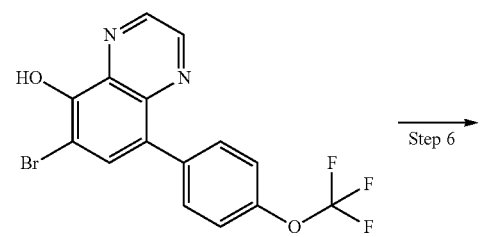

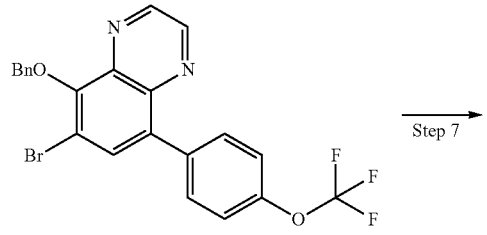

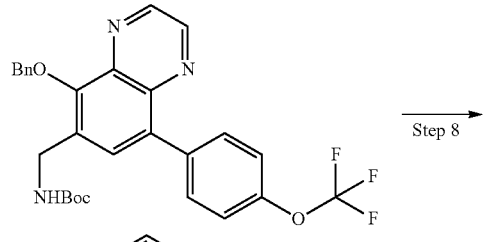

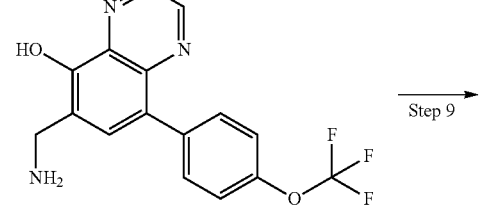

483

-continued

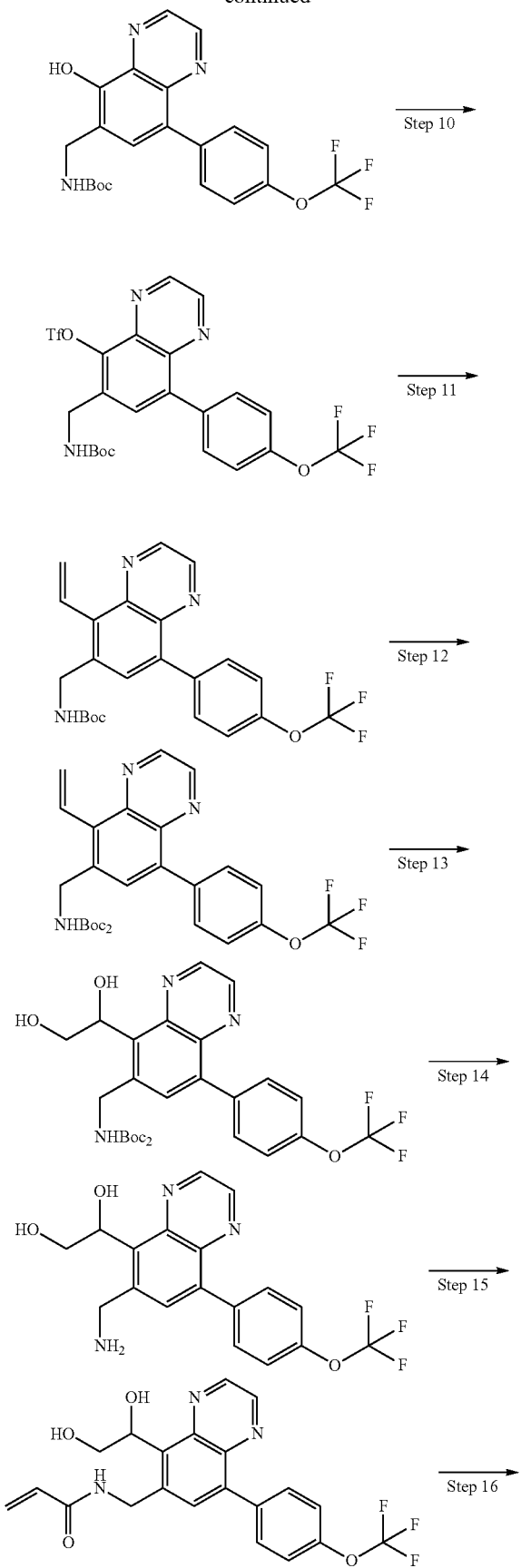

484

-continued

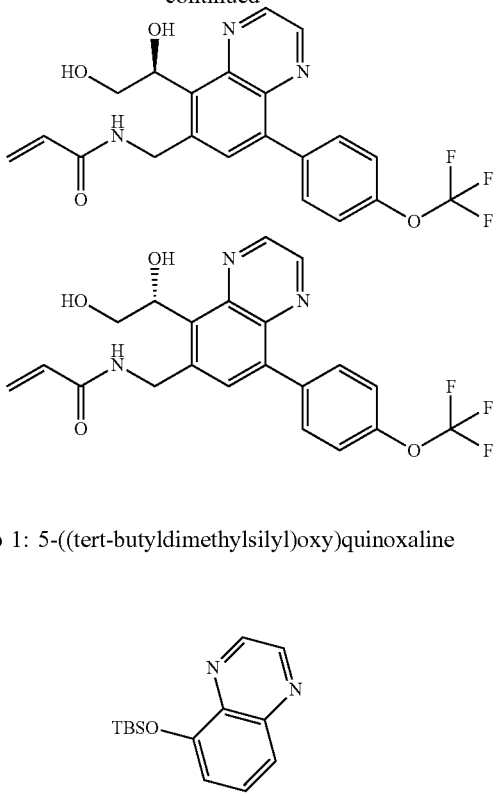

Step 1: 5-((tert-butyldimethylsilyl)oxy)quinoxaline

To a solution of quinoxalin-5-ol (10.0 g, 68.4 mmol) in dichloromethane (50 mL) was added tert-butylchlorodimethylsilane (15.47 g, 102.6 mmol) and imidazole (9.3 g, 136.8 mmol), the mixture was stirred at room temperature for 16 h. The mixture was quenched with water (50 mL) and extracted with DCM (50 mL×2), the organic layer was dried over $Na_2SO_4$ and concentrated under vacuum, the residue was purified by flash chromatography on silica gel (0-3% ethyl acetate in petroleum ether) to afford the title compound (17.0 g, 95%) as a yellow oil. $^1$H NMR (400 MHz, $CDCl_3$): δ 8.82-8.80 (m, 2H), 7.74-7.72 (m, 1H), 7.68-7.63 (m, 1H), 7.23-7.21 (m, 1H), 1.08 (s, 9H), 0.26 (s, 6H); LCMS (ESI): m/z 260.9 $(M+H)^+$.

Step 2: 5-bromo-8-((tert-butyldimethylsilyl)oxy) quinoxaline

To a solution of 5-((tert-butyldimethylsilyl)oxy)quinoxaline (10.0 g, 38.0 mmol) in acetonitrile (50 mL) was added 1-bromo-2,5-pyrrolidinedione (10.25 g, 58.0 mmol), the mixture was stirred at room temperature for 12 h. The mixture was concentrated, and the residue was diluted with ethyl acetate (100 mL), then washed with water (100 mL), the organic layer was dried with $Na_2SO_4$ and concentrated under vacuum, the residue was purified by flash chromatography on silica gel (0-20% ethyl acetate in petroleum ether) to afford the title compound (10.0 g, 77%) as a yellow solid. 2D-NMR confirmed it. $^1$H NMR (400 MHz, CDCl$_3$): δ 8.84 (d, J=1.6 Hz, 1H), 8.74 (d, J=1.6 Hz, 1H), 7.86 (d, J=8.4 Hz, 1H), 7.03 (d, J=8.4 Hz, 1H), 0.96 (s, 9H), 0.15 (s, 6H).

Step 3: 5-((tert-butyldimethylsilyl)oxy)-8-(4-(trifluoromethoxy)phenyl)quinoxaline

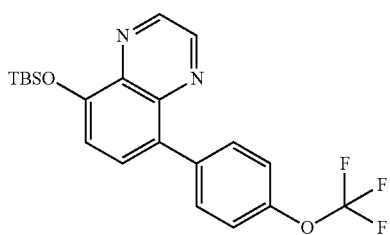

A mixture of K$_3$PO4 (12.5 g, 58.94 mmol), (4-(trifluoromethoxy)phenyl)boronic acid (9.1 g, 44.21 mmol), 5-bromo-8-((tert-butyldimethylsilyl)oxy)quinoxaline (10.0 g, 29.47 mmol) and Pd(dppf)Cl$_2$ (1.08 g, 1.47 mmol) in 1,4-dioxane (50 mL) and water (5 mL) was stirred at 100° C. for 12 h under N2 atmosphere. The mixture was quenched with water (50 mL), extracted with ethyl acetate (50 mL×3), the organic layer was dried over Na$_2$SO$_4$ and concentrated. The residue was purified by flash chromatography on silica gel (0-20% ethyl acetate in petroleum ether) to afford the title compound (6.4 g, 52%) as a yellow solid. $^1$H NMR (400 MHz, CDCl$_3$): δ 8.77-8.75 (m, 2H), 7.64-7.59 (m, 3H), 7.26 (d, J=8.0 Hz, 2H), 7.21 (d, J=8.0 Hz, 1H), 1.02 (s, 9H), 0.23 (s, 6H); LCMS (ESI): m/z 421.1 (M+H)$^+$.

Step 4: 8-(4-(trifluoromethoxy)phenyl)quinoxalin-5-ol

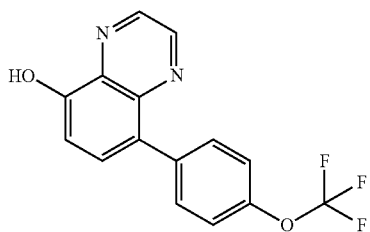 [SMILES: Oc1ccc(-c2ccc(OC(F)(F)F)cc2)c2nccnc12]

To a solution of 5-((tert-butyldimethylsilyl)oxy)-8-(4-(trifluoromethoxy)phenyl)quinoxaline (6.4 g, 15.22 mmol) in THF (30 mL) was added TBAF (22.0 mL, 22.0 mmol, 1M/L in THF). The mixture was stirred at room temperature for 30 min. The mixture was quenched with water (50 mL), extracted with ethyl acetate (30 mL×3), the organic layer was washed with water (50 mL) and brine (50 mL), dried over Na$_2$SO$_4$ and concentrated. The residue was purified by flash chromatography on silica gel (0-30% ethyl acetate in petroleum ether) to afford the title compound (3.8 g, 82%) as a yellow solid. $^1$H NMR (400 MHz, CDCl$_3$): δ 8.88 (d, J=2.0 Hz, 1H), 8.69 (d, J=2.0 Hz, 1H), 7.67 (d, J=8.0 Hz, 1H), 7.62-7.60 (m, 2H), 7.27-7.22 (m, 3H); LCMS (ESI): m/z 306.9 (M+H)$^+$.

Step 5: 6-bromo-8-(4-(trifluoromethoxy)phenyl)quinoxalin-5-ol

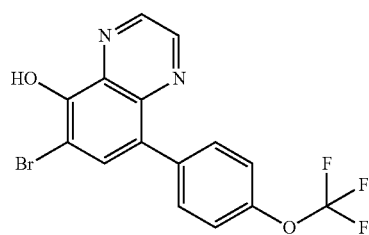 [SMILES: Oc1c(Br)cc(-c2ccc(OC(F)(F)F)cc2)c2nccnc12]

To a solution of 8-(4-(trifluoromethoxy)phenyl)quinoxalin-5-ol (3.8 g, 12.41 mmol) in dichloromethane (30 mL) was added bromine (1.27 mL, 24.82 mmol) at room temperature, the mixture was stirred at room temperature for 1 h. The mixture was quenched with sat. Na$_2$S$_2$O$_4$ (50 mL), extracted with DCM (100 mL×3), the organic layer was dried with Na$_2$SO$_4$ and concentrated to afford the title compound (4.6 g, 96%) as a yellow solid. LCMS (ESI): m/z 384.8 (M+H)$^+$.

Step 6: 5-(benzyloxy)-6-bromo-8-(4-(trifluoromethoxy)phenyl)quinoxaline

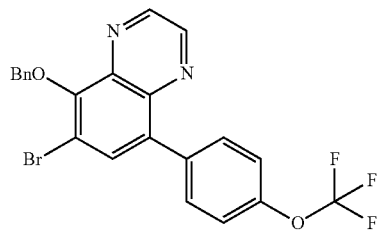 [SMILES: FC(F)(F)Oc1ccc(-c2cc(Br)c(OCc3ccccc3)c3nccnc23)cc1]

To a solution of 6-bromo-8-(4-(trifluoromethoxy)phenyl)quinoxalin-5-ol (4.6 g, 11.94 mmol) in acetonitrile (40 mL) was added K$_2$CO$_3$ (2.48 g, 17.92 mmol) and (bromomethyl)benzene (1.84 mL, 15.53 mmol) at room temperature, the mixture was stirred at room temperature for 12 h. The mixture was quenched with water (50 mL), extracted with ethyl acetate (30 mL×3), the organic layer was washed with brine (30 mL), dried over Na$_2$SO$_4$ and concentrated. The residue was purified by flash chromatography on silica gel (0-20% ethyl acetate in petroleum ether) to afford the title compound (2.0 g, 35%) as a yellow solid. $^1$H NMR (400 MHz, CDCl$_3$): δ 8.85-8.83 (m, 2H), 7.89 (s, 1H), 7.62-7.56 (m, 4H), 7.34-7.24 (m, 5H), 5.45 (s, 2H); LCMS (ESI): m/z 475.0 (M+H)$^+$.

Step 7: tert-butyl ((5-(benzyloxy)-8-(4-(trifluoromethoxy)phenyl)quinoxalin-6-yl)methyl)carbamate

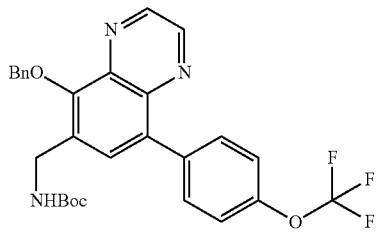 [SMILES: CC(C)(C)OC(=O)NCc1cc(-c2ccc(OC(F)(F)F)cc2)c2nccnc2c1OCc1ccccc1]

A mixture of potassium (((tert-butoxycarbonyl)amino)methyl)trifluoroborate (833 mg, 4.21 mmol), 5-(benzyloxy)-6-bromo-8-(4-(trifluoromethoxy)phenyl)quinoxaline (1.0 g, 2.1 mmol), $Cs_2CO_3$ (1.37 g, 4.21 mmol) and CATACXIUM A Pd G2 (141 mg, 0.21 mmol) in 1,4-dioxane (15 mL) and water (3 mL) was purged with $N_2$ for 3 min. The mixture was stirred at 100° C. for 12 h under $N_2$ atmosphere. After cooling down, the solution was quenched with water (50 mL), extracted with ethyl acetate (50 mL×2), the organic layer was dried over $Na_2SO_4$ and concentrated. The residue was purified by chromatography on silica gel (0-15% ethyl acetate in petroleum ether) to afford the title compound (860 mg, 78%) as a yellow solid. $^1$H NMR (400 MHz, $CDCl_3$): δ 8.85-8.82 (m, 3H), 7.69 (s, 1H), 7.61 (d, J=8.0 Hz, 2H), 7.44-7.38 (m, 2H), 7.34-7.31 (m, 2H), 7.26 (d, J=8.0 Hz, 2H), 5.49 (s, 2H), 4.64 (s, 11H), 4.34 (d, J=4.0 Hz, 2H), 1.46 (s, 9H); LCMS (ESI): m/z 526.0 (M+H)$^+$.

Step 8: 6-(aminomethyl)-8-(4-(trifluoromethoxy)phenyl)quinoxalin-5-ol hydrochloride

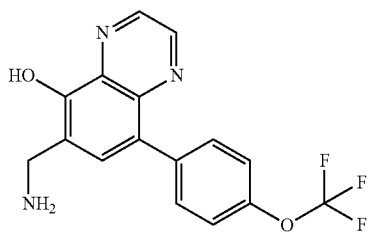 [SMILES: NCc1cc(-c2ccc(OC(F)(F)F)cc2)c2nccnc2c1O]

A solution of tert-butyl ((5-(benzyloxy)-8-(4-(trifluoromethoxy)phenyl)quinoxalin-6-yl)methyl)carbamate (200 mg, 0.38 mmol) in 6 M/L hydrogen chloride (10 mL, 60 mmol) was stirred at 100° C. for 2 h. The mixture was concentrated under vacuum to afford the title compound (128 mg, crude) as a yellow solid. The crude would be used in the next step directly. LCMS (ESI): m/z 335.9 (M+H)$^+$.

Step 9: tert-butyl ((5-hydroxy-8-(4-(trifluoromethoxy)phenyl)quinoxalin-6-yl)methyl)carbamate

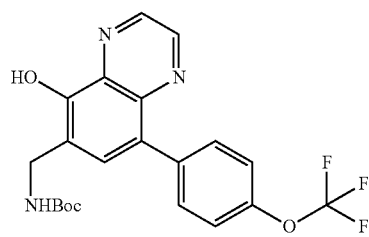 [SMILES: CC(C)(C)OC(=O)NCc1cc(-c2ccc(OC(F)(F)F)cc2)c2nccnc2c1O]

To a solution of $NaHCO_3$ (21 mg, 0.25 mmol) in THF (10 mL) and water (2 mL) was added 6-(aminomethyl)-8-(4-(trifluoromethoxy)phenyl)quinoxalin-5-ol hydrochloride (128 mg, 0.38 mmol) and $Boc_2O$ (55 mg, 0.25 mmol) at room temperature. The mixture was stirred at room temperature for 12 h. The mixture was extracted with ethyl acetate (15 mL×2), the organic layer was washed with brine (15 mL), dried over $Na_2SO_4$ and concentrated. The residue was purified by chromatography on silica gel (0-30% ethyl acetate in petroleum ether) to afford the title compound (100 mg, 60%) as a yellow solid. LCMS (ESI): m/z 436.0 (M+H)$^+$.

Step 10: 6-(((tert-butoxycarbonyl)amino)methyl)-8-(4-(trifluoromethoxy)phenyl)quinoxalin-5-yl trifluoromethanesulfonate

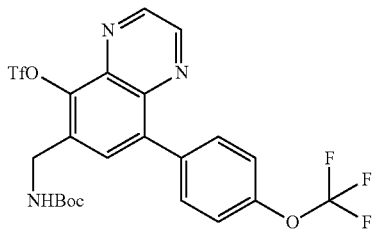 [SMILES: CC(C)(C)OC(=O)NCc1cc(-c2ccc(OC(F)(F)F)cc2)c2nccnc2c1OS(=O)(=O)C(F)(F)F]

To a solution of pyridine (0.09 mL, 1.87 mmol) in dichloromethane (15 mL) was added trifluoromethanesulfonic anhydride (0.53 mL, 3.12 mmol) and tert-butyl ((5-hydroxy-8-(4-(trifluoromethoxy)phenyl)quinoxalin-6-yl)methyl)carbamate (680 mg, 1.56 mmol) at 0° C. The mixture was stirred at 0° C. for 1 h. The mixture was quenched with water (15 mL), extracted with DCM (15 mL×2), the organic layer was washed with water (15 mL) and brine (15 mL), dried over $Na_2SO_4$ and concentrated. The residue was purified by flash chromatography on silica gel (0-20% ethyl acetate in petroleum ether) to afford the title compound (820 mg, 93%) as a white solid. $^1$H NMR (400 MHz, $CDCl_3$): δ 8.98-8.96 (m, 2H), 7.95 (s, 1H), 7.69 (d, J=8.0 Hz, 2H), 7.38 (d, J=8.0 Hz, 2H), 5.15 (s, 1H), 4.71 (d, J=4.0 Hz, 2H), 1.48 (s, 9H); LCMS (ESI): m/z 568.0 (M+H)$^+$.

Step 11: tert-butyl ((8-(4-(trifluoromethoxy)phenyl)-5-vinylquinoxalin-6-yl)methyl)carbamate

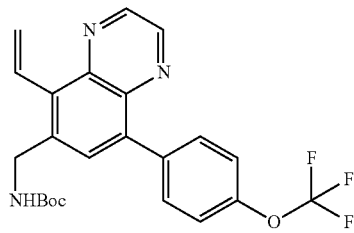 [SMILES: C=Cc1c(CNC(=O)OC(C)(C)C)cc(-c2ccc(OC(F)(F)F)cc2)c2nccnc12]

A solution of 6-(((tert-butoxycarbonyl)amino)methyl)-8-(4-(trifluoromethoxy)phenyl)quinoxalin-5-yl trifluoromethanesulfonate (820 mg, 1.45 mmol), Na$_2$CO$_3$ (459 mg, 4.34 mmol), 4,4,5,5-tetramethyl-2-vinyl-1,3,2-dioxaborolane (668 mg, 4.34 mmol), Pd(dppf)Cl$_2$ (106 mg, 0.14 mmol) in 1,4-dioxane (15 mL) and water (1 mL) was stirred at 100° C. for 12 h. The reaction was quenched by water (15 mL), extracted with ethyl acetate (20 mL×3), the organic layer was washed with brine (10 mL), dried over Na$_2$SO$_4$ and concentrated. The residue was purified by flash chromatography on silica gel (0-30% ethyl acetate in petroleum ether) to afford the title compound (560 mg, 87%) as a gray solid. $^1$H NMR (400 MHz, CDCl$_3$): δ 8.82-8.79 (m, 2H), 7.79 (s, 11H), 7.64 (d, J=8.8 Hz, 2H), 7.37 (dd, J=18.0, 11.6 Hz, 11H), 7.28 (d, J=8.0 Hz, 2H), 5.84 (dd, J=11.6, 1.6 Hz, 1H), 5.60 (d, J=18.0 Hz, 11H), 4.90 (s, 11H), 4.64 (d, J=5.6 Hz, 2H), 1.40 (s, 9H); LCMS (ESI): m/z 446.0 (M+H)$^+$.

Step 12: tert-butyl N-tert-butoxycarbonyl-N-[[8-[4-(trifluoromethoxy)phenyl]-5-vinyl-quinoxalin-6-yl]methyl]carbamate

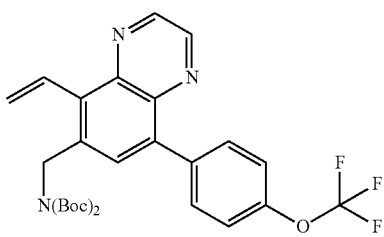

A solution of Boc$_2$O (412 mg, 1.89 mmol), tert-butyl ((8-(4-(trifluoromethoxy)phenyl)-5-vinylquinoxalin-6-yl)methyl)carbamate (560 mg, 1.26 mmol) and DMAP (184 mg, 1.51 mmol) in THF (15 mL) was stirred at 75° C. for 4 hours. The mixture was concentrated. The residue was purified by chromatography on silica gel (0-10% ethyl acetate in petroleum ether) to afford the title compound (660 mg, 96%) as a colorless oil. LCMS (ESI): m/z 546.5 (M+H)$^+$.

Step 13: tert-butyl N-tert-butoxycarbonyl-N-[[5-(1,2-dihydroxyethyl)-8-[4-(trifluoromethyl)phenoxy]-6-quinolyl]methyl]carbamate

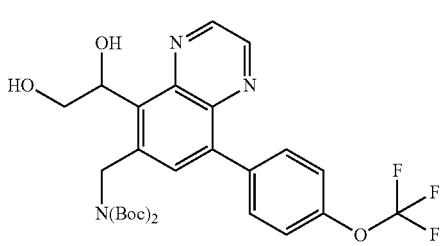

To a solution of NMO (567 mg, 4.84 mmol) and K$_2$OsO$_4$·2H$_2$O (89 mg, 0.24 mmol) in THF (10 mL) and water (1 mL) was added tert-butyl N-tert-butoxycarbonyl-N-[[8-[4-(trifluoromethoxy)phenyl]-5-vinyl-quinoxalin-6-yl]methyl]carbamate (660 mg, 1.21 mmol) at 0° C. The resulting mixture was stirred at room temperature for 2 h. The reaction was quenched with sat.Na$_2$SO$_3$ (15 mL). The reaction mixture was diluted with water (10 mL) and washed with ethyl acetate (20 mL×3). The organic layer was combined and washed with brine (10 mL). The organic layer was dried over Na$_2$SO$_4$ and concentrated under vacuum. The residue was purified by flash chromatography on silica gel (0-50% ethyl acetate in petroleum ether) to afford the title compound (600 mg, 86%) as a white solid. $^1$H NMR (400 MHz, CDCl$_3$): δ 8.94 (d, J=1.6 Hz, 1H), 8.77 (d, J=1.6 Hz, 1H), 7.68 (s, 1H), 7.64 (d, J=8.4 Hz, 2H), 7.35 (d, J=8.4 Hz, 2H), 5.53-5.50 (m, 1H), 5.21-5.08 (m, 2H), 4.10-4.05 (m, 1H), 3.92-3.89 (m, 1H), 3.77-3.74 (m, 1H), 1.90-1.83 (m, 1H), 1.47 (s, 18H); LCMS (ESI): m/z 580.4 (M+H)$^+$.

Step 14: 1-(6-(aminomethyl)-8-(4-(trifluoromethoxy)phenyl) 486uinoxaline-5-yl)ethane-1,2-diol

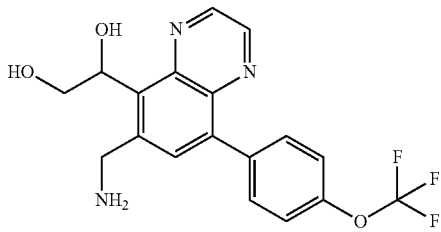 [SMILES: NCc1cc(-c2ccc(OC(F)(F)F)cc2)c2nccnc2c1C(O)CO]

A solution of tert-butyl N-tert-butoxycarbonyl-N-[[5-(1,2-dihydroxyethyl)-8-[4-(trifluoromethyl)phenoxy]-6-quinolyl]methyl]carbamate (600 mg, 1.04 mmol) and con.HCl (3 mL) in THF (10 mL) was stirred at room temperature for 16 h. The reaction was diluted with water (10 mL) and adjusted to pH=7 with sat.NaHCO$_3$. The mixture was extracted with ethyl acetate (20 mL×3). The combined organic layers were dried over Na$_2$SO$_4$ and concentrated in vacuo to afford the title compound (300 mg, crude) as a yellow solid. The crude was used for next step without further purification. LCMS (ESI): m/z 380.1 (M+H)$^+$.

Step 15: N-((5-(1,2-dihydroxyethyl)-8-(4-(trifluoromethoxy)phenyl)quinoxaline-6-yl)methyl)acrylamide

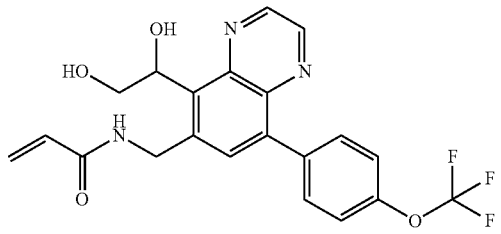 [SMILES: C=CC(=O)NCc1cc(-c2ccc(OC(F)(F)F)cc2)c2nccnc2c1C(O)CO]

To a solution of 1-(6-(aminomethyl)-8-(4-(trifluoromethoxy)phenyl)quinoxalin-5-yl)ethane-1,2-diol (300 mg, 0.79 mmol) and sat.NaHCO$_3$ (0.5 mL) in THF (10 mL) was added acrylicanhydride (110 mg, 0.87 mmol) at 0° C. The mixture was stirred at 0° C. for 1 h. The reaction was diluted with water (10 mL) and extracted with ethyl acetate (10 mL×3), the combined organic layers were dried over Na$_2$SO$_4$ and concentrated in vacuo and the residue was purified by flash chromatography on silica gel (0-100% ethyl acetate in petroleum ether) to afford the title compound (250 mg, 73%) as a white solid. LCMS (ESI): m/z 434.0 (M+H)$^+$.

Step 16: (S)—N-((5-(1,2-dihydroxyethyl)-8-(4-(trifluoromethoxy)phenyl)quinoxalin-6-yl)methyl)acrylamide & (R)—N-((5-(1,2-dihydroxyethyl)-8-(4-(trifluoromethoxy)phenyl)quinoxalin-6-yl)methyl)acrylamide

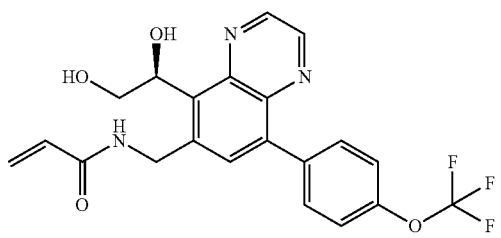

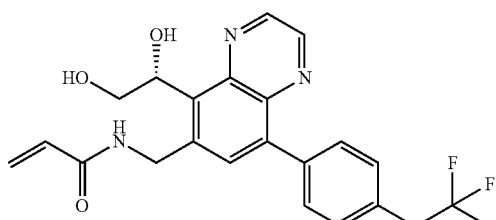

N-((5-(1,2-Dihydroxyethyl)-8-(4-(trifluoromethoxy)phenyl)quinoxalin-6-yl)methyl)acrylamide (250 mg, 0.58 mmol) was separated by SFC with the following conditions: DAICEL CHIRALPAK AD(250 mm*30 mm,10 um); 30% Neu-EtOH to afford the first peak (S)—N-((5-(1,2-dihydroxyethyl)-8-(4-(trifluoromethoxy)phenyl)quinoxalin-6-yl)methyl)acrylamide (86.8 mg, 35%) and the second peak (R)—N-((5-(1,2-dihydroxyethyl)-8-(4-(trifluoromethoxy)phenyl)quinoxalin-6-yl)methyl)acrylamide (72.8 mg, 29%) both as white solid. The first peak: $^1$H NMR (400 MHz, DMSO-d$_6$): δ 8.99 (d, J=1.6 Hz, 1H), 8.96 (d, J=1.6 Hz, 1H), 8.62 (t, J=5.6 Hz, 1H), 7.82 (s, 1H), 7.74 (d, J=8.8 Hz, 2H), 7.51 (d, J=8.4 Hz, 2H), 6.32 (dd, J=17.2, 10.0 Hz, 1H), 6.17-6.09 (m, 2H), 5.81 (d, J=5.6 Hz, 1H), 5.63 (dd, J=10.0, 2.0 Hz, 1H), 5.03 (dd, J=15.6, 6.4 Hz, 1H), 4.94 (t, J=5.6 Hz, 1H), 4.84 (dd, J=15.6, 5.6 Hz, 1H), 3.91-3.87 (m, 1H), 3.71-3.64 (m, 1H); LCMS (ESI): m/z 455.9 (M+Na)$^+$.

The second peak: $^1$H NMR (400 MHz, DMSO-d$_6$): δ 8.99 (d, J=1.6 Hz, 1H), 8.96 (d, J=1.6 Hz, 1H), 8.62 (t, J=5.6 Hz, 1H), 7.82 (s, 1H), 7.74 (d, J=8.8 Hz, 2H), 7.51 (d, J=8.4 Hz, 2H), 6.32 (dd, J=17.2, 10.0 Hz, 1H), 6.17-6.09 (m, 2H), 5.81 (d, J=5.6 Hz, 1H), 5.63 (dd, J=10.0, 2.0 Hz, 1H), 5.03 (dd, J=15.6, 6.4 Hz, 1H), 4.94 (t, J=5.6 Hz, 1H), 4.84 (dd, J=15.6, 5.6 Hz, 1H), 3.91-3.87 (m, 1H), 3.71-3.64 (m, 1H); LCMS (ESI): m/z 455.9 (M+Na)$^+$.

Example 76 (Compound 28)

(R)—N-((5-(1,2-Dihydroxyethyl)-8-(4-(trifluoromethoxy)phenyl)quinoxalin-6-yl)methyl)acrylamide

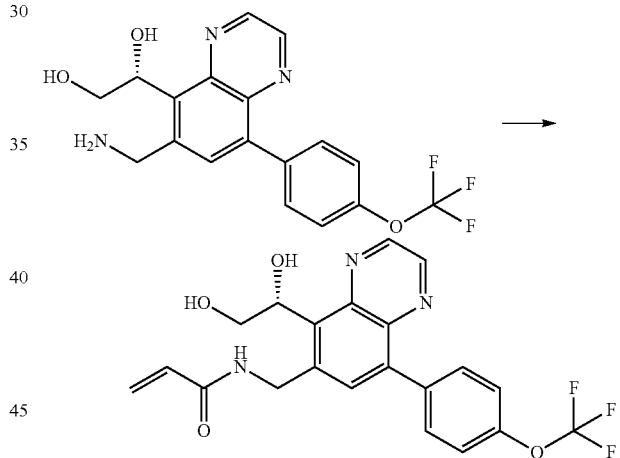

To a solution of (R)-1-(6-(aminomethyl)-8-(4-(trifluoromethoxy)phenyl)quinoxalin-5-yl)ethane-1,2-diol (130.0 g, 342.71 mmol) and sat.NaHCO$_3$ (500 mL) in THF (1.3 L) was added acrylic anhydride (47.54 g, 376.98 mmol) at 0° C. The mixture was stirred at 0° C. for 1 h. The reaction was diluted with water (1 L) and extracted with ethyl acetate (1 L×3), the combined organic layers were dried over Na$_2$SO$_4$ and concentrated in vacuo. The residue was purified by reverse phase chromatography (Phenomenex luna C18 250*50 mm*10 um, water(0.225% FA)-ACN,30% -66%) to afford the title compound (80.0 g, 54%) as a white solid. $^1$H NMR (400 MHz, DMSO-d$_6$): δ 8.99 (d, J=2.0 Hz, 1H), 8.95 (d, J=2.0 Hz, 1H), 8.59 (t, J=6.0 Hz, 1H), 7.82 (s, 1H), 7.73 (d, J=8.8 Hz, 2H), 7.50 (d, J=8.0 Hz, 2H), 6.31 (dd, J=16.8, 10.0 Hz, 1H), 6.16-6.10 (m, 2H), 5.79 (d, J=6.0 Hz, 1H), 5.62 (dd, J=10.0, 2.4 Hz, 1H), 5.02 (dd, J=15.4, 6.4 Hz, 1H), 4.91 (t, J=5.6 Hz, 1H), 4.84 (dd, J=15.4, 5.6 Hz, 1H), 3.91-3.86 (m, 1H), 3.69-3.65 (m, 1H); LCMS (ESI): m/z 434.2 (M+H)$^+$.

Example 77 (Compound 80)

(R)—N-((5-(1,2-Dihydroxyethyl)-8-(4-(trifluoromethoxy)phenyl)quinoxalin-6-yl)methyl)-2-fluoroacrylamide

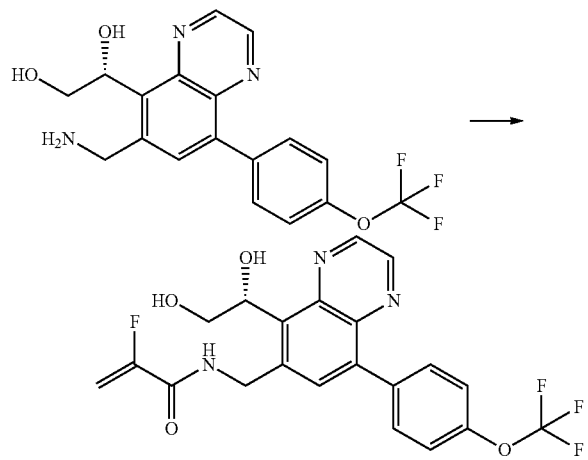

To a solution of (R)-1-(6-(aminomethyl)-8-(4-(trifluoromethoxy)phenyl)quinoxalin-5-yl)ethane-1,2-diol (150 mg, 0.40 mmol) and 2-fluoroacrylic acid (43 mg, 0.47 mmol) in dichloromethane (10 mL) was added ethyl 2-ethoxyquinoline-1(2H)-carboxylate (245 mg, 0.99 mmol) at room temperature. The mixture was stirred at room temperature for 16 hours. The reaction mixture was diluted with ethyl acetate (30 mL), washed with brine (50 mL), dried over $Na_2SO_4$ and concentrated to dryness. The residue was purified by column chromatography on silica gel (0-70% ethyl acetate in petroleum ether) and purified by prep-TLC (75% ethyl acetate in petroleum ether) to afford the title compound (104.4 mg, 58%) as a white solid. $^1$H NMR (400 MHz, DMSO-$d_6$): δ 9.00-8.87 (m, 3H), 7.82 (s, 1H), 7.73 (d, J=8.4 Hz, 2H), 7.51 (d, J=8.0 Hz, 2H), 6.13-6.09 (m, 1H), 5.85 (d, J=5.6 Hz, 1H), 5.57 (dd, J=48.4, 3.6 Hz, 1H), 5.27 (dd, J=15.6, 3.6 Hz, 1H), 5.13-5.02 (m, 1H), 5.00-4.92 (m, 11H), 4.88-4.76 (m, 1H), 3.93-3.86 (m, 1H), 3.72-3.65 (m, 1H); LCMS (ESI): m/z 451.9 (M+H)$^+$.

Example 78 (Compound 81)

(R)—N-((5-(1,2-Dihydroxyethyl)-8-(4-(trifluoromethoxy)phenyl)quinoxalin-6-yl)methyl)cyclobut-1-ene-1-carboxamide

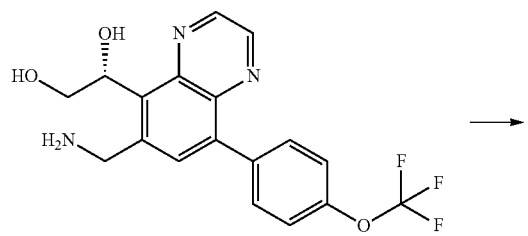

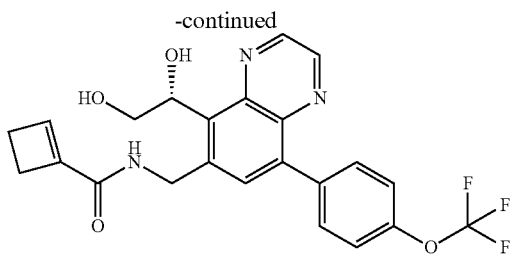

To a solution of (R)-1-(6-(aminomethyl)-8-(4-(trifluoromethoxy)phenyl)quinoxalin-5-yl)ethane-1,2-diol (150 mg, 0.40 mmol) and cyclobut-1-ene-1-carboxylic acid (47 mg, 0.47 mmol) in dichloromethane (10 mL) was added ethyl 2-ethoxyquinoline-1(2H)-carboxylate (245 mg, 0.99 mmol) at room temperature. The mixture was stirred at room temperature for 16 hours. The reaction mixture was diluted with ethyl acetate (30 mL), washed with brine (50 mL), dried over $Na_2SO_4$ and concentrated to dryness. The residue was purified by column chromatography on silica gel (0-80% ethyl acetate in petroleum ether) and purified by prep-TLC (75% ethyl acetate in petroleum ether) to afford the title compound (85.6 mg, 46%) as a white solid. $^1$H NMR (400 MHz, DMSO-$d_6$): δ 9.00-8.92 (m, 2H), 8.41 (t, J=5.6 Hz, 1H), 7.81 (s, 1H), 7.73 (d, J=8.8 Hz, 2H), 7.51 (d, J=8.0 Hz, 2H), 6.59 (s, 1H), 6.10-6.06 (m, 1H), 5.83 (d, J=6.0 Hz, 1H), 5.00-4.91 (m, 2H), 4.80-4.73 (m, 1H), 3.92-3.84 (m, 1H), 3.71-3.63 (m, 1H), 2.62-2.59 (m, 2H), 2.37-2.35 (m, 2H); LCMS (ESI): m/z 460.0 (M+H)$^+$.

Example 79 (Compound 82) & 80 (Compound 83)

(R)—N-((5-(1-Hydroxyethyl)-8-(4-(trifluoromethoxy)phenyl)quinoxalin-6-yl)methyl)acrylamide & (S)—N-((5-(1-hydroxyethyl)-8-(4-(trifluoromethoxy)phenyl)quinoxalin-6-yl)methyl) acrylamide

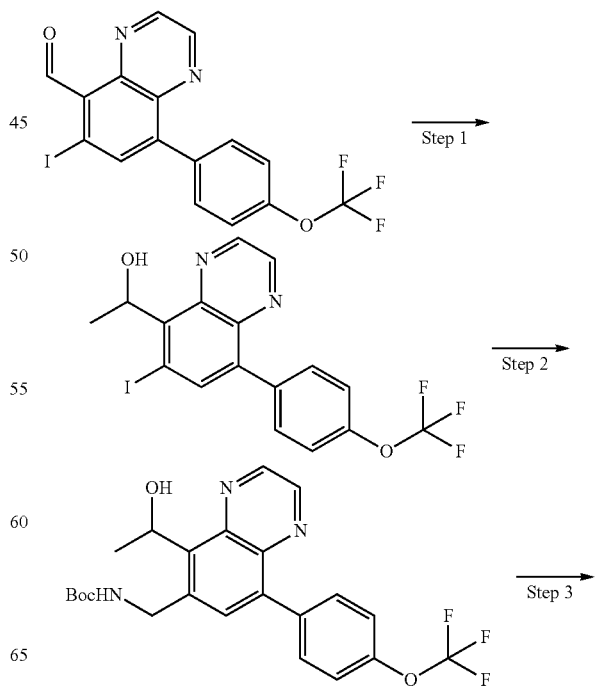

495

-continued

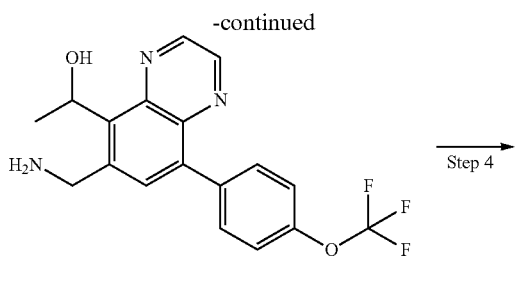

Step 4 →

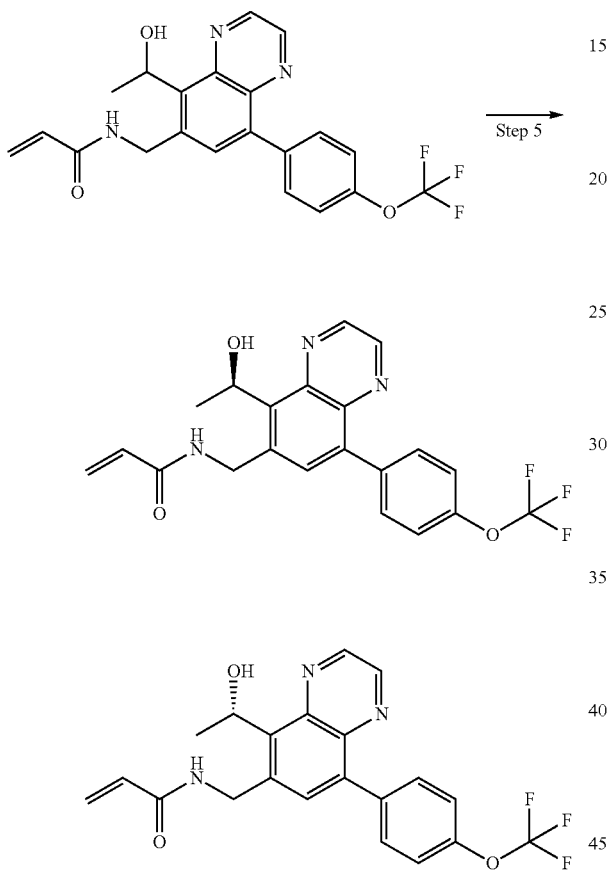

Step 1: 1-(6-iodo-8-(4-(trifluoromethoxy)phenyl)quinoxalin-5-yl)ethan-1-ol

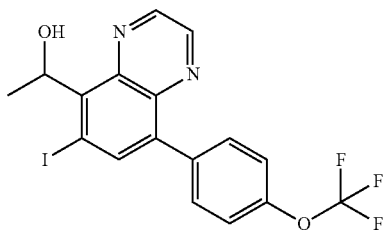

To a solution of 6-iodo-8-(4-(trifluoromethoxy)phenyl)quinoxaline-5-carbaldehyde (300 mg, 0.68 mmol) in THF (5 mL) was added methylmagnesium bromide (0.27 mL, 0.81 mmol, 3.0 mom/L in THF) at 0° C. The resulting mixture was stirred at 0° C. for 1 h. The mixture was quenched with sat.NH₄Cl (10 mL), extracted with ethyl acetate (50 mL×3) and washed with water (50 mL×3). The organic was dried over Na₂SO₄ and concentrated to afford the title compound (300 mg, 97%) as a colorless oil. LCMS (ESI): m/z 461.1 (M+H)⁺.

Step 2: tert-butyl ((5-(1-hydroxyethyl)-8-(4-(trifluoromethoxy)phenyl)quinoxalin-6-yl)methyl)carbamate A mixture of 1-(6-iodo-8-(4-(trifluoromethoxy)phenyl)quinoxalin-5-yl)ethan-1-ol (500 mg, 1.09 mmol), potassium (((tert-butoxycarbonyl)amino)methyl)trifluoroborate (515 mg, 2.17 mmol), CATACXIUM A Pd G2 (73 mg, 0.11 mmol) and Cs₂CO₃ (708 mg, 2.17 mmol) in 1,4-dioxane (10 mL) and water (1 mL) was stirred at 100° C. for 5 h under N₂ atmosphere. The reaction was diluted with water (100 mL) and extracted with ethyl acetate (100 mL×3). The organic layers were washed with brine (150 mL×2), dried over sodium sulfate, filtered and concentrated. The residue was purified by flash chromatography on silica gel (0-50% ethyl acetate in petroleum ether) to afford the title compound (200 mg, 40%) as a yellow solid. LCMS (ESI): m/z 464.2 (M+H)⁺.

Step 3: 1-(6-(aminomethyl)-8-(4-(trifluoromethoxy)phenyl)quinoxalin-5-yl)ethan-1-ol A solution of tert-butyl ((5-(1-hydroxyethyl)-8-(4-(trifluoromethoxy)phenyl)quinoxalin-6-yl)methyl)carbamate (200 mg, 0.43 mmol) in 5% TFA in HFIP (5 mL) was stirred at room temperature for 16 h. The mixture was quenched with water (100 mL) then adjusted pH to 8 with aq. NaHCO₃ solution and extracted with ethyl acetate (100 mL) and washed with water (100 mL×3). The organic layer was dried over Na₂SO₄ and concentrated to afford the title compound (150 mg, crude) as a brown oil. LCMS (ESI): m/z 346.1 (M+H−H₂O )⁺.

Step 4: N-((5-(1-hydroxyethyl)-8-(4-(trifluoromethoxy)phenyl)quinoxalin-6-yl)methyl)acrylamide

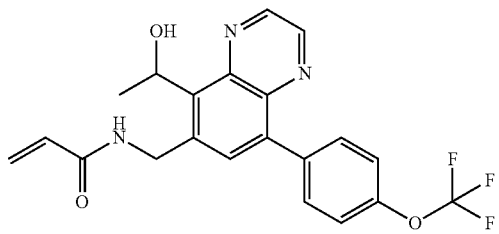

To a solution of 1-(6-(aminomethyl)-8-(4-(trifluoromethoxy)phenyl)quinoxalin-5-yl)ethan-1-ol (150 mg, 0.41 mmol) and sat.NaHCO$_3$ (1 mL) in THF (5 mL) was added acrylic anhydride (78 mg, 0.62 mmol) at 0° C. The resulting mixture was stirred at 0° C. for 1 h. The mixture was diluted with ethyl acetate (100 mL) and washed with water (100 mL×3). The organic layer was dried over Na$_2$SO$_4$ and concentrated. The residue was purified by reverse phase chromatography (Welch Xtimate C18 150*30 mm*5 um, water (0.225% FA)-ACN, 49-79%) to afford the title compound (60 mg, 35%) as a white solid. LCMS (ESI): m/z 400.2 (M+H−H$_2$O )$^+$.

Step 5: (R)—N-((5-(1-hydroxyethyl)-8-(4-(trifluoromethoxy)phenyl)quinoxalin-6-yl)methyl)acrylamide & (S)—N-((5-(1-hydroxyethyl)-8-(4-(trifluoromethoxy)phenyl)quinoxalin-6-yl)methyl)acrylamide

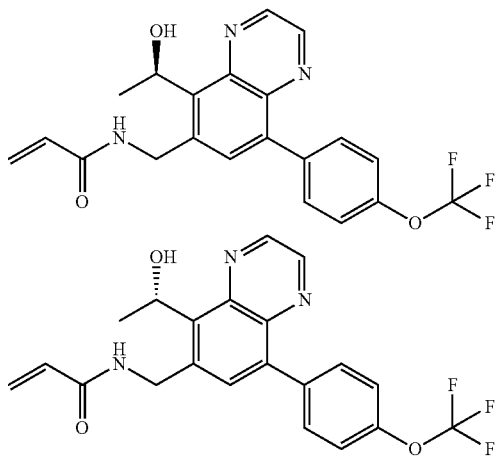

N-((5-(1-Hydroxyethyl)-8-(4-(trifluoromethoxy)phenyl)quinoxalin-6-yl)methyl)acrylamide (60 mg, 0.14 mmol) was separated by SFC (DAICEL CHIRALPAK AD(250 mm*30 mm, 10um), Neu-EtOH,10-10%) to afford the first peak (R)—N-((5-(1-hydroxyethyl)-8-(4-(trifluoromethoxy)phenyl)quinoxalin-6-yl)methyl)acrylamide (23.65 mg, 39%) and the second peak (S)—N-((5-(1-hydroxyethyl)-8-(4-(trifluoromethoxy)phenyl)quinoxalin-6-yl)methyl)acrylamide (23.65 mg, 39%) both as white solid.

The first peak: $^1$H NMR (400 MHz, DMSO-d$_6$): δ 8.99 (d, J=1.6 Hz, 1H), 8.95 (d, J=1.6 Hz, 1H), 8.64 (t, J=6.0 Hz, 1H), 7.83 (s, 1H), 7.73 (d, J=8.4 Hz, 2H), 7.51 (d, J=8.4 Hz, 2H), 6.36-6.23 (m, 2H), 6.13 (dd, J=17.2, 2.4 Hz, 1H), 5.67-5.60 (m, 2H), 5.05 (dd, J=15.2, 6.0 Hz, 1H), 4.84 (dd, J=15.2, 6.0 Hz, 1H), 1.59 (d, J=6.8 Hz, 3H); LCMS (ESI): m/z 440.0 (M+Na)$^+$.

The second peak: $^1$H NMR (400 MHz, DMSO-d$_6$): δ 8.99 (d, J=1.6 Hz, 1H), 8.95 (d, J=1.6 Hz, 1H), 8.64 (t, J=6.0 Hz, 1H), 7.83 (s, 1H), 7.73 (d, J=8.4 Hz, 2H), 7.51 (d, J=8.4 Hz, 2H), 6.36-6.23 (m, 2H), 6.13 (dd, J=17.2, 2.4 Hz, 1H), 5.67-5.60 (m, 2H), 5.05 (dd, J=15.2, 6.0 Hz, 1H), 4.84 (dd, J=15.2, 6.0 Hz, 1H), 1.59 (d, J=6.8 Hz, 3H); LCMS (ESI): m/z 440.0 (M+Na)$^+$.

Example 81 (Compound 84)

N-((5-(Hydroxymethyl)-8-(4-(trifluoromethoxy)phenyl)quinoxalin-6-yl)methyl)acrylamide

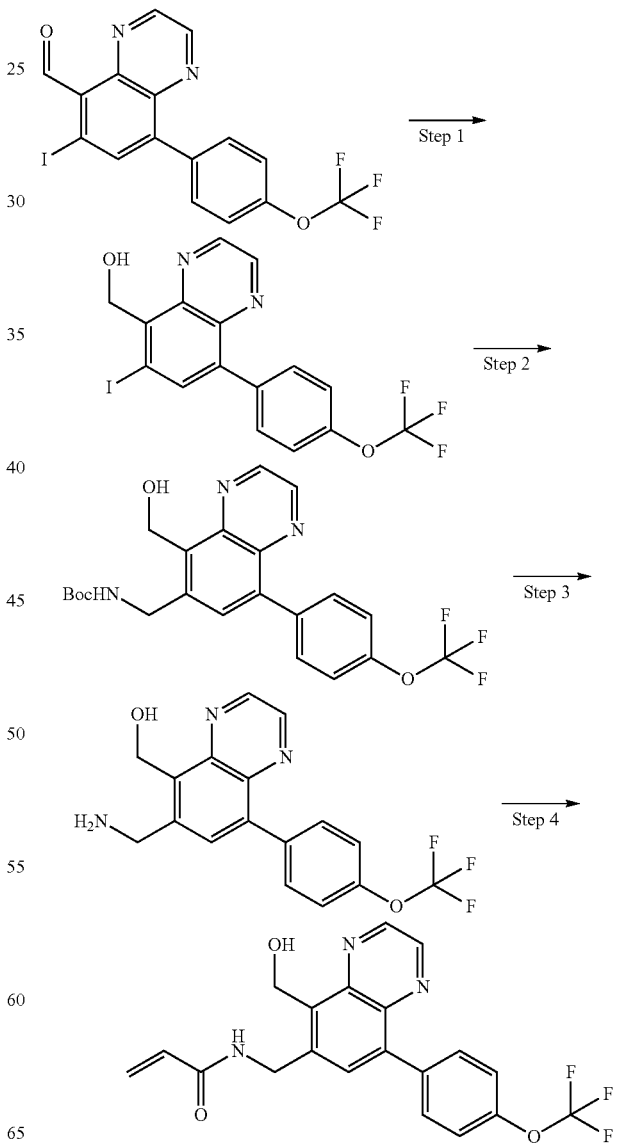

Step 1: (6-iodo-8-(4-(trifluoromethoxy)phenyl)qui-
noxalin-5-yl)methanol

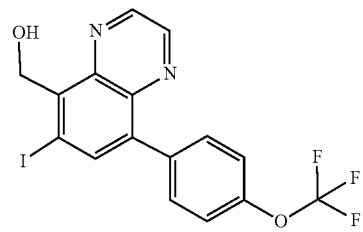 [SMILES: OCc1c(I)cc(-c2ccc(OC(F)(F)F)cc2)c2nccnc12]

To a solution of 6-iodo-8-(4-(trifluoromethoxy)phenyl) quinoxaline-5-carbaldehyde (150 mg, 0.34 mmol) in methanol (3 mL) was added NaBH$_4$ (15 mg, 0.41 mmol) at 0° C. and the mixture was stirred at 0° C. for 10 min. The reaction mixture was quenched by addition of aq.NH$_4$Cl (3 mL). The reaction mixture was diluted with ethyl acetate (30 mL), washed with brine (20 mL), dried over Na$_2$SO$_4$ and concentrated to dryness to afford the title compound (100 mg, crude). The crude product was used directly for next step. LCMS (ESI): m/z 447.0 (M+H)$^+$. Note: quinoxaline could be reduced during reduction reaction.

Step 2: tert-butyl ((5-(hydroxymethyl)-8-(4-(trifluoromethoxy)phenyl)quinoxalin-6-yl)methyl)carbamate

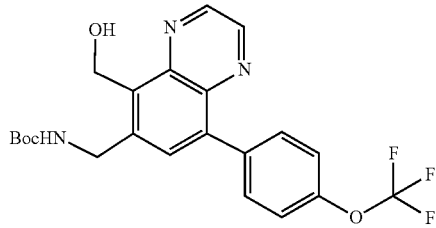 [SMILES: CC(C)(C)OC(=O)NCc1cc(-c2ccc(OC(F)(F)F)cc2)c2nccnc2c1CO]

A mixture of potassium (((tert-butoxycarbonyl)amino)methyl)trifluoroborate (298 mg, 1.26 mmol), (6-iodo- 8-(4-(trifluoromethoxy)phenyl)quinoxalin-5-yl)methanol (187 mg, 0.42 mmol), Cs$_2$CO$_3$ (410 mg, 1.26 mmol) and CATACXIUM A Pd G2 (28 mg, 0.04 mmol) in 1,4-dioxane (5 mL) and water (0.5 mL) was stirred at 80° C. under N$_2$ atmosphere for 16 h. The mixture was diluted with ethyl acetate (80 mL) and washed with water (50 mL). The organic layer was dried over Na$_2$SO$_4$ and concentrated. The residue was purified by flash chromatography on silica gel (0-60% ethyl acetate in petroleum ether) to afford the title compound (100 mg, 53%) as a brown solid. LCMS (ESI): m/z 450.2 (M+H)$^+$.

Step 3: (6-(aminomethyl)-8-(4-(trifluoromethoxy)phenyl)quinoxalin-5-yl)methanol

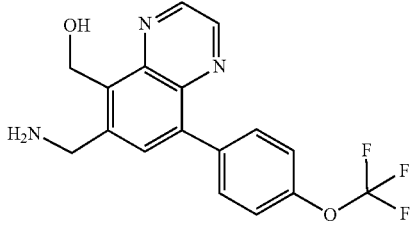 [SMILES: NCc1cc(-c2ccc(OC(F)(F)F)cc2)c2nccnc2c1CO]

To a solution of tert-butyl ((5-(hydroxymethyl)-8-(4-(trifluoromethoxy)phenyl)quinoxalin-6-yl)methyl)carbamate (100 mg, 0.22 mmol) in THF (3 mL) was added con.HCl (1 mL) at 0° C. The reaction mixture was stirred at room temperature for 16 h. The reaction was diluted with water (10 mL) and adjusted to pH=7 with sat.NaHCO$_3$. The mixture was extracted with ethyl acetate (10 mL×3). The combined organic layers were dried over Na$_2$SO$_4$ and concentrated to afford the title compound (50 mg, crude) as a yellow solid. The crude was used for next step without further purification. LCMS (ESI): m/z 350.1 [M+H]$^+$.

Step 4: N-((5-(hydroxymethyl)-8-(4-(trifluoromethoxy)phenyl)quinoxalin-6-yl)methyl)acrylamide

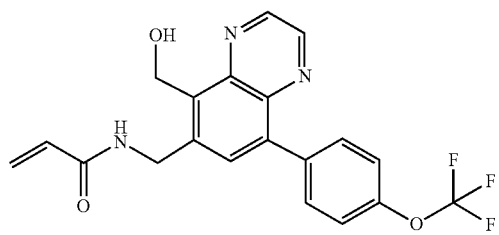 [SMILES: C=CC(=O)NCc1cc(-c2ccc(OC(F)(F)F)cc2)c2nccnc2c1CO]

To a solution of (6-(aminomethyl)-8-(4-(trifluoromethoxy)phenyl)quinoxalin-5-yl)methanol (50 mg, 0.14 mmol) and sat.NaHCO$_3$ (1 mL) in THF (2 mL) was added acrylicanhydride (20 mg, 0.16 mmol) at 0° C. The mixture was stirred at 0° C. for 1 h. The reaction mixture was diluted with water (10 mL) and extracted with ethyl acetate (10 mL×3), the combined organic layers were dried over Na$_2$SO$_4$ and concentrated. The residue was purified by reverse phase chromatography (Welch Xtimate C18 150*30 mm*5 um, water(0.225% FA)-ACN, 35%-65%) to afford the title compound (33 mg, 57%) as a white solid. $^1$H NMR (400 MHz, DMSO-d$_6$): δ 9.04 (d, J=1.6 Hz, 1H), 8.95 (d, J=1.6 Hz, 1H), 8.78 (t, J=5.6 Hz, 1H), 7.86 (s, 1H), 7.76 (d, J=8.4 Hz, 2H), 7.52 (d, J=8.4 Hz, 2H), 6.30 (dd, J=16.8, 10.0 Hz 1H), 6.14 (dd, J=16.8, 2.0 Hz, 1H), 5.64 (dd, J=10.0, 2.0 Hz, 1H), 5.33 (d, J=5.6 Hz, 2H), 5.19-5.11 (m, 1H), 4.81 (d, J=5.6 Hz, 2H); LCMS (ESI): m/z 404.1 (M+H)$^+$.

Example 82 (Compound 85)

N-((5-Cyano- 8-(4-(trifluoromethoxy)phenyl)quinoxalin-6-yl)methyl)acrylamide

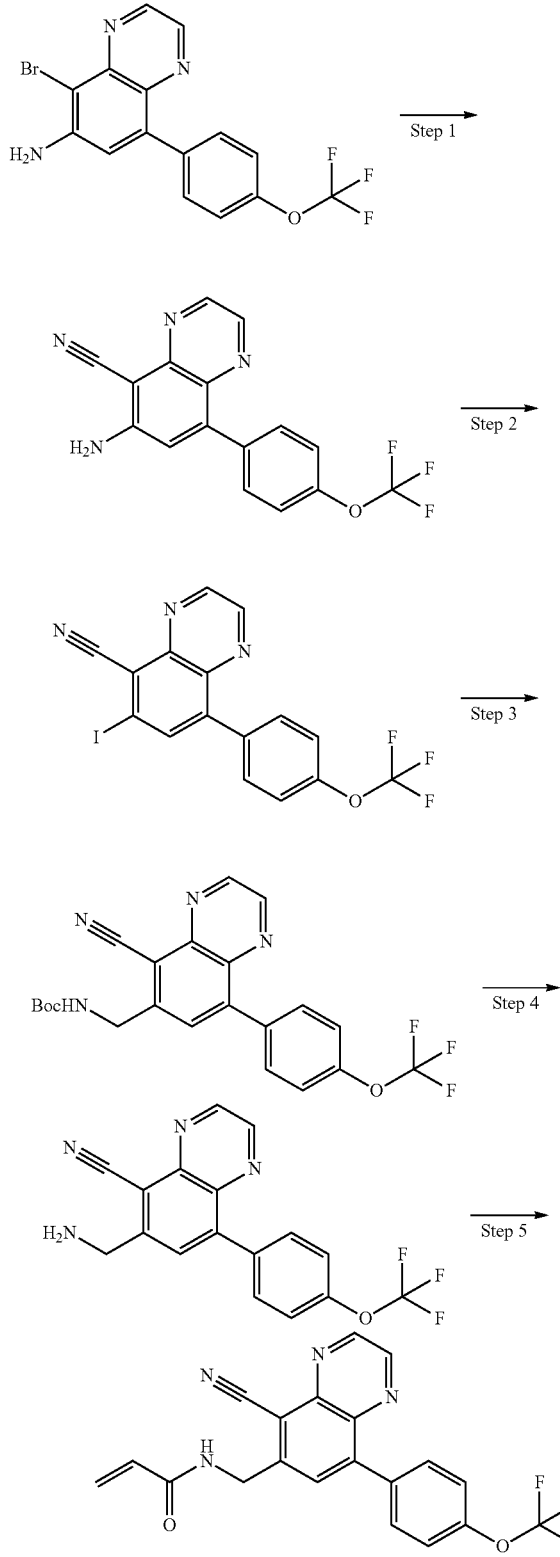

Step 1: 6-amino- 8-(4-(trifluoromethoxy)phenyl)quinoxaline-5-carbonitrile

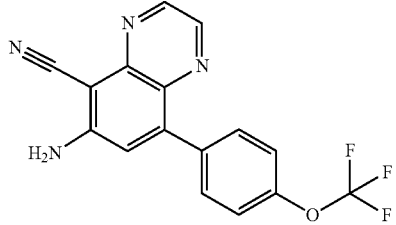 [SMILES: N#Cc1c(N)cc(-c2ccc(OC(F)(F)F)cc2)c2nccnc12]

A mixture of 5-bromo-8-(4-(trifluoromethoxy)phenyl)quinoxalin-6-amine (2.0 g, 5.21 mmol), t-BuXPhos Pd G$_3$ (0.62 g, 0.78 mmol) and Zn(CN)$_2$ (3.06 g, 26.03 mmol) in DMA (5 mL) was stirred at 140° C. for 16 h under N$_2$ atmosphere. The reaction mixture was diluted with water (100 mL) and extracted with ethyl acetate (200 mL×3), the combined organic layers were dried over Na$_2$SO$_4$ and concentrated. The residue was purified by flash chromatography on silica gel (0-20% ethyl acetate in petroleum ether) to afford the title compound (1.2 g, 70%) as a yellow solid. $^1$H NMR (400 MHz, CDCl$_3$): δ 8.84 (d, J=2.0 Hz, 11H), 8.68 (d, J=2.0 Hz, 1H), 7.69-7.63 (m, 2H), 7.37 (d, J=8.0 Hz, 2H), 7.22 (s, 1H), 5.19 (s, 2H).

Step 2: 6-iodo- 8-(4-(trifluoromethoxy)phenyl)quinoxaline-5-carbonitrile

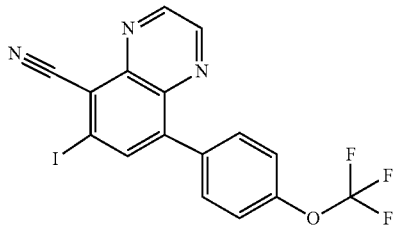 [SMILES: N#Cc1c(I)cc(-c2ccc(OC(F)(F)F)cc2)c2nccnc12]

To a solution of 6-amino- 8-(4-(trifluoromethoxy)phenyl)quinoxaline-5-carbonitrile (870 mg, 2.63 mmol) in acetonitrile (6 mL) and CH$_2$I$_2$ (2 mL) was added t-BuONO (0.47 mL, 3.95 mmol) at room temperature, then the solution was stirred at room temperature for 3 hours. The reaction was diluted with water (100 mL) and extracted with ethyl acetate (100 mL×3). The organics were washed with brine (100 mL×2), dried over sodium sulfate, filtered and concentrated. The residue was purified by flash chromatography on silica gel (0-10% ethyl acetate in petroleum ether) to afford the title compound (600 mg, 58%) as a white solid. $^1$H NMR (400 MHz, CDCl$_3$): δ 9.04 (d, J=1.6 Hz, 1H), 9.01 (d, J=1.6 Hz, 1H), 8.28 (s, 1H), 7.74-7.69 (m, 2H), 7.40 (d, J=8.0 Hz, 2H).

Step 3: tert-butyl ((5-cyano-8-(4-(trifluoromethoxy)phenyl)496uinoxaline-6-yl)methyl)carbamate

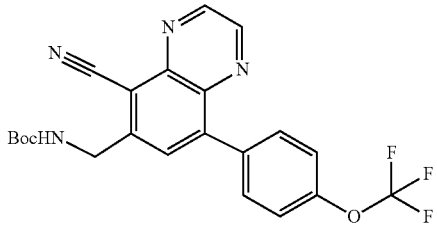 [SMILES: CC(C)(C)OC(=O)NCc1cc(-c2ccc(OC(F)(F)F)cc2)c2nccnc2c1C#N]

A mixture of 6-iodo- 8-(4-(trifluoromethoxy)phenyl)quinoxaline-5-carbonitrile (400 mg, 0.91 mmol), potassium (((tert-butoxycarbonyl)amino)methyl)trifluoroborate (430 mg, 1.81 mmol), CATACXIUM A Pd G$_2$ (61 mg, 0.09 mmol) and Cs$_2$CO$_3$ (591 mg, 1.81 mmol) in 1,4-dioxane (10 mL) and water (1 mL) was stirred at 100° C. for 5 h under N$_2$ atmosphere. The reaction was diluted with water (50 mL) and extracted with ethyl acetate (50 mL×3). The organic layers were washed with brine (50 mL×2), dried over sodium sulfate, filtered and concentrated. The residue was purified by flash chromatography on silica gel (0-50% ethyl acetate in petroleum ether) to afford the title compound (200 mg, 50%) as a yellow solid. $^1$H NMR (400 MHz, CDCl$_3$): δ 9.05 (d, J=1.6 Hz, 1H), 8.99 (d, J=1.6 Hz, 1H), 7.98 (s, 1H), 7.73 (d, J=8.4 Hz, 2H), 7.39 (d, J=8.4 Hz, 2H), 5.38-5.35 (m, 1H), 4.81 (d, J=6.4 Hz, 2H), 1.47 (s, 9H); LCMS (ESI): m/z 445.2 (M+H)$^+$.

Step 4: 6-(aminomethyl)-8-(4-(trifluoromethoxy)phenyl)quinoxaline-5-carbonitrile

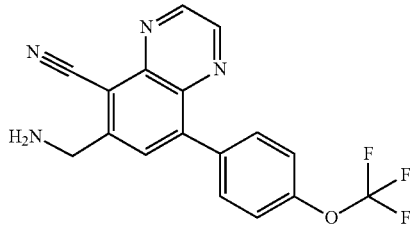 [SMILES: N#Cc1c(CN)cc(-c2ccc(OC(F)(F)F)cc2)c2nccnc12]

A solution of tert-butyl ((5-cyano- 8-(4-(trifluoromethoxy)phenyl)quinoxalin-6-yl)methyl)carbamate (200 mg, 0.45 mmol) and 5% TFA in HFIP (5 mL) was stirred at room temperature for 1 h. The mixture was quenched with water (10 mL) then adjusted pH to 8 with aq.NaHCO$_3$ solution and diluted with ethyl acetate (100 mL) and washed with water (100 mL×3). The organic layer was dried over Na$_2$SO$_4$ and concentrated to afford the title compound (150 mg, crude) as a brown solid. LCMS (ESI): m/z 345.1 (M+H)$^+$.

Step 5: N-((5-cyano- 8-(4-(trifluoromethoxy)phenyl)quinoxalin-6-yl)methyl)acrylamide

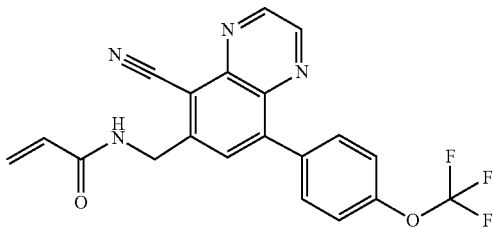 [SMILES: C=CC(=O)NCc1cc(-c2ccc(OC(F)(F)F)cc2)c2nccnc2c1C#N]

To a solution of 6-(aminomethyl)-8-(4-(trifluoromethoxy)phenyl)quinoxaline-5-carbonitrile (150 mg, 0.44 mmol) and sat.NaHCO$_3$ (1 mL) in THF (5 mL) was added acrylic anhydride (55 mg, 0.44 mmol) at 0° C. The resulting mixture was stirred at 0° C. for 1 h. The mixture was diluted with ethyl acetate (30 mL) and washed with water (30 mL×3). The organic was dried over Na$_2$SO$_4$ and concentrated. The residue was purified by reverse phase chromatography (Welch Xtimate C18 150*30 mm*5 um,water(0.225% FA)-ACN,45-75%) to afford the title compound (28.93 mg, 17%) as a white solid. $^1$H NMR (400 MHz, DMSO-d$_6$): δ 9.18 (d, J=1.6 Hz, 1H), 9.12 (d, J=1.6 Hz, 1H), 9.00 (t, J=5.6 Hz, 1H), 7.98 (s, 1H), 7.81-7.78 (m, 2H), 7.57 (d, J=8.0 Hz, 2H), 6.30 (dd, J=17.2, 10.0 Hz, 1H), 6.14 (dd, J=17.2, 2.0 Hz, 1H), 5.66 (dd, J=10.0, 2.0 Hz, 1H), 4.83 (d, J=5.6 Hz, 2H); LCMS (ESI): m/z 399.0 (M+H)$^+$.

Example 83a (Compound 86)

(R)-Cyclobut-1-en-1-yl(3-(5-(1,2-dihydroxyethyl)-8-(4-(trifluoromethoxy)phenyl)quinoxalin-6-yl)azetidin-1-yl)methanone

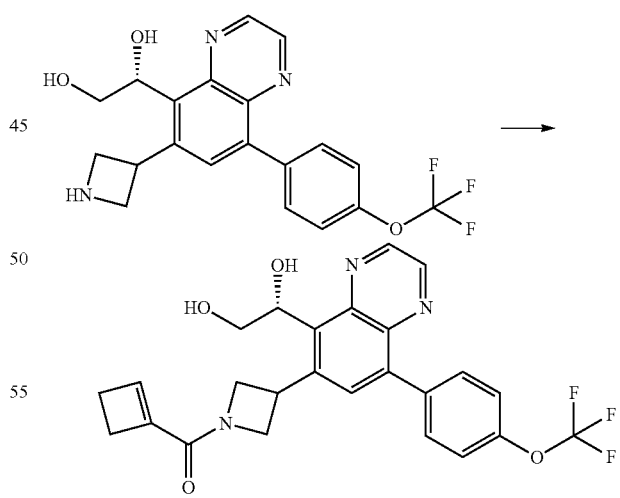

To a stirred solution of (R)-1-(6-(azetidin-3-yl)-8-(4-(trifluoromethoxy)phenyl)quinoxalin-5-yl)ethane-1,2-diol (150 mg, 0.37 mmol) and cyclobutene-1-carboxylic acid (54 mg, 0.56 mmol) in dichloromethane (4 mL) and methyl alcohol (0.5 mL) was added ethyl 2-ethoxyquinoline-1(2H)-carboxylate (137 mg, 0.56 mmol) at room temperature. The mixture was at room temperature stirred for 2 h. The reaction mixture was concentrated and the residue was purified by column chromatography on silica gel (0-5% methanol in dichloromethane) to afford the title compound (37.8 mg, 21%) as a white solid. $^1$H NMR (400 MHz, DMSO-d$_6$): δ 8.99 (d, J=1.6 Hz, 1H), 8.95 (d, J=1.6 Hz, 1H), 8.15, 8.14 (s, 1H total), 7.84 (d, J=8.8 Hz, 2H), 7.51 (d, J=8.4 Hz, 2H), 6.51 (d, J=4.4 Hz, 1H), 6.15 (s, 1H), 5.80-5.75 (m, 1H), 5.17-5.15 (m, 1H), 4.90-4.86 (m, 1H), 4.71-4.64 (m, 1H), 4.54-4.35 (m, 2H), 4.18-4.06 (m, 1H), 3.77-3.73 (m, 1H), 3.65-3.58 (m, 1H), 2.67-2.65 (m, 2H), 2.42-2.40 (m, 2H); LCMS (ESI): m/z 486.2 (M+H)$^+$.

Example 83b (Compound 87)

(S)-Cyclobut-1-en-1-yl(3-(5-(1,2-dihydroxyethyl)-8-(4-(trifluoromethoxy) phenyl)quinoxalin-6-yl)azetidin-1-yl)methanone

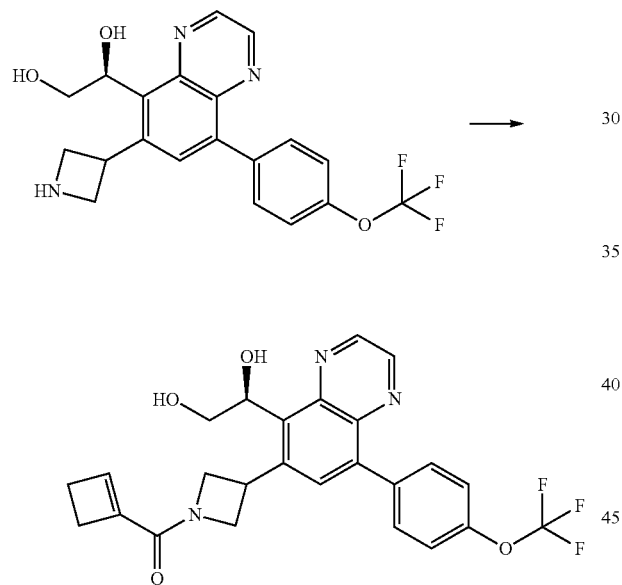

To a solution of (S)-1-(6-(azetidin-3-yl)-8-(4-(trifluoromethoxy)phenyl)quinoxalin-5-yl)ethane-1,2-diol (200 mg, 0.49 mmol) and cyclobut-1-enecarboxylic acid (63 mg, 0.64 mmol) in dichloromethane (4 mL) and methyl alcohol (1 mL) was added ethyl 2-ethoxyquinoline-1(2H)-carboxylate (159 mg, 0.64 mmol) at room temperature. The resulting mixture was stirred at room temperature for 3 h. The mixture was concentrated and the residue was purified by column chromatography on silica gel (0-5% methanol in dichloromethane) to afford the title compound (67 mg, 28%) as a yellow solid. $^1$H NMR (400 MHz, DMSO-d$_6$): δ 8.99 (d, J=1.6 Hz, 1H), 8.95 (d, J=1.6 Hz, 1H), 8.15, 8.14 (s, 1H total), 7.84 (d, J=8.8 Hz, 2H), 7.51 (d, J=8.4 Hz, 2H), 6.51 (d, J=4.4 Hz, 1H), 6.15 (s, 1H), 5.80-5.75 (m, 1H), 5.17-5.15 (m, 1H), 4.90-4.86 (m, 1H), 4.71-4.64 (m, 1H), 4.54-4.35 (m, 2H), 4.18-4.06 (m, 1H), 3.77-3.73 (m, 1H), 3.65-3.58 (m, 1H), 2.67-2.65 (m, 2H), 2.42-2.40 (m, 2H); LCMS (ESI): m/z 486.0 (M+H)$^+$.

Example 84 (Compound 88)

N-((4-(Hydroxymethyl)-7-(4-(trifluoromethoxy)phenyl)-2,3-dihydrobenzofuran-5-yl)methyl)-N-methylacrylamide

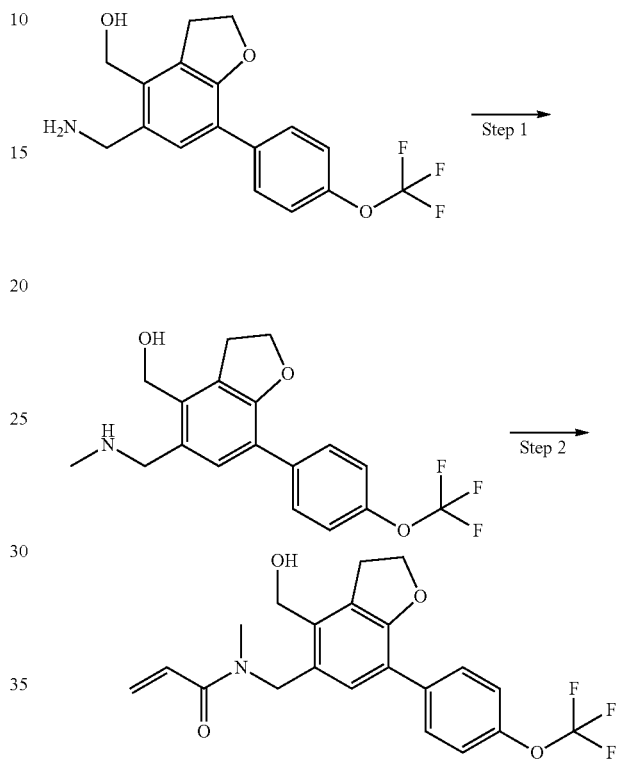

Step 1: (5-((methylamino)methyl)-7-(4-(trifluoromethoxy)phenyl)-2,3-dihydrobenzofuran-4-yl)methanol

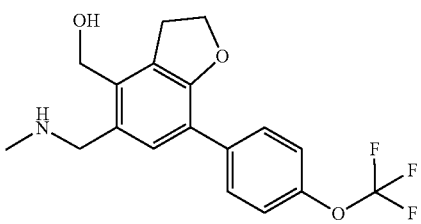 [SMILES: CNCc1cc(-c2ccc(OC(F)(F)F)cc2)c2c(c1CO)CCO2]

A mixture of (5-(aminomethyl)-7-(4-(trifluoromethoxy)phenyl)-2,3-dihydrobenzofuran-4-yl)methanol (200 mg, 0.59 mmol) and methyl trifluoromethanesulfonate (145 mg, 0.88 mmol) in HFIP (2 mL) was stirred at room temperature for 16 h under N$_2$ atmosphere. The reaction was quenched with H$_2$O (4 mL) and extracted with ethyl acetate (10 mL×2), the combined organic layers were dried over Na$_2$SO$_4$ and concentrated to afford the title compound (200 mg, crude) as a yellow oil. The crude was used directly and without other purification. LCMS (ESI): m/z 354.1 (M+H)$^+$.

Step 2: N-((4-(hydroxymethyl)-7-(4-(trifluoromethoxy)phenyl)-2,3-dihydrobenzofuran-5-yl)methyl)-N-methylacrylamide

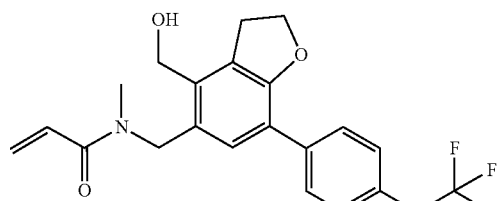

To a solution of (5-((methylamino)methyl)-7-(4-(trifluoromethoxy)phenyl)-2,3-dihydrobenzofuran-4-yl)methanol (200 mg, 0.57 mmol) and sat.NaHCO$_3$ (0.5 mL) in THF (2 mL) was added acryloyl chloride (51 mg, 0.14 mmol) at 0° C. The resulting mixture was stirred at 0° C. for 0.5h. The reaction mixture was quenched with water (5 mL), extracted with ethyl acetate (10 mL×2). Combined organic layers were dried over Na$_2$SO$_4$, filtered and concentrated under vacuum. The residue was purified by reverse phase chromatography (Welch Xtimate C18 150*25 mm*5 um, water(FA)-ACN, 44-74%) and Chiral SFC (Instrument: SFC-12; Column: AD(250 mm*30 mm,10 um); Condition: Neu-ETOH; Begin B:25%; Flow Rate (ml/min): 60) to afford the title compound (29.8 mg, 13%) as a white solid. $^1$H NMR (400 MHz, DMSO-d$_6$): δ 7.74 (d, J=8.8 Hz, 2H), 7.39 (d, J=8.8 Hz, 2H), 7.10-6.97 (m, 1H), 6.75 (dd, J=16.8, 10.4 Hz, 1H), 6.16 (dd, J=16.8, 2.4 Hz, 1H), 5.67 (dd, J=10.4, 2.4 Hz, 11H), 4.82 (s, 11H), 4.74 (s, 2H), 4.62 (t, J=8.8 Hz, 2H), 4.53 (d, J=5.2 Hz, 2H), 3.34 (t, J=8.8 Hz, 2H), 2.95 (s, 3H); LCMS (ESI): m/z 430.0 (M+Na)$^+$.

Example 85 (Compound 89) & 86 (Compound 90)

N-((4-((1S,2S)-1,2-Dihydroxypropyl)-7-(4-(trifluoromethoxy)phenyl)-2,3-dihydrobenzofuran-5-yl)methyl)acrylamide & N-((4-((1R,2R)-1,2-dihydroxypropyl)-7-(4-(trifluoromethoxy)phenyl)-2,3-dihydrobenzofuran-5-yl)methyl)acrylamide

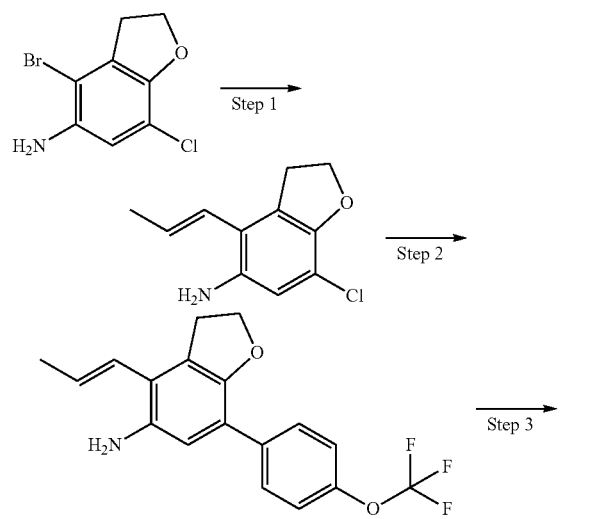

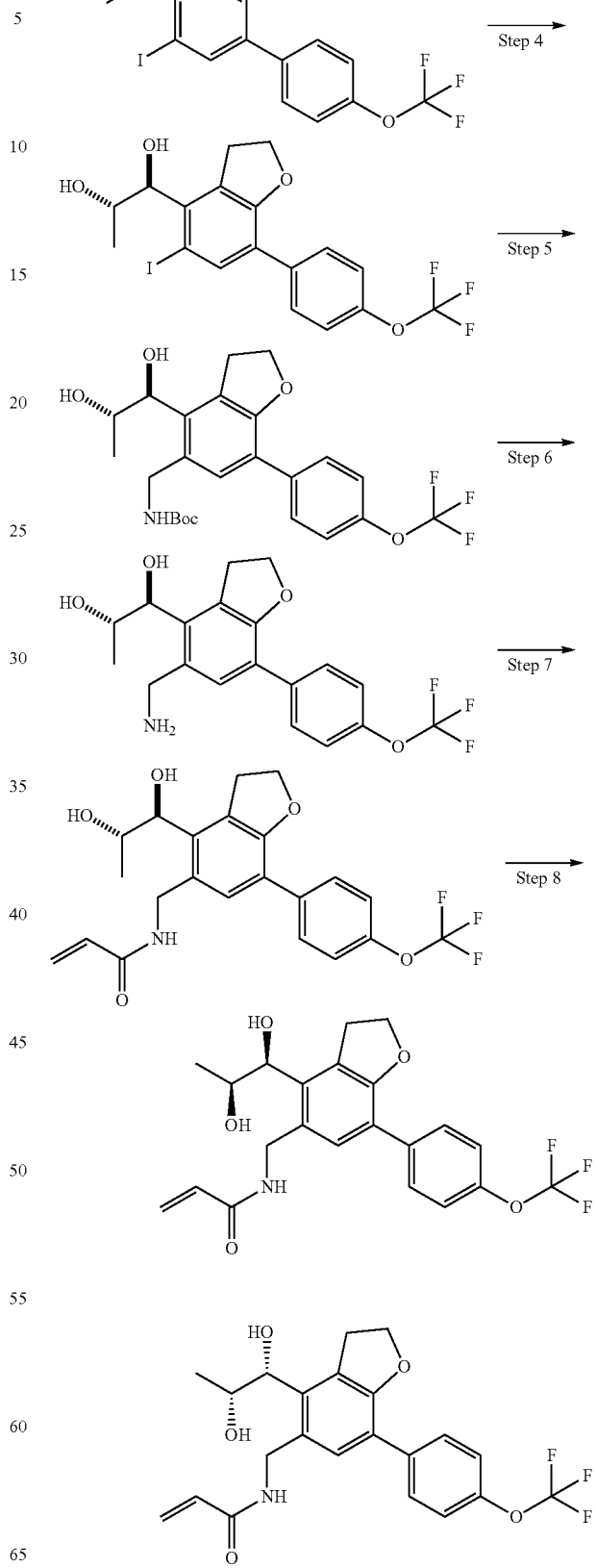

Step 1: (E)-7-chloro-4-(prop-1-en-1-yl)-2,3-dihydrobenzofuran-5-amine

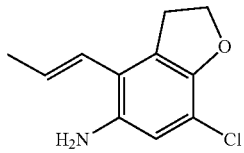

A mixture of 4-bromo-7-chloro-2,3-dihydrobenzofuran-5-amine (1.0 g, 4.0 mmol), (E)-4,4,5,5-tetramethyl-2-(prop-1-en-1-yl)-1,3,2-dioxaborolane (1.0 g, 6.0 mmol), $K_2CO_3$ (853 mg, 8.0 mmol), Pd(dppf)C12 (441 mg, 0.6 mmol) in 1,4-dioxane (10 mL) and water (1 mL) was stirred at 100° C. for 5 h under $N_2$ atmosphere. The reaction mixture was filtered, the filtrate was diluted with water (30 mL) and extracted with ethyl acetate (50 mL×3). The combined organics were washed with brine (50 mL×2), dried over sodium sulfate, filtered and concentrated. The residue was purified by flash chromatography on silica gel (0-8% ethyl acetate in petroleum ether) to afford the title compound (800 mg, 95%) as a yellow solid. $^1$H NMR (400 MHz, $CDCl_3$): δ 6.52 (s, 1H), 6.22 (dd, J=16.4, 1.2 Hz, 1H), 6.06-5.99 (m, 1H), 4.59 (t, J=8.4 Hz, 2H), 3.23 (t, J=8.4 Hz, 2H), 1.92 (dd, J=6.4, 1.6 Hz, 3H).

Step 2: (E)-4-(prop-1-en-1-yl)-7-(4-(trifluoromethoxy)phenyl)-2,3-dihydrobenzofuran-5-amine

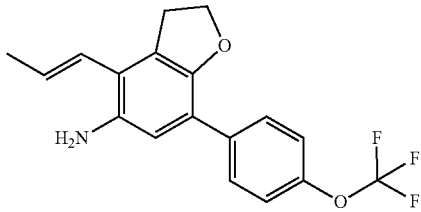 [SMILES: C/C=C/c1c(N)cc(-c2ccc(OC(F)(F)F)cc2)c2c1CCO2]

A reaction mixture of (E)-7-chloro-4-(prop-1-en-1-yl)-2,3-dihydrobenzofuran-5-amine (800 mg, 3.8 mmol), Xphos (172 mg, 0.4 mmol), Xphos Pd $G_2$ (300 mg, 0.4 mmol), (4-(trifluoromethoxy)phenyl)boronic acid (864 mg, 4.2 mmol) and KOAc (1.12 g, 11.45 mmol) in 1,4-dioxane (20 mL) and $H_2O$ (5 mL) was stirred at 100° C. for 4 h under $N_2$ atmosphere. The reaction mixture was concentrated and diluted with ethyl acetate (60 mL), washed with brine (50 mL×5). The organic layers were combined, dried over $Na_2SO_4$, filtered and concentrated. The residue was purified by flash chromatography on silica gel (0-8% ethyl acetate in petroleum ether) to afford the title compound (1.0 g, 78%) as a brown oil. $^1$H NMR (400 MHz, $CDCl_3$): δ 7.69 (d, J=8.8 Hz, 1H), 7.24 (d, J=8.4 Hz, 2H), 6.65 (s, 1H), 6.35 (d, J=16.4 Hz, 11H), 6.15-6.02 (m, 1H), 4.63-4.50 (m, 2H), 3.23 (t, J=8.4 Hz, 2H), 1.99-1.92 (m, 3H).

Step 3: (E)-5-iodo-4-(prop-1-en-1-yl)-7-(4-(trifluoromethoxy)phenyl)-2,3-dihydrobenzofuran

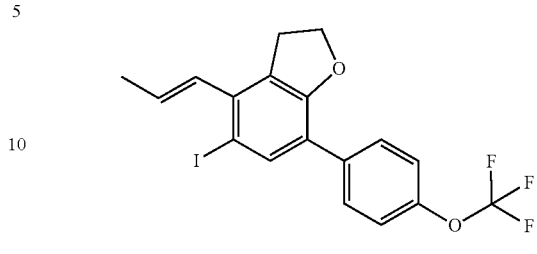

To a solution of (E)-4-(prop-1-en-1-yl)-7-(4-(trifluoromethoxy)phenyl)-2,3-dihydrobenzofuran-5-amine (1.0 g, 2.98 mmol) in acetonitrile (10 mL) was added a solution of HCl (4 M in water, 1.5 mL, 5.96 mmol) slowly at 0° C. Then $NaNO_2$ (216 mg, 3.1 mmol) in water (3 mL) was added slowly and the reaction temperature was kept at 0° C. After addition, the mixture was stirred at 0° C. for 3 minutes. Then the KI (990 mg, 6.0 mmol) in water (10 mL) was added slowly at 0° C. The mixture was stirred at 0° C. for 40 minutes. The mixture was quenched with aq.$Na_2SO_3$ (20 mL) and extracted with ethyl acetate (50 mL×3) and washed with brine (100 mL). The organic layers were dried over anhydrous sodium sulfate and concentrated under reduced. The residue was purified by flash chromatography on silica gel (0-5% ethyl acetate in petroleum ether) to afford the title compound (600 mg, 45%) as a yellow solid. $^1$H NMR (400 MHz, $CDCl_3$): δ 7.74 (s, 1H), 7.67 (d, J=8.8 Hz, 2H), 7.27-7.23 (m, 2H), 6.48 (d, J=16.0 Hz 1H), 6.04-5.93 (m, 1H), 4.62 (t, J=8.8 Hz, 2H), 3.35 (t, J=8.8 Hz, 2H), 1.97 (dd, J=6.4, 2.0 Hz, 3H).

Step 4: cis-1-(5-iodo-7-(4-(trifluoromethoxy)phenyl)-2,3-dihydrobenzofuran-4-yl)propane-1,2-diol

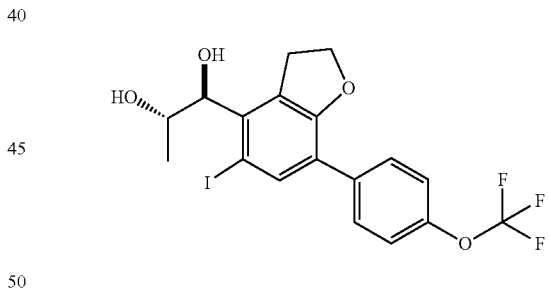

To a solution of (E)-5-iodo-4-(prop-1-en-1-yl)-7-(4-(trifluoromethoxy)phenyl)-2,3-dihydrobenzofuran (600 mg, 1.3 mmol) and NMO in THF (6 mL) and water (2 mL) was added $K_2OsO_4 2H_2O$ (50 mg, 0.30 mmol) at room temperature. The resulting mixture was stirred at room temperature for 16 h. The mixture was diluted with water (50 mL) and extracted with ethyl acetate (50 mL×3) and washed with saturated $Na_2SO_3$ (50 mL). The combined organic layers were dried over anhydrous sodium sulfate and concentrated under reduced. The residue was purified by flash chromatography on silica gel (0-25% ethyl acetate in petroleum ether) to afford the title compound (450 mg, 69%) as a white solid. $^1$H NMR (400 MHz, $CDCl_3$): δ 7.72 (s, 1H), 7.66 (d, J=8.8 Hz, 2H), 7.27-7.23 (m, 2H), 4.90 (dd, J=7.2, 4.0 Hz, 1H), 4.66-4.56 (m, 2H), 4.17-4.10 (m, 1H), 3.73-3.65 (m, 1H), 3.41-3.31 (m, 2H), 2.72 (d, J=4.0 Hz, 1H), 2.37 (d, J=4.0 Hz, 1H), 1.30-1.25 (m, 3H).

Step 5: tert-butyl ((4-(cis-1,2-dihydroxypropyl)-7-(4-(trifluoromethoxy)phenyl)-2,3-dihydrobenzofuran-5-yl)methyl)carbamate

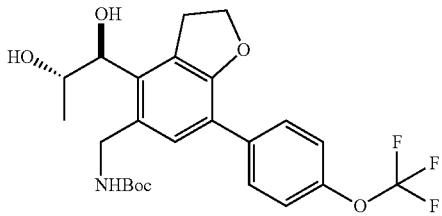 [SMILES: C[C@H](O)[C@@H](O)c1c(CNC(=O)OC(C)(C)C)cc(-c2ccc(OC(F)(F)F)cc2)c2c1CCO2]

A mixture of cis-1-(5-iodo-7-(4-(trifluoromethoxy)phenyl)-2,3-dihydrobenzofuran-4-yl)propane-1,2-diol (300 mg, 0.6 mmol), K₂CO₃ (777 mg, 5.6 mmol), Sphos Pd G₂ (45 mg, 0.06 mmol) and potassium (((tert-butoxycarbonyl)amino)methyl)trifluoroborate (446 mg, 1.8 mmol) in 1,4-dioxane (5 mL) and water (0.6 mL) was purged with N₂ atmosphere for 3 min. The mixture was stirred at 80° C. for 2 h under N₂ atmosphere. The solution was concentrated and the residue was purified by flash chromatography on silica gel (0-20% ethyl acetate in petroleum ether) to afford the title compound (200 mg, 66%) as a yellow solid. LCMS (ESI): m/z 505.9 (M+Na)⁺.

Step 6: cis-1-(5-(Aminomethyl)-7-(4-(trifluoromethoxy)phenyl)-2,3-dihydrobenzofuran-4-yl)propane-1,2-diol 2,2,2-trifluoroacetate

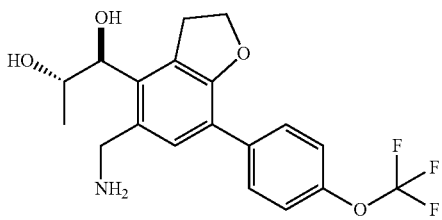 [SMILES: C[C@H](O)[C@@H](O)c1c(CN)cc(-c2ccc(OC(F)(F)F)cc2)c2c1CCO2]

To a stirred solution of tert-butyl ((4-(cis-1,2-dihydroxypropyl)-7-(4-(trifluoromethoxy)phenyl)-2,3-dihydrobenzofuran-5-yl)methyl)carbamate (200 mg, 0.6 mmol) was added 5% TFA in HFIP (1 mL) at room temperature. The mixture was stirred for 2 h at room temperature. The solvent was removed under reduced pressure directly to afford the title compound (130 mg, crude) as yellow oil. LCMS (ESI): m/z 384.2 (M+H)⁺.

Step 7: N-((4-(cis-1,2-dihydroxypropyl)-7-(4-(trifluoromethoxy)phenyl)-2,3-dihydrobenzofuran-5-yl)methyl)acrylamide

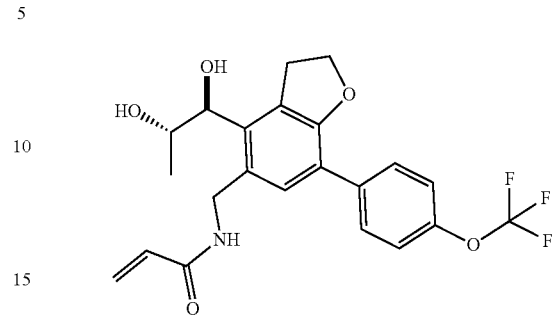

To a solution of cis-1-(5-(aminomethyl)-7-(4-(trifluoromethoxy)phenyl)-2,3-dihydrobenzofuran-4-yl)propane-1,2-diol 2,2,2-trifluoroacetate (130 mg, 0.3 mmol) and sat. NaHCO₃ (2 mL) in THF (5 mL) was added acryloyl chloride (33 mg, 0.3 mmol) at 0° C. The mixture was stirred at 0° C. for 1 h. The mixture was diluted with water (10 mL), extracted with ethyl acetate (20 mL×3), the organic layer was dried over Na₂SO₄ and concentrated under reduced pressure. The residue was purified by reverse phase chromatography (Welch Xtimate C18 150*25 mm*5 um, acetonitrile 37-6 7%/0.225% FA in water) to afford the title compound (80 mg, 53%) as white solid. LCMS (ESI): m/z 460.2 (M+Na)⁺.

Step 8: N-((4-((1S,2S)-1,2-dihydroxypropyl)-7-(4-(trifluoromethoxy)phenyl)-2,3-dihydrobenzofuran-5-yl)methyl)acrylamide & N-((4-((1R,2R)-1,2-dihydroxypropyl)-7-(4-(trifluoromethoxy)phenyl)-2,3-dihydrobenzofuran-5-yl)methyl)acrylamide

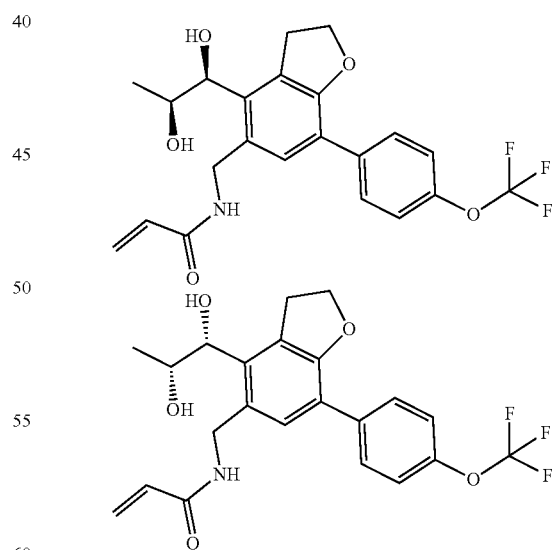

N-((4-(cis-1,2-Dihydroxypropyl)-7-(4-(trifluoromethoxy)phenyl)-2,3-dihydrobenzofuran-5-yl)methyl)acrylamide (80 mg, 0.17 mmol) was separated by Chiral SFC (Instrument: SFC-12; Column: OD(250 mm*30 mm,10 um); Condition: Neu-ETOH; Begin B:15%; Flow Rate (ml/min): 70) to afford the first peak N-((4-((1S,2S)-1,2- dihydroxypropyl)-7-(4-(trifluoromethoxy)phenyl)-2,3-dihydrobenzofuran-5-yl)methyl)acrylamide (29 mg, 35%) and the second peak N-((4-((1R,2R)-1,2-dihydroxypropyl)-7-(4-(trifluoromethoxy)phenyl)-2,3-dihydrobenzofuran-5-yl)methyl)acrylamide (34 mg, 42%) both as white solid.

The first peak: $^1$H NMR (400 MHz, DMSO-$d_6$): δ 8.33 (t, J=5.6 Hz, 1H), 7.75 (d, J=8.8 Hz, 2H), 7.42 (d, J=8.4 Hz, 2H), 7.23 (s, 1H), 6.27 (dd, J=17.2, 10.0 Hz, 1H), 6.10 (dd, J=17.2, 2.4 Hz, 1H), 5.59 (dd, J=10.0, 2.4 Hz, 1H), 5.22 (d, J=3.6 Hz, 1H), 4.71 (d, J=4.8 Hz, 1H), 4.60-4.47 (m, 4H), 4.45-4.36 (m, 1H), 3.92-3.86 (m, 1H), 3.48-3.38 (m, 1H), 3.32-3.24 (m, 1H), 0.95 (d, J=6.4 Hz, 3H); LCMS (ESI): m/z 460.1 (M+Na)$^+$.

The second peak: $^1$H NMR (400 MHz, DMSO-$d_6$): δ 8.33 (t, J=5.6 Hz, 1H), 7.75 (d, J=8.8 Hz, 2H), 7.42 (d, J=8.4 Hz, 2H), 7.23 (s, 1H), 6.27 (dd, J=17.2, 10.0 Hz, 1H), 6.10 (dd, J=17.2, 2.4 Hz, 1H), 5.59 (dd, J=10.0, 2.4 Hz, 1H), 5.22 (d, J=3.6 Hz, 1H), 4.71 (d, J=4.8 Hz, 1H), 4.60-4.47 (m, 4H), 4.45-4.36 (m, 1H), 3.95-3.86 (m, 1H), 3.48-3.38 (m, 1H), 3.32-3.24 (m, 1H), 0.95 (d, J=6.4 Hz, 3H); LCMS (ESI): m/z 460.1 (M+Na)$^+$.

Example 87 & (Compound 91) Example 88 (Compound 92)

(R)—N-((4-(2-Cyano-1-hydroxyethyl)-7-(4-(trifluoromethoxy)phenyl)-2,3-dihydrobenzofuran-5-yl)methyl)acrylamide & (S)—N-((4-(2-cyano-1-hydroxyethyl)-7-(4-(trifluoromethoxy)phenyl)-2,3-dihydrobenzofuran-5-yl)methyl)acrylamide

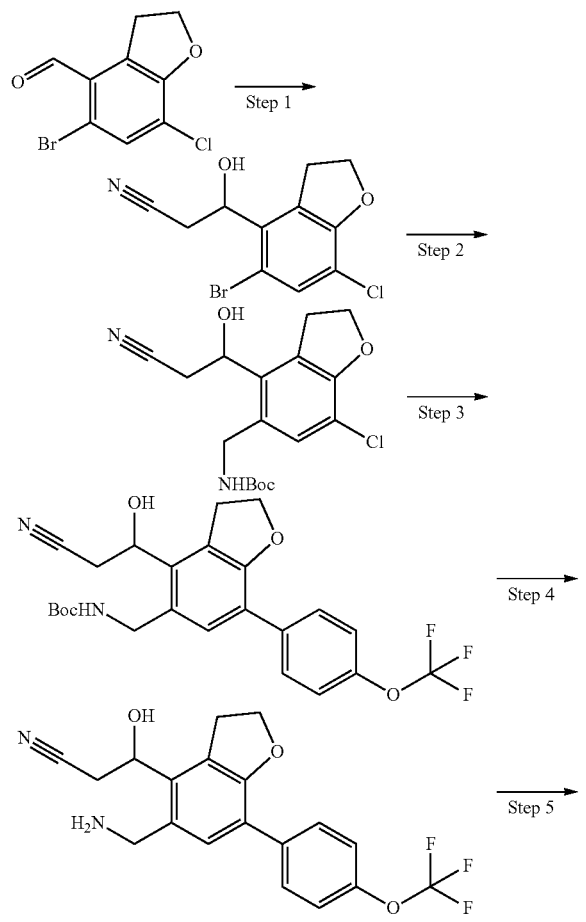

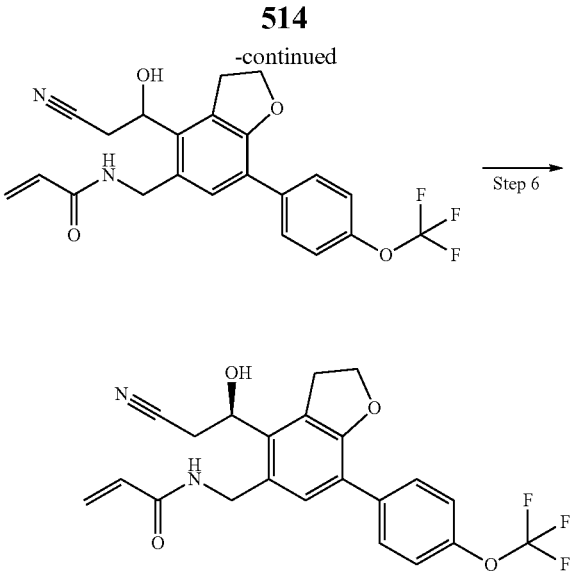

Step 1: 3-(5-bromo-7-chloro-2,3-dihydrobenzofuran-4-yl)-3-hydroxypropanenitrile

To a solution of MeCN (0.2 mL, 3.8 mmol) in THF (5 mL) was added LDA (2.0 M in THF, 2.1 mL, 4.21 mmol) at −78° C. and the reaction was stirred at −78° C. for 0.5h. Then 5-bromo-7-chloro-2,3-dihydrobenzofuran-4-carbaldehyde (500 mg, 1.9 mmol) in THF (5 mL) was added into the solution of at 0° C. After addition, the resulting solution was stirred at 0° C. for 1 h. The mixture was quenched with sat.NH$_4$Cl (20 mL) and extracted with ethyl acetate (50 mL×3), the combined organic layers were washed with water (30 mL×3). The organic was dried over Na$_2$SO$_4$ and concentrated. The residue was purified by chromatography on silica gel (0-5% ethyl acetate in petroleum ether) to afford the title compound (500 mg, 86%) as a white solid. $^1$H NMR (400 MHz, CDCl$_3$): δ 7.36 (s, 1H), 5.48-5.44 (m, 1H), 4.76-4.57 (m, 2H), 3.73-3.62 (m, 1H), 3.59-3.51 (m, 1H), 2.87-2.81 (m, 2H), 2.58 (d, J=5.2 Hz, 1H).

Step 2: tert-butyl ((7-chloro-4-(2-cyano-1-hydroxyethyl)-2,3-dihydrobenzofuran-5-yl)methyl)carbamate

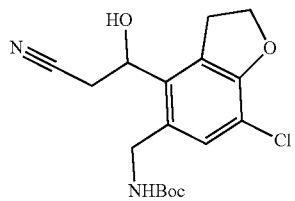 [SMILES: CC(C)(C)OC(=O)NCc1cc(Cl)c2c(c1C(O)CC#N)CCO2]

A mixture of Cs₂CO₃ (646 mg, 1.98 mmol), potassium (((tert-butoxycarbonyl)amino)methyl)trifluoroborate (262 mg, 1.3 mmol), CATACXIUM A Pd G₂ (44 mg, 0.07 mmol) and 3-(5-bromo-7-chloro-2,3-dihydrobenzofuran-4-yl)-3-hydroxypropanenitrile (200 mg, 0.60 mmol) in 1,4-dioxane (12 mL) and water (1.2 mL) was purged with N₂ atmosphere for 3 min. The mixture was stirred at 100° C. for 4 h under N₂ atmosphere. The solution was concentrated. The resulting solution was extracted with ethyl acetate (40 mL×3) and washed with water (40 mL×3). The organic layers were combined, dried over anhydrous sodium sulfate and concentrated under reduced pressure. Then the residue was purified by flash chromatography on silica gel (0-20% ethyl acetate in petroleum ether) to afford the title compound (100 mg, 43%) as a yellow oil. LCMS (ESI): m/z 375.1 (M+Na)⁺.

Step 3: tert-butyl ((4-(2-cyano-1-hydroxyethyl)-7-(4-(trifluoromethoxy)phenyl)-2,3-dihydrobenzofuran-5-yl)methyl)carbamate

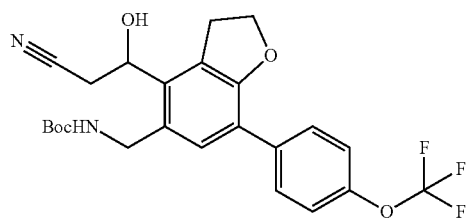 [SMILES: CC(C)(C)OC(=O)NCc1cc(-c2ccc(OC(F)(F)F)cc2)c2c(c1C(O)CC#N)CCO2]

A mixture of tert-butyl ((7-chloro-4-(2-cyano-1-hydroxyethyl)-2,3-dihydrobenzofuran-5-yl)methyl)carbamate (500 mg, 1.4 mmol), Xphos (68 mg, 0.1 mmol), Xphos Pd G₂ (112 mg, 0.1 mmol), (4-(trifluoromethoxy)phenyl)boronic acid (321 mg, 1.5 mmol) and Na₂CO₃ (300 mg, 2.8 mmol) in 1,4-dioxane (10 mL) and water (1 mL) was stirred at 100° C. for 2 h under N₂ atmosphere. The mixture was diluted with water (20 mL) and extracted with ethyl acetate (20 mL×3). The combined organic layers were dried over anhydrous sodium sulfate and concentrated under reduced. The residue was purified by flash chromatography on silica gel (0-15% ethyl acetate in petroleum ether) to afford the title compound (400 mg, 60%) as a yellow oil. LCMS (ESI): m/z 501.2 (M+Na)⁺.

Step 4: 3-(5-(aminomethyl)-7-(4-(trifluoromethoxy)phenyl)-2,3-dihydrobenzofuran-4-yl)-3-hydroxypropanenitrile 2,2,2-trifluoroacetate

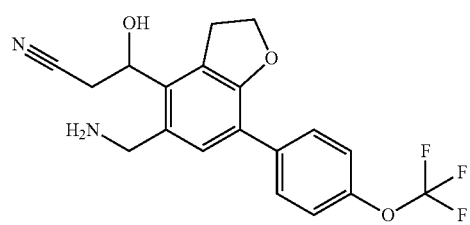 [SMILES: N#CCC(O)c1c(CN)cc(-c2ccc(OC(F)(F)F)cc2)c2c1CCO2]

To a stirred solution of tert-butyl ((4-(2-cyano-1-hydroxyethyl)-7-(4-(trifluoromethoxy)phenyl)-2,3-dihydrobenzofuran-5-yl)methyl)carbamate (400 mg, 0.80 mmol) in DCM (5 mL) was added TFA (2 mL) at room temperature. The mixture was stirred at room temperature for 2 h. The solvent was removed under reduced pressure to afford the title compound (300 mg, crude) as a yellow oil. The crude was used directly without further purification. LCMS (ESI): m/z 379.2 (M+H)⁺.

Step 5: N-((4-(2-cyano-1-hydroxyethyl)-7-(4-(trifluoromethoxy)phenyl)-2,3-dihydrobenzofuran-5-yl)methyl)acrylamide

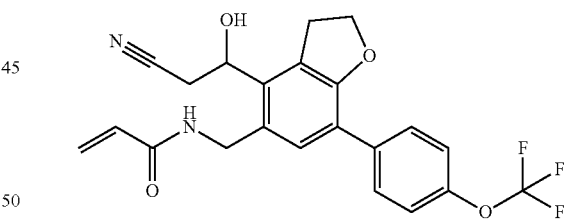

To a solution of 3-(5-(aminomethyl)-7-(4-(trifluoromethoxy)phenyl)-2,3-dihydrobenzofuran-4-yl)-3-hydroxypropanenitrile 2,2,2-trifluoroacetate (250 mg, 0.60 mmol) in THF (5 mL) was added sat.NaHCO₃ (1 mL) and acryloyl chloride (119 mg, 1.3 mmol) at 0° C. The mixture was stirred at 0° C. for 1 h. The mixture was diluted with water (20 mL), extracted with ethyl acetate (40 mL×3), the combined organic layers were washed with brine (50 mL), dried over Na₂SO₄ and concentrated in vacuo. The residue was purified by column chromatography on silica gel (0-20% ethyl acetate in petroleum ether) to afford the title compound (200 mg, 70%) as a white solid. LCMS (ESI): m/z 433.1 (M+H)⁺.

Step 6: (R)—N-((4-(2-cyano-1-hydroxyethyl)-7-(4-(trifluoromethoxy)phenyl)-2,3-dihydrobenzofuran-5-yl)methyl)acrylamide & (S)—N-((4-(2-cyano-1-hydroxyethyl)-7-(4-(trifluoromethoxy)phenyl)-2,3-dihydrobenzofuran-5-yl)methyl)acrylamide

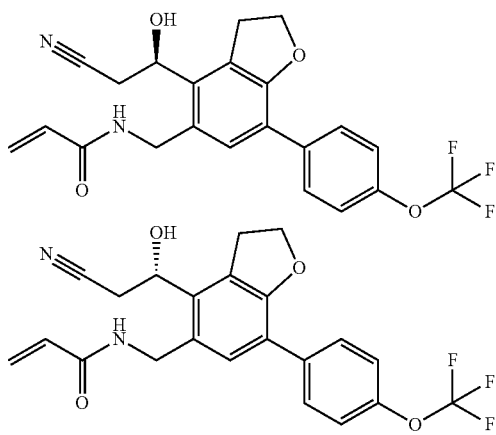

N-((4-(2-Cyano-1-hydroxyethyl)-7-(4-(trifluoromethoxy)phenyl)-2,3-dihydrobenzofuran-5-yl)methyl)acrylamide (200 mg, 0.46 mmol) was separated by Chiral SFC (Instrument: SFC-12; Column: OD(250 mm*30 mm,10 um); Condition: Neu-ETOH; Begin B:15%; Flow Rate (ml/min): 70) to afford the first peak (R)—N-((4-(2-cyano-1-hydroxyethyl)-7-(4-(trifluoromethoxy)phenyl)-2,3-dihydrobenzofuran-5-yl)methyl)acrylamide (48 mg, 23%) and the second peak (S)—N-((4-(2cyano-1-hydroxyethyl)-7-(4-(trifluoromethoxy)phenyl)-2,3-dihydrobenzofuran-5-yl)methyl) acrylamide (44 mg, 22%) both as white solid.

The first peak: $^1$H NMR (400 MHz, DMSO-$d_6$): δ 8.44 (t, J=5.6 Hz, 1H), 7.77-7.74 (m, 2H), 7.44 (d, J=8.8 Hz, 2H), 7.29 (s, 1H), 6.26 (dd, J=17.2, 10.0 Hz, 1H), 6.13 (dd, J=17.2, 2.0 Hz, 1H), 6.02 (d, J=4.0 Hz, 1H), 5.62 (dd, J=10.0, 2.0 Hz, 1H), 5.21-5.14 (m, 1H), 4.61-4.47 (m, 2H), 4.43 (d, J=5.6 Hz, 2H), 3.49-3.39 (m, 2H), 3.04-2.96 (m, 1H), 2.89-2.81 (m, 1H); LCMS (ESI): m/z 455.0 (M+Na)$^+$.

The second peak: $^1$H NMR (400 MHz, DMSO-$d_6$): δ 8.44 (t, J=5.6 Hz, 1H), 7.77-7.74 (m, 2H), 7.44 (d, J=8.8 Hz, 2H), 7.29 (s, 1H), 6.26 (dd, J=17.2, 10.0 Hz, 1H), 6.13 (dd, J=17.2, 2.0 Hz, 1H), 6.02 (d, J=4.0 Hz, 1H), 5.62 (dd, J=10.0, 2.0 Hz, 1H), 5.21-5.14 (m, 1H), 4.61-4.47 (m, 2H), 4.43 (d, J=5.6 Hz, 2H), 3.49-3.39 (m, 2H), 3.04-2.96 (m, 1H), 2.89-2.81 (m, 1H); LCMS (ESI): m/z 455.0 (M+Na)$^+$.

Example 89 (Compound 93) N-((7-(4-Ethynylphenyl)-4-(hydroxymethyl)-2,3-dihydrobenzofuran-5-yl)methyl)acrylamide

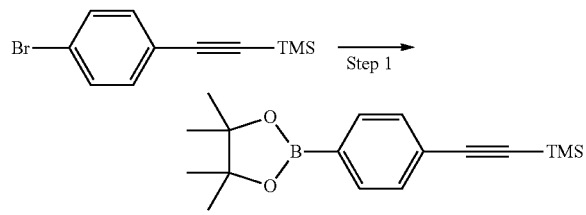

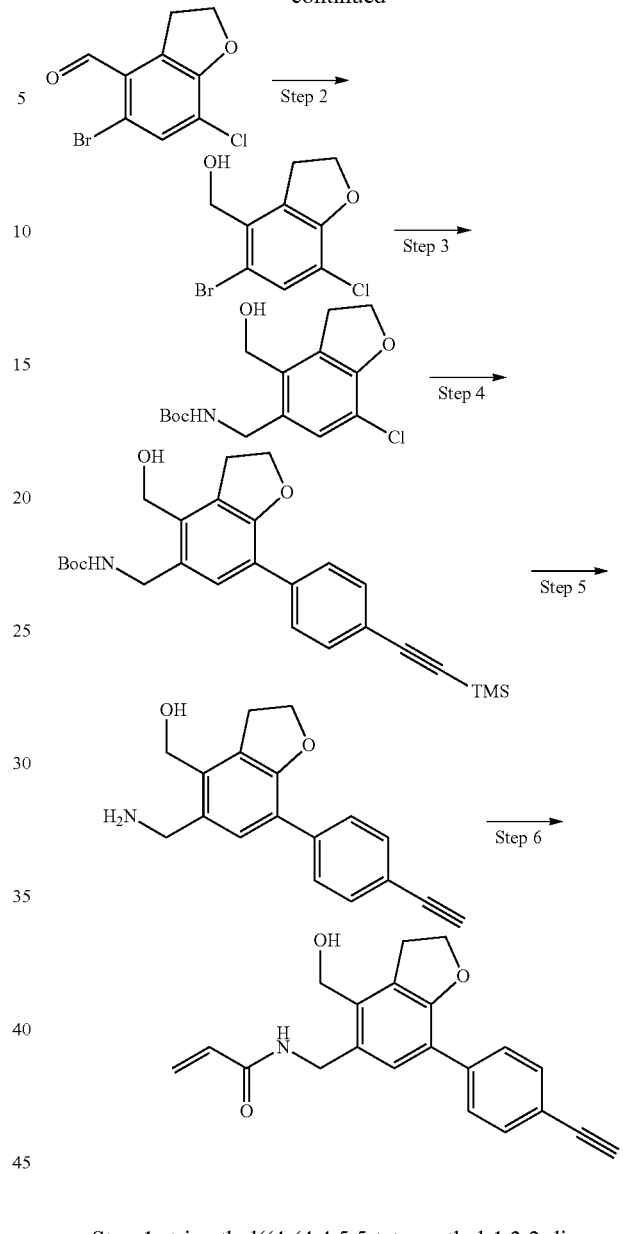

Step 1: trimethyl((4-(4,4,5,5-tetramethyl-1,3,2-dioxaborolan-2-yl)phenyl)ethynyl)silane

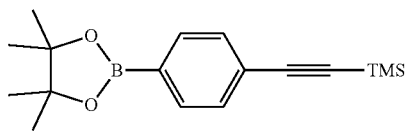 [SMILES: CC1(C)OB(c2ccc(C#C[Si](C)(C)C)cc2)OC1(C)C]

A mixture of ((4-bromophenyl)ethynyl)trimethylsilane (5.0 g, 19.75 mmol), KOAc (5.5 g, 59.24 mmol), Pd(dppf)Cl$_2$ (1.4 g, 1.97 mmol) and B$^2$Pin2 (7.5 g, 29.62 mmol) in 1,4-dioxane (50 mL) was stirred at 80° C. for 16 h under N$_2$ atmosphere. The mixture was quenched with H$_2$O (50 mL), extracted with ethyl acetate (100 mL×2), the organic layer was washed with brine (100 mL), dried over Na$_2$SO$_4$ and concentrated. The residue was purified by column chromatography on silica gel (100% petroleum ether) to afford the title compound (3.9 g, 66%) as a white solid. ¹H NMR (400 MHz, CDCl₃): δ 7.73 (d, J=8.4 Hz, 2H), 7.46 (d, J=8.0 Hz, 2H), 1.35 (s, 12H), 0.26 (s, 9H).

Step 2: (5-bromo-7-chloro-2,3-dihydrobenzofuran-4-yl)methanol

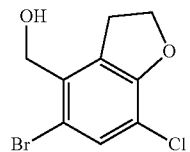

To a solution of 5-bromo-7-chloro-2,3-dihydrobenzofuran-4-carbaldehyde (4.4 g, 14.15 mmol) in THF (50 mL) was added NaBH₄ (642 mg, 16.98 mmol) at 0° C. The mixture was stirred at 0° C. for 1 h. The mixture was quenched with sat.NH₄Cl (50 mL), extracted with ethyl acetate (100 mL×2), the organic layer was washed with brine (50 mL), dried over Na₂SO₄ and concentrated. The residue was purified by column chromatography on silica gel (0-35% ethyl acetate in petroleum ether) to afford the title compound (3.95 g, 100%) as a white solid. ¹H NMR (400 MHz, CDCl₃): δ 7.36 (s, 1H), 4.75-4.69 (m, 4H), 3.43 (t, J=8.4 Hz, 2H), 1.96 (t, J=6.4 Hz, 1H).

Step 3: tert-butyl ((7-chloro-4-(hydroxymethyl)-2,3-dihydrobenzofuran-5-yl)methyl)carbamate

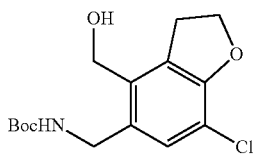 [SMILES: CC(C)(C)OC(=O)NCc1cc(Cl)c2c(c1CO)CCO2]

A mixture of (5-bromo-7-chloro-2,3-dihydrobenzofuran-4-yl)methanol (100 mg, 0.38 mmol), potassium (((tert-butoxycarbonyl)amino)methyl)trifluoroborate (108 mg, 0.46 mmol), Sphos Pd G₂ (25 mg, 0.04 mmol) and Cs₂CO₃ (371 mg, 1.14 mmol) in toluene (5 mL) and water (0.50 mL) was stirred at 80° C. for 16 h under N₂ atmosphere. The mixture was quenched with H₂O (10 mL), extracted with ethyl acetate (10 mL×2), the organic layer was washed with brine (10 mL), dried over Na₂SO₄ and concentrated. The residue was purified by column chromatography on silica gel (0-25% ethyl acetate in petroleum ether) to afford the title compound (52 mg, 44%) as a white solid. ¹H NMR (400 MHz, CDCl₃): δ 7.08 (s, 1H), 5.14-5.12 (m, 1H), 4.70 (t, J=8.8 Hz, 2H), 4.64 (s, 2H), 4.28 (d, J=6.4 Hz, 2H), 3.37 (t, J=8.8 Hz, 2H), 1.43 (s, 9H).

Step 4: tert-butyl ((4-(hydroxymethyl)-7-(4-(((trimethylsilyl)ethynyl)phenyl)-2,3-dihydrobenzofuran-5-yl)methyl)carbamate

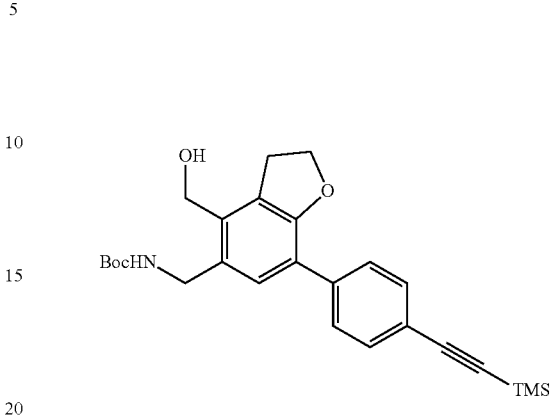

A mixture of tert-butyl ((7-chloro-4-(hydroxymethyl)-2,3-dihydrobenzofuran-5-yl)methyl)carbamate (220 mg, 0.70 mmol), Xphos (33 mg, 0.07 mmol), Xphos Pd G₂ (55 mg, 0.07 mmol) and trimethyl((4-(4,4,5,5-tetramethyl-1,3,2-dioxaborolan-2-yl)phenyl)ethynyl)silane (253 mg, 0.84 mmol) and KOAc (138 mg, 1.40 mmol) in 1,4-dioxane (4 mL) and water (0.40 mL) was stirred at 80° C. for 5 h under N₂ atmosphere. The mixture was quenched with H₂O (5 mL), extracted with ethyl acetate (10 mL×2), the organic layer was washed with brine (10 mL), dried over Na₂SO₄ and concentrated. The residue was purified by column chromatography on silica gel (0-30% ethyl acetate in petroleum ether) to afford the title compound (237 mg, 75%) as a white solid.

¹H NMR (400 MHz, CDCl₃): δ 7.57 (d, J=8.8 Hz, 2H), 7.43 (d, J=8.8 Hz, 2H), 7.22 (s, 11H), 5.15-5.12 (m, 1H), 4.65 (s, 2H), 4.59 (t, J=8.8 Hz, 2H), 4.31-4.29 (m, 2H), 3.35 (t, J=8.8 Hz, 2H), 1.43 (s, 9H), 0.27 (m, 9H).

Step 5: (5-(aminomethyl)-7-(4-ethynylphenyl)-2,3-dihydrobenzofuran-4-yl)methanol

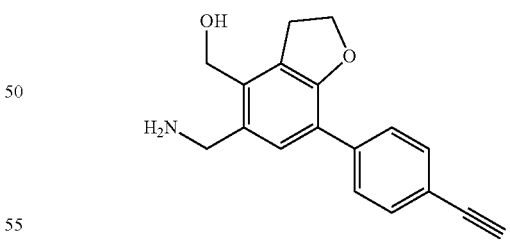

To a mixture of tert-butyl ((4-(hydroxymethyl)-7-(4-((trimethylsilyl)ethynyl)phenyl)-2,3-dihydrobenzofuran-5-yl)methyl)carbamate (50 mg, 0.11 mmol) and 2,6-lutidine (0.04 mL, 0.33 mmol) in DCM (2 mL) was added TMSOTf (0.12 mL, 0.66 mmol) at 0° C. Then the reaction was stirred at room temperature for 2 h under N₂ atmosphere. The reaction mixture was concentrated to afford the title compound (30 mg, crude) as a black oil. The crude product was used directly for next step. LCMS (ESI): m/z 263.2 (M+H-17)⁺.

Step 6: N-((7-(4-ethynylphenyl)-4-(hydroxymethyl)-2,3-dihydrobenzofuran-5-yl)methyl)acrylamide

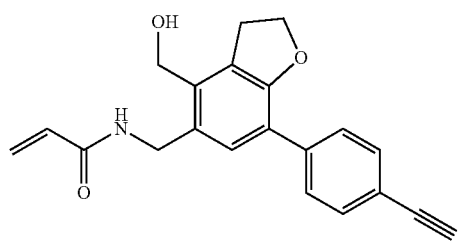

To a mixture of (5-(aminomethyl)-7-(4-ethynylphenyl)-2,3-dihydrobenzofuran-4-yl)methanol (30 mg, 0.11 mmol) and saturated aq.NaHCO$_3$ (0.5 mL) in THF (2 mL) was added acrylicanhydride (20 mg, 0.16 mmol) at 0° C. The resulting mixture was stirred at 0° C. for 2 h. The reaction mixture was dried over Na$_2$SO$_4$, filtered and concentrated. The residue was purified by pre-TLC (50% ethyl acetate in petroleum ether) to afford the title compound (5 mg, 14%) as a white solid. $^1$H NMR (400 MHz, DMSO-d$_6$): δ 8.41 (s, 1H), 7.68 (d, J=8.4 Hz, 2H), 7.53 (d, J=8.0 Hz, 2H), 7.27 (s, 1H), 6.28 (dd, J=16.8, 10.4 Hz, 1H), 6.09 (dd, J=16.8, 2.0 Hz, 1H), 5.59 (dd, J=10.4, 2.0 Hz, 1H), 5.04 (t, J=5.6 Hz, 1H), 4.60 (t, J=8.8 Hz, 2H), 4.51 (d, J=5.6 Hz, 2H), 4.43 (d, J=5.6 Hz, 2H), 4.23 (s, 1H), 3.30-3.28 (m, 2H); LCMS (ESI): m/z 356.0 (M+Na)$^+$.

Example 90 (Compound 94)

N-((7-(4-Ethynylphenyl)-4-(hydroxymethyl)-2,3-dihydrobenzofuran-5-yl)methyl)-N-methylacrylamide

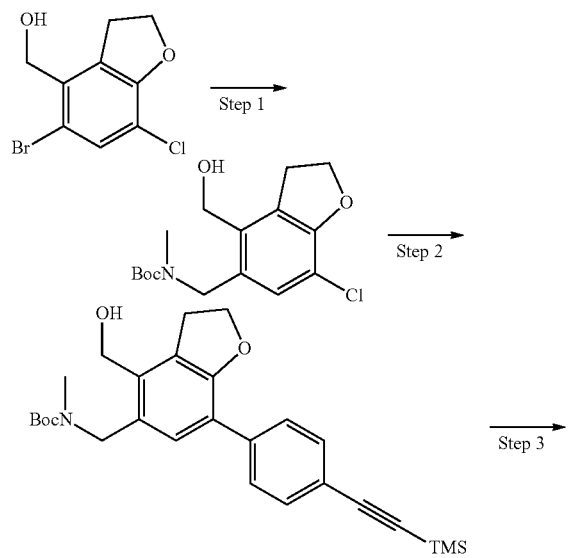

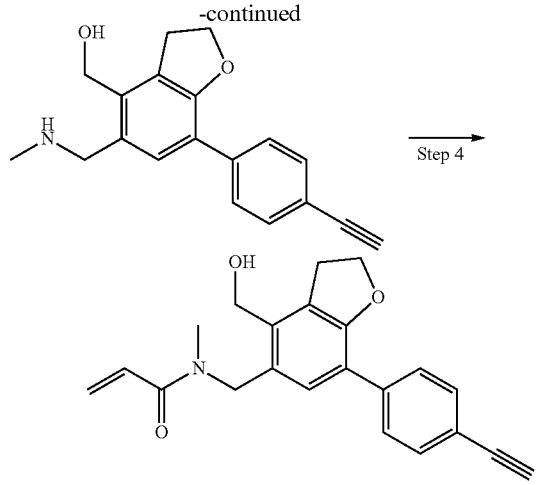

Step 1: tert-butyl ((7-chloro-4-(hydroxymethyl)-2,3-dihydrobenzofuran-5-yl)methyl)(methyl)carbamate

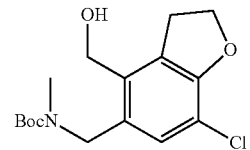 [SMILES: CN(Cc1cc(Cl)c2c(c1CO)CCO2)C(=O)OC(C)(C)C]

A mixture of potassium (((tert-butoxycarbonyl)(methyl)amino)methyl)trifluoroborate (2.29 g, 9.11 mmol), (5-bromo-7-chloro-2,3-dihydrobenzofuran-4-yl)methanol (800 mg, 3.04 mmol), Cs$_2$CO$_3$ (2.97 g, 9.11 mmol) and CATACXIUM A Pd G$_2$ (203 mg, 0.30 mmol) in toluene (10 mL) and water (2 mL) was stirred at 80° C. for 16 h under N$_2$ atmosphere. The mixture was diluted with ethyl acetate (80 mL×3) and washed with water (50 mL×3). The organic layer was dried over Na$_2$SO$_4$ and concentrated. The residue was purified by flash chromatography on silica gel (0-60% ethyl acetate in petroleum ether) to afford the title compound (700 mg, 70%) as a brown solid. $^1$H NMR (400 MHz, CDCl$_3$): δ 7.02 (s, 1H), 4.72 (t, J=8.8 Hz, 2H), 4.69 (d, J=3.6 Hz, 2H), 4.47 (s, 2H), 3.76-3.72 (m, 1H), 3.37 (t, J=8.8 Hz, 2H), 2.85 (s, 3H), 1.48 (s, 9H).

Step 2: tert-butyl ((4-(hydroxymethyl)-7-(4-((trimethylsilyl)ethynyl)phenyl)-2,3-dihydrobenzofuran-5-yl)methyl)(methyl)carbamate

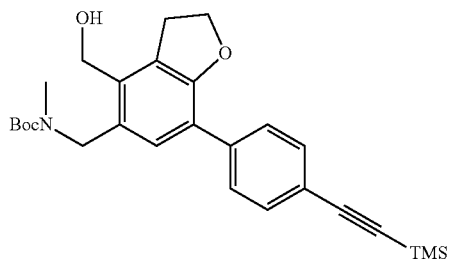 [SMILES: CN(Cc1cc(-c2ccc(C#C[Si](C)(C)C)cc2)c2c(c1CO)CCO2)C(=O)OC(C)(C)C]

A mixture of tert-butyl ((7-chloro-4-(hydroxymethyl)-2,3-dihydrobenzofuran-5-yl)methyl)(methyl)carbamate (700 mg, 2.14 mmol), Xphos Pd G₂ (130 mg, 0.21 mmol), Xphos (101 mg, 0.21 mmol), KOAc (629 mg, 6.41 mmol) and trimethyl((4-(4,4,5,5-tetramethyl-1,3,2-dioxaborolan-2-yl)phenyl)ethynyl)silane (833 mg, 2.78 mmol) in 1,4-dioxane (10 mL) and water (3 mL) was purged with N₂ for 3 min. The mixture was heated to 80° C. for 4 h under N₂ atmosphere. The reaction mixture was diluted with water (20 mL), extracted with ethyl acetate (30 mL×2). The combined organics were dried over Na₂SO₄, filtered and concentrated. The residue was purified by flash chromatography on silica gel (0-60% ethyl acetate in petroleum ether) to afford the title compound (510 mg, 51%) as a white solid. ¹H NMR (400 MHz, CDCl₃): δ 7.65 (d, J=8.0 Hz, 2H), 7.50 (d, J=8.0 Hz, 2H), 7.16 (s, 1H), 4.71-4.64 (m, 4H), 4.59-4.54 (m, 2H), 3.38-3.33 (m, 2H), 2.86 (s, 3H), 1.49 (s, 9H), 0.27 (s, 6H).

Step 3: (7-(4-ethynylphenyl)-5-((methylamino)methyl)-2,3-dihydrobenzofuran-4-yl)methanol

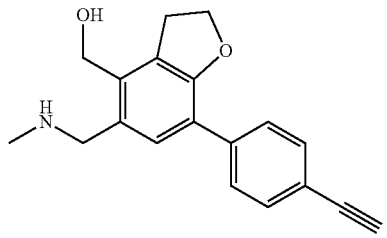 [SMILES: C#Cc1ccc(-c2cc(CNC)c(CO)c3c2OCC3)cc1]

To a mixture of tert-butyl ((4-(hydroxymethyl)-7-(4-((trimethylsilyl)ethynyl)phenyl)-2,3-dihydrobenzofuran-5-yl)methyl)(methyl)carbamate (800 mg, 1.72 mmol) and saturated 2,6-lutidine (3 mL, 25.76 mmol) in DCM (5 mL) was added TMSOTf (6 mL, 33.15 mmol) at 0° C. The resulting mixture was stirred at 0° C. for 2 h. The reaction mixture was concentrated to afford the title compound (500 mg, crude) as a brown solid. The crude product was used directly for next step. LCMS (ESI): m/z 294.2 (M+H)⁺.

Step 4: N-((7-(4-ethynylphenyl)-4-(hydroxymethyl)-2,3-dihydrobenzofuran-5-yl)methyl)-N-methylacrylamide

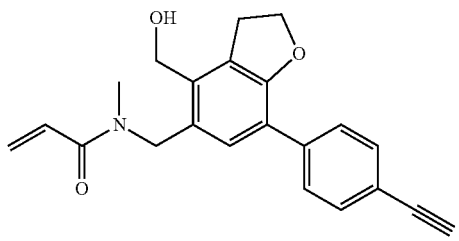 [SMILES: C#Cc1ccc(-c2cc(CN(C)C(=O)C=C)c(CO)c3c2OCC3)cc1]

To a mixture of (7-(4-ethynylphenyl)-5-((methylamino)methyl)-2,3-dihydrobenzofuran-4-yl)methanol (500 mg, 1.7 mmol) and saturated NaHCO₃ (1 mL) in THF (2 mL) was added acrylicanhydride (322 mg, 2.56 mmol) at 0° C. The resulting mixture was stirred at 0° C. for 2 h. The reaction mixture was dried over Na₂SO₄, filtered and concentrated. The residue was purified by reverse phase chromatography (Boston Green ODS 150*30 mm*5 um, water (0.225% FA)-ACN, 42%-72%) to afford the title compound (75 mg, 13%) as a white solid. ¹H NMR (400 MHz, DMSO-d₆, t=75° C.): δ 7.65 (d, J=8.0 Hz, 2H), 7.53-7.46 (m, 2H), 7.03 (s, 1H), 6.74 (dd, J=16.4, 10.0 Hz, 1H), 6.15 (dd, J=16.4, 2.4 Hz, 1H), 5.66 (dd, J=10.0, 2.4 Hz, 1H), 4.80 (s, 1H), 4.73 (s, 2H), 4.61 (t, J=8.8 Hz, 2H), 4.52 (d, J=5.2 Hz, 2H), 4.03 (s, 1H), 3.32 (t, J=8.8 Hz, 2H), 2.95 (s, 3H); LCMS (ESI): m/z 370.0 (M+Na)⁺.

¹H NMR (400 MHz, DMSO-d₆): b 7.67-7.59 (m, 2H), 7.52 (d, J=8.4 Hz, 2H), 7.11, 6.86 (s, 1H total), 6.81-6.75 (m, 1H), 6.19-6.12 (m, 1H), 5.72-5.66 (m, 1H), 5.06-4.95 (m, 1H), 4.78, 4.68 (s, 2H total), 4.62-4.58 (m, 2H), 4.48-4.46 (m, 2H), 4.21 (s, 1H), 3.32 (t, J=8.8 Hz, 2H), 2.97, 2.92 (s, 3H total).

Example 91 (Compound 22)

N-((4-(Hydroxymethyl)-7-(5-isopropoxythiazol-2-yl)-2,3-dihydrobenzofuran-5-yl)methyl)acrylamide

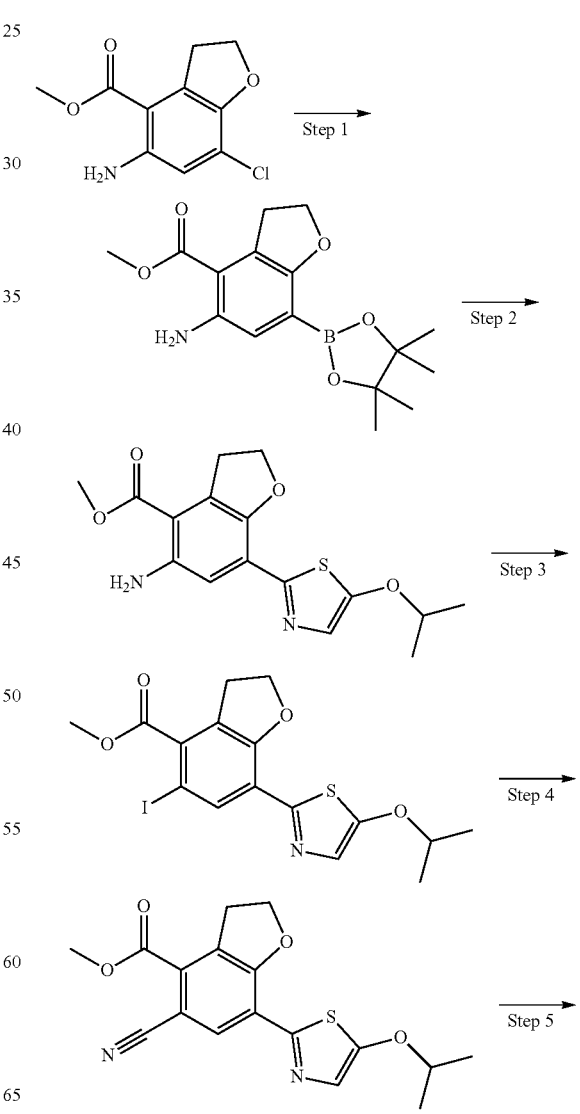

-continued

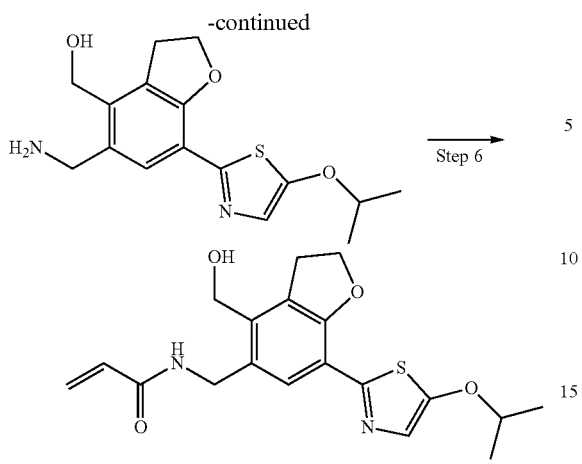

Step 1: methyl 5-amino-7-(4,4,5,5-tetramethyl-1,3,2-dioxaborolan-2-yl)-2,3-dihydrobenzofuran-4-carboxylate

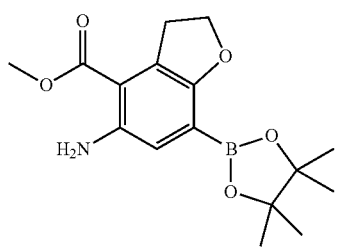

A mixture of methyl 5-amino-7-chloro-2,3-dihydrobenzofuran-4-carboxylate (1.0 g, 4.39 mmol), NiCl$_2$(PMe$_3$)$_2$ (124 mg, 0.44 mmol), CsF (1.33 g, 8.79 mmol), B$^2$Pin2 (1.23 g, 4.83 mmol) in THF (10 mL) was purged N$_2$ for 3 m. Then trimethyl(2,2,2-trifluoroethoxy)silane (1.59 g, 9.23 mmol) was added into it. The reaction mixture was stirred at 100° C. for 16 h. The reaction mixture was used directly for next step. LCM S (ESI): m/z 320.0 (M+H)$^+$.

Step 2: methyl 5-amino-7-(5-isopropoxythiazol-2-yl)-2,3-dihydrobenzofuran-4-carboxylate

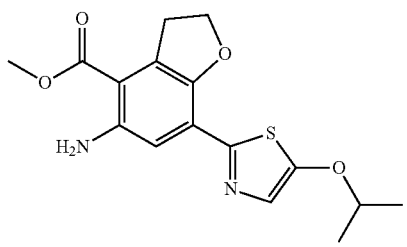 [SMILES: COC(=O)c1c(N)cc(-c2ncc(OC(C)C)s2)c2c1CCO2]

A mixture of methyl 5-amino-7-(4,4,5,5-tetramethyl-1,3,2-dioxaborolan-2-yl)-2,3-dihydrobenzofuran-4-carboxylate (1.4 g, 4.39 mmol), 2-bromo-5-isopropoxythiazole (1.07 g, 4.83 mmol), Na$_2$CO$_3$ (1.39 g, 13.16 mmol), Pd(dppf)Cl$_2$ (321 mg, 0.44 mmol) in 1,4-dioxane (5 mL) and water (1 mL) was stirred at 100° C. for 2 h. The reaction mixture was quenched with water (100 mL), extracted with ethyl acetate (50 mL×3). The organic layer was dried over Na$_2$SO$_4$, filtered and concentrated. The residue was purified flash chromatography on silica gel (0-30% ethyl acetate in petroleum ether) to afford the title compound (930 mg, 63%) as a white solid. $^1$H NMR (400 MHz, CDCl$_3$): δ 7.22 (s, 1H), 7.18 (s, 1H), 4.62 (t, J=8.8 Hz, 2H), 4.39-4.31 (m, 1H), 3.81 (s, 3H), 3.46 (t, J=8.8 Hz, 2H), 1.34 (d, J=6.0 Hz, 6H); LCMS (ESI): m/z 335.1 (M+H)$^+$.

Step 3: methyl 5-iodo-7-(5-isopropoxythiazol-2-yl)-2,3-dihydrobenzofuran-4-carboxylate

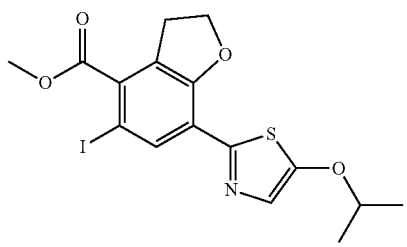 [SMILES: COC(=O)c1c(I)cc(-c2ncc(OC(C)C)s2)c2c1CCO2]

To a mixture of tert-butyl nitrite (0.16 mL, 1.32 mmol) and methyl 5-amino-7-(5-isopropoxythiazol-2-yl)-2,3-dihydrobenzofuran-4-carboxylate (400 mg, 1.2 mmol) in acetonitrile (8 mL) was added diiodomethane (0.98 mL, 12.11 mmol) at 0° C. The mixture was stirred at room temperature for 16 h. The reaction solution was quenched with H$_2$O (10 mL), extracted with ethyl acetate (20 mL), dried over Na$_2$SO$_4$, filtered and concentrated. The residue was purified by flash chromatography on silica gel (0-15% ethyl acetate in petroleum ether) to afford the title compound (130 mg, 24%) as a yellow solid. $^1$H NMR (400 MHz, DMSO-d$_6$): δ 8.31 (s, 1H), 7.40 (s, 1H), 4.78 (t, J=8.8 Hz, 2H), 4.53-4.46 (m, 1H), 3.87 (s, 3H), 3.38 (t, J=8.8 Hz, 2H), 1.33 (d, J=6.4 Hz, 6H).

Step 4: methyl 5-cyano-7-(5-isopropoxythiazol-2-yl)-2,3-dihydrobenzofuran-4-carboxylate

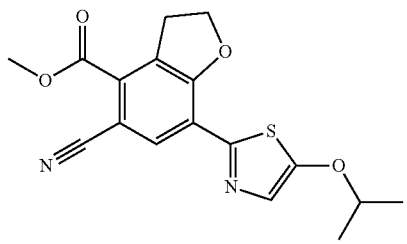 [SMILES: COC(=O)c1c(C#N)cc(-c2ncc(OC(C)C)s2)c2c1CCO2]

To a solution of methyl 5-bromo-7-(5-isopropoxythiazol-2-yl)-2,3-dihydrobenzofuran-4-carboxylate (130 mg, 0.33 mmol) in DMF (5 mL) was added CuCN (322 mg, 3.6 mmol). The mixture was stirred at 80° C. for 16 hours under N$_2$ atmosphere. The reaction mixture was filtered and the filtrate was concentrated under vacuum. The residue was purified by flash chromatography on silica gel (0-15% ethyl acetate in petroleum ether) to afford the title compound (100 mg, 89%) as a yellow solid. $^1$H NMR (400 MHz, DMSO-d$_6$): δ 8.29 (s, 1H), 7.48 (s, 1H), 4.89 (t, J=8.8 Hz, 2H), 4.56-4.48 (m, 1H), 3.91 (s, 3H), 3.56 (t, J=8.8 Hz, 2H), 1.34 (d, J=6.0 Hz, 6H).

Step 5: (5-(aminomethyl)-7-(5-isopropoxythiazol-2-yl)-2,3-dihydrobenzofuran-4-yl)methanol

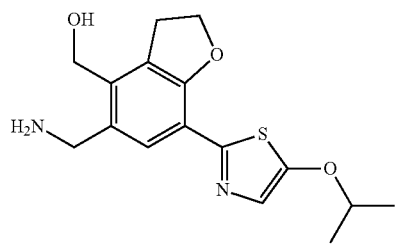 [SMILES: CC(C)Oc1cnc(-c2cc(CN)c(CO)c3c2OCC3)s1]

To a solution of methyl 5-cyano-7-(5-isopropoxythiazol-2-yl)-2,3-dihydrobenzofuran-4-carboxylate (90 mg, 0.26 mmol) in THF (5 mL) was added LAH (50 mg, 1.31 mmol) slowly at 0° C. Then the reaction mixture was stirred at 0° C. for 1 hour. The reaction was quenched with aq.KHSO$_4$ (1 mL) and dried over MgSO$_4$. The mixture was filtered and the filtrate was concentrated in vacuo to afford the title compound (83 mg, crude) as a yellow solid. The crude was used for next step without further purification. LCMS (ESI): m/z 321.1 (M+H)$^+$.

Step 6: N-((4-(hydroxymethyl)-7-(5-isopropoxythiazol-2-yl)-2,3-dihydrobenzofuran-5-yl)methyl)acrylamide

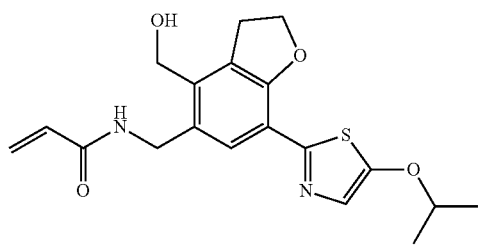 [SMILES: C=CC(=O)NCc1cc(-c2ncc(OC(C)C)s2)c2c(c1CO)CCO2]

A mixture of (5-(aminomethyl)-7-(5-isopropoxythiazol-2-yl)-2,3-dihydrobenzofuran-4-yl)methanol (60 mg, 0.09 mmol), saturated NaHCO$_3$ (0.2 mL) and acryloyl chloride (9 mg, 0.09 mmol) in THF (5 mL) was stirred at 0° C. for 1 h. The mixture was diluted with water (10 mL) and extracted with ethyl acetate (30 mL×3). The organics were washed with brine (20 mL×2), dried over sodium sulfate, filtered and concentrated. The residue was purified by reverse phase chromatography (Boston Green ODS 150*30 mm*5 um, acetonitrile 30%-60%/water(FA)-ACN) to afford the title compound (7.83 mg, 22%) as a white solid. $^1$H NMR (400 MHz, DMSO-d$_6$): δ 8.49 (t, J=5.2 Hz, 1H), 7.76 (s, 1H), 7.28 (s, 1H), 6.26 (dd, J=16.8, 10.4 Hz, 11H), 6.11 (dd, J=16.8, 2.0 Hz, 1H), 5.61 (dd, J=10.4, 2.0 Hz, 1H), 5.08 (t, J=5.6 Hz, 1H), 4.73 (t, J=8.8 Hz, 2H), 4.51 (d, J=5.6 Hz, 2H), 4.47-4.40 (m, 3H), 3.30 (t, J=8.8 Hz, 2H), 1.32 (d, J=6.0 Hz, 6H); LCMS (ESI): m/z 375.0 (M+H)$^+$.

Example 92 (Compound 95) N-((4-Cyano-7-(4-(trifluoromethoxy)phenyl)-2,3-dihydrobenzofuran-5-yl)methyl)-N-methylacrylamide

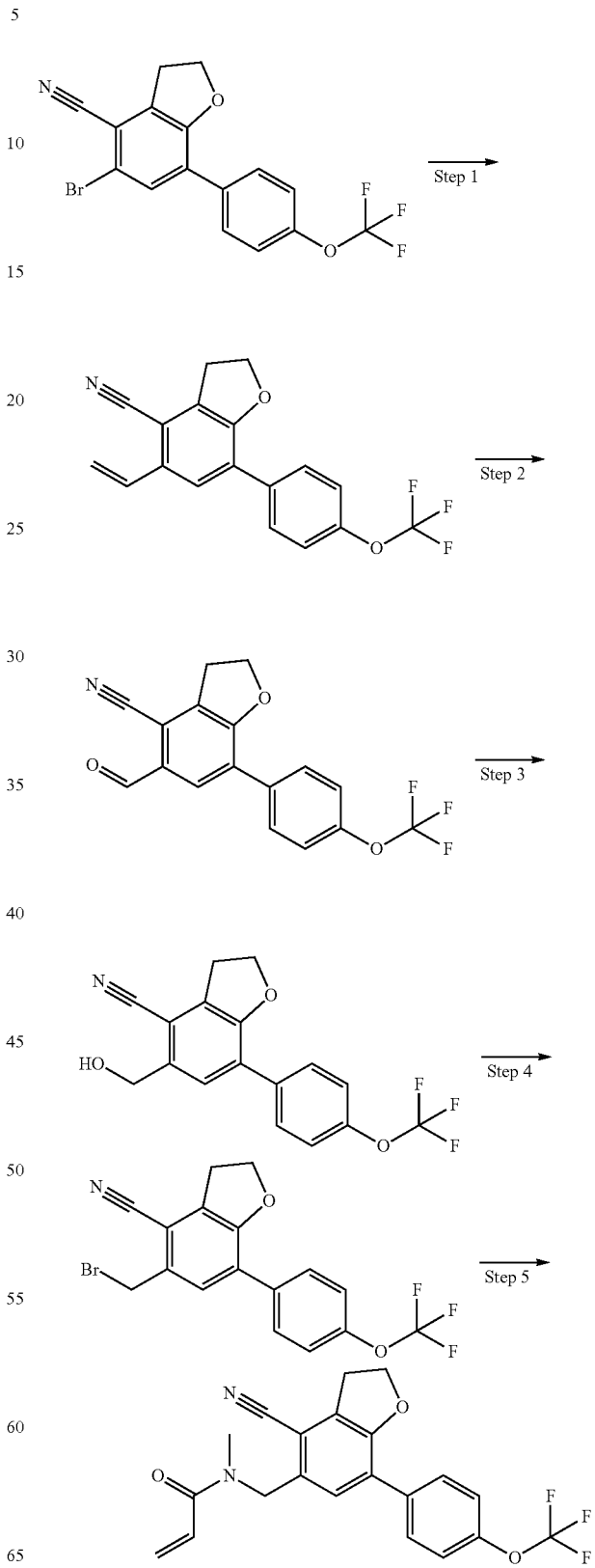

Step 1: 7-(4-(trifluoromethoxy)phenyl)-5-vinyl-2,3-dihydrobenzofuran-4-carbonitrile

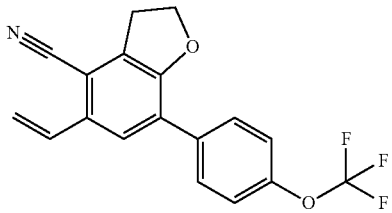 [SMILES: C=Cc1cc(-c2ccc(OC(F)(F)F)cc2)c2c(c1C#N)CCO2]

A mixture of 5-bromo-7-(4-(trifluoromethoxy)phenyl)-2,3-dihydrobenzofuran-4-carbonitrile (6.0 g, 15.62 mmol), 4,4,5,5-tetramethyl-2-vinyl-1,3,2-dioxaborolane (3.61 g, 23.43 mmol), Na$_2$CO$_3$ (3.31 g, 31.24 mmol) and Pd(dppf)Cl$_2$ (1.14 g, 1.56 mmol) in 1,4-dioxane (10 mL) and water (1 mL) was stirred at 100° C. for 8 h under N$_2$ atmosphere. The mixture was diluted with ethyl acetate (500 mL) and washed with water (300 mL×3). The organic was dried over Na$_2$SO$_4$ and concentrated. The residue was purified by flash chromatography on silica gel (0-25% ethyl acetate in petroleum ether) to afford the title compound (4.3 g, 83%) as a white solid. LCMS (ESI): m/z 332.1 (M+H)$^+$.

Step 2: 5-formyl-7-(4-(trifluoromethoxy)phenyl)-2,3-dihydrobenzofuran-4-carbonitrile

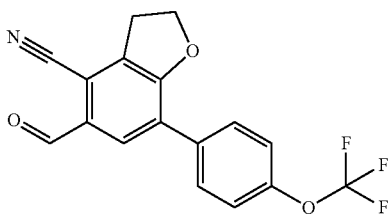 [SMILES: N#Cc1c(C=O)cc(-c2ccc(OC(F)(F)F)cc2)c2c1CCO2]

To a solution of 7-(4-(trifluoromethoxy)phenyl)-5-vinyl-2,3-dihydrobenzofuran-4-carbonitrile (4.3 g, 12.98 mmol) in THF (43 mL) and water (10 mL) was added osmium(VIII) oxide (39 mg, 1.97 mmol) and NaIO$_4$ (11.11 g, 51.92 mmol) at 0° C. The reaction mixture was stirred at room temperature for 2.5h. The resulting mixture was diluted with water (300 mL), extracted with ethyl acetate (300 mL×3), washed with sat.Na$_2$SO$_3$ (200 mL). Combined organic layers were dried over Na$_2$SO$_4$, filtered and concentrated to afford the title compound (1.6 g, 37%) as a brown solid. The crude product was used for next step directly. $^1$H NMR (400 MHz, CDCl$_3$): δ 10.18 (s, 1H), 7.99 (s, 1H), 7.77 (d, J=8.8 Hz, 2H), 7.33 (d, J=8.8 Hz, 2H), 4.90 (t, J=8.8 Hz, 2H), 3.58 (t, J=8.8 Hz, 2H).

Step 3: 5-(hydroxymethyl)-7-(4-(trifluoromethoxy)phenyl)-2,3-dihydrobenzofuran-4-carbonitrile

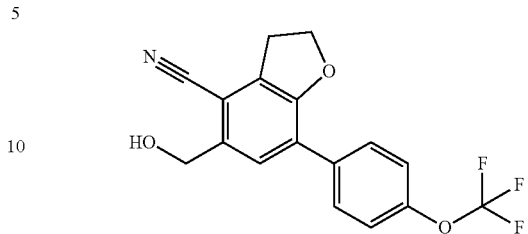

To a solution of 5-formyl-7-(4-(trifluoromethoxy)phenyl)-2,3-dihydrobenzofuran-4-carbonitrile (600 mg, 1.8 mmol) in methanol (3 mL) was added NaBH$_4$ (34 mg, 0.90 mmol) at 0° C. The mixture was stirred at room temperature for 0.5h. The reaction mixture was quenched with water (50 mL), extracted with ethyl acetate (50 mL×3). Combined organic layers were dried over Na$_2$SO$_4$, filtered and concentrated to afford the title compound (600 mg, crude) as a brown solid. The crude product was used directly for next step directly.

Step 4: 5-(bromomethyl)-7-(4-(trifluoromethoxy)phenyl)-2,3-dihydrobenzofuran-4-carbonitrile

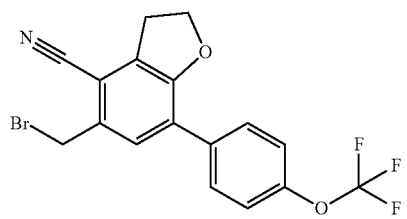 [SMILES: N#Cc1c(CBr)cc(-c2ccc(OC(F)(F)F)cc2)c2c1CCO2]

To a solution of 5-(hydroxymethyl)-7-(4-(trifluoromethoxy)phenyl)-2,3-dihydrobenzofuran-4-carbonitrile (600 mg, 1.79 mmol) in DCM (10 mL) was added PBr$_3$ (0.17 mL, 1.79 mmol) at 0° C. The reaction mixture was stirred at 0° C. for 2.5h. The mixture was concentrated and the residue was purified by flash chromatography column on silica gel (0-40% ethyl acetate in petroleum ether) to afford the title compound (500 mg, 70%) as a yellow solid.

Step 5: N-((4-cyano-7-(4-(trifluoromethoxy)phenyl)-2,3-dihydrobenzofuran-5-yl)methyl)-N-methylacrylamide

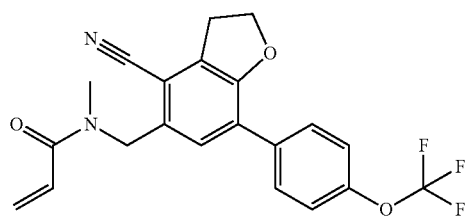 [SMILES: C=CC(=O)N(C)Cc1cc(-c2ccc(OC(F)(F)F)cc2)c2c(c1C#N)CCO2]

To a solution of N-methylacrylamide (21 mg, 0.25 mmol) in THF (3 mL) was added NaH (11 mg, 0.28 mmol, 60% in mineral oil) at 0° C. After stirred at 0° C. for 30 min, 5-(bromomethyl)-7-(4-(trifluoromethoxy)phenyl)-2,3-dihydrobenzofuran-4-carbonitrile (100 mg, 0.25 mmol) was added into it at 0° C. The reaction mixture was stirred at room temperature for 2.5h. The mixture was quenched with water (30 mL), extracted with ethyl acetate (50 mL×3). The organic layers were dried over Na$_2$SO$_4$, filtered, concentrated and the residue was purified by pre-TLC (40% ethyl acetate in petroleum ether) to afford the title compound (19.0 mg, 19%) as a white solid. $^1$H NMR (400 MHz, CDCl$_3$): δ 7.72-7.69 (m, 2H), 7.29 (s, 1H), 7.27-7.25 (m, 2H), 6.67-6.60 (m, 1H), 6.43-6.37 (m, 1H), 5.78-5.76 (m, 1H), 4.83 (s, 2H), 4.78-4.72 (m, 2H), 3.51-3.46 (m, 2H), 3.14 (s, 3H); LCMS (ESI): m/z 403.0 (M+H)$^+$.

Example 93 (Compound 96) & Example 94 (Compound 97)

N-[[7-[4-(Pentafluoro-6-sulfanyl)phenyl]-4-[rac-(1R)-1,2-dihydroxyethyl]-2,3-dihydrobenzofuran-5-yl]methyl]prop-2-enamide & N-[[7-[4-(pentafluoro-6-sulfanyl)phenyl]-4-[rac-(1S)-1,2-dihydroxyethyl]-2,3-dihydrobenzofuran-5-yl]methyl]prop-2-enamide

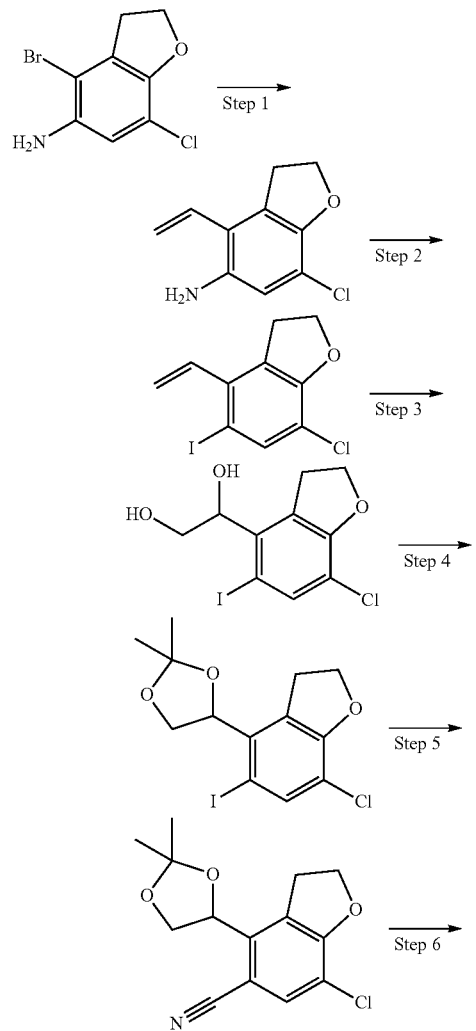

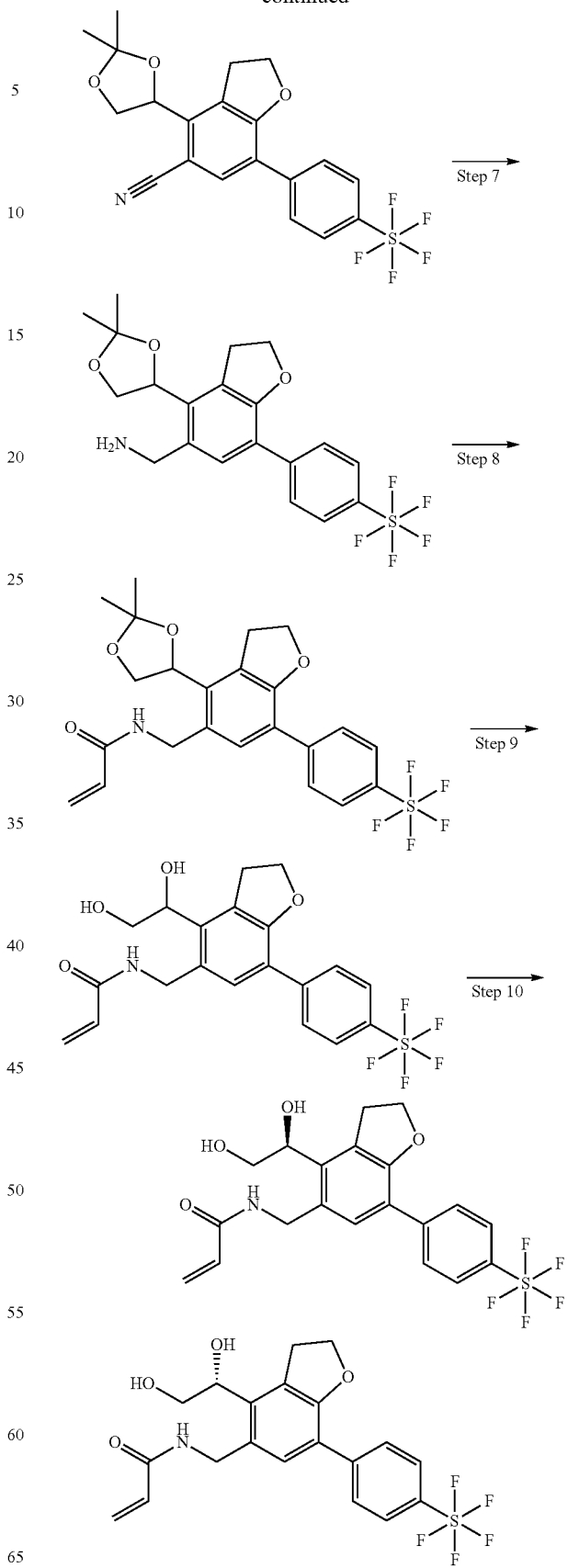

Step 1: 7-chloro-4-vinyl-2,3-dihydrobenzofuran-5-amine

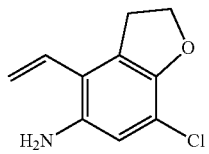

A mixture of 4-bromo-7-chloro-2,3-dihydrobenzofuran-5-amine (6.0 g, 24.1 mmol), 4,4,5,5-tetramethyl-2-vinyl-1,3,2-dioxaborolane (5.5 g, 36.2 mmol), Na$_2$CO$_3$ (5.1 g, 48.3 mmol) and Pd(dppf)Cl$_2$ (2.6 g, 3.6 mmol) in 1,4-dioxane (100 mL) and water (10 mL) was stirred at 100° C. for 8 h under N$_2$ atmosphere. The mixture was diluted with water (100 mL) and extracted with ethyl acetate (100 mL×3) and washed with brine (100 mL×3). The organic layers were dried over anhydrous sodium sulfate and concentrated under reduced. The residue was purified by flash chromatography on silica gel (0-5% ethyl acetate in petroleum ether) to afford the title compound (2.1 g, 45%) as a yellow solid. $^1$H NMR (400 MHz, CDCl$_3$): δ 6.61 (dd, J=18.0, 11.6 Hz, 1H), 6.55 (s, 1H), 5.59-5.50 (m, 2H), 4.61 (t, J=8.8 Hz, 2H), 3.26 (t, J=8.8 Hz, 2H).

Step 2: 7-chloro-5-iodo-4-vinyl-2,3-dihydrobenzofuran

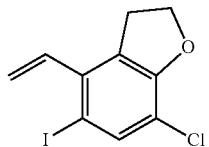

To a solution of 7-chloro-4-vinyl-2,3-dihydrobenzofuran-5-amine (2.0 g, 10.0 mmol) and 4M HCl (5 mL, 20.0 mmol) in acetonitrile (10 mL) was added a solution of NaNO$_2$ (1.4 g, 20 mmol) in water (2 mL) slowly at 0° C. The mixture was stirred at 0° C. for 3 minutes. Then the KI (2.5 g, 15.0 mmol) in water (2 mL) was added slowly into it at 0° C. The mixture was stirred at 0° C. for 40 minutes. The mixture was diluted with water (100 mL), extracted with ethyl acetate (100 mL×3) and washed with brine (100 mL×3). The organic layers were dried over anhydrous sodium sulfate and concentrated under reduced. The residue was purified by flash chromatography on silica gel (0-5% ethyl acetate in petroleum ether) to afford the title compound as a yellow solid. $^1$H NMR (400 MHz, CDCl$_3$): δ 7.64 (s, 1H), 6.72 (dd, J=17.6, 11.6 Hz, 1H), 5.55-5.38 (m, 2H), 4.68 (t, J=8.8 Hz, 2H), 3.40 (t, J=8.8 Hz, 2H).

Step 3: 1-(7-chloro-5-iodo-2,3-dihydrobenzofuran-4-yl)ethane-1,2-diol

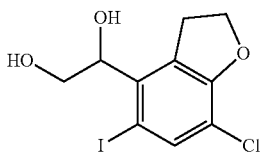 [SMILES: OCC(O)c1c(I)cc(Cl)c2c1CCO2]

To a solution of 7-chloro-5-iodo-4-vinyl-2,3-dihydrobenzofuran (1.0 g, 3.30 mmol) and K$_2$OsO$_4$·2H$_2$O (120 mg, 0.30 mmol) in THF (10 mL) and water (2 mL) was added NMO (788 mg, 6.70 mmol) at room temperature. The resulting mixture was stirred at room temperature for 16 h. The reaction mixture was diluted with ethyl acetate (20 mL) and washed with water (100 mL×2) and brine (100 mL×2). The organic layer was dried over Na$_2$SO$_4$ and concentrated under vacuo to afford the title compound (600 mg, 54%) as a white solid. The crude was used for next step without further purification. $^1$H NMR (400 MHz, CDCl$_3$): s 7.58 (s, 1H), 5.12-5.09 (m, 1H), 4.69-4.60 (m, 2H), 3.82-3.75 (m, 2H), 3.63-3.59 (m, 1H), 3.38-3.33 (m, 1H).

Step 5: 7-chloro-4-(2,2-dimethyl-1,3-dioxolan-4-yl)-5-iodo-2,3-dihydrobenzofuran

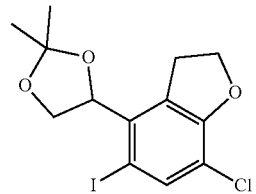 [SMILES: CC1(C)OCC(c2c(I)cc(Cl)c3c2CCO3)O1]

To a solution of 1-(7-chloro-5-iodo-2,3-dihydrobenzofuran-4-yl)ethane-1,2-diol (500 mg, 1.47 mmol) in acetone (5 mL) was added TsOH·H$_2$O (85 mg, 0.40 mmol). The resulting mixture was stirred at 70° C. for 16 h. The reaction mixture was diluted with ethyl acetate (20 mL), washed with water (20 mL×2) and brine (20 mL×2). The organic layer was dried over Na$_2$SO$_4$ and concentrated under vacuo to afford the title compound (400 mg, 72%) as a white solid. The crude was used for next step without further purification. $^1$H NMR (400 MHz, CDCl$_3$): δ 7.58 (s, 1H), 5.36-5.31 (m, 1H), 4.66-4.60 (m, 2H), 4.45-4.40 (m, 1H), 3.75-3.68 (m, 1H), 3.60-3.55 (m, 1H), 3.40-3.36 (m, 1H), 1.57 (s, 3H), 1.47 (s, 3H).

Step 6: 7-chloro-4-(2,2-dimethyl-1,3-dioxolan-4-yl)-2,3-dihydrobenzofuran-5-carbonitrile

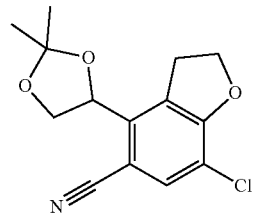 [SMILES: CC1(C)OCC(c2c(C#N)cc(Cl)c3c2CCO3)O1]

A solution of 7-chloro-4-(2,2-dimethyl-1,3-dioxolan-4-yl)-5-iodo-2,3-dihydrobenzofuran (400 mg, 1.0 mmol) and CuCN (188 mg, 2.1 mmol) in DMF (5 mL) was stirred at 100° C. for 16 hours under N$_2$ atmosphere. The reaction mixture was quenched with water (50 mL), ethyl acetate with (50 mL×3). Combined organic layers were dried over Na$_2$SO$_4$, filtered and concentrated. The residue was purified by flash chromatography on silica gel (0-30% ethyl acetate in petroleum ether) to afford the title compound (200 mg, 68%) as a white solid. $^1$H NMR (400 MHz, CDCl$_3$): (7.48 (s, 1H), 5.46-5.43 (m, 1H), 4.79-4.72 (m, 2H), 4.45-4.41 (m, 1H), 3.73-3.69 (m, 1H), 3.66-3.57 (m, 1H), 3.49-3.39 (m, 1H), 1.59 (s, 3H), 1.48 (s, 3H).

Step 7: 4-(2,2-dimethyl-1,3-dioxolan-4-yl)-7-[4-(pentafluoro-6-sulfanyl)phenyl]-2,3-dihydrobenzofuran-5-carbonitrile

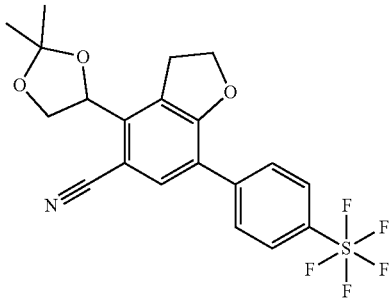 [SMILES: CC1(C)OCC(c2c(C#N)cc(-c3ccc(S(F)(F)(F)(F)F)cc3)c3c2CCO3)O1]

A mixture of 7-chloro-4-(2,2-dimethyl-1,3-dioxolan-4-yl)-2,3-dihydrobenzofuran-5-carbonitrile (200 mg, 0.70 mmol), pentafluoro-[4-(4,4,5,5-tetramethyl-1,3,2-dioxaborolan-2-yl)phenyl]-6-sulfane (283 mg, 0.80 mmol), KOAc (120 mg, 1.4 mmol), Xphos (34.0 mg, 0.07 mmol) and Xphos Pd $G_2$ (57 mg, 0.07 mmol) in 1,4-dioxane (5 mL) and water (0.5 mL) was stirred at 80° C. for 16 h under $N_2$ atmosphere. The reaction was diluted with water (20 mL) and extracted with ethyl acetate (20 mL×2). The organic layers were washed with brine (20 mL×2), dried over sodium sulphate, filtered and concentrated. The residue was purified by chromatography on silica gel (0-30% ethyl acetate in petroleum ether) to afford the title compound (240 mg, 75%) as a light yellow solid. $^1$H NMR (400 MHz, CDCl$_3$): δ 7.83 (d, J=8.8 Hz, 2H), 7.73 (d, J=8.8 Hz, 2H), 7.62 (s, 1H), 5.56-5.49 (m, 11H), 4.77-4.71 (m, 2H), 4.51-4.43 (m, 1H), 3.81-3.77 (m, 11H), 3.66-3.59 (m, 1H), 3.47-3.37 (m, 1H), 1.62 (s, 3H), 1.50 (s, 3H).

Step 8: N-[[4-(2,2-dimethyl-1,3-dioxolan-4-yl)-7-[4-(pentafluoro-6-sulfanyl)phenyl]-2,3-dihydrobenzofuran-5-yl]methyl]prop-2-enamide

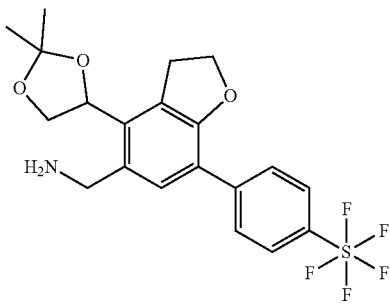 [SMILES: CC1(C)OCC(c2c(CN)cc(-c3ccc(S(F)(F)(F)(F)F)cc3)c3c2CCO3)O1]

To a solution of 4-(2,2-dimethyl-1,3-dioxolan-4-yl)-7-[4-(pentafluoro-6-sulfanyl)phenyl]-2,3-dihydrobenzofuran-5-carbonitrile (240 mg, 0.70 mmol) in MeOH (5 mL) was added Raney Ni (64 mg, 0.70 mmol). The reaction was stirred at room temperature under H$_2$ balloon for 16 h. The mixture was filtered and concentrated to afford the title compound (300 mg, crude) as a brown oil.

Step 9: N-[[4-(2,2-dimethyl-1,3-dioxolan-4-yl)-7-[4-(pentafluoro-6-sulfanyl)phenyl]-2,3-dihydrobenzofuran-5-yl]methyl]prop-2-enamide

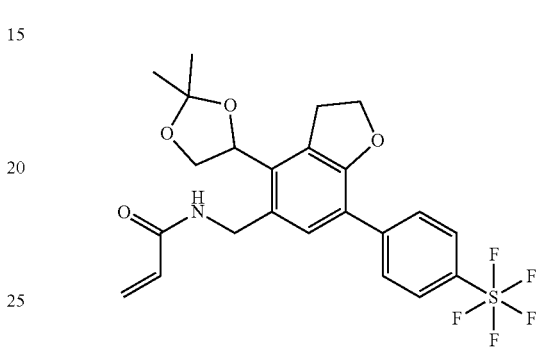

To a solution of N-[[4-(2,2-dimethyl-1,3-dioxolan-4-yl)-7-[4-(pentafluoro-6-sulfanyl)phenyl]-2,3-dihydrobenzofuran-5-yl]methyl]prop-2-enamide (250 mg, 0.50 mmol) and sat.NaHCO$_3$ (1 mL) in THF (5 mL) was added acryloyl chloride (55 mg, 0.60 mmol) at 0° C. The mixture was stirred at 0° C. for 1 h. The mixture was filtered and concentrated to afford the title compound (260 mg, crude). The mixture was used directly and without further purification.

Step 10: N-[[4-(1,2-dihydroxyethyl)-7-[4-(pentafluoro-6-sulfanyl)phenyl]-2,3-dihydrobenzofuran-5-yl]methyl]prop-2-enamide

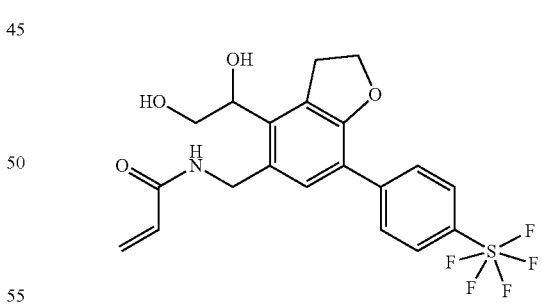

To a solution of N-[[4-(2,2-dimethyl-1,3-dioxolan-4-yl)-7-[4-(pentafluoro-6-sulfanyl)phenyl]-2,3-dihydrobenzofuran-5-yl]methyl]prop-2-enamide (250 mg, 0.50 mmol) in THF (10 mL) was added 4M HCl (2 mL). Then the reaction mixture was stirred at 40° C. for 4 h. The solution was combined, the residue was purified by reverse phase chromatography (Welch Xtimate C18 150*25 mm*5 um, acetonitrile 40-70%/water (NH$_4$HCO$_3$)-CAN) to afford the title compound (100 mg, 43%) as a white solid. LCMS (ESI): m/z 488.1 (M+Na)$^+$.

537

Step 11: N-[[7-[4-(pentafluoro-6-sulfanyl)phenyl]-4-[rac-(1S)-1,2-dihydroxyethyl]-2,3-dihydrobenzofuran-5-yl]methyl]prop-2-enamide & N-[[7-[4-(pentafluoro-6-sulfanyl)phenyl]-4-[rac-(1R)-1,2-dihydroxyethyl]-2,3-dihydrobenzofuran-5-yl]methyl]prop-2-enamide

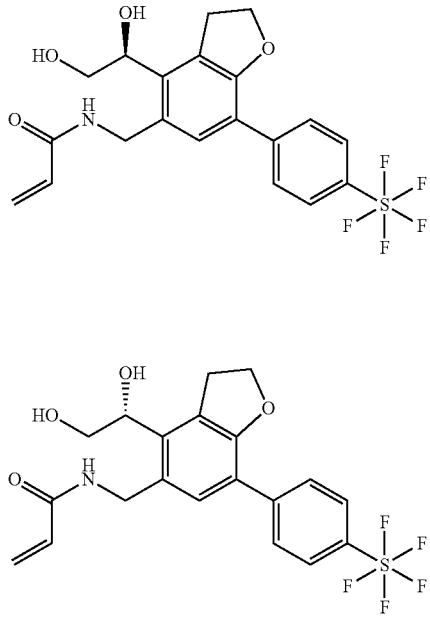

N-[[4-(1,2-Dihydroxyethyl)-7-[4-(pentafluoro-6-sulfanyl)phenyl]-2,3-dihydrobenzofuran-5-yl]methyl]prop-2-enamide (100 mg, 0.22 mmol) was separated by Chiral SFC (Instrument: SFC-12; Column: OD(250 mm*30 mm,10 um); Condition: Neu-ETOH; Begin B:15%; Flow Rate (ml/min): 70) to afford the first peak N-[[7-[4-(pentafluoro-6-sulfanyl)phenyl]-4-[rac-(1R)-1,2-dihydroxyethyl]-2,3-dihydrobenzofuran-5-yl]methyl]prop-2-enamide (35 mg, 34%) and the second peak N-[[7-[4-(pentafluoro-6-sulfanyl)phenyl]-4-[rac-(1R)-1,2-dihydroxyethyl]-2,3-dihydrobenzofuran-5-yl]methyl]prop-2-enamide (30 mg, 30%) both as white solid. The first peak: $^1$H NMR (400 MHz, DMSO-d$_6$): δ 8.35 (t, J=5.2 Hz, 1H), 7.96 (d, J=8.8 Hz, 2H), 7.85 (d, J=8.8 Hz, 2H), 7.27 (s, 1H), 6.26 (dd, J=17.2, 10.0 Hz, 1H), 6.10 (dd, J=17.2, 2.4 Hz, 1H), 5.59 (dd, J=10.0, 2.4, Hz, 1H), 5.32 (d, J=3.2 Hz, 1H), 4.88-4.82 (m, 2H), 4.61-4.49 (m, 3H), 4.37-4.33 (m, 1H), 3.63-3.59 (m, 1H), 3.56-3.49 (m, 2H), 3.45-3.40 (m, 1H); LCMS (ESI): m/z 488.0 (M+Na)$^+$.

The second peak: $^1$H NMR (400 MHz, DMSO-d$_6$): δ 8.35 (t, J=5.2 Hz, 1H), 7.96 (d, J=8.8 Hz, 2H), 7.85 (d, J=8.8 Hz, 2H), 7.27 (s, 1H), 6.26 (dd, J=17.2, 10.0 Hz, 1H), 6.10 (dd, J=17.2, 2.4 Hz, 1H), 5.59 (dd, J=10.0, 2.4, Hz, 1H), 5.32 (d, J=3.2 Hz, 1H), 4.88-4.82 (m, 2H), 4.61-4.49 (m, 3H), 4.37-4.33 (m, 1H), 3.63-3.59 (m, 1H), 3.56-3.49 (m, 2H), 3.45-3.40 (m, 1H); LCMS (ESI): m/z 488.0 (M+Na)$^+$.

538

Example 95 (Compound 98)

N-Ethyl-N-((7-(4-(trifluoromethoxy)phenyl)thiazolo[5,4-d]pyrimidin-5-yl)methyl)acrylamide

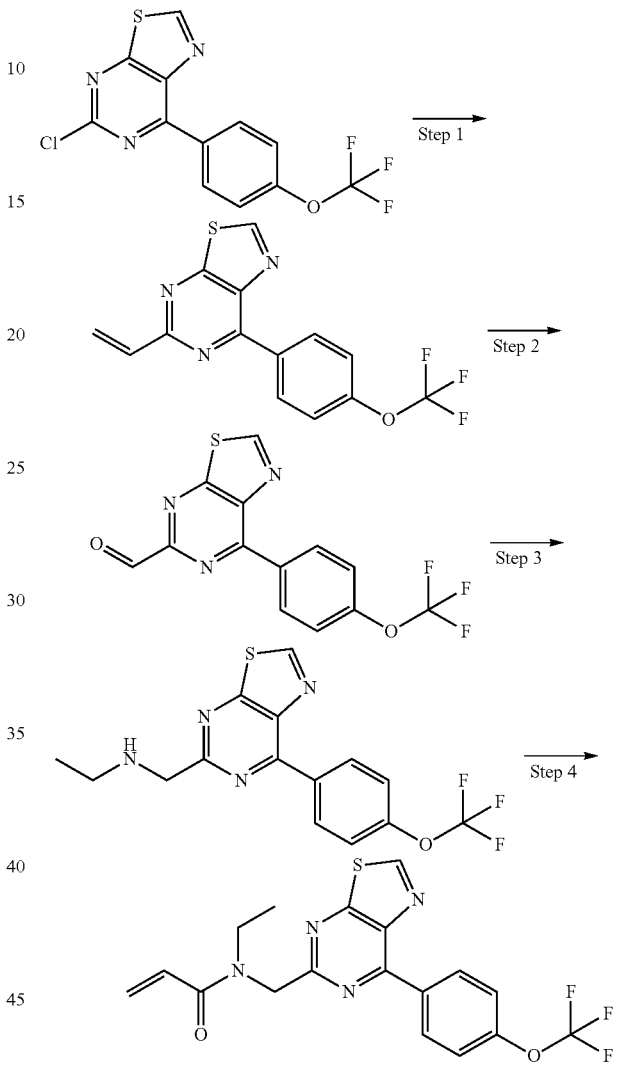

Step 1: 7-(4-(trifluoromethoxy)phenyl)-5-vinylthiazolo[5,4-d]pyrimidine

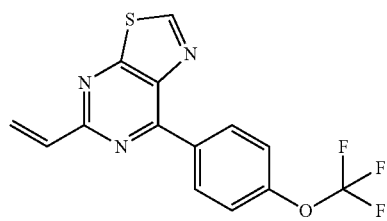 [SMILES: C=Cc1nc(-c2ccc(OC(F)(F)F)cc2)c2ncsc2n1]

A mixture of 5-chloro-7-(4-(trifluoromethoxy)phenyl)thiazolo[5,4-d]pyrimidine (200 mg, 0.60 mmol), 4,4,5,5-tetramethyl-2-vinyl-1,3,2-dioxaborolane (140 mg, 0.90 mmol), Na$_2$CO$_3$ (128 mg, 1.21 mmol) and Pd(dppf)Cl$_2$ (45 mg, 0.06 mmol) in 1,4-dioxane (5 mL) and water (0.5 mL) was stirred at 100° C. for 30 min under N$_2$ atmosphere. The mixture was diluted with ethyl acetate (20 mL) and washed with water (20 mL×3). The organic was dried over Na$_2$SO$_4$ and concentrated. The residue was purified by flash chromatography on silica gel (0-25% ethyl acetate in petroleum ether) to afford the title compound (110 mg, 56%) as a white solid. $^1$H NMR (400 MHz, CDCl$_3$): (9.13 (s, 1H), 8.86-8.80 (m, 2H), 7.42 (d, J=8.4 Hz, 2H), 7.06 (dd, J=17.2, 10.4 Hz, 1H), 6.83 (dd, J=17.2, 1.6 Hz, 1H), 5.86 (dd, J=10.4, 1.6 Hz, 1H); LCMS (ESI): m/z 324.0 (M+H)$^+$.

Step 2: 7-(4-(trifluoromethoxy)phenyl)thiazolo[5,4-d]pyrimidine-5-carbaldehyde

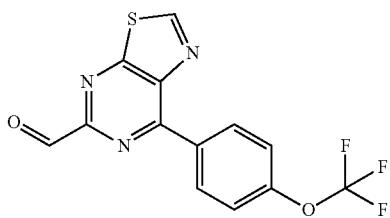 [SMILES: O=Cc1nc(-c2ccc(OC(F)(F)F)cc2)c2ncsc2n1]

To a solution of 7-(4-(trifluoromethoxy)phenyl)-5-vinylthiazolo[5,4-d]pyrimidine (110 mg, 0.34 mmol) in THF (4 mL) and water (0.50 mL) was added OsO$_4$ (10 mg, 0.04 mmol) and NaIO$_4$ (292 mg, 1.36 mmol) at 0° C. The reaction mixture was stirred at room temperature for 2.5h. The reaction mixture was quenched with aq.Na$_2$SO$_3$ (10 mL). The resulting mixture was extracted with ethyl acetate (20 mL×3), combined organic layers were dried over Na$_2$SO$_4$, filtered and concentrated to afford the title compound (110 mg, 99%) as a brown solid. The crude product was used for next step directly. $^1$H NMR (400 MHz, CDCl$_3$): δ: 10.32 (s, 1H), 9.42 (s, 1H), 9.00-8.92 (m, 2H), 7.47-7.41 (m, 2H).

Step 3: N-((7-(4-(trifluoromethoxy)phenyl)thiazolo[5,4-d]pyrimidin-5-yl)methyl)ethanamine

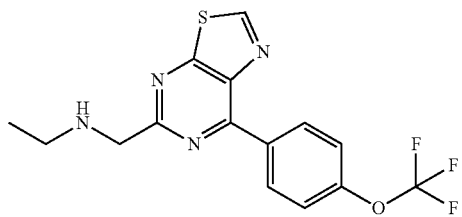 [SMILES: CCNCc1nc(-c2ccc(OC(F)(F)F)cc2)c2ncsc2n1]

To a solution of ethanamine hydrochloride (81 mg, 1.0 mmol) in DCE (5 mL) was added TEA (0.14 mL, 1.0 mmol), then 7-(4-(trifluoromethoxy)phenyl)thiazolo[5,4-d]pyrimidine-5-carbaldehyde (250 mg, 0.50 mmol) and FA (12 mg, 0.25 mmol). The mixture was stirred at room temperature for 2 hours, then NaBH(OAc)$_3$ (159 mg, 0.75 mmol) was added into it. The mixture was stirred at room temperature for 3 hours. The reaction was concentrated under vacuum. The residue was purified by pre-TLC (10% methanol in DCM) to afford the title compound (160 mg, 90%) as a colorless solid. LCMS (ESI): m/z 355.1 (M+H)$^+$.

Step 4: N-ethyl-N-((7-(4-(trifluoromethoxy)phenyl)thiazolo[5,4-d]pyrimidin-5-yl)methyl)acrylamide

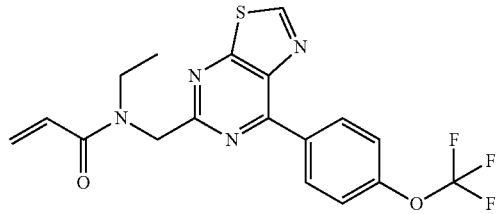 [SMILES: C=CC(=O)N(CC)Cc1nc(-c2ccc(OC(F)(F)F)cc2)c2ncsc2n1]

To a mixture of N-((7-(4-(trifluoromethoxy)phenyl)thiazolo[5,4-d]pyrimidin-5-yl)methyl)ethanamine (160 mg, 0.45 mmol) in THF (5 mL) was added sat.NaHCO$_3$ (0.5 mL) and acryloyl chloride (49 mg, 0.54 mmol) at 0° C., the resulting mixture was stirred at 0° C. for 30 min. The reaction was quenched with water (10 mL) and extracted with ethyl acetate (10 mL×3). The combined organic layers were dried over Na$_2$SO$_4$ and concentrated under vacuum. The resulting residue was purified by reverse phase chromatography (Welch Xtimate C18 150*25 mm*5 um, acetonitrile/water (0.225% FA)-ACN, 59%-89%) to afford the title compound (81.28 mg, 44%) as a colorless oil. $^1$H NMR (400 MHz, DMSO-d$_6$): δ 9.71, 9.68 (s, 1H total), 8.82-8.77 (m, 2H), 7.65-7.61 (m, 2H), 6.90, 6.75 (dd, J=16.8, 10.4 Hz, 1H), 6.16 (dd, J=16.8, 1.2 Hz, 1H), 5.74, 5.56 (dd, J=10.4, 1.2 Hz, 1H), 5.05, 4.93 (s, 2H total), 3.69, 3.53 (q, J=7.2 Hz, 2H), 1.22, 1.06 (t, J=7.2 Hz, 3H); LCMS (ESI): m/z 409.0 (M+H)$^+$.

Example 96 (Compound 99)

1-(3-(7-(4-(Trifluoromethoxy)phenyl)thiazolo[5,4-d]pyrimidin-5-yl)azetidin-1-yl)prop-2-en-1-one

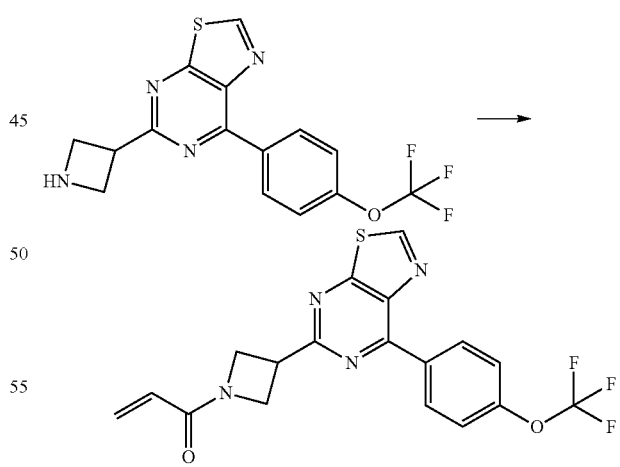

To a mixture of 5-(azetidin-3-yl)-7-(4-(trifluoromethoxy)phenyl)thiazolo[5,4-d]pyrimidine (70 mg, 0.20 mmol) in THF (2 mL) was added sat.NaHCO$_3$ (0.2 mL) and acryloyl chloride (22 mg, 0.24 mmol) at 0° C., the resulting mixture was stirred at 0° C. for 30 min. The reaction was quenched with water (10 mL) and extracted with ethyl acetate (10 mL×3). The combined organic layers were dried over Na$_2$SO$_4$ and concentrated under vacuum. The resulting residue was purified by reverse phase chromatography (Welch Xtimate C18 150*25 mm*5 um, acetonitrile/water(FA)-ACN,56%-86%) to afford the title compound (29.28 mg, 35%) as a colorless oil. ¹H NMR (400 MHz, DMSO-d₆): δ 9.68 (s, 1H), 8.80-8.79 (s, 2H), 7.63-7.61 (m, 2H), 6.40-6.38 (m, 1H), 6.17-6.13 (m, 1H), 5.79-5.58 (m, 1H), 4.71-4.31 (m, 5H); LCMS (ESI): m/z 406.9 (M+H)⁺.

Example 97 (Compound 100)

(E)-4-Hydroxy-1-(3-(7-(4-(trifluoromethoxy)phenyl)thiazolo[5,4-d]pyrimidin-5-yl)azetidin-1-yl)but-2-en-1-one

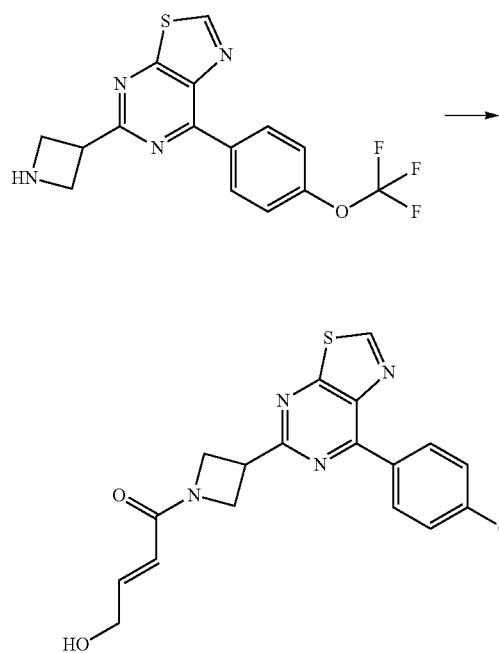

A mixture of 5-(azetidin-3-yl)-7-(4-(trifluoromethoxy)phenyl)thiazolo[5,4-d]pyrimidine (41 mg, 0.12 mmol), (E)-4-hydroxybut-2-enoic acid (15 mg, 0.15 mmol) and ethyl 2-ethoxyquinoline-1(2H)-carboxylate (61 mg, 0.24 mmol) in DCM (20 mL) and methyl alcohol (6 mL) was stirred at room temperature for 16 h. The mixture was diluted with ethyl acetate (10 mL) and washed with water (15 mL). The organic was dried over Na₂SO₄ and concentrated. The residue was purified by reverse phase chromatography (Welch Xtimate C18 150*25 mm*5 um, water (0.225% FA)-ACN, 40%-70%) to afford the title compound (5.0 mg, 9%) as a white solid. ¹H NMR (400 MHz, DMSO-d₆): δ 9.69 (s, 1H), 8.82 (d, J=8.8 Hz, 2H), 7.64 (d, J=8.8 Hz, 2H), 6.78 (dt, J=15.2, 4.0 Hz, 1H), 6.21-6.19 (m, 1H), 5.07 (t, J=5.2 Hz, 1H), 4.69-4.66 (m, 1H), 4.59-4.55 (m, 1H), 4.40-4.36 (m, 1H), 4.32-4.29 (m, 2H), 4.27-4.25 (m, 2H); LCMS (ESI): m/z 437.0 (M+H)⁺.

Example 98 (Compoun 101)

N-((7-(4-(Trifluoromethoxy)phenyl)thiazolo[5,4-d]pyrimidin-5-yl)methyl)acrylamide-2,3,3-d₃

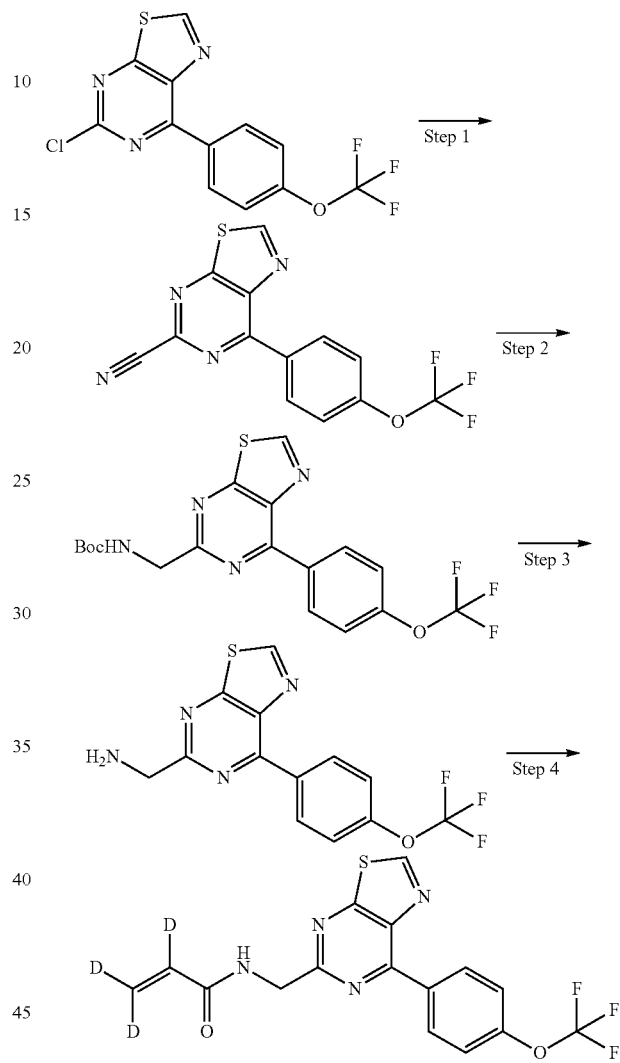

Step 1: 7-(4-(trifluoromethoxy)phenyl)thiazolo[5,4-d]pyrimidine-5-carbonitrile

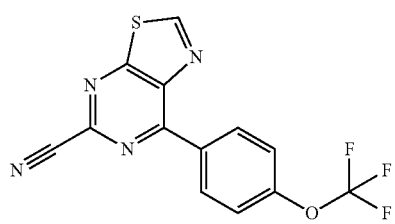 [SMILES: N#Cc1nc(-c2ccc(OC(F)(F)F)cc2)c2ncsc2n1]

To a mixture of 5-chloro-7-(4-(trifluoromethoxy)phenyl)thiazolo[5,4-d]pyrimidine (1.0 g, 3.01 mmol) in DMA (12 mL) was added Pd(PPh₃)₄ (349 mg, 0.30 mmol) and Zn(CN)₂ (1.42 g, 12.06 mmol). The mixture was stirred at

543

180° C. in MW for 30 min. The reaction was diluted with ethyl acetate (100 mL) and washed with brine (50 mL×3). The organic layer was dried over Na₂SO₄, filtered and concentrated. The residue was purified by flash chromatography on silica gel (0-30% ethyl acetate in petroleum ether) to afford the title compound (600 mg, 62%) as a yellow solid.

$^1$H NMR (400 MHz, DMSO-d$_6$): δ 9.98 (s, 1H), 8.83-8.76 (m, 2H), 7.66 (d, J=8.4 Hz, 2H); LCMS (ESI): m/z 323.1 (M+H)$^+$.

Step 2: tert-butyl ((7-(4-(trifluoromethoxy)phenyl) thiazolo[5,4-d]pyrimidin-5-yl)methyl)carbamate

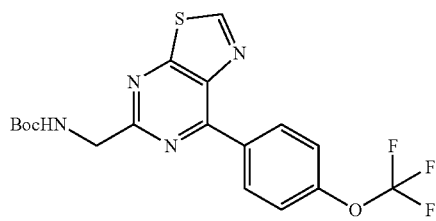 [SMILES: CC(C)(C)OC(=O)NCc1nc(-c2ccc(OC(F)(F)F)cc2)c2ncsc2n1]

A solution 7-(4-(trifluoromethoxy)phenyl)thiazolo[5,4-d]pyrimidine-5-carbonitrile (300 mg, 0.93 mmol) in methanol (10 mL) was added Boc₂O (1.22 g, 5.59 mmol) and Raney-Ni (1.0 g, 12.54 mmol). The reaction was stirred at room temperature under H₂ (15 psi) for 1 day. The mixture was filtered and the filtrate was concentrated. The residue was purified by flash chromatography on silica gel (0-30% ethyl acetate in petroleum ether) to afford to afford the title compound (75 mg, 19%) as a colorless oil. $^1$H NMR (400 MHz, CDCl₃): δ 9.16 (s, 1H), 8.83 (d, J=8.8 Hz, 2H), 7.43 (d, J=8.8 Hz, 2H), 4.79 (d, J=4.4 Hz, 2H), 1.52 (s, 9H); LCMS (ESI): m/z 427.1 (M+H)$^+$.

Step 3: (7-(4-(trifluoromethoxy)phenyl)thiazolo[5,4-d]pyrimidin-5-yl)methanamine

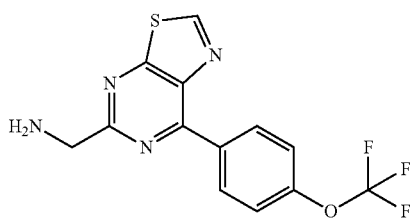 [SMILES: NCc1nc(-c2ccc(OC(F)(F)F)cc2)c2ncsc2n1]

To a mixture of tert-butyl((7-(4-(trifluoromethoxy)phenyl)thiazolo[5,4-d]pyrimidin-5-yl)methyl)carbamate (75 mg, 0.18 mmol) in dichloromethane (3 mL) was added TFA (0.3 mL) at 0° C. The solution was stirred at room temperature for 1 h. The reaction was quenched with ammonia (1 mL). The mixture was concentrated under vacuum to afford the title compound (57 mg, crude) as a white solid. LCMS (ESI): m/z 327.0 (M+H)$^+$.

544

Step 4: N-((7-(4-(trifluoromethoxy)phenyl)thiazolo[5,4-d]pyrimidin-5-yl)methyl)acrylamide-2,3,3-d₃

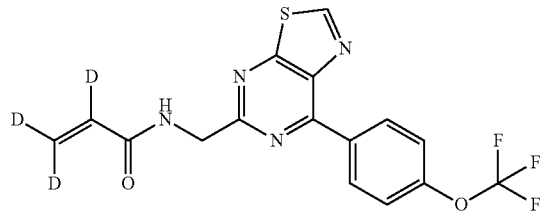

To a solution of (7-(4-(trifluoromethoxy)phenyl)thiazolo[5,4-d]pyrimidin-5-yl)methanamine (57 mg, 0.17 mmol) and 2,3,3-trideuterioprop-2-enoic acid (20 mg, 0.26 mmol) in DMF (1.5 mL) was added HATU (150 mg, 0.39 mmol) and DIEA (0.14 mL, 0.79 mmol) at room temperature. The mixture was stirred at room temperature for 2 h. The mixture was concentrated and the residue was purified by reverse phase chromatography (Welch Xtimate C18 150*25 mm*5 um, 49%-79% water(FA)-ACN) to afford the title compound (22.65 mg, 33%) as a white solid. $^1$H NMR (400 MHz, DMSO-d$_6$): δ 9.69 (s, 1H), 8.88-8.80 (m, 3H), 7.64 (d, J=8.0 Hz, 2H), 4.77 (d, J=6.0 Hz, 2H); LCMS (ESI): m/z 384.0 (M+H)$^+$.

Example 99 (Compound 102)

N-((7-(3-Isopropylbicyclo[1.1.1]pentan-1-yl)thiazolo[5,4-d]pyrimidin-5-yl)methyl)acrylamide

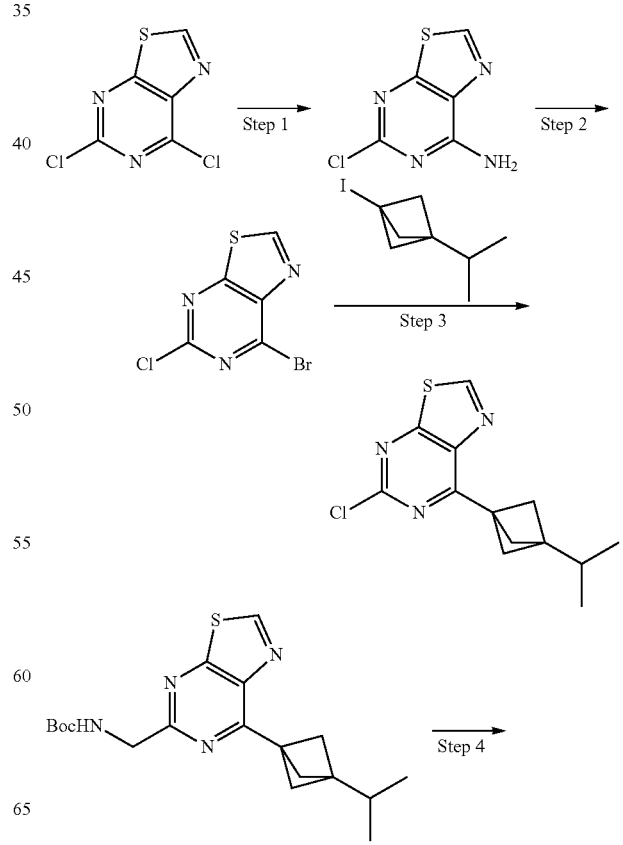

-continued

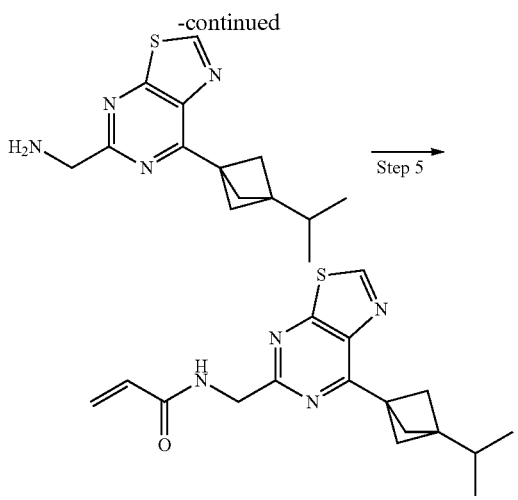

Step 1: 5-chlorothiazolo[5,4-d]pyrimidin-7-amine

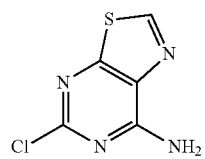

To a solution of 5,7-dichlorothiazolo[5,4-d]pyrimidine (2.0 g, 9.71 mmol) in THF (30 mL) was added NH$_3$H$_2$O (10 mL) at room temperature. The mixture was stirred at room temperature for 2 h. The mixture was diluted with water (30 mL) and washed with ethyl acetate (10 mL×3). The organic layer was dried over Na$_2$SO$_4$ and concentrated to afford the title compound (1.5 g, 83%) as a white solid. LCMS (ESI): m/z 187.0 (M+H)$^+$.

Step 2: 7-bromo-5-chlorothiazolo[5,4-d]pyrimidine

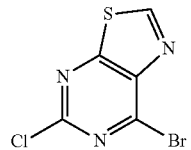 [SMILES: Clc1nc(Br)c2ncsc2n1]

To a solution of t-BuONO (0.96 mL, 8.04 mmol) and CuBr (2.31 g, 16.08 mmol) in acetonitrile (20 mL) was added 5-chlorothiazolo[5,4-d]pyrimidin-7-amine (1.5 g, 8.04 mmol) at room temperature, and then the reaction was stirred at 60° C. for 2 hours. The reaction was diluted with water (50 mL) and extracted with ethyl acetate (50 mL×2). The organic layers were washed with brine (50 mL), dried over Na$_2$SO$_4$, filtered and concentrated. The resulting residue was purified by flash chromatography on silica gel (0-20% ethyl acetate in petroleum ether) to afford the title compound (600 mg, 30%) as white solid. LCMS (ESI): m/z 249.9 (M+H)$^+$.

Step 3: 5-chloro-7-(3-isopropylbicyclo[1.1.1]pentan-1-yl)thiazolo[5,4-d]pyrimidine

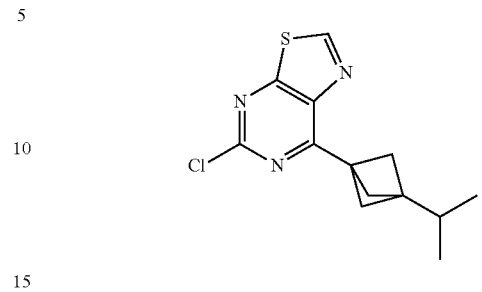

To a mixture of 1-iodo-3-isopropylbicyclo[1.1.1]pentane (142 mg, 0.60 mmol), 7-bromo-5-chlorothiazolo[5,4-d]pyrimidine (100 mg, 0.40 mmol) in DME (8 mL) was added Na$_2$CO$_3$ (106 mg, 1.0 mmol), Ir[dF(CF$_3$)ppy]$_2$(dtbbpy)PF$_6$ (5 mg, 0.01 mmol) and TTMSS (120 mg, 0.48 mmol). The solution NiCl$_2$-glyme (9 mg, 0.04 mmol) and dtbbpy (16 mg, 0.06 mmol) in DME (2 mL) was added into the mixture in glove box at room temperature. The reaction mixture was stirred under a Lumidox Screen Kit at room temperature for 16 hours. The solution was quenched with water (10 mL) and extracted with ethyl acetate (10 mL×3), dried over Na$_2$SO$_4$ and concentrated. The residue was purified by reverse phase chromatography (Welch Xtimate C18 150*30 mm*5 um, 70%-100% water (NH$_3$H$_2$O +NH$_4$HCO$_3$)-ACN) to afford the title compound (5 mg, 5%) as a white solid. 2D-NMR confirmed it. $^1$H NMR (400 MHz, CDCl$_3$): δ 9.06 (s, 1H), 2.23 (s, 6H), 1.88-1.78 (m, 1H), 0.92 (d, J=6.8 Hz, 6H); LCMS (ESI): m/z 280.1 (M+H)$^+$.

Step 4: tert-butyl ((7-(3-isopropylbicyclo[1.1.1]pentan-1-yl)thiazolo[5,4-d]pyrimidin-5-yl)methyl)carbamate

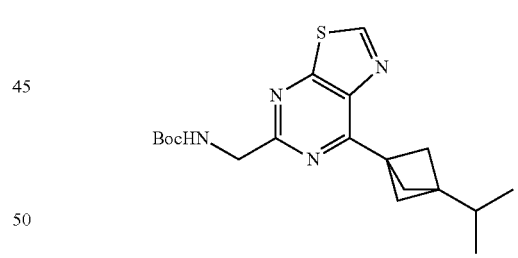

A mixture of potassium (((tert-butoxycarbonyl)amino)methyl)trifluoroborate (542 mg, 2.27 mmol), 5-chloro-7-(3-isopropylbicyclo[1.1.1]pentan-1-yl)thiazolo[5,4-d]pyrimidine (180 mg, 0.57 mmol), CATACXIUM A Pd G$_2$ (38 mg, 0.06 mmol) and Cs$_2$CO$_3$ (556 mg, 1.71 mmol) in 1,4-dioxane (7 mL) and water (0.70 mL) was stirred at 100° C. for 5 h under N$_2$ atmosphere. The mixture was quenched with water (30 mL), extracted with ethyl acetate (30 mL×3) and washed with brine (30 mL). The organic layer was dried over Na$_2$SO$_4$. After filtration, the filtrate was concentrated under reduced pressure. Then the residue was purified by flash chromatography on silica gel (0-20% ethyl acetate in petroleum ether) to afford the title compound (34 mg, 16%) as a yellow solid. LCMS (ESI): m/z 375.1 (M+H)$^+$.

547

Step 5: (7-(3-isopropylbicyclo[1.1.1]pentan-1-yl)thiazolo[5,4-d]pyrimidin-5-yl)methanamine

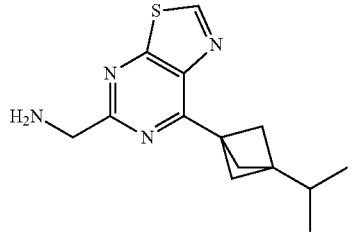 [SMILES: CC(C)C12CC(c3nc(CN)nc4scnc34)(C1)C2]

To a mixture of tert-butyl ((7-(3-isopropylbicyclo[1.1.1]pentan-1-yl)thiazolo[5,4-d]pyrimidin-5-yl)methyl)carbamate (34 mg, 0.09 mmol) in DCM (2 mL) was added TFA (0.2 mL) at room temperature, the resulting mixture was stirred at room temperature for 2 h. The reaction was quenched with $NH_3$—$H_2O$ (1 mL). The mixture was concentrated under vacuum to afford the title compound (24 mg, crude) as a white solid. LCMS (ESI): m/z 275.1 (M+H)$^+$.

Step 6: N-((7-(3-isopropylbicyclo[1.1.1]pentan-1-yl)thiazolo[5,4-d]pyrimidin-5-yl)methyl)acrylamide

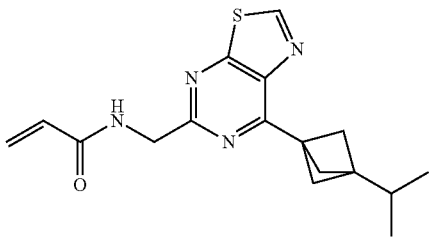 [SMILES: C=CC(=O)NCc1nc(C23CC(C(C)C)(C2)C3)c2ncsc2n1]

To a mixture of (7-(3-isopropylbicyclo[1.1.1]pentan-1-yl)thiazolo[5,4-d]pyrimidin-5-yl)methanamine (24 mg, 0.09 mmol) and sat.NaHCO$_3$ (0.2 mL) in THF (2 mL) was added acryloyl chloride (9 mg, 0.10 mmol) at 0° C., the mixture was stirred at 0° C. for 30 min. The reaction was quenched with water (5 mL) and extracted with ethyl acetate (5 mL×3). The combined organic layers were dried over Na$_2$SO$_4$ and concentrated under vacuum. The resulting residue was purified by reverse phase chromatography (Boston Green ODS 150*30 mm*5 um, acetonitrile 50% -80%/water (FA)-ACN) to afford the title compound (6.8 mg, 24%) as white solid. $^1$H NMR (400 MHz, DMSO-d$_6$): δ 9.53 (s, 1H), 8.76 (t, J=6.0 Hz, 1H), 6.38 (dd, J=16.8, 10.0 Hz, 1H), 6.11 (dd, J=16.8, 2.0 Hz, 1H), 5.64 (dd, J=10.0, 2.0 Hz, 1H), 4.64 (d, J=6.0 Hz, 2H), 2.13 (s, 6H), 1.81-1.74 (m, 1H), 0.89 (d, J=6.8 Hz, 6H); LCMS (ESI): m/z 328.9 (M+H)$^+$.

548

Example 100 (Compound 103)

N-Methyl-N-[[7-[4-(pentafluoro-6-sulfanyl)phenyl]thiazolo[5,4-d]pyrimidin-5-yl]methyl]prop-2-enamide

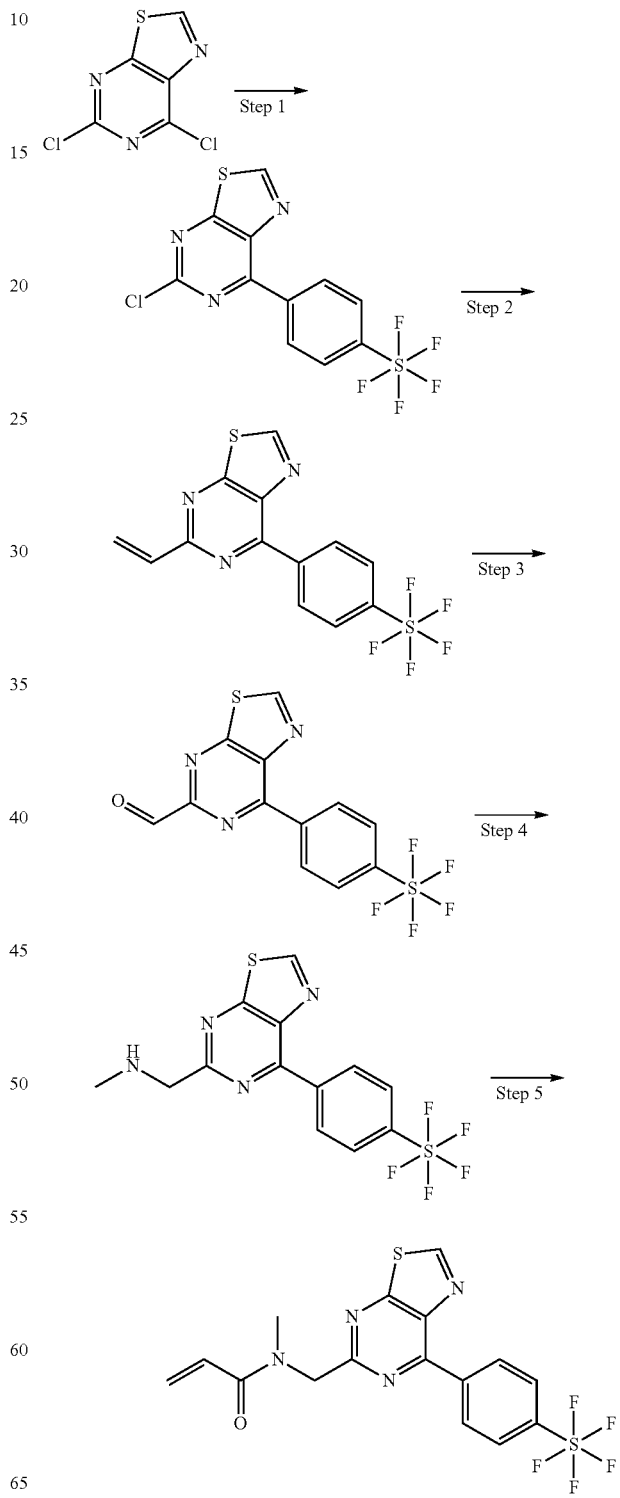

Step 1: [4-(5-chlorothiazolo[5,4-d]pyrimidin-7-yl)phenyl]-pentafluoro-6-sulfane

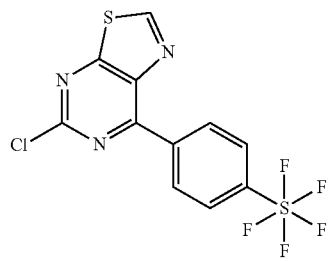 [SMILES: FS(F)(F)(F)(F)c1ccc(-c2nc(Cl)nc3scnc23)cc1]

To a solution of K₃P04 (2.06 g, 9.71 mmol), pentafluoro-[4-(4,4,5,5-tetramethyl-1,3,2-dioxaborolan-2-yl)phenyl]-6-sulfane (1.44 g, 4.37 mmol) in 1,4-dioxane (20 mL) and water (2 mL) was added 5,7-dichlorothiazolo[5,4-d]pyrimidine (1.0 g, 4.85 mmol) and Pd(dppf)C12 (356 mg, 0.49 mmol). The reaction mixture was stirred at 80° C. for 3 h under N₂ atmosphere. The mixture was diluted with water (30 mL) and extracted with ethyl acetate (200 mL×3) and washed with brine (100 mL). The organic layers were dried over anhydrous sodium sulfate and concentrated under reduced. The residue was purified by flash chromatography on silica gel (0-30% ethyl acetate in petroleum ether) to afford the title compound (1.1 g, 61%) as a white solid. $^1$H NMR (400 MHz, CDCl₃): δ 9.23 (s, 1H), 8.87 (d, J=8.8 Hz, 2H), 7.97 (d, J=8.8 Hz, 2H); LCMS (ESI): m/z 373.9 (M+H)⁺.

Step 2: pentafluoro-[4-(5-vinylthiazolo[5,4-d]pyrimidin-7-yl)phenyl]-6-sulfane

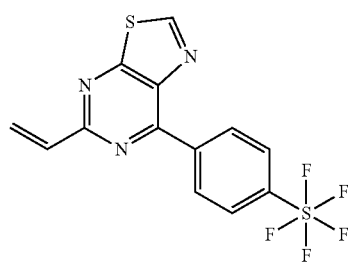 [SMILES: C=Cc1nc(-c2ccc(S(F)(F)(F)(F)F)cc2)c2ncsc2n1]

A mixture of [4-(5-chlorothiazolo[5,4-d]pyrimidin-7-yl)phenyl]-pentafluoro-6-sulfane (500 mg, 1.34 mmol), 4,4,5,5-tetramethyl-2-vinyl-1,3,2-dioxaborolane (309 mg, 2.01 mmol), Na₂CO₃ (284 mg, 2.68 mmol), Pd(dppf)Cl₂ (98 mg, 0.13 mmol) in 1,4-dioxane (10 mL) and water (1 mL) was stirred at 100° C. for 1 h under N₂ atmosphere. The mixture was diluted with ethyl acetate (100 mL) and washed with water (100 mL×3). The organic layer was dried over Na₂SO₄ and concentrated. The residue was purified by flash chromatography on silica gel (0-25% ethyl acetate in petroleum ether) to afford the title compound (300 mg, 61%) as a white solid. $^1$H NMR (400 MHz, CDCl₃): δ 9.16 (s, 1H), 8.85 (d, J=8.8 Hz, 2H), 8.00-7.93 (m, 2H), 7.07 (dd, J=17.2, 10.4, Hz, 1H), 6.84 (dd, J=17.2, 2.0 Hz, 1H), 5.88 (dd, J=10.4, 2.0 Hz, 1H); LCMS (ESI): m/z 366.0 (M+H)⁺.

Step 3: 7-[4-(pentafluoro-6-sulfanyl)phenyl]thiazolo[5,4-d]pyrimidine-5-carbaldehyde

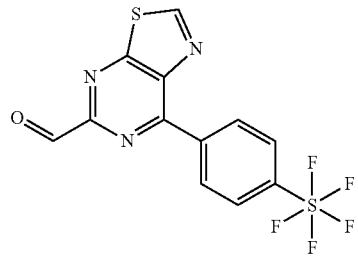 [SMILES: O=Cc1nc(-c2ccc(S(F)(F)(F)(F)F)cc2)c2ncsc2n1]

To a solution of pentafluoro-[4-(5-vinylthiazolo[5,4-d]pyrimidin-7-yl)phenyl]-6-sulfane (150 mg, 0.41 mmol) in THF (3 mL) and water (1 mL) was added NaIO₄ (352 mg, 1.64 mmol) and K₂OsO₄·2H₂O (31 mg, 0.08 mmol) at 0° C. The reaction was stirred at room temperature for 2.5h. The reaction mixture was quenched with aq.Na₂SO₃ (50 mL). The resulting mixture was extracted with ethyl acetate (100 mL×3), combined organic layers were dried over Na₂SO₄, filtered and concentrated. The residue was purified by flash chromatography on silica gel (0-30% ethyl acetate in petroleum ether) to afford the title compound (90 mg, 60%) as a yellow solid. $^1$H NMR (400 MHz, CDCl₃): δ 10.34 (s, 1H), 9.46 (s, 1H), 8.98 (d, J=9.2 Hz, 2H), 8.00 (d, J=9.2 Hz, 2H).

Step 4: N-methyl-1-[7-[4-(pentafluoro-6-sulfanyl)phenyl]thiazolo[5,4-d]pyrimidin-5-yl]methanamine

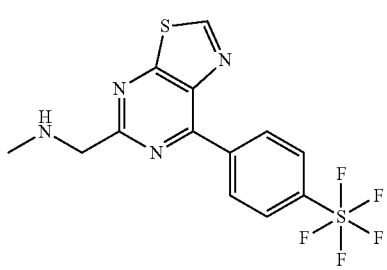 [SMILES: CNCc1nc(-c2ccc(S(F)(F)(F)(F)F)cc2)c2ncsc2n1]

To a solution of methylamine hydrochloride (33 mg, 0.49 mmol) in 1,2-dichloroethane (3 mL) were added TEA (0.48 mL, 3.46 mmol), 7-[4-(pentafluoro-6-sulfanyl)phenyl]thiazolo[5,4-d]pyrimidine-5-carbaldehyde (90 mg, 0.25 mmol) and one drop HOAc. The reaction solution was stirred at room temperature for 1 h. Then NaBH(OAc)₃ (78 mg, 0.37 mmol) was added into it. The mixture was stirred at room temperature for 5 hours. The reaction was concentrated under vacuum. The reaction was diluted with water (50 mL) and extracted with ethyl acetate (100 mL×3). The organics were washed with brine (20 mL×2), dried over sodium sulfate, filtered and concentrated to afford the title compound (90 mg, crude) as a white solid. LCMS (ESI): m/z 383.0 (M+H)⁺.

Step 5: N-methyl-N-[[7-[4-(pentafluoro-6-sulfanyl)phenyl]thiazolo[5,4-d]pyrimidin-5-yl]methyl]prop-2-enamide

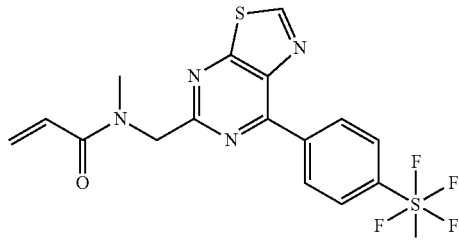

To a solution of N-methyl-1-[7-[4-(pentafluoro-6-sulfanyl)phenyl]thiazolo[5,4-d]pyrimidin-5-yl]methanamine (80 mg, 0.21 mmol) in THF (2 mL) were added sat.NaHCO$_3$ (1 mL) and acryloyl chloride (0.02 mL, 0.21 mmol) at 0° C. The mixture was stirred at room temperature for 1 h. The reaction was diluted with water (20 mL) and extracted with ethyl acetate (30 mL×3). The organics were washed with brine (10 mL×2), dried over sodium sulfate, filtered and concentrated. The residue was purified by reverse phase chromatography (Welch Xtimate C18 150*25 mm*5 um, water (0.225%- FA)-ACN, 43%-72%) to afford the title compound (29.64 mg, 32%) as a white solid. $^1$H NMR (400 MHz, DMSO-d$_6$): δ 9.74, 9.72 (s, 1H total), 8.82 (d, J=8.8 Hz, 2H), 8.21-8.18 (m, 2H), 6.98-6.83 (m, 1H), 6.19-6.14 (m, 1H), 5.78-5.60 (m, 1H), 5.10, 4.99 (s, 2H total), 3.31, 3.06 (s, 3H total); LCMS (ESI): m/z 437.1 (M+H)$^+$.

Example 101 (Compound 104)

N-((7-(5-Oxo-4,5-dihydro-1,2,4-oxadiazol-3-yl)-4-(4-(trifluoromethoxy)phenyl)benzo[d]thiazol-6-yl)methyl)acrylamide

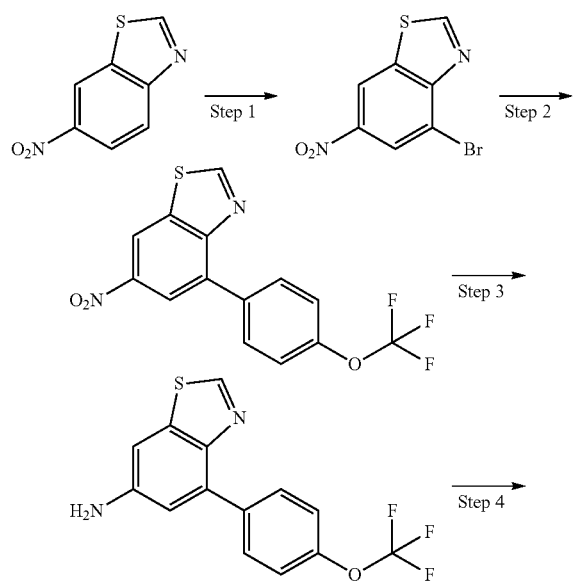

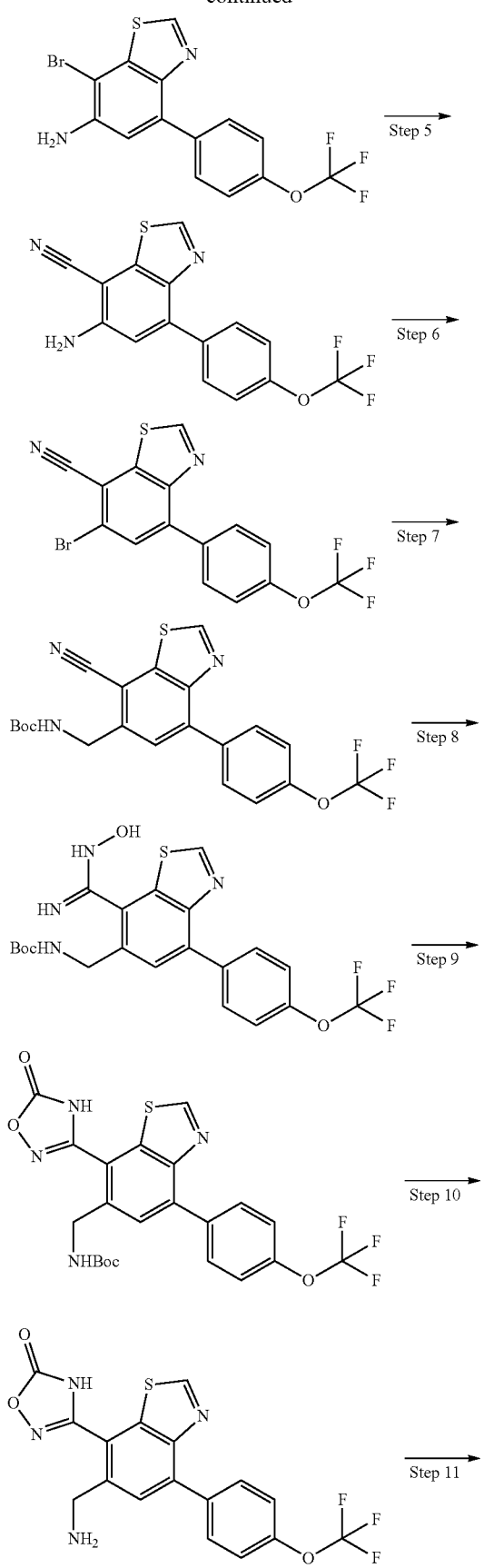

553

-continued

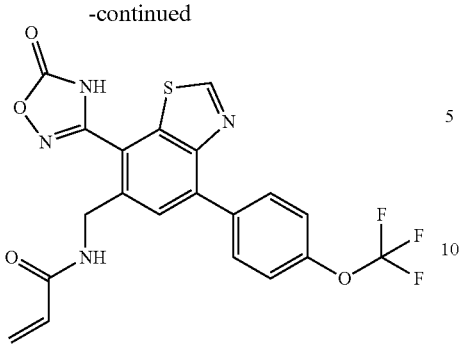

Step 1: 4-bromo-6-nitrobenzo[d]thiazole

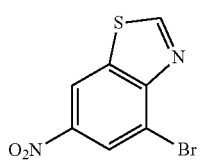

To a solution of 6-nitrobenzo[d]thiazole (10.0 g, 55.5 mmol) in $H_2SO_4$ (50 mL) was added NBS (10.87 g, 61.05 mmol) at 0° C. Then the mixture was stirred at 60° C. for 5 h. The mixture was quenched with water (500 mL) and extracted with ethyl acetate (1 L×3). The organic layer was washed with water (500 mL×3), dried over $Na_2SO_4$, filtered and concentrated. The residue was washed by ethyl acetate (50 mL) to afford the title compound (10.0 g, 69%) as a white solid. $^1$H NMR (400 MHz, CDCl$_3$): δ 9.37 (s, 1H), 8.89 (d, J=2.0 Hz, 1H), 8.64 (d, J=2.0 Hz, 1H).

Step 2: 6-nitro-4-(4-(trifluoromethoxy)phenyl)benzo[d]thiazole

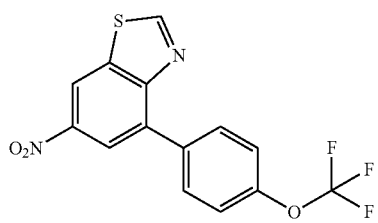

A mixture of 4-bromo-6-nitrobenzo[d]thiazole (4.90 g, 18.91 mmol), (4-(trifluoromethoxy)phenyl)boronic acid (4.67 g, 22.7 mmol), Pd(dppf)Cl$_2$ (1.38 g, 1.89 mmol) and K$_2$CO$_3$ (7.84 g, 56.74 mmol) in 1,4-dioxane (50 mL) and water (5 mL) was stirred at 100° C. for 2 hours under N$_2$ atmosphere. The reaction mixture was concentrated under vacuum. The residue was purified by flash chromatography on silica gel (0-25% ethyl acetate in petroleum ether ) to afford the title compound (5.0 g, 78%) as a yellow solid. $^1$H NMR (400 MHz, CDCl$_3$): δ 9.32 (s, 1H), 8.92 (d, J=2.4 Hz, 1H), 8.48 (d, J=2.4 Hz, 1H), 7.94-7.13 (m, 2H), 7.41 (d, J=8.0 Hz, 2H); LCMS (ESI): m/z 341.0 (M+H)$^+$.

554

Step 3: 4-(4-(trifluoromethoxy)phenyl)benzo[d]thiazol-6-amine

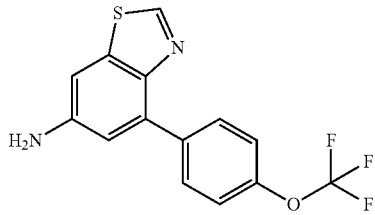 [SMILES: O=[N+]([O-])c1cc(-c2ccc(OC(F)(F)F)cc2)c2ncsc2c1]

A solution of 6-nitro-4-(4-(trifluoromethoxy)phenyl)benzo[d]thiazole (5.0 g, 14.69 mmol) and 10% Pd/C (1.56 g, 14.69 mmol) in ethanol (100 mL) under H$_2$ (15 psi) was stirred at room temperature for 16 h. The reaction mixture was filtered and concentrated to afford the title compound (4.2 g, 92%) as a yellow solid. $^1$H NMR (400 MHz, CDCl$_3$): δ 8.75 (s, 1H), 7.84-7.81 (m, 2H), 7.34 (d, J=8.0 Hz, 2H), 7.20 (d, J=2.4 Hz, 1H), 6.93 (d, J=2.4 Hz, 1H), 3.93 (s, 2H); LCMS (ESI): m/z 311.0 (M+H)$^+$.

Step 4: 7-bromo-4-(4-(trifluoromethoxy)phenyl)benzo[d]thiazol-6-amine

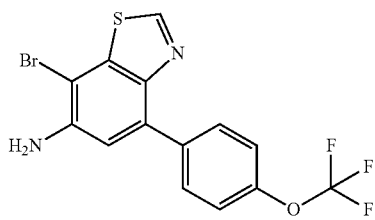 [SMILES: Nc1cc(-c2ccc(OC(F)(F)F)cc2)c2ncsc2c1Br]

To a solution of 4-(4-(trifluoromethoxy)phenyl)benzo[d]thiazol-6-amine (4.2 g, 13.54 mmol) in DCM (50 mL) was added NBS (2.41 g, 13.54 mmol) at 0° C., and the solution was stirred at 0° C. for 1 h. The reaction solution was concentrated. The residue was purified by flash chromatography on silica gel eluting with (0-25% ethyl acetate in petroleum ether) to afford the title compound (3.8 g, 72%) as a yellow solid. $^1$H NMR (400 MHz, CDCl$_3$): δ 8.79 (s, 1H), 7.79 (d, J=8.4 Hz, 2H), 7.34 (d, J=8.4 Hz, 2H), 7.00 (s, 1H), 4.31 (s, 2H); LCMS (ESI): m/z 389.0 (M+H)$^+$.

Step 5: 6-amino-4-(4-(trifluoromethoxy)phenyl)benzo[d]thiazole-7-carbonitrile

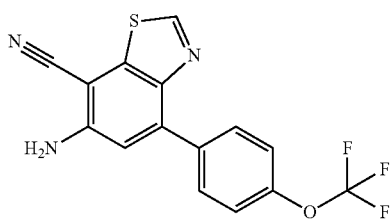 [SMILES: N#Cc1c(N)cc(-c2ccc(OC(F)(F)F)cc2)c2ncsc12]

A mixture of 7-bromo-4-(4-(trifluoromethoxy)phenyl)benzo[d]thiazol-6-amine (2.0 g, 5.14 mmol), t-BuXphos Pd G$_3$ (408 mg, 0.51 mmol) and Zn(CN)$_2$ (3.02 g, 25.69 mmol)

in DMA (20 mL) was stirred at 135° C. for 16 hours under N₂ atmosphere. The reaction solution was quenched with water (200 mL), extracted with ethyl acetate (200 mL), dried over Na₂SO₄, filtered and concentrated. The residue was purified by flash chromatography on silica gel (0-25% ethyl acetate in petroleum ether) to afford the title compound (1.3 g, 75%) as a yellow solid. ¹H NMR (400 MHz, CDCl₃): δ 8.82 (s, 1H), 7.85-7.78 (m, 2H), 7.36 (d, J=8.4 Hz, 2H), 6.93 (s, 1H), 4.74 (s, 2H); LCMS (ESI): m/z 335.9 (M+H)⁺.

Step 6: 6-bromo-4-(4-(trifluoromethoxy)phenyl)benzo[d]thiazole-7-carbonitrile

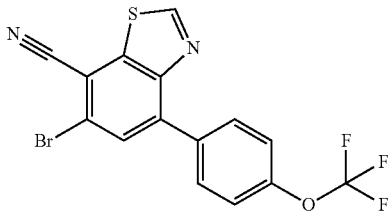 [SMILES: N#Cc1c(Br)cc(-c2ccc(OC(F)(F)F)cc2)c2ncsc12]

To a solution of CuBr (5.16 g, 35.76 mmol) and 6-amino-4-(4-(trifluoromethoxy)phenyl)benzo[d]thiazole-7-carbonitrile (6.0 g, 17.88 mmol) in acetonitrile (50 mL) was added tert-butyl nitrite (2.1 mL, 17.88 mmol) at room temperature, then the solution was stirred at 60° C. for 2 hours. The reaction was diluted with water (50 mL) and extracted with ethyl acetate (50 mL×3). The organics were washed with brine (50 mL×2), dried over sodium sulfate, filtered and concentrated. The resulting residue was purified by flash chromatography on silica gel (0-30% ethyl acetate in petroleum ether) to afford the title compound (5.0 g, 62%) as a white solid. ¹H NMR (400 MHz, CDCl₃): δ 9.06 (s, 1H), 7.84-7.79 (m, 3H), 7.32 (d, J=8.0 Hz, 2H); LCMS (ESI): m/z 398.8 (M+H)⁺.

Step 7: tert-butyl ((7-cyano-4-(4-(trifluoromethoxy)phenyl)benzo[d]thiazol-6-yl)methyl)carbamate

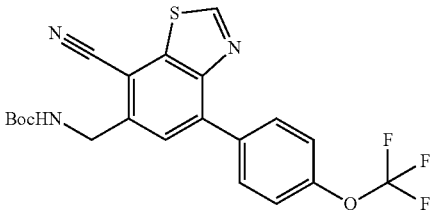 [SMILES: CC(C)(C)OC(=O)NCc1cc(-c2ccc(OC(F)(F)F)cc2)c2ncsc2c1C#N]

A mixture of 6-bromo-4-(4-(trifluoromethoxy)phenyl)benzo[d]thiazole-7-carbonitrile (300 mg, 0.75 mmol), Cs₂CO₃ (490 mg, 1.5 mmol), CATACXIUM A Pd G₂ (101 mg, 0.15 mmol) and potassium (((tert-butoxycarbonyl)amino)methyl)trifluoroborate (446 mg, 2.25 mmol) in 1,4-dioxane (10 mL) and water (1 mL) was purged with N₂ atmosphere for 3 min at room temperature. The mixture was stirred at 100° C. for 12 h under N₂ atmosphere. After cooling down, the solution was quenched with water (10 mL), extracted with ethyl acetate (10 mL×2), the organic layer was washed with brine (10 mL), dried over Na₂SO₄, concentrated and the residue was purified by flash chromatography on silica gel (0-25% ethyl acetate in petroleum ether) to afford the title compound (200 mg, 59%) as a yellow solid. LCMS (ESI): m/z 472.0 (M+Na)⁺.

Step 8: tert-butyl ((7-(N-hydroxycarbamimidoyl)-4-(4-(trifluoromethoxy)phenyl)benzo[d]thiazol-6-yl)methyl)carbamate

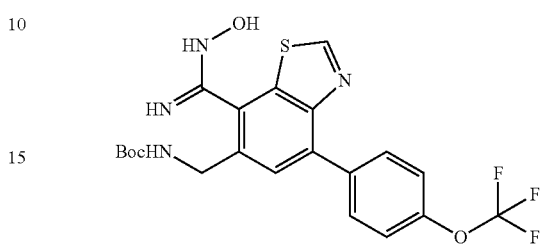

A mixture of TEA (0.19 mL, 1.33 mmol), hydroxylamine hydrochloride (46 mg, 0.67 mmol) in ethanol (10 mL) was stirred at room temperature for 15 min, then tert-butyl ((7-cyano-4-(4-(trifluoromethoxy)phenyl)benzo[d]thiazol-6-yl)methyl)carbamate (100 mg, 0.22 mmol) was added into it, the mixture was stirred at 90° C. for 16 h. The reaction was filtered and the filtrate was concentrated. The residue was quenched with water (10 mL), extracted with ethyl acetate (10 mL×2), the organic layer was washed with brine (10 mL), dried over Na₂SO₄ and concentrated to afford the title compound (105 mg, crude) as a yellow solid. The crude would be used in the next step directly. LCMS (ESI): m/z 483.0 (M+H)⁺.

Step 9: tert-butyl ((7-(5-oxo-4,5-dihydro-1,2,4-oxadiazol-3-yl)-4-(4-(trifluoromethoxy)phenyl)benzo[d]thiazol-6-yl)methyl)carbamate

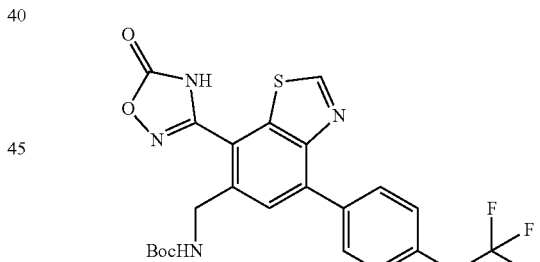

A mixture of DBU (0.16 mL, 1.09 mmol) and tert-butyl ((7-(N-hydroxycarbamimidoyl)-4-(4-(trifluoromethoxy)phenyl)benzo[d]thiazol-6-yl)methyl)carbamate (105 mg, 0.22 mmol) in DCM (10 mL) was stirred at room temperature for 15 min, then CDI (353 mg, 2.18 mmol) was added into it, the mixture was stirred at room temperature for 1 h. The reaction was filtered and the filtrate was concentrated. The residue was diluted with water (10 mL), extracted with ethyl acetate (10 mL×2), the organic layer was washed with brine (10 mL), dried over Na₂SO₄, concentrated and the residue was purified by prep-TLC (10% methanol in DCM) to afford the title compound (80 mg, 82%) as a yellow solid. ¹H NMR (400 MHz, CDCl₃): δ 9.09 (s, 1H), 7.82 (d, J=8.0 Hz, 2H), 7.51 (s, 11H), 7.32 (d, J=8.0 Hz, 2H), 5.67 (s, 1H), 4.36 (d, J=6.0 Hz, 2H), 1.35 (s, 9H) LCMS (ESI): m/z 509.0 (M+H)⁺.

Step 10: 3-(6-(aminomethyl)-4-(4-(trifluoromethoxy)phenyl)benzo[d]thiazol-7-yl)-1,2,4-oxadiazol-5(4H)-one 2,2,2-trifluoroacetate

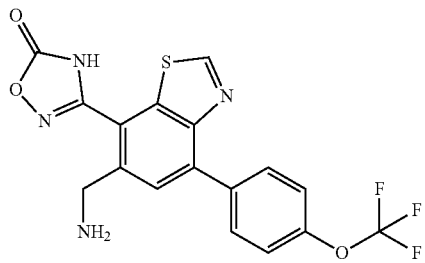 [SMILES: NCc1cc(-c2ccc(OC(F)(F)F)cc2)c2ncsc2c1-c1noc(=O)[nH]1]

A mixture of tert-butyl ((7-(5-oxo-4,5-dihydro-1,2,4-oxadiazol-3-yl)-4-(4-(trifluoromethoxy)phenyl)benzo[d]thiazol-6-yl)methyl)carbamate (80 mg, 0.16 mmol) and 5% TFA in HFIP (6 mL) was stirred at room temperature for 1 h. The mixture was concentrated to afford the title compound (82 mg, crude) as a yellow solid. The crude was used for the next step directly.

Step 11: N-((7-(5-oxo-4,5-dihydro-1,2,4-oxadiazol-3-yl)-4-(4-(trifluoromethoxy)phenyl)benzo[d]thiazol-6-yl)methyl)acrylamide

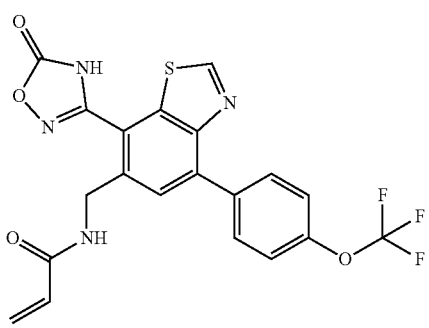 [SMILES: C=CC(=O)NCc1cc(-c2ccc(OC(F)(F)F)cc2)c2ncsc2c1-c1noc(=O)[nH]1]

To a mixture of 3-(6-(aminomethyl)-4-(4-(trifluoromethoxy)phenyl)benzo[d]thiazol-7-yl)-1,2,4-oxadiazol-5(4H)-one 2,2,2-trifluoroacetate (82 mg, 0.16 mmol) and sat.NaHCO$_3$ (0.4 mL) in THF (6 mL) was added acetyl chloride (18 mg, 0.19 mmol) at 0° C., the resulting mixture was stirred at 0° C. for 1 h. The reaction was quenched with water (10 mL) and extracted with ethyl acetate (10 mL×3). The combined organic layers were dried over Na$_2$SO$_4$ and concentrated under vacuum. The residue was purified by prep-TLC (5% methanol in DCM) to afford the crude product which was purified by reverse phase chromatography (Welch Xtimate C18 150*30 mm*5 um; 54%-84% water(FA)-ACN) to afford the title compound (10.40 mg, 16%) as a white solid. $^1$H NMR (400 MHz, DMSO-d$_6$): δ 13.29 (s, 1H), 9.53 (s, 1H), 8.94 (t, J=5.6 Hz, 1H), 8.01 (d, J=8.0 Hz, 2H), 7.83 (s, 1H), 7.58 (d, J=8.0 Hz, 2H), 6.25 (dd, J=17.2, 10.0 Hz, 1H), 6.12 (dd, J=17.2, 2.4 Hz, 1H), 5.65 (dd, J=10.0, 2.4 Hz, 1H), 4.69 (d, J=5.6 Hz, 2H); LCMS (ESI): m/z 463.0 (M+H)$^+$.

Example 102 (Compound 105) & Example 103 (Compound 106)

(S)—N-((7-(1,2-Dihydroxyethyl)-4-(4-(trifluoromethoxy)phenyl)benzo[d]oxazol-6-yl)methyl)acrylamide & (R)—N-((7-(1,2-dihydroxyethyl)-4-(4-(trifluoromethoxy)phenyl)benzo[d]oxazol-6-yl)methyl)acrylamide

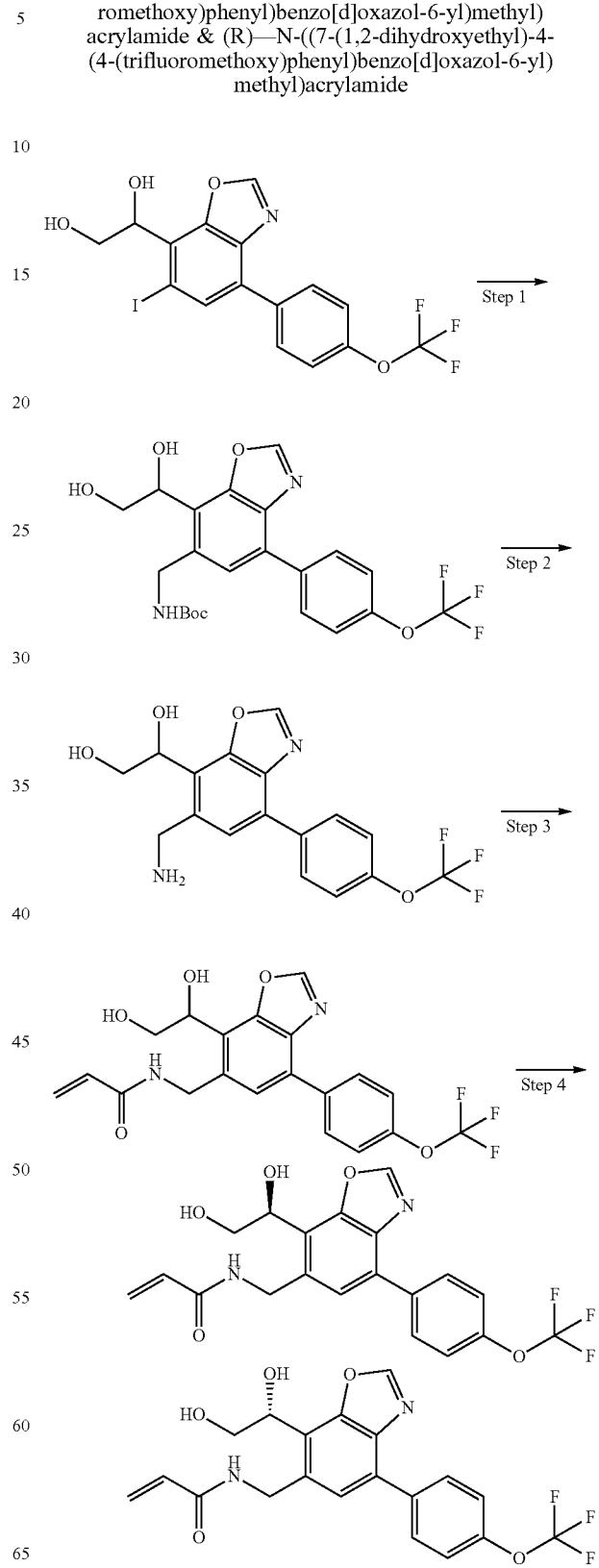

Step 1: tert-butyl ((7-(1,2-dihydroxyethyl)-4-(4-(trifluoromethoxy)phenyl)benzo [d]oxazol-6-yl)methyl)carbamate

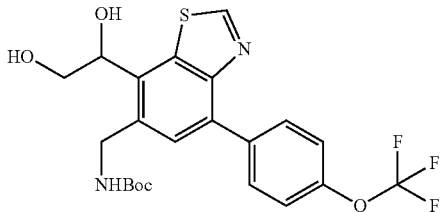 [SMILES: CC(C)(C)OC(=O)NCc1cc(-c2ccc(OC(F)(F)F)cc2)c2ncsc2c1C(O)CO]

A mixture of 1-(6-iodo-4-(4-(trifluoromethoxy)phenyl)benzo[d]oxazol-7-yl)ethane-1,2-diol (200 mg, 0.52 mmol), $K_2CO_3$ (647 mg, 4.69 mmol), potassium (((tert-butoxycarbonyl)amino)methyl)trifluoroborate (370 mg, 1.56 mmol) and Sphos Pd $G_2$ (37 mg, 0.05 mmol) in 1,4-dioxane (3 mL) and water (0.60 mL) was purged with $N_2$ atmosphere for 3 min. The mixture was stirred at 80° C. for 2 h under $N_2$ atmosphere. After cooling down, the solution was concentrated and the residue was purified by flash chromatography on silica gel (0-20% ethyl acetate in petroleum ether) to afford the title compound (80 mg, 35%) as a yellow solid. LCMS (ESI): m/z 469.3 (M+H)+.

Step 2: 1-(6-(aminomethyl)-4-(4-(trifluoromethoxy)phenyl)benzo[d]oxazol-7-yl)ethane-1,2-diol 2,2,2-trifluoroacetate

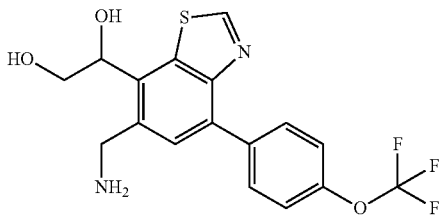 [SMILES: NCc1cc(-c2ccc(OC(F)(F)F)cc2)c2ncsc2c1C(O)CO]

A mixture of tert-butyl ((7-(1,2-dihydroxyethyl)-4-(4-(trifluoromethoxy)phenyl)benzo [d]oxazol-6-yl)methyl)carbamate (80 mg, 0.17 mmol) and 5% TFA in HFIP (5 mL) was stirred at room temperature for 2 h. The reaction mixture was concentrated to afford the crude title compound (60 mg, crude) as a yellow solid. The crude product was used directly.

Step 3: N-((7-(1,2-dihydroxyethyl)-4-(4-(trifluoromethoxy)phenyl)benzo[d]oxazol-6-yl)methyl)acrylamide

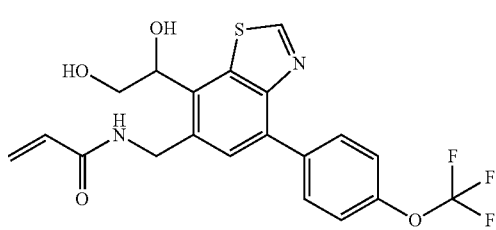

To a mixture of 1-(6-(aminomethyl)-4-(4-(trifluoromethoxy)phenyl)benzo[d]oxazol-7-yl)ethane-1,2-diol 2,2,2-trifluoroacetate (60 mg, 0.16 mmol) in THF (3 mL) was added saturated aq.$NaHCO_3$ (1 mL) and acryloyl chloride (0.03 mL, 0.33 mmol) at 0° C. The mixture was stirred at 0° c for 2 h under $N_2$ atmosphere. The solution was diluted with water (20 mL), extracted with ethyl acetate (20 mL×2). The combined organic layers were dried over $Na_2SO_4$ and concentrated. The residue was purified by flash chromatography on silica gel (0-30% EE (EtOH: ethyl acetate=1:3) in petroleum ether) to afford the title compound (25.0 mg, 36%) as a white solid. LCMS (ESI): m/z 405.2 (M+H−18)+.

Step 4: (S)—N-((7-(1,2-dihydroxyethyl)-4-(4-(trifluoromethoxy)phenyl)benzo[d]oxazol-6-yl)methyl)acrylamide & (R)—N-((7-(1,2-dihydroxyethyl)-4-(4-(trifluoromethoxy)phenyl)benzo[d]oxazol-6-yl)methyl)acrylamide N-((7-(1,2-Dihydroxyethyl)-4-(4-(trifluoromethoxy)phenyl)benzo[d]oxazol-6-yl)methyl)acrylamide (25 mg, 0.059 mmol) was separated by SFC (DAICEL CHIRALPAK AD(250 mm*30 mm,10 um), Neu-MeOH, 25%) to afford the first peak (S)—N-((7-(1,2-dihydroxyethyl)-4-(4-(trifluoromethoxy)phenyl)benzo[d]oxazol-6-yl)methyl)acrylamide (10.49 mg, 42%) and the second peak (R)—N-((7-(1,2-dihydroxyethyl)-4-(4-(trifluoromethoxy)phenyl)benzo[d]oxazol-6-yl)methyl)acrylamide (6.36 mg, 25%) both as white solid.

The first peak: $^1$H NMR (400 MHz, DMSO-$d_6$): δ 8.82 (s, 1H), 8.52 (t, J=5.6 Hz, 1H), 8.10-8.02 (m, 2H), 7.59 (s, 1H), 7.54 (d, J=8.0 Hz, 2H), 6.27 (dd, J=17.2, 10.0 Hz, 1H), 6..14 (dd, J=17.2, 2.0 Hz, 1H), 5.65-5.59 (m, 2H), 5.24-5.19 (m, 1H), 4.95 (t, J=5.6 Hz, 1H), 4.78-4.70 (m, 1H), 4.68-4.58 (m, 1H), 3.90-3.83 (m, 1H), 3.79-3.69 (m, 1H); LCMS (ESI): m/z 445.0 (M+Na)+. The second peak: $^1$H NMR (400 MHz, DMSO-$d_6$): δ 8.82 (s, 1H), 8.52 (t, J=5.6 Hz, 1H), 8.10-8.02 (m, 2H), 7.59 (s, 1H), 7.54 (d, J=8.0 Hz, 2H), 6.27 (dd, J=17.2, 10.0 Hz, 1H), 6..14 (dd, J=17.2, 2.0 Hz, 1H), 5.65-5.59 (m, 2H), 5.24-5.19 (m, 1H), 4.95 (t, J=5.6 Hz, 1H), 4.78-4.70 (m, 1H), 4.68-4.58 (m, 1H), 3.90-3.83 (m, 1H), 3.79-3.69 (m, 1H); LCMS (ESI): m/z 445.0 (M+Na)+.

Example 104 (Compound 107) & Example 105 (Compound 108)

(S)—N-((7-(1,2-Dihydroxyethyl)-4-(4-(trifluoromethoxy)phenyl)benzo[d]oxazol-6-yl)methyl)-N-methylacrylamide & (R)—N-((7-(1,2-dihydroxyethyl)-4-(4-(trifluoromethoxy)phenyl)benzo[d]oxazol-6-yl)methyl)-N-methylacrylamide

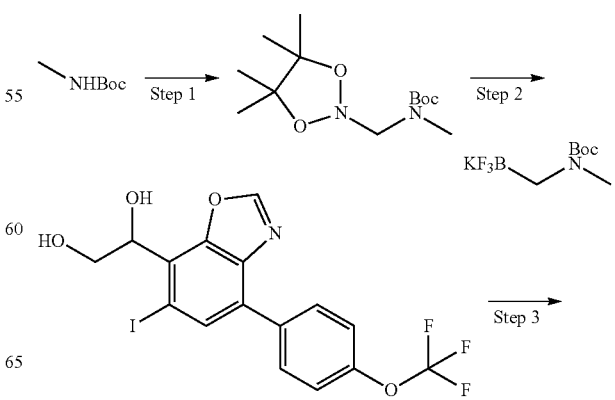

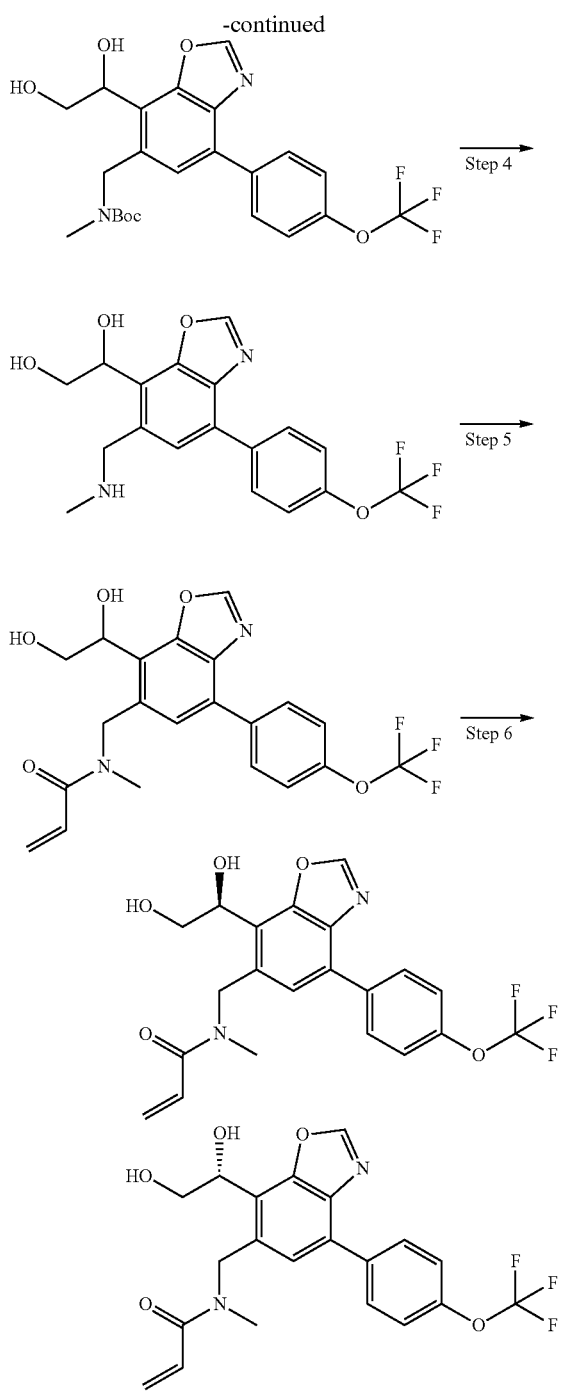

Step 1: tert-butyl methyl((4,4,5,5-tetramethyl-1,3,2-dioxaborolan-2-yl)methyl)carbamate

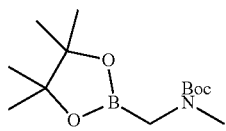

To the mixture of tert-butyl methylcarbamate (1.0 g, 7.62 mmol) in THF (10 mL) was added n-BuLi (3.66 mL, 9.15 mmol, 2.5 M/L in hexane) at −78° C. dropwise. After stirred for 10 min, 2-(iodomethyl)-4,4,5,5-tetramethyl-1,3,2-dioxaborolane (2.04 g, 7.62 mmol) in THF (5 mL) was added into it at −78° C. The resulting mixture was stirred at room temperature for 16 h. The reaction mixture was quenched with aq.NH$_4$Cl (20 mL), extracted with ethyl acetate (50 mL×3). The combined organic layers were dried over Na$_2$SO$_4$, filtered and concentrated. The residue was purified by flash chromatography on silica gel (0-20% ethyl acetate in petroleum ether) to afford the title compound (300 mg, 15%) as a colorless oil. $^1$H NMR (400 MHz, CDCl$_3$): δ 2.85 (s, 3H), 2.42 (s, 2H), 1.52 (s, 9H), 1.23 (s, 12H).

Step 2: potassium (((tert-butoxycarbonyl)(methyl)amino)methyl)trifluoroborate

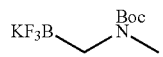

To a solution of tert-butyl methyl((4,4,5,5-tetramethyl-1,3,2-dioxaborolan-2-yl)methyl)carbamate (300 mg, 1.11 mmol) in acetone (3 mL) and water (1 mL) was added KHF$_2$ (259 mg, 3.32 mmol). The mixture was stirred at room temperature for 2 h. The reaction mixture was concentrated and the residue was lyophilized to afford the crude title compound (270 mg, crude) as a white solid. The crude product was used for next step directly.

Step 3: tert-butyl ((7-(1,2-dihydroxyethyl)-4-(4-(trifluoromethoxy)phenyl)benzo[d]oxazol-6-yl)methyl)(methyl)carbamate

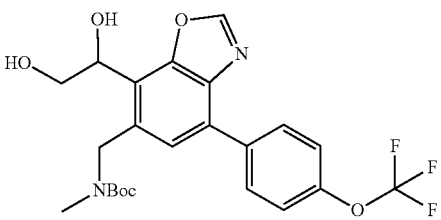 [SMILES: CN(Cc1cc(-c2ccc(OC(F)(F)F)cc2)c2ncoc2c1C(O)CO)C(=O)OC(C)(C)C]

A mixture of 1-(6-iodo-4-(4-(trifluoromethoxy)phenyl)benzo[d]oxazol-7-yl)ethane-1,2-diol (200 mg, 0.43 mmol), Sphos Pd G$_2$ (30 mg, 0.04 mmol), potassium (((tert-butoxycarbonyl)(methyl)amino)methyl)trifluoroborate (216 mg, 0.86 mmol) and K$_2$CO$_3$ (178 mg, 1.30 mmol) in 1,4-dioxane (3 mL) and water (0.5 mL) was purged with N$_2$ atmosphere for 3 min. The mixture was stirred at 80° C. for 4 h under N$_2$ atmosphere. After cooling down. The reaction mixture was diluted with water (40 mL), extracted with ethyl acetate (30 mL×3). Combined organic layers were dried over Na$_2$SO$_4$ and concentrated. The residue was purified by flash chromatography on silica gel (0-50% ethyl acetate in petroleum ether) to afford the title compound (150 mg, 72%) as a brown solid. LCMS (ESI): m/z 483.2 (M+H)$^+$.

Step 4: 1-(6-((methylamino)methyl)-4-(4-(trifluoromethoxy)phenyl)benzo[d]oxazol-7-yl)ethane-1,2-diol 2,2,2-trifluoroacetate

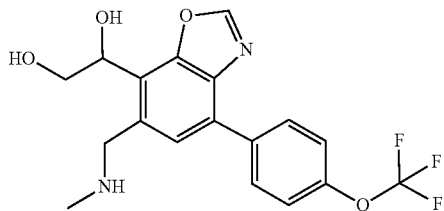 [SMILES: CNCc1cc(-c2ccc(OC(F)(F)F)cc2)c2ncoc2c1C(O)CO]

A mixture of tert-butyl ((7-(1,2-dihydroxyethyl)-4-(4-(trifluoromethoxy)phenyl)benzo[d]oxazol-6-yl)methyl)(methyl)carbamate (200 mg, 0.41 mmol) and 5% TFA in HFIP (3 mL) was stirred at room temperature for 2 h. The reaction was concentrated to afford the title compound (150 mg, crude) as a brown solid. The crude was used directly without any purification. LCMS (ESI): m/z 383.1 (M+H)$^+$.

Step 5: N-((7-(1,2-dihydroxyethyl)-4-(4-(trifluoromethoxy)phenyl)benzo[d]oxazol-6-yl)methyl)-N-methylacrylamide

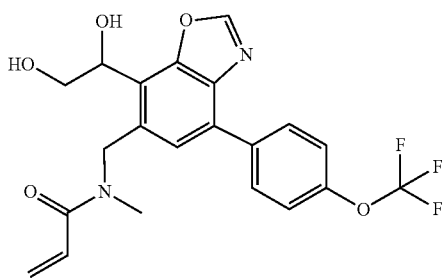 [SMILES: C=CC(=O)N(C)Cc1cc(-c2ccc(OC(F)(F)F)cc2)c2ncoc2c1C(O)CO]

To the mixture of 1-(6-((methylamino)methyl)-4-(4-(trifluoromethoxy)phenyl)benzo[d]oxazol-7-yl)ethane-1,2-diol 2,2,2-trifluoroacetate (150 mg, 0.39 mmol) in THF (3 mL) was added saturated aq.NaHCO$_3$ (1.0 mL) and acrylicanhydride (0.09 mL, 0.78 mmol) at 0° C. The mixture was stirred at 0° C. for 2 h. The solution was diluted with water (20 mL), extracted with ethyl acetate (20 mL×2). The organic layer was dried over anhydrous sodium sulfate and concentrated. The residue was purified by reverse phase chromatography (Boston Prime C18 150*30 mm*5 um, water (NH$_4$HCO$_3$)-ACN, 30%-60%) to afford title compound (50 mg, 29%) as a white solid. LCMS (ESI): m/z 437.2 (M+H)$^+$.

Step 6: (S)—N-((7-(1,2-dihydroxyethyl)-4-(4-(trifluoromethoxy)phenyl)benzo[d]oxazol-6-yl)methyl)-N-methylacrylamide &®—N-((7-(1,2-dihydroxyethyl)-4-(4-(trifluoromethoxy)phenyl)benzo[d]oxazol-6-yl)methyl)-N-methylacrylamide

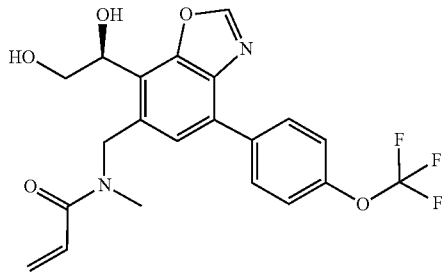

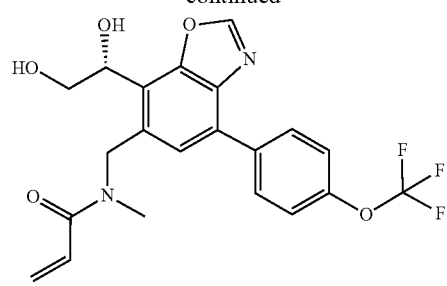

N-((7-(1,2-Dihydroxyethyl)-4-(4-(trifluoromethoxy)phenyl)benzo[d]oxazol-6-yl)methyl)-N-methylacrylamide (50 mg, 0.11 mmol) was separated by SFC (DAICEL CHIRALPAK IG (250 mm*30 mm,10 um),Neu-MeOH,30%) to afford the first peak (S)—N-((7-(1,2-dihydroxyethyl)-4-(4-(trifluoromethoxy)phenyl)benzo[d]oxazol-6-yl)methyl)-N-methylacrylamide (11.25 mg, 23%) and the second peak (R)—N-((7-(1,2-dihydroxyethyl)-4-(4-(trifluoromethoxy)phenyl)benzo[d]oxazol-6-yl)methyl)-N-methylacrylamide (11.09 mg, 22%) both as white solid.

The first peak: $^1$H NMR (400 MHz, DMSO-d$_6$): 38.84, 8.83 (s, 1H total), 8.04-7.98 (m, 2H), 7.53 (d, J=7.6 Hz, 2H), 7.37, 7.16 (s, 1H total), 6.88-6.70 (m, 1H), 6.20 (dd, J=16.8, 2.4 Hz, 1H), 5.74-5.56 (m, 2H), 5.28-5.14 (m, 1H), 5.11-4.86 (m, 3H), 3.84-3.65 (m, 2H), 3.02, 2.98 (s, 3H total); LCMS (ESI): m/z 459.0 (M+Na)$^+$.

The second peak: $^1$H NMR (400 MHz, DMSO-d$_6$): δ 8.84, 8.83 (s, 1H total), 8.04-7.98 (m, 2H), 7.53 (d, J=7.6 Hz, 2H), 7.37, 7.16 (s, 1H total), 6.88-6.70 (m, 1H), 6.20 (dd, J=16.8, 2.4 Hz, 1H), 5.74-5.56 (m, 2H), 5.28-5.14 (m, 1H), 5.11-4.86 (m, 3H), 3.84-3.65 (m, 2H), 3.02, 2.98 (s, 3H total); LCMS (ESI): m/z 459.0 (M+Na)$^+$.

Example 106 (Compound 109) & Example 107 (Compound 110)

(S)—N-((7-(1,2-Dihydroxyethyl)-4-(4-(trifluoromethyl)phenyl)benzo[d]oxazol-6-yl)methyl)acrylamide & (R)—N-((7-(1,2-dihydroxyethyl)-4-(4-(trifluoromethyl)phenyl)benzo[d]oxazol-6-yl)methyl)acrylamide

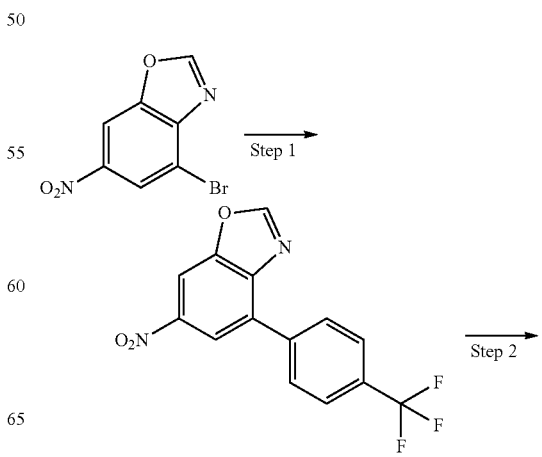

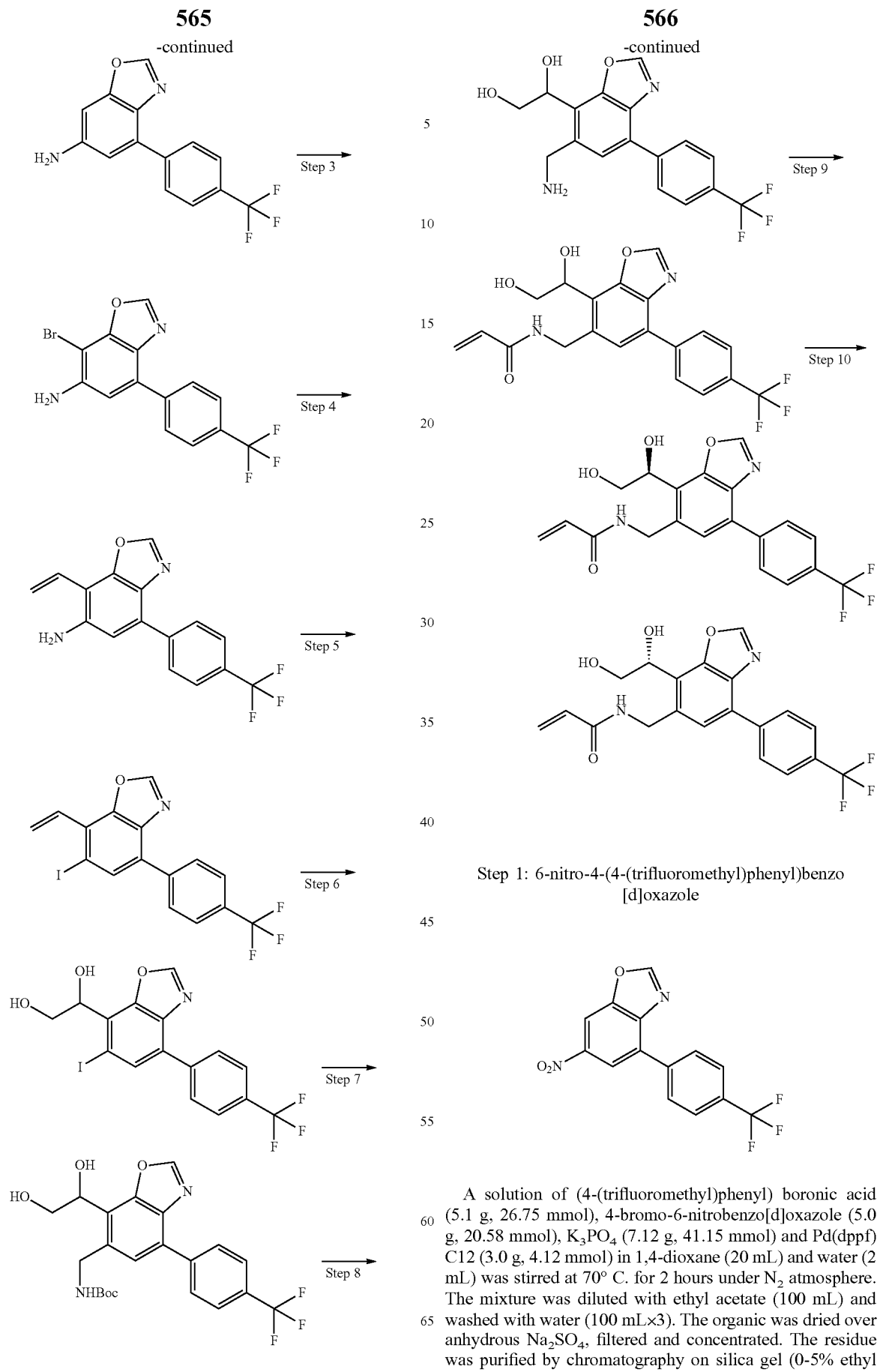

Step 1: 6-nitro-4-(4-(trifluoromethyl)phenyl)benzo[d]oxazole

A solution of (4-(trifluoromethyl)phenyl) boronic acid (5.1 g, 26.75 mmol), 4-bromo-6-nitrobenzo[d]oxazole (5.0 g, 20.58 mmol), $K_3PO_4$ (7.12 g, 41.15 mmol) and Pd(dppf)C12 (3.0 g, 4.12 mmol) in 1,4-dioxane (20 mL) and water (2 mL) was stirred at 70° C. for 2 hours under $N_2$ atmosphere. The mixture was diluted with ethyl acetate (100 mL) and washed with water (100 mL×3). The organic was dried over anhydrous $Na_2SO_4$, filtered and concentrated. The residue was purified by chromatography on silica gel (0-5% ethyl acetate in petroleum ether) to afford the title compound (1.6 g, 24%) as a yellow solid. $^1$H NMR (400 MHz, DMSO-d$_6$): δ 9.22 (s, 1H), 8.84 (d, J=2.0 Hz, 1H), 8.56 (d, J=2.0 Hz, 1H), 8.30 (d, J=8.4 Hz, 2H), 7.94 (d, J=8.4 Hz, 2H).

Step 2: 4-(4-(trifluoromethyl)phenyl)benzo[d]oxazol-6-amine

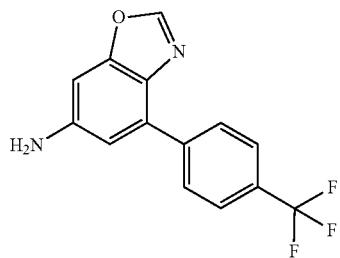 [SMILES: Nc1cc(-c2ccc(C(F)(F)F)cc2)c2ncoc2c1]

To a solution of 6-nitro-4-(4-(trifluoromethyl)phenyl)benzo[d]oxazole (4.4 g, 14.28 mmol) in ethanol (30 mL) was added 10% Pd/C (3.0 g, 2.86 mmol), the mixture was stirred at room temperature for 15 hours under H2 (15 psi). The mixture was filtrated and washed with methanol, the solution was concentrated under vacuo to afford the title compound (2.2 g, 55%) as a yellow solid. LCMS (ESI): m/z 278.8 (M+H)$^+$.

Step 3: 7-bromo-4-(4-(trifluoromethyl)phenyl)benzo[d]oxazol-6-amine

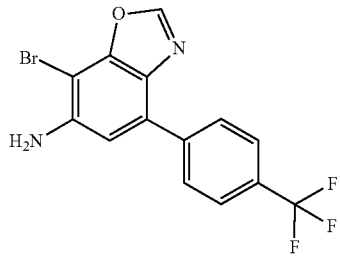 [SMILES: Nc1cc(-c2ccc(C(F)(F)F)cc2)c2ncoc2c1Br]

To a solution of 4-(4-(trifluoromethyl)phenyl)benzo[d]oxazol-6-amine (1.3 g, 4.74 mmol) in dichloromethane (40 mL) was added NBS (0.8 g, 4.74 mmol) at 0° C., the solution was stirred at 0° C. for 2 hours, The solution was quenched with water (50 mL) and extracted with DCM (50 mL×3), the organic layer was dried with anhydrous Na$_2$SO$_4$, filtrated and concentrated under vacuo, the residue was purified by column chromatography on silica gel (0-5% ethyl acetate in petroleum ether) to afford the title compound (1.1 g, 65%) as a yellow solid. LCMS (ESI): m/z 356.8 (M+H)$^+$.

Step 4: 4-(4-(trifluoromethyl)phenyl)-7-vinylbenzo[d]oxazol-6-amine

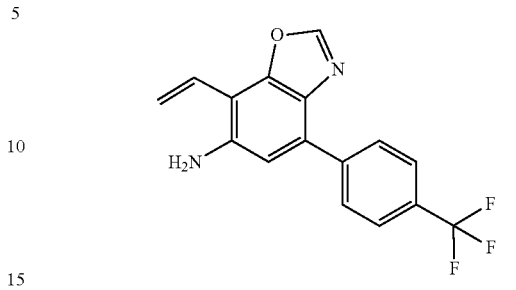

A solution of 7-bromo-4-(4-(trifluoromethyl)phenyl)benzo[d]oxazol-6-amine (1.1 g, 3.11 mmol), tributyl(vinyl)stannane (2.0 mL, 6.87 mmol) and Pd(PPh$_3$)$_4$(700 mg, 0.62 mmol) in 1,4-dioxane (30 mL) was stirred at 100° C. for 16 hours under N$_2$ atmosphere. The reaction mixture was diluted with ethyl acetate (40 mL) and washed with saturated brine (20 mL×3) and KF solution (30 mL). The organic layer was dried over anhydrous Na$_2$SO$_4$ and concentrated under reduced pressure. The residue was purified by column chromatography on silica gel (0-10% ethyl acetate in petroleum ether) to afford the title compound (660 mg, 70%) as a yellow solid. $^1$H NMR (400 MHz, DMSO-d$_6$): δ 8.57 (s, 1H), 8.16 (d, J=8.0 Hz, 2H), 7.87 (d, J=8.0 Hz, 2H), 7.11 (s, 1H), 6.98 (dd, J=18.0, 11.6 Hz, 1H), 6.15 (dd, J=18.0, 2.0 Hz, 1H), 5.73 (s, 2H), 5.54 (dd, J=11.6, 2.0 Hz, 1H); LCMS (ESI): m/z 304.9 (M+H)$^+$.

Step 5: 6-iodo-4-(4-(trifluoromethyl)phenyl)-7-vinylbenzo[d]oxazole

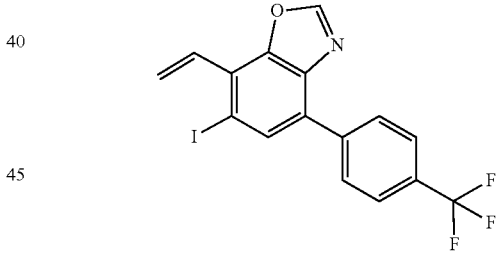

To a solution of 4-(4-(trifluoromethyl)phenyl)-7-vinylbenzo[d]oxazol-6-amine (330 mg, 1.08 mmol) in acetonitrile (2 mL) was added 6 M HCl (0.36 mL) at 0° C. and the mixture was stirred at 0° C. for 15 minutes, then NaNO$_2$ (7 mg, 1.14 mmol) in water (5 mL) was added into it at 0° C. Then the solution was stirred at 0° C. for 30 minutes, then KI (360 mg, 2.17 mmol) in water (5 mL) was added drop wise at 0° C. The reaction mixture was stirred at 0° C. for 15 minutes, the reaction mixture was quenched with cold water (50 mL), washed with sat.Na$_2$S$_2$O$_3$ (50 mL) and extracted with ethyl acetate (50 mL×3), the organic layer was dried over anhydrous Na$_2$SO$_4$ and concentrated, the residue was purified by column chromatography on silica gel (0-3% ethyl acetate in petroleum ether) to afford the title compound (150 mg, 33%). $^1$H NMR (400 MHz, DMSO-d$_6$): δ 8.92 (s, 1H), 8.25 (d, J=8.0 Hz, 2H), 8.21 (s, 1H), 7.89 (d, J=8.0 Hz, 2H), 6.90 (dd, J1=17.6, 11.2 Hz, 1H), 6.34 (d, J=17.6 Hz, 1H), 5.85 (d, J=11.2 Hz, 1H).

Step 6: 1-(6-iodo-4-(4-(trifluoromethyl)phenyl)benzo[d]oxazol-7-yl)ethane-1,2-diol

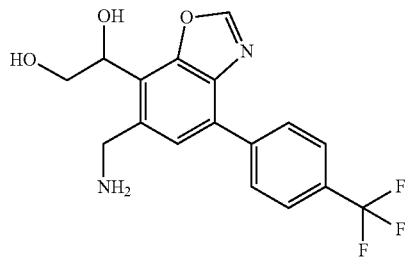 [SMILES: NCc1cc(-c2ccc(C(F)(F)F)cc2)c2ncoc2c1C(O)CO]

To a solution of 6-iodo-4-(4-(trifluoromethyl)phenyl)-7-vinylbenzo[d]oxazole (150 mg, 0.36 mmol) and $K_2OsO_4 \cdot 2H_2O$ (13 mg, 0.04 mmol) in THF (6 mL) and water (1.2 mL) was added NMO (55 mg, 0.47 mmol) at room temperature. The resulting mixture was stirred at room temperature for 16 hours. The reaction mixture was diluted with ethyl acetate (50 mL) and washed with water (20 mL) and $Na_2S_2O_3$ solution (20 mL). The organic layer was dried over anhydrous $Na_2SO_4$ and concentrated under vacuo. The residue was purified by column chromatography on silica gel (0-50% ethyl acetate in petroleum ether) to afford the title compound (100 mg, 62%) as a white solid. LCMS (ESI): m/z 450.1 $(M+H)^+$.

Step 7: tert-butyl ((7-(1,2-dihydroxyethyl)-4-(4-(trifluoromethyl)phenyl)benzo[d]oxazol-6-yl)methyl)carbamate

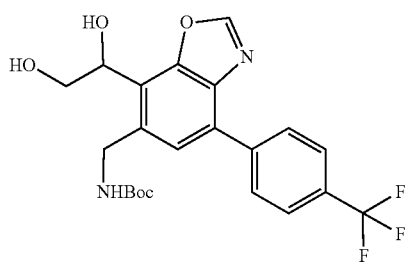 [SMILES: CC(C)(C)OC(=O)NCc1cc(-c2ccc(C(F)(F)F)cc2)c2ncoc2c1C(O)CO]

A mixture of 1-(6-iodo-4-(4-(trifluoromethyl)phenyl)benzo[d]oxazol-7-yl)ethane-1,2-diol (300 mg, 0.67 mmol), potassium (((tert-butoxycarbonyl)amino)methyl)trifluoroborate (475 mg, 2.00 mmol), $K_2CO_3$ (554 mg, 4.01 mmol) and Sphos Pd $G_2$ (48 mg, 0.07 mmol) in 1,4-dioxane (10 mL) and water (3 mL) was stirred at 100° C. for 4 hours under $N_2$ atmosphere. The mixture was diluted with ethyl acetate (20 mL) and water (20 mL×2). The organic layer was dried over $Na_2SO_4$ and concentrated. The residue was purified by prep-TLC (60% ethyl acetate in petroleum ether) to afford the title compound (210 mg, 69%) as white solid. LCMS (ESI): m/z 475.2 $(M+Na)^+$.

Step 8: 1-(6-(aminomethyl)-4-(4-(trifluoromethyl)phenyl)benzo[d]oxazol-7-yl)ethane-1,2-diol

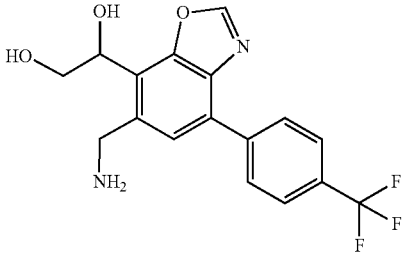 [SMILES: NCc1cc(-c2ccc(C(F)(F)F)cc2)c2ncoc2c1C(O)CO]

To a mixture of tert-butyl ((7-(1,2-dihydroxyethyl)-4-(4-(trifluoromethyl)phenyl)benzo[d]oxazol-6-yl)methyl)carbamate (210 mg, 0.46 mmol) in dichloromethane (6 mL) was added 2,6-dimethylpyridine (149 mg, 1.39 mmol) and trimethylsilyl trifluoromethanesulfonate (620 mg, 2.79 mmol) at 0° C., the mixture was stirred at 0° C. for 3 hours. The mixture was concentrated under vacuum to afford the title compound (163 mg, crude). The crude compound was used for the next step directly. LCMS (ESI): m/z 353.0 $(M+H)^+$.

Step 9: N-((7-(1,2-dihydroxyethyl)-4-(4-(trifluoromethyl)phenyl)benzo[d]oxazol-6-yl)methyl)acrylamide

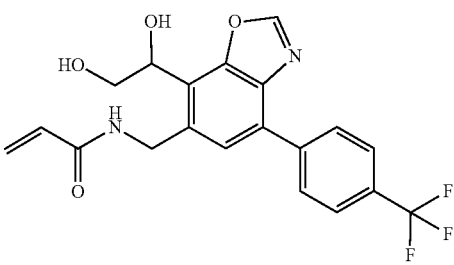 [SMILES: C=CC(=O)NCc1cc(-c2ccc(C(F)(F)F)cc2)c2ncoc2c1C(O)CO]

To a solution of 1-(6-(aminomethyl)-4-(4-(trifluoromethyl)phenyl)benzo[d]oxazol-7-yl)ethane-1,2-diol (190 mg, 0.41 mmol) in THF (3 mL) was added sat.$NaHCO_3$ (2 mL) and acryloyl chloride (0.05 mL, 0.65 mmol) and at 0° C. Then the reaction was stirred at 0° C. for 30 minutes. The reaction was diluted with water (10 mL) and extracted with ethyl acetate (20 mL×3). The organic layer was dried over anhydrous $Na_2SO_4$, filtered and concentrated. The residue was purified by pre-TLC (petroleum ether: ethyl acetate: ethanol=8:3:1) to afford the title compound (50 mg, 23%) as a brown solid. LCMS (ESI): m/z 428.9 $(M+Na)^+$.

Step 10: (S)—N-((7-(1,2-dihydroxyethyl)-4-(4-(trifluoromethyl)phenyl)benzo[d]oxazol-6-yl)methyl)acrylamide & (R)—N-((7-(1,2-dihydroxyethyl)-4-(4-(trifluoromethyl)phenyl)benzo[d]oxazol-6-yl)methyl)acrylamide

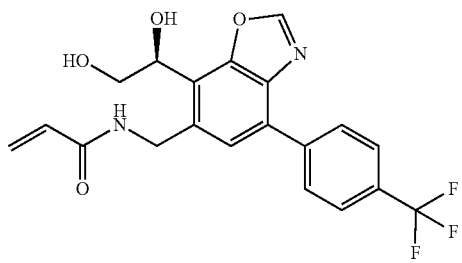

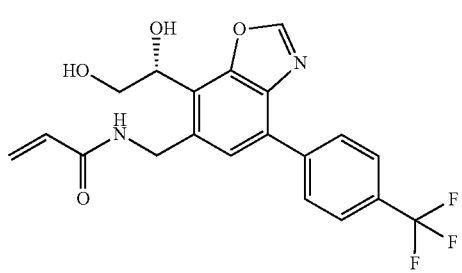

N-((7-(1,2-dihydroxyethyl)-4-(4-(trifluoromethyl)phenyl)benzo[d]oxazol-6-yl)methyl)acrylamide (50 mg, 0.12 mmol) was separated by Chiral SFC (Instrument: SFC-22; Column: DAICEL CHIRALPAK AD(250 mm*30 mm,10 um); Condition: 0.1% NH$_3$H$_2$O MEOH; Begin B: 25%; Flow Rate (mL/min): 60) to afford the first peak (S)—N-((7-(1,2-dihydroxyethyl)-4-(4-(trifluoromethyl)phenyl)benzo[d]oxazol-6-yl)methyl)acrylamide (10.90 mg, 44%) and the second peak (R)—N-((7-(1,2-dihydroxyethyl)-4-(4-(trifluoromethyl)phenyl)benzo[d]oxazol-6-yl)methyl)acrylamide (8.90 mg, 32%) both as white solid.

The first peak: $^1$H NMR (400 MHz, DMSO-d$_6$): δ 8.84 (s, 1H), 8.53 (t, J=6.0 Hz, 1H), 8.18 (d, J=8.0 Hz, 2H), 7.89 (d, J=8.0 Hz, 2H), 7.65 (s, 1H), 6.28 (dd, J=16.8, 10.0 Hz, 1H), 6.13 (dd, J=16.8, 2.4 Hz, 1H), 5.63-5.61 (m, 2H), 5.20-5.18 (m, 1H), 4.94-4.92 (m, 1H), 4.74-4.60 (m, 2H), 3.89-3.84 (m, 1H), 3.75-3.70 (m, 1H); LCMS (ESI): m/z 429.2 (M+Na)$^+$.

The second peak: $^1$H NMR (400 MHz, DMSO-d$_6$): δ 8.84 (s, 1H), 8.53 (t, J=6.0 Hz, 1H), 8.18 (d, J=8.0 Hz, 2H), 7.89 (d, J=8.0 Hz, 2H), 7.65 (s, 1H), 6.28 (dd, J=16.8, 10.0 Hz, 1H), 6.13 (dd, J=16.8, 2.4 Hz, 1H), 5.63-5.61 (m, 2H), 5.20-5.18 (m, 1H), 4.94-4.92 (m, 1H), 4.74-4.60 (m, 2H), 3.89-3.84 (m, 1H), 3.75-3.70 (m, 1H); LCMS (ESI): m/z 429.2 (M+Na)$^+$.

Example 108 & (Compound 1H) Example 109 (Compound 112)

(S)—N-((7-(2-Oxooxazolidin-5-yl)-4-(4-(trifluoromethoxy)phenyl)benzo[d]oxazol-6-yl)methyl)acrylamide & (R)—N-((7-(2-oxooxazolidin-5-yl)-4-(4-(trifluoromethoxy)phenyl)benzo[d]oxazol-6-yl)methyl)acrylamide

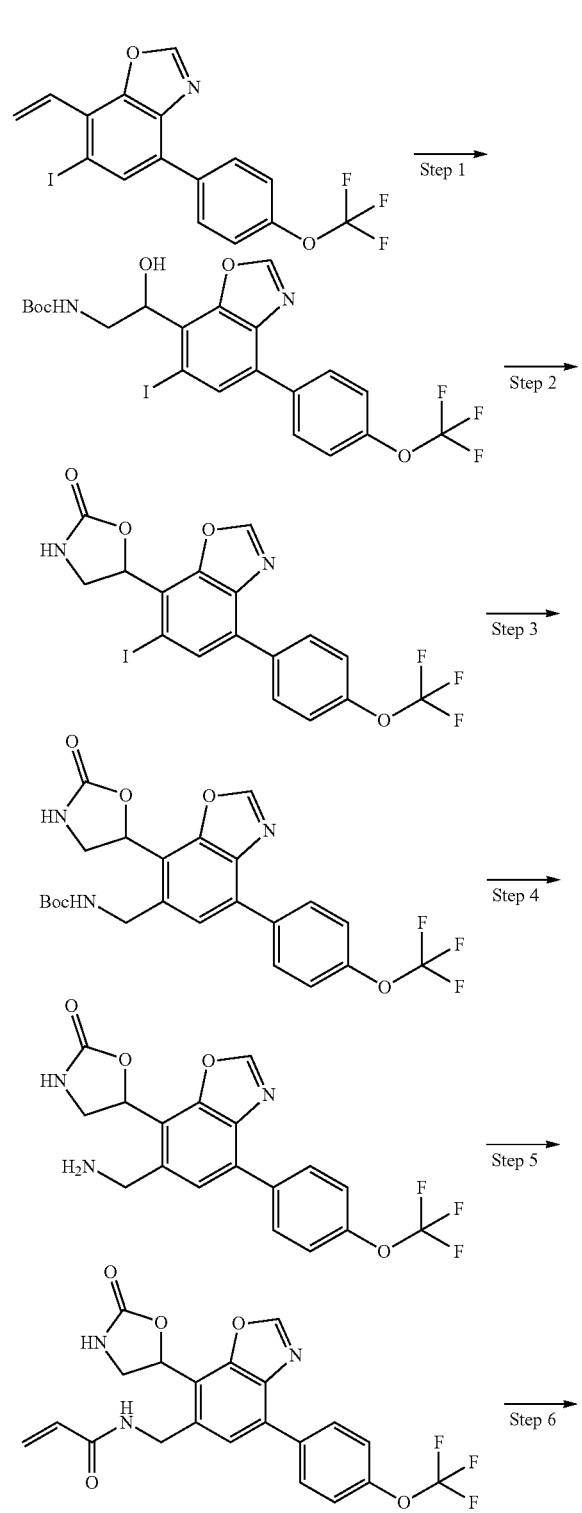

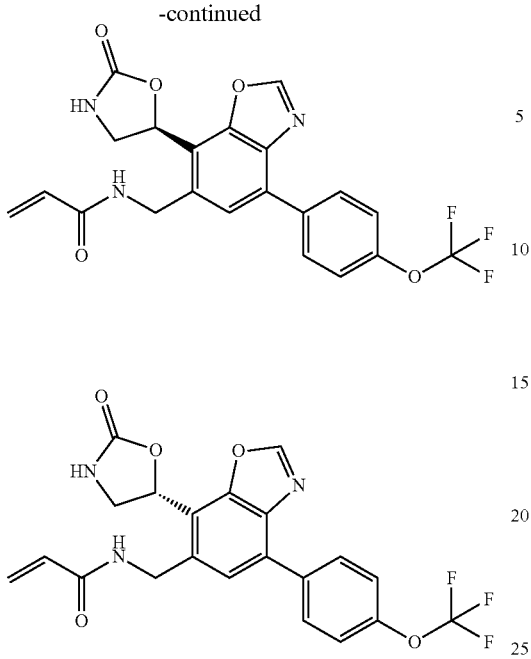

Step 1: tert-butyl (2-hydroxy-2-(6-iodo-4-(4-(trifluoromethoxy)phenyl)benzo[d]oxazol-7-yl)ethyl)carbamate A solution of tert-butyl carbamate (816 mg, 6.96 mmiol) and M sodium hydroxide (6.96 mL, 6.96 mmol) in propan-1-ol (5 mL) was stirred at room temperature for 5 mins. Then tert-butyl hypochlorite (0.78 mL, 6.96 mmol) was added into it and the reaction solution was stirred at room temperature for 4 mins. This reaction was then placed in an ice-bath. (DHQD)$_2$PHAL (109 mg, 0.14 mmol) and (DHQ)$_2$PHAL (109 mg, 0.14 mmol) in propan-1-ol (5 mL) and 6-iodo-4-(4-(trifluoromethoxy)phenyl)-7-vinylbenzo[d]oxazole (1.0 g, 2.32 mmol) in propan-1-ol (5 mL) were added sequentially, and then the solution was stirred for 6 mins. K$_2$OsO$_4$·2H$_2$O (35 mg, 0.09 mmol) was added into the solution directly at 0° C. The reaction mixture was stirred at room temperature for 16 h. The mixture was quenched with the saturated Na$_2$SO$_3$ solution (5 mL). The resulting solution was extracted with ethyl acetate (50 mL×3) and water (35 mL×2). The organic layers were dried over Na$_2$SO$_4$ and concentrated. The residue was purified by flash chromatography on silica gel (0-30% ethyl acetate in petroleum ether) to afford the title compound (560 mg, 42%) as a white solid. LCMS (ESI): m/z 465.0 (M+H)$^+$.

Step 2: 5-(6-iodo-4-(4-(trifluoromethoxy)phenyl)benzo[d]oxazol-7-yl)oxazolidin-2-one

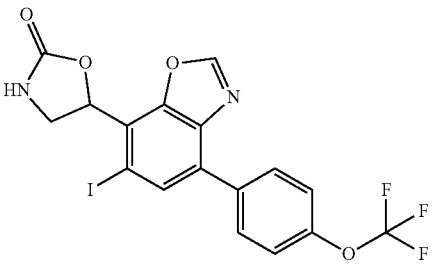

To a solution of tert-butyl (2-hydroxy-2-(6-iodo-4-(4-(trifluoromethoxy)phenyl)benzo[d]oxazol-7-yl)ethyl)carbamate (560 mg, 0.99 mmol) in 1,2-dichloroethane (10 mL) was added bis(trichloromethyl) carbonate (442 mg, 1.49 mmol) in toluene (5 mL) at room temperature for 2 mins. Then the solution was stirred at 80° C. for 16 hours. The mixture was concentrated and the residue was purified by flash chromatography on silica gel (0-50% ethyl acetate in petroleum ether) to afford the title compound (310 mg, 64%) as a white solid. 2D-NMR confirmed it. LCMS (ESI): m/z 491.0 (M+H)$^+$.

Step 3: tert-butyl ((7-(2-oxooxazolidin-5-yl)-4-(4-(trifluoromethoxy)phenyl)benzo [d]oxazol-6-yl)methyl)carbamate

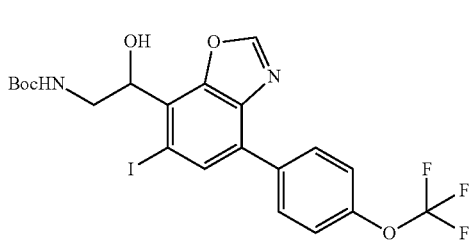 [SMILES: CC(C)(C)OC(=O)NCC(O)c1c(I)cc(-c2ccc(OC(F)(F)F)cc2)c2ncoc12]

A mixture of 5-(6-iodo-4-(4-(trifluoromethoxy)phenyl)benzo[d]oxazol-7-yl)oxazolidin-2-one (150 mg, 0.31 mmol), potassium ((((tert-butoxycarbonyl)amino)methyl)trifluoroborate (145 mg, 0.61 mmol), Cs$_2$CO$_3$ (199 mg, 0.61 mmol) and CATACXIUM A Pd G$_2$ (20 mg, 0.03 mmol) in toluene (3 mL) and water (0.20 mL) was stirred at 100° C. for 4 h under N$_2$ atmosphere. The mixture was diluted with water (20 mL), extracted with ethyl acetate (15 mL×2). The combined organic layers were washed with brine (20 mL×3), dried over anhydrous sodium sulfate and concentrated under vacuum. The residue was purified by prep-TLC (60% ethyl acetate in petroleum ether) to afford the title compound (40 mg, 27%) as a white solid. LCMS (ESI): m/z 494.2 (M+H)$^+$.

Step 4: 5-(6-(aminomethyl)-4-(4-(trifluoromethoxy)phenyl)benzo[d]oxazol-7-yl)oxazolidin-2-one A mixture of tert-butyl ((7-(2-oxooxazolidin-5-yl)-4-(4-(trifluoromethoxy)phenyl)benzo[d]oxazol-6-yl)methyl)carbamate (140 mg, 0.28 mmol), 2,6-lutidine (0.1 mL, 0.85 mmol) and TMSOTf (0.31 mL, 1.7 mmol) was stirred at 0° C. for 3 h. The reaction mixture was concentrated to afford the title compound (110 mg, crude) as a brown solid. The crude product was used directly for next step directly. LCMS (ESI): m/z 394.1 (M+H)⁺.

Step 5: N-((7-(2-oxooxazolidin-5-yl)-4-(4-(trifluoromethoxy)phenyl)benzo[d]oxazol-6-yl)methyl)acrylamide

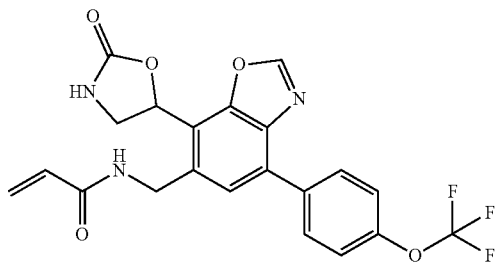 [SMILES: C=CC(=O)NCc1cc(-c2ccc(OC(F)(F)F)cc2)c2ncoc2c1C1CNC(=O)O1]

To a mixture of 5-(6-(aminomethyl)-4-(4-(trifluoromethoxy)phenyl)benzo[d]oxazol-7-yl)oxazolidin-2-one (110 mg, 0.28 mmol) and saturated aq.NaHCO₃ (1 mL) in THF (3 mL) was added acrylicanhydride (0.06 mL, 0.56 mmol) at 0° C. The mixture was stirred at 0° C. for 2 h under N₂ atmosphere. The solution was diluted with water (20 mL), extracted with ethyl acetate (20 mL×2). Combined organic layers were dried over Na₂SO₄ and concentrated. The residue was purified by reverse phase chromatography (Welch Xtimate C18 150*25 mm*5 um, water (NH₄HCO₃)-ACN, 30%-60%) to afford the title compound (50 mg, 40%) as a white solid. LCMS (ESI): m/z 448.1 (M+H)⁺.

Step 6: (S)—N-((7-(2-oxooxazolidin-5-yl)-4-(4-(trifluoromethoxy)phenyl)benzo[d]oxazol-6-yl)methyl)acrylamide & (R)—N-((7-(2-oxooxazolidin-5-yl)-4-(4-(trifluoromethoxy)phenyl)benzo[d]oxazol-6-yl)methyl)acrylamide

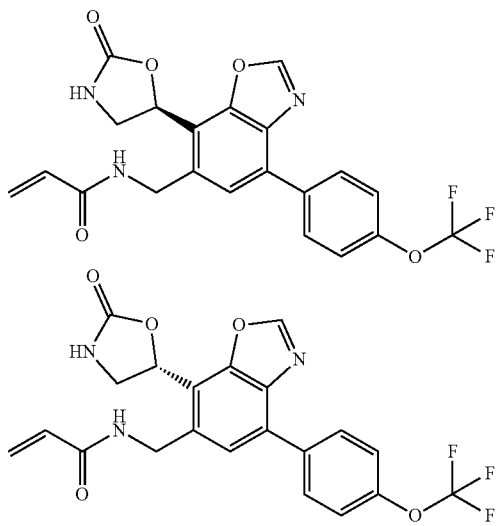

N-((7-(2-Oxooxazolidin-5-yl)-4-(4-(trifluoromethoxy)phenyl)benzo[d]oxazol-6-yl)methyl)acrylamide (50 mg, 0.11 mmol) was separated by SFC (DAICEL CHIRALPAK IG (250 mm*30 mm,10 um), 0.1% NH₃H₂O ETOH, 50%) to afford the first peak (S)—N-((7-(2-oxooxazolidin-5-yl)-4-(4-(trifluoromethoxy)phenyl)benzo[d]oxazol-6-yl)methyl)acrylamide (22.7 mg, 45%) and the second peak (R)—N-((7-(2-oxooxazolidin-5-yl)-4-(4-(trifluoromethoxy)phenyl)benzo[d]oxazol-6-yl)methyl)acrylamide (22.03 mg, 44%) both as white solid.

The first peak: ¹H NMR (400 MHz, DMSO-d₆): δ 8.92 (s, 1H), 8.71 (t, J=5.6 Hz, 1H), 8.12-8.08 (m, 2H), 7.90 (s, 1H), 7.69 (s, 1H), 7.56 (d, J=8.0 Hz, 2H), 6.24-6.10 (m, 3H), 5.62 (dd, J=10.0, 2.4 Hz, 1H), 4.70-4.63 (m, 1H), 4.60-4.52 (m, 1H), 3.89 (t, J=9.2 Hz, 1H), 3.58 (t, J=8.4 Hz, 1H); LCMS (ESI): m/z 470.0 (M+Na)⁺.

The second peak: ¹H NMR (400 MHz, DMSO-d₆): δ 8.92 (s, 1H), 8.71 (t, J=5.6 Hz, 1H), 8.12-8.08 (m, 2H), 7.90 (s, 1H), 7.69 (s, 1H), 7.56 (d, J=8.0 Hz, 2H), 6.24-6.10 (m, 3H), 5.62 (dd, J=10.0, 2.4 Hz, 1H), 4.70-4.63 (m, 1H), 4.60-4.52 (m, 1H), 3.89 (t, J=9.2 Hz, 1H), 3.58 (t, J=8.4 Hz, 1H); LCMS (ESI): m/z 470.0 (M+Na)⁺.

Example 110 (Compound 113) N-((7-(Hydroxymethyl)-4-(4-(trifluoromethoxy)phenyl)benzo[d]oxazol-6-yl)methyl)acrylamide

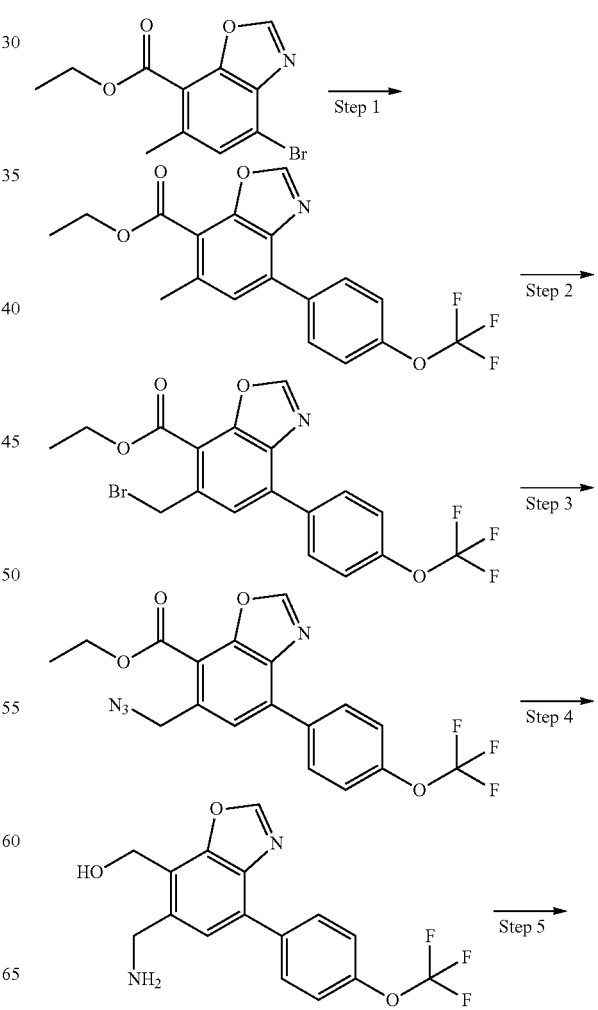

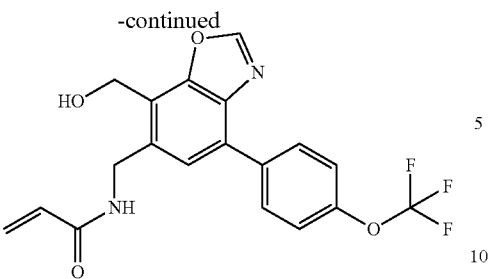

Step 1: ethyl6-methyl-4-(4-(trifluoromethoxy)phenyl)benzo[d]oxazole-7-carboxylate

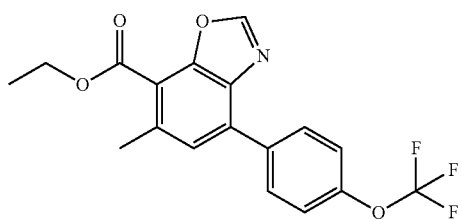 [SMILES: CCOC(=O)c1c(C)cc(-c2ccc(OC(F)(F)F)cc2)c2ncoc12]

A solution of ethyl 4-bromo-6-methylbenzo[d]oxazole-7-carboxylate (7.0 g, 24.64 mmol), $K_3PO_4$ (10.46 g, 49.28 mmol), (4-(trifluoromethoxy)phenyl)boronic acid (7.61 g, 36.96 mmol) and Pd(dppf)$Cl_2$ (1.8 g, 2.46 mmol) in 1,4-dioxane (100 mL) and water (5 mL) was stirred at 90° C. for 3 h under $N_2$ atmosphere. The mixture was diluted with ethyl acetate (500 mL) and washed with water (500 mL×3). The organic layer was dried over $Na_2SO_4$ and concentrated. The residue was purified by flash chromatography on silica gel (0-15% ethyl acetate in petroleum ether) to afford the title compound (7.5 g, 83%) as a white solid. $^1$H NMR (400 MHz, $CDCl_3$): δ 8.18 (s, 1H), 8.02-7.97 (m, 2H), 7.42 (s, 1H), 7.37 (d, J=8.4 Hz, 2H), 4.51 (q, J=7.2 Hz, 2H), 2.75 (s, 3H), 1.48 (t, J=7.2 Hz, 3H); LCMS (ESI): nm/z 366.2 (M+H)$^+$.

Step 2: ethyl6-(bromomethyl)-4-(4-(trifluoromethoxy)phenyl)benzo[d]oxazole-7-carboxylate

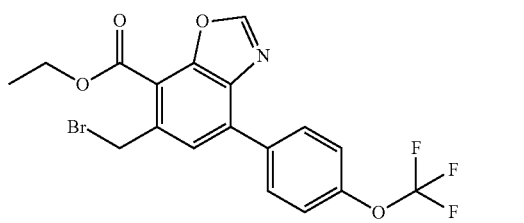 [SMILES: CCOC(=O)c1c(CBr)cc(-c2ccc(OC(F)(F)F)cc2)c2ncoc12]

To a mixture of ethyl6-(bromomethyl)-4-(4-(trifluoromethoxy)phenyl)benzo[d]oxazole-7-carboxylate (2.0 g, 5.47 mmol) in CC14 (20 mL) was added AIBN (180 mg, 1.09 mmol) and NBS (1.17 g, 6.57 mmol) at 0° C. The reaction was stirred at 80° C. for 16 h. The mixture was diluted with ethyl acetate (200 mL) and washed with water (100 mL×3). The organic layer was dried over $Na_2SO_4$ and concentrated. The residue was purified by chromatography on silica gel (0-10% ethyl acetate in petroleum ether) to afford the title compound (2.2 g, 91%) as a yellow solid. LCMS (ESI): m/z 444.0 (M+H)$^+$.

Step 3: ethyl 6-(azidomethyl)-4-(4-(trifluoromethoxy)phenyl)benzo[d]oxazole-7-carboxylate

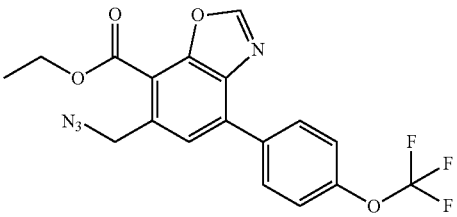 [SMILES: CCOC(=O)c1c(CN=[N+]=[N-])cc(-c2ccc(OC(F)(F)F)cc2)c2ncoc12]

To a mixture of ethyl 6-(bromomethyl)-4-(4-(trifluoromethoxy)phenyl)benzo[d]oxazole-7-carboxylate (2.2 g, 4.95 mmol) in DMF (20 mL) was added $NaN_3$ (330 mg, 5.08 mmol) at room temperature. Then the reaction was stirred at room temperature for 16 hours. The reaction solution was quenched with water (200 mL), extracted with ethyl acetate (300 mL), dried over $MgSO_4$, filtered and concentrated to afford the title compound (2.0 g, 99%) as a yellow oil. LCMS (ESI): m/z 407.1 (M+H)$^+$.

Step 4: (6-(aminomethyl)-4-(4-(trifluoromethoxy)phenyl)benzo[d]oxazol-7-yl)methanol

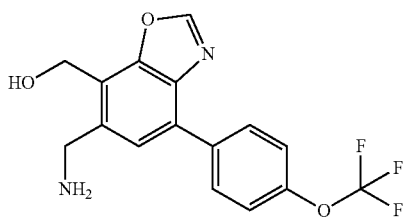 [SMILES: NCc1cc(-c2ccc(OC(F)(F)F)cc2)c2ncoc2c1CO]

To a mixture of ethyl 6-(azidomethyl)-4-(4-(trifluoromethoxy)phenyl)benzo[d]oxazole-7-carboxylate (500 mg, 1.23 mmol) in THF (20 mL) was added $LiAlH_4$ (0.49 mL, 1.23 mmol, 2.5 M in THF) at 0° C. Then the reaction was stirred at 0° C. for 1 h. The reaction was quenched with water (1 mL) and aq.NaOH solution (1 mL, 2M). The organic layer was dried over $Na_2SO_4$ and concentrated to afford the title compound (400 mg, crude) as a brown oil. LCMS (ESI): m/z 339.1 (M+H)$^+$.

Step 5: N-((7-(hydroxymethyl)-4-(4-(trifluoromethoxy)phenyl)benzo[d]oxazol-6-yl)methyl)acrylamide

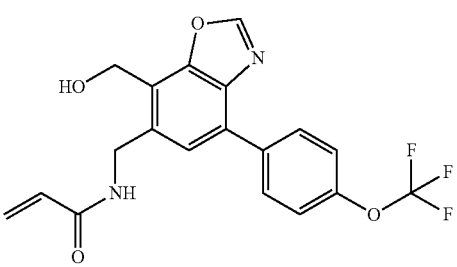 [SMILES: C=CC(=O)NCc1cc(-c2ccc(OC(F)(F)F)cc2)c2ncoc2c1CO]

To a solution of (6-(aminomethyl)-4-(4-(trifluoromethoxy)phenyl)benzo[d]oxazol-7-yl)methanol (400 mg, 1.18 mmol) and sat.NaHCO₃ (1 mL) in THF (5 mL) was added acryloyl chloride (107 mg, 1.18 mmol) at 0° C. The resulting mixture was stirred at 0° C. for 1 h. The mixture was diluted with ethyl acetate (30 mL) and washed with water (30 mL×3). The organic was dried over Na₂SO₄ and concentrated. The residue was purified by flash chromatography on silica gel (0-35% ethyl acetate/EtOH(3/1) in petroleum ether) to afford the title compound (80 mg, 17%) as a white solid.

¹H NMR (400 MHz, DMSO-$d_6$): δ 8.85 (s, 1H), 8.64-8.62 (m, 1H), 8.09 (d, J=8.4 Hz, 2H), 7.63 (s, 1H), 7.54 (d, J=8.4 Hz, 2H), 6.27 (dd, J=17.2, 10.0 Hz, 1H), 6.12 (dd, J=17.2, 2.0 Hz, 1H), 5.62 (dd, J=10.0, 2.0 Hz, 1H), 5.36 (t, J=5.2 Hz, 1H), 4.88 (d, J=5.6 Hz, 2H), 4.66 (d, J=5.6 Hz, 2H); LCMS (ESI): m/z 414.9 (M+Na)⁺.

Example 111 (Compound 114) N-((7-(Hydroxymethyl)-4-(6-(trifluoromethoxy)pyridin-3-yl)benzo[d]oxazol-6-yl)methyl)acrylamide

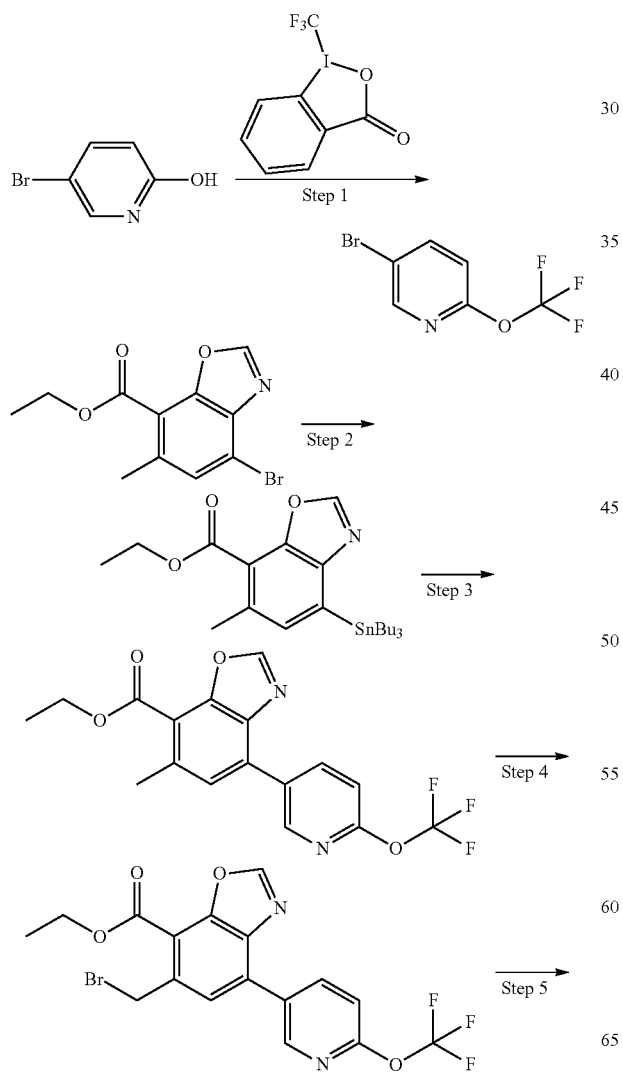

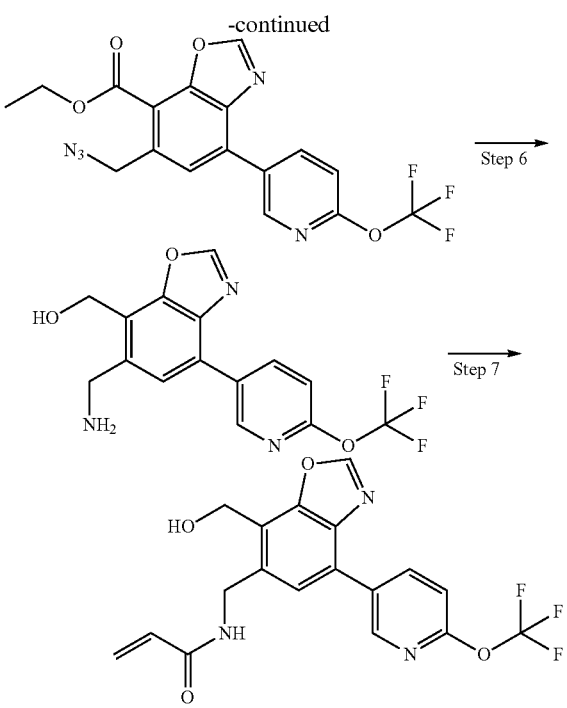

Step 1: 5-bromo-2-(trifluoromethoxy)pyridine

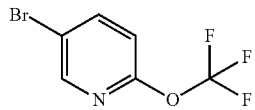 [SMILES: FC(F)(F)Oc1ccc(Br)cn1]

To a solution of 1-trifluoromethyl-1,2-benziodoxol-3-(1H)-one (35.0 g, 110.74 mmol) in McNO₂ (580 mL) was added 5-bromopyridin-2-ol (57.82 g, 332.30 mmol) at room temperature. The solution was stirred at 100° C. for 5 hours under N₂ atmosphere. The reaction mixture was concentrated and the residue was purified by flash column chromatography on silica gel (100% petroleum ether) to afford the title compound (3.8 g, 14%) as a colorless oil. ¹H NMR (400 MHz, CDCl₃): δ 8.39 (d, J=2.4 Hz, 1H), 7.90 (dd, J=8.4, 2.4 Hz, 11H), 6.95 (d, J=8.4 Hz, 1H).

Step 2: ethyl 6-methyl-4-(tributylstannyl)benzo[d]oxazole-7-carboxylate

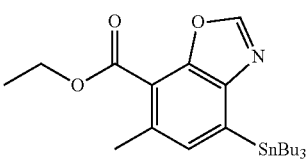

A mixture of ethyl 4-bromo-6-methylbenzo[d]oxazole-7-carboxylate (3.0 g, 10.56 mmol), Pd(PPh₃)₂Cl₂ (741 mg, 1.06 mmol) and 1,1,1,2,2,2-hexabutyldistannane (6.94 mL, 13.73 mmol) in 1,4-dioxane (50 mL) was stirred at 100° C. for 16 hours under N₂ atmosphere. The mixture was quenched with water (300 mL), extracted with ethyl acetate (300 mL). The organic layer was washed with water (300 mL×3). The organic was dried over Na₂SO₄ and concentrated. The residue was purified by flash chromatography on silica gel (0-15% ethyl acetate in petroleum ether) to afford the title compound (3.8 g, 73%) as a yellow oil.

Step 3: ethyl 6-methyl-4-(6-(trifluoromethoxy)pyridin-3-yl)benzo[d]oxazole-7-carboxylate

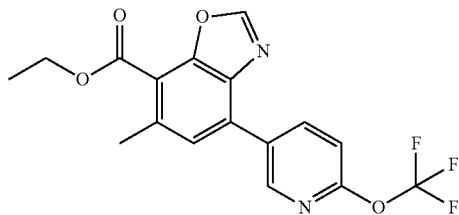 [SMILES: CCOC(=O)c1c(C)cc(-c2ccc(OC(F)(F)F)nc2)c2ncoc12]

A mixture of ethyl 6-methyl-4-(tributylstannyl)benzo[d]oxazole-7-carboxylate (1.5 g, 3.03 mmol), Pd(PPh₃)₂Cl₂ (213 mg, 0.30 mmol), CsF (1.36 g, 9.1 mmol), CuCl (30 mg, 0.30 mmol) and 5-bromo-2-(trifluoromethoxy)pyridine (881 mg, 3.64 mmol) in 1,4-dioxane (20 mL) was stirred at 100° C. for 16 hours under N₂ atmosphere. The mixture was quenched with water (100 mL), extracted with ethyl acetate (100 mL). The organic layer was washed with water (100 mL×3). The organic layer was dried over Na₂SO₄ and concentrated. The residue was purified by flash chromatography on silica gel (0-10% ethyl acetate in petroleum ether) to afford the title compound (1.0 g, 90%) as a white solid. ¹H NMR (400 MHz, CDCl₃): δ 8.87 (d, J=2.0 Hz, 1H), 8.47 (dd, J=8.4, 2.0 Hz, 1H), 8.19 (s, 1H), 7.44 (s, 1H), 7.18 (d, J=8.4 Hz, 1H), 4.52 (q, J=7.2 Hz, 2H), 2.77 (s, 3H), 1.48 (t, J=7.2 Hz, 3H); LCMS (ESI): m/z 367.1 (M+H)⁺.

Step 4: ethyl 6-(bromomethyl)-4-(6-(trifluoromethoxy)pyridin-3-yl)benzo[d]oxazole-7-carboxylate

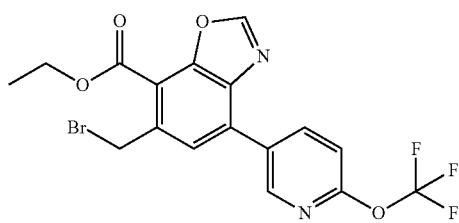 [SMILES: CCOC(=O)c1c(CBr)cc(-c2ccc(OC(F)(F)F)nc2)c2ncoc12]

To a mixture of ethyl 6-methyl-4-(6-(trifluoromethoxy)pyridin-3-yl)benzo[d]oxazole-7-carboxylate (900 mg, 2.46 mmol) in CCl4 (10 mL) was added AIBN (80 mg, 0.49 mmol) and NBS (524 mg, 2.95 mmol) at 0° C. The reaction solution was stirred at 80° C. for 16 hours. The solution was concentrated. The residue was purified by flash chromatography on silica gel (0-10% ethyl acetate in petroleum ether) to afford the title compound (900 mg, 82%) as a yellow solid. LCMS (ESI): m/z 445.0 (M+H)⁺.

Step 5: ethyl 6-(azidomethyl)-4-(6-(trifluoromethoxy)pyridin-3-yl)benzo[d]oxazole-7-carboxylate

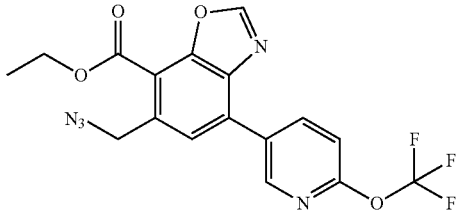

To a mixture of ethyl 6-(bromomethyl)-4-(6-(trifluoromethoxy)pyridin-3-yl)benzo[d]oxazole-7-carboxylate (500 mg, 1.12 mmol) in DMF (10 mL) was added NaN₃ (80 mg, 1.24 mmol) at room temperature. Then the reaction was stirred at room temperature for 16 hours. The reaction solution was quenched with water (200 mL), extracted in ethyl acetate (300 mL), dried over MgSO₄, filtered and concentrated to afford the title compound (0.40 g, 87%) as a yellow solid. LCMS (ESI): m/z 408.1 (M+H)⁺.

Step 6: (6-(aminomethyl)-4-(6-(trifluoromethoxy)pyridin-3-yl)benzo[d]oxazol-7-yl)methanol

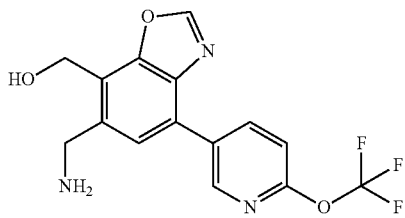

To a mixture of ethyl 6-(azidomethyl)-4-(6-(trifluoromethoxy)pyridin-3-yl)benzo[d]oxazole-7-carboxylate (100 mg, 0.25 mmol) in THF (5 mL) was added LiAlH₄ (0.22 mL, 0.54 mmol, 2.5 mol/L in THF) at 0° C. Then the reaction was stirred at 0° C. for 1 hour. The reaction was quenched with water (1 mL) and sat.NaHCO₃ solution (1 mL). The organic was dried over Na₂SO₄ and concentrated to afford the title compound (80 mg, crude) as a brown liquid. LCMS (ESI): m/z 340.1 (M+H)⁺.

Step 7: N-((7-(hydroxymethyl)-4-(6-(trifluoromethoxy)pyridin-3-yl)benzo[d]oxazol-6-yl)methyl)acrylamide

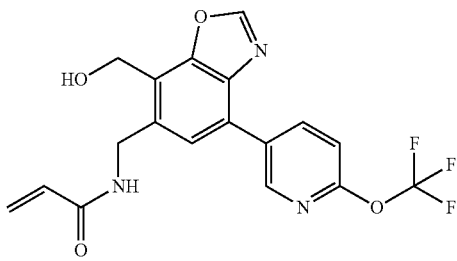 [SMILES: C=CC(=O)NCc1cc(-c2ccc(OC(F)(F)F)nc2)c2ncoc2c1CO]

To a solution of (6-(aminomethyl)-4-(6-(trifluoromethoxy)pyridin-3-yl)benzo[d]oxazol-7-yl)methanol (80 mg, 0.24 mmol) in THF (5 mL) was added sat.NaHCO₃ solution (1 mL) and acryloyl chloride (25 mg, 0.28 mmol) at 0° C. Then the reaction was stirred at 0° C. for 30 min. The reaction was diluted with water (20 mL) and extracted with ethyl acetate (100 mL×3). The organic layers were washed with brine (100 mL×2), dried over sodium sulfate, filtered and concentrated. The residue was purified by flash chromatography on silica gel (0-50% ethyl acetate in petroleum ether) and by reverse phase chromatography (Welch Xtimate C18 150*25 mm*5 um,water (NH₄HCO₃)-ACN,30-60%) to afford the title compound (6.28 mg, 7%) as a white solid. ¹H NMR (400 MHz, DMSO-d₆): δ 8.94 (d, J=2.4 Hz, 1H), 8.89 (s, 1H), 8.61-8.57 (m, 1H), 7.70 (s, 1H), 7.49 (d, J=8.4 Hz, 1H), 6.27 (dd, J=17.2, 10.0 Hz, 1H), 6.12 (dd, J=17.2, 2.4 Hz, 1H), 5.62 (dd, J=10.0, 2.4 Hz, 1H), 5.40-5.39 (m, 1H), 4.88 (d, J=5.2 Hz, 2H), 4.67 (d, J=6.0 Hz, 2H); LCMS (ESI): m/z 416.0 (M+Na)⁺.

Example 112 (Compound 115)

Cyclobut-1-en-1-yl(3-(9-methyl-6-(4-(trifluoromethoxy)phenyl)-9H-purin-2-yl)azetidin-1-yl)methanone

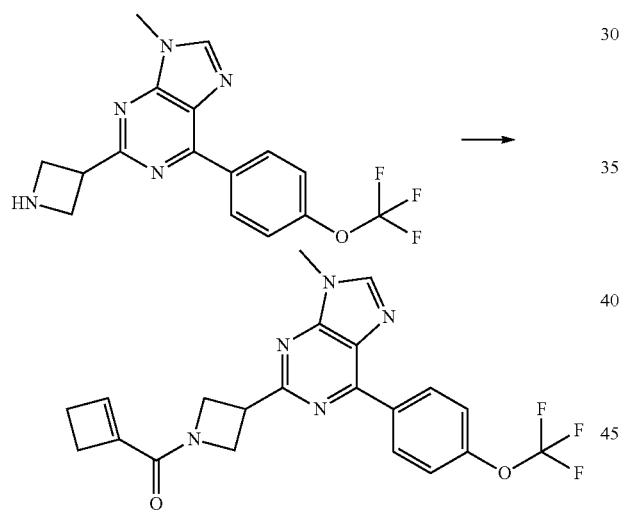

To a solution of HATU (253 mg, 0.67 mmol) and DIPEA (115 mg, 0.89 mmol) and cyclobut-1-ene-1-carboxylic acid (65 mg, 0.67 mmol) in DMF (2 mL) was added 2-(azetidin-3-yl)-9-methyl-6-(4-(trifluoromethoxy)phenyl)-9H-purine (155 mg, 0.44 mmol) at 0° C. The mixture was stirred at room temperature for 16 h. The reaction mixture was quenched with H₂O (10 mL), extracted with ethyl acetate (20 mL×3), the combined organic layers were washed with water (10 mL×3), dried over Na₂SO₄ and concentrated. The residue was purified by reverse phase chromatography (Welch Xtimate C18 150*30 mm*5 um, water(FA)-ACN, 50-80%) to afford the title compound (62.8 mg, 33%) as a white solid. ¹H NMR (400 MHz, DMSO-d₆): δ 8.96 (d, J=8.8 Hz, 2H), 8.64 (s, 1H), 7.61 (d, J=8.8 Hz, 2H), 6.53 (s, 1H), 4.77-4.73 (m, 1H), 4.63-4.59 (m, 1H), 4.43-4.25 (m, 3H), 3.87 (s, 3H), 2.68-2.65 (m, 2H), 2.44-2.42 (m, 2H); LCMS (ESI): m/z 430.0 (M+H)⁺. Example 113 (Compound 116)

(E)-9-Methyl-2-(1-(prop-1-en-1-ylsulfonyl)azetidin-3-yl)-6-(4-(trifluoromethoxy)phenyl)-9H-purine

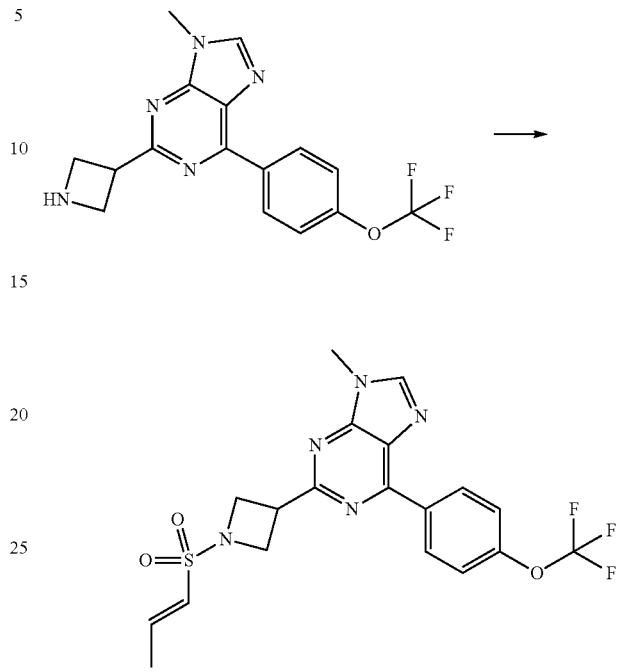

A mixture of TEA (130 mg, 1.29 mmol) and (E)-prop-1-ene-1-sulfonyl chloride (72 mg, 0.52 mmol) and 2-(azetidin-3-yl)-9-methyl-6-(4-(trifluoromethoxy)phenyl)-9H-purine (150 mg, 0.43 mmol) in DMF (1.5 mL) was stirred at room temperature for 16 h. The reaction mixture was quenched with H₂O (10 mL) and extracted with ethyl acetate (20 mL×3), the combined organic layers were washed with water (10 mL×3), dried over Na₂SO₄ and concentrated. The residue was purified by reverse phase chromatography (Welch Xtimate C18 150*30 mm*5 um, water (FA)-ACN, 49-79%) to afford the title compound (23.3 mg, 12%) as a white solid. ¹H NMR (400 MHz, DMSO-d₆): δ 8.98 (d, J=9.2 Hz, 2H), 8.65 (s, 1H), 7.62 (d, J=8.4 Hz, 2H), 6.85-6.73 (m, 2H), 4.27-4.19 (m, 5H), 3.87 (s, 3H), 1.91 (d, J=5.6 Hz, 3H); LCMS (ESI): m/z 453.9 (M+H)⁺.

Example 114 (Compound 117)

(E)-4-Hydroxy-1-(3-(9-methyl-6-(4-(trifluoromethoxy)phenyl)-9H-purin-2-yl)azetidin-1-yl)but-2-en-1-one

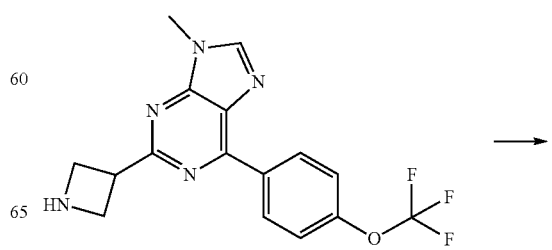

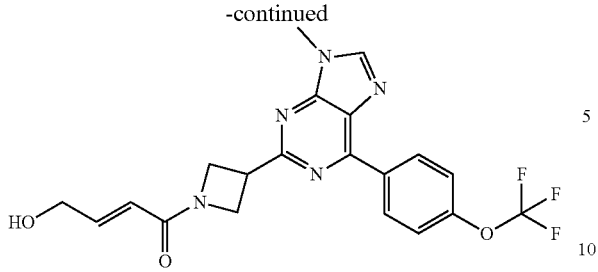

To a solution of 2-(azetidin-3-yl)-9-methyl-6-(4-(trifluoromethoxy)phenyl)-9H-purine (190 mg, 0.54 mmol), (E)-4-hydroxybut-2-enoic acid (67 mg, 0.65 mmol) and DIPEA (0.28 mL, 1.63 mmol) in DMF (5 mL) was added HATU (414 mg, 1.09 mmol) at room temperature, the resulting solution was stirred at room temperature for 2 h. The resulting residue was purified by reverse phase chromatography (Welch Xtimate C18 150*30 mm*5 um, acetonitrile 37-67%/water(0.225% FA)-ACN) to afford the title compound (42.8 mg, 18%) as a white solid. $^1$H NMR (400 MHz, DMSO-d$_6$): δ 8.95 (d, J=8.8 Hz, 2H), 8.63 (s, 1H), 7.60 (d, J=8.4 Hz, 2H), 6.81-6.75 (m, 1H), 6.23-6.19 (m, 1H), 4.70-4.54 (m, 2H), 4.41-4.36 (m, 1H), 4.31-4.20 (m, 2H), 4.16-4.14 (m, 2H), 3.86 (s, 3H); LCMS (ESI): m/z 434.0 (M+H)$^+$.

Example 115 (Compound 118)

2-Fluoro-1-(3-(9-methyl-6-(4-(trifluoromethoxy)phenyl)-9H-purin-2-yl)azetidin-1-yl)prop-2-en-1-one

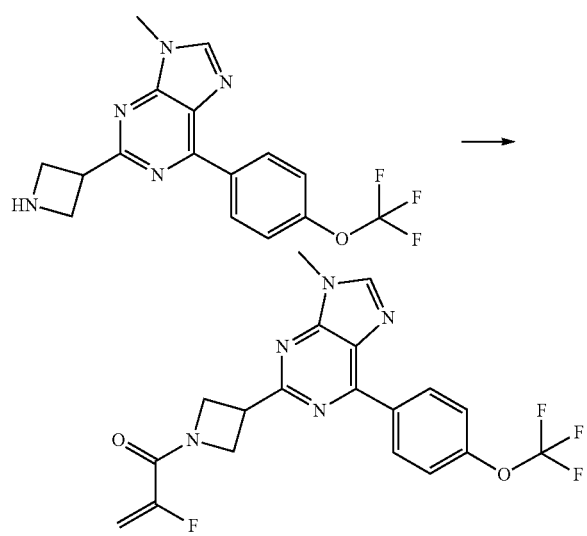

To a solution of 2-(azetidin-3-yl)-9-methyl-6-(4-(trifluoromethoxy)phenyl)-9H-purine (200 mg, 0.57 mmol), 2-fluoroacrylic acid (62 mg, 0.69 mmol) and DIEA (0.3 mL, 1.72 mmol) in DMF (2 mL) was added HATU (435 mg, 1.15 mmol) at 0° C., the resulting solution was stirred at room temperature for 2 h. The resulting solution was purified by reverse phase chromatography (Welch Xtimate C18 150*30 mm*5 um, acetonitrile 37-67%/water (0.225% FA)-ACN) to afford the title compound (50.1 mg, 21%) as a white solid. $^1$H NMR (400 MHz, DMSO-d$_6$): δ 8.97 (d, J=9.2 Hz, 2H), 8.65 (s, 1H), 7.62 (d, J=8.0 Hz, 2H), 5.52 (dd, J=48.4, 3.6 Hz, 1H, 1H), 5.33 (dd, J=16.8, 3.6 Hz, 1H), 4.90-4.86 (m, 1H), 4.77-4.67 (m, 1H), 4.50-4.44 (m, 1H), 4.42-4.37 (m, 1H), 4.33-4.25 (m, 1H), 3.87 (s, 3H); LCMS (ESI): m/z 421.9 (M+H)$^+$.

Example 116 (Compound 119)

Bicyclo[1.1.0]butan-1-yl(3-(9-methyl-6-(4-(trifluoromethoxy)phenyl)-9H-purin-2-yl)azetidin-1-yl)methanone

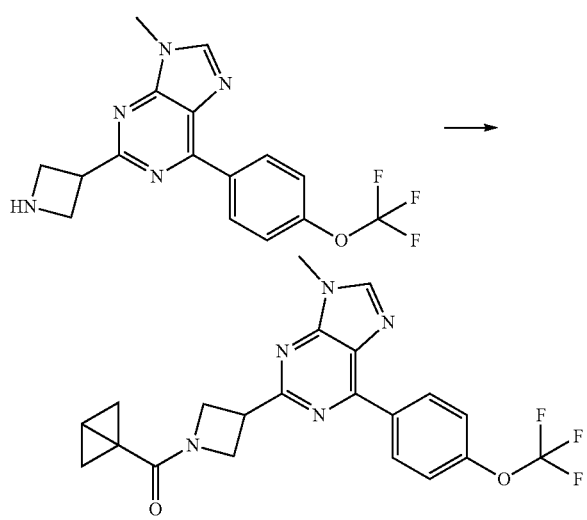

To a stirred solution of 2-(azetidin-3-yl)-9-methyl-6-(4-(trifluoromethoxy)phenyl)-9H-purine (80 mg, 0.23 mmol) and DIPEA (89 mg, 0.69 mmol) in THF (2 mL) was added 4-nitrophenyl bicyclo[1.1.0]butane-1-carboxylate (61 mg, 0.27 mmol) at 0° C. The mixture was stirred at room temperature for 1 h. The mixture was concentrated and the residue was purified by column chromatography on silica gel (0-3% methanol in dichloromethane) and then prep-TLC (5% methanol in dichloromethane) to afford the title compound (48 mg, 48%) as a white solid. I H NMR (400 MHz, DMSO-d$_6$): δ 8.98 (d, J=8.8 Hz, 2H), 8.64 (s, 1H), 7.62 (d, J=8.4 Hz, 2H), 4.76-4.71 (m, 1H), 4.62-4.59 (m, 1H), 4.35-4.23 (m, 3H), 3.88 (s, 3H), 2.25-2.22 (m, 2H), 2.18-2.16 (m, 1H), 1.04-1.02 (m, 2H); LCMS (ESI): m/z 430.1 (M+H)$^+$.

Example 117 (Compound 120)

(E)-2-Methyl-1-(3-(9-methyl-6-(4-(trifluoromethoxy)phenyl)-9H-purin-2-yl)azetidin-1-yl)but-2-en-1-one

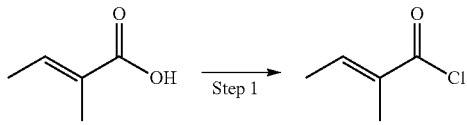

-continued

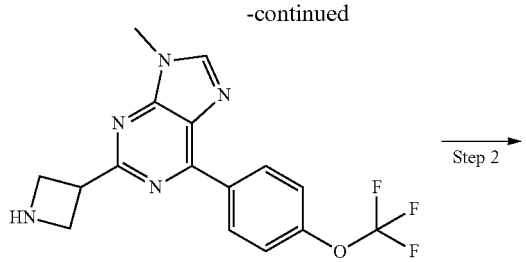

Step 2

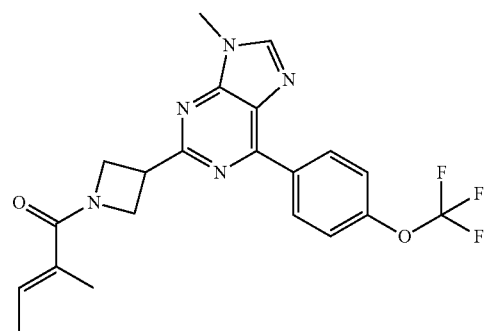

Step 1: (E)-2-methylbut-2-enoyl chloride

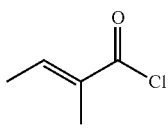

A solution of (E)-2-methylbut-2-enoic acid (800 mg, 7.99 mmol) in SOCl$_2$ (10 mL, 7.99 mmol) was stirred at 100° C. for 1 h. The mixture was concentrated to afford the title compound (940 mg, crude) as a colorless oil, which was used directly for next step without further purification.

Step 2: (E)-2-methyl-1-(3-(9-methyl-6-(4-(trifluoromethoxy)phenyl)-9H-purin-2-yl)azetidin-1-yl)but-2-en-1-one

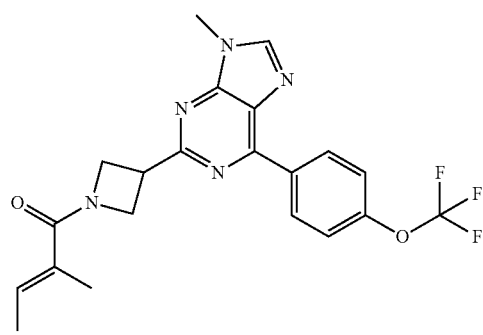 [SMILES: C/C=C(\C)C(=O)N1CC(c2nc(-c3ccc(OC(F)(F)F)cc3)c3ncn(C)c3n2)C1]

To a solution of 2-(azetidin-3-yl)-9-methyl-6-(4-(trifluoromethoxy)phenyl)-9H-purine (150 mg, 0.43 mmol) and DIPEA (0.45 mL, 2.58 mmol) in dichloromethane (4 mL) was added (E)-2-methylbut-2-enoyl chloride (204 mg, 1.72 mmol) dropwise at 0° C., the mixture was stirred at 0° C. for 2 h. The mixture was quenched with methanol (0.5 mL) and concentrated, the residue was purified by column chromatography on silica gel (0-3% methanol in dichloromethane) to afford the title compound (95 mg, 50%) as a white solid. $^1$H NMR (400 MHz, DMSO-d$_6$): δ 9.00-8.92 (m, 2H), 8.63 (s, 1H), 7.60 (d, J=8.4 Hz, 2H), 6.11-6.03 (m, 1H), 4.68-4.25 (m, 4H), 4.24-4.16 (m, 1H), 3.86 (s, 3H), 1.75 (s, 3H), 1.72 (d, J=6.8 Hz, 3H); LCMS (ESI): m/z 432.0 (M+H)$^+$.

Example 118 (Compound 121)

(E)-1-(3-(9-Methyl-6-(4-(trifluoromethoxy)phenyl)-9H-purin-2-yl)azetidin-1-yl)but-2-en-1-one

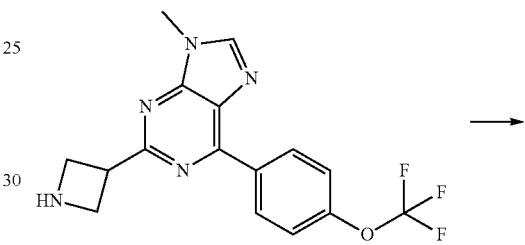

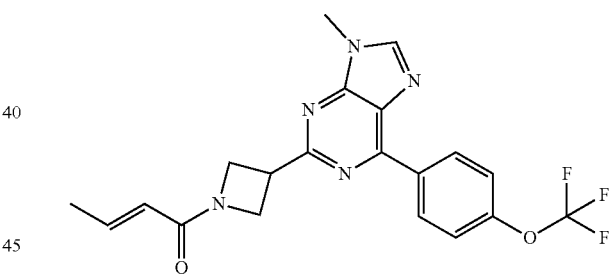

A solution of 2-(azetidin-3-yl)-9-methyl-6-(4-(trifluoromethoxy)phenyl)-9H-purine (90 mg, 0.26 mmol), (E)-but-2-enoic acid (97 mg, 0.31 mmol) and HATU (147 mg, 0.39 mmol) in DMF (3 mL) was added N-ethyl-N-isopropylpropan-2-amine (0.18 mL, 1.03 mmol) at 0° C. The reaction was stirred at 0° C. for 1 hour. The reaction was quenched with water (10 mL). The mixture was extracted with ethyl acetate (20 mL×3). The organic layers were dried over anhydrous sodium sulfate and concentrated under reduced. The residue was purified by reverse phase chromatography (Welch Xtimate C18 150*30 mm*5 um, water (0.225% FA)-CAN, 54-84%) to afford the title compound (25 mg, 23%) as a light brown solid. $^1$H NMR (400 MHz, DMSO-d$_6$): δ 8.96 (d, J=8.8 Hz, 2H), 8.64 (s, 1H), 7.61 (d, J=8.4 Hz, 2H), 6.73-6.65 (m, 1H), 6.12-6.07 (m, 1H), 4.68-4.54 (m, 2H), 4.39-4.22 (m, 3H), 3.87 (s, 3H), 1.84 (dd, J=6.8, 1.6 Hz, 3H); LCMS (ESI): m/z 418.0 (M+H)$^+$.

Example 119 (Compound 122) & Example 120 (Compound 123)

(R)-1-(3-(9-Methyl-6-(4-(trifluoromethoxy)phenyl)-9H-purin-2-yl)pyrrolidin-1-yl)prop-2-en-1-one & (S)-1-(3-(9-methyl-6-(4-(trifluoromethoxy)phenyl)-9H-purin-2-yl)pyrrolidin-1-yl)prop-2-en-1-one

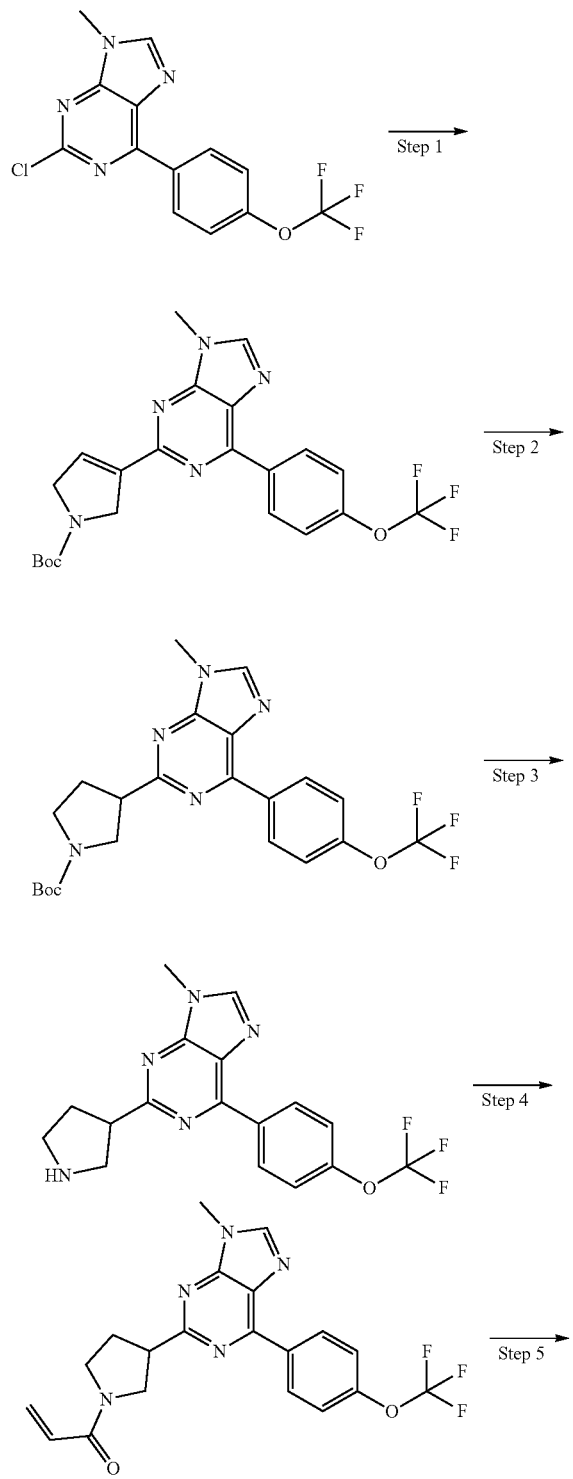

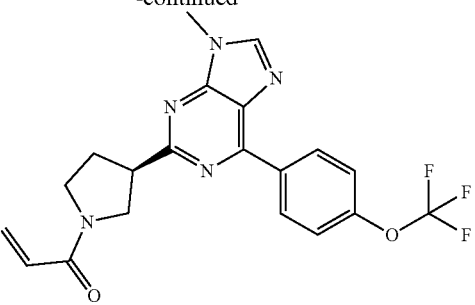

Step 1: tert-butyl 3-(9-methyl-6-(4-(trifluoromethoxy)phenyl)-9H-purin-2-yl)-2,5-dihydro-1H-pyrrole-1-carboxylate A mixture of 2-chloro-9-methyl-6-(4-(trifluoromethoxy)phenyl)-9H-purine (300 mg, 0.91 mmol), Xphos Pd G$_2$ (144 mg, 0.18 mmol), Xphos (43 mg, 0.09 mmol), tert-butyl 3-(4,4,5,5-tetramethyl-1,3,2-dioxaborolan-2-yl)-2,5-dihydro-1H-pyrrole-1-carboxylate (404 mg, 1.37 mmol), KOAc (179 mg, 1.83 mmol) in 1,4-dioxane (10 mL) and water (1 mL) was stirred at 80° C. for 5 hours under N$_2$ atmosphere. The reaction mixture was filtered, the filtrate was diluted with water (100 mL) and extracted with dichloromethane (100 mL×3). The organics were washed with brine (100 mL×2), dried over sodium sulfate, filtered and concentrated. The residue was purified by flash chromatography on silica gel (0-10% ethyl acetate in petroleum ether) to afford the title compound (327 mg, 78%) as a white solid. $^1$H NMR (400 MHz, CDCl$_3$): δ 8.94-8.89 (m, 2H), 8.10, 8.09 (s, 1H total), 7.42-7.38 (m, 2H), 7.07-6.96 (m, 1H), 4.80-4.68 (m, 2H), 4.48-4.39 (m, 2H), 3.95, 3.92 (s, 3H total), 1.59, 1.54 (s, 9H); LCMS (ESI): m/z 462.2 (M+H)$^+$.

Step 2: tert-butyl 3-(9-methyl-6-(4-(trifluoromethoxy)phenyl)-9H-purin-2-yl)pyrrolidine-1-carboxylate

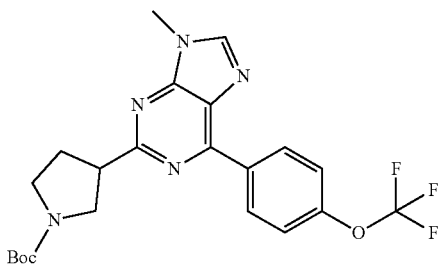 [SMILES: Cn1cnc2c(-c3ccc(OC(F)(F)F)cc3)nc(C3CCN(C(=O)OC(C)(C)C)C3)nc21]

To a mixture of tert-butyl 3-(9-methyl-6-(4-(trifluoromethoxy)phenyl)-9H-purin-2-yl)-2,5-dihydro-1H-pyrrole-1-carboxylate (327 mg, 0.71 mmol) in ethanol (5 mL) was added 10% Pd on carbon (151 mg, 0.14 mmol). The mixture was stirred at room temperature under $H_2$ (15 psi) for 16 h. The reaction mixture was filtered over a short diatomite liner. The filtrate was concentrated. The residue was purified by chromatography on silica gel (0-15% ethyl acetate in petroleum ether) to afford the title compound (268 mg, 82%) as a yellow solid. $^1$H NMR (400 MHz, CDCl$_3$): δ 8.89 (d, J=8.8 Hz, 2H), 8.08 (s, 1H), 7.39 (d, J=6.4 Hz, 2H), 3.98-3.57 (m, 8H), 2.42-2.40 (m, 2H), 1.49 (s, 9H); LCMS (ESI): m/z 464.2 (M+H)$^+$.

Step 3: 9-methyl-2-(pyrrolidin-3-yl)-6-(4-(trifluoromethoxy)phenyl)-9H-purine 2,2,2-trifluoroacetate

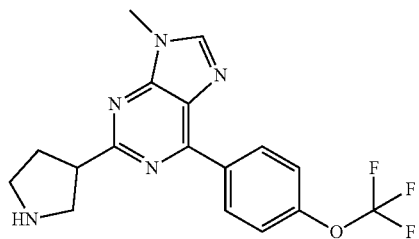 [SMILES: Cn1cnc2c(-c3ccc(OC(F)(F)F)cc3)nc(C3CCNC3)nc21]

To a stirred solution of tert-butyl 3-(9-methyl-6-(4-(trifluoromethoxy)phenyl)-9H-purin-2-yl)pyrrolidine-1-carboxylate (268 mg, 0.56 mmol) in DCM (3 mL) was added 2,2,2-trifluoroacetic acid (0.21 mL) at 0° C. The mixture was stirred at room temperature for 2 h. The solvent was removed under reduced pressure directly to afford the title compound (110 mg, crude) as a yellow oil. The reaction was used directly without further purification. LCMS (ESI): m/z 364.1 (M+H)$^+$.

Step 4: 1-(3-(9-methyl-6-(4-(trifluoromethoxy)phenyl)-9H-purin-2-yl)pyrrolidin-1-yl)prop-2-en-1-one

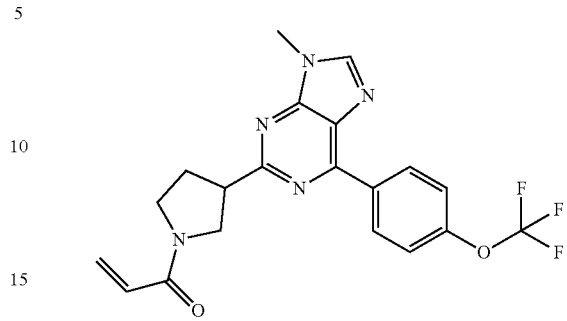

To a solution of 9-methyl-2-(pyrrolidin-3-yl)-6-(4-(trifluoromethoxy)phenyl)-9H-purine 2,2,2-trifluoroacetate (110 mg, 0.29 mmol) and sat.NaHCO$_3$ (1 mL) in THF (2 mL) was added acryloyl chloride (303 mg, 3.35 mmol) at 0° C. The mixture was stirred at room temperature for 16 h. The reaction mixture was diluted with water (200 mL) and extracted with ethyl acetate (20 mL×3). The organics were washed with brine (20 mL×2), dried over sodium sulfate, filtered and concentrated. The residue was purified by reverse phase chromatography (Welch Xtimate C18 150*30 mm*5 um, acetonitrile 40-70%/water (FA)-ACN) to give the title compound (120 mg, 96%) as a white solid. LCMS (ESI): m/z 418.2 (M+H)$^+$.

Step 4: (R)-1-(3-(9-methyl-6-(4-(trifluoromethoxy)phenyl)-9H-purin-2-yl)pyrrolidin-1-yl)prop-2-en-1-one & (S)-1-(3-(9-methyl-6-(4-(trifluoromethoxy)phenyl)-9H-purin-2-yl)pyrrolidin-1-yl)prop-2-en-1-one

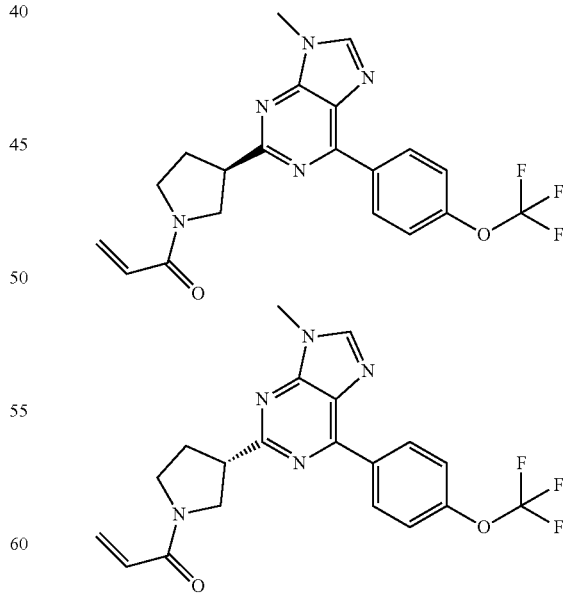

1-(3-(9-Methyl-6-(4-(trifluoromethoxy)phenyl)-9H-purin-2-yl)pyrrolidin-1-yl)prop-2-en-1-one (120 mg, 0.29 mmol) was separated by Chiral SFC (Instrument: SFC-16; Column: AS(250 mm*30 mm,10 um); Condition: Neu- ETOH; Begin B:20%; Flow Rate (ml/min): 60) to afford the first peak (R)-1-(3-(9-methyl-6-(4-(trifluoromethoxy)phenyl)-9H-purin-2-yl)pyrrolidin-1-yl)prop-2-en-1-one (40.6 mg, 34%) and the second peak (S)-1-(3-(9-methyl-6-(4-(trifluoromethoxy)phenyl)-9H-purin-2-yl)pyrrolidin-1-yl)prop-2-en-1-one (45.0 mg, 37%) both as white solid.

The first peak: $^1$H NMR (400 MHz, DMSO-$d_6$): δ 8.99-8.96 (m, 2H), 8.64, 8.63 (s, 1H total), 7.55 (d, J=8.8 Hz, 2H), 6.70-6.59 (m, 11H), 6.20-6.15 (m, 1H), 5.72-5.68 (m, 1H), 4.14-4.04 (m, 1H), 3.96-3.87 (m, 6H), 3.77-3.68 (m, 1H), 3.60-3.48 (m, 0.5H), 2.43-2.37 (m, 1.5H); LCMS (ESI): m/z 418.0 (M+H)$^+$.

The second peak: $^1$H NMR (400 MHz, DMSO-$d_6$): δ 8.99-8.96 (m, 2H), 8.64, 8.63 (s, 1H total), 7.55 (d, J=8.8 Hz, 2H), 6.70-6.59 (m, 1H), 6.20-6.15 (m, 1H), 5.72-5.68 (m, 1H), 4.14-4.04 (m, 1H), 3.96-3.87 (m, 6H), 3.77-3.68 (m, 1H), 3.60-3.48 (m, 0.5H), 2.43-2.37 (m, 1.5H); LCMS (ESI): m/z 418.0 (M+H)$^+$.

Example 121 (Compound 124) 1-(4-(9-Methyl-6-(4-(trifluoromethoxy)phenyl)-9H-purin-2-yl)piperazin-1-yl)prop-2-en-1-one

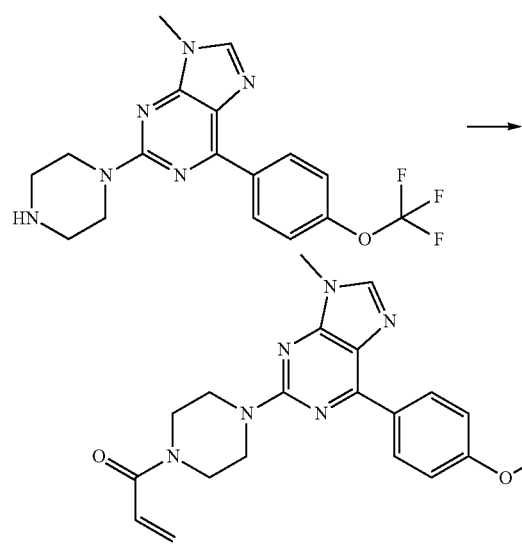

To a solution of 9-methyl-2-(piperazin-1-yl)-6-(4-(trifluoromethoxy)phenyl)-9H-purine 2,2,2-trifluoroacetate (100 mg, 0.26 mmol) and sat.NaHCO$_3$ solution (3 mL) in THF (4 mL) was added acrylic anhydride (0.07 mL, 0.63 mmol) at 0° C. The reaction solution was stirred at 0° C. for 1 hour. The mixture was quenched with water (20 mL) and extracted with ethyl acetate (20 mL×3). The organic layers were dried over anhydrous sodium sulfate and concentrated under reduced. The residue was purified by reverse phase chromatography (Welch Xtimate C18 150*30 mm*5 um, water (0.225% FA)-CAN, 58-88%) to afford the title compound (25 mg, 21%). $^1$H NMR (400 MHz, DMSO-$d_6$): δ 8.91 (d, J=8.8 Hz, 2H), 8.26 (s, 1H), 7.57 (d, J=8.4 Hz, 2H), 6.89 (dd, J=16.8, 10.8 Hz, 1H), 6.17 (dd, J=16.8, 2.0 Hz, 1H), 5.73 (d, J=10.8, 2.0 Hz, 1H), 3.92-3.90 (m, 4H), 3.73-3.69 (m, 7H); LCMS (ESI): m/z 433.0 (M+H)$^+$.

Example 122 (Compound 125)

(E)-4-Hydroxy-1-(4-(9-methyl-6-(4-(trifluoromethoxy)phenyl)-9H-purin-2-yl)piperazin-1-yl)but-2-en-1-one

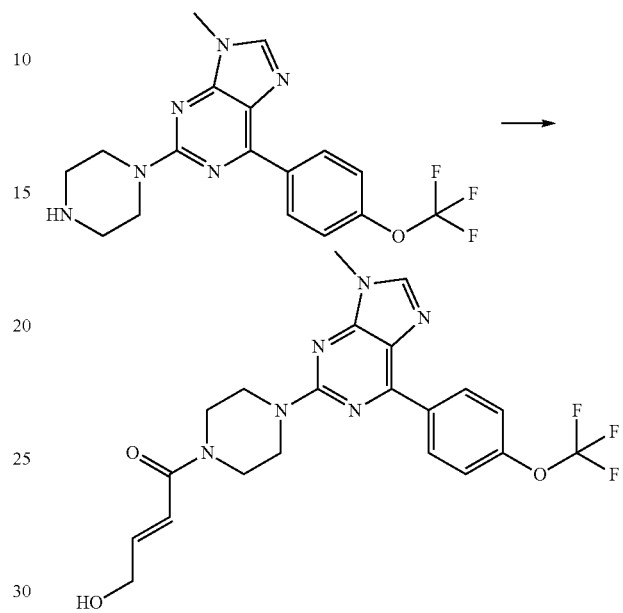

To a solution of 9-methyl-2-(piperazin-1-yl)-6-(4-(trifluoromethoxy)phenyl)-9H-purine (1.6 g, 4.08 mmol), (E)-4-hydroxybut-2-enoic acid (625 mg, 6.13 mmol) in dichloromethane (80 mL) was added ethyl 2-ethoxyquinoline-1(2H)-carboxylate (2.0 g, 8.17 mmol) at room temperature. And the solution was stirred at room temperature for 16 hours. The solution was diluted with water (50 mL) and extracted with DCM (100 mL×2). The combined organic layers were washed with brine (120 mL), dried over sodium sulfate and concentrated under reduced pressure. The residue was purified by reverse phase chromatography (Wetch Xtimate C18 150*30 mm*5 um, acetonitrile 50-80% /water (0.225% FA)-ACN) to afford the title compound (550 mg, 29%) as a white solid. $^1$H NMR (400 MHz, DMSO-$d_6$): δ 8.89 (d, J=8.8 Hz, 2H), 8.24 (s, 1H), 7.55 (d, J=8.4 Hz, 2H), 6.83-6.77 (m, 1H), 6.68-6.62 (m, 1H), 5.06 (t, J=5.2 Hz, 1H), 4.17-4.15 (m, 2H), 3.90-3.88 (m, 4H), 3.71-3.69 (m, 7H); LCMS (ESI): m/z 463.0 (M+H)$^+$.

Example 123 (Compound 126)

2-Fluoro-1-(4-(9-methyl-6-(4-(trifluoromethoxy)phenyl)-9H-purin-2-yl)piperazin-1-yl)prop-2-en-1-one

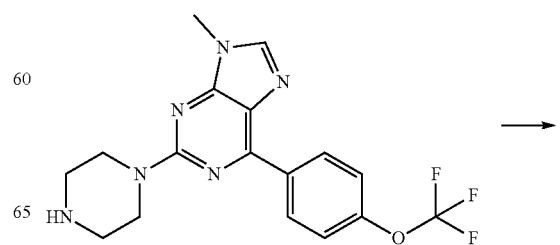

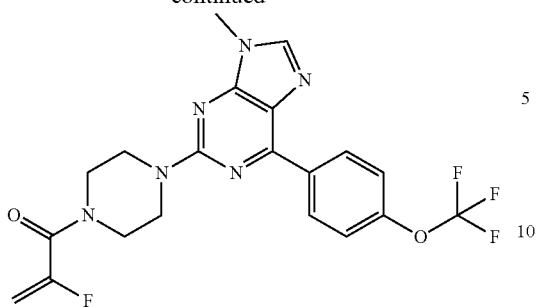

To a solution of 9-methyl-2-(piperazin-1-yl)-6-(4-(trifluoromethoxy)phenyl)-9H-purine (1.0 g, 2.72 mmol), 2-fluoroacrylic acid (368 mg, 4.08 mmol) in DCM (10 mL) and methanol (2 mL) was added ethyl 2-ethoxyquinoline-1(2H)-carboxylate (1.35 g, 5.44 mmol) at 0° C. The reaction solution was stirred at room temperature for 16 hours. The mixture was diluted with water (30 mL), extracted with ethyl acetate (60 mL×3) and washed with brine (60 mL). The organic layers were dried over anhydrous sodium sulfate and concentrated under reduced. The residue was purified by reverse phase chromatography (Wetch Xtimate C18 150*30 mm*5 um 60-90% acetonitrile in formic/water) to afford the title compound (270 mg, 23%). $^1$H NMR (400 MHz, DMSO-$d_6$): δ 8.90 (d, J=8.8 Hz, 2H), 8.26 (s, 1H), 7.55 (d, J=8.4 Hz, 2H), 5.37-5.16 (m, 2H), 3.95-3.93 (m, 4H), 3.72-3.68 (m, 7H); LCMS (ESI): m/z 451.0 (M+H)$^+$.

Example 124 (Compound 127)

N-(1-(9-Methyl-6-(4-(trifluoromethoxy)phenyl)-9H-purin-2-yl)azetidin-3-yl)acrylamide

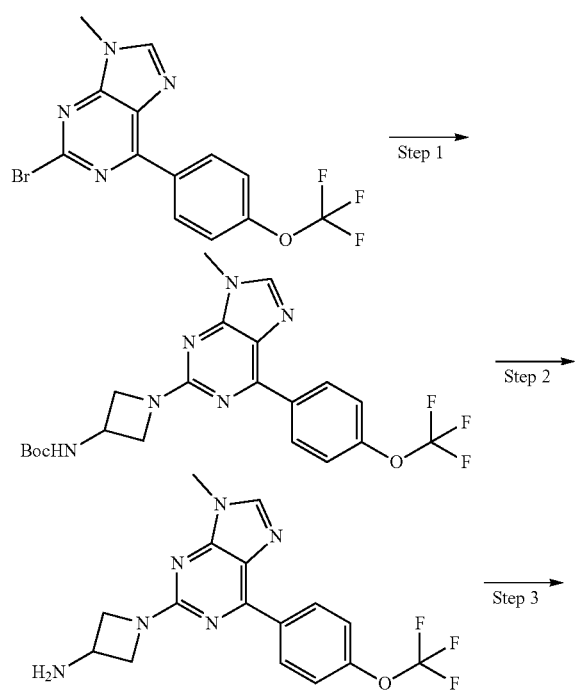

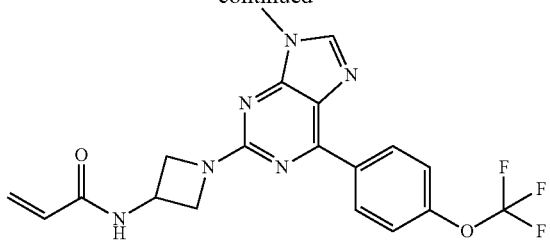

Step 1: tert-butyl (1-(9-methyl-6-(4-(trifluoromethoxy)phenyl)-9H-purin-2-yl)azetidin-3-yl)carbamate

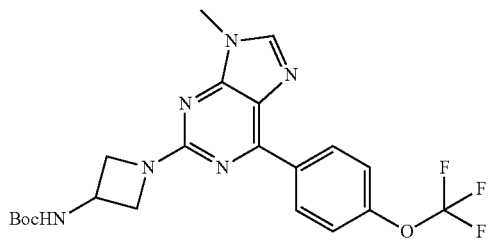 [SMILES: Cn1cnc2c(-c3ccc(OC(F)(F)F)cc3)nc(N3CC(NC(=O)OC(C)(C)C)C3)nc21]

A mixture of 2-bromo-9-methyl-6-(4-(trifluoromethoxy)phenyl)-9H-purine (300 mg, 0.68 mmol), tert-butyl azetidin-3-ylcarbamate (118 mg, 0.68 mmol), RuPhos Pd G$_3$ (32 mg, 0.03 mmol), RuPhos (48 mg, 0.1 mmol), Cs$_2$CO$_3$ (445 mg, 1.4 mmol) in 1,4-dioxane (20 mL) was stirred at 100° C. for 2 hours under N$_2$ atmosphere. The reaction was quenched with water (60 mL) and extracted with ethyl acetate (20 mL×3), the combined organic layers were dried over Na$_2$SO$_4$ and concentrated. The residue was purified by chromatography on silica gel (0-50% ethyl acetate in petroleum ether) to afford the title compound (300 mg, 95%) as a yellow solid. $^1$H NMR (400 MHz, DMSO-$d_6$): $^S$ 8.88 (d, J=8.8 Hz, 2H), 8.24 (s, 1H), 7.61-7.57 (m, 2H), 4.43-4.41 (m, 1H), 4.34-4.32 (m, 2H), 3.98-3.96 (m, 2H), 3.71 (s, 3H), 1.41 (s, 9H); LCMS (ESI): m/z 465.0 (M+H)$^+$.

Step 2: 1-(9-methyl-6-(4-(trifluoromethoxy)phenyl)-9H-purin-2-yl)azetidin-3-amine

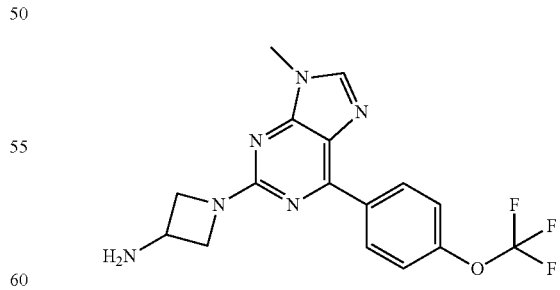

To the tert-butyl (1-(9-methyl-6-(4-(trifluoromethoxy)phenyl)-9H-purin-2-yl)azetidin-3-yl)carbamate (300 mg, 0.67 mmol) was added 5% TFA/HFIP (20 mL) at 0° C. The mixture was stirred at 0° C. for 30 min. The reaction was quenched with NaHCO$_3$ solution (30 mL) and extracted with ethyl acetate (50 mL). The combined organic layers were Step 5: N-(1-(9-methyl-6-(4-(trifluoromethoxy)phenyl)-9H-purin-2-yl)azetidin-3-yl)acrylamide

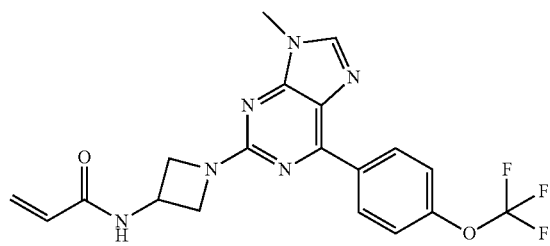 [SMILES: C=CC(=O)NC1CN(c2nc(-c3ccc(OC(F)(F)F)cc3)c3ncn(C)c3n2)C1]

To a solution of 1-(9-methyl-6-(4-(trifluoromethoxy)phenyl)-9H-purin-2-yl)azetidin-3-amine (200 mg, 0.55 mmol) in THF (10 mL) was added sat.NaHCO$_3$ (2 mL) and acryloyl chloride (0.07 mL, 0.82 mmol) at 0° C. The mixture was stirred at 0° C. for 30 min. The reaction mixture was quenched with water (30 mL), extracted with ethyl acetate (30 mL×2). The combined organic layers were washed with brine (50 mL), dried over Na$_2$SO$_4$ and concentrated. The resulting residue was purified by reverse phase chromatography (Welch Xtimate C18 150*25 mm*5 um, acetonitrile 40-70%/water (0.225% FA)-ACN) to afford the title compound (87.50 mg, 33%) as a white solid.

$^1$H NMR (400 MHz, DMSO-d$_6$): b 8.91-8.89 (m, 2H), 8.83 (d, J=7.2 Hz, 1H), 8.25 (s, 1H), 7.56 (d, J=8.4 Hz, 2H), 6.23 (dd, J=17.2, 10.0 Hz, 1H), 6.14 (dd, J=17.2, 2.4 Hz, 1H), 5.64 (dd, J=10.0, 2.4 Hz, 1H), 4.72-4.67 (m, 1H), 4.43-4.40 (m, 2H), 4.00-3.98 (m, 2H), 3.71 (s, 3H); LCMS (ESI): m/z 419.0 (M+H)$^+$.

Example 125 (Compound 128)

(E)-1-(4-Hydroxybut-2-enoyl)-3-(9-methyl-6-(4-(trifluoromethoxy)phenyl)-9H-purin-2-yl)azetidine-3-carbonitrile

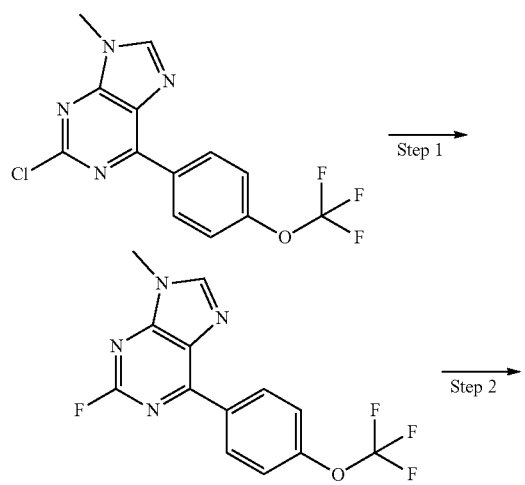

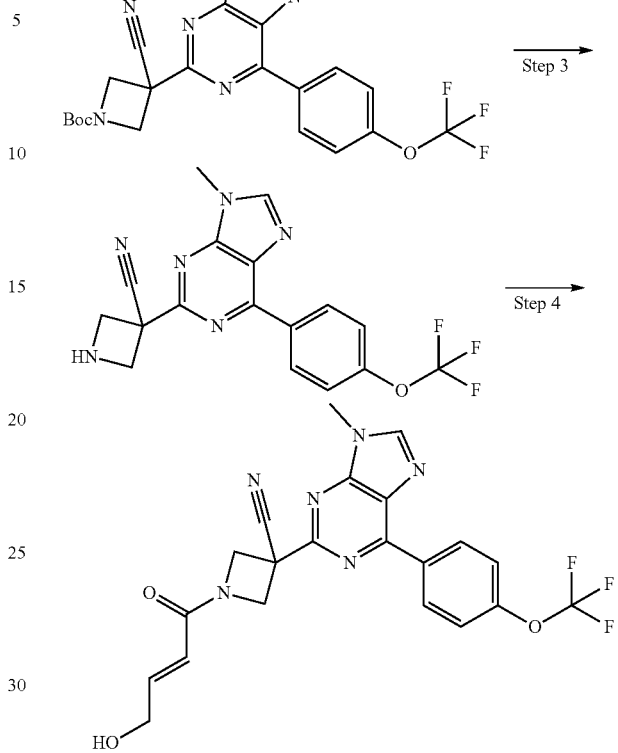

Step 1: 2-fluoro-9-methyl-6-(4-(trifluoromethoxy)phenyl)-9H-purine

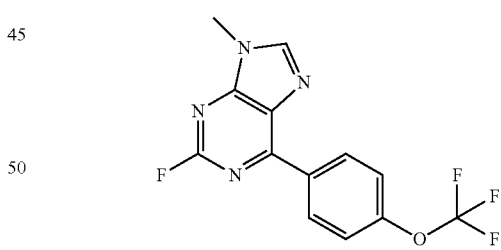

A mixture of 2-chloro-9-methyl-6-(4-(trifluoromethoxy)phenyl)-9H-purine (1.0 g, 3.04 mmol) and potassium fluoride (8.8 g, 152.12 mmol) in dimethyl sulfoxide (10 mL) was stirred at 140° C. for 16 h. The reaction was filtered, the filtrate was diluted with ethyl acetate (50 mL) and washed with brine (50 mL×3). The organic layer was dried over Na$_2$SO$_4$ and concentrated in vacuo. The residue was purified by chromatography on silica gel (0-50% ethyl acetate in petroleum ether) to afford the title compound (800 mg, 84%) as a yellow solid. $^1$H NMR (400 MHz, CDCl$_3$): δ 8.90 (d, J=8.8 Hz, 2H), 8.10 (s, 1H), 7.40 (d, J=8.0 Hz, 2H), 3.92 (s, 3H); LCMS (ESI): m/z 312.9 (M+H)$^+$.

Step 2: tert-butyl 3-cyano-3-(9-methyl-6-(4-(trifluoromethoxy)phenyl)-9H-purin-2-yl)azetidine-1-carboxylate

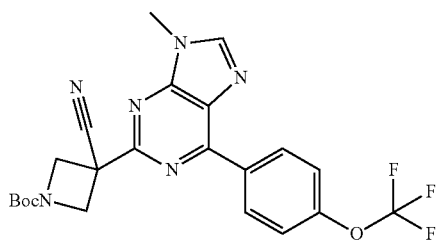 [SMILES: Cn1cnc2c(-c3ccc(OC(F)(F)F)cc3)nc(C3(C#N)CN(C(=O)OC(C)(C)C)C3)nc21]

To a solution of tert-butyl 3-cyanoazetidine-1-carboxylate (400 mg, 2.2 mmol) in THF (15 mL) was added LDA (1.21 mL, 2.41 mmol, 2.0 mol/L in THF) at −78° C., after addition, the solution was stirred at −78° C. for 30 min, a solution of 2-fluoro-9-methyl-6-(4-(trifluoromethoxy)phenyl)-9H-purine (343 mg, 1.1 mmol) in THF (4 mL) was added into it at −78° C., the resulting solution was stirred at −78° C. for 1 h, then warmed to room temperature and the solution was stirred for 12 h. The mixture was quenched with sat.NH$_4$Cl (10 mL), extracted with ethyl acetate (10 mL×2), the organic layer was washed with brine (10 mL), dried over Na$_2$SO$_4$ and concentrated. The residue was purified by chromatography on silica gel (10-40% ethyl acetate in petroleum ether) to afford the title compound (200 mg, 38%) as a white solid. $^1$H NMR (400 MHz, CDCl$_3$): δ 8.89 (d, J=8.8 Hz, 2H), 8.11 (s, 1H), 7.33 (d, J=8.0 Hz, 2H), 4.60-4.57 (m, 2H), 3.98 (d, J=7.6 Hz, 2H), 3.91 (s, 3H), 1.43 (s, 9H); LCMS (ESI): m/z 475.0 (M+H)$^+$.

Step 3: 3-(9-methyl-6-(4-(trifluoromethoxy)phenyl)-9H-purin-2-yl)azetidine-3-carbonitrile

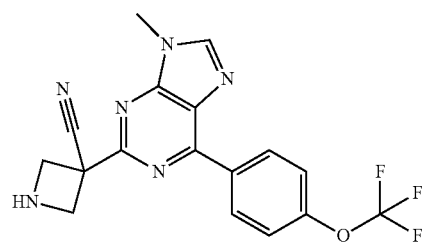 [SMILES: Cn1cnc2c(-c3ccc(OC(F)(F)F)cc3)nc(C3(C#N)CNC3)nc21]

A solution of tert-butyl 3-cyano-3-(9-methyl-6-(4-(trifluoromethoxy)phenyl)-9H-purin-2-yl)azetidine-1-carboxylate (120 mg, 0.25 mmol) and 5% TFA in HFIP (6 mL) was stirred at room temperature for 2 h. The mixture was concentrated in vacuo to afford the crude product and the residue was diluted with sat.NaHCO$_3$ (5 mL), extracted with ethyl acetate (10 mL×2), the organic layer was dried over Na$_2$SO$_4$ and concentrated to afford the title compound (94 mg, crude) as a yellow oil and used directly.

Step 4: (E)-1-(4-hydroxybut-2-enoyl)-3-(9-methyl-6-(4-(trifluoromethoxy)phenyl)-9H-purin-2-yl)azetidine-3-carbonitrile

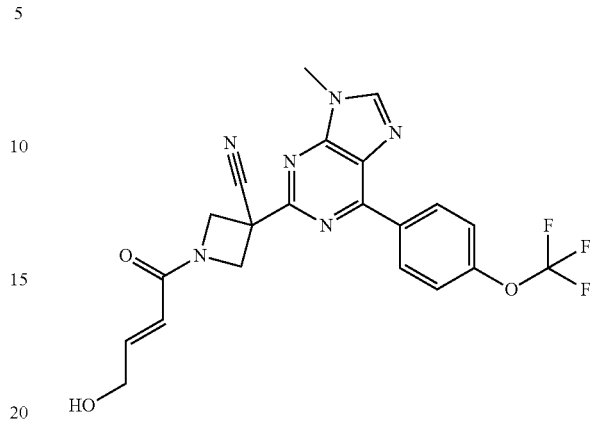

To a solution of 3-(9-methyl-6-(4-(trifluoromethoxy)phenyl)-9H-purin-2-yl)azetidine-3-carbonitrile (94 mg, 0.25 mmol), HATU (143 mg, 0.38 mmol) and (E)-4-hydroxybut-2-enoic acid (31 mg, 0.3 mmol) in DMF (5 mL) was added DIPEA (0.13 mL, 0.75 mmol) at room temperature, the resulting solution was stirred at room temperature for 12 h. The reaction was diluted with ethyl acetate (10 mL) and washed with brine (10 mL×3), the organic layer was dried over Na$_2$SO$_4$ and concentrated in vacuo. The residue was purified by prep-TLC (5% methanol in DCM) to afford the title compound (25 mg, 210%) as a white solid. $^1$H NMR (400 MHz, DMSO-d$_6$): δ 8.98 (d, J=9.2 Hz, 2H), 8.77 (s, 1H), 7.65 (d, J=8.4 Hz, 2H), 6.87 (dt, J=15.2, 4.0 Hz, 1H), 6.22 (d, J=15.2 Hz, 1H), 5.10 (t, J=5.2 Hz, 1H), 5.03-4.94 (m, 2H), 4.70-4.63 (m, 2H), 4.18-4.16 (m, 2H), 3.90 (s, 3H); LCMS (ESI): m/z 458.9 (M+H)$^+$.

Example 126 (Compound 129)

1-((9-Methyl-6-(4-(trifluoromethoxy)phenyl)-9H-purin-2-yl)methyl)-3-methylenepyrrolidin-2-one

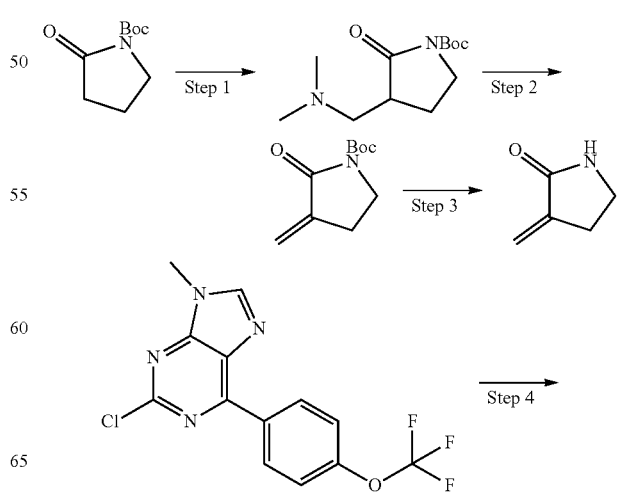

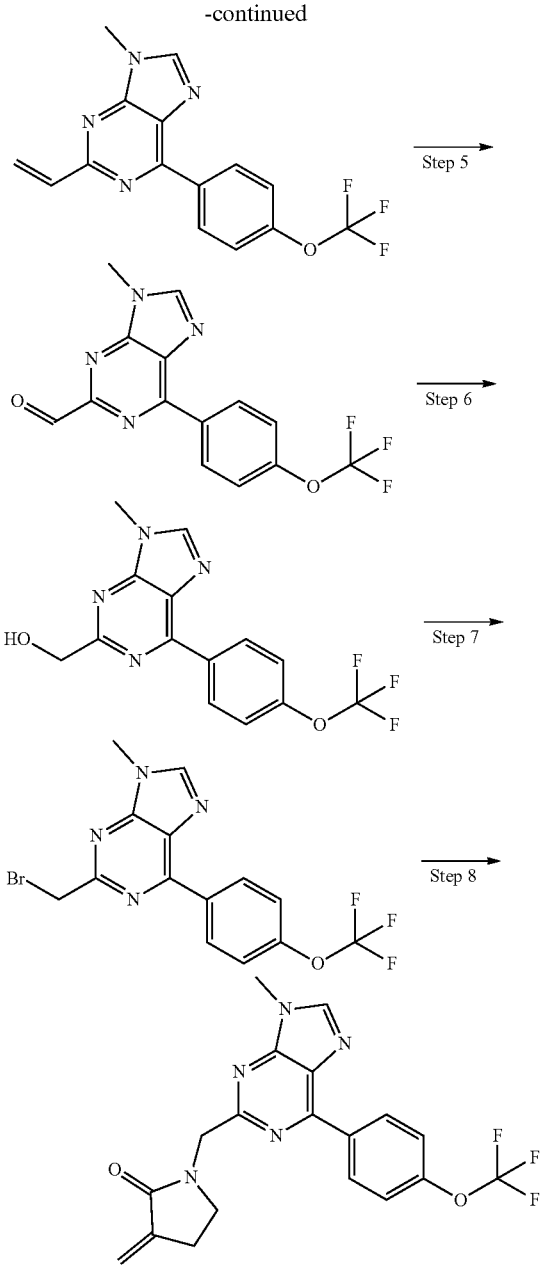

Step 5

Step 6

Step 7

Step 8

Step 1: tert-butyl 3-((dimethylamino)methyl)-2-oxopyrrolidine-1-carboxylate

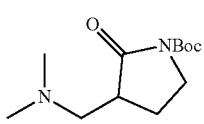 [SMILES: CN(C)CC1CCN(C(=O)OC(C)(C)C)C1=O]

To a solution of tert-butyl 2-oxopyrrolidine-1-carboxylate (2.0 g, 10.8 mmol) in THF (25 mL) was added LiHMDS (14.04 mL, 14.04 mmol, 1.0 M/L in THF) at −78° C. for 10 min. The solution was stirred at −78° C. for 1 h and N-methyl-N-methylenemethanaminium iodide (3.0 g, 16.2 mmol) was added into it at −78° C. The mixture was stirred at −78° C. for 1 h and warmed up to 0° C. The reaction was quenched with saturated aqueous NH$_4$Cl (100 mL) and water (50 mL) and extracted with ethyl acetate (150 mL×3). The organic extracts were combined, dried over MgSO$_4$, filtered and concentrated in vacuo to afford the title compound (2.5 g, 93%) as a brown oil. The crude product was used directly for next step.

Step 2: tert-butyl 3-methylene-2-oxopyrrolidine-1-carboxylate

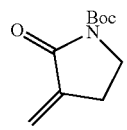

To a solution of tert-butyl 3-((dimethylamino)methyl)-2-oxopyrrolidine-1-carboxylate (2.5 g, 10.32 mmol) in ethanol (100 mL) was added 3-bromoprop-1-ene (0.89 mL, 10.32 mmol) and Na$_2$CO$_3$ (1.09 g, 10.32 mmol) at room temperature. The mixture was stirred at room temperature for 3d. The mixture was diluted with ethyl acetate (100 mL) and the residual solid Na$_2$CO$_3$ was removed by filtration. The reaction was then quenched with saturated aqueous NH$_4$Cl (200 mL) and extracted with ethyl acetate (300 mL). The organic layers were combined, dried over MgSO$_4$ and concentrated in vacuo. The residue was purified by flash column chromatography on silica gel (0-30% ethyl acetate in petroleum ether) to afford the title compound (1.3 g, 51%) as a slightly yellow oil that solidified on standing. $^1$H NMR (400 MHz, CDCl$_3$): δ 6.22-6.19 (m, 1H), 5.51-5.46 (m, 1H), 3.78-3.69 (m, 2H), 2.80-2.71 (m, 2H), 1.57 (s, 9H).

Step 3: 3-methylenepyrrolidin-2-one

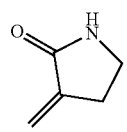

A solution of tert-butyl 3-methylene-2-oxopyrrolidine-1-carboxylate (1.3 g, 6.59 mmol) and TFA (2.54 mL, 32.96 mmol) in DCM (20 mL) was stirred at room temperature for 2 h. The reaction mixture was quenched with aq.NaHCO$_3$ (10 mL), extracted with ethyl acetate (20 mL×3). Combined organic layers were dried over Na$_2$SO$_4$, filtered and concentrated to afford the title compound (400 mg, 63%) as a light yellow solid. $^1$H NMR (400 MHz, CDCl$_3$): δ 6.82 (s, 1H), 6.00 (t, J=2.8 Hz, 1H), 5.38 (s, 11H), 3.45 (t, J=6.8 Hz, 2H), 2.90-2.82 (m, 2H).

Step 4: 9-methyl-6-(4-(trifluoromethoxy)phenyl)-2-vinyl-9H-purine

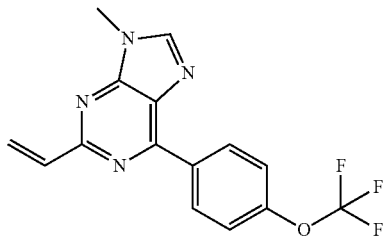 [SMILES: C=Cc1nc(-c2ccc(OC(F)(F)F)cc2)c2ncn(C)c2n1]

A solution of Xphos (276 mg, 0.58 mmol), Xphos Pd G$_2$ (550 mg, 0.58 mmol), 4,4,5,5-tetramethyl-2-vinyl-1,3,2-dioxaborolane (1.34 g, 8.67 mmol), KOAc (568 mg, 5.78 mmol) and 2-chloro-9-methyl-6-(4-(trifluoromethoxy)phenyl)-9H-purine (1.9 g, 5.78 mmol) in 1,4-dioxane (60 mL) and water (3 mL) was stirred at 100° C. for 6 h. The mixture was diluted with ethyl acetate (500 mL) and washed with water (300 mL×3). The organic layer was dried over Na$_2$SO$_4$ and concentrated. The residue was purified by flash chromatography on silica gel (0-15% ethyl acetate in petroleum ether) to afford the title compound (1.6 g, 79%) as a white solid. $^1$H NMR (400 MHz, CDCl$_3$): (S 8.91 (d, J=8.8 Hz, 2H), 8.08 (s, 1H), 7.40 (d, J=8.4 Hz, 2H), 7.03 (dd, J=17.6, 10.4 Hz, 1H), 6.77 (dd, J=17.2, 1.6 Hz, 1H), 5.76 (dd, J=10.4, 1.6 Hz, 1H), 5.95 (s, 3H); LCMS (ESI): m/z 320.9 (M+H).

Step 5: 9-methyl-6-(4-(trifluoromethoxy)phenyl)-9H-purine-2-carbaldehyde

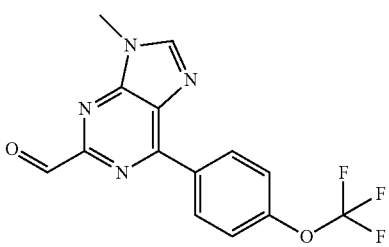 [SMILES: Cn1cnc2c(-c3ccc(OC(F)(F)F)cc3)nc(C=O)nc21]

To a solution of 9-methyl-6-(4-(trifluoromethoxy)phenyl)-2-vinyl-9H-purine (1.8 g, 5.62 mmol) and NaIO$_4$ (4.81 g, 22.48 mmol) in THF (20 mL) was added K$_2$OsO$_4$·2H$_2$O (190 mg, 0.56 mmol) at 0° C. The resulting mixture was stirred at room temperature for 12 h. The mixture was diluted with ethyl acetate (50 mL), washed with Na$_2$SO$_3$ solution (10 mL) and water (30 mL×3). The organic was dried over Na$_2$SO$_4$ and concentrated to afford the title compound (1.2 g, 66%) as a white solid. $^1$H NMR (400 MHz, DMSO-d$_6$): δ 10.14 (s, 1H), 9.02 (d, J=8.8 Hz, 2H), 8.90 (s, 1H), 7.65 (d, J=8.8 Hz, 2H), 3.96 (s, 3H); LCMS (ESI): m/z 323.0 (M+H)$^+$.

Step 6: (9-methyl-6-(4-(trifluoromethoxy)phenyl)-9H-purin-2-yl)methanol

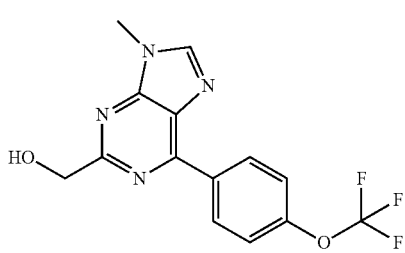 [SMILES: Cn1cnc2c(-c3ccc(OC(F)(F)F)cc3)nc(CO)nc21]

To a solution of 9-methyl-6-(4-(trifluoromethoxy)phenyl)-9H-purine-2-carbaldehyde (1.0 g, 3.1 mmol) in THF (10 mL) was added NaBH$_4$ (117 mg, 3.1 mmol) at 0° C. The mixture was stirred at 0° C. for 35 min. The reaction was quenched with sat.NH$_4$C$_1$ (10 mL) and extracted with ethyl acetate (10 mL), the organic layer was dried with Na$_2$SO$_4$ and concentrated under vacuum. The residue was purified by column chromatography on silica gel (0-50% ethyl acetate in petroleum ether) to afford the title compound (510 mg, 47%) as a yellow solid. $^1$H NMR (400 MHz, DMSO-d$_6$): δ 9.01 (d, J=8.8 Hz, 2H), 8.62 (s, 1H), 7.60 (d, J=8.8 Hz, 2H), 5.36 (t, J=6.4 Hz, 1H), 4.76 (d, J=6.4 Hz, 2H), 3.88 (s, 3H); LCMS (ESI): m/z 325.1 (M+H)$^+$.

Step 7: 2-(bromomethyl)-9-methyl-6-(4-(trifluoromethoxy)phenyl)-9H-purine

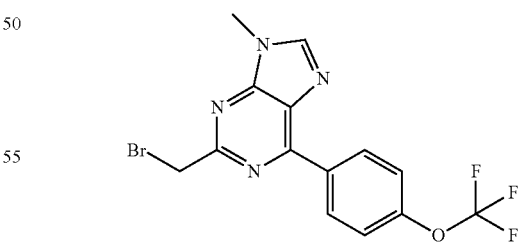

To a solution of (9-methyl-6-(4-(trifluoromethoxy)phenyl)-9H-purin-2-yl)methanol (200 mg, 0.62 mmol) in DCM (5 mL) was added PBr$_3$ (0.03 mL, 0.31 mmol) at 0° C. The reaction was stirred at 0° C. for 2 h. The reaction mixture was concentrated under vacuum to afford the title product (200 mg, crude) as a yellow solid which was used directly for the next step.

605

Step 8: 1-((9-methyl-6-(4-(trifluoromethoxy)phenyl)-9H-purin-2-yl)methyl)-3-methylenepyrrolidin-2-one

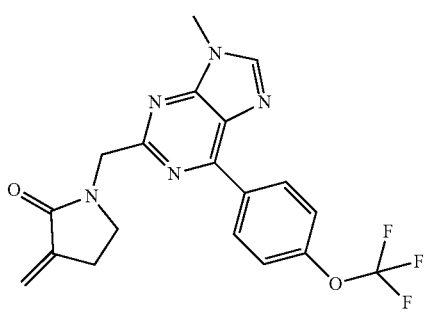 [SMILES: C=C1CCN(Cc2nc(-c3ccc(OC(F)(F)F)cc3)c3ncn(C)c3n2)C1=O]

To a solution of 3-methylenepyrrolidin-2-one (50 mg, 0.52 mmol) in THF (2 mL) was added NaH (60% in mineral oil, 42 mg, 1.03 mmol) at 0° C., the mixture was stirred at 0° C. for 30 min. And then 2-(bromomethyl)-9-methyl-6-(4-(trifluoromethoxy)phenyl)-9H-purine (200 mg, 0.52 mmol) in THF (2 mL) was added into it at 0° C., the mixture was stirred at room temperature for 12 h. The reaction was quenched with ice water (20 mL) and extracted with ethyl acetate (20 mL×2), the organic layer was dried with Na$_2$SO$_4$ and concentrated under vacuum, the residue was purified by reverse phase chromatography (Boston Green ODS 150*30 mm*5umwater(0.225% FA)-ACN,45%-75%) to afford the title compound (25.3 mg, 12%) as white solid. $^1$H NMR (400 MHz, DMSO-d$_6$): δ 9.00-8.92 (m, 2H), 8.69 (s, 1H), 7.64 (d J=8.0 Hz, 2H), 5.86-5.83 (m, 1H), 5.46-5.43 (m, 1H), 4.90 (s, 2H), 3.90 (s, 3H), 3.67 (t, J=6.8 Hz, 2H), 2.93-2.83 (m, 2H); LCMS (ESI): m/z 403.9(M+H)$^+$.

Example 127 (Compound 130) N-((9-Methyl-6-(4-(trifluoromethyl)piperidin-1-yl)-9H-purin-2-yl)methyl)acrylamide

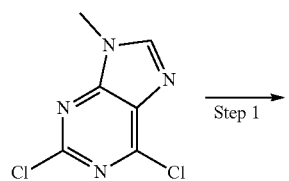

Step 1 →

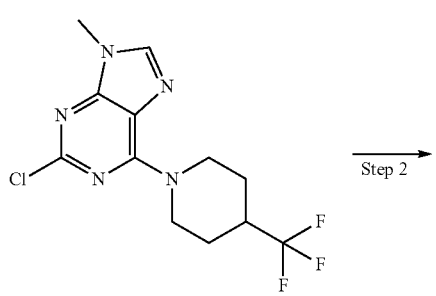

606

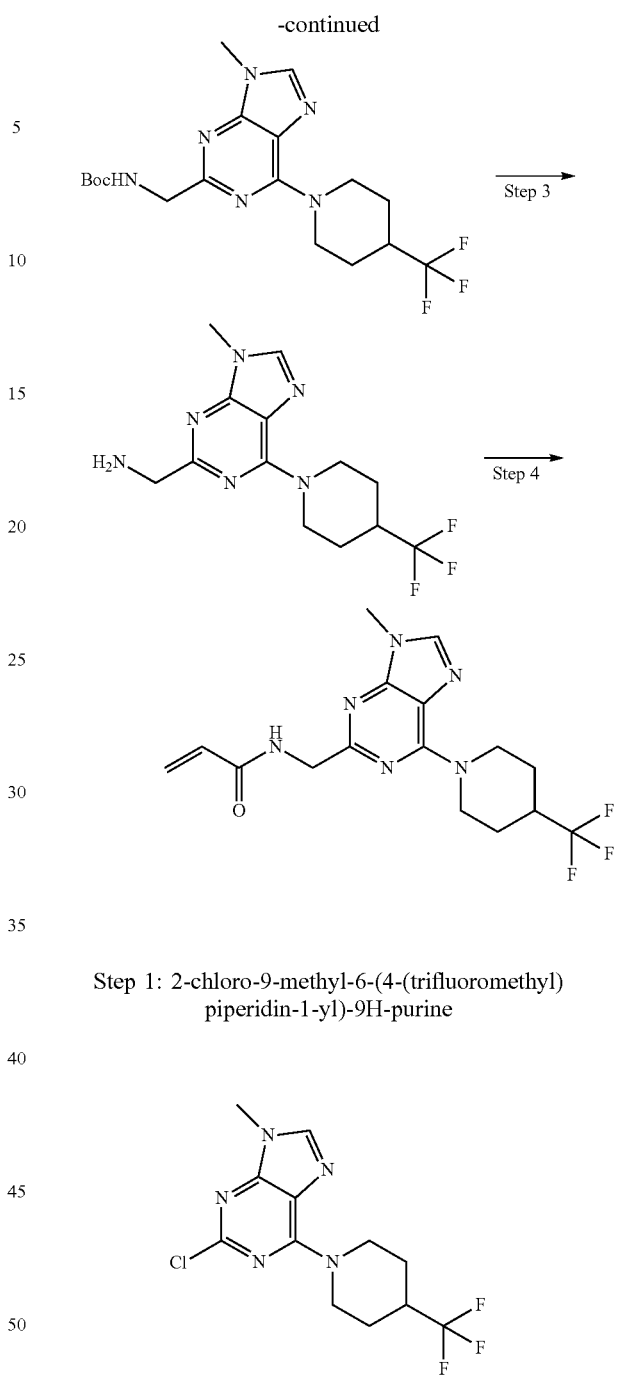

Step 1: 2-chloro-9-methyl-6-(4-(trifluoromethyl)piperidin-1-yl)-9H-purine

A mixture of 2,6-dichloro-9-methyl-9H-purine (200 mg, 0.99 mmol) and 4-(trifluoromethyl)piperidine (226 mg, 1.48 mmol) in acetonitrile (4 mL) was stirred at room temperature for 16 hours. The mixture was quenched with water (20 mL), extracted with ethyl acetate (20 mL×3), the organic layer was washed with water (40 mL×3), dried over Na$_2$SO$_4$ and concentrated. The residue was purified by flash chromatography on silica gel (0-24% ethyl acetate in petroleum ether) to afford the title compound (200 mg, 64% ) as a white solid.. $^1$H NMR (400 MHz, CDCl$_3$): δ 7.68 (s, 1H), 5.59-5.56 (m, 2H), 3.79 (s, 3H), 3.10-3.06 (m, 2H), 2.44-2.35 (m, 1H), 2.03-2.00 (m, 2H), 1.71-1.61 (m, 2H); LCMS (ESI): m/z 319.9 (M+H)$^+$.

Step 2: tert-butyl ((9-methyl-6-(4-(trifluoromethyl) piperidin-1-yl)-9H-purin-2-yl)methyl)carbamate

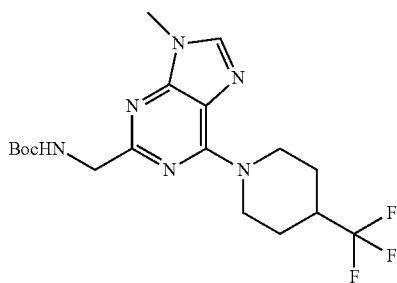 [SMILES: Cn1cnc2c(N3CCC(C(F)(F)F)CC3)nc(CNC(=O)OC(C)(C)C)nc21]

A mixture of 2-chloro-9-methyl-6-(4-(trifluoromethyl)piperidin-1-yl)-9H-purine (200 mg, 0.63 mmol), CATACXIUM A Pd G$_2$ (42 mg, 0.06 mmol), Cs$_2$CO$_3$ (611 mg, 1.88 mmol) and potassium (((tert-butoxycarbonyl)amino) methyl)trifluoroborate (223 mg, 0.94 mmol) in 1,4-dioxane (4 mL) and water (0.4 mL) was stirred at 100° C. for 16 hours under N$_2$ atmosphere. The solution was quenched with water (20 mL) and extracted with ethyl acetate (20 mL×3), the combined organic layers were washed with water (40 mL×3), dried over Na$_2$SO$_4$, filtered and concentrated. The residue was purified by flash chromatography on silica gel (0-50% ethyl acetate in petroleum ether) to afford the title compound (140 mg, 54%) as a yellow oil. $^1$H NMR (400 MHz, CDCl$_3$): δ 7.69 (s, 1H), 5.64-5.59 (m, 3H), 4.42-4.40 (m, 2H), 3.80 (s, 3H ), 3.07-3.00 (m, 2H), 2.41-2.37 (m, 1H), 2.05-2.00 (m, 2H), 1.70-1.63 (m, 2H), 1.50 (s, 9H); LCMS (ESI): m/z 415.1 (M+H)$^+$.

Step 3: (9-methyl-6-(4-(trifluoromethyl)piperidin-1-yl)-9H-purin-2-yl)methanamine 2,2,2-trifluoroacetate

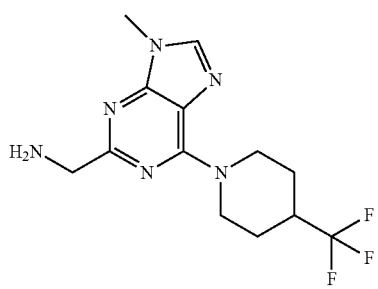 [SMILES: Cn1cnc2c(N3CCC(C(F)(F)F)CC3)nc(CN)nc21]

A solution of tert-butyl ((9-methyl-6-(4-(trifluoromethyl) piperidin-1-yl)-9H-purin-2-yl)methyl)carbamate (140 mg, 0.34 mmol) and 5% TFA in HFIP (5 mL) was stirred at room temperature for 16 hours. The mixture was concentrated directly to afford the title compound (140 mg, crude) as a yellow oil. LCMS (ESI): m/z 314.9 (M+H)$^+$.

Step 4: N-((9-methyl-6-(4-(trifluoromethyl)piperidin-1-yl)-9H-purin-2-yl)methyl)acrylamide

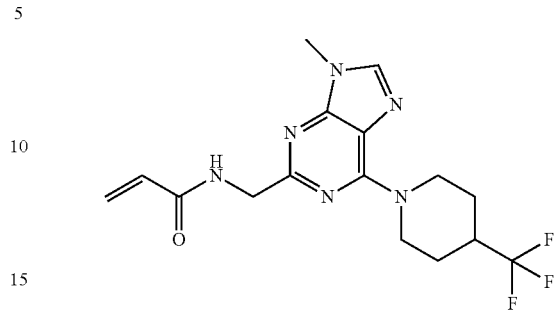

To a solution of (9-methyl-6-(4-(trifluoromethyl)piperidin-1-yl)-9H-purin-2-yl)methanamine 2,2,2-trifluoroacetate (140 mg, 0.33 mmol) in THF (4 mL) was added acrylic anhydride (45 mg, 0.36 mmol) and sat.NaHCO$_3$ (3 mL) at 0° C. The mixture was stirred at 0° C. for 1 hour. The reaction was quenched with water (10 mL) and extracted with ethyl acetate (20 mL×3), the combined organic layers were washed with water (40 mL×3), dried over Na$_2$SO$_4$, filtered and concentrated. The residue was purified by reverse phase chromatography (Boston Green ODS 150*30 mm*5 um/water(0.225% FA)-ACN/30%-60%) to afford the title compound (62 mg, 52%) as a white solid. $^1$H NMR (400 MHz, DMSO-d$_6$) δ 8.46 (t, J=5.6 Hz, 1H), 8.11 (s, 1H), 6.39 (dd, J=17.2, 10.4 Hz, 1H), 6.10 (dd, J=17.2, 2.0 Hz, 1H), 5.61 (dd, J=10.4, 2.0 Hz, 1H), 5.58-5.48 (m, 2H), 4.37 (d, J=6.0 Hz, 2H), 3.71 (s, 3H), 3.10-3.03 (m, 2H), 2.75-2.67 (m, 1H), 1.93-1.90 (m, 2H), 1.45-1.35 (m, 2H); LCMS (ESI): m/z 369.0 (M+H)$^+$.

Example 128 (Compound 131) N-((9-Methyl-6-(4-(trifluoromethoxy)piperidin-1-yl)-9H-purin-2-yl) methyl)acrylamide

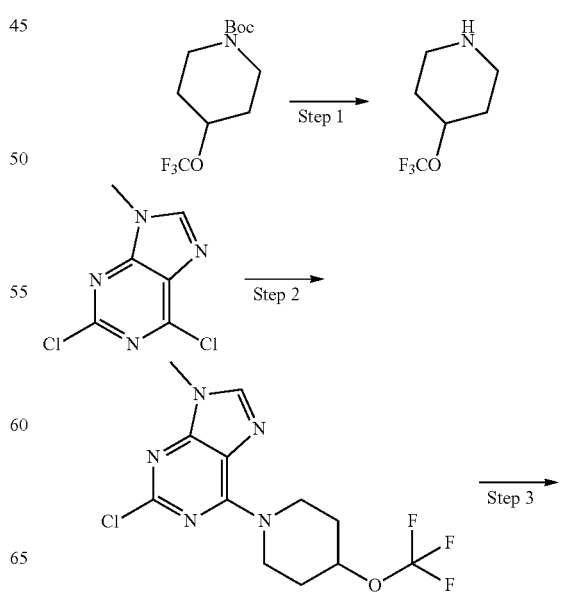

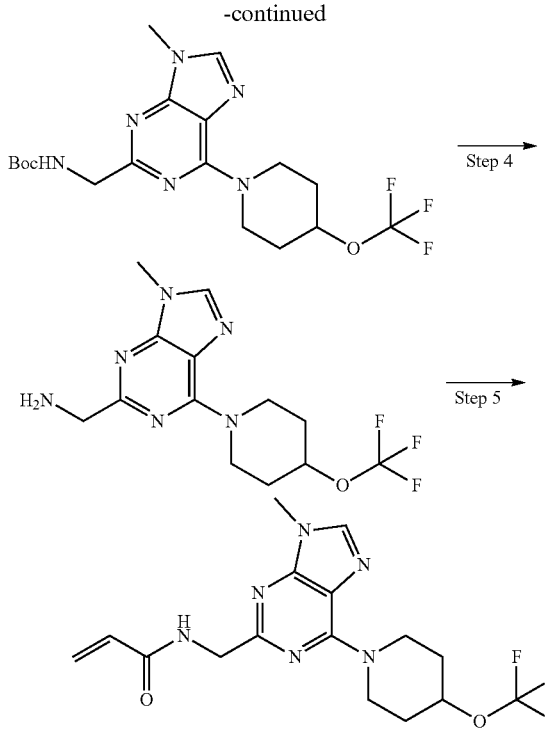

Step 1: 4-(trifluoromethoxy)piperidine 2,2,2-trifluoroacetate

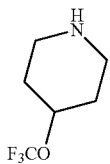

To a solution of tert-butyl 4-(trifluoromethoxy)piperidine-1-carboxylate (330 mg, 1.23 mmol) was added 5% TFA in HFIP (4 mL) at room temperature, the solution was stirred at room temperature for 16 hours, the solution was concentrated under vacuo to afford the title compound (207 mg, crude), the residue was used directly for the next.

Step 2: 2-chloro-9-methyl-6-(4-(trifluoromethoxy) piperidin-1-yl)-9H-purine

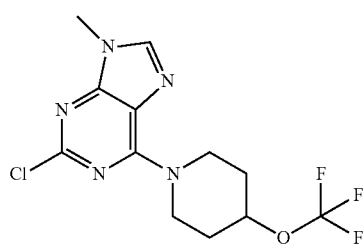 [SMILES: Cn1cnc2c(N3CCC(OC(F)(F)F)CC3)nc(Cl)nc21]

To a solution of 4-(trifluoromethoxy)piperidine 2,2,2-trifluoroacetate (207 mg, 1.11 mmol) in acetonitrile (10 mL) was added DIPEA (0.64 mL, 3.67 mmol) and 2,6-dichloro-9-methyl-9H-purine (173 mg, 0.86 mmol) at room temperature, the solution was stirred at room temperature for 6 hours. The solution was diluted with water (50 mL) and extracted with ethyl acetate (50 mL×3), the organic layer was dried with anhydrous Na$_2$SO$_4$, filtered and concentrated under vacuo, the residue was purified by column chromatography on silica gel (0-20% ethyl acetate in petroleum ether) to afford the title compound as a white solid. $^1$H NMR (400 MHz, CDCl$_3$): δ 7.68 (s, 1H), 4.60-4.10 (m, 5H), 3.79 (s, 3H), 2.09-2.04 (m, 2H), 1.97-1.92 (m, 2H); LCMS (ESI): m/z 336.1 (M+H)$^+$.

Step 3: tert-butyl ((9-methyl-6-(4-(trifluoromethoxy)piperidin-1-yl)-9H-purin-2-yl)methyl) carbamate

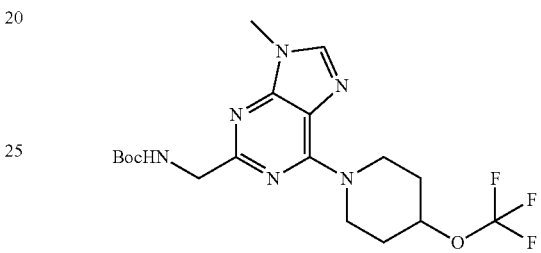

A mixture of 2-chloro-9-methyl-6-(4-(trifluoromethoxy) piperidin-1-yl)-9H-purine (200 mg, 0.60 mmol), CAT-ACXIUM A Pd G$_2$ (39 mg, 0.06 mmol), Cs$_2$CO$_3$ (582 mg, 1.79 mmol) and potassium (((tert-butoxycarbonyl)amino) methyl)trifluoroborate (212 mg, 0.89 mmol) in 1,4-dioxane (5 mL) and water (0.5 mL) was stirred at 120° C. for 4 hours under N$_2$ atmosphere. The solution was quenched with water (20 mL) and extracted with ethyl acetate (20 mL×2), the combined organic layers were washed with water (40 mL), dried over Na$_2$SO$_4$, filtered and concentrated. The residue was purified by flash chromatography on silica gel (0-50% ethyl acetate in petroleum ether) to afford the title compound (140 mg, 54%) as a yellow solid. $^1$H NMR (400 MHz, CDCl$_3$): δ 7.69 (s, 1H), 5.63 (s, 1H), 4.65-4.62 (m, 2H), 4.59-4.54 (m, 1H), 4.42 (d, J=4.8 Hz, 2H), 4.10-4.06 (m, 2H), 3.80 (s, 3H), 2.09-2.05 (m, 2H), 1.95-1.88 (m, 2H), 1.50 (s, 9H); LCMS (ESI): m/z 431.0 (M+H)$^+$.

Step 4: (9-methyl-6-(4-(trifluoromethoxy)piperidin-1-yl)-9H-purin-2-yl)methanamine 2,2,2-trifluoroacetate

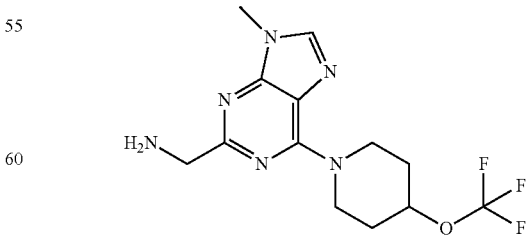

A solution of tert-butyl ((9-methyl-6-(4-(trifluoromethoxy)piperidin-1-yl)-9H-purin-2-yl)methyl)carbamate (110 mg, 0.26 mmol) and 5% TFA in HFIP (2 mL) was stirred at room temperature for 2 hours, the solution was concentrated under vacuo to afford the title compound (84 mg, crude) and directly used for the next.

Step 5: N-((9-methyl-6-(4-(trifluoromethoxy)piperidin-1-yl)-9H-purin-2-yl)methyl)acrylamide

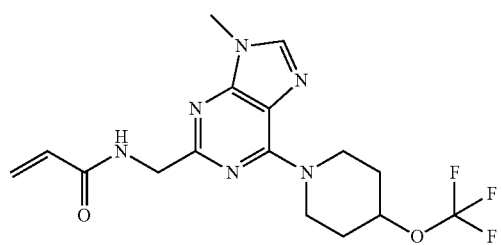 [SMILES: C=CC(=O)NCc1nc(N2CCC(OC(F)(F)F)CC2)c2ncn(C)c2n1]

To a solution of (9-methyl-6-(4-(trifluoromethoxy)piperidin-1-yl)-9H-purin-2-yl)methanamine 2,2,2-trifluoroacetate (84 mg, 0.25 mmol) in THF (3 mL) was added sat. NaHCO$_3$ (2 mL) and acryloyl chloride (0.03 mL, 0.38 mmol) at 0° C., the mixture was stirred at 0° C. for 30 minutes, the solution was quenched with water (10 mL) and extracted with ethyl acetate (10 mL×3), the organic layer was dried with anhydrous Na$_2$SO$_4$, filtered and concentrated under vacuo. The residue was purified by reverse phase chromatography (Boston Green ODS 150*30 mm*5 um, water(0.225% FA)-CAN, 60%-90%) to afford the title compound (31.9 mg, 32%) as a white solid.

$^1$H NMR (400 MHz, DMSO-d$_6$): δ 8.46 (t, J=5.6 Hz, 1H), 8.11 (s, 1H), 6.39 (dd, J=17.2 Hz, 10.4 Hz, 1H), 6.10 (dd, J=17.2 Hz, 2.4 Hz, 1H), 5.61 (dd, J=10.4 Hz, 2.0 Hz, 1H), 4.78-4.73 (m, 3H), 4.37 (d, J=5.6 Hz, 2H), 3.86-3.81 (m, 2H), 3.71 (s, 3H), 2.07-2.03 (m, 2H), 1.73-1.67 (m, 2H), LCMS (ESI): m/z 384.9 (M+H)$^+$.

Example 129 (Compound 132) 1-(3-(9-(Difluoromethyl)-6-(4-(trifluoromethoxy)phenyl)-9H-purin-2-yl)azetidin-1-yl)-2-fluoroprop-2-en-1-one

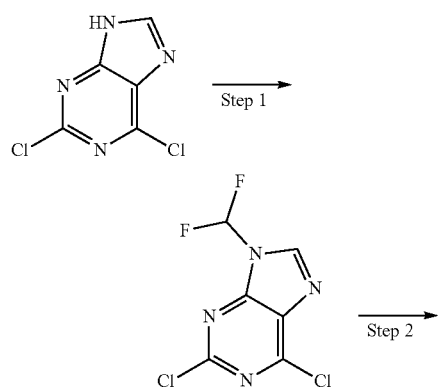

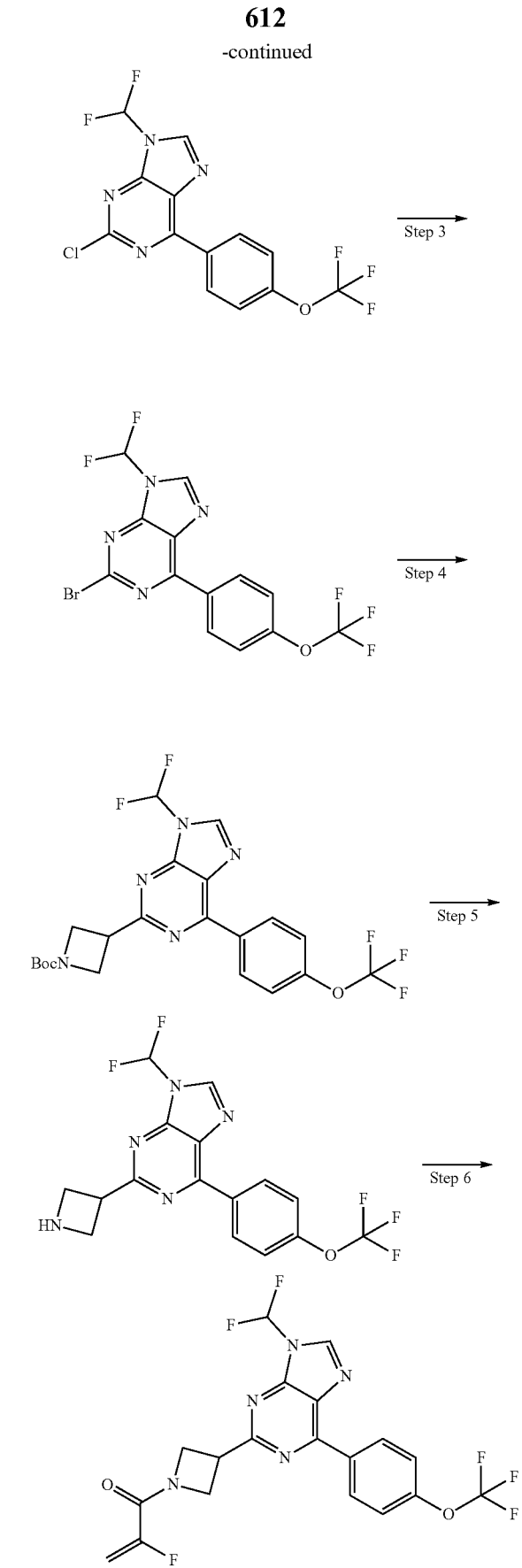

Step 1: 2,6-dichloro-9-(difluoromethyl)-9H-purine

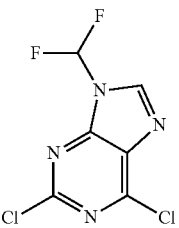 [SMILES: FC(F)n1cnc2c(Cl)nc(Cl)nc21]

A mixture of 2,6-dichloro-9H-purine (10.0 g, 52.91 mmol), K$_3$PO$_4$ (22.5 g, 105.82 mmol) and ethyl 2-bromo-2,2-difluoroacetate (10.0 mL, 79.37 mmol) in DMF (100 mL) was stirred at room temperature for 3 h. The mixture was diluted with ethyl acetate (200 mL), washed with water (200 mL×2) and brine (100 mL). The organic layer was dried over Na$_2$SO$_4$ and evaporated in vacuo. The residue was purified by flash chromatography on silica gel (0-20% ethyl acetate in petroleum ether) to afford the title compound (2.4 g, 19%) as a white oil. $^1$H NMR (400 MHz, CDCl$_3$): b 8.47 (s, 1H), 7.62 (t, J=58.8 Hz, 1H).

Step 2: 2-chloro-9-(difluoromethyl)-6-(4-(trifluoromethoxy)phenyl)-9H-purine

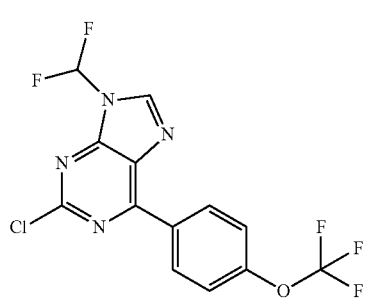 [SMILES: FC(F)n1cnc2c(-c3ccc(OC(F)(F)F)cc3)nc(Cl)nc21]

A solution of 2,6-dichloro-9-(difluoromethyl)-9H-purine (1.0 g, 4.18 mmol) and (4-(trifluoromethoxy)phenyl)boronic acid (430 mg, 2.09 mmol), K$_3$P04 (1.8 g, 8.37 mmol) and Pd(dppf)Cl$_2$ (306 mg, 0.42 mmol) in 1,4-dioxane (10 mL) and water (1 mL) was stirred at 90° C. for 2 hours under N$_2$ atmosphere. The resulting solution was diluted with water (150 mL), extracted with ethyl acetate (100 mL). The combined organic layers were dried over Na$_2$SO$_4$ and concentrated in vacuo. The residue was purified by flash chromatography on silica gel (0-10% ethyl acetate in petroleum ether) to afford the title compound (1.5 g, 98%) as a white solid. $^1$H NMR (400 MHz, CDCl$_3$): δ 8.81 (d, J=8.8 Hz, 2H), 8.36 (s, 1H), 7.58 (t, J=59.2 Hz, 1H), 7.33 (d, J=8.8 Hz, 2H).

Step 3: 2-bromo-9-(difluoromethyl)-6-(4-(trifluoromethoxy)phenyl)-9H-purine

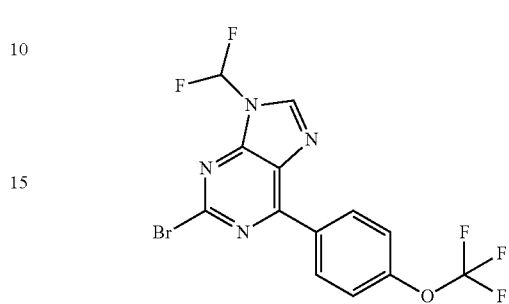

A mixture of 33% HBr in AcOH (3 mL) and 2-chloro-9-(difluoromethyl)-6-(4-(trifluoromethoxy)phenyl)-9H-purine (1.5 g, 4.11 mmol) was stirred at 80° C. for 5 h. The reaction mixture was concentrated under reduced pressure. The mixture was diluted with water (100 mL) and adjusted to pH=8 by sat.NaHCO$_3$. The mixture was extracted with ethyl acetate (100 mL×5), the combined organic layers were dried over Na$_2$SO$_4$ and concentrated in vacuo to afford the title compound (1.0 g, crude) as a white solid. The crude was used for next step without further purification. LCMS (ESI): m/z 409.0 (M+H)$^+$.

Step 4: tert-butyl3-(9-(difluoromethyl)-6-(4-(trifluoromethoxy)phenyl)-9H-purin-2-yl)azetidine-1-carboxylate

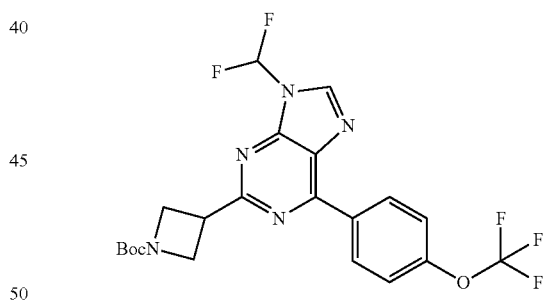

In a glove box, to a mixture of 2-bromo-9-(difluoromethyl)-6-(4-(trifluoromethoxy)phenyl)-9H-purine (250 mg, 0.64 mmol), Na$_2$CO$_3$ (170 mg, 1.59 mmol) in DME (10 mL) was added NiCl$_2$·glyme (14 mg, 0.06 mmol), tert-butyl 3-bromoazetidine-1-carboxylate (226 mg, 0.96 mmol) and dtbbpy (25 mg, 0.10 mmol). The solution of TTMSS (190 mg, 0.760 mmol) and Ir[dF(CF$_3$)ppy]$_2$(dtbbpy)PF$_6$ (7 mg, 0.01 mmol) in DME (4 mL) was added into the mixture at room temperature. The reaction mixture was stirred under a Lumidox Screen Kit at room temperature for 16 hours. Added water (20 mL) and extracted with ethyl acetate (40 ml×3), the combined organic layers were dried over sodium sulfate, concentrated. The residue was purified by pre-TLC (30% ethyl acetate in petroleum ether) to afford the title compound (250 mg, 84%) as a green solid. LCMS (ESI): m/z 430.0 (M+H−56)$^+$.

Step 5: 2-(azetidin-3-yl)-9-(difluoromethyl)-6-(4-(trifluoromethoxy)phenyl)-9H-purine

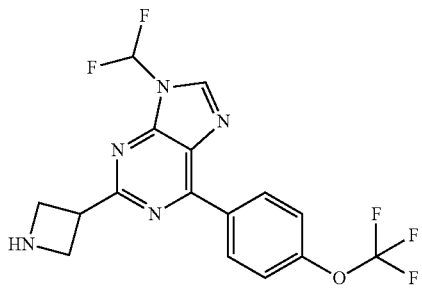 [SMILES: FC(F)n1cnc2c(-c3ccc(OC(F)(F)F)cc3)nc(C3CNC3)nc21]

A mixture of tert-butyl 3-(9-(difluoromethyl)-6-(4-(trifluoromethoxy)phenyl)-9H-purin-2-yl)azetidine-1-carboxylate (220 mg, 0.45 mmol) and 5% TFA in HFIP (20 mL) was stirred at room temperature for 16 h. The reaction was diluted with water (50 mL) and adjusted to pH=8 with sat.NaHCO$_3$, the mixture was extracted with ethyl acetate (50 mL×3), the combined organic layers were dried over Na$_2$SO$_4$ and concentrated under vacuum to afford the title compound (170 mg, crude) as a white solid. The crude was used for next step without further purification.

Step 6: 1-(3-(9-(difluoromethyl)-6-(4-(trifluoromethoxy)phenyl)-9H-purin-2-yl)azetidin-1-yl)-2-fluoroprop-2-en-1-one

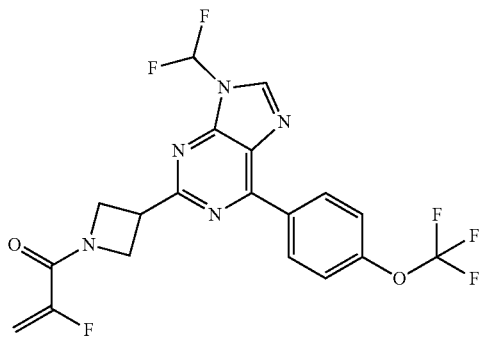 [SMILES: C=C(F)C(=O)N1CC(c2nc(-c3ccc(OC(F)(F)F)cc3)c3ncn(C(F)F)c3n2)C1]

A mixture of 2-(azetidin-3-yl)-9-(difluoromethyl)-6-(4-(trifluoromethoxy)phenyl)-9H-purine (220 mg, 0.63 mmol), 2-fluoroacrylic acid (86 mg, 0.95 mmol) and ethyl 2-ethoxyquinoline-1(2H)-carboxylate (235 mg, 0.95 mmol) in DCM (10 mL) and methanol (2 mL) was stirred at room temperature for 16 h. The mixture was diluted with ethyl acetate (100 mL) and washed with water (100 mL×3). The organic was dried over Na$_2$SO$_4$ and concentrated. The residue was purified by reverse phase chromatography (Welch Xtimate C18 150*30 mm*5 um, water(0.225% FA)-ACN, 42-72%) to afford the title compound (25.6 mg, 9%) as a white solid. $^1$H NMR (400 MHz, DMSO-d$_6$): δ 9.09 (s, 1H), 8.93 (d, J=8.8 Hz, 2H), 8.18 (t, J=58.4 Hz, 1H), 7.66 (d, J=8.8 Hz, 2H), 5.53 (dd, J=48.4, 3.6 Hz, 1H), 5.34 (dd, J=16.4, 3.6 Hz, 1H), 4.92-4.81 (m, 1H), 4.77-4.70 (m, 1H), 4.52-4.44 (m, 1H), 4.42-4.29 (m, 2H); LCMS (ESI): m/z 458.0 (M+H)$^+$.

Example 130 (Compound 133)

N-((9-Methyl-2-(4-(trifluoromethoxy)phenyl)-9H-purin-6-yl)methyl)acrylamide

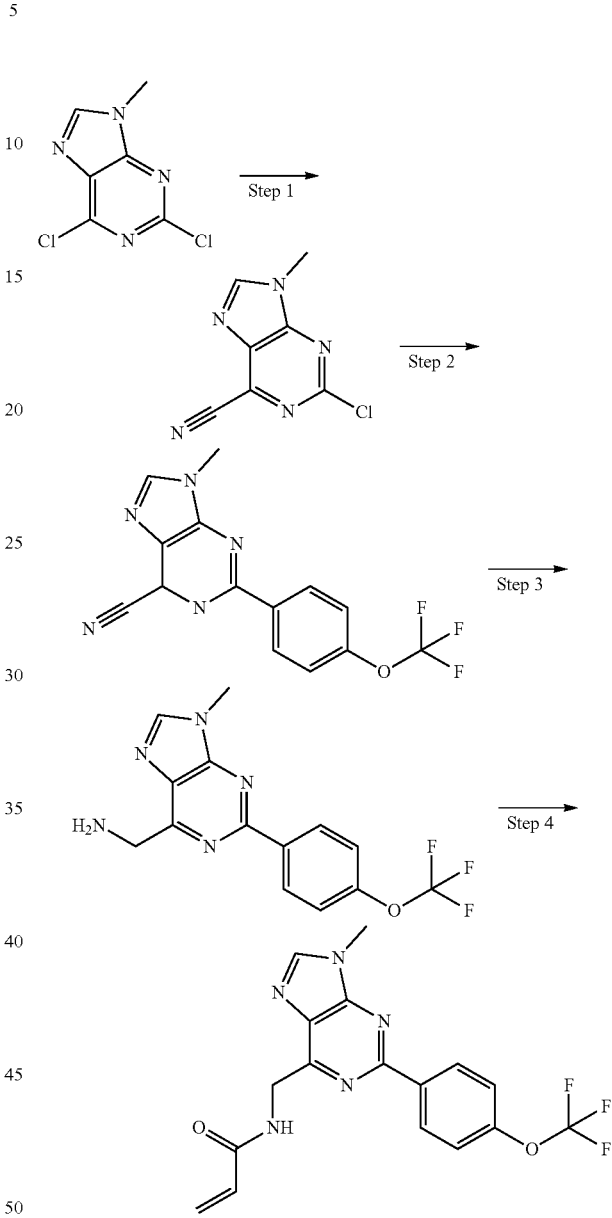

Step 1: 2-chloro-9-methyl-9H-purine-6-carbonitrile

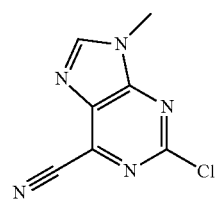

To a solution of 2,6-dichloro-9-methyl-9H-purine (2.0 g, 9.85 mmol) in DMF (20 mL) and H$_2$O (4 mL) was added DABCO (110 mg, 0.98 mmol) and NaCN (579 mg, 11.82 mmol) at 0° C. The mixture was stirred at 0° C. for 2 h under N₂ atmosphere. The reaction was poured into water (25 mL) and extracted with ethyl acetate (20 mL×3). The combined organic phase was washed with brine (40 mL×2), dried with anhydrous Na₂SO₄, filtered and concentrated in vacuum. The residue was purified by column chromatography on silica gel (50-100% ethyl acetate in petroleum ether) to afford the title compound (1.35 g, 70%) as a pink solid. ¹H NMR (400 MHz, CDCl₃): δ 8.29 (s, 1H), 3.98 (s, 3H).

Step 2: 9-methyl-2-(4-(trifluoromethoxy)phenyl)-9H-purine-6-carbonitrile

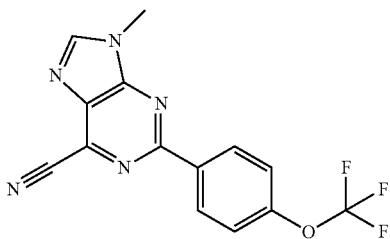 [SMILES: Cn1cnc2c(C#N)nc(-c3ccc(OC(F)(F)F)cc3)nc21]

To a solution of 2-chloro-9-methyl-9H-purine-6-carbonitrile (1.35 g, 6.97 mmol) and (4-(trifluoromethoxy)phenyl boronic acid (2.15 g, 10.46 mmol) in dioxane (15 mL) and H₂O (3 mL) was added K₃PO₄ (4.44 g, 20.92 mmol) and Xphos Pd G₂ (548 mg, 0.69 mmol). The mixture was stirred at 100° C. for 16 h under N₂ atmosphere. The reaction was poured into water (20 mL). The aqueous phase was extracted with ethyl acetate (15 mL×3). The combined organic phase was washed with brine (10 mL×2), dried with anhydrous Na₂SO₄, filtered and concentrated in vacuum. The residue was purified by column chromatography on silica gel (50-100% ethyl acetate in petroleum ether) to afford the title compound (750 mg, 33%) as a yellow solid. ¹H NMR (400 MHz, CDCl₃): δ 8.57 (d, J=8.8 Hz, 2H), 8.25 (s, 1H), 7.34 (d, J=8.4 Hz, 2H), 4.03 (s, 3H).

Step 3: (9-methyl-2-(4-(trifluoromethoxy)phenyl)-9H-purin-6-yl)methanamine

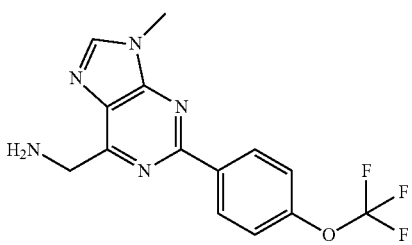 [SMILES: Cn1cnc2c(CN)nc(-c3ccc(OC(F)(F)F)cc3)nc21]

To a solution of 9-methyl-2-(4-(trifluoromethoxy)phenyl)-9H-purine-6-carbonitrile (750 mg, 2.35 mmol) and NiCl₂·6H₂O (558 mg, 2.35 mmol) in methanol (12 mL) was added NaBH₄ (266 mg, 7.05 mmol) at 0° C. The mixture was stirred at room temperature for 1 h under N₂ atmosphere. The reaction was poured into ice aq.NH₄Cl (10 mL) and extracted with ethyl acetate (20 mL×3). The combined organic phase was dried with anhydrous Na₂SO₄, filtered and concentrated in vacuum to afford the title compound (700 mg, crude) as a gray solid. LCMS (ESI): m/z 324.1 (M+H)⁺.

Step 4: N-((9-methyl-2-(4-(trifluoromethoxy)phenyl)-9H-purin-6-yl)methyl)acrylamide

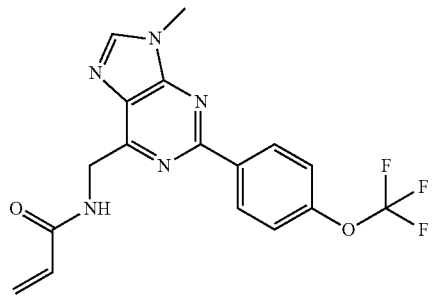 [SMILES: C=CC(=O)NCc1nc(-c2ccc(OC(F)(F)F)cc2)nc2c1ncn2C]

To a solution of (9-methyl-2-(4-(trifluoromethoxy)phenyl)-9H-purin-6-yl)methanamine (600 mg, 1.86 mmol) and NaHCO₃ (467 mg, 5.57 mmol) in THF (10 mL) and H₂O (2 mL) was added acryloyl chloride (167 mg, 1.86 mmol) at 0° C. The mixture was stirred at room temperature for 2 h under N₂ atmosphere. The reaction was poured into water (15 mL) and extracted with ethyl acetate (10 mL×3). The combined organic phase was dried with anhydrous Na₂SO₄, filtered and concentrated in vacuum. The residue was purified by reverse phase chromatography (Phenomenex C18 75*30 mm*3 um/water (FA)-ACN/35%-60%) to afford the title compound (72.55 mg, 10%) as a white solid. ¹H NMR (400 MHz, DMSO-d₆): δ 8.78 (t, J=5.2 Hz, 1H), 8.60 (d, J=8.8 Hz, 2H), 8.54 (s, 1H), 7.52 (d, J=8.4 Hz, 2H), 6.44 (dd, J=17.2, 10.4 Hz, 1H), 6.14 (dd, J=17.2, 2.4 Hz, 1H), 5.65 (dd, J=10.4, 2.0 Hz, 1H), 4.90 (d, J=6.0 Hz, 2H), 3.90 (s, 3H); LCMS (ESI): m/z 378.1 (M+H)⁺.

Example 131 (Compound 134)

6-(1-(2-Fluoroacryloyl)azetidin-3-yl)-8-(4-(trifluoromethoxy)phenyl)pyrido[3,4-b]pyrazin-5(6H)-one

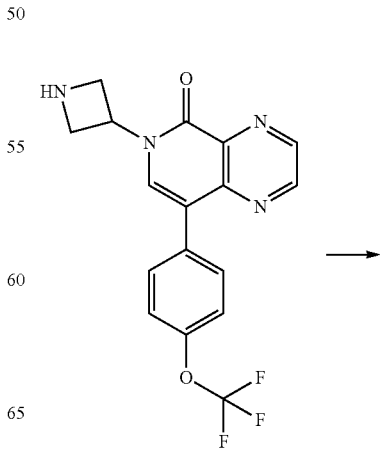

-continued

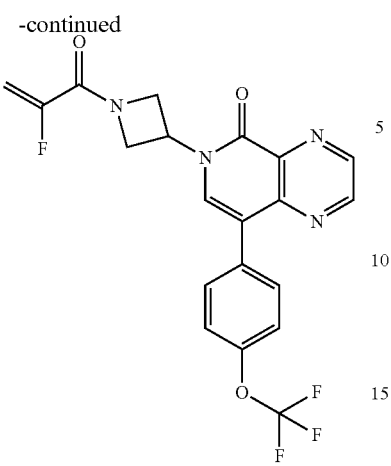

-continued

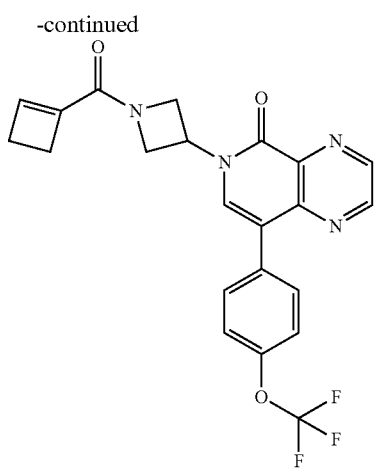

To a mixture of 2-fluoroacrylic acid (18 mg, 0.19 mmol) and ethyl 2-ethoxyquinoline-1(2H)-carboxylate (82 mg, 0.33 mmol) in DCM (3 mL) was added 6-(azetidin-3-yl)-8-(4-(trifluoromethoxy)phenyl)pyrido[3,4-b]pyrazin-5(6H)-one (60 mg, 0.16 mmol) in methanol (0.5 mL) at 0° C. The mixture was stirred at room temperature for 2 h under $N_2$ atmosphere. The reaction mixture was poured into brine (10 mL) and extracted with ethyl acetate (10 mL×3), dried over $Na_2SO_4$ and concentrated under reduced pressure to give a residue. The residue was purified by reverse phase chromatography (Waters Xbridge BEH C18 100*30 mm*10 um; 20%-50% water (NH$_4$HCO$_3$)-CAN) to afford the title compound (50.8 mg, 67%) as a white solid. $^1$H NMR (400 MHz, DMSO-d$_6$): δ 9.00 (d, J=2.0 Hz, 1H), 8.91 (d, J=2.0 Hz, 1H), 8.13 (s, 1H), 7.78-7.71 (m, 2H), 7.47 (d, J=8.0 Hz, 2H), 5.67-5.59 (m, 1H), 5.51 (dd, J=48.4, 3.6 Hz, 1H), 5.31 (d, J=16.4, 3.6 Hz, 1H), 4.84-4.75 (m, 2H), 4.45-4.39 (m, 2H); LCMS (ESI): m/z 435.1 (M+H)$^+$.

To a solution of 6-(azetidin-3-yl)-8-(4-(trifluoromethoxy) phenyl)pyrido[3,4-b]pyrazin-5(6H)-one (150 mg, 0.41 mmol) and cyclobut-1-ene-1-carboxylic acid (81 mg, 0.83 mmol) in dichloromethane (2 mL) and methyl alcohol (0.4 mL) was added ethyl 2-ethoxyquinoline-1(2H)-carboxylate (154 mg, 0.62 mmol) at 0° C. The resulting mixture was stirred at room temperature for 3 h. The mixture was concentrated and the residue was purified by column chromatography on silica gel (0-5% methanol in dichloromethane) to afford the title compound (28 mg, 15%) as a yellow solid. $^1$H NMR (400 MHz, DMSO-d$_6$): 3 9.00 (d, J=2.0 Hz, 1H), 8.91 (d, J=2.0 Hz, 1H), 8.07 (s, 1H), 7.77-7.73 (m, 2H), 7.47 (d, J=8.0 Hz, 2H), 6.52 (s, 1H), 5.63-5.58 (m, 1H), 4.73-4.69 (m, 2H), 4.40-4.36 (m, 2H), 2.67-2.65 (m, 2H), 2.44-2.42 (m, 2H); LCMS (ESI): m/z 443.0 (M+H)$^+$.

Example 132 (Compound 135)

6-(1-(Cyclobut-1-ene-1-carbonyl)azetidin-3-yl)-8-(4-(trifluoromethoxy)phenyl) pyrido[3,4-b]pyrazin-5 (6H)-one Example 133 (Compound 136)

5-(1-(2-Fluoroacryloyl)azetidin-3-yl)-3-methyl-7-(4-(trifluoromethoxy)phenyl)-3,5-dihydro-4H-imidazo [4,5-c]pyridin-4-one

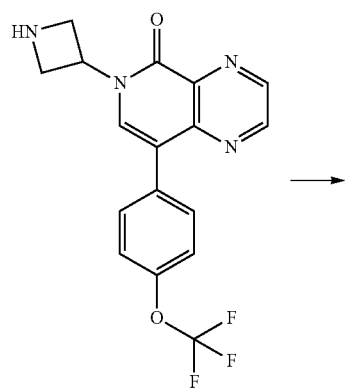

→

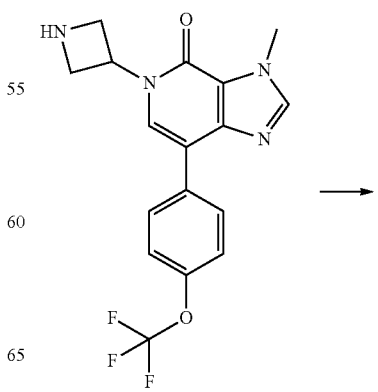

→

621

-continued

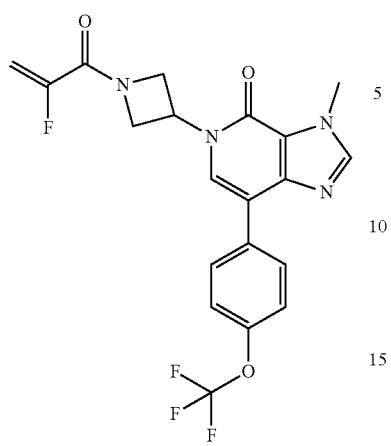

622

-continued

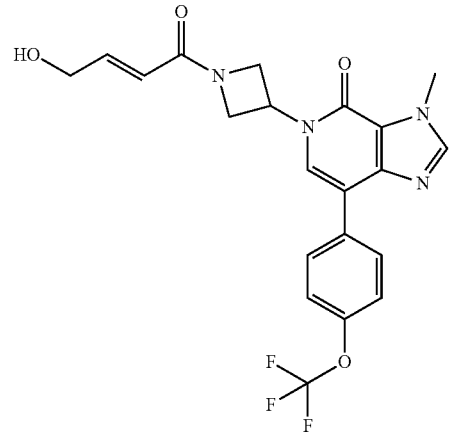

A mixture of 5-(azetidin-3-yl)-3-methyl-7-(4-(trifluoromethoxy)phenyl)-3,5-dihydro-4H-imidazo[4,5-c]pyridin-4-one (130 mg, 0.36 mmol), 2-fluoroacrylic acid (38 mg, 0.43 mmol) and ethyl 2-ethoxyquinoline-1(2H)-carboxylate (132 mg, 0.54 mmol) in DCM (2 mL) was stirred at room temperature for 16 hours. The solution was quenched with water (10 mL) and extracted with ethyl acetate (20 mL×3), the combined organic layers were washed with water (40 mL×3), dried over $Na_2SO_4$, filtered and concentrated. The residue was purified by reverse phase chromatography (Welch Xtimate C18 150*30 mm*5 um/water (FA)-ACN/43%-73%) to afford the title compound (42 mg, 27%) as a white solid. $^1$H NMR (400 MHz, DMSO-$d_6$): δ 8.25 (s, 1H), 8.12 (d, J=9.2 Hz, 2H), 7.85 (s, 1H), 7.44 (d, J=8.4 Hz, 2H), 5.67-5.61 (m, 1H), 5.50 (dd, J=48.4, 3.6 Hz, 1H), 5.32 (dd, J=16.8, 3.6 Hz, 11H), 4.82-4.74 (m, 2H), 4.42-4.37 (m, 2H), 4.06 (s, 3H); LCMS (ESI): m/z 437.3 (M+H)$^+$.

Example 134 (Compound 137)

(E)-5-(1-(4-Hydroxybut-2-enoyl)azetidin-3-yl)-3-methyl-7-(4-(trifluoromethoxy)phenyl)-3,5-dihydro-4H-imidazo[4,5-c]pyridin-4-one A mixture of 5-(azetidin-3-yl)-3-methyl-7-(4-(trifluoromethoxy)phenyl)-3,5-dihydro-4H-imidazo[4,5-c]pyridin-4-one (170 mg, 0.47 mmol), (E)-4-hydroxybut-2-enoic acid (57 mg, 0.56 mmol) and ethyl 2-ethoxyquinoline-1(2H)-carboxylate (173 mg, 0.70 mmol) in DCM (3 mL) was stirred at room temperature for 16 hours. The solution was quenched with water (10 mL) and extracted it with ethyl acetate (10 mL×3), the combined organic layers were washed with water (20 mL×3), dried over $Na_2SO_4$, filtered and concentrated. The residue was purified by reverse phase chromatography (Welch Xtimate C18 150*30 mm*5 um/water(0.225% FA)-ACN/35%-65%) to afford the title compound (23.90 mg, 12%) as a white solid. $^1$H NMR (400 MHz, DMSO-$d_6$): δ 8.25 (s, 1H), 8.12 (d, J=9.2 Hz, 2H), 7.81 (s, 1H), 7.44 (d, J=8.0 Hz, 2H), 6.80-6.74 (m, 1H), 6.20-6.15 (m, 1H), 5.64-5.57 (m, 1H), 5.06 (t, J=5.2 Hz, 1H), 4.68-4.58 (m, 2H), 4.34 (d, J=7.2 Hz, 2H), 4.16-4.13 (m, 2H), 4.06 (s, 3H); LCMS (ESI): m/z 449.0 (M+H)$^+$.

Example 135 (Compound 138) & Example 136 (Compound 139)

(R)—N-((7-(1-Hydroxyethyl)-1-methyl-4-(4-(trifluoromethoxy)phenyl)-1H-benzo[d]imidazol-6-yl)methyl)acrylamide & (S)—N-((7-(1-hydroxyethyl)-1-methyl-4-(4-(trifluoromethoxy)phenyl)-1H-benzo[d]imidazol-6-yl)methyl)acrylamide

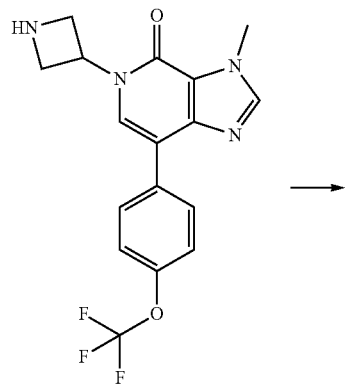

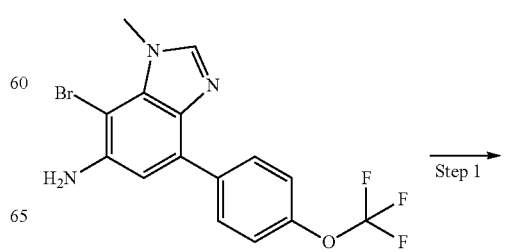

Step 1

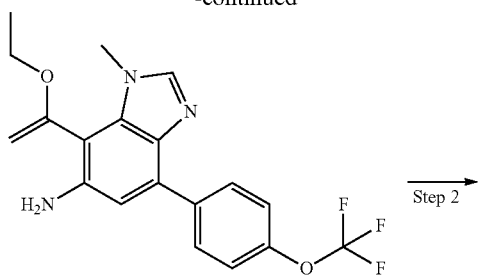

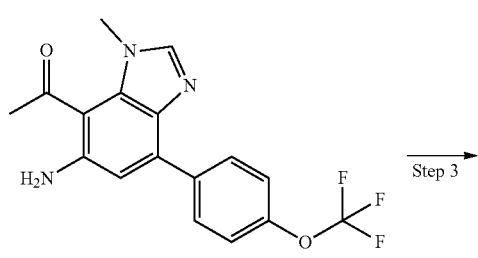

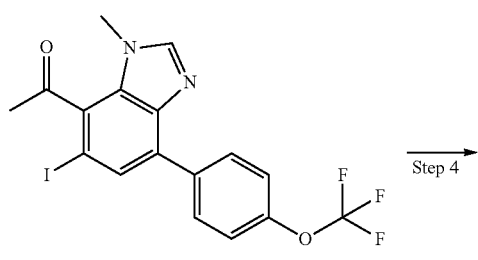

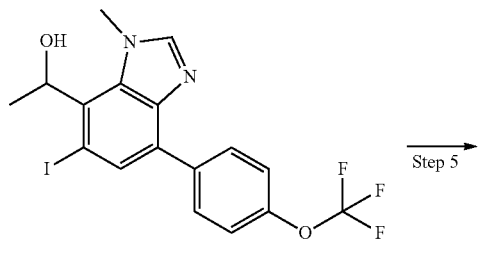

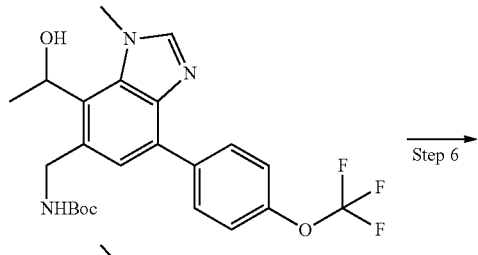

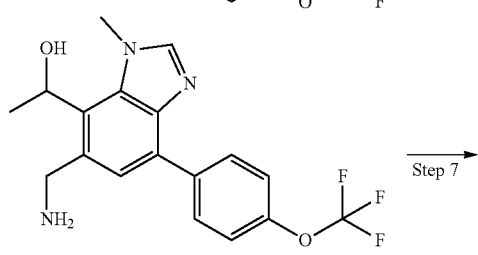

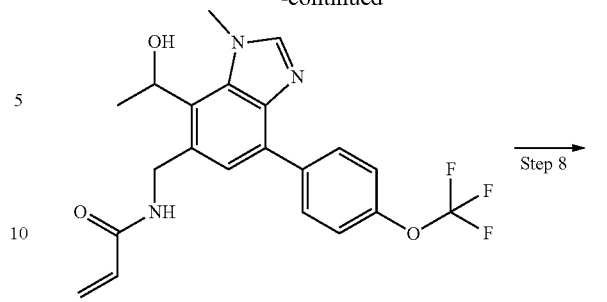

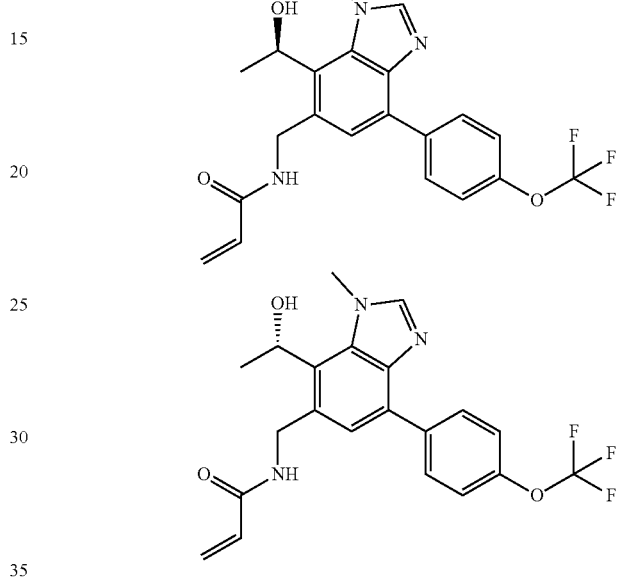

Step 1: (7-ethoxyvinyl-1-methyl-4-(4-(trifluoromethoxy)phenyl)-1H-benzo[d]imidazol-6-yl)methanol

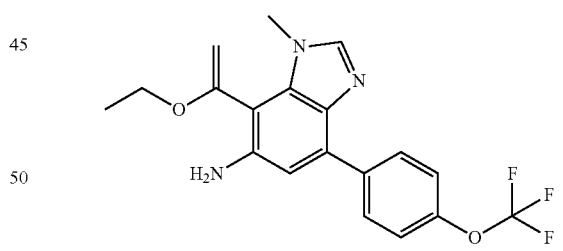

A mixture of Pd(PPh$_3$)$_2$Cl$_2$ (1.1 g, 1.55 mmol), tributyl(1-ethoxyvinyl)stannane (8.4 g, 23.31 mmol), 7-bromo-1-methyl-4-(4-(trifluoromethoxy)phenyl)-1H-benzo[d]imidazol-6-amine (6.0 g, 15.54 mmol) and Cs$_2$CO$_3$ (4.7 g, 31.07 mmol) in 1,4-dioxane (60 mL) was stirred at 120° C. for 16 h under N$_2$ atmosphere. The mixture was diluted with ethyl acetate (500 mL) and washed with water (500 mL×3). The organic layer was dried over Na$_2$SO$_4$ and concentrated. The residue was purified by chromatography on silica gel (0-20% ethyl acetate in petroleum ether) to afford the title compound (4.8 g, 82%) as a yellow oil. $^1$H NMR (400 MHz, CDCl$_3$): δ 7.92 (d, J=8.8 Hz, 2H), 7.67 (s, 1H), 7.32 (d, J=8.8 Hz, 2H), 6.82 (s, 1H), 4.71 (d, J=2.0 Hz, 1H), 4.46 (d, J=2.0 Hz, 1H), 4.00 (q, J=7.2 Hz, 2H), 3.83 (s, 3H), 1.43 (t, J=7.2 Hz, 3H); LCMS (ESI): m/z 378.2 (M+H)⁺.

Step 2: 1-(6-amino-1-methyl-4-(4-(trifluoromethoxy)phenyl)-1H-benzo[d]imidazol-7-yl)ethan-1-one

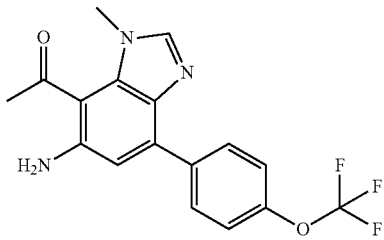 [SMILES: CC(=O)c1c(N)cc(-c2ccc(OC(F)(F)F)cc2)c2ncn(C)c12]

A mixture of 7-(1-ethoxyvinyl)-1-methyl-4-(4-(trifluoromethoxy)phenyl)-1H-benzo[d]imidazol-6-amine (4.8 g, 13.41 mmol) and con.HCl (20 mL) in THF (50 mL) was stirred at 0° C. for 2 h. The reaction was diluted with water (500 mL) and adjusted to pH=8 with sat.NaHCO₃, the mixture was extracted with ethyl acetate (300 mL×3), the combined organic layers were dried over Na₂SO₄ and concentrated under vacuum to afford the title compound (4.4 g, 99%) as a yellow oil. The crude was used for next step without further purification. ¹H NMR (400 MHz, CDCl₃): δ 7.95 (d, J=8.8 Hz, 2H), 7.78 (s, 1H), 7.36 (d, J=8.4 Hz, 2H), 6.75 (s, 1H), 3.78 (s, 3H), 2.60 (s, 3H); LCMS (ESI): m/z 350.1 (M+H)⁻.

Step 3: 1-(6-iodo-1-methyl-4-(4-(trifluoromethoxy)phenyl)-1H-benzo[d]imidazol-7-yl)ethan-1-one

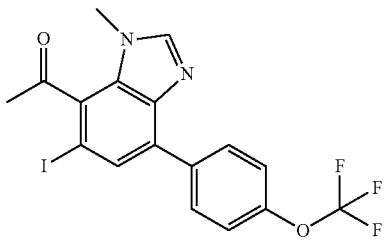 [SMILES: CC(=O)c1c(I)cc(-c2ccc(OC(F)(F)F)cc2)c2ncn(C)c12]

To a solution of 1-(6-amino-1-methyl-4-(4-(trifluoromethoxy)phenyl)-1H-benzo[d]imidazol-7-yl)ethan-1-one (4.4 g, 12.60 mmol) and CH₂I₂ (8.8 mL, 109.24 mmol) in acetonitrile (50 mL) was added t-BuONO (2.3 mL, 18.89 mmol) at room temperature, the resulting solution was stirred at 70° C. for 2 h. The reaction was diluted with water (300 mL) and extracted with ethyl acetate (200 mL×3), the combined organic layers were dried over Na₂SO₄ and concentrated under vacuum. The residue was purified by chromatography on silica gel (0-25% ethyl acetate in petroleum ether) to afford the title compound (2.8 g, 48%) as a yellow oil. ¹H NMR (400 MHz, CDCl₃): δ 7.94 (d, J=8.8 Hz, 2H), 7.84 (s, 1H), 7.80 (s, 1H), 7.36 (d, J=8.8 Hz, 2H), 3.74 (s, 3H), 2.83 (s, 3H); LCMS (ESI): m/z 461.0 (M+H)⁺.

Step 4: 1-(6-iodo-1-methyl-4-(4-(trifluoromethoxy)phenyl)-1H-benzo[d]imidazol-7-yl)ethan-1-ol

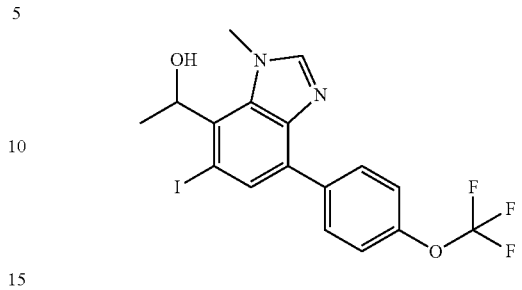

To a solution of 1-(6-iodo-1-methyl-4-(4-(trifluoromethoxy)phenyl)-1H-benzo[d]imidazol-7-yl)ethan-1-one (2.4 g, 5.22 mmol) in methanol (30 mL) was added NaBH₄ (790 mg, 20.86 mmol) at 0° C., then the resulting solution was stirred at room temperature for 2 hours. The reaction was quenched with sat.NH₄Cl (200 mL) and extracted with ethyl acetate (200 mL×3). The combined organic layers were dried over sodium sulfate, filtered and concentrated. The resulting residue was purified by reverse phase chromatography (Welch Xtimate C18 150*30 mm*5 um, acetonitrile 60-90%/water(0.225% FA)-ACN) to afford the title compound (1.1 g, 46%) as a white solid. ¹H NMR (400 MHz, DMSO-d₆): δ 8.22 (s, 1H), 8.07 (d, J=8.8 Hz, 2H), 7.83 (s, 1H), 7.46 (d, J=8.0 Hz, 2H), 6.01 (s, 1H), 5.39 (q, J=6.8 Hz, 1H), 4.22 (s, 3H), 1.53 (d, J=6.8 Hz, 3H); LCMS (ESI): m/z 462.9 (M+H)⁺.

Step 5: tert-butyl ((7-(1-hydroxyethyl)-1-methyl-4-(4-(trifluoromethoxy)phenyl)-1H-benzo[d]imidazol-6-yl)methyl)carbamate

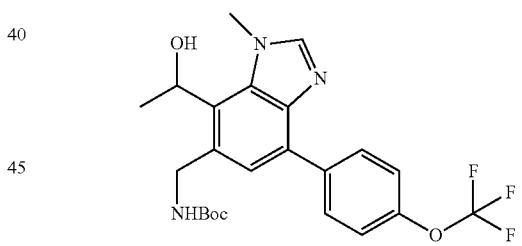

A mixture of CATACXIUM A Pd G₂ (159 mg, 0.24 mmol), 1-(6-iodo-1-methyl-4-(4-(trifluoromethoxy)phenyl)-1H-benzo[d]imidazol-7-yl)ethan-1-ol (1.1 g, 2.38 mmol), Cs₂CO₃ (2.3 g, 7.14 mmol) and potassium (((tert-butoxycarbonyl)amino)methyl)trifluoroborate (1.7 g, 7.14 mmol) in 1,4-dioxane (20 mL) and water (2 mL) was stirred at 100° C. for 2 h under N₂ atmosphere. The reaction mixture was diluted with water (100 mL) and extracted with ethyl acetate (100 mL×3), the combined organic layers were dried over Na₂SO₄ and concentrated under vacuum. The residue was purified by flash chromatography on silica gel (0-50% ethyl acetate in petroleum ether) to afford the title compound (740 mg, 67%) as a pink solid. ¹H NMR (400 MHz, DMSO-d₆): δ 8.18 (s, 1H), 8.10 (d, J=8.8 Hz, 2H), 7.47 (d, J=8.0 Hz, 2H), 7.37 (s, 1H), 7.21 (t, J=6.0 Hz, 1H), 5.60-5.56 (m, 1H), 5.54 (d, J=3.2 Hz, 1H), 4.57-4.39 (m, 2H), 4.16 (s, 3H), 1.56 (d, J=6.8 Hz, 3H), 1.39 (s, 9H); LCMS (ESI): m/z 466.2 (M+H)⁺.

Step 6: 1-(6-(aminomethyl)-1-methyl-4-(4-(trifluoromethoxy)phenyl)-1H-benzo[d]imidazol-7-yl)ethan-1-ol

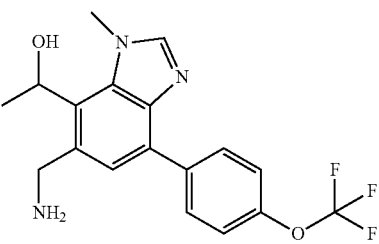 [SMILES: CC(O)c1c(CN)cc(-c2ccc(OC(F)(F)F)cc2)c2ncn(C)c12]

A solution of tert-butyl ((7-(1-hydroxyethyl)-1-methyl-4-(4-(trifluoromethoxy)phenyl)-1H-benzo[d]imidazol-6-yl)methyl)carbamate (690 mg, 1.48 mmol) and 5% TFA in HFIP (10 mL) was stirred at room temperature for 2 h. The reaction was diluted with water (100 mL) and adjusted to pH=8 with sat.NaHCO$_3$, the mixture was extracted with ethyl acetate (50 mL×3), the combined organic layers were dried over Na$_2$SO$_4$ and concentrated under vacuum to afford the title compound (540 mg, crude) as a brown oil. The crude was used for next step without further purification. LCMS (ESI): m/z 366.1 (M+H)$^+$.

Step 7: N-((7-(1-hydroxyethyl)-1-methyl-4-(4-(trifluoromethoxy)phenyl)-1H-benzo[d]imidazol-6-yl)methyl)acrylamide

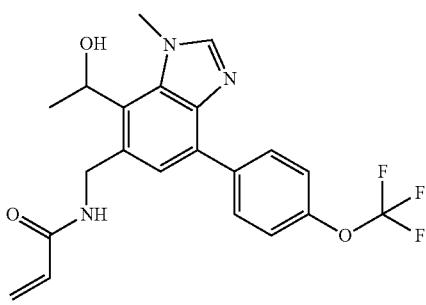

To a mixture of 1-(6-(aminomethyl)-1-methyl-4-(4-(trifluoromethoxy)phenyl)-1H-benzo[d]imidazol-7-yl)ethan-1-ol (540 mg, 1.48 mmol) and sat.NaHCO$_3$ (5 mL) in THF (10 mL) was added acryloyl chloride (147 mg, 1.63 mmol) at 0° C., the resulting mixture was stirred at room temperature for 1 h. The reaction was diluted with water (30 mL) and extracted with ethyl acetate (30 mL×3), the organic layers were dried over Na$_2$SO$_4$ and concentrated in vacuo. The resulting residue was purified by reverse phase chromatography (Welch Xtimate C18 150*30 mm*5 um, acetonitrile 29-59%/water (FA)-ACN) to afford the title compound (240 mg, 39%) as white solid. LCMS (ESI): m/z 420.2 (M+H)$^+$.

Step 8: (R)—N-((7-(1-hydroxyethyl)-1-methyl-4-(4-(trifluoromethoxy)phenyl)-1H-benzo[d]imidazol-6-yl)methyl)acrylamide & (S)—N-((7-(1-hydroxyethyl)-1-methyl-4-(4-(trifluoromethoxy)phenyl)-1H-benzo[d]imidazol-6-yl)methyl)acrylamide

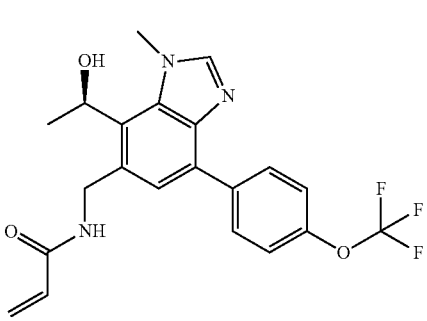

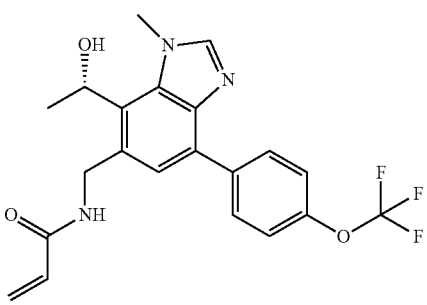

N-((7-(1-Hydroxyethyl)-1-methyl-4-(4-(trifluoromethoxy)phenyl)-1H-benzo[d]imidazol-6-yl)methyl)acrylamide (240 mg, 0.57 mmol) was separated by SFC (Phenomenex-Cellulose-2 (250 mm*30 mm,10 um), 20-20%/Neu-MeOH) to afford the first peak (R)—N-((7-(1-hydroxyethyl)-1-methyl-4-(4-(trifluoromethoxy)phenyl)-1H-benzo[d]imidazol-6-yl)methyl)acrylamide (91.77 mg, 38%) and the second peak (S)—N-((7-(1-hydroxyethyl)-1-methyl-4-(4-(trifluoromethoxy)phenyl)-1H-benzo[d]imidazol-6-yl)methyl)acrylamide (87.13 mg, 36%) as both white solid.

The first peak: $^1$H NMR (400 MHz, DMSO-d$_6$): δ 8.44 (t, J=5.2 Hz, 1H), 8.21 (s, 1H), 8.09 (d, J=8.8 Hz, 2H), 7.47 (d, J=8.0 Hz, 2H), 7.40 (s, 1H), 6.28 (dd, J=16.8, 10.0 Hz, 1H), 6.13 (dd, J=16.8, 3.6 Hz 1H, 1H), 5.65-5.57 (m, 2H), 5.55-5.46 (m, 1H), 4.77 (dd, J=14.8, 6.4 Hz, 1H), 4.60 (dd, J=14.8, 4.8 Hz, 1H), 4.17 (s, 3H), 1.54 (d, J=6.4 Hz, 3H); LCMS (ESI): m/z 420.0 (M+H)$^+$.

The second peak: $^1$H NMR (400 MHz, DMSO-d$_6$): δ 8.44 (t, J=5.2 Hz, 1H), 8.21 (s, 1H), 8.09 (d, J=8.8 Hz, 2H), 7.47 (d, J=8.0 Hz, 2H), 7.40 (s, 11H), 6.28 (dd, J=16.8, 10.0 Hz, 1H), 6.13 (dd, J=16.8, 3.6 Hz 1H, 11H), 5.65-5.57 (m, 2H), 5.55-5.46 (m, 1H), 4.77 (dd, J=14.8, 6.4 Hz, 11H), 4.60 (dd, J=14.8, 4.8 Hz, 1H), 4.17 (s, 3H), 1.54 (d, J=6.4 Hz, 3H); LCMS (ESI): m/z 420.0 (M+H)$^+$.

Example 137 (Compound 140)

N-((7-((2-Hydroxyethyl)amino)-1-methyl-4-(4-(trifluoromethoxy)phenyl)-1H-benzo[d]imidazol-6-yl)methyl)acrylamide

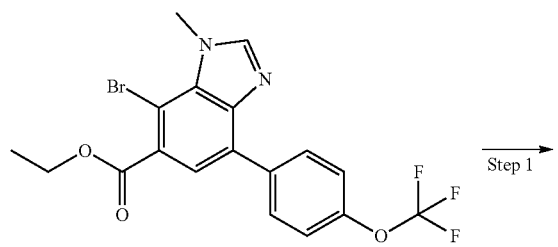

Step 1 →

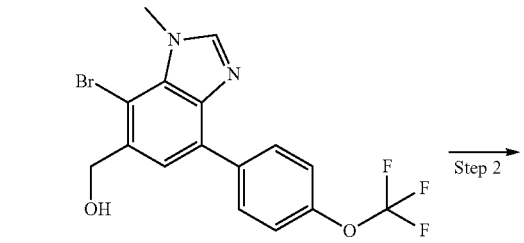

Step 2 →

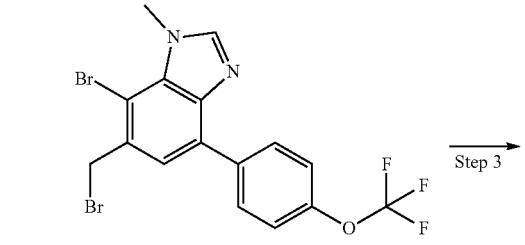

Step 3 →

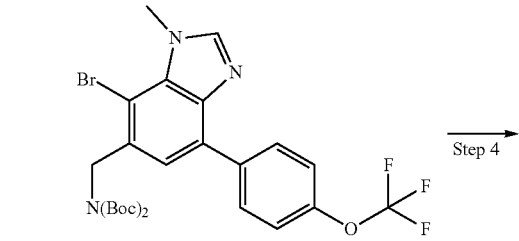

Step 4 →

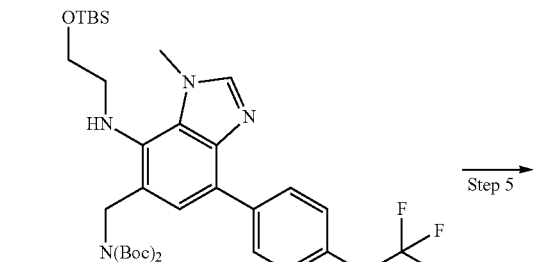

Step 5 →

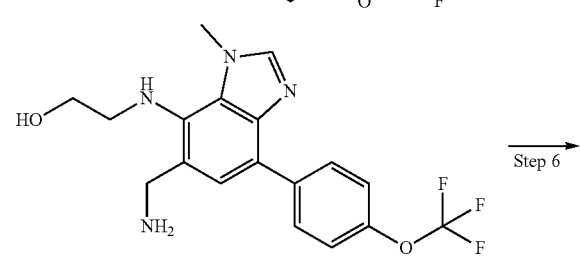

Step 6 →

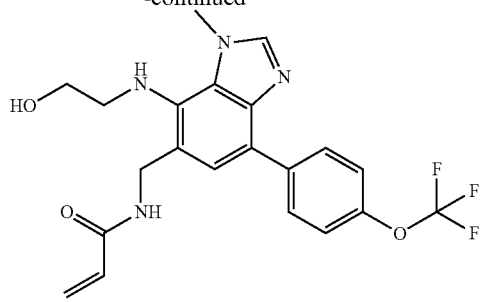

-continued

Step 1: (7-bromo-1-methyl-4-(4-(trifluoromethoxy)phenyl)-1H-benzo[d]imidazol-6-yl)methanol

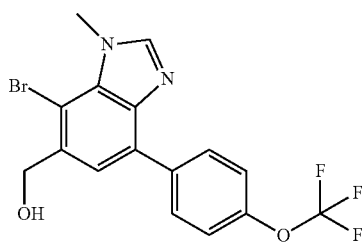 [SMILES: Cn1cnc2c(-c3ccc(OC(F)(F)F)cc3)cc(CO)c(Br)c21]

To a solution of ethyl 7-bromo-1-methyl-4-(4-(trifluoromethoxy)phenyl)-1H-benzo[d]imidazole-6-carboxylate (4.0 g, 9.03 mmol) in THF (10 mL) was added slowly DIBAL-H (18 mL, 18.05 mmol, 1.0 M/L in THF) at 0° C. dropwise. After addition, the resulting solution was stirred at 0° C. for 2 h. The reaction was quenched with sat.KHSO$_4$ (5 mL), and then the mixture was dried over MgSO$_4$ and filtered. The filtrate was concentrated in vacuo to afford the title compound (3.4 g, 94%) as a yellow solid. The crude product was used for next step without further purification. $^1$H NMR (400 MHz, DMSO-d$_6$): δ 8.29 (s, 1H), 8.14 (d, J=8.8 Hz, 2H), 7.62 (s, 1H), 7.49 (d, J=8.0 Hz, 2H), 5.47 (t, J=5.6 Hz, 1H), 4.70 (d, J=5.6 Hz, 2H), 4.15 (s, 3H); LCMS (ESI): m/z 401.0 (M+H)$^+$.

Step 2: 7-bromo-6-(bromomethyl)-1-methyl-4-(4-(trifluoromethoxy)phenyl)-1H-benzo[d]imidazole

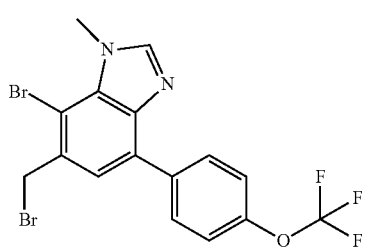 [SMILES: Cn1cnc2c(-c3ccc(OC(F)(F)F)cc3)cc(CBr)c(Br)c21]

To a solution of (7-bromo-1-methyl-4-(4-(trifluoromethoxy)phenyl)-1H-benzo[d]imidazol-6-yl)methanol (700 mg, 1.74 mmol) in DCM (10 mL) was added PBr$_3$ (0.082 mL, 0.87 mmol) at 0° C., the reaction mixture was stirred at 0° C. for 2 h. The reaction was diluted with water (50 mL) and adjusted to pH=8 with sat.NaHCO$_3$, the mixture was extracted with ethyl acetate (50 mL×3), the combined organic layers were dried over $Na_2SO_4$ and concentrated in vacuo to afford the title compound (700 mg, 86%) as a yellow solid. The crude product was used for next step without further purification. $^1$H NMR (400 MHz, $CDCl_3$): δ 7.95 (d, J=8.8 Hz, 2H), 7.89 (s, 1H), 7.47 (s, 1H), 7.35 (d, J=8.4 Hz, 2H), 4.85 (s, 2H), 4.23 (s, 3H); LCMS (ESI): m/z 465.0 (M+H)$^+$.

Step 3: tert-butyl N-[[4-bromo-3-methyl-7-[4-(trifluoromethoxy)phenyl]benzimidazol-5-yl]methyl]-N-tert-butoxycarbonyl-carbamate

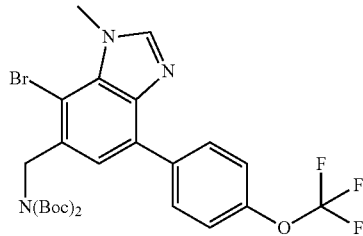

A mixture of 7-bromo-6-(bromomethyl)-1-methyl-4-(4-(trifluoromethoxy)phenyl)-1H-benzo[d]imidazole (700 mg, 1.51 mmol), $Cs_2CO_3$ (983 mg, 3.02 mmol) and $Boc_2NH$ (492 mg, 2.26 mmol) in DMF (10 mL) was stirred at room temperature for 16 h. The reaction was diluted with water (100 mL) and extracted with ethyl acetate (100 mL×3), the combined organic layers were washed with brine (100 mL×3), the organic was dried over $Na_2SO_4$ and concentrated in vacuo. The residue was purified by chromatography on silica (0-25% ethyl acetate in petroleum ether) to afford the title compound (530 mg, 59%) as a yellow oil. $^1$H NMR (400 MHz, $CDCl_3$): δ 7.90 (d, J=8.8 Hz, 2H), 7.84 (s, 1H), 7.32 (d, J=8.4 Hz, 2H), 7.17 (s, 1H), 5.05 (s, 2H), 4.22 (s, 3H), 1.46 (s, 18H).

Step 4: tert-butyl N-tert-butoxycarbonyl-N-[[4-[2-[tert-butyl(dimethyl)silyl]oxyethylamino]-3-methyl-7-[4-(trifluoromethoxy)phenyl]benzimidazol-5-yl]methyl]carbamate

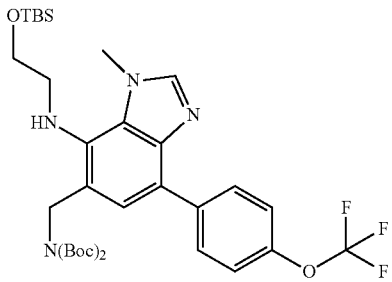

A mixture of Xantphos (51 mg, 0.09 mmol), $Pd_2(dba)_3$ (81 mg, 0.09 mmol), 2-((tert-butyldimethylsilyl)oxy) ethanamine (310 mg, 1.77 mmol), $Cs_2CO_3$ (863 mg, 2.65 mmol) and tert-butyl N-[[4-bromo-3-methyl-7-[4-(trifluoromethoxy)phenyl]benzimidazol-5-yl]methyl]-N-tert-butoxycarbonyl-carbamate (530 mg, 0.88 mmol) in 1,4-dioxane (10 mL) was stirred at 100° C. for 16 h under $N_2$ atmosphere. The reaction mixture was filtered and the filtrate was concentrated in vacuo. The residue was purified by chromatography on silica gel (0-20% ethyl acetate in petroleum ether) to afford the title compound (400 mg, 65%) as a yellow solid. $^1$H NMR (400 MHz, $CDCl_3$): δ 7.94 (d, J=8.8 Hz, 2H), 7.82 (s, 1H), 7.43 (s, 1H), 7.30 (d, J=8.0 Hz, 2H), 5.00 (s, 2H), 4.74 (s, 1H), 4.20 (s, 3H), 3.82 (t, J=4.8 Hz, 2H), 3.13 (t, J=4.8 Hz, 2H), 1.48 (s, 18H), 0.95 (s, 9H), 0.12 (s, 6H); LCMS (ESI): m/z 695.3 (M+H)$^+$.

Step 5: 2-((6-(aminomethyl)-1-methyl-4-(4-(trifluoromethoxy)phenyl)-1H-benzo[d]imidazol-7-yl) amino)ethan-1-ol

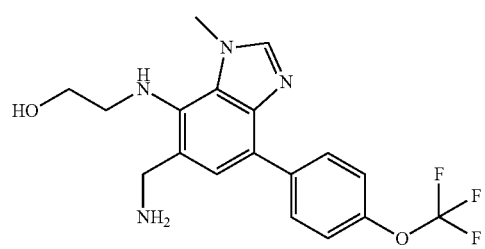 [SMILES: Cn1cnc2c(-c3ccc(OC(F)(F)F)cc3)cc(CN)c(NCCO)c21]

A solution of tert-butyl N-tert-butoxycarbonyl-N-[[4-[2-[tert-butyl(dimethyl)silyl]oxyethylamino]-3-methyl-7-[4-(trifluoromethoxy)phenyl]benzimidazol-5-yl]methyl]carbamate (350 mg, 0.50 mmol) and con.HCl (2 mL) in THF (4 mL) was stirred at room temperature for 2 h. The reaction was diluted with water (50 mL) and adjusted to pH=8 with sat.$NaHCO_3$, the mixture was extracted with ethyl acetate (50 mL×3), the combined organic layers were dried over $Na_2SO_4$ and concentrated in vacuo to afford the title compound (110 mg, crude) as a yellow oil. The crude was used for next step without further purification. LCMS (ESI): m/z 381.1 (M+H)$^+$.

Step 6: N-((7-((2-hydroxyethyl)amino)-1-methyl-4-(4-(trifluoromethoxy)phenyl)-1H-benzo[d]imidazol-6-yl)methyl)acrylamide

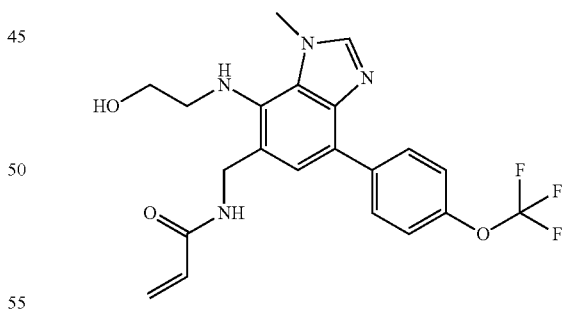

To a mixture of 2-((6-(aminomethyl)-1-methyl-4-(4-(trifluoromethoxy)phenyl)-1H-benzo[d]imidazol-7-yl)amino) ethan-1-ol (110 mg, 0.29 mmol) and sat.$NaHCO_3$ (2 mL) in THF (5 mL) was added acrylic anhydride (36 mg, 0.29 mmol) at 0° C., after addition, the resulting mixture was stirred at room temperature for 2 h. The reaction was diluted with water (50 mL) and extracted with ethyl acetate (50 mL×3), the combined organic layers were dried over $Na_2SO_4$ and concentrated under vacuum. The resulting residue was purified by reverse phase chromatography (Welch Xtimate C18 150*30 mm*5 um, acetonitrile 17-47%/water (FA)-ACN) to afford the title compound (26 mg, 21%) as a white solid. $^1$H NMR (400 MHz, DMSO-$d_6$): δ 8.67 (t, J=5.6 Hz, 1H), 8.14-8.07 (m, 3H), 7.44 (d, J=8.4 Hz, 2H), 7.34 (s, 1H), 6.23 (dd, J=17.2, 10.0 Hz, 1H), 6.12 (dd, J=17.2, 2.0 Hz, 1H), 5.61 (dd, J=10.0, 2.0 Hz, 1H), 4.86-4.77 (m, 1H), 4.74-4.63 (m, 1H), 4.52 (d, J=6.0 Hz, 2H), 4.12 (s, 3H), 3.62-3.58 (m, 2H), 3.10-3.04 (m, 2H); LCMS (ESI): m/z 435.0 (M+H)$^+$.

Example 138 (Compound 141) Methyl 2-(1-methyl-4-(4-(trifluoromethoxy)phenyl)-1H-benzo[d]imidazole-6-carboxamido)acrylate

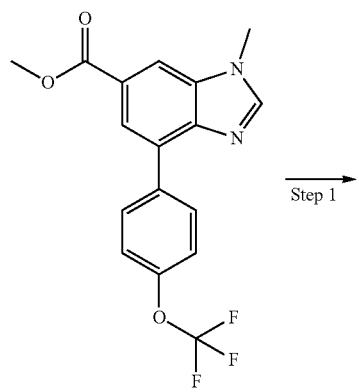

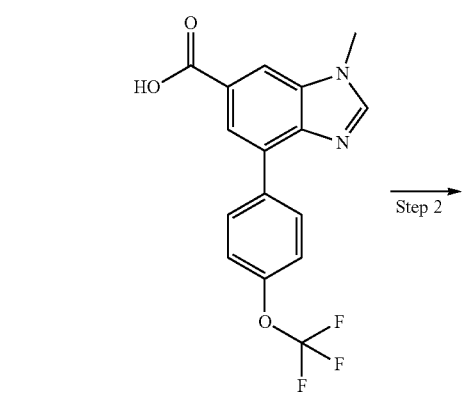

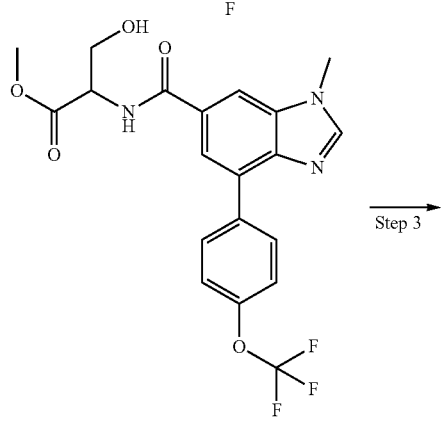

-continued

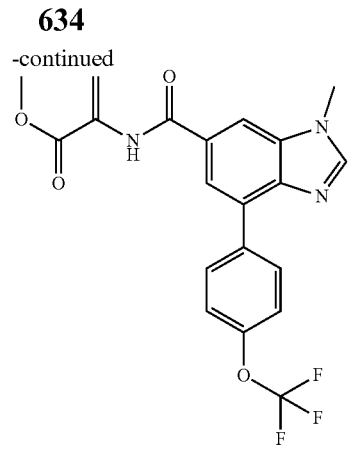

Step 1: 1-methyl-4-(4-(trifluoromethoxy)phenyl)-1H-benzo[d]imidazole-6-carboxylic acid

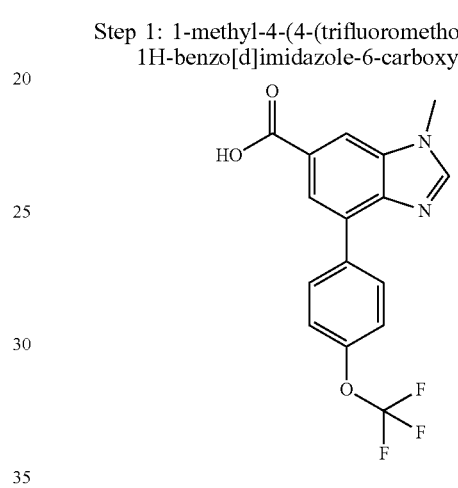

To a stirred solution of methyl 1-methyl-4-(4-(trifluoromethoxy)phenyl)-1H-benzo[d]imidazole-6-carboxylate (5.0 g, 14.27 mmol) in THF (90 mL) and water (30 mL) was added lithium hydroxide monohydrate (1.2 g, 28.55 mmol) at room temperature. The mixture was stirred at 60° C. for 3 h. The mixture was diluted with water (60 mL), adjusted with 2M HCl to pH=3, extracted with ethyl acetate (80 mL×3). The combined organic layer was dried over anhydrous Na$_2$SO$_4$, filtered and concentrated to afford the title compound (4.6 g, crude) as a yellow solid. LCMS (ESI): m/z 336.9 (M+H)$^+$.

Step 2: methyl 3-hydroxy-2-(1-methyl-4-(4-(trifluoromethoxy)phenyl)-1H-benzo[d]imidazole-6-carboxamido)propanoate

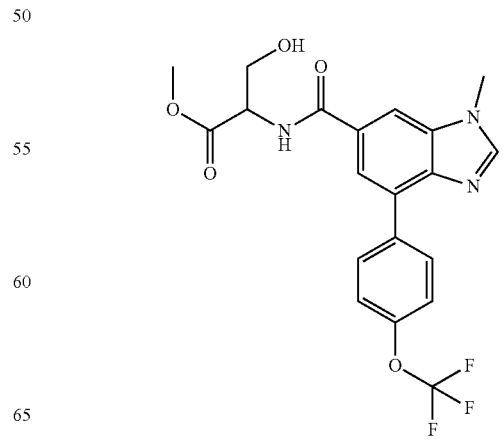

A solution of 1-methyl-4-(4-(trifluoromethoxy)phenyl)-1H-benzo[d]imidazole-6-carboxylic acid (4.0 g, 11.9 mmol), DIEA (6.22 mL, 35.69 mmol), HOBt (2.4 g, 17.84 mmol) and EDCI (3.4 g, 17.84 mmol) in DMF (80 mL) was stirred at room temperature for 30 min. Then methyl 2-amino-3-hydroxypropanoate hydrochloride (2.04 g, 13.08 mmol) was added into it. The reaction was stirred at room temperature for 2 h. The reaction was quenched with water (50 mL) and extracted with ethyl acetate (100 mL×2). The combined organic layer was washed with brine (50 mL×2), dried over anhydrous $Na_2SO_4$, filtered and concentrated. The residue was purified by column chromatography on silica gel (0-2% methanol in dichloromethane) to afford the title compound (3.0 g, 58%) as a yellow solid. $^1$H NMR (400 MHz, DMSO-$d_6$): δ 8.78 (d, J=7.6 Hz, 1H), 8.43 (s, 1H), 8.29-8.27 (m, 2H), 8.20 (d, J=1.2 Hz, 1H), 8.06 (s, 1H), 7.52 (d, J=8.0 Hz, 2H), 5.12 (t, J=6.0 Hz, 1H), 4.66-4.61 (m, 1H), 3.95 (s, 3H), 3.87-3.82 (m, 2H), 3.67 (s, 3H).

Step 3: methyl 2-(1-methyl-4-(4-(trifluoromethoxy)phenyl)-1H-benzo[d]imidazole-6-carboxamido)acrylate

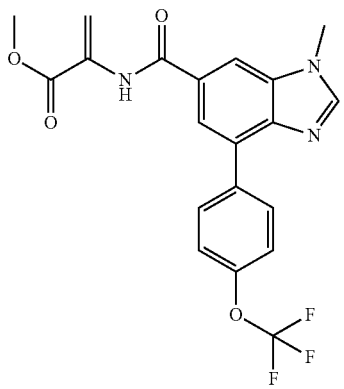 [SMILES: C=C(NC(=O)c1cc(-c2ccc(OC(F)(F)F)cc2)c2ncn(C)c2c1)C(=O)OC]

To a stirred solution of methyl 3-hydroxy-2-(1-methyl-4-(4-(trifluoromethoxy)phenyl)-1H-benzo[d]imidazole-6-carboxamido)propanoate (630 mg, 1.44 mmol) in dichloromethane (12 mL) was added EDCI (304 mg, 1.58 mmol) and CuCl (157 mg, 1.58 mmol) at room temperature. The mixture was stirred at room temperature for 2 h. The mixture was quenched with water (50 mL) and extracted with ethyl acetate (100 mL×2). The combined organic layer was washed with brine (50 mL), dried over anhydrous $Na_2SO_4$, filtered and concentrated. The residue was purified by reverse phase chromatography (Welch Xtimate C18 150*30 mm*5 um, acetonitrile 52-82%/water (0.225% FA)-CAN to afford the title compound (65.2 mg, 11%) as a white solid. $^1$H NMR (400 MHz, DMSO-$d_6$): δ 10.11 (s, 1H), 8.46 (s, 1H), 8.30-8.27 (m, 2H), 8.22 (d, J=1.6 Hz, 1H), 8.06 (d, J=1.6 Hz, 1H), 7.53 (d, J=8.4 Hz, 2H), 5.86-5.84 (m, 1H), 5.75 (s, 1H), 3.96 (s, 3H), 3.75 (s, 3H); LCMS (ESI): m/z 420.0 (M+H)$^+$.

Example 139 (Compound 142) N-(3-Amino-3-oxo-prop-1-en-2-yl)-1-methyl-4-(4-(trifluoromethoxy)phenyl)-1H-benzo[d]imidazole-6-carboxamide

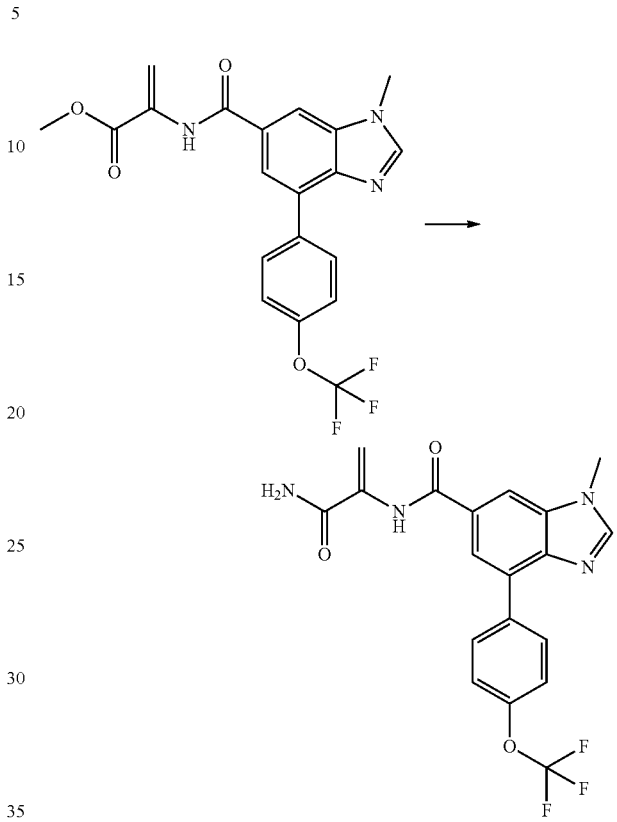

A mixture of methyl 2-(1-methyl-4-(4-(trifluoromethoxy)phenyl)-1H-benzo[d]imidazole-6-carboxamido)acrylate (300 mg, 0.72 mmol) in 7 N $NH_3$ in methanol (10 mL, 70 mmol) was stirred at room temperature for 1 h. The reaction mixture was quenched with water (50 mL), extracted with ethyl acetate (50 mL×2). The combined organic was dried over $Na_2SO_4$, filtered and concentrated. The residue was purified by column chromatography on silica gel (0-5% methanol in dichloromethane) and then purified by reverse phase chromatography (Welch Xtimate C18 150*30 mm*5 um, acetonitrile 28-48%/water (0.225% FA)-CAN) to afford the title compound (40 mg, 14%) as a white solid. $^1$H NMR (400 MHz, DMSO-$d_6$): δ 9.56 (s, 1H), 8.45 (s, 1H), 8.28-8.25 (m, 2H), 8.17 (d, J=1.6 Hz, 11H), 7.98 (d, J=1.6 Hz, 11H), 7.94 (s, 11H), 7.55-7.46 (m, 3H), 6.13 (s, 1H), 5.65 (s, 1H), 3.96 (s, 3H); LCMS (ESI): m/z 405.2 (M+H)$^+$.

Example 140 (Compound 143) N-((7-Cyano-4-(2-fluoro-4-(trifluoromethoxy)phenyl)-1-methyl-1H-benzo[d]imidazol-6-yl)methyl)acrylamide

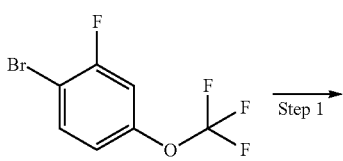

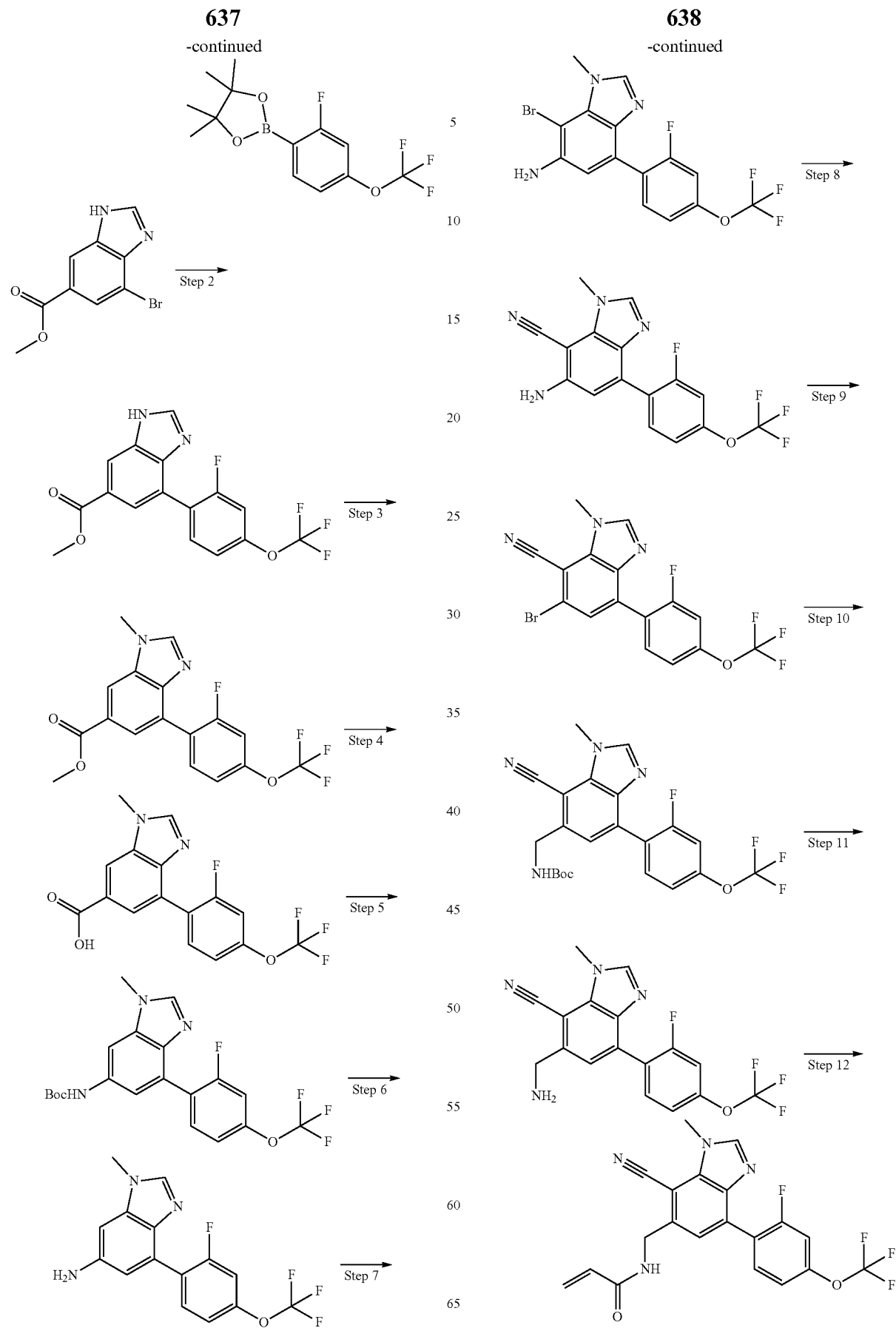

Step 1: 2-(2-fluoro-4-(trifluoromethoxy)phenyl)-4,4,5,5-tetramethyl-1,3,2-dioxaborolane

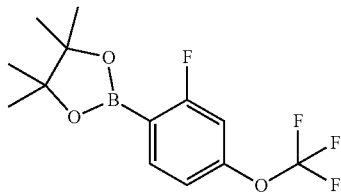 [SMILES: CC1(C)OB(c2ccc(OC(F)(F)F)cc2F)OC1(C)C]

A solution of 1-bromo-2-fluoro-4-(trifluoromethoxy)benzene (10.0 g, 38.61 mmol), KOAc (9.47 g, 96.53 mmol), 4,4,4',4',5,5,5',5'-octamethyl-2,2'-bi(1,3,2-dioxaborolane) (11.77 g, 46.33 mmol) and Pd(dppf)Cl$_2$ (2.83 g, 3.86 mmol) in 1,4-dioxane (100 mL) was stirred at 100° C. for 16 h under N$_2$ atmosphere. The mixture was diluted with ethyl acetate (200 mL) and washed with water (100 mL×3). The organic layer was dried over Na$_2$SO$_4$ and concentrated. The residue was purified by chromatography on silica gel (0-10% ethyl acetate in petroleum ether) to afford the title compound (9.0 g, 76%) as a white solid. $^1$H NMR (400 MHz, CDCl$_3$): δ 7.78 (dd, J=8.0, 6.8 Hz, 1H), 7.01 (d, J=8.0 Hz, 1H), 6.93 (dd, J=9.6, 0.8 Hz, 1H), 1.37 (s, 12H).

Step 2: methyl 4-(2-fluoro-4-(trifluoromethoxy)phenyl)-1H-benzo[d]imidazole-6-carboxylate

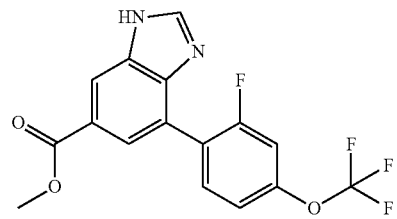

A solution of methyl 4-bromo-1H-benzo[d]imidazole-6-carboxylate (7.0 g, 27.44 mmol), K$_3$PO$_4$ (11.65 g, 54.89 mmol), 2-(2-fluoro-4-(trifluoromethoxy)phenyl)-4,4,5,5-tetramethyl-1,3,2-dioxaborolane (9.0 g, 29.41 mmol) and Pd(dppf)Cl$_2$ (2.01 g, 2.74 mmol) in 1,4-dioxane (100 mL) and water (10 mL) was stirred at 100° C. for 3 h under N$_2$ atmosphere. The mixture was diluted with ethyl acetate (500 mL) and washed with water (500 mL×3). The organic layer was dried over Na$_2$SO$_4$ and concentrated. The residue was purified by chromatography on silica gel (0-50% ethyl acetate in petroleum ether) to afford the title compound (2.5 g, 26%) as a white solid. $^1$H NMR (400 MHz, CDCl$_3$): δ 8.43 (d, J=1.2 Hz, 1H), 8.18 (s, 1H), 8.08 (s, 11H), 7.67 (t, J=8.4 Hz, 11H), 7.14 (dd, J=8.4, 0.8 Hz, 11H), 7.06 (d, J=9.6 Hz, 11H), 3.97 (s, 3H).

Step 3: methyl 4-(2-fluoro-4-(trifluoromethoxy)phenyl)-1-methyl-1H-benzo[d]imidazole-6-carboxylate

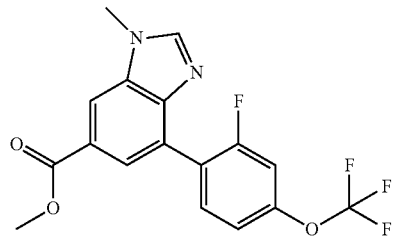 [SMILES: COC(=O)c1cc(-c2ccc(OC(F)(F)F)cc2F)c2ncn(C)c2c1]

To a solution of methyl 4-(2-fluoro-4-(trifluoromethoxy)phenyl)-1H-benzo[d]imidazole-6-carboxylate (2.5 g, 7.06 mmol) and K$_3$P04 (3.0 g, 14.11 mmol) in DMF (50 mL) was added CH$_3$I (1.1 g, 7.76 mmol) at 0° C. Then the reaction was stirred at room temperature for 16 h. The reaction was diluted with water (500 mL) and extracted with ethyl acetate (500 mL×3), the combined organic layers were washed with brine (500 mL×3), and the organic layer was dried over Na$_2$SO$_4$ and concentrated in vacuo. The residue was purified by flash chromatography on silica gel (0-50% ethyl acetate in petroleum ether) to afford the title compound (1.8 g, 69%) as a white solid. LCMS (ESI): m/z 369.1 (M+H)$^+$.

Step 4: 4-(2-fluoro-4-(trifluoromethoxy)phenyl)-1-methyl-1H-benzo[d]imidazole-6-carboxylic acid

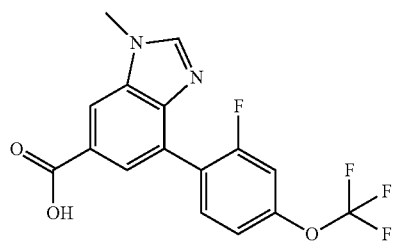 [SMILES: Cn1cnc2c(-c3ccc(OC(F)(F)F)cc3F)cc(C(=O)O)cc21]

A solution of methyl 4-(2-fluoro-4-(trifluoromethoxy)phenyl)-1-methyl-1H-benzo[d]imidazole-6-carboxylate (1.8 g, 4.89 mmol) and lithium hydroxide monohydrate (1.03 g, 24.44 mmol) in THF (20 mL) and water (5 mL) was stirred at room temperature for 16 h. The reaction was adjusted pH to 4 with aq. HCl (2N), extracted with ethyl acetate (200 mL). The organic layer was dried over Na$_2$SO$_4$ and concentrated in vacuo to afford the title compound (1.7 g, 98%) as a white solid. LCMS (ESI): m/z 355.1 (M+H)$^+$ Step 5: tert-butyl (4-(2-fluoro-4-(trifluoromethoxy) phenyl)-1-methyl-1H-benzo[d]imidazol-6-yl)carbamate

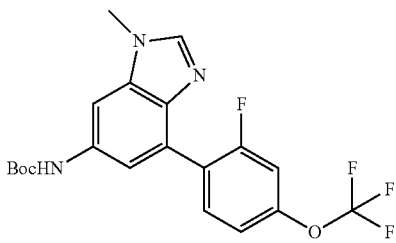 [SMILES: Cn1cnc2c(-c3ccc(OC(F)(F)F)cc3F)cc(NC(=O)OC(C)(C)C)cc21]

To a mixture of 4-(2-fluoro-4-(trifluoromethoxy)phenyl)-1-methyl-1H-benzo[d]imidazole-6-carboxylic acid (1.7 g, 4.8 mmol) in t-BuOH (110 mL) was added DPPA (1.03 mL, 4.8 mmol) and TEA (0.74 mL, 5.28 mmol) at room temperature. The mixture was stirred at 80° C. for 16 hours. The reaction was diluted with water (100 mL) and extracted with ethyl acetate (200 mL×3), the combined organic layers were washed with brine (200 mL×3), and the organic layer was dried over $Na_2SO_4$ and concentrated in vacuo. The residue was purified by chromatography on silica gel (0-35% ethyl acetate in petroleum ether) to afford the title compound (850 mg, 42%) as a yellow solid. $^1$H NMR (400 MHz, $CDCl_3$): δ 7.96 (s, 1H), 7.89-7.81 (m, 2H), 7.19-7.09 (m, 2H), 7.02 (s, 1H), 6.71 (s, 1H), 3.86 (s, 3H), 1.56 (s, 9H).

Step 6: 4-(2-fluoro-4-(trifluoromethoxy)phenyl)-1-methyl-1H-benzo[d]imidazol-6-amine

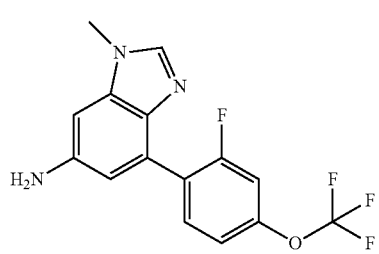 [SMILES: Cn1cnc2c(-c3ccc(OC(F)(F)F)cc3F)cc(N)cc21]

To a solution of tert-butyl (4-(2-fluoro-4-(trifluoromethoxy)phenyl)-1-methyl-1H-benzo[d]imidazol-6-yl) carbamate (850 mg, 2.0 mmol) in DCM (10 mL) was added TFA (2 mL) at 0° C. The mixture was stirred at room temperature for 16 h. The reaction was diluted with aq.NaHCO$_3$ (30 mL), extracted with ethyl acetate (200 mL×3). The organic layer was dried over $Na_2SO_4$ and concentrated to afford the title compound (600 mg, crude). The crude product would be directly used in the next step without purification. LCMS (ESI): m/z 326.1 (M+H)$^+$.

Step 7: 7-bromo-4-(2-fluoro-4-(trifluoromethoxy) phenyl)-1-methyl-1H-benzo[d]imidazol-6-amine To a solution of 4-(2-fluoro-4-(trifluoromethoxy)phenyl)-1-methyl-1H-benzo[d]imidazol-6-amine (600 mg, 1.84 mmol) in DCM (10 mL) was added NBS (328 mg, 1.84 mmol) at 0° C. The mixture was stirred at 0° C. for 1 h. The reaction was diluted with water (20 mL) and extracted with ethyl acetate (100 mL×3). The organic layer was washed with brine (50 mL×2), dried over sodium sulfate, filtered and concentrated. The residue was purified by flash chromatography on silica gel (0-35% ethyl acetate in petroleum ether) to afford the title compound (600 mg, 81%) as a white solid. $^1$H NMR (400 MHz, $CDCl_3$): δ 7.74 (t, J=8.4 Hz, 1H), 7.67 (s, 1H), 7.16-7.07 (m, 2H), 6.87 (d, J=1.6 Hz, 1H), 4.13 (s, 3H).

Step 8: 6-amino-4-(2-fluoro-4-(trifluoromethoxy) phenyl)-1-methyl-1H-benzo[d]imidazole-7-carbonitrile A mixture of 7-bromo-4-(2-fluoro-4-(trifluoromethoxy) phenyl)-1-methyl-1H-benzo[d]imidazol-6-amine (600 mg, 1.48 mmol), t-BuXphos Pd G$_3$ (177 mg, 0.22 mmol) and Zn(CN)$_2$ (872 mg, 7.42 mmol) in DMA (5 mL) was stirred at 140° C. for 16 h under N$_2$ atmosphere. The reaction mixture was diluted with water (100 mL) and extracted with ethyl acetate (100 mL×3), the combined organic layers were dried over $Na_2SO_4$ and concentrated in vacuo. The residue was purified by flash chromatography on silica gel (0-35% ethyl acetate in petroleum ether) to afford the title compound (350 mg, 67%) as a yellow solid. $^1$H NMR (400 MHz, $CDCl_3$): δ 7.80 (t, J=8.4 Hz, 1H), 7.71 (s, 1H), 7.19-7.07 (m, 2H), 6.79 (d, J=1.6 Hz, 1H), 4.59 (s, 2H), 4.08 (s, 3H).

Step 9: 6-bromo-4-(2-fluoro-4-(trifluoromethoxy)phenyl)-1-methyl-1H-benzo[d]imidazole-7-carbonitrile

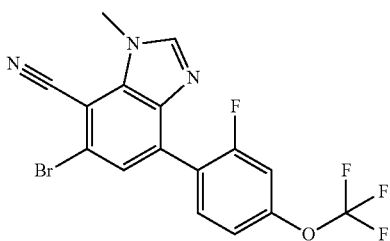

To a solution of 6-amino-4-(2-fluoro-4-(trifluoromethoxy)phenyl)-1-methyl-1H-benzo[d]imidazole-7-carbonitrile (350 mg, 1.0 mmol) and CuBr (287 mg, 2.0 mmol) in acetonitrile (8 mL) was added t-BuONO (0.18 mL, 1.5 mmol) at room temperature, then the solution was stirred at 60° C. for 3 hours. The reaction was diluted with water (200 mL) and extracted with ethyl acetate (200 mL×3). The organic layers were washed with brine (150 mL×2), dried over sodium sulfate, filtered and concentrated. The residue was purified by flash chromatography on silica gel (0-25% ethyl acetate in petroleum ether) to afford the title compound (200 mg, 48%) as a white solid. $^1$H NMR (400 MHz, CDCl$_3$) δ 7.96 (s, 1H), 7.81 (t, J=8.4 Hz, 1H), 7.69 (d, J=1.6 Hz, 1H), 7.22-7.12 (m, 2H), 4.20 (s, 3H).

Step 10: tert-butyl ((7-cyano-4-(2-fluoro-4-(trifluoromethoxy)phenyl)-1-methyl-1H-benzo[d]imidazol-6-yl)methyl)carbamate

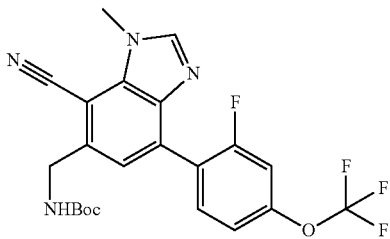 [SMILES: Cn1cnc2c(-c3ccc(OC(F)(F)F)cc3F)cc(CNC(=O)OC(C)(C)C)c(C#N)c21]

A mixture of 6-bromo-4-(2-fluoro-4-(trifluoromethoxy)phenyl)-1-methyl-1H-benzo[d]imidazole-7-carbonitrile (200 mg, 0.48 mmol), potassium (((tert-butoxycarbonyl)amino)methyl)trifluoroborate (229 mg, 0.97 mmol), CATACXIUM A Pd G$_2$ (33 mg, 0.05 mmol) and Cs$_2$CO$_3$ (315 mg, 0.97 mmol) in 1,4-dioxane (10 mL) and water (1 mL) was stirred at 100° C. for 5 h under N$_2$ atmosphere. The reaction was diluted with water (200 mL) and extracted with ethyl acetate (200 mL×3). The organic layers were washed with brine (150 mL×2), dried over sodium sulfate, filtered and concentrated. The residue was purified by flash chromatography on silica gel (0-50% ethyl acetate in petroleum ether) to afford the title compound (120 mg, 54%) as a white solid. $^1$H NMR (400 MHz, CDCl$_3$): δ 7.95 (s, 1H), 7.80 (t, J=8.4 Hz, 1H), 7.54 (s, 1H), 7.21-7.11 (m, 2H), 5.22 (s, 1H), 4.68 (d, J=6.0 Hz, 2H), 4.20 (s, 3H), 1.46 (s, 9H).

Step 11: 6-(aminomethyl)-4-(2-fluoro-4-(trifluoromethoxy)phenyl)-1-methyl-1H-benzo[d]imidazole-7-carbonitrile 2,2,2-trifluoroacetate

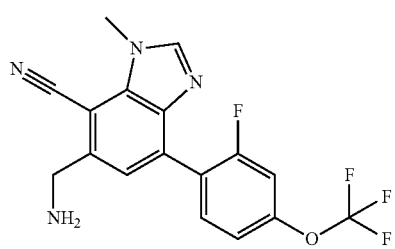 [SMILES: Cn1cnc2c(-c3ccc(OC(F)(F)F)cc3F)cc(CN)c(C#N)c21]

A solution of tert-butyl ((7-cyano-4-(2-fluoro-4-(trifluoromethoxy)phenyl)-1-methyl-1H-benzo[d]imidazol-6-yl)methyl)carbamate (100 mg, 0.22 mmol) and 5% TFA in HFIP (2 mL) was stirred at room temperature for 16 h. The mixture was concentrated to afford the title compound (100 mg, crude) as a brown oil. LCMS (ESI): m/z 365.1 (M+H)$^+$.

Step 12: N-((7-cyano-4-(2-fluoro-4-(trifluoromethoxy)phenyl)-1-methyl-1H-benzo[d]imidazol-6-yl)methyl)acrylamide

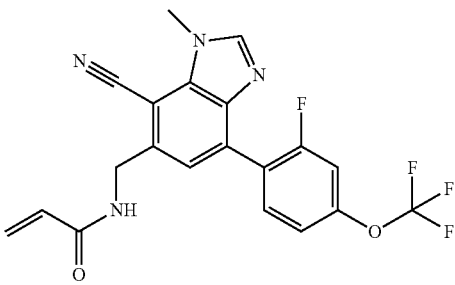

To a solution of 6-(aminomethyl)-4-(2-fluoro-4-(trifluoromethoxy)phenyl)-1-methyl-1H-benzo[d]imidazole-7-carbonitrile 2,2,2-trifluoroacetate (100 mg, 0.21 mmol) and sat. NaHCO$_3$ (1 mL) in THF (5 mL) was added acrylic anhydride (26 mg, 0.21 mmol) at 0° C. The resulting mixture was stirred at 0° C. for 1 h. The mixture was diluted with ethyl acetate (100 mL) and washed with water (100 mL×3). The organic layer was dried over Na$_2$SO$_4$ and concentrated. The residue was purified by reverse phase chromatography (Welch Xtimate C18 150*30 mm*5 um,water(0.225% FA)-ACN,34-64%) to afford the title compound (8.7 mg, 10%) as a white solid. $^1$H NMR (400 MHz, DMSO-d$_6$): δ 8.82 (t, J=5.6 Hz, 1H), 8.42 (s, 1H), 7.85 (t, J=8.4 Hz, 1H), 7.59 (d, J=10.8 Hz, 1H), 7.46-7.39 (m, 2H), 6.28 (dd, J=16.8, 10.4 Hz, 1H), 6.13 (dd, J=16.8, 2.0 Hz, 1H), 5.64 (dd, J=10.4, 2.0 Hz, 1H), 4.68 (d, J=5.6 Hz, 2H), 4.13 (s, 3H); LCMS (ESI): m/z 419.0 (M+H)$^+$.

Example 141 (Compound 144) N-(2-(7-Cyano-1-methyl-4-(4-(trifluoromethoxy)phenyl)-1H-benzo[d]imidazol-6-yl)ethyl)-N-methylacrylamide

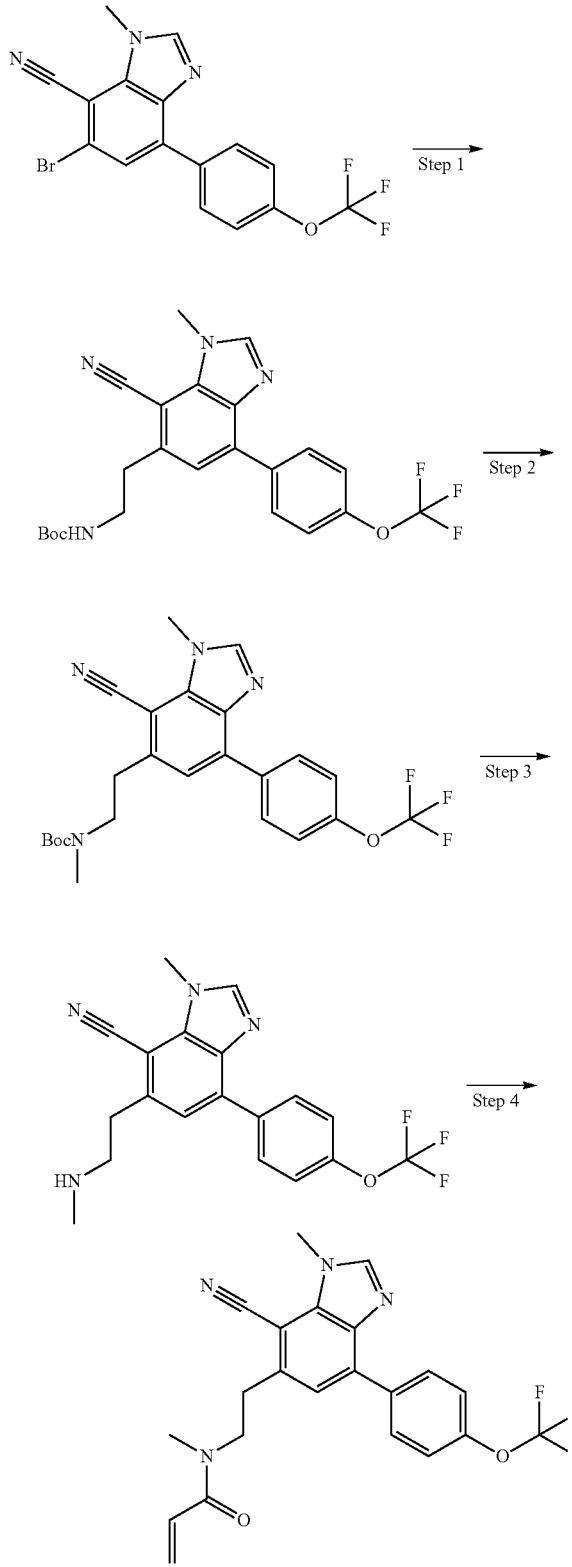

Step 1: tert-butyl (2-(7-cyano-1-methyl-4-(4-(trifluoromethoxy)phenyl)-1H-benzo[d]imidazol-6-yl)ethyl)carbamate

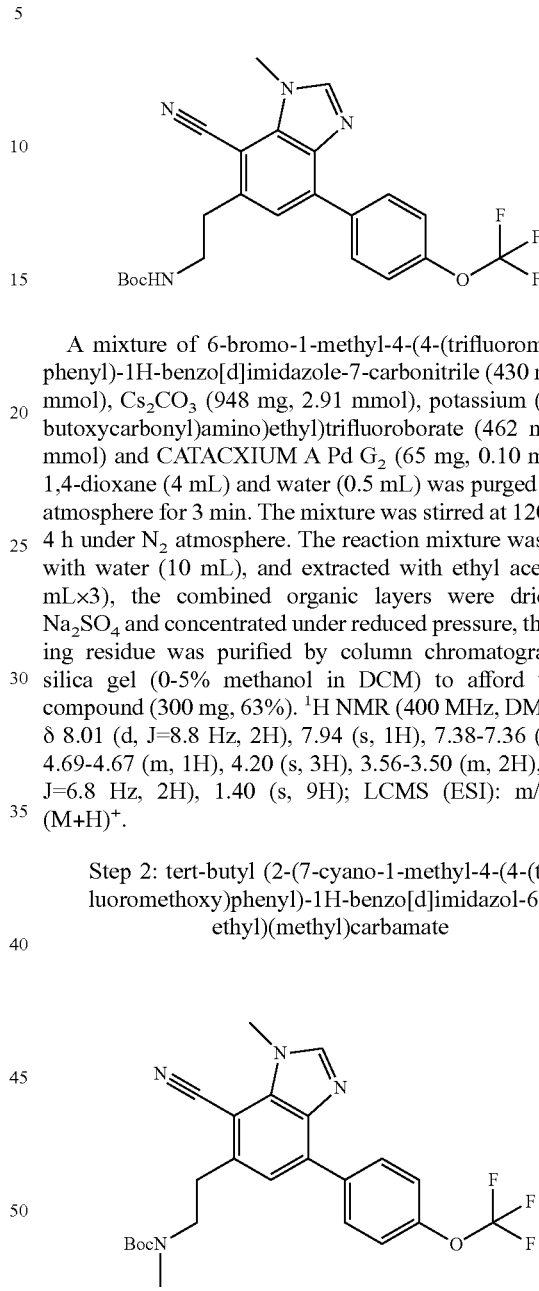

A mixture of 6-bromo-1-methyl-4-(4-(trifluoromethoxy)phenyl)-1H-benzo[d]imidazole-7-carbonitrile (430 mg, 0.97 mmol), $Cs_2CO_3$ (948 mg, 2.91 mmol), potassium (2-((tert-butoxycarbonyl)amino)ethyl)trifluoroborate (462 mg, 1.94 mmol) and CATACXIUM A Pd $G_2$ (65 mg, 0.10 mmol) in 1,4-dioxane (4 mL) and water (0.5 mL) was purged with $N_2$ atmosphere for 3 min. The mixture was stirred at 120° C. for 4 h under $N_2$ atmosphere. The reaction mixture was diluted with water (10 mL), and extracted with ethyl acetate (10 mL×3), the combined organic layers were dried over $Na_2SO_4$ and concentrated under reduced pressure, the resulting residue was purified by column chromatography on silica gel (0-5% methanol in DCM) to afford the title compound (300 mg, 63%). $^1$H NMR (400 MHz, DMSO-$d_6$): δ 8.01 (d, J=8.8 Hz, 2H), 7.94 (s, 1H), 7.38-7.36 (m, 3H), 4.69-4.67 (m, 1H), 4.20 (s, 3H), 3.56-3.50 (m, 2H), 3.24 (t, J=6.8 Hz, 2H), 1.40 (s, 9H); LCMS (ESI): m/z 461.2 (M+H)$^+$.

Step 2: tert-butyl (2-(7-cyano-1-methyl-4-(4-(trifluoromethoxy)phenyl)-1H-benzo[d]imidazol-6-yl)ethyl)(methyl)carbamate To a mixture of tert-butyl (2-(7-cyano-1-methyl-4-(4-(trifluoromethoxy)phenyl)-1H-benzo[d]imidazol-6-yl)ethyl)carbamate (320 mg, 0.69 mmol) in DMF (5 mL) was added NaH (60% in mineral oil, 56 mg, 1.39 mmol) at 0° C., and the solution was stirred at 0° C. for 30 min under $N_2$ atmosphere. Then MeI (296 mg, 2.08 mmol) was added into the mixture at 0° C. The reaction was stirred at room temperature for 3 hours under the protection of nitrogen. The reaction was diluted with water (10 mL) and extracted with ethyl acetate (10 mL×2). The combined organics were washed with brine (10 mL×2), dried over sodium sulfate, filtered and concentrated. The residue was purified by flash chromatography on silica gel (0-30% ethyl acetate in petroleum ether) to afford the title compound (300 mg, 91%) as a white solid. LCMS (ESI): m/z 475.3 (M+H)⁺.

Step 4: 1-methyl-6-(2-(methylamino)ethyl)-4-(4-(trifluoromethoxy)phenyl)-1H-benzo[d]imidazole-7-carbonitrile

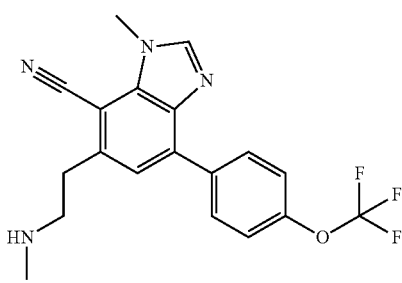 [SMILES: CNCCc1cc(-c2ccc(OC(F)(F)F)cc2)c2ncn(C)c2c1C#N]

To a stirred solution of tert-butyl (2-(7-cyano-1-methyl-4-(4-(trifluoromethoxy)phenyl)-1H-benzo[d]imidazol-6-yl)ethyl)(methyl)carbamate (300 mg, 0.63 mmol) in DCM (5 mL) was added TFA (2 mL) at room temperature. The mixture was stirred at room temperature for 2 h. The reaction was diluted water (50 mL) and adjusted to pH=8 with sat.NaHCO₃, the mixture was extracted with ethyl acetate (40 mL×3), the combined organic layers were dried over Na₂SO₄ and concentrated under reduced pressure to afford the title compound (200 mg, crude) as a white solid. The crude was used for next step without further purification. LCMS (ESI): m/z 375.1 (M+H).

Step 5: N-(2-(7-cyano-1-methyl-4-(4-(trifluoromethoxy)phenyl)-1H-benzo[d]imidazol-6-yl)ethyl)-N-methylacrylamide

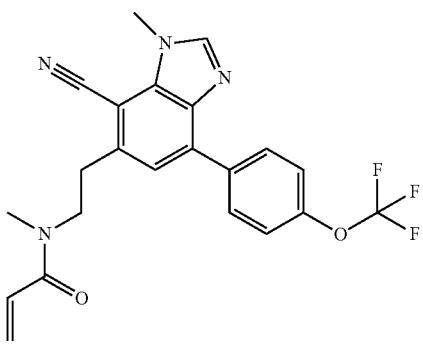 [SMILES: C=CC(=O)N(C)CCc1cc(-c2ccc(OC(F)(F)F)cc2)c2ncn(C)c2c1C#N]

To a solution of 1-methyl-6-(2-(methylamino)ethyl)-4-(4-(trifluoromethoxy)phenyl)-1H-benzo[d]imidazole-7-carbonitrile (35 mg, 0.1 mmol) in THF (3 mL) was added sat.NaHCO₃ (0.5 ml) and acryloyl chloride (17 mg, 0.2 mmol) at 0° C., the mixture was stirred at 0° C. for 30 mins. The solution was diluted with water (10 mL) and extracted with ethyl acetate (20 mL×3), the combined organic layers were dried over anhydrous Na₂SO₄, filtered and concentrated under vacuo, the residue was purified by reverse phase chromatography (Welch Xtimate C18 150*30 mm*5 um, water(FA)-ACN, 39-69%) to afford the title compound (28 mg, 65%) as a white solid. ¹H NMR (400 MHz, DMSO-d₆): δ 8.41 (s, 1H), 8.24 (d, J=8.8 Hz, 2H), 7.70-7.50 (m, 3H), 6.69-6.58 (m, 1H), 6.08-5.86 (m, 1H), 5.69-5.37 (m, 1H), 4.11 (s, 3H), 3.76-3.70 (m, 2H), 3.22-3.16 (m, 2H), 3.06, 2.96 (s, 3H total); LCMS (ESI): m/z 429.1 (M+H).

Example 142 (Compound 145)

2-Fluoro-1-(3-(1-methyl-4-(4-(trifluoromethoxy)phenyl)-1H-benzo[d]imidazol-6-yl)azetidin-1-yl)prop-2-en-1-one

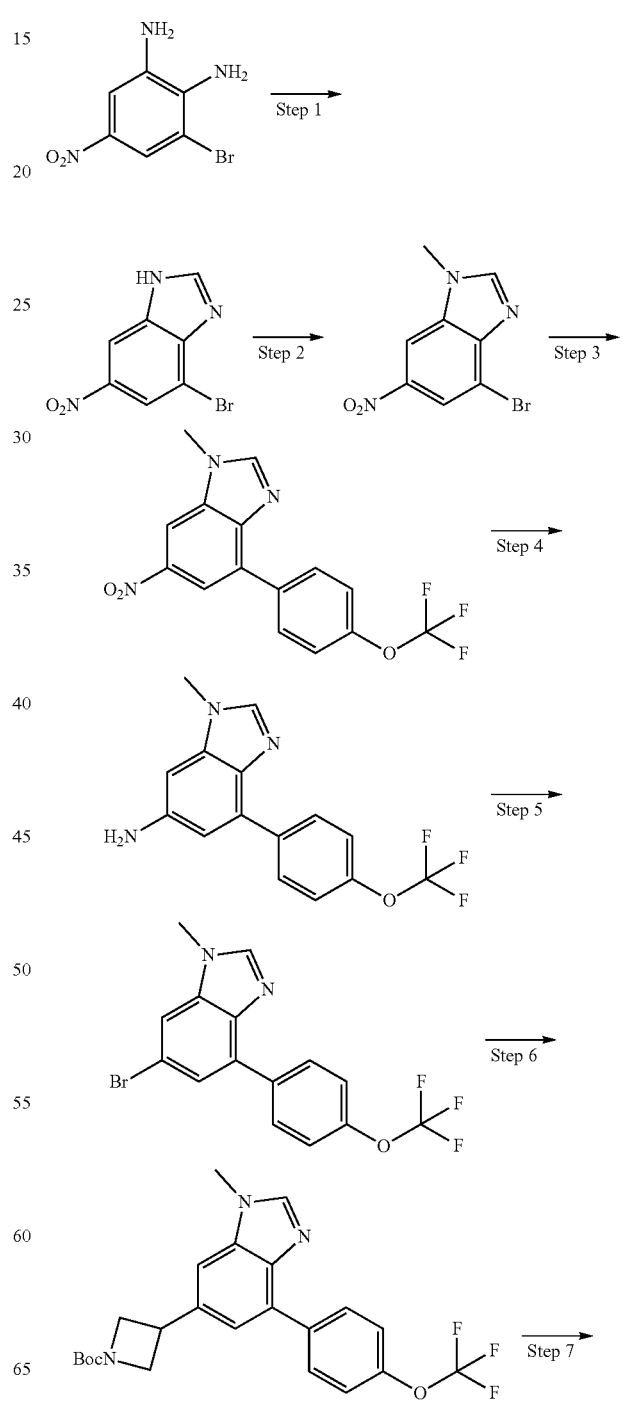

-continued

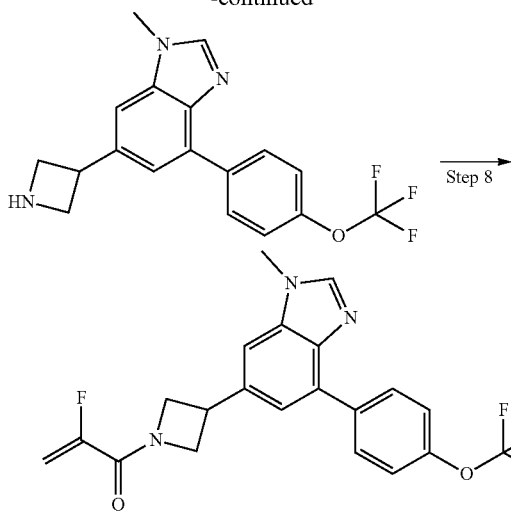

Step 1: 4-bromo-6-nitro-1H-benzo[d]imidazole

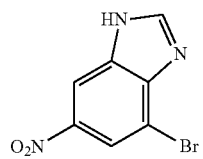

To a 500 mL round bottomed flask was added 3-bromo-5-nitrobenzene-1,2-diamine (13.0 g, 56.1 mmol) and FA (200 mL, 56.01 mmol). The solution was heated to reflux overnight. The reaction was quenched with water (100 mL) and adjusted to pH 14 with 6N NaOH. The reaction mixture was diluted with ethyl acetate (500 mL) and filtered. The filtrate was washed with brine (500 mL×3), dried over $Na_2SO_4$ and concentrated to dryness. After filtration, the filtrate was concentrated to afford the title compound (11.4 g, 88%) as a yellow solid. $^1$H NMR (400 MHz, DMSO-$d_6$): δ 8.55 (s, 1H), 8.47 (s, 1H), 8.22 (s, 1H); LCMS (ESI): m/z 242.0 (M+H)$^+$.

Step 2: 4-bromo-1-methyl-6-nitro-1H-benzo[d]imidazole

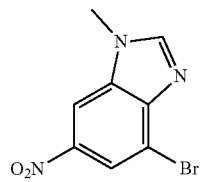

To a solution of 4-bromo-6-nitro-1H-benzo[d]imidazole (11.4 g, 47.1 mmol) in DMF (120 mL) was added saturated $K_2CO_3$ (40 mL) and MeI (2.91 mL, 47.1 mmol). The mixture was stirred at room temperature for 16 h. The reaction was quenched with water (100 mL). The mixture was diluted with ethyl acetate (300 mL), washed with brine (200 mL×3). The organic layer was dried over $Na_2SO_4$ and concentrated. The residue was purified by flash chromatography on silica gel (0-40% ethyl acetate in petroleum ether to afford the title compound (5.7 g, 47%) as a white solid, 2D-NMR confirmed it. $^1$H NMR (400 MHz, DMSO-$d_6$): δ 8.70 (s, 1H), 8.65 (s, 1H), 8.31 (s, 1H), 3.99 (s, 3H).

Step 3: 1-methyl-6-nitro-4-(4-(trifluoromethoxy)phenyl)-1H-benzo[d]imidazole

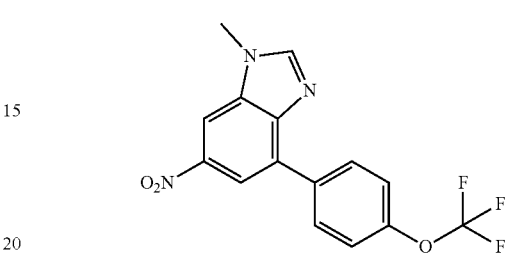

A mixture of 4-bromo-1-methyl-6-nitro-1H-benzo[d]imidazole (5.7 g, 22.26 mmol) and (4-(trifluoromethoxy)phenyl)boronic acid (9.17 g, 44.5 mmol), $Na_2CO_3$ (4.7 g, 44.5 mmol) and Pd(dppf)$Cl_2$ (1.63 g, 2.2 mmol) in 1,4-dioxane (70 mL) and water (5 mL) was stirred at 110° C. for 2 hours under $N_2$ atmosphere. The reaction mixture was quenched with water (200 mL) and extracted with ethyl acetate (300 mL×2). The combined organic layers were dried over $Na_2SO_4$ and concentrated. The residue was purified by flash chromatography on silica gel (0-20% ethyl acetate in petroleum ether) to afford the title compound (5.7 g, 76%) as a yellow solid. $^1$H NMR (400 MHz, DMSO-$d_6$): δ 8.66 (d, J=2.0 Hz, 1H), 8.64 (s, 1H), 8.31-8.25 (m, 3H), 7.54 (d, J=8.4 Hz, 2H), 4.02 (s, 3H); LCMS (ESI): m/z 337.9 (M+H)$^+$.

Step 4: 1-methyl-4-(4-(trifluoromethoxy)phenyl)-1H-benzo[d]imidazol-6-amine

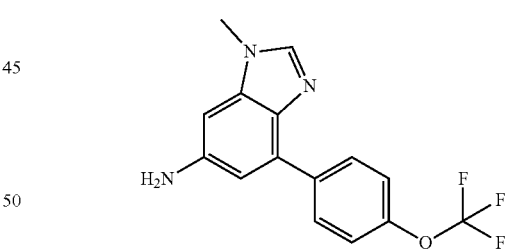

A mixture of 1-methyl-6-nitro-4-(4-(trifluoromethoxy)phenyl)-1H-benzo[d]imidazole (1.7 g, 5.04 mmol), iron (2.82 g, 50.41 mmol) and $NH_4Cl$ (1.35 g, 25.2 mmol) in ethanol (40 mL) and water (4 mL) was stirred at 80° C. for 2 h under $N_2$ atmosphere. After cooling for room temperature, the acetic acid (10 mL) was added into the mixture and the solution was stirred for 20 min. The reaction was quenched with saturated $NaHCO_3$ (80 mL) and extracted with ethyl acetate (100 mL×2), the combined organic layers were dried over $Na_2SO_4$ and concentrated. The residue was purified by flash chromatography on silica gel (0-20% ethyl acetate in petroleum ether) to afford the title compound (1.5 g, 97%) as a yellow solid. $^1$H NMR (400 MHz, DMSO-$d_6$): δ 8.14 (d, J=8.8 Hz, 2H), 7.91 (s, 1H), 7.44 (d, J=8.0 Hz, 2H), 6.82 (s, 1H), 6.62 (s, 1H), 5.10 (s, 2H), 3.71 (s, 3H); LCMS (ESI): m/z 307.9 (M+H)⁺.

Step 5: 6-bromo-1-methyl-4-(4-(trifluoromethoxy)phenyl)-1H-benzo[d]imidazole

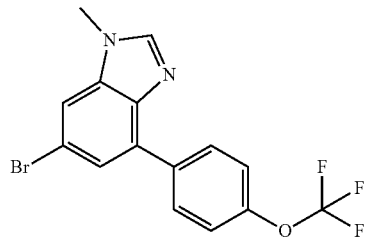 [SMILES: Cn1cnc2c(-c3ccc(OC(F)(F)F)cc3)cc(Br)cc21]

To a solution of 1-methyl-4-(4-(trifluoromethoxy)phenyl)-1H-benzo[d]imidazol-6-amine (1.5 g, 4.9 mmol), and tert-butyl nitrite (1.16 mL, 9.7 mmol) in acetonitrile (15 mL) was added CuBr (1.4 g, 9.8 mmol) at room temperature. Then the solution was stirred at 65° C. for 2 hours under $N_2$ atmosphere. The reaction mixture was quenched with water (50 mL), extracted with water (100 mL×3). Combined organic layers were dried over $Na_2SO_4$, filtered and concentrated. The residue was purified by flash chromatography on silica gel (0-20% ethyl acetate in petroleum ether) to afford the title compound (1.0 g, 55%) as a green solid. ¹H NMR (400 MHz, DMSO-$d_6$): δ 8.31 (s, 1H), 8.23 (d, J=8.8 Hz, 2H), 7.91 (s, 1H), 7.62 (s, 1H), 7.48 (d, J=8.0 Hz, 2H), 3.88 (s, 3H); LCMS (ESI): m/z 370.9 (M+H)⁺.

Step 6: tert-butyl 3-(1-methyl-4-(4-(trifluoromethoxy)phenyl)-1H-benzo[d]imidazol-6-yl)azetidine-1-carboxylate

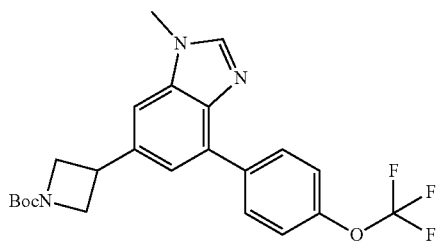 [SMILES: Cn1cnc2c(-c3ccc(OC(F)(F)F)cc3)cc(C3CN(C(=O)OC(C)(C)C)C3)cc21]

A mixture of 6-bromo-1-methyl-4-(4-(trifluoromethoxy)phenyl)-1H-benzo[d]imidazole (300 mg, 0.80 mmol) and $Na_2CO_3$ (202 mg, 1.9 mmol) in DME (10 mL) was added Ir[dF(CF$_3$)ppy]$_2$(dtbbpy)PF$_6$ (9 mg, 0.007 mmol), TTMSS (228 mg, 0.91 mmol) and tert-butyl 3-bromoazetidine-1-carboxylate (271 mg, 1.1 mmol). The solution of NiCl$_2$-glyme (17 mg, 0.07 mmol) and dtbbpy (31 mg, 0.15 mmol) in DME (4 mL) was added the above mixture in glove box at room temperature. The reaction mixture was stirred under a Lumidox Screen Kit for 16 hours at room temperature. The reaction mixture was quenched with water (40 mL), extracted with water (20 mL×3). The organic layer was dried over $Na_2SO_4$ and concentrated. The residue was purified by flash chromatography on silica gel (0-30% ethyl acetate in petroleum ether) to afford the title compound (300 mg, 83%) as a white solid. ¹H NMR (400 MHz, DMSO-$d_6$): δ 8.25-8.22 (m, 3H), 7.61 (s, 1H), 7.48-7.44 (m, 2H), 7.42 (s, 1H), 4.32-4.30 (m, 2H), 4.05-4.02 (m, 3H), 3.89 (s, 3H), 1.39 (s, 9H); LCMS (ESI): m/z 448.0 (M+H)⁺.

Step 7: 6-(azetidin-3-yl)-1-methyl-4-(4-(trifluoromethoxy)phenyl)-1H-benzo[d]imidazole hydrochloride

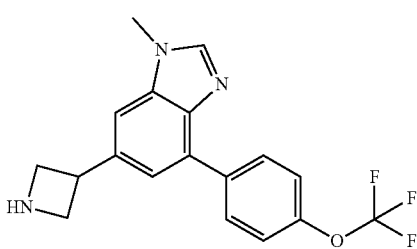 [SMILES: Cn1cnc2c(-c3ccc(OC(F)(F)F)cc3)cc(C3CNC3)cc21]

A solution of tert-butyl 3-(1-methyl-4-(4-(trifluoromethoxy)phenyl)-1H-benzo[d]imidazol-6-yl)azetidine-1-carboxylate (320 mg, 0.72 mmol) and 5% TFA in HFIP (20 mL) was stirred at room temperature for 1 h. The reaction was concentrated under vacuum. The residue was diluted with water (10 mL), and the solution was adjusted with saturated aqueous NaHCO$_3$ to pH 7, and extracted with ethyl acetate (50 mL×3). The organic layer was dried over anhydrous sodium sulfate and concentrated under vacuum to afford (220 mg, crude). LCMS (ESI): m/z 347.9 (M+H)⁺.

Step 8: 2-fluoro-1-(3-(1-methyl-4-(4-(trifluoromethoxy)phenyl)-1H-benzo[d]imidazol-6-yl)azetidin-1-yl)prop-2-en-1-one

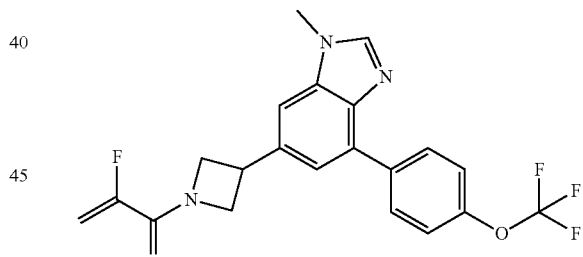

To a mixture of 6-(azetidin-3-yl)-1-methyl-4-(4-(trifluoromethoxy)phenyl)-1H-benzo[d]imidazole (300 mg, 0.86 mmol) in dichloromethane (10 mL) and methyl alcohol (2 mL) was added 2-fluoroacrylic acid (117 mg, 1.3 mmol) and ethyl 2-ethoxyquinoline-1(2H)-carboxylate (321 mg, 1.3 mmol). The reaction mixture was stirred at room temperature for 4 h. The reaction mixture was quenched with water (60 mL), extracted with ethyl acetate (20 mL×3). The organic was dried over $Na_2SO_4$ and concentrated. The residue was purified by reverse phase chromatography (Welch Xtimate C18 150*25 mm*5 um, water(0.225% FA)-ACN, 42%-72%) to afford the title compound (28.5 mg, 8%) as a white solid. ¹H NMR (400 MHz, DMSO-$d_6$): δ 8.29-8.25 (m, 3H), 7.70 (s 1H), 7.51-7.48 (m, 3H), 5.40 (dd, J=48.8, 3.6 Hz, 1H), 5.31 (dd, J=16.4, 3.6 Hz, 1H), 4.83-4.80 (m, 1H), 4.58-4.56 (m, 1H), 4.48-4.45 (m, 1H), 4.18-4.11 (m, 2H), 3.90 (s, 3H); LCMS (ESI): m/z 419.9 (M+H)⁺.

Example 143 (Compound 146)

N—((8-(4-(Trifluoromethyl)phenoxy)quinolin-6-yl)methyl)acrylamide

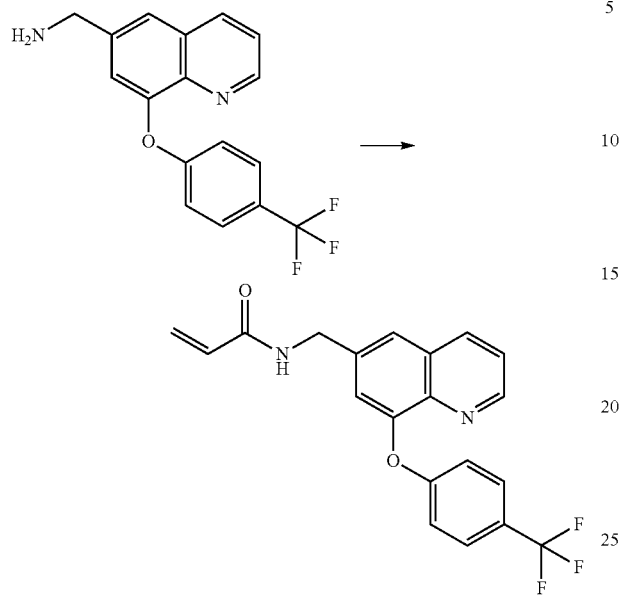

To a solution of (8-(4-(trifluoromethyl)phenoxy)quinolin-6-yl)methanamine (110 mg, 0.35 mmol) in THF (5 mL) was added sat.NaHCO₃ (2 mL) and acrylic anhydride (0.06 mL, 0.52 mmol) at 0° C. The solution was stirred at 0° C. for 2 hours. The reaction mixture was diluted with water (30 mL) and extracted with ethyl acetate (15 mL×3), the combined organic layers were washed with brine (15 mL×3). The organic layer was dried over Na₂SO₄ and concentrated in vacuo. The residue was purified by reverse phase chromatography (Boston Green ODS 150*30 mm*5 um/water (FA)-CAN/40%-70%) to afford the title compound (46.3 mg, 36%) as a white solid. $^1$H NMR (400 MHz, DMSO-$d_6$): δ 8.80-8.77 (m, 2H), 8.45 (dd, J=8.8, 1.6 Hz, 1H), 7.78 (d, J=1.6 Hz, 1H), 7.66 (d, J=8.8 Hz, 2H), 7.58 (dd, J=8.4, 4.0 Hz, 1H), 7.50 (d, J=1.6 Hz, 1H), 7.01 (d, J=8.4 Hz, 2H), 6.31 (dd, J=17.2, 10.4 Hz 1H), 6.15 (dd, J=17.2, 2.0 Hz 1H), 5.66 (dd, J=10.4, 2.0 Hz, 1H), 4.57 (d, J=6.0 Hz, 2H); LCMS (ESI): m/z 373.0 (M+H)⁺.

Example 144 (Compound 147) & Example 145 (Compound 148)

(S)—N-((5-(1,2-Dihydroxyethyl)-8-(4-(trifluoromethyl)phenoxy)quinolin-6-yl)methyl)acrylamide & (R)—N-((5-(1,2-dihydroxyethyl)-8-(4-(trifluoromethyl)phenoxy)quinolin-6-yl)methyl)acrylamide

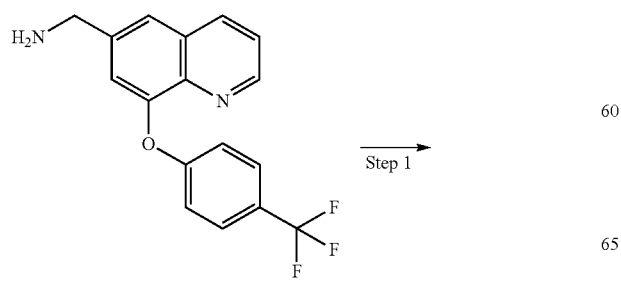

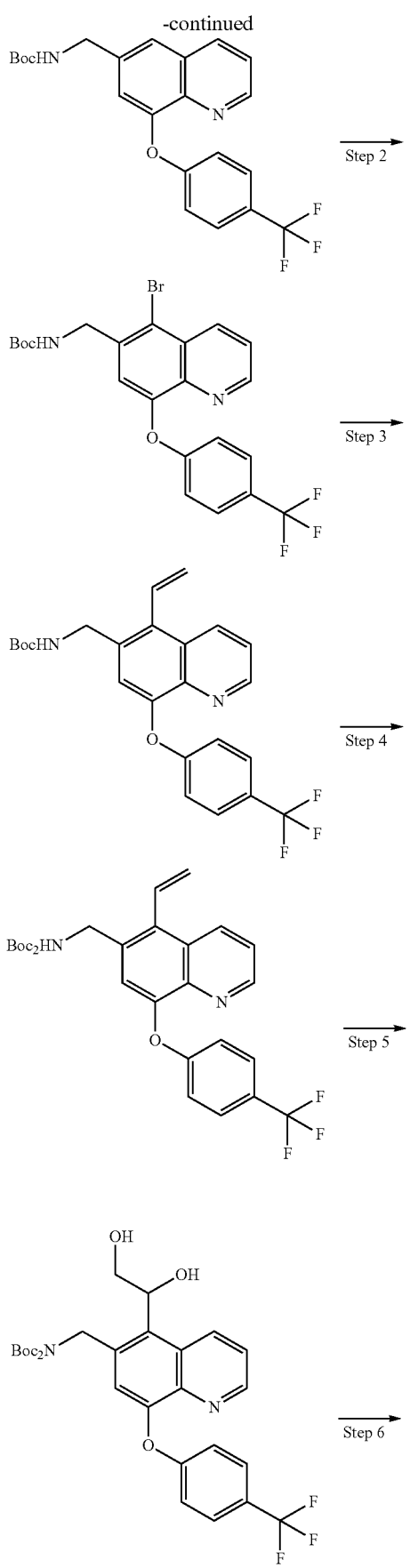

655

-continued

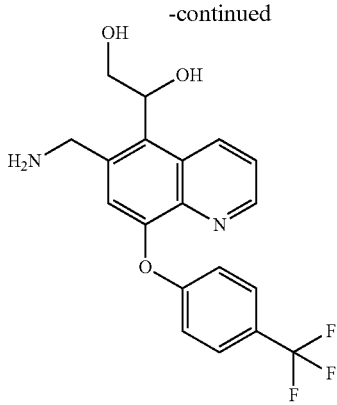

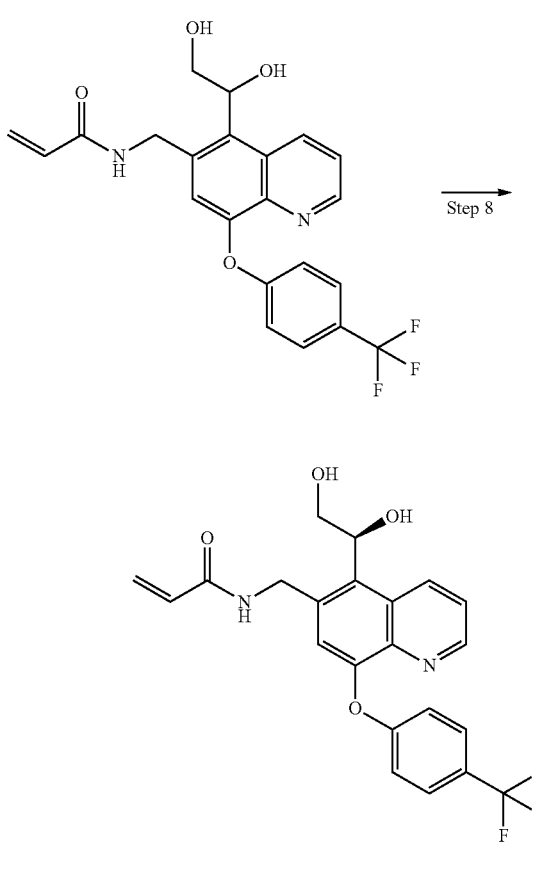

656

Step 1: tert-butyl ((8-(4-(trifluoromethyl)phenoxy)
quinolin-6-yl)methyl)carbamate

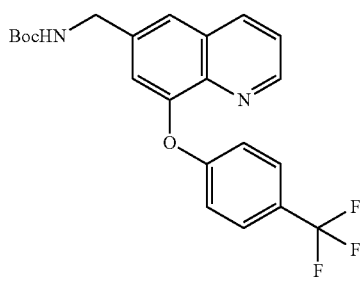 [SMILES: CC(C)(C)OC(=O)NCc1cc(Oc2ccc(C(F)(F)F)cc2)c2ncccc2c1]

A solution of (8-(4-(trifluoromethyl)phenoxy)quinolin-6-yl)methanamine (6.0 g, 18.85 mmol), Boc₂O (4.53 g, 20.74 mmol) and DMAP (230 mg, 1.89 mmol) in dichloromethane (70 mL) was stirred at room temperature for 16 hours. The solution was concentrated. The residue was purified by flash chromatography on silica gel (0-25% ethyl acetate in petroleum ether) to afford the title compound (4.5 g, 57%) as a white solid. LCMS (ESI): m/z 419.2 (M+H)⁺.

Step 2: tert-butyl ((5-bromo-8-(4-(trifluoromethyl)
phenoxy)quinolin-6-yl)methyl)carbamate

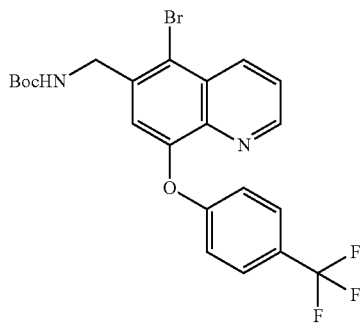 [SMILES: CC(C)(C)OC(=O)NCc1cc(Oc2ccc(C(F)(F)F)cc2)c2ncccc2c1Br]

A solution of tert-butyl ((8-(4-(trifluoromethyl)phenoxy)quinolin-6-yl)methyl)carbamate (3.5 g, 8.37 mmol) and NBS (1.78 g, 10.04 mmol) in acetonitrile (30 mL) was stirred at room temperature for 16 hours. The organic layer was concentrated under vacuum to afford the title compound (3.0 g, crude) as a white solid. LCMS (ESI): m/z 497.1 (M+H)⁺.

Step 3: tert-butyl ((8-(4-(trifluoromethyl)phenoxy)-
5-vinylquinolin-6-yl)methyl)carbamate

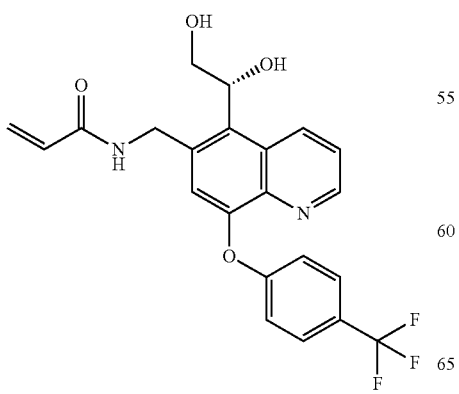

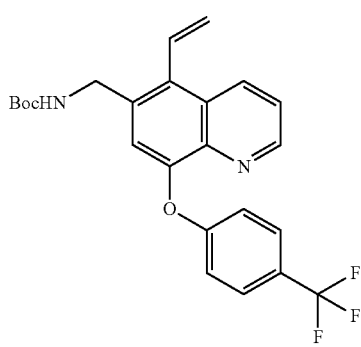 [SMILES: C=Cc1c(CNC(=O)OC(C)(C)C)cc(Oc2ccc(C(F)(F)F)cc2)c2ncccc12]

A mixture of Pd(dppf)Cl₂ (295 mg, 0.40 mmol), 4,4,5,5-tetramethyl-2-vinyl-1,3,2-dioxaborolane (744 mg, 4.83 mmol), tert-butyl ((5-bromo-8-(4-(trifluoromethyl)phenoxy)quinolin-6-yl)methyl)carbamate (2.0 g, 4.02 mmol) and Na₂CO₃(853 mg, 8.04 mmol) in 1,4-dioxane (24 mL) and water (2.4 mL) was stirred at 120° C. for 2.5 h under N₂ atmosphere. The mixture was diluted with water (50 mL) and extracted with ethyl acetate (100 mL×3) and washed with brine (20 mL). The organic layers were dried over anhydrous sodium sulfate and concentrated under reduced. The residue was purified by flash chromatography on silica gel (0-30% ethyl acetate in petroleum ether) to afford the title compound (980 mg, 55%) as a white solid. ¹H NMR (400 MHz, CDCl₃): δ 8.92 (dd, J=4.0, 1.2 Hz, 1H), 8.51 (dd, J=8.8, 1.6 Hz, 1H), 7.59 (d, J=8.4 Hz, 2H), 7.47 (dd, J=8.8, 4.0 Hz, 1H), 7.30 (s, 1H), 7.14 (d, J=8.8 Hz, 2H), 7.04 (dd, J=17.6, 11.6 Hz, 1H), 5.89 (dd, J=11.6, 1.6 Hz, 1H), 5.47 (dd, J=17.6, 1.6 Hz, 1H), 4.86 (s, 1H), 4.49 (d, J=5.6 Hz, 2H), 1.40 (s, 9H).

Step 4: tert-butyl N-tert-butoxycarbonyl-N-[[8-[4-(trifluoromethyl)phenoxy]-5-vinyl-6-quinolyl]methyl]carbamate

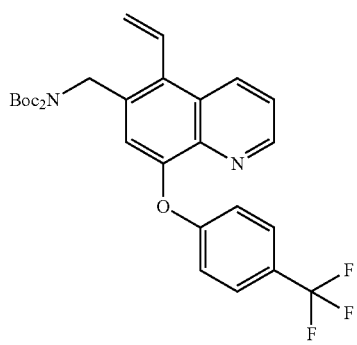

A solution of Boc₂O (569 mg, 2.6 mmol), DMAP (367 mg, 3.0 mmol) and tert-butyl ((8-(4-(trifluoromethyl)phenoxy)-5-vinylquinolin-6-yl)methyl)carbamate (890 mg, 2.0 mmol) in THF (10 mL) was stirred at room temperature for 4 hours. The solution was concentrated. The residue was purified by flash chromatography on silica gel (0-25% ethyl acetate in petroleum ether) to afford the title compound (650 mg, 60%) as colorless oil. LCMS (ESI): m/z 545.3 (M+H)⁺.

Step 5: tert-butyl N-tert-butoxycarbonyl-N-[[5-(1,2-dihydroxyethyl)-8-[4-(trifluoromethyl)phenoxy]-6-quinolyl]methyl]carbamate

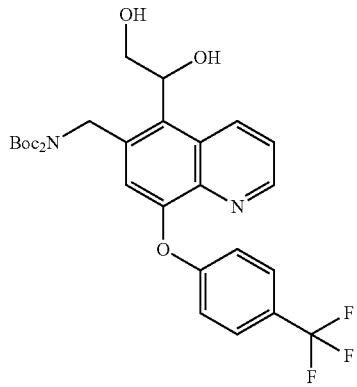

To a solution of tert-butyl N-tert-butoxycarbonyl-N-[[8-[4-(trifluoromethyl)phenoxy]-5-vinyl-6-quinolyl]methyl]carbamate (600 mg, 1.1 mmol) and NMO (259 mg, 2.2 mmol) in THF (6 mL) and water (2 mL) was added K₂OsO₄·2H₂O (41 mg, 0.11 mmol) at 0° C. The mixture was stirred at room temperature for 16 h. The reaction mixture was diluted with ethyl acetate (20 mL) and was washed with sat.Na₂SO₃ (20 mL), the organic layer was dried over Na₂SO₄ and concentrated in vacuo. The residue was purified by flash chromatography on silica gel (0-50% ethyl acetate in petroleum ether) to afford the title compound (300 mg, 47%) as a white solid. ¹H NMR (400 MHz, CDCl₃): δ 8.98 (d, J=8.8 Hz, 1H), 8.92 (dd, J=4.0, 1.2 Hz, 1H), 7.59 (d, J=8.8 Hz, 2H), 7.48 (dd, J=8.8, 4.0 Hz, 1H), 7.14 (d, J=8.8 Hz, 2H), 7.13 (s, 1H), 5.80-5.71 (m, 1H), 5.15 (d, J=16.0 Hz, 1H), 5.04 (d, J=16.0 Hz, 1H), 4.22-4.14 (m, 1H), 3.89-3.80 (m, 1H), 3.46-3.40 (m, 1H), 2.48-2.41 (m, 1H), 1.39 (s, 18H).

Step 6: 1-(6-(aminomethyl)-8-(4-(trifluoromethyl)phenoxy)quinolin-5-yl)ethane-1,2-diol

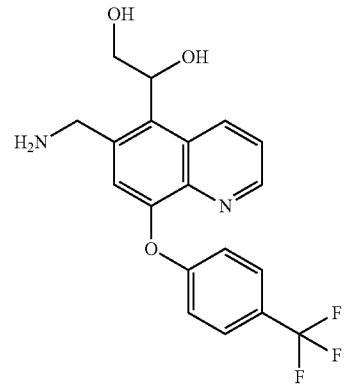 [SMILES: NCc1cc(Oc2ccc(C(F)(F)F)cc2)c2ncccc2c1C(O)CO]

A solution of tert-butyl N-tert-butoxycarbonyl-N-[[5-(1,2-dihydroxyethyl)-8-[4-(trifluoromethyl)phenoxy]-6-quinolyl]methyl]carbamate (600 mg, 1.04 mmol) and con.HCl (3 mL) in THF (10 mL) was stirred at room temperature for 16 h. The reaction was diluted with water (10 mL) and adjusted to pH to 7 with sat.NaHCO₃. The mixture was extracted with ethyl acetate (10 mL×3). The combined organic layers were dried over Na₂SO₄ and concentrated in vacuo to afford the title compound (300 mg, crude) as a yellow solid. LCMS (ESI): m/z 379.1 (M+H)⁺.

Step 7: N-((5-(1,2-dihydroxyethyl)-8-(4-(trifluoromethyl)phenoxy)quinolin-6-yl)methyl)acrylamide

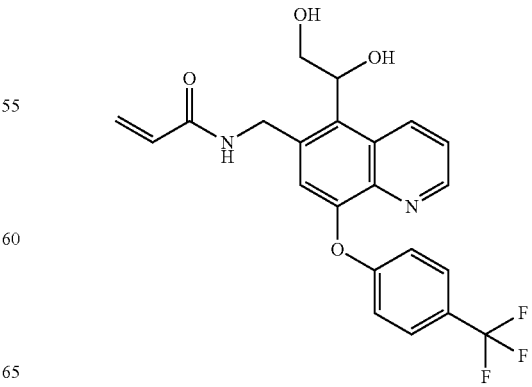

To a mixture of sat.NaHCO$_3$ (3 mL) and 1-(6-(aminomethyl)-8-(4-(trifluoromethyl)phenoxy)quinolin-5-yl)ethane-1,2-diol (200 mg, 0.53 mmol) in THF (6 mL) was added acryloyl chloride (53 mg, 0.58 mmol) at 0° C. The mixture was stirred at 0° C. for 1 h. The reaction mixture was diluted with water (20 mL) and extracted with ethyl acetate (15 mL×3), the combined organic layers were dried over Na$_2$SO$_4$ and concentrated in vacuo. The resulting residue was purified by reverse phase chromatography (Welch Xtimate C18 150*30 mm*5 um, acetonitrile 18-48%/water (FA)-ACN) to afford the title compound (180 mg, 79%) as a white solid. LCMS (ESI): m/z 433.1 (M+H)$^+$.

Step 8: (S)—N—((5-(1,2-dihydroxyethyl)-8-(4-(trifluoromethyl)phenoxy)quinolin-6-yl)methyl)acrylamide & (R)—N—((5-(1,2-dihydroxyethyl)-8-(4-(trifluoromethyl)phenoxy)quinolin-6-yl)methyl)acrylamide

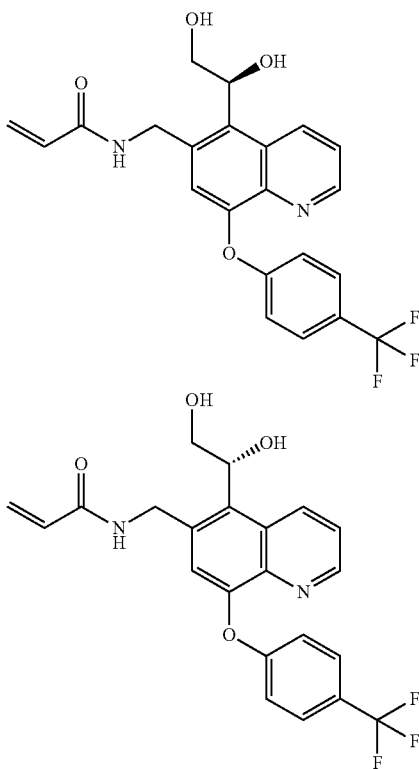

N-((5-(1,2-Dihydroxyethyl)-8-(4-(trifluoromethyl)phenoxy)quinolin-6-yl)methyl)acrylamide (180 mg, 0.42 mmol) was separated by Chiral SFC(Instrument: SFC-16; Column: OD(250 mm*30 mm,10 um); Condition: 0.1% NH$_4$OH-IPA; Begin B:50%; Flow Rate (ml/min): 80) to afford the first peak (S)—N-((5-(1,2-dihydroxyethyl)-8-(4-(trifluoromethyl)phenoxy)quinolin-6-yl)methyl)acrylamide (32 mg, 18%) and the second peak (R)—N-((5-(1,2-dihydroxyethyl)-8-(4-(trifluoromethyl)phenoxy)quinolin-6-yl)methyl)acrylamide (47 mg, 26%) both as white solid.

The first peak: $^1$H NMR (400 MHz, DMSO-d$_6$): δ 9.14 (d, J=8.0 Hz, 1H), 8.75 (d, J=4.0 Hz, 1H), 8.57 (s, 1H), 7.64 (d, J=8.4 Hz, 2H), 7.52 (dd, J=8.8, 4.0 Hz, 1H), 7.44 (s, 1H), 6.96 (d, J=8.8 Hz, 2H), 6.27 (dd, J=17.2, 10.4 Hz, 1H), 6.12 (dd, J=17.2, 2.0 Hz, 1H), 5.82 (d, J=3.6 Hz, 1H), 5.62 (dd, J=10.4, 2.0 Hz, 1H), 5.46-5.43 (m, 1H), 4.96 (t, J=5.2 Hz, 1H), 4.81-4.76 (m, 1H), 4.60-4.55 (m, 1H), 3.94-3.88 (m, 1H), 3.76-3.71 (m, 1H); LCMS (ESI): m/z 433.0 (M+H)$^+$.

The second peak: $^1$H NMR (400 MHz, DMSO-d$_6$): δ 9.14 (d, J=8.0 Hz, 1H), 8.75 (d, J=4.0 Hz, 1H), 8.57 (s, 1H), 7.64 (d, J=8.4 Hz, 2H), 7.52 (dd, J=8.8, 4.0 Hz, 1H), 7.44 (s, 1H), 6.96 (d, J=8.8 Hz, 2H), 6.27 (dd, J=17.2, 10.4 Hz, 1H), 6.12 (dd, J=17.2, 2.0 Hz, 1H), 5.82 (d, J=3.6 Hz, 1H), 5.62 (dd, J=10.4, 2.0 Hz, 1H), 5.46-5.43 (m, 1H), 4.96 (t, J=5.2 Hz, 1H), 4.81-4.76 (m, 1H), 4.60-4.55 (m, 1H), 3.94-3.88 (m, 1H), 3.76-3.71 (m, 1H); LCMS (ESI): m/z 433.0 (M+H)$^+$.

Example 146

TR-FRET Assay

His-tagged TEAD proteins are pre-incubated with TEAD project compounds for 30 minutes or 4 hours at room temperature. Biotinylated lipid pocket probes are then added to the TEAD/Compound mixture and incubated for 60 minutes at room temperature. The lipid pocket probe competes with the test compound for the TEAD lipid pocket until equilibrium is reached. After 60 minutes, Europium labelled anti-His (Perkin Elmer #AD0110) and XL665 labelled streptavidin (CIS Bio 610SAXAC) are added to the TEAD/test compound/lipid pocket mixture and incubated for 30 minutes or 4 hours. TR-FRET values are then measured using an EnVision multi-label plate reader (Perkin Elmer Cat #2104-001 0A.) If the lipid pocket probe binds to TEAD as expected, a TR-FRET signal results from the proximity of anti-His Eu and XL665. If a TEAD lipid pocket binder such as binds and displaces the lipid pocket probe, the disruption of the TEAD:probe interaction results in a decrease in TR-FRET signal. The potency of compounds as TEAD lipid pocket binders is determined by IC$_{50}$ value generated using a non-linear 4 parameter curve fit.

The IC$_{50}$ data for selected compounds are presented in Table 3 (4 hours) below. Note that the "Compound Number" in Table 3 corresponds to the "Compound Number" in Table 1.

TABLE 3

| Compound Number | Lipid HTRF TEAD1 IC$_{50}$ [uM] | Lipid HTRF TEAD2 IC$_{50}$ [uM] | Lipid HTRF TEAD3 IC$_{50}$ [uM] | Lipid HTRF TEAD4 IC$_{50}$ [uM] |
|---|---|---|---|---|
| 1 | 0.0057 | 0.031 | 0.0048 | 0.0034 |
| 2 | 0.067 | 0.155 | 0.1205 | 0.081 |
| 3 | 0.48 | 0.35 | 0.7 | 0.74 |
| 4 | 6 | 50 | 50 | 50 |
| 5 | 0.127333 | 0.226667 | 0.29 | 0.27 |
| 6 | 0.31 | 6.25 | 2.15 | 0.515 |
| 7 | 0.018 | 0.64 | 0.23 | 0.04 |
| 8 | 0.018 | 0.032 | 0.029 | 0.024 |
| 9 | 0.046 | 0.43 | 0.11 | 0.088 |

TABLE 3-continued

| Compound Number | Lipid HTRF TEAD1 IC$_{50}$ [uM] | Lipid HTRF TEAD2 IC$_{50}$ [uM] | Lipid HTRF TEAD3 IC$_{50}$ [uM] | Lipid HTRF TEAD4 IC$_{50}$ [uM] |
|---|---|---|---|---|
| 10 | 0.14 | 1.3 | 0.41 | 0.094 |
| 11 | 0.078 | 0.1 | 0.074 | 0.0081 |
| 12 | 0.016833 | 0.018333 | 0.0265 | 0.015167 |
| 13 | 0.086 | 0.32 | 0.17 | 0.035 |
| 14 | 5.5 | 1.8 | 24 | 1.4 |
| 15 | 0.13 | 0.3 | 0.07 | 0.005 |
| 16 | 0.024 | 0.051 | 0.037 | 0.037 |
| 17 | 13 | 3.7 | 50 | 5.7 |
| 18 | 1.2 | 1.1 | 50 | 0.8 |
| 19 | 0.004 | 0.0039 | 0.008 | 0.0032 |
| 20 | 0.0145 | 0.0235 | 0.0245 | 0.0175 |
| 21 | 0.077 | 0.19 | 0.072667 | 0.0119 |
| 22 | 0.15 | 0.3 | 0.37 | 0.16 |
| 23 | 0.69 | 0.37 | 3.9 | 0.16 |
| 24 | 0.032 | 0.12 | 0.039 | 0.027 |
| 25 | 0.0044 | 0.0039 | 0.0056 | 0.0037 |
| 26 | 0.14 | 0.062 | 0.51 | 0.18 |
| 27 | 0.0245 | 0.015 | 0.0405 | 0.0067 |
| 28 | 0.0597 | 0.0153 | 0.39 | 0.193 |
| 29 | 0.0167 | 0.00887 | 0.054 | 0.0123 |
| 30 | 0.1 | 0.016 | 0.59 | 0.053 |
| 31 | 0.047 | 0.012 | 4.4 | 0.055 |
| 32 | 0.032 | 0.01 | 2.5 | 0.054 |
| 33 | 0.14 | 0.0078 | 0.26 | 0.079 |
| 34 | 0.19 | 0.059 | 3.6 | 0.062 |
| 35 | 0.011 | 0.73 | 0.79 | 0.33 |
| 36 | 0.044 | 0.1 | 0.089 | 0.037 |
| 37 | 0.1 | 0.96 | 0.23 | 0.082 |
| 38 | 0.02 | 0.033 | 0.026 | 0.0068 |
| 39 | 0.008 | 0.009 | 0.0505 | 0.0245 |
| 43 | 0.01 | 0.0098 | 0.022 | 0.016 |
| 44 | 0.011 | 0.016 | 0.018 | 0.054 |
| 45 | 0.048 | 0.018 | 1.2 | 0.38 |
| 46 | 0.022 | 0.00615 | 0.079 | 0.125 |
| 47 | 0.022 | 0.0115 | 0.175 | 0.135 |
| 48 | 0.022 | 0.0145 | 1.035 | 0.145 |
| 49 | 0.0092 | 0.011 | 0.011 | 0.004 |
| 50 | 0.012 | 0.011 | 0.037 | 0.034 |
| 51 | 0.019 | 0.012 | 0.11 | 0.02 |
| 52 | 0.025 | 0.046 | 0.079 | 0.043 |
| 55 | 0.02 | 0.0044 | 0.24 | 0.0072 |
| 56 | 0.048 | 0.035 | 0.099 | 0.013 |
| 57 | 0.0525 | 0.009 | 2.1 | 0.014 |
| 58 | 0.0069 | 0.006 | 0.093 | 0.0035 |
| 59 | 0.018 | 0.037 | 0.38 | 0.081 |
| 62 | 0.0031 | 0.0031 | 0.0046 | 0.002 |
| 63 | 0.11 | 0.076 | 0.31 | 0.08 |
| 64 | 0.27 | 0.51 | 0.7 | 0.044 |
| 67 | 0.093 | 0.34 | 0.42 | 0.14 |
| 68 | 0.85 | 3 | 0.86 | 0.59 |
| 69 | 0.04 | 0.1 | 0.097 | 0.0075 |
| 70 | 0.33 | 0.057 | 1.3 | 0.26 |
| 71 | 0.089 | 0.04 | 14 | 0.12 |
| 72 | 0.031 | 0.034 | 3.8 | 0.06 |
| 73 | 0.058 | 0.04 | 0.22 | 0.039 |
| 74 | 0.016 | 0.017 | 0.34 | 0.0039 |
| 75 | 0.009 | 0.013 | 0.16 | 0.0035 |
| 76 | 1 | 0.23 | 1.3 | 0.26 |
| 77 | 0.011 | 0.004 | 0.11 | 0.0025 |
| 78 | 0.95 | 0.14 | 50 | 0.65 |
| 79 | 0.98 | 0.04 | 1.9 | 0.57 |
| 80 | 0.13 | 0.11 | 0.84 | 0.74 |
| 81 | 0.031 | 0.021 | 0.22 | 0.013 |
| 82 | 0.069 | 0.015 | 1.8 | 0.24 |
| 83 | 0.044 | 0.006 | 0.19 | 0.095 |
| 84 | 0.026666667 | 0.021 | 0.038666667 | 0.048 |
| 85 | 0.078 | 0.120666667 | 0.127333333 | 0.088666667 |
| 86 | 0.12 | 0.038 | 0.23 | 0.032 |
| 87 | 0.05 | 0.016 | 0.14 | 0.011 |
| 88 | 0.0044 | 0.0067 | 0.0074 | 0.0031 |
| 89 | 0.16 | 0.034 | 4.8 | 0.15 |
| 90 | 0.17 | 0.029 | 0.4 | 0.063 |
| 91 | 0.14 | 0.034 | 11 | 0.063 |
| 92 | 0.76 | 0.016 | 1.6 | 0.34 |
| 93 | 0.88 | 0.54 | 1.1 | 0.49 |
| 94 | 0.044 | 0.067 | 0.056 | 0.013 |

TABLE 3-continued

| Compound Number | Lipid HTRF TEAD1 IC$_{50}$ [uM] | Lipid HTRF TEAD2 IC$_{50}$ [uM] | Lipid HTRF TEAD3 IC$_{50}$ [uM] | Lipid HTRF TEAD4 IC$_{50}$ [uM] |
|---|---|---|---|---|
| 95 | 0.0086 | 0.0088 | 0.0095 | 0.0038 |
| 96 | 0.043 | 0.033 | 0.072 | 0.023 |
| 97 | 0.027 | 0.019 | 0.59 | 0.018 |
| 98 | 0.71 | 0.14 | 0.68 | 0.048 |
| 99 | 0.0037 | 0.0043 | 0.0031 | 0.0027 |
| 100 | 0.017 | 0.061 | 0.02 | 0.006 |
| 101 | 0.177666667 | 0.275 | 0.216 | 0.015125 |
| 102 | 0.12 | 0.31 | 0.11 | 0.023 |
| 103 | 0.055 | 0.12 | 0.057 | 0.0038 |
| 104 | 0.095 | 0.08 | 0.027 | 0.04 |
| 105 | 0.13 | 0.03 | 0.074 | 0.09 |
| 106 | 0.18 | 0.024 | 1 | 0.18 |
| 107 | 0.1 | 0.02 | 0.78 | 0.036 |
| 108 | 0.13 | 0.076 | 0.047 | 0.024 |
| 109 | 0.15 | 0.058 | 0.071 | 0.17 |
| 110 | 0.14 | 0.047 | 0.97 | 0.26 |
| 111 | 0.16 | 0.07 | 50 | 0.29 |
| 112 | 2.4 | 0.36 | 50 | 0.52 |
| 113 | 0.024 | 0.024 | 0.044 | 0.031 |
| 114 | 0.48 | 0.35 | 0.7 | 0.74 |
| 115 | 0.0075 | 0.00485 | 0.009 | 0.00225 |
| 116 | 0.0053 | 0.0087 | 0.06 | 0.0033 |
| 117 | 0.0185 | 0.1055 | 0.105 | 0.00615 |
| 118 | 0.0095 | 0.072 | 0.09 | 0.0067 |
| 119 | 0.58 | 1.3 | 12 | 0.16 |
| 120 | 0.7 | 0.84 | 50 | 0.22 |
| 121 | 0.073 | 0.83 | 0.75 | 0.064 |
| 122 | 0.093 | 0.066 | 0.58 | 0.013 |
| 123 | 0.017 | 0.0078 | 0.08 | 0.0039 |
| 124 | 0.0105 | 0.0325 | 0.079 | 0.049 |
| 125 | 0.4 | 4 | 1.8 | 2.3 |
| 126 | 0.2 | 0.37 | 1.1 | 0.32 |
| 127 | 0.026 | 0.028 | 0.42 | 0.023 |
| 128 | 0.011 | 0.021 | 0.0099 | 0.0027 |
| 129 | 0.6 | 1.1 | 1.35 | 0.0245 |
| 130 | 0.41 | 1 | 0.44 | 0.14 |
| 131 | 0.4 | 1.6 | 1.2 | 0.081 |
| 132 | 0.0069 | 0.15 | 0.1 | 0.024 |
| 133 | 0.052 | 0.36 | 0.42 | 0.028 |
| 134 | 0.2 | 1.7 | 0.31 | 0.65 |
| 135 | 0.2 | 0.11 | 0.15 | 0.036 |
| 136 | 0.018 | 0.03 | 0.047 | 0.012 |
| 137 | 0.075 | 0.094 | 0.095 | 0.014 |
| 138 | 0.06 | 0.01 | 3.6 | 0.092 |
| 139 | 0.16 | 0.0068 | 0.38 | 0.1 |
| 140 | 0.027 | 0.047 | 3 | 0.043 |
| 141 | 0.058 | 0.098 | 1.6 | 0.015 |
| 142 | 0.57 | 1.4 | 7.6 | 0.12 |
| 143 | 0.026 | 0.022 | 0.069 | 0.0095 |
| 144 | 0.094 | 0.039 | 1.3 | 0.023 |
| 145 | 0.0069 | 0.019 | 0.24 | 0.012 |
| 146 | 0.0076 | 0.048 | 0.021 | 0.023 |
| 147 | 0.11 | 0.019 | 0.61 | 0.89 |
| 148 | 0.036 | 0.0087 | 0.47 | 0.54 |

Example 147: Synthesis for Compound K1, Compound K2, and Compound K3

An exemplary synthesis of Compound K1 is described in US2018/0334454A1 (see, e.g., Example 41 on pages 210-212 of US2018/0334454A1).

An exemplary synthesis of Compound K2 is described in WO2021/124222A1 (see, e.g., Method 1 Synthetic Scheme as described on pages 111 to 114 of WO2021/124222A1).

An exemplary synthesis of Compound K3 is described in US2019/0144444A1 (see, e.g., Example 478 on pages 668-669 of US2019/0144444A1).

Any references detailed in this section are incorporated herein by reference in their entirety, and specifically with respect to methods of making compounds detailed therein. Preparation of 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one (Compound K1/Example 41 of US2018/0334454A1)

Step 1: 2,6-Dichloro-5-fluoronicotinamide (Intermediate S)

To a mixture of 2,6-dichloro-5-fluoronicotinic acid (4.0 g, 19.1 mmol, AstaTech Inc., Bristol, Pa.) in dichloromethane (48 mL) was added oxalyl chloride (2M solution in DCM, 11.9 mL, 23.8 mmol), followed by a catalytic amount of DMF (0.05 mL). The reaction was stirred at room temperature overnight and then was concentrated. The residue was dissolved in 1,4-dioxane (48 mL) and cooled to 0° C. Ammonium hydroxide solution (28.0-30% NH$_3$ basis, 3.6 mL, 28.6 mmol) was added slowly via syringe. The resulting mixture was stirred at 0° C. for 30 min and then was concentrated. The residue was diluted with a 1:1 mixture of EtOAc/Heptane and agitated for 5 min, then was filtered. The filtered solids were discarded, and the remaining mother liquor was partially concentrated to half volume and filtered. The filtered solids were washed with heptane and dried in a reduced-pressure oven (45° C.) overnight to provide 2,6-dichloro-5-fluoronicotinamide. $^1$H NMR (400 MHz, DMSO-d$_6$) δ ppm 8.23 (d, J=7.9 Hz, 1H) 8.09 (br s, 1H)$^+$. 7.93 (br s, 1H). m/z (ESI, +ve ion): 210.9 (M+H)$^+$.

Step 2: 2,6-Dichloro-5-fluoro-N-((2-isopropyl-4-methylpyridin-3-yl)carbamoyl)nicotinamide To an ice-cooled slurry of 2,6-dichloro-5-fluoronicotinamide (Intermediate S, 5.0 g, 23.9 mmol) in THF (20 mL) was added oxalyl chloride (2 M solution in DCM, 14.4 mL, 28.8 mmol) slowly via syringe. The resulting mixture was heated at 750 C. for 1 h, then heating was stopped, and the reaction was concentrated to half volume. After cooling to 0° C., THF (20 mL) was added, followed by a solution of 2-isopropyl-4-methylpyridin-3-amine (Intermediate R, 3.59 g, 23.92 mmol) in THF (10 mL), dropwise via cannula. The resulting mixture was stirred at 0° C. for 1 h and then was quenched with a 1:1 mixture of brine and saturated aqueous ammonium chloride. The mixture was extracted with EtOAc (3×) and the combined organic layers were dried over anhydrous sodium sulfate and concentrated to provide 2,6-dichloro-5-fluoro-N-((2-isopropyl-4-methylpyridin-3-yl)carbamoyl)nicotinamide. This material was used without further purification in the following step. m/z (ESI, +ve ion): 385.1 (M+H)$^+$.

Step 3: 7-Chloro-6-fluoro-1-(2-isopropyl-4-methylpyridin-3-yl)pyrido[2,3-d]pyrimidine-2,4(1H,3H)-dione To an ice-cooled solution of 2,6-dichloro-5-fluoro-N-((2-isopropyl-4-methylpyridin-3-yl)carbamoyl)nicotinamide (9.2 g, 24.0 mmol) in THF (40 mL) was added KHMDS (1 M solution in THF, 50.2 mL, 50.2 mmol) slowly via syringe. The ice bath was removed and the resulting mixture was stirred for 40 min at room temperature. The reaction was quenched with saturated aqueous ammonium chloride and extracted with EtOAc (3×). The combined organic layers were dried over anhydrous sodium sulfate and concentrated. The residue was purified by silica gel chromatography (eluent: 0-50% 3:1 EtOAc-EtOH/heptane) to provide 7-chloro-6-fluoro-1-(2-isopropyl-4-methylpyridin-3-yl)pyrido[2,3-d]pyrimidine-2,4(1H,3H)-dione. $^1$H NMR (400 MHz, DMSO-d$_6$) δ ppm 12.27 (br s, 1H), 8.48-8.55 (m, 2H), 7.29 (d, J=4.8 Hz, 1H), 2.87 (quin, J=6.6 Hz, 1H), 1.99-2.06 (m, 3H), 1.09 (d, J=6.6 Hz, 3H), 1.01 (d, J=6.6 Hz, 3H). $^{19}$F NMR (376 MHz, DMSO-d$_6$) δ: -126.90 (s, 1F). m/z (ESI, +ve ion): 349.1 (M+H)$^+$.

Step 4: 4,7-Dichloro-6-fluoro-1-(2-isopropyl-4-methylpyridin-3-yl)pyrido[2,3-d]pyrimidin-2(1H)-one To a solution of 7-chloro-6-fluoro-1-(2-isopropyl-4-methylpyridin-3-yl)pyrido[2,3-d]pyrimidine-2,4(1H,3H)-dione (4.7 g, 13.5 mmol) and DIPEA (3.5 mL, 20.2 mmol) in acetonitrile (20 mL) was added phosphorus oxychloride (1.63 mL, 17.5 mmol), dropwise via syringe. The resulting mixture was heated at 800 C. for 1 h, and then was cooled to room temperature and concentrated to provide 4,7-dichloro-6-fluoro-1-(2-isopropyl-4-methylpyridin-3-yl)pyrido[2,3-d]pyrimidin-2(1H)-one. This material was used without further purification in the following step. m/z (ESI, +ve ion): 367.1 (M+H)$^+$.

Step 5: (S)-tert-Butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate To an ice-cooled solution of 4,7-dichloro-6-fluoro-1-(2-isopropyl-4-methylpyridin-3-yl)pyrido[2,3-d]pyrimidin-2(1H)-one (13.5 mmol) in acetonitrile (20 mL) was added DIPEA (7.1 mL, 40.3 mmol), followed by (S)-4-N-Boc-2-methyl piperazine (3.23 g, 16.1 mmol, Combi-Blocks, Inc., San Diego, Calif., USA). The resulting mixture was warmed to room temperature and stirred for 1 h, then was diluted with cold saturated aqueous sodium bicarbonate solution (200 mL) and EtOAc (300 mL). The mixture was stirred for an additional 5 min, the layers were separated, and the aqueous layer was extracted with more EtOAc (1×). The combined organic layers were dried over anhydrous sodium sulfate and concentrated. The residue was purified by silica gel chromatography (eluent: 0-50% EtOAc/heptane) to provide (S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate. m/z (ESI, +ve ion): 531.2 (M+H)$^+$.

Step 6: (3S)-tert-Butyl 4-(6-fluoro-7-(2-fluoro-6-hydroxyphenyl)-1-(2-isopropyl-4-methylpyridin-3-yl)-2-oxo-1,2-dihydropyrido [2,3-d]pyrimidin-4-yl)-3-methylpiperazine-1-carboxylate A mixture of (S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (4.3 g, 8.1 mmol), potassium trifluoro(2-fluoro-6-hydroxyphenyl)borate (Intermediate Q, 2.9 g, 10.5 mmol), potassium acetate (3.2 g, 32.4 mmol) and [1,1'-bis(diphenylphosphino)ferrocene]dichloropalladium(II), complex with dichloromethane (661 mg, 0.81 mmol) in 1,4-dioxane (80 mL) was degassed with nitrogen for 1 min. De-oxygenated water (14 mL) was added, and the resulting mixture was heated at 90° C. for 1 h. The reaction was allowed to cool to room temperature, quenched with half-saturated aqueous sodium bicarbonate, and extracted with EtOAc (2×) and DCM (1×). The combined organic layers were dried over anhydrous sodium sulfate and concentrated. The residue was purified by silica gel chromatography (eluent: 0-60% 3:1 EtOAc-EtOH/heptane) to provide (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 10.19 (br s, 1H), 8.38 (d, J=5.0 Hz, 1H), 8.26 (dd, J=12.5, 9.2 Hz, 1H), 7.23-7.28 (m, 1H), 7.18 (d, J=5.0 Hz, 1H), 6.72 (d, J=8.0 Hz, 1H), 6.68 (t, J=8.9 Hz, 1H), 4.77-4.98 (m, 1H), 4.24 (brt, J=14.2 Hz, 1H), 3.93-4.08 (m, 1H), 3.84 (br d, J=12.9 Hz, 1H), 3.52-3.75 (m, 1H), 3.07-3.28 (m, 1H), 2.62-2.74 (m, 1H), 1.86-1.93 (m, 3H), 1.43-1.48 (m, 9H), 1.35 (dd, J=10.8, 6.8 Hz, 3H), 1.26-1.32 (m, 1H), 1.07 (dd, J=6.6, 1.7 Hz, 3H), 0.93 (dd, J=6.6, 2.1 Hz, 3H). $^{19}$F NMR (376 MHz, DMSO-d$_6$) δ : -115.65 (s, 1F), -128.62 (s, 1F). m/z (ESI, +ve ion): 607.3 (M+H)$^+$.

Step 7: 6-Fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one Trifluoroacetic acid (25 mL, 324 mmol) was added to a solution of (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (6.3 g, 10.4 mmol) in DCM (30 mL). The resulting mixture was stirred at room temperature for 1 h and then was concentrated. The residue was dissolved in DCM (30 mL), cooled to 0° C., and sequentially treated with DIPEA (7.3 mL, 41.7 mmol) and a solution of acryloyl chloride (0.849 mL, 10.4 mmol) in DCM (3 mL; added dropwise via syringe). The reaction was stirred at 0° C. for 10 min, then was quenched with half-saturated aqueous sodium bicarbonate and extracted with DCM (2×). The combined organic layers were dried over anhydrous sodium sulfate and concentrated. The residue was purified by silica gel chromatography (eluent: 0-100% 3:1 EtOAc-EtOH/heptane) to provide 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one (Compound K1). $^1$H NMR (400 MHz, DMSO-$d_6$) δ ppm 10.20 (s, 1H), 8.39 (d, J=4.8 Hz, 1H), 8.24-8.34 (m, 1H), 7.23-7.32 (m, 1H), 7.19 (d, J=5.0 Hz, 1H), 6.87 (td, J=16.3, 11.0 Hz, 1H), 6.74 (d, J=8.6 Hz, 1H), 6.69 (t, J=8.6 Hz, 1H), 6.21 (br d, J=16.2 Hz, 1H), 5.74-5.80 (m, 1H), 4.91 (br s, 1H), 4.23-4.45 (m, 2H), 3.97-4.21 (m, 1H), 3.44-3.79 (m, 2H), 3.11-3.31 (m, 1H), 2.67-2.77 (m, 1H), 1.91 (s, 3H), 1.35 (d, J=6.8 Hz, 3H), 1.08 (d, J=6.6 Hz, 3H), 0.94 (d, J=6.8 Hz, 3H). $^{19}$F NMR (376 MHz, DMSO-$d_6$) δ ppm −115.64 (s, 1F), −128.63 (s, 1F). m/z (ESI, +ve ion): 561.2 (M+H)$^+$. Preparation of a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one and a(S)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one (Compound K2/Example 1 of WO2021/124222A1)

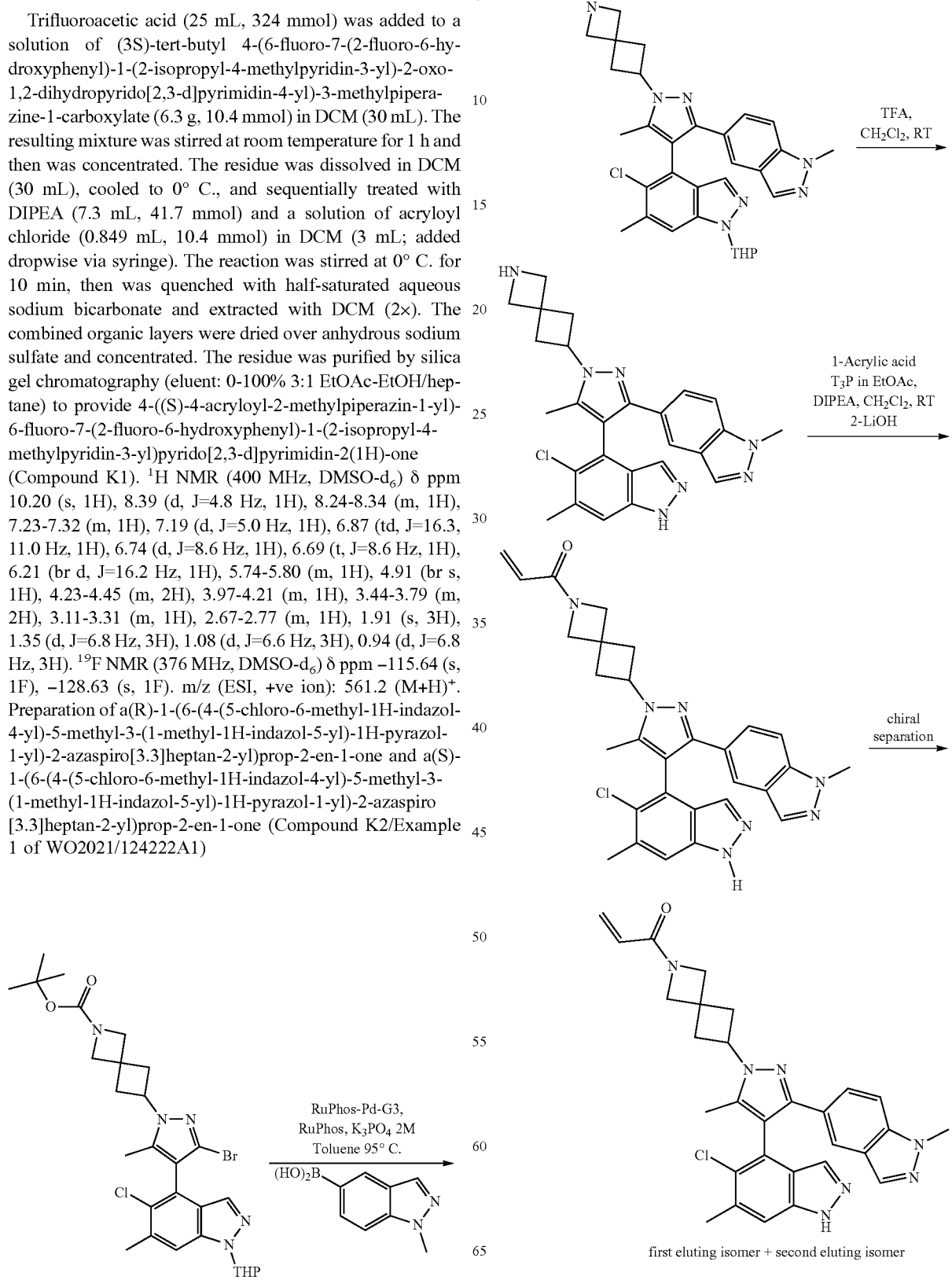

Step 1: Tert-butyl 6-(4-(5-chloro-6-methyl-1-(tetrahydro-2H-pyran-2-yl)-1H-indazol-4-yl)-5-methyl-3-(1-methyl-1H-indazol-5-yl)-1H-pyrazol-1-yl)-2-azaspiro[3.3]heptane-2-carboxylate In a 500 mL flask, tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 10 g, 16.5 mmol), (1-methyl-1H-indazol-5-yl)boronic acid (6.12 g, 33.1 mmol), RuPhos (1.16 g, 2.48 mmol) and RuPhos-Pd-G$_3$ (1.66 g, 1.98 mmol) were suspended in toluene (165 mL) under argon. K$_3$PO$_4$ (2M, 24.8 mL, 49.6 mmol) was added and the reaction mixture was placed in a preheated oil bath (95° C.) and stirred for 45 min. The reaction mixture was poured into a sat. aq. NH$_4$CI solution and was extracted with EtOAc (×3). The combined organic layers were washed with a sat. aq. NaHCO$_3$ solution, dried (phase separator) and concentrated under reduced pressure. The crude residue was diluted with THE (50 mL), SiliaMetS® Thiol (15.9 mmol) was added and the mixture swirled for 1 h at 40° C. The mixture was filtered, the filtrate was concentrated and the crude residue was purified by normal phase chromatography (eluent: MeOH in CH$_2$Cl$_2$ from 0 to 2%), the purified fractions were again purified by normal phase chromatography (eluent: MeOH in CH$_2$Cl$_2$ from 0 to 2%) to give the title compound as a beige foam. UPLC-MS-3: Rt=1.23 min; MS m/z [M+H]$^+$; 656.3/658.3.

Step 2: 5-Chloro-6-methyl-4-(5-methyl-3-(1-methyl-11H-indazol-5-yl)-1-(2-azaspiro[3.3]heptan-6-yl)-1H-pyrazol-4-yl)-1H-indazole TFA (19.4 mL, 251 mmol) was added to a solution of tert-butyl 6-(4-(5-chloro-6-methyl-1-(tetrahydro-2H-pyran-2-yl)-1H-indazol-4-yl)-5-methyl-3-(1-methyl-1H-indazol-5-yl)-1H-pyrazol-1-yl)-2-azaspiro[3.3]heptane-2-carboxylate (Step 1, 7.17 g, 10.0 mmol) in CH$_2$Cl$_2$ (33 mL). The reaction mixture was stirred at RT under nitrogen for 1.5 h. The RM was concentrated under reduced pressure to give the title compound as a trifluoroacetate salt, which was used without purification in the next step. UPLC-MS-3: Rt=0.74 min; MS m/z [M+H]$^+$; 472.3/474.3.

Step 3: 1-(6-(4-(5-Chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one A mixture of acrylic acid (0.69 mL, 10.1 mmol), propylphosphonic anhydride (50% in EtOAc, 5.94 mL, 7.53 mmol) and DIPEA (21.6 mL, 126 mmol) in CH$_2$Cl$_2$ (80 mL) was stirred for 20 min at RT and then added (dropping funnel) to an ice-cooled solution of 5-chloro-6-methyl-4-(5-methyl-3-(1-methyl-1H-indazol-5-yl)-1-(2-azaspiro[3.3]heptan-6-yl)-1H-pyrazol-4-yl)-1H-indazole trifluoroacetate (Step 2, 6.30 mmol) in CH$_2$Cl$_2$ (40 mL). The reaction mixture was stirred at RT under nitrogen for 15 min. The RM was poured into a sat. aq. NaHCO$_3$ solution and extracted with CH$_2$C12 (×3). The combined organic layers were dried (phase separator) and concentrated. The crude residue was diluted with THF (60 mL) and LiOH (2N, 15.7 mL, 31.5 mmol) was added. The mixture was stirred at RT for 30 min until disappearance (UPLC) of the side product resulting from the reaction of the acryloyl chloride with the free NH group of the indazole then was poured into a sat. aq. NaHCO$_3$ solution and extracted with CH$_2$Cl$_2$ (3×). The combined organic layers were dried (phase separator) and concentrated. The crude residue was purified by normal phase chromatography (eluent: MeOH in CH$_2$Cl$_2$ from 0 to 5%) to give the title compound. The isomers were separated by chiral SFC (C—SFC-1; mobile phase: CO$_2$/[IPA+0.1% Et$_3$N]: 69/31) to give Example 1a: a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one as the second eluting peak (white powder): $^1$H NMR (600 MHz, DMSO-d$_6$.) 6 13.1 (s, 1H), 7.89 (s, 1H), 7.59 (s, 1H), 7.55 (s, 1H), 7.42 (m, 2H), 7.30 (d, 11H), 6.33 (m, 11H), 6.12 (m, 1H), 5.68 (m, 1H), 4.91 (m, 1H), 4.40 (s, 1H), 4.33 (s, 1H), 4.11 (s, 1H), 4.04 (s, 1H), 3.95 (s, 3H), 2.96-2.86 (m, 2H), 2.83-2.78 (m, 2H), 2.49 (s, 3H), 2.04 (s, 3H); UPLC-MS-4: Rt=4.22 min; MS m/z [M+H]$^+$ 526.3/528.3: C—SFC-3 (mobile phase: CO$_2$/[IPA+0.1% Et$_3$N]: 67/33): Rt=2.23 min. The compound of Example 1a of WO2021/124222A1 is also referred to as "Compound X" of WO2021/124222A1.

The other isomer Example 1b of WO2021/124222A1; a(S)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one was obtained as the first eluting peak: C—SFC-3 (mobile phase: CO$_2$/[IPA+0.1% Et$_3$N]: 67/33): Rt=1.55 min.

Preparation of 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile (Compound K3/Example 478 of US2019/0144444A1) [0724]2-fluoroprop-2-enoyl chloride. To a solution of 2-fluoroprop-2-enoic acid (400 mg, 4.44 mmol, 1 eq) in DCM (4 mL) was added (COCl)$_2$ (846 mg, 6.66 mmol, 583 μL, 1.5 eq) and DMF (32.5 mg, 444 umol, 34.2 uL, 0.1 eq). The mixture was stirred at 25° C. for 2 hrs. The reaction mixture was concentrated under reduced pressure to remove a part of solvent and give a residue in DCM. Compound 2-fluoroprop-2-enoyl chloride (400 mg, crude) was obtained as a yellow liquid and used into the next step without further purification.

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile. To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, 528 umol, 1 eq, HCl) in DCM (5 mL) was added DIEA (1.73 g, 13.4 mmol, 2.33 mL, 25.4 eq) and 2-fluoroprop-2-enoyl chloride (286 mg, 2.64 mmol, 5 eq) in DCM (5 mL). The mixture was stirred at 0° C. for 1 hour. The reaction mixture was concentrated under reduced pressure to give a residue. The residue was purified by column chromatography (Al$_2$O$_3$, Dichloromethane/Methanol=10/1 to 10/1). The residue was purified by prep-HPLC (column: Gemini 150*25 5u; mobile phase: [water (0.05% ammonia hydroxide v/v) - ACN]; B %: 55%-85%, 12 min). The residue was purified by prep-HPLC (column: Phenomenex Synergi C18 150 * 30 mm*4 um; mobile phase: [water (0.225% FA) - ACN]; B %: 20%-50%, 10.5 min). The residue was concentrated under reduced pressure to remove ACN, and then lyophlization. Title compound 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile (Compound K3/EXAMPLE 478 of US2019/0144444A1, 24.1 mg, 36.7 umol, 7% yield, 99.1% purity, FA) was obtained as a brown solid.

SFC condition: "AD - 3S_3_5_40_3 ML Column: Chiralpak AD - 3 100×4.6 mm I.D., 3 um Mobile phase: methanol (0.05% DEA) in CO$_2$ from 5% to 40% Flow rate: 3 mL/min Wavelength: 220 nm".

$^1$H NMR (400 MHz, Acetic) δ=7.82 (d, J=8.0 Hz, 1H), 7.69 (d, J=8.0 Hz, 1H), 7.56 (d, J=7.6 Hz, 1H), 7.49 (t, J=7.6 Hz, 1H), 7.41-7.30 (m, 2H), 5.58-5.25 (m, 2H), 5.17-4.59 (m, 4H), 4.57-4.28 (m, 3H), 4.24-3.78 (m, 4H), 3.67-3.13 (m, 7H), 3.08 (br d, J=2.4 Hz, 3H), 2.98 (br d, J=6.4 Hz, 1H), 2.83-2.61 (m, 1H), 2.45-2.29 (m, 1H), 2.24-2.08 (m, 3H).

Preparation of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4/Example 17a &17b of US2021/0230142A9) and 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4-S)

Synthetic Route

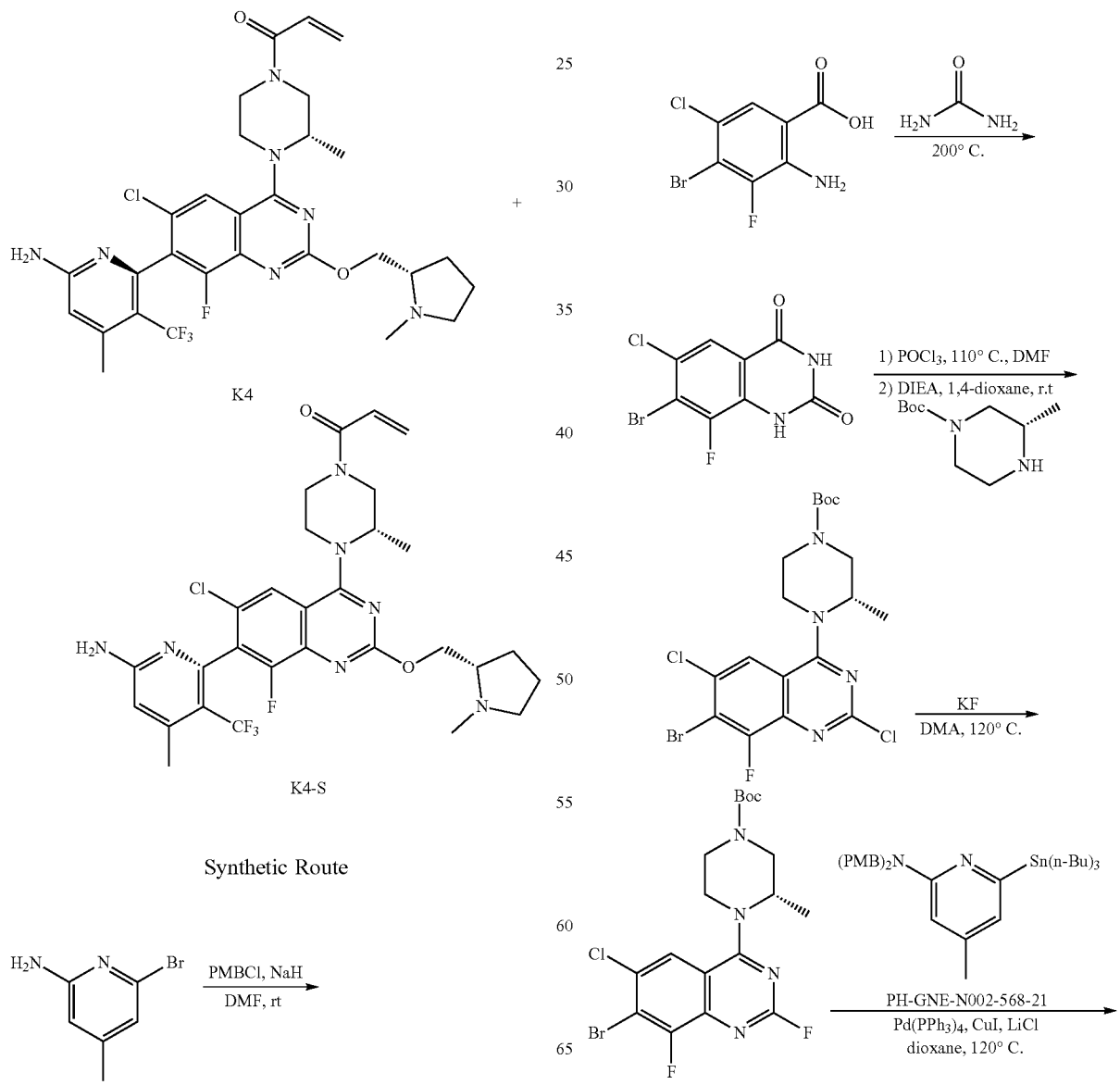

-continued

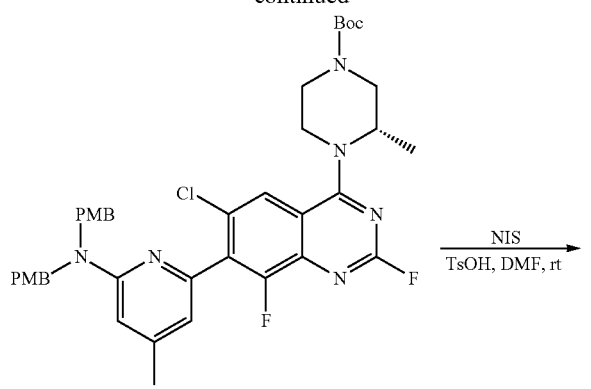

-continued

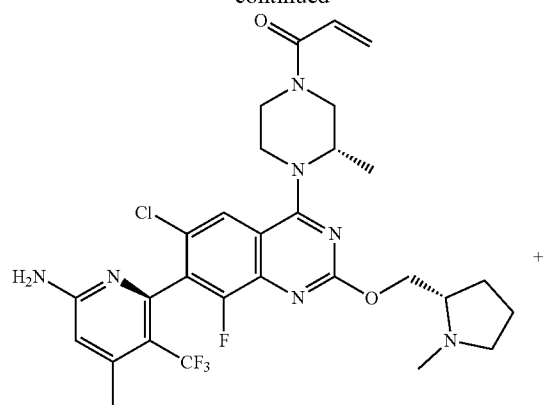

Step 1: 6-bromo-N,N-bis(4-methoxybenzyl)-4-methylpyridin-2-amine

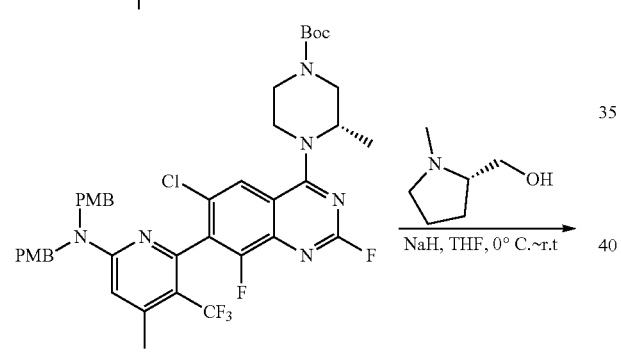

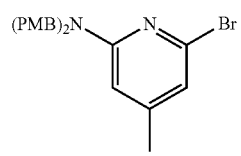

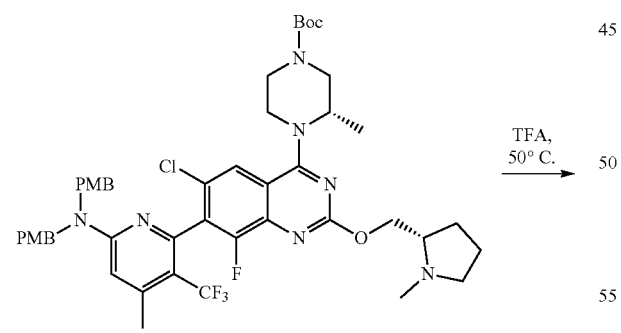

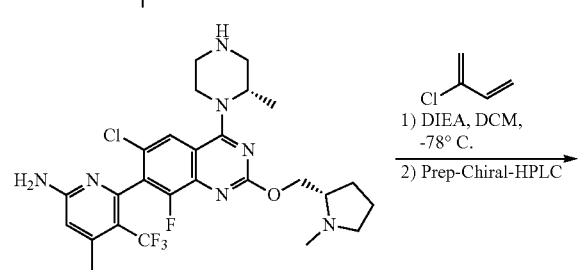

To a solution of 6-bromo-4-methylpyridin-2-amine (30.0 g, 160 mmol) in N,N-dimethylformamide (500 mL) was added slowly sodium hydride (19.0 g, 792 mmol) at 0° C. and stirred at 25° C. for 1 hour. Then 4-methoxybenzylchloride (56.0 g, 359 mmol) was added into the reaction system and stirred at 25° C. for 2 hours. After completion, the reaction system was quenched with saturated ammonium chloride solution (500 mL) and diluted with ethyl acetate (2.5 L). The mixture was washed with brine (5×500 mL) and the organic layers were combined, dried with $Na_2SO_4$, evaporated under vacuum. The residue was applied onto a silica gel column eluting with petroleum ether/ethyl acetate (15%) to afford 6-bromo-N,N-bis(4-methoxybenzyl)-4-methylpyridin-2-amine (60 g, 140 mmol, 87.5% yield) as an off-white solid. LC-MS: (ESI, m/z): 427.1 [M+H]$^+$.

Step 2: N,N-bis[(4-methoxyphenyl)methyl]-4-methyl-6-tributylstannyl-pyridin-2-amine

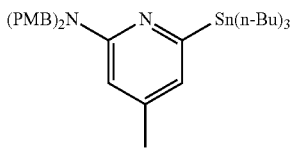

Under nitrogen, a solution of 6-bromo-N,N-bis[(4-methoxyphenyl)methyl]-4-methyl-pyridin-2-amine (35.0 g, 82 mmol), hexabutylditin (143.0 g, 247 mmol), tris(dibenzylideneacetone)dipalladium (7.53 g, 8.2 mmol), tricyclohexyl phosphine (4.6 g, 16.4 mmol) and Lithium chloride (17.3 g, 412 mmol) in 1,4-dioxane (220 mL) was stirred at 110° C. for 5 hours. After completion, the reaction system was concentrated under vacuum. The residue was purified by flash chromatography on silica gel eluting with petroleum ether/ethyl acetate (10/1) to afford N,N-bis[(4-methoxyphenyl)methyl]-4-methyl-6-tributylstannyl-pyridin-2-amine (45 g, 71 mmol, 86.2% yield) as a red oil. LC-MS: (ESI, m/z): 639.3 [M+H]$^+$.

Step 3: 2-amino-4-bromo-5-chloro-3-fluoro-benzoic acid

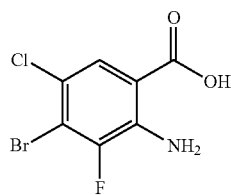 [SMILES: Nc1c(C(=O)O)cc(Cl)c(Br)c1F]

A solution of 2-amino-4-bromo-3-fluoro-benzoic acid (100.0 g, 427 mmol) and N-chlorosuccinimide (66.0 g, 494 mmol) in N,N-dimethylformamide (1 L) was stirred at 80° C. for 2 hours. After completion, the system was poured into water (2.0 L), a large amount of solids were precipitated. Then the solids were collected after filtration. The solids were washed with hot water (1 L). Then the solids were dried under infrared lamp to afford 2-amino-4-bromo-5-chloro-3-fluoro-benzoic acid (100 g, 373 mmol, 87.2% yield) as off-white solid. LC-MS: (ESI, m/z): 265.9 [M–H]$^+$.

Step 4: 7-bromo-6-chloro-8-fluoroquinazoline-2,4(1H,3H)-dione

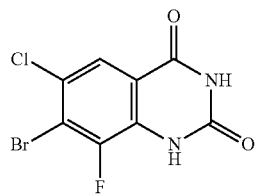

A solution of 2-amino-4-bromo-5-chloro-3-fluoro-benzoic acid (120.0 g, 447 mmol) in urea (806.0 g, 13.4 mol) was stirred at 200° C. for 1.5 hours. After completion, the reaction system was cooled to 80° C., and water (1.5 L) was added into the system with stirring for 20 mins. After filtration, the solids were collected and washed with hot water (1 L). Then the solids were dried under infrared lamp to afford 7-bromo-6-chloro-8-fluoroquinazoline-2,4(1H,3H)-dione (120 g, 409 mmol, 91.5% yield) as a light brown solid. LC-MS: (ESI, m/z): 290.9 [M–H]$^+$.

Step 5: tert-butyl (3S)-4-(7-bromo-2,6-dichloro-8-fluoroquinazolin-4-yl)-3-methylpiperazine-1-carboxylate

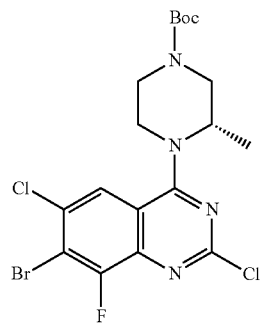 [SMILES: C[C@H]1CN(C(=O)OC(C)(C)C)CCN1c1nc(Cl)nc2c(F)c(Br)c(Cl)cc12]

A solution of 7-bromo-6-chloro-8-fluoro-quinazoline-2,4-diol (65.0 g, 222 mmol) and DMF (500.0 mg, 6.85 mmol) in POCl$_3$ (1.0 L) was stirred at 110° C. for 60 hours. After the starting material was completely, the resulting mixture was concentrated under vacuum. Then 1,4-dioxane (1.0 L), N,N-diisopropylethylamine (286.0 g, 2217 mmol) and tert-butyl (3S)-3-methyl-1-piperazinecarboxylate (90.0 g, 449 mmol) was added into the reaction system and stirred at 25° C. for 1 hours. After completion, the solvent was concentrated under vacuum. The residue was purified by flash chromatography on silica gel eluting with petroleum ether/ethyl acetate (20%) to afford tert-butyl (3S)-4-(7-bromo-2,6-dichloro-8-fluoroquinazolin-4-yl)-3-methylpiperazine-1-carboxylate (65 g, 132 mmol, 59.4% yield) as a yellow solid. LC-MS: (ESI, m/z): 493.0 [M+H]$^+$.

Step 6: tert-butyl (3S)-4-(7-bromo-6-chloro-2,8-difluoroquinazolin-4-yl)-3-methylpiperazine-1-carboxylate

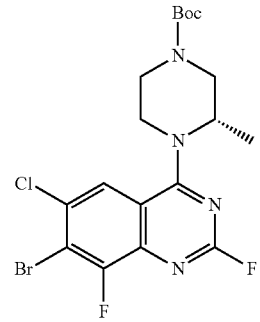 [SMILES: C[C@H]1CN(C(=O)OC(C)(C)C)CCN1c1nc(F)nc2c(F)c(Br)c(Cl)cc12]

A mixture of tert-butyl (3S)-4-(7-bromo-2,6-dichloro-8-fluoroquinazolin-4-yl)-3-methylpiperazine-1-carboxylate (30.0 g, 61 mmol) and potassium fluoride (71.0 g, 1224 mmol) in N,N-dimethylacetamide (300 mL) was stirred at 120° C. for 18 hours. After completion, the reaction system was cooled to room temperature. Then ethyl acetate (1.5 L) was added into the system and the mixture was washed with water (3×500 mL). The organic layer was dried over anhydrous sodium sulfate and concentrated under vacuum. The residue was purified by flash chromatography on silica gel eluting with petroleum ether/ethyl acetate (20%) to afford tert-butyl (3S)-4-(7-bromo-6-chloro-2,8-difluoroquinazolin-4-yl)-3-methylpiperazine-1-carboxylate (23 g, 48 mmol, 79.3% yield) as a yellow solid. LC-MS: (ESI, m/z): 477.0 [M+H]).

Step 7: tert-butyl (3S)-4-(7-(6-(bis(4-methoxybenzyl)amino)-4-methylpyridin-2-yl)-6-chloro-2,8-difluoroquinazolin-4-yl)-3-methylpiperazine-1-carboxylate

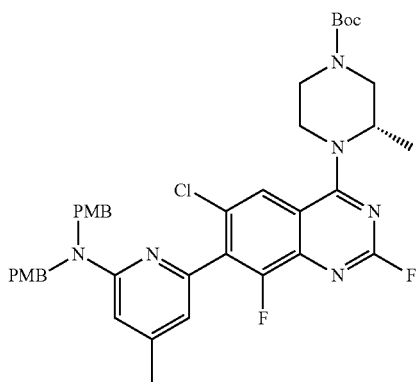

Under nitrogen, a solution of tert-butyl (3S)-4-(7-bromo-6-chloro-2,8-difluoroquinazolin-4-yl)-3-methylpiperazine-1-carboxylate (23.0 g, 48 mmol), N,N-bis[(4-methoxyphenyl)methyl]-4-methyl-6-tributylstannyl-pyridin-2-amine (62.0 g, 97 mmol), tetrakis(triphenylphosphine)palladium (11.2 g, 9.7 mmol), cuprous iodide (2.8 g, 15 mmol) and Lithium chloride (5.0 g, 119 mmol) in 1,4-dioxane (320 mL) was stirred at 120° C. for 16 hours. After completion, the reaction system was diluted with water (100 mL) and extracted with ethyl acetate (100 mL). Then the organic layers were combined, dried over anhydrous sodium sulfate and concentrated under vacuum. The residue was purified by flash chromatography on silica gel eluting with petroleum ether/ethyl acetate (30%) to afford tert-butyl (3S)-4-(7-(6-(bis(4-methoxybenzyl)amino)-4-methylpyridin-2-yl)-6-chloro-2,8-difluoroquinazolin-4-yl)-3-methylpiperazine-1-carboxylate (18.5 g, 25 mmol, 51.6% yield) as a yellow solid. LC-MS: (ESI, m/z): 745.3 [M+H]+.

Step 8: tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate

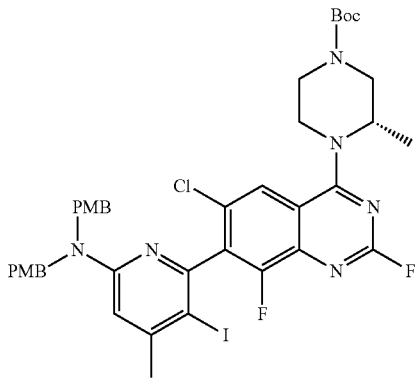

A solution of tert-butyl (3S)-4-(7-(6-(bis(4-methoxybenzyl)amino)-4-methylpyridin-2-yl)-6-chloro-2,8-difluoroquinazolin-4-yl)-3-methylpiperazine-1-carboxylate (18.5 g, 25 mmol), p-toluenesulfonic acid (171.0 mg, 0.99 mmol) and N-iodosuccinimide (28.0 g, 125 mmol) in N,N-dimethylformamide (350 mL) was stirred at 25° C. for 5 hours. After completion, the reaction system was diluted with ethyl acetate (1.5 L) and washed with saturated sodium thiosulfate solution (4×350 mL). The organic layer was dried over anhydrous sodium sulfate and concentrated under vacuum. The residue was purified by flash chromatography on silica gel eluting with petroleum ether/ethyl acetate (25%) to afford tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate (16 g, 18.4 mmol, 74% yield) as a yellow solid. LC-MS: (ESI, m/z): 871.2 [M+H]+.

Step 9: tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate

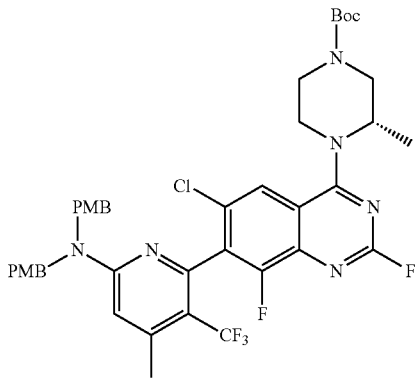

Under nitrogen, a solution of tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate (16.0 g, 18.4 mmol), methyl 2,2-difluoro-2-(fluorosulfonyl)acetate (88.3 g, 460 mmol) and cuprous iodide (42.0 g, 221 mmol) in N,N-dimethylacetamide (400 mL) was stirred at 90° C. for 18 hours. After completion, the reaction system was diluted with ethyl acetate (2.0 L) and washed with brine (4×350 mL). The organic layer was dried over anhydrous sodium sulfate and concentrated under vacuum. The residue was purified by flash chromatography on silica gel eluting with petroleum ether/ethyl acetate (30%) to afford tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate (12.2 g, 15 mmol, 81.7% yield) as a yellow solid. LC-MS: (ESI, m/z): 813.3 [M+H]$^+$.

Step 10: tert-butyl (3S)-4-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazine-1-carboxylate

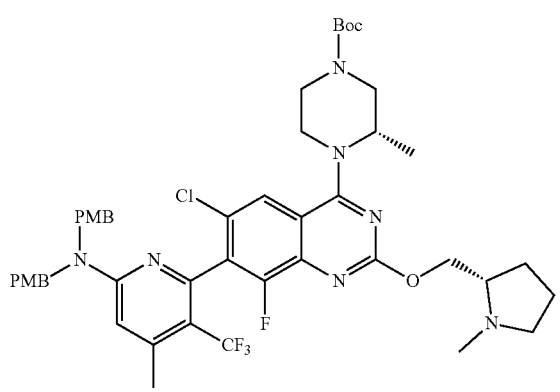

To a solution of (S)-(1-methylpyrrolidin-2-yl)methanol (4.32 g, 37.5 mmol) in tetrahydrofuran (300 mL) was added slowly sodium hydride (2.1 g, 87.5 mmol) at 0° C. and stirred for 1 h at 25° C. Then tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate (12.2 g, 15 mmol) was added into the reaction system and stirred at 25° C. for 1 hours. After completion, the reaction system was quenched with methanol (50 mL). Then the mixture was concentrated under vacuum and the residue was purified by flash chromatography on silica gel eluting with dichloromethane/methanol (6/94) to afford tert-butyl (3S)-4-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazine-1-carboxylate (8.6 g, 9.5 mmol, 63.1% yield) as a brown solid. LC-MS: (ESI, m/z): 908.4 [M+H]$^+$.

Step 11: 6-(6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine

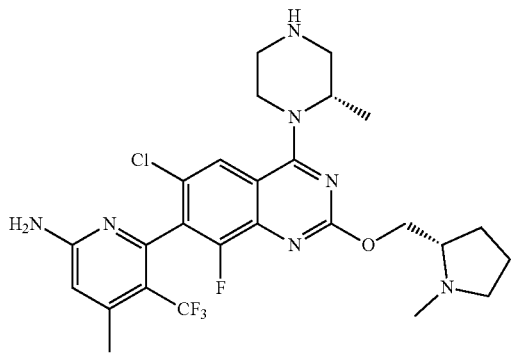 [SMILES: Cc1cc(N)nc(-c2c(Cl)cc3c(N4CCNC[C@@H]4C)nc(OC[C@@H]4CCCN4C)nc3c2F)c1C(F)(F)F]

A solution of tert-butyl (3S)-4-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazine-1-carboxylate (8.6 g, 9.5 mmol) in trifluoroacetic acid (100 mL) was stirred at 50° C. for 4 hours. After completion, the reaction system was concentrated under vacuum. The residue was dissolved with dichloromethane (50 mL) and the pH was adjusted to pH=9 with N,N-diisopropylethylamine. After concentrated under vacuum, the residue was purified by a reversed-phase chromatography directly with the following conditions: Column, C18 silica gel; mobile phase, A: water, B:ACN, B % (5%-40% in 30 min); Detector, UV 254 nm to afford 6-(6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine (3.5 g, 6.17 mmol, 65.1% yield) as a yellow solid. LC-MS: (ESI, m/z): 568.2 [M+H]$^+$.

Step 12: 1—((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4) and 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4-S)

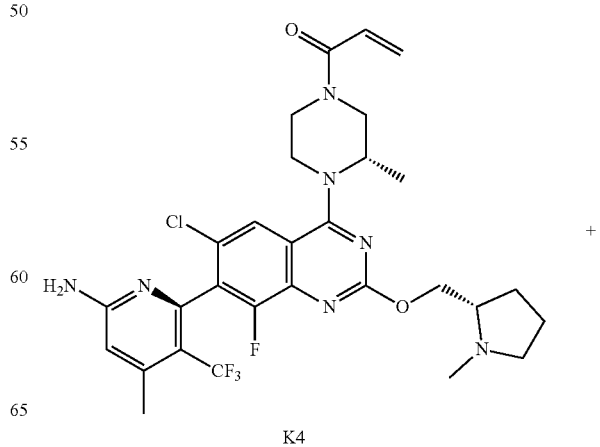

K4

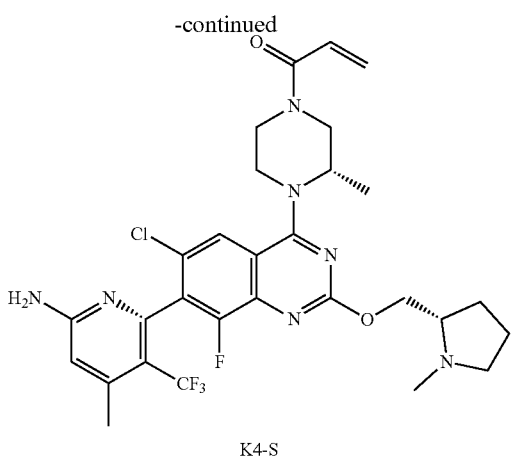

K4-S

K4: LC-MS: (ESI, m/z): 622.2 [M+H]+, $^1$H NMR: (400 MHz, CDCl$_3$, ppm) δ 7.64 (s, 1H), 6.70-6.55 (m, 1H), 6.48 (s, 1H), 6.42-6.35 (m, 1H), 5.82-5.75 (m, 1H), 4.90-4.79 (m, 2H), 4.78-4.40 (m, 3H), 4.35-4.28 (m, 1H), 4.18-4.00 (m, 1H), 3.99-3.76 (m, 1H), 3.72-3.45 (m, 2H), 3.31-2.98 (m, 2H), 2.81-2.70 (m, 1H), 2.55-2.45 (m, 6H), 2.35-2.25 (m, 1H), 2.11-2.01 (m, 1H), 1.95-1.72 (m, 3H), 1.36-1.34 (m, 3H).

K4-S: LC-MS: (ESI, m/z): 622.2 [M+H]+, $^1$H NMR: (400 MHz, CDCl$_3$, ppm) δ 7.63 (s, 1H), 6.70-6.55 (m, 1H), 6.50 (s, 1H), 6.42-6.35 (m, 1H), 5.82-5.75 (m, 1H), 4.85-4.70 (m, 2H), 4.78-4.68 (m, 2H), 4.65-4.55 (m, 1H), 4.50-4.40 (m, 1H), 4.30-4.10 (m, 1H), 4.05-3.75 (m, 1H), 3.80-3.76 (m, 2H), 3.25-3.08 (m, 2H), 2.85-2.75 (m, 11H), 2.60-2.45 (m, 6H), 2.40-2.25 (m, 1H), 2.15-2.05 (m, 1H), 1.95-1.72 (m, 3H), 1.45-1.32 (m, 3H).

| Example No. | $^1$H NMR | MS (M + H)$^+$ |
|---|---|---|
| K4 | $^1$H NMR: (400 MHz, CDCl$_3$, ppm) δ 7.64 (s, 1H), 6.70-6.55 (m, 1H), 6.48 (s, 1H), 6.42-6.35 (m, 1H), 5.82-5.75 (m, 1H), 4.90-4.79 (m, 2H), 4.78-4.40 (m, 3H), 4.35-4.28 (m, 1H), 4.18-4.00 (m, 1H), 3.99-3.76 (m, 1H), 3.72-3.45 (m, 2H), 3.31-2.98 (m, 2H), 2.81-2.70 (m, 1H), 2.55-2.45 (m, 6H), 2.35-2.25 (m, 1H), 2.11-2.01 (m, 1H), 1.95-1.72 (m, 3H), 1.36-1.34 (m, 3H). | 622.2 |
| K4-S | $^1$H NMR: (400 MHz, CDCl$_3$, ppm) δ 7.63 (s, 1H), 6.70-6.55 (m, 1H), 6.50 (s, 1H), 6.42-6.35 (m, 1H), 5.82-5.75 (m, 1H), 4.85-4.70 (m, 2H), 4.78-4.68 (m, 2H), 4.65-4.55 (m, 1H), 4.50-4.40 (m, 1H), 4.30-4.10 (m, 1H), 4.05-3.75 (m, 1H), 3.80-3.76 (m, 2H), 3.25-3.08 (m, 2H), 2.85-2.75 (m, 1H), 2.60-2.45 (m, 6H), 2.40-2.25 (m, 1H), 2.15-2.05 (m, 1H), 1.95-1.72 (m, 3H), 1.45-1.32 (m, 3H). | 622.2 |

To a solution of 6-(6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine (2.5 g, 4.4 mmol) and N,N-diisopropylethylamine (2.9 g, 22.5 mmol) in dichloromethane (120 mL) was added acryloyl chloride (359.0 mg, 3.97 mmol) at −78° C. and stirred at −78° C. for 25 mins. The reaction was quenched by water and extracted with dichloromethane. The organic layers were combined. The organic layer was dried over anhydrous sodium sulfate and concentrated under vacuum. The residue was purified by a reversed-phase chromatography directly with the following conditions: Column, C18 silica gel; mobile phase, A: water, B:ACN, B % (5%- 60% in 30 min); Detector, UV 254 nm to afford 1-[(3S)-4-[7-[6-amino-4-methyl-3-(trifluoromethyl)-2-pyridyl]-6-chloro-8-fluoro-2-[[(2S)-1-methylpyrrolidin-2-yl]methoxy]quinazolin-4-yl]-3-methyl-piperazin-1-yl]prop-2-en-1-one (1.3 g, 2.09 mmol, 47.5% yield) as a brown solid. The mixture of diastereoisomer was separated by Prep-Chiral-HPLC with the following condition: Column, CHIRALPAK IC-3 0.46*5 Cm 3 um; mobile phase, (Hex: dichloromethane=3:1) (0.1% DEA): EtOH=50:50; Detector, 254 nm; Flow, 1.0 ml/min; Temperature: 25° C. to afford 657.7 mg of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4) as a white solid and 352.1 mg of 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4-S) as a white solid.

Figure 2:
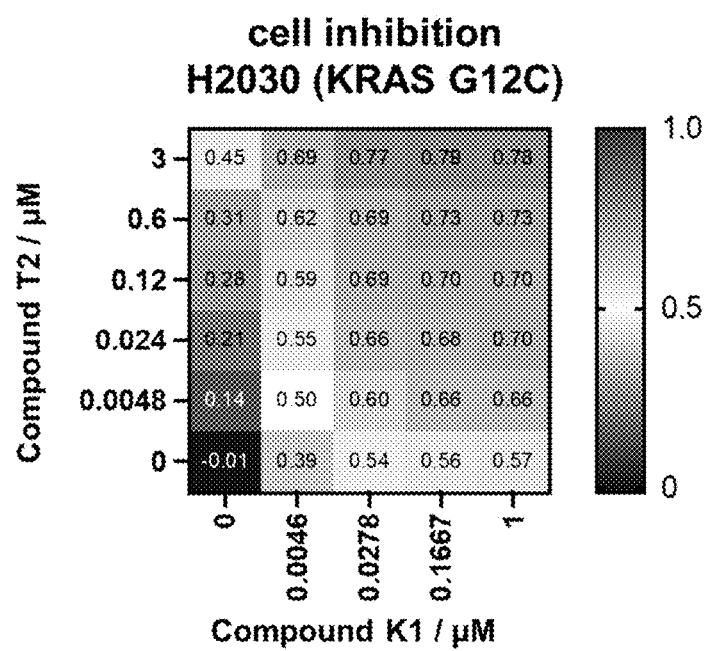
FIG. 2 depicts % inhibition of H2030 cells (KRAS G12C) following administration of a combination comprising Compound T2 (a YAP/TAZ-TEAD inhibitor) and Compound K1 (a KRAS inhibitor).
Figure 3:
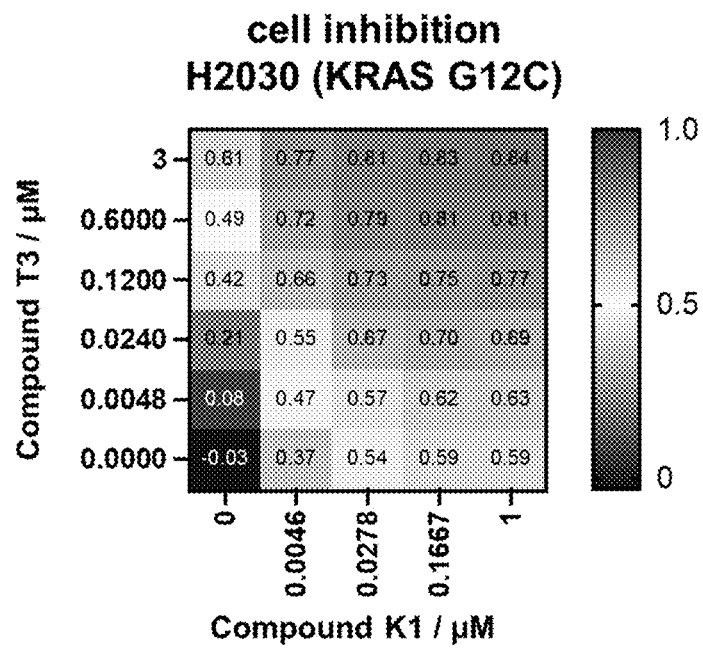
FIG. 3 depicts % inhibition of H2030 cells (KRAS G12C) following administration of a combination comprising Compound T3 (a YAP/TAZ-TEAD inhibitor) and Compound K1 (a KRAS inhibitor).
Figure 4:
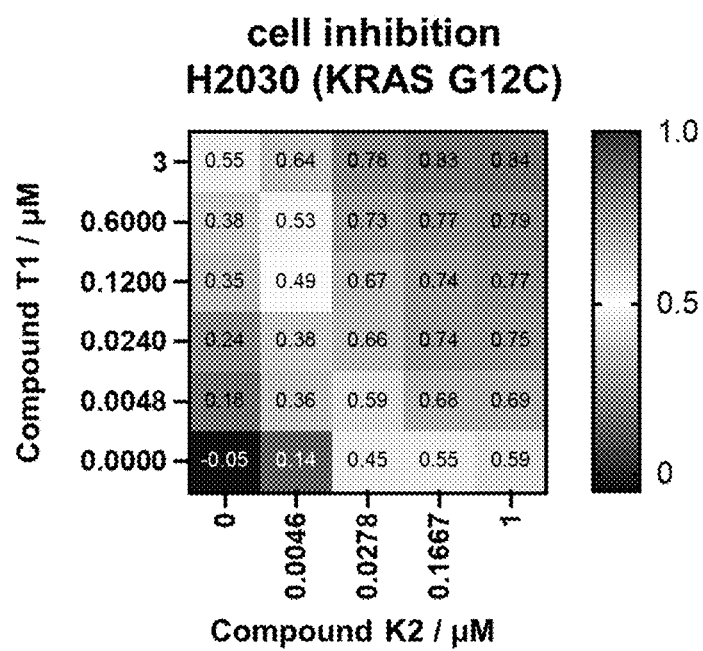
FIG. 4 depicts % inhibition of H2030 cells (KRAS G12C) following administration of a combination comprising Compound T1 (a YAP/TAZ-TEAD inhibitor) and Compound K2 (a KRAS inhibitor).
Figure 5:
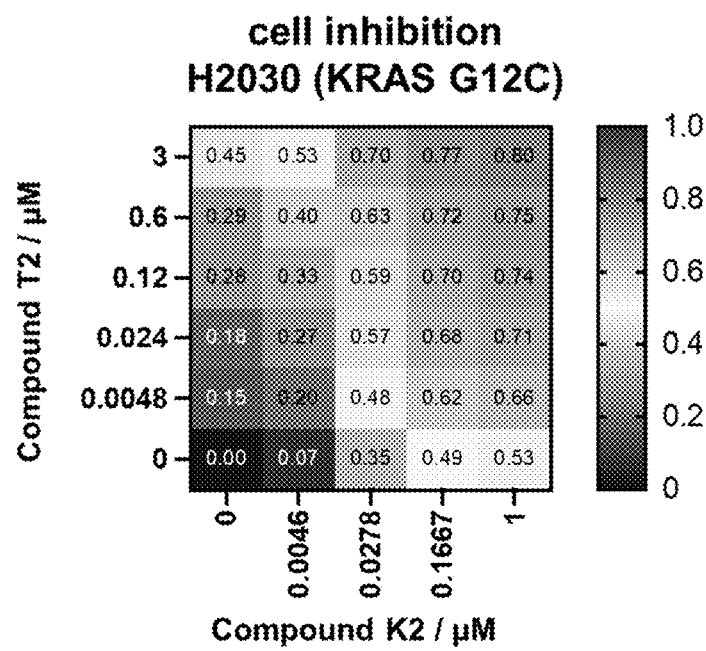
FIG. 5 depicts % inhibition of H2030 cells (KRAS G12C) following administration of a combination comprising Compound T2 (a YAP/TAZ-TEAD inhibitor) and Compound K2 (a KRAS inhibitor).
Figure 6:
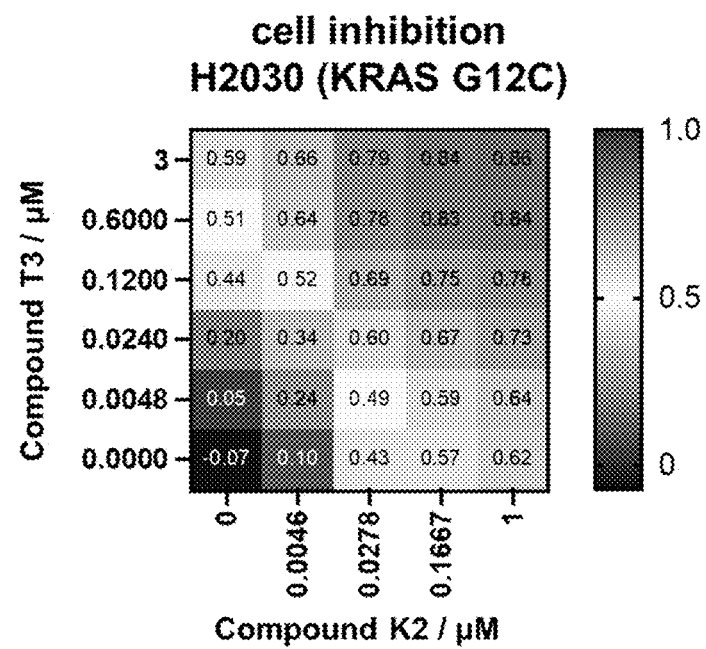
FIG. 6 depicts % inhibition of H2030 cells (KRAS G12C) following administration of a combination comprising Compound T3 (a YAP/TAZ-TEAD inhibitor) and Compound K2 (a KRAS inhibitor).
Figure 7:
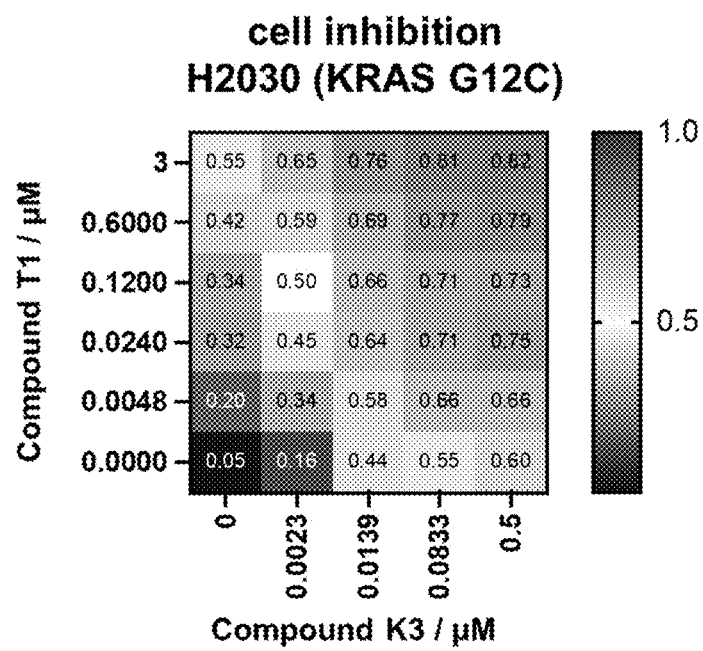
FIG. 7 depicts % inhibition of H2030 cells (KRAS G12C) following administration of a combination comprising Compound T1 (a YAP/TAZ-TEAD inhibitor) and Compound K3 (a KRAS inhibitor).
Figure 8:
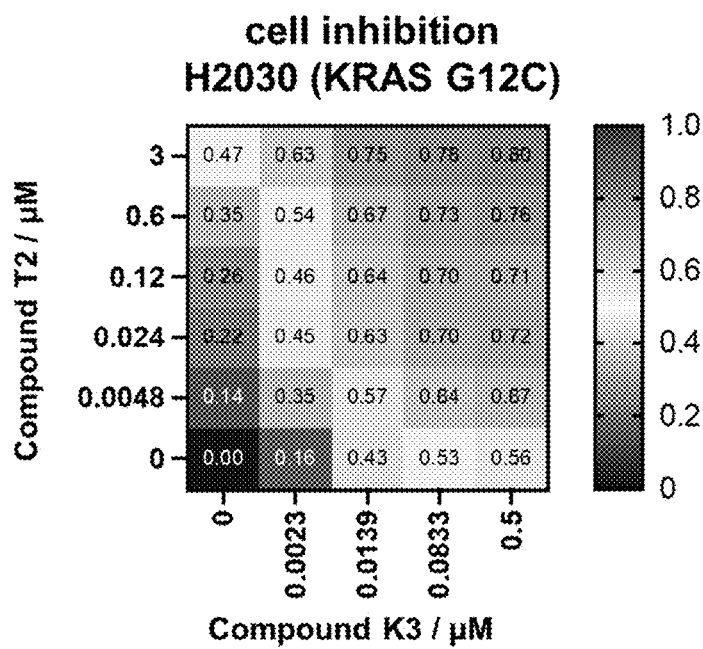
FIG. 8 depicts % inhibition of H2030 cells (KRAS G12C) following administration of a combination comprising Compound T2 (a YAP/TAZ-TEAD inhibitor) and Compound K3 (a KRAS inhibitor).
Figure 9:
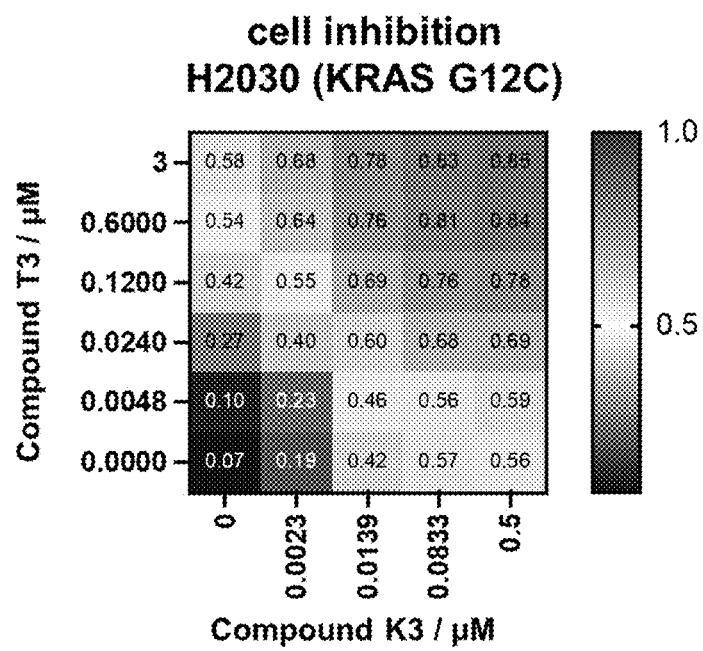
FIG. 9 depicts % inhibition of H2030 cells (KRAS G12C) following administration of a combination comprising Compound T3 (a YAP/TAZ-TEAD inhibitor) and Compound K3 (a KRAS inhibitor).
Figure 10:
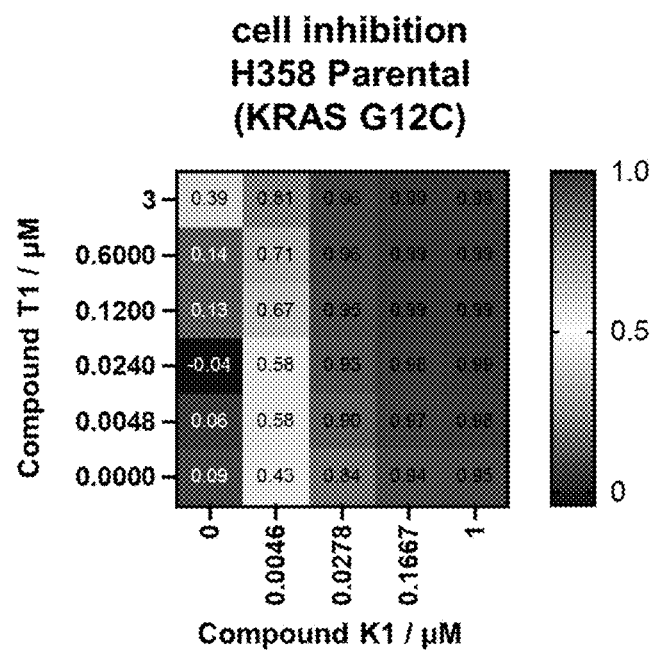
FIG. 10 depicts % inhibition of H358 parental cells (KRAS G12C) following administration of a combination comprising Compound T1 (a YAP/TAZ-TEAD inhibitor) and Compound K1 (a KRAS inhibitor).
Figure 11:
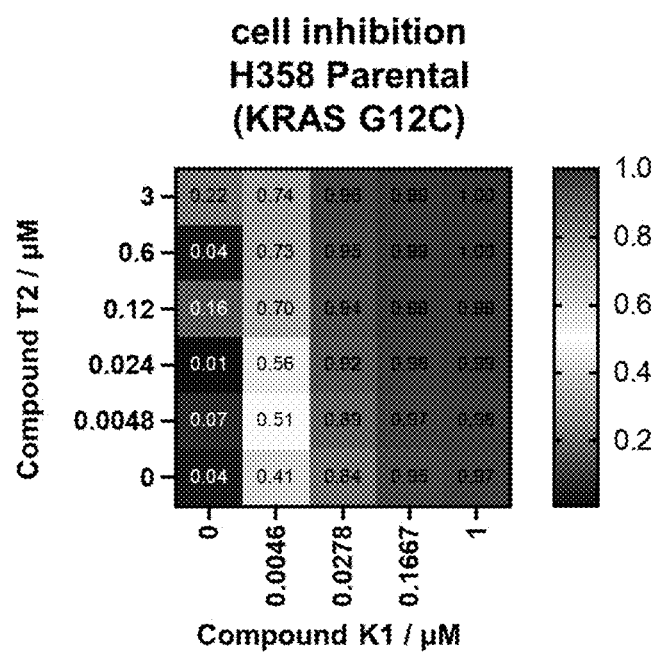
FIG. 11 depicts % inhibition of H358 parental cells (KRAS G12C) following administration of a combination comprising Compound T2 (a YAP/TAZ-TEAD inhibitor) and Compound K1 (a KRAS inhibitor).
Figure 12:
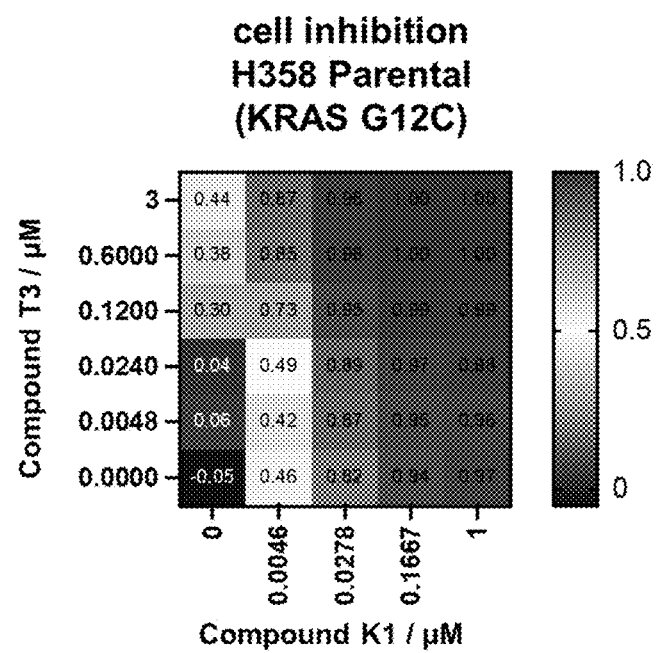
FIG. 12 depicts % inhibition of H358 parental cells (KRAS G12C) following administration of a combination comprising Compound T3 (a YAP/TAZ-TEAD inhibitor) and Compound K1 (a KRAS inhibitor).
Figure 13:
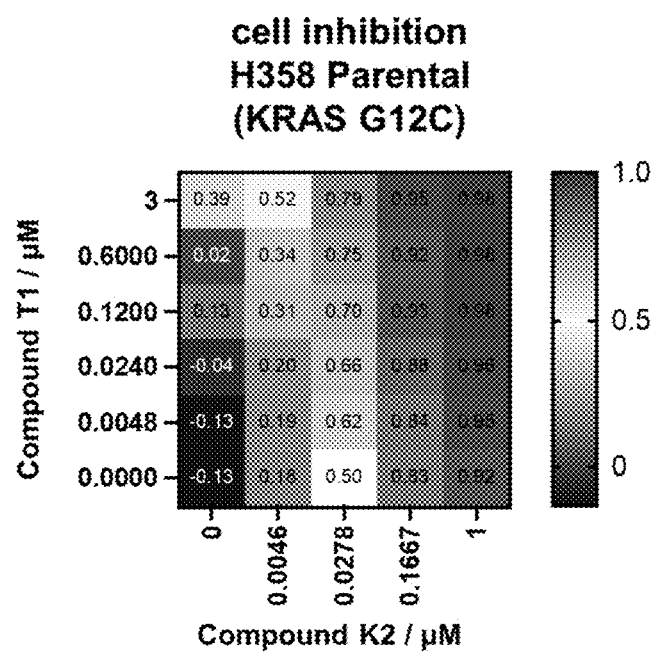
FIG. 13 depicts % inhibition of H358 parental cells (KRAS G12C) following administration of a combination comprising Compound T1 (a YAP/TAZ-TEAD inhibitor) and Compound K2 (a KRAS inhibitor).
Figure 14:
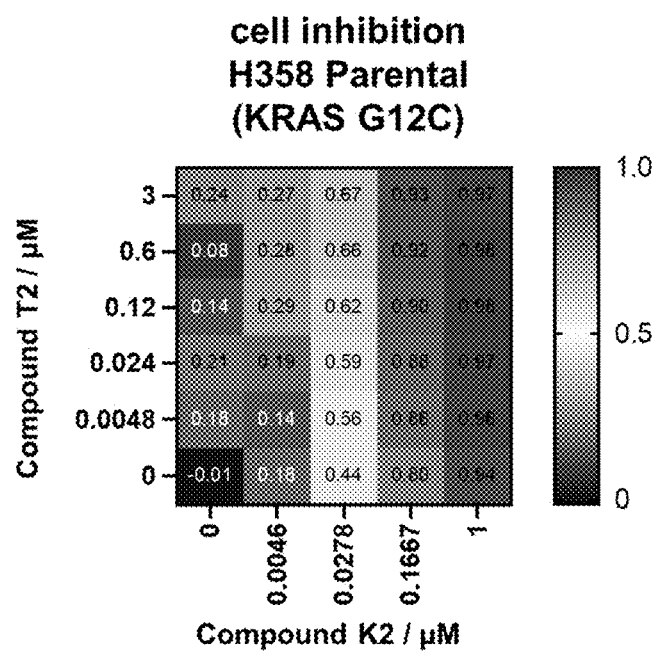
FIG. 14 depicts % inhibition of H358 parental cells (KRAS G12C) following administration of a combination comprising Compound T2 (a YAP/TAZ-TEAD inhibitor) and Compound K2 (a KRAS inhibitor).
Figure 15:
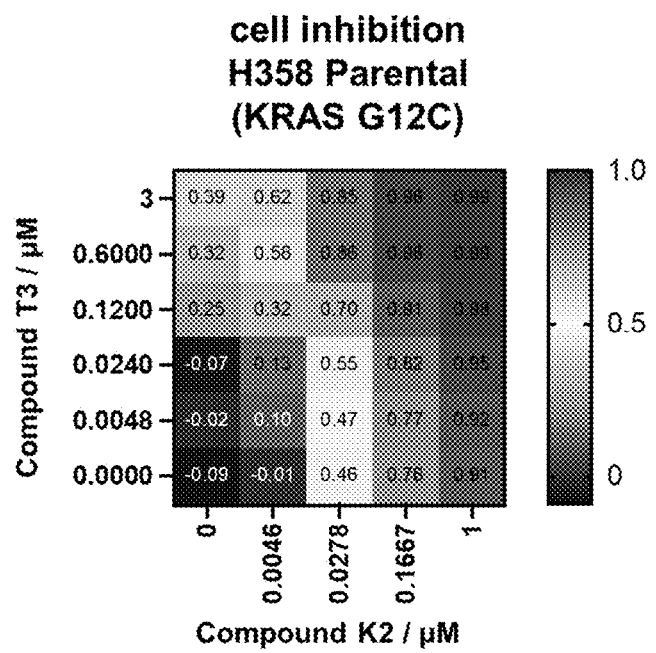
FIG. 15 depicts % inhibition of H358 parental cells (KRAS G12C) following administration of a combination comprising Compound T3 (a YAP/TAZ-TEAD inhibitor) and Compound K2 (a KRAS inhibitor).
Figure 16:
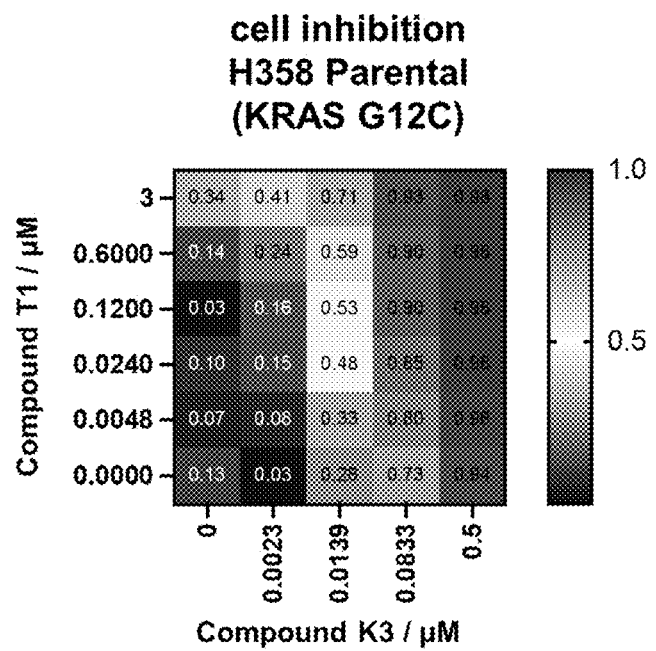
FIG. 16 depicts % inhibition of H358 parental cells (KRAS G12C) following administration of a combination comprising Compound T1 (a YAP/TAZ-TEAD inhibitor) and Compound K3 (a KRAS inhibitor).
Figure 17:
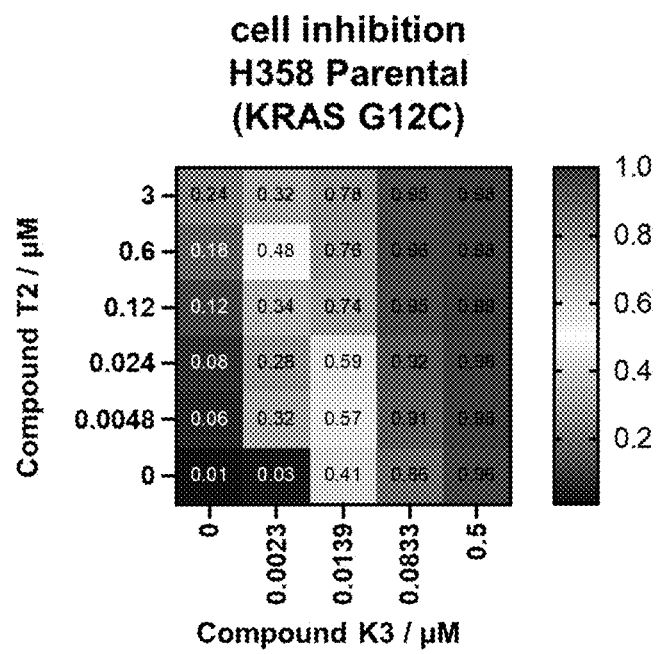
FIG. 17 depicts % inhibition of H358 parental cells (KRAS G12C) following administration of a combination comprising Compound T2 (a YAP/TAZ-TEAD inhibitor) and Compound K3 (a KRAS inhibitor).
Figure 18:
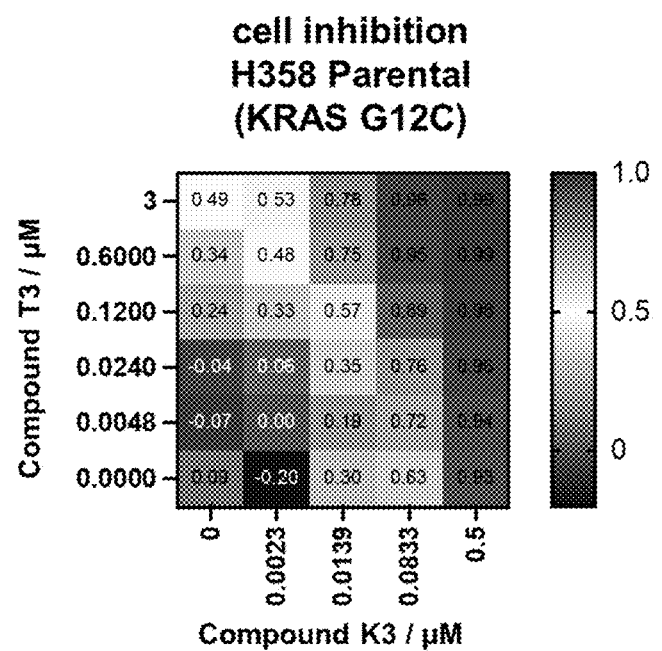
FIG. 18 depicts % inhibition of H358 parental cells (KRAS G12C) following administration of a combination comprising Compound T3 (a YAP/TAZ-TEAD inhibitor) and Compound K3 (a KRAS inhibitor).
Figure 19:
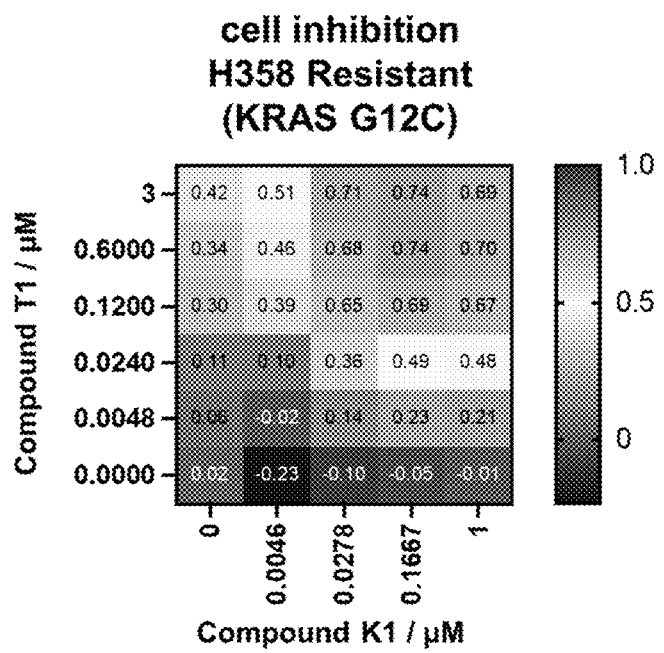
FIG. 19 depicts % inhibition of H358 resistant cells (KRAS G12C) following administration of a combination comprising Compound T1 (a YAP/TAZ-TEAD inhibitor) and Compound K1 (a KRAS inhibitor).
Figure 20:
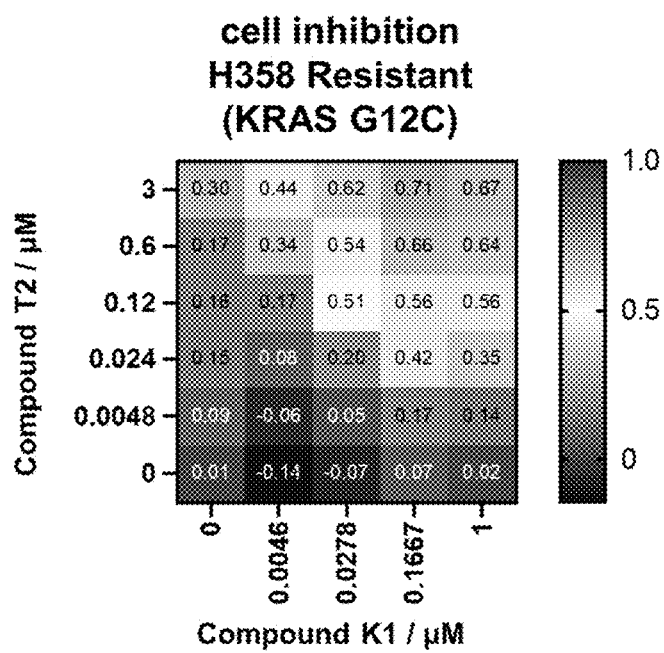
FIG. 20 depicts % inhibition of H358 resistant cells (KRAS G12C) following administration of a combination comprising Compound T2 (a YAP/TAZ-TEAD inhibitor) and Compound K1 (a KRAS inhibitor).
Figure 21:
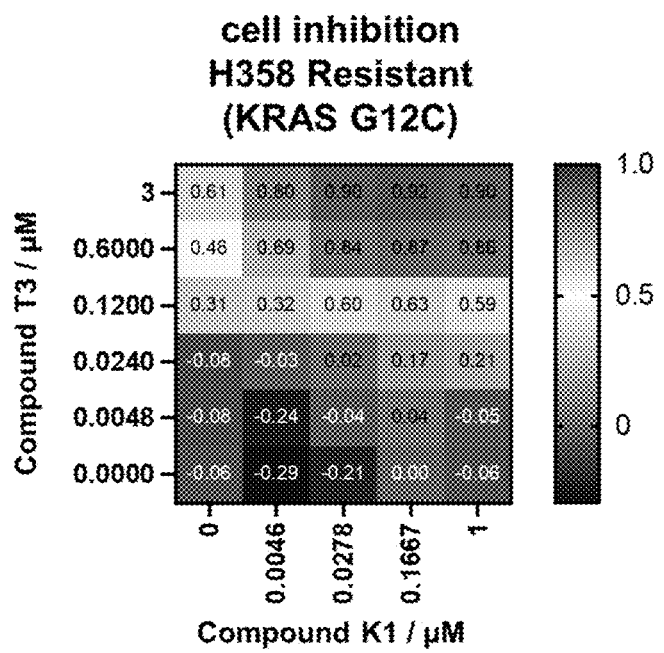
FIG. 21 depicts % inhibition of H358 resistant cells (KRAS G12C) following administration of a combination comprising Compound T3 (a YAP/TAZ-TEAD inhibitor) and Compound K1 (a KRAS inhibitor).
Figure 22:
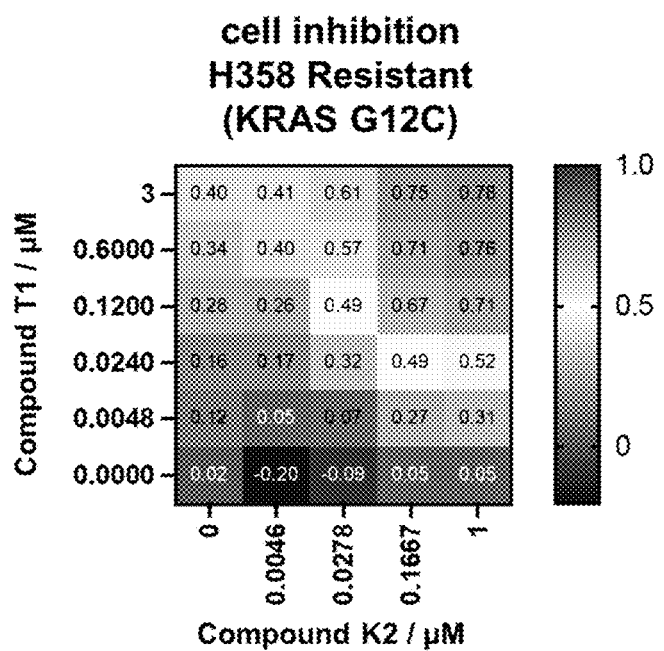
FIG. 22 depicts % inhibition of H358 resistant cells (KRAS G12C) following administration of a combination comprising Compound T1 (a YAP/TAZ-TEAD inhibitor) and Compound K2 (a KRAS inhibitor).
Figure 23:
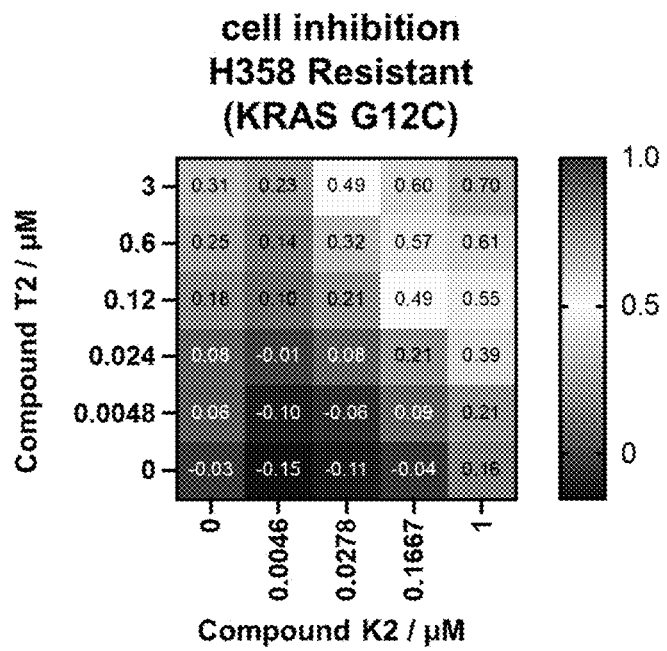
FIG. 23 depicts % inhibition of H358 resistant cells (KRAS G12C) following administration of a combination comprising Compound T2 (a YAP/TAZ-TEAD inhibitor) and Compound K2 (a KRAS inhibitor).
Figure 24:
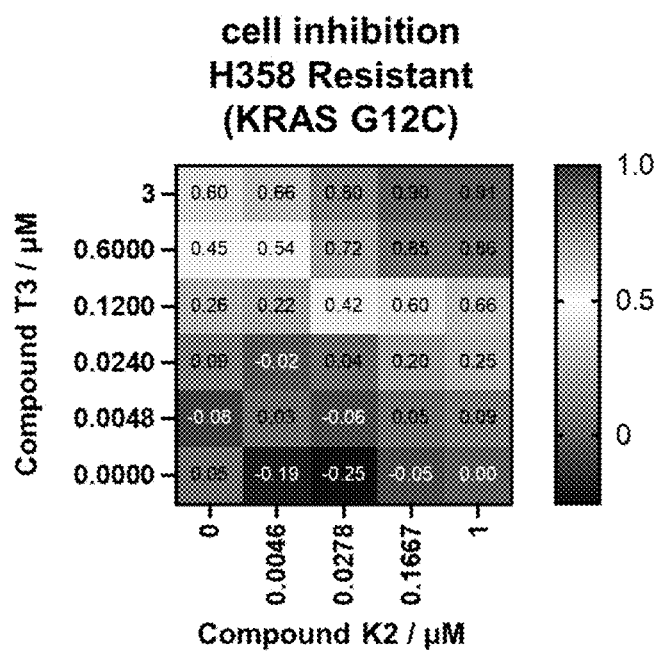
FIG. 24 depicts % inhibition of H358 resistant cells (KRAS G12C) following administration of a combination comprising Compound T3 (a YAP/TAZ-TEAD inhibitor) and Compound K2 (a KRAS inhibitor).
Figure 25:
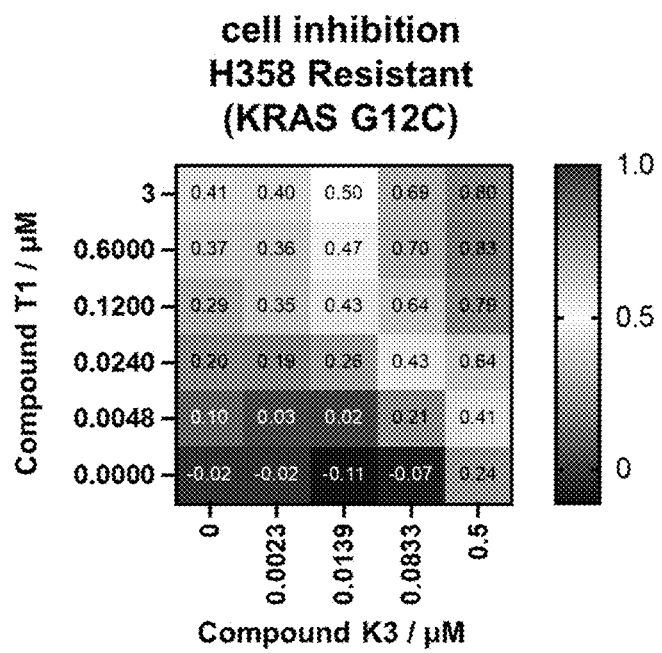
FIG. 25 depicts % inhibition of H358 resistant cells (KRAS G12C) following administration of a combination comprising Compound T1 (a YAP/TAZ-TEAD inhibitor) and Compound K3 (a KRAS inhibitor).
Figure 26:
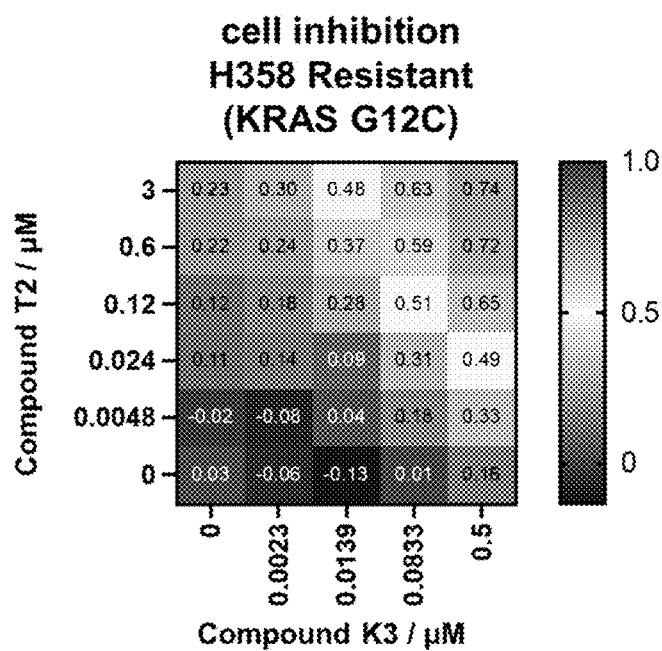
FIG. 26 depicts % inhibition of H358 resistant cells (KRAS G12C) following administration of a combination comprising Compound T2 (a YAP/TAZ-TEAD inhibitor) and Compound K3 (a KRAS inhibitor).
Figure 27:
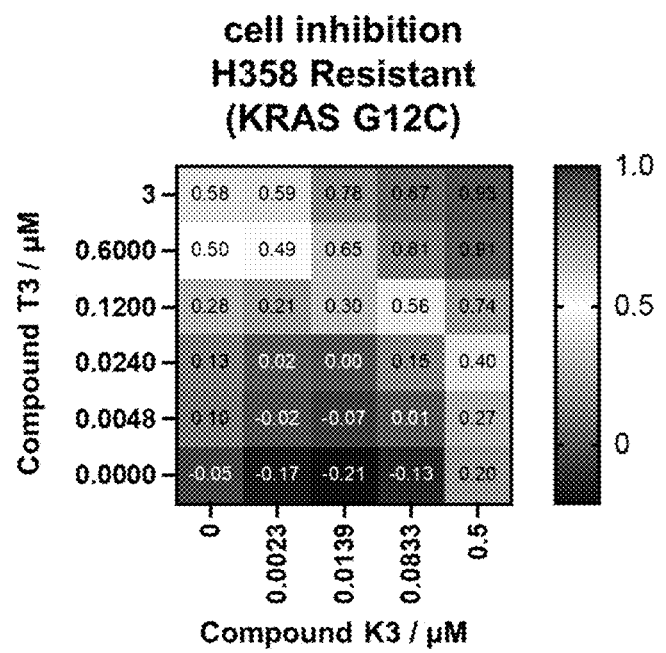
FIG. 27 depicts % inhibition of H358 resistant cells (KRAS G12C) following administration of a combination comprising Compound T3 (a YAP/TAZ-TEAD inhibitor) and Compound K3 (a KRAS inhibitor).
Figure 28:
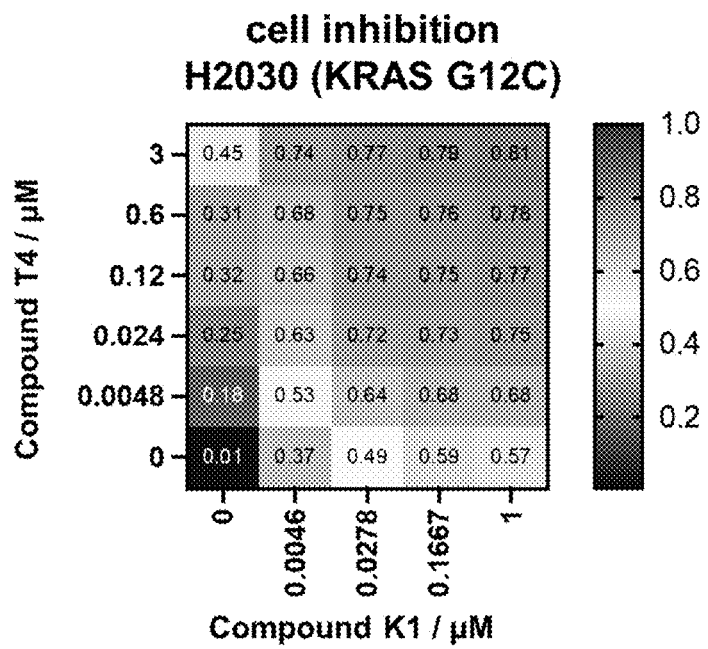
FIG. 28 depicts % inhibition of H2030 cells (KRAS G12C) following administration of a combination comprising Compound T4 (a YAP/TAZ-TEAD inhibitor) and Compound K1 (a KRAS inhibitor).
Figure 29:
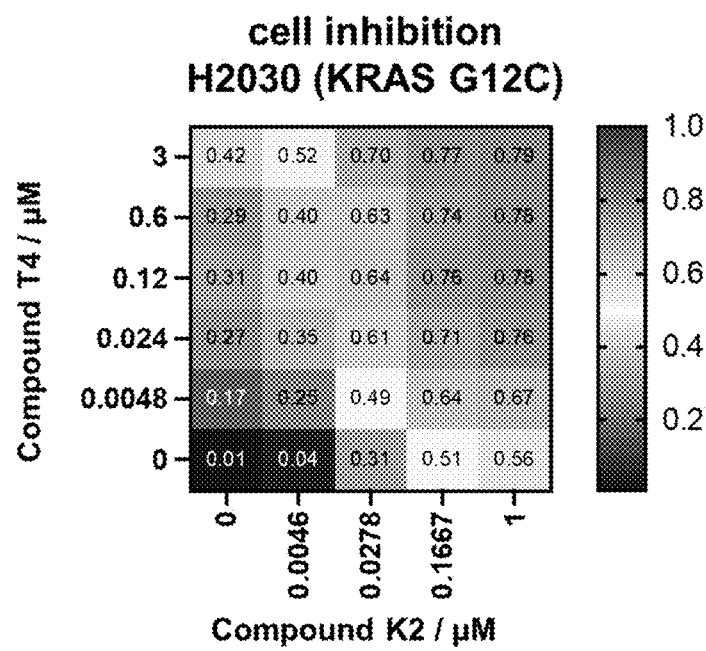
FIG. 29 depicts % inhibition of H2030 cells (KRAS G12C) following administration of a combination comprising Compound T4 (a YAP/TAZ-TEAD inhibitor) and Compound K2 (a KRAS inhibitor).
Figure 30:
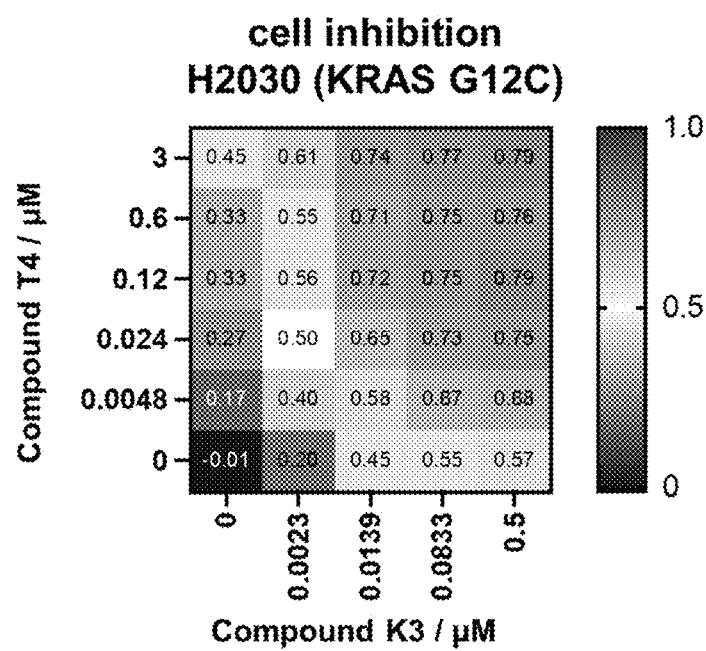
FIG. 30 depicts % inhibition of H2030 cells (KRAS G12C) following administration of a combination comprising Compound T4 (a YAP/TAZ-TEAD inhibitor) and Compound K3 (a KRAS inhibitor).
Figure 31:
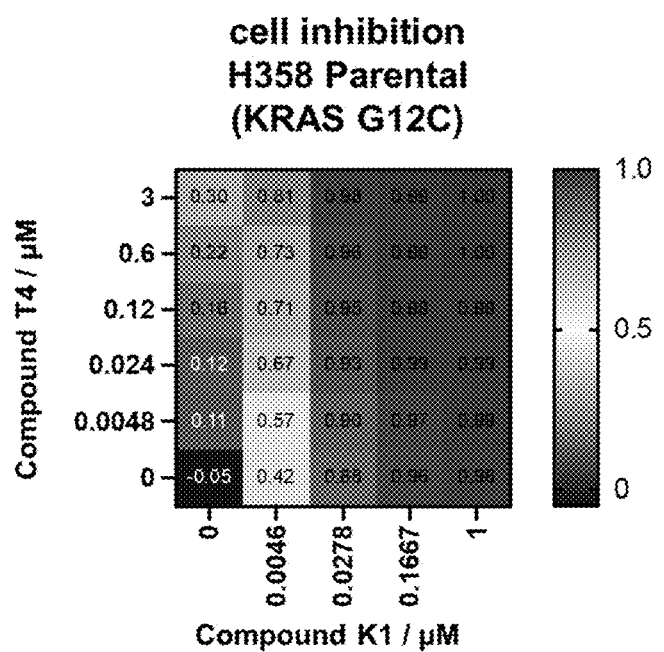
FIG. 31 depicts % inhibition of H358 Parental cells (KRAS G12C) following administration of a combination comprising Compound T4 (a YAP/TAZ-TEAD inhibitor) and Compound K1 (a KRAS inhibitor).
Figure 32:
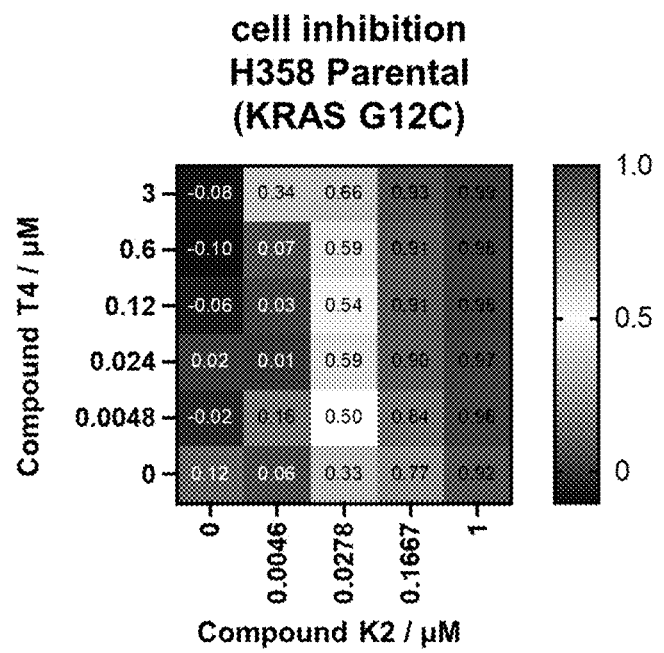
FIG. 32 depicts % inhibition of H358 Parental cells (KRAS G12C) following administration of a combination comprising Compound T4 (a YAP/TAZ-TEAD inhibitor) and Compound K2 (a KRAS inhibitor).
Figure 33:
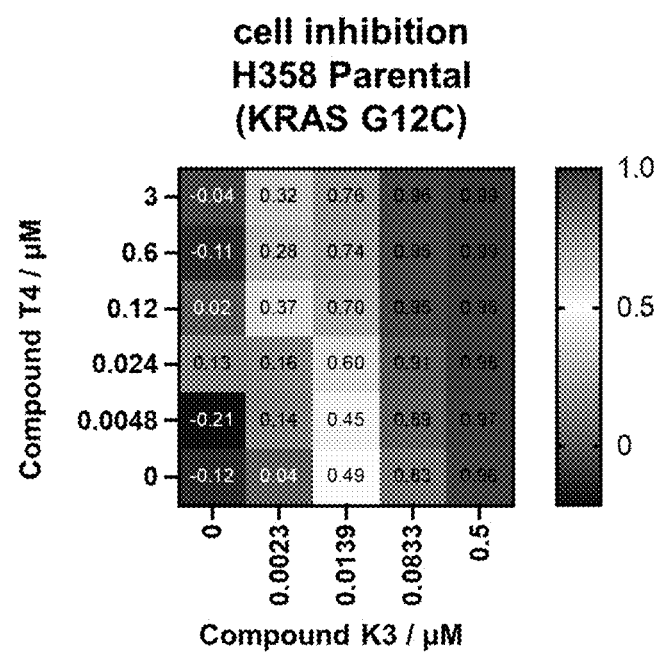
FIG. 33 depicts % inhibition of H358 Parental cells (KRAS G12C) following administration of a combination comprising Compound T4 (a YAP/TAZ-TEAD inhibitor) and Compound K3 (a KRAS inhibitor).
Figure 34:
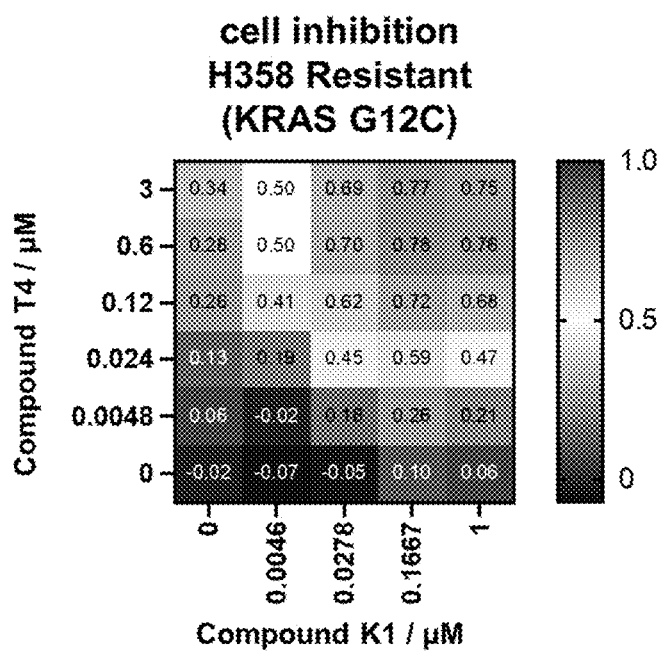
FIG. 34 depicts % inhibition of H358 Resistant cells (KRAS G12C) following administration of a combination comprising Compound T4 (a YAP/TAZ-TEAD inhibitor) and Compound K1 (a KRAS inhibitor).
Figure 35:
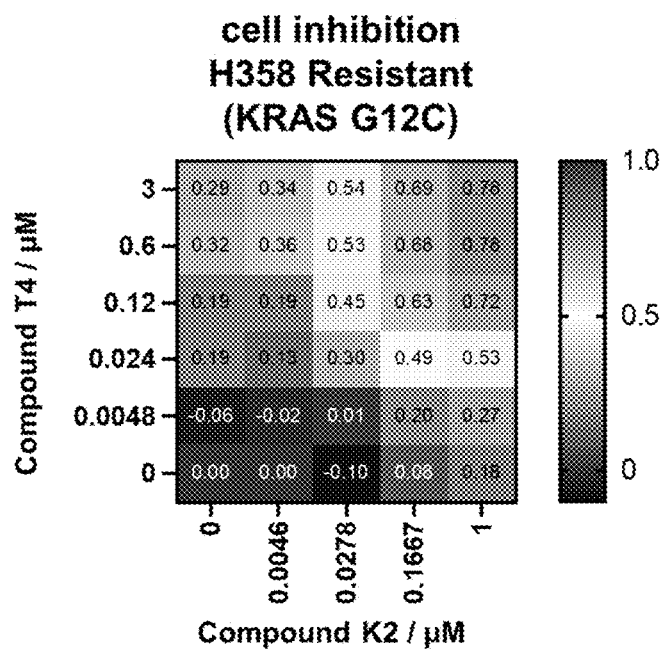
FIG. 35 depicts % inhibition of H358 Resistant cells (KRAS G12C) following administration of a combination comprising Compound T4 (a YAP/TAZ-TEAD inhibitor) and Compound K2 (a KRAS inhibitor).
Figure 36:
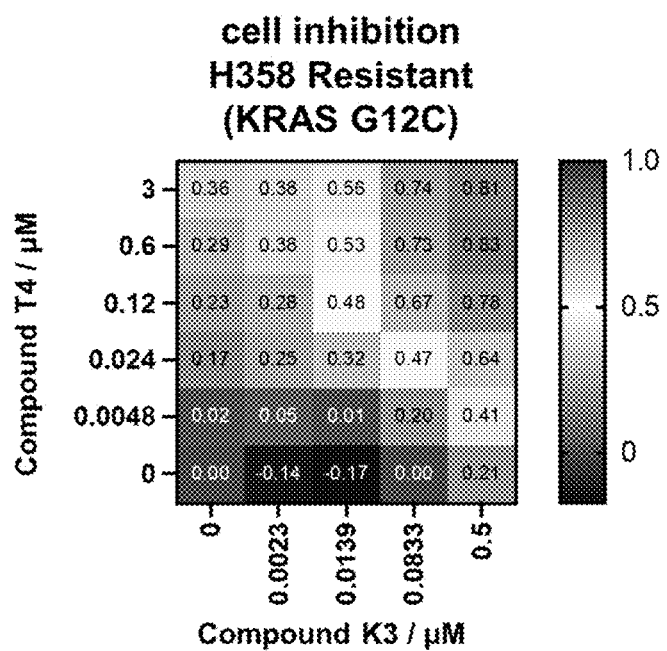
FIG. 36 depicts % inhibition of H358 Resistant cells (KRAS G12C) following administration of a combination comprising Compound T4 (a YAP/TAZ-TEAD inhibitor) and Compound K3 (a KRAS inhibitor).
Figure 37:
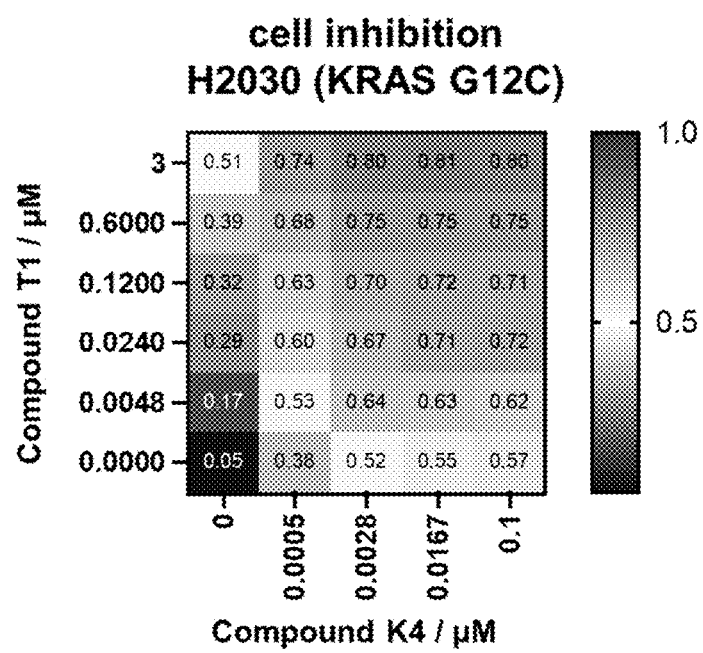
FIG. 37 depicts % inhibition of H2030 cells (KRAS G12C) following administration of a combination comprising Compound T1 (a YAP/TAZ-TEAD inhibitor) and Compound K4 (a KRAS inhibitor).
Figure 38:
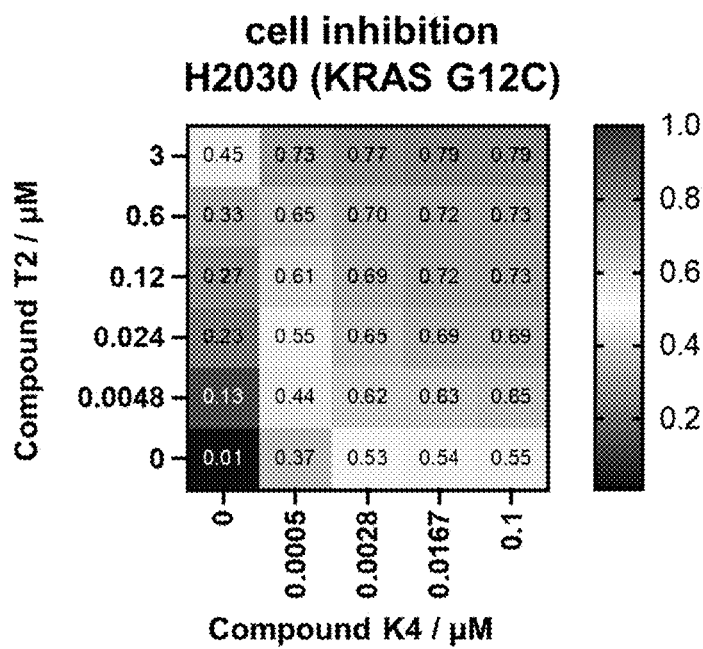
FIG. 38 depicts % inhibition of H2030 cells (KRAS G12C) following administration of a combination comprising Compound T2 (a YAP/TAZ-TEAD inhibitor) and Compound K4 (a KRAS inhibitor).
Figure 39:
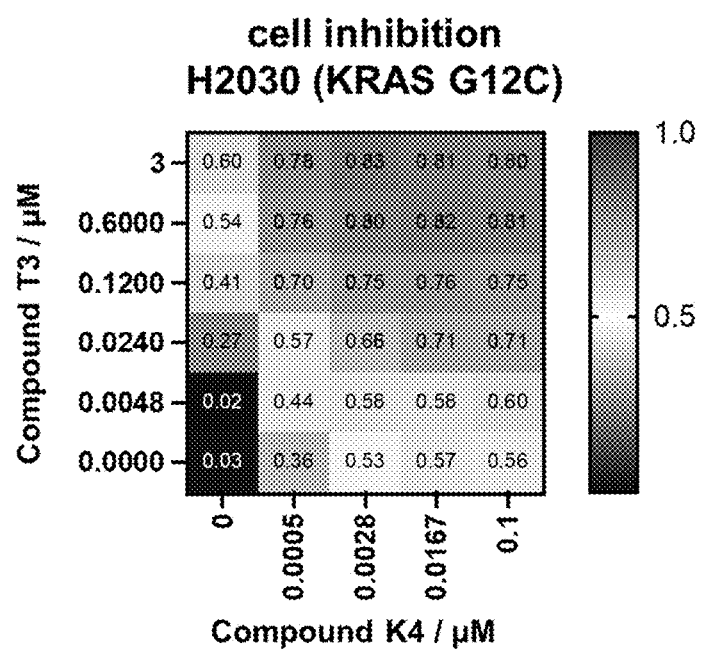
FIG. 39 depicts % inhibition of H2030 cells (KRAS G12C) following administration of a combination comprising Compound T3 (a YAP/TAZ-TEAD inhibitor) and Compound K4 (a KRAS inhibitor).
Figure 40:
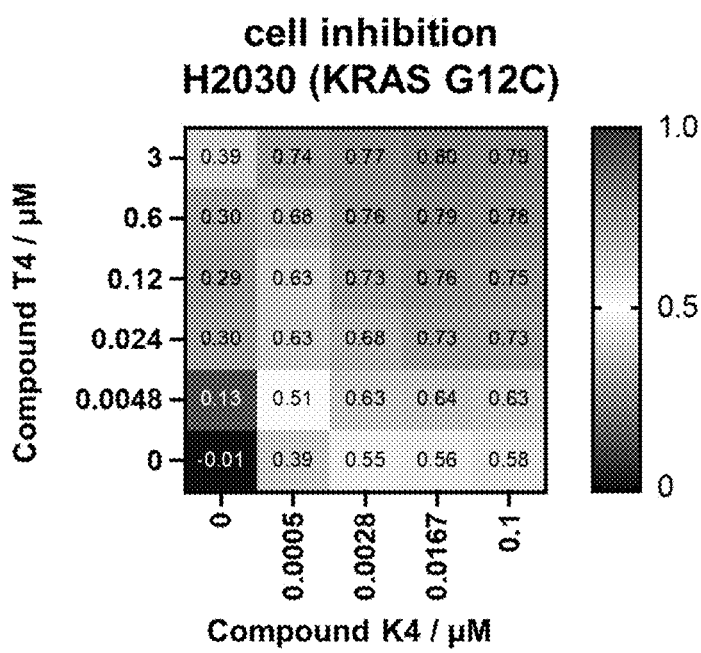
FIG. 40 depicts % inhibition of H2030 cells (KRAS G12C) following administration of a combination comprising Compound T4 (a YAP/TAZ-TEAD inhibitor) and Compound K4 (a KRAS inhibitor).
Figure 41:
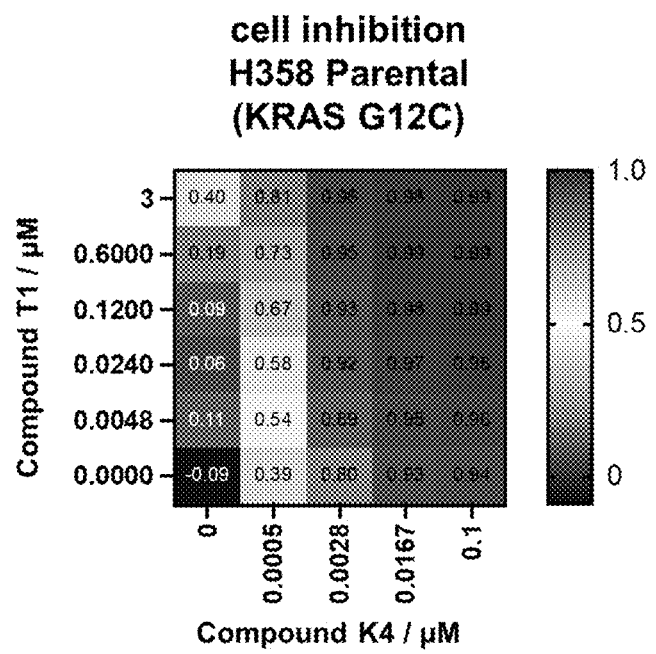
FIG. 41 depicts % inhibition of H358 Parental cells (KRAS G12C) following administration of a combination comprising Compound T1 (a YAP/TAZ-TEAD inhibitor) and Compound K4 (a KRAS inhibitor).
Figure 42:
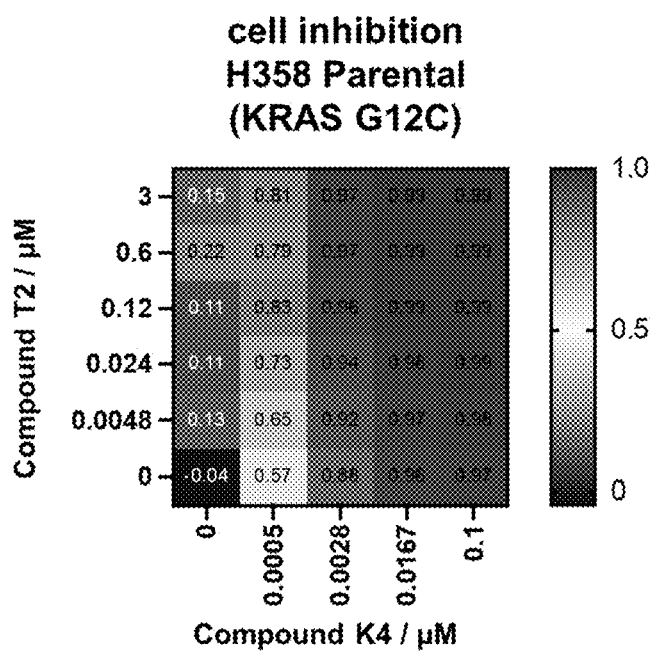
FIG. 42 depicts % inhibition of H358 Parental cells (KRAS G12C) following administration of a combination comprising Compound T2 (a YAP/TAZ-TEAD inhibitor) and Compound K4 (a KRAS inhibitor).
Figure 43:
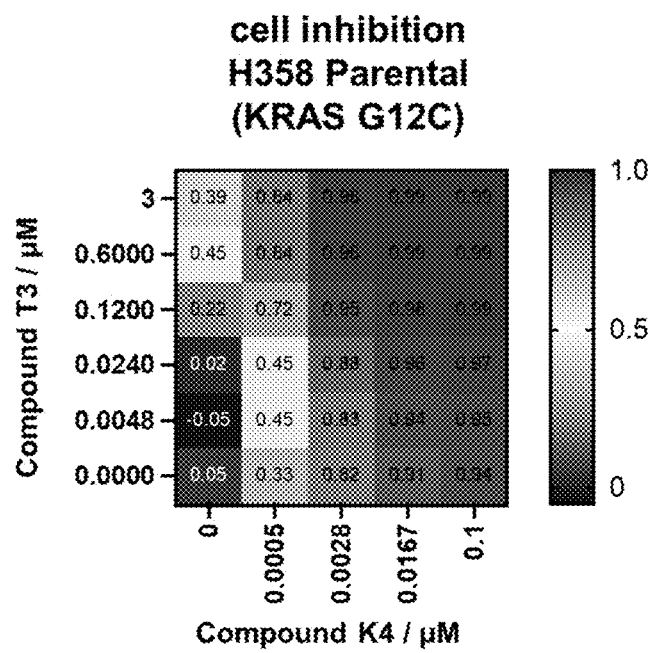
FIG. 43 depicts % inhibition of H358 Parental cells (KRAS G12C) following administration of a combination comprising Compound T3 (a YAP/TAZ-TEAD inhibitor) and Compound K4 (a KRAS inhibitor).
Figure 44:
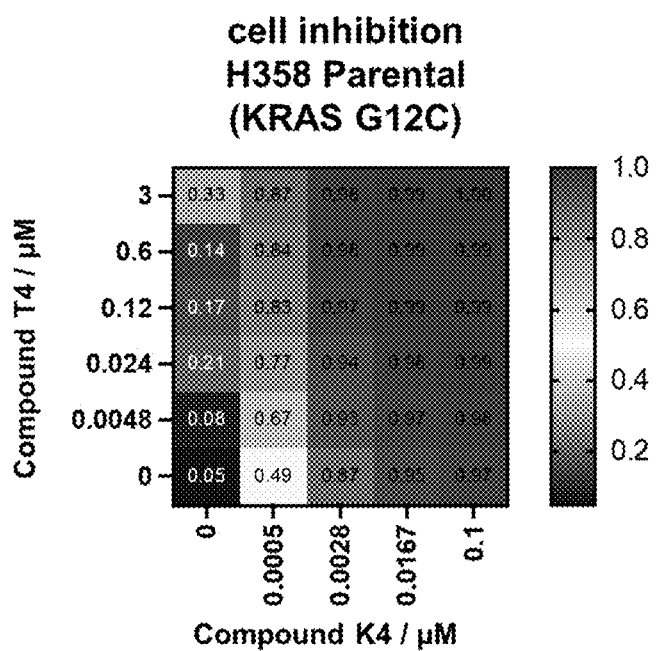
FIG. 44 depicts % inhibition of H358 Parental cells (KRAS G12C) following administration of a combination comprising Compound T4 (a YAP/TAZ-TEAD inhibitor) and Compound K4 (a KRAS inhibitor).
Figure 45:
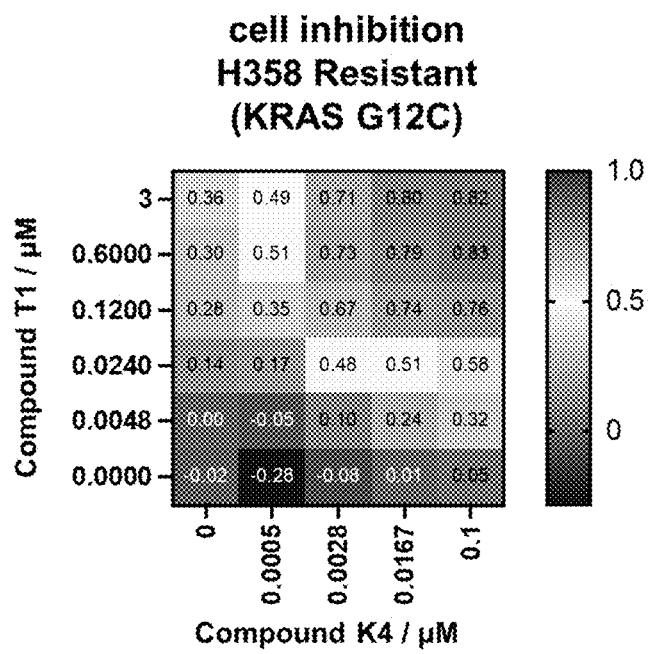
FIG. 45 depicts % inhibition of H358 Resistant cells (KRAS G12C) following administration of a combination comprising Compound T1 (a YAP/TAZ-TEAD inhibitor) and Compound K4 (a KRAS inhibitor).
Figure 46:
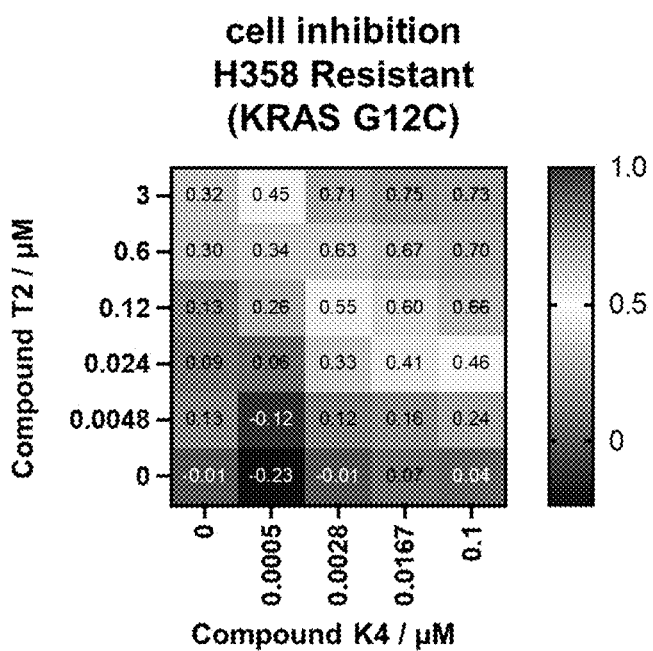
FIG. 46 depicts % inhibition of H358 Resistant cells (KRAS G12C) following administration of a combination comprising Compound T2 (a YAP/TAZ-TEAD inhibitor) and Compound K4 (a KRAS inhibitor).
Figure 47:
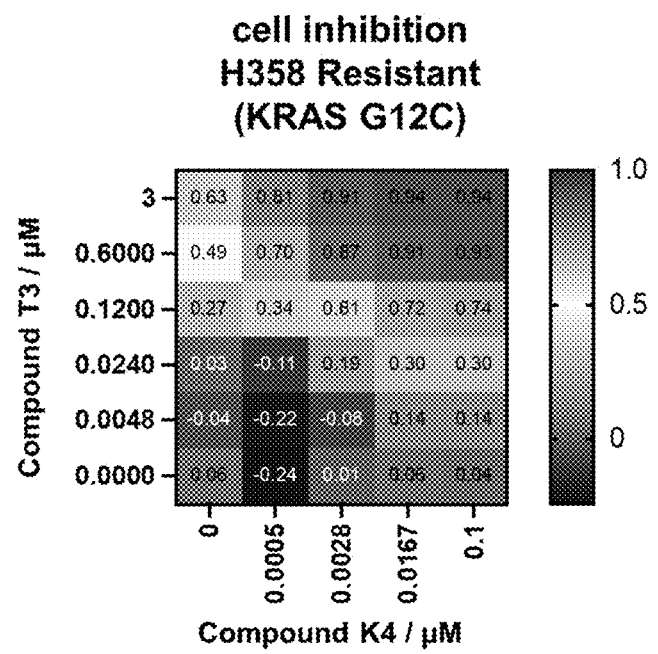
FIG. 47 depicts % inhibition of H358 Resistant cells (KRAS G12C) following administration of a combination comprising Compound T3 (a YAP/TAZ-TEAD inhibitor) and Compound K4 (a KRAS inhibitor).
Figure 48:
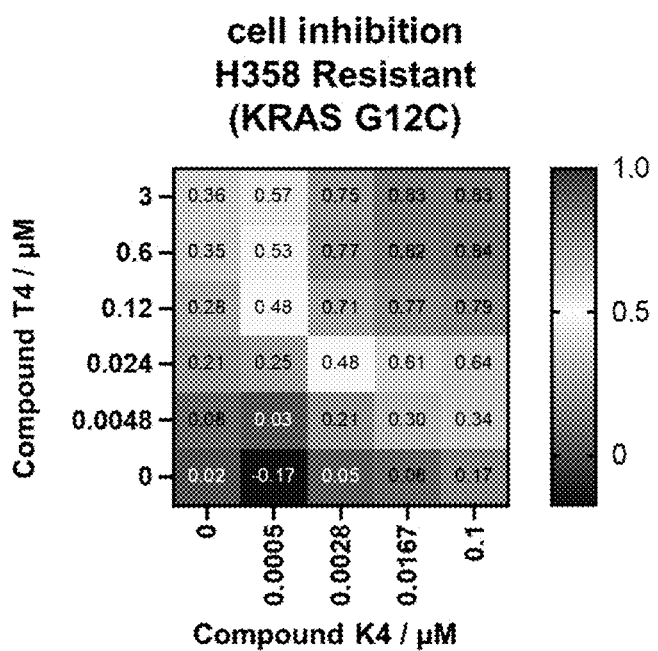
FIG. 48 depicts % inhibition of H358 Resistant cells (KRAS G12C) following administration of a combination comprising Compound T4 (a YAP/TAZ-TEAD inhibitor) and Compound K4 (a KRAS inhibitor).

Example 78: biological examples for combination of one or more TEAD inhibitors and one or more KRAS inhibitors EXAMPLE B-1: Drug Combination Assay Cells were seeded in 96-well plates 16h before treatment at a density of 1000 cells per well. Then, cells were treated with varying concentrations of compound(s) as indicated in FIGS. 1-48, either a single agent or in combination, for six days. The relative number of viable cells was estimated using CellTiter-Glo Luminescent Cell Viability Assay (Promega, G7573) as a proportion from 0, representing no cells inhibited, to 1.0 representing all cells inhibited. Total luminescence was detected on a Wallac Multilabel Reader (Perkin-Elmer).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

It is to be understood that the invention is not limited to the particular embodiments and aspects of the disclosure described above, as variations of the particular embodiments and aspects may be made and still fall within the scope of the appended claims. All documents cited to or relied upon herein are expressly incorporated by reference.

What is claimed is:

1. A compound of formula (II-A-1):

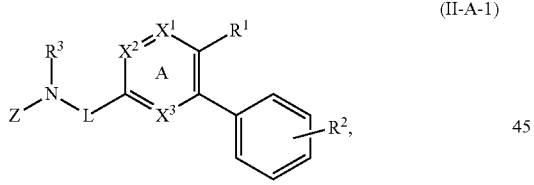

(II-A-1)

or a stereoisomer or tautomer thereof, or a pharmaceutically acceptable salt thereof, wherein:

L is methylene optionally substituted with one or more $C_{1-6}$alkyl;

$X^1$ is C, and $X^1$ is taken together with $R^1$ and the atoms to which they are attached, to form a 5 to 6 membered heteroarylfused to ring A;
  wherein the 5 to 6 membered heteroaryl is optionally substituted with one or more $R^t$,
  wherein $R^t$ is independently, at each occurrence, selected from the group consisting of halo, $C_{1-15}$alkyl, halo$C_{1-15}$alkyl, $C_{6-20}$aryl, 5 to 15 membered heteroaryl, $C_{3-20}$cycloalkyl, 3 to 15 membered heterocyclyl, —OH, —CN, oxo, $C_{1-15}$alkoxy, —NR$^d$COR$^e$, —CONR$^d$R$^e$, —SO$_2$R$^d$, —SO$_2$NR$^d$R$^e$, —NR$^d$SO$_2$R$^e$, and —NR$^d$R$^e$; and
  wherein R$^d$ and R$^e$ are each independently H or $C_{1-6}$alkyl, and wherein the $C_{1-6}$alkyl of R$^d$ or R$^e$ is optionally substituted with one or more substituents selected from the group consisting of halo, oxo, —OH and —CN;

$X^2$ is CR$^s$, wherein R$^s$ is selected from the group consisting of H, halo, $C_{1-15}$alkyl, hydroxyl$C_{1-6}$alkynyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —NR$^d$COR$^e$, —CONR$^d$R$^e$, —SO$_2$R$^d$, —S(O)NHR$^d$, —SO$_2$NR$^d$R$^e$, —NR$^d$SO$_2$R$^e$, and —NR$^d$R$^e$;
  wherein the $C_{1-15}$alkyl and $C_{1-15}$alkoxy of R$^s$ are each independently optionally substituted with one or more R$^{t1}$, wherein R$^{t1}$ is independently at each occurrence halo, oxo, —OH, —CN, 5-6 membered heteroaryl, or —NR$^d$R$^e$, wherein R$^d$ and R$^e$ are each independently H or $C_{1-6}$alkyl, and wherein the $C_{1-6}$alkyl of R$^d$ or R$^e$ is optionally substituted with one or more substituents selected from the group consisting of halo, oxo, —OH and —CN; and
  wherein the $C_{6-20}$aryl, 5 to 15 membered heteroaryl, $C_{3-20}$cycloalkyl, and 3 to 15 membered heterocyclyl of R$^s$ are each independently optionally substituted with one or more R$^{t2}$, wherein R$^{t2}$ is independently at each occurrence selected from the group consisting of halo, oxo, —OH, —CN and $C_{1-6}$alkyl; and
  wherein R$^d$ and R$^e$ are each independently H or $C_{1-6}$alkyl, and wherein the $C_{1-6}$alkyl of R$^d$ or R$^e$ is optionally substituted with one or more substituents selected from the group consisting of halo, oxo, —OH and —CN;

X³ is CH;

R² is halo; S(Rʸ)₅, wherein each Rʸ is halo; or C₁₋₆alkoxy optionally substituted with one or more halo; R³ is H or C₁₋₆alkyl; and Z is —OH, —NRᵈRᵉ, C₁₋₆alkoxy, —C(O)Rᵃ, or —S(O)₂Rᵇ, wherein Rᵈ and Rᵉ are each independently H or C₁₋₆alkyl, and wherein the C₁₋₆alkyl of Rᵈ or Rᵉ is optionally substituted with one or more substituents selected from the group consisting of halo, oxo, —OH and —CN;

Rᵃ and Rᵇ are each independently i) C₂₋₆alkenyl optionally substituted with one or more substituents selected from the group consisting of deuterium, C₁₋₆alkyl, hydroxyl C₁₋₆alkyl, halo and haloC₁₋₆alkyl; ii) C₁₋₆alkyl, optionally substituted with one or more halo; or iii) cyclobutenyl or bicyclobutanyl.

2. The compound of claim 1, or a stereoisomer or tautomer thereof, or a pharmaceutically acceptable salt thereof, wherein Z is —C(O)Rᵃ or —S(O)₂Rᵇ, Rᵃ and Rᵇ are each independently i) C₂₋₆alkenyl optionally substituted with one or more substituents selected from the group consisting of deuterium, C₁₋₆alkyl, hydroxyl C₁₋₆alkyl, halo and haloC₁₋₆alkyl; ii) C₁₋₆alkyl, optionally substituted with one or more halo; or iii) cyclobutenyl or bicyclobutanyl.

3. The compound of claim 2, or a stereoisomer or tautomer thereof, or a pharmaceutically acceptable salt thereof, wherein Z is —C(O)Rᵃ and Rᵃ is (i) ethenyl optionally substituted with one or more substituents selected from the group consisting of deuterium and halo;

(ii) cyclobutenyl; or (iii) bicyclobutanyl.

4. The compound of claim 2, or a stereoisomer or tautomer thereof, or a pharmaceutically acceptable salt thereof, wherein Z is

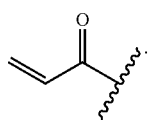 [SMILES: *C(=O)C=C]

5. The compound of claim 1, or a stereoisomer or tautomer thereof, or a pharmaceutically acceptable salt thereof, wherein R² is halomethoxy.

6. The compound of claim 1, or a stereoisomer or tautomer thereof, or a pharmaceutically acceptable salt thereof, wherein R² is trifluoromethoxy.

7. The compound of claim 1, or a stereoisomer or tautomer thereof, or a pharmaceutically acceptable salt thereof, wherein Z is —C(O)Rᵃ and Rᵃ is (i) C₂₋₆alkenyl optionally substituted with one or more substituents selected from the group consisting of deuterium, C₁₋₆alkyl, halo and haloC₁₋₆alkyl; or (ii) C₁₋₆alkyl, optionally substituted with one or more halo; and B is phenyl substituted with one or more R², wherein R² is C₁₋₆alkoxy optionally substituted with one or more halo.

8. The compound of claim 1, or a stereoisomer or tautomer thereof, or a pharmaceutically acceptable salt thereof, wherein the compound is a compound of formula (II-A-20):

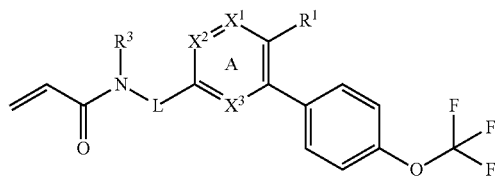

(II-A-20)

or a stereoisomer or tautomer thereof, or a pharmaceutically acceptable salt thereof.

9. The compound of claim 1, or a stereoisomer or tautomer thereof, or a pharmaceutically acceptable salt thereof, wherein R³ is H.

10. The compound of claim 1, or a stereoisomer or tautomer thereof, or a pharmaceutically acceptable salt thereof, wherein X² is CRˢ, wherein Rˢ is C-1.5alkyl, 5 to 15 membered heteroaryl, —CN, or C-1.5alkoxy;

wherein the C-1.5alkyl and C-1.5alkoxy of Rˢ are each independently optionally substituted with one or more Rᵗ¹, wherein Rᵗ¹ is independently at each occurrence halo, oxo, —OH, —CN, 5-6 membered heteroaryl, or —NRᵈRᵉ, wherein Rᵈ and Rᵉ are each independently H or C₁₋₆alkyl, and wherein the C₁₋₆alkyl of Rᵈ or Rᵉ is optionally substituted with one or more substituents selected from the group consisting of halo, oxo, —OH and —CN; and wherein the 5 to 15 membered heteroaryl of Rˢ is optionally substituted with one or more Rᵗ², wherein Rᵗ² is independently at each occurrence selected from the group consisting of halo, oxo, —OH, —CN and C₁₋₆alkyl.

11. The compound of claim 1, or a stereoisomer or tautomer thereof, or a pharmaceutically acceptable salt thereof, wherein the 5 to 6 membered heteroaryl fused to ring A is selected from the group consisting of:

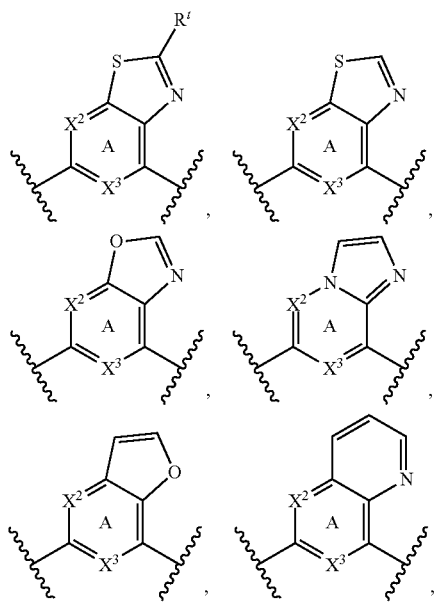

-continued

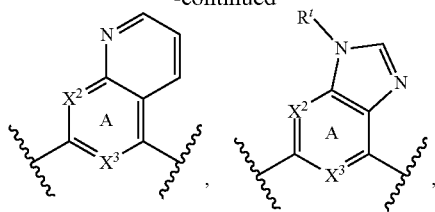

-continued

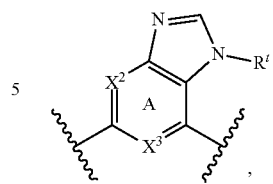

and

12. A compound selected from the group consisting of:

| Compound Number | Structure | Compound Name |
|---|---|---|
| 16 | 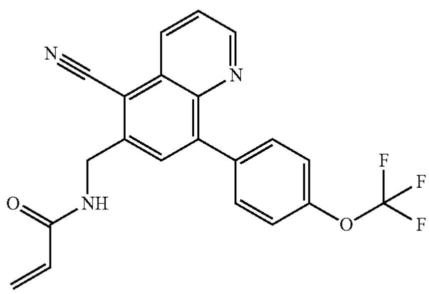 [SMILES: C=CC(=O)NCc1cc(-c2ccc(OC(F)(F)F)cc2)c2ncccc2c1C#N] | N-[[5-cyano-8-[4-(trifluoromethoxy)phenyl]-6-quinolyl]methyl]prop-2-enamide |
| 27 | 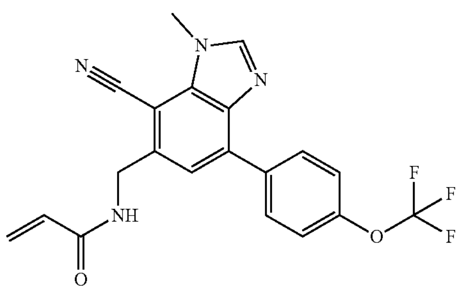 [SMILES: C=CC(=O)NCc1cc(-c2ccc(OC(F)(F)F)cc2)c2ncn(C)c2c1C#N] | N-[[4-cyano-3-methyl-7-[4-(trifluoromethoxy)phenyl]benzimidazol-5-yl]methyl]prop-2-enamide |
| 28 | 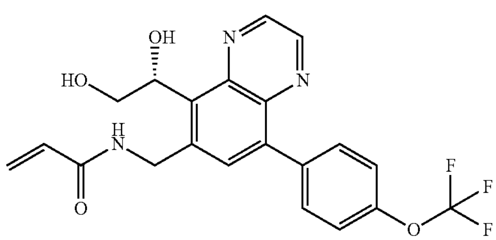 | N-[5-[(1R)-1,2-dihydroxyethyl]-8-[4-(trifluoromethoxy)phenyl]quinoxalin-6-yl]methyl]prop-2-enamide |
| 29 | 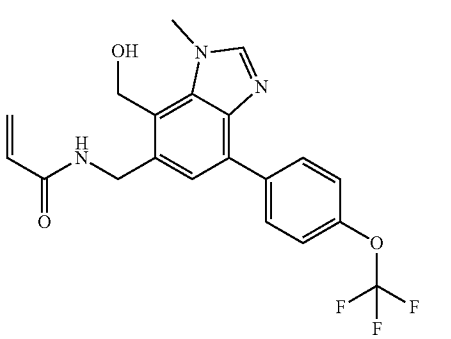 [SMILES: C=CC(=O)NCc1cc(-c2ccc(OC(F)(F)F)cc2)c2ncn(C)c2c1CO] | N-[[4-(hydroxymethyl)-3-methyl-7-[4-(trifluoromethoxy)phenyl]benzimidazol-5-yl]methyl]prop-2-enamide |

| Compound Number | Structure | Compound Name |
|---|---|---|
| 30 | 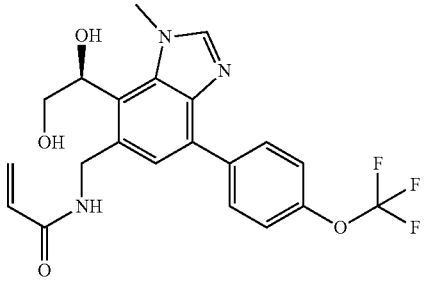 [SMILES: C=CC(=O)NCc1cc(-c2ccc(OC(F)(F)F)cc2)c2ncn(C)c2c1[C@H](O)CO] | N-[[3-methyl-4-[(1S)-1,2-dihydroxyethyl]-7-[4-(trifluoromethoxy)phenyl]benzimidazol-5-yl]methyl]prop-2-enamide |
| 31 | 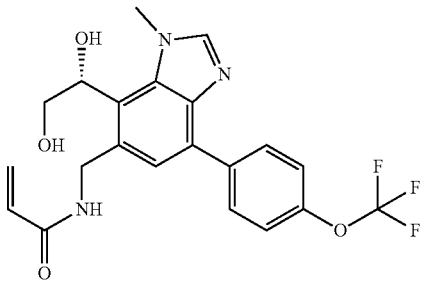 [SMILES: C=CC(=O)NCc1cc(-c2ccc(OC(F)(F)F)cc2)c2ncn(C)c2c1[C@@H](O)CO] | N-[[3-methyl-4-[(1R)-1,2-dihydroxyethyl]-7-[4-(trifluoromethoxy)phenyl]benzimidazol-5-yl]methyl]prop-2-enamide |
| 32 | 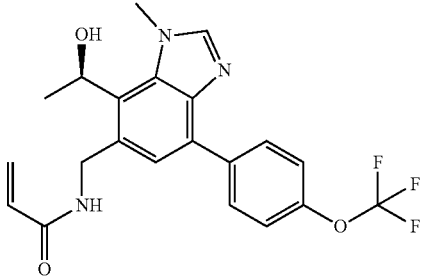 [SMILES: C=CC(=O)NCc1cc(-c2ccc(OC(F)(F)F)cc2)c2ncn(C)c2c1[C@@H](C)O] | N-[[3-methyl-4-[(1R)-1-hydroxyethyl]-7-[4-(trifluoromethoxy)phenyl]benzimidazol-5-yl]methyl]prop-2-enamide |
| 33 | 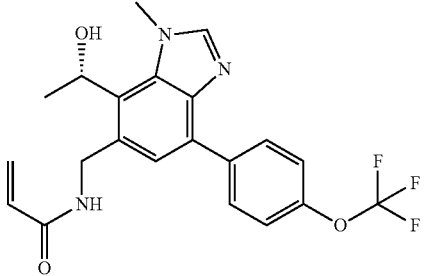 [SMILES: C=CC(=O)NCc1cc(-c2ccc(OC(F)(F)F)cc2)c2ncn(C)c2c1[C@H](C)O] | N-[[3-methyl-4-[(1S)-1-hydroxyethyl]-7-[4-(trifluoromethoxy)phenyl]benzimidazol-5-yl]methyl]prop-2-enamide |
| 34 | 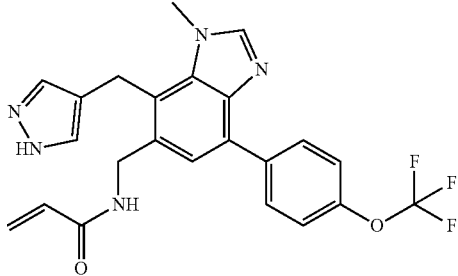 [SMILES: C=CC(=O)NCc1cc(-c2ccc(OC(F)(F)F)cc2)c2ncn(C)c2c1Cc1cn[nH]c1] | N-[[3-methyl-4-(1H-pyrazol-4-ylmethyl)-7-[4-(trifluoromethoxy)phenyl]benzimidazol-5-yl]methyl]prop-2-enamide |

-continued

| Compound Number | Structure | Compound Name |
|---|---|---|
| 39 | 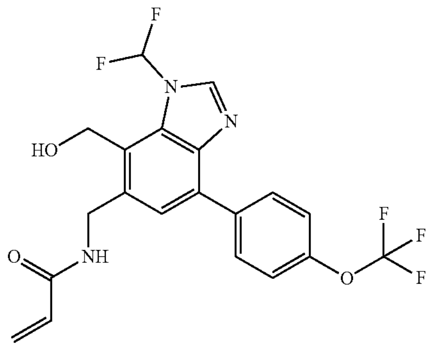 [SMILES: C=CC(=O)NCc1cc(-c2ccc(OC(F)(F)F)cc2)c2ncn(C(F)F)c2c1CO] | N-[3-(difluoromethyl)-4-(hydroxymethyl)-7-[4-(trifluoromethoxy)phenyl]benzimidazol-5-yl]methyl]prop-2-enamide |
| 40 | 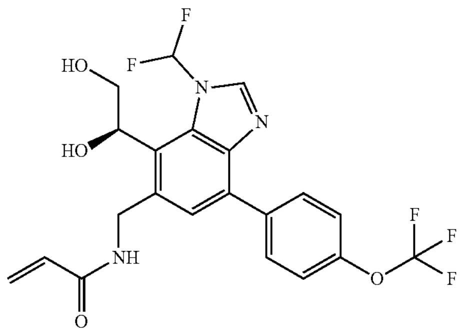 [SMILES: C=CC(=O)NCc1cc(-c2ccc(OC(F)(F)F)cc2)c2ncn(C(F)F)c2c1[C@@H](O)CO] | (R)-N-((1-(difluoromethyl)-7-(1,2-dihydroxyethyl)-4-(4-(trifluoromethoxy)phenyl)-1H-benzo[d]imidazol-6-yl)methyl)acrylamide |
| 41 | 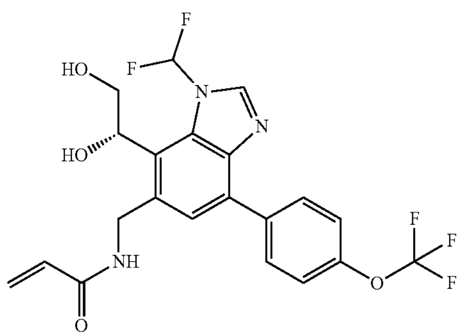 [SMILES: C=CC(=O)NCc1cc(-c2ccc(OC(F)(F)F)cc2)c2ncn(C(F)F)c2c1[C@H](O)CO] | (S)-N-((1-(difluoromethyl)-7-(1,2-dihydroxyethyl)-4-(4-(trifluoromethoxy)phenyl)-1H-benzo[d]imidazol-6-yl)methyl)acrylamide |
| 43 | 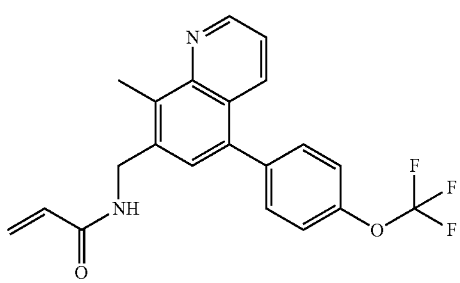 [SMILES: C=CC(=O)NCc1cc(-c2ccc(OC(F)(F)F)cc2)c2cccnc2c1C] | N-[8-methyl-5-[4-(trifluoromethoxy)phenyl]-7-quinolyl]methyl]prop-2-enamide |
| 44 | 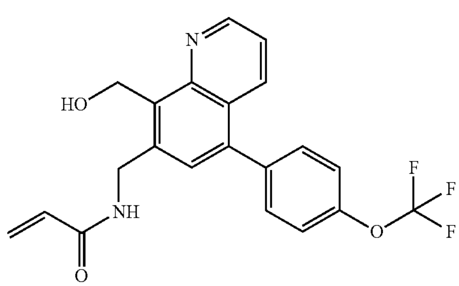 [SMILES: C=CC(=O)NCc1cc(-c2ccc(OC(F)(F)F)cc2)c2cccnc2c1CO] | N-[8-(hydroxymethyl)-5-[4-(trifluoromethoxy)phenyl]-7-quinolyl]methyl]prop-2-enamide |

| Compound Number | Structure | Compound Name |
|---|---|---|
| 45 | 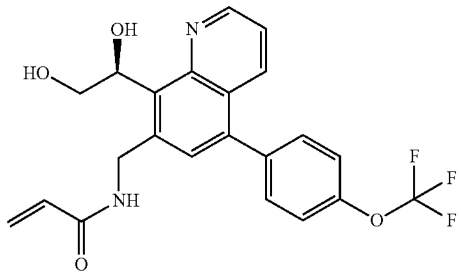 [SMILES: C=CC(=O)NCc1cc(-c2ccc(OC(F)(F)F)cc2)c2cccnc2c1[C@H](O)CO] | (S)-N-((8-(1,2-dihydroxyethyl)-5-(4-(trifluoromethoxy)phenyl)quinolin-7-yl)methyl)acrylamide |
| 46 | 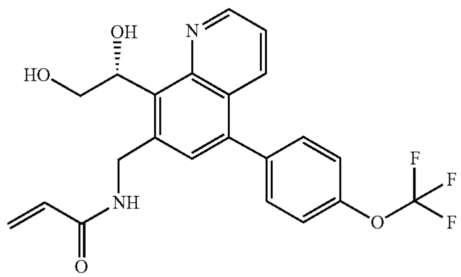 [SMILES: C=CC(=O)NCc1cc(-c2ccc(OC(F)(F)F)cc2)c2cccnc2c1[C@@H](O)CO] | (R)-N-((8-(1,2-dihydroxyethyl)-5-(4-(trifluoromethoxy)phenyl)quinolin-7-yl)methyl)acrylamide |
| 47 | 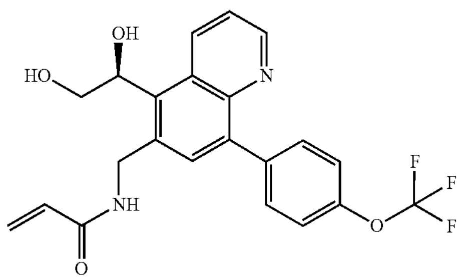 [SMILES: C=CC(=O)NCc1cc(-c2ccc(OC(F)(F)F)cc2)c2ncccc2c1[C@H](O)CO] | (S)-N-((5-(1,2-dihydroxyethyl)-8-(4-(trifluoromethoxy)phenyl)quinolin-6-yl)methyl) acrylamide |
| 48 | 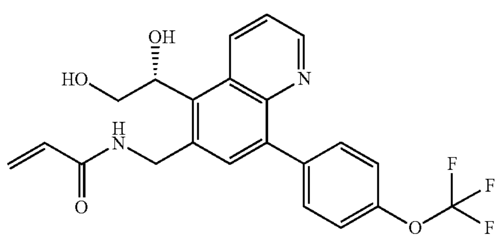 [SMILES: C=CC(=O)NCc1cc(-c2ccc(OC(F)(F)F)cc2)c2ncccc2c1[C@@H](O)CO] | (R)-N-((5-(1,2-dihydroxyethyl)-8-(4-(trifluoromethoxy)phenyl)quinolin-6-yl)methyl) acrylamide |
| 49 | 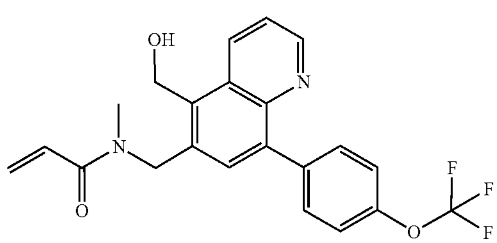 [SMILES: C=CC(=O)N(C)Cc1cc(-c2ccc(OC(F)(F)F)cc2)c2ncccc2c1CO] | N-[[5-(hydroxymethyl)-8-[4-(trifluoromethoxy)phenyl]-6-quinolyl]methyl]-N-methyl-prop-2-enamide |
| 50 | 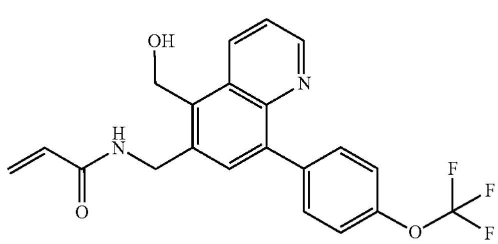 [SMILES: C=CC(=O)NCc1cc(-c2ccc(OC(F)(F)F)cc2)c2ncccc2c1CO] | N-[[5-(hydroxymethyl)-8-[4-(trifluoromethoxy)phenyl]-6-quinolyl]methyl]prop-2-enamide |

-continued

| Compound Number | Structure | Compound Name |
|---|---|---|
| 51 | 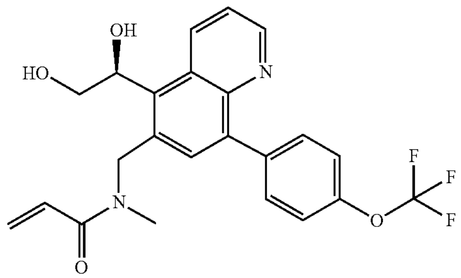 [SMILES: C=CC(=O)N(C)Cc1cc(-c2ccc(OC(F)(F)F)cc2)c2ncccc2c1[C@H](O)CO] | N-[5-[(1S)-1,2-dihydroxyethyl]-8-[4-(trifluoromethoxy)phenyl]-6-quinolyl]methyl]-N-methyl-prop-2-enamide |
| 52 | 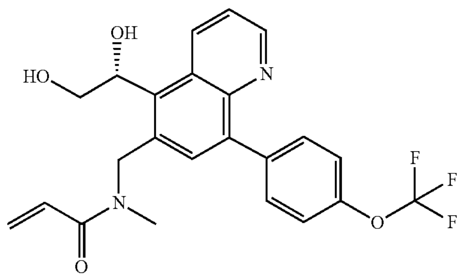 [SMILES: C=CC(=O)N(C)Cc1cc(-c2ccc(OC(F)(F)F)cc2)c2ncccc2c1[C@@H](O)CO] | N-[5-[(1R)-1,2-dihydroxyethyl]-8-[4-(trifluoromethoxy)phenyl]-6-quinolyl]methyl]-N-methyl-prop-2-enamide |
| 57 | 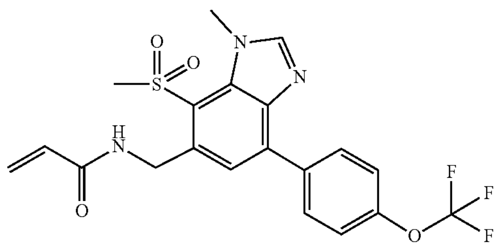 [SMILES: C=CC(=O)NCc1cc(-c2ccc(OC(F)(F)F)cc2)c2ncn(C)c2c1S(C)(=O)=O] | N-[[3-methyl-4-methylsulfonyl-7-[4-(trifluoromethoxy)phenyl]benzimidazol-5-yl]methyl]prop-2-enamide |
| 58 | 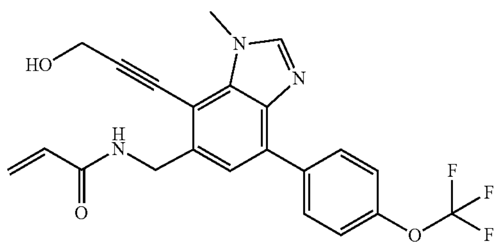 [SMILES: C=CC(=O)NCc1cc(-c2ccc(OC(F)(F)F)cc2)c2ncn(C)c2c1C#CCO] | N-[4-(3-hydroxyprop-1-ynyl)-3-methyl-7-[4-(trifluoromethoxy)phenyl]benzimidazol-5-yl]methyl]prop-2-enamide |
| 60 | 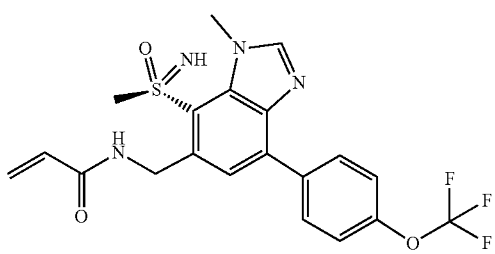 [SMILES: C=CC(=O)NCc1cc(-c2ccc(OC(F)(F)F)cc2)c2ncn(C)c2c1[S@@](C)(=N)=O] | (S)-N-((1-methyl-7-(S-methylsulfonimidoyl)-4-(4-(trifluoromethoxy)phenyl)-1H-benzo[d]imidazol-6-yl)methyl)acrylamide |
| 61 | 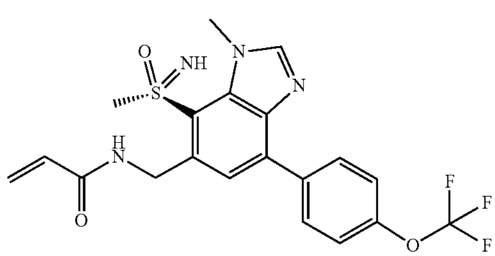 [SMILES: C=CC(=O)NCc1cc(-c2ccc(OC(F)(F)F)cc2)c2ncn(C)c2c1[S@](C)(=N)=O] | (R)-N-((1-methyl-7-(S-methylsulfonimidoyl)-4-(4-(trifluoromethoxy)phenyl)-1H-benzo[d]imidazol-6-yl)methyl)acrylamide |

-continued

| Compound Number | Structure | Compound Name |
|---|---|---|
| 63 | 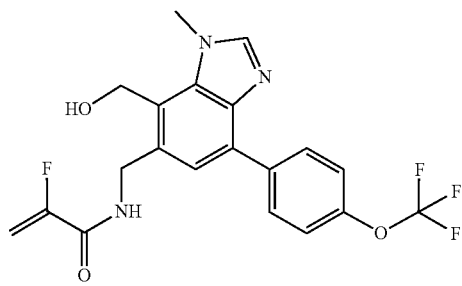 [SMILES: C=C(F)C(=O)NCc1cc(-c2ccc(OC(F)(F)F)cc2)c2ncn(C)c2c1CO] | 2-fluoro-N-[[4-(hydroxymethyl)-3-methyl-7-[4-(trifluoromethoxy)phenyl]benzimidazol-5-yl]methyl]prop-2-enamide |
| 64 | 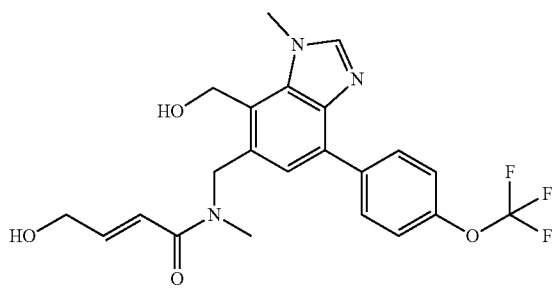 [SMILES: CN(Cc1cc(-c2ccc(OC(F)(F)F)cc2)c2ncn(C)c2c1CO)C(=O)/C=C/CO] | (E)-4-hydroxy-N-[[4-(hydroxymethyl)-3-methyl-7-[4-(trifluoromethoxy)phenyl]benzimidazol-5-yl]methyl]-N-methyl-but-2-enamide |
| 65 | 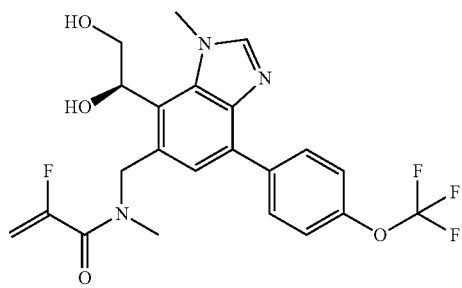 [SMILES: C=C(F)C(=O)N(C)Cc1cc(-c2ccc(OC(F)(F)F)cc2)c2ncn(C)c2c1[C@@H](O)CO] | (R)-N-((7-(1,2-dihydroxyethyl)-1-methyl-4-(4-(trifluoromethoxy)phenyl)-1H-benzo[d]imidazol-6-yl)methyl)-2-fluoro-N-methylacrylamide |
| 66 | 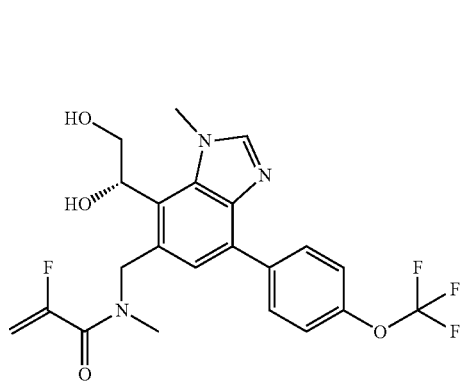 [SMILES: C=C(F)C(=O)N(C)Cc1cc(-c2ccc(OC(F)(F)F)cc2)c2ncn(C)c2c1[C@H](O)CO] | (S)-N-((7-(1,2-dihydroxyethyl)-1-methyl-4-(4-(trifluoromethoxy)phenyl)-1H-benzo[d]imidazol-6-yl)methyl)-2-fluoro-N-methylacrylamide |
| 68 | 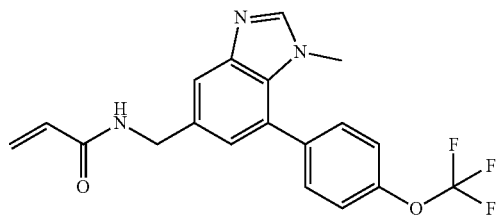 [SMILES: C=CC(=O)NCc1cc(-c2ccc(OC(F)(F)F)cc2)c2c(c1)ncn2C] | N-[[1-methyl-7-[4-(trifluoromethoxy)phenyl]benzimidazol-5-yl]methyl]prop-2-enamide |

-continued

| Compound Number | Structure | Compound Name |
|---|---|---|
| 72 | 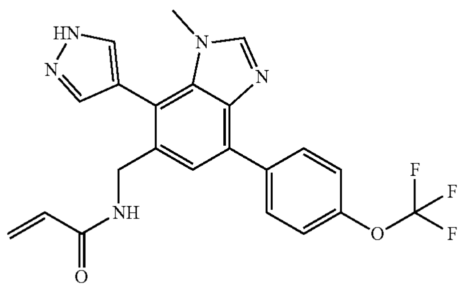 [SMILES: C=CC(=O)NCc1cc(-c2ccc(OC(F)(F)F)cc2)c2ncn(C)c2c1-c1cn[nH]c1] | N-[[3-methyl-4-(1H-pyrazol-4-yl)-7-[4-(trifluoromethoxy)phenyl]benzimidazol-5-yl]methyl]prop-2-enamide |
| 74 | 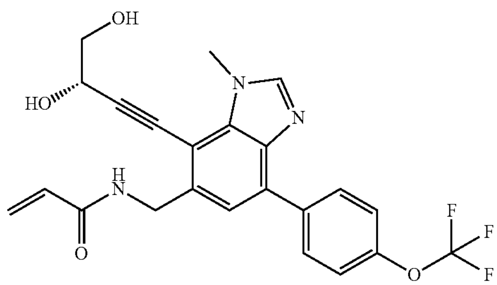 [SMILES: C=CC(=O)NCc1cc(-c2ccc(OC(F)(F)F)cc2)c2ncn(C)c2c1C#C[C@H](O)CO] | (S)-N-((7-(3,4-dihydroxybut-1-yn-1-yl)-1-methyl-4-(4-(trifluoromethoxy)phenyl)-1H-benzo[d]imidazol-6-yl)methyl)acrylamide |
| 75 | 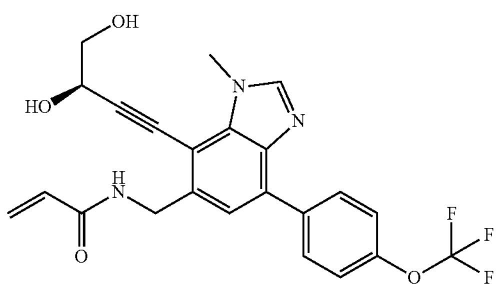 [SMILES: C=CC(=O)NCc1cc(-c2ccc(OC(F)(F)F)cc2)c2ncn(C)c2c1C#C[C@@H](O)CO] | (R)-N-((7-(3,4-dihydroxybut-1-yn-1-yl)-1-methyl-4-(4-(trifluoromethoxy)phenyl)-1H-benzo[d]imidazol-6-yl)methyl)acrylamide |
| 76 | 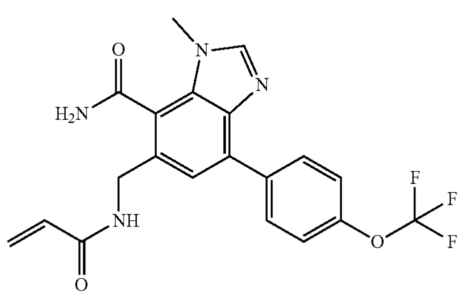 [SMILES: C=CC(=O)NCc1cc(-c2ccc(OC(F)(F)F)cc2)c2ncn(C)c2c1C(N)=O] | 3-methyl-5-[(prop-2-enoylamino)methyl]-7-[4-(trifluoromethoxy)phenyl]benzimidazole-4-carboxamide |
| 77 | 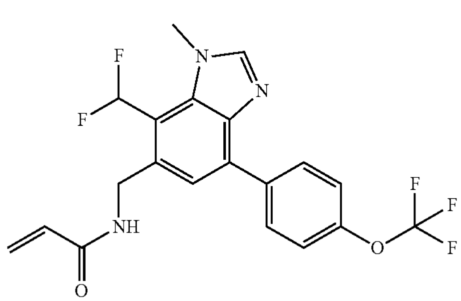 [SMILES: C=CC(=O)NCc1cc(-c2ccc(OC(F)(F)F)cc2)c2ncn(C)c2c1C(F)F] | N-[[4-(difluoromethyl)-3-methyl-7-[4-(trifluoromethoxy)phenyl]benzimidazol-5-yl]methyl]prop-2-enamide |

| Compound Number | Structure | Compound Name |
|---|---|---|
| 78 | 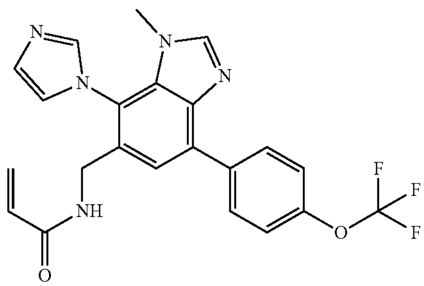 [SMILES: C=CC(=O)NCc1cc(-c2ccc(OC(F)(F)F)cc2)c2ncn(C)c2c1-n1ccnc1] | N-((7-(1H-imidazol-1-yl)-1-methyl-4-(4-(trifluoromethoxy)phenyl)-1H-benzo[d]imidazol-6-yl)methyl)acrylamide |
| 79 | 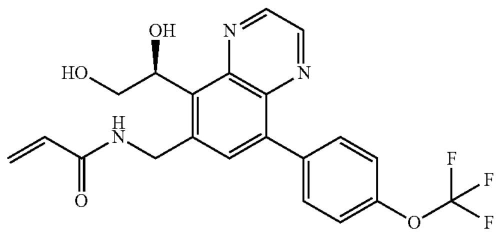 [SMILES: C=CC(=O)NCc1cc(-c2ccc(OC(F)(F)F)cc2)c2nccnc2c1[C@H](O)CO] | (S)-N-((5-(1,2-Dihydroxyethyl)-8-(4-(trifluoromethoxy)phenyl)quinoxalin-6-yl)methyl)acrylamide |
| 80 | 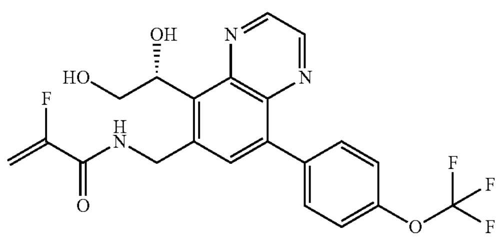 [SMILES: C=C(F)C(=O)NCc1cc(-c2ccc(OC(F)(F)F)cc2)c2nccnc2c1[C@@H](O)CO] | (R)-N-((5-(1,2-Dihydroxyethyl)-8-(4-(trifluoromethoxy)phenyl)quinoxalin-6-yl)methyl)-2-fluoroacrylamide |
| 81 | 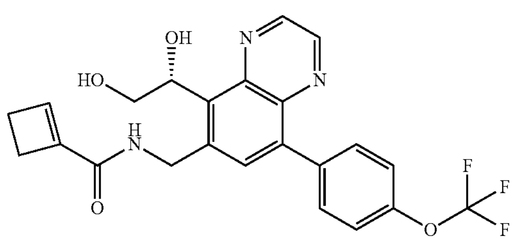 [SMILES: O=C(NCc1cc(-c2ccc(OC(F)(F)F)cc2)c2nccnc2c1[C@@H](O)CO)C1=CCC1] | (R)-N-((5-(1,2-Dihydroxyethyl)-8-(4-(trifluoromethoxy)phenyl)quinoxalin-6-yl)methyl)cyclobut-1-ene-1-carboxamide |
| 82 | 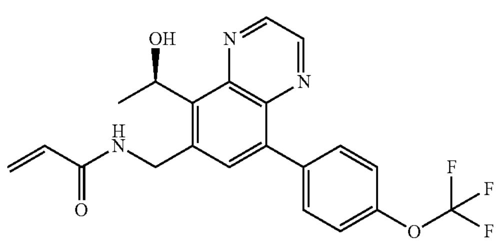 [SMILES: C=CC(=O)NCc1cc(-c2ccc(OC(F)(F)F)cc2)c2nccnc2c1[C@@H](C)O] | (R)-N-((5-(1-Hydroxyethyl)-8-(4-(trifluoromethoxy)phenyl)quinoxalin-6-yl)methyl)acrylamide |
| 83 | 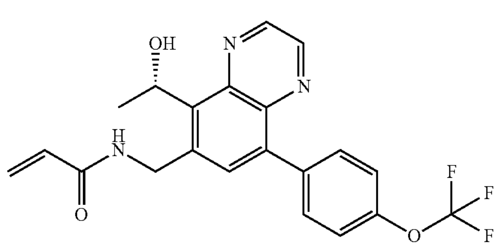 [SMILES: C=CC(=O)NCc1cc(-c2ccc(OC(F)(F)F)cc2)c2nccnc2c1[C@H](C)O] | (S)-N-((5-(1-hydroxyethyl)-8-(4-(trifluoromethoxy)phenyl)quinoxalin-6-yl)methyl)acrylamide |

| Compound Number | Structure | Compound Name |
|---|---|---|
| 84 | 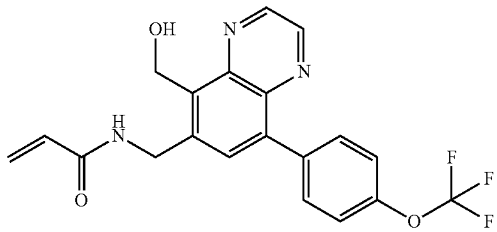 [SMILES: C=CC(=O)NCc1cc(-c2ccc(OC(F)(F)F)cc2)c2nccnc2c1CO] | N-((5-(Hydroxymethyl)-8-(4-(trifluoromethoxy)phenyl)quinoxalin-6-yl)methyl)acrylamide |
| 85 | 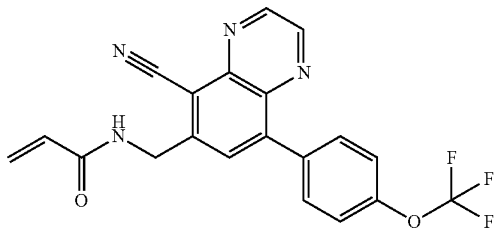 [SMILES: C=CC(=O)NCc1cc(-c2ccc(OC(F)(F)F)cc2)c2nccnc2c1C#N] | N-((5-Cyano-8-(4-(trifluoromethoxy)phenyl)quinoxalin-6-yl)methyl)acrylamide |
| 104 | 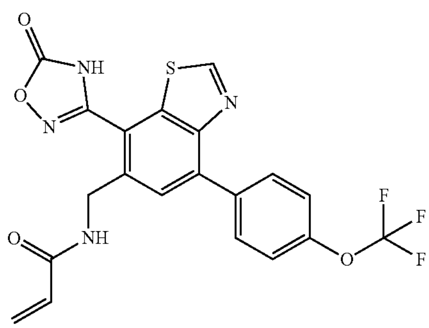 [SMILES: C=CC(=O)NCc1cc(-c2ccc(OC(F)(F)F)cc2)c2ncsc2c1-c1noc(=O)[nH]1] | N-((7-(5-Oxo-4,5-dihydro-1,2,4-oxadiazol-3-yl)-4-(4-(trifluoromethoxy)phenyl)benzo[d]thiazol-6-yl)methyl)acrylamide |
| 105 | 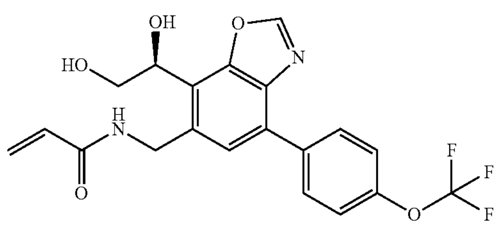 [SMILES: C=CC(=O)NCc1cc(-c2ccc(OC(F)(F)F)cc2)c2ncoc2c1[C@H](O)CO] | (S)-N-((7-(1,2-Dihydroxyethyl)-4-(4-(trifluoromethoxy)phenyl)benzo[d]oxazol-6-yl)methyl)acrylamide |
| 106 | 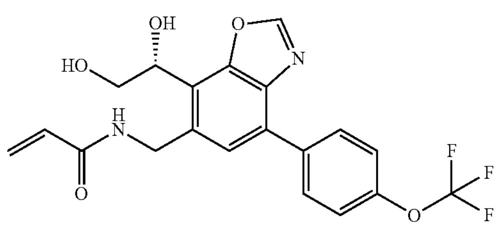 | (R)-N-((7-(1,2-dihydroxyethyl)-4-(4-(trifluoromethoxy)phenyl)benzo[d]oxazol-6-yl)methyl)acrylamide |
| 107 | 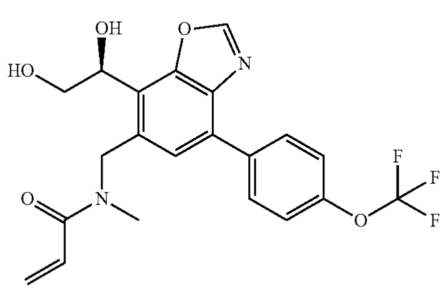 [SMILES: C=CC(=O)N(C)Cc1cc(-c2ccc(OC(F)(F)F)cc2)c2ncoc2c1[C@H](O)CO] | (S)-N-((7-(1,2-Dihydroxyethyl)-4-(4-(trifluoromethoxy)phenyl)benzo[d]oxazol-6-yl)methyl)-N-methylacrylamide |

-continued

| Compound Number | Structure | Compound Name |
|---|---|---|
| 108 | 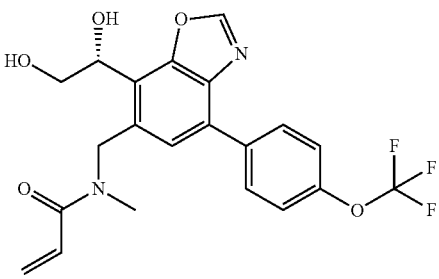 [SMILES: C=CC(=O)N(C)Cc1cc(-c2ccc(OC(F)(F)F)cc2)c2ncoc2c1[C@@H](O)CO] | (R)-N-((7-(1,2-dihydroxyethyl)-4-(4-(trifluoromethoxy)phenyl)benzo[d]oxazol-6-yl)methyl)-N-methylacrylamide |
| 109 | 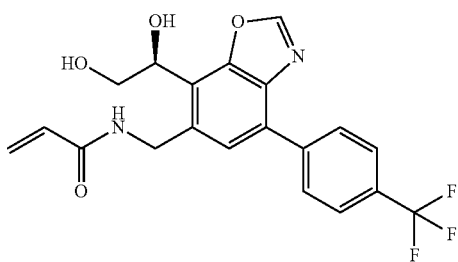 [SMILES: C=CC(=O)NCc1cc(-c2ccc(C(F)(F)F)cc2)c2ncoc2c1[C@H](O)CO] | (S)-N-((7-(1,2-Dihydroxyethyl)-4-(4-(trifluoromethyl)phenyl)benzo[d]oxazol-6-yl)methyl)acrylamide |
| 110 | 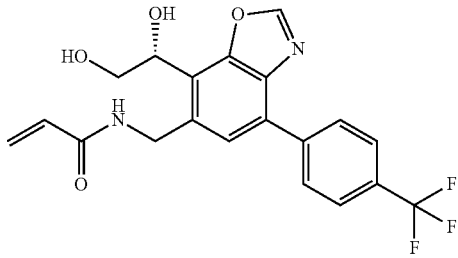 [SMILES: C=CC(=O)NCc1cc(-c2ccc(C(F)(F)F)cc2)c2ncoc2c1[C@@H](O)CO] | (R)-N-((7-(1,2-dihydroxyethyl)-4-(4-(trifluoromethyl)phenyl)benzo[d]oxazol-6-yl)methyl)acrylamide |
| 111 | 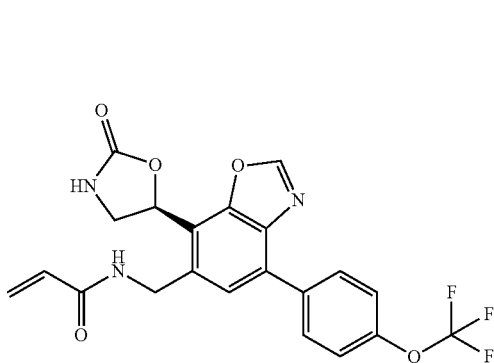 [SMILES: C=CC(=O)NCc1cc(-c2ccc(OC(F)(F)F)cc2)c2ncoc2c1[C@H]1CNC(=O)O1] | (S)-N-((7-(2-Oxooxazolidin-5-yl)-4-(4-(trifluoromethoxy)phenyl)benzo[d]oxazol-6-yl)methyl)acrylamide |
| 112 | 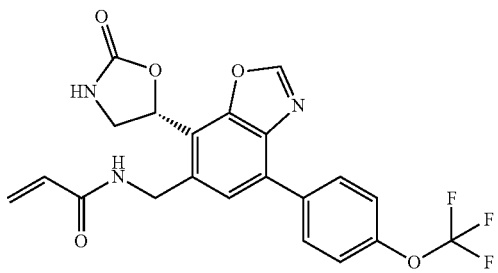 [SMILES: C=CC(=O)NCc1cc(-c2ccc(OC(F)(F)F)cc2)c2ncoc2c1[C@@H]1CNC(=O)O1] | (R)-N-((7-(2-oxooxazolidin-5-yl)-4-(4-(trifluoromethoxy)phenyl)benzo[d]oxazol-6-yl)methyl)acrylamide |

-continued

| Compound Number | Structure | Compound Name |
|---|---|---|
| 113 | 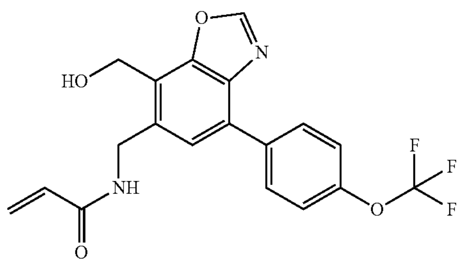 [SMILES: C=CC(=O)NCc1cc(-c2ccc(OC(F)(F)F)cc2)c2ncoc2c1CO] | N-((7-(Hydroxymethyl)-4-(4-(trifluoromethoxy)phenyl)benzo[d]oxazol-6-yl)methyl)acrylamide |
| 138 | 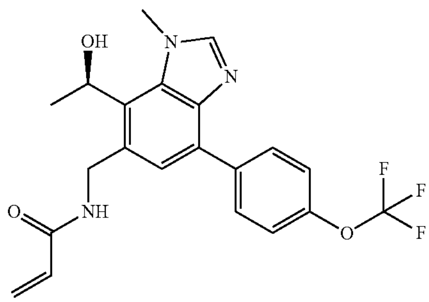 [SMILES: C=CC(=O)NCc1cc(-c2ccc(OC(F)(F)F)cc2)c2ncn(C)c2c1[C@@H](C)O] | (R)-N-((7-(1-Hydroxyethyl)-1-methyl-4-(4-(trifluoromethoxy)phenyl)-1H-benzo[d]imidazol-6-yl)methyl)acrylamide |
| 139 | 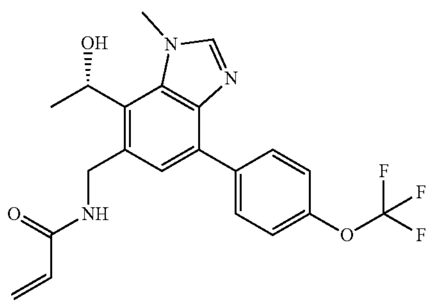 [SMILES: C=CC(=O)NCc1cc(-c2ccc(OC(F)(F)F)cc2)c2ncn(C)c2c1[C@H](C)O] | (S)-N-((7-(1-hydroxyethyl)-1-methyl-4-(4-(trifluoromethoxy)phenyl)-1H-benzo[d]imidazol-6-yl)methyl)acrylamide |
| 140 | 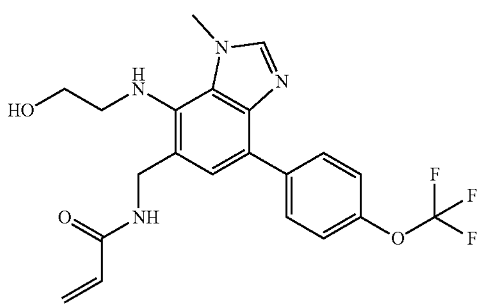 [SMILES: C=CC(=O)NCc1cc(-c2ccc(OC(F)(F)F)cc2)c2ncn(C)c2c1NCCO] | N-((7-((2-Hydroxyethyl)amino)-1-methyl-4-(4-(trifluoromethoxy)phenyl)-1H-benzo[d]imidazol-6-yl)methyl)acrylamide, and |
| 143 | 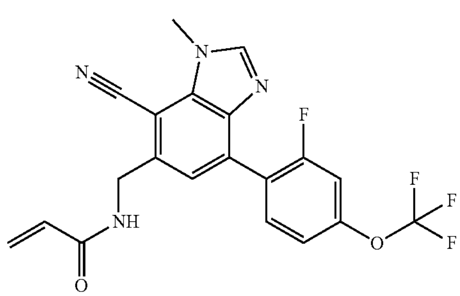 [SMILES: C=CC(=O)NCc1cc(-c2ccc(OC(F)(F)F)cc2F)c2ncn(C)c2c1C#N] | N-((7-Cyano-4-(2-fluoro-4-(trifluoromethoxy)phenyl)-1-methyl-1H-benzo[d]imidazol-6-yl)methyl)acrylamide |

13. The compound of claim 1, or a stereoisomer or tautomer thereof, or a pharmaceutically acceptable salt thereof, wherein $R^s$ is selected from the group consisting of —CN, —CH$_3$,

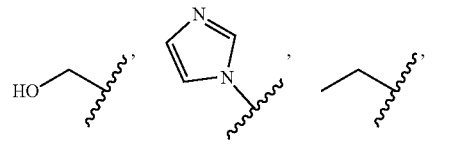

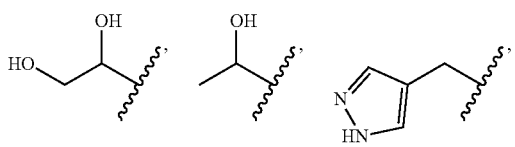

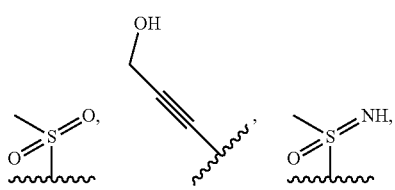

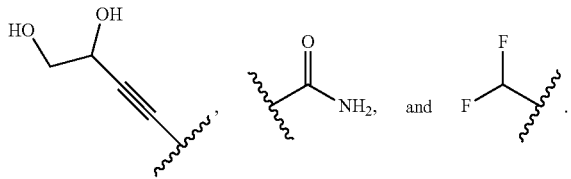

14. The compound of claim 12, wherein the compound is:

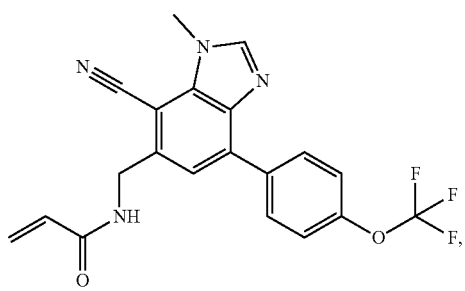 [SMILES: C=CC(=O)NCc1cc(-c2ccc(OC(F)(F)F)cc2)c2ncn(C)c2c1C#N]

or a pharmaceutically acceptable salt thereof.

15. The compound of claim 12, wherein the compound is:

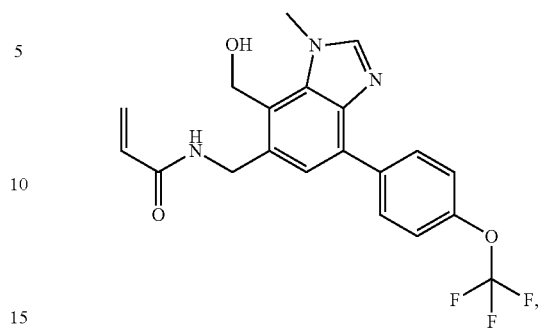

or a pharmaceutically acceptable salt thereof.

16. The compound of claim 12, wherein the compound is:

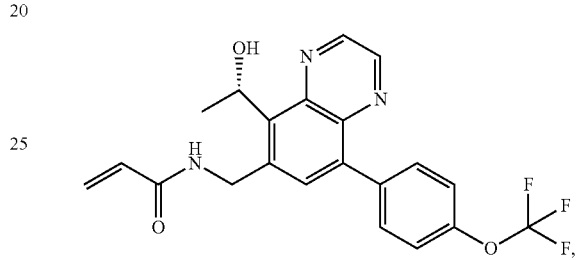

or a pharmaceutically acceptable salt thereof.

17. The compound of claim 12, wherein the compound is:

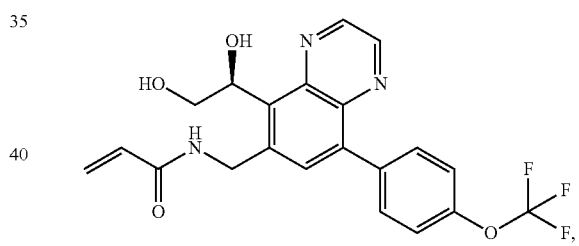

or a pharmaceutically acceptable salt thereof.

18. A pharmaceutical composition, comprising (i) a compound as described in claim 1, or a stereoisomer, tautomer, or pharmaceutically acceptable salt thereof, and (ii) a pharmaceutically acceptable carrier, diluent, or excipient.

19. A composition, comprising: (i) one or more TEAD inhibitors, or a pharmaceutically acceptable salt thereof; and (ii) one or more KRAS inhibitors, or a pharmaceutically acceptable salt thereof,
wherein the one or more TEAD inhibitors are any one of the compounds of claim 1.

20. A kit, comprising: (i) one or more TEAD inhibitors, or a pharmaceutically acceptable salt thereof; (ii) one or more KRAS inhibitors, or a pharmaceutically acceptable salt thereof; and (iii) instructions for administering the combination to treat cancer in a subject in need thereof;
wherein the one or more TEAD inhibitors are any one of the compounds of claim 1.

* * * * *